US012286430B2

(12) United States Patent
Xue et al.

(10) Patent No.: US 12,286,430 B2
(45) Date of Patent: Apr. 29, 2025

(54) BCL-2 INHIBITOR

(71) Applicant: BEIGENE, LTD., Grand Cayman (KY)

(72) Inventors: Hai Xue, Beijing (CN); Yunhang Guo, Beijing (CN); Zhiwei Wang, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 206 days.

(21) Appl. No.: 17/916,845

(22) PCT Filed: Apr. 14, 2021

(86) PCT No.: PCT/CN2021/087225
§ 371 (c)(1),
(2) Date: Oct. 4, 2022

(87) PCT Pub. No.: WO2021/208963
PCT Pub. Date: Oct. 21, 2021

(65) Prior Publication Data
US 2023/0159522 A1 May 25, 2023

(30) Foreign Application Priority Data

| Apr. 15, 2020 | (WO) | PCT/CN2020/084992 |
| Jul. 6, 2020 | (WO) | PCT/CN2020/100472 |
| Oct. 30, 2020 | (WO) | PCT/CN2020/125580 |
| Feb. 7, 2021 | (WO) | PCT/CN2021/075831 |
| Apr. 9, 2021 | (WO) | PCT/CN2021/086189 |

(51) Int. Cl.
| C07D 471/04 | (2006.01) |
| A61P 35/00 | (2006.01) |
| C07D 409/12 | (2006.01) |
| C07D 519/00 | (2006.01) |

(52) U.S. Cl.
CPC ............ C07D 471/04 (2013.01); A61P 35/00 (2018.01); C07D 409/12 (2013.01); C07D 519/00 (2013.01); C07B 2200/05 (2013.01); C07B 2200/07 (2013.01)

(58) Field of Classification Search
CPC .................................................. C07D 471/04
USPC ........................................................ 514/157
See application file for complete search history.

(56) References Cited

U.S. PATENT DOCUMENTS

| 11,420,968 B2 | 8/2022 | Guo et al. |
| 2002/0055631 A1 | 5/2002 | Augeri et al. |
| 2011/0124628 A1 | 5/2011 | Bruncko et al. |
| 2011/0237553 A1 | 9/2011 | Ding et al. |
| 2011/0312969 A1 | 12/2011 | East et al. |
| 2012/0189539 A1 | 7/2012 | Wang et al. |
| 2012/0214796 A1 | 8/2012 | Ding et al. |
| 2013/0245005 A1 | 9/2013 | Sorba et al. |
| 2020/0397895 A1 | 12/2020 | Levy et al. |
| 2021/0269433 A1 | 9/2021 | Guo et al. |
| 2022/0402915 A1 | 12/2022 | Guo et al. |
| 2023/0002369 A1 | 1/2023 | Xue et al. |
| 2024/0122932 A1 | 4/2024 | Hilger et al. |
| 2024/0317743 A1 | 9/2024 | Yu et al. |

FOREIGN PATENT DOCUMENTS

| CN | 102448959 A | 5/2012 |
| CN | 102947283 A | 2/2013 |
| CN | 103237797 A | 8/2013 |
| CN | 103562202 A | 2/2014 |
| CN | 106565706 A | 4/2017 |
| CN | 106749233 A | 5/2017 |
| CN | 110143974 A | 8/2019 |
| CN | 110177788 A | 8/2019 |
| WO | WO-0224636 A2 | 3/2002 |
| WO | WO-2005049593 A2 | 6/2005 |
| WO | WO-2006023778 A2 | 3/2006 |
| WO | WO-2006127364 A1 | 11/2006 |
| WO | WO-2007040650 A2 | 4/2007 |
| WO | WO-2008030836 A2 | 3/2008 |
| WO | WO-2009036051 A1 | 3/2009 |
| WO | WO-2009152082 A1 | 12/2009 |
| WO | WO-2009155386 A1 | 12/2009 |
| WO | WO-2010065824 A2 | 6/2010 |
| WO | WO-2010065865 A2 | 6/2010 |
| WO | WO-2010067067 A1 | 6/2010 |
| WO | WO-2010083441 A2 | 7/2010 |
| WO | WO-2010083442 A1 | 7/2010 |
| WO | WO-2010138588 A2 | 12/2010 |
| WO | WO-2011029842 A1 | 3/2011 |
| WO | WO-2011068561 A1 | 6/2011 |
| WO | WO-2011119345 A2 | 9/2011 |
| WO | WO-2011149492 A1 | 12/2011 |
| WO | WO-2011150016 A1 | 12/2011 |
| WO | WO-2012017251 A1 | 2/2012 |
| WO | WO-2012058392 A1 | 5/2012 |
| WO | WO-2012073184 A1 | 6/2012 |
| WO | WO-2012103059 A2 | 8/2012 |

(Continued)

OTHER PUBLICATIONS

Adams, J. M. et al. (2007) The Bcl-2 apoptotic switch in cancer development and therapy. Oncogene 26:1324-1337.
Anderson, M. A. et al. (2014) Targeting BCL2 for the treatment of lymphoid malignancies. Semin. Hematol., 51:219-227.
Ashkenazi, A. et al, "From basic apoptosis discoveries to advanced selective BCL-2 family inhibitors," Nature Reviews Drug Discovery. Apr. 2017, vol. 16, No. 4, pp. 273-284.
Balar, A. V. et al., "Atezolizumab as first-line treatment in cisplatin-ineligible patients with locally advanced and metastatic urothelial carcinoma: a single-arm, multicentre, phase 2 trial," Lancet, 2017;389(10064):67-76.
Blombery, P. et al., "Acquisition of the recurrent Gly101Val mutation in BCL2 confers resistance to venetoclax in patients with progressive chronic lymphocytic leukemia," Cancer Discovery, Mar. 2019, vol. 9, No. 3, pp. 342-353.

(Continued)

Primary Examiner — Niloofar Rahmani
(74) Attorney, Agent, or Firm — McNeill PLLC

(57) ABSTRACT

Disclosed herein is a compound of Formula (I) for inhibiting both Bcl-2 wild type and mutated Bcl-2, in particular, Bcl-2 G101V and D103Y, and a method of using the compound disclosed herein for treating dysregulated apoptotic diseases.

24 Claims, 1 Drawing Sheet

(56) References Cited

FOREIGN PATENT DOCUMENTS

| WO | WO-2012162365 A1 | 11/2012 |
| --- | --- | --- |
| WO | WO-2013053045 A1 | 4/2013 |
| WO | WO-2013096049 A1 | 6/2013 |
| WO | WO-2013096050 A1 | 6/2013 |
| WO | WO-2013096051 A1 | 6/2013 |
| WO | WO-2013096055 A1 | 6/2013 |
| WO | WO-2013096060 A1 | 6/2013 |
| WO | WO-2013185202 A1 | 12/2013 |
| WO | WO-2014113413 A1 | 7/2014 |
| WO | WO-2014158528 A1 | 10/2014 |
| WO | WO-2014173289 A1 | 10/2014 |
| WO | WO-2016024230 A1 | 2/2016 |
| WO | WO-2017132474 A1 | 8/2017 |
| WO | WO-2018009444 A1 | 1/2018 |
| WO | WO-2018027097 A1 | 2/2018 |
| WO | WO-2018041248 A1 | 3/2018 |
| WO | WO-2018127130 A1 | 7/2018 |
| WO | WO-2018192462 A1 | 10/2018 |
| WO | WO-2019001383 A1 | 1/2019 |
| WO | WO-2019040550 A1 | 2/2019 |
| WO | WO-2019040573 A1 | 2/2019 |
| WO | 2019210828 * | 4/2019 |
| WO | WO-2019081559 A1 | 5/2019 |
| WO | WO-2019210828 A1 | 11/2019 |
| WO | WO-2020024834 A1 | 2/2020 |
| WO | WO-2020024916 A1 | 2/2020 |
| WO | WO-2020140005 A2 | 7/2020 |
| WO | WO-2021083135 A1 | 5/2021 |
| WO | WO-2021110102 A1 | 6/2021 |
| WO | WO-2021208963 A1 | 10/2021 |
| WO | 2022213335 A1 | 10/2022 |
| WO | WO-2022256489 A1 | 12/2022 |
| WO | 2023030363 A1 | 3/2023 |
| WO | 2023218410 A1 | 11/2023 |
| WO | 2024017354 A1 | 1/2024 |

OTHER PUBLICATIONS

Bold, R. et al., "BCL2 expression correlates with metastatic potential in pancreatic cancer cell lines," Cancer: Interdisciplinary International Journal of the American Cancer Society, Sep. 1, 2001, vol. 92, No. 5, pp. 1122-1129.

Cang S. et al., "ABT-199 (venetoclax) and BCL-2 inhibitors in clinical development," Journal of Hematology & Oncology, Dec. 2015, vol. 8, No. 1, pp. 1-8.

Chipuk, J. et al., "The BCL-2 family reunion," Molecular Cell, Feb. 12, 2010, vol. 37, No. 3, pp. 299-310.

Cookson, B. et al., "Pro-inflammatory programmed cell death," Trends in Microbiology, Mar. 1, 2001, vol. 9, No. 3, pp. 113-114.

Coultas, L. et al., "The role of the Bcl-2 protein family in cancer," Seminars in Cancer Biology, Apr. 1, 2003, vol. 13, No. 2, pp. 115-123.

Czabotar, P. E. et al. (2014) Control of apoptosis by the BCL-2 protein family: implications for physiology and therapy. Nat. Rev. Mol. Cell Biol., 15: 49-63.

Dinardo, C.D., et al., "Venetoclax combined with decitabine or azacitidine in treatment-naive, elderly patients with acute myeloid leukemia," Blood, 2019, vol. 133, No. 1, pp. 7-17.

Egle, A. et al. (2004) VavP-Bcl2 transgenic mice develop follicular lymphoma preceded by germinal center hyperplasia. Blood, 103:2276-2283.

Hanahan, D and R.A. Weinberg (Mar. 4, 2011) "Hallmarks of cancer: The next generation" Cell, 144(5):646-674.

Hennessy, E., "Selective inhibitors of Bcl-2 and Bcl-xL: Balancing antitumor activity with on-target toxicity," Bioorganic & Medicinal Chemistry Letters, May 1, 2016, vol. 26, No. 9, pp. 2105-2114.

Hillmen, P., et al., "Ibrutinib Plus Venetoclax in Relapsed/Refractory Chronic Lymphocytic Leukemia: The CLARITY Study," J Clin Oncol, 2019, vol. 3, No. 30, pp. 2722-2729.

International Search Report and Written Opinion for International Application No. PCT/CN2019/085001, mailed Jul. 26, 2019, 12 pages.

International Search Report and Written Opinion for International Application No. PCT/CN2020/123939, mailed Jan. 4, 2021, 15 pages.

International Search Report and Written Opinion for International Application No. PCT/CN2020/133636, mailed Feb. 26, 2021, 13 pages.

International Search Report and Written Opinion for International Application No. PCT/CN2021/087225, mailed Jul. 14, 2021, 11 pages.

International Search Report and Written Opinion for International Application No. PCT/US2022/031782, mailed Aug. 29, 2022, 13 pages.

International Search Report and Written Opinion for International Application No. PCT/US2022/031903, mailed Aug. 25, 2022, 13 pages.

Jain, N., Ibrutinib and Venetoclax for First-Line Treatment of CLL Reply, N Engl J Med, 2019, vol. 381, No. 8, p. 789.

Kerr, J. F. R. et al., "Apoptosis: A Basic Biological Phenomenon With Wide-Ranging Implications In Tissue Kinetics," Br. J. Cancer, 26:239-257, 1972.

Kondo, S. et al. (2008) Rescue of renal hypoplasia and cystic dysplasia in Bcl-2 -/- mice expressing Bcl-2 in ureteric bud derived epithelia. Dev. Dyn., 237:2450-2459.

Letai, A., "Diagnosing and exploiting cancer's addiction to blocks in apoptosis," Nature Reviews Cancer, Feb. 2008, vol. 8, No. 2, pp. 121-132.

Liu, X. et al. (2018) "Development of high potent and selective Bcl-2 inhibitors bearing the structural elements of natural product artemisinin," European Journal of Medicinal Chemistry, 159:149-165.

Lochmuller, C. H. et al., "Chromatographic resolution of enantiomers selective review," J. Chromatogr., vol. 113, No. 3, Oct. 1975, pp. 283-302.

Masood, A., "Small molecule inhibitors of bcl-2 family proteins for pancreatic cancer therapy," Cancers, Mar. 24, 2011, vol. 3, No. 2, pp. 1527-1549.

Mohammad, R., "Small-molecule inhibitors of Bcl-2 family proteins as therapeutic agents in cancer," Recent patents on anti-cancer drug discovery, Jan. 1, 2008, vol. 3, No., 1, pp. 20-30.

Placzek, W.J., et al., "A survey of the anti-apoptotic Bcl-2 subfamily expression in cancer types provides a platform to predict the efficacy of Bcl-2 antagonists in cancer therapy," Cell Death Dis, 2010, vol. 1, pp. e40.

Poeta G. et al., "Deregulation of the mitochondrial apoptotic machinery and development of molecular targeted drugs in acute myeloid leukemia," Current Cancer Drug Targets, May 1, 2008, vol. 8, No. 3, pp. 207-222.

Roberts, A. W. (2016) Targeting apoptotic pathways to treat lymphoid malignancies. Rinsho Ketsueki 57:2054-2058.

Roberts, A. W. et al. (2017) Targeting BCL2 With BH3 Mimetics: Basic Science and Clinical Application of Venetoclax in Chronic Lymphocytic Leukemia and Related B Cell Malignancies. Clin. Pharmacol. Ther., 101:89-98.

Roberts, et al., "Targeting BCL2 with Venetoclax in Relapsed Chronic Lymphocytic Leukemia", N Engl J Med (Jan. 2016); 374:311-322.

Schenk, R. L. et al. (2017) BCL-2: Long and winding path from discovery to therapeutic target. Biochem. Biophys. Res. Commun., 482:459-469.

Seymour, J.F., et al., "Venetoclax plus rituximab in relapsed or refractory chronic lymphocytic leukaemia: a phase lb study," Lancet Oncol, 2017, vol. 18, No. 2, pp. 230-240.

Tam, C. S. et al., "Phase 1 study of the selective BTK inhibitor zanubrutinib in B-cell malignancies and safety and efficacy evaluation in CLL," The American Society of Hematology, vol. 134, No. 11, pp. 851-859 (2019).

Tausch, E. et al. (2019) Venetoclax resistance and acquired BCL2 mutations in chronic lymphocytic leukemia. Haematologica, 104:e434-e437.

(56) References Cited

OTHER PUBLICATIONS

Tsujimoto, Y. et al., "Analysis of the structure, transcripts, and protein products of bcl-2, the gene involved in human follicular lymphoma," Proc Natl Acad Sci, 1986, vol. 83, No. 14, pp. 5214-5218.
Veis, D. J. et al. (1993) Bcl-2-deficient mice demonstrate fulminant lymphoid apoptosis, polycystic kidneys, and hypopigmented hair. Cell, 75:229-240.
Vogelstein, B. et al., "Cancer genes and the pathways they control," Nature Medicine. Aug. 1, 2004, vol. 10, No. 8, pp. 789-799.
Wilson, WH, et al., "Navitoclax, a targeted high-affinity inhibitor of BCL-2, in lymphoid malignancies: a phase 1 dose-escalation study of safety, pharmacokinetics, pharmacodynamics, and antitumour activity," Lancet Oncol., Dec. 2010; vol. 11, No. 12, pp. 1149-1159.
Written Opinion for Singapore Application No. 11202009933W, dated Mar. 10, 2022, 7 pages.
Yamamura, K. et al., "Accelerated disappearance of melanocytes in bcl-2-deficient mice," Cancer Res vol. 56, pp. 3546-3550 (Aug. 1996).
Extended European Search Report EESR issued in EP Application No. 21789482.3, Sep. 29, 2023, 6 pgs.
Hilger, James, et al. U.S. Appl. No. 18/524,170, filed Nov. 30, 2023.
Yu, Desheng, et al., U.S. Appl. No. 18/589,022, filed Feb. 27, 2024.
Gandhi et al., 2011, "Phase I study of Navitoclax (ABT-263), a novel Bcl-2 family inhibitor, in patients with small-cell lung cancer and other solid tumors", J. Clin. Oncol., 29(7): 909-916.
Blombery et al., 2019, "Characterization of a novel venetoclax resistance mutation (BCL2 Phe104lle) observed in follicular lymphoma", Br J Haematol., 186(6): e188-e191.
Davids et al., 2018, "Comprehensive safety analysis of Venetoclax monotherapy for patients with relapsed / refractory chronic lymphocytic leukemia", Clinical Cancer Research, 24(18): 4371-4379.
Daniel et al., 2017, "BCL-2 as a therapeutic target in chronic lymphocytic leukemia." Clinical Advances in Hematology & Oncology, 15(3): 210-218.

* cited by examiner

BCL-2 INHIBITOR

CROSS-REFERENCE TO RELATED APPLICATIONS

This application is a U.S. National Stage Application under 35 U.S.C. § 371 of International Application No. PCT/CN2021/087225, filed Apr. 14, 2021, which claims priority to Patent Application Nos. PCT/CN2020/084992 (CN), filed Apr. 15, 2020, PCT/CN2020/100472 (CN), filed on Jul. 6, 2020, PCT/CN2020/125580 (CN), filed on Oct. 30, 2020, PCT/CN2021/075831 (CN), filed on Feb. 7, 2021, and PCT/CN2021/086189 (CN), filed Apr. 9, 2021.

FIELD OF THE DISCLOSURE

Disclosed herein is a compound of Formula (I) for inhibiting both Bcl-2 wild type and mutated Bcl-2, and a method of using the compound disclosed herein for treating dysregulated apoptotic diseases.

BACKGROUND OF THE DISCLOSURE

The B cell lymphoma 2 (Bcl-2) gene family, a group of proteins homologous to the Bcl-2 protein, encodes more than 20 proteins that regulate the intrinsic apoptosis pathway. Bcl-2 family proteins, consisting of pro-apoptotic and anti-apoptotic molecules, can be classified into the following three subfamilies according to sequence homology within four BH domains (BH1, BH2, BH3 and BH4): (1) a subfamily shares sequence homology within all four BH domains, such as Bcl-2, Bcl-xl and Bcl-w which are anti-apoptotic; (2) a subfamily shares sequence homology within BH1, BH2 and BH4, such as Bax and Bak which are pro-apoptotic; (3) a subfamily shares sequence homology only within BH3, such as Bik, Bid and HRK which are pro-apoptotic. The BH1, BH2, and BH4 domains are required for anti-apoptotic activity. In contrast, the BH3 domain is essential and, itself, sufficient for pro-apoptotic activity.

Similar to oncogene addiction, in which tumor cells rely on a single dominant gene for survival, tumor cells may also become dependent on Bcl-2 in order to survive. Bcl-2 overexpress is found frequently in acute myeloid leukemia (AML), acute lymphocytic leukemia (ALL), relapsed/refractory chronic lymphocytic leukemia (CLL), follicular lymphoma (FL), non-Hodgkin lymphoma (NHL) and solid tumors such as pancreatic, prostate, breast, and small cell and non-small cell lung cancers (Cancer 2001, 92, 1122-1129; Cancer Biol. 2003; 13:115-23; Curr. Cancer Drug Targets 2008, 8, 207-222; Cancers 2011, 3, 1527-1549). Dysregulated apoptotic pathways have also been implicated in the pathology of other significant diseases such as neurodegenerative conditions (up-regulated apoptosis), e.g., Alzheimer's disease; and proliferative diseases (down-regulated apoptosis), e.g., cancers, autoimmune diseases, and pro-thrombotic conditions. Target to either Bcl-2 or Bcl-xl, a number of small-molecule BH3 mimetics have been reported. Some of the Bcl-2 small molecule inhibitors have been investigated at various stages of drug development: the Bcl-2/Bcl-xl inhibitor ABT-263 (navitoclax, WO2009155386) has shown promising clinical activity in lymphoid malignancies such as chronic lymphocytic leukemia. However, its efficacy in these settings is limited by platelet death and attendant thrombocytopenia caused by Bcl-xl inhibition (Lancet Oncol. 2010, 11, 1149; J. Clin. Oncol. 2011, 29, 909; J. Clin. Oncol. 2012, 30, 488). The new generation of the Bcl-2 selective inhibitor venetoclax (ABT-199/GDC-0199) was proceeded, which demonstrated robust activity in these cancers but also spared platelets (Journal of Hematology & Oncology 2015, 8, 129; Clinical Advances in Hematology & Oncology 2017, 15, 210). S55746 (also known as BCL201), APG-101, APG-1252 are being studied at the clinical trial stage. Currently, Venetoclax (formerly ABT-199) is the only Bcl-2 selective inhibitor approved by the FDA for the treatment of patients who have relapsed or refractory chronic lymphocytic leukemia (CLL) with the 17p deletion.

Despite the high clinical activity and favorable safety profile, patients can develop acquired resistance to venetoclax over time with continuous treatment. Recently, a novel Gly101Val (G101V) mutation in Bcl2 was identified after the patients were treated with the Bcl-2 inhibitor venetoclax (ABT-199) for 19 to 42 months (Cancer Discov. 2019, 9, 342-353; Haematologica 104, e434-e437, 2019). Blombery et al demonstrated that the Gly101Val mutation in Bcl-2 confers acquired refractoriness by reducing the binding affinity of venetoclax without disrupting the binding of pro-apoptotic proteins to Bcl-2. The novel Gly101 Val mutation in Bcl-2 was identified at progression in 7 of 15 patients, but not at study entry. The Bcl-2 Asp103Tyr (D103Y) mutation observed in CLL patients was also predicted to impede the binding of Bcl-2 to venetoclax leading to reduced fitness of the patient (Haematologica 104, e434-e437, 2019). Bcl-2 Phe104Ile (F104I) mutation in FL (follicular lymphoma) patient treated with venetoclax was also described to be associated with significantly reduced binding to venetoclax and is sufficient to confer cellular resistance (Br J Haematol, 186(6): e188-e191, 2019).

In addition, wild type Bcl-2 is important for the survival of neutrophil precursors, thereby neutropenia was the most common adverse effect in the therapy of Bcl-2 inhibitor. In CLL patients treated with venetoclax, the onset of neutropenia was commonly observed during dose ramp-up, although its incidence was decreased with time prolonged on therapy. (Clin Cancer Res; 24(18), 2018). That is to say, the excessive inhibition of wild type Bcl-2 protein could present on-target toxicity and side effect of neutropenia.

WO2019210828 disclosed a novel class of Bcl-2 inhibitors. There is still a strong need for new small molecules that inhibit both wild type Bcl-2 proteins and Bcl-2 mutations found in patients with progression after long term treatment by venetoclax, such as G101V and D103Y mutations.

SUMMARY OF THE DISCLOSURE

The inventors of the present disclosure found that the compounds disclosed herein exhibit almost equal inhibitory activity against both wild type Bcl-2 and Bcl-2 mutations including G101V and D103Y, suggesting a new type of potential Bcl-2 inhibitors without the resistance concerns. The present disclosure also presents the potential possibility of the new therapy in an effective and safe dose for clinically relapse patients with mutations after treatment with venetoclax.

Disclosed herein is a compound of Formula (I)

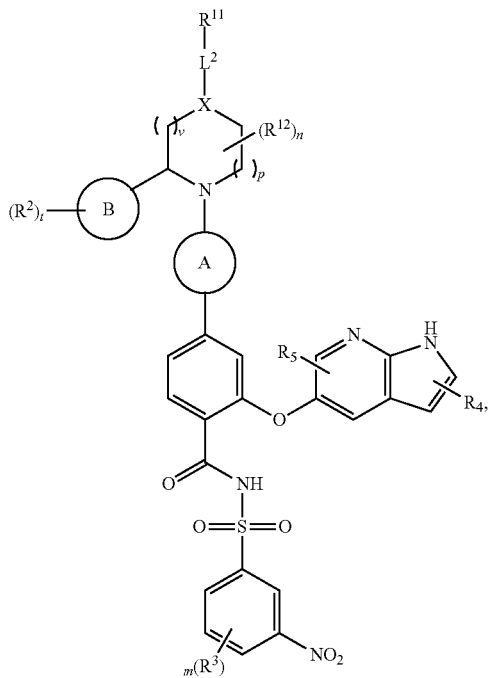

or a pharmaceutically acceptable salt thereof, or a stereoisomer thereof,
wherein
X is independently selected from N or CH;
p is an integer selected from 1 or 2;
v is an integer selected from 1 or 2;
m is an integer selected from 1, 2, or 3;
n is an integer selected from 0, 1, or 2;
t is an integer selected from 1 or 2;
Ring A is

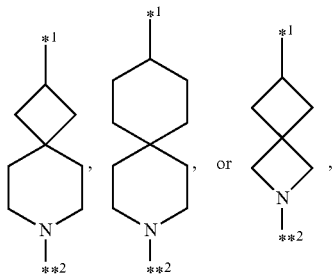

wherein **2 refers to the position attached to the phenyl moiety of Formula (I);

Ring B is an aryl or 5- or 6-membered heteroaryl;
$L^2$ is a direct bond, —$(CR^aR^b)_q$—, —O—, —S—, —S(O)—, —$SO_2$—, —C(O)—, C(O)O—, —OC(O)—, —$NR^a$—, —$C(O)NR^a$—, —$NR^aC(O)$—, —$NR^aC(O)O$—, —$NR^aC(O)NR^b$—, —$SO_2NR^a$—, —$NR^aSO_2$—, —$NR^aS(O)_2NR^b$—, —$NR^aS(O)NR^b$—, —$C(O)NR^aSO_2$—, —$C(O)NR^aSO$—, —$C(=NR^a)NR^b$—, or cycloalkyl, wherein q is a number of 1 to 7;
$R^{11}$ is —$C_{1-3}$alkyl, —$C_{3-10}$cycloalkyl, aryl, 5- or 6-membered monocyclic heteroaryl, 7- to 10-membered bicyclic heteroaryl, 3- to 6-membered monocyclic heterocyclyl, 7- to 14-membered bicyclic heterocyclyl, each of which is independently optionally substituted with 1, 2, 3 or 4 substituents $R^{11X}$, $R^{11X}$, at each occurrence, is independently halogen, —$C_{1-8}$alkyl, halo$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^{11a}$, —$SO_2R^{11a}$, —$COR^{11a}$, —$CO_2R^{11a}$, —$CONR^{11a}R^{11b}$, —$C(=NR^{11a})NR^{11b}R^{11c}$, —$NR^{11a}R^{11b}$, —$NR^{11a}COR^{11b}$, —$NR^{11a}CONR^{11b}R^{11c}$, —$NR^{11a}CO_2R^{11b}$, —$NR^{11a}SONR^{11b}R^{11c}$, —$NR^{11a}SO_2NR^{11b}R^{11c}$, —$P(=O)R^{11a}R^{11b}$, or —$NR^{11a}SO_2R^{11b}$, wherein said $C_{3-8}$cycloalkyl, heterocyclyl, aryl, or heteroaryl is optionally substituted with halogen, —$C_{1-8}$alkyl, -halo$C_{1-8}$alkyl, —$C_{1-8}$alkoxyl, or -halo$C_{1-8}$alkoxyl;

$R^{11a}$, $R^{11b}$, and $R^{11c}$ are each independently hydrogen, —$C_{1-8}$alkyl, -halo$C_{1-8}$alkyl, —$C_{2-8}$alkenyl, —$C_{2-8}$alkynyl, —$C_{3-8}$cycloalkyl, heterocyclyl, aryl, or heteroaryl, wherein said $C_{3-8}$cycloalkyl, heterocyclyl, aryl, or heteroaryl is optionally substituted with halogen, —$C_{1-8}$alkyl, -halo$C_{1-8}$alkyl, —$C_{1-8}$alkoxyl, or -halo$C_{1-8}$alkoxyl;

$R^{12}$ is hydrogen, halogen, —$C_{1-8}$alkyl, halo$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^{1a}$, —$SO_2R^{1a}$, —$COR^{1a}$, —$CO_2R^{1a}$, —$CONR^{1a}R^{1b}$, —$C(=NR^{1a})NR^{1b}R^{1c}$, —$NR^{1a}R^{1b}$, —$NR^{1a}COR^{1b}$, —$NR^{1a}CONR^{1b}R^{1c}$, —$NR^{1a}CO_2R^{1b}$, —$NR^{1a}SONR^{1b}R^{1c}$, —$NR^{1a}SO_2NR^{1b}R^{1c}$, or —$NR^{1a}SO_2R^{1b}$;

$R^{1a}$ and $R^{1b}$, are each independently hydrogen, —$C_{1-8}$alkyl, -halo$C_{1-8}$alkyl, —$C_{2-8}$alkenyl, —$C_{2-8}$alkynyl, cycloalkyl, heterocyclyl, aryl, or heteroaryl;

$R^{1c}$ is hydrogen, —$C_{1-8}$alkyl, -halo$C_{1-8}$alkyl, —$C_{2-8}$alkenyl, —$C_{2-8}$alkynyl, cycloalkyl, heterocyclyl, aryl, or heteroaryl;

$R^2$ is independently selected from halogen, —$C_{1-8}$alkyl, —$C_{2-8}$alkenyl, —$C_{2-8}$alkynyl or -$C_{3-6}$cycloalkyl; wherein said —$C_{1-8}$alkyl, —$C_{2-8}$alkenyl, —$C_{2-8}$alkynyl or —$C_{3-6}$cycloalkyl are each independently optionally substituted with halogen, hydroxy, $C_{1-6}$alkoxy, or amino, —$C_{1-8}$alkyl, —$C_{2-8}$alkenyl, —$C_{2-8}$alkynyl, $C_{3-6}$cycloalkyl or $C_{3-6}$heterocyclyl;

$R^3$ is -$L^1$-CyC,
wherein
$L^1$ is a direct bond, —$(CR^aR^b)_{1-4}$—, —O—$(CR^aR^b)_{0-3}$—, —NH—$(CR^aR^b)_{1-3}$, or —NH;
CyC is cycloalkyl, or heterocyclyl, each of which is optionally substituted with one, two, three or four substituents $R^{3a}$;

$R^{3a}$ is independently selected from hydrogen, halogen, cyano, oxo, —$OR^{3b}$, —$NR^{3b}R^{3c}$, —$COR^{3b}$, —$SO_2R^{3b}$, —$C_{1-8}$alkyl, —$C_{2-8}$alkenyl, —$C_{2-8}$alkynyl, -cycloalkyl, or heterocyclyl, each of said —$C_{1-8}$alkyl, and heterocyclyl is optionally substituted with one or two substituents $R^{3c}$ which is selected from hydrogen, halogen, cyano, —$OR^{3f}$, —$C_{1-8}$alkyl, -cycloalkyl, or heterocyclyl;

wherein $R^{3b}$, and $R^{3c}$ are each independently hydrogen, —$C_{1-8}$alkyl, -cycloalkyl, or heterocyclyl, said —$C_{1-8}$alkyl is optionally substituted with one or two substituents $R^{5e}$ which is hydrogen, —$NR^3R^{3g}$, -cycloalkyl, or heterocyclyl;

$R^{3f}$ and $R^{3g}$ are each independently hydrogen or —$C_{1-8}$alkyl;

or, two adjacent $R^3$ on the phenyl ring together with the phenyl ring form a benzo ring, said ring is optionally substituted with heteroaryl;

$R^a$ and $R^b$ are independently hydrogen, —$C_{1-8}$alkyl, —$C_{2-8}$alkenyl, —$C_{2-8}$alkynyl, cycloalkyl, heterocyclyl, aryl, or heteroaryl; and, $R^4$ and $R^5$ are each independently hydrogen, halogen, cyano, —$NO_2$, —$C_{1-8}$alkyl, —$C_{2-8}$alkenyl, or —$C_{2-8}$alkynyl.

In some embodiments, X is N.

In some embodiments, ring B is phenyl, furanyl, isoxazolyl, pyridinyl, pyrazolyl, or pyrimidinyl.

In some embodiments, $R^2$ is halo, —$C_{1-6}$alkyl or —$C_{3-4}$cycloalkyl; wherein said —$C_{1-6}$alkyl and —$C_{3-4}$cycloalkyl are each independently optionally substituted with hydrogen, —$C_{1-3}$alkyl, $C_{3-6}$cycloalkyl or $C_{3-6}$heterocyclyl.

In some embodiments, $R^2$ is fluoro, methyl, isopropyl, isobutyl, cyclopropyl, cyclobutyl or morpholinomethyl.

In some embodiments, n is 0, and $L^2$ is —$(CH_2)_q$—, or —O—, wherein q is a number of 1-3, preferably 1.

In some embodiments, $R^1$ is —$C_{3-10}$cycloalkyl, aryl, 5- or 6-membered monocyclic heteroaryl, 7- to 10-membered bicyclic heteroaryl, 3- to 6-membered monocyclic heterocyclyl, 7- to 14-membered bicyclic heterocyclyl, each of which is independently optionally substituted with 1, 2, or 3 substituents $R^{11X}$, wherein $R^{11X}$ is defined as with formula (I).

In some embodiments, $R^{11}$ is cyclopropyl, cyclobutyl, cyclopentyl, cyclohexyl, or 3- to 6 membered heterocycloalkyl containing 1 or 2 heteroatoms selected from oxygen and nitrogen atoms.

In some embodiments, $R^{11}$ is selected from cyclohexyl, bicyclo[1.1.1]pentanyl, tetrahydro-2H-pyran-1-yl, tetrahydro-2H-pyran-2-yl, tetrahydro-2H-pyran-3-yl, tetrahydro-2H-pyran-4-yl oxazol-2-yl, oxazol-4-ylmethyl or oxazol-5-yl.

In some embodiments, $R^{11}$ is selected from phenyl or 8- to 10-membered bicyclic aryl, optionally substituted with 1, 2 or 3 substituents $R^{11X}$.

In some embodiments, $R^{11}$ is selected from phenyl or 8- to 10-membered bicyclic aryl, optionally substituted with 1 to 2 substituents $R^{11X}$.

In some embodiments, $R^{11}$ is chromanyl, benzo[b][1,4]dioxinyl), 5,6,7,8-tetrahydronaphthalenyl, octahydro-5H-2,5-methanoindenyl (preferably octahydro-5H-2,5-methanoinden-5-yl), 2,3,4,5-tetrahydrobenzo[b]oxepinyl (preferably 2,3,4,5-tetrahydrobenzo[b]oxepin-7-yl), adamantanyl (preferably adamantan-1-yl), each of which is optionally substituted with 1 or 2 $R^{11X}$.

In some embodiments, $R^{11X}$ is halogen, cyano, hydroxy, —$C_{1-8}$alkyl, halo$C_{1-8}$alkyl, —$C_{2-6}$ alkenyl, —$C_{2-8}$alkynyl, $C_{1-6}$alkoxyl, halo$_{1-6}$alkoxyl, $C_{3-6}$cycloalkyl, heterocyclyl, $C_{3-6}$ cycloalkoxyl, —$NH_2$, —$NH(C_{1-8}$alkyl), —$N(C_{1-8}$alkyl)$_2$ or heterocyclyl-O—.

In some embodiments, $R^{11X}$ is —$OR^{11a}$, wherein $R^{11a}$ is —$C_{1-8}$alkyl, preferably methyl (—$CH_3$), ethyl, propyl, isopropyl, butyl, or tert-butyl. In some embodiments, $R^{11X}$ is —$OR^{11a}$, wherein $R^{11a}$ is —$C_{1-8}$alkyl optionally enriched in deuterium, e.g., -$CD_3$, or -$CD_2CD_3$.

In some embodiments, $R^{11X}$ is —$OR^{11a}$, wherein $R^{11a}$ is $C_{3-6}$cycloalkyl, preferably cyclopropyl, cyclobutyl, cyclopentyl, or cyclohexyl.

In some embodiments, $R^{11}$ is phenyl substituted with one, two or three substitutions $R^{11X}$ independently selected from a) cyano, fluoro, chloro, bromo, methyl, ethyl, propyl, isopropyl, butyl, tert-butyl, methoxy, ethoxy, propoxy, isopropoxy, butoxy, tert-butoxy, trifluoromethyl, trifluoromethoxy, cyclopropyl, cyclobutyl, cyclopentyl, cyclohexyl, oxetan-3-yl, —$NH_2$, or —$NH(CH_3)$; or, b) —$OR^{11a}$, wherein $R^{11a}$ is $C_{3-6}$cycloalkyl, preferably cyclopropyl, cyclobutyl, cyclopentyl, or cyclohexyl.

In some embodiments, $R^{11}$ is phenyl substituted with cyano, fluoro, chloro, bromo, methyl, ethyl, propyl, isopropyl, butyl, tert-butyl, methoxy, ethoxy, propoxy, isopropoxy, butoxy, tert-butoxy, difluoromethyl, trifluoromethyl, or trifluoromethoxy.

In some embodiments, $R^{11}$ is phenyl substituted with cyclopropyl, cyclobutyl, cyclopentyl, or cyclohexyl.

In some embodiments, $R^{11X}$ is cyclohexyl, 4-methoxylcyclohexyl, bicyclo[1.1.1]pentan-1-yl, tetrahydro-2H-pyran-4-yl, oxazol-4-yl, phenyl, 2-fluorophenyl, 3-fluorophenyl, 4-fluorophenyl, 4-chlorophenyl, 2,4-difluorophenyl, 3,5-difluorophenyl, 3,4-difluorophenyl, 4-cyanophenyl, 4-methylphenyl, 4-(trifluoromethyl)phenyl, 2-methoxylphenyl, 3-methoxylphenyl, 4-methoxylphenyl, 4-ethoxylphenyl, 4-methoxylphenyl, 4-(trifluoromethoxyl)phenyl, 2,4-dimethoxylphenyl, 2,3-dimethoxylphenyl, 3,4-dimethoxylphenyl, 3,5-dimethoxylphenyl, 3,4,5-trimethoxylphenyl, chroman-6-yl, chroman-4-yl, 2,3-dihydrobenzo[b][1,4]dioxin-6-yl, 2,3-dihydrobenzo[b][1,4]dioxin-5-yl, or 5,6,7,8-tetrahydronaphthalen-2-yl, or 5,6,7,8-tetrahydronaphthalen-1-yl, bicyclo[4.2.0]octa-1(6),2,4-trien-7-yl.

In some embodiments, $R^{11}$ is furanyl, isoxazolyl, pyridinyl, pyrazolyl, pyrimidinyl, quinoxalinyl, benzo[b]thiophenyl, benzofuranyl, or 2,3-dihydrobenzofuran-5-yl.

In some embodiments, $R^{11}$ is furan-2-yl, isoxazol-4-yl, pyridin-3-yl, pyridin-2-yl, 1H-pyrazol-4-yl, pyrimidin-2-yl, benzo[b]thiophen-5-yl, benzo[b]thiophen-4-yl, benzofuran-5-yl, benzofuran-4-yl, 2,3-dihydrobenzo[b][1,4]dioxin-5-yl, benzo[b][1,4]oxazin-5-yl, dihydro-[1,4]dioxino[2,3-b]pyridin-8-yl, or 3,4-dihydro-2H-benzo[b][1,4]dioxepin-7-yl.

In some embodiments, $R^{11}$-$L^2$- is selected from furan-2-ylmethyl, isoxazol-4-ylmethyl, (pyridin-3-yl)methyl, (6-methoxypyridin-3-yl)methyl, (5-methoxypyridin-2-yl)methyl, (1-methyl-1H-pyrazol-4-yl)methyl, (3-methoxy-1-methyl-1H-pyrazol-4-yl)methyl, (1-cyclopropyl-1H-pyrazol-4-yl)methyl, (5-methoxypyrimidin-2-yl)methyl, benzo[b]thiophen-5-ylmethyl, benzo[b]thiophen-4-ylmethyl, benzofuran-5-ylmethyl, or benzofuran-4-ylmethyl.

In some embodiments, $R^{11}$-$L^2$- is cyclopropyl, cyclobutyl, cyclopentyl, cyclohexyl or 1,2,3,4-tetrahydronaphthalen-1-yl, 3-phenylcyclobut-1-yl, 3-phenylcyclopent-1-yl, 4-phenylcyclohex-1-yl or 3-(4-methoxylphenyl)cyclopent-1-yl.

In some embodiments, $R^{11}$-$L^2$- is -3- to 6-membered monocyclic heterocyclyl selected from oxetanyl, tetrahydrofuranyl, or tetrahydro-2H-pyranyl, preferably oxetan-3-yl, tetrahydrofuran-3-yl, and tetrahydro-2H-pyran-4-yl.

In some embodiments, $R^{12}$ is hydrogen.

In some embodiments, $L^2$ is —$SO_2$— or —CO—, and $R^{11}$ is —$C_{1-3}$alkyl or phenyl, each of which is optionally substituted with $C_{1-3}$alkoxyl.

In some embodiments, $R^a$ is hydrogen or methyl.

In some embodiments, m is 1, $R^3$ is -$L^1$-CyC, and $L^1$ is a direct bond, —$(CH_2)_{0-2}$—, —$N(CH_2)_{0-2}$, or —$O(CH_2)_{0-2}$.

In some embodiments, CyC is $C_{3-6}$cycloalkyl selected from monocyclic $C_{3-8}$cycloalkyl or bridged cycloalkyl

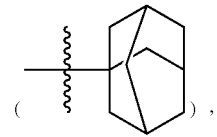 [SMILES: *C12CC3CC(CC(C3)C1)C2]

each of which is optionally substituted with one or two substituents $R^{3a}$.

In some embodiments, CyC is cyclobutyl, cyclopentyl or cyclohexyl, each of which is optionally substituted with one or two substituents $R^{3a}$.

In some embodiments, CyC is:
a) heterocyclyl selected from monocyclic 4 to 9-membered heterocyclyl groups containing one nitrogen or oxygen or sulfur heteroatom as ring member; monocyclic 4 to 9-membered heterocyclyl groups containing two heteroatoms selected from oxygen, sulfur, and nitrogen as ring members,
b) 5 to 10-membered spiro heterocyclyl comprising one or two heteroatoms selected from nitrogen, sulfur, and oxygen as ring members, or,
c) 5 to 10-membered bridged heterocyclyl comprising one or two heteroatoms selected from nitrogen, sulfur, and oxygen as ring members;
each of which is optionally substituted with one, two, three or four substituents $R^{3a}$.

In some embodiments, CyC is monocyclic 4 to 6-membered heterocyclyl groups containing one nitrogen or oxygen or sulfur heteroatom as the ring members.

In some embodiments, Cyc is selected from oxetanyl, tetrahydrofuranyl, tetrahydropyranyl, azetidinyl, pyrrolidinyl, and piperdinyl.

In some embodiments, CyC is selected from oxetan-2-yl, Oxetan-3-yl, tetrahydrofuran-4-yl, tetrahydrofuran-2-yl, tetrahydrofuran-3-yl, tetrahydropyran-2-yl, tetrahydropyran-3-yl, tetrahydropyran-4-yl, azetidin-3-yl, azetidin-2-yl, pyrrolidin-2-yl, pyrrolidin-3-yl, piperdin-4-yl, piperdin-2-yl, and piperdin-3-yl.

In some embodiments, CyC is a monocyclic 6-membered heterocyclyl group containing two heteroatoms selected from oxygen and nitrogen as ring members.

In some embodiments, CyC is dioxanyl, morpholino, morpholinyl, or piperzinyl.

In some embodiments, CyC is 1,3-dioxan-2-yl, 1,3-dioxan-4-yl, 1,4-dioxan-2-yl, morpholin-1-yl, morpholin-2-yl, or morpholin-3-yl.

In some embodiments, CyC is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members.

In some embodiments, CyC is

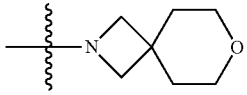

(7-oxa-2-azaspiro[3.5]nonan-2-yl), or

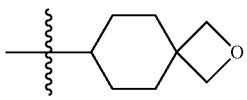 [SMILES: *C1CCC2(CC1)COC2]

(2-oxaspiro[3.5]nonan-7-yl.

In some embodiments, $R^{3a}$ is independently selected from hydrogen, halogen, cyano, oxo, —$OR^{3b}$, —$NR^{3b}R^{3c}$, —C(=O)$R^{3b}$, —$SO_2R^{3b}$, —$C_{1-6}$alkyl, monocyclic $C_{3-6}$cycloalkyl, or monocyclic 4 to 9-membered heterocyclyl group containing one or two heteroatoms selected from nitrogen or oxygen or sulfur heteroatom as ring members, each of said —$C_{1-6}$alkyl and monocyclic 4 to 9-membered heterocyclyl group is optionally substituted with one or two substituents $R^{3e}$.

In some embodiments, cycloalkyl as $R^{3a}$ is $C_{3-6}$cycloalkyl; more preferably cyclopropyl.

In some embodiments, heterocyclyl as $R^{3a}$ is 4 to 6-membered heterocyclyl groups containing one or two heteroatoms selected from nitrogen or oxygen or sulfur heteroatom as ring members.

In some embodiments, heterocyclyl as $R^{3a}$ is oxetanyl, tetrahydrofuranyl, tetrahydropyranyl, piperzinyl, or morpholinyl.

In some embodiments, heterocyclyl as $R^{3a}$ is oxetan-3-yl, tetrahydrofuran-3-yl, tetrahydro-2H-pyran-4-yl, or morphin-4-yl.

In some embodiments, heterocyclyl as $R^{3e}$ is a monocyclic 4 to 9-membered heterocyclyl group containing one or two heteroatoms selected from nitrogen or oxygen or sulfur heteroatom as ring members.

In some embodiments, heterocyclyl as $R^{3e}$ is tetrahydropyran-4-yl.

In some embodiments, $R^{3a}$ is —$NR^{3b}R^{3b}$, wherein $R^{3b}$ is hydrogen, and $R^{3c}$ is heterocyclyl.

In some embodiments, $R^{3a}$ is —$NR^{3b}R^{3c}$, wherein $R^{3b}$ is hydrogen, and $R^{3c}$ is tetrahydro-pyran-4-yl.

In some embodiments, $R^{3a}$ is —$NR^{3b}R^{3c}$, wherein $R^{3b}$ and $R^{3c}$ are each independently hydrogen or —$C_{3-6}$alkyl substituted with cycloalkyl, preferably —$C_{1-6}$alkyl substituted with monocyclic $C_{3-6}$cycloalkyl.

In some embodiments, $R^{3a}$ is —$OR^{3b}$ or —$SO_2R^{3b}$, wherein $R^{3b}$ is hydrogen or $C_{1-8}$alkyl, preferably methyl.

In some embodiments, $R^{3a}$ is —$COR^{3b}$, wherein $R^{3b}$ is hydrogen or $C_{1-6}$alkyl optionally substituted with —$NR^{3f}R^{3g}$, wherein $R^{3f}$ and $R^{3g}$ are each independently hydrogen or $C_{1-6}$alkyl, preferably methyl.

In some embodiments, two adjacent $R^3$ on the phenyl ring together with the phenyl ring form indazolyl which is substituted with tetrahydropyranyl.

In some embodiments, m is 1 and $R^3$ is selected from the group consisting of:

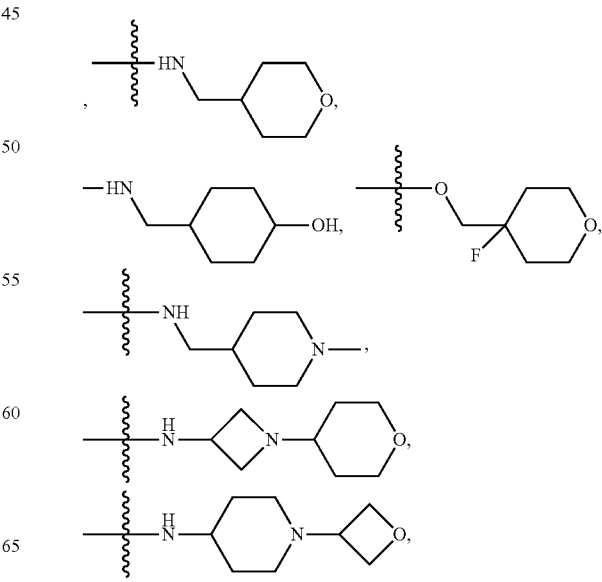

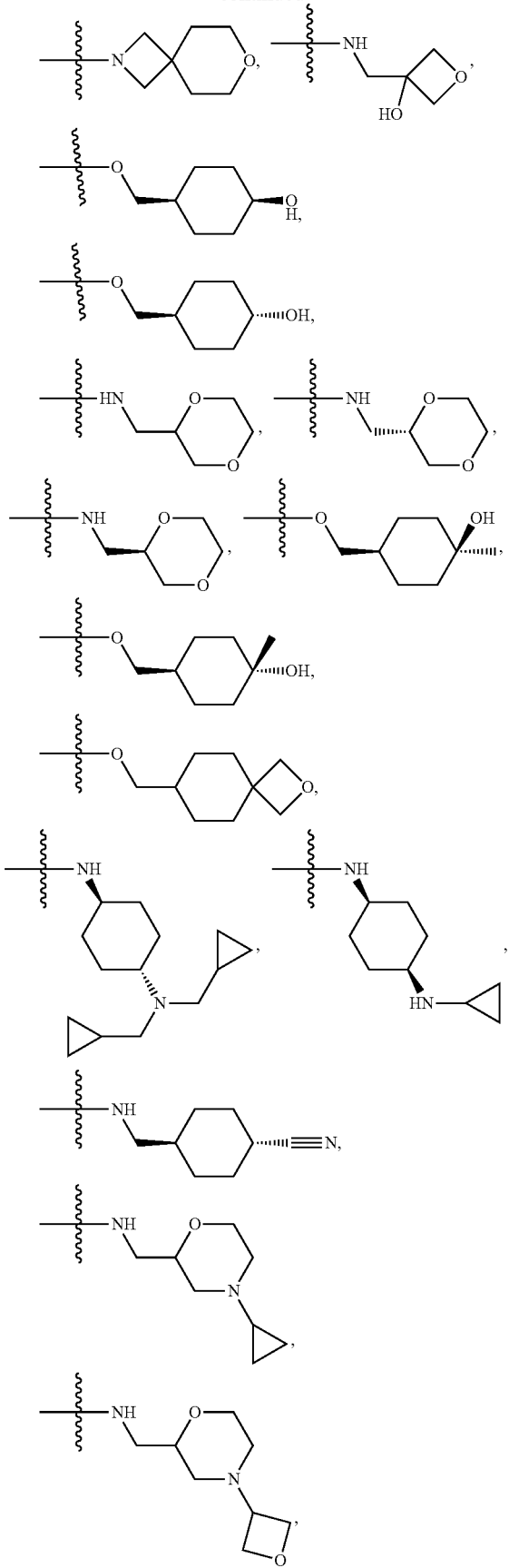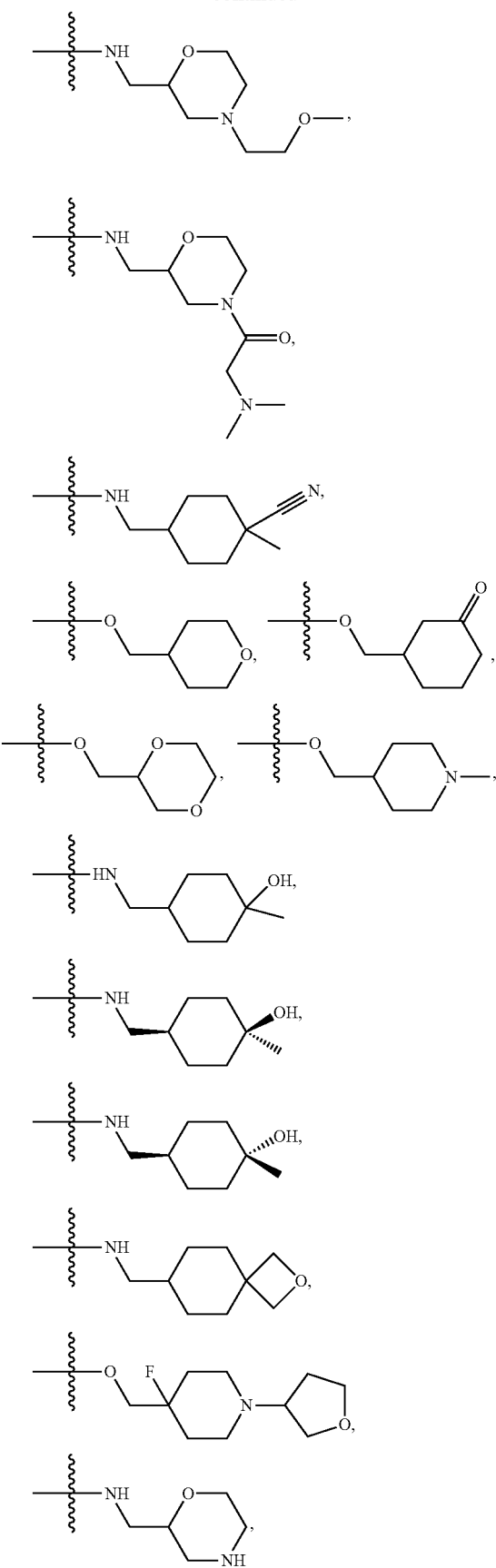

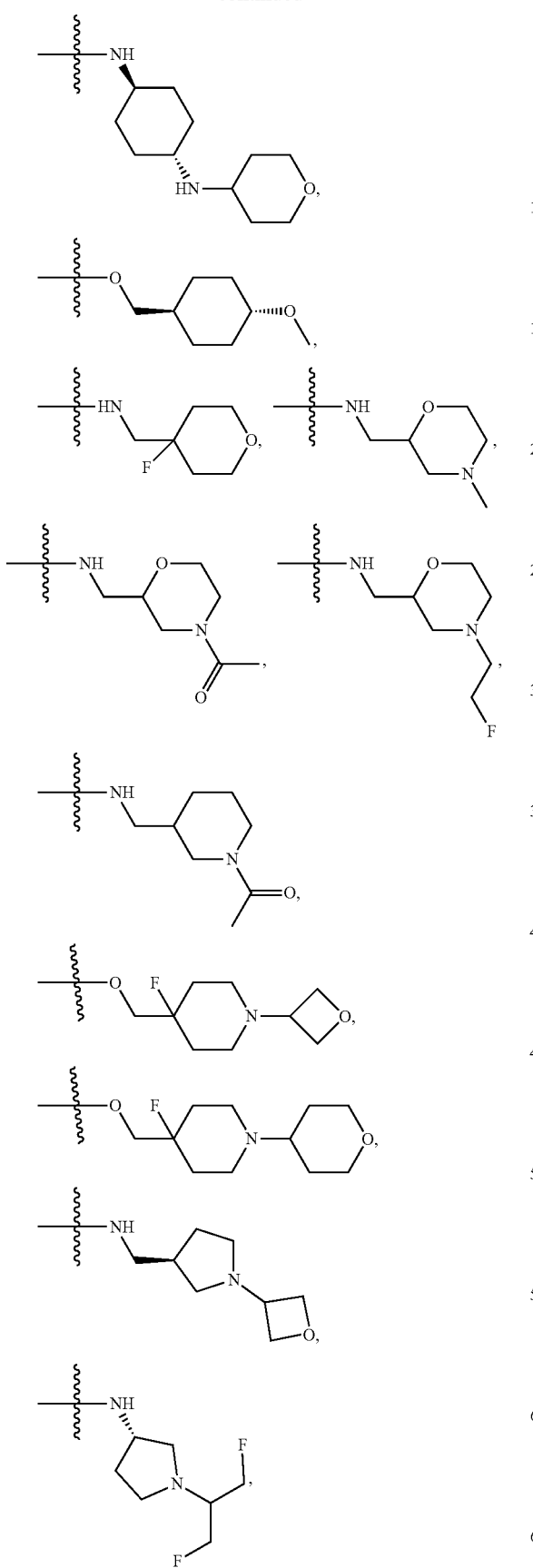
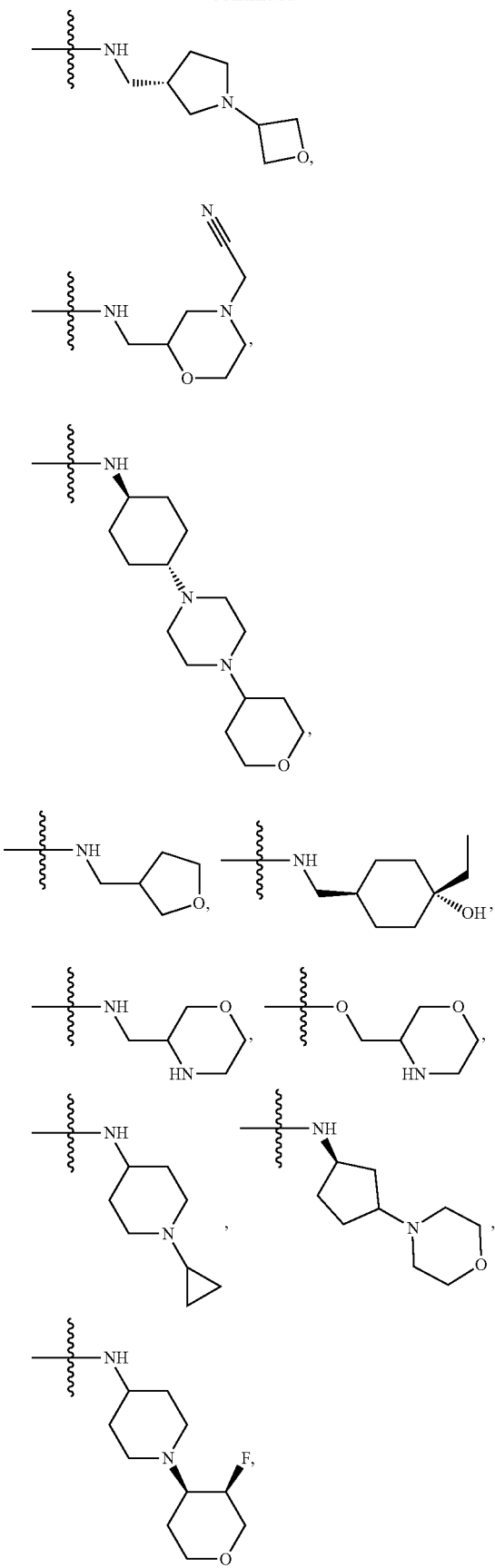

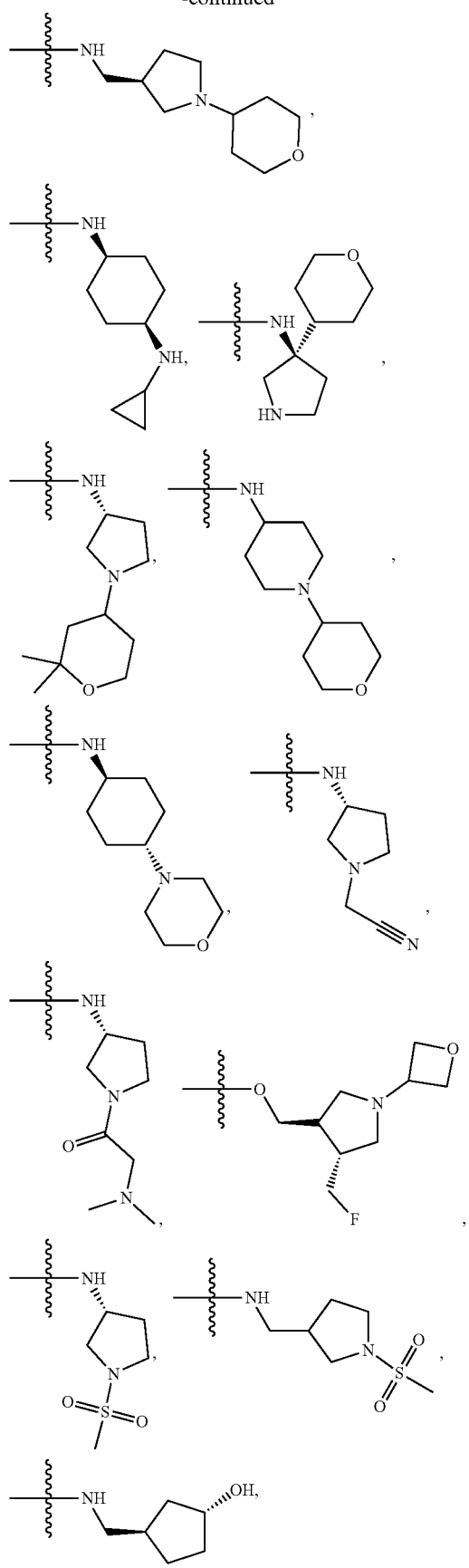
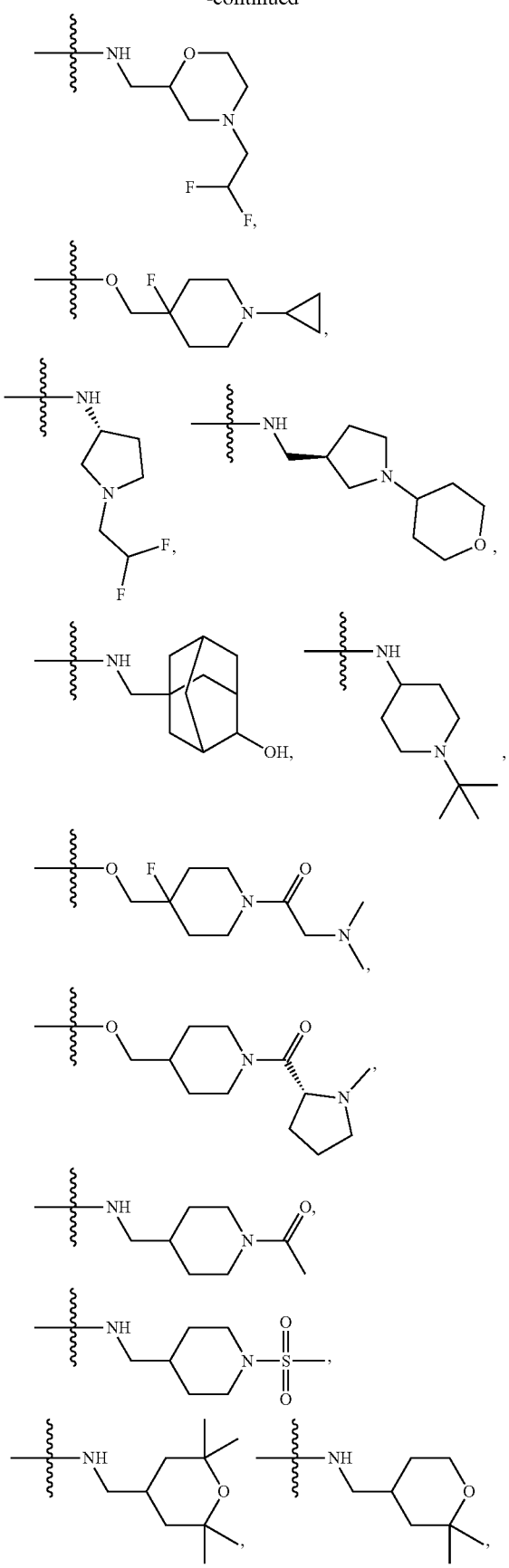

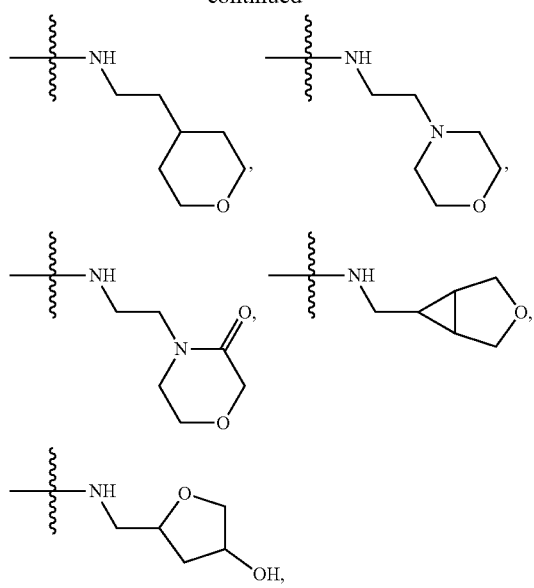
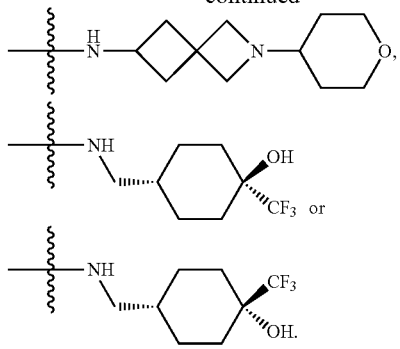
In some embodiments, $R^4$ is halogen selected from fluoro (—F), chloro (—Cl) or bromo (—Br), preferably fluoro (—F).
In some embodiments, $R^4$ is at position 3 of the pyrrolo[2,3-b]pyridin-5-yl ring.
In some embodiments, the compound is selected from the exemplified compounds.
In some embodiments, the compound is selected from
i)
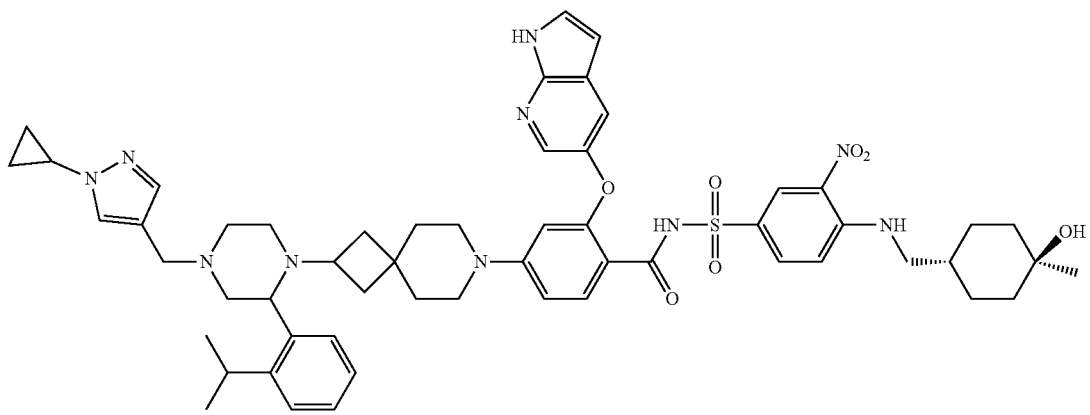
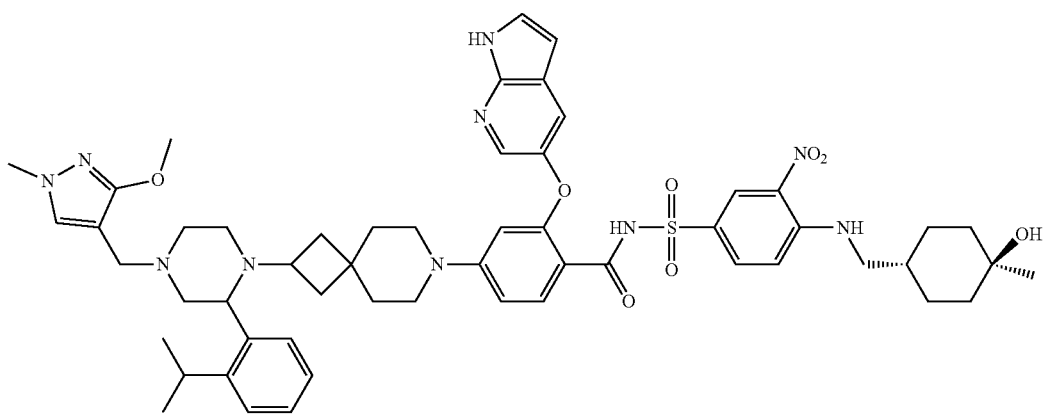

-continued
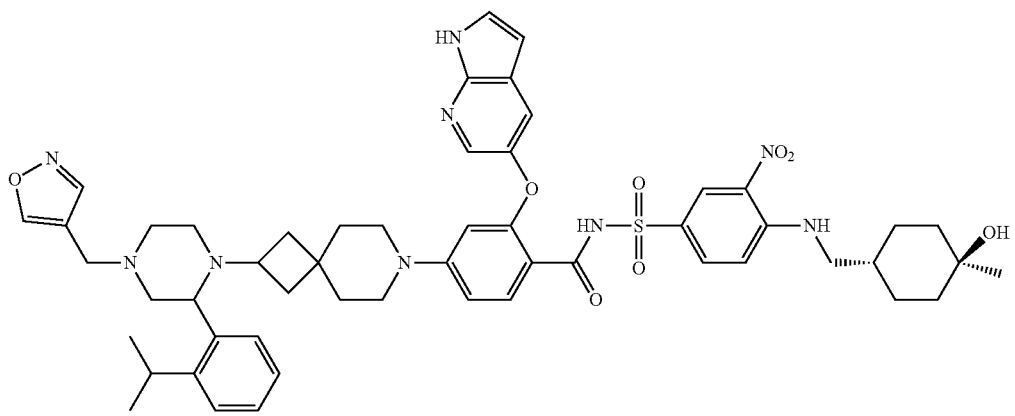
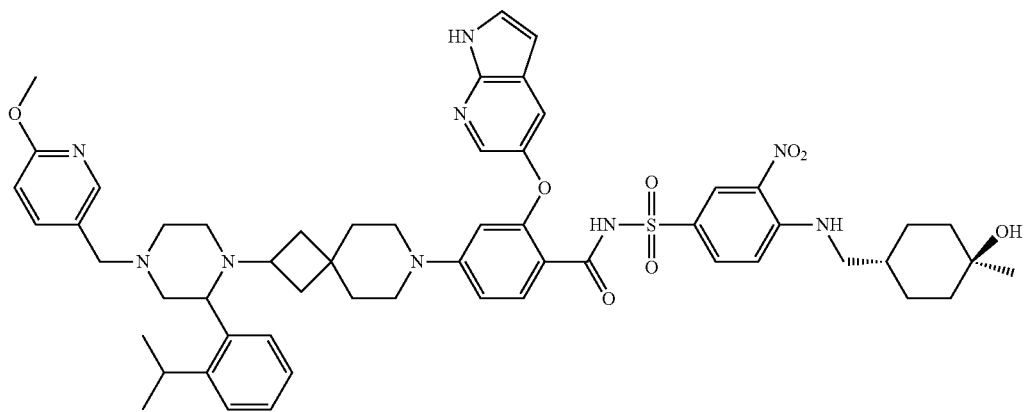
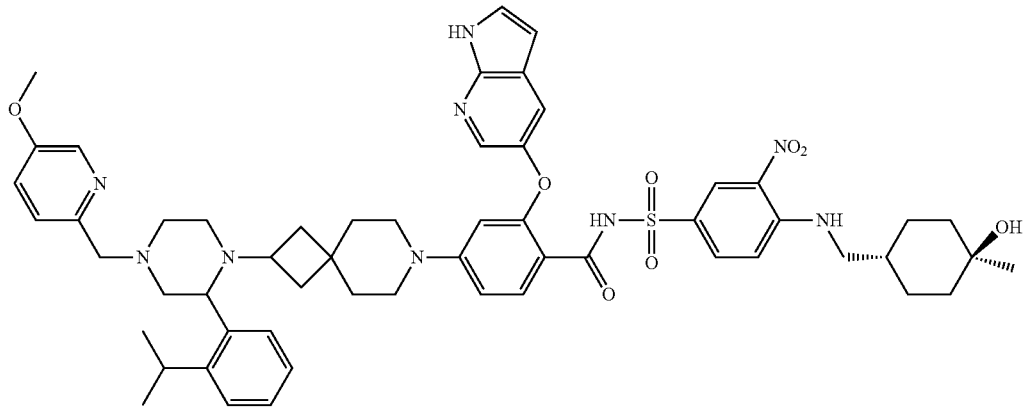
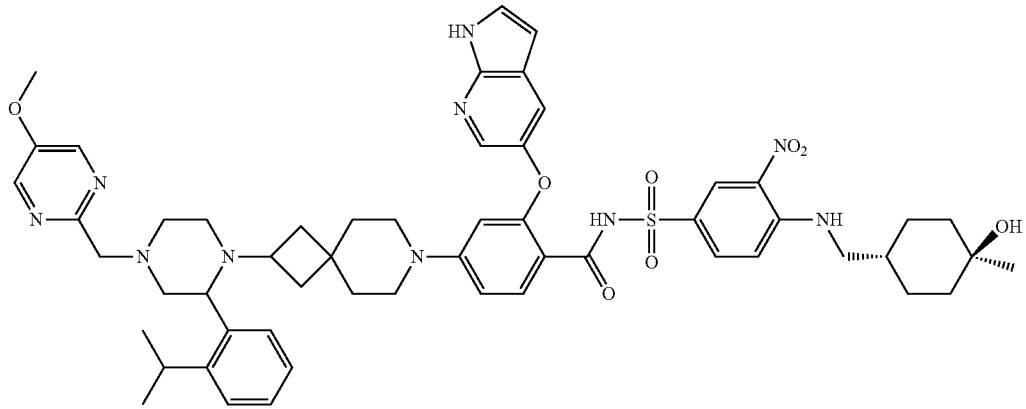

-continued
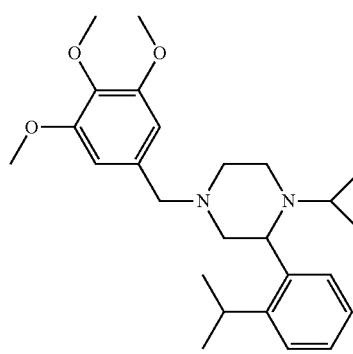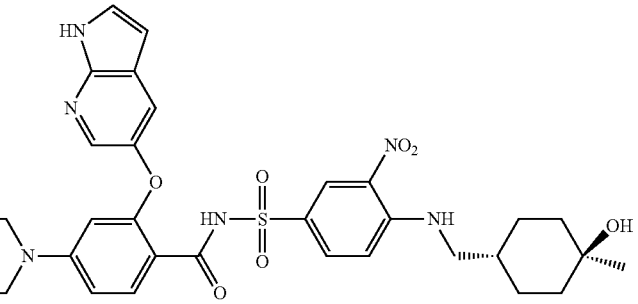
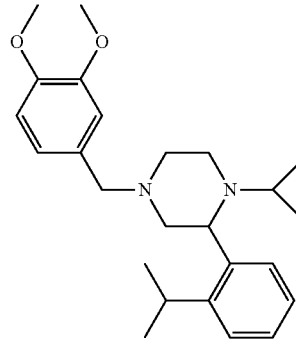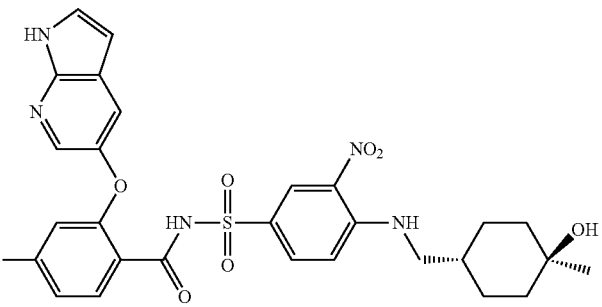
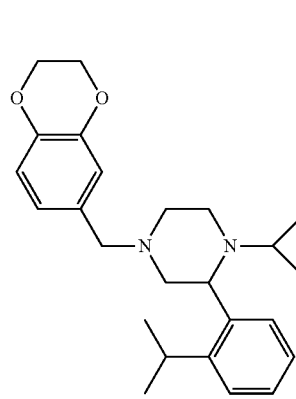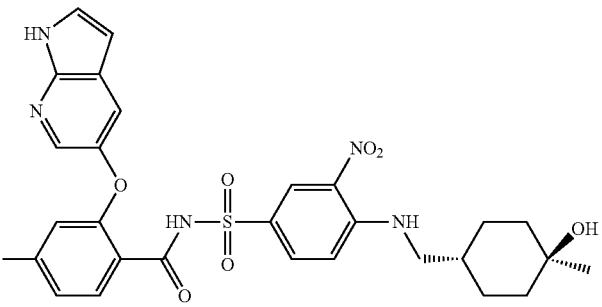
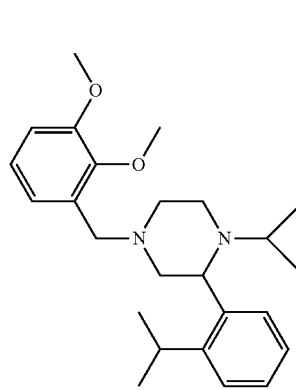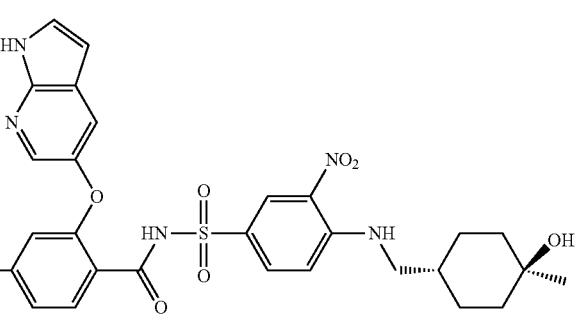

-continued
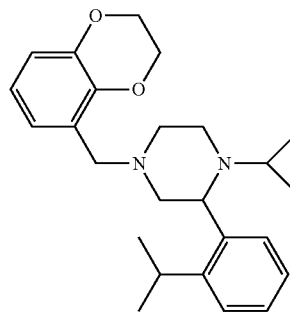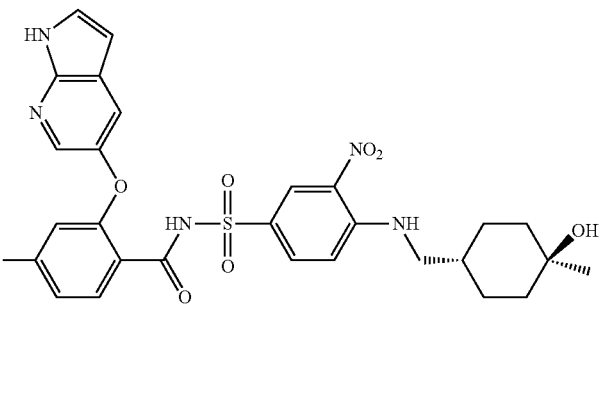
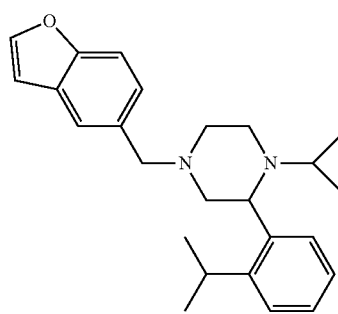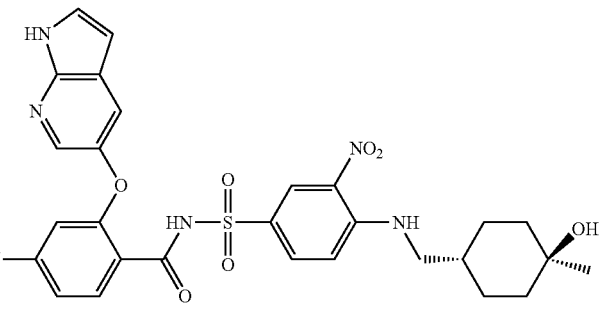
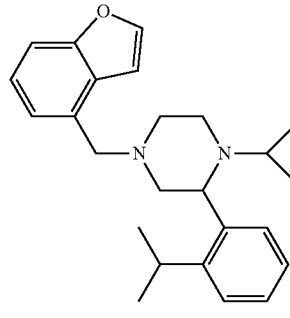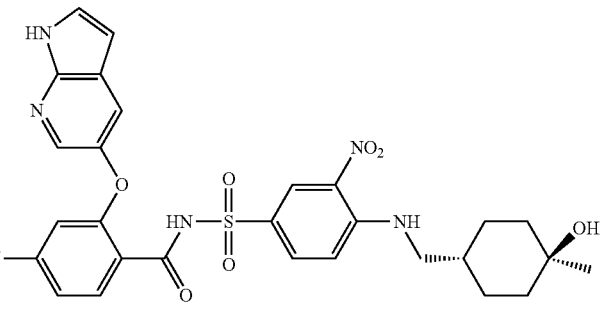
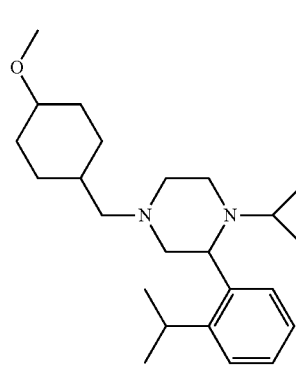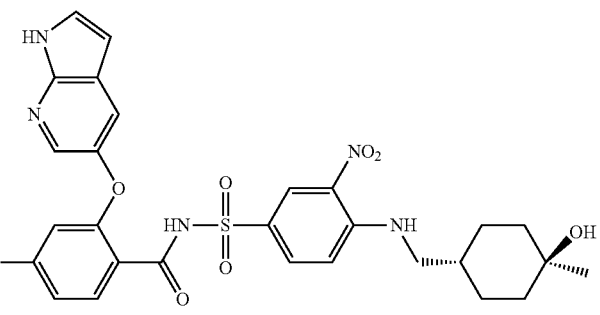

-continued
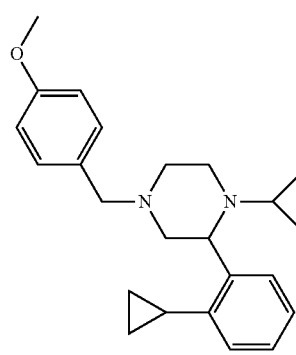
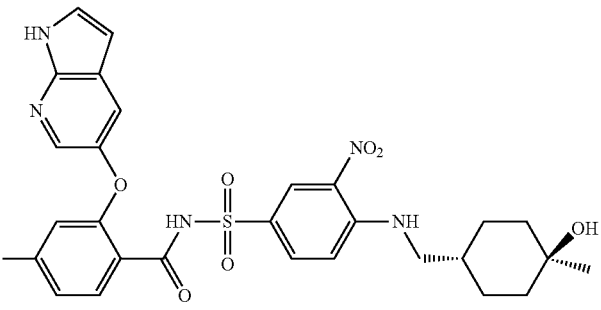
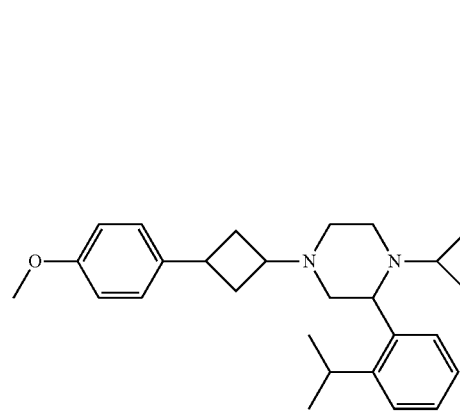
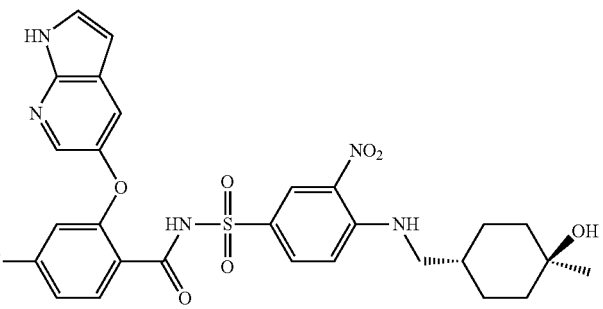
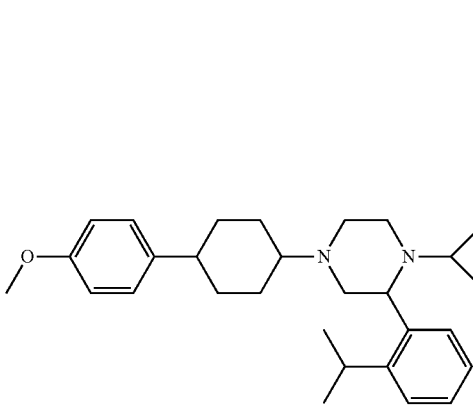
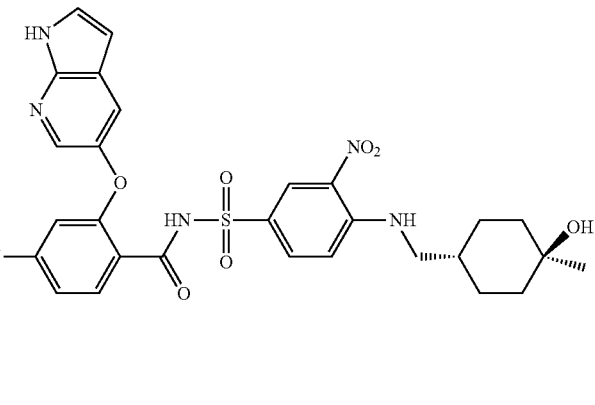
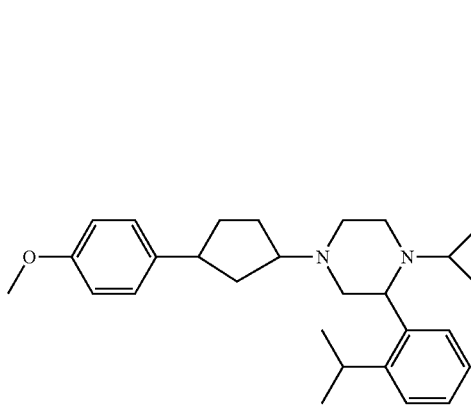
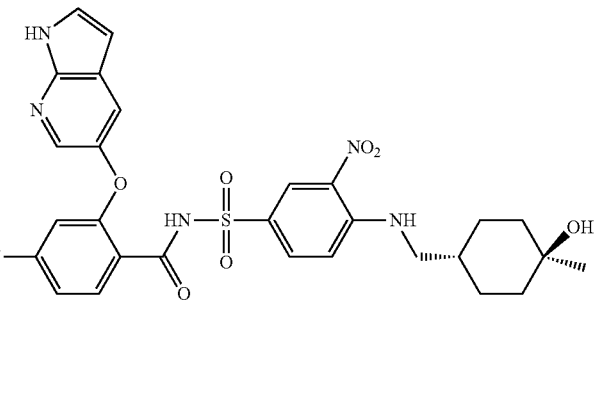

-continued
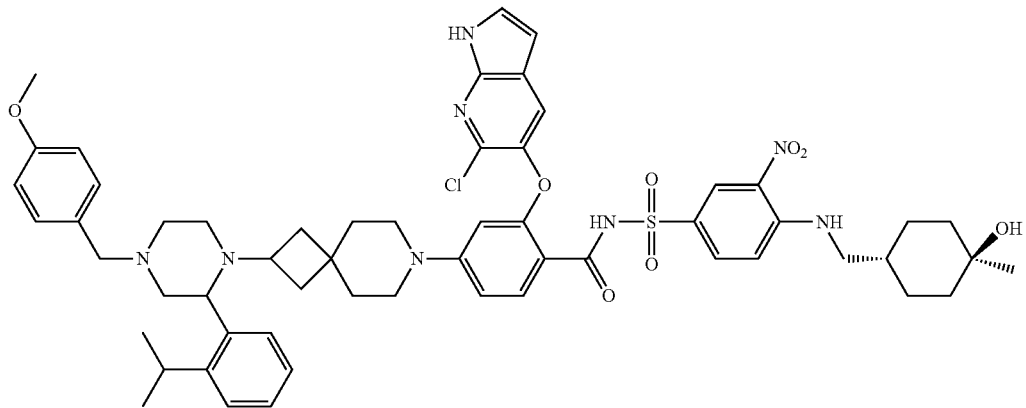
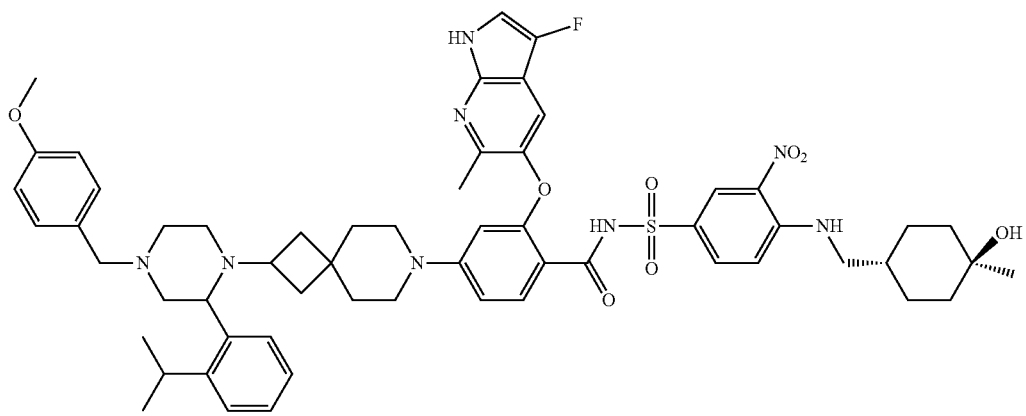
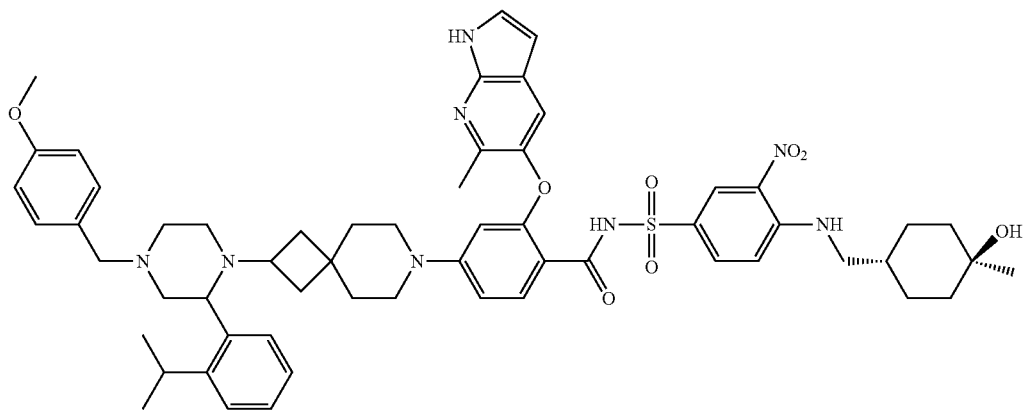
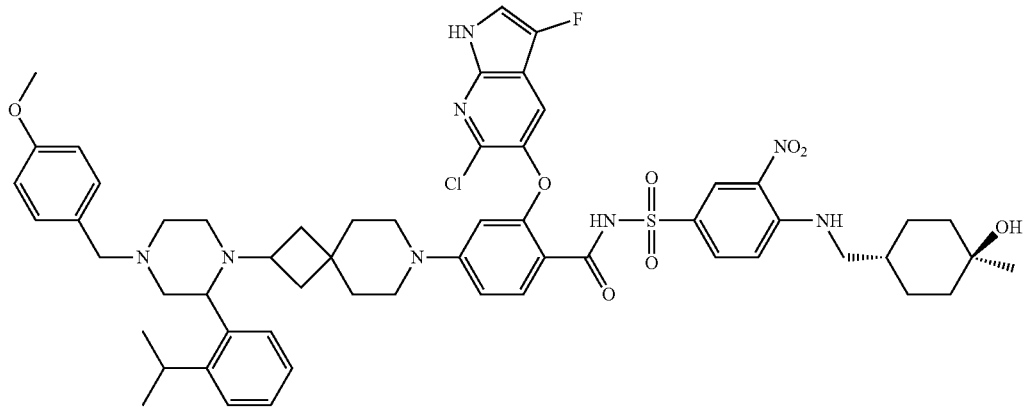

-continued
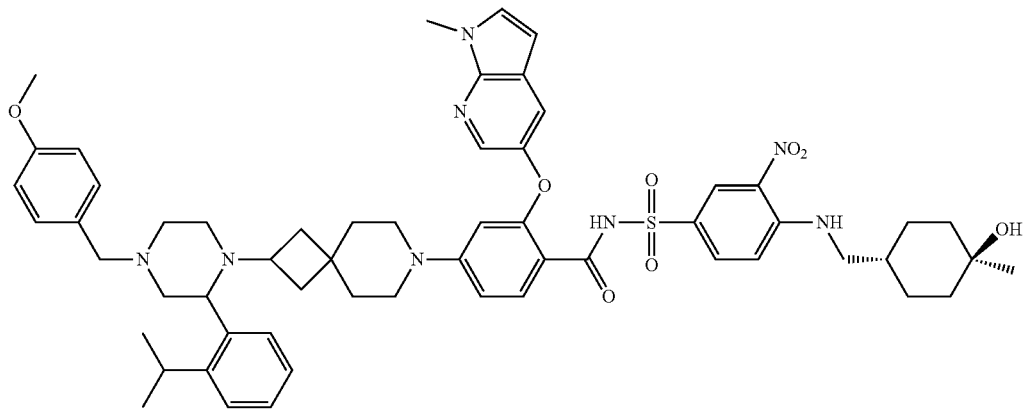
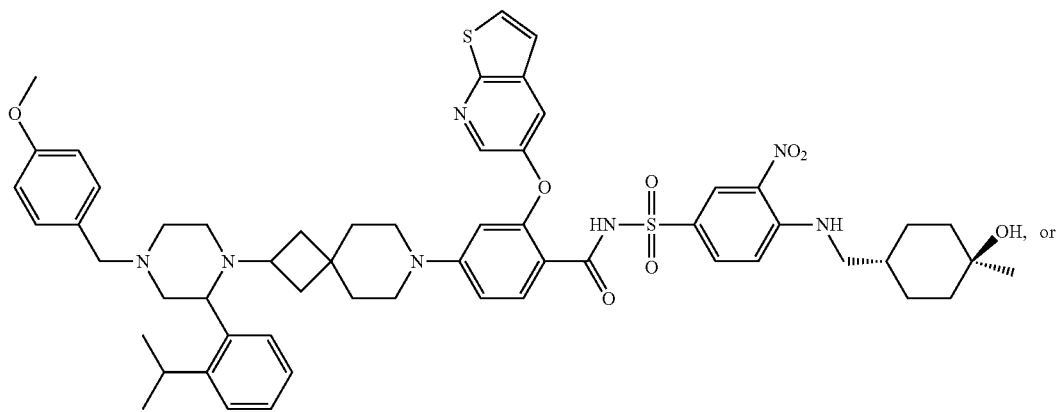
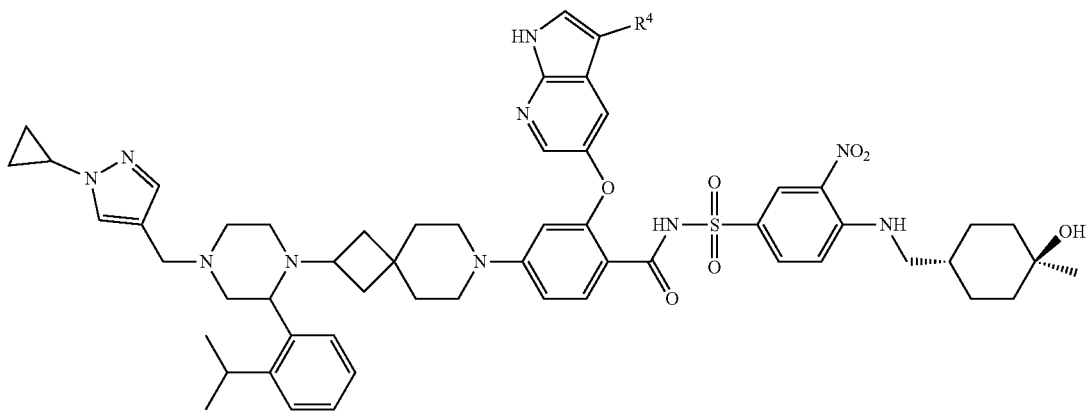
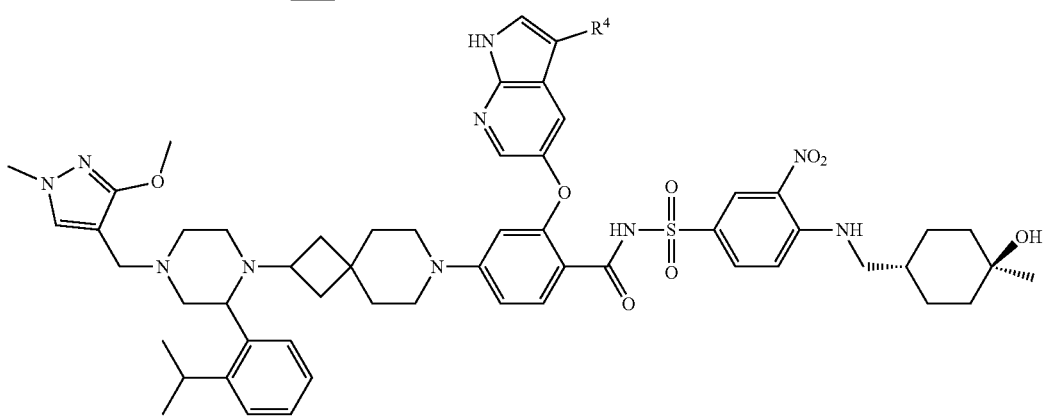

-continued
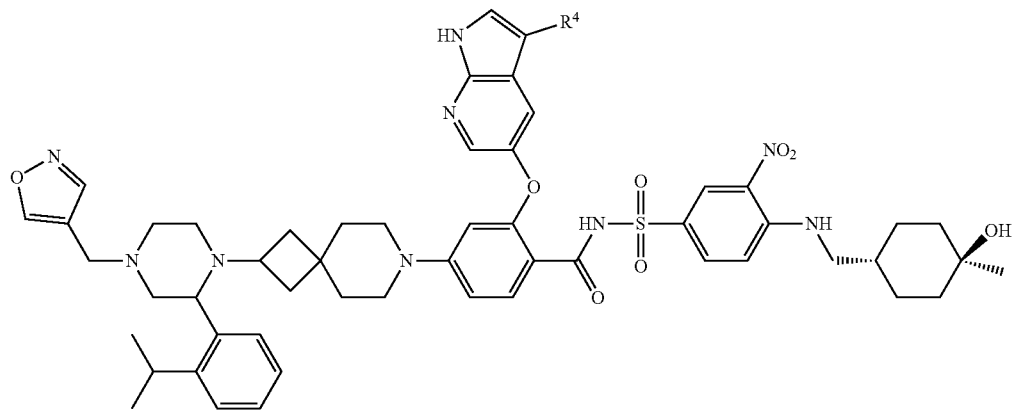
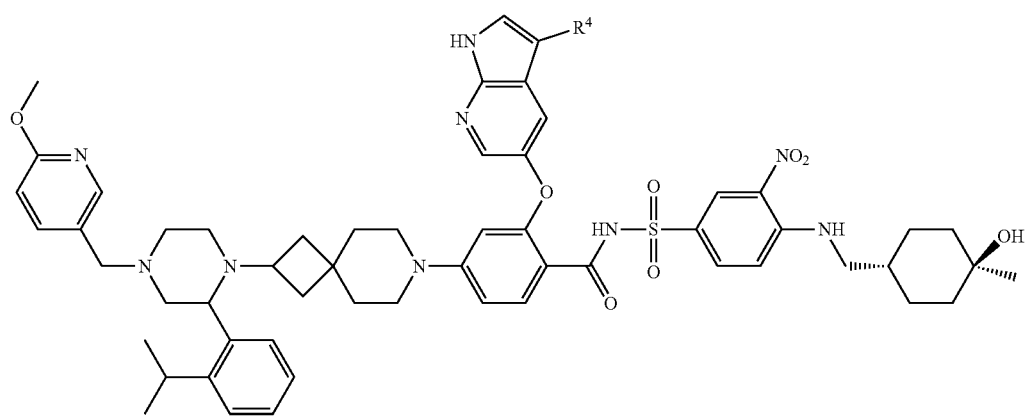
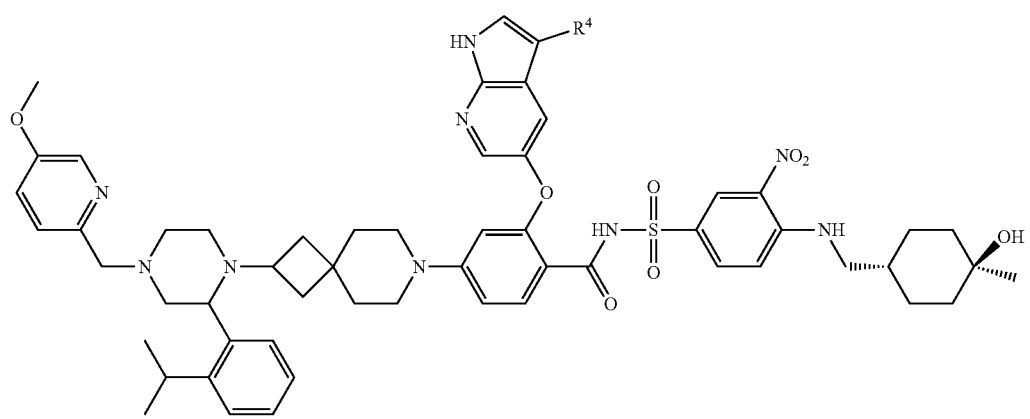
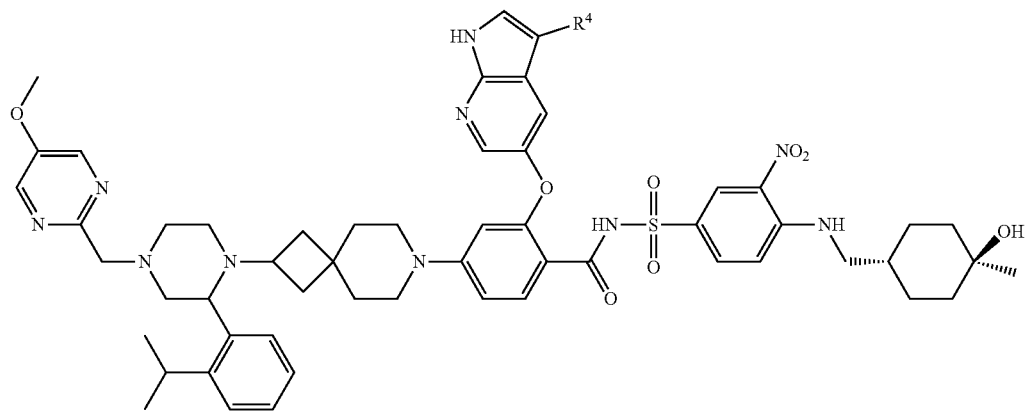

-continued
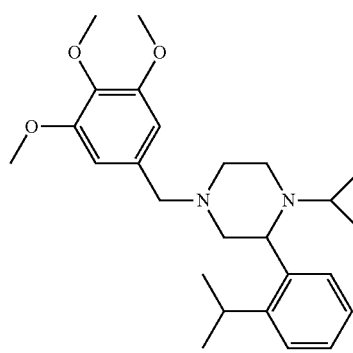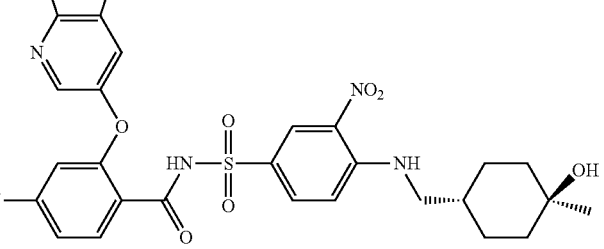
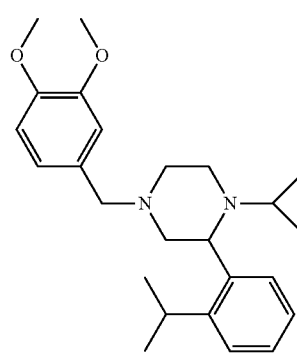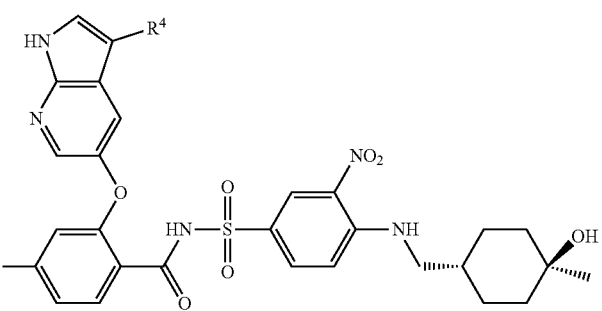
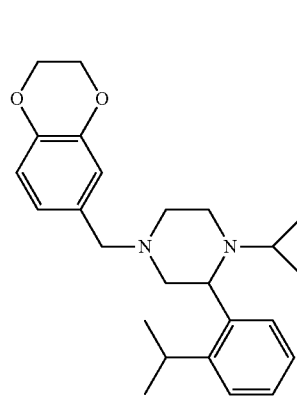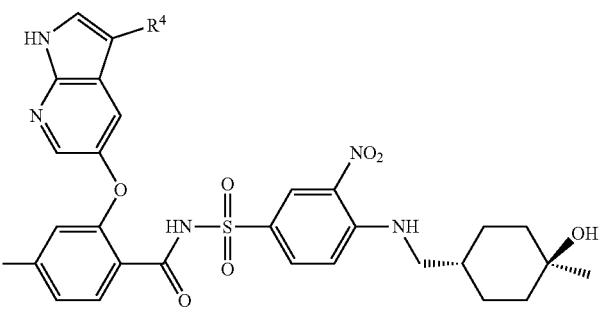
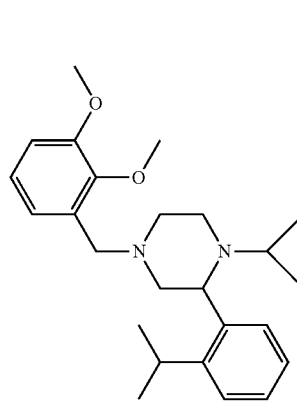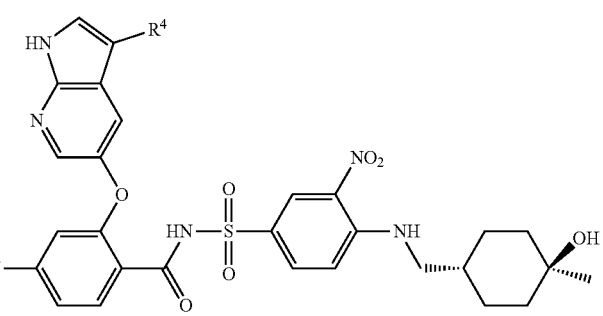

-continued
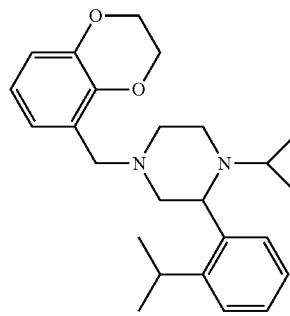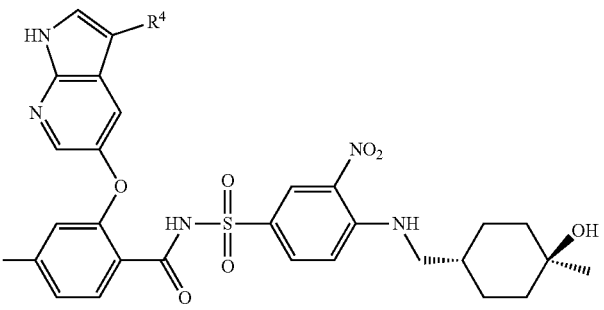
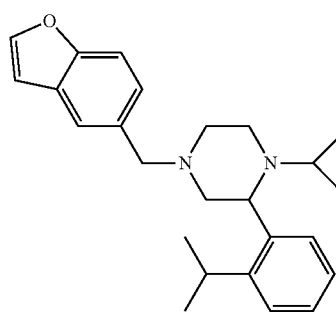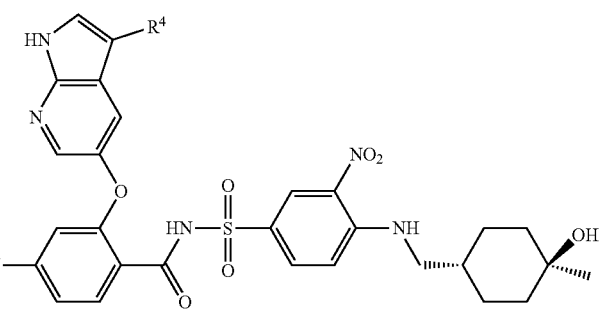
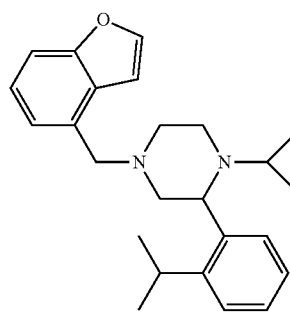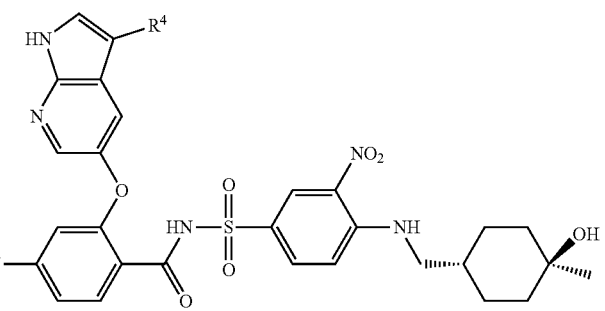
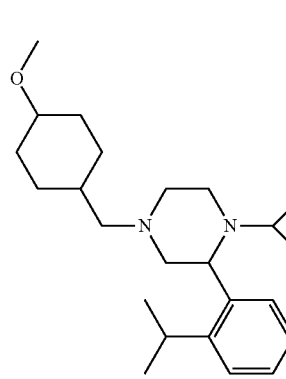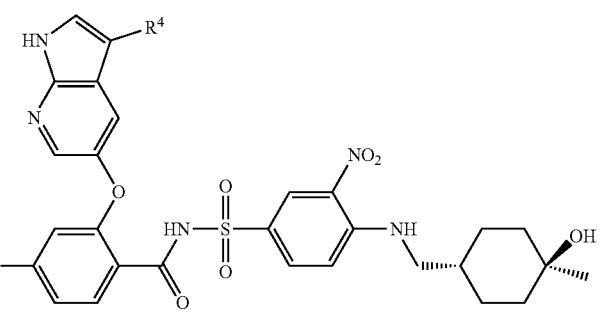

-continued
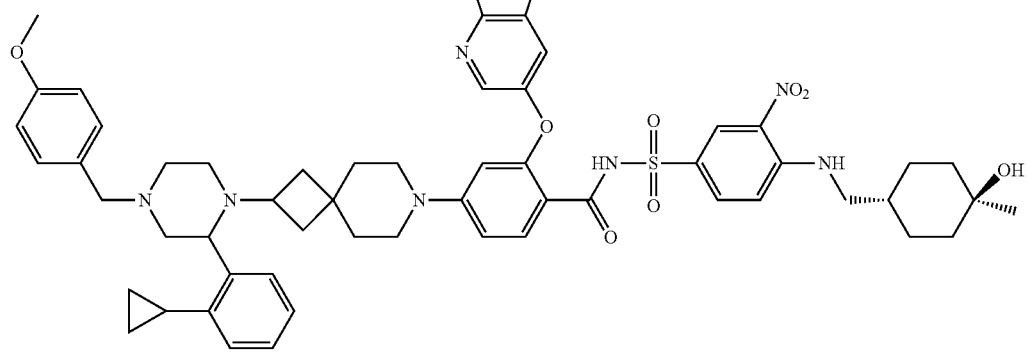
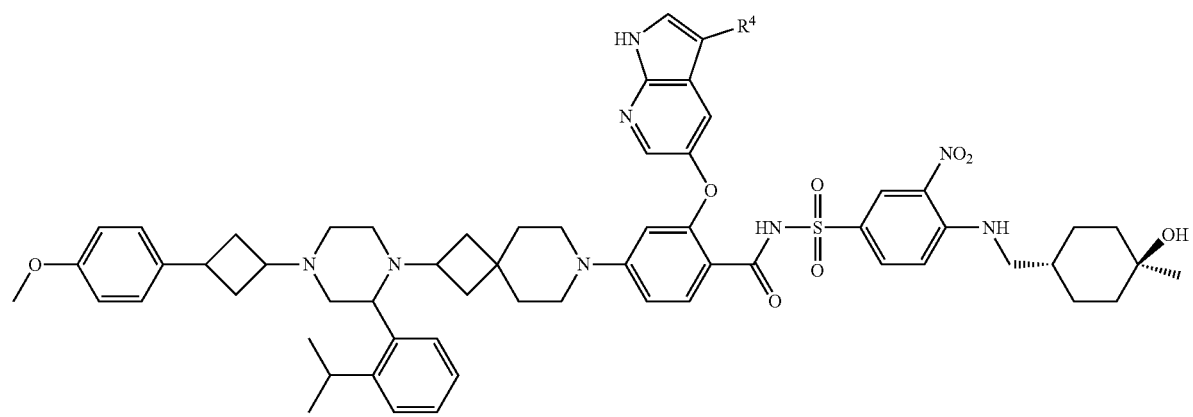
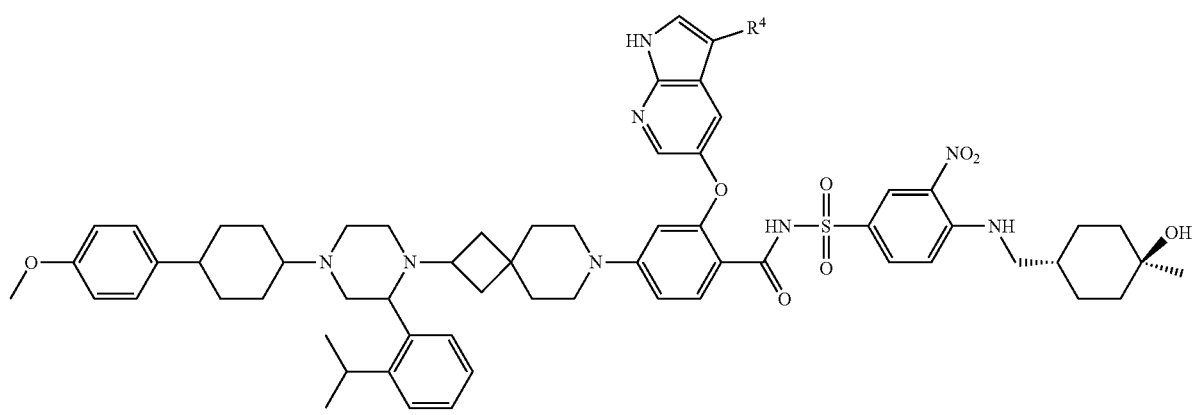
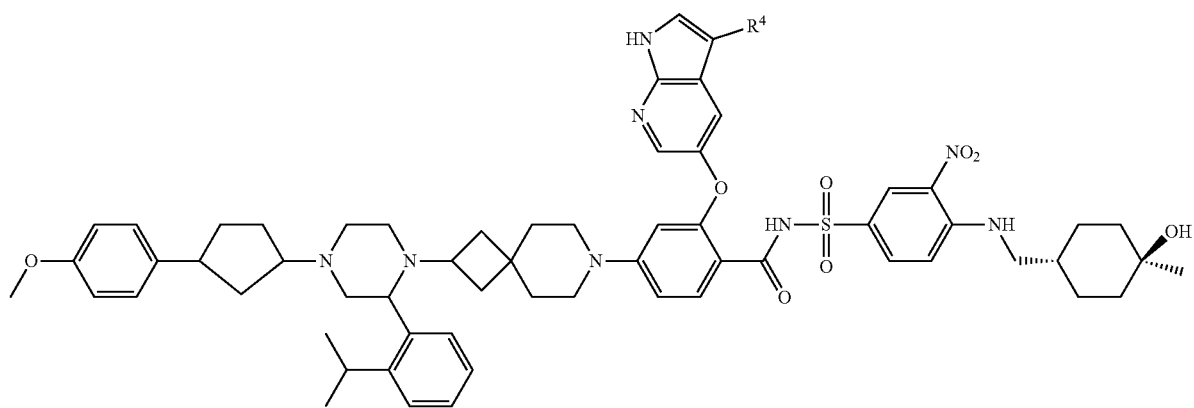

-continued
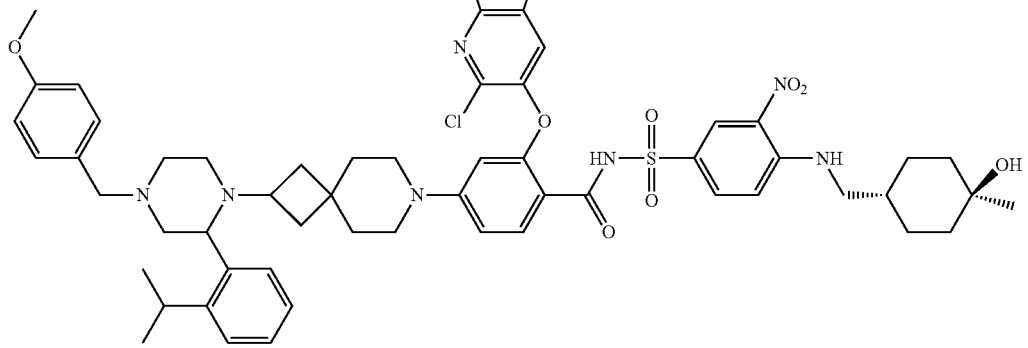
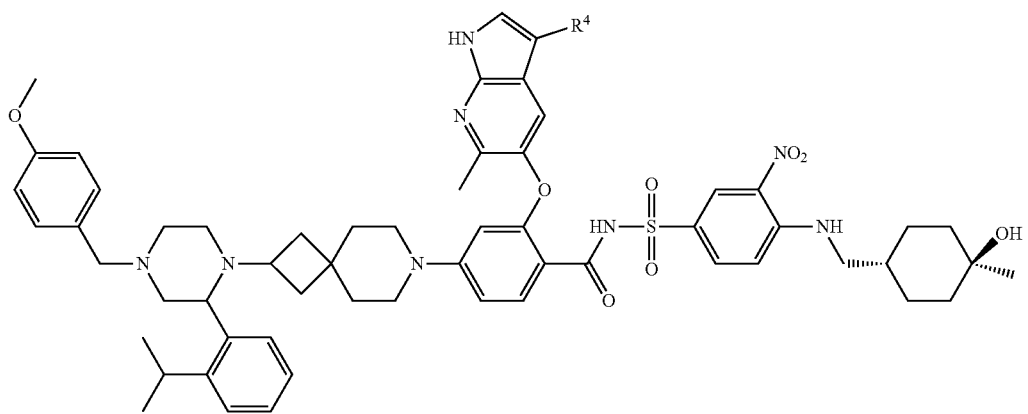
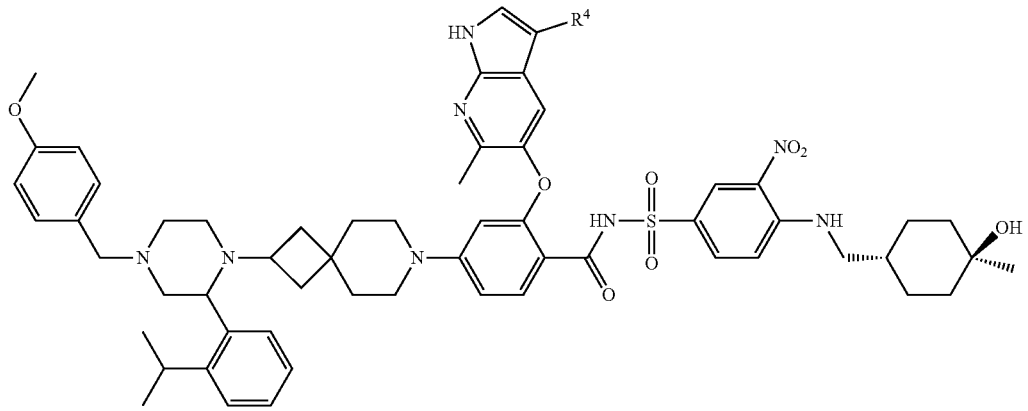
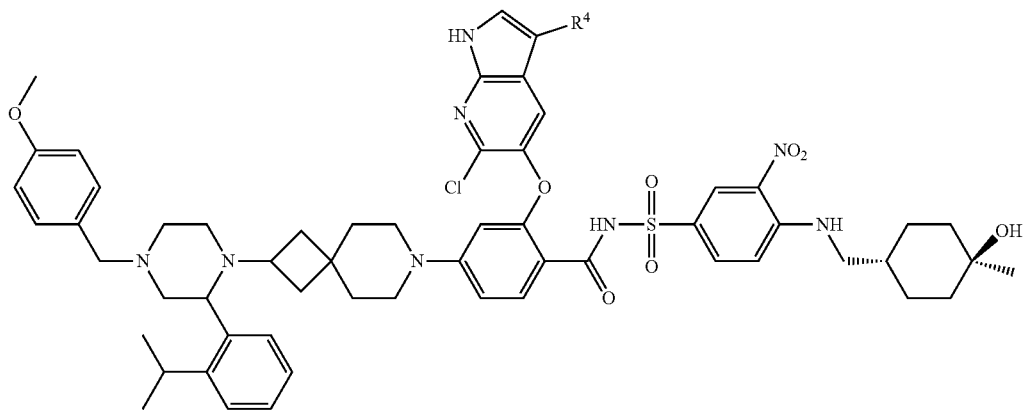

-continued
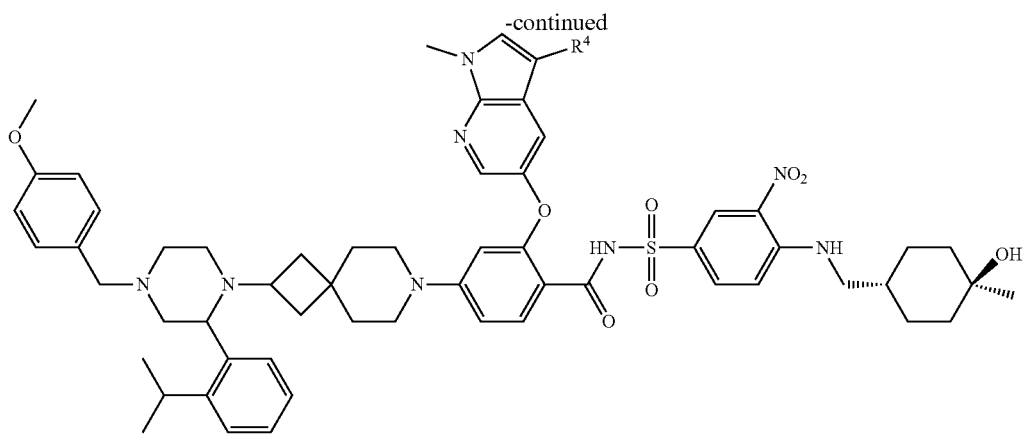
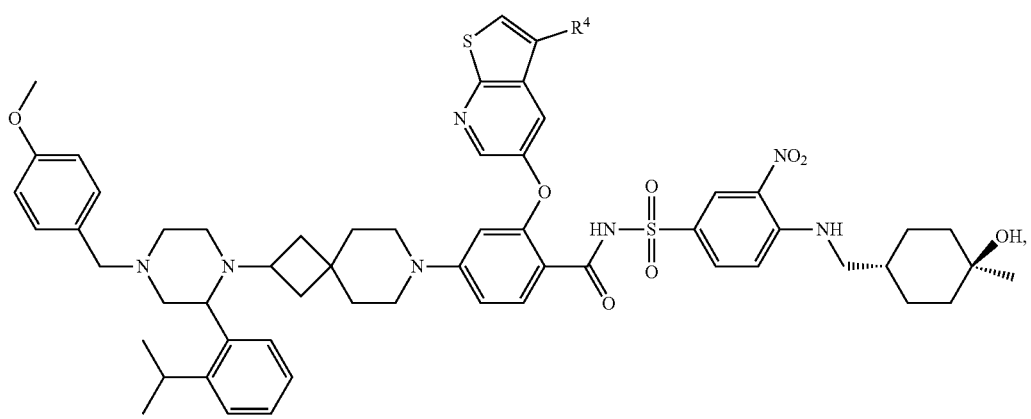
wherein R⁴ is halogen selected from fluoro (—F), chloro (—Cl) or bromo (—Br).
In some embodiments, the compound is
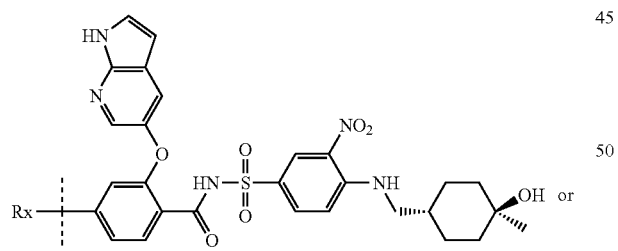
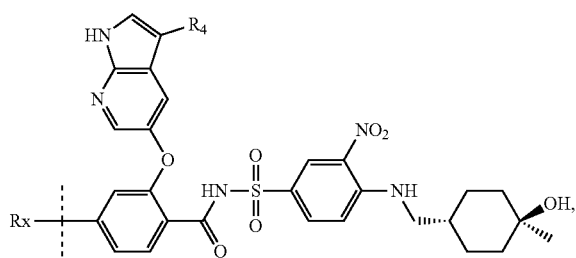
wherein R⁴ is halogen selected from fluoro (—F), chloro (—Cl) or bromo (—Br), an x is selected rom
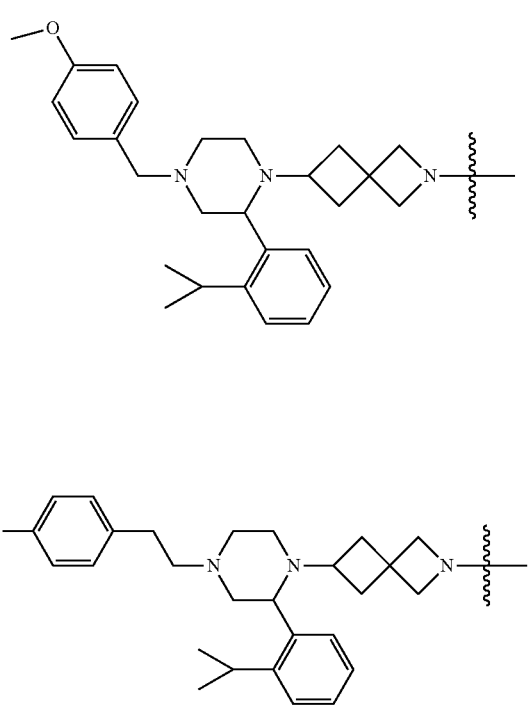

-continued
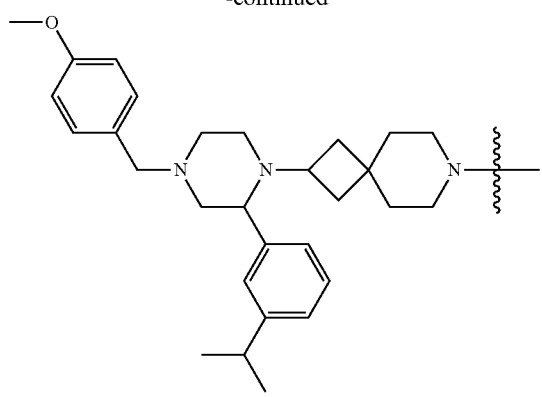
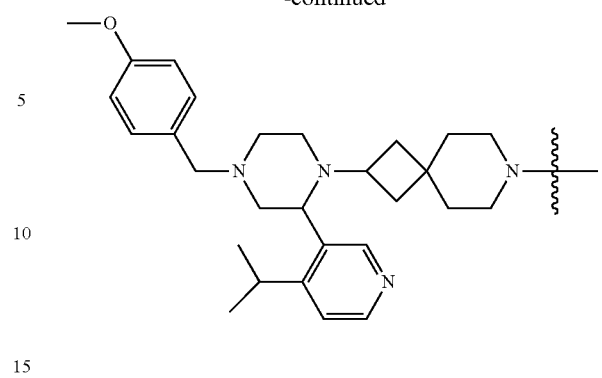
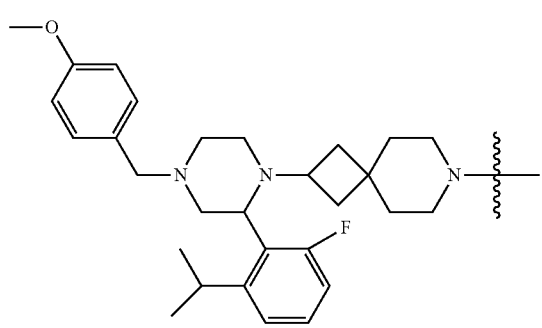
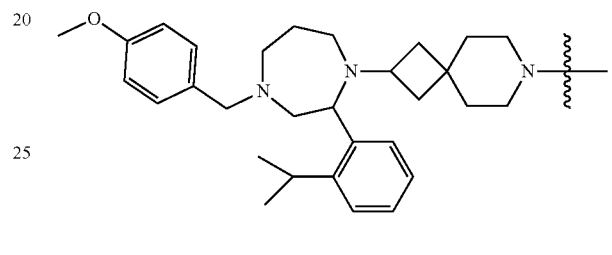
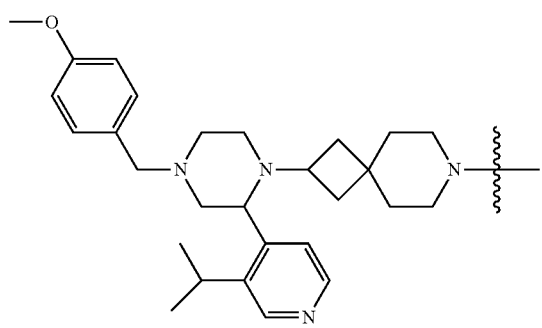
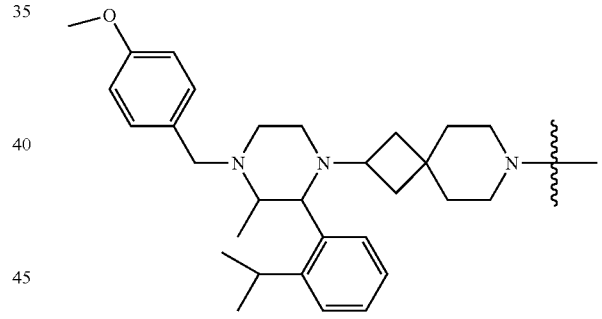
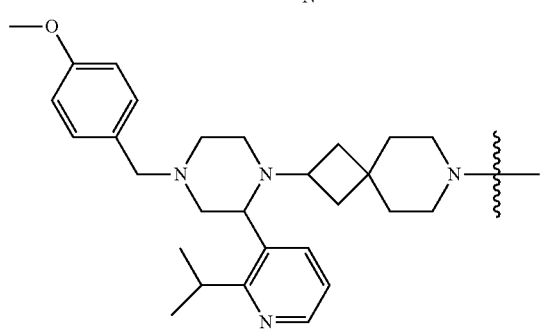
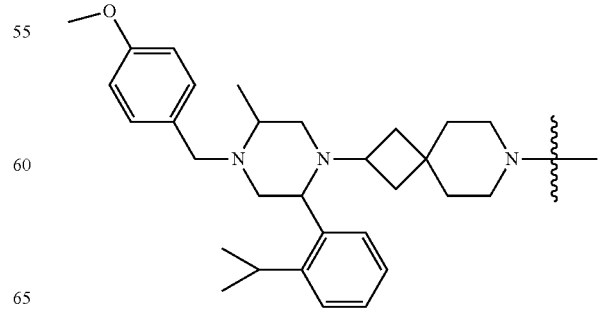

In some embodiments, the compound is selected from
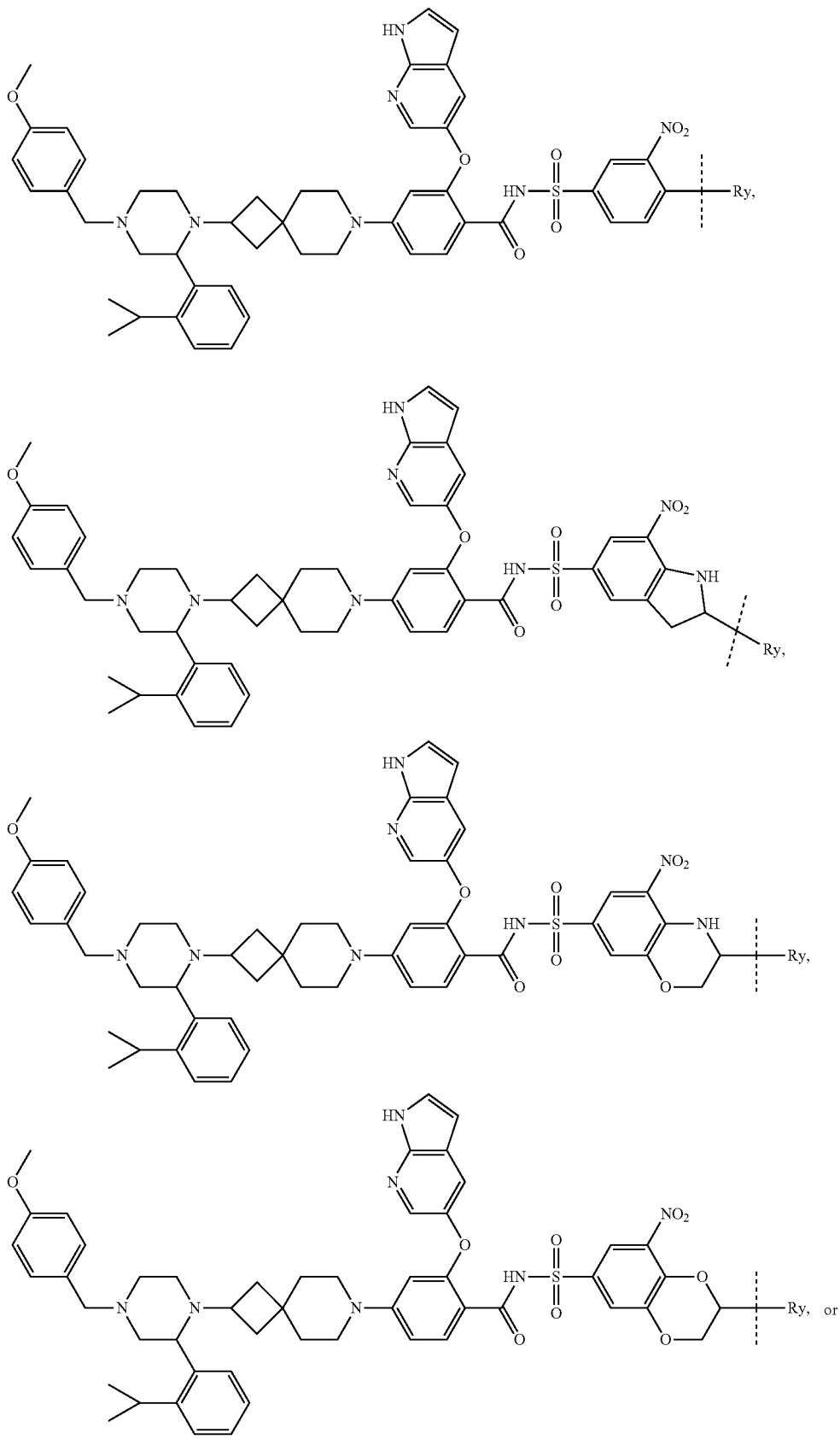

-continued
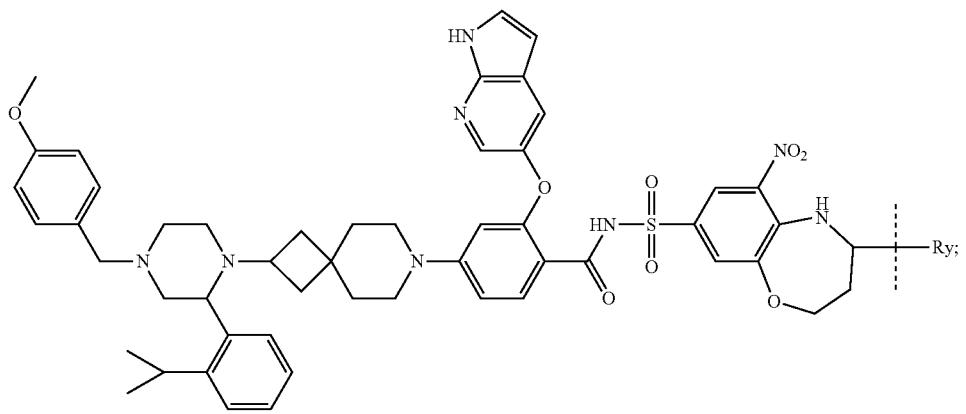
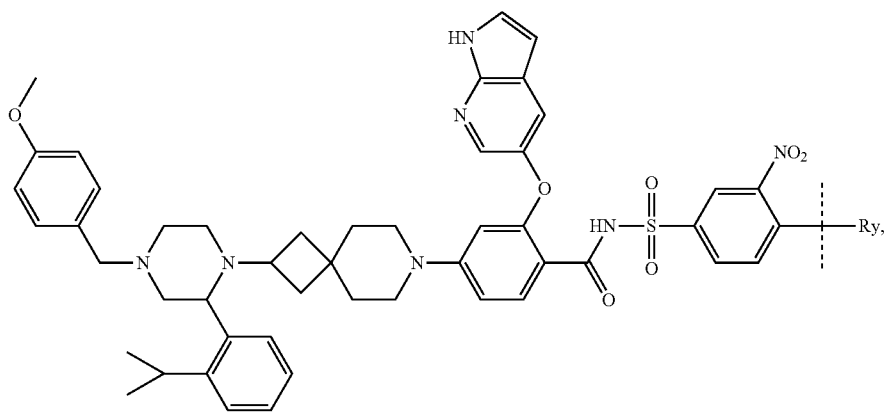
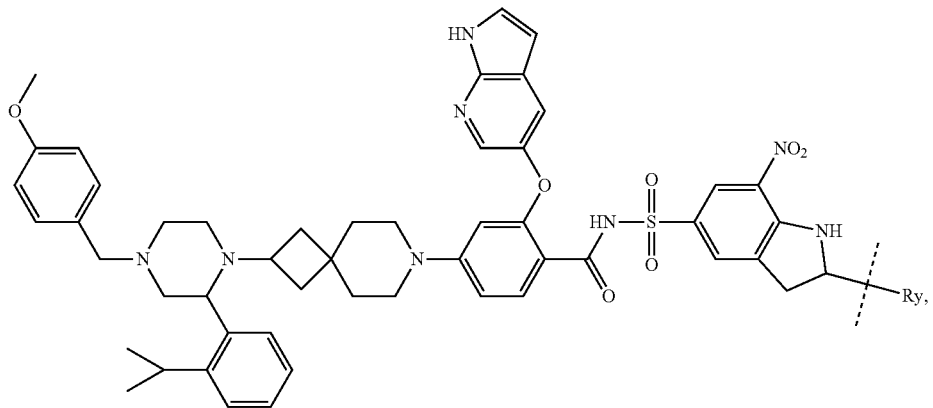
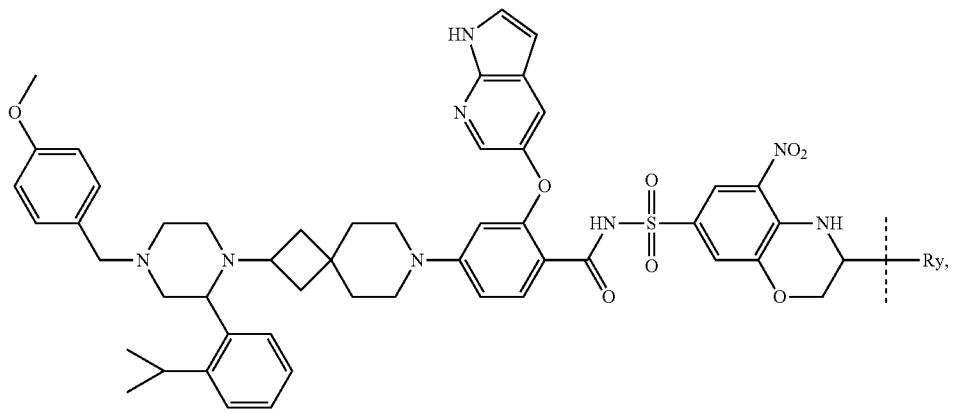

-continued
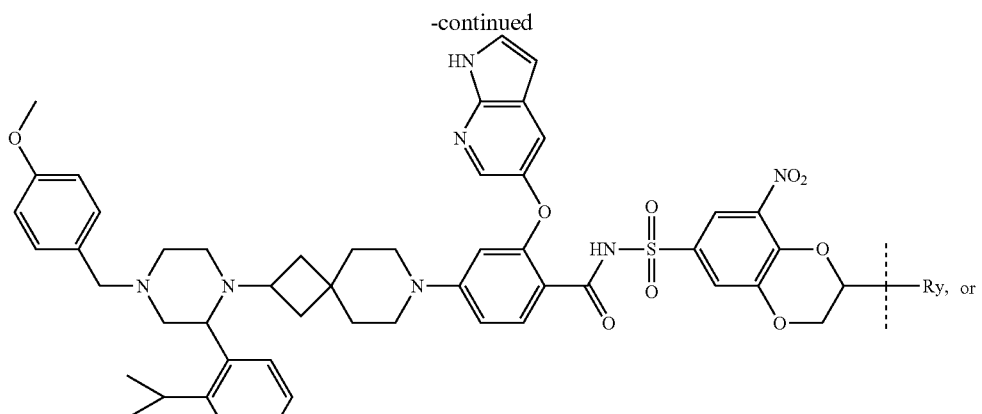
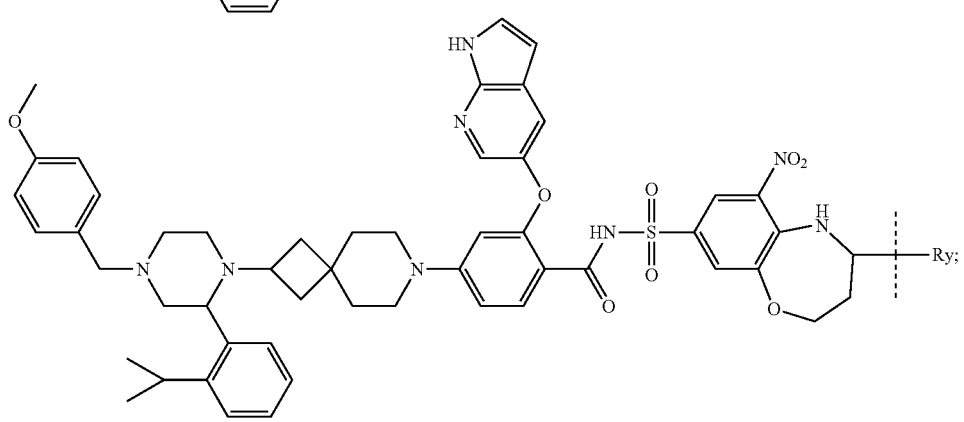
wherein the pyrrole ring on the pyrrolo[2,3-b]pyridin-5-yl ring is optionally substituted with one substitution R⁴ selected from fluoro (—F), chloro (—Cl) or bromo (—Br). and, Ry is selected from
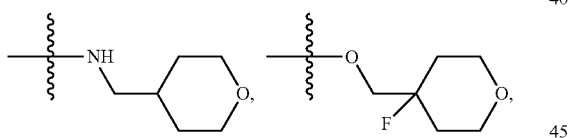
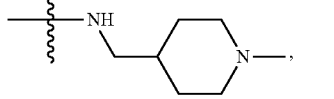
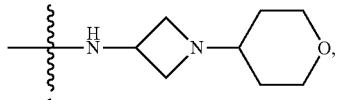
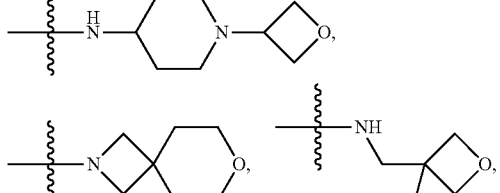
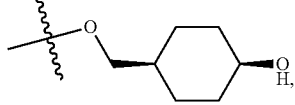
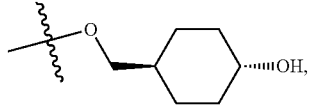
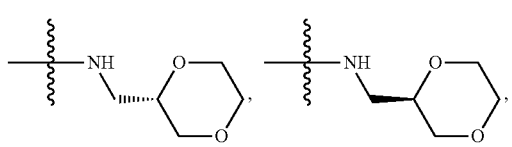
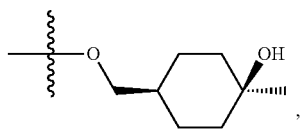
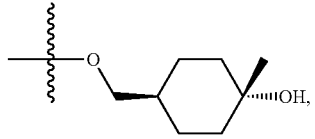
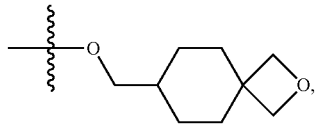

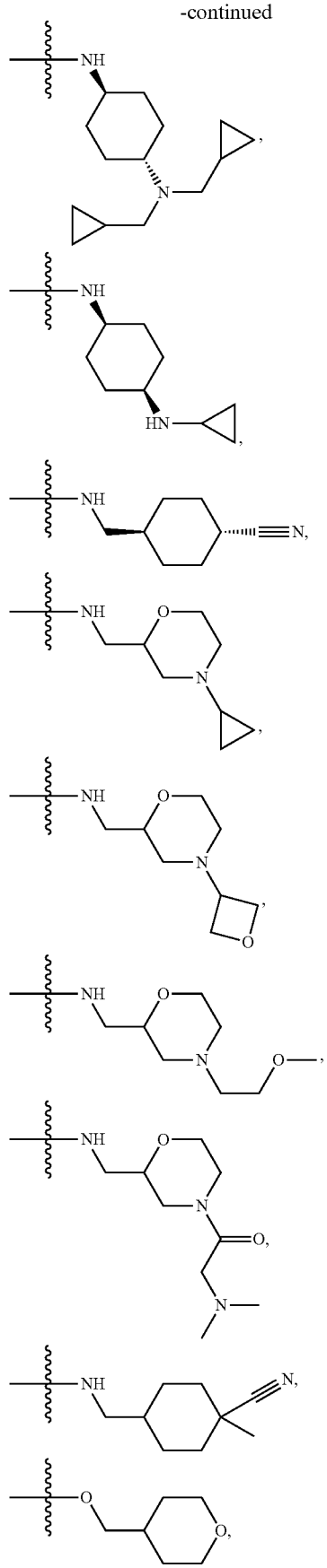
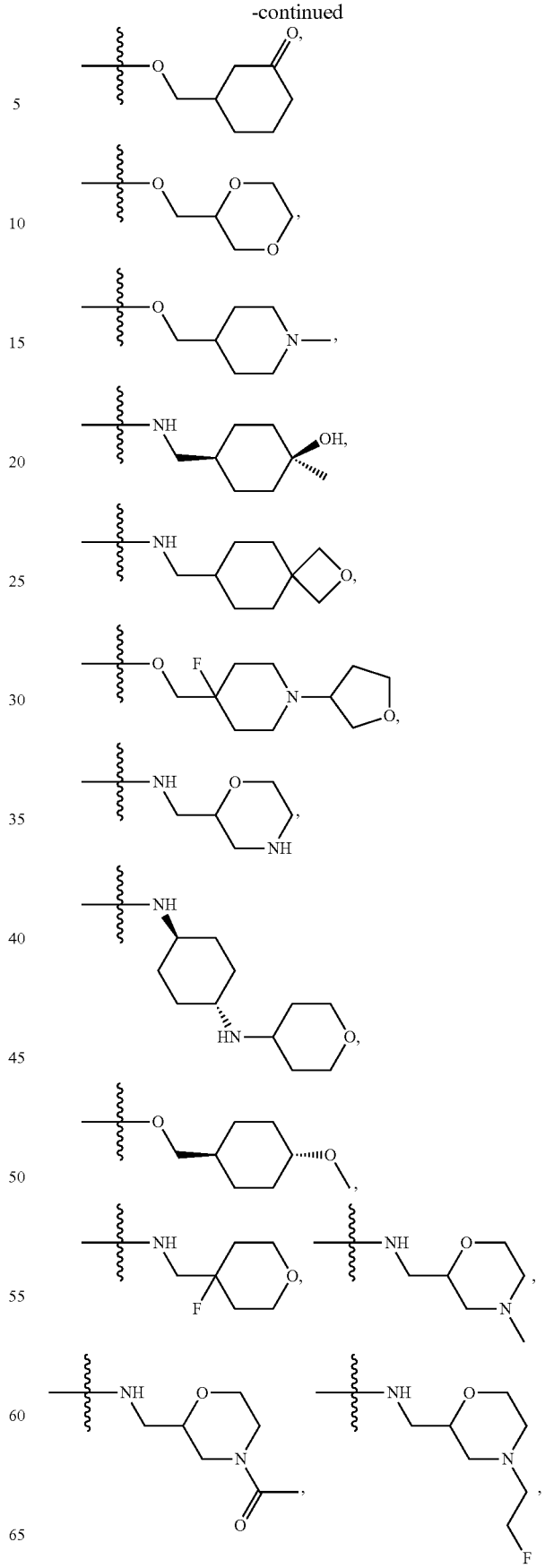

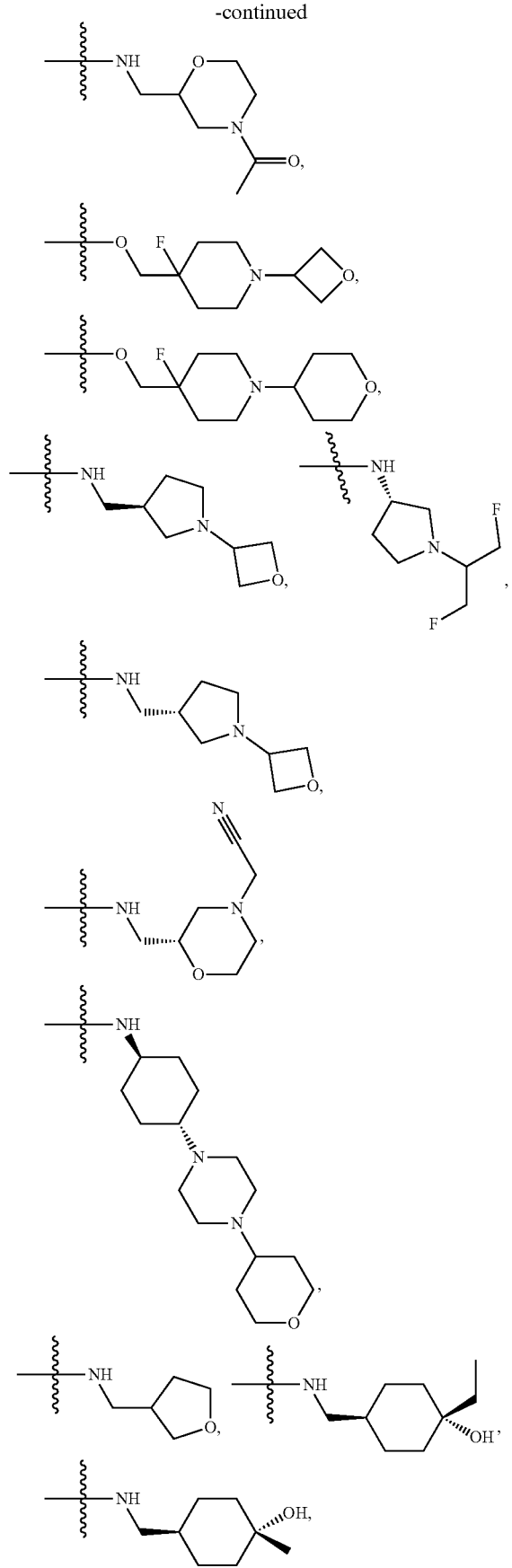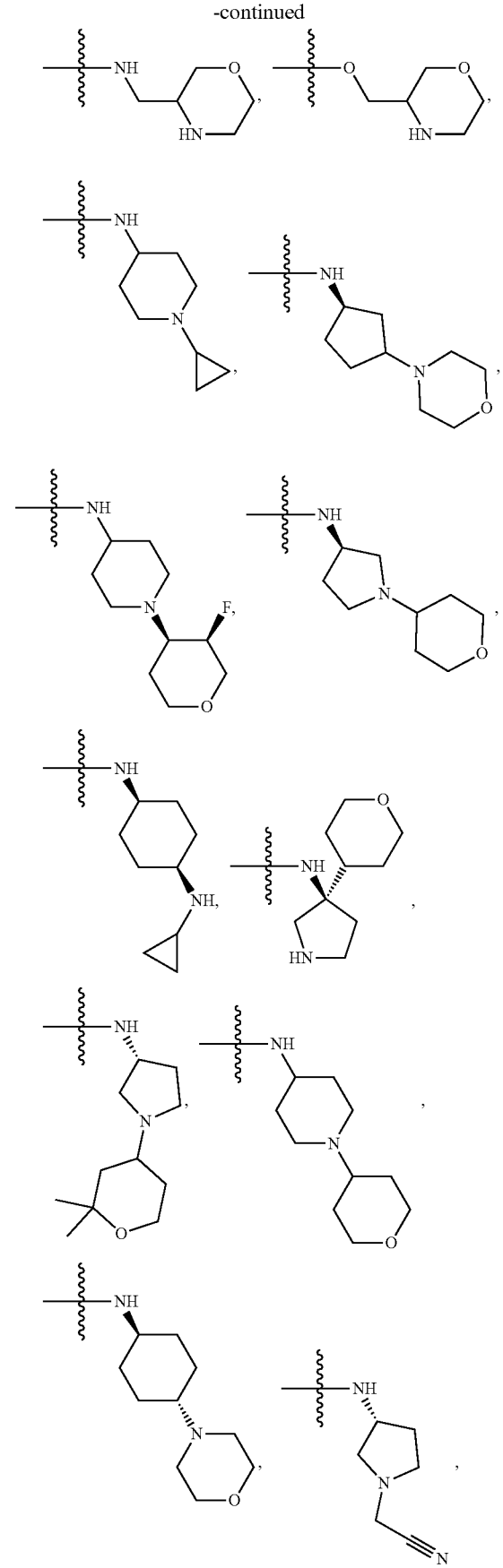

53
-continued

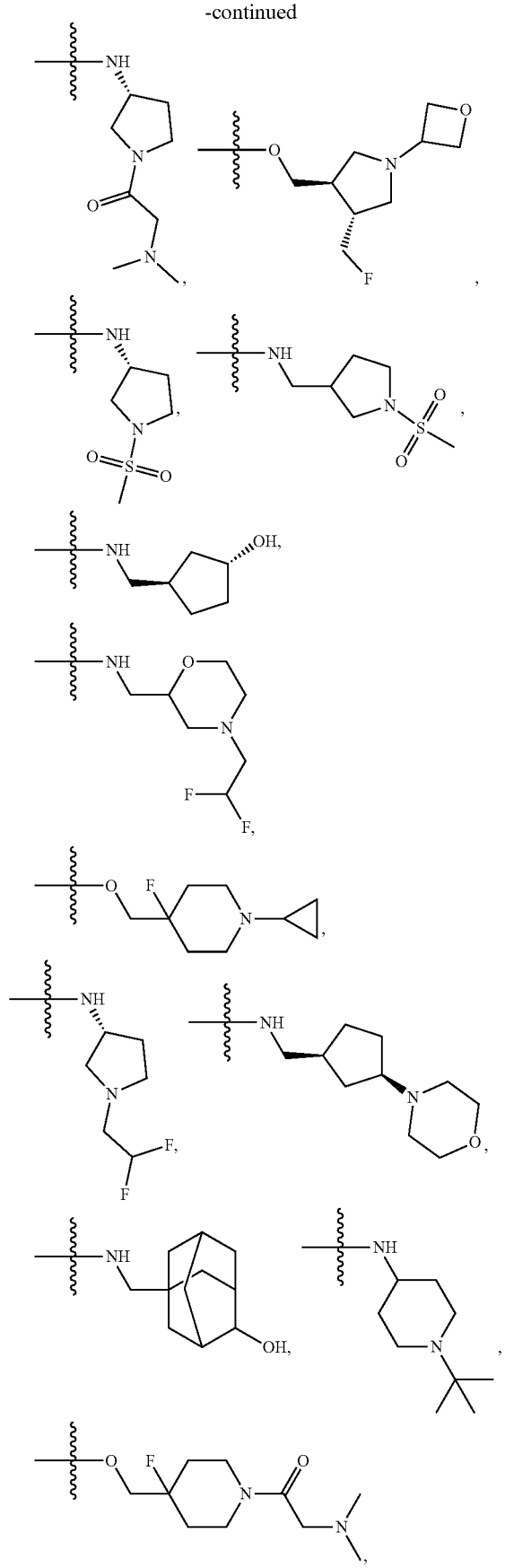

54
-continued

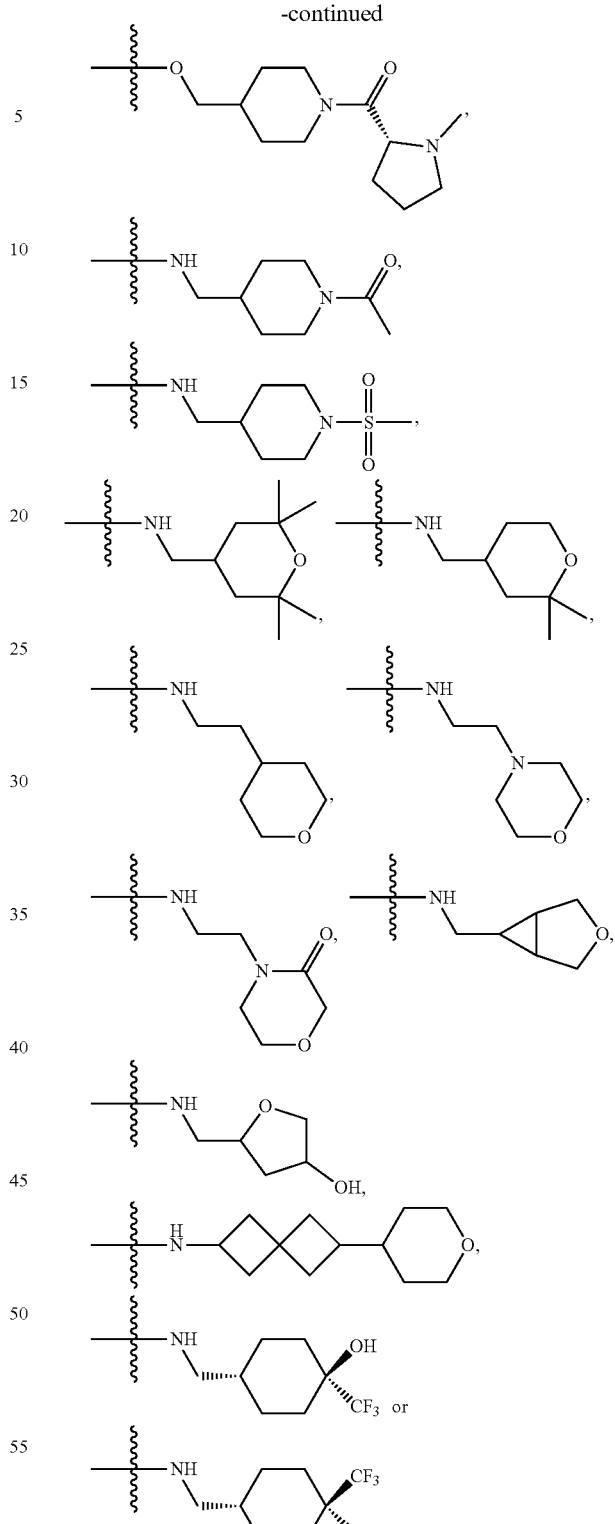

The compounds disclosed herein have an additional aromatic or carbon cyclic moiety attached by a linker —L$_2$— (especially —CH$_2$—, —O—) to the phenylpiperazine or phenylpiperidine moiety in the molecule. This key structural feature not only imparts the comparable or slightly better inhibitory activity for Bcl-2 wild type protein, but also, unexpectedly, exhibit robust potency for Bcl2 mutants including G101V and D103Y. The ratio of $IC_{50}$ of Bcl-2 G101V/Bcl-2 wt is much low. These results suggest the compounds disclosed herein are a type of new potential Bcl-2 inhibitors without resistance concerns from mutations such as G101V and D103Y. From the aspect of neutropenia adverse effect, these compounds present the possibility of a new therapy in an effective and safe dose for clinically relapse patients with mutations after the treatment with venetoclax.

In human and mouse species, the compounds of the present disclosure show long in vitro half-life ($T_{1/2}$) and low intrinsic clearance ($CL_{int}$), and the metabolic stability in liver microsome of compounds in the present disclosure are significantly increased.

Also, the compounds in the present disclosure have significantly good PK, AUC, and Cmax in mouse. And, the CL value in iv dosing of compounds in the present disclosure is also much low, which is consistent with its in vitro clearance data.

Disclosed herein is a pharmaceutical composition, comprising a compound disclosed herein or a pharmaceutically acceptable salt thereof, or a stereoisomer thereof, and at least one of pharmaceutically acceptable excipients.

Disclosed herein is a method for treating dysregulated apoptotic diseases, comprising administering a subject in need thereof a therapeutically effective amount of a compound disclosed herein, or a pharmaceutically acceptable salt thereof, or a stereoisomer thereof. In some embodiments, the dysregulated apoptotic disease is a neurodegenerative condition, proliferative disease, and pro-thrombotic condition. In other embodiments, the proliferative disease is cancer. In some embodiments, the dysregulated apoptotic disease is associated with mutation of Bcl-2. In other embodiments, the mutation of Bcl-2 comprises Bcl-2 G101V and/or Bcl-2 D103Y. In yet another embodiment, the mutation of Bcl-2 is Bcl-2 G101V or Bcl-2 D103Y.

DETAILED DESCRIPTION OF THE DISCLOSURE

Definitions

Figure 1A:
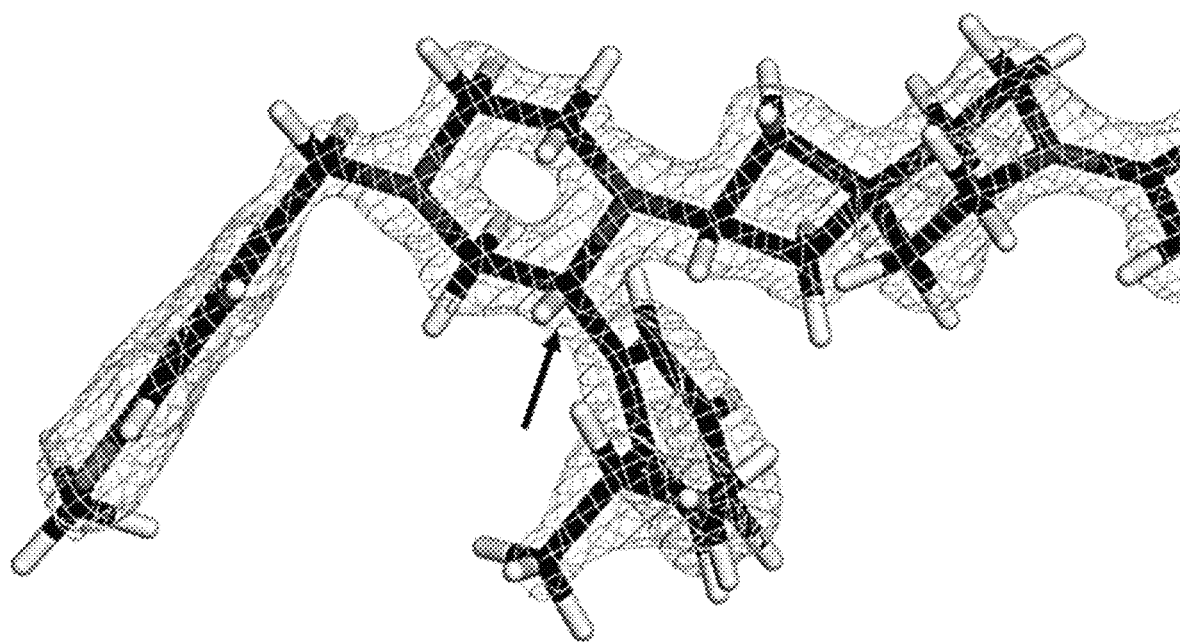
FIG. 1A. The conformation of Example 19a synthesized from intermediate 19-1a in Method A and its electron density map. Example 19a is shown as stick and colored in black, while the density map is shown as mesh in gray. The absolute stereochemistry of arrow pointed carbon is assigned as (R)-configuration.
Figure 1B:
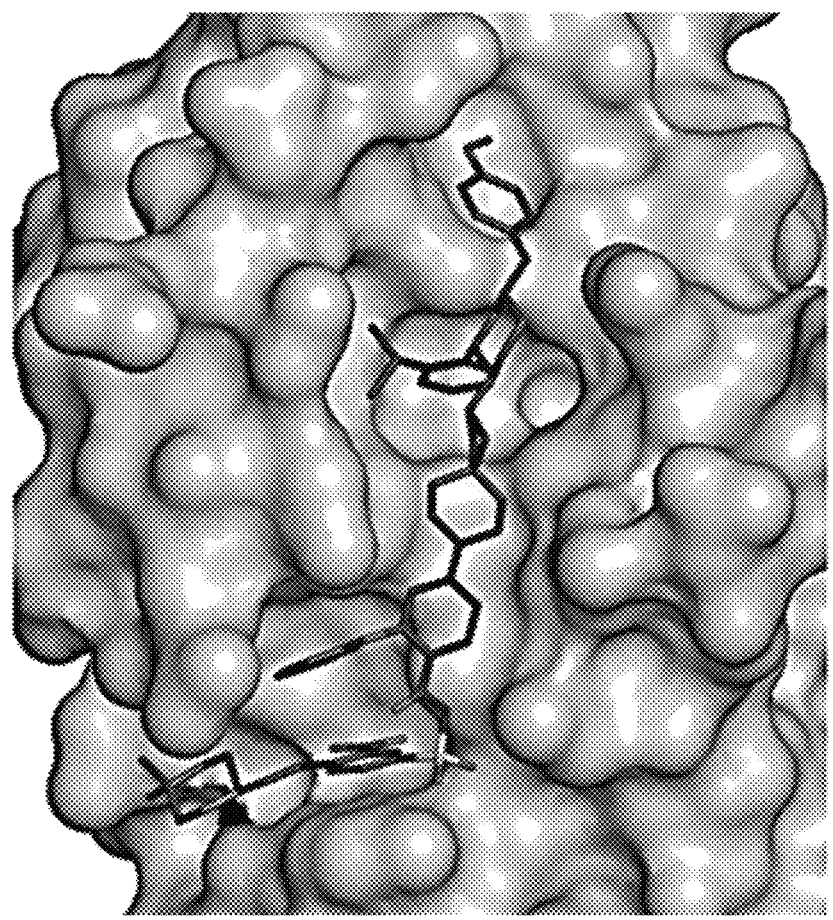
FIG. 1B. Co-crystal structure of Example 19a with Bcl-2 G101V mutant.

Unless specifically defined elsewhere in this document, all other technical and scientific terms used herein have the meaning commonly understood by one of ordinary skill in the art.

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. The alkyl group can be optionally enriched in deuterium, e.g., $-CD_3$, $-CD_2CD_3$ and the like.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$alkyl or halo $C_4$alkyl, but not limited to $-CF_3$, $-CH_2Cl$, $-CH_2CF_3$, $-CCl_2$, $CF_3$, and the like.

The term "alkyloxy" or "alkoxy" refers to an alkyl group as defined above attached to the parent molecular moiety through an oxygen atom. Examples of an alkyloxy, e.g., $C_{1-6}$alkyloxy or C v alkyloxy include, but not limited to, methoxy, ethoxy, isopropoxy, propoxy, n-butoxy, tert-butoxy, pentoxy and hexoxy and the like.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, cyclohexyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo [2.2.1]heptane, bicyclo[2.2.2]octane, and bicyclo[3.2.2] nonane. Further Examples of the bicyclic cycloalkyl groups include those arranged as a bicyclic ring selected from [5,6] and [6,6] ring systems, such as

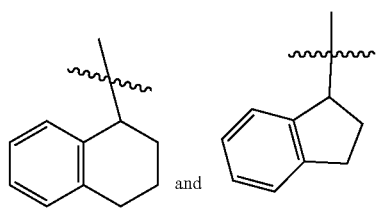 [SMILES: *C1CCCc2ccccc21 ; *C1CCc2ccccc21]

and wherein the wavy lines indicate the points of attachment. The ring may be saturated or have at least one double bond (i.e. partially unsaturated), but is not fully conjugated, and is not aromatic, as aromatic is defined herein.

The term "spiro cycloalkyl" refers to a cyclic structure which contains carbon atoms and is formed by at least two rings sharing one atom. The term "7 to 10 membered spiro cycloalkyl" refers to a cyclic structure which contains 7 to 10 carbon atoms and is formed by at least two rings sharing one atom.

The term "fused cycloalkyl" refers to a fused ring which contains carbon atoms and is formed by two or more rings sharing two adjacent atoms. The term "4 to 10 membered fused cycloalkyl" refers to a fused ring which contains 4 to 10 ring carbon atoms and is formed by two or more rings sharing two adjacent atoms.

Examples include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1,2,3,4-tetralyl, 1,4-dihydronaphthyl, etc. Preferred embodiments are 8 to 9 membered fused cyclyl, which refer to cyclic structures containing 8 to 9 ring atoms within the above examples.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

Examples include but are not limited to octahydro-5H-2,5-methanoindenyl (preferably octahydro-5H-2,5-methanoinden-5-yl), or adamantanyl (preferably adamantan-1-yl).

The term "aryl" used alone or in combination with other terms refers to a group selected from:
a) 5- and 6-membered carbocyclic aromatic rings, e.g., phenyl;
b) bicyclic ring systems such as 7 to 12 membered bicyclic ring systems, wherein at least one ring is carbocyclic and aromatic, e.g., naphthyl and indanyl; and,
c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" refers to a group selected from:
a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
b) 8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides. The term "C-linked heteroaryl" as used herein means that the heteroaryl group is connected to the core molecule by a bond from a C-atom of the heteroaryl ring The terms "aromatic heterocyclic ring" and "heteroaryl" are used interchangeably throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur, and oxygen.

Examples of the heteroaryl group or the monocyclic or bicyclic aromatic heterocyclic ring include, but are not limited to, (as numbered from the linkage position assigned priority 1)pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzofuranyl, benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heterocyclyl", "heterocycle" or "heterocyclic" are interchangeable and refer to a non-aromatic heterocyclyl group comprising one or more heteroatoms selected from the group consisting of NH, O, S, SO or $SO_2$ heteroatoms as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from the group consisting of NH, O, S, SO or $SO_2$. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "spiro heterocyclyl" or "heterospirocyclyl" refers to a 5 to 20-membered polycyclic heterocyclyl with rings connected through one common carbon atom (called a spiro atom), comprising one or more heteroatoms selected from the group consisting of NH, O, S, SO or $SO_2$ heteroatoms as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 10-membered. According to the number of common spiro atoms, a spiro heterocyclyl is divided into mono-spiro heterocyclyl, di-spiro heterocyclyl, or polyspiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include, but not limited to the following groups: 2,3-dihydrospiro[indene-1,2'-pyrrolidine](e.g., 2,3-dihydrospiro[indene-1,2'-pyrrolidine]-1'-yl), 1,3-dihydrospiro[indene-2,2'-pyrrolidine](e.g., 1,3-dihydrospiro[indene-2,2'-pyrrolidine]-1'-yl), azaspiro[2.4]heptane (e.g., 5-azaspiro[2.4]heptane-5-yl), azaspiro[3.4]octane (e.g., 6-azaspiro[3.4]octane-6- yl), 2-oxa-6-azaspiro[3.4]octane (e.g., 2-oxa-6-azaspiro[3.4]octane-6-yl), azaspiro[3.4]octane (e.g., 6-azaspiro[3.4]octan-6-yl), azaspiro[3.4]octane (e.g., 6-azaspiro[3.4]octan-6-yl), 7-azaspiro[3.5]nonane (e.g., 7-azaspiro[3.5]nonan-7-yl), 2-azaspiro[3.5]nonane (e.g., 2-azaspiro[3.5]nonan-2-yl),1,7-dioxaspiro[4.5]decane, 2-oxa-7-aza-spiro[4.4]nonane (e.g., 2-oxa-7-aza-spiro[4.4]non-7-yl), 7-oxa-spiro[3.5]nonyl and 5-oxa-spiro[2.4]heptyl.

The term "fused heterocyclic group" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from the group consisting of NH, O, S, SO or $SO_2$ heteroatoms as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin, dihydrobenzofuranyl, benzo[d][1,3]dioxolyl or 2,3,4,5-tetrahydrobenzo[b]oxepinyl (preferably 2,3,4,5-tetrahydrobenzo[b]oxepin-7-yl).

The term "bridged heterocyclyl" refers to a 5- to 14-membered polycyclic heterocyclic alkyl group, wherein every two rings in the system share two disconnected atoms, comprising one or more heteroatoms selected from the group consisting of NH, O, S, SO or $SO_2$ heteroatoms as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

The heterocyclyl ring may be fused to aryl, heteroaryl or cycloalkyl ring, wherein the ring structure is connected to the parent heterocyclic group together.

The term "heterocyclyl-O—" as used refers to a heterocyclyl as defined above attached to the parent molecular moiety through an oxygen atom.

"C-linked heterocyclyl" as used refers to a heterocyclyl group which is connected to the other part of the molecule by a direct bond from a carbon atom of the heterocyclyl ring.

"N-linked heterocyclyl" as used refers to a heterocyclyl group which is connected to the other part of the molecule by a direct bond from a nitrogen atom of the heterocyclyl ring.

Compounds disclosed herein may contain an asymmetric center and may thus exist as enantiomers. "Enantiomers" refer to two stereoisomers of a compound which are nonsuperimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, a reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations.

Cis formation means that both substituents are found on the upper side of the 2 substituent placements on the carbon, while trans would mean that they were on opposing sides.

It may be advantageous to separate reaction products from one another and/or from starting materials. The desired product of each step or series of steps is separated and/or purified (hereinafter separated) to the desired degree of homogeneity by the techniques common in the art.

Typically such separations involve multiphase extraction, crystallization from a solvent or solvent mixture, distillation, sublimation, or chromatography. Chromatography can involve any number of methods including, for example reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review*." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer Irving W, Ed. *Drug Stereochemistry: Analytical Methods and Pharmacology*. New York: Marcel Dekker Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administered via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

EXAMPLES

The present invention is further exemplified, but not limited to, by the following examples that illustrate the invention.

In the following examples, the abbreviations below are used:

AcOH or HOAc Acetic acid
aq. Aqueous
BINAP (2,2'-bis(diphenylphosphino)-1,1'-binaphthyl)
$BH_3$ Borane
Brine Saturated aqueous sodium chloride solution
$Boc_2O$ di(tert-butyl) carbonate
BSA Bovine serum albumin
DAST Diethylaminosulfur trifluoride
DBN 1,5-Diazabicyclo[4.3.0]non-5-ene
DBU 1,8-Diazabicyclo[5.4.0]undec-7-ene
DCE 1,2-Dichloroethane
DCM Dichloromethane
DMAP 4-Dimethylaminopyridine
$CH_3MgBr$ Methyl magnesium bromide
DIPEA N,N-Diisopropylethylamine
DMF N,N-Dimethylformamide
DMAC Dimethylacetamide
DMSO Dimethyl sulfoxide
EA Ethyl acetate
EDCI 1-Ethyl-3-(3-dimethylaminopropyl)carbodiimide Hydrochloride
EDTA Ethylenediaminetetraacetic acid
EtOH Ethyl alcohol
h or hr Hour
HATU 1-[Bis(dimethylamino)methylene]-1H-1,2,3-triazolo[4,5-b]pyridinium 3-oxide hexafluorophosphate
Hex Hexane
$^1H$ NMR Proton Nuclear Magnetic Resonance
$H_2O_2$ Hydrogen peroxide
HOBt Hydroxybenzotriazole
IPA (i-PrOH) Isopropyl alcohol
KOAc Potassium Acetate
LAH Lithium aluminum hydride
LC-MS Liquid chromatography- mass spectrometry
LDA Lithium diisopropylamide
MeOH Methanol
MsOH Methanesulfonic acid
Min Minutes
n-BuLi n-Butyllithium
NaH Sodium hydride
$NaBH(OAc)_3$ Sodium triacetoxyborohydride
$NaBH_3CN$ Sodium cyanoborohydride
$NH_4Cl$ Ammonium chloride
Pd/C Palladium on carbon powder
$Pd(dppf)Cl_2$ [1,1'-Bis(diphenylphosphino)ferrocene]dichloropalladium(II)
$Pd(PPh_3)_4$ Tetrakis(triphenylphosphine)palladium(O)
$Pd(OAc)_2$ Palladium acetate
$Pd(OH)_2/C$ Palladium hydroxide on carbon powder
PE Petroleum ether
pH -lg(hydrogen ion concentration)
Prep-HPLC Preparative high-pressure liquid chromatography
Prep-MPLC Preparative medium pressure liquid chromatography Prep-SFC Preparative supercritical fluid chromatography Pre-TLC Preparative thin layer chromatography p-TsOH p-Toluenesulfonic acid r.t. or RT room temperature sat. Saturated t-BuOK Potassium tert-butoxide TBS tert-butyldimethylsilyl THF Tetrahydrofuran TEA Triethylamine TFA Trifluoroacetic acid TsCl 4-methylbenzenesulfonyl chloride The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on a Agilent instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; d6-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LC-MS spectrometer (Agilent 1260) Detector: MWD (190-400 nm), Mass detector: 6120 SQ Mobile phase: A: acetonitrile with 0.1% Formic acid, B: water with 0.1% Formic acid Column: Poroshell 120 EC-C18, 4.6×50 mm, 2.7 μm Gradient method: Flow rate: 1.8 mL/min

| Time (min) | A (%) | B (%) |
|---|---|---|
| 0.00 | 5 | 95 |
| 1.5 | 95 | 5 |
| 2.0 | 95 | 5 |
| 2.1 | 5 | 95 |
| 3.0 | 5 | 95 |

Preparative HPLC was conducted on a column (150×21.2 mm ID, 5 μm, Gemini NX—C18) at a different flow rate and injection volume, at room temperature and UV Detection at 214 nm and 254 nm.

Preparation of Intermediates

Intermediate 2-1: 2-(4-ethyl-2-(2-isopropylphenyl) piperazin-1-yl)-7-azaspiro[3.5]nonane

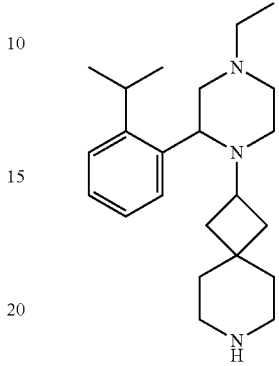

Intermediate 2-1

Step 1: tert-butyl 4-ethyl-2-(2-isopropylphenyl)-3-oxopiperazine-1-carboxylate.

To a solution of tert-butyl 2-(2-isopropylphenyl)-3-oxopiperazine-1-carboxylate (2.0 g, 6.28 mmol) in THF (20 mL) was added NaH (301.47 mg, 7.54 mmol) at 0° C., the mixture was stirred at 0° C. for 10 min, then $C_2H_5I$ (1.18 g, 7.54 mmol) was added at 0° C. The mixture was stirred at 50° C. for 16 hrs. The reaction mixture was poured into $H_2O$ (20 mL), extracted with EtOAc (20 mL×3). The combined organic layers were washed with brine, dried over $Na_2SO_4$, filtered and concentrated under reduced pressure. The residue was purified by MPLC. The compound tert-butyl 4-ethyl-2-(2-isopropylphenyl)-3-oxopiperazine-1-carboxylate (1.7 g, yield: 78%) was obtained as a yellow oil. $^1$H NMR (400 MHz, $CDCl_3$) δ ppm: 7.36 (m, 1H), 7.31-7.28 (m, 1H), 7.15-7.10 (m, 1H), 7.09-7.06 (m, 1H), 5.97 (s, 1H), 3.75-3.64 (m, 1H), 3.62-3.53 (m, 2H), 3.46-3.27 (m, 4H), 1.46 (s, 9H), 1.29 (m, 3H), 1.25-1.23 (m, 3H), 1.18 (m, 3H).

Step 2: 1-ethyl-3-(2-isopropylphenyl)piperazin-2-one.

A mixture of tert-butyl 4-ethyl-2-(2-isopropylphenyl)-3-oxopiperazine-1-carboxylate (1.7 g, 4.91 mmol) in DCM (10 mL) and TFA (10 mL) was stirred at 25° C. for 2 hrs. The reaction mixture was concentrated under reduced pressure. The residue was diluted with $H_2O$ (10 mL) and added $Na_2CO_3$ to pH=9. The mixture was extracted with DCM (10 mL×3). The combined organic layers were washed with brine, dried over $Na_2SO_4$, filtered and concentrated under reduced pressure. The compound 1-ethyl-3-(2-isopropylphenyl)piperazin-2-one (1.2 g, yield: 99%) was obtained as a yellow oil. MS (ESI, m/e) [M+1]$^+$247.1.

Step 3: tert-butyl 2-(4-ethyl-2-(2-isopropylphenyl)-3-oxopiperazin-1-yl)-7-azaspiro[3.5]nonane-7-carboxylate.

To a solution of 1-ethyl-3-(2-isopropylphenyl)piperazin-2-one (1.2 g, 4.87 mmol) and tert-butyl 2-oxo-7-azaspiro [3.5]nonane-7-carboxylate (1.4 g, 5.85 mmol) in DCE (20 mL) was added AcOH (585 mg, 9.74 mmol) and NaBH $(OAc)_3$ (2.06 g, 9.74 mmol) at 20° C. The mixture was stirred at 50° C. for 12 hrs. The reaction mixture was poured into aq. $Na_2CO_3$ (20 mL), extracted with and DCM (20 mL×3). The combined organic layers were washed with brine, dried over $Na_2SO_4$, filtered and concentrated under reduced pressure. The residue was purified by MPLC to give tert-butyl 2-(4-ethyl-2-(2-isopropylphenyl)-3-oxopiperazin- 1-yl)-7-azaspiro[3.5]nonane-7-carboxylate (1.2 g, yield: 52%) as a yellow oil. MS (ESI, m/e) [M+1]$^+$470.3.

Step 4: tert-butyl 2-(4-ethyl-2-(2-isopropylphenyl)piperazin-1-yl)-7-azaspiro[3.5]nonane-7-carboxylate.

A mixture of tert-butyl 2-(4-ethyl-2-(2-isopropylphenyl)-3-oxopiperazin-1-yl)-7-azaspiro[3.5]nonane-7-carboxylate (1.2 g, 2.56 mmol) in BH$_3$·THF (10 mL) was stirred at 70° C. for 12 hrs. The reaction mixture was quenched by MeOH (10 mL) at 0° C. and stirred at 25° C. for 30 min. The mixture was concentrated under reduced pressure to give tert-butyl 2-(4-ethyl-2-(2-isopropylphenyl)piperazin-1-yl)-7-azaspiro[3.5]nonane-7-carboxylate (1.1 g, crude) was obtained as a colorless oil. MS (ESI, m/e) [M+1]$^+$456.3.

Step 5: 2-(4-ethyl-2-(2-isopropylphenyl)piperazin-1-yl)-7-azaspiro[3.5]nonane.

A mixture of tert-butyl 2-(4-ethyl-2-(2-isopropylphenyl)piperazin-1-yl)-7-azaspiro[3.5]nonane-7-carboxylate (1.1 g, 2.41 mmol) in DCM (5 mL) and TFA (5 mL) was stirred at 25° C. for 1 hr. The reaction mixture was concentrated under reduced pressure. The residue was purified by prep-HPLC (TFA condition) according to HPLC. The residue was diluted with H$_2$O (10 mL) and added Na$_2$CO$_3$ to pH=9. The mixture was extracted with EtOAc (10 mL×3). The combined organic layers were washed with brine, dried over Na$_2$SO$_4$, filtered and concentrated under reduced pressure. The compound 2-(4-ethyl-2-(2-isopropylphenyl)piperazin-1-yl)-7-azaspiro[3.5]nonane (440 mg, yield: 51%) was obtained as a yellow oil. $^1$H NMR (400 MHz, CDCl$_3$) δ ppm: 7.50 (m, 1H), 7.26-7.20 (m, 2H), 7.16-7.10 (m, 1H), 3.66 (m, 2H), 3.45-3.35 (m, 1H), 3.01 (t, 2H), 2.94-2.88 (m, 1H), 2.75-2.61 (m, 5H), 2.46-2.38 (m, 2H), 2.35-2.21 (m, 2H), 2.11 (t, 1 H), 1.79 (m, 1H), 1.74-1.65 (m, 1H), 1.49-1.37 (m, 4H), 1.32 (m, 1H), 1.24 (d, J=6.8 Hz, 3H), 1.20 (d, J=6.8 Hz, 3H), 1.10-1.05 (m, 3H). MS (ESI, m/e) [M+1]$^+$356.2.

Intermediate 4-1: 2-(4-cyclopropyl-2-(2-isopropylphenyl)piperazin-1-yl)-7-azaspiro[3.5]nonane

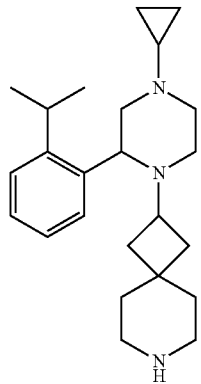

Intermediate 4-1

Step 1: tert-butyl 2-(4-cyclopropyl-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.5 g, 3.4 mmol) in MeOH (20 mL) was added (1-ethoxy-cyclopropoxy)trimethylsilane (2.96 g, 17 mmol), HOAc (1.43 g, 23.8 mmol), 4A MS (500 mg) and NaBH$_3$CN (641 mg, 10.2 mmol). The mixture was stirred at 25° C. for 12 hrs. The mixture was poured into aqueous NaHCO$_3$ (20 mL), extracted with EtOAc (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=20/1 to 10/1) to give tert-butyl 2-(4-cyclopropyl-2-(2-isopropylphenyl)-6-oxopiperazin-1-yl)-7-azaspiro[3.5]nonane-7-carboxylate (1.1 g, yield: 70%) as yellow oil. $^1$H NMR (400 MHz, CDCl$_3$) δ ppm: 7.31-7.28 (m, 1H), 7.26-7.22 (m, 1H), 7.11 (m, 1H), 6.99 (d, J=8.0 Hz, 1H), 4.99 (br t, 1H), 4.26-4.14 (m, 1H), 3.49-3.42 (m, 1H), 3.38-3.32 (m, 1H), 3.39-3.31 (m, 1H), 3.30-3.12 (m, 6H), 3.07 (m, 1H), 2.71 (m, 1H), 2.20 (br s, 1H), 1.98 (br t, 1H), 1.84 (br s, 1H), 1.64 (m, 2H), 1.41 (s, 9H), 1.39-1.32 (m, 3H), 1.29 (m, 6H), 0.45-0.39 (m, 1H), 0.34 (m, 2H), −0.01 (br s, 1H).

Step 2: tert-butyl 2-(4-cyclopropyl-2-(2-isopropylphenyl)piperazin-1-yl)-7-azaspiro[3.5]nonane-7-carboxylate.

The mixture of tert-butyl 2-(4-cyclopropyl-2-(2-isopropylphenyl)-6-oxopiperazin-1-yl)-7-azaspiro[3.5]nonane-7-carboxylate (1.1 g, 2.28 mmol) and BH$_3$·THF (10 mL, 10 mmol) was heated to 70° C. for 12 hrs. After cooling to 0° C., the mixture was quenched with MeOH (10 mL) carefully. The mixture was concentrated in vacuum to give tert-butyl 2-(4-cyclopropyl-2-(2-isopropylphenyl)piperazin-1-yl)-7-azaspiro[3.5]nonane-7-carboxylate (0.8 g, yield: 80%) as yellow oil, which was used into the next step without further purification. MS (ESI, m/e) [M+1]$^+$468.4.

Step 3: 2-(4-cyclopropyl-2-(2-isopropylphenyl)piperazin-1-yl)-7-azaspiro[3.5]nonane.

To a solution of tert-butyl 2-(4-cyclopropyl-2-(2-isopropylphenyl)piperazin-1-yl)-7-azaspiro[3.5]nonane-7-carboxylate (800 mg, 1.7 mmol) in DCM (30 mL) was added TFA (10 mL). The mixture was stirred at 25° C. for 2 hrs. After concentrating under reduced pressure, the residue was dissolved into water (20 mL). Then the mixture was extracted with EtOAc (20 mL×3). The combined organic phases were washed with brine (20 mL×2), dried with anhydrous Na$_2$SO$_4$, filtered and concentrated in vacuum to give 2-(4-cyclopropyl-2-(2-isopropylphenyl)piperazin-1-yl)-7-azaspiro[3.5]nonane (405 mg, yield: 64%) as yellow solid. $^1$H NMR (400 MHz, CDCl$_3$) δ ppm: 7.52 (br s, 1H), 7.26-7.19 (m, 2H), 7.16-7.11 (m, 1H), 3.57 (m, 1H), 3.38 (m, 1H), 3.03 (br t, 2H), 2.94-2.87 (m, 1H), 2.81 (m, 1H), 2.67-2.58 (m, 4H), 2.56-2.48 (m, 1H), 2.39 (br t, 1H), 2.22 (br t, 1H), 1.93 (br s, 1H), 1.75 (br s, 1H), 1.68 (m, 1H), 1.64-1.60 (m, 1H), 1.42-1.28 (m, 6H), 1.24 (m, 3H), 1.20 (m, 3H), 0.44 (m, 2H), 0.41 (m, 2H). MS (ESI, m/e) [M+1]$^+$368.3

Intermediate 5-1: 2-(4-cyclobutyl-2-(2-isopropylphenyl)piperazin-1-yl)-7-azaspiro[3.5]nonane

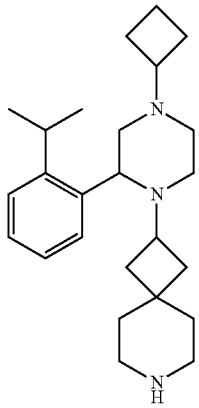

Intermediate 5-1

Step 1: tert-butyl 2-(4-cyclobutyl-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added cyclobutanone (0.24 g, 3.40 mmol) and HOAc (0.27 g, 4.52 mmol). After stirred at 25° C. for 1 hr, then NaBH(OAc)$_3$ (0.96 g, 4.52 mmol) was added. The mixture was stirred at 25° C. for 12 hrs. Then aqueous NH$_4$Cl (20 mL) was added to the mixture, and then the mixture was extracted with DCM (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=5/1) to give tert-butyl 2-(4-cyclobutyl-2-(2-isopropylphenyl)-6-oxopiperazin-1-yl)-7-azaspiro[3.5]nonane-7-carboxylate (0.85 g, yield: 76%) as a yellow solid. $^1$H NMR (400 MHz, CDCl$_3$) δ ppm: 7.33-7.27 (m, 2H), 7.19-7.14 (m, 1H), 7.08 (m, 1H), 5.05 (m, 1H), 3.29-3.10 (m, 8H), 2.81-2.72 (m, 2H), 2.35 (m, 1H), 2.25-2.19 (m, 1H), 2.04-1.75 (m, 6H), 1.68-1.52 (m, 5H), 1.41 (s, 9H), 1.38-1.35 (m, 2H), 1.29 (d, J=6.8 Hz, 3H), 1.27-1.25 (m, 3H).

Step 2: tert-butyl 2-(4-cyclobutyl-2-(2-isopropylphenyl)piperazin-1-yl)-7-azaspiro[3.5]nonane-7-carboxylate.

The mixture of tert-butyl 2-(4-cyclobutyl-2-(2-isopropylphenyl)-6-oxopiperazin-1-yl)-7-azaspiro[3.5]nonane-7-carboxylate (850 mg, 1.71 mmol) and BH$_3$·THF (20 mL, 17.1 mmol) was heated to 70° C. for 12 hrs. Then MeCOH (10 mL) was added to the mixture carefully, and concentrated in vacuum to give tert-butyl 2-(4-cyclobutyl-2-(2-isopropylphenyl)piperazin-1-yl)-7-azaspiro[3.5]nonane-7-carboxylate (800 mg, yield: 97%) was obtained as yellow oil, which was used directly without further purification. MS (ESI, m/e) [M+1]$^+$482.4.

Step 3: 2-(4-cyclobutyl-2-(2-isopropylphenyl)piperazin-1-yl)-7-azaspiro[3.5]nonane.

To a solution of tert-butyl 2-(4-cyclobutyl-2-(2-isopropylphenyl)piperazin-1-yl)-7-azaspiro[3.5]nonane-7-carboxylate (700 mg, 1.45 mmol) in MeOH (20 mL) was added HCl/MeOH (10 mL). The mixture was stirred at 25° C. for 1 hr. The mixture was concentrated in vacuum under reduced pressure to give 2-(4-cyclobutyl-2-(2-isopropylphenyl)piperazin-1-yl)-7-azaspiro[3.5]nonane (400 mg, yield: 83%) as a yellow solid. $^1$H NMR (400 MHz, CDCl$_3$) δ ppm: 8.84 (m, 2H), 8.11 (br s, 1H), 7.45 (m, 2H), 7.31 (m, 1H), 5.32 (br s, 1H), 3.60-3.48 (m, 4H), 3.38 (m, 4H), 2.84-2.75 (m, 4H), 2.44-2.34 (m, 3H), 2.24-2.13 (m, 4H), 1.77-1.60 (m, 5H), 1.52 (br s, 2H), 1.44-1.41 (m, 2H), 1.29 (d, J=6.8 Hz, 3H), 1.18 (d, J=6.8 Hz, 3H). MS (ESI, m/e) [M+1]$^+$ 382.4.

Intermediate 6-1: 2-(2-(2-isopropylphenyl)-4-(oxetan-3-yl)piperazin-1-yl)-7-azaspiro[3.5]nonane

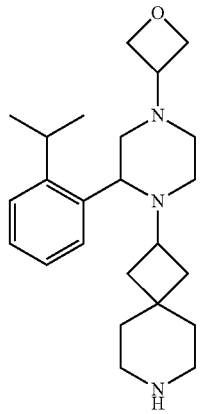

Intermediate 6-1

Step 1: tert-butyl 2-(2-(2-isopropylphenyl)piperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (3.6 g, 8.15 mmol) in BH$_3$·THF (40 mL) was stirred at 70° C. for 12 hrs. The reaction mixture was quenched by MeOH (40 mL) at 0° C. and stirred at 25° C. for 30 min. The mixture was concentrated to give tert-butyl 2-(2-(2-isopropylphenyl)piperazin-1-yl)-7-azaspiro[3.5]nonane-7-carboxylate (3.6 g, crude) as a white solid. MS (ESI, m/e) [M+1]$^+$428.3.

Step 2: tert-butyl 2-(2-(2-isopropylphenyl)-4-(oxetan-3-yl)piperazin-1-yl)-7-azaspiro[3.5]nonane-7-carboxylate.

To a solution of tert-butyl 2-(2-(2-isopropylphenyl)piperazin-1-yl)-7-azaspiro[3.5]nonane-7-carboxylate (1.0 g, 2.34 mmol) and oxetan-3-one (219.08 mg, 3.04 mmol) in MeOH (20 mL) was added NaBH$_3$CN (191.04 mg, 3.04 mmol). The mixture was stirred at 45° C. for 36 hrs. The reaction mixture was diluted with aqueous Na$_2$CO$_3$ (40 mL) and extracted with EtOAc (40 mL×3). The combined organic layers were dried over Na$_2$SO$_4$, filtered and concentrated under reduced pressure. The residue was purified by MPLC. The compound tert-butyl 2-(2-(2-isopropylphenyl)-4-(oxetan-3-yl)piperazin-1-yl)-7-azaspiro[3.5]nonane-7-carboxylate (420 mg, yield: 37%) was obtained as a yellow oil. MS (ESI, m/e) [M+1]$^+$484.3.

Step 3: 2-(2-(2-isopropylphenyl)-4-(oxetan-3-yl)piperazin-1-yl)-7-azaspiro[3.5]nonane.

A mixture of tert-butyl 2-(2-(2-isopropylphenyl)-4-(oxetan-3-yl)piperazin-1-yl)-7-azaspiro[3.5]nonane-7-carboxylate (420 mg, 868.33 umol) in DCM (3 mL) and TFA (1 mL) was stirred at 25° C. for 2 hrs. The reaction mixture was concentrated under reduced pressure. The residue was purified by prep-HPLC (TFA condition) according to HPLC. The residue was dilute with H$_2$O (5 mL) and added Na$_2$CO$_3$ to pH=9 and extracted with EtOAc (5 mL×3). The combined organic layers were dried over Na$_2$SO$_4$, filtered and concentrated under reduced pressure to give 2-(2-(2-isopropylphenyl)-4-(oxetan-3-yl)piperazin-1-yl)-7-azaspiro[3.5]nonane (203 mg, yield: 61%) as a yellow oil. $^1$H NMR (400 MHz, CDCl$_3$) δ ppm: 7.52-7.41 (m, 1H), 7.27-7.19 (m, 2H), 7.16-7.11 (m, 1H), 4.71-4.62 (m, 2H), 4.62-4.55 (m, 2H), 3.75-3.63 (m, 1H), 3.53-3.45 (m, 11H), 3.44-3.35 (m, 1H), 3.11-3.02 (m, 1H), 2.98-2.89 (m, 1H), 2.84 (m, 1H), 2.72-2.57 (m, 4H), 2.53 (m, 1 H), 2.33 (m, 1H), 2.25-2.16 (m, 1H), 2.10-2.04 (m, 11H), 1.92-1.75 (m, 4H), 1.72-1.63 (m, 1H), 1.44-1.31 (m, 4H), 1.27 (d, J=6.8 Hz, 3H), 1.21 (d, J=6.8 Hz, 3H). MS (ESI, m/e) [M+1]$^+$384.2.

Intermediate 6-1a: 2-(2-(2-isopropylphenyl)-4-(oxetan-3-yl)piperazin-1-yl)-7-azaspiro[3.5]nonane was purification by SFC (Instrument: Waters SFC 80 preparative SFC; Column: Chiralcel OD, 250×30 mm i.d. 10 um; Mobile phase: A for C02 and B for MeOH (0.1% NH$_3$·H$_2$O); Gradient: B%=30% isocratic mode; Flow rate: 60 g/min; Wavelength: 220 nm; Column temperature: 40° C.; System back pressure: 100 bar).

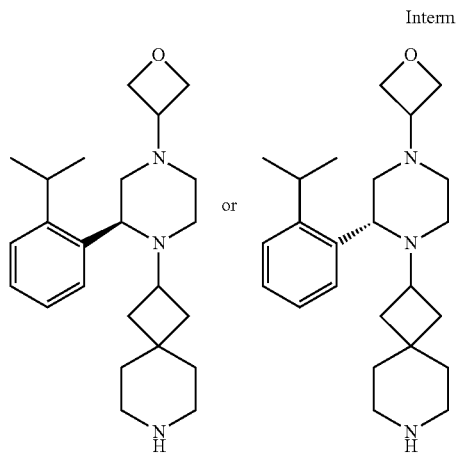

Intermediate 6-1a (R or S)-2-(2-(2-isopropylphenyl)-4-(oxetan-3-yl)piperazin-1-yl)-7-azaspiro[3.5]nonane (728 mg, retention time: 1.40 min ) was obtained, yield: 32.1%. $^1$H NMR (400 MHz, CDCl$_3$) δ ppm: 7.45 (d, J=6.0 Hz, 1H), 7.27-7.19 (m, 2H), 7.16-7.08 (m, 1H), 6.45-6.05 (m, 1H), 4.72-4.62 (m, 2H), 4.61-4.52 (m, 2H), 3.68 (d, J=9.0 Hz, 1H), 3.48 (m, 1H), 3.37 (s, 1H), 3.01 (d, J=11.2 Hz, 1H), 2.97-2.68 (m, 6H), 2.53 (d, J=11.2 Hz, 1H), 2.35-2.25 (m, 1H), 2.24-2.13 (m, 1H), 2.05 (t, J=10.6 Hz, 1H), 1.82 (d, J=3.4 Hz, 1H), 1.76-1.68 (m, 1H), 1.65-1.45 (m, 4H), 1.38-1.29 (m, 1H), 1.25 (d, J=6.8 Hz, 3H), 1.20 (d, J=6.3 Hz, 3H), 1.15 (d, J=5.1 Hz, 1H). MS (ESI, m/e) [M+1]$^+$384.2.

Intermediate 6-1b: (S or R)-2-(2-(2-isopropylphenyl)-4-(oxetan-3-yl)piperazin-1-yl)-7-azaspiro[3.5]nonane (649 mg, retention time: 1.51 min, yield: 28.6%) was obtained. MS (ESI, m/e) [M+1]$^+$384.2

Intermediate 7-1: 2-(4-cyclopentyl-2-(2-isopropylphenyl)piperazin-1-yl)-7-azaspiro[3.5]nonane

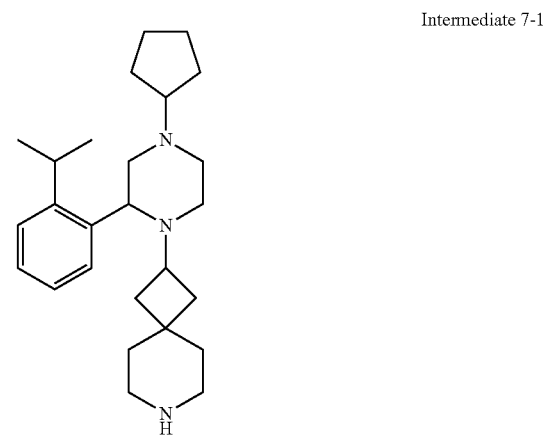 [SMILES: CC(C)c1ccccc1C1CN(C2CCCC2)CCN1C1CC2(CCNCC2)C1]

Intermediate 7-1

Step 1: tert-butyl 2-(4-cyclopentyl-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (15 mL) was added cyclopentanone (285.7 mg, 3.40 mmol) and AcOH (272.0 mg, 5.57 mmol) at 25° C. for 30 min, then NaBH(OAc)$_3$ (1.44 g, 6.79 mmol) was added at 25° C. The mixture was stirred at 25° C. for 12 hrs. The reaction mixture was poured into aq. NaHCO$_3$ (50 mL), extracted with DCM (50 mL×2). The combined organic layers were washed with brine, dried over Na$_2$SO$_4$, filtered and concentrated under reduced pressure. The residue was purified by column chromatography (silica gel, eluent: PE/EA (v/v)=10/1 to 0/1) to give tert-butyl 2-(4-cyclopentyl-2-(2-isopropylphenyl)-6-oxopiperazin-1-yl)-7-azaspiro[3.5]nonane-7-carboxylate (1.0 g, 1.96 mmol, yield: 86%) as a yellow oil. $^1$H NMR (400 MHz, CDCl$_3$) δ ppm: 7.33-7.28 (m, 1H), 7.25 (br s, 1H), 7.16 (m, 1H), 7.09 (s, 1H), 5.06 (br s, 1H), 3.37-3.08 (m, 7H), 3.00-2.89 (m, 1H), 2.58-2.43 (m, 2H), 2.27-2.18 (m, 1H), 2.04-1.95 (m, 1H), 1.94-1.83 (m, 1H), 1.74 (br s, 2H), 1.67-1.46 (m, 8H), 1.42 (s, 9H), 1.40-1.31 (m, 4H), 1.31-1.26 (m, 7H), 1.25-1.09 (m, 2H).

Step 2: tert-butyl 2-(4-cyclopentyl-2-(2-isopropylphenyl)piperazin-1-yl)-7-azaspiro[3.5]nonane-7-carboxylate.

To a mixture of tert-butyl 2-(4-cyclopentyl-2-(2-isopropylphenyl)-6-oxopiperazin-1-yl)-7-azaspiro[3.5]nonane-7-carboxylate (1.0 g, 1.96 mmol) in THF (10 mL) was added BH$_3$·THF (20 mL, 1 M) at 25° C. The mixture was stirred at 70° C. for 12 hrs. The reaction mixture was cooled to 0-5° C. Then MeOH (10 mL) was added dropwise at 5° C. to quench the reaction. The mixture was concentrated under reduced pressure to give tert-butyl 2-(4-cyclopentyl-2-(2-isopropylphenyl)piperazin-1-yl)-7-azaspiro[3.5]nonane-7-carboxylate (1.0 g, crude) as a white solid, which was used directly for next step without further reaction. MS (ESI, m/e) [M+1]$^+$496.5

Step 3: 2-(4-cyclopentyl-2-(2-isopropylphenyl)piperazin-1-yl)-7-azaspiro[3.5]nonane.

To a solution of tert-butyl 2-(4-cyclopentyl-2-(2-isopropylphenyl)piperazin-1-yl)-7-azaspiro[3.5]nonane-7-carboxylate (1.0 g, 2.02 mmol) in MeOH (5 mL) was added HCl/MeOH (10 mL, 4 M) at 25° C. The mixture was stirred at 25° C. for 1 hr. The reaction mixture was concentrated to remove most of MeOH. Then HCl/H$_2$O (1M) solution was added to adjust the pH =2-3, extracted with EtOAc (10 mL). The aqueous phase was added sat. Na$_2$CO$_3$ to pH=9-10, extracted with EtOAc (20 mL×3). The combined organic layers were washed with brine, dried over Na$_2$SO$_4$, filtered and concentrated under reduced pressure to give 2-(4-cyclopentyl-2-(2-isopropylphenyl)piperazin-1-yl)-7-azaspiro[3.5]nonane (577 mg, 1.46 mmol, yield: 72%) as a yellow oil. $^1$H NMR (400 MHz, CDC$_3$) δ ppm: 7.52 (br d, J=7.2 Hz, 1 H), 7.26-7.10 (m, 3H), 3.67 (in, 1H), 348-3.33 (m, 1H), 3.05 (m, 2H), 2.96-2.86 (m, 1H), 2.78 (m, 1H), 2.69-2.57 (m, 4H), 2.48 (m, 1H), 2.36-2.24 (m, 2H), 2.18-2.10 (m, 2H), 1.91-1.85 (m, 1H), 1.77 (m, 2H), 1.72-1.63 (m, 3H), 1.57-1.49 (m, 2H), 1.49-1.29 (m, 8H), 1.25 (d, J=6.8 Hz, 3H), 1.20 (d, J=6.8 Hz, 3H). MS (ESI, m/e) [M+1]$^+$396.4.

Intermediate 8-1: 2-(2-(2-isopropylphenyl)-4-(tetrahydrofuran-3-yl)piperazin-1-yl)-7-azaspiro[3.5]nonane

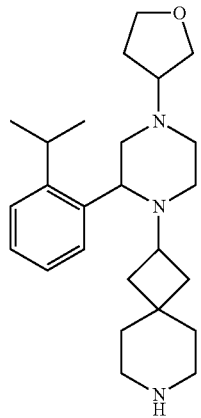

Intermediate 8-1

Step 1: tert-butyl 2-(2-(2-isopropylphenyl)-6-oxo-4-(tetrahydrofuran-3-yl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) and dihydrofuran-3(2H)-one (292.4 mg, 3.40 mmol) in DCE (10 mL) was added HOAc (271.9 mg, 4.53 mmol). The solution was stirred at 25° C. for 5 min and added NaBH(OAc)$_3$ (1.06 g, 4.98 mmol). The solution was stirred at 25° C. for 12 hrs. The reaction was added aqueous NaHCO$_3$ to pH=7, extracted with DCM (10 mL×3).

The combined organic layers were dried over Na$_2$SO$_4$, filtered and evaporated under reduced pressure. The residue was purified by column chromatography (silica gel, eluent: PE/EA (v/v)=10/1 to 1/1) to give tert-butyl 2-(2-(2-isopropylphenyl)-6-oxo-4-(tetrahydrofuran-3-yl)piperazin-1-yl)-7-azaspiro[3.5]nonane-7-carboxylate (1.0 g, yield: 86.3%) as yellow oil.

Step 2: tert-butyl 2-(2-(2-isopropylphenyl)-4-(tetrahydrofuran-3-yl)piperazin-1-yl)-7-azaspiro[3.5]nonane-7-carboxylate.

To a solution of tert-butyl 2-(2-(2-isopropylphenyl)-6-oxo-4-(tetrahydrofuran-3-yl)piperazin-1-yl)-7-azaspiro[3.5]nonane-7-carboxylate (1.0 g, 1.95 mmol) in THF (15 mL) was added BH$_3$·THF (15 mL). The solution was stirred at 70° C. for 12 hrs. After cooling to room temperature, MeOH (10 mL) was added to quench the reaction. The reaction was evaporated under reduced pressure to give tert-butyl 2-(2-(2-isopropylphenyl)-4-(tetrahydrofuran-3-yl)piperazin-1-yl)-7-azaspiro[3.5]nonane-7-carboxylate (700 mg, crude) as a white solid, which was used directly without further purification. MS (ESI, m/e) [M+1]$^+$498.4.

Step 3: 2-(2-(2-isopropylphenyl)-4-(tetrahydrofuran-3-yl)piperazin-1-yl)-7-azaspiro[3.5]nonane.

To a solution of tert-butyl 2-(2-(2-isopropylphenyl)-4-(tetrahydrofuran-3-yl)piperazin-1-yl)-7-azaspiro[3.5]nonane-7-carboxylate (0.7 g, 1.41 mmol) in DCM (10 mL) was added TFA (5 mL). Then the solution was stirred at 25° C. for 2 hrs. The mixture was poured into aqueous NaHCO$_3$ to adjust the pH=7, extracted with DCM (10 mL×3). The combined organic phases were dried over Na$_2$SO$_4$, filtered and evaporated under reduced pressure to give 2-(2-(2-isopropylphenyl)-4-(tetrahydrofuran-3-yl)piperazin-1-yl)-7-azaspiro[3.5]nonane (342 mg) as a yellow oil. $^1$H NMR (400 MHz, CDCl$_3$) b ppm: 7.50 (s, 1H), 7.28-7.14 (m, 4H), 3.93-3.66 (m, 5H), 3.03-2.64 (m, 4H), 2.64-2.85 (m, 5H), 2.77-2.46 (m, 3H), 2.17-1.66 (m, 7H), 1.45-1.36 (m, 4H), 1.20-1.36 (m, 3H). MS (ESI, m/e) [M+1]$^+$398.3.

Intermediate 9-1: 2-(4-cyclohexyl-2-(2-isopropylphenyl)piperazin-1-yl)-7-azaspiro[3.5]nonane

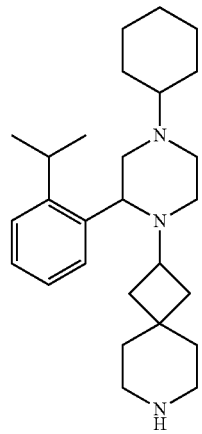

Intermediate 9-1

Step 1: tert-butyl 2-(4-cyclohexyl-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added cyclohexanone (0.34 g, 3.40 mmol) and HOAc (0.27 g, 4.52 mmol). After stirred at 25° C. for 1 hr, then NaBH(OAc)$_3$ (0.96 g, 4.52 mmol) was added. The mixture was stirred at 25° C. for 12 hrs. Then aqueous NH$_4$Cl (20 mL) was added to the mixture, and then the mixture was extracted with DCM (20 mL×3). The combined organic phase was washed with brine (20 mL×2), dried with anhydrous Na$_2$SO$_4$, filtered and concentrated in vacuum. The residue was purified by column chromatography (silica gel, eluent: PE/EA (v/v)=5/1) to give tert-butyl 2-(4-cyclohexyl-2-(2-isopropylphenyl)-6-oxopiperazin-1-yl)-7-azaspiro[3.5]nonane-7-carboxylate (750 mg, yield: 63%) was obtained as yellow solid. $^1$H NMR (400 MHz, CDCl$_3$) δ ppm: 7.32-7.28 (m, 1H), 7.25 (br s, 1H), 7.14 (t, 1H), 7.09-7.06 (m, 1H), 5.01 (br s, 1H), 4.26-4.15 (m, 1H), 3.38 (m, 2H), 3.26-3.13 (m, 6H), 2.95 (m, 1H), 2.62 (m, 1H), 2.20 (br s, 2H), 1.98 (br s, 1H), 1.84 (br s, 1H), 1.68 (br s, 3H), 1.61 (br s, 6H), 1.42 (s, 10H), 1.35 (m, 2H), 1.31-1.28 (m, 6H), 1.12 (br s, 2H).

Step 2: tert-butyl 2-(4-cyclohexyl-2-(2-isopropylphenyl)piperazin-1-yl)-7-azaspiro[3.5]nonane-7-carboxylate.

The mixture of tert-butyl 2-(4-cyclohexyl-2-(2-isopropylphenyl)-6-oxopiperazin-1-yl)-7-azaspiro[3.5]nonane-7-carboxylate (0.75 g, 1.43 mmol) and BH$_3$·THF (14 mL, 14.3 mmol) was heated to 70° C. for 12 hrs. Then MeOH (10 mL) was added to the mixture carefully and concentrated in vacuum to give tert-butyl 2-(4-cyclohexyl-2-(2-isopropylphenyl)piperazin-1-yl)-7-azaspiro[3.5]nonane-7-carboxylate (0.7 g, yield: 96%) as a yellow oil, , which was used directly without further purification. MS (ESI, m/e) [M+1]$^+$ 510.4.

Step 3: 2-(4-cyclohexyl-2-(2-isopropylphenyl)piperazin-1-yl)-7-azaspiro[3.5]nonane.

To a solution of tert-butyl 2-(4-cyclohexyl-2-(2-isopropylphenyl)piperazin-1-yl)-7-azaspiro[3.5]nonane-7-carboxylate (700 mg, 1.37 mmol,) in MeOH (20 mL) was added HCl/MeOH solution (10 mL). The mixture was stirred at 25° C. for 1 hr. After removed the solvent, the residue was dissolved into water (20 mL). The mixture was adjusted the pH=9-10 using aqueous Na$_2$CO$_3$. The mixture was extracted with EtOAc (20 mL×3). The combined organic phases were washed with brine (20 mL×2), dried with anhydrous Na$_2$SO$_4$, filtered and concentrated in vacuum to give 2-(4-cyclohexyl-2-(2-isopropylphenyl)piperazin-1-yl)-7-azaspiro[3.5]nonane (380 mg, yield: 68%) as a yellow solid. $^1$H NMR (400 MHz, CDCl$_3$) δ ppm: 7.50 (m, 1H), 7.26-7.19 (m, 2H), 7.15-7.11 (m, 1H), 3.61 (br d, J=8.4 Hz, 1H), 3.40 (br s, 1H), 3.05 (m, 1H), 2.97 (m, 1H), 2.93-2.87 (m, 1H), 2.75-2.56 (m, 6H), 2.50 (m, 1H), 2.36-2.18 (m, 5H), 1.89 (br s, 2H), 1.76 (br s, 3H), 1.69 (m, 1H), 1.60 (m, 1H), 1.39-1.30 (m, 5H), 1.25 (m, 3H), 1.20 (m, 7H). MS (ESI, m/e) [M+1]+410.4.

Intermediate 10-1: 2-(2-(2-isopropylphenyl)-4-(tetrahydro-2H-pyran-4-yl)piperazin-1-yl)-7-azaspiro[3.5]nonane

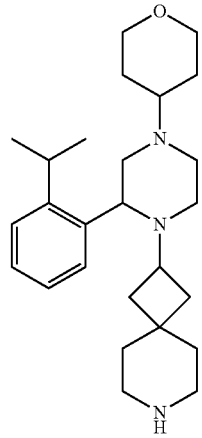

Intermediate 10-1

Step 1: tert-butyl 2-(2-(2-isopropylphenyl)-6-oxo-4-(tetrahydro-2H-pyran-4-yl) piperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), dihydro-2H-pyran-4(3H)-one (340.06 mg, 3.40 mmol) and HOAc (271.97 mg, 4.53 mmol) in DCE (20 mL) was stirred at 25° C. for 30 min.

Then NaBH(OAc)$_3$ (1.44 g, 6.79 mmol) was added in portions to the mixture and stirred at 25° C. for 12 hrs. The reaction mixture was poured into ice-water (20 mL), adjust the pH=8 with NaHCO$_3$. The resulting mixture was extracted with DCM (30 mL×3). The combined organic phases were dried with anhydrous Na$_2$SO$_4$, filtered and concentrated. The crude was purified by column chromatography (silica gel, eluent: PE/EA (v/v)=3/1 to 1/1) to give tert-butyl 2-(2-(2-isopropylphenyl)-6-oxo-4-(tetrahydro-2H-pyran-4-yl)piperazin-1-yl)-7-azaspiro[3.5]nonane-7-carboxylate (1.05 g, yield: 88%) as a yellow solid. $^1$H NMR (400 MHz, CDCl$_3$) δ ppm: 7.30 (m, 1H), 7.14 (m, 1H), 7.09-7.01 (m, 1H), 5.02 (m, 1 H), 4.25 (s, 1H), 3.95-3.81 (m, 2H), 3.54-3.04 (m, 10H), 2.98-2.93 (m, 1H), 2.70-2.65 (m, 1H), 2.45-2.34 (m, 1H), 2.26-2.17 (m, 1H), 1.97 (m, 1H), 1.82 (s, 1H), 1.66-1.59 (m, 2H), 1.57-1.52 (m, 1H), 1.46-1.40 (m, 12H), 1.37-1.33 (m, 2H), 1.32-1.27 (m, 6H).

Step 2: tert-butyl 2-(2-(2-isopropylphenyl)-4-(tetrahydro-2H-pyran-4-yl)piperazin-1-yl)-7-azaspiro[3.5]nonane-7-carboxylate To a solution of tert-butyl 2-(2-(2-isopropylphenyl)-6-oxo-4-(tetrahydro-2H-pyran-4-yl)piperazin-1-yl)-7-azaspiro[3.5]nonane-7-carboxylate (900 mg, 1.71 mmol) in THF (15 mL) was added BH$_3$·THF (30 mL, 30 mmol) dropwise at 20° C. The mixture was heated to 70° C. for 20 hrs. The reaction was quenched by ethanol (5 mL), concentrated in vacuum to give tert-butyl 2-(2-(2-isopropylphenyl)-4-(tetrahydro-2H-pyran-4-yl)piperazin-1-yl)-7-azaspiro[3.5]nonane-7-carboxylate (876 mg, crude) as a colorless oil, which was used directly for next step without further purification. MS (ESI, m/e) [M+1]$^+$512.4.

Step 3: 2-(2-(2-isopropylphenyl)-4-(tetrahydro-2H-pyran-4-yl)piperazin-1-yl)-7-azaspiro[3.5]nonane.

To a solution of tert-butyl 2-(2-(2-isopropylphenyl)-4-(tetrahydro-2H-pyran-4-yl)piperazin-1-yl)-7-azaspiro[3.5]nonane-7-carboxylate (900 mg, 1.76 mmol) in MeOH (2 mL) was added HCl/MeOH solution (20 mL, 4M). The solution was stirred at 25° C. for 4 hrs. The reaction solution was concentrated in vacuum. The crude was purified by prep-HPLC and lyophilization. The residue was free with sat. NaHCO$_3$ (20 mL), extracted with EtOAc (50 mL×3). The combined organic phases were dried with anhydrous Na$_2$SO$_4$, filtered and concentrated in vacuum to give 2-(2-(2-isopropylphenyl)-4-(tetrahydro-2H-pyran-4-yl)piperazin-1-yl)-7-azaspiro[3.5]nonane (390 mg, yield: 54%) as a white gum. $^1$H NMR (400 MHz, CDCl$_3$) δ ppm: 7.50 (d, J=5.6 Hz, 1H), 7.27-7.20 (m, 2H), 7.17-7.11 (m, 1H), 4.03-4.00 (td, 2H), 3.63 (m, 1H), 3.35-3.25 (m, 3H), 3.13-2.99 (m, 2H), 2.91 (m, 1H), 2.75 (m, 1H), 2.70-2.51 (m, 4H), 2.46-2.33 (m, 2H), 2.33-2.20 (m, 2H), 1.90-1.72 (m, 4H), 1.71-1.63 (m, 1H), 1.65-1.55 (m, 2H), 1.48-1.01 (m, 14H). MS (ESI, m/e) [M+1]412.5.

Intermediate 11-1: 2-(4-isobutyl-2-(2-isopropylphenyl)piperazin-1-yl)-7-azaspiro[3.5]nonane

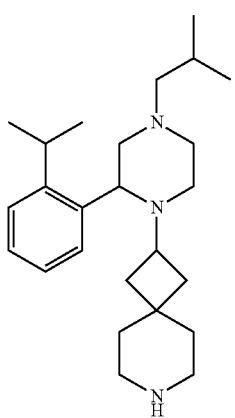

Intermediate 11-1

Step 1: tert-butyl 2-(4-isobutyl-2-(2-isopropylphenyl)-3-oxopiperazin-1-yl)-7-azaspiro[3.5]nonane-7-carboxylate.

To a solution of tert-butyl 2-(2-(2-isopropylphenyl)-3-oxopiperazin-1-yl)-7-azaspiro[3.5]nonane-7-carboxylate (2.0 g, 4.53 mmol) in THF (20 mL) was added NaH (362.28 mg, 9.06 mmol) at 0° C. The mixture was stirred at 0° C. for 10 min. Then 1-iodo-2-methylpropane (1.67 g, 9.06 mmol) was added at 0° C. The mixture was stirred at 65° C. for 48 hr.

The reaction mixture was poured into H$_2$O (20 mL), extracted with EtOAc (20 mL×3). The combined organic layers were washed with brine, dried over Na$_2$SO$_4$, filtered and concentrated under reduced pressure. The residue was purified by MPLC. The compound tert-butyl 2-(4-isobutyl-2-(2-isopropylphenyl)-3-oxopiperazin-1-yl)-7-azaspiro[3.5]nonane-7-carboxylate (1.1 g, 2.21 mmol, yield: 48%) was obtained as a yellow solid $^1$H NMR (400 MHz, CDCl$_3$) δ ppm: 7.27-7.21 (m, 3H), 7.12-7.06 (m, 1H), 4.81 (m, 1H), 4.09 (s, 1H), 3.52-3.39 (m, 2H), 3.29 (m, 1H), 3.27-3.23 (m, 2H), 3.19-3.15 (m, 2H), 3.13 (m, 1H), 2.97 (m, 1H), 2.38 (m, 1H), 1.96-1.88 (m, 1H), 1.71-1.60 (m, 2H), 1.45 (m, 2H), 1.42 (s, 9H), 1.41-1.37 (m, 2H), 1.32 (s, 1H), 1.30 (d, J=6.8 Hz, 3H), 1.18 (d, J=6.8 Hz, 3H), 1.14 (m, 6H).

Step 2: tert-butyl 2-(4-isobutyl-2-(2-isopropylphenyl)piperazin-1-yl)-7-azaspiro[3.5]nonane-7-carboxylate.

A mixture of tert-butyl 2-(4-isobutyl-2-(2-isopropylphenyl)-3-oxopiperazin-1-yl)-7-azaspiro[3.5]nonane-7-carboxylate (1.1 g, 2.21 mmol) in BH$_3$·THF (10 mL) was stirred at 70° C. for 12 hrs. The reaction mixture was quenched by MeOH (5 mL) at 0° C. and stirred at 25° C. for 30 min. Then the mixture was concentrated under reduced pressure to afford tert-butyl 2-(4-isobutyl-2-(2-isopropylphenyl)piperazin-1-yl)-7-azaspiro[3.5]nonane-7-carboxylate (1.05 g, crude) as a colorless oil. MS (ESI, m/e) [M+1]$^+$484.3.

Step 3: 2-(4-isobutyl-2-(2-isopropylphenyl)piperazin-1-yl)-7-azaspiro[3.5]nonane.

A mixture of tert-butyl 2-(4-isobutyl-2-(2-isopropylphenyl)piperazin-1-yl)-7-azaspiro[3.5]nonane-7-carboxylate (1.05 g, 2.17 mmol) in HCl/EtOAc (10 mL) was stirred at 25° C. for 2 hrs. The reaction mixture was concentrated under reduced pressure. The residue was purified by prep-HPLC (HCl condition) according to HPLC. The residue was dilute with H$_2$O (10 mL) and added Na$_2$CO$_3$ to pH=9. The mixture was extracted with EtOAc (10 mL×3). The combined organic layers were washed with brine, dried over Na$_2$SO$_4$, filtered and concentrated under reduced pressure. The compound 2-(4-isobutyl-2-(2-isopropylphenyl)piperazin-1-yl)-7-azaspiro[3.5]nonane (461 mg, 1.18 mmol, yield: 54.26%) was obtained as a yellow oil. $^1$H NMR (400 MHz, CDCl$_3$) δ ppm: 7.50 (d, J=4.5 Hz, 1H), 7.27-7.19 (m, 2H), 7.16-7.10 (m, 1H), 3.62 (m, 1H), 3.41 (m, 1H), 2.99 (m, 1H), 2.95-2.85 (m, 2H), 2.71-2.54 (m, 5H), 2.34-2.19 (m, 2H), 2.14-2.04 (m, 3H), 1.85 (s, 2H), 1.80-1.72 (m, 2H), 1.72-1.64 (m, 1H), 1.43-1.29 (m, 5H), 1.27 (d, J=6.8 Hz, 3H), 1.21 (d, J=6.8 Hz, 3H), 0.88 (m, 6H). MS (ESI, m/e) [M+1]$^+$384.4.

Intermediate 12-1: 2-(2-(2-isopropylphenyl)-4-neopentylpiperazin-1-yl)-7-azaspiro[3.5]nonane

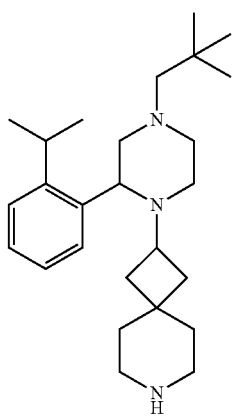

Intermediate 12-1

Step 1: 2-isopropylbenzaldehyde.

To a solution of 1-bromo-2-isopropylbenzene (20 g, 0.1 mol) in THF (200 mL) was added n-BuLi (44 mL, 0.11 mol, 2.5 M in hexane) dropwise at −78° C. After stirring for 1 hr at −78° C., DMF (8.0 g, 0.11 mol) was added to the mixture. The mixture was stirred at −60° C. for 1 hr. Then aqueous NH$_4$Cl (1M, 100 mL) was added to the mixture. The mixture was extracted with EtOAc (300 mL×3). The combined organic phases were washed with brine (100 mL×2), dried with anhydrous Na₂SO₄, filtered and concentrated in vacuum. The residue was purified by column chromatography (silica gel, eluent: PE). The compound 2-isopropylbenzaldehyde (14 g, yield: 94%) was obtained as a yellow oil. $^1$H NMR (400 MHz, CDCl₃) δ ppm: 10.38 (s, 1H), 7.83 (dd, J=8.0 Hz, 1.6 Hz, 1H), 7.60-7.53 (m, 1H), 7.49-7.45 (m, 1H), 7.36 (t, 1H), 3.99 (t, 1H), 1.32 (d, J=6.8 Hz, 6H).

Step 2: (E)-N-(2-isopropylbenzylidene)-2-methylpropane-2-sulfinamide.

To a solution of 2-isopropylbenzaldehyde (20 g, 0.135 mol) in THF (200 mL) was added 2-methylpropane-2-sulfinamide (18 g, 0.148 mmol). After cooling to 0° C., Ti(OEt)₄ (62 g, 0.27 mol) was added. The mixture was stirred at 25° C. for 12 hrs. The reaction mixture was quenched by water (100 mL) carefully, and then filtered through a celite pad. The filtrate was extracted with EtOAc (100 mL×3) and washed with brine (100 mL). The combined organic layers were dried over Na₂SO₄, filtered and concentrated under reduced pressure. The residue was purified by column chromatography (silica gel, eluent: PE/EA (v/v)=100/1 to 20/1).The compound (E)-N-(2-isopropylbenzylidene)-2-methylpropane-2-sulfinamide (32.5 g, yield: 96%) was obtained as a yellow oil. $^1$H NMR (400 MHz, CDCl₃) δ ppm: 9.00 (s, 1H), 7.96 (dd, J=8.0 Hz, 2.0 Hz, 1H), 7.51-7.45 (m, 1H), 7.44-7.40 (m, 1 H), 7.32-7.27 (m, 1H), 3.72 (t, 11H), 1.33-1.25 (m, 15H).

Step 3: N-(1-(2-isopropylphenyl)-2-nitroethyl)-2-methylpropane-2-sulfinamide.

To a solution of (E)-N-(2-isopropylbenzylidene)-2-methylpropane-2-sulfinamide (32 g, 0.13 mol) in THF (300 mL) was added t-BuOK (21 g, 0.19 mol) in several portions at 0° C. After stirring for 1 hr at 0° C., nitromethane (77 g, 1.27 mmol) was added. The mixture was stirred at 25° C. for 12 hrs. Then water (100 mL) was added to the mixture, and then the mixture was extracted EtOAc (100 mL×3). The organic layer was dried, filtered and concentrated under reduced pressure. The residue was purified by column chromatography (silica gel, eluent: PE/EA (v/v)=10/1 to 2/1) to give N-(1-(2-isopropylphenyl)-2-nitroethyl)-2-methylpropane-2-sulfinamide (26.5 g, yield: 67%) as a yellow oil. $^1$H NMR (400 MHz, CDCl₃) δ ppm: 7.40-7.34 (m, 2H), 7.34-7.28 (m, 1H), 7.26-7.21 (m, 1H), 5.53-5.44 (m, 1H), 4.88-4.78 (m, 1H), 4.76-4.65 (m, 1H), 4.30-4.20 (m, 1H), 3.35-3.22 (m, 1H), 1.34-1.26 (m, 6H), 1.27-1.20 (m, 9H)

Step 4: N-(2-amino-1-(2-isopropylphenyl)ethyl)-2-methylpropane-2-sulfinamide

To a solution of N-(1-(2-isopropylphenyl)-2-nitroethyl)-2-methylpropane-2-sulfinamide (23 g, 0.074 mol) in MeOH (200 mL) was added Raney-Ni (5.0 g). The mixture was stirred at 25° C. under H₂ (15 psi) atmosphere for 12 hrs. After filtration through a celite pad, the filtrate was concentrated under reduced pressure to give N-(2-amino-1-(2-isopropylphenyl)ethyl)-2-methylpropane-2-sulfinamide (17.6 g, yield: 84%) as a brown solid, which was used into the next step without further purification. MS (ESI, m/e) [M+1]+283.1.

Step 5: N-(2-((tert-butylsulfinyl)amino)-2-(2-isopropylphenyl)ethyl)-4-methylbenzenesulfonamide.

To a solution of N-(2-amino-1-(2-isopropylphenyl)ethyl)-2-methylpropane-2-sulfinamide (23 g, 0.081 mol) in DCM (300 mL) was added TEA (24.5 g, 0.243 mol). After cooling to 0° C., TsCl (17 g, 0.09 mol) was added in several portions. The mixture was stirred at 25° C. for 2 hrs. Then aqueous NH₄Cl (1M, 100 mL) was added to the mixture, and then the mixture was extracted with DCM (100 mL×3). The combined organic phases were washed with brine (100 mL×2), dried with anhydrous Na₂SO₄, filtered and concentrated in vacuum. The residue was purified by column chromatography (silica gel, eluent: PE/EA (v/v)=20/1 to 5/1) to give N-(2-((tert-butylsulfinyl)amino)-2-(2-isopropylphenyl) ethyl)-4-methylbenzenesulfonamide (23 g, yield: 65%) was obtained as a yellow solid. $^1$H NMR (400 MHz, CDC₃) δ ppm: 7.79 (d, J=8.4 Hz, 2H), 7.32-7.26 (m, 4H), 7.20-7.12 (m, 1H), 4.82-4.69 (m, 1H), 4.25 (br s, 1H), 3.14 (br d, J=7.6 Hz, 4H), 3.07-2.97 (m, 1 H), 2.41 (s, 3H), 1.42 (t, 6H), 1.23 (s, 9H).

Step 6: N-(2-amino-2-(2-isopropylphenyl)ethyl)-4-methylbenzenesulfonamide.

To a solution of N-(2-((tert-butylsulfinyl)amino)-2-(2-isopropylphenyl)ethyl)-4-methylbenzenesulfonamide (5.0 g, 11 mmol) in MeOH (20 mL) was added HCl (gas) in MeOH (10 mL, 4M). The mixture was stirred at 25° C. for 1 hr. The mixture was concentrated under reduced pressure. The residue was dissolved into water (50 mL), and then added aqueous Na₂CO₃ to adjust the pH=9. The mixture was extracted with EtOAc (50 mL×2). The combined organic layers were dried over Na₂SO₄, filtered and concentrated in vacuum to give N-(2-amino-2-(2-isopropylphenyl)ethyl)-4-methylbenzenesulfonamide (3.8 g, yield: 99%) as a yellow oil. $^1$H NMR (400 MHz, CDCl₃) δ ppm: 7.74 (d, J=8.0 Hz, 2H), 7.32-7.23 (m, 5H), 7.21-7.13 (m, 1H), 4.36 (m, 1H), 3.17-3.03 (m, 2H), 2.93 (dd, J=12.8, 8.8 Hz, 1H), 2.43 (s, 3H), 1.21-1.18 (m, 6H).

Step 7: tert-butyl 2-((1-(2-isopropylphenyl)-2-(4-methylphenyl)sulfonamido)ethyl)amino)-7-azaspiro[3.5]nonane-7-carboxylate.

To a solution of N-(2-amino-2-(2-isopropylphenyl)ethyl)-4-methylbenzenesulfonamide (4.0 g, 0.012 mol) in DCE (50 mL) was added tert-butyl 2-oxo-7-azaspiro[3.5]nonane-7-carboxylate (3.2 g, 0.013 mol) and HOAc (1.44 g, 0.024 mol). After stirring at 25° C. for 1 hr, then NaBH(OAc)₃ (5.1 g, 0.024 mol) was added. The mixture was stirred at 25° C. for 12 hrs. Then aqueous NH₄Cl (50 mL) was added to the mixture, extracted with DCM (50 mL×3). The combined organic phases were washed with brine (50 mL×2), dried with anhydrous Na₂SO₄, filtered and concentrated in vacuum. The residue was purified by column chromatography (silica gel, eluent: PE/EA (v/v)=10/1 to 5/1) to give tert-butyl 2-((1-(2-isopropylphenyl)-2-(4-methylphenyl)sulfonamido)ethyl)amino)-7-azaspiro[3.5]nonane-7-carboxylate (4.3 g, yield: 64%) as a yellow solid. $^1$H NMR (400 MHz, CDCl₃) δ ppm: 7.73 (d, J=8.0 Hz, 2H), 7.32-7.25 (m, 4H), 7.19-7.13 (m, 2H), 4.02 (m, 1H), 3.30-3.22 (m, 4H), 3.09-2.98 (m, 3H), 2.88 (m, 1H), 2.43 (s, 3H), 2.02-1.88 (m, 2H), 1.75 (br s, 3H), 1.44 (s, 9H), 1.40 (m, 3H), 1.17 (m, 6H).

Step 8: tert-butyl 2-(2-chloro-N-(1-(2-isopropylphenyl)-2-(4-methylphenyl)sulfonamido)ethyl)acetamido)-7-azaspiro[3.5]nonane-7-carboxylate.

To a solution of tert-butyl 2-((1-(2-isopropylphenyl)-2-(4-methylphenyl)sulfonamido)ethyl)amino)-7-azaspiro[3.5] nonane-7-carboxylate (4.3 g, 7.74 mmol) in THF (50 mL) was added TEA (1.56 g, 15.48 mmol). After cooling to 0° C., 2-chloroacetyl chloride (0.96 g, 8.51 mmol) was added dropwise. The mixture was stirred at 25° C. for 2 hrs. The mixture was poured into aqueous NH₄Cl (1M, 50 mL), extracted with EtOAc (50 mL×3). The combined organic phases were washed with brine (50 mL×2), dried with anhydrous Na₂SO₄, filtered and concentrated in vacuum. The residue was purified by column chromatography (silica gel, eluent: PE/EA (v/v)=20/1 to 5/1) to give tert-butyl 2-(2-chloro-N-(1-(2-isopropylphenyl)-2-(4-methylphenyl) sulfonamido)ethyl)acetamido)-7-azaspiro[3.5]nonane-7-carboxylate (4.6 g, yield: 94%) was obtained as a yellow solid. ¹H NMR (400 MHz, CDCl₃) δ ppm: 7.74 (d, J=8.0 Hz, 2H), 7.32-7.27 (m, 4H), 7.20 (m, 1H), 7.15-7.10 (m, 1H), 5.31-5.20 (m, 1H), 5.08 (br s, 1H), 4.22 (d, J=2.8 Hz, 2H), 4.13 (m, 2H), 3.30 (m, 2H), 3.23 (m, 3H), 2.38 (s, 3H), 2.05 (s, 3H), 1.65 (br s, 3H), 1.48-1.45 (m, 3H), 1.44 (s, 9H), 1.27 (m, 6H).

Step 9: tert-butyl 2-(2-(2-isopropylphenyl)-6-oxo-4-tosylpiperazin-1-yl)-7-azaspiro[3.5]nonane-7-carboxylate.

To a solution of tert-butyl 2-(2-chloro-N-(1-(2-isopropylphenyl)-2-(4-methylphenyl)sulfonamido)ethyl)acetamido)-7-azaspiro[3.5]nonane-7-carboxylate (4.6 g, 7.28 mmol) in DMF (50 mL) was added K₂CO₃ (2.0 g, 14.55 mmol). The mixture was stirred at 60° C. for 1 hr. Then water (50 mL) was added to the mixture, and then the mixture was extracted with EtOAc (50 mL×3). The combined organic phases were washed with brine (50 mL×2), dried with anhydrous Na₂SO₄, filtered and concentrated in vacuum. The residue was purified by column chromatography (silica gel, eluent: PE/EA (v/v)=20/1 to 5/1) to give tert-butyl 2-(2-(2-isopropylphenyl)-6-oxo-4-tosylpiperazin-1-yl)-7-azaspiro[3.5]nonane-7-carboxylate (2.6 g, yield: 62%) as a yellow solid. ¹H NMR (400 MHz, CDCl₃) δ ppm: 7.47 (d, J=8.4 Hz, 2H), 7.36-7.30 (m, 2H), 7.23 (d, J=8.4 Hz, 2H), 7.16-7.10 (m, 1H), 6.89 (d, J=7.75 Hz, 1H), 5.07 (t, 1H), 4.30 (br s, 1H), 4.16-4.10 (m, 1H), 3.97-3.88 (m, 1H), 3.81-3.70 (m, 1H), 3.39 (m, 2H), 3.27-3.21 (m, 2H), 3.21-3.13 (m, 2H), 3.12-3.06 (m, 1H), 2.99-2.85 (m, 1H), 2.41 (s, 3H), 2.22-2.14 (m, 1H), 1.85 (br t, 1H), 1.73-1.58 (m, 2H), 1.46 (m, 2H), 1.41 (s, 9H), 1.30-1.26 (m, 6H).

Step 10: tert-butyl 2-(2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxo-4-tosylpiperazin-1-yl)-7-azaspiro[3.5]nonane-7-carboxylate (2.6 g, 4.47 mmol) in MeOH (50 mL) was added Mg (1.07 g, 44.7 mmol). The mixture was stirred at 100° C. for 2 hrs. The mixture was diluted with water (50 mL) and EtOAc (50 mL), and then filtered through a celite pad. The filtrate was extracted with EtOAc (50 mL×3). The combined organic phases were washed with brine (50 mL×2), dried with anhydrous Na₂SO₄, filtered and concentrated under reduced pressure to give tert-butyl 2-(2-(2-isopropylphenyl)-6-oxopiperazin-1-yl)-7-azaspiro[3.5]nonane-7-carboxylate (1.3 g, yield: 66%) as a brown oil. ¹H NMR (400 MHz, CDCl₃) δ ppm: 7.40-7.36 (d, J=7.2 Hz, 1H), 7.32 (t, 1H), 7.20 (t, 1H), 7.00 (d, J=8.0 Hz, 1H), 5.02 (br s, 1H), 4.55 (br s, 1H), 3.60 (m, 2H), 3.49 (s, 1H), 3.33 (m, 1H), 3.29-3.24 (m, 2H), 3.21-3.11 (m, 3H), 2.97-2.91 (m, 1H), 2.27-2.20 (m, 1H), 1.90 (br t, 1H), 1.74-1.64 (m, 5H), 1.47-1.44 (m, 2H), 1.42 (s, 9H), 1.29 (t, 6H).

Step 11: tert-butyl 2-(2-(2-isopropylphenyl)-4-neopentyl-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added pivalaldehyde (0.29 g, 3.40 mmol) and HOAc (0.27 g, 4.52 mmol). After stirring at 25° C. for 1 hr, then NaBH(OAc)₃ (0.96 g, 4.52 mmol) was added. The mixture was stirred at 25° C. for 12 hrs. The mixture was poured into aqueous NH₄Cl (1M, 20 mL), extracted with DCM (20 mL×3). The combined organic phases were washed with brine (20 mL×2), dried with anhydrous Na₂SO₄, filtered and concentrated in vacuum. The residue was purified by column chromatography (silica gel, eluent: PE/EA (v/v)=20/1 to 5/1) to give tert-butyl 2-(2-(2-isopropylphenyl)-4-neopentyl-6-oxopiperazin-1-yl)-7-azaspiro[3.5]nonane-7-carboxylate (0.68 g, yield: 59%) as a yellow solid. ¹H NMR (400 MHz, CDCl₃) δ ppm: 7.29-7.27 (m, 2H), 7.15-7.10 (m, 2H), 4.93 (br s, 1H), 4.45 (br s, 1H), 3.55 (br d, J=16.76 Hz, 1H), 3.50 (s, 1H), 3.31-3.07 (m, 8H), 2.96 (m, 1H), 2.76 (m, 1H), 2.22 (m, 1H), 2.01 (br s, 2H), 1.94 (m, 1H), 1.74 (br s, 2H), 1.49-1.45 (m, 3H), 1.42 (s, 9H), 1.30-1.26 (m, 6H), 0.53 (br s, 9H).

Step 12: tert-butyl 2-(2-(2-isopropylphenyl)-4-neopentylpiperazin-1-yl)-7-azaspiro[3.5]nonane-7-carboxylate.

The mixture of tert-butyl 2-(2-(2-isopropylphenyl)-4-neopentyl-6-oxopiperazin-1-yl)-7-azaspiro[3.5]nonane-7-carboxylate (680 mg, 1.33 mmol) and BH₃·THF (13 mL, 13.3 mmol) was heated to 70° C. for 12 hrs. After cooling to 0° C., the mixture was quenched with MeOH (10 mL) carefully. The mixture was concentrated in vacuum to give tert-butyl 2-(2-(2-isopropylphenyl)-4-neopentylpiperazin-1-yl)-7-azaspiro[3.5]nonane-7-carboxylate (0.6 g, yield: 91%) as yellow oil, which was used into the next step without further purification. MS (ESI, m/e) [M+1]+498.4

Step 13: 2-(2-(2-isopropylphenyl)-4-neopentylpiperazin-1-yl)-7-azaspiro[3.5]nonane.

To a solution of tert-butyl 2-(2-(2-isopropylphenyl)-4-neopentylpiperazin-1-yl)-7-azaspiro[3.5]nonane-7-carboxylate (600 mg, 1.21 mmol) in MeOH (20 mL) was added HCl/MeOH (10 mL, 4M) solution. The mixture was stirred at 25° C. for 1 hr. After concentrating under reduced pressure, the residue was dissolved into water (20 mL). The mixture was adjusted to the pH=9-10 with aqueous Na₂CO₃. The mixture was extracted with EtOAc (20 mL×3). The combined organic phases were washed with brine (20 mL×2), dried with anhydrous Na₂SO₄, filtered and concentrated in vacuum to give 2-(2-(2-isopropylphenyl)-4-neopentylpiperazin-1-yl)-7-azaspiro[3.5]nonane (400 mg, 83.5% yield) as yellow solid. ¹H NMR (400 MHz, CDCl₃) δ ppm: 7.49 (m, 1H), 7.26-7.18 (m, 2H), 7.15-7.10 (m, 1H), 3.61 (m, 1H), 3.41 (br s, 1H), 2.97-2.88 (m, 2H), 2.82 (m, 1H), 2.68-2.52 (m, 6H), 2.39 (br t, 1H), 2.32-2.26 (m, 1H), 2.11-2.01 (m, 3H), 1.78-1.72 (m, 1H), 1.69 (m, 1H), 1.45-1.30 (m, 5H), 1.28 (m, 3H), 1.19 (m, 3H), 0.85 (s, 9H). MS (ESI, m/e) [M+1]⁺398.4.

Intermediate 13-1: 2-(2-(2-isopropylphenyl)-4-(2-methoxyethyl)piperazin-1-yl)-7-azaspiro[3.5]nonane

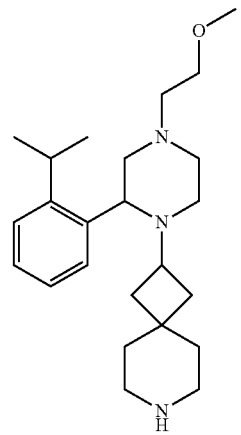

Intermediate 13-1

Step 1: tert-butyl 2-(2-isopropylphenyl)-4-(2-methoxyethyl)-3-oxopiperazine-1-carboxylate.

A mixture of tert-butyl 2-(2-isopropylphenyl)-3-oxopiperazine-1-carboxylate (1.5 g, 4.7 mmol) and 1-bromo-2-methoxyethane (0.72 g, 5.2 mmol) in THF (15 mL) at 20°

C. was added NaH (136 mg, 5.6 mmol) in portions. The mixture was stirred at 50° C. for 24 hrs. The mixture was quenched by MeOH (2 mL), concentrated under reduced pressure. The residue was poured into brine (20 mL), extracted with EtOAc (20 mL×3). The combined organic layers were dried over $Na_2SO_4$, filtered and concentrated under reduced pressure to give tert-butyl 2-(2-isopropylphenyl)-4-(2-methoxyethyl)-3-oxopiperazine-1-carboxylate (1.5 g, crude) as a yellow oil, which was used directly for next step without further purification.

Step 2: 3-(2-isopropylphenyl)-1-(2-methoxyethyl)piperazin-2-one.

A solution of tert-butyl 2-(2-isopropylphenyl)-4-(2-methoxyethyl)-3-oxopiperazine-1-carboxylate (1.4 g, 3.8 mmol) in TFA (5 mL) and DCM (5 mL) was stirred at 27° C. for 2 hrs. The mixture was concentrated under reduced pressure. The residue was poured into sat. $NaHCO_3$ (30 mL), extracted with EtOAc (30 mL×3). The combined organic layers were dried over $Na_2SO_4$, filtered and concentrated under reduced pressure to give 3-(2-isopropylphenyl)-1-(2-methoxyethyl)piperazin-2-one (1.0 g, crude) as a yellow oil, which was used directly for next step without further purification.

Step 3: tert-butyl 2-(2-(2-isopropylphenyl)-4-(2-methoxyethyl)-3-oxopiperazin-1-yl)-7-azaspiro[3.5]nonane-7-carboxylate.

To a solution of 3-(2-isopropylphenyl)-1-(2-methoxyethyl)piperazin-2-one (1.0 g, 3.7 mmol) in DCE (10 mL) was added tert-butyl 2-oxo-7-azaspiro[3.5]nonane-7-carboxylate (874 mg, 3.7 mmol) and $NaBH(OAc)_3$ (1.6 g, 7.3 mmol). The mixture was stirred at 27° C. for 10 hrs.

The mixture was poured into sat. $NaHCO_3$ (50 mL), extracted with DCM (20 mL×3). The combined organic layers were dried over $Na_2SO_4$, filtered and concentrated under reduced pressure to give tert-butyl 2-(2-(2-isopropylphenyl)-4-(2-methoxyethyl)-3-oxopiperazin-1-yl)-7-azaspiro[3.5]nonane-7-carboxylate (1.6 g, crude) as a yellow oil, which was used directly for next step without further purification.

Step 4: tert-butyl 2-(2-(2-isopropylphenyl)-4-(2-methoxyethyl)piperazin-1-yl)-7-azaspiro[3.5]nonane-7-carboxylate.

A solution of tert-butyl 2-(2-(2-isopropylphenyl)-4-(2-methoxyethyl)-3-oxopiperazin-1-yl)-7-azaspiro[3.5]nonane-7-carboxylate (1.4 g, 2.8 mmol) in $BH_3$-THF (10 mL) was stirred at 70° C. for 10 hrs. The mixture was quenched by MeOH (10 mL) and concentrated under reduced pressure to give tert-butyl 2-(2-(2-isopropylphenyl)-4-(2-methoxyethyl)piperazin-1-yl)-7-azaspiro[3.5]nonane-7-carboxylate (2.4 g, crude) as a yellow oil, which was used directly for next step without further purification.

Step 5: 2-(2-(2-isopropylphenyl)-4-(2-methoxyethyl)piperazin-1-yl)-7-azaspiro[3.5]nonane.

A solution of tert-butyl 2-(2-(2-isopropylphenyl)-4-(2-methoxyethyl)piperazin-1-yl)-7-azaspiro[3.5]nonane-7-carboxylate (1.3 g, 2.7 mmol) in TFA (3 mL) and DCM (6 mL) was stirred at 20° C. for 2 hrs. The mixture was concentrated under reduced pressure. The residue was purified by prep-HPLC (TFA). The compound 2-(2-(2-isopropylphenyl)-4-(2-methoxyethyl) piperazin-1-yl)-7-azaspiro[3.5]nonane (791 mg, yield: 77%) was obtained as a colorless oil. $^1$H NMR (400 MHz, $CH_3OH$-$d_4$) δ ppm: 7.48 (br, 1H), 7.32-7.27 (m, 1H), 7.23 (m, 1H), 7.18-7.09 (m, 1H), 3.74 (m, 1H), 3.55-3.50 (m, 2H), 3.44 (m, 1H), 3.33-3.31 (m, 3H), 3.09-2.99 (m, 2H), 2.93 (m, 1H), 2.76-2.69 (m, 1H), 2.67-2.45 (m, 6H), 2.42-2.22 (m, 3H), 1.88-1.79 (m, 1H), 1.72-1.63 (m, 1H), 1.44-1.25 (m, 8H), 1.20 (d, J=6.8 Hz, 3H), 1.15-1.03 (m, 1H). MS (ESI, m/e) $[M+1]^+$386.4.

Intermediate 13-1a: (R or S)-2-(2-(2-isopropylphenyl)-4-(2-methoxyethyl)piperazin-1-yl)-7-azaspiro[3.5]nonane Intermediate 13-1a

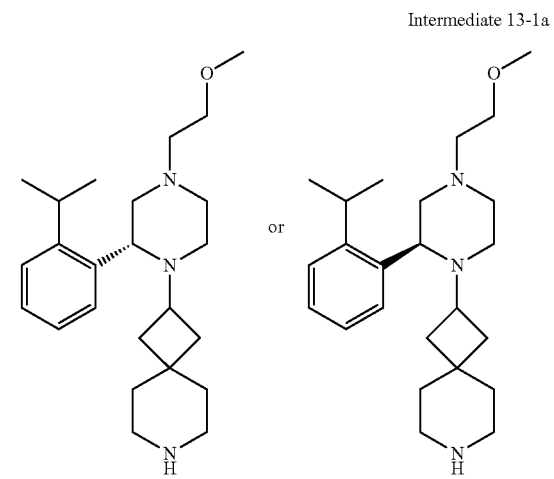 [SMILES: COCCN1CCN(C2CC3(CCNCC3)C2)[C@H](c2ccccc2C(C)C)C1 ; COCCN1CCN(C2CC3(CCNCC3)C2)[C@@H](c2ccccc2C(C)C)C1]

2-(2-(2-isopropylphenyl)-4-(2-methoxyethyl)piperazin-1-yl)-7-azaspiro[3.5]nonane was separated by SFC (Instrument: Waters SFC80 preparative SFC; Column: Phenomenex-Cellulose-2(250×30 mm i.d. 10 uM); Mobile phase: A for $CO_2$ and B for MeOH (0.1% $NH_3 \cdot H_2O$); Gradient: B%=40%; Flow rate: 70 g/min; Wavelength: 220 nm; Column temperature: 40° C.; System back pressure: 100 bar). (R or S)-2-(2-(2-isopropylphenyl)-4-(2-methoxyethyl)piperazin-1-yl)-7-azaspiro[3.5]nonane (452 mg, retention time: 1.59 min) was obtained, yield: 30%. $^1$H NMR (400 MHz, $CDCl_3$) δ ppm: 7.50 (s, 1H), 7.25-7.20 (m, 2H), 7.13 (m, 1H), 3.73-3.67 (m, 1H), 3.50 (m, 2H), 3.40 (br s, 1H), 3.33 (s, 3H), 3.00 (m, 2H), 2.93-2.87 (m, 1H), 2.74-2.65 (m, 4H), 2.58 (t, 2H), 2.33 (m, 2H), 2.23-2.14 (m, 2H), 1.80-1.75 (m, 2H), 1.44-1.34 (m, 6H), 1.22 (m, 6H). MS (ESI, m/e) $[M+1]^+$386.3.

Intermediate 13-1b: (S or R)-2-(2-(2-isopropylphenyl)-4-(2-methoxyethyl)piperazin-1-yl)-7-azaspiro[3.5]nonane (441 mg, retention time: 1.78 min, yield: 29%) was obtained. MS (ESI, m/e) [M+1]$^+$ 386.3

Intermediate 15-1: 2-(4-(cyclopentylmethyl)-2-(2-isopropylphenyl)piperazin-1-yl)-7-azaspiro[3.5]nonane

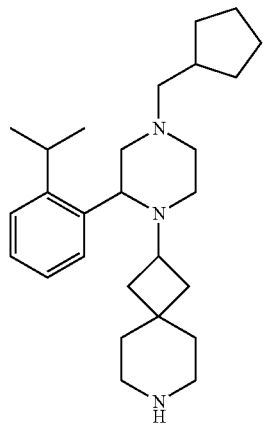

Intermediate 15-1

Step 1: tert-butyl 2-(4-(cyclopentylmethyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol), cyclopentanecarbaldehyde (333 mg, 3.40 mmol) and AcOH (339 mg, 5.66 mmol) in DCE (10 mL) was added NaBH(OAc)$_3$ (959 mg, 4.53 mmol) at 25° C. The mixture was stirred at 25° C. for 12 hrs. The reaction mixture was quenched by sat. Na$_2$CO$_3$ (10 mL), extracted with EtOAc (10 mL×3). The combined organic layers were washed with brine, dried with anhydrous Na$_2$SO$_4$, filtered and concentrated under reduced pressure. The crude product was purified by column chromatography (silica gel, eluent: PE/EA (v/v)=50/1 to 0/1) to give tert-butyl 2-(4-(cyclopentylmethyl)-2-(2-isopropylphenyl)-6-oxopiperazin-1-yl)-7-azaspiro[3.5]nonane-7-carboxylate (1.0 g, yield: 84%) as a pale yellow oil.

Step 2: tert-butyl 2-(4-(cyclopentylmethyl)-2-(2-isopropylphenyl)piperazin-1-yl)-7-azaspiro[3.5]nonane-7-carboxylate.

To a mixture of tert-butyl 2-(4-(cyclopentylmethyl)-2-(2-isopropylphenyl)-6-oxopiperazin-1-yl)-7-azaspiro[3.5]nonane-7-carboxylate (1.0 g, 1.91 mmol) was added BH$_3$·THF (57 mL, 57.28 mmol) in THF (20 mL) at 0° C. The mixture was stirred at 80° C. for 12 hrs. The reaction solution was added MeOH (20 mL) at 0° C. to quench the reaction and concentrated under reduced pressure to give tert-butyl 2-(4-(cyclopentylmethyl)-2-(2-isopropylphenyl)piperazin-1-yl)-7-azaspiro[3.5]nonane-7-carboxylate (1.0 g, crude) as a yellow oil, which was used directly for next step without further purification.

Step 3: 2-(4-(cyclopentylmethyl)-2-(2-isopropylphenyl)piperazin-1-yl)-7-azaspiro[3.5]nonane.

To a mixture of tert-butyl 2-(4-(cyclopentylmethyl)-2-(2-isopropylphenyl)piperazin-1-yl)-7-azaspiro[3.5]nonane-7-carboxylate (1.0 g, 1.96 mmol) was added HCl/MeOH (40 mL) at 0° C. for 2 hrs. The reaction mixture poured into saturated Na$_2$CO$_3$ (40 mL), extracted with EtOAc (40 mL×3). The combined organic phases were washed with brine (40 mL×2), dried with anhydrous Na$_2$SO$_4$, filtered and concentrated under reduced pressure to give 2-(4-(cyclopentylmethyl)-2-(2-isopropylphenyl)piperazin-1-yl)-7-azaspiro[3.5]nonane (712 mg, yield: 88%) as a pale pink oil. $^1$H NMR (400 MHz, CDCl$_3$) δ ppm: 7.58-7.46 (m, 1H), 7.26-7.19 (m, 2H), 7.17-7.10 (in, 1H), 3.68-3.59 (m, 1H), 3.42 (s, 1H), 3.03-2.88 (m, 3H), 2.73-2.57 (m, 5H), 2.28 (m, 4H), 2.16-2.09 (m, 1H), 1.79-1.64 (m, 9H), 1.61-1.56 (m, 2H), 1.41-1.30 (m, 6H), 1.28-1.25 (d, J=6.8 Hz, 3H), 1.20-1.22 (d, J=6.8 Hz, 3H), 1.16 (m, 2H). MS (ESI, m/e) [M+1]$^+$ 410.3.

Intermediate 16-1: 2-(4-(cyclohexylmethyl)-2-(2-isopropylphenyl)piperazin-1-yl)-7-azaspiro[3.5]nonane

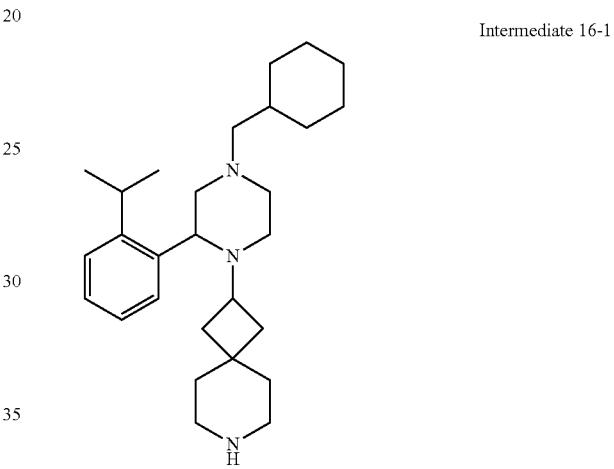

Intermediate 16-1

Step 1: tert-butyl 2-(4-(cyclohexylmethyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added cyclohexanecarbaldehyde (0.38 g, 3.40 mmol) and HOAc (0.27 g, 4.52 mmol). After stirred at 25° C. for 1 hr, then NaBH(OAc)$_3$ (0.96 g, 4.52 mmol) was added. The mixture was stirred at 25° C. for 12 hrs. Then aqueous NH$_4$Cl (20 mL) was added to the mixture, and then the mixture was extracted with DCM (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=5/1) to give tert-butyl 2-(4-(cyclohexylmethyl)-2-(2-isopropylphenyl)-6-oxopiperazin-1-yl)-7-azaspiro[3.5]nonane-7-carboxylate (1.0 g, yield: 83%) was obtained as yellow solid. MS (ESI, m/e) [M+1]$^+$538.4.

Step 2: tert-butyl 2-(4-(cyclohexylmethyl)-2-(2-isopropylphenyl)piperazin-1-yl)-7-azaspiro[3.5]nonane-7-carboxylate.

The mixture of tert-butyl 2-(4-(cyclohexylmethyl)-2-(2-isopropylphenyl)-6-oxopiperazin-1-yl)-7-azaspiro[3.5]nonane-7-carboxylate (1.0 g, 1.86 mmol) and BH$_3$·THF (19 mL, 18.6 mmol) was heated to 70° C. for 12 hrs. Then MeOH (10 mL) was added to the mixture carefully. The mixture was concentrated in vacuum to give tert-butyl 2-(4-(cyclohexylmethyl)-2-(2-isopropylphenyl)piperazin-1- yl)-7-azaspiro[3.5]nonane-7-carboxylate (0.6 g, yield: 65%) as yellow oil, which was used directly for the next step without further purification. MS (ESI, m/e) [M+1]⁺524.4

Step 3: 2-(4-(cyclohexylmethyl)-2-(2-isopropylphenyl) piperazin-1-yl)-7-azaspiro[3.5]nonane.

To a solution of tert-butyl 2-(2-(2-isopropylphenyl)piperazin-1-yl)-7-azaspiro[3.5]nonane-7-carboxylate (600 mg, 0.99 mmol) in MeOH (20 mL) was added HCl/MeOH (10 mL, 4M) solution. The mixture was stirred at 25° C. for 1 hr. After removed the solvent, the residue was dissolved into water (20 mL). The mixture was adjusted the pH to 9-10 using aqueous Na₂CO₃. The mixture was extracted with EtOAc (20 mL×3). The combined organic phase was washed with brine (20 mL×2), dried with anhydrous Na₂SO₄, filtered and concentrated in vacuum to give 2-(4-(cyclohexylmethyl)-2-(2-isopropylphenyl)piperazin-1-yl)-7-azaspiro[3.5]nonane (450 mg, yield: 83%) as a yellow solid. ¹H NMR (400 MHz, CDCl₃) δ ppm: 7.49 (br s, 1H), 7.25-7.19 (m, 2H), 7.15-7.10 (m, 1H), 3.62 (m, 1H), 3.46-3.34 (m, 1H), 3.02 (m, 1H), 3.00 (m, 1H), 2.94-2.86 (m, 2H), 2.66-2.57 (m, 5H), 2.31-2.21 (m, 2H), 2.15-2.09 (m, 2H), 1.81-1.73 (m, 3H), 1.71-1.63 (m, 5H), 1.45 (m, 2H), 1.35-1.29 (m, 5H), 1.28-1.25 (d, J=6.8 Hz, 3H), 1.21 (d, J=6.8 Hz, 3H), 1.16 (m, 3H), 0.91-0.83 (m, 2H). MS (ESI, m/e) [M+1]⁺424.5.

Intermediate 17-1: 2-(2-(2-isopropylphenyl)-4-((tetrahydro-2H-pyran-4-yl)methyl)piperazin-1-yl)-7-azaspiro[3.5]nonane

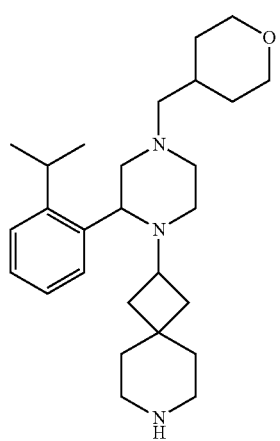

Intermediate 17-1

Step 1: tert-butyl 2-(2-(2-isopropylphenyl)-6-oxo-4-((tetrahydro-2H-pyran-4-yl)methyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g,2.06 mmol) in DCE (10 mL) was added AcOH (339 mg, 5.66 mmol), tetrahydro-2H-pyran-4-carbaldehyde (387 mg, 3.40 mmol) and NaBH(OAc)₃ (959 mg, 4.53 mmol) at 25° C. The mixture was stirred at 25° C. for 12 hrs. The reaction mixture was poured into saturated Na₂CO₃ (10 mL), extracted with EtOAc (10 mL×3). The combined organic layers were washed with brine, dried with anhydrous Na₂SO₄, filtered and concentrated under reduced pressure. The crude product was purified by column chromatography (silica gel, eluent: PE/EA (v/v)=50/1 to 0/1) to give tert-butyl 2-(2-(2-isopropylphenyl)-6-oxo-4-((tetrahydro-2H-pyran-4-yl)methyl)piperazin-1-yl)-7-azaspiro[3.5]nonane-7-carboxylate (1.0 g, yield: 82%) as a pale yellow oil.

Step 2: tert-butyl 2-(2-(2-isopropylphenyl)-4-((tetrahydro-2H-pyran-4-yl)methyl)piperazin-1-yl)-7-azaspiro [3.5]nonane-7-carboxylate.

To a mixture of tert-butyl 2-(2-(2-isopropylphenyl)-6-oxo-4-((tetrahydro-2H-pyran-4-yl)methyl)piperazin-1-yl)-7-azaspiro[3.5]nonane-7-carboxylate (700 mg, 1.30 mmol) was added BH₃.THF (38 mL, 38.91 mmol) in THF (20 mL) at 80° C. for 12 hrs. The reaction was quenched by MeOH (20 mL) and concentrated under reduced pressure to give tert-butyl 2-(2-(2-isopropylphenyl)-4-((tetrahydro-2H-pyran-4-yl)methyl)piperazin-1-yl)-7-azaspiro[3.5]nonane-7-carboxylate (660 mg, crude) as a yellow gum, which was used directly for next step without further purification.

Step 3: 2-(2-(2-isopropylphenyl)-4-((tetrahydro-2H-pyran-4-yl)methyl)piperazin-1-yl)-7-azaspiro[3.5]nonane.

To a mixture of tert-butyl 2-(2-(2-isopropylphenyl)-4-((tetrahydro-2H-pyran-4-yl)methyl)piperazin-1-yl)-7-azaspiro[3.5]nonane-7-carboxylate (700 mg, 1.30 mmol) was added HCl/MeOH (40 mL) solution at 0° C. for 2 hrs. The reaction mixture poured into sat. Na₂CO₃ (40 mL). The mixture was extracted with EtOAc (40 mL×3). The combined organic phases were washed with brine, dried with anhydrous Na₂SO₄, filtered and concentrated under reduced pressure to give 2-(2-(2-isopropylphenyl)-4-((tetrahydro-2H-pyran-4-yl)methyl)piperazin-1-yl)-7-azaspiro[3.5] nonane (541 mg, yield: 75%) as a pale pink oil. ¹H NMR (400 MHz, CDCl₃) δ ppm: 7.59-7.44 (m, 1H), 7.26-7.19 (m, 2H), 7.17-7.10 (m, 1H), 4.04-3.91 (m, 2H), 3.60 (m, 1H), 3.45-3.30 (m, 3H), 3.04-2.97 (m, 1H), 2.96-2.84 (m, 2H), 2.67-2.57 (m, 4H), 2.31-2.24 (m, 2H), 2.23-2.16 (m, 2H), 2.14-2.07 (m, 1H), 1.85-1.67 (m, 5H) 1.41-1.28 (m, 4H), 1.21 (d, J=6.8 Hz, 3H). MS (ESI, m/e) [M+1]⁺426.4.

Intermediate 18-1: 2-(4-(bicyclo[1.1.1]pentan-1-ylmethyl)-2-(2-isopropylphenyl)piperazin-1-yl)-7-azaspiro[3.5]nonane

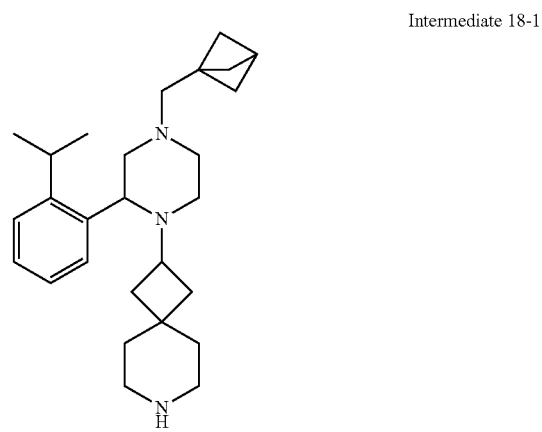 [SMILES: CC(C)c1ccccc1C1CN(CC23CC(C2)C3)CCN1C1CC2(CCNCC2)C1]

Intermediate 18-1

Step 1: tert-butyl 2-(2-(2-isopropylphenyl)-4-(3-(methoxycarbonyl)bicyclo[1.1.1]pentane-1-carbonyl)-6-oxopiperazin-1-yl)-7-azaspiro[3.5]nonane-7-carboxylate.

To a mixture of tert-butyl 2-(2-(2-isopropylphenyl)-6-oxopiperazin-1-yl)-7-azaspiro[3.5]nonane-7-carboxylate (2.5 g, 5.66 mmol) and 3-(methoxycarbonyl)bicyclo[1.1.1] pentane-1-carboxylic acid (1.16 g, 6.76 mmol) and HOBt (1.15 g, 8.49 mmol) and TEA (1.14 g, 11.32 mmol) in THF (30 mL) was added EDCI (1.63 g, 8.49 mmol) at 0° C. The mixture was stirred at 20° C. for 12 hrs. The mixture was quenched with H₂O (20 mL), extracted with DCM (100 mL). The combined organic layers were washed with brine (10 mL), dried over anhydrous Na₂SO₄, filtered and concentrated under reduced pressure. The crude product was purified by column chromatography (silica gel, eluent: PE/EA (v/v)=1/8) to give tert-butyl 2-(2-(2-isopropylphenyl)-4-(3-(methoxycarbonyl)bicyclo[I1.1.1]pentane-1-carbonyl)-6-oxopiperazin-1-yl)-7-azaspiro[3.5]nonane-7-carboxylate (2.8 g, yield: 85%) as a white solid. MS (ESI, m/e) [M-55]⁺538.3.

Step 2: 3-(4-(7-(tert-butoxycarbonyl)-7-azaspiro[3.5]nonan-2-yl)-3-(2-isopropylphenyl)-5-oxopiperazine-1-carbonyl)bicyclo[1.1.1]pentane-1-carboxylic acid.

A mixture of tert-butyl 2-(2-(2-isopropylphenyl)-4-(3-(methoxycarbonyl)bicyclo[1.1.1]pentane-1-carbonyl)-6-oxopiperazin-1-yl)-7-azaspiro[3.5]nonane-7-carboxylate (2.8 g, 4.71 mmol) and LiOH·H₂O (0.79 g, 18.86 mmol) in MeOH (50 mL) and H₂O (10 mL) was stirred at 20° C. for 5 hrs. The mixture was concentrated under reduced pressure. The residue was diluted with H₂O (30 mL), acidified by citric acid to pH=4-5 and filtered. The filtrate was extracted with EtOAc (100 mL×2). The organic phase was washed with brine (10 mL), dried over Na₂SO₄, filtered and concentrated under reduced pressure to afford 3-(4-(7-(tert-butoxycarbonyl)-7-azaspiro[3.5]nonan-2-yl)-3-(2-isopropylphenyl)-5-oxopiperazine-1-carbonyl)bicyclo[1.1.1]pentane-1-carboxylic acid (0.6 g, crude) as a white solid. MS (ESI, m/e) [M+Na]⁺602.3.

Step 3: tert-butyl 2-(2-(2-isopropylphenyl)-6-oxo-4-(3-(((2-thioxopyridin-1(2H)-yl)oxy)carbonyl)bicyclo[1.1.1]pentane-1-carbonyl)piperazin-1-yl)-7-azaspiro[3.5]nonane-7-carboxylate A mixture of 3-(4-(7-(tert-butoxycarbonyl)-7-azaspiro[3.5]nonan-2-yl)-3-(2-isopropylphenyl)-5-oxopiperazine-1-carbonyl)bicyclo[1.1.1]pentane-1-carboxylic acid (0.5 g, 0.86 mmol) and 1-hydroxypyridine-2(1H)-thione (142 mg, 1.12 mmol), DCC (231 mg, 1.12 mmol) in DCM (13 mL) was stirred at 0° C. for 2 hrs. The mixture was filtered and concentrated under reduced pressure to afford tert-butyl 2-(2-(2-isopropylphenyl)-6-oxo-4-(3-(((2-thioxopyridin-1(2H)-yl)oxy)carbonyl)bicyclo[1.1.1]pentane-1-carbonyl)piperazin-1-yl)-7-azaspiro[3.5]nonane-7-carboxylate (0.5 g, crude) as a yellow solid, which was used directly without further purification. MS (ESI, m/e) [M+1]+689.1.

Step 4: tert-butyl 2-(4-(bicyclo[1.1.1]pentane-1-carbonyl)-2-(2-isopropylphenyl)-6-oxopiperazin-1-yl)-7-azaspiro[3.5]nonane-7-carboxylate.

A mixture of tert-butyl 2-(2-(2-isopropylphenyl)-6-oxo-4-(3-(((2-thioxopyridin-1(2H)-yl)oxy)carbonyl)bicyclo[1.1.1]pentane-1-carbonyl)piperazin-1-yl)-7-azaspiro[3.5]nonane-7-carboxylate (2.0 g, 2.63 mmol) and Bu₃SnH (2.3 g, 7.9 mmol), AIBN (36 mg, 0.22 mmol) in toluene (35 mL) was stirred at 60° C. for 1 hr under W lamp (300 W). The mixture was quenched with KF solution (50 mL), extracted with EtOAc (100 mL×3). The combined organic phases were washed with brine (10 mL), dried over Na₂SO₄, filtered and concentrated under reduced pressure. The residue was purified by prep-HPLC (0.1% TFA, then neutralized) to afford tert-butyl 2-(4-(bicyclo[1.1.1]pentane-1-carbonyl)-2-(2-isopropylphenyl)-6-oxopiperazin-1-yl)-7-azaspiro[3.5]nonane-7-carboxylate (0.95 g) as an off-white solid. MS (ESI, m/e) [M+Na]+558.4.

Step 5: tert-butyl 2-(4-(bicyclo[1.1.1]pentan-1-ylmethyl)-2-(2-isopropylphenyl)piperazin-1-yl)-7-azaspiro[3.5]nonane-7-carboxylate.

A mixture of tert-butyl 2-(4-(bicyclo[1.1.1]pentane-1-carbonyl)-2-(2-isopropylphenyl)-6-oxopiperazin-1-yl)-7-azaspiro[3.5]nonane-7-carboxylate (0.95 g, 1.77 mmol) and BH₃·THF (1M, 10 mL) in THF (5 mL) was stirred at 70° C. for 12.4 hrs. The reaction mixture was cooled to 25° C. and quenched with MeOH (20 mL) slowly. The mixture was concentrated under reduced pressure to give tert-butyl 2-(4-(bicyclo[1.1.1]pentan-1-ylmethyl)-2-(2-isopropylphenyl)piperazin-1-yl)-7-azaspiro[3.5]nonane-7-carboxylate (1.0 g, crude) as a white solid, which was used directly without further purification. MS (ESI, m/e) [M+1]⁺508.5.

Step 6: 2-(4-(bicyclo[1.1.1]pentan-1-ylmethyl)-2-(2-isopropylphenyl)piperazin-1-yl)-7-azaspiro[3.5]nonane.

A mixture of tert-butyl 2-(4-(bicyclo[1.1.1]pentan-1-ylmethyl)-2-(2-isopropylphenyl)piperazin-1-yl)-7-azaspiro[3.5]nonane-7-carboxylate (1.0 g, 1.97 mmol) in HCl/MeOH (8 mL, 4 M) was stirred at 20° C. for 3 hrs. The mixture was concentrated under reduced pressure and purified by prep-HPLC (0.1% TFA), then adjusted pH=9 by Na₂CO₃ solution. The solution was extracted with EtOAc (20 mL×2). The combined organics were washed with brine (5 mL), dried over Na₂SO₄, filtered and concentrated under reduced pressure to give 2-(4-(bicyclo[1.1.1]pentan-1-ylmethyl)-2-(2-isopropylphenyl)piperazin-1-yl)-7-azaspiro[3.5]nonane (327 mg, yield: 40%) as a light yellow solid. ¹H NMR (400 MHz, CDCl₃) δ ppm: 7.57-7.40 (m, 1H), 7.26-7.19 (m, 2H), 7.16-7.10 (m, 1H), 3.70-3.59 (m, 1H), 3.51-3.31 (m, 1H), 3.03-2.86 (m, 4H), 2.77-2.65 (m, 5H), 2.46-2.43 (m, 1H), 2.40-2.37 (m, 2H), 2.34-2.28 (m, 2H), 2.21-2.05 (m, 2H), 1.75 (m, 8H), 1.48-1.30 (m, 5H), 1.28-1.24 (m, 3H), 1.23-1.20 (m, 3H). MS (ESI, m/e) [M+1]⁺408.4.

Intermediate 20-1: 2-(4-(furan-3-ylmethyl)-2-(2-isopropylphenyl)piperazin-1-yl)-7-azaspiro[3.5]nonane

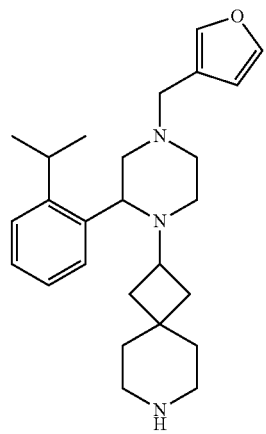

Intermediate 20-1

Step 1: tert-butyl 2-(4-(furan-3-ylmethyl)-2-(2-isopropylphenyl)-6-oxopiperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), furan-3-carbaldehyde (326.37 mg, 3.40 mmol,) and HOAc (271.97 mg, 4.53 mmol) in DCE (20 mL) was stirred at 25° C. for 30 min. Then NaBH(OAc)₃ (1.44 g, 6.79 mmol) was added in portions to the above mixture and stirred at 25° C. for 10 hrs. The reaction mixture was poured into ice-water (20 mL), adjust the pH=8 with NaHCO₃. The resulting mixture was extracted with DCM (50 mL×3). The combined organic phases were dried with anhydrous Na₂SO₄, filtered and concentrated under reduced pressure. The crude was purified by column chromatography (silica gel, eluent: PE/EA (v/v)=2/1 to 1/1) to give tert-butyl 2-(4-(furan-3-ylmethyl)-2-(2-isopropylphenyl)-6-oxopiperazin-1-yl)-7-azaspiro[3.5]nonane-7-carboxylate (1.05 g, 89% yield) as a pale yellow solid. ¹H NMR (400 MHz, CDCl₃) δ ppm: 7.29 (m, 2H), 7.23-7.14 (m, 2H), 7.12-7.07 (m, 1H), 6.91 (s, 1H), 5.86 (s, 1H), 4.97 (s, 1H), 4.38 (s, 1H), 3.53-3.38 (m, 2H), 3.32-2.98 (m, 7H), 2.75-2.64 (m, 2H), 2.28-2.18 (m, 1H), 1.94 (m, 1H), 1.83-1.74 (m, 1H), 1.72-1.62 (m, 2H), 1.50-1.46 (m, 1H), 1.42 (s, 9H), 1.36-1.30 (m, 2H), 1.25 (d, J=6.8 Hz, 3H), 1.10 (d, J=6.8 Hz, 3H).

Step 2: tert-butyl 2-(4-(furan-3-ylmethyl)-2-(2-isopropylphenyl)piperazin-1-yl)-7-azaspiro[3.5]nonane-7-carboxylate.

To a solution of tert-butyl 2-(4-(furan-3-ylmethyl)-2-(2-isopropylphenyl)-6-oxopiperazin-1-yl)-7-azaspiro[3.5]nonane-7-carboxylate (1.05 g, 2.01 mmol) in THF (15 mL) was added BH₃·THF (30 mL, 30 mmol) dropwise at 25° C. The mixture was heated to 70° C. for 15 hrs. The reaction was quenched by ethanol (10 mL), concentrated under reduced pressure to give tert-butyl 2-(4-(furan-3-ylmethyl)-2-(2-isopropylphenyl)piperazin-1-yl)-7-azaspiro[3.5]nonane-7-carboxylate (1.02 g, crude) as a white solid. MS (ESI, m/e) [M+1]+508.4.

Step 3: 2-(4-(furan-3-ylmethyl)-2-(2-isopropylphenyl)piperazin-1-yl)-7-azaspiro[3.5]nonane.

To a solution of tert-butyl 2-(4-(furan-3-ylmethyl)-2-(2-isopropylphenyl)piperazin-1-yl)-7-azaspiro[3.5]nonane-7-carboxylate (200 mg, 393.93 umol) in DCM (3 mL) was added TFA (3 mL) dropwise at 25° C. The solution was stirred at 25° C. for 12 hrs. The reaction solution was concentrated in vacuum. The crude was purified by prep-HPLC and lyophilization. The residue was free with sat. Na₂CO₃ (20 mL), extracted with EtOAc (30 mL×5). The combined organic phases were dried with anhydrous Na₂SO₄, filtered and concentrated in vacuum to give 2-(4-(furan-3-ylmethyl)-2-(2-isopropylphenyl)piperazin-1-yl)-7-azaspiro[3.5]nonane (265 mg, 0.52 mmol, yield: 27%) as a white gum. ¹H NMR (400 MHz, CDCl₃) δ ppm: 7.46 (s, 1H), 7.36 (m, 1H), 7.31 (s, 1H), 7.26-7.20 (m, 2H), 7.15-7.09 (m, 1H), 6.38 (m, 1H), 3.64 (m, 1H), 3.40 (s, 3H), 3.03-2.85 (m, 4H), 2.83-2.70 (m, 4H), 2.67 (s, 1H), 2.33-2.24 (m, 2H), 2.15 (m, 1H), 1.83-1.68 (m, 2H), 1.60-1.51 (m, 2H), 1.37-1.31 (m, 1H), 1.30-1.20 (m, 5H), 1.17 (d, J=6.8 Hz, 3H). MS (ESI, m/e) [M+1]+408.3.

Intermediate 21-1: 4-((3-(2-isopropylphenyl)-4-(7-azaspiro[3.5]nonan-2-yl)piperazin-1-yl)methyl)oxazole Intermediate 21-1

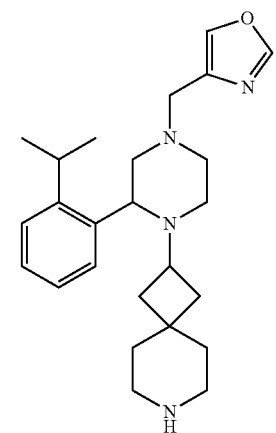

Step 1: tert-butyl 2-(2-(2-isopropylphenyl)-4-(oxazol-4-ylmethyl)piperazin-1-yl)-7-azaspiro[3.5]nonane-7-carboxylate.

To a solution of tert-butyl 2-(2-(2-isopropylphenyl)piperazin-1-yl)-7-azaspiro[3.5]nonane-7-carboxylate (1.0 g, 2.26 mmol) in DCE (15 mL) was added oxazole-4-carbaldehyde (329.7 mg, 3.40 mmol) and AcOH (272 mg, 4.53 mmol) at 25° C. for 30 min. Then NaBH(OAc)₃ (1.2 g, 5.66 mmol) was added at 25° C. The mixture was stirred at 25° C. for 12 hrs. The reaction mixture was poured into sat. NH₄Cl (50 mL), extracted with DCM (50 mL×2). The combined organic phases were washed with brine (20 mL×2), dried with anhydrous Na₂SO₄, filtered and concentrated in vacuum. The residue was purified by column chromatography (silica gel, eluent: PE/EA (v/v)=10/1 to EA/MeOH (v/v)=10/1) to give tert-butyl 2-(2-(2-isopropylphenyl)-4-(oxazol-4-ylmethyl)piperazin-1-yl)-7-azaspiro[3.5]nonane-7-carboxylate (360 mg, 707.69 umol, yield: 30.26%) as a yellow oil. MS (ESI, m/e) [M+1]+509.3.

Step 2: 4-((3-(2-isopropylphenyl)-4-(7-azaspiro[3.5]nonan-2-yl)piperazin-1-yl)methyl)oxazole.

To a solution of tert-butyl 2-(2-(2-isopropylphenyl)-4-(oxazol-4-ylmethyl)piperazin-1-yl)-7-azaspiro[3.5]nonane-7-carboxylate (300 mg, 1.32 mmol) in DCM (2 mL) was added TFA (0.5 mL) at 25° C. The mixture was stirred at 25° C. for 2 hrs. The reaction mixture was poured into sat. Na₂CO₃ (20 mL), extracted with EtOAc (50 mL×3). The combined organic phases were washed with brine (20 mL×2), dried with anhydrous Na₂SO₄, filtered and concentrated in vacuum to give 4-((3-(2-isopropylphenyl)-4-(7-azaspiro[3.5]nonan-2-yl)piperazin-1-yl)methyl)oxazole (390 mg, 374.47 umol, yield: 63%) as a yellow oil. ¹H NMR (400 MHz, CDCl₃) δ ppm: 7.83 (s, 1H), 7.55 (s, 1H), 7.53-7.45 (m, 1H), 7.26-7.09 (m, 3H), 3.72-3.64 (m, 1H), 3.59-3.46 (m, 2H), 3.42-3.34 (m, 1H), 3.07-2.95 (m, 2H), 2.95-2.86 (m, 1H), 2.73 (m, 1H), 2.69-2.55 (m, 4H), 2.43-2.29 (m, 2H), 2.25 (m, 1H), 1.71 (m, 4H), 1.37-1.29 (m, 4H), 1.25 (d, J=6.8 Hz, 3H), 1.17 (d, J=6.8 Hz, 3H). MS (ESI, m/e) [M+1]+409.3.

Intermediate 22-1: 2-(2-(2-isopropylphenyl)-4-((1-methyl-1H-pyrazol-4-yl)methyl)piperazin-1-yl)-7-azaspiro[3.5]nonane

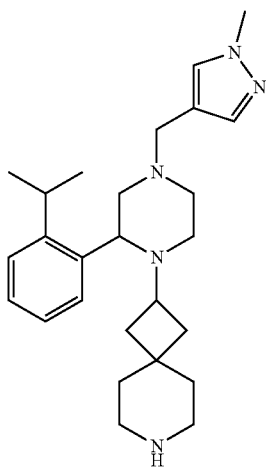

Intermediate 22-1

Step 1: tert-butyl 2-(2-(2-isopropylphenyl)-4-((1-methyl-1H-pyrazol-4-yl)methyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.2 g, 2.72 mmol) in DCE (10 mL) was added AcOH (326.36 mg, 5.43 mmol) and 1-methyl-1H-pyrazole-4-carbaldehyde (329.14 mg, 2.99 mmol). The mixture was stirred at 25° C. for 1 hr. Then NaBH(OAc)₃ (1.73 g, 8.15 mmol) was added and stirred at 25° C. for another 12 hrs. The reaction mixture was poured into saturated NaHCO₃ (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give tert-butyl 2-(2-(2-isopropylphenyl)-4-((1-methyl-1H-pyrazol-4-yl)methyl)-6-oxopiperazin-1-yl)-7-azaspiro[3.5]nonane-7-carboxylate (0.9 g, yield: 62%) as a yellow oil.

Step 2: tert-butyl 2-(2-(2-isopropylphenyl)-4-((1-methyl-1H-pyrazol-4-yl)methyl)piperazin-1-yl)-7-azaspiro[3.5]nonane-7-carboxylate.

A mixture of 2-(2-(2-isopropylphenyl)-4-((1-methyl-1H-pyrazol-4-yl)methyl)-6-oxopiperazin-1-yl)-7-azaspiro[3.5]nonane-7-carboxylate (0.9 g, 1.68 mmol) and BH₃·THF (16.80 mL, 16.8 mmol) in THF (20 mL) was stirred at 70° C. for 12 hrs. The reaction solution was quenched by MeOH (20 mL) and stirred at 0° C. for 1 hr. The mixture was concentrated under reduced pressure to give tert-butyl 2-(2-(2-isopropylphenyl)-4-((1-methyl-1H-pyrazol-4-yl)methyl)piperazin-1-yl)-7-azaspiro[3.5]nonane-7-carboxylate as a white oil, which was used directly for next step without further purification. MS (ESI, m/e) [M+1]+522.4.

Step 3: 2-(2-(2-isopropylphenyl)-4-((1-methyl-1H-pyrazol-4-yl)methyl)piperazin-1-yl)-7-azaspiro[3.5]nonane.

A mixture of tert-butyl 2-(2-(2-isopropylphenyl)-4-((1-methyl-1H-pyrazol-4-yl)methyl)piperazin-1-yl)-7-azaspiro[3.5]nonane-7-carboxylate (900 mg, 1.73 mmol) and HCl (4.31 mL, 17.25 mmol) in MeOH (10 mL) was stirred at 25° C. for 2 hrs. The reaction solution was concentrated under reduced pressure. The reaction mixture was poured into saturated NaHCO₃ (10 mL), extracted with EtOAc (20 mL×2). The combined organic layers were washed with brine, dried with anhydrous Na₂SO₄, filtered and concentrated under reduced pressure to give 2-(2-(2-isopropylphenyl)-4-((1-methyl-1H-pyrazol-4-yl)methyl)piperazin-1-yl)-7-azaspiro[3.5]nonane (518 mg, yield: 71%) as a yellow solid. ¹H NMR (400 MHz, CDCl₃) δ ppm: 7.47 (br s, 1H), 7.38 (s, 1H), 7.25-7.19 (m, 2H), 7.13 (t, 1H), 3.85 (s, 4H), 3.65 (m, 1H), 3.49 (s, 2H), 3.44-3.32 (m, 3H), 3.02 (m, 1H), 2.70-2.55 (m, 6H), 2.31-2.05 (m, 4H), 1.71-1.60 (m, 3H), 1.25 (m, 4H), 1.17 (m, 6H). MS (ESI, m/e) [M+1]+422.4.

Intermediate 22-1a: (R or S)-2-(2-(2-isopropylphenyl)-4-((1-methyl-JH-pyrazol-4-yl)methyl)piperazin-1-yl)-7-azaspiro[3.5]nonane

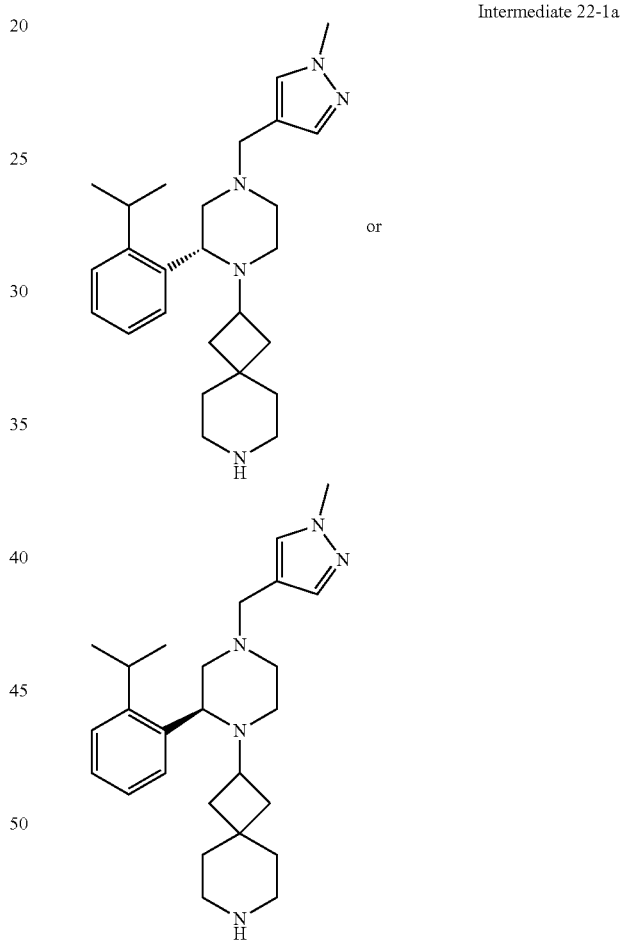

Intermediate 22-1a

Tert-butyl 2-(2-(2-isopropylphenyl)-6-oxopiperazin-1-yl)-7-azaspiro[3.5]nonane-7-carboxylate (20 g, 45.29 mmol) was separated by SFC (Instrument: Thar SFC350 preparative SFC; Column: REGIS(s,s)WHELK-O1, 250×50 mm i.d.: 10 um; Mobile phase: A for CO2 and B for MeOH(0.1% NH3·H2O); Gradient: B %=45%; Flow rate: 200 g/min; Wavelength: 220 nm; Column temperature: 40° C.; System back pressure: 100 bar). (R or S)-tert-butyl 2-(2-(2-isopropylphenyl)-6-oxopiperazin-1-yl)-7-azaspiro[3.5]nonane-7-carboxylate (retention time: 2.55 min, 8.4 g) was obtained, yield: 43%. (S or R)-tert-butyl 2-(2-(2-isopropylphenyl)-6-oxopiperazin-1-yl)-7-azaspiro[3.5]nonane-7-carboxylate (retention time: 2.73 min, 8.3 g) was obtained, yield: 42%.

Step 1: tert-butyl (R or S)-2-(2-(2-isopropylphenyl)-4-((1-methyl-1H-pyrazol-4-yl)methyl)-6-oxopiperazin-1-yl)-7-azaspiro[3.5]nonane-7-carboxylate.

To a solution of tert-butyl (R or S)-2-(2-(2-isopropylphenyl)-6-oxopiperazin-1-yl)-7-azaspiro[3.5]nonane-7-carboxylate (1.0 g, 2.26 mmol) and 1-methyl-1H-pyrazole-4-carbaldehyde (274.28 mg, 2.49 mmol) in DCE (10 mL) was added AcOH (271.97 mg, 4.53 mmol) and NaBH(OAc)$_3$ (1.44 g, 6.79 mmol). The mixture was stirred at 25° C. for 12 hrs. The reaction mixture was extracted with aq. Na$_2$CO$_3$ (10 mL) and DCM (10 mL×3), dried over Na$_2$SO$_4$, filtered and concentrated under reduced pressure. The residue was purified by MPLC. The compound tert-butyl (R or S)-2-(2-(2-isopropylphenyl)-4-((1-methyl-1H-pyrazol-4-yl)methyl)-6-oxopiperazin-1-yl)-7-azaspiro[3.5]nonane-7-carboxylate (950 mg, 1.77 mmol, yield: 78%) was obtained as a yellow oil. $^1$H NMR (400 MHz, CDCl$_3$) δ ppm: 7.35-7.30 (m, 2H), 7.22-7.17 (m, 1H), 7.10 (m, 1H), 7.07 (s, 1H), 6.37 (s, 1H), 4.96 (s, 1H), 4.43 (s, 1H), 3.66 (s, 3H), 3.53-3.45 (m, 2H), 3.29-3.12 (m, 6H), 3.02 (m, 1H), 2.66 (s, 2H), 2.29-2.19 (m, 1H), 1.92 (m, 1H), 1.82-1.67 (m, 2H), 1.53-1.45 (m, 2H), 1.41 (s, 9H), 1.36-1.31 (m, 2H), 1.24 (m, 3H), 1.03 (m, 3H).

Step 2: tert-butyl (R or S)-2-(2-(2-isopropylphenyl)-4-((1-methyl-1H-pyrazol-4-yl)methyl)piperazin-1-yl)-7-azaspiro[3.5]nonane-7-carboxylate.

A mixture of tert-butyl (R or S)-2-(2-(2-isopropylphenyl)-4-((1-methyl-1 H-pyrazol-4-yl)methyl)-6-oxopiperazin-1-yl)-7-azaspiro[3.5]nonane-7-carboxylate (950 mg, 1.77 mmol) in BH$_3$·THF (15 mL) was stirred at 70° C. for 12 hrs. The reaction mixture was quenched by MeOH (20 mL) at 0° C. and stirred at 25° C. for 30 min. Then the mixture was concentrated under reduced pressure to afford tert-butyl (R or S)-2-(2-(2-isopropylphenyl)-4-((1-methyl-1H-pyrazol-4-yl)methyl)piperazin-1-yl)-7-azaspiro[3.5]nonane-7-carboxylate (900 mg, 1.73 mmol, crude) as a white solid. MS (ESI, m/e) [M+1]+522.3.

Step 3: (R or S)-2-(2-(2-isopropylphenyl)-4-((1-methyl-1H-pyrazol-4-yl)methyl)piperazin-1-yl)-7-azaspiro[3.5]nonane.

A mixture of tert-butyl (R or S)-2-(2-(2-isopropylphenyl)-4-((1-methyl-1H-pyrazol-4-yl)methyl)piperazin-1-yl)-7-azaspiro[3.5]nonane-7-carboxylate (900 mg, 1.73 mmol) in HCl/MeOH (10 mL) solution was stirred at 25° C. for 2 hrs. The reaction mixture was concentrated under reduced pressure to remove solvent. The residue was dilute with H$_2$O (10 mL), and added Na$_2$CO$_3$ to pH=9, the mixture was extracted with EtOAc (10 mL×3), dried over Na$_2$SO$_4$, filtered and concentrated under reduced pressure to remove solvent. The compound (R or S)-2-(2-(2-isopropylphenyl)-4-((1-methyl-1H-pyrazol-4-yl)methyl)piperazin-1-yl)-7-azaspiro[3.5]nonane (492 mg, 1.07 mmol, yield: 62.24%) was obtained as a white solid. $^1$H NMR (400 MHz, CDCl$_3$) δ ppm: 7.47 (m, 1H), 7.38 (s, 1H), 7.27-7.20 (m, 3H), 7.15-7.09 (m, 1H), 3.84 (s, 3H), 3.69-3.60 (m, 1H), 3.48-3.35 (m, 3H), 2.99 (m, 1H), 2.96-2.86 (m, 2H), 2.68 (m, 5H), 2.26 (m, 2H), 2.22-2.06 (m, 2H), 1.83-1.73 (m, 1H), 1.67 (m, 1H), 1.50-1.32 (m, 5H), 1.24 (m, 3H), 1.17 (in, 3H). MS (ESI, m/e) [M+1]+422.3.

Following the similar procedure of Intermediate 22-1a: (S or R)-2-(2-(2-isopropylphenyl)-4-((1-methyl-1H-pyrazol-4-yl)methyl)piperazin-1-yl)-7-azaspiro[3.5]nonane was obtained (607 mg, intermediate 22-1b) with (S or R)-tert-butyl 2-(2-(2-isopropylphenyl)-6-oxopiperazin-1-yl)-7-azaspiro[3.5]nonane-7-carboxylate as starting material, yield: 82%. MS (ESI, m/e) [M+1]+422.4.

Intermediate 23-1: 2-(4-benzyl-2-(2-isopropylphenyl)piperazin-1-yl)-7-azaspiro[3.5]nonane

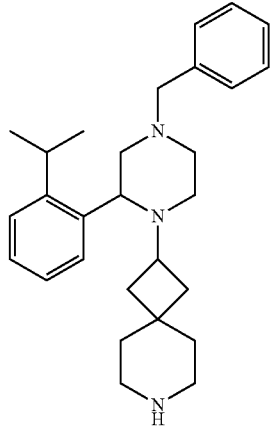

Intermediate 23-1

Step 1: tert-butyl 2-(4-benzyl-2-(2-isopropylphenyl)-6-oxopiperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), benzaldehyde (360.46 mg, 3.40 mmol) and AcOH (271.97 mg, 4.53 mmol) in DCE (20 mL) was stirred at 25° C. for 30 min. Then NaBH(OAc)$_3$ (1.44 g, 6.79 mmol) was added in portions to the mixture and stirred at 20° C. for 3 hrs. The mixture was washed with sat. NaHCO$_3$ (20 mL×2), dried with anhydrous Na$_2$SO$_4$, filtered and concentrated. The crude was purified by column chromatography (silica gel, eluent: PE/EA (v/v)=5/1 to 1/1) to give tert-butyl 2-(4-benzyl-2-(2-isopropylphenyl)-6-oxopiperazin-1-yl)-7-azaspiro[3.5]nonane-7-carboxylate (1.0 g, 1.88 mmol, yield: 83%) as a white solid. $^1$H NMR (400 MHz, CDCl$_3$) δ ppm: 7.33-7.29 (m, 1H), 7.26-7.17 (m, 2H), 7.16-7.04 (m, 4H), 6.85 (d, J=6.8 Hz, 2H), 4.95 (s, 1H), 4.43 (s, 1H), 3.61 (m, 1H), 3.52 (m, 1H), 3.35-3.12 (m, 7H), 2.96 (m, 1H), 2.73-2.56 (m, 2H), 2.23 (m, 1H), 1.94 (m, 1H), 1.67-1.82 (m, 2H), 1.48 (m, 2H), 1.42 (s, 9H), 1.33 (s, 1H), 1.21 (d, J=6.8 Hz, 3H), 0.92 (d, J=6.8 Hz, 3H).

Step 2: tert-butyl 2-(4-benzyl-2-(2-isopropylphenyl)piperazin-1-yl)-7-azaspiro[3.5]nonane-7-carboxylate.

To a solution of tert-butyl 2-(4-benzyl-2-(2-isopropylphenyl)-6-oxopiperazin-1-yl)-7-azaspiro[3.5]nonane-7-carboxylate (1.0 g, 1.88 mmol) in THF (10 mL) was added BH$_3$·THF (30 mL, 30 mmol) dropwise at 25° C. The mixture was heated to 75° C. for 12 hrs. The reaction was quenched by ethanol (10 mL), concentrated under reduced pressure to give tert-butyl 2-(4-benzyl-2-(2-isopropylphenyl)piperazin-1-yl)-7-azaspiro[3.5]nonane-7-carboxylate (970 mg, crude) as a white solid. MS (ESI, m/e) [M+1]+518.5.

Step 3: 2-(4-benzyl-2-(2-isopropylphenyl)piperazin-1-yl)-7-azaspiro[3.5]nonane.

To a solution of tert-butyl 2-(4-benzyl-2-(2-isopropylphenyl)piperazin-1-yl)-7-azaspiro[3.5]nonane-7-carboxylate (970 mg, 1.82 mmol) in MeOH (10 mL) was added HCl/MeOH (10 mL, 4M) dropwise at 25° C. The solution was stirred at 20° C. for 4 hrs. The reaction solution was concentrated in vacuum. The residue was diluted with HCl (5 mL, 1M), extracted with EtOAc (10 mL×2). The aqueous phase was adjusted the pH=8 with NaHCO₃, extracted with EtOAc (20 mL×5). The combined organic phases were dried with anhydrous Na$_2$SO$_4$, filtered and concentrated to give 2-(4-benzyl-2-(2-isopropylphenyl)piperazin-1-yl)-7-azaspiro[3.5]nonane (529 mg, 1.27 mmol, yield: 68%) as a white solid. $^1$H NMR (400 MHz, CDCl$_3$) δ ppm: 7.47 (d, J=4.4 Hz, 1H), 7.28 (m, 4H), 7.24-7.15 (m, 3H), 7.14-7.06 (m, 1H), 3.83-3.56 (m, 2H), 3.51 (s, 2H), 3.37 (d, J=6.8 Hz, 1H), 3.01-2.86 (m, 3H), 2.80-2.59 (m, 5H), 2.38-2.25 (m, 2H), 2.22-2.13 (m, 1H), 1.84-1.54 (m, 3H), 1.53-1.39 (m, 4H), 1.35-1.28 (m, 1H), 1.25-1.22 (d, J=6.8 Hz, 3H), 1.12 (d, J=6.8 Hz, 3H). MS (ESI, m/e) [M+1]$^+$418.4.

Intermediate 24-1: 2-(2-(2-isopropylphenyl)-4-(1-phenylethyl)piperazin-1-yl)-7-azaspiro[3.5]nonane Intermediate 24-1

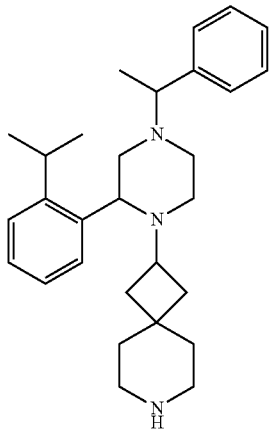

Step 1: tert-butyl 2-(2-(2-isopropylphenyl)-6-oxo-4-(1-phenylethyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DMF (10 mL) was added (1-bromoethyl)benzene (0.84 g, 4.53 mmol) and Cs$_2$CO$_3$ (2.21 g, 6.79 mmol). The mixture was stirred at 80° C. for 2 hrs. The mixture was added saturated NH$_4$Cl (50 mL), extracted with EtOAc (30 mL×3). The combined organic phases were dried over anhydrous Na$_2$SO$_4$, filtered and concentrated in vacuum. The residue was purified by column chromatography (silica gel, eluent: PE/EA (v/v)=5/1) to give tert-butyl 2-(2-(2-isopropylphenyl)-6-oxo-4-(1-phenylethyl)piperazin-1-yl)-7-azaspiro[3.5]nonane-7-carboxylate (1.2 g, yield: 73%) as a colorless oil.

Step 2: tert-butyl 2-(2-(2-isopropylphenyl)-4-(1-phenylethyl)piperazin-1-yl)-7-azaspiro[3.5]nonane-7-carboxylate.

A mixture of tert-butyl 2-(2-(2-isopropylphenyl)-6-oxo-4-(1-phenylethyl)piperazin-1-yl)-7-azaspiro[3.5]nonane-7-carboxylate (1.1 g, 2.02 mmol) and BH$_3$·THF(10 mL) in THF (10 mL) was stirred at 70° C. for 16 hrs. After cooling to 0° C., the mixture was added MeOH (20 mL) dropwise and concentrated under reduced pressure to give tert-butyl 2-(2-(2-isopropylphenyl)-4-(1-phenylethyl)piperazin-1-yl)-7-azaspiro[3.5]nonane-7-carboxylate (1.1 g, crude) as a colorless oil, which was used directly next step without purification. MS (ESI, m/e) [M+1]$^+$532.4.

Step 3: 2-(2-(2-isopropylphenyl)-4-(1-phenylethyl)piperazin-1-yl)-7-azaspiro[3.5]nonane.

A mixture of tert-butyl 2-(2-(2-isopropylphenyl)-4-(1-phenylethyl)piperazin-1-yl)-7-azaspiro[3.5]nonane-7-carboxylate (1.0 g, 1.88 mmol) in HCl/EtOAc (10 mL, 4M) was stirred at 20° C. for 16 hrs. After removed the solvent, the residue was purified by prep-HPLC (TFA). The mixture was concentrated in vacuum, added H$_2$O (50 mL) and adjusted the pH=11 using aqueous NaOH (2 M). The mixture was extracted with EtOAc (10 mL×3). The combined organic phases were dried with anhydrous Na$_2$SO$_4$, filtered and concentrated under reduced pressure to give 2-(2-(2-isopropylphenyl)-4-(1-phenylethyl)piperazin-1-yl)-7-azaspiro [3.5]nonane (537 mg, yield: 66%) as a white gum. $^1$H NMR (400 MHz, CDCl$_3$) δ ppm: 7.57-7.35 (m, 2H), 7.31 (m, 2H), 7.27-7.22 (m, 3H), 7.18-7.05 (m, 2H), 3.69-3.53 (m, 1H), 3.40-3.34 (m, 1H), 3.16-3.05 (m, 1H), 3.02-2.82 (m, 3H), 2.75-2.52 (m, 5H), 2.46-2.25 (m, 3H), 2.24-2.09 (m, 2H), 1.71-1.64 (m, 1H), 1.37 (m, 3H), 1.33 (m, 3H), 1.31-1.26 (m, 2H), 1.22 (m, 3H), 1.01 (m, 1H). MS (ESI, m/e) [M+1]$^+$432.4.

Intermediate 25-1: 2-(2-(2-isopropylphenyl)-4-(1,2,3,4-tetrahydronaphthalen-1-yl)piperazin-1-yl)-7-azaspiro[3.5]nonane Intermediate 25-1

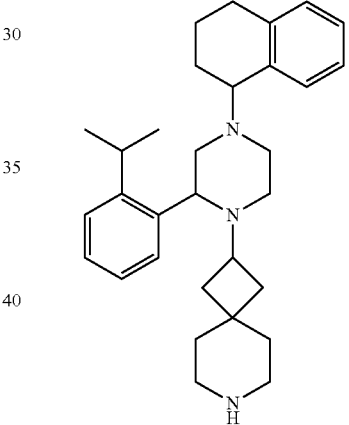

Step 1: 1,2,3,4-tetrahydronaphthalen-1-ol.

To a solution of 3,4-dihydronaphthalen-1(2H)-one (8.0 g, 54.72 mmol) in THF (100 mL) was added NaBH$_4$ (8.24 g, 219 mmol) at 0° C. The mixture was stirred at 20° C. for 4 hrs. The mixture was poured into H$_2$O (80 mL), extracted with EtOAc (50 mL×2). The combined organic phases were dried over anhydrous Na$_2$SO$_4$, filtered and concentrated in vacuum to give 1,2,3,4-tetrahydronaphthalen-1-ol (6.0 g, yield: 74%) as a yellow oil, which was used directly for next step without further purification.

Step 2: 1-bromo-1,2,3,4-tetrahydronaphthalene.

A mixture of 1,2,3,4-tetrahydronaphthalen-1-ol (4.0 g, 26.99 mmol) and TMSBr (4.96 g, 32.39 mmol) was stirred to 20° C. for 16 hrs. The mixture was poured into H$_2$O (50 mL), extracted with EtOAc (20 mL×3). The combined organic phases were dried over anhydrous Na$_2$SO$_4$, filtered and concentrated in vacuum. The residue was purified by column chromatography (silica gel, eluent: PE/EA (v/v)=5/1) to give 1-bromo-1,2,3,4-tetrahydronaphthalene (5.0 g, yield: 87%) as a yellow oil.

Step 3: tert-butyl 2-(2-(2-isopropylphenyl)-6-oxo-4-(1,2,3,4-tetrahydronaphthalen-1-yl)piperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), 1-bromo-1,2,3,4-tetrahydronaphthalene (956 mg, 14.53 mmol) and Cs$_2$CO$_3$ (2.21 g, 6.79 mmol) in DMF (10 mL) was stirred at 80° C. for 16 hrs. The mixture was poured into saturated NH$_4$Cl (50 mL), extracted with EtOAc (30 mL×2). The combined organic phases were dried over anhydrous Na$_2$SO$_4$, filtered and concentrated in vacuum. The residue was purified by column chromatography (silica gel, eluent: PE/EA (v/v)=6/1) to give tert-butyl 2-(2-(2-isopropylphenyl)-6-oxo-4-(1,2,3,4-tetrahydronaphthalen-1-yl)piperazin-1-yl)-7-azaspiro[3.5]nonane-7-carboxylate (0.9 g, yield: 69%) as a yellow oil. MS (ESI, m/e) [M+1]$^+$572.4.

Step 4: tert-butyl 2-(2-(2-isopropylphenyl)-4-(1,2,3,4-tetrahydronaphthalen-1-yl)piperazin-1-yl)-7-azaspiro[3.5]nonane-7-carboxylate.

A mixture of tert-butyl 2-(2-(2-isopropylphenyl)-6-oxo-4-(1,2,3,4-tetrahydronaphthalen-1-yl)piperazin-1-yl)-7-azaspiro[3.5]nonane-7-carboxylate (0.8 g, 1.4 mmol) and BH$_3$·THF (5 mL, 5 mmol) in THF (5 mL) was stirred at 70° C. for 16 hrs. After cooling to 0° C., the mixture was added MeOH (10 mL) dropwise and concentrated under reduced pressure to give tert-butyl 2-(2-(2-isopropylphenyl)-4-(1,2,3,4-tetrahydronaphthalen-1-yl)piperazin-1-yl)-7-azaspiro[3.5]nonane-7-carboxylate (0.8 g, crude) as a colorless oil, which was used directly next step without purification.

Step 5: 2-(2-(2-isopropylphenyl)-4-(1,2,3,4-tetrahydronaphthalen-1-yl)piperazin-1-yl)-7-azaspiro[3.5]nonane.

A mixture of tert-butyl 2-(2-(2-isopropylphenyl)-4-(1,2,3,4-tetrahydronaphthalen-1-yl) piperazin-1-yl)-7-azaspiro[3.5]nonane-7-carboxylate (700 mg, 1.25 mmol) in HCl/EtOAc (10 mL, 4M) was stirred at 20° C. for 3 hrs. After removed the solvent, the residue was purified by prep-HPLC (TFA). The mixture was concentrated in vacuum and adjusted the pH=9-10 using aqueous NaOH (1 M). The mixture was extracted with EtOAc (10 mL×3). The combined organic phases were dried with anhydrous Na$_2$SO$_4$, filtered and concentrated in vacuum to give 2-(2-(2-isopropylphenyl)-4-(1,2,3,4-tetrahydronaphthalen-1-yl)piperazin-1-yl)-7-azaspiro[3.5]nonane (365 mg, yield: 64%) as a white solid. $^1$H NMR (400 MHz, CDCl$_3$) δ ppm: 7.76 (m, 1H), 7.57-7.42 (m, 1H), 7.24-7.12 (m, 4H), 7.09-6.98 (m, 2H), 3.89-3.39 (m, 4H), 3.16-2.85 (m, 4H), 2.73-2.60 (m, 6H), 2.55-2.33 (m, 2H), 2.24-2.15 (m, 1H), 1.95 (m, 2H), 1.73-1.62 (m, 4H), 1.37-1.22 (m, 11H), 1.02 (m, 1H). MS (ESI, m/e) [M+1]$^+$458.3.

Intermediate 26-1: 2-(2-(2-isopropylphenyl)-4-phenethylpiperazin-1-yl)-7-azaspiro[3.5]nonane

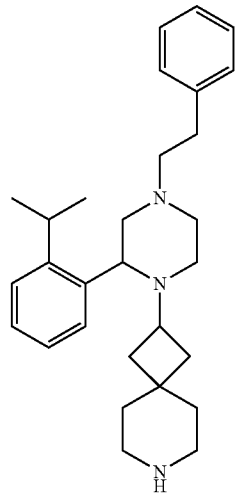

Intermediate 26-1

Step 1: tert-butyl 2-(2-(2-isopropylphenyl)-6-oxo-4-phenethylpiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (700 mg, 1.59 mmol) in DCE (10 mL) was added 2-phenylacetaldehyde (285.7 mg, 2.38 mmo), HOAc (190.38 mg, 3.17 mmol) and NaBH(OAc)$_3$ (739.1 mg, 3.49 mmol). The solution was stirred at 25° C. for 12 hrs. The reaction was poured into sat. NaHCO$_3$ until pH=7, extracted with DCM (10 mL×3). The combined organic layers were washed with brine, dried over Na$_2$SO$_4$, filtered and concentrated under reduced pressure. The residue was purified by column chromatography (silica gel, eluent: PE/EA (v/v)=10/1 to 2/1) to give tert-butyl 2-(2-(2-isopropylphenyl)-6-oxo-4-phenethylpiperazin-1-yl)-7-azaspiro[3.5]nonane-7-carboxylate (0.5 g, yield: 58%) as a yellow oil. $^1$H NMR (400 MHz, CDCl$_3$) δ ppm: 7.34-7.28 (m, 2H), 7.25-7.03 (m, 6H), 6.85 (d, J=7.2 Hz, 2H), 4.95 (br s, 1H), 4.42 (br s, 1H), 3.68-3.46 (m, 2H), 3.37-3.09 (m, 7H), 2.97 (t, 1H), 2.73-2.56 (m, 2H), 2.32-2.18 (m, 1H), 2.02-1.85 (m, 1H), 1.83-1.67 (m, 2H), 1.42 (s, 9H), 1.22 (d, J=6.8 Hz, 3H), 0.93 (d, J=6.8 Hz, 3H).

Step 2: tert-butyl 2-(2-(2-isopropylphenyl)-4-phenethylpiperazin-1-yl)-7-azaspiro[3.5]nonane-7-carboxylate.

A solution of tert-butyl 2-(2-(2-isopropylphenyl)-6-oxo-4-phenethylpiperazin-1-yl)-7-azaspiro[3.5]nonane-7-carboxylate (0.6 g, 1.1 mmol) in BH$_3$·THF (10 mL, 1M) was stirred at 70° C. for 12 hrs. The reaction was quenched by MeOH (5 mL) at 0° C. and stirred at 25° C. for 30 min. The mixture was concentrated under reduced pressure to give tert-butyl 2-(2-(2-isopropylphenyl)-4-phenethylpiperazin-1-yl)-7-azaspiro[3.5]nonane-7-carboxylate (600 mg, crude) as a yellow oil. MS (ESI, m/e) [M+1]$^+$532.5.

Step 3: 2-(2-(2-isopropylphenyl)-4-phenethylpiperazin-1-yl)-7-azaspiro[3.5]nonane.

A solution of tert-butyl 2-(2-(2-isopropylphenyl)-4-phenethylpiperazin-1-yl)-7-azaspiro[3.5]nonane-7-carboxylate (0.6 g, 1.1 mmol) in TFA (1 mL) and DCM (10 mL) was stirred at 20° C. for 12 hrs. The reaction mixture was poured into aq. Na$_2$CO$_3$ (300 mL), extracted with DCM (20 mL×3). The combined organic layers were washed with brine, dried over Na$_2$SO$_4$, filtered and concentrated under reduced pressure. The crude product was purified by prep-HPLC (HCQ) to give 2-(2-(2-isopropylphenyl)-4-phenethylpiperazin-1-yl)-7-azaspiro[3.5]nonane (130 mg, HCl salt, yield: 27% via two steps) as a white solid. ¹H NMR (400 MHz, CH₃OH-d₄) δ ppm: 7.96 (d, J=7.6 Hz, 1H), 7.51-7.49 (m, 2H), 7.36-7.26 (m, 5H), 5.25 (s, 1H), 4.05 (m, 1H), 3.85-3.54 (m, 4H), 3.54-3.31 (m, 4H), 3.20-3.17 (m, 2H), 3.03-2.95 (m, 4H), 2.33 (m, 1H), 1.75-1.71 (m, 3H), 1.64-1.61 (m, 2H), 1.38 (d, J=6.8 Hz, 3H), 1.28 (d, J=6.8 Hz, 3H). MS (ESI, m/e) [M+1]⁺432.4.

Intermediate 28-1: 2-(4-(4-fluorobenzyl)-2-(2-isopropylphenyl)piperazin-1-yl)-7-azaspiro[3.5]nonane

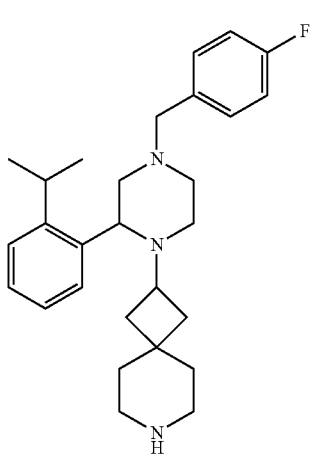

Intermediate 28-1

Step 1: tert-butyl 2-(4-(4-fluorobenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (700 mg, 1.59 mmol) in DCE (10 mL) was added 4-fluorobenzaldehyde (671.9 mg, 3.17 mmol), HOAc (190.38 mg, 3.17 mmol) and NaBH(OAc)₃ (190.38 mg, 3.17 mmol). The solution was stirred at 25° C. for 12 hrs. The reaction was added sat. NaHCO₃ until pH=7, extracted with DCM (10 mL×3). The combined organic layers were washed with brine, dried over Na₂SO₄, filtered and concentrated under reduced pressure. The residue was purified by column chromatography (silica gel, eluent: PE/EA (v/v)=10/1 to 2/1) to give tert-butyl 2-(4-(4-fluorobenzyl)-2-(2-isopropylphenyl)-6-oxopiperazin-1-yl)-7-azaspiro[3.5]nonane-7-carboxylate (0.5 g, yield: 57.3%) as a yellow oil. ¹H NMR (400 MHz, CDCl₃) δ ppm: 7.23-7.03 (m, 3H), 6.70-6.67 (m, 4H), 4.85 (s, 3H), 4.37 (s, 1H), 3.51-3.43 (m, 2H), 3.20-3.04 (m, 6H), 2.57-2.54 (m, 1H), 2.20-2.10 (m, 2H), 1.82-1.91 (m, 1H), 1.66-1.58 (m, 2H), 1.45-1.38 (m, 2H), 1.20-1.17 (m, 2H), 1.34 (s, 9H), 1.14 (d, J=6.8 Hz, 3H), 0.85 (d, J=6.8 Hz, 3H).

Step 2: tert-butyl 2-(4-(4-fluorobenzyl)-2-(2-isopropylphenyl)piperazin-1-yl)-7-azaspiro[3.5]nonane-7-carboxylate.

To a solution of tert-butyl 2-(4-(4-fluorobenzyl)-2-(2-isopropylphenyl)-6-oxopiperazin-1-yl)-7-azaspiro[3.5]nonane-7-carboxylate (0.5 g, 0.91 mmol) in BH₃·THF (10 mL) was stirred at 60° C. for 12 hrs. The reaction mixture was quenched by MeOH (10 mL) at 0° C. and stirred at 25° C. for 30 min. The mixture was concentrated under reduced pressure to give tert-butyl 2-(4-(4-fluorobenzyl)-2-(2-isopropylphenyl)piperazin-1-yl)-7-azaspiro[3.5]nonane-7-carboxylate (600 mg, crude) as a yellow oil, which was used directly without further purification. MS (ESI, m/e) [M+1]⁺ 536.4.

Step 3: 2-(4-(4-fluorobenzyl)-2-(2-isopropylphenyl)piperazin-1-yl)-7-azaspiro[3.5]nonane.

To a solution of tert-butyl 2-(4-(4-fluorobenzyl)-2-(2-isopropylphenyl)piperazin-1-yl)-7-azaspiro[3.5]nonane-7-carboxylate (0.6 g, 1.12 mmol) in DCM (10 mL) was added TFA (1 mL). The solution was stirred at 25° C. for 12 hrs. The mixture was concentrated under reduced pressure. The residue was poured into aq. Na₂CO₃ (30 mL), extracted with DCM (20 mL×3). The combined organic layers were washed with brine, dried over Na₂SO₄, filtered and concentrated under reduced pressure to give 2-(4-(4-fluorobenzyl)-2-(2-isopropylphenyl)piperazin-1-yl)-7-azaspiro[3.5] nonane (300 mg, yield: 62%) as a yellow solid. ¹H NMR (400 MHz, CDCl₃) δ ppm: 7.47 (s, 1H), 7.25-7.12 (m, 3H), 6.99-6.95 (m, 2H), 3.64-3.63 (m, 1H), 3.48 (s, 1H), 2.98-2.87 (m, 2H), 2.65-2.59 (m, 4H), 2.30-2.29 (m, 3H), 1.92 (m, 4H), 1.75 (m, 1H), 1.65 (t, 1H), 1.35-1.32 (m, 4H), 1.25 (d, J=6.8 Hz, 3H), 1.13 (d, J=6.8 Hz, 3H). MS (ESI, m/e) [M+1]⁺436.3.

Intermediate 28-1a: (R or S)-2-(4-(4-fluorobenzyl)-2-(2-isopropylphenyl)piperazin-1-yl)-7-azaspiro[3.5]nonane

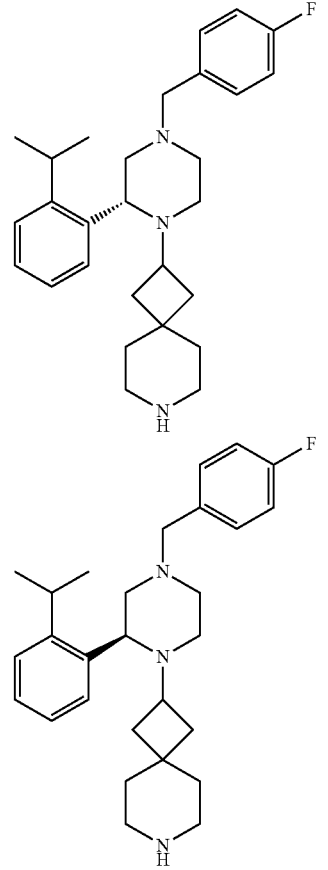

Intermediate 28-1a or

Step 1: tert-butyl (R or S)-2-(4-(4-fluorobenzyl)-2-(2-isopropylphenyl)-6-oxopiperazin-1-yl)-7-azaspiro[3.5]nonane-7-carboxylate.

To a solution of tert-butyl (R or S)-2-(2-(2-isopropylphenyl)-6-oxopiperazin-1-yl)-7-azaspiro[3.5]nonane-7-carboxylate (1.0 g, 2.26 mmol) in DCE (10 mL) was added 4-fluorobenzaldehyde (353.97 mg, 2.49 mmol), HOAc (271.97 mg, 4.53 mmol) and NaBH(OAc)$_3$ (1.44 g, 6.79 mmol). The mixture was stirred at 25° C. for 12 hrs. The reaction was added sat. NaHCO$_3$ until pH=9, extracted with DCM (10 mL×3). The combined organic layers were washed with brine, dried over Na$_2$SO$_4$, filtered and concentrated under reduced pressure. The residue was purified by column chromatography (silica gel, eluent: PE/EA (v/v)= 10/1 to 2/1) to give tert-butyl (R or S)-2-(4-(4-fluorobenzyl)-2-(2-isopropylphenyl)-6-oxopiperazin-1-yl)-7-azaspiro[3.5]nonane-7-carboxylate (0.9 g, yield: 72%) as a yellow oil.

Step 2: tert-butyl (R or S)-2-(4-(4-fluorobenzyl)-2-(2-isopropylphenyl)piperazin-1-yl)-7-azaspiro[3.5]nonane-7-carboxylate.

To a solution of tert-butyl (R or S)-2-(4-(4-fluorobenzyl)-2-(2-isopropylphenyl)-6-oxopiperazin-1-yl)-7-azaspiro[3.5]nonane-7-carboxylate (0.9 g, 1.64 mmol) in BH$_3$·THF (16.5 mL) was stirred at 70° C. for 12 hrs. The reaction mixture was quenched with MeOH (10 mL) at 0° C. and stirred at 25° C. for 30 min. The mixture was concentrated under reduced pressure to give tert-butyl (R or S)-2-(4-(4-fluorobenzyl)-2-(2-isopropylphenyl)piperazin-1-yl)-7-azaspiro[3.5]nonane-7-carboxylate (1.0 g, crude) as a yellow oil, which was used directly without further purification. MS (ESI, m/e) [M+1]536.5.

Step 3: (R or S)-2-(4-(4-fluorobenzyl)-2-(2-isopropylphenyl)piperazin-1-yl)-7-azaspiro[3.5]nonane.

To a solution of tert-butyl (R or S)-2-(4-(4-fluorobenzyl)-2-(2-isopropylphenyl)piperazin-1-yl)-7-azaspiro[3.5]nonane-7-carboxylate (1.0 g, 1.87 mmol) in MeOH (10 mL) was added HCl (4.67 mL). The mixture was stirred at 25° C. for 2 hrs. The mixture was concentrated under reduced pressure. The residue was poured into saturated Na$_2$CO$_3$ (30 mL), extracted with DCM (20 mL×3). The combined organic layers were washed with brine, dried over Na$_2$SO$_4$, filtered and concentrated under reduced pressure to give (R or S)-2-(4-(4-fluorobenzyl)-2-(2-isopropylphenyl)piperazin-1-yl)-7-azaspiro[3.5]nonane (435 mg, yield: 58%) as a yellow solid. $^1$H NMR (400 MHz, CDCl$_3$) δ ppm: 7.48 (br s, 1H), 7.27-7.18 (m, 2H), 7.16-7.10 (m, 1H), 6.97 (t, 2H), 3.63 (m, 1H), 3.48 (s, 2H), 3.36 (br s, 1H), 3.05-2.97 (m, 1H), 2.94-2.84 (m, 2H), 2.66-2.56 (m, 3H), 2.35-2.25 (m, 2H), 2.20-2.13 (m, 2H), 1.86-1.57 (m, 4H), 1.28-1.47 (m, 5H), 1.24-1.27 (d, J=6.8 Hz, 3H), 1.13 (d, J=6.8 Hz, 3H). MS (ESI, m/e) [M+1]$^+$436.3

Intermediate 29-1: 2-(4-(4-chlorobenzyl)-2-(2-isopropylphenyl)piperazin-1-yl)-7-azaspiro[3.5]nonane

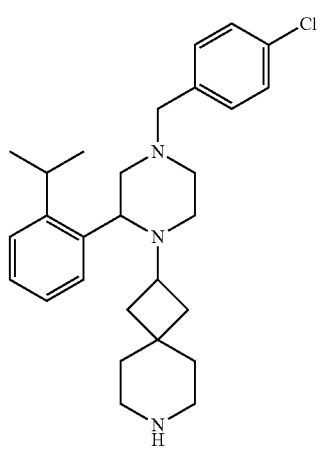

Intermediate 29-1

Step 1: tert-butyl 2-(4-(4-chlorobenzyl)-2-(2-isopropylphenyl)-6-oxopiperazin-1-yl)-7-azaspiro[3.5]nonane-7-carboxylate.

To a solution of tert-butyl2-(2-(2-isopropylphenyl)-6-oxopiperazin-1-yl)-7-azaspiro[3.5]nonane-7-carboxylate (1.2 g, 2.72 mmol) in DCE (10 mL) was added AcOH (326.36 mg, 5.43 mmol) and 4-chlorobenzaldehyde (420.71 mg, 2.99 mmol). The mixture was stirred at 25° C. for 1 hr. Then NaBH(OAc)$_3$ (1.73 g, 8.15 mmol) was added to the solution. The mixture was stirred at 25° C. for another 12 hrs. The reaction mixture was poured into sat. NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl 2-(4-(4-chlorobenzyl)-2-(2-isopropylphenyl)-6-oxopiperazin-1-yl)-7-azaspiro[3.5]nonane-7-carboxylate (1.2 g, 2.12 mmol, yield: 78%) as a yellow oil.

Step 2: tert-butyl 2-(4-(4-chlorobenzyl)-2-(2-isopropylphenyl)piperazin-1-yl)-7-azaspiro[3.5]nonane-7-carboxylate.

A mixture of tert-butyl 2-(4-(4-chlorobenzyl)-2-(2-isopropylphenyl)-6-oxopiperazin-1-yl)-7-azaspiro[3.5]nonane-7-carboxylate (1.2 g, 2.12 mmol) and BH$_3$·THF (21.19 mL, 21.19 mmol) in THF (10 mL) was stirred at 70° C. for 12 hrs. The reaction solution was quenched by MeOH (10 mL) and concentrated under reduced pressure to give tert-butyl 2-(4-(4-chlorobenzyl)-2-(2-isopropylphenyl)piperazin-1-yl)-7-azaspiro[3.5]nonane-7-carboxylate (1.2 g, crude), which was used directly for next step without further reaction.

Step 3: 2-(4-(4-chlorobenzyl)-2-(2-isopropylphenyl)piperazin-1-yl)-7-azaspiro[3.5]nonane.

To a mixture of tert-butyl 2-(4-(4-chlorobenzyl)-2-(2-isopropylphenyl)piperazin-1-yl)-7-azaspiro[3.5]nonane-7-carboxylate (1.2 g, 2.17 mmol) and HCl (5.43 mL, 21.73 mmol) in MeOH (30 mL) was stirred at 25° C. for 2 hrs. The reaction solution was concentrated under reduced pressure. The reaction mixture was poured into sat. NaHCO$_3$ (50 mL), extracted with EtOAc (100 mL×2). The combined organic layers were washed with brine, dried with anhydrous Na$_2$SO$_4$, filtered and concentrated under reduced pressure to give 2-(4-(4-chlorobenzyl)-2-(2-isopropylphenyl)piperazin- 1-yl)-7-azaspiro[3.5]nonane (445 mg, 1.36 mmol, yield: 45%) as an off-white solid. $^1$H NMR (400 MHz, CDCl$_3$) δ ppm: 7.49 (br s, 1H), 7.36-7.28 (m, 2H), 7.26-7.11 (m, 5H), 3.65 (br d, J=8.8 Hz, 1H), 3.50 (s, 3H), 3.05-2.97 (m, 2H), 2.96-2.86 (m, 3H), 2.68-2.58 (m, 7H), 2.36-2.14 (m, 4H), 1.71-1.64 (m, 3H), 1.28 (m, 4H), 1.16 (m, 6H). MS (ESI, m/e) [M+1]$^+$452.3.

Intermediate 29-1a: (R or S)-2-(4-(4-chlorobenzyl)-2-(2-isopropylphenyl)piperazin-1-yl)-7-azaspiro[3.5]nonane Intermediate 29-1a

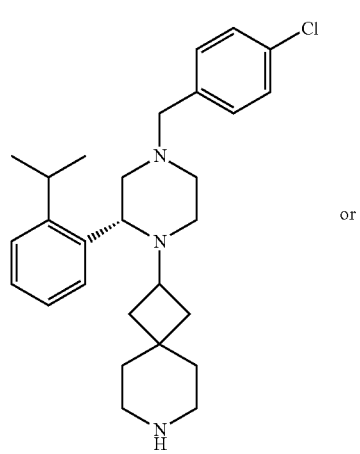

or

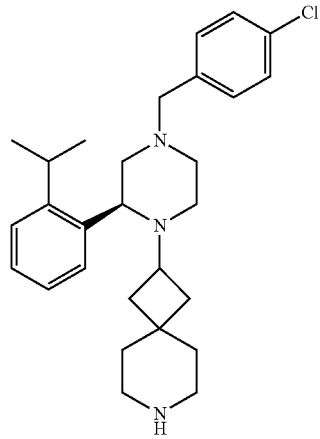

Step 1: tert-butyl (R or S)-2-(4-(4-chlorobenzyl)-2-(2-isopropylphenyl)-6-oxopiperazin-1-yl)-7-azaspiro[3.5]nonane-7-carboxylate.

To a solution of tert-butyl (R or S)-2-(2-(2-isopropylphenyl)-6-oxopiperazin-1-yl)-7-azaspiro[3.5]nonane-7-carboxylate (1.0 g, 2.26 mmol) in DCE (15 mL) was added AcOH (271.97 mg, 4.53 mmol) and 4-chlorobenzaldehyde (477.46 mg, 3.40 mmol). The mixture was stirred at 20° C. for 30 min, then NaBH(OAc)$_3$ (959.86 mg, 4.53 mmol) was added and stirred at 20° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl (R or S)-2-(4-(4-chlorobenzyl)-2-(2-isopropylphenyl)-6-oxopiperazin-1-yl)-7-azaspiro[3.5]nonane-7-carboxylate (1.0 g, yield: 78%) as a yellow oil.

Step 2: tert-butyl (R or S)-2-(4-(4-chlorobenzyl)-2-(2-isopropylphenyl)piperazin-1-yl)-7-azaspiro[3.5]nonane-7-carboxylate.

A mixture of tert-butyl (R or S)-2-(4-(4-chlorobenzyl)-2-(2-isopropylphenyl)-6-oxopiperazin-1-yl)-7-azaspiro[3.5]nonane-7-carboxylate (1.0 g, 1.77 mmol) and BH$_3$·THF (17.66 mL, 17.66 mmol) in THF (15 mL) was stirred at 70° C. for 12 hrs. The reaction solution was quenched with MeOH (10 mL) and concentrated under reduced pressure to give tert-butyl (R or S)-2-(4-(4-chlorobenzyl)-2-(2-isopropylphenyl)piperazin-1-yl)-7-azaspiro[3.5]nonane-7-carboxylate (1.0 g, crude), which was used directly for next step without further reaction.

Step 3: (R or S)-2-(4-(4-chlorobenzyl)-2-(2-isopropylphenyl)piperazin-1-yl)-7-azaspiro[3.5]nonane.

To a mixture of tert-butyl (R or S)-2-(4-(4-chlorobenzyl)-2-(2-isopropylphenyl)piperazin-1-yl)-7-azaspiro[3.5]nonane-7-carboxylate (1.0 g, 1.81 mmol) in MeOH (5 mL) was added HCl/MeOH solution (5 mL, 4M). The mixture was stirred at 20° C. for 2 hrs. The reaction solution was concentrated under reduced pressure. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure to give (R or S)-2-(4-(4-chlorobenzyl)-2-(2-isopropylphenyl)piperazin-1-yl)-7-azaspiro[3.5]nonane (322 mg, yield: 39%) as a yellow solid. $^1$H NMR (400 MHz, CDCl$_3$) δ ppm: 7.50 (br s, 1H), 7.27 (s, 4H), 7.25-7.19 (m, 2H), 7.15 (d, J=6.8 Hz, 1H), 3.67 (br s, 2H), 3.45-3.29 (m, 11H), 3.04-2.87 (m, 3H), 2.69-2.56 (m, 5H), 2.36-2.27 (m, 2H), 2.24-2.16 (m, 11H), 1.78 (s, 1H), 1.73-1.63 (m, 2H), 1.33 (m, 3H), 1.28 (br d, J=6.8 Hz, 4H), 1.16 (br d, J=6.4 Hz, 4H). MS (ESI, m/e) [M+1]$^+$452.4.

Intermediate 30-1: 2-(2-(2-isopropylphenyl)-4-(4-methylbenzyl)piperazin-1-yl)-7-azaspiro[3.5]nonane Intermediate 30-1

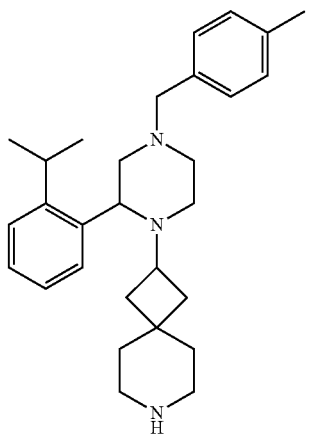

Step 1: tert-butyl 2-(2-(2-isopropylphenyl)-4-(4-methylbenzyl)-6-oxopiperazin-1-yl)-7-azaspiro[3.5]nonane-7-carboxylate.

To a solution of tert-butyl2-(2-(2-isopropylphenyl)-6-oxopiperazin-1-yl)-7-azaspiro[3.5]nonane-7-carboxylate (1.2 g, 2.72 mmol) in DCE (10 mL) was added AcOH (326.36 mg, 5.43 mmol) and 4-methylbenzaldehyde (359.13 mg, 2.72 mmol). The mixture was stirred at 25° C. for 1 hr. Then NaBH(OAc)₃ (1.73 g, 8.15 mmol) was added to the solution. The mixture was stirred at 25° C. for another 12 hrs. The reaction mixture was poured into sat. NaHCO₃ (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give tert-butyl 2-(2-(2-isopropylphenyl)-4-(4-methylbenzyl)-6-oxopiperazin-1-yl)-7-azaspiro[3.5]nonane-7-carboxylate (1.18 g, 2.16 mmol, yield: 79.6%) as a yellow oil.

Step 2: tert-butyl 2-(2-(2-isopropylphenyl)-4-(4-methylbenzyl)piperazin-1-yl)-7-azaspiro[3.5]nonane-7-carboxylate.

A mixture of tert-butyl 2-(2-(2-isopropylphenyl)-4-(4-methylbenzyl)-6-oxopiperazin-1-yl)-7-azaspiro[3.5]nonane-7-carboxylate (1.18 g, 2.16 mmol) and BH₃·THF (21.62 mL, 21.62 mmol) in THF (10 mL) was stirred at 70° C. for 12 hrs. The reaction solution was quenched by MeOH (10 mL), concentrated under reduced pressure to give tert-butyl 2-(2-(2-isopropylphenyl)-4-(4-methylbenzyl)piperazin-1-yl)-7-azaspiro[3.5]nonane-7-carboxylate (1.18 g, crude), which was used directly for next step without further purification.

Step 3: 2-(2-(2-isopropylphenyl)-4-(4-methylbenzyl)piperazin-1-yl)-7-azaspiro[3.5]nonane.

To a mixture of tert-butyl 2-(2-(2-isopropylphenyl)-4-(4-methylbenzyl)piperazin-1-yl)-7-azaspiro[3.5]nonane-7-carboxylate (1.18 g, 2.22 mmol) and HCl (5.55 mL, 22.19 mmol) in MeOH (30 mL) was stirred at 25° C. for 2 hrs. The reaction solution was concentrated under reduced pressure. The reaction mixture was poured into sat. NaHCO₃ (50 mL), extracted with EtOAc (100 mL×2). The combined organic layers were washed with brine, dried with anhydrous Na₂SO₄, filtered and concentrated under reduced pressure to give 2-(2-(2-isopropylphenyl)-4-(4-methylbenzyl)piperazin-1-yl)-7-azaspiro[3.5]nonane (589 mg, 1.36 mmol, yield: 61.5%) as an off-white solid. ¹H NMR (400 MHz, CDCl₃) δ ppm: 7.48 (br s, 1H), 7.25-7.16 (m, 4H), 7.15-7.07 (m, 3H), 3.65 (m, 1H), 3.54-3.44 (m, 2H), 3.02-2.87 (m, 3H), 2.69-2.57 (m, 5H), 2.36-2.21 (m, 6H), 1.79-1.62 (m, 4H), 1.39-1.21 (m, 9H), 1.15 (m, 4H). MS (ESI, m/e) [M+1]⁺432.3.

Intermediate 31-1: 2-(2-(2-isopropylphenyl)-4-(4-methoxyphenethyl)piperazin-1-yl)-7-azaspiro[3.5]nonane

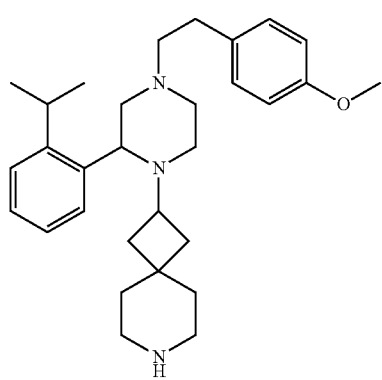

Intermediate 31-1

Step 1: tert-butyl 2-(2-(2-isopropylphenyl)-4-(4-methoxyphenethyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added 2-(4-methoxyphenyl)acetaldehyde (510 g, 3.40 mmol) and HOAc (0.27 g, 4.52 mmol). After stirred at 25° C. for 1 hr, then NaBH(OAc)₃ (0.96 g, 4.52 mmol) was added. The mixture was stirred at 25° C. for 12 hrs. Then aqueous NH₄Cl (20 mL) was added to the mixture and extracted with DCM (20 mL×3). The combined organic phases were washed with brine (20 mL×2), dried with anhydrous Na₂SO₄, filtered and concentrated in vacuum. The residue was purified by column chromatography (silica gel, eluent: PE/EA (v/v)=1/1) to give tert-butyl 2-(2-(2-isopropylphenyl)-4-(4-methoxyphenethyl)-6-oxopiperazin-1-yl)-7-azaspiro[3.5]nonane-7-carboxylate (0.85 g, yield: 65%) as a yellow solid. ¹H NMR (400 MHz, CDCl₃) δ ppm: 7.36-7.29 (m, 2H), 7.19-7.13 (m, 1H), 7.08-7.05 (m, 1H), 6.90 (br d, J=8.4 Hz, 2H), 6.73 (d, J=8.4 Hz, 2H), 5.05 (m, 1H), 4.23 (br s, 1H), 3.77 (s, 3H), 3.39 (m, 1H), 3.27-3.15 (m, 6H), 2.88 (m, 1H), 2.67 (m, 1H), 2.61-2.48 (m, 4H), 2.22 (m, 1H), 1.97 (br s, 1H), 1.82 (br s, 1H), 1.61 (br s, 1H), 1.42 (s, 1 OH), 1.33-1.38 (m, 2H), 1.29 (m, 6H).

Step 2: tert-butyl 2-(2-(2-isopropylphenyl)-4-(4-methoxyphenethyl)piperazin-1-yl)-7-azaspiro[3.5]nonane-7-carboxylate.

The mixture of tert-butyl 2-(2-(2-isopropylphenyl)-4-(4-methoxyphenethyl)-6-oxopiperazin-1-yl)-7-azaspiro[3.5]nonane-7-carboxylate (0.85 g, 1.48 mmol) and BH₃·THF (15 mL, 14.8 mmol) was heated to 70° C. for 12 hrs. The MeOH (10 mL) was added to the mixture carefully, and concentrated in vacuum to give tert-butyl 2-(2-(2-isopropylphenyl)-4-(4-methoxyphenethyl)piperazin-1-yl)-7-azaspiro[3.5]nonane-7-carboxylate (0.8 g, yield: 96%) as a yellow oil, which was used into the next step without further purification. MS (ESI, m/e) [M+1]+562.4.

Step 3: 2-(2-(2-isopropylphenyl)-4-(4-methoxyphenethyl)piperazin-1-yl)-7-azaspiro[3.5]nonane.

To a solution of tert-butyl 2-(2-(2-isopropylphenyl)-4-(4-methoxyphenethyl)piperazin-1-yl)-7-azaspiro[3.5]nonane-7-carboxylate (800 mg, 1.42 mmol) in MeOH (20 mL) was added HCl/MeOH (10 mL) solution. The mixture was stirred at 25° C. for 1 hr. After removed the solvent, the residue was dissolved into water (20 mL). The mixture was adjusted the pH=9-10 using aqueous Na₂CO₃. Then the mixture was extracted with EtOAc (20 mL×3). The combined organic phase was washed with brine (20 mL×2), dried with anhydrous Na₂SO₄, filtered and concentrated in vacuum to give 2-(2-(2-isopropylphenyl)-4-(4-methoxyphenethyl)piperazin-1-yl)-7-azaspiro[3.5]nonane (600 mg, yield: 91%) as a yellow solid. ¹H NMR (400 MHz, CDCl₃) δ ppm: 7.51 (br s, 1H), 7.27-7.21 (m, 2H), 7.17-7.07 (m, 3H), 6.81 (d, J=8.4 Hz, 2H), 4.55-4.28 (m, 1H), 3.78 (s, 3H), 3.67 (m, 1H), 3.41 (br s, 1H), 3.03 (m, 2H), 2.94-2.87 (m, 1H), 2.80-2.68 (m, 6H), 2.60-2.52 (m, 2H), 2.41-2.13 (m, 4H), 1.79 (br s, 1H), 1.70 (m, 1H), 1.51-1.38 (m, 4H), 1.23 (m, 6H), 1.15 (br s, 1H). MS (ESI, m/e) [M+1]⁺462.5.

Intermediate 34-1: 2-(4-(4-methoxybenzyl)-2-(o-tolyl)piperazin-1-yl)-7-azaspiro[3.5]nonane

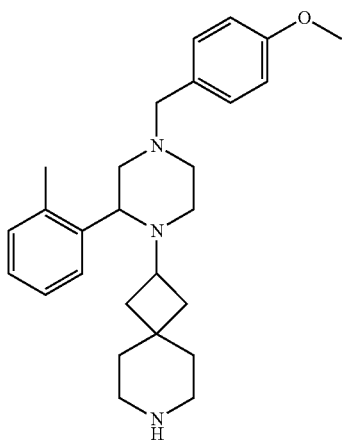

Intermediate 34-1

Step 1: tert-butyl (2-((4-methoxybenzyl) (2-oxo-2-(o-tolyl)ethyl)amino)ethyl)carbamate.

To a solution of 1-bromo-2-methylbenzene (2.8 g, 16.39 mmol) in THF (30 mL) was added n-BuLi (6.37 mL, 15.92 mmol, 2.5 M) at −78° C. and the mixture was stirred at −78° C. for 10 min. Then tert-butyl 4-(4-methoxybenzyl)-2-oxopiperazine-1-carboxylate (5.0 g, 15.61 mmol) in THF (20 mL) was added and the mixture was stirred at −78° C. for 2 hrs. The reaction mixture was quenched with aq. NH$_4$Cl (50 mL) and extracted with EtOAc (50 mL×3), washed with brine, dried over Na$_2$SO$_4$, filtered and concentrated under reduced pressure. The residue was purified by MPLC. The compound tert-butyl (2-((4-methoxybenzyl)(2-oxo-2-(o-tolyl)ethyl)amino)ethyl)carbamate (3.1 g, 7.51 mmol, yield: 48.15%) was obtained as yellow oil. MS (ESI, m/e) [M+1]$^+$413.3.

Step 2: 1-(4-methoxybenzyl)-5-(o-tolyl)-1,2,3,6-tetrahydropyrazine.

A mixture of tert-butyl (2-((4-methoxybenzyl)(2-oxo-2-(o-tolyl)ethyl)amino)ethyl)carbamate (2.1 g, 5.09 mmol) in DCM (20 mL) was added TFA (5.8 g, 50.91 mmol). The mixture was stirred at 20° C. for 12 hrs. The residue was diluted with H$_2$O (20 mL) and added Na$_2$CO$_3$ to pH=9, extracted with EtOAc (20 mL×3), washed with brine, dried over Na$_2$SO$_4$, filtered and concentrated under reduced pressure to give 1-(4-methoxybenzyl)-5-(o-tolyl)-1,2,3,6-tetrahydropyrazine (1.4 g, 4.76 mmol, crude) as a yellow oil. MS (ESI, m/e) [M+1]+295.3.

Step 3: 1-(4-methoxybenzyl)-3-(o-tolyl)piperazine.

To a solution of 1-(4-methoxybenzyl)-5-(o-tolyl)-1,2,3,6-tetrahydropyrazine (1.4 g, 4.76 mmol) in MeOH (20 mL) was added NaBH$_4$ (719.66 mg, 19.02 mmol). The mixture was stirred at 25° C. for 12 hrs. The mixture was quenched by H$_2$O and concentrated under reduced pressure. The residue was diluted with H$_2$O (20 mL) and extracted with DCM (20 mL×3), washed with brine, dried over Na$_2$SO$_4$, filtered and concentrated under reduced pressure. The residue was purified by MPLC. The compound 1-(4-methoxybenzyl)-3-(o-tolyl)piperazine (550 mg, 1.75 mmol, yield: 39.02%) was obtained as a yellow oil. MS (ESI, m/e) [M+1]$^+$297.3

Step 4: tert-butyl 2-(4-(4-methoxybenzyl)-2-(o-tolyl)piperazin-1-yl)-7-azaspiro[3.5]nonane-7-carboxylate.

To a solution of 1-(4-methoxybenzyl)-3-(o-tolyl)piperazine (520 mg, 1.75 mmol) and tert-butyl 2-oxo-7-azaspiro[3.5]nonane-7-carboxylate (419.83 mg, 1.75 mmol) in DCE (10 mL) was added AcOH (210.7 mg, 3.15 mmol) and NaBH(OAc)$_3$ (1.12 g, 5.36 mmol). The mixture was stirred at 25° C. for 12 hrs. The reaction mixture was extracted with aq. Na$_2$CO3 (20 mL) and DCM (10 mL×3), dried over Na$_2$SO$_4$, filtered and concentrated under reduced pressure. The residue was purified by MPLC. The compound tert-butyl 2-(4-(4-methoxybenzyl)-2-(o-tolyl)piperazin-1-yl)-7-azaspiro[3.5]nonane-7-carboxylate (630 mg, 1.21 mmol, yield: 69.1%) was obtained as a yellow oil. MS (ESI, m/e) [M+1]$^+$520.6

Step 5: 2-(4-(4-methoxybenzyl)-2-(o-tolyl)piperazin-1-yl)-7-azaspiro[3.5]nonane.

A mixture of tert-butyl 2-(4-(4-methoxybenzyl)-2-(o-tolyl)piperazin-1-yl)-7-azaspiro[3.5]nonane-7-carboxylate (630 mg, 1.21 mmol) in HCl/MeOH (10 mL) was stirred at 25° C. for 2 hrs. The reaction mixture was concentrated under reduced pressure to remove solvent. The residue was purified by prep-HPLC (TFA condition) according to HPLC. The residue was dilute with H$_2$O (10 mL), and added Na$_2$CO$_3$ to pH=9, the mixture was extracted with EtOAc (10 mL×3), dried over Na$_2$SO$_4$, filtered and concentrated under reduced pressure to remove solvent.

The compound 2-(4-(4-methoxybenzyl)-2-(o-tolyl)piperazin-1-yl)-7-azaspiro[3.5]nonane (109 mg, 294.83 umol, yield: 20.57%) was obtained as a yellow oil. $^1$H NMR (400 MHz, CDCl$_3$) δ ppm: 7.45 (m, 1H), 7.22 (m, 2H), 7.17-7.06 (m, 2H), 7.11-7.06 (m, 1H), 6.83 (m, 2H), 3.79 (s, 3H), 3.51 (m, 1H), 3.46 (s, 2H), 3.02-2.96 (m, 1H), 2.90 (m, 2H), 2.69-2.62 (m, 3H), 2.61-2.54 (m, 2H), 2.35 (s, 3H), 2.27 (m, 2H), 2.15 (m, 1H), 1.79-1.72 (m, 1H), 1.68-1.62 (m, 1H), 1.37-1.26 (m, 5H), 1.20-1.12 (m, 1H). MS (ESI, m/e) [M+1]$^+$420.3.

Intermediate 35-1: 2-(2-(2-isobutylphenyl)-4-(4-methoxybenzyl)piperazin-1-yl)-7-azaspiro[3.5]nonane

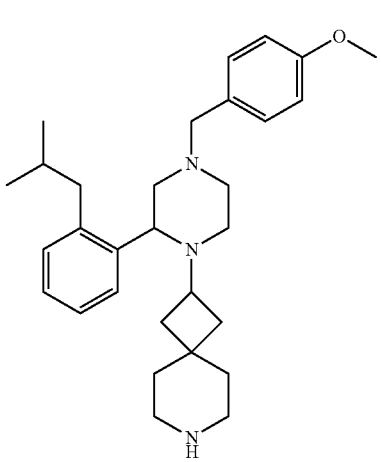

Intermediate 35-1

Step 1: tert-butyl 4-(4-methoxybenzyl)-2-(2-(2-methylprop-1-en-1-yl)phenyl)piperazine-1-carboxylate.

To a solution of tert-butyl 2-(2-bromophenyl)-4-(4-methoxybenzyl)piperazine-1-carboxylate (0.8 g, 1.73 mmol) and 4,4,5,5-tetramethyl-2-(2-methylprop-1-en-1-yl)-1,3,2-dioxaborolane (208 mg, 2.08 mmol) in dioxane (20 mL) and H₂O (4 mL) was added Cs₂CO₃ (1.13 g, 3.46 mmol) and Pd(dppl)Cl₂·CH₂Cl₂ (143 mg, 0.173 mmol) under N₂. The mixture was stirred at 100° C. for 3 hrs. The reaction mixture was filtered and concentrated under reduced pressure.

The residue was purified by MPLC. The compound tert-butyl 4-(4-methoxybenzyl)-2-(2-(2-methylprop-1-en-1-yl)phenyl)piperazine-1-carboxylate (0.63 g, yield: 83%) was obtained as a brown oil. MS (ESI, m/e) [M+1]⁺437.3.

Step 2: tert-butyl 2-(2-isobutylphenyl)-4-(4-methoxybenzyl)piperazine-1-carboxylate.

To a solution of tert-butyl 4-(4-methoxybenzyl)-2-(2-(2-methylprop-1-en-1-yl)phenyl)piperazine-1-carboxylate (0.63 g, 1.44 mmol) in MeOH (20 mL) was added Pt/C (0.5 g). The mixture was stirred at 25° C. under H₂ (15 Psi) for 12 hrs. The solution was filtered and concentrated under reduced pressure. The compound tert-butyl 2-(2-isobutylphenyl)-4-(4-methoxybenzyl)piperazine-1-carboxylate (0.6 g, yield: 95%) was obtained as a yellow oil. MS (ES1, m/e) [M+1]⁺439.3.

Step 3: 3-(2-isobutylphenyl)-1-(4-methoxybenzyl)piperazine.

To a solution of tert-butyl 2-(2-isobutylphenyl)-4-(4-methoxybenzyl)piperazine-1-carboxylate (0.6 g, 1.37 mmol) in MeOH (10 mL) was added HCl/MeOH solution (5 mL, 4 M). The mixture was stirred at 20° C. for 2 hrs. The solution was concentrated under reduced pressure. The residue was dilute with H₂O (50 mL) and added aqueous Na₂CO₃ solution to pH=9. The aqueous layer was extracted with EtOAc (50 mL×3). The combined organic layers were dried and concentrated under reduced pressure. The compound 3-(2-isobutylphenyl)-1-(4-methoxybenzyl)piperazine (0.42 g, yield: 91%) was obtained as a red oil. MS (ESI, m/e) [M+1]⁺339.3.

Step 4: tert-butyl 2-(2-(2-isobutylphenyl)-4-(4-methoxybenzyl)piperazin-1-yl)-7-azaspiro[3.5]nonane-7-carboxylate.

To a solution of 3-(2-isobutylphenyl)-1-(4-methoxybenzyl)piperazine (420 mg, 1.24 mmol) in DCE (20 mL) was added tert-butyl 2-oxo-7-azaspiro[3.5]nonane-7-carboxylate (356 mg, 1.49 mmol) and HOAc (149 mg, 2.48 mmol). After stirred at 25° C. for 1 hr, then NaBH(OAc)₃ (0.79 g, 3.72 mmol) was added. The mixture was stirred at 25° C. for 12 hrs. Then aqueous NaHCO₃ (50 mL) was added to the mixture, and then the mixture was extracted with DCM (20 mL×3). The combined organic phases were washed with brine (20 mL×2), dried with anhydrous Na₂SO₄, filtered and concentrated in vacuum. The residue was purified by column chromatography (silica gel, eluent: PE/EA (v/v)=5/1) to give tert-butyl 2-(2-(2-isobutylphenyl)-4-(4-methoxybenzyl)piperazin-1-yl)-7-azaspiro[3.5]nonane-7-carboxylate (400 mg, yield: 58%) as yellow oil. MS (ESI, m/e) [M+1]⁺562.5.

Step 5: 2-(2-(2-isobutylphenyl)-4-(4-methoxybenzyl)piperazin-1-yl)-7-azaspiro[3.5]nonane.

To a solution of tert-butyl 2-(2-(2-isobutylphenyl)-4-(4-methoxybenzyl)piperazin-1-yl)-7-azaspiro[3.5]nonane-7-carboxylate (400 mg, 0.71 mmol) in MeOH (10 mL) was added HCl/MeOH (5 mL, 4 M). The mixture was stirred at 20° C. for 2 hrs. The solution was concentrated under reduced pressure. The residue was dilute with H₂O (50 mL) and added aqueous Na₂CO3 solution to pH=9. The aqueous layer was extracted with EtOAc (50 mL×3).

The combined organic layers were dried with anhydrous Na₂SO₄ and concentrated under reduced pressure. The compound 2-(2-(2-isobutylphenyl)-4-(4-methoxybenzyl)piperazin-1-yl)-7-azaspiro[3.5]nonane (300 mg, yield: 91%) was obtained as a brown solid. ¹H NMR (400 MHz, CDCl₃) δ ppm: 7.48 (m, 1H), 7.21 (m, 2H), 7.15-7.10 (m, 2H), 7.05-7.00 (m, 1H), 6.82 (m, 2H), 3.78 (s, 3H), 3.48-3.38 (m, 2H), 2.99 (m, 1H), 2.89 (m, 2H), 2.70-2.57 (m, 6H), 2.45-2.38 (m, 1H), 2.36-2.22 (m, 3H), 2.23-2.06 (m, 1H), 1.82-1.60 (m, 4H), 1.44-1.36 (m, 4H), 1.30-1.23 (m, 2H), 0.91 (d, J=6.4 Hz, 3H), 0.82 (d, J=6.4 Hz, 3H). MS (ESI, m/e) [M+1]⁺462.3

Intermediate 36-1: 2-(2-(2-cyclopentylphenyl)-4-(4-methoxybenzyl)piperazin-1-yl)-7-azaspiro[3.5]nonane

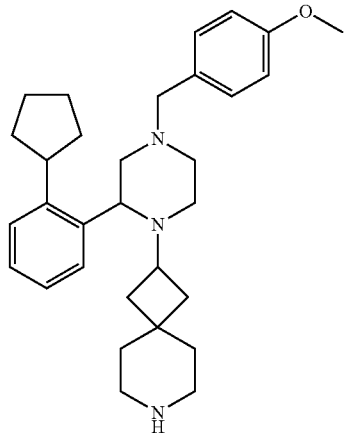

Intermediate 36-1

Step 1: tert-butyl (2-((2-(2-bromophenyl)-2-oxoethyl)(4-methoxybenzyl)amino)ethyl) carbamate.

To a solution of 1-bromo-2-iodobenzene (10 g, 35 mmol) in THF (100 mL) was added i-PrMgCl·LiCl (30 Ml, 1M in THF) at −70° C. After stirred for 0.5 hr, tert-butyl 4-(4-methoxybenzyl)-2-oxopiperazine-1-carboxylate (10.5 g, 33 mmol) was added. The mixture was stirred at 20° C. for 3 hrs. The reaction mixture was quenched by addition NH₄Cl (100 mL) at 0° C. and extracted with EtOAc (50 mL×3). The combined organic layers were washed with brine (50 mL×2), dried over Na₂SO₄, filtered and concentrated under reduced pressure. The residue was purified by column chromatography (silica gel, eluent: PE/EA (v/v)=10/1) to give tert-butyl (2-((2-(2-bromophenyl)-2-oxoethyl)(4-methoxybenzyl)amino)ethyl)carbamate (14 g, yield: 84%) as a yellow oil. ¹H NMR (400 MHz, CDCl₃) δ ppm: 7.85 (dd, J=1.6, 8.0 Hz, 1H), 7.54 (dd, J=1.2, 8.0 Hz, 1H), 7.33-7.28 (m, 1H), 7.22 (m, 2H), 7.10 (m, 1H), 6.88-6.82 (d, J=8.4 Hz, 2H), 4.47 (s, 1H), 3.91 (m, 1H), 3.81 (s, 3H), 3.57-3.44 (m, 3H), 2.97-2.88 (m, 2H), 2.64-2.55 (m, 2H), 1.27 (m, 2H), 1.14 (s, 9H).

Step 2: 3-(2-bromophenyl)-1-(4-methoxybenzyl)piperazine.

To a solution of tert-butyl (2-((2-(2-bromophenyl)-2-oxoethyl)(4-methoxybenzyl)amino)ethyl)carbamate (5.0 g, 10 mmol) in DCM (25 mL) was added TFA (25 mL). The mixture was stirred at 20° C. for 30 min. After removed the solvent under reduced pressure, the residue was dissolved into DCE (50 mL). Then NaBH(OAc)₃ (2.2 g, 10 mmol) was added. The mixture was stirred at 20° C. for 1 hr. The reaction mixture was concentrated under reduced pressure to remove solvent. The reaction mixture was extracted with DCM (10 mL×3), then washed with aq. NaHCO₃ (10 mL×2) and dried over Na₂SO₄, filtered and concentrated to give 3-(2-bromophenyl)-1-(4-methoxybenzyl)piperazine (3.5 g, yield: 99%) as a brown oil, which was used into next step without further purification. MS (ESI, m/e) [M+1]+361.2, 363.2.

Step 3: tert-butyl 2-(2-bromophenyl)-4-(4-methoxybenzyl)piperazine-1-carboxylate.

To a solution of 3-(2-bromophenyl)-1-(4-methoxybenzyl)piperazine (3.4 g, 9.4 mmol) in DCM (50 mL) was added TEA (1.9 g, 18.8 mmol). Then Boc$_2$O (2.5 g, 11.29 mmol) was added. The mixture was stirred at 20° C. for 12 hrs. The reaction mixture was quenched by addition NH$_4$Cl (50 mL) at 0° C., and then extracted with EtOAc (20 mL×3). The combined organic layers were washed with brine (20 mL×2), dried over Na$_2$SO$_4$, filtered and concentrated under reduced pressure. The residue was purified by column chromatography (silica gel, eluent: PE/EA (v/v)=10/1) to give tert-butyl 2-(2-bromophenyl)-4-(4-methoxybenzyl)piperazine-1-carboxylate (2.9 g, yield: 68%) as a yellow oil. $^1$H NMR (400 MHz, CDCl$_3$) δ ppm: 7.58 (m, 1H), 7.52 (m, 1H), 7.31-7.27 (m, 1H), 7.13-7.09 (m, 1H), 7.06 (d, J=8.4 Hz, 2H), 6.79-6.75 (m, 2H), 5.33 (m, 1H), 3.94-3.89 (m, 1H), 3.78 (s, 3H), 3.53-3.46 (m, 1H), 3.43 (m, 2H), 3.00 (m, 1H), 2.84 (m, 1H), 2.52 (m, 1H), 2.22 (m, 1H), 1.31 (s, 9H).

Step 4: tert-butyl 2-(2-(cyclopent-1-en-1-yl)phenyl)-4-(4-methoxybenzyl)piperazine-1-carboxylate.

To a solution of tert-butyl 2-(2-bromophenyl)-4-(4-methoxybenzyl)piperazine-1-carboxylate (1.0 g, 2.17 mmol) and 2-(cyclopent-1-en-1-yl)-4,4,5,5-tetramethyl-1,3,2-dioxaborolane (0.5 g, 2.6 mmol) in dioxane (20 mL) and H$_2$O (4 mL) was added Cs$_2$CO$_3$ (1.4 g, 4.34 mmol) and Pd(dppf)Cl$_2$·CH$_2$Cl$_2$ (180 mg, 0.217 mmol) under N$_2$. The mixture was stirred at 100° C. for 3 hrs. The reaction mixture was filtered and concentrated under reduced pressure to give a residue. The residue was purified by MPLC. The compound tert-butyl 2-(2-(cyclopent-1-en-1-yl)phenyl)-4-(4-methoxybenzyl)piperazine-1-carboxylate (0.73 g, yield: 75%) was obtained as a white solid. MS (ESI, m/e) [M+1]$^+$ 449.4.

Step 5: tert-butyl 2-(2-cyclopentylphenyl)-4-(4-methoxybenzyl)piperazine-1-carboxylate.

To a solution of tert-butyl 2-(2-(cyclopent-1-en-1-yl)phenyl)-4-(4-methoxybenzyl)piperazine-1-carboxylate (0.73 g, 1.63 mmol) in MeOH (20 mL) was added Pt/C (0.5 g). The mixture was stirred at 25° C. under H$_2$ (15 Psi) for 12 hr. The solution was filtered and concentrated under reduced pressure. The compound tert-butyl 2-(2-cyclopentylphenyl)-4-(4-methoxybenzyl)piperazine-1-carboxylate (0.7 g, yield: 96%) was obtained as a yellow oil. MS (ESI, m/e) [M+1]$^+$ 451.3.

Step 6: 3-(2-cyclopentylphenyl)-1-(4-methoxybenzyl)piperazine.

To a solution of tert-butyl 2-(2-cyclopentylphenyl)-4-(4-methoxybenzyl)piperazine-1-carboxylate (0.89 g, 1.98 mmol) in MeOH (10 mL) was added HCl/MeOH (5 mL, 4 M). The mixture was stirred at 20° C. for 2 hrs. The solution was concentrated under reduced pressure. The residue was dilute with H$_2$O (50 mL) and added Na$_2$CO$_3$ solution to pH=9. The aqueous layer was extracted with EtOAc (50 mL×3). The combined organic layer was dried and concentrated under reduced pressure. The compound 3-(2-cyclopentylphenyl)-1-(4-methoxybenzyl)piperazine (0.6 g, yield: 87%) was obtained as a red oil. MS (ESI, m/e) [M+1]+ 351.3.

Step 7: tert-butyl 2-(2-(2-cyclopentylphenyl)-4-(4-methoxybenzyl)piperazin-1-yl)-7-azaspiro[3.5]nonane-7-carboxylate.

To a solution of 3-(2-cyclopentylphenyl)-1-(4-methoxybenzyl)piperazine (600 mg, 1.71 mmol) in DCE (20 mL) was added tert-butyl 2-oxo-7-azaspiro[3.5]nonane-7-carboxylate (491 mg, 2.05 mmol) and HOAc (205 mg, 3.42 mmol). After stirred at 25° C. for 1 hr, the NaBH(OAc)$_3$ (1.09 g, 5.13 mmol) was added. The mixture was stirred at 25° C. for 12 hrs. Then aqueous NaHCO$_3$ (50 mL) was added to the mixture, and then the mixture was extracted with DCM (20 mL×3). The combined organic phase was washed with brine (20 mL×2), dried with anhydrous Na$_2$SO$_4$, filtered and concentrated in vacuum. The residue was purified by column chromatography (silica gel, eluent: PE/EA (v/v)=5/1) to give tert-butyl 2-(2-(2-cyclopentylphenyl)-4-(4-methoxybenzyl)piperazin-1-yl)-7-azaspiro[3.5]nonane-7-carboxylate (700 mg, yield: 71%) was obtained as yellow oil. MS (ESI, m/e) [M+1]$^+$574.4.

Step 8: 2-(2-(2-cyclopentylphenyl)-4-(4-methoxybenzyl)piperazin-1-yl)-7-azaspiro[3.5]nonane.

To a solution of tert-butyl 2-(2-(2-cyclopentylphenyl)-4-(4-methoxybenzyl)piperazin-1-yl)-7-azaspiro[3.5]nonane-7-carboxylate (700 mg, 1.22 mmol) in MeOH (10 mL) was added HCl/MeOH (5 mL, 4 M) solution. The mixture was stirred at 20° C. for 2 hrs. The solution was concentrated under reduced pressure. The residue was dilute with H$_2$O (50 mL) and added Na$_2$CO3 solution to pH=9. The aqueous layer was extracted with EtOAc (50 mL×3). The combined organic layers were dried and concentrated under reduced pressure. The compound 2-(2-(2-cyclopentylphenyl)-4-(4-methoxybenzyl)piperazin-1-yl)-7-azaspiro[3.5]nonane (500 mg, yield: 87%) was obtained as a brown solid. $^1$H NMR (400 MHz, CDCl$_3$) δ ppm: 7.48 (s, 1H), 7.25-7.18 (m, 4H), 7.15-7.08 (m, 1H), 6.85-6.81 (m, 2H), 3.79 (s, 3H), 3.71-3.59 (m, 1H), 3.50-3.42 (m, 2H), 3.41-3.26 (m, 1H), 2.99 (m, 1H), 2.94-2.84 (m, 2H), 2.75-2.55 (m, 5H), 2.32-2.23 (m, 2H), 2.16 (m, 1H), 2.04-1.96 (m, 1H), 1.89-1.73 (m, 4H), 1.72-1.56 (m, 4H), 1.55-1.20 (m, 7H), 1.19-1.07 (m, 1H). MS (ESI, m/e) [M+1]$^+$474.4.

Intermediate 37-1: 4-(2-(4-(4-methoxybenzyl)-1-(7-azaspiro[3.5]nonan-2-yl)piperazin-2-yl)benzyl)morpholine

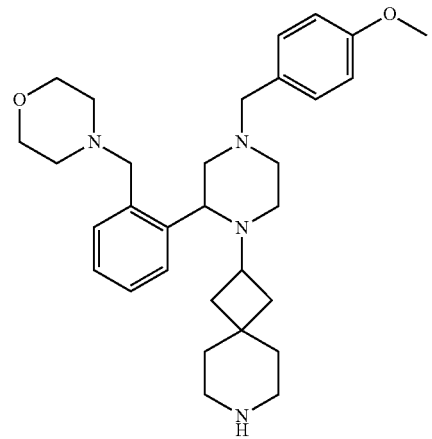

Intermediate 37-1

Step 1: tert-butyl 4-(4-methoxybenzyl)-2-(2-vinylphenyl)piperazine-1-carboxylate.

To a solution of tert-butyl 2-(2-bromophenyl)-4-(4-methoxybenzyl)piperazine-1-carboxylate (1.0 g, 2.17 mmol) and Potassium vinyl trifluoroborate (406.44 mg, 3.03 mmol) in dioxane (10 mL) and H$_2$O (1 mL) was added Cs$_2$CO$_3$ (1.41 g, 4.33 mmol) and Pd(dppf)Cl2 (158.59 mg, 216.74 umol) under N$_2$. The mixture was stirred at 90° C. for 12 hrs. The reaction mixture was filtered and concentrated. The residue was extracted with H$_2$O (10 mL) and EtOAc (10 mL×3), dried over Na$_2$SO$_4$, filtered and concentrated. The residue was purified by MPLC.

The compound tert-butyl 4-(4-methoxybenzyl)-2-(2-vinylphenyl)piperazine-1-carboxylate (800 mg, 1.96 mmol, yield: 90.35%) was obtained as a yellow oil. $^1$H NMR (400 MHz, CDCl$_3$) δ ppm: 7.84-7.80 (m, 11H), 7.47-7.42 (m, 1H), 7.26-7.22 (m, 2H), 7.16 (m, 2H), 7.08 (m, 1H), 6.82 (d, J=8.8 Hz, 2H), 5.51 (m, 1H), 5.37 (m, 1H), 5.21 (m, 1H), 3.87-3.81 (m, 1H), 3.80 (s, 3H), 3.48-3.38 (m, 2H), 3.25-3.15 (m, 1H), 3.07 (m, 1H), 2.79 (m, 1H), 2.45 (m, 1H), 2.17 (m, 1H), 1.41 (s, 9H).

Step 2: tert-butyl 2-(2-formylphenyl)-4-(4-methoxybenzyl)piperazine-1-carboxylate.

To a solution of tert-butyl 4-(4-methoxybenzyl)-2-(2-vinylphenyl)piperazine-1-carboxylate (800 mg, 1.96 mmol) in THF (5 mL) and H$_2$O (5 mL) was added K$_2$OsO$_4$·H$_2$O (28.86 mg, 78.33 umol) and NaIO$_4$ (1.68 g, 7.83 mmol) at 5° C. and the mixture was stirred at 25° C. for 3 hrs. The reaction mixture was diluted with H$_2$O (10 mL) and extracted with EtOAc (10 mL×3), washed with aq·Na$_2$SO$_3$ (10 mL), dried over Na$_2$SO$_4$, filtered and concentrated under reduced pressure to afford tert-butyl 2-(2-formylphenyl)-4-(4-methoxybenzyl)piperazine-1-carboxylate (800 mg, 1.95 mmol, yield: 99.52%) was obtained as a yellow oil. MS (ESI, m/e) [M+1]$^+$411.2.

Step 3: tert-butyl 4-(4-methoxybenzyl)-2-(2-(morpholinomethyl)phenyl)piperazine-1-carboxylate.

To a solution of tert-butyl 2-(2-formylphenyl)-4-(4-methoxybenzyl)piperazine-1-carboxylate (800 mg, 1.95 mnol), morpholine (203.74 mg, 2.34 mmol) AcOH (234.06 mg, 3.90 mmol) and NaBH(OAc)$_3$ (1.24 g, 5.85 mmol) was added in DCE (10 mL). The mixture was stirred at 25° C. for 12 hrs. The reaction mixture was poured into aqueous Na$_2$CO$_3$ (10 mL) and extracted with DCM (10 mL×3), dried over Na$_2$SO$_4$, filtered and concentrated under reduced pressure. The residue was purified by MPLC. The compound tert-butyl 4-(4-methoxybenzyl)-2-(2-(morpholinomethyl)phenyl)piperazine-1-carboxylate (400 mg, 830.52 umol, yield: 42.62%) was obtained as a yellow oil. $^1$H NMR (400 MHz, CDCl$_3$) δ ppm: 7.83 (d, J=8.0 Hz, 1H), 7.25 (d, J=2.8 Hz, 1H), 7.21-7.15 (m, 2H), 7.10 (d, J=8.4 Hz, 2H), 6.73 (d, J=8.8 Hz, 2H), 5.27 (d, J=2.4 Hz, 1H), 3.92 (m, 1H), 3.89-3.83 (m, 1H), 3.75 (s, 3H), 3.57-3.47 (m, 4H), 3.45-3.28 (m, 3H), 3.07 (d, J=12.8 Hz, 1H), 2.91 (d, J=11.2 Hz, 2H), 2.44 (m, 1H), 2.41-2.25 (m, 3H), 2.23-2.16 (m, 2H), 1.30 (s, 9H).

Step 4: 4-(2-(4-(4-methoxybenzyl)piperazin-2-yl)benzyl)morpholine.

A mixture of tert-butyl 4-(4-methoxybenzyl)-2-(2-(morpholinomethyl)phenyl)piperazine-1-carboxylate (400 mg, 830.52 umol) in HCl/EtOAc (5 mL) was stirred at 25° C. for 6 hrs. The reaction mixture was concentrated to remove solvent. The residue was diluted with H$_2$O (5 mL), and added Na$_2$CO$_3$ to pH=9, the mixture was extracted with EtOAc (5 mL×3), dried over Na$_2$SO$_4$, filtered and concentrated under reduced pressure to remove solvent. The compound 4-(2-(4-(4-methoxybenzyl)piperazin-2-yl)benzyl)morpholine (300 mg, 786.35 umol, yield: 94.68%) was obtained as a yellow oil. MS (ESI, m/e) [M+1]$^+$382.2.

Step 5: tert-butyl 2-(4-(4-methoxybenzyl)-2-(2-(morpholinomethyl)phenyl)piperazin-1-yl)-7-azaspiro[3.5]nonane-7-carboxylate.

To a solution of 4-(2-(4-(4-methoxybenzyl)piperazin-2-yl)benzyl)morpholine (300 mg, 786.35 umol), tert-butyl 2-oxo-7-azaspiro[3.5]nonane-7-carboxylate (225.82 mg, 943.62 umol), AcOH (94.44 mg, 1.57 mmol) and NaBH(OAc)$_3$ (499.58 mg, 2.36 mmol) was added in DCE (6 mL). The mixture was stirred at 25° C. for 48 hrs. The reaction mixture was extracted with aqueous Na$_2$CO$_3$ (10 mL) and DCM (10 mL×3), dried over Na$_2$SO$_4$, filtered and concentrated.

The residue was purified by prep-HPLC (TFA condition). The compound tert-butyl 2-(4-(4-methoxybenzyl)-2-(2-(morpholinomethyl)phenyl)piperazin-1-yl)-7-azaspiro[3.5]nonane-7-carboxylate (255 mg, 421.61 umol, yield: 53.62%) was obtained as a white solid. MS (ESI, m/e) [M+1]$^+$605.4.

Step 6: 4-(2-(4-(4-methoxybenzyl)-1-(7-azaspiro[3.5]nonan-2-yl)piperazin-2-yl)benzyl)morpholine.

A mixture of tert-butyl 2-(4-(4-methoxybenzyl)-2-(2-(morpholinomethyl)phenyl)piperazin-1-yl)-7-azaspiro[3.5]nonane-7-carboxylate (255 mg, 421.61 umol) in DCM (4 mL) and TFA (2 mL) was stirred at 25° C. for 1 hr. The reaction mixture was dilute with H$_2$O (5 mL) and added aqueous Na$_2$CO$_3$ to pH=9. The mixture was extracted with DCM (5 mL×3), dried over Na$_2$SO$_4$, filtered and concentrated under reduced pressure to remove solvent. The compound 4-(2-(4-(4-methoxybenzyl)-1-(7-azaspiro[3.5]nonan-2-yl)piperazin-2-yl)benzyl)morpholine (135 mg, 267.48 umol, yield: 63.44%) was obtained as a yellow solid. $^1$H NMR (400 MHz, CDCl$_3$) δ ppm: 7.58 (d, J=7.6 Hz, 1H), 7.25-7.19 (m, 3H), 7.17-7.09 (m, 2H), 6.83 (d, J=8.8 Hz, 2H), 3.78 (s, 3H), 3.66-3.50 (m, 5H), 3.39 (s, 2H), 3.32 (m, 1H), 3.22 (m, 1H), 2.97 (m, 2H), 2.85 (m, 1H), 2.76-2.59 (m, 5H), 2.42-2.22 (m, 6H), 2.01 (m, 1H), 1.84-1.76 (m, 1H), 1.70-1.63 (m, 1H), 1.46-1.32 (m, 4H), 1.29-1.23 (m, 1H), 1.11-1.03 (m, 1H). MS (ESI, m/e) [M+1]$^+$505.4.

Intermediate 39-1: 2-(2-(2-isopropylphenyl)-4-(4-(trifluoromethoxy)benzyl)piperazin-1-yl)-7-azaspiro[3.5]nonane

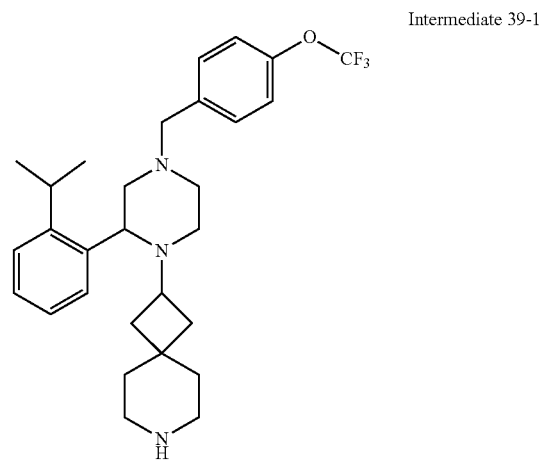 [SMILES: CC(C)c1ccccc1C1CN(Cc2ccc(OC(F)(F)F)cc2)CCN1C1CC2(CCNCC2)C1]

Intermediate 39-1

Step 1: tert-butyl 2-(2-(2-isopropylphenyl)-6-oxo-4-(4-(trifluoromethoxy)benzyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (900 mg, 2.04 mmol) in DCE (10 mL) was added AcOH (244.77 mg, 4.08 mmol) and 4-(trifluoromethoxy)benzaldehyde (426.21 mg, 2.24 mmol) at 25° C.

The mixture was stirred at 25° C. for 1 hr. Then NaBH(OAc)$_3$ (1.3 g, 6.11 mmol) was added and stirred at 25° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl 2-(2-(2-isopropylphenyl)-6-oxo-4-(4-(trifluoromethoxy)benzyl)piperazin-1-yl)-7-azaspiro[3.5]nonane-7-carboxylate (820 mg, yield: 64%) as a yellow oil.

Step 2: tert-butyl 2-(2-(2-isopropylphenyl)-4-(4-(trifluoromethoxy)benzyl)piperazin-1-yl)-7-azaspiro[3.5]nonane-7-carboxylate.

A mixture of tert-butyl 2-(2-(2-isopropylphenyl)-6-oxo-4-(4-(trifluoromethoxy)benzyl)piperazin-1-yl)-7-azaspiro[3.5]nonane-7-carboxylate (800 mg, 1.30 mmol) and BH$_3$·THF (12.99 mL, 12.99 mmol) in THF was stirred at 70° C. for 12 hrs. The reaction solution was quenched by MeOH (10 mL, concentrated under reduced pressure to give tert-butyl 2-(2-(2-isopropylphenyl)-4-(4-(trifluoromethoxy)benzyl)piperazin-1-yl)-7-azaspiro[3.5]nonane-7-carboxylate (800 mg, crude) as a yellow oil, which was used directly for next step without further purification.

Step 3: 2-(2-(2-isopropylphenyl)-4-(4-(trifluoromethoxy)benzyl)piperazin-1-yl)-7-azaspiro[3.5]nonane.

To a mixture of tert-butyl 2-(2-(2-isopropylphenyl)-4-(4-(trifluoromethoxy)benzyl) piperazin-1-yl)-7-azaspiro[3.5]nonane-7-carboxylate (800 mg, 1.33 mmol) and HCl/MeOH (15 mL, 4M) in MeOH (10 mL) was stirred at 25° C. for 2 hrs. The reaction solution was concentrated under reduced pressure. The residue was poured into saturated NaHCO$_3$ (10 mL), extracted with EtOAc (20 mL×2). The combined organic layers were washed with brine, dried with anhydrous Na$_2$SO$_4$, filtered and concentrated under reduced pressure to give 2-(2-(2-isopropylphenyl)-4-(4-(trifluoromethoxy)benzyl)piperazin-1-yl)-7-azaspiro[3.5]nonane (606 mg, yield 90%) as a white solid. $^1$H NMR (400 MHz, CDCl$_3$) δ ppm: 7.48 (br s, 1H), 7.33 (br s, 2H), 7.23 (br s, 2H), 7.14 (br s, 3H), 3.71-3.27 (m, 4H), 3.07-2.85 (m, 3H), 2.61 (br s, 5H), 2.37-2.11 (m, 2H), 1.91-1.52 (m, 4H), 1.47-0.82 (m, 12H). MS (ESI, m/e) [M+1]$^+$502.4.

Intermediate 40-1: 2-(4-(4-ethoxybenzyl)-2-(2-isopropylphenyl)piperazin-1-yl)-7-azaspiro[3.5]nonane

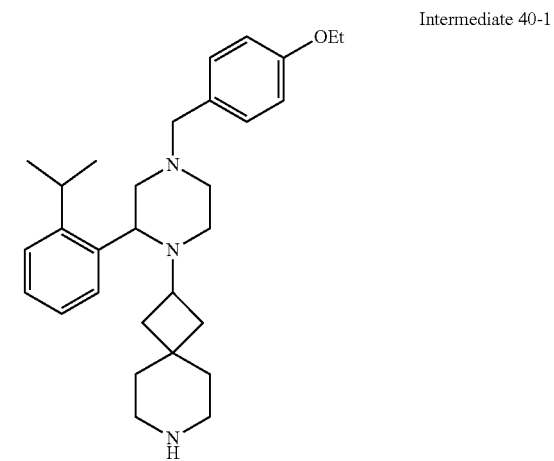 [SMILES: CC(C)c1ccccc1C1CN(Cc2ccc(C#N)cc2)CCN1C1CC2(CCNCC2)C1]

Intermediate 40-1

Step 1: tert-butyl 2-(4-(4-ethoxybenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (900 mg, 2.04 mmol) in DCE (10 mL) was added AcOH (244.77 mg, 4.08 mmol) and 4-ethoxybenzaldehyde (333.66 mg, 2.24 mmol) at 25° C. The mixture was stirred at 25° C. for 1 hr. Then NaBH(OAc)$_3$ (1.3 g, 6.11 mmol) was added and stirred at 25° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl 2-(4-(4-ethoxybenzyl)-2-(2-isopropylphenyl)-6-oxopiperazin-1-yl)-7-azaspiro[3.5]nonane-7-carboxylate (800 mg, yield: 68%) as a yellow oil.

Step 2: tert-butyl 2-(4-(4-ethoxybenzyl)-2-(2-isopropylphenyl)piperazin-1-yl)-7-azaspiro[3.5]nonane-7-carboxylate.

A mixture of tert-butyl 2-(4-(4-ethoxybenzyl)-2-(2-isopropylphenyl)-6-oxopiperazin-1-yl)-7-azaspiro[3.5]nonane-7-carboxylate (800 mg, 1.39 mmol) and BH$_3$·THF (13.89 mL, 13.89 mmol) in THF was stirred at 70° C. for 12 hrs. The reaction solution was quenched by MeOH (10 mL), concentrated under reduced pressure to give tert-butyl 2-(4-(4-ethoxybenzyl)-2-(2-isopropylphenyl)piperazin-1-yl)-7-azaspiro[3.5]nonane-7-carboxylate (800 mg, crude) as a yellow oil, which was used directly for next step without further purification.

Step 3: 2-(4-(4-ethoxybenzyl)-2-(2-isopropylphenyl)piperazin-1-yl)-7-azaspiro[3.5]nonane.

To a mixture of tert-butyl 2-(4-(4-ethoxybenzyl)-2-(2-isopropylphenyl)piperazin-1-yl)-7-azaspiro[3.5]nonane-7-carboxylate (800 mg, 1.42 mmol) and HCl (3.56 mL, 14.24 mmol) in MeOH (10 mL) was stirred at 25° C. for 2 hrs. The reaction solution was concentrated under reduced pressure. The residue was poured into saturated NaHCO$_3$ (10 mL), extracted with EtOAc (20 mL×2). The combined organic layers were washed with brine, dried with anhydrous Na$_2$SO$_4$, filtered and concentrated under reduced pressure to give 2-(4-(4-ethoxybenzyl)-2-(2-isopropylphenyl)piperazin-1-yl)-7-azaspiro[3.5]nonane (562 mg, yield: 62%) as a white solid. )H NMR (400 MHz, CDCl₃) δ ppm: 7.48 (br s, 1H), 7.25-7.16 (m, 4H), 7.15-7.07 (m, 1H), 6.81 (d, J=8.4 Hz, 2H), 4.01 (q, 2H), 3.64 (m, 1H), 3.50-3.31 (m, 3H), 3.01-2.84 (m, 3H), 2.70-2.52 (m, 5H), 2.33-2.23 (m, 2H), 2.21-2.07 (m, 2H), 1.79-1.61 (m, 2H), 1.43-1.32 (m, 6H), 1.31-1.21 (m, 5H), 1.14 (d, J=6.8 Hz, 4H). MS (ESI, m/e) [M+1]⁺462.4.

Intermediate 41-1: 2-(2-(2-isopropylphenyl)-4-(4-(trifluoromethyl)benzyl)piperazin-1-yl)-7-azaspiro[3.5]nonane

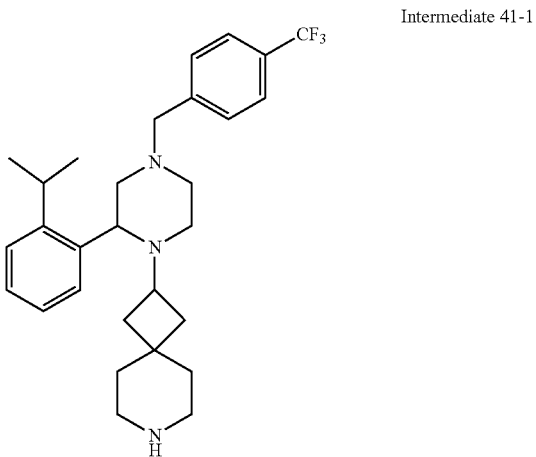

Intermediate 41-1

Step 1: tert-butyl 2-(2-(2-isopropylphenyl)-6-oxo-4-(4-(trifluoromethyl)benzyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (800 mg, 1.87 mmol) in DCE (10 mL) was added AcOH (337 mg, 5.61 mmol) and 4-(trifluoromethyl)benzaldehyd (179 mg, 2.03 mmol). The mixture was stirred at 20° C. for 1 hr, then NaBH(OAc)₃ (1.19 g, 5.61 mmol) was added. The mixture was stirred at 20° C. for 16 hrs. Then saturated NaHCO₃ (10 mL) and EtOAc (10 mL) were added. The mixture was stirred at 20° C. for 0.2 hr. The organic layer was separated, dried over Na₂SO₄, evaporated in vacuo. The residue was purified by column chromatography (silica gel, eluent: PE/EA (v/v)=10/1 to 1/1) to afford tert-butyl 2-(2-(2-isopropylphenyl)-6-oxo-4-(4-(trifluoromethyl)benzyl) piperazin-1-yl)-7-azaspiro[3.5]nonane-7-carboxylate (500 mg, yield: 49%) as yellow solid. MS (ESI, m/e) [M+1]⁺ 600.5

Step 2: tert-butyl 2-(2-(2-isopropylphenyl)-4-(4-(trifluoromethyl)benzyl)piperazin-1-yl)-7-azaspiro[3.5]nonane-7-carboxylate.

The mixture of tert-butyl 2-(2-(2-isopropylphenyl)-6-oxo-4-(4-(trifluoromethyl)benzyl) piperazin-1-yl)-7-azaspiro[3.5]nonane-7-carboxylate (500 mg, 0.88 mmol) and BH₃·THF (8.8 mL, 8.8 mmol) was heated to 70° C. for 12 hrs. After cooling to 0° C., the mixture was quenched with MeOH (10 mL). The mixture was concentrated in vacuum to give tert-butyl 2-(2-(2-isopropylphenyl)-4-(4-(trifluoromethyl)benzyl)piperazin-1-yl)-7-azaspiro[3.5] nonane-7-carboxylate (400 mg, yield: 80%) as yellow solid, which was used into the next step without further purification. MS (ESI, m/e) [M+1]⁺586.3.

Step 3: 2-(2-(2-isopropylphenyl)-4-(4-(trifluoromethyl) benzyl)piperazin-1-yl)-7-azaspiro[3.5]nonane.

To a solution of tert-butyl 2-(2-(2-isopropylphenyl)-4-(4-(trifluoromethyl)benzyl)piperazin-1-yl)-7-azaspiro[3.5] nonane-7-carboxylate (400 mg, 0.68 mmol) in MeOH (10 mL) was added HCl/MeOH solution (10 mL). The mixture was stirred at 25° C. for 2 hrs. After concentrating in vacuum, the residue was dissolved into water (20 mL). The mixture was adjusted the pH=9-10 using aqueous Na₂CO₃. The mixture was extracted with EtOAc (20 mL×3). The combined organic phases were washed with brine (20 mL×2), dried with anhydrous Na₂SO₄, filtered and concentrated in vacuum to give 2-(2-(2-isopropylphenyl)-4-(4-(trifluoromethyl)benzyl)piperazin-1-yl)-7-azaspiro[3.5] nonane (220 mg, yield: 66%) as a brown solid. ¹H NMR (400 MHz, CDCl₃) δ ppm: 7.55-7.43 (m, 5H), 7.27-7.21 (m, 2H), 7.14-7.11 (m, 1H), 3.66-3.56 (m, 3H), 3.48-3.25 (m, 1H), 3.22-3.02 (m, 1H), 2.91-2.87 (m, 2H), 2.64-2.61 (m, 5H), 2.45-2.20 (m, 4H), 1.80-1.60 (m, 2H), 1.38-1.12 (m, 13H). MS (ESI, m/e) [M+1]⁺486.3

Intermediate 42-1: 4-((3-(2-isopropylphenyl)-4-(7-azaspiro[3.5]nonan-2-yl)piperazin-1-yl)methyl)benzonitrile

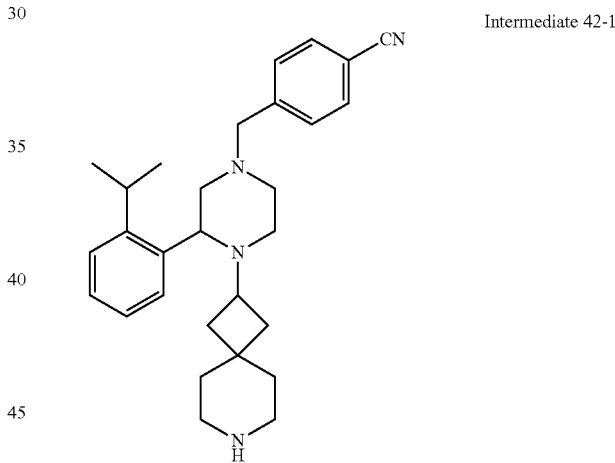

Intermediate 42-1

Step 1: tert-butyl2-(2-(2-isopropylphenyl)piperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol) and BH₃·THF (22.64 mL, 22.64 mmol) in THF (20 mL) was stirred at 70° C. for 12 hrs. The reaction solution was quenched by MeOH (20 mL) and stirred at 0° C. for 1 hr. The mixture was concentrated under reduced pressure to give tert-butyl2-(2-(2-isopropylphenyl)piperazin-1-yl)-7-azaspiro[3.5]nonane-7-carboxylate (900 mg, crude) as a white oil, which was used directly for next step without further purification. MS (ESI, m/e) [M+1]⁺428.3.

Step 2: tert-butyl 2-(4-(4-cyanobenzyl)-2-(2-isopropylphenyl)piperazin-1-yl)-7-azaspiro[3.5]nonane-7-carboxylate.

To a solution of tert-butyl2-(2-(2-isopropylphenyl)piperazin-1-yl)-7-azaspiro[3.5]nonane-7-carboxylate (900 mg, 2.10 mmol) in DCE (10 mL) was added AcOH (252.78 mg, 4.21 mmol) and 4-formylbenzonitrile (303.59 mg, 2.32 mmol). The mixture was stirred at 25° C. for 1 hr, then NaBH(OAc)₃ (1.34 g, 6.31 mmol) was added and stirred at 25° C. for another 12 hrs. The reaction mixture was poured into saturated NaHCO₃ (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give tert-butyl 2-(4-(4-cyanobenzyl)-2-(2-isopropylphenyl)piperazin-1-yl)-7-azaspiro[3.5]nonane-7-carboxylate (270 mg, yield: 23%) as a yellow oil.

Step 3: 4-((3-(2-isopropylphenyl)-4-(7-azaspiro[3.5]nonan-2-yl)piperazin-1-yl)methyl)benzonitrile A mixture of 2-(4-(4-cyanobenzyl)-2-(2-isopropylphenyl)piperazin-1-yl)-7-azaspiro[3.5]nonane-7-carboxylate (270 mg, 497.46 mol) and TFA (0.38 mL, 4.97 mmol) in DCM (10 mL) was stirred at 25° C. for 2 hrs. The reaction solution was concentrated under reduced pressure. The reaction mixture was poured into saturated NaHCO₃ (10 mL), extracted with EtOAc (20 mL×2). The combined organic layers were washed with brine, dried with anhydrous Na₂SO₄, filtered and concentrated under reduced pressure to give 4-((3-(2-isopropylphenyl)-4-(7-azaspiro[3.5]nonan-2-yl)piperazin-1-yl)methyl)benzonitrile (102 mg, yield: 46.32%) as a yellow solid. ¹H NMR (400 MHz, CDCl₃) δ ppm: 7.59 (d, J=8.4 Hz, 2H), 7.45 (d, J=8.0 Hz, 3H), 7.26-7.19 (m, 3H), 7.15-7.09 (m, 1H), 3.65-3.59 (m, 1H), 3.56 (m, 2H), 3.35 (br s, 3H), 3.02-2.83 (m, 3H), 2.72 (m, 5H), 2.59 (m, 1H), 2.39-2.26 (m, 3H), 2.26-2.15 (m, 2H), 1.96 (s, 2H), 1.46 (m, 3H), 1.30-1.23 (m, 6H), 1.13 (br d, J=6.8 Hz, 3H), 0.88 (m, 3H). MS (ESI, m/e) [M+1]⁺443.3.

Intermediate 43-1: 2-(4-(3-fluorobenzyl)-2-(2-isopropylphenyl)piperazin-1-yl)-7-azaspiro[3.5]nonane

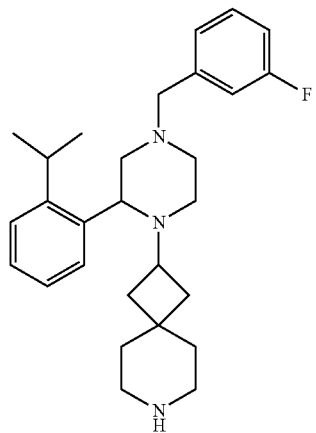

Intermediate 43-1

Step 1: tert-butyl 2-(2-(2-isopropylphenyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mol) in THF (20 mL) was added LiAlH₄ (0.17 g, 4.53 mol) in portions at 0° C. The mixture was stirred at 20° C. for 1 hr. Then H₂O (10 mL) was added to the mixture, extracted with ethyl acetate (20 mL×3). The combined organic phases were washed with brine (10 mL×2), dried with anhydrous Na₂SO₄, filtered and concentrated in vacuum to give tert-butyl 2-(2-(2-isopropylphenyl)piperazin-1-yl)-7-azaspiro[3.5]nonane-7-carboxylate (0.9 g, yield: 94%) as a yellow oil. MS (ESI, m/e) [M+1]⁺428.4.

Step 2: tert-butyl 2-(4-(3-fluorobenzyl)-2-(2-isopropylphenyl)piperazin-1-yl)-7-azaspiro[3.5]nonane-7-carboxylate.

To a solution of tert-butyl 2-(2-(2-isopropylphenyl)piperazin-1-yl)-7-azaspiro[3.5]nonane-7-carboxylate (0.9 g, 2.1 mmol) in DCE (20 mL) was added 3-fluorobenzaldehyde (0.31 g, 2.5 mmol) and HOAc (0.25 g, 4.2 mmol). After stirred at 25° C. for 1 hr, NaBH(OAc)₃ (0.89 g, 4.2 mmol) was added. The mixture was stirred at 25° C. for 12 hrs. Then aqueous NH₄Cl (20 mL) was added to the mixture and extracted with DCM (20 mL×3). The combined organic phases were washed with brine (20 mL×2), dried with anhydrous Na₂SO₄, filtered and concentrated in vacuum. The residue was purified by column chromatography (silica gel, eluent: PE/EA (v/v)=5/1) to give tert-butyl 2-(4-(3-fluorobenzyl)-2-(2-isopropylphenyl)piperazin-1-yl)-7-azaspiro[3.5]nonane-7-carboxylate (0.5 g, yield: 45%) as a yellow solid. MS (ESI, m/e) [M+1]536.5.

Step 3: 2-(4-(3-fluorobenzyl)-2-(2-isopropylphenyl)piperazin-1-yl)-7-azaspiro[3.5]nonane.

To a solution of tert-butyl 2-(4-(3-fluorobenzyl)-2-(2-isopropylphenyl)piperazin-1-yl)-7-azaspiro[3.5]nonane-7-carboxylate (500 mg, 0.934 mmol) in MeOH (20 mL) was added HCl/MeOH solution (10 mL). The mixture was stirred at 25° C. for 1 hr. After removed the solvent, the residue was dissolved into water (20 mL). The mixture was adjusted the pH=9-10 by aqueous Na₂CO₃. The mixture was extracted with EtOAc (20 mL×3). The combined organic phases were washed with brine (20 mL×2), dried with anhydrous Na₂SO₄, filtered and concentrated in vacuum to give 2-(4-(3-fluorobenzyl)-2-(2-isopropylphenyl)piperazin-1-yl)-7-azaspiro[3.5]nonane (370 mg, yield: 91%) as a yellow solid. ¹H NMR (400 MHz, CDCl₃) δ ppm: 7.47 (br s, 1H), 7.23-7.19 (m, 3H), 7.14-7.10 (m, 1H), 7.10-7.05 (m, 2H), 6.91 (m, 1H), 3.64 (m, 1H), 3.51 (s, 2H), 3.38 (m, 1H), 3.02-2.96 (m, 1H), 2.95-2.87 (m, 2H), 2.75-2.61 (m, 5H), 2.35-2.27 (m, 2H), 2.18 (m, 1H), 1.81-1.73 (m, 1H), 1.70 (m, 1H), 1.48-1.37 (m, 4H), 1.36-1.32 (m, 2H), 1.25 (m, 3H), 1.15-1.12 (m, 3H). MS (ESI, m/e) [M+1]⁺436.3.

Intermediate 44-1: 2-(2-(2-isopropylphenyl)-4-(3-methoxybenzyl)piperazin-1-yl)-7-azaspiro[3.5]nonane

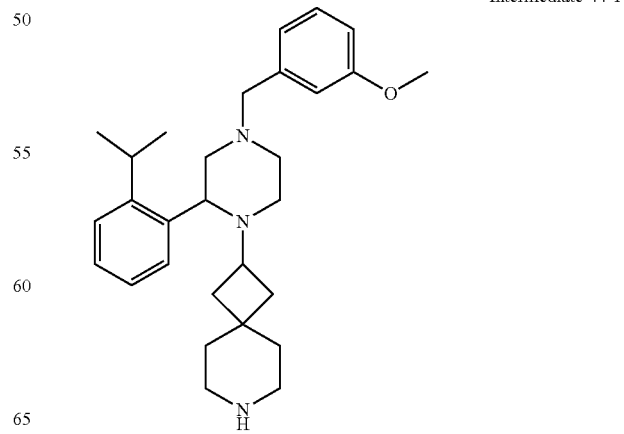

Intermediate 44-1

Step 1: tert-butyl 2-(2-(2-isopropylphenyl)-4-(3-methoxybenzyl)piperazin-1-yl)-7-azaspiro[3.5]nonane-7-carboxylate.

To a solution of tert-butyl 2-(2-(2-isopropylphenyl)piperazin-1-yl)-7-azaspiro[3.5]nonane-7-carboxylate (1.0 g, 2.34 mmol) in DCE (10 mL) was added AcOH (280 mg, 4.68 mmol) and 3-methoxybenzaldehyde (477 mg, 3.51 mmol) at 25° C. The mixture was stirred at 25° C. for 1 hr, then NaBH(OAc)$_3$ (991 mg, 4.68 mmol) was added and stirred at 25° C. for another 12 hrs. The reaction mixture was quenched by saturated Na$_2$CO$_3$ (10 mL), extracted with EtOAc (10 mL×3). The combined organic layers were washed with brine, dried with anhydrous Na$_2$SO$_4$, filtered and concentrated under reduced pressure. The crude product was purified by column chromatography (silica gel, eluent: PE/EA (v/v)=50/1 to 0/1) to give tert-butyl 2-(2-(2-isopropylphenyl)-4-(3-methoxybenzyl)piperazin-1-yl)-7-azaspiro[3.5]nonane-7-carboxylate (0.3 g, 0.547 mmol, 23% yield) as a pale yellow oil.

Step 2: 2-(2-(2-isopropylphenyl)-4-(3-methoxybenzyl)piperazin-1-yl)-7-azaspiro[3.5]nonane.

To a mixture of tert-butyl 2-(2-(2-isopropylphenyl)-4-(3-methoxybenzyl)piperazin-1-yl)-7-azaspiro[3.5]nonane-7-carboxylate (300 mg, 0.547 mmol) was added HCl/MeOH (10 mL, 4M) solution at 0° C. for 2 hrs. The reaction mixture poured into saturated Na$_2$CO$_3$ (10 ml), extracted with EtOAc (10 mL×3). The combined organic phases were washed with brine (10 mL×2), dried with anhydrous Na$_2$SO$_4$, filtered and concentrated under reduced pressure to give 2-(2-(2-isopropylphenyl)-4-(3-methoxybenzyl)piperazin-1-yl)-7-azaspiro[3.5]nonane (183 mg, yield: 75%) as a pale pink oil. $^1$H NMR (400 MHz, CDCl$_3$) δ ppm: 7.55-7.44 (m, 1H), 7.25-7.19 (m, 3H), 7.15-7.09 (m, 1H), 6.91-6.88 (m, 2H), 6.77 (m, 1H), 3.80 (s, 3H), 3.65 (d, J=9.2 Hz, 1H), 3.50 (s, 2H), 3.37 (m, 1H), 3.03-2.89 (m, 3H), 2.69-2.60 (m, 5H), 2.33-2.28 (m, 2H), 2.24-2.11 (m, 3H), 1.76 (m, 1H), 172-1.64 (m, 1H), 1.42-1.31 (m, 4H), 1.27-1.25 (d, J=6.8 Hz, 3H), 1.15 (d, J=6.8 Hz, 3H). MS (ESI, m/e) [M+1]+ 448.2.

Intermediate 46-1: 2-(4-(2-fluorobenzyl)-2-(2-isopropylphenyl)piperazin-1-yl)-7-azaspiro[3.5]nonane Intermediate 46-1

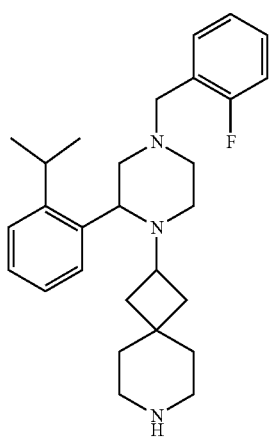

Step 1: tert-butyl 2-(4-(2-fluorobenzyl)-2-(2-isopropylphenyl)-6-oxopiperazin-1-yl)-7-azaspiro[3.5]nonane-7-carboxylate.

To a solution of tert-butyl2-(2-(2-isopropylphenyl)piperazin-1-yl)-7-azaspiro[3.5]nonane-7-carboxylate (1.0 g, 2.26 mmol) in DCE (10 mL) was added AcOH (271.97 mg, 4.53 mmol) and 2-fluorobenzaldehyde (342.88 mg, 2.76 mmol). The mixture was stirred at 25° C. for 1 hr, then NaBH(OAc)$_3$ (1.44 g, 6.79 mmol) was added and stirred at 25° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl 2-(4-(2-fluorobenzyl)-2-(2-isopropylphenyl)-6-oxopiperazin-1-yl)-7-azaspiro[3.5]nonane-7-carboxylate (1.2 g, yield: 96%) as a yellow oil.

Step 2: tert-butyl 2-(4-(2-fluorobenzyl)-2-(2-isopropylphenyl)piperazin-1-yl)-7-azaspiro[3.5]nonane-7-carboxylate.

A mixture of tert-butyl 2-(4-(2-fluorobenzyl)-2-(2-isopropylphenyl)-6-oxopiperazin-1-yl)-7-azaspiro[3.5]nonane-7-carboxylate (1.2 g, 2.18 mmol) and BH$_3$·THF (24.01 mL, 24.01 mmol) in THF (20 mL) was stirred at 70° C. for 12 hrs. The reaction solution was quenched by MeOH (20 mL) and stirred at 0° C. for 1 hr. The mixture was concentrated under reduced pressure to give tert-butyl 2-(4-(2-fluorobenzyl)-2-(2-isopropylphenyl)piperazin-1-yl)-7-azaspiro[3.5]nonane-7-carboxylate (1.07 mg, crude) as a white oil, which was used directly for next step without further purification. MS (ESI, m/e) [M+1]$^+$536.4.

Step 3: 2-(4-(2-fluorobenzyl)-2-(2-isopropylphenyl)piperazin-1-yl)-7-azaspiro[3.5]nonane.

A mixture of tert-butyl 2-(4-(2-fluorobenzyl)-2-(2-isopropylphenyl)piperazin-1-yl)-7-azaspiro[3.5]nonane-7-carboxylate (1.07 mg, 2 mmol) and HCl (4.99 mL, 19.97 mmol) in MeOH (10 mL) was stirred at 25° C. for 2 hrs. The reaction solution was concentrated under reduced pressure. The reaction mixture was poured into saturated NaHCO$_3$ (10 mL), extracted with EtOAc (20 mL×2). The combined organic layers were washed with brine, dried with anhydrous Na$_2$SO$_4$, filtered and concentrated under reduced pressure to give 2-(4-(2-fluorobenzyl)-2-(2-isopropylphenyl)piperazin-1-yl)-7-azaspiro[3.5]nonane (481 mg, yield: 55.28%) as a yellow solid. )H NMR (400 MHz, CDC$_3$) δ ppm: 7.46 (hr s, 1H), 7.37 (t, 1H), 7.26-7.17 (m, 3H), 7.16-6.96 (m, 3H), 3.72-3.54 (m, 3H), 3.39 (br s, 1H), 3.00 (br d, J=11.2 Hz, 1H), 2.96-2.85 (m, 2H), 2.73-2.57 (m, 6H), 2.44-2.35 (m, 1H), 2.33-2.21 (m, 2H), 1.80-1.71 (m, 1H), 1.71-1.60 (m, 1H), 1.46-1.30 (m, 4H), 1.29-1.21 (m, 4H), 1.15 (d, J=6.8 Hz, 4H). MS (ESI, m/e) [M+1]$^+$436.3.

Intermediate 47-1: 2-(2-(2-isopropylphenyl)-4-(2-methoxybenzyl)piperazin-1-yl)-7-azaspiro[3.5]nonane

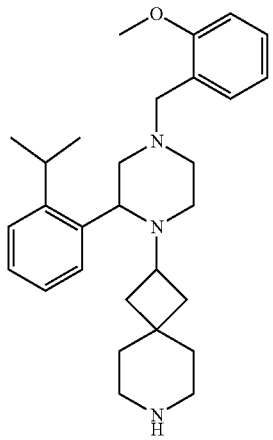

Intermediate 47-1

Step 1: tert-butyl 2-(2-(2-isopropylphenyl)-4-(2-methoxybenzyl)piperazin-1-yl)-7-azaspiro[3.5]nonane-7-carboxylate.

To a solution of tert-butyl 2-(2-(2-isopropylphenyl)piperazin-1-yl)-7-azaspiro[3.5]nonane-7-carboxylate (1.0 g, 2.34 mmol) and 2-methoxybenzaldehyde (477.5 mg, 3.51 mmol) in DCE (10 mL) was added HOAc (280.6 mg, 4.68 mmol,). The solution was stirred at 25° C. for 30 min.

Then NaBH(OAc)$_3$ (1.09 g, 5.14 mmol) was added to the above reaction and stirred at 25° C. for 12 hrs. The reaction was added sat. NaHCO$_3$ until pH=7, extracted with DCM (10 mL×3). The combined organic layers were washed with brine, dried over Na$_2$SO$_4$, filtered and concentrated under reduced pressure. The residue was purified by column chromatography (silica gel, eluent: PE/EA (v/v)=5/1 to 1/1) to give tert-butyl 2-(2-(2-isopropylphenyl)-4-(2-methoxybenzyl)piperazin-1-yl)-7-azaspiro[3.5]nonane-7-carboxylate (230 mg, yield: 18%) as yellow oil.

Step 2: 2-(2-(2-isopropylphenyl)-4-(2-methoxybenzyl)piperazin-1-yl)-7-azaspiro[3.5]nonane To a solution of tert-butyl 2-(2-(2-isopropylphenyl)-4-(2-methoxybenzyl)piperazin-1-yl)-7-azaspiro[3.5]nonane-7-carboxylate (230 mg, 0.42 mmol) in MeOH (10 mL) was added HCl/MeOH (2 mL) solution. Then the solution was stirred at 25° C. for 12 hrs. The mixture was concentrated under reduced pressure. The residue was poured into aq. Na$_2$CO$_3$ (30 mL), extracted with DCM (20 mL×3). The combined organic layers were washed with brine, dried over Na$_2$SO$_4$, filtered and concentrated under reduced pressure to give 2-(2-(2-isopropylphenyl)-4-(2-methoxybenzyl)piperazin-1-yl)-7-azaspiro[3.5]nonane (146 mg, yield: 78%) as a yellow oil. $^1$H NMR (400 MHz, CDCl$_3$) δ ppm: 7.47 (s, 1H), 7.34 (s, 1H), 7.27-7.18 (m, 5H), 6.90-6.83 (m, 2H), 3.78 (s, 3H), 3.67-3.58 (m, 4H), 2.99-2.71 (m, 3H), 2.65-2.60 (m, 5H), 2.32-2.25 (m, 3H), 1.69-1.60 (m, 3H), 1.35-1.25 (m, 9H), 1.16 (d, J=6.8 Hz, 3H). MS (ESI, m/e) [M+1]+448.3.

Intermediate 48-1: 2-(4-(2,4-dimethoxybenzyl)-2-(2-isopropylphenyl)piperazin-1-yl)-7-azaspiro[3.5]nonane

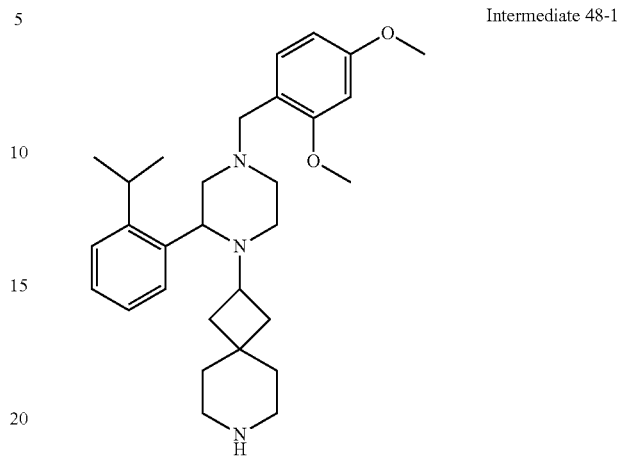

Intermediate 48-1

Step 1: tert-butyl 2-(4-(2,4-dimethoxybenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.2 g, 2.72 mmol) in DCE (10 mL) was added AcOH (326.36 mg, 5.43 mmol) and 2,4-dimethoxybenzaldehyde (496.71 mg, 2.99 mmol), The mixture was stirred at 25° C. for 1 hr. A solution of was added NaBH(OAc)$_3$ (1.73 mg, 8.15 mmol), then stirred at 25° C. for another 12 hrs. The reaction mixture was extracted with EtOAc (100 mL×2) at PH=9. The combined organic layers were washed with brine, dried with Na$_2$SO$_4$, filtered and concentrated in vacuum. The crude product was purified by column chromatography (silica gel, eluent: PE/EA (v/v)=5/1 to 2/1) to give tert-butyl 2-(4-(2,4-dimethoxybenzyl)-2-(2-isopropylphenyl)-6-oxopiperazin-1-yl)-7-azaspiro[3.5]nonane-7-carboxylate (1.2 g, 2.72 mmol, yield: 75%) as a white solid.

Step 2: 2-(4-(2,4-dimethoxybenzyl)-2-(2-isopropylphenyl)piperazin--yl)-7-azaspiro[3.5]nonane-7-carboxylate.

To a mixture of tert-butyl 2-(4-(2,4-dimethoxybenzyl)-2-(2-isopropylphenyl)-6-oxopiperazin-1-yl)-7-azaspiro[3.5]nonane-7-carboxylate (1.2 g, 2.03 mmol) and BH$_3$·THF (20.28 mL, 20.28 mmol, 1M) in THF (10 mL) was stirred at 70° C. for 12 hrs. The reaction solution was quenched by MeOH (10 mL), concentrated under reduced pressure to give tert-butyl 2-(4-(2,4-dimethoxybenzyl)-2-(2-isopropylphenyl)piperazin-1-yl)-7-azaspiro[3.5]nonane-7-carboxylate (1.2 g, crude) as a white gum, which was used directly for next step without further reaction.

Step 3: 2-(4-(2,4-dimethoxybenzyl)-2-(2-isopropylphenyl)piperazin--yl)-7-azaspiro[3.5]nonane.

To a mixture of tert-butyl 2-(4-(2,4-dimethoxybenzyl)-2-(2-isopropylphenyl) piperazin-1-yl)-7-azaspiro[3.5]nonane-7-carboxylate (1.2 g, 2.08 mmol) and HCl/MeOH (30 mL, 4M) was stirred at 25° C. for 2 hrs. The reaction solution was concentrated under reduced pressure. The residue was poured into aqueous NaHCO$_3$ to adjust the pH=9, extracted with EtOAc (100 mL×2). The combined organic layers were washed with brine, dried with anhydrous Na$_2$SO$_4$, filtered and concentrated under reduced pressure to give 2-(4-(2,4-dimethoxybenzyl)-2-(2-isopropylphenyl)piperazin-1-yl)-7-azaspiro[3.5]nonane (651 mg, 1.36 mmol, yield: 65.2%) as a white solid. $^1$H NMR (400 MHz, CDCl$_3$) δ ppm: 7.47 (br s, 1H), 7.26-7.17 (m, 4H), 7.15-7.07 (m, 1H), 6.45-6.39 (m, 2H), 3.78 (m, 6H), 3.72-3.62 (m, 2H), 3.59-3.46 (m, 3H), 3.41 (br s, 1H), 3.07-2.83 (m, 4H), 2.75-2.54 (m, 7H), 2.42-2.16 (m, 4H), 2.00-1.61 (m, 6H), 1.28-1.23 (m, 6H), 1.17 (d, J=6.8 Hz, 5H). MS (ESI, m/e) [M+1]⁺478.3.

Intermediate 48-1a: (R or S)-2-(4-(2,4-dimethoxybenzyl)-2-(2-isopropylphenyl)piperazin-1-yl)-7-azaspiro[3.5]nonane

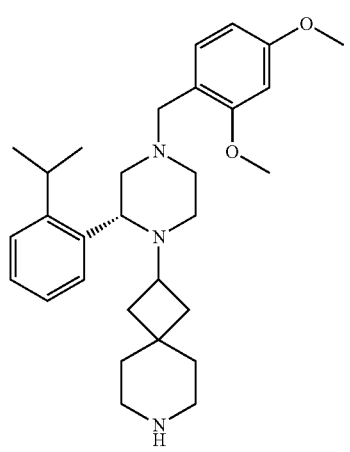

Intermediate 48-1a or

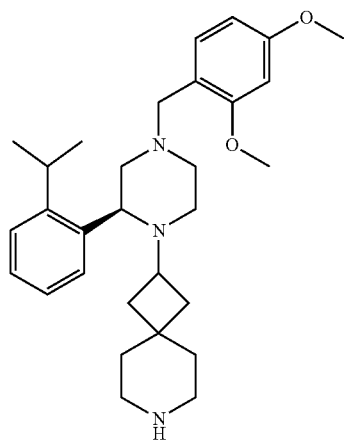

Step 1: tert-butyl (R or S)-2-(4-(2,4-dimethoxybenzyl)-2-(2-isopropylphenyl)-6-oxopiperazin-1-yl)-7-azaspiro[3.5]nonane-7-carboxylate.

To a solution of tert-butyl (R or S)-2-(2-(2-isopropylphenyl)-6-oxopiperazin-1-yl)-7-azaspiro[3.5]nonane-7-carboxylate (1.0 g, 2.26 mmol) in DCE (15 mL) was added AcOH (271.97 mg, 4.53 mmol) and 2,4-dimethoxybenzaldehyde (564.44 mg, 3.40 mmol), The mixture was stirred at 20° C. for 30 min. A solution of was added NaBH(OAc)₃ (959.86 mg, 4.53 mmol), stirred at 20° C. for another 12 hrs. The reaction mixture was extracted with EtOAc (100 mL×2) at pH=9. The combined organic layers were washed with brine, dried with Na₂SO₄, filtered and concentrated in vacuum. The crude product was purified by column chromatography (silica gel, eluent: PE/EA (v/v)=5/1 to 2/1) to give tert-butyl (R or S)-2-(4-(2,4-dimethoxybenzyl)-2-(2-isopropylphenyl)-6-oxopiperazin-1-yl)-7-azaspiro[3.5]nonane-7-carboxylate (1.13 g, yield 84%) as a white oil.

Step 2: tert-butyl (R or S)-2-(4-(2,4-dimethoxybenzyl)-2-(2-isopropylphenyl)piperazin-1-yl)-7-azaspiro[3.5]nonane-7-carboxylate.

To a mixture of tert-butyl (R or S)-2-(4-(2,4-dimethoxybenzyl)-2-(2-isopropylphenyl)-6-oxopiperazin-1-yl)-7-azaspiro[3.5]nonane-7-carboxylate (1.13 g, 1.91 mmol) and BH₃·THF (19.09 mL, 19.09 mmol, 1M) in THF (15 mL) was stirred at 70° C. for 12 hrs. The reaction solution was quenched with MeOH (10 mL), concentrated under reduced pressure to give tert-butyl (R or S)-2-(4-(2,4-dimethoxybenzyl)-2-(2-isopropylphenyl)piperazin-1-yl)-7-azaspiro[3.5]nonane-7-carboxylate (1.0 g, crude) as a white gum, which was used directly for next step without further reaction.

Step 3: (R or S)-2-(4-(2,4-dimethoxybenzyl)-2-(2-isopropylphenyl)piperazin-1-yl)-7-azaspiro[3.5]nonane.

To a mixture of tert-butyl (R or S)-2-(4-(2,4-dimethoxybenzyl)-2-(2-isopropylphenyl)piperazin-1-yl)-7-azaspiro[3.5]nonane-7-carboxylate (1.0 g, 1.73 mmol) in MeOH (10 mL) was added HCl/MeOH solution (10 mL, 4M). The mixture was stirred at 20° C. for 3 hrs. The reaction solution was concentrated under reduced pressure. The residue was poured into aqueous NaHCO₃ to adjust the pH=9, extracted with EtOAc (100 mL×2). The combined organic layers were washed with brine, dried with anhydrous Na₂SO₄, filtered and concentrated under reduced pressure to give (R or S)-2-(4-(2,4-dimethoxybenzyl)-2-(2-isopropylphenyl)piperazin-1-yl)-7-azaspiro[3.5]nonane (500 mg, yield: 60.5%) as a yellow solid.

¹H NMR (400 MHz, CDCl₃) δ ppm: 7.47 (br s, 1H), 7.26-7.17 (m, 3H), 7.15-7.06 (m, 1H), 6.51-6.30 (m, 2H), 3.81 (s, 1H), 3.79 (s, 3H), 3.76 (s, 3H), 3.66 (br s, 1H), 3.60-3.46 (m, 2H), 3.40 (br s, 1H), 3.02-2.84 (m, 3H), 2.73-2.55 (m, 4H), 2.39-2.19 (m, 4H), 2.15 (m, 1H), 1.75 (m, 1H), 1.84-1.68 (m, 1H), 1.67-1.65 (m, 1H), 1.69-1.61 (m, 1H), 1.43-1.28 (m, 4H), 1.25 (d, J=6.8 Hz, 4H), 1.17 (d, J=6.8 Hz, 4H). MS (ESI, m/e) [M+1]⁺478.5.

Intermediate 49-1: 2-(4-(3,5-dimethoxybenzyl)-2-(2-isopropylphenyl)piperazin-1-yl)-7-azaspiro[3.5]nonane

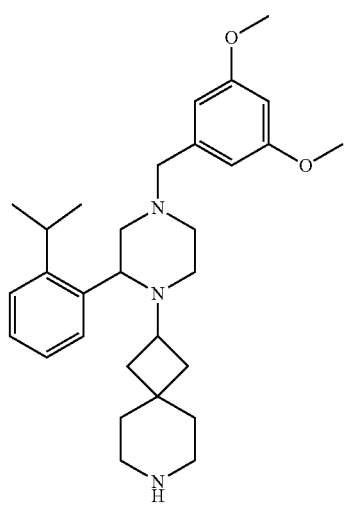

Intermediate 49-1

Step 1: tert-butyl 2-(4-(3,5-dimethoxybenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added 3,5-dimethoxybenzaldehyde (0.56 g, 3.40 mmol) and HOAc (0.27 g, 4.52 mmol). After stirred at 25° C. for 1 hr, then NaBH(OAc)$_3$ (0.96 g, 4.52 mmol) was added. The mixture was stirred at 25° C. for 12 hrs. Then aqueous NH$_4$Cl (20 mL) was added to the mixture, extracted with DCM (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=1/1) to give tert-butyl 2-(4-(3,5-dimethoxybenzyl)-2-(2-isopropylphenyl)-6-oxopiperazin-1-yl)-7-azaspiro[3.5]nonane-7-carboxylate (1.1 g, yield: 82%) as a yellow solid. $^1$H NMR (400 MHz, CDCl$_3$) δ ppm: 7.27 (s, 2H), 7.18-7.13 (m, 2H), 6.24 (s, 1H), 6.12 (s, 2H), 4.94 (br s, 1H), 4.41 (br s, 1H), 3.63-3.57 (m, 2H), 3.55 (s, 6H), 3.29-3.08 (m, 7H), 3.02-2.94 (m, 1H), 2.75-2.64 (m, 2H), 2.26-2.19 (m, 1H), 1.92 (m, 1H), 1.74-1.63 (m, 3H), 1.49-1.44 (m, 2H), 1.42 (s, 9H), 1.34-1.29 (m, 2H), 1.23 (d, J=6.8 Hz, 3H), 0.98 (d, J=6.8 Hz, 3H).

Step 2: tert-butyl 2-(4-(3,5-dimethoxybenzyl)-2-(2-isopropylphenyl)piperazin-1-yl)-7-azaspiro[3.5]nonane-7-carboxylate.

The mixture of tert-butyl 2-(4-(3,5-dimethoxybenzyl)-2-(2-isopropylphenyl)-6-oxopiperazin-1-yl)-7-azaspiro[3.5]nonane-7-carboxylate (1.1 g, 1.86 mmol) and BH$_3$·THF (18 mL, 18.6 mmol) was heated to 70° C. for 12 hrs. MeOH (10 mL) was added to the mixture carefully, and concentrated in vacuum to tert-butyl 2-(4-(3,5-dimethoxybenzyl)-2-(2-isopropylphenyl)piperazin-1-yl)-7-azaspiro[3.5]nonane-7-carboxylate (0.9 g, yield: 84%) as a yellow oil, which was used into the next step without further purification. MS (ESI, m/e) [M+1]$^+$578.4.

Step 3: 2-(4-(3,5-dimethoxybenzyl)-2-(2-isopropylphenyl)piperazin-1-yl)-7-azaspiro[3.5]nonane.

To a solution of tert-butyl 2-(4-(3,5-dimethoxybenzyl)-2-(2-isopropylphenyl)piperazin-1-yl)-7-azaspiro[3.5]nonane-7-carboxylate (900 mg, 1.56 mmol) in MeOH (20 mL) was added HCl/MeOH (10 mL). The mixture was stirred at 25° C. for 1 hr. After removed the solvent, the residue was dissolved into water (20 mL). The mixture was adjusted the pH=9-10 using aqueous Na$_2$CO$_3$. The mixture was extracted with EtOAc (20 mL×3). The combined organic phases were washed with brine (20 mL×2), dried with anhydrous Na$_2$SO$_4$, filtered and concentrated in vacuum to give 2-(4-(3,5-dimethoxybenzyl)-2-(2-isopropylphenyl)piperazin-1-yl)-7-azaspiro[3.5]nonane (550 mg, yield: 74%) as a yellow solid. $^1$H NMR (400 MHz, CDCl$_3$) δ ppm: 7.48 (br s, 1H), 7.25-7.17 (m, 2H), 7.15-7.09 (m, 1H), 6.50 (m, 2H), 6.33 (s, 1H), 3.77 (s, 6H), 3.65 (m, 1H), 3.46 (s, 2H), 3.41 (m, 1H), 3.00 (m, 1H), 2.96-2.87 (m, 2H), 2.72-2.54 (m, 5H), 2.35-2.26 (m, 2H), 2.20-2.14 (m, 1H), 1.93 (br s, 1H), 1.79-1.72 (m, 1H), 1.70-1.64 (m, 1H), 1.41-1.29 (m, 5H), 1.26 (br d, J=6.8 Hz, 3H), 1.15 (br d, J=6.8 Hz, 3H). MS (ESI, m/e) [M+1]$^+$478.4.

Intermediate 50-1: 2-(4-(2,4-difluorobenzyl)-2-(2-isopropylphenyl)piperazin-1-yl)-7-azaspiro[3.5]nonane

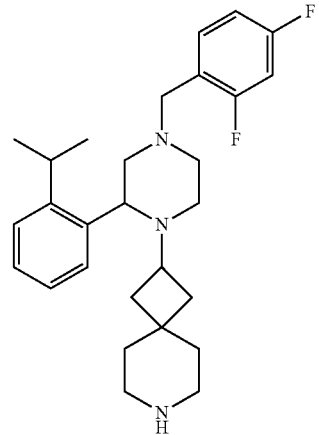

Intermediate 50-1

Step 1: tert-butyl 2-(4-(2,4-difluorobenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.2 g, 2.72 mmol) in DCE (10 mL) was added AcOH (326.36 mg, 5.43 mmol) and 2,4-difluorobenzaldehyde (424.76 mg, 2.99 mmol). The mixture was stirred at 25° C. for 1 hr, then NaBH(OAc)$_3$ (1.73 g, 8.15 mmol) was added and stirred at 25° C. for another 12 hrs. The reaction mixture was poured into sat. NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl 2-(4-(2,4-difluorobenzyl)-2-(2-isopropylphenyl)-6-oxopiperazin-1-yl)-7-azaspiro[3.5]nonane-7-carboxylate (1.0 g, 1.76 mmol, yield: 64%) as a yellow oil.

Step 2: tert-butyl 2-(4-(2,4-difluorobenzyl)-2-(2-isopropylphenyl)piperazin-1-yl)-7-azaspiro[3.5]nonane-7-carboxylate.

To a mixture of tert-butyl 2-(4-(2,4-difluorobenzyl)-2-(2-isopropylphenyl)-6-oxopiperazin-1-yl)-7-azaspiro[3.5]nonane-7-carboxylate ((1.0 g, 1.76 mmol) and BH$_3$ (19.38 mL, 19.38 mmol) in THF (10 mL) was stirred at 70° C. for 12 hrs. The reaction solution was quenched by MeOH (10 mL), concentrated under reduced pressure to give tert-butyl 2-(4-(2,4-difluorobenzyl)-2-(2-isopropylphenyl)piperazin-1-yl)-7-azaspiro[3.5]nonane-7-carboxylate (1.2 g, crude), which was used directly for next step without further reaction.

Step 3: 2-(4-(2,4-difluorobenzyl)-2-(2-isopropylphenyl)piperazin-1-yl)-7-azaspiro[3.5]nonane.

A mixture of tert-butyl 2-(4-(2,4-difluorobenzyl)-2-(2-isopropylphenyl)piperazin-1-yl)-7-azaspiro[3.5]nonane-7-carboxylate (1.2 g, 2.17 mmol) and HCl/MeOH (35 mL, 4M) was stirred at 25° C. for 2 hrs. The reaction solution was concentrated under reduced pressure. The reaction mixture was poured into sat. NaHCO$_3$ (50 mL), extracted with EtOAc (100 mL×2). The combined organic layers were washed with brine, dried with anhydrous Na$_2$SO$_4$, filtered and concentrated under reduced pressure to give 2-(4-(2,4-difluorobenzyl)-2-(2-isopropylphenyl)piperazin-1-yl)-7-azaspiro[3.5]nonane (515 mg, 1.14 mmol, yield: 52%) as a yellow solid. $^1$H NMR (400 MHz, CDCl$_3$) δ ppm: 7.46 (br s, 1H), 7.38-7.30 (m, 1H), 7.23 (m, 2H), 7.16-7.09 (m, 1H), 6.85-6.72 (m, 2H), 3.65-3.51 (m, 3H), 3.37 (br s, 1H), 3.00 (m, 1H), 2.90 (m, 2H), 2.69-2.56 (m, 5H), 2.42-2.21 (m, 4H), 1.80-1.61 (m, 2H), 1.44-1.28 (m, 5H), 1.25 (br d, J=6.8 Hz, 3H), 1.15 (br d, J=6.8 Hz, 3H). MS (ESI, m/e) [M+1]$^+$ 454.3.

Intermediate 51-1: 2-(4-(3,5-difluorobenzyl)-2-(2-isopropylphenyl)piperazin-1-yl)-7-azaspiro[3.5]nonane

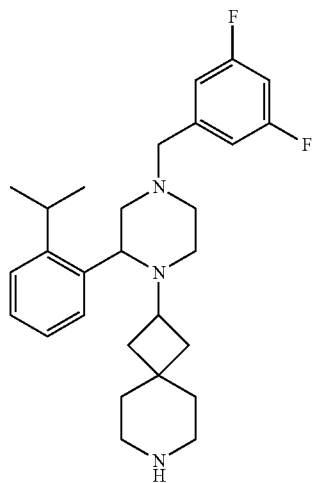

Class B-451

Step 1: tert-butyl 2-(4-(3,5-difluorobenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (800 mg, 1.87 mmol) in DCE (10 mL) was added AcOH (337 mg, 5.61 mmol) and 3,5-difluorobenzaldehyde (292 mg, 2.06 mmol). The mixture was stirred at 20° C. for 1 hr. Then NaBH(OAc)$_3$ (1.19 g, 5.61 mmol) was added. The mixture was stirred at 20° C. for 16 hrs. Then saturated NaHCO$_3$ (10 mL) and EtOAc (10 mL) were added. The mixture was stirred at 20° C. for 0.2 hr. The organic layer was separated, dried over Na$_2$SO$_4$, evaporated in vacuo. The residue was purified by column chromatography (silica gel, eluent: PE/EA (v/v)=10/1 to 1/1) to afford tert-butyl 2-(4-(3,5-difluorobenzyl)-2-(2-isopropylphenyl)-6-oxopiperazin-1-yl)-7-azaspiro[3.5]nonane-7-carboxylate (500 mg, yield: 50%) as yellow solid. MS (ESI, m/e) [M+1]$^+$568.5

Step 2: tert-butyl 2-(4-(3,5-difluorobenzyl)-2-(2-isopropylphenyl)piperazin-1-yl)-7-azaspiro[3.5]nonane-7-carboxylate.

The mixture of tert-butyl 2-(4-(3,5-difluorobenzyl)-2-(2-isopropylphenyl)-6-oxopiperazin-1-yl)-7-azaspiro[3.5]nonane-7-carboxylate (500 mg, 0.88 mmol) and BH$_3$·THF (8.8 mL, 8.8 mmol) was heated to 70° C. for 12 hrs. After cooling to 0° C., the mixture was quenched with MeOH (10 mL). The mixture was concentrated in vacuum to give tert-butyl 2-(4-(3,5-difluorobenzyl)-2-(2-isopropylphenyl)piperazin-1-yl)-7-azaspiro[3.5]nonane-7-carboxylate (400 mg, yield: 80%) as yellow solid which was used into the next step without further purification. MS (ESI, m/e) [M+1]$^+$ 554.2.

Step 3: 2-(4-(3,5-difluorobenzyl)-2-(2-isopropylphenyl)piperazin-1-yl)-7-azaspiro[3.5]nonane.

To a solution of tert-butyl 2-(4-(3,5-difluorobenzyl)-2-(2-isopropylphenyl)piperazin-1-yl)-7-azaspiro[3.5]nonane-7-carboxylate (400 mg, 0.71 mmol) in MeOH (10 mL) was added HCl/MeOH (10 mL). The mixture was stirred at 25° C. for 2 hrs After concentrating in vacuum, the residue was dissolved into water (20 mL). The mixture was adjusted the pH=9-10 with aqueous Na$_2$CO$_3$. The mixture was extracted with EtOAc (20 mL×3). The combined organic phases were washed with brine (20 mL×2), dried with anhydrous Na$_2$SO$_4$, filtered and concentrated in vacuum to give 2-(4-(3,5-difluorobenzyl)-2-(2-isopropylphenyl)piperazin-1-yl)-7-azaspiro[3.5]nonane (225 mg, yield: 70%) as a brown solid. $^1$H NMR (400 MHz, CDCl$_3$) δ ppm: 7.52-7.47 (s, 1H), 7.27-7.21 (m, 2H), 7.14-7.12 (m, 1H), 6.89-6.87 (m, 2H), 6.68-6.66 (m, 1H), 3.65-3.63 (m, 1H), 3.48-3.47 (m, 2H), 3.46-3.38 (m, 1H), 3.22-3.02 (m, 1H), 3.02-2.88 (m, 2H), 2.67-2.60 (m, 5H), 2.32-2.22 (m, 2H), 2.22-2.15 (m, 1H), 1.80-1.60 (m, 2H), 1.38-1.14 (m, 13H). MS (ESI, m/e) [M+1]$^+$454.3

Intermediate 52-1: 2-(4-(3,4-difluorobenzyl)-2-(2-isopropylphenyl)piperazin-1-yl)-7-azaspiro[3.5]nonane

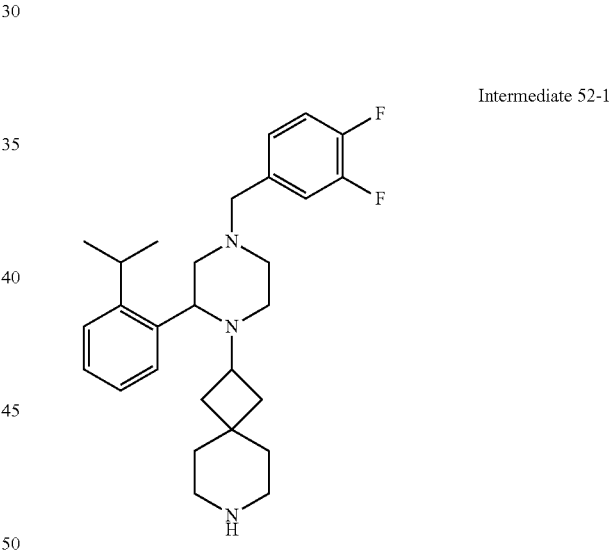

Intermediate 52-1

Step 1: tert-butyl 2-(4-(3,4-difluorobenzyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (880 mg, 1.99 mmol) in DCE (10 mL) was added AcOH (239.33 mg, 3.99 mmol) and 3,4-difluorobenzaldehyde (311.49 mg, 2.19 mmol). The mixture was stirred at 25° C. for 1 hr. Then NaBH(OAc)$_3$ (1.27 g, 5.98 mmol) was added and stirred at 25° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The residue was purified by column chromatography (silica gel, eluent: PE/EA (v/v)=5/1 to 2/1) to give tert-butyl 2-(4-(3,4-difluorobenzyl)-2-(2-isopropylphenyl)-6-oxopiperazin-1-yl)-7-azaspiro[3.5]nonane-7-carboxylate (1.0 g, yield: 85%) as a yellow oil.

Step 2: tert-butyl 2-(4-(3,4-difluorobenzyl)-2-(2-isopropylphenyl)piperazin-1-yl)-7-azaspiro[3.5]nonane-7-carboxylate.

A mixture of tert-butyl 2-(4-(3,4-difluorobenzyl)-2-(2-isopropylphenyl)-6-oxopiperazin-1-yl)-7-azaspiro[3.5]nonane-7-carboxylate (1.0 g, 1.76 mmol) and BH$_3$·THF (17.61 mL, 17.61 mmol) in THF (15 mL) was stirred at 70° C. for 12 hrs. The reaction solution was quenched by MeOH (10 mL), concentrated under reduced pressure to give tert-butyl 2-(4-(3,4-difluorobenzyl)-2-(2-isopropylphenyl)piperazin-1-yl)-7-azaspiro[3.5]nonane-7-carboxylate (750 mg, crude) as a yellow oil, which was used directly for next step without further purification.

Step 3: 2-(4-(3,4-difluorobenzyl)-2-(2-isopropylphenyl)piperazin-1-yl)-7-azaspiro[3.5]nonane.

To a mixture of tert-butyl 2-(4-(3,4-difluorobenzyl)-2-(2-isopropylphenyl)piperazin-1-yl)-7-azaspiro[3.5]nonane-7-carboxylate (750 mg, 1.35 mmol) and HCl (3.39 mL, 13.54 mmol) in MeOH (10 mL) was stirred at 25° C. for 2 hrs. The reaction solution was concentrated under reduced pressure. The residue was poured into saturated NaHCO$_3$ (10 mL), extracted with EtOAc (20 mL×2). The combined organic layers were dried with anhydrous Na$_2$SO$_4$, filtered and concentrated under reduced pressure to give 2-(4-(3,4-difluorobenzyl)-2-(2-isopropylphenyl)piperazin-1-yl)-7-azaspiro[3.5]nonane (423 mg, yield: 68%) as a white solid. $^1$H NMR (400 MHz, CDCl$_3$) δ ppm: 7.47 (br s, 1H), 7.26-6.96 (m, 6H), 3.63 (m, 1H), 3.51-3.28 (m, 3H), 3.09-2.79 (m, 3H), 2.70-2.53 (m, 5H), 2.36-2.23 (m, 3H), 2.21-1.97 (m, 3H), 1.80-1.63 (m, 2H), 1.46-1.21 (m, 10H), 1.14 (br d, J=6.8 Hz, 4H). MS (ESI, m/e) [M+1]$^+$454.3.

Intermediate 52-1a: (R or S)-2-(4-(3,4-difluorobenzyl)-2-(2-isopropylphenyl)piperazin-1-yl)-7-azaspiro[3.5]nonane Intermediate 52-1a

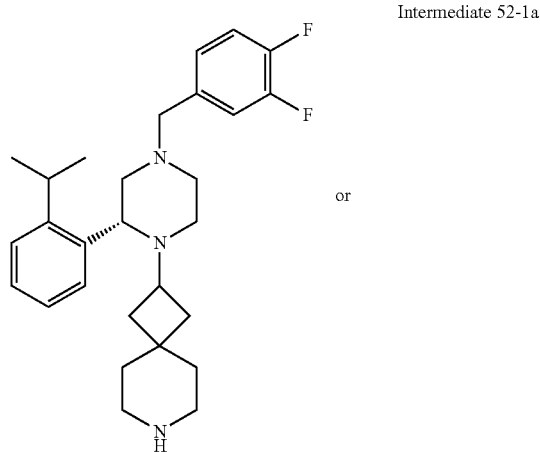 [SMILES: CC(C)c1ccccc1C1CN(Cc2ccc(F)c(F)c2)CCN1C1CC2(CCNCC2)C1]

or

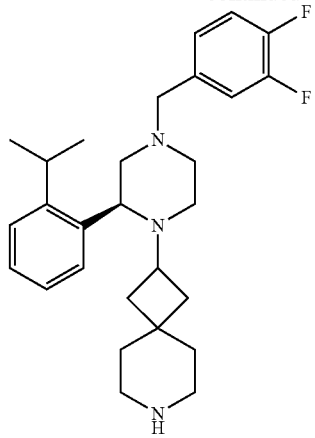

Step 1: tert-butyl (R or S)-2-(4-(3,4-difluorobenzyl)-2-(2-isopropylphenyl)-6-oxopiperazin-1-yl)-7-azaspiro[3.5]nonane-7-carboxylate.

To a solution of tert-butyl (R or S)-2-(2-(2-isopropylphenyl)-6-oxopiperazin-1-yl)-7-azaspiro[3.5]nonane-7-carboxylate (1.0 g, 2.26 mmol) in DCE (10 mL) was added AcOH (271.97 mg, 4.53 mmol) and 3,4-difluorobenzaldehyde (309.15 mg, 2.49 mmol). The mixture was stirred at 25° C. for 1 hour, then NaBH(OAc)$_3$ (1.44 g, 6.79 mmol) was added, stirred at 25° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The residue was purified by column chromatography (silica gel, eluent: PE/EA (v/v)=5/1 to 2/1) to give tert-butyl (R or S)-2-(4-(3,4-difluorobenzyl)-2-(2-isopropylphenyl)-6-oxopiperazin-1-yl)-7-azaspiro[3.5]nonane-7-carboxylate (1.15 g, yield: 88%) as a yellow oil.

Step 2: tert-butyl (R or S)-2-(4-(3,4-difluorobenzyl)-2-(2-isopropylphenyl)piperazin-1-yl)-7-azaspiro[3.5]nonane-7-carboxylate.

A mixture of tert-butyl (R or S)-2-(4-(3,4-difluorobenzyl)-2-(2-isopropylphenyl)-6-oxopiperazin-1-yl)-7-azaspiro[3.5]nonane-7-carboxylate (1.15 g, 2.03 mmol) and BH$_3$·THF (20.26 mL, 20.26 mmol) in THF was stirred at 70° C. for 12 hrs. The reaction solution was quenched with MeOH (10 mL), concentrated under reduced pressure to give t tert-butyl (R or S)-2-(4-(3,4-difluorobenzyl)-2-(2-isopropylphenyl)piperazin-1-yl)-7-azaspiro[3.5]nonane-7-carboxylate (1.1 g, crude) as a yellow oil, which was used directly for next step without further purification.

Step 3: (R or S)-2-(4-(3,4-difluorobenzyl)-2-(2-isopropylphenyl)piperazin-1-yl)-7-azaspiro[3.5]nonane.

To a mixture of tert-butyl (R or S)-2-(4-(3,4-difluorobenzyl)-2-(2-isopropylphenyl)piperazin-1-yl)-7-azaspiro[3.5]nonane-7-carboxylate (1.1 g, 1.99 mmol) and HCl (4.97 mL, 19.87 mmol) in MeOH (10 mL) was stirred at 25° C. for 2 hrs. The reaction solution was concentrated under reduced pressure. The residue was poured into saturated NaHCO$_3$ (10 mL), extracted with EtOAc (20 mL×2). The combined organic layers were dried with anhydrous Na$_2$SO$_4$, filtered and concentrated under reduced pressure to give (R or S)-2-(4-(3,4-difluorobenzyl)-2-(2-isopropylphenyl)piperazin-1-yl)-7-azaspiro[3.5]nonane (420 mg, yield: 47%) as a yellow solid. $^1$H NMR (400 MHz, CDCl$_3$) δ ppm: 7.48 (br s, 1H), 7.26-7.15 (m, 3H), 7.15-7.04 (m, 2H), 7.01 (m, 1H), 3.63 (m, 1H), 3.45 (s, 2H), 3.39 (m, 1H), 3.01 (m, 1H), 2.95-2.85 (m, 2H), 2.71-2.57 (m, 4H), 2.36-2.24 (m, 3H), 2.23-2.12 (m, 3H), 1.82-1.55 (m, 2H), 1.45-1.30 (m, 5H), 1.26 (d, J=6.8 Hz, 3H), 1.14 (d, J=6.8 Hz, 3H). MS (ESI, m/e) [M+1]$^+$454.3.

Intermediate 53-1: 2-(4-(chroman-6-ylmethyl)-2-(2-isopropylphenyl)piperazin-1-yl)-7-azaspiro[3.5]nonane

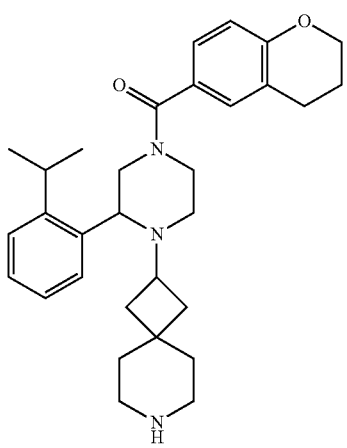

Intermediate 53-1

Step 1: tert-butyl 2-(4-(chroman-6-ylmethyl)-2-(2-isopropylphenyl)-6-oxopiperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), chroman-6-carbaldehyde (404 mg, 2.49 mmol) and AcOH (271.97 mg, 4.53 mmol) in DCE (20 mL) was stirred at 20° C. for 30 min. Then NaBH(OAc)$_3$ (1.44 g, 6.79 mmol) was added to the above mixture in portions, and stirred at 30° C. for 2 hrs. The reaction mixture was diluted with DCM (30 mL), washed with sat. NaHCO$_3$ (30 mL). The organic layer was dried with anhydrous Na$_2$SO$_4$, filtered and concentrated under reduced pressure. The residue was purified by column chromatography (silica gel, eluent: PE/EA (v/v)=3/1 to 1/1) to give tert-butyl 2-(4-(chroman-6-ylmethyl)-2-(2-isopropylphenyl)-6-oxopiperazin-1-yl)-7-azaspiro[3.5]nonane-7-carboxylate (1.25 g, yield: 94%) as a white solid. $^1$H NMR (400 MHz, CDCl$_3$) δ ppm: 7.34-7.28 (m, 1H), 7.27 (s, 1H), 7.24-7.16 (m, 1H), 7.15-7.09 (m, 1H), 6.68-6.58 (m, 1H), 6.57-6.50 (m, 1H), 6.40 (s, 1H), 4.93 (s, 1H), 4.44 (s, 1H), 4.15-4.10 (m, 1H), 3.59-3.46 (m, 2H), 3.33-3.06 (m, 6H), 2.97 (t, 1H), 2.63 (s, 2H), 2.56-2.36 (m, 2H), 2.23 (t, 1H), 1.98-1.83 (m, 3H), 1.81-1.57 (m, 3H), 1.54-1.38 (m, 11H), 1.37-1.29 (m, 3H), 1.25-1.17 (m, 3H), 0.95 (d, J=6.8 Hz, 3H). MS (ESI, m/e) [M+1]$^+$588.4.

Step 2: tert-butyl 2-(4-(chroman-6-ylmethyl)-2-(2-isopropylphenyl)piperazin-1-yl)-7-azaspiro[3.5]nonane-7-carboxylate.

To a solution of tert-butyl 2-(4-(chroman-6-ylmethyl)-2-(2-isopropylphenyl)-6-oxopiperazin-1-yl)-7-azaspiro[3.5]nonane-7-carboxylate (1.25 g, 2.13 mmol) in THF (15 mL) was added BH$_3$·THF (30 mL, 30 mmol) dropwise at 20° C. The mixture was heated to 70° C. for 12 hrs. The reaction was quenched by methanol (5 mL), concentrated under reduced pressure to give tert-butyl 2-(4-(chroman-6-ylmethyl)-2-(2-isopropylphenyl)piperazin-1-yl)-7-azaspiro[3.5]nonane-7-carboxylate (1.22 g, crude) as a white solid. MS (ESI, m/e) [M+1]$^+$574.5.

Step 3: 2-(4-(chroman-6-ylmethyl)-2-(2-isopropylphenyl)piperazin-1-yl)-7-azaspiro[3.5]nonane.

To a solution of tert-butyl 2-(4-(chroman-6-ylmethyl)-2-(2-isopropylphenyl)piperazin-1-yl)-7-azaspiro[3.5]nonane-7-carboxylate (1.20 g, 2.09 mmol) in MeOH (5 mL) was added HCl/MeOH (20 mL, 4M) dropwise at 20° C. The solution was stirred at 20° C. for 2 hrs. The reaction solution was concentrated in vacuum. The residue was diluted with HCl (10 mL, 1M), extracted with EtOAc (20 mL×2). The aqueous phase was adjusted the Ph=8 with NaHCO$_3$, extracted with EtOAc/MeOH (20/1, 40 mL×5). The combined organic phases were dried with anhydrous Na$_2$SO$_4$, filtered and concentrated under reduced pressure to give 2-(4-(chroman-6-ylmethyl)-2-(2-isopropylphenyl)piperazin-1-yl)-7-azaspiro[3.5]nonane (740 mg, yield: 75%) as a white solid. $^1$H NMR (400 MHz, CDCl$_3$) δ ppm: 7.47 (s, 1H), 7.17-7.25 (m, 2H), 7.08-7.15 (m, 1H), 6.92-7.04 (m, 2H), 6.70 (d, J=8.19 Hz, 1H), 4.12-4.21 (m, 2H), 3.57-3.80 (m, 3H), 3.41 (s, 3H), 2.83-3.05 (m, 3H), 2.56-2.82 (m, 7H), 2.21-2.33 (m, 2H), 2.08-2.19 (m, 1H), 1.92-2.03 (m, 2H), 1.60-1.80 (m, 2H), 1.35-1.54 (m, 4H), 1.28-1.34 (m, 1H), 1.24 (d, J=6.85 Hz, 3H), 1.14 (d, J=6.85 Hz, 3H). MS (ESI, m/e) [M+1]$^+$474.4.

Intermediate 54-1: 2-(2-(2-isopropylphenyl)-4-((5,6,7,8-tetrahydronaphthalen-2-yl)methyl)piperazin-1-yl)-7-azaspiro[3.5]nonane

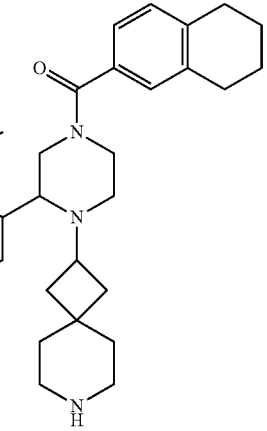

Intermediate 54-1

Step 1: 5,6,7,8-tetrahydronaphthalene-2-carbaldehyde and 5,6,7,8-tetrahydronaphthalene-1-carbaldehyde.

A solution of 1,2,3,4-tetrahydronaphthalene (3.0 g, 22.69 mmol) in DCM (50 mL) was cooled to 0° C. with vigorous stirring, SnCl$_4$ (10.4 g, 39.94 mmol) was added all at once via syringe, followed by the dropwise introduction of dichloro(methoxy)methane (2.61 g, 22.69 mmol) over 10 min. After the addition, the reaction was stirred at 0° C. for 0.5 hr. The color of mixture turned to deep red, and then turned to yellow. The reaction mixture was quenched by ice.

The organic phase was washed with water (30 mL×3), dried with anhydrous Na$_2$SO$_4$, filtered and concentrated under reduced pressure to give the mixture of 5,6,7,8-tetrahydronaphthalene-2-carbaldehyde and 5,6,7,8-tetrahydronaphthalene-1-carbaldehyde (3.3 g, crude) as a dark yellow oil. $^1$H NMR (400 MHz, CDCl$_3$) δ ppm: 10.39-9.83 (m, 1H), 7.67-7.56 (m, 1H), 7.34-7.20 (m, 1H), 7.12-7.04 (m, 1H), 1.69-3.37 (m, 8H).

Step 2: tert-butyl 2-(2-(2-isopropylphenyl)-6-oxo-4-((5,6,7,8-tetrahydronaphthalen-2-yl)methyl)piperazin-1-yl)-7-azaspiro[3.5]nonane-7-carboxylate and tert-butyl 2-(2-(2-isopropylphenyl)-6-oxo-4-((5,6,7,8-tetrahydronaphthalen-1-yl)methyl)piperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), AcOH (271.97 mg, 4.53 mmol) and the mixture of 5,6,7,8-tetrahydronaphthalene-2-carbaldehyde and 5,6,7,8-tetrahydronaphthalene-1-carbaldehyde (435.35 mg, 2.72 mmol) in DCE (20 mL) was stirred at 20° C. for 30 min. NaBH(OAc)$_3$ (1.44 g, 6.79 mmol) was added to the above mixture in portions, and then stirred at 20° C. for 3 hrs. The reaction mixture was diluted with DCM (30 mL), washed with sat. Na$_2$CO$_3$, dried with anhydrous Na$_2$SO$_4$, filtered and concentrated under reduced pressure. The residue was purified by prep-HPLC, adjusted the pH=8 with NaHCO$_3$, concentrated, extracted with EtOAc (50 mL×3). The combined organic phases were dried with anhydrous Na$_2$SO$_4$, filtered and concentrated under reduced pressure to give tert-butyl 2-(2-(2-isopropylphenyl)-6-oxo-4-((5,6,7,8-tetrahydronaphthalen-2-yl)methyl)piperazin-1-yl)-7-azaspiro[3.5]nonane-7-carboxylate (500 mg, 0.86 mmol) as a pale yellow solid. $^1$H NMR (400 MHz, CDCl$_3$) δ ppm: 7.33-7.27 (m, 2H), 7.22-7.17 (m, 1H), 7.15-7.10 (m, 1H), 6.82 (d, J=7.6 Hz, 1H), 6.65 (d, J=7.6 Hz, 1H), 6.51 (s, 1H), 4.96 (s, 1H), 4.49-4.31 (m, 1H), 3.62-3.48 (m, 2H), 3.28-3.12 (m, 6H), 3.03-2.92 (m, 1H), 2.71-2.61 (m, 4H), 2.55-2.40 (m, 2H), 2.27-2.19 (m, 1H), 1.93 (t, 1H), 1.81-1.68 (m, 6H), 1.56-1.41 (m, 11H), 1.36-1.31 (m, 2H), 1.22 (d, J=6.8 Hz, 3H), 0.95 (d, J=6.8 Hz, 3H).

tert-butyl 2-(2-(2-isopropylphenyl)-6-oxo-4-((5,6,7,8-tetrahydronaphthalen-1-yl)methyl)piperazin-1-yl)-7-azaspiro[3.5]nonane-7-carboxylate (370 mg, 0.63 mmol) as a white solid. $^1$H NMR (400 MHz, CDCl$_3$) δ ppm: 7.27-7.16 (m, 3H), 7.12 (td, 1H), 7.03 (d, J=7.6 Hz, 1H), 6.96-6.81 (m, 2H), 6.72 (m, 1H), 4.92 (s, 1H), 4.48 (s, 1H), 3.57-3.49 (m, 2H), 3.30-3.04 (m, 6H), 2.94 (m, 1H), 2.73-2.57 (m, 4H), 2.36-2.10 (m, 4H), 1.90 (t, 1H), 1.71 (m, 2H), 1.63-1.58 (m, 1H), 1.55-1.41 (m, 13H), 1.36-1.29 (m, 2H), 1.20 (d, J=6.8 Hz, 3H), 0.91 (d, J=6.8 Hz, 3H).

Step 3: tert-butyl 2-(2-(2-isopropylphenyl)-4-((5,6,7,8-tetrahydronaphthalen-2-yl)methyl)piperazin-1-yl)-7-azaspiro[3.5]nonane-7-carboxylate.

To a solution of tert-butyl 2-(2-(2-isopropylphenyl)-6-oxo-4-((5,6,7,8-tetrahydronaphthalen-2-yl)methyl)piperazin-1-yl)-7-azaspiro[3.5]nonane-7-carboxylate (500 mg, 0.86 mmol) in THF (8 mL) was added BH$_3$·THF (16 mL, 16 mmol) dropwise at 20° C. The mixture was heated to 70° C. for 12 hrs. The reaction was quenched by methanol (5 mL), concentrated under reduced pressure to give tert-butyl 2-(2-(2-isopropylphenyl)-4-((5,6,7,8-tetrahydronaphthalen-2-yl)methyl)piperazin-1-yl)-7-azaspiro[3.5]nonane-7-carboxylate (488 mg, crude) as a white solid. MS (ESI, m/e) [M+1]$^+$572.5.

Step 4: 2-(2-(2-isopropylphenyl)-4-((5,6,7,8-tetrahydronaphthalen-2-yl)methyl)piperazin-1-yl)-7-azaspiro[3.5]nonane.

To a solution of tert-butyl 2-(2-(2-isopropylphenyl)-4-((5,6,7,8-tetrahydronaphthalen-2-yl)methyl)piperazin-1-yl)-7-azaspiro[3.5]nonane-7-carboxylate (488 mg, 0.85 mmol) in MeOH (5 mL) was added HCl/MeOH (15 mL, 4M) dropwise at 20° C. The solution was stirred at 20° C. for 2 hrs. The reaction solution was concentrated under reduced pressure. The residue was diluted with HCl (10 mL, 1M), extracted with EtOAc (10 mL×2). The aqueous phase was adjusted the pH=8 with NaHCO$_3$, extracted with EtOAc (20 mL×3). The combined organic phases were dried with anhydrous Na$_2$SO$_4$, filtered and concentrated under reduced pressure to give 2-(2-(2-isopropylphenyl)-4-((5,6,7,8-tetrahydronaphthalen-2-yl)methyl)piperazin-1-yl)-7-azaspiro[3.5]nonane (311 mg, yield: 77%) as a white solid. $^1$H NMR (400 MHz, CDCl$_3$) δ ppm: 7.47 (s, 1H), 7.26-7.15 (m, 2H), 7.11 (t, 1H), 6.99 (m, 3H), 3.66 (m, 1H), 3.48-3.30 (m, 3H), 3.03-2.82 (m, 3H), 2.82-2.39 (m, 10H), 2.37-2.08 (m, 3H), 1.79-1.60 (m, 6H), 1.41-1.11 (m, 12H). MS (ESI, m/e) [M+1]$^+$472.4.

Intermediate 55-1: 2-(2-(2-isopropylphenyl)-4-((5,6,7,8-tetrahydronaphthalen-2-yl)methyl)piperazin-1-yl)-7-azaspiro[3.5]nonane

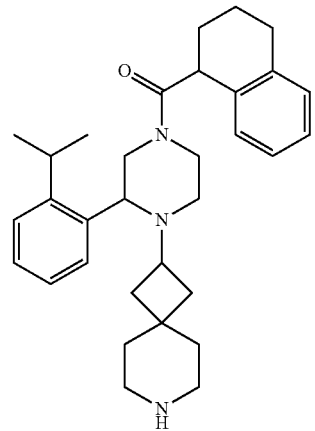

Intermediate 55-1

Step 1: tert-butyl 2-(2-(2-isopropylphenyl)-4-((5,6,7,8-tetrahydronaphthalen-1-yl)methyl)piperazin-1-yl)-7-azaspiro[3.5]nonane-7-carboxylate.

To a solution of tert-butyl 2-(2-(2-isopropylphenyl)-6-oxo-4-((5,6,7,8-tetrahydronaphthalen-1-yl)methyl)piperazin-1-yl)-7-azaspiro[3.5]nonane-7-carboxylate (370 mg, 0.63 mmol) in THF (6 mL) was added BH$_3$·THF (12 mL, 12 mmol) dropwise at 20° C. The mixture was heated to 70° C. for 12 hrs. The reaction was quenched by methanol (5 mL), concentrated under reduced pressure to give tert-butyl 2-(2-(2-isopropylphenyl)-4-((5,6,7,8-tetrahydronaphthalen-1-yl)methyl)piperazin-1-yl)-7-azaspiro[3.5]nonane-7-carboxylate (361 mg, crude) as a white solid, which was used directly for next step without further purification. MS (ESI, m/e) [M+1]$^+$572.5.

Step 2: 2-(2-(2-isopropylphenyl)-4-((5,6,7,8-tetrahydronaphthalen-2-yl)methyl)piperazin-1-yl)-7-azaspiro[3.5]nonane.

To a solution of tert-butyl 2-(2-(2-isopropylphenyl)-4-((5,6,7,8-tetrahydronaphthalen-1-yl)methyl)piperazin-1-yl)-7-azaspiro[3.5]nonane-7-carboxylate (361 mg, 0.63 mmol) in MeOH (5 mL) was added HCl/MeOH (10 mL, 4M) dropwise at 20° C. The solution was stirred at 20° C. for 2 hrs. The reaction solution was concentrated under reduced pressure. The residue was diluted with HCl (10 mL, 1M), extracted with EtOAc (10 mL×2). The aqueous phase was adjusted the pH=8 with NaHCO$_3$, extracted with EtOAc (20 mL×3). The combined organic phases were dried over anhydrous Na$_2$SO$_4$, filtered and concentrated in vacuum to give 2-(2-(2-isopropylphenyl)-4-((5,6,7,8-tetrahydronaphthalen-2-yl)methyl)piperazin-1-yl)-7-azaspiro[3.5]nonane (245 mg, yield: 83%) as a white solid. $^1$H NMR (400 MHz, CDCl$_3$) δ ppm: 7.51 (s, 1H), 7.21 (m, 2H), 7.16-7.09 (m, 2H), 7.02 (t, 1H), 6.99-6.92 (m, 1H), 3.64 (s, 2H), 3.45-3.36 (m, 2H), 3.08-2.86 (m, 3H), 2.82-2.45 (m, 10H), 2.39-2.14 (m, 3H), 1.83-1.63 (m, 6H), 1.42-1.06 (m, 12H). MS (ESI, m/e) [M+1]$^+$472.4. MS (ESI, m/e) [M+1]$^+$472.4.

Intermediate 57-1: 2-(4-(chroman-4-ylmethyl)-2-(2-isopropylphenyl)piperazin-1-yl)-7-azaspiro[3.5]nonane Intermediate 57-1

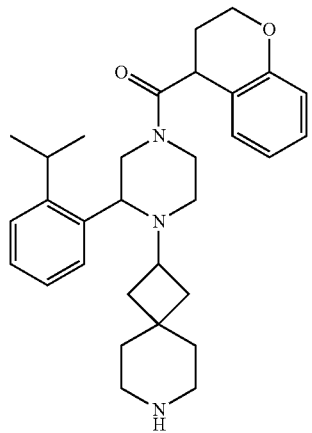

Step 1: chroman-4-carbonitrile.

To a solution of chroman-4-one (2.0 g, 13.50 mmol) in DME (20 mL) and t-BuOH (5 mL) was added TosMIC (11.9 g, 40.50 mmol) and t-BuOK (4.5 g, 40.50 mmol) at 0° C. The mixture was stirred at 20° C. for 12 hrs. The reaction mixture was poured into water (20 mL), extracted with EtOAc (50 mL×3). The combined organic phases were washed with brine (20 mL×2), dried with anhydrous Na$_2$SO$_4$, filtered and concentrated in vacuum. The crude product was purified by column chromatography (silica gel, eluent: PE/EA (v/v)=100/1 to 1/1) to give chroman-4-carbonitrile (800 mg, 5.03 mmol, yield: 37%) as a yellow oil. MS (ESI, m/e) [M+1]$^+$ 160.0.

Step 2: chroman-4-carboxylic acid.

To a mixture of chroman-4-carbonitrile (1.6 g, 10.06 mmol) in MeOH (30 mL) and H$_2$O (5 mL) was added NaOH (2.0 g, 50.26 mmol) at 20° C. The mixture was stirred at 100° C. for 12 hrs.

The reaction solution was added HCl (1 M) to pH=1, extracted with EtOAc (50 mL×3). The combined organic phases were washed with brine (20 mL), dried with anhydrous Na$_2$SO$_4$, filtered and concentrated in vacuum to give chroman-4-carboxylic acid (850 mg, crude) as a yellow oil.

$^1$H NMR (400 MHz, DMSO-d6) δ ppm: 12.77-12.47 (m, 1H), 7.20 (d, J=7.6 Hz, 1H), 7.16-7.09 (m, 1H), 6.85 (m, 1H), 6.79-6.74 (m, 1H), 4.20-4.09 (m, 2H), 3.75 (m, 1H), 2.21-2.01 (m, 2H).

Step 3: tert-butyl 2-(4-(chroman-4-carbonyl)-2-(2-isopropylphenyl)-6-oxopiperazin-1-yl)-7-azaspiro[3.5]nonane-7-carboxylate.

To a solution of chroman-4-carboxylic acid (646 mg, 3.62 mmol) in DMF (20 mL) was added DIEA (585 mg, 4.53 mmol), HATU (1.03 g, 2.72 mmol) and tert-butyl 2-(2-(2-isopropylphenyl)-6-oxopiperazin-1-yl)-7-azaspiro[3.5]nonane-7-carboxylate (1.0 g, 2.26 mmol) was added at 20° C. for 3 hrs. The reaction mixture was poured into water (50 mL), extracted with EtOAc (50 mL×3). The combined organic phases were washed with brine, dried with anhydrous Na$_2$SO$_4$, filtered and concentrated in vacuum. The residue was purified by column chromatography (silica gel, eluent: PE/EA (v/v)=100/1 to 1/1) to give tert-butyl 2-(4-(chroman-4-carbonyl)-2-(2-isopropylphenyl)-6-oxopiperazin-1-yl)-7-azaspiro[3.5]nonane-7-carboxylate (1.1 g, 1.83 mmol, yield: 82%) as a white solid. $^1$H NMR (400 MHz, DMSO-d6) δ ppm: 7.50-7.39 (m, 1H), 7.37-7.19 (m, 2H), 7.17 (s, 1H), 7.04-6.90 (m, 1H), 6.89-6.69 (m, 2H), 6.68-6.54 (m, 1H), 5.41-5.27 (m, 1H), 4.82-4.45 (m, 2H), 4.37-4.15 (m, 1H), 4.13-3.94 (m, 2H), 3.92-3.70 (m, 1H), 3.60-3.38 (m, 2H), 3.20 (br s, 2H), 3.09 (br s, 2H), 2.17-1.73 (m, 4H), 1.68-1.52 (m, 2H), 1.49-1.39 (m, 2H), 1.35 (s, 9H), 1.30-1.15 (m, 8H), 0.91-0.56 (m, 1H).

Step 4: tert-butyl 2-(4-(chroman-4-ylmethyl)-2-(2-isopropylphenyl)piperazin-1-yl)-7-azaspiro[3.5]nonane-7-carboxylate.

A solution of tert-butyl 2-(4-(chroman-4-carbonyl)-2-(2-isopropylphenyl)-6-oxopiperazin-1-yl)-7-azaspiro[3.5]nonane-7-carboxylate (1.1 g, 1.83 mmol) in BH$_3$·THF (20 mL, 1 M in THF) 20° C. for 12 hrs. The reaction mixture was cooled to 0° C. Then MeOH (10 mL) was added dropwise at 0° C. and concentrated in vacuum to give tert-butyl 2-(4-(chroman-4-ylmethyl)-2-(2-isopropylphenyl)piperazin-1-yl)-7-azaspiro[3.5]nonane-7-carboxylate (1.05 g, crude) as a white solid. MS (ESI, m/e) [M+1]$^+$574.4.

Step 5: 2-(4-(chroman-4-ylmethyl)-2-(2-isopropylphenyl)piperazin-1-yl)-7-azaspiro[3.5]nonane.

To a solution of tert-butyl 2-(4-(chroman-4-ylmethyl)-2-(2-isopropylphenyl)piperazin-1-yl)-7-azaspiro[3.5]nonane-7-carboxylate (1.0 g, 1.74 mmol) in MeOH (5 mL) was added HCl/MeOH (20 mL, 4 M) at 20° C. The mixture was stirred at 20° C. for 2 hrs. The reaction mixture was concentrated in vacuum, poured into H$_2$O (20 mL) and extracted with EtOAc (20 mL). The aqueous phase was added sat. Na$_2$CO$_3$ to pH=10, extracted with EtOAc (50 mL×3).

The combined organic phases were washed with brine (20 mL×2), dried with anhydrous Na$_2$SO$_4$, filtered and concentrated in vacuum to give 2-(4-(chroman-4-ylmethyl)-2-(2-isopropylphenyl)piperazin-1-yl)-7-azaspiro[3.5]nonane (615 mg, 374.47 umol, yield: 74%) as a white solid. $^1$H NMR (400 MHz, CDCl$_3$) δ ppm: 7.61-7.40 (m, 1H), 7.28-6.98 (m, 5H), 6.92-6.72 (m, 2H), 4.21-4.10 (m, 2H), 3.73-3.59 (m, 1H), 3.49-3.33 (m, 1H), 3.07-2.80 (m, 4H), 2.65-2.44 (m, 6H), 2.37-2.07 (m, 4H), 2.05-1.87 (m, 2H), 1.82-1.64 (m, 2H), 1.39-1.14 (m, 13H). MS (ESI, m/e) [M+1]$^+$ 474.4.

Intermediate 58-1: 2-(4-(benzo[b]thiophen-5-ylmethyl)-2-(2-isopropylphenyl)piperazin-1-yl)-7-azaspiro[3.5]nonane

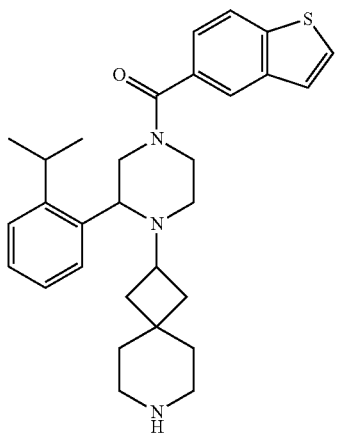

Intermediate 58-1

Step 1: benzo[b]thiophene-5-carbaldehyde

To a solution of 5-bromobenzo[b]thiophene (1.0 g, 4.69 mmol) in THF (30 mL) was added i-PrMgCl·LiCl (25 mL, 32.50 mmol) at −60° C. The mixture was stirred at 25° C. for 12 hrs.

Then DMF (5 mL) was added dropwise. The reaction mixture was quenched by aq. NH$_4$Cl (50 mL) and extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=20/1 to 10/1) to give benzo[b]thiophene-5-carbaldehyde (452 mg, yield: 59%) as a yellow oil.

Step 2: tert-butyl 2-(4-(benzo[b]thiophen-5-ylmethyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (10 mL) was added AcOH (271.97 mg, 4.53 mmol) and benzo[b]thiophene-5-carbaldehyde (404.05 mg, 2.49 mmol), The mixture was stirred at 25° C. for 1 hr, then NaBH(OAc)$_3$ (1.44 g, 6.79 mmol) was added. The mixture was stirred at 25° C. for another 12 hrs. The reaction mixture was poured into sat.

NaHCO$_3$ (50 mL), extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give tert-butyl 2-(4-(benzo[b]thiophen-5-ylmethyl)-2-(2-isopropylphenyl)-6-oxopiperazin-1-yl)-7-azaspiro[3.5]nonane-7-carboxylate (1.2 g, 2.04 mmol, yield: 90%) as a yellow oil.

Step 3: tert-butyl 2-(4-(benzo[b]thiophen-4-ylmethyl)-2-(2-isopropylphenyl)piperazin-1-yl)-7-azaspiro[3.5]nonane-7-carboxylate.

To a mixture of tert-butyl 2-(4-(benzo[b]thiophen-5-ylmethyl)-2-(2-isopropylphenyl)-6-oxopiperazin-1-yl)-7-azaspiro[3.5]nonane-7-carboxylate (1.2 g, 2.04 mmol) and BH$_3$·THF (20.41 mL, 20.41 mmol) in THF was stirred at 70° C. for 12 hrs. The reaction solution was quenched by MeOH (10 mL), concentrated under reduced pressure to give tert-butyl 2-(4-(benzo[b]thiophen-5-ylmethyl)-2-(2-isopropylphenyl)piperazin-1-yl)-7-azaspiro[3.5]nonane-7-carboxylate (1.26 g, crude) as a yellow oil, which was directly for next step without further reaction. MS (ESI, m/e) [M+1]$^+$ 574.3.

Step 4: 2-(4-(benzo[b]thiophen-5-ylmethyl)-2-(2-isopropylphenyl)-7-azaspiro[3.5]nonane.

To a mixture of tert-butyl 2-(4-(benzo[b]thiophen-5-ylmethyl)-2-(2-isopropylphenyl)piperazin-1-yl)-7-azaspiro[3.5]nonane-7-carboxylate (1.26 g, 2.20 mmol) and TFA (5.1 mL, 43.92 mmol) was stirred at 25° C. for 2 hrs. The reaction solution was concentrated under reduced pressure. The mixture was poured into sat. NaHCO$_3$ (50 mL), extracted with EtOAc (100 mL×2). The combined organic layers were washed with brine, dried with anhydrous Na$_2$SO$_4$, filtered and concentrated under reduced pressure. The residue was purified by prep-HPLC (TFA condition) according to HPLC. The residue was diluted with H$_2$O (20 mL), and added Na$_2$CO$_3$ to pH=9, the mixture was extracted with EtOAc (20 mL×3). The combined organic layers were washed with brine, dried over Na$_2$SO$_4$, filtered and concentrated under reduced pressure to give 2-(4-(benzo[b]thiophen-5-ylmethyl)-2-(2-isopropylphenyl)piperazin-1-yl)-7-azaspiro[3.5]nonane (132 mg, 278.65 μmol, yield: 13%) as a yellow solid. $^1$H NMR (400 MHz, CDCl$_3$) δ ppm: 7.80 (d, J=8.4 Hz, 1H), 7.75 (s, 1H), 7.48 (br s, 1H), 7.42 (d, J=5.6 Hz, 1H), 7.33 (m, 2H), 7.18-7.25 (m, 2H), 7.09-7.15 (m, 1H), 3.64 (m, 2H), 3.30-3.48 (m, 1H), 2.86-3.02 (m, 2H), 2.72 (m, 4H), 2.20-2.38 (m, 3H), 1.62-1.83 (m, 3H), 1.42 (br s, 4H), 1.23-1.28 (m, 4H), 1.13 (m, 4H), 0.89 (br s, 2H). MS (ESI, m/e) [M+1]$^+$474.3.

Intermediate 59-1: 2-(4-(benzo[b]thiophen-4-ylmethyl)-2-(2-isopropylphenyl)piperazin-1-yl)-7-azaspiro[3.5]nonane

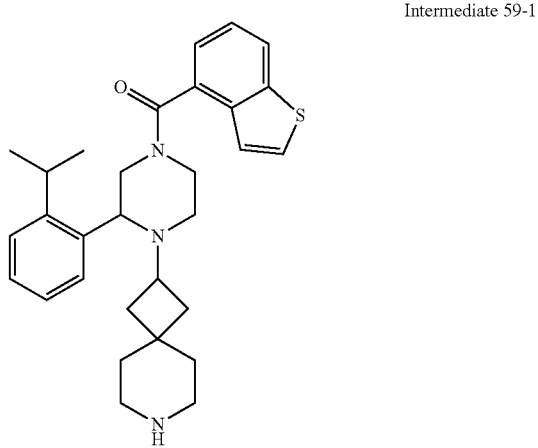 [SMILES: CC(C)c1ccccc1C1CN(C(=O)c2cccc3sccc23)CCN1C1CC2(CCNCC2)C1]

Intermediate 59-1

Step 1: benzo[b]thiophen-4-ylmethanol.

To a solution of benzo[b]thiophene-4-carboxylic acid (900 mg, 5.05 mmol) in DCM (10 mL) was added LAH (383.36 mg, 10.10 mmol) at 0° C. The mixture was stirred at 25° C. for 1 hr. The reaction mixture was quenched by aq. NaOH (0.8 mL, 25%) and extracted with EtOAc (100 mL×2). The combined organic layers were washed with brine, dried with anhydrous Na$_2$SO$_4$, filtered and concentrated under reduced pressure. The crude product was purified by column chromatography (silica gel, eluent: PE/EA (v/v)=5/1 to 2/1) to give benzo[b]thiophen-4-ylmethanol (800 mg, 4.87 mmol, yield: 96%) as a yellow oil.

Step 2: benzo[b]thiophene-4-carbaldehyde.

To a mixture of benzo[b]thiophen-4-ylmethanol (800 mg, 4.87 mmol) and MnO₂ (4.24 g, 48.71 mmol) in DCM (10 mL) was stirred at 50° C. for 3 hrs. The reaction was filtrated and extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give benzo[b]thiophene-4-carbaldehyde (625 mg, 3.85 mmol, yield: 79%) as a yellow oil. ¹H NMR (400 MHz, CDCl₃) δ ppm: 10.29-10.20 (s, 1H), 8.39 (d, J=5.6 Hz, 1H), 8.14 (d, J=8.0 Hz, 1H), 7.86 (d, J=7.6 Hz, 1H), 7.73 (d, J=5.6 Hz, 1H), 7.58-7.46 (m, 1H).

Step 3: tert-butyl 2-(4-(benzo[b]thiophen-4-ylmethyl)-2-(2-isopropylphenyl)-6-oxopiperazin-1-yl)-7-azaspiro[3.5]nonane-7-carboxylate To a solution of tert-butyl 2-(2-(2-isopropylphenyl)-6-oxopiperazin-1-yl)-7-azaspiro[3.5]nonane-7-carboxylate (1.2 g, 2.72 mmol) in DCE (10 mL) was added AcOH (326.36 mg, 5.43 mmol) and benzo[b]thiophene-4-carbaldehyde (484.86 mg, 2.99 mmol). The mixture was stirred at 25° C. for 1 hr, the NaBH(OAc)₃ (1.73 g, 8.15 mmol) was added to the solution. The mixture was stirred at 25° C. for another 12 hrs. The reaction mixture was poured into sat. NaHCO₃ (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give tert-butyl 2-(4-(benzo[b]thiophen-4-ylmethyl)-2-(2-isopropylphenyl)-6-oxopiperazin-1-yl)-7-azaspiro[3.5]nonane-7-carboxylate (900 mg, 1.53 mmol, yield: 56%) as a yellow oil.

Step 4: tert-butyl 2-(4-(benzo[b]thiophen-4-ylmethyl)-2-(2-isopropylphenyl)piperazin-1-yl)-7-azaspiro[3.5]nonane-7-carboxylate.

To a mixture of tert-butyl 2-(4-(benzo[b]thiophen-4-ylmethyl)-2-(2-isopropylphenyl)-6-oxopiperazin-1-yl)-7-azaspiro[3.5]nonane-7-carboxylate (900 mg, 1.53 mmol) and BH₃ (15.31 mL, 15.31 mmol) in DCM (10 mL) was stirred at 70° C. for 12 hrs. The reaction solution was quenched by MeOH (10 mL), concentrated under reduced pressure to give 2-(4-(benzo[b]thiophen-4-ylmethyl)-2-(2-isopropylphenyl)piperazin-1-yl)-7-azaspiro[3.5]nonane-7-carboxylate (850 mg, crude), which was used directly for next step without further purification.

Step 5: 2-(4-(benzo[b]thiophen-4-ylmethyl)-2-(2-isopropylphenyl)piperazin-1-yl)-7-azaspiro[3.5]nonane.

To a mixture of 2-(4-(benzo[b]thiophen-4-ylmethyl)-2-(2-isopropylphenyl)piperazin-1-yl)-7-azaspiro[3.5]nonane-7-carboxylate (850 mg, 1.48 mmol) and HCl (3.70 mL, 14.81 mmol) in MeOH (30 mL) was stirred at 25° C. for 2 hrs. The reaction solution was concentrated under reduced pressure. The residue was poured into sat. NaHCO₃ (50 mL), extracted with EtOAc (100 mL×2). The combined organic layers were washed with brine, dried with anhydrous Na₂SO₄, filtered and concentrated under reduced pressure. The residue was purified by prep-HPLC (TFA condition) according to HPLC. The residue was diluted with H₂O (20 mL), and added Na₂CO₃ to pH=9, the mixture was extracted with EtOAc (20 mL×3). The combined organic layers were washed with brine, dried over Na₂SO₄, filtered and concentrated under reduced pressure to give 2-(4-(benzo[b]thiophen-4-ylmethyl)-2-(2-isopropylphenyl)piperazin-1-yl)-7-azaspiro[3.5]nonane (183 mg, 386.31 μmol, yield: 26%) as a yellow oil. ¹H NMR (400 MHz, CDCl₃) δ ppm: 7.78 (d, J=7.6 Hz, 1H), 7.71-7.63 (m, 1H), 7.52-7.43 (m, 2H), 7.32-7.29 (m, 1H), 7.23-7.20 (m, 2H), 7.15-7.07 (m, 2H), 3.83 (s, 2H), 3.63 (m, 1H), 3.02-2.87 (m, 4H), 2.71-2.61 (m, 6H), 2.41-2.24 (m, 4H), 1.70-1.62 (m, 2H), 1.35 (m, 4H), 1.25 (br s, 3H), 1.14 (d, J=6.8 Hz, 3H), 1.07 (d, J=6.8 Hz, 3H). MS (ESI, m/e) [M+1]474.3.

Intermediate 60-1: (3-(2-isopropylphenyl)-4-(7-azaspiro[3.5]nonan-2-yl)piperazin-1-yl)(phenyl)methanone

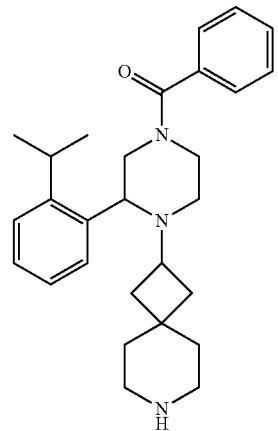

Intermediate 60-1

Step 1: tert-butyl 2-(4-benzoyl-2-(2-isopropylphenyl)piperazin-1-yl)-7-azaspiro[3.5]nonane-7-carboxylate.

To a solution of tert-butyl 2-(2-(2-isopropylphenyl)piperazin-1-yl)-7-azaspiro[3.5]nonane-7-carboxylate (1.1 g, 2.57 mmol) in DCM (10 mL) was added TEA (1.04 g, 10.29 mmol) at 25° C. for 30 min. Then benzoyl chloride (723.2 mg, 5.14 mmol) was added dropwise at 0° C. The mixture was stirred at 0° C. for 1 hr. The reaction mixture was poured into sat. NH₄Cl (50 mL), extracted with DCM 50 mL) and concentrated under reduced pressure. The crude product was purified by column chromatography (silica gel, eluent: PE/EA (v/v)=100/1 to 10/1) to give tert-butyl 2-(4-benzoyl-2-(2-isopropylphenyl)piperazin-1-yl)-7-azaspiro[3.5]nonane-7-carboxylate (700 mg, 1.32 mmol, yield: 51%) as a yellow oil. ¹H NMR (400 MHz, CDCl₃) δ ppm: 7.54-7.29 (m, 6H), 7.25-7.02 (m, 3H), 4.81-4.67 (m, 1H), 4.55-4.43 (m, 1H), 3.83 (br d, J=7.2 Hz, 1H), 3.46 (br s, 2H), 3.28-3.07 (m, 7H), 3.03-2.92 (m, 2H), 2.33-2.18 (m, 1H), 1.85-1.52 (m, 4H), 1.41 (s, 9H), 1.36-1.10 (m, 12H), 0.94 (br s, 2H).

Step 2: (3-(2-isopropylphenyl)-4-(7-azaspiro[3.5]nonan-2-yl)piperazin-1-yl)(phenyl)methanone To a mixture of tert-butyl 2-(4-benzoyl-2-(2-isopropylphenyl)piperazin-1-yl)-7-azaspiro[3.5]nonane-7-carboxylate (700 mg, 1.32 mmol) in DCM (100 mL) was added TFA (3 mL) at 25° C. The mixture was stirred at 25° C. for 45 min. The reaction solution was added water (40 mL), extracted with EtOAc (50 mL). The aqueous phase was adjusted the pH to 9-10 with sat.

Na₂CO₃. The resulting mixture was extracted with EtOAc (50 mL×3). The combined organic phases were washed with brine, dried with anhydrous Na₂SO₄, filtered and concentrated under reduced pressure to give (3-(2-isopropylphenyl)-4-(7-azaspiro[3.5]nonan-2-yl)piperazin-1-yl)(phenyl) methanone (390 mg, 903.59 umol, yield: 68%) as a yellow oil. ¹H NMR (400 MHz, CDCl₃) δ ppm: 7.83 (d, J=7.2 Hz, 1H), 7.57-7.30 (m, 7H), 7.22-7.09 (m, 2H), 4.74 (m, 1H), 4.41-4.79 (m, 1H), 3.63-3.39 (m, 2H), 3.21-3.07 (m, 2H), 3.07-2.83 (m, 2H), 2.75-2.49 (m, 4H), 2.31-2.13 (m, 1H), 1.69 (m, 2H), 1.42-1.15 (m, 10H), 1.06-0.81 (m, 1H). MS (ESI, m/e) [M+1]⁺432.3.

Intermediate 61-1: (3-(2-isopropylphenyl)-4-(7-azaspiro[3.5]nonan-2-yl)piperazin-1-yl)(4-methoxyphenyl)methanone

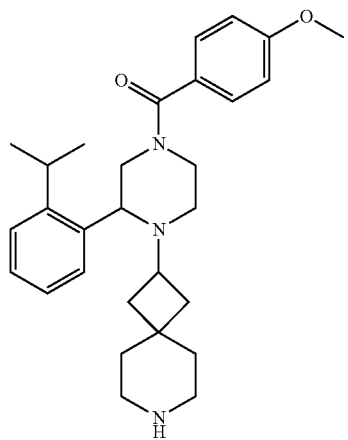

Intermediate 61-1

Step 1: tert-butyl 2-(2-(2-isopropylphenyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (2.0 g, 4.53 mmol) in THF (20 mL) was added BH₃·THF (30 mL, 22.5 mmol). The mixture was heated to 70° C. and stirred at 70° C. for 12 hrs. After cooling to 0° C., the mixture was quenched with MeOH (10 mL). The mixture was concentrated in vacuum to give crude product which was purified by column chromatography to afford tert-butyl 2-(2-(2-isopropylphenyl)piperazin-1-yl)-7-azaspiro[3.5]nonane-7-carboxylate (0.7 g, yield: 50%) as a white solid. MS (ESI, m/e) [M+1]⁺428.5

Step 2: tert-butyl 2-(2-(2-isopropylphenyl)-4-(4-methoxybenzoyl)piperazin--yl)-7-azaspiro[3.5]nonane-7-carboxylate.

To a solution of tert-butyl 2-(2-(2-isopropylphenyl) piperazin-1-yl)-7-azaspiro[3.5]nonane-7-carboxylate (700 mg, 1.64 mmol) and 4-methoxybenzoic acid (274 mg, 1.8 mmol) in DCM (10 mL) was added HATU (685 mg, 1.8 mmol) and Et₃N (364 mg, 3.6 mmol).

The mixture was stirred at 25° C. for 16 hrs. The mixture was poured into H₂O (20 mL), extracted with DCM (20 mL). The combined organic phases were washed with brine (20 mL), dried with anhydrous Na₂SO₄, filtered and concentrated in vacuum. The residue was purified by column chromatography (silica gel, eluent: PE/EA (v/v)=20/1 to 2/1) to give tert-butyl 2-(2-(2-isopropylphenyl)-4-(4-methoxybenzoyl)piperazin-1-yl)-7-azaspiro[3.5]nonane-7-carboxylate (0.4 g, yield: 60%) as yellow oil. MS (ESI, m/e) [M+1]⁺562.3.

Step 3: (3-(2-isopropylphenyl)-4-(7-azaspiro[3.5]nonan-2-yl)piperazin-1-yl)(4-methoxyphenyl)methanone.

To a solution of tert-butyl 2-(2-(2-isopropylphenyl)-4-(4-methoxybenzoyl)piperazin-1-yl)-7-azaspiro[3.5]nonane-7-carboxylatein (400 mg, 0.71 mmol) in MeOH (10 mL) was added HCl/MeOH (10 mL). The mixture was stirred at 25° C. for 2 hrs. After concentrating in vacuum, the residue was dissolved into water (20 mL). The mixture was adjusted the pH=9-10 with aqueous Na₂CO₃. The mixture was extracted with EtOAc (20 mL×3). The combined organic phases were washed with brine (20 mL×2), dried with anhydrous Na₂SO₄, filtered and concentrated in vacuum to give (3-(2-isopropylphenyl)-4-(7-azaspiro[3.5]nonan-2-yl)piperazin-1-yl)(4-methoxyphenyl)methanone (305 mg, yield: 93%) as a white solid. ¹H NMR (400 MHz, CDCl₃) δ ppm: 7.45-7.38 (m, 3H), 7.27-7.14 (m, 3H), 7.00-6.87 (m, 2H), 3.80 (s, 3H), 3.52-3.48 (m, 3H), 3.10-2.91 (m, 3H), 2.70-2.55 (m, 4H), 2.25-2.17 (m, 1H), 1.80-1.61 (m, 2H), 1.52-0.89 (m, 14H). MS (ESI, n/e) [M+1]⁺462.3

Intermediate 62-1: 2-(2-(2-isopropylphenyl)-4-(methylsulfonyl)piperazin-1-yl)-7-azaspiro[3.5]nonane

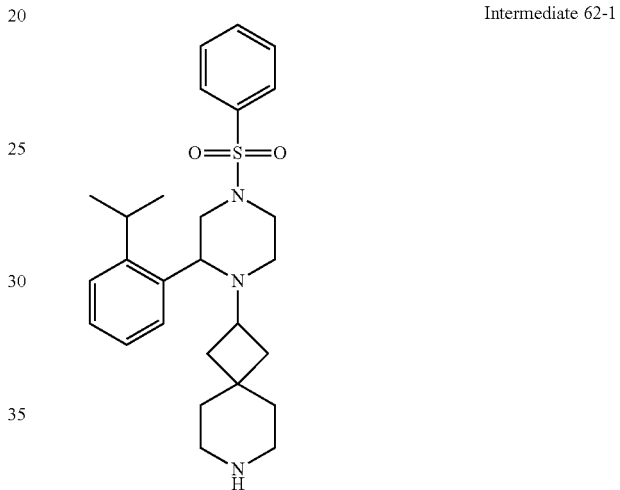

Intermediate 62-1

Step 1: tert-butyl 2-(2-(2-isopropylphenyl)-6-oxo-4-(phenylsulfonyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (0.5 g, 1.13 mmol) in DCM (6 mL) was added TEA (206 mg, 2.04 mmol). After cooling to 0° C., benzene sulfonyl chloride (300 mg, 1.7 mmol) was added. The mixture was stirred at 25° C. for 2 hrs. The mixture was poured into water (10 mL), extracted with DCM (20 mL×3). The combined organic phases were concentrated in vacuum. The residue was purified by column chromatography (silica gel, eluent: PE/EA (v/v)=20/1 to 10/1) to give tert-butyl 2-(2-(2-isopropylphenyl)-6-oxo-4-(phenylsulfonyl)piperazin-1-yl)-7-azaspiro[3.5]nonane-7-carboxylate (0.6 g, yield: 91%) as a yellow oil. MS (ESI, n/e) [M+1]⁺582.3

Step 2: tert-butyl 2-(2-(2-isopropylphenyl)-4-(phenylsulfonyl)piperazin-1-yl)-7-azaspiro[3.5]nonane-7-carboxylate.

The mixture of tert-butyl 2-(2-(2-isopropylphenyl)-6-oxo-4-(phenylsulfonyl) piperazin-1-yl)-7-azaspiro[3.5]nonane-7-carboxylate (0.6 g, 1.03 mmol) and BH₃·THF (5 mL, 5 mmol) was heated to 70° C. for 12 hrs. After cooling to 0° C., the mixture was quenched with MeOH (10 mL).

The mixture was concentrated in vacuum to give tert-butyl 2-(2-(2-isopropylphenyl)-4-(phenylsulfonyl)piperazin-1-yl)-7-azaspiro[3.5]nonane-7-carboxylate (0.45 g, yield: 65%) as yellow oil. MS (ESI, m/e) [M+1]⁺568.2.

Step 3: 2-(2-(2-isopropylphenyl)-4-(phenylsulfonyl)piperazin-1-yl)-7-azaspiro[3.5]nonane.

To a solution of tert-butyl 2-(2-(2-isopropylphenyl)-4-(phenylsulfonyl)piperazin-1-yl)-7-azaspiro[3.5]nonane-7-carboxylate (450 mg, 0.79 mmol) in MeOH (10 mL) was added HCl/MeOH (10 mL). The mixture was stirred at 25° C. for 2 hrs. After concentrating in vacuum, the residue was dissolved into water (20 mL). The mixture was adjusted the pH=9-10 with aqueous $Na_2CO_3$. The mixture was extracted with EtOAc (20 mL×3). The combined organic phases were washed with brine (20 mL×2), dried with anhydrous $Na_2SO_4$, filtered and concentrated in vacuum to give 2-(2-(2-isopropylphenyl)-4-(phenylsulfonyl)piperazin-1-yl)-7-azaspiro[3.5]nonane (310 mg, yield: 94%) as a white solid. $^1$H NMR (400 MHz, $CDCl_3$) δ ppm: 7.74-7.72 (m, 2H), 7.61 (m, 1H), 7.55-7.53 (m, 2H), 7.28-7.25 (m, 3H), 7.09-7.07 (m, 1H), 3.83-3.80 (m, 1H), 3.74-3.71 (m, 1H), 3.52-3.49 (m, 1H), 3.03-3.00 (m, 1H), 2.88-2.85 (m, 1H), 2.62-2.60 (m, 6H), 2.38-2.35 (m, 3H), 1.77-1.74 (m, 1H), 1.59-1.56 (m, 1H), 1.34-1.24 (m, 11H). MS (ESI, m/e) [M+1]$^+$468.3

Intermediate 63-1: 2-(2-(2-isopropylphenyl)-4-(1-phenylbut-2-yn-1-yl)piperazin-1-yl)-7-azaspiro[3.5]nonane

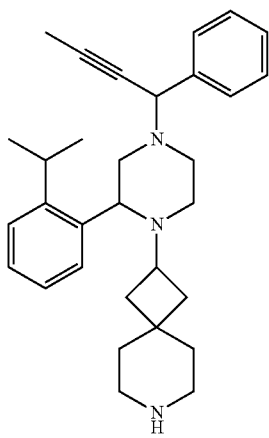

Intermediate 63-1

Step 1: 1-phenylbut-2-yn-1-ol.

To a solution of benzaldehyde (4.0 g, 37.69 mmol) in THF (100 mL) was added dropwise prop-1-yn-1-yl magnesium bromide in THF (0.5 M) (90.5 mL, 45.23 mmol) at −70° C. The mixture was warmed to 20° C. and stirred at 20° C. for 12 hrs. After cooling to 0° C., the mixture was quenched with saturated $NH_4Cl$ aqueous (100 mL). The mixture was extracted with EtOAc (50 mL×2). The organic layer was dried over $Na_2SO_4$, evaporated in vacuum to give 1-phenylbut-2-yn-1-ol (5.0 g, yield: 90%) as a yellow oil. $^1$H NMR (400 MHz, $CDCl_3$) δ ppm: 7.46-7.44 (d, J=6.8 Hz, 2H), 7.31-7.24 (m, 3H), 5.34 (s, 1H), 2.17 (s, 1H), 1.83 (s, 3H).

Step 2: 1-phenylbut-2-yn-1-yl methanesulfonate.

To a solution of 1-phenylbut-2-yn-1-ol (2.5 g, 17 mmol) and $Et_3N$ (5.1 g, 51 mmol) in DCM (25 mL) was added MsCl (2.15 g, 18.8 mmol) at 25° C. The mixture was stirred at 25° C. for 1 hr. The mixture was poured into $H_2O$ (20 mL), extracted with DCM (20 mL). The combined organic phases were washed with brine (20 mL), dried with anhydrous $Na_2SO_4$, filtered and concentrated in vacuum to give the residue (2.6 g, yield: 95%) as a yellow oil which was used directly in the next step without further purification.

Step 3: tert-butyl 2-(2-(2-isopropylphenyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (2.0 g, 4.53 mmol) in THF (20 mL) was added $BH_3$·THF (30 mL, 22.5 mmol). The mixture was heated to 70° C. and stirred at 70° C. for 12 hrs. After cooling to 0° C., the mixture was quenched with MeOH (10 mL). The mixture was concentrated in vacuum to give crude product which was purified by column chromatography to afford tert-butyl 2-(2-(2-isopropylphenyl)piperazin-1-yl)-7-azaspiro[3.5]nonane-7-carboxylate (0.7 g, yield: 50%) as a white solid.

Step 4: tert-butyl 2-(2-(2-isopropylphenyl)-4-(1-phenylbut-2-yn-1-yl)piperazin-1-yl)-7-azaspiro[3.5]nonane-7-carboxylate.

To a solution of tert-butyl 2-(2-(2-isopropylphenyl) piperazin-1-yl)-7-azaspiro[3.5]nonane-7-carboxylate (0.7 g, 1.64 mmol) in $CH_3CN$ (20 mL) was added $K_2CO_3$ (0.68 g, 4.91 mmol) and 1-phenylbut-2-yn-1-yl methanesulfonate (0.55 g, 2.46 mmol). The mixture was stirred at 50° C. for 1 hr. After concentrating in vacuum, the residue was dissolved into water (20 mL).

The mixture was extracted with EtOAc (10 mL×3). The combined organic phases were washed with brine (10 mL×2), dried with anhydrous $Na_2SO_4$, filtered and concentrated in vacuum to give tert-butyl 2-(2-(2-isopropylphenyl)-4-(1-phenylbut-2-yn-1-yl)piperazin-1-yl)-7-azaspiro[3.5]nonane-7-carboxylate (240 mg, yield: 27%) as a yellow oil.

Step 5: 2-(2-(2-isopropylphenyl)-4-(1-phenylbut-2-yn-1-yl)piperazin-1-yl)-7-azaspiro[3.5]nonane.

To a solution of tert-butyl 2-(2-(2-isopropylphenyl)-4-(1-phenylbut-2-yn-1-yl) piperazin-1-yl)-7-azaspiro[3.5]nonane-7-carboxylate (240 mg, 0.43 mmol) in MeOH (10 mL) was added HCl/MeOH (10 mL). The mixture was stirred at 25° C. for 2 hrs. After concentrating in vacuum, the residue was dissolved into water (10 mL). The mixture was adjusted the pH=9-10 using aqueous $Na_2CO_3$. The mixture was extracted with EtOAc (10 mL×3). The combined organic phases were washed with brine (10 mL×2), dried with anhydrous $Na_2SO_4$, filtered and concentrated in vacuum to give 2-(2-(2-isopropylphenyl)-4-(1-phenylbut-2-yn-1-yl)piperazin-1-yl)-7-azaspiro[3.5]nonane (170 mg, yield: 73%) as a yellow solid. $^1$H NMR (400 MHz, $CDCl_3$) δ ppm: 7.54-7.28 (m, 5H), 7.25-7.08 (m, 4H), 4.71-4.50 (d, 1H), 3.68-3.51 (m, 1H), 3.49-3.20 (m, 1H), 3.10-2.93 (m, 1H), 2.92-2.89 (m, 2H), 2.71-2.65 (m, 6H), 2.42-2.19 (m, 3H), 1.90 (s, 3H), 1.72-1.66 (m, 2H), 1.50-1.10 (m, 11H), 1.02-0.98 (m, 2H). MS (ESI, m/e) [M+1]$^+$456.4.

Intermediate 64-1: 2-(2-(2-isopropylphenyl)-4-(3-phenylcyclopentyl)piperazin-1-yl)-7-azaspiro[3.5]nonane

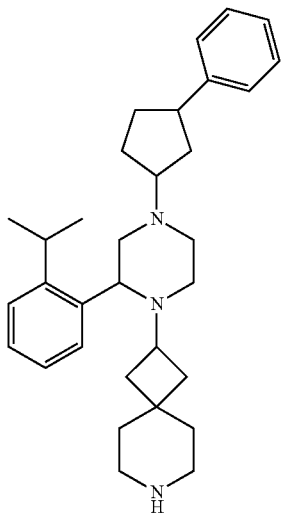

Intermediate 64-1

Step 1: 3-phenylcyclopentan-1-one.

To a solution of cyclopent-2-en-1-one (3.0 g, 36 mmol) in Toluene (80 mL) and CHCl₃ (0.4 mL) was added phenylboronic acid (5.27 g, 43 mmol), Pd(OAc)₂ (0.81 g, 3.6 mmol), PPh₃ (1.9 g, 7.2 mmol) and Cs₂CO₃ (23 g, 72 mmol). The mixture was heated to 80° C. for 4 hrs. After cooled to room temperature, the mixture was filtered. The filtrate was concentrated in vacuum.

The residue was purified by column chromatography (silica gel, eluent: PE/EA (v/v)=10/1) to give 3-phenylcyclopentan-1-one (2.8 g, yield: 48%) as a brown oil. ¹H NMR (400 MHz, CDCl₃) δ ppm: 7.39-7.34 (m, 2H), 7.28 (m, 3H), 3.52-3.38 (m, 1H), 2.70 (m, 1H), 2.52-2.29 (m, 4H), 2.09-1.95 (m, 1H).

Step 2: tert-butyl 2-(2-(2-isopropylphenyl)-6-oxo-4-(3-phenylcyclopentyl)piperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DCE (20 mL) was added 3-phenyl-cyclopentan-1-one (540 mg, 3.40 mmol) and HOAc (0.27 g, 4.52 mmol). After stirred at 25° C. for 1 hr, the NaBH(OAc)₃ (0.96 g, 4.52 mmol) was added. The mixture was stirred at 25° C. for 12 hrs. Then aqueous NH₄Cl (20 mL) was added to the mixture, extracted with DCM (20 mL×3). The combined organic phase was washed with brine (20 mL×2), dried with anhydrous Na₂SO₄, filtered and concentrated in vacuum. The residue was purified by column chromatography (silica gel, eluent: PE/EA (v/v)=1/1) to give tert-butyl 2-(2-(2-isopropylphenyl)-6-oxo-4-(3-phenylcyclopentyl)piperazin-1-yl)-7-azaspiro[3.5]nonane-7-carboxylate (0.66 g, yield: 50%) as yellow solid. ¹H NMR (400 MHz, CDCl₃) δ ppm: 7.33-7.27 (m, 3H), 7.26-7.24 (m, 1H), 7.21-7.14 (m, 3H), 7.13-7.07 (m, 2H), 5.09 (br d, J=5.25 Hz, 1H), 4.25-4.10 (m, 1H), 3.44-3.10 (m, 8H), 3.09-2.88 (m, 2H), 2.82-2.65 (m, 1H), 2.64-2.47 (m, 1H), 2.32-2.09 (m, 2H), 2.05-1.95 (m, 2H), 1.94-1.78 (m, 2H), 1.76-1.51 (m, 5H), 1.42 (s, 9H), 1.39-1.35 (m, 2H), 1.31-1.25 (m, 6H).

Step 3: tert-butyl 2-(2-(2-isopropylphenyl)-4-(3-phenylcyclopentyl)piperazin-1-yl)-7-azaspiro[3.5]nonane-7-carboxylate.

The mixture of tert-butyl 2-(2-(2-isopropylphenyl)-6-oxo-4-(3-phenylcyclopentyl)piperazin-1-yl)-7-azaspiro[3.5]nonane-7-carboxylate (0.66 g, 1.13 mmol) and BH₃·THF (11 mL, 11.3 mmol) was heated to 70° C. for 12 hrs. Then MeOH (10 mL) was added in drops to quench the reaction. The mixture was concentrated under reduced pressure to give tert-butyl 2-(2-(2-isopropylphenyl)-4-(3-phenylcyclopentyl)piperazin-1-yl)-7-azaspiro[3.5]nonane-7-carboxylate (0.6 g, yield: 93%) as yellow oil, which was used directly without further purification. MS (ESI, m/e) [M+1]⁺572.4.

Step 4: 2-(2-(2-isopropylphenyl)-4-(3-phenylcyclopentyl)piperazin-1-yl)-7-azaspiro[3.5]nonane.

To a solution of tert-butyl 2-(2-(2-isopropylphenyl)-4-(3-phenylcyclopentyl)piperazin-1-yl)-7-azaspiro[3.5]nonane-7-carboxylate (600 mg, 1.05 mmol) in MeOH (20 mL) was added HCl/MeOH (10 mL). The mixture was stirred at 25° C. for 1 hr. After removed the solvent, the residue was dissolved into water (20 mL). The mixture was adjusted the pH=9-10 using aqueous.

Na₂CO₃ Then the mixture was extracted with EtOAc (20 mL×3). The combined organic phases were washed with brine (20 mL×2), dried with anhydrous Na₂SO₄, filtered and concentrated under reduced pressure to give 2-(2-(2-isopropylphenyl)-4-(3-phenylcyclopentyl)piperazin-1-yl)-7-azaspiro[3.5]nonane (450 mg, yield: 91%) as a yellow solid. ¹H NMR (400 MHz, CDCl₃) δ ppm: 7.52 (br s, 1H), 7.32-7.28 (m, 1H), 7.26-7.11 (m, 7H), 3.70 (br s, 1H), 3.40 (br s, 1H), 3.13-3.00 (m, 3H), 2.92 (br s, 1H), 2.80 (m, 1H), 2.72-2.60 (m, 5H), 2.39-2.25 (m, 3H), 2.23-2.03 (m, 4H), 1.98-1.85 (m, 1H), 1.78 (m, 2H), 1.73-1.57 (m, 3H), 1.46-1.32 (m, 5H), 1.26-1.17 (m, 6H). MS (ESI, m/e) [M+1]⁺ 472.5.

Intermediate 65-1: 2-(2-(2-isopropylphenyl)-4-phenylpiperazin-1-yl)-7-azaspiro[3.5]nonane

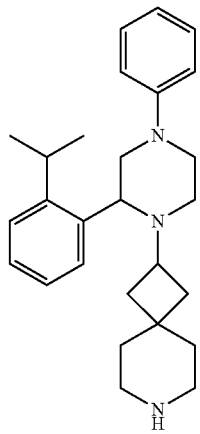

Intermediate 65-1

Step 1: tert-butyl 2-(2-isopropylphenyl)-3-oxo-4-phenylpiperazine-1-carboxylate.

To a solution of tert-butyl 2-(2-isopropylphenyl)-3-oxopiperazine-1-carboxylate (1.5 g, 4.7 mmol) in DCE (150 mL), was added phenylboronic acid (2.3 g, 18.8 mmol), Cu(OAc)₂ (1.4 g, 9.4 mmol), 4A MS (1.5 g) and TEA (9.5 g, 94.2 mmol). The mixture was stirred at 75° C. for 12 hrs under 02. The mixture was filtered and concentrated to afford a residue, extracted with 1M HCl (50 mL) and EA (20 mL×3).The combined organic layer was dried and concentrated to afford a residue, purified by column chromatography (silica gel, eluent: PE/EA (v/v)=20/1). The compound tert-butyl 2-(2-isopropylphenyl)-3-oxo-4-phenylpiperazine-1-carboxylate (1.2 g, yield: 64%) was obtained as a brown oil.

Step 2: 3-(2-isopropylphenyl)-1-phenylpiperazin-2-one.

A solution of tert-butyl 2-(2-isopropylphenyl)-3-oxo-4-phenylpiperazine-1-carboxylate (1.1 g, 2.8 mmol) in TFA (5 mL) and DCM (5 mL) was stirred at 27° C. for 2 hrs. The mixture was concentrated to afford a residue, extracted with EA (30 mL×3) and sat. NaHCO$_3$ (30 mL). The combined organic layer was dried and concentrated to give 3-(2-isopropylphenyl)-1-phenylpiperazin-2-one (0.82 g, crude) as a brown oil, used directly.

Step 3: tert-butyl 2-(2-(2-isopropylphenyl)-3-oxo-4-phenylpiperazin-1-yl)-7-azaspiro[3.5]nonane-7-carboxylate.

To a solution of 3-(2-isopropylphenyl)-1-phenylpiperazin-2-one (820 mg, 2.8 mmol) in DCE (10 mL), was added tert-butyl 2-oxo-7-azaspiro[3.5]nonane-7-carboxylate (666 mg, 2.8 mmol) and NaBH(OAc)$_3$ (1.2 g, 5.6 mmol). The mixture was stirred at 27° C. for 10 hrs. The mixture was extracted with sat. NaHCO$_3$ (50 mL) and DCM (20 mL×3) to give tert-butyl 2-(2-(2-isopropylphenyl)-3-oxo-4-phenylpiperazin-1-yl)-7-azaspiro[3.5]nonane-7-carboxylate (1.3 g, crude) as a yellow oil, used directly.

Step 4: tert-butyl 2-(2-(2-isopropylphenyl)-4-phenylpiperazin-1-yl)-7-azaspiro[3.5]nonane-7-carboxylate.

A solution of tert-butyl 2-(2-(2-isopropylphenyl)-3-oxo-4-phenylpiperazin-1-yl)-7-azaspiro[3.5]nonane-7-carboxylate (1.2 g, 2.3 mmol) in BH3-THF (10 mL) was stirred at 70° C. for 10 hrs. The mixture was quenched by MeOH (10 mL) and concentrated to give tert-butyl 2-(2-(2-isopropylphenyl)-4-phenylpiperazin-1-yl)-7-azaspiro[3.5]nonane-7-carboxylate (2.1 g, crude) as a yellow oil, used directly.

Step 5: 2-(2-(2-isopropylphenyl)-4-phenylpiperazin-1-yl)-7-azaspiro[3.5]nonane.

A solution of tert-butyl 2-(2-(2-isopropylphenyl)-4-phenylpiperazin-1-yl)-7-azaspiro[3.5]nonane-7-carboxylate (1.1 g, 2.2 mmol) in TFA (3 mL) and DCM (6 mL) was stirred at 20° C. for 2 hrs. The mixture was concentrated to afford a residue, purified by prep-HPLC (TFA). The compound 2-(2-(2-isopropylphenyl)-4-phenylpiperazin-1-yl)-7-azaspiro[3.5]nonane (570 mg, 65% yield) was obtained as a white solid. $^1$H NMR (400 MHz, METHANOL-d4) δ ppm: 7.53 (d, J=7.6 Hz, 1H), 7.36-7.31 (m, 1H), 7.29-7.14 (m, 4H), 6.93 (d, J=7.9 Hz, 2H), 6.83 (t, J=7.3 Hz, 1H), 3.82-3.70 (m, 2H), 3.49 (br d, J=6.3 Hz, 1H), 3.35 (td, J=2.6 Hz, 12.2 Hz, 1H), 3.17 (td, J=2.5 Hz, 11.5 Hz, 1H), 3.03-2.91 (m, 2H), 2.85 (dd, J=10.8 Hz, 12.1 Hz, 1H), 2.68-2.48 (m, 4H), 2.39 (dt, J=3.0 Hz, 11.8 Hz, 1H), 1.92-1.83 (m, 1H), 1.75-1.68 (m, 1H), 1.46-1.28 (m, 9H), 1.24 (d, J=6.9 Hz, 3H), 1.18-1.10 (m, 1H). MS (ESI, m/e) [M+1]$^+$404.4.

Intermediate 66-1: 2-(2-(2-isopropylphenyl)-4-(methylsulfonyl)piperazin-1-yl)-7-azaspiro[3.5] nonane

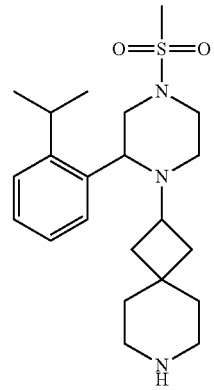

Intermediate 66-1

Step 1: tert-butyl 2-(2-(2-isopropylphenyl)-4-(methylsulfonyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.1 g, 2.5 mmol) in DCM (20 mL) was added TEA (506 mg, 5.0 mmol). After cooling to 0° C., MsCl (340 mg, 3.0 mmol) was added. The mixture was stirred at 25° C. for 2 hrs. The mixture was poured into aqueous NH$_4$Cl (I M, 20 mL), extracted with DCM (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=20/1 to 10/1) to give tert-butyl 2-(2-(2-isopropylphenyl)-4-(methylsulfonyl)-6-oxopiperazin-1-yl)-7-azaspiro[3.5]nonane-7-carboxylate (1.07 g, yield: 82%) as yellow oil. (H NMR (400 MHz, CDCl$_3$) δ ppm: 7.41-7.37 (m, 1H), 7.36-7.31 (m, 11H), 7.18 (t, 1H), 6.97 (d, J=7.6 Hz, 1H), 5.11 (br s, 1H), 4.52 (br s, 1H), 4.18-4.08 (m, 2H), 4.01-3.94 (m, 11H), 3.71-3.54 (m, 2H), 3.30-3.09 (m, 5H), 2.37 (s, 3H), 2.26 (m, 11H), 1.93 (br t, 1H), 1.82-1.70 (m, 2H), 1.59 (m, 1H), 1.53-1.46 (m, 2H), 1.42 (s, 9H), 1.36 (m, 3H), 1.30 (m, 3H).

Step 2: tert-butyl 2-(2-(2-isopropylphenyl)-4-(methylsulfonyl)piperazin-1-yl)-7-azaspiro[3.5]nonane-7-carboxylate.

The mixture of tert-butyl 2-(2-(2-isopropylphenyl)-4-(methylsulfonyl)-6-oxopiperazin-1-yl)-7-azaspiro[3.5] nonane-7-carboxylate (1.07 g, 2.06 mmol) and BH$_3$·THF (10 mL, 10 mmol) was heated to 70° C. for 12 hrs. After cooling to 0° C., the mixture was quenched with MeOH (10 mL). The mixture was concentrated in vacuum to give tert-butyl 2-(2-(2-isopropylphenyl)-4-(methylsulfonyl)piperazin-1-yl)-7-azaspiro[3.5]nonane-7-carboxylate (0.8 g, yield: 80%) as yellow oil, which was used into the next step without further purification. MS (ESI, m/e) [M+1]+506.3.

Step 3: 2-(2-(2-isopropylphenyl)-4-(methylsulfonyl)piperazin-1-yl)-7-azaspiro[3.5]nonane.

To a solution of tert-butyl 2-(2-(2-isopropylphenyl)-4-(methylsulfonyl)piperazin-1-yl)-7-azaspiro[3.5]nonane-7-carboxylate (800 mg, 1.58 mmol) in MeOH (20 mL) was added HCl/MeOH (10 mL). The mixture was stirred at 25° C. for 2 hrs. After concentrating in vacuum, the residue was dissolved into water (20 mL). The mixture was adjusted the pH=9-10 using aqueous Na$_2$CO$_3$. The mixture was extracted with EtOAc (20 mL×3). The combined organic phases were washed with brine (20 mL×2), dried with anhydrous Na$_2$SO$_4$, filtered and concentrated in vacuum to give 2-(2-(2-isopropylphenyl)-4-(methylsulfonyl)piperazin-1-yl)-7-azaspiro[3.5]nonane (570 mg, yield: 89%) as a yellow solid. $^1$H NMR (400 MHz, CDCl$_3$) δ ppm: 7.45 (m, 11H), 7.31-7.27 (m, 2H), 7.18-7.13 (m, 1H), 3.80 (m, 1H), 3.67 (m, 1H), 3.50 (m, 1H), 3.35 (br s, 1H), 3.12 (m, 1H), 2.99-2.91 (m, 2H), 2.77 (s, 3H), 2.67-2.57 (m, 4H), 2.33 (m, 1H), 1.91-1.75 (m, 3H), 1.66-1.60 (m, 1H), 1.39-1.29 (m, 5H), 1.25 (m, 3H), 1.20-1.13 (m, 3H), 1.16 (br s, 1H). MS (ESI, m/e) [M+1]$^+$406.3.

Intermediate 67-1: 2-(4-benzyl-2-(2-isopropylphenyl)piperidin-1-yl)-7-azaspiro[3.5]nonane.

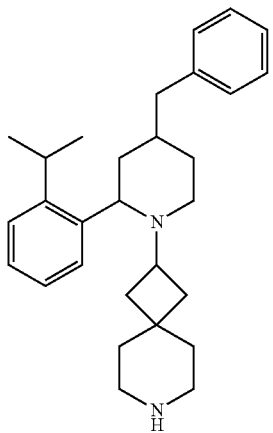

Intermediate 67-1

Step 1: benzyl 2-(2-isopropylphenyl)-4-oxo-3,4-dihydropyridine-1(2H)-carboxylate.

To a solution of 4-methoxypyridine (1.82 g, 17 mmol) in dry THF (50 mL) was added benzyl carbonochloridate (3.2 mL, 22 mmol) in drops at −20° C. The mixture was stirred at −20° C. for 1 hr. To another flask was added magnesite (0.9 g, 38 mmol) in THF (20 mL) at 25° C. under N$_2$. A small amount of I$_2$ (22 mg, 0.17 mmol) was added, then 1-bromo-2-isopropylbenzene (5.0 g, 25 mmol) was added in drops. The mixture was heated to 70° C. for 1 hr until the brown color disappeared completely. The obtained Grignard Reagent solution was added dropwise to the above pyridinium salt at −20° C. The mixture was stirred at −20° C. for 1 hr. The mixture was poured into HCl (1 M, 50 mL), extracted with EtOAc (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=10/1) to give benzyl 2-(2-isopropylphenyl)-4-oxo-3,4-dihydropyridine-1(2H)-carboxylate (5.5 g, yield: 92%) as a brown oil. $^1$H NMR (400 MHz, CDCl$_3$) δ ppm: 8.23 (d, J=8.4 Hz, 1H), 7.36-7.32 (m, 1H), 7.31-7.22 (m, 4H), 7.15-7.06 (m, 2H), 7.05-7.00 (m, 1H), 5.97 (d, J=8.4 Hz, 1H), 5.37 (d, J=8.4 Hz, 1H), 5.22-5.11 (m, 2H), 3.38 (m, 1H), 3.06 (t, 1H), 2.24 (m, 1H), 1.23 (d, J=6.8 Hz, 3H), 1.05 (m, 3H).

Step 2: benzyl 2-(2-isopropylphenyl)-4-oxopiperidine-1-carboxylate.

To a solution of benzyl 2-(2-isopropylphenyl)-4-oxo-3,4-dihydropyridine-1(2H)-carboxylate (5.5 g, 0.016 mmol) in HOAc (20 mL) was added zinc (10 g, 0.16 mmol,) at 25° C. The mixture was stirred at 25° C. for 12 hrs. After filtered the mixture, the filtrated was concentrated in vacuum. The residue was dissolved into EtOAc (50 mL) and washed with saturated NaHCO$_3$ (30 mL×2), brine (30 mL×2). The organic layer was dried over anhydrous Na$_2$SO$_4$, filtered and concentrated in vacuum. The residue was purified by column chromatography (silica gel, eluent: PE/EA (v/v)=1/1) to give benzyl 2-(2-isopropylphenyl)-4-oxopiperidine-1-carboxylate (5.4 g, yield: 96%) as brown oil. $^1$H NMR (400 MHz, CDCl$_3$) δ ppm: 7.33-7.28 (m, 5H), 7.23-7.11 (m, 4H), 5.87 (br s, 1H), 5.26-5.20 (m, 1H), 5.19-5.06 (m, 1H), 4.30 (br s, 1H), 3.35-3.11 (m, 2H), 2.87-2.80 (m, 2H), 2.59-2.46 (m, 2H), 1.20 (d, J=6.8 Hz, 3H), 1.03 (d, J=5.2 Hz, 3H).

Step 3: benzyl (E)-4-benzylidene-2-(2-isopropylphenyl)piperidine-1-carboxylate

The mixture of benzyltriphenylphosphonium bromide (4.44 g, 10.24 mmol) in THF (40 mL) was added NaH (0.41 g, 10.24 mmol) at 0° C. in several portions. After stirred at 25° C. for 1 hr, benzyl 2-(2-isopropylphenyl)-4-oxopiperidine-1-carboxylate (3.0 g, 8.54 mmol) in THF (10 mL) was added. The mixture was stirred at 25° C. for 12 hrs. The mixture was poured into aqueous NH$_4$Cl (10 mL) carefully, extracted with EtOAc (50 mL×2). The organic layers were dried over anhydrous Na$_2$SO$_4$, filtered and concentrated in vacuum. The residue was purified by column chromatography (silica gel, eluent: PE/EA (v/v)=10/1) to give benzyl (E)-4-benzylidene-2-(2-isopropylphenyl)piperidine-1-carboxylate (0.8 g, yield: 22%) as a yellow oil. MS (ESI, m/e) [M+1]$^+$426.4.

Step 4: 4-benzyl-2-(2-isopropylphenyl)piperidine.

To a solution of benzyl (E)-4-benzylidene-2-(2-isopropylphenyl)piperidine-1-carboxylate (800 mg, 1.88 mmol) in MeOH (30 mL) was added Pd(OH)$_2$/C (0.5 g). The mixture was stirred under H$_2$ (15 psi) atmosphere at 30° C. for 12 hrs. After filtered, the filtrate was concentrated in vacuum to give 4-benzyl-2-(2-isopropylphenyl)piperidine (450 mg, yield: 82%) as a yellow oil, which was used for next step without further purification. MS (ESI, m/e) [M+1]$^+$294.4.

Step 5: tert-butyl 2-(4-benzyl-2-(2-isopropylphenyl)piperidin-1-yl)-7-azaspiro[3.5]nonane-7-carboxylate.

A solution of 4-benzyl-2-(2-isopropylphenyl)piperidine (450 mg, 1.54 mmol), tert-butyl 2-oxo-7-azaspiro[3.5]nonane-7-carboxylate (611 mg, 2.3 mmol) and AcOH (185 mg, 3.08 mmol) in DCE (20 mL) was stirred at 25° C. for 1 hr, then NaBH(OAc)$_3$ (954 mg, 4.5 mmol) was added in portions and stirred at 25° C. for 12 hrs. The mixture was poured into saturated NaHCO$_3$ (20 mL), extracted with DCM (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=5/1) to give tert-butyl 2-(4-benzyl-2-(2-isopropylphenyl)piperidin-1-yl)-7-azaspiro[3.5]nonane-7-carboxylate (300 mg, yield: 38%) as a brown oil. MS (ESI, m/e) [M+1]$^+$517.4.

Step 6: 2-(4-benzyl-2-(2-isopropylphenyl)piperidin-1-yl)-7-azaspiro[3.5]nonane.

To a solution of tert-butyl 2-(4-benzyl-2-(2-isopropylphenyl)piperidin-1-yl)-7-azaspiro[3.5]nonane-7-carboxylate (300 mg, 0.58 mmol) in MeOH (20 mL) was added HCl/MeOH solution (10 mL). The mixture was stirred at 25° C. for 1 hr. After removed the solvent, the residue was poured into water (20 mL). The mixture was adjusted the pH to 9-10 using aqueous Na$_2$CO$_3$. The mixture was extracted with EtOAc (20 mL×3). The combined organic phase was washed with brine (20 mL×2), dried with anhydrous Na$_2$SO$_4$, filtered and concentrated in vacuum. The residue was purified by prep-HPLC (TFA) to give 2-(4-benzyl-2-(2-isopropylphenyl)piperidin-1-yl)-7-azaspiro[3.5]nonane (200 mg, yield: 83%) as a TFA salt. $^1$H NMR (400 MHz, CDCl$_3$) δ ppm: 7.58 (d, J=8.0 Hz, 1H), 7.47-7.38 (m, 2H), 7.33-7.23 (m, 5H), 7.22-7.17 (m, 1H), 4.84 (br s, 1H), 3.82 (m, 1H), 3.58-3.44 (m, 2H), 3.42-3.34 (m, 1H), 3.07-2.93 (m, 6H), 2.49-2.31 (m, 3H), 2.27-2.11 (m, 2H), 1.91 (m, 1H), 1.76-1.50 (m, 6H), 1.41 (d, J=6.8 Hz, 3H), 1.19 (d, J=6.8 Hz, 3H), 0.94-0.87 (m, 1H). MS (ESI, m/e) [M+1]$^+$ 417.4.

Intermediate 68-1: 2-(2-(2-isopropylphenyl)-4-phenoxypiperidin-1-yl)-7-azaspiro[3.5]nonane Intermediate 68-1

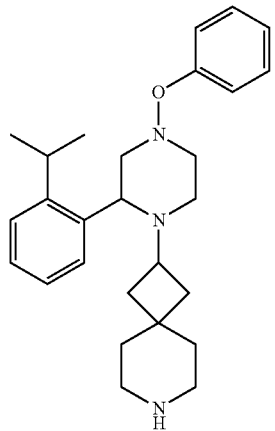

Step 1: benzyl 4-hydroxy-2-(2-isopropylphenyl)piperidine-1-carboxylate.

To a solution of benzyl 2-(2-isopropylphenyl)-4-oxopiperidine-1-carboxylate (2.6 g, 7.4 mmol) in MeOH (20 mL) was added NaBH$_4$ (0.56 g, 14.8 mmol) in several portions at 0° C. The mixture was stirred at 25° C. for 1 hr. The mixture was poured into H$_2$O (20 mL), extracted with EtOAc (20 mL×2). The combined organic layers were dried with anhydrous Na$_2$SO$_4$, filtered and concentrated in vacuum. The residue was purified by column chromatography (silica gel, eluent: PE/EA (v/v)=10/1) to give benzyl 4-hydroxy-2-(2-isopropylphenyl)piperidine-1-carboxylate (2.02 g, yield: 78%) as a brown oil. MS (ESI, m/e) [M+1]$^+$354.4.

Step 2: benzyl 2-(2-isopropylphenyl)-4-phenoxypiperidine-1-carboxylate.

To a solution of benzyl 4-hydroxy-2-(2-isopropylphenyl) piperidine-1-carboxylate (2.02 g, 5.71 mmol) in THF (50 mL) was added phenol (0.59 g, 6.59 mmol) and PPh$_3$ (1.95 g, 7.42 mmol).

After cooled to 0° C., DIAD (1.5 g, 7.42 mmol) was added dropwise. The mixture was stirred at 0-25° C. for 12 hrs. The solvent was removed by concentration under reduced pressure. The residue was purified by column chromatography (silica gel, eluent: PE/EA (v/v)=10/1) to give benzyl 2-(2-isopropylphenyl)-4-phenoxypiperidine-1-carboxylate (1.5 g, yield: 61%) as brown oil. MS (ESI, m/e) [M+1]$^+$430.4.

Step 3: 2-(2-isopropylphenyl)-4-phenoxypiperidine.

To a solution of benzyl 2-(2-isopropylphenyl)-4-phenoxypiperidine-1-carboxylate (1.5 g, 3.5 mmol) in MeOH (30 mL) was added Pd(OH)$_2$/C (0.5 g). The mixture was stirred at 30° C. for 12 hrs under H$_2$ (15 psi). After filtered the mixture, the filtrate was concentrated in vacuum to give 2-(2-isopropylphenyl)-4-phenoxypiperidine (1.0 g, yield: 99%) as yellow oil, which was used for next step without further purification. MS (ESI, m/e) [M+1]$^+$286.4.

Step 4: tert-butyl 2-(2-(2-isopropylphenyl)-4-phenoxypiperidin-1-yl)-7-azaspiro[3.5]nonane-7-carboxylate.

To a solution of 2-(2-isopropylphenyl)-4-phenoxypiperidine (1.0 g, 3.39 mmol) in DCE (20 mL) was added tert-butyl 2-oxo-7-azaspiro[3.5]nonane-7-carboxylate (1.8 g, 6.77 mmol) and AcOH (410 mg, 6.77 mmol). After stirred at 25° C. for 1 hr, then NaBH(OAc)$_3$ (2.15 g, 10.17 mmol) was added in portions. The mixture was stirred at 25° C. for 12 hrs. The mixture was poured into saturated NaHCO$_3$ (20 mL), extracted with DCM (20 mL×3). The combined organic phases were washed with brine (20 mL×2), dried with anhydrous Na$_2$SO$_4$, filtered and concentrated in vacuum. The residue was purified by column chromatography (silica gel, eluent: PE/EA (v/v)=5/1) to give tert-butyl 2-(2-(2-isopropylphenyl)-4-phenoxypiperidin-1-yl)-7-azaspiro[3.5]nonane-7-carboxylate (400 mg, yield: 23%) as a brown oil. MS (ESI, m/e) [M+1]$^+$519.4.

Step 5: 2-(2-(2-isopropylphenyl)-4-phenoxypiperidin-1-yl)-7-azaspiro[3.5]nonane.

To a solution of tert-butyl 2-(2-(2-isopropylphenyl)-4-phenoxypiperidin-1-yl)-7-azaspiro[3.5]nonane-7-carboxylate (300 mg, 0.58 mmol) in MeOH (20 mL) was added HCl/MeOH (10 mL, 4M) solution. The mixture was stirred at 25° C. for 2 hrs. After removed the solvent, the residue was dissolved into H$_2$O (20 mL). The mixture was adjusted the pH=9-10 using aqueous Na$_2$CO$_3$. The mixture was extracted with EtOAc (20 mL×3). The combined organic phases were washed with brine (20 mL×2), dried with anhydrous Na$_2$SO$_4$, filtered and concentrated in vacuum to give 2-(2-(2-isopropylphenyl)-4-phenoxypiperidin-1-yl)-7-azaspiro[3.5]nonane (160 mg, yield: 41%) as a yellow solid. $^1$H NMR (400 MHz, CDCl$_3$) δ ppm: 7.58-7.44 (m, 1H), 7.28-7.09 (m, 5H), 7.02-6.84 (m, 3H), 4.67 (br s, 1H), 3.92 (br d, J=8.4 Hz, 11H), 3.43-3.26 (m, 1H), 3.04-2.85 (m, 2H), 2.71-2.58 (m, 4H), 2.55-2.47 (m, 1H), 2.18-2.11 (m, 1H), 2.18-2.10 (m, 1H), 2.06-1.89 (m, 3H), 1.84-1.76 (m, 1H), 1.73-1.66 (m, 1H), 1.48-1.30 (m, 5H), 1.26 (d, J=6.8 Hz, 3H), 1.09 (m, 1H), 1.06-0.97 (d, J=6.8 Hz, 3H). MS (ESI, m/e) [M+1]$^+$419.4.

Intermediate 70-1: 2-(4-((1-cyclopropyl-JH-pyrazol-4-yl)methyl)-2-(2-isopropylphenyl)piperazin-1-yl)-7-azaspiro[3.5]nonane

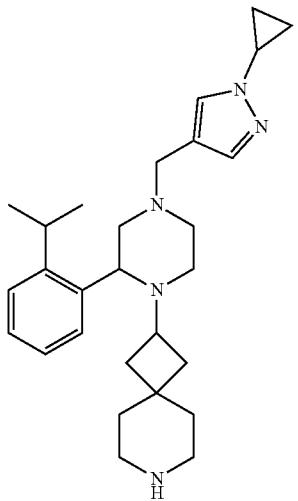

Intermediate 70-1

Step 1: ethyl 1-cyclopropyl-1H-pyrazole-4-carboxylate.

To a mixture of ethyl 1H-pyrazole-4-carboxylate (5.0 g, 35.68 mmol), cyclopropylboronic acid (5.82 g, 67.79 mmol), dipyridyl (5.57 g, 35.68 mmol), 4A MS (1.0 g) and $Na_2CO_3$ (7.18 g, 67.79 mmol) in DCE (150 mL) was added $Cu(OAc)_2$ (6.48 g, 35.68 mmol). The mixture was stirred at 70° C. for 16 hrs under $O_2$ (15 psi). The mixture was diluted with EtOAc (300 mL), filtered through a Celite. The filtrate was concentrated under reduced pressure. The crude was purified by column chromatography (silica gel, eluent: PE/EA (v/v)=10/1 to 2/1) to give ethyl 1-cyclopropyl-1H-pyrazole-4-carboxylate (5.95 g, yield: 93%) as a pale yellow oil. MS (ESI, m/e) [M+1]$^+$181.2.

Step 2: (1-cyclopropyl-1H-pyrazol-4-yl)methanol.

To a solution of ethyl 1-cyclopropyl-1H-pyrazole-4-carboxylate (5.9 g, 32.74 mmol) in THF (80 mL) was added LAH (1.24 g, 32.74 mmol) in portions at 0° C. The mixture was stirred at 20° C. for 2 hrs. The mixture was poured into aq. NaOH (4M, 50 mL), filtered through a Celite, extracted with EtOAc (100 mL×3). The combined organic phases were washed with brine, dried with anhydrous $Na_2SO_4$, filtered and concentrated to give (1-cyclopropyl-1H-pyrazol-4-yl)methanol (2.6 g, crude) as a yellow oil. MS (ESI, m/e) [M+1]$^+$139.2.

Step 3: 1-cyclopropyl-1H-pyrazole-4-carbaldehyde.

A mixture of (1-cyclopropyl-1H-pyrazol-4-yl) methanol (2.6 g, 18.82 mmol) and $MnO_2$ (16.36 g, 188.18 mmol) in DCM (60 mL) was stirred at 20° C. for 20 hrs. The mixture was diluted with DCM (200 mL), filtered through a Celite. The filtrate was concentrated under reduced pressure to give 1-cyclopropyl-1H-pyrazole-4-carbaldehyde (2.4 g, crude) as yellow oil.

Step 4: tert-butyl 2-(4-((1-cyclopropyl-1H-pyrazol-4-yl)methyl)-2-(2-isopropylphenyl)-6-oxopiperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), 1-cyclopropyl-1H-pyrazole-4-carbaldehyde (462.46 mg, 3.40 mmol) and AcOH (271.97 mg, 4.53 mmol) in DCE (20 mL) was stirred at 20° C. for 0.5 hr, then $NaBH(OAc)_3$ (1.44 g, 6.79 mmol) was added to the above mixture in portions, and stirred at 20° C. for 12 hrs. The mixture was poured into saturated $NaHCO_3$ (30 mL), extracted with DCM (30 mL×2). The combined organic phases were dried with $Na_2SO_4$, filtered and concentrated under reduced pressure. The crude was purified by column chromatography (silica gel, eluent: EA/MeOH (v/v)=1/0 to 100/1) to give tert-butyl 2-(4-((1-cyclopropyl-1H-pyrazol-4-yl)methyl)-2-(2-isopropylphenyl)-6-oxopiperazin-1-yl)-7-azaspiro[3.5]nonane-7-carboxylate (1.2 g, yield: 94%) as a yellow solid. $^1$H NMR (400 MHz, $CDCl_3$) δ ppm: 7.35-7.29 (m, 2H), 7.23-7.17 (m, 1H), 7.11 (d, J=8.0 Hz, 1H), 7.06 (s, 1H), 6.59 (s, 1H), 4.96 (s, 1H), 4.41 (s, 1H), 3.53-3.41 (m, 2H), 3.36 (m, 1H), 3.30-3.10 (m, 6H), 3.03 (m, 1H), 2.74-2.58 (m, 2H), 2.28-2.17 (m, 1H), 1.93 (m, 1H), 1.83-1.54 (m, 3H), 1.52-1.40 (m, 11H), 1.36-1.33 (m, 1H), 1.26-1.22 (m, 3H), 1.12-1.00 (m, 4H), 0.89 (d, J=5.6 Hz, 3H).

Step 5: tert-butyl 2-(4-((1-cyclopropyl-1H-pyrazol-4-yl)methyl)-2-(2-isopropylphenyl)piperazin-1-yl)-7-azaspiro[3.5]nonane-7-carboxylate.

To a solution of tert-butyl 2-(4-((1-cyclopropyl-1 H-pyrazol-4-yl)methyl)-2-(2-isopropylphenyl)-6-oxopiperazin-1-yl)-7-azaspiro[3.5]nonane-7-carboxylate (1.2 g, 2.14 mmol) in THF (15 mL) was added $BH_3 \cdot THF$ (30 mL, 30 mmol, 1 M in THF) dropwise at 20° C. The mixture was heated to 75° C. for 12 hrs. The reaction was quenched by MeOH (5 mL), concentrated under reduced pressure to give tert-butyl 2-(4-((1-cyclopropyl-1H-pyrazol-4-yl)methyl)-2-(2-isopropylphenyl)piperazin-1-yl)-7-azaspiro[3.5]nonane-7-carboxylate (1.17 g, crude) as a white solid. MS (ESI, m/e) [M+1]$^+$ 548.5.

Step 6: 2-(4-((1-cyclopropyl-1H-pyrazol-4-yl)methyl)-2-(2-isopropylphenyl)piperazin-1-yl)-7-azaspiro[3.5]nonane.

A solution of tert-butyl 2-(4-((1-cyclopropyl-1 H-pyrazol-4-yl)methyl)-2-(2-isopropylphenyl)piperazin-1-yl)-7-azaspiro[3.5]nonane-7-carboxylate (1.17 g, 2.14 mmol) in HCl/EtOAc (20 mL, 4M) was stirred at 20° C. for 4 hrs. The reaction solution was dried in vacuum. The residue was diluted with HCl (1M, 10 mL), extracted with EtOAc (10 mL×2). The aqueous phases were adjusted the pH=10 with aqueous $Na_2CO_3$, extracted with EtOAc (30 mL×3). The combined organic phases were washed with brine, dried with $Na_2SO_4$, filtered and concentrated under reduced pressure to give 2-(4-((1-cyclopropyl-1H-pyrazol-4-yl)methyl)-2-(2-isopropylphenyl)piperazin-1-yl)-7-azaspiro[3.5] nonane (507 mg, yield: 53%) as a yellow solid. $^1$H NMR (400 MHz, $CDCl_3$) δ ppm: 7.46 (s, 1H), 7.35 (d, J=7.6 Hz, 2H), 7.26-7.19 (m, 2H), 7.15-7.09 (m, 1H), 4.56 (s, 1H), 3.75-3.48 (m, 3H), 3.44-3.29 (m, 3H), 3.04-2.83 (m, 3H), 2.68 (m, 4H), 2.32-2.20 (m, 2H), 2.17-2.08 (m, 1H), 1.81-1.61 (m, 2H), 1.49-1.32 (m, 4H), 1.23 (d, J=7.02 Hz, 3H), 1.16 (d, J=6.8 Hz, 3H), 1.12-1.04 (m, 3H), 1.04-0.93 (m, 3H). MS (ESI, m/e) [M+1]$^+$448.3.

Intermediate 71-1: 2-(2-(2-isopropylphenyl)-4-((3-methoxy-1-methyl-1H-pyrazol-4-yl)methyl)piperazin-1-yl)-7-azaspiro[3.5]nonane

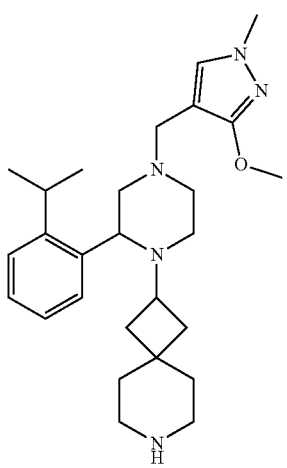

Intermediate 71-1

Step 1: methyl 3-hydroxy-1 H-pyrazole-4-carboxylate.

To a solution of dimethyl 2-(methoxymethylene)malonate (30 g, 172.26 mmol) in MeOH (300 mL) was added $N_2H_4 \cdot H_2O$ (8.62 g, 172.26 mmol) dropwise at 20° C. The mixture was heated to 70° C. for 12 hrs. The reaction mixture was filtered, and the solid was washed with petroleum ether. The filter cake was dried in vacuum to give methyl 3-hydroxy-1H-pyrazole-4-carboxylate (23.5 g, crude) as a white solid. $^1$H NMR (400 MHz, DMSO-$d_6$) δ ppm: 12.30 (s, 1H), 10.47-9.71 (m, 1H), 7.93 (s, 1H), 3.67 (s, 3H).

Step 2: methyl 3-methoxy-1-methyl-1H-pyrazole-4-carboxylate.

To a mixture of methyl 3-hydroxy-1H-pyrazole-4-carboxylate (10 g, 70.37 mmol) and MeI (20.47 g, 144.25 mmol) in DMF (200 mL) was added NaH (7.04 g, 175.92 mmol) in portions at 0° C. under $N_2$ protection. The mixture was stirred at 20° C. for 2 hrs. The mixture was poured into saturated $NH_4Cl$ (300 mL), extracted with EtOAc (500 mL×3). The combined organic phases were washed with brine (1 L), dried with anhydrous $Na_2SO_4$, filtered and concentrated under reduced pressure. The crude was diluted with $H_2O$ (50 mL), ultrasonic 10 min, filtered. The filter cake was washed with petroleum ether, dried in vacuum to give methyl 3-methoxy-1-methyl-1H-pyrazole-4-carboxylate (4.8 g, crude) as a yellow solid, which was used directly for next step without further purification. $^1$H NMR (400 MHz, DMSO-$d_6$) δ ppm: 8.09 (s, 1H), 3.82 (s, 3H), 3.71 (s, 3H), 3.66 (s, 3H).

Step 3: (3-methoxy-1-methyl-1H-pyrazol-4-yl)methanol.

To a solution of methyl 3-methoxy-1-methyl-1H-pyrazole-4-carboxylate (4.8 g, 28.21 mmol) in THF (72 mL) was added LiAlH$_4$ (1.07 g, 28.21 mmol) in portions at 0° C. The mixture was stirred at 20° C. for 2 hrs. The reaction mixture was poured into aqueous NaOH (4M, 50 mL), filtered through a Celite, extracted with EtOAc (100 mL×3). The combined organic phases were washed with brine (50 mL), dried with anhydrous $Na_2SO_4$, filtered and concentrated under reduced pressure to give (3-methoxy-1-methyl-1 H-pyrazol-4-yl)methanol (2.7 g, crude) as a yellow oil, which was used directly for next step without further purification. $^1$H NMR (400 MHz, CDCl$_3$) δ ppm: 7.16 (s, 1H) 4.47 (s, 2H) 3.92 (s, 3H) 3.72 (s, 3H)

Step 4: 3-methoxy-1-methyl-1H-pyrazole-4-carbaldehyde.

A mixture of (3-methoxy-1-methyl-1H-pyrazol-4-yl) methanol (2.6 g, 18.29 mmol) and MnO$_2$ (15.9 g, 182.90 mmol) in DCM (60 mL) was stirred at 20° C. for 20 hrs. The reaction mixture was diluted with DCM (200 mL), filtered through a Celite. The filtrate was concentrated under reduced pressure to give 3-methoxy-1-methyl-1H-pyrazole-4-carbaldehyde (2.4 g, crude) as a green solid, which was used directly for next step without further purification. $^1$H NMR (400 MHz, CDCl$_3$) δ ppm: 9.72 (s, 1H), 7.67 (s, 1H), 3.94-4.04 (m, 3H), 3.78 (s, 3H).

Step 5: tert-butyl 2-(2-(2-isopropylphenyl)-4-((3-methoxy-1-methyl-1H-pyrazol-4-yl)methyl)-6-oxopiperazin-1-yl)-7-azaspiro[3.5]nonane-7-carboxylate.

A mixture of tert-butyl 2-(2-(2-isopropylphenyl)-6-oxopiperazin-1-yl)-7-azaspiro[3.5]nonane-7-carboxylate (1.0 g, 2.26 mmol), 3-methoxy-1-methyl-1H-pyrazole-4-carbaldehyde (476.01 mg, 3.40 mmol) and AcOH (271.97 mg, 4.53 mmol) in DCE (20 mL) was stirred at 20° C. for 0.5 hr, then NaBH(OAc)$_3$ (1.44 g, 6.79 mmol) was added to the above mixture in portions and stirred at 20° C. for 12 hrs. The mixture was poured into saturated NaHCO$_3$ (30 mL), extracted with DCM (30 mL×2). The combined organic phases were dried with anhydrous Na$_2$SO$_4$, filtered and concentrated under reduced pressure. The crude was purified by column chromatography (silica gel, eluent: EA/MeOH (v/v)=1/0 to 100/1) to give tert-butyl 2-(2-(2-isopropylphenyl)-4-((3-methoxy-1-methyl-1H-pyrazol-4-yl)methyl)-6-oxopiperazin-1-yl)-7-azaspiro[3.5]nonane-7-carboxylate (1.16 g, yield: 91%) as a yellow solid. $^1$H NMR (400 MHz, CDCl$_3$) δ ppm: 7.31 (d, J=3.2 Hz, 2H), 7.27-7.15 (m, 2H), 7.12-7.06 (m, 1H), 6.18 (s, 1H), 4.98 (s, 1H), 4.35 (s, 1H), 3.81 (s, 3H), 3.52 (s, 3H), 3.46-3.03 (m, 10H), 2.76-2.60 (m, 2H), 2.37-2.15 (m, 1H), 1.97-1.91 (m, 1H), 1.78 (s, 1H), 1.66 (m, 1H), 1.51-1.41 (m, 10H), 1.34 (d, J=4.88 Hz, 1H), 1.26 (d, J=6.8 Hz, 3H), 1.11 (d, J=6.8 Hz, 3H).

Step 6: tert-butyl 2-(2-(2-isopropylphenyl)-4-((3-methoxy-1-methyl-1H-pyrazol-4-yl)methyl)piperazin-1-yl)-7-azaspiro[3.5]nonane-7-carboxylate.

To a solution of tert-butyl 2-(2-(2-isopropylphenyl)-4-((3-methoxy-1-methyl-1H-pyrazol-4-yl)methyl)-6-oxopiperazin-1-yl)-7-azaspiro[3.5]nonane-7-carboxylate (1.16 g, 2.05 mmol) in THF (15 mL) was added BH$_3$·THF (30 mL, 30 mmol, 1 M in THF) dropwise at 20° C. The mixture was heated to 75° C. for 12 hrs. The reaction was quenched by MeOH (5 mL), concentrated in vacuum to give tert-butyl 2-(2-(2-isopropylphenyl)-4-((3-methoxy-1-methyl-1H-pyrazol-4-yl)methyl)piperazin-1-yl)-7-azaspiro[3.5]nonane-7-carboxylate (1.13 g, crude) as a white solid. MS (ESI, m/e) [M+1]$^+$552.5.

Step 7: 2-(2-(2-isopropylphenyl)-4-((3-methoxy-1-methyl-1 H-pyrazol-4-yl)methyl)piperazin-1-yl)-7-azaspiro [3.5]nonane.

To a solution of tert-butyl 2-(2-(2-isopropylphenyl)-4-((3-methoxy-1-methyl-1H-pyrazol-4-yl)methyl)piperazin-1-yl)-7-azaspiro[3.5]nonane-7-carboxylate (1.13 g, 2.05 mmol) in DCM (25 mL) was added TFA (5 mL) dropwise at 20° C. The mixture was stirred at 20° C. for 12 hrs.

The reaction mixture was concentrated under reduced pressure. The crude was purified by prep-HPLC, the solution was concentrated, adjust the pH=10 with Na$_2$CO$_3$, extracted with EtOAc (50 mL×5). The combined organic phases were dried with anhydrous Na$_2$SO$_4$, filtered and concentrated to give 2-(2-(2-isopropylphenyl)-4-((3-methoxy-1-methyl-1H- pyrazol-4-yl)methyl)piperazin-1-yl)-7-azaspiro[3.5]nonane (472 mg, yield: 51%) as a white solid. ¹H NMR (400 MHz, CDCl₃) δ ppm: 7.45 (s, 1H), 7.25-7.20 (m, 2H), 7.16-7.08 (m, 1H), 7.06 (s, 1H), 3.86 (s, 3H), 3.69 (s, 4H), 3.37 (m, 3H), 3.00-2.64 (m, 8H), 2.38-2.11 (m, 3H), 1.79 (s, 1H), 1.72-1.64 (m, 1H), 1.60-1.40 (m, 4H), 1.32-1.07 (m, 9H). MS (ESI, m/e) [M+1]⁺452.4.

Intermediate 72-1: 2-(2-(2-isopropylphenyl)-4-((6-methoxypyridin-3-yl)methyl)piperazin-1-yl)-7-azaspiro[3.5]nonane

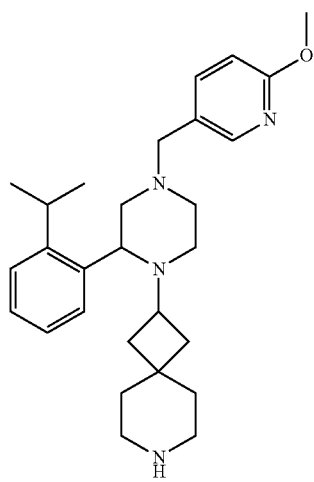

Intermediate 72-1

Step 1: tert-butyl 2-(2-(2-isopropylphenyl)-4-((6-methoxypyridin-3-yl)methyl)-6-oxopiperazin-1-yl)-7-azaspiro[3.5]nonane-7-carboxylate.

A solution of tert-butyl 2-(2-(2-isopropylphenyl)-6-oxopiperazin-1-yl)-7-azaspiro[3.5]nonane-7-carboxylate (1.5 g, 3.4 mmol), 6-methoxynicotinaldehyde (698.7 mg, 5.1 mmol) and AcOH (509.9 mg, 8.49 mmol) in DCE (15 mL) was stirred at 25° C. for 15 min, then NaBH(OAc)₃(1.44 g, 6.79 mmol) was added in portions. The mixture was stirred at 20° C. for 12 hrs. The mixture was poured into saturated NaHCO₃ to adjust the pH=8, extracted with DCM (50 mL×3). The combined organic phases were washed with brine (20 mL), dried over Na₂SO₄ and concentrated under reduced pressure. The residue purified by column chromatography (silica gel, eluent: PE/EA (v/v)=5/1 to 0/1) to give tert-butyl 2-(2-(2-isopropylphenyl)-4-((6-methoxypyridin-3-yl)methyl)-6-oxopiperazin-1-yl)-7-azaspiro[3.5]nonane-7-carboxylate (1.6 g, yield: 83%) as a yellow oil. ¹H NMR (400 MHz, CDCl₃) δ ppm: 7.82 (d, J=2.0 Hz, 1H), 7.33-7.27 (m, 2H), 7.22-7.16 (m, 1H), 7.12-7.07 (m, 1H), 6.91 (m, 1H), 6.42 (d, J1=8.4 Hz, 1H), 4.94 (br s, 1H), 4.42 (br s, 1H), 3.87 (s, 3H), 3.54-3.45 (m, 2H), 3.33-3.08 (m, 7H), 2.98 (m, 11H), 2.74-2.66 (m, 1H), 2.62-2.55 (m, 1H), 2.28-2.17 (m, 11H), 1.98-1.88 (m, 1H), 1.81-1.66 (m, 2H), 1.53-1.40 (m, 12H), 1.22 (d, J=6.8 Hz, 3H), 0.97 (d, J=6.8 Hz, 3H).

Step 2: tert-butyl 2-(2-(2-isopropylphenyl)-4-((6-methoxypyridin-3-yl)methyl)piperazin-1-yl)-7-azaspiro [3.5]nonane-7-carboxylate.

To a solution of tert-butyl 2-(2-(2-isopropylphenyl)-4-((6-methoxypyridin-3-yl)methyl)-6-oxopiperazin-1-yl)-7-azaspiro[3.5]nonane-7-carboxylate (1.2 g, 2.13 mmol) in THF (10 mL) was added BH₃·THF (10 mL). The solution was stirred at 70° C. for 12 hrs. After cooling to 0° C., then MeOH (30 mL) was added dropwise at 0° C. The mixture was concentrated under reduced pressure to give tert-butyl 2-(2-(2-isopropylphenyl)-4-((6-methoxypyridin-3-yl) methyl)piperazin-1-yl)-7-azaspiro[3.5]nonane-7-carboxylate (1.6 g, crude) as a white solid. MS (ESI, m/e) [M+1]+ 549.5.

Step 3: 2-(2-(2-isopropylphenyl)-4-((6-methoxypyridin-3-yl)methyl)piperazin-1-yl)-7-azaspiro[3.5]nonane.

To a solution of tert-butyl 2-(2-(2-isopropylphenyl)-4-((6-methoxypyridin-3-yl)methyl) piperazin-1-yl)-7-azaspiro [3.5]nonane-7-carboxylate (1.6 g, 2.92 mmol) in DCM (20 mL) was added TFA (5 mL) at 25° C. The solution was stirred at 25° C. for 5 hrs. The reaction mixture was poured into aqueous Na₂CO₃ (20 mL), extracted with DCM (50 mL×3). The combined organic layers were washed with brine, dried with anhydrous Na₂SO₄, filtered and concentrated under reduced pressure to give 2-(2-(2-isopropylphenyl)-4-((6-methoxypyridin-3-yl)methyl)piperazin-1-yl)-7-azaspiro[3.5]nonane (1.31 g, yield: 100%) as a white solid. ¹H NMR (400 MHz, CDCl₃) δ ppm: 8.93 (br.s, 1H), 8.01 (s, 1H), 7.58-7.55 (m, 1H), 7.45 (s, 1H), 7.24-7.11 (m, 3H), 6.76-6.68 (m, 1H), 4.43-4.39 (m, 1H), 3.91 (s, 3H), 3.61-3.44 (m, 4H), 2.95-2.83 (m, 9H), 2.30-2.20 (m, 3H), 1.91-1.57 (m, 8H), 1.27-1.13 (m, 8H). MS (ESI, m/e) [M+1]⁺ 449.4.

Intermediate 73-1: 2-(2-(2-cyclopropylphenyl)-4-(4-methoxybenzyl)piperazin-1-yl)-7-azaspiro[3.5] nonane

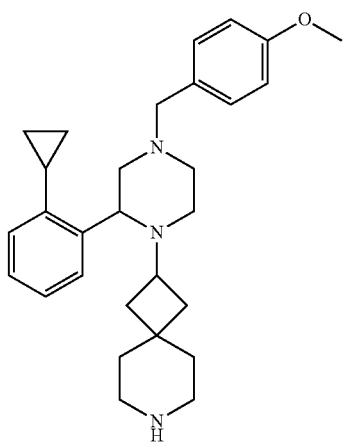

Intermediate 73-1

Step 1: 1-bromo-2-cyclopropylbenzene.

A mixture of 1-bromo-2-iodobenzene (50 g, 176.74 mmol), cyclopropylboronic acid (45.54 g, 530.21 mmol), K₂CO₃ (73.28 g, 530.21 mmol) and Pd(dppf)Cl₂ (6.64 g, 8.84 mmol) in dioxane (500 mL) was stirred at 75° C. for 48 hrs under N₂. The mixture was diluted with EtOAc (500 mL), filtered with Celite, and the filtrate was concentrated under reduced pressure. The residue was purified by column chromatography (silica gel, eluent: PE) to give 1-bromo-2-cyclopropylbenzene (28.9 g, yield: 83%) as a pale-yellow oil. ¹H NMR (400 MHz, CDCl₃) δ ppm: 7.77 (d, J=8.4 Hz, 2H), 7.33 (d, J=8.0 Hz, 2H), 5.06-4.97 (m, 1H), 3.71 (t, J=4.8 Hz, 2H), 3.13-3.06 (m, 2H), 2.44 (s, 3H), 2.03 (s, 1H).

Step 2: tert-butyl (2-((2-(2-cyclopropylphenyl)-2-oxoethyl)(4-methoxybenzyl)amino)ethyl)carbamate.

To a solution of 1-bromo-2-cyclopropylbenzene (5.07 g, 25.75 mmol) in THF (170 mL) was added n-BuLi (8.92 mL, 2.5 M) dropwise at −70° C. The solution was stirred at −70° C. for 10 min. A solution of tert-butyl 4-(4-methoxybenzyl)-2-oxopiperazine-1-carboxylate (5.5 g, 17.17 mmol) in THF (30 mL) was added dropwise at −70° C. The solution was stirred at −70° C. for 4 hrs. The mixture was poured into saturated NH₄Cl (100 mL), extracted with EtOAc (100 mL×2).

The combined organic phases were dried over Na₂SO₄, filtered and concentrated under reduced pressure. The residue was purified by column chromatography (silica gel, eluent: PE/EA (v/v)=25/1 to 15/1, 0.2% DCM) to give tert-butyl (2-((2-(2-cyclopropylphenyl)-2-oxoethyl)(4-methoxybenzyl)amino)ethyl)carbamate (5.2 g, yield: 69%) as a yellow oil. ¹H NMR (400 MHz, CDCl₃) δ ppm: 7.37-7.31 (m, 1H), 7.25-7.15 (m, 4H), 7.00 (d, J=7.6 Hz, 1H), 6.85 (d, J=8.4 Hz, 2H), 5.18 (s, 1H), 3.82-3.72 (m, 7H), 3.23 (d, J=5.6 Hz, 2H), 2.79 (t, J=5.2 Hz, 2H), 2.34-2.10 (m, 1H), 1.45 (s, 9H), 0.93-0.85 (m, 2H), 0.65-0.59 (m, 2H).

Step 3: 3-(2-cyclopropylphenyl)-1-(4-methoxybenzyl)piperazine

A solution of tert-butyl (2-((2-(2-cyclopropylphenyl)-2-oxoethyl)(4-methoxybenzyl)amino)ethyl)carbamate (5.2 g, 11.86 mmol) and TFA (15 mL) in DCM (45 mL) was stirred at 20° C. for 12 hrs. The solvent was removed by evaporation under reduced pressure. The residue was dissolved into DCE (60 mL) and NaBH(OAc)₃ (6.76 g, 31.91 mmol) was added in portions. The solution was stirred at 20° C. for 6 hrs. The mixture was poured into aqueous NaHCO₃ to adjust the pH=8, extracted the solution with DCM (50 mL×3). The combined organic phases were washed with brine, dried over Na₂SO₄, filtered and concentrated under reduced pressure. The residue was purified by column chromatography (silica gel, eluent: PE/EA (v/v)=2/1 to EA/MeOH(v/v)=10/1) to give 3-(2-cyclopropylphenyl)-1-(4-methoxybenzyl)piperazine (3.8 g, yield: 99%) as a yellow oil. ¹H NMR (400 MHz, CDCl₃) δ ppm: 7.57-7.49 (m, 1H), 7.27-7.22 (m, 2H), 7.20-7.15 (m, 2H), 7.04-6.98 (m, 1H), 6.86 (d, J=8.8 Hz, 2H), 4.67 (d, J=9.6 Hz, 1H), 3.80 (s, 3H), 3.72-3.54 (m, 2H), 3.25-2.89 (m, 4H), 2.43 (s, 1H), 2.31-2.18 (m, 1H), 2.00-1.92 (m, 1H), 1.02-0.81 (m, 2H), 0.63-0.73 (m, 1H), 0.42-0.54 (m, 1H). MS (ESI, m/e) [M+1]⁺323.2.

Step 4: tert-butyl 2-(2-(2-cyclopropylphenyl)-4-(4-methoxybenzyl)piperazin-1-yl)-7-azaspiro[3.5]nonane-7-carboxylate.

To a solution of 3-(2-cyclopropylphenyl)-1-(4-methoxybenzyl)piperazine (1.5 g, 4.65 mmol), tert-butyl 2-oxo-7-azaspiro[3.5]nonane-7-carboxylate (2.89 g, 12.10 mmol) and NaBH₃CN (877.0 mg, 13.96 mmol) in MeOH (10 mL) and AcOH (1 mL) was stirred at 65° C. for 24 hrs. The mixture was poured into aqueous Na₂CO₃ (20 mL) to adjust the pH=10, extract with EtOAc (30 mL×2). The combined organic phases were washed with brine, dried over Na₂SO₄, filtered and concentrated under reduced pressure. The residue by column chromatography (silica gel, eluent: PE/EA (v/v)=3/1 to 0/1) to give tert-butyl 2-(2-(2-cyclopropylphenyl)-4-(4-methoxybenzyl)piperazin-1-yl)-7-azaspiro[3.5]nonane-7-carboxylate (1.3 g, yield: 51%) as a yellow oil. MS (ESI, m/e) [M+1]⁺546.5.

Step 5: 2-(2-(2-cyclopropylphenyl)-4-(4-methoxybenzyl)piperazin-1-yl)-7-azaspiro[3.5]nonane.

To a solution of tert-butyl 2-(2-(2-cyclopropylphenyl)-4-(4-methoxybenzyl)piperazin-1-yl)-7-azaspiro[3.5]nonane-7-carboxylate (1.3 g, 2.38 mmol) in DCM (15 mL) was added TFA (5 mL). The solution was stirred at 20° C. for 2 hrs. The mixture was concentrated under reduced pressure. The residue was poured into aqueous HCl (10 mL, 1M), extract with EtOAc (10 mL×2). The combined organic phases were discarded. The aqueous layer was adjusted the pH=10 with Na₂CO₃, extract with EtOAc (10 mL×5). The combined organic phases were washed with brine, dried over Na₂SO₄, filtered and concentrated under reduced pressure to give 2-(2-(2-cyclopropylphenyl)-4-(4-methoxybenzyl)piperazin-1-yl)-7-azaspiro[3.5]nonane (400 mg, yield: 38%) as a yellow gum. ¹H NMR (400 MHz, CDCl₃) δ ppm: 7.47 (s, 1H), 7.22 (d, J=8.4 Hz, 2H), 7.16-7.10 (m, 2H), 6.98 (s, 1H), 6.83 (d, J=8.8 Hz, 2H), 3.94 (s, 1H), 3.79 (s, 3H), 3.54-3.41 (m, 2H), 3.04-2.88 (m, 3H), 2.75-2.60 (m, 5H), 2.30 (s, 3H), 1.84-1.78 (m, 1H), 1.67-1.61 (m, 1H), 1.55 (d, J=5.6 Hz, 1H), 1.44-1.31 (m, 5H), 1.14-1.08 (m, 1H), 0.95-0.88 (m, 2H), 0.59 (s, 2H). MS (ESI, m/e) [M+1]⁺ 446.5.

Intermediate 74-1: 2-(4-(2,3-dimethoxybenzyl)-2-(2-isopropylphenyl)piperazin-1-yl)-7-azaspiro[3.5]nonane

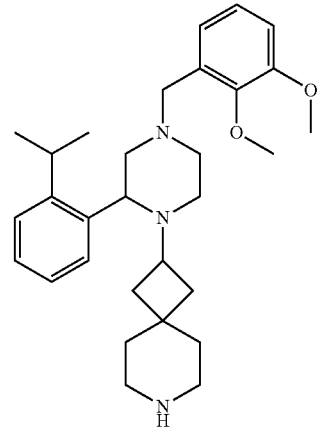

Intermediate 74-1

Step 1: tert-butyl 2-(4-(2,3-dimethoxybenzyl)-2-(2-isopropylphenyl)-6-oxopiperazin-1-yl)-7-azaspiro[3.5]nonane-7-carboxylate.

A solution of tert-butyl 2-(2-(2-isopropylphenyl)-6-oxopiperazin-1-yl)-7-azaspiro[3.5]nonane-7-carboxylate (1.0 g, 2.26 mmol), 2,3-dimethoxybenzaldehyde (333 mg, 3.40 mmol) and AcOH (339 mg, 5.66 mmol) in DCE (20 mL) was stirred at 25° C. for 1 hr, then NaBH(OAc)₃ (959 mg, 4.53 mmol) was added in portions and stirred at 25° C. for 11 hrs. The reaction mixture was quenched by saturated Na₂CO₃ (20 mL), extracted with EtOAc (20 mL×3).

The combined organic layers were washed with brine, dried with anhydrous Na₂SO₄, filtered and concentrated under reduced pressure. The crude product was purified by column chromatography (silica gel, eluent: PE/EA (v/v)= 50/1 to 0/1) to give tert-butyl 2-(4-(2,3-dimethoxybenzyl)-2-(2-isopropylphenyl)-6-oxopiperazin-1-yl)-7-azaspiro[3.5]nonane-7-carboxylate (1.0 g, yield: 74%) as a pale yellow oil.

Step 2: tert-butyl 2-(4-(2,3-dimethoxybenzyl)-2-(2-isopropylphenyl)piperazin-1-yl)-7-azaspiro[3.5]nonane-7-carboxylate.

A mixture of tert-butyl 2-(4-(2,3-dimethoxybenzyl)-2-(2-isopropylphenyl)-6-oxopiperazin-1-yl)-7-azaspiro[3.5]nonane-7-carboxylate (1.0 g, 1.69 mmol) and BH₃·THF (50 mL, 50.69 mmol) in THF (20 mL) was stirred at 70° C. for 12 hrs. After cooling to 0° C., the reaction solution was quenched by MeOH (20 mL) and stirred at 0° C. for 1 hr. The mixture was concentrated to give tert-butyl 2-(4-(2,3-dimethoxybenzyl)-2-(2-isopropylphenyl)piperazin-1-yl)-7-azaspiro[3.5]nonane-7-carboxylate (1.3 g, crude) as a white solid, which was used directly for next step without further purification. MS (ESI, m/e) [M+1]+578.5.

Step 3: 2-(4-(2,3-dimethoxybenzyl)-2-(2-isopropylphenyl)piperazin-1-yl)-7-azaspiro[3.5]nonane.

A mixture of tert-butyl 2-(4-(2,3-dimethoxybenzyl)-2-(2-isopropylphenyl)piperazin-1-yl)-7-azaspiro[3.5]nonane-7-carboxylate (1.3 g, 2.25 mmol) in HCl/MeOH solution (20 mL) was stirred at 20° C. for 3 hrs. The reaction mixture poured into saturated $Na_2CO_3$ (40 mL), extracted with EtOAc (40 mL×3). The combined organic phases were washed with brine, dried with anhydrous $Na_2SO_4$, filtered and concentrated under reduced pressure to give 2-(4-(2,3-dimethoxybenzyl)-2-(2-isopropylphenyl)piperazin-1-yl)-7-azaspiro[3.5]nonane (610 mg, yield: 56%) as a pale pink oil. $^1$H NMR (400 MHz, $CDCl_3$) δ ppm: 7.54-7.44 (m, 1H), 7.25-7.18 (m, 2H), 7.14-7.09 (m, 1H), 7.01-6.96 (m, 2H), 6.84-6.77 (m, 1H), 4.13-4.09 (m, 1H), 3.85 (s, 3H), 3.81 (s, 3H), 3.74-3.64 (m, 1H), 3.62-3.53 (m, 2H), 3.39 (m, 1H), 3.00-2.87 (m, 3H), 2.75-2.60 (m, 6H), 2.39-2.22 (m, 3H), 1.80-1.62 (m, 3H), 1.44-1.33 (m, 4H), 1.26-1.24 (m, 3H), 1.16 (d, J=6.80 Hz, 3H). MS (ESI, m/e) [M+1]$^+$478.3.

Intermediate 75-1: 2-(2-(2-isopropylphenyl)-4-(3,4,5-trimethoxybenzyl)piperazin-1-yl)-7-azaspiro[3.5]nonane

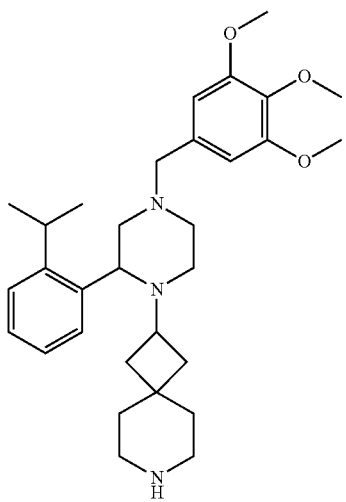

Intermediate 75-1

Step 1: tert-butyl 2-(2-(2-isopropylphenyl)-6-oxo-4-(3,4,5-trimethoxybenzyl)piperazin-1-yl)-7-azaspiro[3.5]nonane-7-carboxylate.

A solution of tert-butyl 2-(2-(2-isopropylphenyl)-6-oxopiperazin-1-yl)-7-azaspiro[3.5]nonane-7-carboxylate (1.0 g, 2.26 mmol), 3,4,5-trimethoxybenzaldehyde (666 mg, 3.40 mmol) and AcOH (339 mg, 5.66 mmol) in DCE (20 mL) was stirred at 25° C. for 1 hr, then NaBH(OAc)$_3$ (959 mg, 4.53 mmol) was added in portions and stirred at 25° C. for 12 hrs. The reaction mixture was quenched by saturated $Na_2CO_3$ (20 mL), extracted with EtOAc (20 mL×3).

The combined organic layers were washed with brine, dried with anhydrous $Na_2SO_4$, filtered and concentrated under reduced pressure. The crude product was purified by column chromatography (silica gel, eluent: PE/EA (v/v)= 50/1 to 0/1) to give tert-butyl 2-(2-(2-isopropylphenyl)-6-oxo-4-(3,4,5-trimethoxybenzyl)piperazin-1-yl)-7-azaspiro[3.5]nonane-7-carboxylate (1.0 g, yield: 71%) as a pale yellow oil Step 2: tert-butyl 2-(2-(2-isopropylphenyl)-4-(3,4,5-trimethoxybenzyl)piperazin-1-yl)-7-azaspiro[3.5]nonane-7-carboxylate.

A mixture of tert-butyl 2-(2-(2-isopropylphenyl)-6-oxo-4-(3,4,5-trimethoxybenzyl)piperazin-1-yl)-7-azaspiro[3.5]nonane-7-carboxylate (1.0 g, 1.61 mmol) and BH$_3$·THF (48 mL, 48.25 mmol) in THF (15 mL) was stirred at 70° C. for 12 hrs. After cooling to 0° C., the mixture was quenched by MeOH (20 mL) and stirred at 0° C. for 1 hr. The mixture was concentrated under reduced pressure to give tert-butyl 2-(2-(2-isopropylphenyl)-4-(3,4,5-trimethoxybenzyl)piperazin-1-yl)-7-azaspiro[3.5]nonane-7-carboxylate (1.3 g, crude) as a white solid, which was used directly for next step without further reaction. MS (ESI, m/e) [M+1]+608.5.

Step 3: 2-(2-(2-isopropylphenyl)-4-(3,4,5-trimethoxybenzyl)piperazin-1-yl)-7-azaspiro[3.5]nonane.

A mixture of tert-butyl 2-(4-(2,3-dimethoxybenzyl)-2-(2-isopropylphenyl)piperazin-1-yl)-7-azaspiro[3.5]nonane-7-carboxylate (1.3 g, 2.14 mmol) in HCl/MeOH solution (20 mL) was stirred at 20° C. for 3 hrs. The reaction mixture poured into saturated $Na_2CO_3$ (40 mL), extracted with EtOAc (40 mL×3). The combined organic phases were dried with anhydrous $Na_2SO_4$, filtered and concentrated under reduced pressure to give 2-(2-(2-isopropylphenyl)-4-(3,4,5-trimethoxybenzyl)piperazin-1-yl)-7-azaspiro[3.5]nonane (630 mg, yield: 56%) as a pale pink oil. $^1$H NMR (400 MHz, $CDCl_3$) δ ppm: 7.54-7.46 (m, 1H), 7.26-7.18 (m, 2H), 7.15-7.10 (m, 1H), 6.56 (s, 2H), 3.85 (s, 6H), 3.81 (s, 3H), 3.76-3.61 (m, 2H), 3.54-3.32 (m, 3H), 3.08-2.99 (m, 1H), 2.98-2.88 (m, 2H), 2.70-2.50 (m, 5H), 2.38-2.27 (m, 2H), 2.18-2.10 (m, 1H), 1.82-1.73 (m, 1H), 1.72-1.64 (m, 2H), 1.42-1.28 (m, 5H), 1.27 (d, J=6.8 Hz, 3H), 1.15 (d, J=6.8 Hz, 3H). MS (ESI, m/e) [M+1]$^+$508.3.

Intermediate 76-1: 2-(2-(2-ethylphenyl)-4-(4-methoxybenzyl)piperazin-1-yl)-7-azaspiro[3.5]nonane

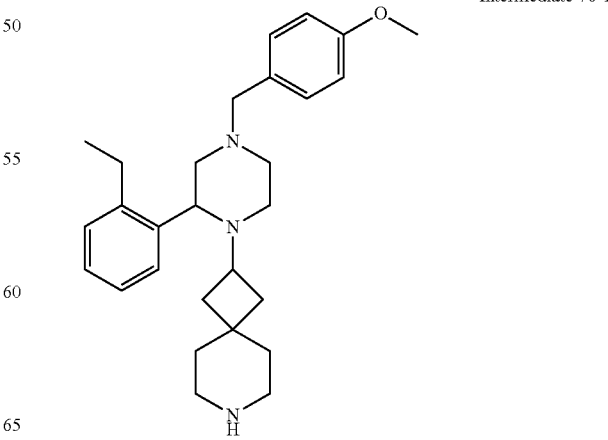

Intermediate 76-1

Step 1: 4-(4-methoxybenzyl)piperazin-2-one.

A solution of piperazin-2-one (25.0 g, 249.7 mmol), PMBCHO (37.4 g, 274.6 mmol) and HOAc (30.0 g, 499.4 mmol) in DCE (250 mL) was stirred at 20° C. for 0.5 hr, then NaBH(OAc)$_3$ (79.4 g, 374.5 mmol) was added in portions and stirred at 20° C. for 12 hrs. The mixture was poured into saturated NaHCO$_3$ to adjust the pH=8, extracted with DCM (100 mL×3). The combined organic phases were washed with brine, dried over Na$_2$SO$_4$, filtered and concentrated under reduced pressure. The residue was purified by column chromatography (silica gel, eluent: PE/EA (v/v)=10/1 to 0/1) to give 4-(4-methoxybenzyl)piperazin-2-one (44 g, yield: 80%) as a yellow solid. $^1$H NMR (400 MHz, CDCl$_3$) δ ppm: 7.22 (d, J=8.8 Hz, 2H), 6.87 (d, J=8.8 Hz, 2H), 6.37 (brs, 1H), 3.81 (s, 3H), 3.52 (s, 2H), 3.34 (t, J=4.0 Hz, 2H), 3.14 (s, 2H), 2.62 (t, J=5.6 Hz, 2H).

Step 2: tert-butyl 4-(4-methoxybenzyl)-2-oxopiperazine-1-carboxylate.

To a solution of 4-(4-methoxybenzyl)piperazin-2-one (44 g, 199.7 mmol) and DMAP (4.88 g, 39.9 mmol) in THF (500 mL) was added Boc$_2$0 (87.2 g, 399.5 mmol) was added in portions. The solution was stirred at 20° C. for 12 hrs. The mixture was poured into H$_2$O (100 mL), extracted with EtOAc (100 mL×3). The combined organic phases were washed with brine, dried over Na$_2$SO$_4$, filtered and concentrated under reduced pressure. The residue was purified by column chromatography (silica gel, eluent: PE/EA (v/v)=10/1 to 1/1) to give tert-butyl 4-(4-methoxybenzyl)-2-oxopiperazine-1-carboxylate (44 g, yield: 69%) as a yellow solid. $^1$H NMR (400 MHz, CDCl$_3$) δ ppm: 7.23-7.20 (m, 2H), 6.88-6.86 (m, 2H), 3.81 (s, 3H), 3.67-3.64 (m, 2H), 3.49 (s, 2H), 3.23 (s, 2H), 2.66 (t, J=5.2 Hz, 2H).

Step 3: tert-butyl (2-((2-(2-ethylphenyl)-2-oxoethyl)(4-methoxybenzyl)amino)ethyl)carbamate.

To a solution of 1-bromo-2-ethylbenzene (5.2 g, 28.09 mmol) in THF (100 mL) was added n-BuLi (9.7 mL, 2.5M) dropwise at −70° C. The solution was stirred at −70° C. for 0.5 hr. A solution of tert-butyl 4-(4-methoxybenzyl)-2-oxopiperazine-1-carboxylate (6.0 g, 18.73 mmol) in THF (20 mL) was added dropwise at −70° C. The solution was stirred at −70° C. for 2 hrs. The mixture was poured into saturated NH$_4$Cl (50 mL), extracted with EtOAc (50 mL×3). The combined organic phases were washed with brine, dried over Na$_2$SO$_4$, filtered and concentrated under reduced pressure. The residue was purified by column chromatography (silica gel, eluent: PE/EA (v/v)=20/1 to 5/1) to give tert-butyl (2-((2-(2-ethylphenyl)-2-oxoethyl)(4-methoxybenzyl) amino)ethyl)carbamate (6.5 g, yield: 81%) as a yellow oil. $^1$H NMR (400 MHz, CDCl$_3$) δ ppm: 7.40-7.21 (m, 6H), 6.88-6.85 (m, 2H), 5.19 (s, 1H), 3.82-3.74 (m, 7H), 3.25-3.23 (m, 2H), 2.79-2.73 (m, 3H), 1.47 (s, 9H), 1.29-1.19 (m, 5H).

Step 4: 3-(2-ethylphenyl)-1-(4-methoxybenzyl)piperazine

A solution of tert-butyl (2-((2-(2-ethylphenyl)-2-oxoethyl)(4-methoxybenzyl)amino)ethyl) carbamate (4.0 g, 9.38 mmol) and TFA (10 mL) in DCM (20 mL) was stirred at 20° C. for 3 hrs.

The solvent was removed by evaporation under reduced pressure. The residue was dissolved into MeOH (20 mL) and NaBH$_3$CN (2.95 g, 46.89 mmol) was added in portions. The solution was stirred at 20° C. for 12 hrs. The mixture was poured into aqueous NaHCO$_3$ to adjust the pH=8, extracted the solution with DCM (50 mL×3). The combined organic phases were washed with brine, dried over Na$_2$SO$_4$, filtered and concentrated under reduced pressure. The residue was purified by column chromatography (silica gel, eluent: PE/EA (v/v)=2/1 to EA/MeOH (v/v)=10/1) to give 3-(2-ethylphenyl)-1-(4-methoxybenzyl)piperazine (2.2 g, yield: 75%) as a yellow oil. $^1$H NMR (400 MHz, CDCl$_3$) δ ppm: 7.51 (d, J=7.2 Hz, 1H), 7.25-7.16 (m, 5H), 6.87 (d, J=8.8 Hz, 2H), 4.34 (d, J=8.8 Hz, 1H), 3.80 (s, 3H), 3.64 (s, 1H), 3.18-2.96 (m, 4H), 2.70-2.66 (m, 2H), 2.48-2.38 (m, 2H), 1.17-1.13 (m, 3H). MS (ESI, m/e) [M+1]+311.3.

Step 5: tert-butyl 2-(2-(2-ethylphenyl)-4-(4-methoxybenzyl)piperazin-1-yl)-7-azaspiro[3.5]nonane-7-carboxylate.

To a solution of 3-(2-ethylphenyl)-1-(4-methoxybenzyl) piperazine (2.2 g, 7.09 mmol), tert-butyl 2-oxo-7-azaspiro [3.5]nonane-7-carboxylate (1.87 g, 7.80 mmol) and NaBH$_3$CN (890.7 mg, 14.17 mmol) in MeOH (20 mL) and AcOH (2 mL) was stirred at 65° C. for 12 hrs. The mixture was poured into aqueous NaHCO$_3$ (20 mL) to adjust the pH=8, extract with EtOAc (30 mL×3). The combined organic phases were washed with brine, dried over Na$_2$SO$_4$, filtered and concentrated under reduced pressure. The residue was purified by column chromatography (silica gel, eluent: PE/EA (v/v)=10/1 to 0/1) to give tert-butyl 2-(2-(2-ethylphenyl)-4-(4-methoxybenzyl)piperazin-1-yl)-7-azaspiro[3.5]nonane-7-carboxylate (1.2 g, yield: 31%) as a yellow oil. MS (ESI, m/e) [M+1]$^+$534.5.

Step 6: 2-(2-(2-ethylphenyl)-4-(4-methoxybenzyl)piperazin-1-yl)-7-azaspiro[3.5]nonane.

To a solution of tert-butyl 2-(2-(2-ethylphenyl)-4-(4-methoxybenzyl)piperazin-1-yl)-7-azaspiro[3.5]nonane-7-carboxylate (1.2 g, 2.25 mmol) in DCM (10 mL) was added TFA (5 mL).

The solution was stirred at 20° C. for 2 hrs. The mixture was concentrated under reduced pressure.

The residue was poured into aqueous HCl (20 mL, 1M), extract with EtOAc (10 mL×2). The combined organic phases were discarded. The aqueous layer was adjusted the pH=8 with NaHCO$_3$ solution, extract with EtOAc (20 mL×3). The combined organic phases were washed with brine, dried over Na$_2$SO$_4$, filtered and concentrated under reduced pressure to give 2-(2-(2-ethylphenyl)-4-(4-methoxybenzyl)piperazin-1-yl)-7-azaspiro[3.5]nonane (413 mg, yield: 43%) as a yellow solid. $^1$H NMR (400 MHz, CDCl$_3$) δ ppm: 7.47 (d, J=4.0 Hz, 1H), 7.22-7.11 (m, 5H), 6.84-6.80 (m, 2H), 3.78 (s, 3H), 3.52-3.45 (m, 3H), 2.99-2.61 (m, 10H), 2.27-2.10 (m, 3H), 1.75-1.60 (m, 2H), 1.35-1.18 (m, 6H), 1.16-1.10 (m, 4H). MS (ESI, m/e) [M+1]$^+$434.4.

Intermediate 77-1: 2-(2-(2-isopropylphenyl)-4-(4-(4-methoxyphenyl)cyclohexyl)piperazin-1-yl)-7-azaspiro[3.5]nonane

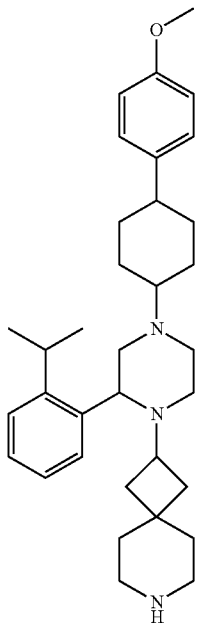

Intermediate 77-1

Step 1: 4-(4-methoxyphenyl)cyclohexan-1-one.

To a solution of 4-(4-hydroxyphenyl)cyclohexan-1-one (1.0 g, 5.26 mmol) in DMF (10 mL) was added $K_2CO_3$ (2.54 g, 18.40 mmol) and iodomethane (7.64 g, 52.57 mmol). The mixture was stirred at 80° C. for 12 hrs. The reaction mixture was poured into $H_2O$ (50 mL), extracted with EtOAc (100 mL×2). The combined organic layers were washed with brine, dried with anhydrous $Na_2SO_4$, filtered and concentrated under reduced pressure. The crude product was purified by column chromatography (silica gel, eluent: PE/EA (v/v)=5/1 to 2/1) to give 4-(4-methoxyphenyl)cyclohexan-1-one (1.05 g, yield: 98%) as a white solid.

Step 2: tert-butyl 2-(2-(2-isopropylphenyl)-4-(4-(4-methoxyphenyl)cyclohexyl)-6-oxopiperazin-1-yl)-7-azaspiro[3.5]nonane-7-carboxylate A solution of tert-butyl 2-(2-(2-isopropylphenyl)-6-oxopiperazin-1-yl)-7-azaspiro[3.5]nonane-7-carboxylate (1.0 g, 2.34 mmol), 4-(4-methoxyphenyl)cyclohexanone (525.44 mg, 2.57 mmol) in DCE (10 mL) and AcOH (280.86 mg, 4.68 mmol) was stirred at 25° C. for 1 hr, then NaBH(OAc)$_3$ (1.49 g, 7.02 mmol) was added and stirred at 25° C. for another 11 hrs.

The mixture was poured into saturated NaHCO$_3$ (50 mL), extracted with EtOAc (100 mL×2).

The combined organic layers were washed with brine, dried with anhydrous Na$_2$SO$_4$, filtered and concentrated under reduced pressure. The residue was purified by column chromatography (silica gel, eluent: PE/EA (v/v)=5/1 to 2/1) to give tert-butyl 2-(2-(2-isopropylphenyl)-4-(4-(4-methoxyphenyl)cyclohexyl)-6-oxopiperazin-1-yl)-7-azaspiro[3.5]nonane-7-carboxylate (1.24 g, yield: 87%) as a white solid.

Step 3: tert-butyl 2-(2-(2-isopropylphenyl)-4-(4-(4-methoxyphenyl)cyclohexyl)piperazin-1-yl)-7-azaspiro[3.5]nonane-7-carboxylate A mixture of tert-butyl 2-(2-(2-isopropylphenyl)-4-(4-(4-methoxyphenyl)cyclohexyl)-6-oxopiperazin-1-yl)-7-azaspiro[3.5]nonane-7-carboxylate (1.24 g, 1.97 mmol) and BH$_3$·THF (19.69 mL, 19.69 mmol) in THF (20 mL) was stirred at 70° C. for 12 hrs. The reaction solution was quenched by MeOH (20 mL) and stirred at 0° C. for 1 hr. The mixture was concentrated under reduced pressure to give tert-butyl 2-(2-(2-isopropylphenyl)-4-(4-(4-methoxyphenyl)cyclohexyl)piperazin-1-yl)-7-azaspiro[3.5]nonane-7-carboxylate (1.28 g, crude) as a white soil, which was used directly for next step without further purification.

Step 4: 2-(2-(2-isopropylphenyl)-4-(4-(4-methoxyphenyl)cyclohexyl)piperazin-1-yl)-7-azaspiro[3.5]nonane.

A mixture of tert-butyl 2-(2-(2-isopropylphenyl)-4-(4-(4-methoxyphenyl)cyclohexyl)piperazin-1-yl)-7-azaspiro[3.5]nonane-7-carboxylate (1.28 mg, 2.08 mmol) and HCl (5.21 mL, 20.78 mmol) in MeOH (10 mL) was stirred at 25° C. for 2 hrs. The reaction solution was concentrated under reduced pressure. The reaction mixture was poured into saturated NaHCO$_3$ (10 mL), extracted with EtOAc (20 mL×2). The combined organic layers were washed with brine, dried with anhydrous Na$_2$SO$_4$, filtered and concentrated under reduced pressure to give 2-(2-(2-isopropylphenyl)-4-(4-(4-methoxyphenyl)cyclohexyl)piperazin-1-yl)-7-azaspiro[3.5]nonane (885 mg, yield: 82%) as a white solid. $^1$H NMR (400 MHz, CDCl$_3$) δ ppm: 7.51 (br s, 1H), 7.26-7.08 (m, 5H), 6.89-6.80 (m, 2H), 3.83-3.77 (m, 3H), 3.68-3.56 (m, 1H), 3.42 (br s, 1H), 3.13-2.99 (m, 2H), 2.95-2.74 (m, 2H), 2.68-2.57 (m, 4H), 2.31-2.16 (m, 3H), 2.12-1.98 (m, 2H), 1.96-1.88 (m, 2H), 1.86-1.67 (m, 5H), 1.63-1.50 (m, 3H), 1.46-1.32 (m, 5H), 1.30-1.25 (m, 4H), 1.24-1.14 (m, 4H). MS (ESI, m/e) [M+1]$^+$516.3.

Intermediate 78-1: 2-(4-((2,3-dihydrobenzo[b][1,4]dioxin-6-yl)methyl)-2-(2-isopropylphenyl)piperazin-1-yl)-7-azaspiro(3.5]nonane

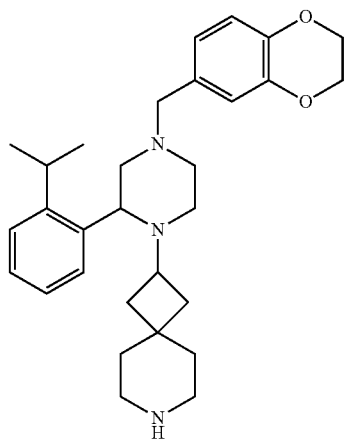

Intermediate 78-1

Step 1: tert-butyl 2-(4-((2,3-dihydrobenzo[b][1,4]dioxin-6-yl)methyl)-2-(2-isopropylphenyl)-6-oxopiperazin-1-yl)-7-azaspiro[3.5]nonane-7-carboxylate.

A solution of tert-butyl 2-(2-(2-isopropylphenyl)-6-oxopiperazin-1-yl)-7-azaspiro[3.5]nonane-7-carboxylate (1.0 g, 2.26 mmol), 2,3-dihydrobenzo[b][1,4]dioxine-6-carbaldehyde (333 mg, 3.40 mmol) and AcOH (339 mg, 5.66 mmol) in DCE (20 mL) was stirred 25° C. for 1 hr, then NaBH(OAc)$_3$ (959 mg, 4.53 mmol) was added and stirred at 25° C. for 11 hrs.

The reaction mixture was quenched by saturated Na$_2$CO$_3$ (20 mL), extracted with EtOAc (50 mL×3). The combined organic layers were washed with brine, dried with anhydrous Na$_2$SO$_4$, filtered and concentrated under reduced pressure. The residue was purified by column chromatography (silica gel, eluent: PE/EA (v/v)=50/1 to 0/1) to give tert-butyl 2-(4-((2,3-dihydrobenzo[b][1,4]dioxin-6-yl)methyl)-2-(2-isopropylphenyl)-6-oxopiperazin-1-yl)-7-azaspiro[3.5]nonane-7-carboxylate (1.0 g, yield: 74%) as a yellow oil.

Step 2: tert-butyl 2-(4-((2,3-dihydrobenzo[b][1,4]dioxin-6-yl)methyl)-2-(2-isopropylphenyl)piperazin-1-yl)-7-azaspiro[3.5]nonane-7-carboxylate.

A mixture of tert-butyl 2-(4-((2,3-dihydrobenzo[b][1,4]dioxin-6-yl)methyl)-2-(2-isopropylphenyl)-6-oxopiperazin-1-yl)-7-azaspiro[3.5]nonane-7-carboxylate (1.0 g, 1.70 mmol) and BH$_3$·THF (50 mL, 50.87 mmol) in THF (20 mL) was stirred at 70° C. for 12 hrs. After cooling to 0° C., the reaction solution quenched with MeOH (20 mL) and stirred at 0° C. for 1 hr. The mixture was concentrated under reduced pressure to give tert-butyl 2-(4-((2,3-dihydrobenzo[b][1,4]dioxin-6-yl)methyl)-2-(2-isopropylphenyl)piperazin-1-yl)-7-azaspiro[3.5]nonane-7-carboxylate (1.3 g, crude) as a white solid, which was used directly for next step without further purification. MS (ESI, m/e) [M+1]$^+$576.5.

Step 3: 2-(4-((2,3-dihydrobenzo[b][1,4]dioxin-6-yl)methyl)-2-(2-isopropylphenyl)piperazin-1-yl)-7-azaspiro[3.5]nonane.

To a mixture of tert-butyl 2-(4-((2,3-dihydrobenzo[b][1,4]dioxin-6-yl)methyl)-2-(2-isopropylphenyl)piperazin-1-yl)-7-azaspiro[3.5]nonane-7-carboxylate (1.0 g, 2.25 mmol) was added HCl/MeOH solution (20 ml) at 20° C. for 3 hrs. The reaction mixture poured into sat. Na$_2$CO$_3$ (40 ml). The mixture was extracted with EtOAc (40 mL×3). The combined organic phases were washed with brine (40 mL×2), dried with anhydrous Na$_2$SO$_4$, filtered and concentrated under reduced pressure to give 2-(4-((2,3-dihydrobenzo[b][1,4]dioxin-6-yl)methyl)-2-(2-isopropylphenyl)piperazin-1-yl)-7-azaspiro[3.5]nonane (430 mg, 0.904 mmol, 40% yield) as a pale pink oil. $^1$H NMR (400 MHz, CDCl$_3$) δ ppm: 7.48 (br s, 1H), 7.25-7.18 (m, 2H), 7.15-7.09 (m, 1H), 6.83 (s, 1H), 6.77 (s, 2H), 4.23 (s, 4H), 3.64 (m, 1H), 3.52-3.33 (m, 2H), 3.03-2.84 (m, 3H), 2.71-2.54 (m, 5H), 2.28 (d, J=7.6 Hz, 2H), 2.19-2.13 (m, 1H), 1.78-1.71 (m, 1H), 1.69-1.63 (m, 1H), 1.39-1.23 (m, 8H), 1.15 (d, J=6.8 Hz, 4H). MS (ESI, m/e) [M+1]$^+$476.4.

Intermediate 79-1: 2-(4-((2,3-dihydrobenzo[b][1,4]dioxin-5-yl)methyl)-2-(2-isopropylphenyl)piperazin-1-yl)-7-azaspiro[3.5]nonane

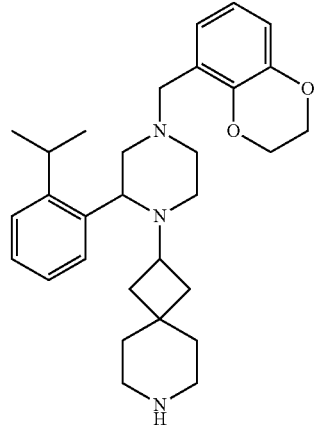

Intermediate 79-1

Step 1: tert-butyl 2-(4-(2,3-dihydrobenzo[b][1,4]dioxine-5-carbonyl)-2-(2-isopropylphenyl)-6-oxopiperazin-1-yl)-7-azaspiro[3.5]nonane-7-carboxylate.

To a solution of tert-butyl 2-(2-(2-isopropylphenyl)-6-oxopiperazin-1-yl)-7-azaspiro[3.5]nonane-7-carboxylate (1.0 g, 2.26 mmol) in DMF (10 mL) was added DIEA (386.69 mg, 2.49 mmol) and 2,3-dihydrobenzo[b][1,4]dioxine-5-carboxylic acid (407.96 mg, 2.26 mmol) at 25° C., then HATU (336.58 mg, 2.49 mmol) was added, stirred at 25° C. for another 12 hrs. The reaction mixture was poured into saturated NaHCO$_3$ (50 mL), extracted with EtOAc (100 mL×2). The combined organic layers were washed with brine, dried with anhydrous Na$_2$SO$_4$, filtered and concentrated under reduced pressure. The residue was purified by column chromatography (silica gel, eluent: PE/EA (v/v)=5/1 to 2/1) to give tert-butyl 2-(4-(2,3-dihydrobenzo[b][1,4]dioxine-5-carbonyl)-2-(2-isopropylphenyl)-6-oxopiperazin-1-yl)-7-azaspiro[3.5]nonane-7-carboxylate (1.1 g, yield: 80%) as a yellow oil.

Step 2: tert-butyl 2-(4-((2,3-dihydrobenzo[b][1,4]dioxin-5-yl)methyl)-2-(2-isopropylphenyl)piperazin-1-yl)-7-azaspiro[3.5]nonane-7-carboxylate.

A mixture of tert-butyl 2-(4-(2,3-dihydrobenzo[b][1,4]dioxine-5-carbonyl)-2-(2-isopropylphenyl)-6-oxopiperazin-1-yl)-7-azaspiro[3.5]nonane-7-carboxylate (1.1 g, 1.82 mmol) and BH$_3$·THF (18.22 mL, 18.22 mmol) in THF (20 mL) was stirred at 70° C. for 12 hrs. The reaction solution was quenched with MeOH (20 mL) and stirred at 0° C. for 1 hr. The mixture was concentrated under reduced pressure to give tert-butyl 2-(4-((2,3-dihydrobenzo[b][1,4]dioxin-5-yl)methyl)-2-(2-isopropylphenyl)piperazin-1-yl)-7-azaspiro[3.5]nonane-7-carboxylate (800 mg, crude) as a yellow oil, which was used directly for next step without further purification. MS (ESI, m/e) [M+1]$^+$576.4.

Step 3: 2-(4-((2,3-dihydrobenzo[b][1,4]dioxin-5-yl)methyl)-2-(2-isopropylphenyl)piperazin-1-yl)-7-azaspiro[3.5]nonane.

A mixture of tert-butyl 2-(4-((2,3-dihydrobenzo[b][1,4]dioxin-5-yl)methyl)-2-(2-isopropylphenyl)piperazin-1-yl)-7-azaspiro[3.5]nonane-7-carboxylate (800 mg, 1.39 mmol) and HCl (3.47 mL, 3.47 mmol) in MeOH (10 mL) was stirred at 25° C. for 2 hrs. The reaction solution was concentrated under reduced pressure. The reaction mixture was poured into saturated NaHCO$_3$ (10 mL), extracted with EtOAc (20 mL×2). The combined organic layers were washed with brine, dried with anhydrous Na$_2$SO$_4$, filtered and concentrated under reduced pressure to give 2-(4-((2,3-dihydrobenzo[b][1,4]dioxin-5-yl)methyl)-2-(2-isopropylphenyl)piperazin-1-yl)-7-azaspiro[3.5]nonane (213 mg, yield: 33%) as a yellow solid. $^1$H NMR (400 MHz, CDCl$_3$) δ ppm: 7.47 (br s, 1H), 7.25-7.17 (m, 2H), 7.15-7.08 (m, 1H), 6.91 (d, J=4.8 Hz, 1H), 6.80-6.72 (m, 2H), 4.23 (s, 4H), 3.67 (br s, 1H), 3.62-3.51 (m, 2H), 3.41 (br s, 1H), 3.03-2.83 (m, 3H), 2.72 (m, 4H), 2.43-2.24 (m, 3H), 1.76 (br s, 1H), 1.72-1.64 (m, 1H), 1.39 (br s, 4H), 1.25 (d, J=6.8 Hz, 5H), 1.17 (d, J=6.8 Hz, 4H), 0.89 (hr s, 1H). MS (ESI, m/e) [M+1]$^+$476.5.

Intermediate 79-1a: (R)-2-(4-((2,3-dihydrobenzo[b][1,4]dioxin-5-yl)methyl)-2-(2-isopropylphenyl)piperazin-1-yl)-7-azaspiro[3.5]nonane; and Intermediate 79-1b: (S)-2-(4-((2,3-dihydrobenzo[b][1,4]dioxin-5-yl)methyl)-2-(2-isopropylphenyl)piperazin-1-yl)-7-azaspiro[3.5]nonane

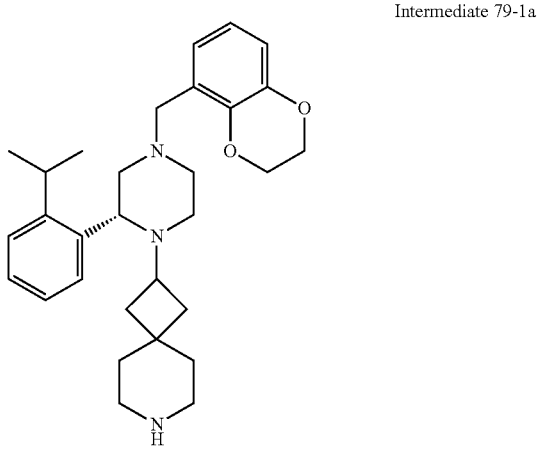 [SMILES: CC(C)c1ccccc1C1CN(Cc2cccc3c2OCCO3)CCN1C1CC2(CCNCC2)C1]

Intermediate 79-1a

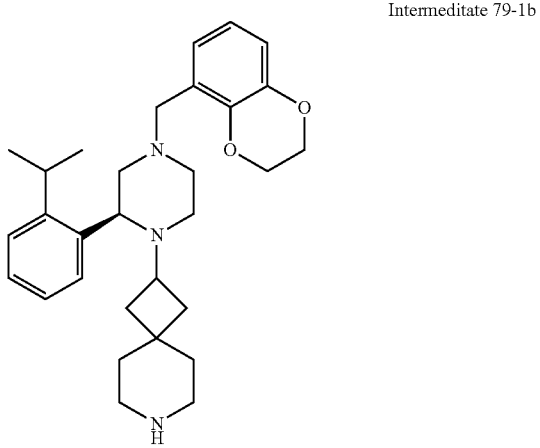

Intermeditate 79-1b

The compound 2-(4-((2,3-dihydrobenzo[b][1,4]dioxin-5-yl)methyl)-2-(2-isopropylphenyl)piperazin-1-yl)-7-azaspiro[3.5]nonane (1.3 g, 2.73 mmol) was separated by SFC (Instrument: Thar SFC80 preparative SFC; Column: DAICEL Chiralpak IE 250×30 mm i.d. 10u; Mobile phase: A for CO$_2$ and B for EtOH (0.1% NH$_3$H$_2$O); Gradient: B%=54% isocratic elution mode; Flow rate: 80 g/min; Wavelength: 220 nm; Column temperature: 40° C.; System back pressure: 100 bar).

Intermediate 79-1a: The compound (R)-2-(4-((2,3-dihydrobenzo[b][1,4]dioxin-5-yl)methyl)-2-(2-isopropylphenyl)piperazin-1-yl)-7-azaspiro[3.5]nonane (381 mg, 800.98 umol, yield: 29%, purity: 92.6%) was obtained as a yellow solid (retention time: 2.31 min). $^1$H NMR (400 MHz, CDCl$_3$) δ ppm: 7.54-7.43 (m, 1H), 7.25-7.19 (m, 2H), 7.14-7.09 (m, 1H), 6.92-6.90 (m, 1H), 6.80-6.71 (m, 2H), 4.23 (s, 4H), 3.71-3.64 (m, 1H), 3.63-3.52 (m, 2H), 3.47-3.37 (m, 1H), 3.07-2.81 (m, 4H), 2.71 (br s, 1H), 2.68-2.55 (m, 4H), 2.43-2.22 (m, 3H), 2.22-2.04 (m, 1H), 1.80-1.73 (m, 1H), 1.69-1.63 (m, 1H), 1.43-1.29 (m, 5H), 1.27-1.25 (d, J=6.8 Hz, 3H), 1.17 (d, J=6.8 Hz, 3H). MS (ESI, m/e) [M+1]$^+$476.5.

Intermediate 79-1b: The compound (S)-2-(4-((2,3-dihydrobenzo[b][1,4]dioxin-5-yl)methyl)-2-(2-isopropylphenyl)piperazin-1-yl)-7-azaspiro[3.5]nonane (272 mg, 571.83 umol, yield: 21%, purity: 96.6%) was obtained as a yellow solid (retention time: 3.13 min). $^1$H NMR (400 MHz, CDCl$_3$) δ ppm: 7.52-7.42 (m, 1H), 7.26-7.18 (m, 2H), 7.15-7.08 (m, 1H), 6.91-6.90 (m, 1H), 6.80-6.72 (m, 2H), 4.23 (s, 4H), 3.71-3.64 (m, 1H), 3.63-3.51 (m, 2H), 3.47-3.35 (m, 1H), 3.06-2.85 (m, 3H), 2.72 (m, 1H), 2.66-2.56 (m, 3H), 2.47-2.19 (m, 3H), 1.89-1.60 (m, 4H), 1.46-1.27 (m, 5H), 1.26 (d, J=6.8 Hz, 3H), 1.17 (d, J=6.8 Hz, 3H). MS (ESI, m/e) [M+1]$^+$476.5.

Intermediate 80-1: 2-((2(R or S)-2-(2-isopropylphenyl)-4-(3-(4-methoxyphenyl)cyclopentyl)piperazin-1-yl)-7-azaspiro[3.5]nonane

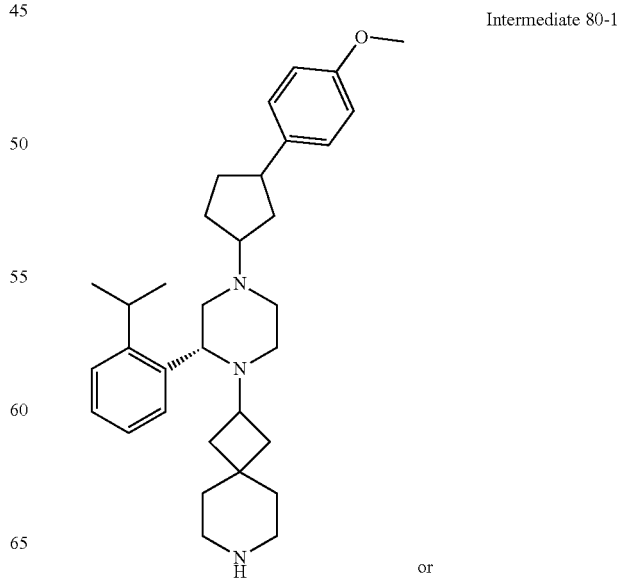

Intermediate 80-1 or

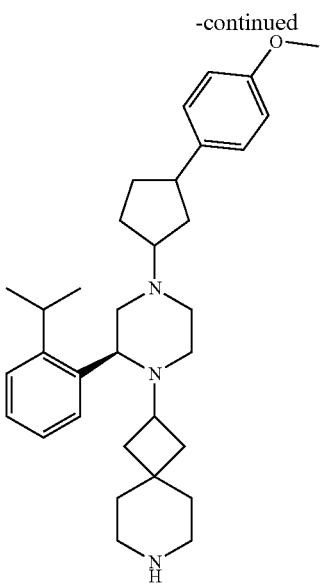

Step 1: 3-(4-methoxyphenyl)cyclopentan-1-one

To a solution of cyclopent-2-en-1-one (1.0 g, 12.18 mmol) in toluene (50 mL) and CHCl₃ (0.25 ml) was added Cs₂CO₃ (7.94 g, 24.36 mmol), (4-methoxyphenyl)boronic acid (2.22 g, 14.62 mmol), PPh₃ (638.94 mg, 2.44 mmol) and Pd(OAc)₂ (638.94 mg, 2.44 mmol) was added under N₂. The mixture was stirred at 80° C. for 24 hrs. The reaction mixture was poured into H₂O (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=10/1 to 5/1) to give 3-(4-methoxyphenyl)cyclopentan-1-one (1.5 g, yield: 65%) as a yellow oil.

Step 2: tert-butyl 2-(2 (R or S)-2-(2-isopropylphenyl)-4-(3-(4-methoxyphenyl)cyclopentyl)-6-oxopiperazin-1-yl)-7-azaspiro[3.5]nonane-7-carboxylate.

To a solution of tert-butyl (R or S)-2-(2-(2-isopropylphenyl)-6-oxopiperazin-1-yl)-7-azaspiro[3.5]nonane-7-carboxylate (1.0 g, 2.26 mmol) in DCE (10 mL) was added AcOH (271.97 mg, 4.68 mmol) and 3-(4-methoxyphenyl)cyclopentanone (473.84 mg, 2.49 mmol). The mixture was stirred at 25° C. for 1 hr, then NaBH(OAc)₃ (1.44 g, 6.79 mmol) was added and stirred at 25° C. for another 11 hrs. The reaction mixture was poured into saturated NaHCO₃ (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give tert-butyl 2-(2 (R or S)-2-(2-isopropylphenyl)-4-(3-(4-methoxyphenyl)cyclopentyl)-6-oxopiperazin-1-yl)-7-azaspiro[3.5]nonane-7-carboxylate (1.2 g, yield: 86%) as a yellow solid.

Step 3: tert-butyl 2-(2(R or S)-2-(2-isopropylphenyl)-4-(3-(4-methoxyphenyl)cyclopentyl)piperazin-1-yl)-7-azaspiro[3.5]nonane-7-carboxylate.

A mixture of tert-butyl 2-((2R or 2S)-2-(2-isopropylphenyl)-4-(3-(4-methoxyphenyl)cyclopentyl)-6-oxopiperazin-1-yl)-7-azaspiro[3.5]nonane-7-carboxylate (1.2 g, 1.95 mmol) and BH₃·THF (19.49 mL, 19.49 mmol) in THF (20 mL) was stirred at 70° C. for 12 hrs. The reaction solution was quenched by MeOH (20 mL) and stirred at 0° C. for 1 hr. The mixture was concentrated under reduced pressure to give tert-butyl 2-(2 (R or S)-2-(2-isopropylphenyl)-4-(3-(4-methoxyphenyl)cyclopentyl)piperazin-1-yl)-7-azaspiro[3.5]nonane-7-carboxylate (1.2 g, crude) as a white oil, which was used directly for next step without further purification.

Step 4: 2-(2 (R or S)-2-(2-isopropylphenyl)-4-(3-(4-methoxyphenyl)cyclopentyl)piperazin-1-yl)-7-azaspiro[3.5]nonane.

A mixture of tert-butyl 2-((2R or 2S)-2-(2-isopropylphenyl)-4-(3-(4-methoxyphenyl)cyclopentyl)piperazin-1-yl)-7-azaspiro[3.5]nonane-7-carboxylate (1.2 g, 1.99 mmol) and HCl(4.98 mL, 19.94 mmol) in MeOH (10 mL) was stirred at 25° C. for 2 hrs. The reaction solution was concentrated under reduced pressure. The reaction mixture was poured into saturated NaHCO₃ (50 mL), extracted with EtOAc (50 mL×2). The combined organic layers were washed with brine, dried with anhydrous Na₂SO₄, filtered and concentrated under reduced pressure to give 2-(2 (R or S)-2-(2-isopropylphenyl)-4-(3-(4-methoxyphenyl)cyclopentyl)piperazin-1-yl)-7-azaspiro[3.5]nonane. (565 mg, yield: 56%) as a yellow solid. ¹H NMR (400 MHz, CDCl₃) δ ppm: 7.44 (br s, 1H), 7.28-7.22 (m, 1H), 7.21-7.08 (m, 4H), 6.85-6.77 (m, 2H), 3.74-3.68 (m, 3H), 3.50 (br s, 1H), 3.09-2.69 (m, 5H), 2.68-2.55 (m, 3H), 2.15 (m, 2H), 1.84-2.04 (m, 4H), 1.71-1.34 (m, 6H), 1.30-1.20 (m, 8H), 1.19-1.03 (m, 5H), 0.87-0.81 (m, 2H). MS (ESI, m/e) [M+1]⁺502.5.

Intermediate 81-1: 2-(4-(3,4-dimethoxybenzyl)-2-(2-isopropylphenyl)piperazin-1-yl)-7-azaspiro[3.5]nonane

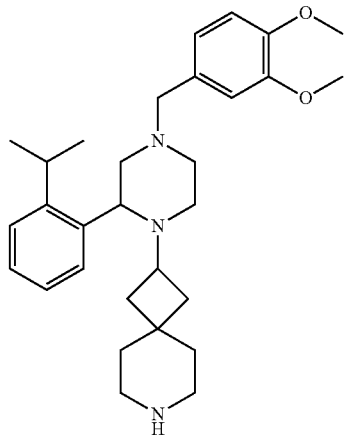

Intermediate 81-1

The synthesis procedures were similar to Intermediate 4-1. The compound 2-(4-(3,4-dimethoxybenzyl)-2-(2-isopropylphenyl)piperazin-1-yl)-7-azaspiro[3.5]nonane was a white solid.

¹H NMR (400 MHz, CDCl₃) δ ppm: 7.49 (m, 1H), 7.21 (m, 2H), 7.15-7.07 (m, 1H), 6.89 (s, 1H), 6.82-6.73 (m, 2H), 3.89-3.87 (m, 3H), 3.85 (s, 3H), 3.68-3.60 (m, 1H), 3.46 (m, 2H), 3.42-3.30 (m, 1H), 3.01 (m, 1H), 2.95-2.86 (m, 2H), 2.70-2.52 (m, 5H), 2.29 (m, 2H), 2.15 (m, 1H), 1.81-1.72 (m, 1H), 1.70-1.63 (m, 1H), 1.38-1.27 (m, 5H), 1.25 (m, 3H), 1.14 (m, 4H). MS (ESI, m/e) [M+1]⁺478.5.

Intermediate 82-1: 2-(2-(2-isopropylphenyl)-4-(4-(methylsulfonyl)benzyl)piperazin-1-yl)-7-azaspiro[3.5]nonane

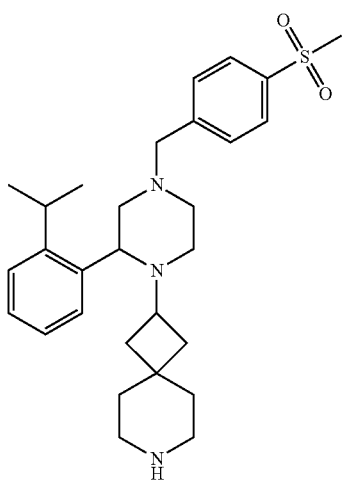

Intermediate 82-1

The synthesis procedures were similar to Intermediate 4-1. The compound 2-(2-(2-isopropylphenyl)-4-(4-(methylsulfonyl)benzyl)piperazin-1-yl)-7-azaspiro[3.5]nonane was a yellow solid. $^1$H NMR (400 MHz, CDCl$_3$) δ ppm: 7.87 (d, J=8.4 Hz, 2H), 7.58-7.45 (m, 3H), 7.25-7.19 (m, 2H), 7.16-7.10 (m, 1H), 3.69-3.55 (m, 3H), 3.37 (br s, 1H), 3.03 (s, 4H), 2.95-2.84 (m, 2H), 2.70-2.54 (m, 5H), 2.41-2.29 (m, 2H), 2.28-2.18 (m, 1H), 1.77 (br s, 1H), 1.71-1.62 (m, 11H), 1.45-1.29 (m, 5H), 1.29-1.24 (m, 4H), 1.13 (d, J=6.8 Hz, 4H). MS (ESI, m/e) [M+1]$^+$496.3.

Intermediate 83-1: 6-(2-(2-isopropylphenyl)-4-(4-methoxybenzyl)piperazin-1-yl)-2-azaspiro[3.3]heptane

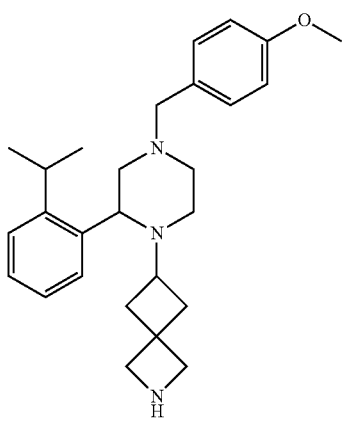

Intermediate 83-1

The synthesis procedures were similar to Intermediate 12-1. The compound 6-(2-(2-isopropylphenyl)-4-(4-methoxybenzyl)piperazin-1-yl)-2-azaspiro[3.3]heptane was a yellow solid. $^1$H NMR (400 MHz, CDCl$_3$) δ ppm: 7.46 (br s, 1H), 7.25-7.18 (m, 4H), 7.14-7.08 (m, 1H), 6.82 (m, 2H), 3.78 (s, 3H), 3.62 (m, 1H), 3.55-3.49 (m, 1H), 3.48-3.30 (m, 5H), 2.90 (m, 2H), 2.70-2.61 (m, 2H), 2.29-2.21 (m, 2H), 2.17-2.06 (m, 2H), 2.02-1.94 (m, 1H), 1.59 (m, 1H), 1.38 (m, 1H), 1.24 (br d, J=6.8 Hz, 3H), 1.13 (br d, J=6.8 Hz, 3H), 0.89-0.84 (m, 1H). MS (ESI, m/e) [M+1]$^+$420.5.

Intermediate 96-1: 2-(4-(benzofuran-5-ylmethyl)-2-(2-isopropylphenyl)piperazin-1-yl)-7-azaspiro[3.5]nonane

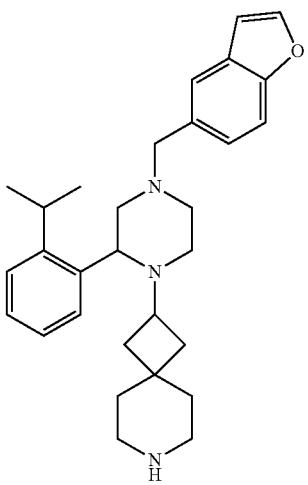

Intermediate 96-1

The synthesis procedures were similar to Intermediate 4-1. The compound 2-(4-(benzofuran-5-ylmethyl)-2-(2-isopropylphenyl)piperazin-1-yl)-7-azaspiro[3.5]nonane was a white solid. $^1$H NMR (400 MHz, CDCl$_3$) δ ppm: 7.60 (d, J=2.0 Hz, 1H), 7.55-7.46 (m, 2H), 7.42 (d, J=8.4 Hz, 1H), 7.26-7.18 (m, 3H), 7.16-7.08 (m, 1H), 6.71 (d, J=2.0 Hz, 1H), 4.17-4.07 (m, 1H), 3.75-3.63 (m, 1H), 3.63-3.54 (m, 2H), 3.47-3.31 (m, 1H), 3.04-2.87 (m, 3H), 2.75-2.50 (m, 5H), 2.37-2.11 (m, 4H), 2.05 (s, 2H), 1.79-1.64 (m, 2H), 1.31-1.22 (m, 9H), 1.12 (br d, J=6.8 Hz, 3H). MS (ESI, m/e) [M+1]$^+$458.5.

Intermediate 97-1: 2-(2-(2-isopropylphenyl)-4-(pyridin-3-ylmethyl)piperazin-1-yl)-7-azaspiro[3.5]nonane

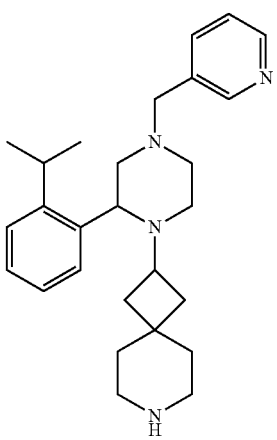

Intermediate 97-1

The synthesis procedures were similar to Intermediate 4-1. The compound 2-(2-(2-isopropylphenyl)-4-(pyridin-3-ylmethyl)piperazin-1-yl)-7-azaspiro[3.5]nonane was a yellow solid. ¹H NMR (400 MHz, CDCl₃) δ ppm: 8.60-8.45 (m, 2H), 7.69-7.61 (m, 1H), 7.54-7.43 (m, 1H), 7.25-7.19 (m, 3H), 7.15-7.10 (m, 1H), 3.67-3.60 (m, 1H), 3.52 (s, 2H), 3.37 (m, 1H), 3.03-2.98 (m, 1H), 2.93-2.86 (m, 2H), 2.66-2.56 (m, 5H), 2.38-2.17 (m, 4), 1.78-1.73 (m, 1H), 1.72-1.60 (m, 2H), 1.37-1.28 (m, 5H), 1.25 (d, J=6.8 Hz, 3H), 1.13 (d, J=6.8 Hz, 3H). MS (ESI, m/e) [M+1]⁺419.5.

Intermediate 98-1: 6-(2-(2-isopropylphenyl)-4-(4-methoxyphenethyl)piperazin-1-yl)-2-azaspiro[3.3]heptane

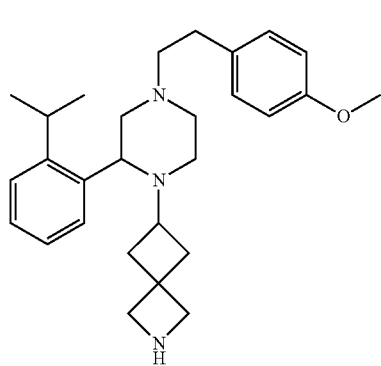

Intermediate 98-1

The synthesis procedures were similar to Intermediate 4-1. The compound 6-(2-(2-isopropylphenyl)-4-(4-methoxyphenethyl)piperazin-1-yl)-2-azaspiro[3.3]heptane was a yellow solid. ¹H NMR (400 MHz, CDCl₃) δ ppm: 7.52 (br d, J=5.6 Hz, 1H), 7.20-7.27 (m, 2H), 7.12-7.17 (m, 1H), 7.06-7.11 (m, 2H), 6.82 (d, J=8.8 Hz, 2H), 3.78 (s, 3H), 3.67 (m, 1H), 3.31-3.54 (m, 4H), 2.95-3.07 (m, 3H), 2.70-2.80 (m, 4H), 2.52-2.61 (m, 2H), 2.31 (m, 2H), 2.14-2.25 (m, 2H), 2.07-2.15 (m, 1H), 2.02 (m, 1H), 1.59-1.73 (m, 1H), 1.34-1.46 (m, 1H), 1.25-1.28 (d, J=6.8 Hz, 3H), 1.22 (d, J=6.8 Hz, 3H). MS (ESI, m/e) [M+1]⁺434.5.

Intermediate 99-1: 2-(2-(2-isopropylphenyl)-4-(4-methoxybenzyl)-5-methylpiperazin-1-yl)-7-azaspiro[3.5]nonane

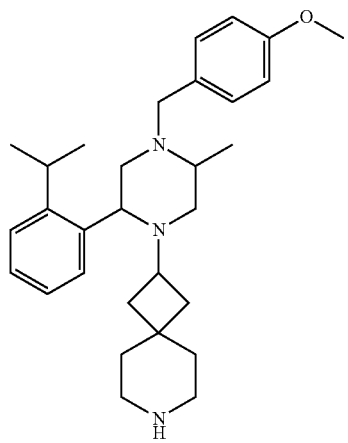

Intermediate 99-1

The synthesis procedures were similar to Intermediate 12-1. The compound 2-(2-(2-isopropylphenyl)-4-(4-methoxybenzyl)-5-methylpiperazin-1-yl)-7-azaspiro[3.5]nonane was a yellow solid. ¹H NMR (400 MHz, CDCl₃) δ ppm: 7.62-7.50 (m, 1H), 7.25-7.17 (m, 3H), 7.15-7.08 (m, 1H), 6.82 (d, J=8.4 Hz, 2H), 3.79 (s, 3H), 3.63-3.45 (m, 3H), 3.37 (br s, 1H), 3.12-3.00 (m, 1H), 2.94-2.87 (m, 1H), 2.80 (m, 1H), 2.72-2.59 (m, 4H), 2.57 (m, 1H), 2.42-2.32 (m, 2H), 1.74-1.67 (m, 1H), 1.66-1.59 (m, 1H), 1.39-1.29 (m, 5H), 1.26 (br s, 1H), 1.23 (m, 7H), 1.11 (d, J=6.8 Hz, 3H). MS (ESI, m/e) [M+1]⁺462.5.

Intermediate 100-1: 2-(2-(2-isopropylphenyl)-4-((4-methoxycyclohexyl)methyl)piperazin-1-yl)-7-azaspiro[3.5]nonane

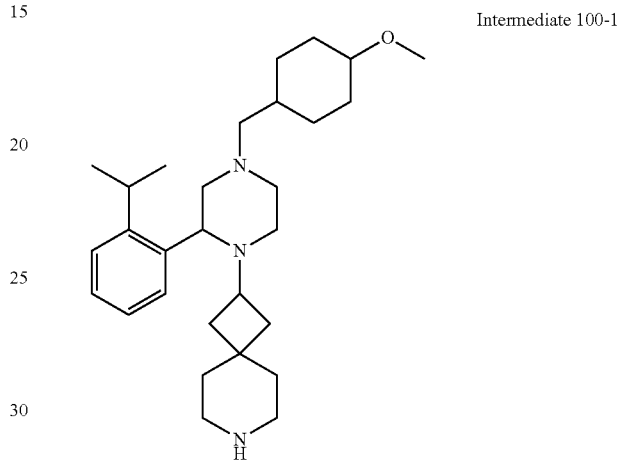

Intermediate 100-1

The synthesis procedures were similar to Intermediate 4-1. The compound 2-(2-(2-isopropylphenyl)-4-((4-methoxycyclohexyl)methyl)piperazin-1-yl)-7-azaspiro[3.5]nonane was a yellow solid. ¹H NMR (400 MHz, CDCl₃) δ ppm: 7.49 (br s, 1H), 7.26-7.19 (m, 2H), 7.15-7.10 (m, 1H), 3.61 (m, 1H), 3.39 (br s, 1H), 3.34 (s, 3H), 3.32-3.26 (m, 1H), 3.11-3.03 (m, 1H), 2.99 (m, 1H), 2.89 (m, 2H), 2.71-2.56 (m, 5H), 2.25 (m, 2H), 2.16-2.04 (m, 5H), 1.88-1.80 (m, 2H), 1.76 (m, 1H), 1.71-1.66 (m, 1H), 1.45-1.33 (m, 6H), 1.26 (m, 4H), 1.20 (d, J=6.8 Hz, 3H), 0.96-0.83 (d, J=6.8 Hz, 3H). MS (ESI, m/e) [M+1]⁺454.5.

Intermediate 101-1: 6-(2-isopropylphenyl)-4-(4-methoxybenzyl)-1-(7-azaspiro[3.5]nonan-2-yl)piperazin-2-one

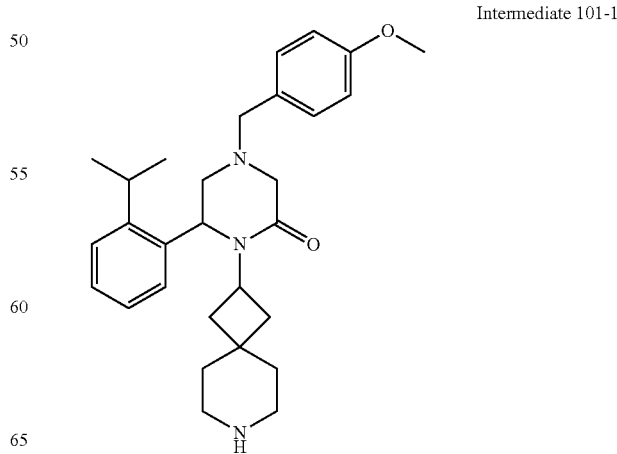

Intermediate 101-1

The synthesis procedures were similar to Intermediate 4-1. The compound 6-(2-isopropylphenyl)-4-(4-methoxybenzyl)-1-(7-azaspiro[3.5]nonan-2-yl)piperazin-2-one was a white solid. ¹H NMR (400 MHz, CDCl₃) δ ppm: 7.30-7.28 (m, 2H), 7.21-7.17 (m, 1H), 7.12-7.10 (d, J=7.6 Hz, 1H), 6.78-6.75 (d, J=8.4 Hz, 2H), 6.63-6.61 (d, J=8.4 Hz, 2H), 4.96-4.94 (t, 1H), 4.42 (m, 1H), 3.73 (s, 3H), 3.51 (t, 2H), 3.27 (d, J=7.6 Hz, 1H), 3.27 (d, J=16.4 Hz, 1H), 3.12 (d, J=16.4 Hz, 1H), 2.97-2.88 (m, 1H), 2.68-2.59 (m, 6H), 2.25 (t, 1H), 1.95-1.80 (t, 1H), 1.70-1.66 (m, 3H), 1.45 (m, 2H), 1.33 (m, 2H), 1.39-1.32 (m, 4H), 1.22 (d, J=6.8 Hz, 3H), 0.95 (d, J=6.8 Hz, 3H). MS (ESI, m/e) [M+1]⁺462.4.

Intermediate 102-1: 2-(4-(2-chloro-4-methoxybenzyl)-2-(2-isopropylphenyl)piperazin-1-yl)-7-azaspiro[3.5]nonane

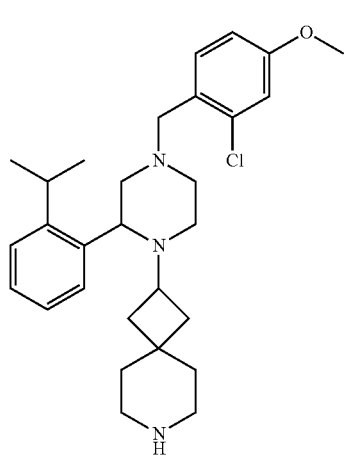

Intermediate 102-1

The synthesis procedures were similar to Intermediate 4-1. The compound 2-(4-(2-chloro-4-methoxybenzyl)-2-(2-isopropylphenyl)piperazin-1-yl)-7-azaspiro[3.5]nonane was a yellow solid. ¹H NMR (400 MHz, CDCl₃) δ ppm: 7.49 (br s, 1H), 7.35 (d, J=8.4 Hz, 1H), 7.25-7.18 (m, 2H), 7.15-7.09 (m, 1H), 6.88 (d, J=2.8 Hz, 1H), 6.78-6.74 (m, 1H), 4.71 (s, 1H), 4.50 (s, 1H), 3.81 (s, 1H), 3.78-3.77 (m, 3H), 3.64 (m, 1H), 3.57 (s, 2H), 3.43-3.34 (m, 1H), 3.02-2.86 (m, 3H), 2.79-2.57 (m, 5H), 2.44-2.36 (m, 1H), 2.31-2.23 (m, 2H), 1.81-1.71 (m, 1H), 1.71-1.65 (m, 1H), 1.52-1.29 (m, 5H), 1.25 (d, J=6.8 Hz, 3H), 1.15 (d, J=6.8 Hz, 3H). MS (ESI, m/e) [M+1]⁺482.5.

Intermediate 103-1: 2-(4-(2-chlorobenzyl)-2-(2-isopropylphenyl)piperazin-1-yl)-7-azaspiro[3.5]nonane

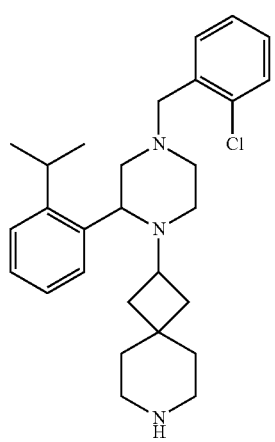

Intermediate 103-1

The synthesis procedures were similar to Intermediate 4-1. The compound 2-(4-(2-chlorobenzyl)-2-(2-isopropylphenyl)piperazin-1-yl)-7-azaspiro[3.5]nonane was a yellow solid. ¹H NMR (400 MHz, CDCl₃) δ ppm: 7.51-7.47 (m, 1H), 7.32 (m, 1H), 7.27-7.05 (in, 4 11), 3.69 (m, 1H), 3.64 (s, 2 11), 3.39 (br s, 1H), 3.05-2.99 (m, 11H), 2.99-2.89 (m, 2H), 2.74-2.53 (m, 5H), 2.50-2.41 (m, 1H), 2.37-2.25 (m, 2H), 1.76 (m, 1H), 1.72-1.64 (m, 2H), 1.44-1.29 (m, 5H), 1.27 (d, J=6.8 Hz, 3H), 1.15 (br d, J=6.8 Hz, 3H). MS (ESI, m/e) [M+1]⁺452.4.

Intermediate 95-1: methyl 4-fluoro-2-((3-fluoro-1H-pyrrolo[2,3-b]pyridin-5-yl)oxy)benzoate

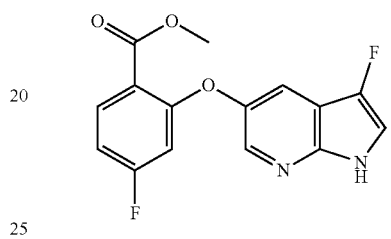

Step 1: Synthesis of 5-bromo-3-fluoro-1H-pyrrolo[2,3-b]pyridine

To a solution of 5-bromo-1H-pyrrolo[2,3-b]pyridine (15.0 g, 76.13 mmol) in MeCN (375 mL) and AcOH (75 mL) was added Selectfluor fluorinating reagent (40.4 g, 114.19 mmol) at 20° C. The solution was stirred at 90° C. for 12 hrs. After the solvent was removed by evaporation under vacuum, the residue was poured into aqueous NaHCO₃. The mixture was adjusted the pH value to 8 and was extracted with EtOAc (200 mL×3). The combined organic layers were washed with brine, dried over anhydrous Na₂SO₄, filtered and concentrated under reduced pressure. The crude product was purified by column chromatography (silica gel, eluent: PE/EA (v/v)=10/1 to 5/1) to give 5-bromo-3-fluoro-1H-pyrrolo[2,3-b]pyridine (10 g, crude), which was used directly for next step.

Step 2: synthesis of 3-fluoro-5-methoxy-1H-pyrrolo[2,3-b]pyridine

To a solution of 5-bromo-3-fluoro-1H-pyrrolo[2,3-b]pyridine (10 g, 46.51 mmol) in DMF (320 mL) was added MeONa (348.8 mL, 5.6 M) and CuBr (13.34 g, 93.01 mmol). The mixture was stirred at 145° C. for 2 hrs. The mixture was cooled to room temperature, poured into aqueous NH₃·H₂O (500 mL, 17%) and then extracted with EtOAc (200 mL×3). The combined organic layers were washed with brine, dried with anhydrous Na₂SO₄, filtered and concentrated under reduced pressure. The crude product was purified by column chromatography (silica gel, eluent: PE/EA (v/v)=50/1 to 10/1) to give 3-fluoro-5-methoxy-1H-pyrrolo[2,3-b]pyridine (1.2 g), yield: 9% in the two steps. ¹H NMR (400 MHz, CDCl₃) δ ppm: 9.03 (br, 1H), 8.12 (d, J=2.4 Hz, 1H), 7.43 (d, J=2.4 Hz, 1H), 7.08-7.03 (m, 1H), 3.91 (s, 3H).

Step 3: synthesis of 3-fluoro-1H-pyrrolo[2,3-b]pyridin-5-ol

To a solution of 3-fluoro-5-methoxy-1H-pyrrolo[2,3-b]pyridine (1.4 g, 8.43 mmol) in DCM (20 mL) was added BBr₃ (8.4 g, 33.7 mmol) dropwise at −30° C. The mixture was stirred at 25° C. for 2 hrs. The mixture was poured into aqueous NaHCO₃ solution (50 mL, 4 M), extracted with DCM (50 mL×3). The combined organic layers were washed with brine, dried with anhydrous Na₂SO₄, filtered and concentrated under reduced pressure. The crude product was purified by column chromatography (silica gel, eluent: PE/EA (v/v)=50/1 to 10/1) to give 3-fluoro-1H-pyrrolo[2,3-b]pyridin-5-ol (0.5 g, yield: 39%).

Step 4: synthesis of methyl 4-fluoro-2-((3-fluoro-1H-pyrrolo[2,3-b]pyridin-5-yl)oxy)benzoate To a solution of 3-fluoro-1H-pyrrolo[2,3-b]pyridin-5-ol (0.5 g, 3.29 mmol) in DGDE (5 mL) was added methyl 2,4-difluorobenzoate (1.13 g, 6.57 mmol) and K₃PO₄ (1.4 g, 6.57 mmol).

The mixture was stirred at 135° C. for 3 hrs. The mixture was cooled to room temperature and then poured into H₂O (20 mL), extracted with EtOAc (20 mL×3). The combined organic layers were washed with brine, dried with anhydrous Na₂SO₄, filtered and concentrated under reduced pressure. The crude product was purified by column chromatography (silica gel, eluent: PE/EA (v/v)=10/1) to give methyl 4-fluoro-2-((3-fluoro-1H-pyrrolo[2,3-b]pyridin-5-yl)oxy)benzoate (0.35 g, yield: 35%) as a yellow solid. ¹H NMR (400 MHz, CDCl₃) δ ppm: 8.59 (br, 1H), 8.22 (d, J=2.8 Hz, 1H), 8.01-7.97 (m, 1H), 7.63 (d, J=2.8 Hz, 1H), 7.16-7.14 (m, 1H), 6.88-6.84 (m, 1H), 6.56-6.53 (m, 1H), 3.89 (s, 3H). MS (ESI, m/e) [M+1]⁺305.3.

Intermediate 104-1: 2-(2-(2-isopropylphenyl)-4-(4-methoxybenzyl)-3-methylpiperazin-1-yl)-7-azaspiro[3.5]nonane Intermediate 104-1

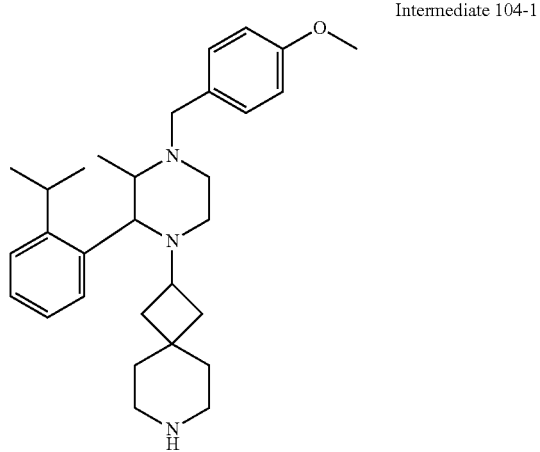 [SMILES: COc1ccc(CN2CCN(C3CC4(CCNCC4)C3)C(c3ccccc3C(C)C)C2C)cc1]

The synthesis procedures were similar to Intermediate 12-1. The compound 2-(2-(2-isopropylphenyl)-4-(4-methoxybenzyl)-3-methylpiperazin-1-yl)-7-azaspiro[3.5]nonane. 1 H NMR (400 MHz, CDCl₃) δ ppm: 7.61-7.59 (m, 1H), 7.30-7.28 (m, 2H), 7.26-7.22 (m, 2H), 7.20-7.15 (m, 1H), 7.11-7.06 (m, 1H), 6.86-6.84 (m, 2H), 3.92-3.91 (m, 1H), 3.80 (s, 3H), 3.69-3.67 (m, 1H), 3.45-3.42 (m, 1H), 3.28-3.18 (m, 2H), 2.98-2.96 (m, 1H), 2.84-2.82 (m, 1H), 2.77-2.75 (m, 1H), 2.65-2.63 (m, 4H), 2.53-2.43 (m, 2H), 1.83-1.81 (m, 1H), 1.67-1.64 (m, 2H), 1.57-1.52 (m, 11H), 1.47-1.45 (m, 1H), 1.38-1.36 (m, 4H), 1.23-1.21 (m, 4H), 1.09 (d, J=6.8 Hz, 3H), 0.85 (d, J=6.8 Hz, 3H). MS (ESI, m/e) [M+1]⁺462.5.

Intermediate 105-1: 2-(2-cyclopropylphenyl)-N-(4-methoxybenzyl)-N-methyl-1-(7-azaspiro[3.5]nonan-2-yl)piperidin-4-amine Intermediate 105-1

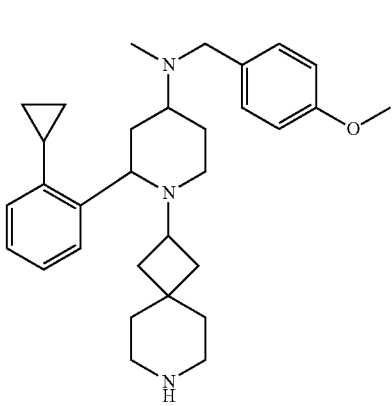

Step 1: benzyl 2-(2-cyclopropylphenyl)-4-oxo-3,4-dihydropyridine-1(2H)-carboxylate.

A small amount of I₂ (10 mg, catalyst) was added to the solution of Mg (0.9 g, 38 mmol) in THF (20 mL) at 25° C. under N₂, then 1-bromo-2-cyclopropylbenzene (5.0 g, 25 mmol) was added in drops. The mixture was heated to 70° C. for 1 hr until the brown color disappeared. The solution of Grignard Reagent was added dropwise to the pyridinium salt obtained from 4-methoxypyridine (1.85 g, 0.017 mol) and benzyl carbonochloridate (3.2 mL, 0.022 mol) in dry THF (50 mL) at −20° C. The mixture was stirred at −20° C. for 1 hr. The HCl (1 M, 50 mL) was added to the mixture, extracted with EtOAc (20 mL×3). The combined organic phases were washed with brine (20 mL*2), dried with anhydrous Na₂SO₄, filtered and concentrated in vacuum. The residue was purified by column chromatography (silica gel, eluent: PE/EA (v/v)=10/1) to give benzyl 2- (2-cyclopropylphenyl)-4-oxo-3,4-dihydropyridine-1(2H)-carboxylate (4.0 g, yield: 68%) as a brown oil. 1H NMR (400 MHz, CDCl₃) δ ppm: 8.20 (d, J=8.4 Hz, 1H), 7.40-7.27 (m, 3H), 7.21-7.08 (m, 5H), 6.26 (br d, J=8.8 Hz, 1H), 5.47 (d, J=8.4 Hz, 1H), 5.20-5.11 (m, 2H), 3.23-3.17 (m, 1H), 2.72 (d, J=16.4 Hz, 1H), 1.80 (br s, 1H), 0.98-0.83 (m, 2H), 0.72-0.49 (m, 2H).

Step 2: benzyl 2-(2-cyclopropylphenyl)-4-oxopiperidine-1-carboxylate.

To a solution of benzyl 2-(2-cyclopropylphenyl)-4-oxo-3,4-dihydropyridine-1(2H)-carboxylate (4.0 g, 11.51 mmol) in AcOH (40 mL) was added Zn (7.53 g, 115.14 mmol). The mixture was stirred at 25° C. for 12 hrs. After filtered the mixture, the filtrated was concentrated in vacuum. The residue was dissolved into EtOAc (80 mL), the organic layer was washed with NaHCO₃ aqueous (30 mL×2) and brine (30 mL×2). The organic layer was dried, filtered and concentrated in vacuum. The residue was purified by column chromatography (silica gel, eluent: PE/EA (v/v)=1/1) to give benzyl 2-(2-cyclopropylphenyl)-4-oxopiperidine-1-carboxylate (3.9 g, yield: 96%) as a brown oil, which was used directly for next step without further purification.

Step 3: benzyl 2-(2-cyclopropylphenyl)-4-((4-methoxybenzyl)(methyl)amino)piperidine-1-carboxylate A mixture of benzyl 2-(2-cyclopropylphenyl)-4-oxopiperidine-1-carboxylate (3.88 g, 10.88 mmol), 1-(4-methoxyphenyl)-N-methylmethanamine (1.8 g, 11.76 mmol) and AcOH (1.31 g, 21.75 mmol) in DCE (20 mL) was stirred at 25° C. for 1 hr. Then NaBH(OAc)₃ (6.91 g, 32.63 mmol) was added and stirred at 25° C. for another 12 hrs. The reaction mixture was poured into saturated NaHCO₃ (50 mL), extracted with EtOAc (100 mL×2). The combined organic layers were washed with brine, dried with Na₂SO₄, filtered and concentrated under reduced pressure. The crude product was purified by column chromatography (silica gel, eluent: PE/EA (v/v)=5/1 to 2/1) to give benzyl 2-(2-cyclopropylphenyl)-4-((4-methoxybenzyl)(methyl)amino)piperidine-1-carboxylate (3.3 g, yield: 79%) as a yellow oil. MS (ESI, m/e) [M+1]⁺485.3

Step 4: 2-(2-cyclopropylphenyl)-N-(4-methoxybenzyl)-N-methylpiperidin-4-amine.

To a solution of benzyl 2-(2-cyclopropylphenyl)-4-((4-methoxybenzyl)(methyl)amino) piperidine-1-carboxylate (3.3 g, 6.81 mmol) in DCM (10 mL) was added TMSI (5.45 g, 27.24 mmol) at 0° C. The mixture was stirred at 35° C. for 2 hrs. The reaction mixture was poured into water (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give 2-(2-cyclopropylphenyl)-N-(4-methoxybenzyl)-N-methylpiperidin-4-amine (1.77 g, yield: 74%) as a yellow oil. MS (ESI, m/e) [M+1]⁺351.3.

Step 5: tert-butyl 2-(2-(2-cyclopropylphenyl)-4-((4-methoxybenzyl)(methyl)amino)piperidin-1-yl)-7-azaspiro[3.5]nonane-7-carboxylate.

To a solution of 2-(2-cyclopropylphenyl)-N-(4-methoxybenzyl)-N-methylpiperidin-4-amine (1.0 g, 2.85 mmol) in DCE (10 mL) was added AcOH (342.67 mg, 5.71 mmol) and tert-butyl 2-oxo-7-azaspiro[3.5]nonane-7-carboxylate (750.51 mg, 3.14 mmol). The mixture was stirred at 25° C. for 1 hr. Then NaBH(OAc)₃ (1.81 g, 8.56 mmol) was added and stirred at 25° C. for another 12 hrs. The reaction mixture was poured into saturated NaHCO₃ (50 mL), extracted with EtOAc (100 mL×2). The combined organic layers were washed with brine, dried with anhydrous Na₂SO₄, filtered and concentrated under reduced pressure. The crude product was purified by column chromatography (silica gel, eluent: PE/EA (v/v)=5/1 to 2/1) to give tert-butyl 2-(2-(2-cyclopropylphenyl)-4-((4-methoxybenzyl)(methyl)amino)piperidin-1-yl)-7-azaspiro[3.5]nonane-7-carboxylate (870 mg, yield: 60%) as a yellow oil.

Step 6: 2-(2-cyclopropylphenyl)-N-(4-methoxybenzyl)-N-methyl-1-(7-azaspiro[3.5]nonan-2-yl)piperidin-4-amine.

A mixture of tert-butyl 2-(2-(2-cyclopropylphenyl)-4-((4-methoxybenzyl)(methyl)amino) piperidin-1-yl)-7-azaspiro[3.5]nonane-7-carboxylate (870 mg, 1.52 mmol) and HCl (3.79 mL, 15.16 mmol) in MeOH (10 mL) was stirred at 25° C. for 2 hrs. The reaction solution was concentrated under reduced pressure. The reaction mixture was poured into saturated NaHCO₃ (50 mL), extracted with EtOAc (50 mL×2). The combined organic layers were washed with brine, dried with anhydrous Na₂SO₄, filtered and concentrated under reduced pressure to give 2-(2-cyclopropylphenyl)-N-(4-methoxybezyl)-N-methyl-1-(7-azaspiro[3.5]nonan-2-yl)piperidin-4-amine (482 mg, yield: 67%) as a yellow solid. 1H NMR (400 MHz, CDCl₃) δ ppm: 7.53 (br s, 1H), 7.26-19 (m, 2H), 7.18-7.07 (m, 2H), 7.05-6.91 (m, 1H), 6.89-6.81 (m, 2H), 3.82-3.80 (m, 3H), 3.57-3.44 (m, 2H), 3.21-3.19 (m, 1H), 3.03-2.95 (m, 1H), 2.90-2.84 (m, 1H), 2.74-2.51 (m, 5H), 2.21-2.11 (m, 4H), 2.04-1.62 (m, 7H), 1.55-1.19 (m, 6H), 1.10-1.00 (m, 1H), 0.99-0.85 (m, 2H), 0.72-0.61 (m, 2H). MS (ESI, m/e) [M+1]⁺474.34.

Intermediate 107-1: 2-(4-((3,4-dihydro-2H-benzo[b][1,4]dioxepin-6-yl)methyl)-2-(2-isopropylphenyl)piperazin-1-yl)-7-azaspiro[3.5]nonane

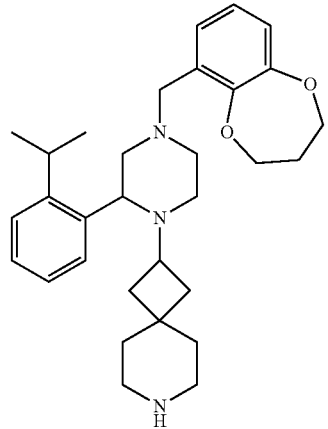

Intermediate 107-1

The synthesis procedures were similar to Intermediate 4-1. The compound 2-(4-((3,4-dihydro-2H-benzo[b][1,4]dioxepin-6-yl)methyl)-2-(2-isopropylphenyl)piperazin-1-yl)-7-azaspiro[3.5]nonane was a yellow solid. ¹H NMR (400 MHz, CDCl₃) δ ppm: 7.47 (s, 1H), 7.26-7.18 (m, 2H), 7.15-7.07 (m, 1H), 7.05-6.96 (m, 1H), 6.94-6.78 (m, 2H), 4.17-4.13 (m, 4H), 3.81-3.17 (m, 6H), 3.08-2.85 (m, 3H), 2.75-2.64 (m, 4H), 2.44-2.10 (m, 5H), 1.83-1.59 (m, 2H), 1.42-1.39 (m, 4H), 1.32-1.22 (m, 5H),1.16 (d, J=6.8 Hz, 3H). MS (ESI, m/e) [M+1]⁺490.2.

Intermediate 114-1: 4-((3-(2-isopropylphenyl)-4-(7-azaspiro[3.5]nonan-2-yl)piperazin-1-y)methyl)-N,N-dimethylaniline

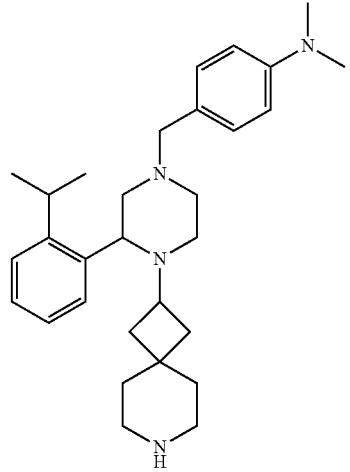

Intermediate 114-1

The synthesis procedures were similar to Intermediate 4-1. The compound 4-((3-(2-isopropylphenyl)-4-(7-azaspiro[3.5]nonan-2-yl)piperazin-1-yl)methyl)-N,N-dimethylaniline was a yellow solid. ¹H NMR (400 MHz, CDCl₃) δ ppm: 7.56-7.41 (m, 1H), 7.25-7.19 (m, 2H), 7.18-7.10 (m, 3H), 6.68 (d, J=8.8 Hz, 2H), 3.66-3.64 (m, 1H), 3.52-3.35 (m, 3H), 2.99-2.87 (m, 9H), 2.72-2.59 (m, 5H), 2.29-2.24 (m, 2H), 2.21-2.10 (m, 2H), 1.76-1.74 (m, 1H), 1.69-1.63 (m, 1H), 1.36 (m, 5H), 1.25 (d, J=6.8 Hz, 3H), 1.16 (br d, J=6.8 Hz, 3H). MS (ESI, m/e) [M+1]⁺461.6.

Intermediate 115-1: 2-(4-(benzo[d][1,3]dioxol-4-ylmethyl)-2-(2-isopropylphenyl)piperazin-1-yl)-7-azaspiro[3.5]nonane

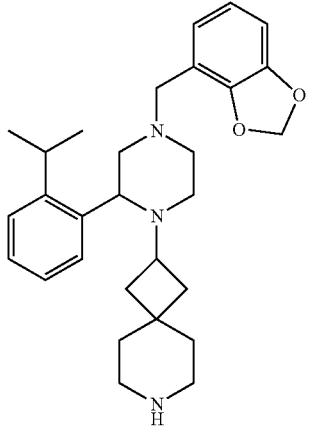

Intermediate 115-1

The synthesis procedures were similar to Intermediate 4-1. The compound 2-(4-(benzo[d][1,3]dioxol-4-ylmethyl)-2-(2-isopropylphenyl)piperazin-1-yl)-7-azaspiro[3.5]nonane was a white solid. ¹H NMR (400 MHz, CDCl₃) δ ppm: 7.46 (s, 1H), 7.26-7.18 (m, 2H), 7.15-7.08 (m, 1H), 6.84-6.68 (m, 3H), 5.91 (s, 2H), 3.69-3.63 (m, 1H), 3.56 (s, 2H), 3.39 (s, 1H), 3.12-2.80 (m, 5H), 2.75-2.55 (m, 5H), 2.43-2.18 (m, 3H), 1.81-1.71 (m, 1H), 1.68-1.62 (m, 1H), 1.47-1.32 (m, 4H), 1.24 (d, J=6.8 Hz, 3H), 1.16 (d, J=6.8 Hz, 4H). MS (ESI, m/e) [M+1]⁺462.5.

Intermediate 119-1: 2-(4-(3-chloro-2-methoxybenzyl)-2-(2-isopropylphenyl)piperazin-1-yl)-7-azaspiro[3.5]nonane

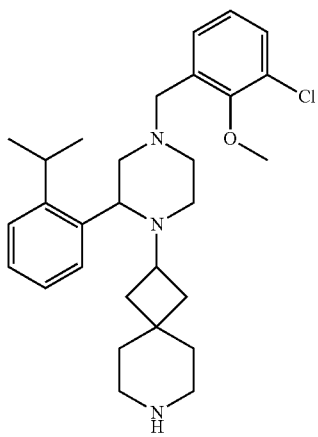

Intermediate 119-1

The synthesis procedures were similar to Intermediate 4-1. The compound 2-(4-(3-chloro-2-methoxybenzyl)-2-(2-isopropylphenyl)piperazin-1-yl)-7-azaspiro[3.5]nonane was a white solid. ¹H NMR (400 MHz, CDCl₃) δ ppm: 7.41 (br s, 1H), 7.23-7.21 (m, 1H), 7.17-7.13 (m, 3H), 7.06-7.04 (m, 1H), 6.93-6.89 (m, 1H), 3.78 (s, 3H), 3.59-3.47 (m, 3H), 3.44 (br. s, 3H), 2.93-2.82 (m, 3H), 2.61-2.53 (m, 5H), 2.53-2.17 (m, 3H), 1.75-1.55 (m, 2H), 1.29-1.06 (m, 12H). MS (ESI, m/e) [M+1]⁺482.5.

Intermediate 121-1: 2-(4-(4-fluoro-3-methoxybenzyl)-2-(2-isopropylphenyl)piperazin-1-yl)-7-azaspiro[3.5]nonane

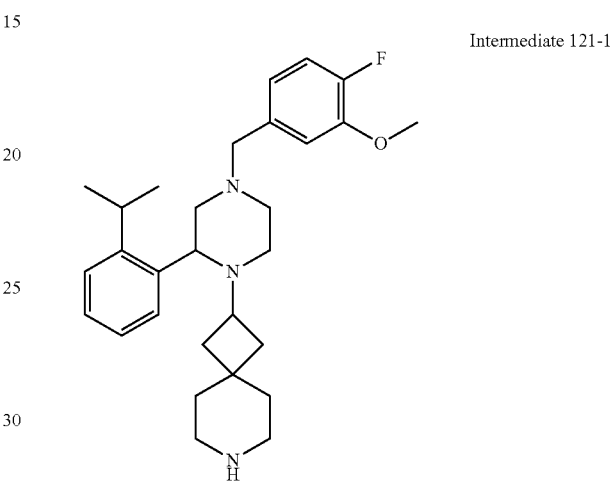

Intermediate 121-1

The synthesis procedures were similar to Intermediate 4-1. The compound 2-(4-(4-fluoro-3-methoxybenzyl)-2-(2-isopropylphenyl)piperazin-1-yl)-7-azaspiro[3.5]nonane was a yellow solid. ¹H NMR (400 MHz, CDCl₃) δ ppm: 7.61-7.42 (m, 1H), 7.25-7.19 (m, 2H), 7.15-7.10 (m, 1H), 7.00-6.94 (m, 2H), 6.82-6.79 (m, 1H), 3.89 (s, 3H), 3.65-3.63 (m, 1H), 3.48-3.35 (m, 3H), 3.03-2.98 (m, 1H), 2.94-2.87 (m, 2H), 2.74-2.52 (m, 6H), 2.36-2.25 (m, 2H), 2.19-2.13 (m, 1H) 1.77 (br s, 1H), 1.71-1.64 (m, 1H), 1.46-1.29 (m, 6H), 1.26 (d, J=6.8 Hz, 3H), 1.14 (d, J=6.8 Hz, 3H). MS (ESI, m/e) [M+1]⁺466.5.

Intermediate 122-1: 2-(4-(benzo[d][1,3]dioxol-5-ylmethyl)-2-(2-isopropylphenyl)piperazin-1-yl)-7-azaspiro[3.5]nonane

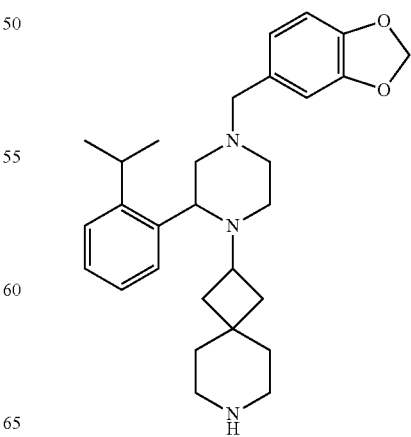

Intermediate 122-1

The synthesis procedures were similar to Intermediate 18-1. The compound 2-(4-(benzo[d][1,3]dioxol-5-ylmethyl)-2-(2-isopropylphenyl)piperazin-1-yl)-7-azaspiro[3.5]nonane was a yellow solid. ¹H NMR (400 MHz, CDCl₃) δ ppm: 7.54-7.40 (m, 1H), 7.25-7.18 (m, 2H), 7.16-7.06 (m, 1H), 6.84 (s, 1H), 6.76-6.67 (m, 2H), 5.91 (s, 2H), 5.87-5.66 (m, 1H), 3.71-3.54 (m, 1H), 3.48-3.29 (m, 3H), 2.97-2.95 (m, 1H), 2.93-2.83 (m, 2H), 2.78-2.62 (m, 4H), 2.31-2.21 (m, 2H), 2.21-2.11 (m, 1H), 1.83-1.74 (m, 1H), 1.72-1.61 (m, 1H), 1.55-1.36 (m, 4H), 1.31-1.21 (m, 5H), 1.14 (d, J=6.8 Hz, 4H). MS (ESI, m/e) [M+1]⁺462.4.

Intermediate 123-1: methyl 2-((3-chloro-1H-pyrrolo[2,3-b]pyridin--yl)oxy)-4-fluorobenzoate

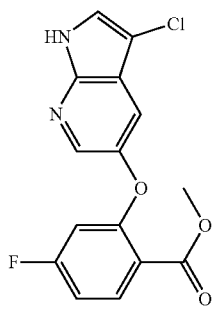

Intermediate 123-1

To the mixture of methyl 2-((1H-pyrrolo[2,3-b]pyridin-5-yl)oxy)-4-fluorobenzoate (10 g, 34.93 mmol) in DMF (100 mL) was added N-Chlorosuccinimide (4.88 g, 36.68 mmol) was stirred for 16 hrs at room temperature. The reaction was poured to brine (500 mL), filtered, and washed with water (200 mL×3), The solid precipitated was filtered and dried in vacuo to give a crude.

The residue was taken in DCM (50 mL) and stirred for 30 mins. Then filtered and dried in vacuo to give the title product (9.3 g, yield: 83.02%) as off-white solid. ¹H NMR (400 MHz, DMSO-d₆) δ ppm: 12.13 (s, 1H), 8.20-8.15 (m, 1H), 7.98-7.92 (m, 1H), 7.79-7.74 (m, 1H), 7.58 (s, 1H), 7.15-7.07 (m, 1H), 6.86-6.79 (m, 1H), 3.79 (s, 1H). MS (ESI, m/e) [M+1]⁺321.1.

Intermediate 131-1: 2-(2-(2-isopropylphenyl)-4-(pyridin-2-ylmethyl)piperazin-1-yl)-7-azaspiro[3.5]nonane

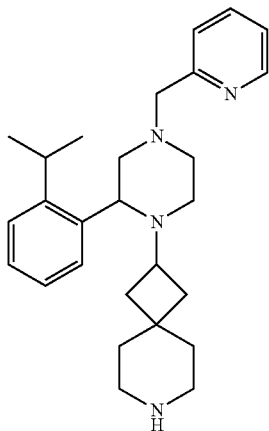

Intermediate 131-1

The synthesis procedures were similar to Intermediate 4-1. The compound 2-(2-(2-isopropylphenyl)-4-(pyridin-2-ylmethyl)piperazin-1-yl)-7-azaspiro[3.5]nonane was a yellow solid. ¹H NMR (400 MHz, CDCl₃) δ ppm: 8.56 (d, J=4.0 Hz, 1H), 7.64-7.60 (m, 1H), 7.49 (br s, 1H), 7.37 (d, J=7.6 Hz, 1H), 7.19-7.25 (m, 2H), 7.16-7.10 (m, 2H), 3.75-3.65 (m, 3H), 3.38 (br s, 1H), 3.00-2.98 (m, 1H), 2.96-2.89 (m, 2H), 2.72-2.64 (m, 3H), 2.64-2.59 (m, 2H), 2.44-2.35 (m, 2H), 2.33-2.22 (m, 2H), 2.15 (br s, 1H), 1.80-1.73 (m, 1H), 1.70-1.64 (m, 1H), 1.37-1.34 (m, 5H), 1.25 (d, J=6.8 Hz, 3H), 1.14 (d, J=6.8 Hz, 3H). MS (ESI, m/e) [M+1]⁺419.2.

Intermediate 132-1: 5-((3-(2-isopropylphenyl)-4-(7-azaspiro[3.5]nonan-2-yl)piperazin-1-yl)methyl)-2-methoxybenzonitrile

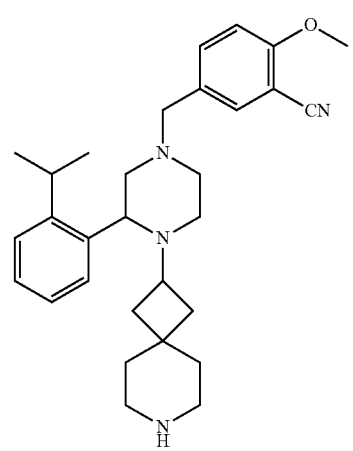

Intermediate 132-1

The synthesis procedures were similar to Intermediate 109-1. The compound 5-((3-(2-isopropylphenyl)-4-(7-azaspiro[3.5]nonan-2-yl)piperazin-1-yl)methyl)-2-methoxybenzonitrile was a white solid. ¹H NMR (400 MHz, CDCl₃) δ ppm: 7.57 (s, 1H), 7.45-7.43 (m, 2H), 7.25-7.20 (m, 2H), 7.14-7.11 (m, 1H), 6.88 (br d, J=8.4 Hz, 1H), 3.91 (s, 3H), 3.81-3.76 (m, 1H), 3.66-3.59 (m, 1H), 3.45 (br s, 1H), 3.35 (br s, 1H), 2.96-2.71 (m, 6H), 2.61 (s, 1H), 2.29-2.27 (m, 2H), 2.17 (br s, 1H), 1.86-1.69 (m, 3H), 1.38-1.29 (m, 4H), 1.27-1.26 (m, 2H), 1.15 (br d, J=6.8 Hz, 6H). MS (ESI, m/e) [M+1]⁺473.6.

Intermediate 134-1: 2-(4-(3-fluoro-4-methoxybenzyl)-2-(2-isopropylphenyl)piperazin-1-yl)-7-azaspiro[3.5]nonane

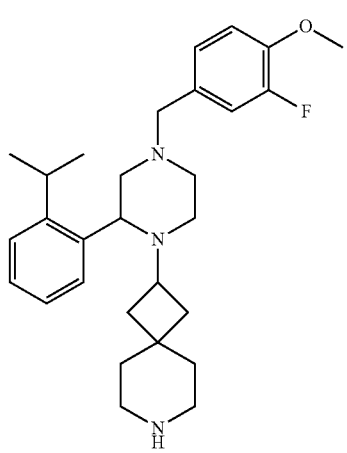

Intermediate 134-1

The synthesis procedures were similar to Intermediate 4-1. The compound 2-(4-(3-fluoro-4-methoxybenzyl)-2-(2-isopropylphenyl)piperazin-1-yl)-7-azaspiro[3.5]nonane was a yellow solid. $^1$H NMR (400 MHz, CDCl$_3$) δ ppm: 7.48 (br s, 1H), 7.26-7.17 (m, 2H), 7.16-7.06 (m, 2H), 6.97 (d, J=8.4 Hz, 1H), 6.90-6.82 (m, 1H), 3.91-3.80 (m, 3H), 3.68-3.58 (m, 1H), 3.51-3.26 (m, 3H), 3.05-2.85 (m, 311), 2.70-2.53 (m, 5H), 2.34-2.25 (m, 2H), 2.18-2.14 (m, 1H), 1.87-1.71 (m, 2H), 1.70-1.64 (m, 1H), 1.38-1.28 (m, 5H), 1.26 (d, J=6.8 Hz, 3H), 1.15 (d, J=6.8 Hz, 3H). MS (ESI, m/e) [M+1]$^+$466.3.

Intermediate 148-1: 2-(4-(3-chloro-4,5-dimethoxybenzyl)-2-(2-isopropylphenyl)piperazin-1-yl)-7-azaspiro[3.5]nonane Intermediate 148-1

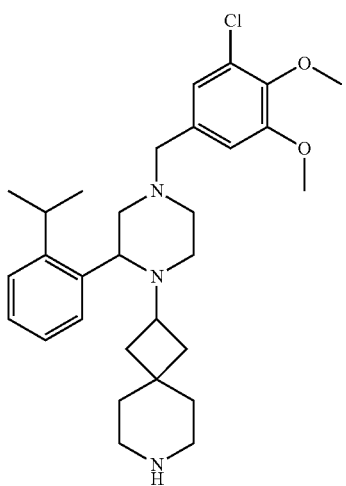

The synthesis procedures were similar to Intermediate 4-1. The compound 2-(4-(3-chloro-4,5-dimethoxybenzyl)-2-(2-isopropylphenyl)piperazin-1-yl)-7-azaspiro[3.5]nonane was a light yellow solid. $^1$H NMR (400 MHz, CDCl$_3$) δ ppm: 7.48-7.46 (m, 1H), 7.23-7.21 (m, 2H), 7.16-7.09 (m, 1H), 6.99-6.94 (m, 11H), 6.80 (s, 1H), 3.88-3.81 (m, 7H), 3.66-3.64 (m, 1H), 3.50-3.36 (m, 3H) 3.09-2.83 (m, 3H), 2.69-2.60 (m, 5H), 2.39-2.27 (m, 2H), 2.16-2.14 (m, 1H), 1.81-1.64 (m, 1H), 1.47-1.33 (m, 4H), 1.29-1.25 (m, 4H), 1.15 (d, J=6.8 Hz, 4H). MS (ESI, m/e) [M+1]$^+$512.4.

Intermediate 149-1: 6-(4-((2,3-dihydrobenzo[b][1,4]dioxin-5-yl)methyl)-2-(2-isopropylphenyl)piperazin-1-yl)-2-azaspiro[3.3]heptane Intermediate 149-1

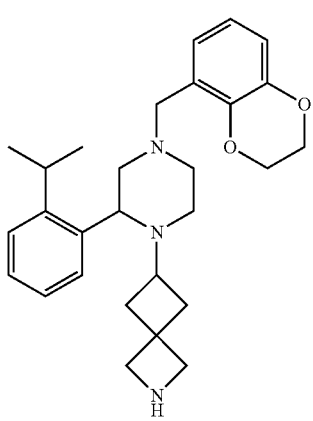

Step 1: 1-((2,3-dihydrobenzo[b][1,4]dioxin-5-yl)methyl)-3-(2-isopropylphenyl)piperazine.

A mixture of 2-(2-isopropylphenyl)piperazine (2.6 g, 12.7 mmol), 2,3-dihydrobenzo[b][1,4]dioxine-5-carbaldehyde (1.9 g, 11.6 mmol) and NaBH(OAc)$_3$ (4.9 g, 23.2 mmol) in DCM (20 mL) was stirred at 20° C. for 12 hrs. The mixture was adjusted pH=7 by aqueous Na$_2$CO$_3$ extracted with DCM (20 mL×2). The combined organic layers were washed with brine, dried over anhydrous Na$_2$SO$_4$, filtered and concentrated in vacuum. The crude product was purified by column chromatography (silica gel, eluent: EA) to give 1-((2,3-dihydrobenzo[b][1,4]dioxin-5-yl)methyl)-3-(2-isopropylphenyl)piperazine (3.2 g, yield: 78%) as a yellow solid. MS (ESI, m/e) [M+1]+353.3.

Step 2: tert-butyl 6-(4-((2,3-dihydrobenzo[b][1,4]dioxin-5-yl)methyl)-2-(2-isopropylphenyl)piperazin-1-yl)-2-azaspiro[3.3]heptane-2-carboxylate.

A mixture of I-((2,3-dihydrobenzo[b][1,4]dioxin-5-yl)methyl)-3-(2-isopropylphenyl)piperazine (3.2 g, 8.97 mmol), tert-butyl 6-oxo-2-azaspiro[3.3]heptane-2-carboxylate (1.9 g, 8.97 mmol), AcOH (1.1 g, 17.9 mmol) and NaBH$_3$CN (1.1 g, 17.9 mmol) in MeOH (30 mL) was stirred at 75° C. for 12 hrs. The mixture was adjusted pH=7 by aqueous Na$_2$CO$_3$, extracted with DCM (40 mL×2). The combined organic layers were washed with brine (50 mL), dried over anhydrous Na$_2$SO$_4$, filtered and concentrated in vacuum. The crude product was purified by column chromatography (silica gel, eluent: EA) to give tert-butyl 6-(4-((2,3-dihydrobenzo[b][1,4]dioxin-5-yl)methyl)-2-(2-isopropylphenyl)piperazin-1-yl)-2-azaspiro[3.3]heptane-2-carboxylate (2.0 g, yield: 41%) as a yellow solid. MS (ESI, m/e) [M+1]$^+$548.5.

Step 3: 6-(4-((2,3-dihydrobenzo[b][1,4]dioxin-5-yl)methyl)-2-(2-isopropylphenyl)piperazin-1-yl)-2-azaspiro[3.3]heptane.

A mixture of tert-butyl 6-(4-((2,3-dihydrobenzo[b][1,4]dioxin-5-yl)methyl)-2-(2-isopropylphenyl)piperazin-1-yl)-2-azaspiro[3.3]heptane-2-carboxylate (2.0 g, 3.65 mmol) in HCl/MeOH (40 mL) was stirred at 20° C. for 2 hrs. The reaction mixture was poured into saturated NaHCO$_3$ (50 mL), extracted with EtOAc (50 mL×2). The combined organic layers were washed with brine, dried with anhydrous Na$_2$SO$_4$, filtered and concentrated under reduced pressure. The residue was purified by prep-HPLC (Instrument: Shimadzu LC-8A preparative HPLC Column: Phenomenex luna C18 (250×70 mm, 15 um) Mobile phase: A for H$_2$O (0.09% TFA) and B for CAN Gradient: B from 15% to 45% in 20 min Flow rate: 130 mL/min Wavelength: 220&254 nm) to give 6-(4-((2,3-dihydrobenzo[b][1,4]dioxin-5-yl)methyl)-2-(2-isopropylphenyl)piperazin-1-yl)-2-azaspiro[3.3]heptane (500 mg, yield: 31%) as a yellow solid. MS (ESI, m/e) [M+1]+448.6

Intermediate 149-1a: (R)-6-(4-((2,3-dihydrobenzo[b][1,4]dioxin-5-yl)methyl)-2-(2-isopropylphenyl)piperazin-1-yl)-2-azaspiro[3.3]heptane; and, Intermediate 149-1b: (S)-6-(4-((2,3-dihydrobenzo[b][1,4]dioxin-5-yl)methyl)-2-(2-isopropylphenyl)piperazin-1-yl)-2-azaspiro[3.3]heptane Intermediate 149-1a

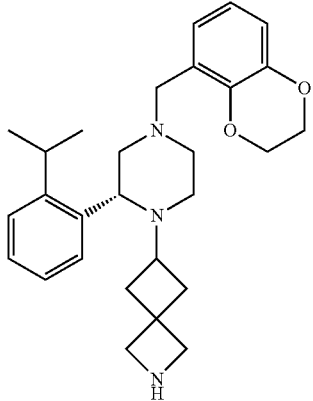

Intermediate 149-1b

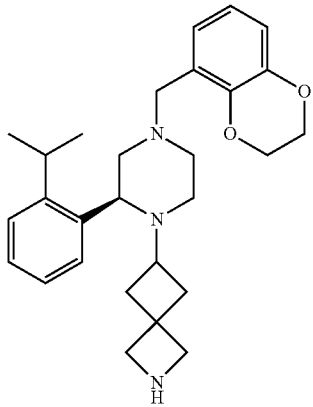

The compound 6-(4-((2,3-dihydrobenzo[b][1,4]dioxin-5-yl)methyl)-2-(2-isopropylphenyl)piperazin-1-yl)-2-azaspiro[3.3]heptane (500 mg, 1.12 mmol) was separated by SFC (Instrument: Waters SFC 80 preparative SFC; Column: Chiralpak IG, 250×30 mm i.d. 10 um; Mobile phase: A for $CO_2$ and B for EtOH(0.1% $NH_3H_2O$); Gradient: B%=30% isocratic mode; Flow rate:60 g/min; Wavelength:220 nm; Column temperature: 40° C.; System back pressure: 100 bar).

Intermediate 149-1a: The compound (R)-6-(4-((2,3-dihydrobenzo[b][1,4]dioxin-5-yl)methyl)-2-(2-isopropylphenyl)piperazin-1-yl)-2-azaspiro[3.3]heptane (205 mg, 0.56 mmol, yield: 40%, purity: 95%) was obtained as a white solid (faster peak, retention time: 1.23 min). $^1$H NMR (400 MHz, $CDCl_3$) δ ppm: 7.40-7.39 (m, 1H), 7.31-7.27 (m, 2H), 7.17-7.09 (m, 1H), 6.93-6.79 (m, 3H), 4.25 (s, 4H), 4.07-3.93 (m, 2H), 3.92-3.81 (m, 2H), 3.79-3.64 (m, 3H), 3.34-3.22 (m, 2H), 3.15-3.04 (m, 1H), 2.95 (m, 1H), 2.82-2.69 (m, 2H), 2.66-2.52 (m, 2H), 2.29-2.19 (m, 1H), 2.16-2.06 (m, 1H), 1.72-1.61 (m, 1H), 1.46-1.34 (m, 1H), 1.27 (m, 4H), 1.23 (br d, J=6.4 Hz, 3H), 1.18 (d, J=6.8 Hz, 3H), 0.95-0.79 (m, 1H). MS (ESI, m/e) [M+1]$^+$448.5.

Intermediate 149-1b: The compound (S)-6-(4-((2,3-dihydrobenzo[b][1,4]dioxin-5-yl)methyl)-2-(2-isopropylphenyl)piperazin-1-yl)-2-azaspiro[3.3]heptane (155 mg, 0.34 mmol, yield: 31%, purity: 85%) was obtained as a white solid (slower peak, retention time: 1.29 min). $^1$H NMR (400 MHz, $CDCl_3$) δ ppm: 7.51-7.40 (m, 1H), 7.25-7.16 (m, 2H), 7.14-7.05 (m, 1H), 6.94-6.86 (m, 1H), 6.80-6.69 (m, 2H), 4.23-4.22 (m, 4H), 3.70-3.62 (m, 1H), 3.60-3.51 (m, 2H), 3.46-3.31 (m, 2H), 3.04-2.83 (m, 4H), 2.75-2.64 (m, 2H), 2.45-2.17 (m, 3H), 2.01-1.82 (m, 4H), 1.64-1.51 (m, 1H), 1.25-1.21 (m, 3H), 1.16 (t, J=6.4 Hz, 3H), 0.66 (d, J=6.0 Hz, 1H). MS (ESI, m/e) [M+1]$^+$448.6.

Intermediate 150-1: 2-(2-isopropylphenyl)-N-(4-methoxyphenyl)-N-methyl-1-(7-azaspiro[3.5]nonan-2-yl)piperidin-4-amine Intermediate 150-1

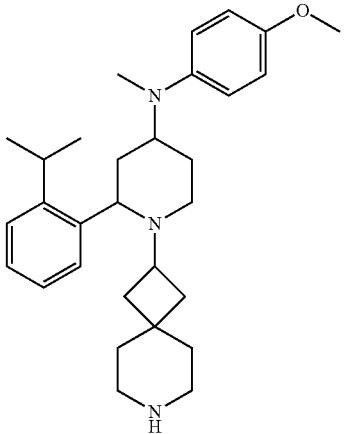

The synthesis procedures were similar to Intermediate 105-1. The compound 2-(2-isopropylphenyl)-N-(4-methoxyphenyl)-N-methyl-1-(7-azaspiro[3.5]nonan-2-yl)piperidin-4-amine was a yellow solid. $^1$H NMR (400 MHz, $CDCl_3$) δ ppm: 7.50-7.48 (m, 1H), 7.23-7.15 (m, 2H), 7.14-7.07 (m, 1H), 7.06-7.04 (m, 1H), 6.86-6.77 (m, 3H), 3.97-3.96 (m, 1H), 3.78-3.74 (m, 3H), 3.35-3.27 (m, 1H), 3.26-3.18 (m, 1H), 2.97-2.96 (m, 1H), 2.87-2.80 (m, 1H), 2.74 (s, 1H), 2.68 (s, 3H), 2.65-2.64 (m, 1H), 2.62-2.60 (m, 2H), 2.04-1.97 (m, 1H), 1.93-1.83 (m, 3H), 1.82-1.76 (m, 2H), 1.74-1.63 (m, 2H), 1.40-1.29 (m, 5H), 1.29-1.25 (m, 2H), 1.22 (d, J=6.8 Hz, 3H), 1.17 (br s, 1H), 1.01 (d, J=6.8 Hz, 2H). MS (ESI, m/e) [M+1]+462.6.

Intermediate 152-1: 2-(4-(3-fluoro-4,5-dimethoxybenzyl)-2-(2-isopropylphenyl)piperazin-1-yl)-7-azaspiro[3.5]nonane Intermediate 152-1

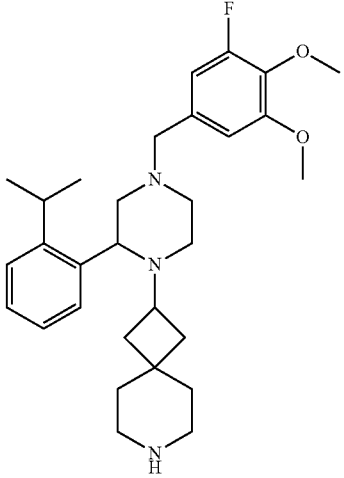

The synthesis procedures were similar to Intermediate 4-1. The compound 2-(4-(3-fluoro-4,5-dimethoxybenzyl)-2-(2-isopropylphenyl)piperazin-1-yl)-7-azaspiro[3.5]nonane was a light yellow solid. $^1$H NMR (400 MHz, CDCl$_3$) δ ppm: 7.49-7.47 (m, 1H), 7.26-7.18 (m, 2H), 7.16-7.08 (m, 1H), 6.74-6.66 (m, 2H), 3.88-3.86 (m, 6H), 3.71-3.59 (m, 2H), 3.49-3.35 (m, 3H), 3.05-2.89 (m, 3H) 2.69-2.51 (m, 5H) 2.34-2.27 (m, 2H), 2.18-2.14 (m, 1H), 1.72-1.62 (m, 3H), 1.45-1.32 (m, 4H), 1.15 (d, J=6.8 Hz, 4H), 0.96-0.94 (m, 1H). MS (ESI, m/e) [M+1]$^+$496.6.

Intermediate 154-1: 2-(2-(2-isopropylphenyl)-4-((5-methoxypyrazin-2-yl)methyl)piperazin-1-yl)-7-azaspiro[3.5]nonane

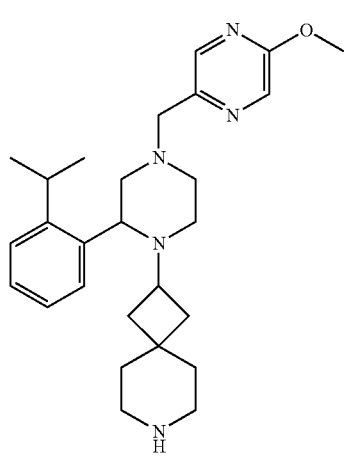

Intermediate 154-1

The synthesis procedures were similar to Intermediate 4-1. The compound 2-(2-(2-isopropylphenyl)-4-((5-methoxypyrazin-2-yl)methyl)piperazin-1-yl)-7-azaspiro[3.5]nonane was a white solid. $^1$H NMR (400 MHz, CDCl$_3$) δ ppm: 8.20 (d, J=1.6 Hz, 1H), 8.14-8.10 (m, 1H), 8.06 (d, J=1.2 Hz, 1H), 7.49 (br s, 1H), 7.26-7.19 (m, 2H), 7.15-7.08 (m, 1H), 3.95 (s, 3H), 3.75-3.53 (m, 3H), 3.47-3.26 (m, 1H), 3.04-2.84 (m, 3H), 2.73-2.58 (m, 5H), 2.44-2.25 (m, 3H), 1.81-1.71 (m, 1H), 1.70-1.62 (m, 1H), 1.48-1.32 (m, 4H), 1.29-1.20 (m, 5H), 1.15 (d, J=6.8 Hz, 4H). MS (ESI, m/e) [M+1]$^+$405.6.

Intermediate 175-1: 1-(3,4-bis(methoxy-d$_3$)benzyl)-3-(2-isopropylphenyl)piperazine

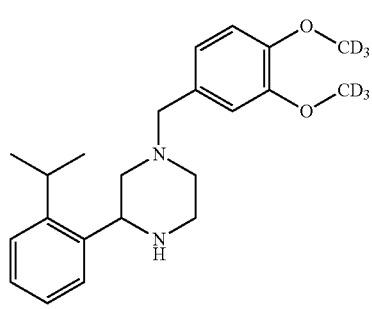

Intermediate 178-1

Step 1: 3,4-bis(methoxy-d$_3$)benzaldehyde.

A mixture of 3,4-dihydroxybenzaldehyde (1.2 g, 8.7 mmol) and K$_2$CO$_3$ (6.0 g, 43.4 mmol) and CD$_3$1 (2.72 g, 19.11 mmol) in CH$_3$CN (40 mL) was stirred at 70° C. for 2 hrs. The mixture was added water (20 mL), extracted with Ethyl acetate (20 mL×2). The combined organic layers were washed with brine (50 mL), dried over anhydrous Na$_2$SO$_4$, filtered and concentrated under reduced pressure. The crude product was purified by column chromatography (silica gel, eluent: PE/EA (v/v)=5/1) to give 3,4-dimethoxy-d$_3$-benzaldehyde (1.0 g, yield: 80%) as a colorless oil. $^1$H NMR (400 MHz, CDCl$_3$) δ ppm: 9.78 (s, 1H), 7.47-7.45 (m, 2H), 7.41 (d, J=0.8 Hz, 1H), 6.99-6.97 (d, J=8.4 Hz, 2H).

Step 2: 1-(3,4-bis(methoxy-d3)benzyl)-3-(2-isopropylphenyl)piperazine.

A mixture of 2-(2-isopropylphenyl)piperazine (0.5 g, 2.45 mmol) and 3,4-dimethoxy-d3-benzaldehyde (0.44 g, 2.45 mmol) and NaBH(OAc)$_3$ (1.04 g, 4.5 mmol), in DCM (10 mL) was stirred at 20° C. for 2 hrs. The mixture was adjusted pH=9 with K$_2$CO$_3$ solution, extracted with DCM (20 mL×2). The combined organic layers were washed with brine, dried over anhydrous Na$_2$SO$_4$, filtered and concentrated under reduced pressure. The crude product was purified by column chromatography (silica gel, eluent: EA) to give 1-(3,4-dimethoxy-d$_3$-benzyl)-3-(2-isopropylphenyl)piperazine (0.4 g, yield: 40%) as a yellow oil. $^1$H NMR (400 MHz, CDCl$_3$) δ ppm: 7.53-7.51 (m, 1H), 7.24-7.12 (m, 3H), 6.90-6.89 (m, 1H), 6.82-6.75 (m, 2H), 4.19-4.17 (m, 1H), 3.54-3.41 (m, 2H), 3.26-3.24 (m, 1H), 3.11-3.09 (m, 2H), 2.85-2.76 (m, 2H), 2.22-2.12 (m, 1H), 1.99-1.94 (m, 2H), 1.24-1.20 (d, J=6.8 Hz, 3H), 1.13-1.11 (d, J=6.8 Hz, 3H). MS (ESI, m/e) [M+1]$^+$361.2.

Intermediate 178-1: 2-(4-(3-cyclopropoxybenzyl)-2-(2-isopropylphenyl)piperazin-1-yl)-7-azaspiro[3.5]nonane

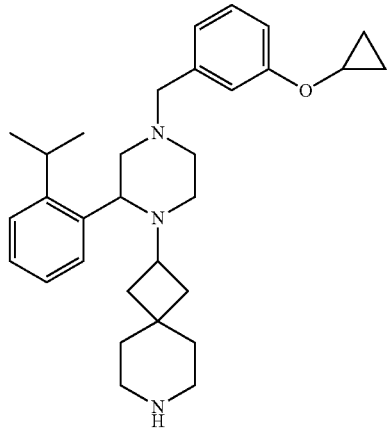

Intermediate 178-1

The synthesis procedures were similar to Intermediate 149-1. The compound 2-(4-(3-cyclopropoxybenzyl)-2-(2-isopropylphenyl)piperazin-1-yl)-7-azaspiro[3.5]nonane was an off-white solid. $^1$H NMR (400 MHz, CDCl$_3$) δ ppm: 7.53-7.41 (m, 1H), 7.26-7.17 (m, 3H), 7.15-7.09 (m, 1H), 7.01-6.99 (m, 1H), 6.95-6.89 (m, 2H), 3.76-3.71 (m, 1H), 3.69-3.62 (m, 1H), 3.54-3.49 (m, 2H), 3.45-3.30 (m, 1H), 3.04-2.87 (m, 3H), 2.72-2.56 (m, 5H), 2.37-2.24 (m, 2H), 2.22-2.15 (m, 1H), 1.75-1.71 (m, 1H), 1.69-1.67 (m, 1H), 1.41-1.29 (m, 5H), 1.28-1.22 (m, 4H), 1.19-1.10 (m, 4H), 0.79-0.72 (m, 4H). MS (ESI, m/e) [M+1]$^+$474.3.

Intermediate 182-1: 1-((benzo[d][1,3]dioxol-5-yl-2,2-d2)methyl)-3-(2-isopropylphenyl)piperazine

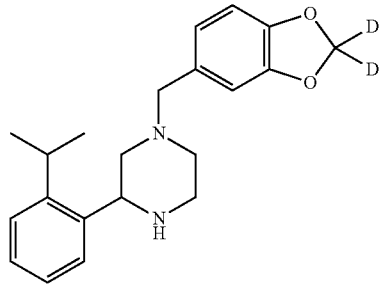

Intermediate 182-1

Step 1: benzo[d][1,3]dioxole-2,2-d2-5-carbaldehyde

A mixture of 3,4-dihydroxybenzaldehyde (0.5 g, 3.6 mmol) and Cs$_2$CO$_3$ (5.9 g, 18.1 mmol) and CD$_2$Cl$_2$ (1.0 g, 11 mmol) in DMSO (5 mL) was stirred at 130° C. for 2 hrs. The mixture was added water (20 mL), extracted with Ethyl acetate (20 mL×2). The combined organic layers were washed with brine (50 mL), dried over anhydrous Na$_2$SO$_4$, filtered and concentrated under reduced pressure. The crude product was purified by column chromatography (silica gel, eluent: PE/EA (v/v)=5/1) to give benzo[d][1,3]dioxole-d2-5-carbaldehyde (0.5 g, yield: 92%) as a colorless oil.

Step 2: 1-((benzo[d][1,3]dioxol-5-yl-2,2-d2)methyl)-3-(2-isopropylphenyl)piperazine A mixture of 2-(2-isopropylphenyl)piperazine (0.5 g, 2.45 mmol) and benzo[d][1,3]dioxole-d2-5-carbaldehyde (0.42 g, 2.45 mmol) and NaBH(OAc)$_3$ (1.04 g, 4.5 mmol), in DCM (10 mL) was stirred at 20° C. for 2 hrs. The mixture was adjusted pH=9 by K$_2$CO$_3$ solution, extracted with DCM (20 mL×2). The combined organic layers were washed with brine, dried over anhydrous Na$_2$SO$_4$, filtered and concentrated under reduced pressure. The crude product was purified by column chromatography (silica gel, eluent: EA) to give 1-((benzo[d][1,3]dioxol-5-yl-2,2-d2)methyl)-3-(2-isopropylphenyl)piperazine (0.47 g, yield: 74%) as a brown oil. $^1$H NMR (400 MHz, CDCl$_3$) δ ppm: 7.59-7.57 (m, 1H), 7.29-7.20 (m, 2H), 7.16-7.14 (m, 1H), 6.84 (s, 1H), 6.82-6.75 (m, 2H), 4.33-4.30 (m, 1H), 3.54-3.48 (m, 2H), 3.38-3.34 (m, 1H), 3.15-3.09 (m, 1H), 2.86-2.82 (m, 1H), 2.38-2.36 (m, 1H), 2.25-2.21 (m, 1H), 2.02-2.00 (m, 1H), 1.26-1.23 (d, J=6.8 Hz, 3H), 1.13-1.12 (d, J=6.8 Hz, 3H). MS (ESI, m/e) [M+1]$^+$341.2.

Intermediate 186-1: 2-(4-(3-cyclopropoxy-4-methoxybenzyl)-2-(2-isopropylphenyl)piperazin-1-yl)-7-azaspiro[3.5]nonane

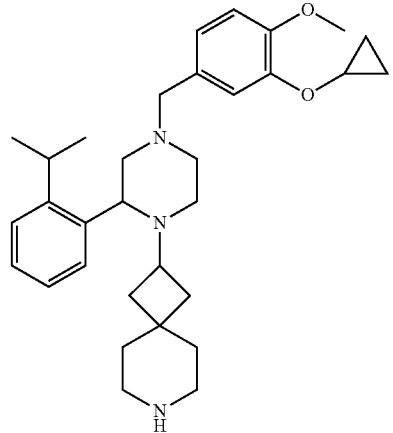

Intermediate 186-1

The synthesis procedures were similar to Intermediate 149-1. The compound 2-(4-(3-cyclopropoxy-4-methoxybenzyl)-2-(2-isopropylphenyl)piperazin-1-yl)-7-azaspiro [3.5]nonane was a yellow oil. $^1$H NMR (400 MHz, CDCl$_3$) δ ppm: 7.56-7.43 (m, 1H), 7.26-7.18 (m, 3H), 7.15-7.09 (m, 1H), 6.86-6.81 (m, 1H), 6.79-6.75 (m, 1H), 3.86-3.81 (m, 3H), 3.77-7.75 (m, 1H), 3.69-3.60 (m, 1H), 3.49 (s, 2H), 3.39 (s, 1H), 3.05-2.98 (m, 1H), 2.95-2.88 (m, 2H), 2.70-2.54 (m, 5H), 2.36-2.25 (m, 2H), 2.23-2.12 (m, 1H), 1.81-1.72 (m, 11H), 1.70-1.63 (m, 3H), 1.41-1.29 (m, 5H), 1.26 (d, J=6.8 Hz, 3H), 1.15 (d, J=6.8 Hz, 3H), 0.87-0.81 (m, 2H), 0.81-0.75 (m, 2H). MS (ESI, m/e) [M+1]$^+$503.4.

Intermediate 193-1: 2-(4-((3,4-dimethoxyphenyl)methyl-d2)-2-(2-isopropylphenyl)piperazin-1-yl)-7-azaspiro[3.5]nonane

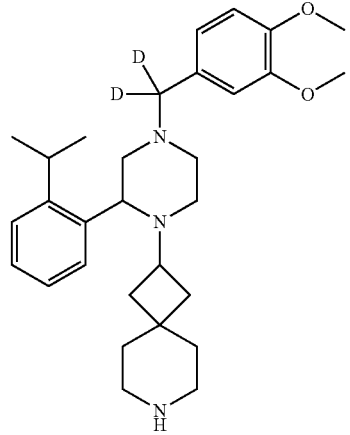

Intermediate 193-1

Step 1: methyl 3,4-dimethoxybenzoate

To a solution of 3,4-dimethoxybenzoic acid (2.0 g, 10.98 mmol) in MeOH (20 mL) was added H$_2$SO$_4$ (3.23 g, 32.94 mmol). The solution was stirred at 80° C. for 2 hrs. The reaction was concentrated under reduced pressure. The residue was poured into saturated NaHCO$_3$ (20 mL), extracted with EtOAc (40 mL×3). The combined organic layers were washed with brine, dried over Na₂SO₄, filtered and concentrated under reduced pressure. The residue was purified by column chromatography (silica gel, eluent: PE/EA (v/v)=5/1 to 1/1) to give 3,4-dimethoxybenzoate (2.0 g, yield: 93%) as a yellow solid. H NMR (400 MHz, CDC₃) δ ppm: 7.70-7.68 (m, 1H), 7.55 (d, J=2.0 Hz, 1H), 6.91-6.88 (m, 1H), 3.94 (d, 6H), 3.90 (s, 3H).

Step 2: (3,4-dimethoxyphenyl)methan-d2-ol

To a solution of 3,4-dimethoxybenzoate (2.0 g, 10.19 mmol) in DCM (10 mL) was added LiAlD₄ (513.35 mg, 12.23 mmol) at 0° C. The solution was stirred at 20° C. for 2 hrs. The reaction was quenched by saturated NH₄Cl (30 mL), extracted with EA (10 mL×3). The combined organic layers were washed with brine, dried over Na₂SO₄, filtered and concentrated under reduced pressure. The residue was purified by column chromatography (silica gel, eluent: PE/EA (v/v)=5/1 to 2/1) to give (3,4-dimethoxyphenyl)methan-d2-ol (1.3 g, yield: 79%) as a yellow solid. ¹H NMR (400 MHz, CDCl₃) δ ppm: 6.96-6.83 (m, 3H), 4.64-4.59 (m, 1H), 3.90-3.89 (in, 6H).

Step 3: (3,4-dimethoxyphenyl)methyl-d₂ methanesulfonate

To a solution of (3,4-dimethoxyphenyl)methan-d2-ol (1.3 g, 7.64 mmol) in DCM (103 mL) was added TEA (2.32 g, 22.91 mmol) and MsCl (1.31 g, 11.46 mmol) at 0° C. The reaction was poured into aqueous NH4Cl (30 mL), extracted with DCM (30 mL×3). The combined organic layers were washed with brine, dried over Na₂SO₄, filtered and concentrated under reduced pressure to give (3,4-dimethoxyphenyl)methyl-d₂ methanesulfonate (1.9 g, crude) as a yellow oil, which was used directly for next step without further purification.

Step 4: tert-butyl 2-(4-((3,4-dimethoxyphenyl)methyl-d2)-2-(2-isopropylphenyl)piperazin-1-yl)-7-azaspiro[3.5]nonane-7-carboxylate To a solution of tert-butyl 2-(2-(2-isopropylphenyl)-6-oxopiperazin-1-yl)-7-azaspiro[3.5]nonane-7-carboxylate (1.0 g, 2.26 mmol) in DMA (10 mL) was added K₂CO₃ (625.92 mg, 4.53 mmol) and (3,4-dimethoxyphenyl)methyl-d₂ methanesulfonate (618.47 mg, 2.49 mmol). The mixture was stirred at 80° C. for 3 hrs. The reaction was poured into H₂O (50 mL), extracted with DCM (30 mL×3). The combined organic layers were washed with brine, dried over Na₂SO₄, filtered and concentrated under reduced pressure. The residue was purified by column chromatography (silica gel, eluent: PE/EA (v/v)=10/1 to 2/1) to give tert-butyl 2-(4-((3,4-dimethoxyphenyl)methyl-d₂)-2-(2-isopropylphenyl)piperazin-1-yl)-7-azaspiro[3.5]nonane-7-carboxylate (0.835 g, yield: 62%) as a yellow oil.

Step 5: 2-(4-((3,4-dimethoxyphenyl)methyl-d2)-2-(2-isopropylphenyl)piperazin-1-yl)-7-azaspiro[3.5]nonane.

To a solution of tert-butyl 2-(4-((3,4-dimethoxyphenyl)methyl-d2)-2-(2-isopropylphenyl)piperazin-1-yl)-7-azaspiro[3.5]nonane-7-carboxylate (0.835 g, 1.44 mmol) in MeOH (3.6 mL) was added HCl/MeOH (3.6 mL, 4M). The solution was stirred at 25° C. for 2 hrs. The mixture was concentrated under reduced pressure. The residue was poured into saturated Na₂CO3 (30 mL), extracted with DCM (20 mL×3). The combined organic layers were washed with brine, dried over Na₂SO₄, filtered and concentrated under reduced pressure to give 2-(4-((3,4-dimethoxyphenyl)methyl-d₂)-2-(2-isopropylphenyl)piperazin-1-yl)-7-azaspiro[3.5]nonane (425 mg, yield: 62%) as a yellow solid. ¹H NMR (400 MHz, CDCl₃) δ ppm: 7.48 (br s, 1H), 7.24-7.09 (m, 3H), 6.89 (s, 1H), 6.84-6.74 (m, 2H), 3.88-3.85 (m, 6H), 3.65-3.64 (m, 1H), 3.43-3.38 (m, 1H), 3.06- 2.97 (m, 1H), 2.91-2.90 (m, 2H), 2.68-2.55 (m, 5H), 2.34-2.24 (m, 2H), 2.18-2.16 (m, 1H), 1.75-1.62 (m, 4H), 1.33-1.30 (m, 5H), 1.27-1.25 (m, 3H), 1.15-1.13 (m, 3H). MS (ESI, m/e) [M+1]⁺480.4.

Intermediate 194-1: 2-(4-((5,6-dimethoxypyridin-2-yl)methyl)-2-(2-isopropylphenyl)piperazin-1-yl)-7-azaspiro[3.5]nonane

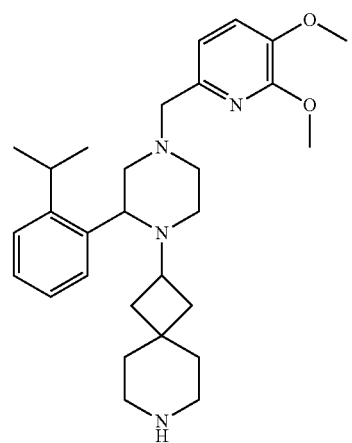

Intermediate 194-1

Step 1: 6-iodo-2,3-dimethoxypyridine

To a solution of 2-bromo-6-iodo-3-methoxypyridine (2.5 g, 7.96 mmol) in DMF (20 mL) was added MeONa (602.33 mg, 11.15 mmol, 5.4 M) at 20° C. The solution was stirred at 100° C. for 2 hrs. The reaction was added H₂O (50 mL), extracted with MTBE (50 mL×3). The combined organic layers were washed with brine, dried over Na₂SO₄, filtered and concentrated under reduced pressure. The residue was purified by column chromatography (silica gel, eluent: PE/EA (v/v)=50/1 to 10/1) to give 6-iodo-2,3-dimethoxypyridine (2.5 g, yield: 85%) as a white oil.

Step 2: 5,6-dimethoxypicolinaldehyde

To a solution of 6-iodo-2,3-dimethoxypyridine (2.4 g, 9.05 mmol) in THE (20 mL) was added n-BuLi (4.35 mL, 10.87 mmol, 2.5 M) at −70° C. The solution was stirred at −70° C. for 0.5 hr. DMF (1.99 g, 27.16 mmol) was added in drops at −70° C. The solution was stirred at −70° C. for 1.5 hrs. The reaction was added saturated NH₄Cl (20 mL), extracted with EtOAc (50 mL×3). The combined organic layers were washed with brine, dried over Na₂SO₄, filtered and concentrated under reduced pressure. The residue was purified by column chromatography (silica gel, eluent: PE/EA (v/v)=30/1 to 5/1) to give 5,6-dimethoxypicolinaldehyde (1.0 g, yield: 66%) as a white solid.

Step 3: tert-butyl 2-(4-((5,6-dimethoxypyridin-2-yl)methyl)-2-(2-isopropylphenyl)piperazin-1-yl)-7-azaspiro[3.5]nonane-7-carboxylate To a solution of tert-butyl 2-(2-(2-isopropylphenyl)piperazin-1-yl)-7-azaspiro[3.5]nonane-7-carboxylate (1.0 g, 2.34 mmol) and 5,6-dimethoxypicolinaldehyde (390.91 mg, 2.34 mmol) in DCM (15 mL) was added AcOH (280.86 mg, 4.68 mmol) and NaBH(OAc)₃ (991.25 mg, 4.68 mmol). The solution was stirred at 20° C. for 12 hrs. The reaction was added saturated NaHCO₃ until pH=7, extracted with DCM (10 mL×3). The combined organic layers were washed with brine, dried over Na₂SO₄, filtered and concentrated under reduced pressure. The residue was purified by column chromatography ((silica gel, eluent: PE/EA (v/v)=20/1 to EA) to give tert-butyl 2-(4-((5,6-dimethoxypyridin-2-yl)methyl)-2-(2-isopropylphenyl)piperazin-1-yl)-7-azaspiro[3.5]nonane-7-carboxylate (790 mg, yield: 58%) as a brown oil.

Step 4: 2-(4-((5,6-dimethoxypyridin-2-yl)methyl)-2-(2-isopropylphenyl)piperazin-1-yl)-7-azaspiro[3.5]nonane.

To a solution of tert-butyl 2-(4-((5,6-dimethoxypyridin-2-yl)methyl)-2-(2-isopropylphenyl) piperazin-1-yl)-7-azaspiro[3.5]nonane-7-carboxylate (740 mg, 1.28 mmol) in DCM (2 mL) was added TFA (10 mL). The solution was stirred at 20° C. for 2 hrs. The mixture was concentrated under reduced pressure. The residue was poured into aq. Na$_2$CO$_3$ (30 mL), extracted with DCM (20 mL×3). The combined organic layers were washed with brine, dried over Na$_2$SO$_4$, filtered and concentrated under reduced pressure to give 2-(4-((5,6-dimethoxypyridin-2-yl)methyl)-2-(2-isopropylphenyl)piperazin-1-yl)-7-azaspiro[3.5]nonane (510 mg, yield: 83%) as a white oil. $^1$H NMR (400 MHz, CDCl$_3$) δ ppm: 7.54-7.42 (m, 1H), 7.26-7.18 (m, 2H), 7.15-7.09 (m, 1H), 6.98 (d, J=8.0 Hz, 1H), 6.88 (d, J=8.0 Hz, 1H), 3.99-3.95 (m, 3H), 3.85 (s, 3H), 3.74-3.64 (m, 1H), 3.57 (s, 2H), 3.40 (s, 1H), 3.01 (d, J=9.2 Hz, 2H), 2.93-2.89 (m, 1H), 2.74 (d, J=11.2 Hz, 1H), 2.71-2.55 (m, 4H), 2.51-2.24 (m, 5H), 1.84-1.72 (m, 1H), 1.71-1.64 (m, 1H), 1.45-1.32 (m, 4H), 1.25 (d, J=6.8 Hz, 3H), 1.17 (d, J=6.8 Hz, 3H). MS (ESI, m/e) [M+1]$^+$479.4.

Intermediate 200-1: 5-((3-(2-isopropylphenyl)-4-(7-azaspiro[3.5]nonan-2-yl)piperazin-1-yl)methyl)-4-methyl-3,4-dihydro-2H-benzo[b][1,4]oxazine

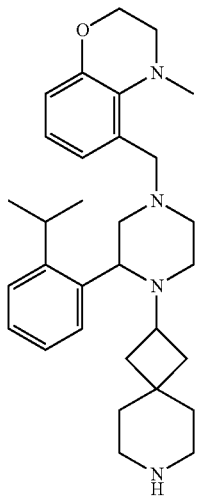

Intermediate 200-1

The synthesis procedures were similar to Intermediate 18-1. The compound 5-((3-(2-isopropylphenyl)-4-(7-azaspiro[3.5]nonan-2-yl)piperazin-1-yl)methyl)-4-methyl-3,4-dihydro-2H-benzo[b][1,4]oxazine was a white solid. $^1$H NMR (400 MHz, CDCl$_3$) δ ppm: 7.50 (br s, 1H), 7.24-7.18 (m, 2H), 7.14-7.10 (m, 1H), 7.06 (d, J=6.8 Hz, 1H), 6.88 (t, J=8.0 Hz, 1H), 6.74 (d, J=8.0 Hz, 1H), 4.17-4.15 (m, 2H), 3.62-3.60 (m, 1H), 3.54 (d, J=13.2 Hz, 2H), 3.43-3.32 (m, 1H), 3.07-3.03 (m, 2H), 3.00-2.98 (m, 2H), 2.94-2.88 (m, 1H), 2.78 (s, 3H), 2.75-2.60 (m, 6H), 2.43-2.33 (m, 2H), 2.31-2.20 (m, 3H), 1.76 (d, J=2.4 Hz, 1H), 1.70 (d, J=9.2 Hz, 1H), 1.42-1.34 (m, 4H), 1.27 (d, J=6.8 Hz, 3H), 1.15 (d, J=6.8 Hz, 3H). MS (ESI, m/e) [M+1]489.4

Intermediate 201-1: 2-(4-((2,2-dimethylbenzo[d][1,3]dioxol-4-yl)methyl)-2-(2-isopropylphenyl)piperazin-1-yl)-7-azaspiro[3.5]nonane

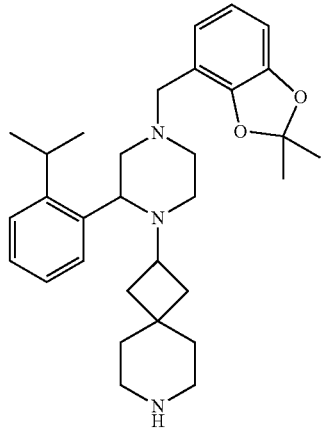

Intermediate 201-1

The synthesis procedures were similar to Intermediate 149-1. The compound 2-(4-((2,2-dimethylbenzo[d][1,3]dioxol-4-yl)methyl)-2-(2-isopropylphenyl)piperazin-1-yl)-7-azaspiro[3.5]nonane was a white solid. $^1$H NMR (400 MHz, CDCl$_3$) δ ppm: 7.43 (br d, J=4.4 Hz, 1H), 7.26-7.18 (m, 2H), 7.12-7.07 (m, 1H), 6.79-6.69 (m, 2H), 6.62 (d, J=7.6 Hz, 1H), 4.85-4.42 (m, 2H), 3.65 (br d, J=8.4 Hz, 1H), 3.57 (s, 2H), 3.47-3.29 (m, 1H), 3.02-2.85 (m, 3H), 2.83-2.65 (m, 5H), 2.42-2.24 (m, 3H), 1.79 (d, J=3.6 Hz, 1H), 1.72-1.66 (m, 1H), 1.60 (s, 6H), 1.52-1.41 (m, 4H), 1.35-1.29 (m, 1H), 1.24 (d, J=6.8 Hz, 3H), 1.17 (d, J=6.8 Hz, 3H). MS (ESI, m/e) [M+1]$^+$490.6.

Intermediate 203-1: 2-(2-(2-isopropylphenyl)-4-((8-methoxy-2,3-dihydrobenzo[b][1,4]dioxin-5-yl)methyl)piperazin-1-yl)-7-azaspiro[3.5]nonane

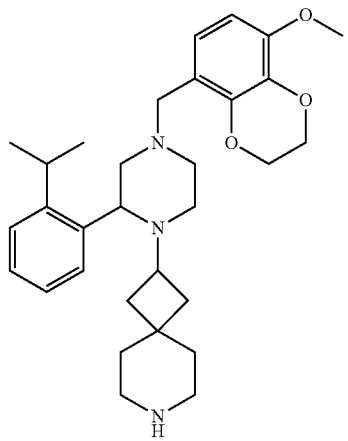

Intermediate 203-1

The synthesis procedures were similar to Intermediate 149-1. The compound 2-(2-(2-isopropylphenyl)-4-((8- methoxy-2,3-dihydrobenzo[b][1,4]dioxin-5-yl)methyl)piperazin-1-yl)-7-azaspiro[3.5]nonane was a yellow solid. ¹H NMR (400 MHz, CDCl₃) δ ppm: 7.45 (br s, 1H), 7.27-7.18 (m, 2H), 7.15-7.07 (m, 1H), 6.80 (d, J=8.4 Hz, 1H), 6.44 (d, J=8.4 Hz, 1H), 4.34-4.27 (m, 2H), 4.26-4.20 (m, 2H), 3.85 (s, 3H), 3.68-3.65 (m, 1H), 3.59-3.47 (m, 2H), 3.37 (br s, 1H), 3.00-2.68 (m, 8H), 2.41-2.19 (m, 3H), 1.80 (br s, 1H), 1.74-1.67 (m, 1H), 1.63-1.45 (m, 4H), 1.36-1.27 (m, 1H), 1.25-1.21 (d, J=6.8 Hz, 3H), 1.17 (d, J=6.8 Hz, 3H). MS (ESI, m/e) [M+1]⁺506.3.

Intermediate 212-1: 1-(5-((3-(2-isopropylphenyl)-4-(7-azaspiro[3.5]nonan-2-yl)piperazin-1-yl)methyl)-2-methoxyphenyl)ethan-1-one

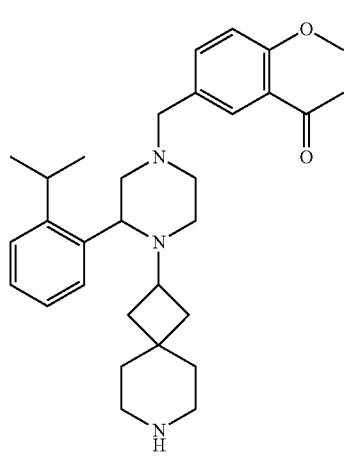

Intermediate 212-1

The synthesis procedures were similar to Intermediate 149-1. The compound 1-(5-((3-(2-isopropylphenyl)-4-(7-azaspiro[3.5]nonan-2-yl)piperazin-1-yl)methyl)-2-methoxyphenyl)ethan-1-one was a yellow oil. ¹H NMR (400 MHz, CDCl₃) δ ppm: 7.66 (s, 1H), 7.50-7.39 (m, 2H), 7.24-7.18 (m, 2H), 7.15-7.07 (m, 1H), 6.89 (d, J=8.4 Hz, 1H), 3.89 (s, 3H), 3.64 (d, J=10.8 Hz, 1H), 3.47 (s, 2H), 3.38 (s, 1H), 3.04-2.86 (m, 4H), 2.64 (s, 4H), 2.60 (s, 3H), 2.28 (s, 2H), 2.23-2.15 (m, 1H), 1.75-1.62 (m, 4H), 1.38-1.28 (m, 5H), 1.25 (d, J=6.8 Hz, 3H), 1.14 (d, J=6.8 Hz, 3H). MS (ESI, m/e) [M+1]⁺490.4

Intermediate 213-1: 2-(4-(benzofuran-4-ylmethyl)-2-(2-isopropylphenyl)piperazin-1-yl)-7-azaspiro[3.5]nonane

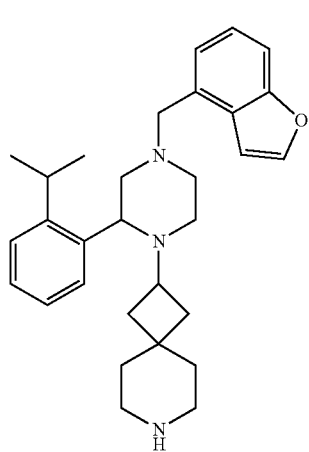

Intermediate 213-1

The synthesis procedures were similar to Intermediate 149-1. The compound 2-(4-(benzofuran-4-ylmethyl)-2-(2-isopropylphenyl)piperazin-1-yl)-7-azaspiro[3.5]nonane was a yellow solid. ¹H NMR (400 MHz, CDCl₃) δ ppm: 7.61 (d, J=2.4 Hz, 1H), 7.54-7.44 (m, 1H), 7.39 (d, J=8.0 Hz, 11H), 7.25-7.15 (m, 4H), 7.15-7.08 (m, 11H), 7.02 (d, J=1.6 Hz, 1H), 3.80-3.72 (m, 2H), 3.65 (br d, J=8.8 Hz, 1H), 3.44-3.25 (m, 1H), 3.04-2.85 (m, 3H), 2.77-2.54 (m, 5H), 2.42-2.17 (m, 3H), 1.81-1.62 (m, 2H), 1.44-1.28 (m, 5H), 1.25 (d, J=6.8 Hz, 3H), 1.16-1.14 (m, 1H), 1.08 (d, J=6.8 Hz, 3H). MS (ESI, m/e) [M+1]⁺458.3.

Intermediate 216-1: 5-((3-(2-isopropylphenyl)-4-(7-azaspiro[3.5]nonan-2-yl)piperazin-1-yl)methyl)-4-methyl-2H-benzo[b][1,4]oxazin-3(4H)-one

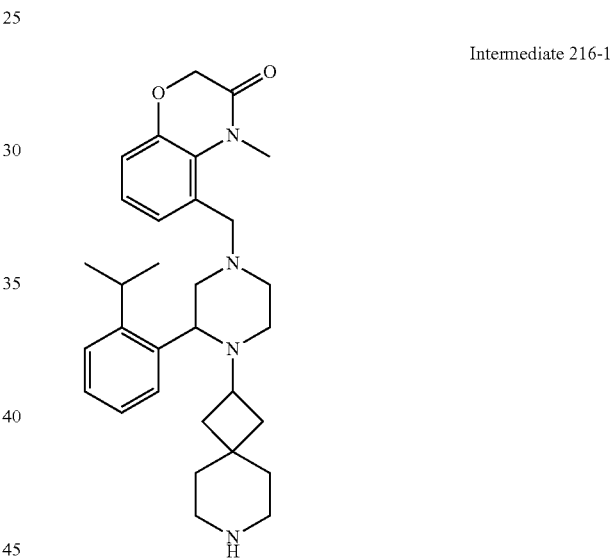

Intermediate 216-1

The synthesis procedures were similar to Intermediate 149-1. The compound 5-((3-(2-isopropylphenyl)-4-(7-azaspiro[3.5]nonan-2-yl)piperazin-1-yl)methyl)-4-methyl-2H-benzo[b][1,4]oxazin-3(4H)-one was a white solid. ¹H NMR (400 MHz, CDCl₃) δ ppm: 7.41 (br s, 1H), 7.23-7.14 (m, 2H), 7.12-7.07 (m, 1H), 7.05-7.03 (m, 1H), 7.00-6.93 (m, 2H), 4.51 (d, J=14.4 Hz, 1H), 4.35 (d, J=14.4 Hz, 1H), 3.73-3.66 (m, 1H), 3.53 (d, J=14.0 Hz, 1H), 3.43 (br s, 1H), 3.39 (s, 3H), 3.35-3.20 (m, 2H), 2.93 (br d, J=11.2 Hz, 1H), 2.88-2.79 (m, 2H), 2.46-2.33 (m, 5H), 2.25-2.18 (m, 1H), 2.15-2.08 (m, 1H), 1.99 (s, 1H), 1.79-1.49 (m, 3H), 1.21-1.17 (m, 5H), 1.17-1.11 (m, 3H), 1.03 (d, J=6.8 Hz, 3H). MS (ESI, m/e) [M+1]⁺503.4.

Intermediate 223-1: 2-((2R)-4-((3,4-dimethoxybicy-clo[4.2.0]octa-1(6),2,4-trien-7-yl)methyl)-2-(2-iso-propylphenyl)piperazin-1-yl)-7-azaspiro[3.5]nonane

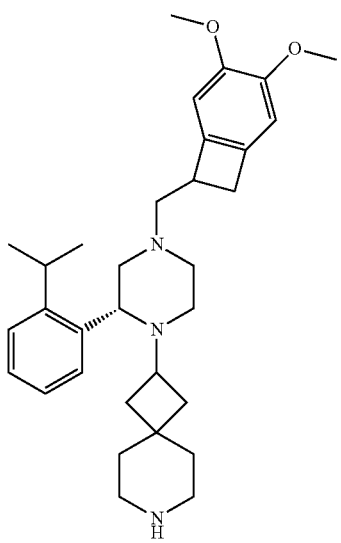
Intermediate 223-1

The synthesis procedures were similar to Intermediate 149-1. The compound 2-((2R)-4-((3,4-dimethoxybicyclo[4.2.0]octa-1(6),2,4-trien-7-yl)methyl)-2-(2-isopropylphenyl)piperazin-1-yl)-7-azaspiro[3.5]nonane was a white solid. $^1$H NMR (400 MHz, DMSO-d$_6$) δ ppm: 7.46-7.44 (m, 1H), 7.27-7.24 (m, 1H), 7.19 (t, J=7.2 Hz, 1H), 7.13-7.09 (m, 1H), 6.75-6.70 (m, 2H), 6.67 (s, 1H), 3.69-3.66 (m, 6H), 3.63 (s, 2H), 3.56-3.46 (m, 3H), 3.20-3.09 (m, 2H), 2.95-2.93 (m, 2H), 2.87 (d, J=7.6 Hz, 1H), 2.69-2.61 (m, 4H), 2.46-2.38 (m, 5H), 2.22-2.19 (m, 2H), 2.12-2.06 (m, 1H), 1.62 (s, 3H), 1.22 (d, J=6.8 Hz, 3H), 1.16 (d, J=6.8 Hz, 3H), 1.06 (s, 1H). MS (ESI, m/e) [M+1]$^+$504.3.

Intermediate 235-1: 2-(2-(5-fluoro-2-isopropylphe-nyl)-4-(4-methoxybenzyl)piperazin-1-yl)-7-azaspiro[3.5]nonane

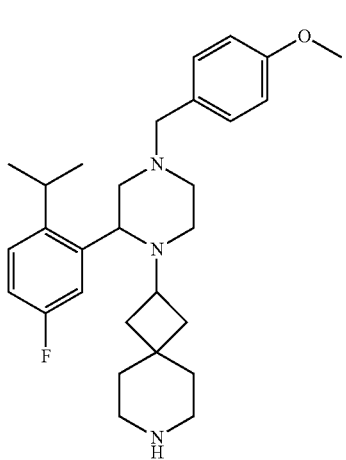
Intermediate 235-1

The compound 2-(2-(5-fluoro-2-isopropylphenyl)-4-(4-methoxybenzyl)piperazin-1-yl)-7-azaspiro[3.5]nonane was a yellow solid. $^1$H NMR (400 MHz, CDCl$_3$) δ ppm: 7.27-7.17 (m, 4H), 6.89-6.82 (m, 3H), 3.79 (s, 3H), 3.62-3.60 (m, 2H), 3.46-3.45 (m, 2H), 3.35-3.25 (m, 1H), 2.89-2.82 (m, 3H), 2.66-2.59 (m, 5H), 2.27-2.26 (m, 2H), 2.10-2.05 (m, 1H), 1.36-1.31 (m, 5H), 1.23-1.21 (d, J=6.8 Hz, 3H), 1.13-1.11 (d, J=6.8 Hz, 3H). MS (ESI, m/e) [M+1]$^+$466.2.

Intermediate 239-1: (R)-2-(2-(2-isopropylphenyl)-4-((7-methoxy-2,3-dihydrobenzofuran-5-yl)methyl)piperazin-1-yl)-7-azaspiro[3.5]nonane

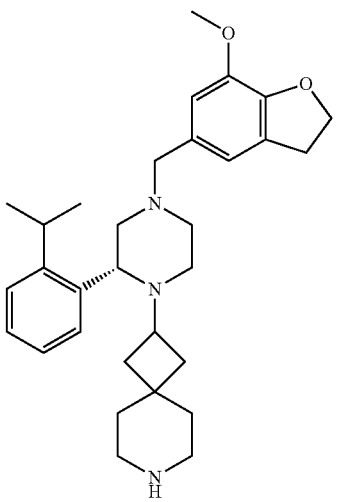
Intermediate 239-1

The compound (R)-2-(2-(2-isopropylphenyl)-4-((7-methoxy-2,3-dihydrobenzofuran-5-yl)methyl)piperazin-1-yl)-7-azaspiro[3.5]nonane was a yellow oil. $^1$H NMR (400 MHz, CDCl$_3$) δ ppm: 7.56-7.43 (m, 1H), 7.26-7.23 (m, 2H), 7.16-7.09 (m, 1H), 6.74 (d, J=14.8 Hz, 2H), 4.60 (t, J=8.8 Hz, 2H), 3.86 (s, 3H), 3.70-3.60 (m, 1H), 3.44 (d, J=2.8 Hz, 2H), 3.18 (t, J=8.8 Hz, 2H), 3.02 (d, J=5.6 Hz, 1H), 3.06-2.82 (m, 3H), 2.70-2.56 (m, 5H), 2.34-2.25 (m, 2H), 2.15 (t, J=10.0 Hz, 1H), 1.78-1.75 (m, 1H), 1.67 (s, 3H), 1.41-1.29 (m, 5H), 1.26 (d, J=6.8 Hz, 3H), 1.15 (d, J=6.8 Hz, 3H). MS (ESI, m/e) [M+1]$^+$490.3.

Intermediate 241-1: (R)-3-(2-isopropylphenyl)-1-((5-methoxypyridin-2-yl)methyl)piperazine

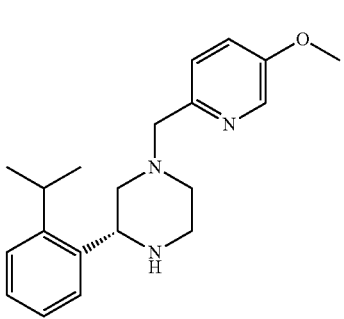
Intermediate 241-1

The synthesis procedures were similar to Intermediate 182-1. The compound (R)-3-(2-isopropylphenyl)-1-((5-methoxypyridin-2-yl)methyl)piperazine was a yellow oil. ¹H NMR (400 MHz, CDCl₃) δ ppm: 8.28 (d, J=2.8 Hz, 1H), 7.57-7.52 (m, 1H), 7.31 (d, J=8.4 Hz, 1H), 7.27-7.20 (m, 2H), 7.19-7.14 (m, 2H), 4.29-4.26 (m, 1H), 3.88-3.82 (m, 3H), 3.67 (d, J=2.0 Hz, 2H), 3.30-3.26 (m, 1H), 3.20-3.09 (m, 2H), 2.94-2.82 (m, 2H), 2.35-2.30 (m, 1H), 2.17-2.12 (m, 1H), 1.23 (d, J=6.8 Hz, 3H), 1.16 (d, J=6.8 Hz, 3H). MS (ESI, m/e) [M+1]⁺326.1.

Intermediate 247-1: 2-(2-(5-chloro-2-isopropylphenyl)-4-(4-methoxybenzyl)piperazin-1-yl)-7-azaspiro[3.5]nonane Intermediate 247-1

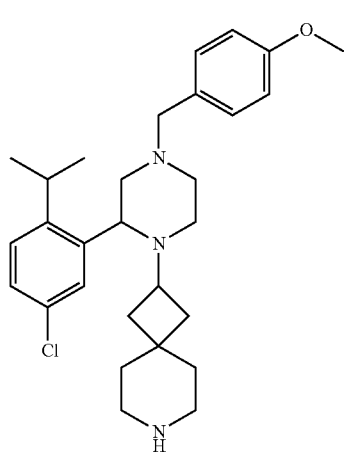

The compound 2-(2-(5-chloro-2-isopropylphenyl)-4-(4-methoxybenzyl)piperazin-1-yl)-7-azaspiro[3.5]nonane was a yellow oil. ¹H NMR (400 MHz, CDCl₃) δ ppm: 7.27 (s, 1H), 7.22-7.20 (m, 2H), 7.16 (m, 2H), 6.84-6.82 (m, 2H), 4.32-4.28 (m, 1H), 3.61 (s, 3H), 3.46-3.45 (m, 2H), 2.89-2.62 (m, 8H), 2.27-2.25 (m, 2H), 1.65-1.63 (m, 4H), 1.55-1.53 (m, 4H), 1.36-1.35 (m, 2H), 1.23-1.21 (d, J=6.8 Hz, 3H), 1.12-1.10 (d, J=6.8 Hz, 3H). MS (ESI, m/e) [M+1]⁺ 482.2.

Intermediate 259-1: 2-((2R)-4-(((1R,3S,5R)-adamantan-2-yl)methyl)-2-(2-isopropylphenyl)piperazin-1-yl)-7-azaspiro[3.5]nonane Intermediate 259-1

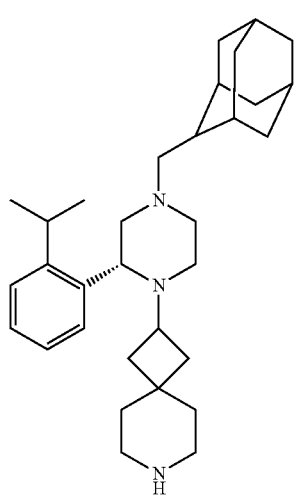

The synthesis procedures were similar to Intermediate 18-1. The compound 2-((2R)-4-(((1R,3S,5R)-adamantan-2-yl)methyl)-2-(2-isopropylphenyl)piperazin-1-yl)-7-azaspiro[3.5]nonane was a white solid. ¹H NMR (400 MHz, CDCl₃) δ ppm: 7.41 (br s, 1H), 7.19-7.09 (m, 2H), 7.09-7.00 (m, 1H), 3.56-3.54 (m, 1H), 3.40-3.23 (m, 1H), 3.01 (br s, 3H), 2.93-2.80 (m, 3H), 2.71-2.51 (m, 5H), 2.39-2.33 (m, 1H), 2.29-2.16 (m, 3H), 2.05-1.97 (m, 1H), 1.81-1.60 (m, 14H), 1.50-1.38 (m, 2H), 1.38-1.27 (m, 4H), 1.18 (d, J=6.8 Hz, 3H), 1.12 (d, J=6.8 Hz, 3H). MS (ESI, m/e) [M+1]⁺476.3.

Intermediate 260-1: (R)-2-(2-(2-isopropylphenyl)-4-(3-methoxy-4-methylbenzyl)piperazin-1-yl)-7-azaspiro[3.5]nonane Intermediate 260-1

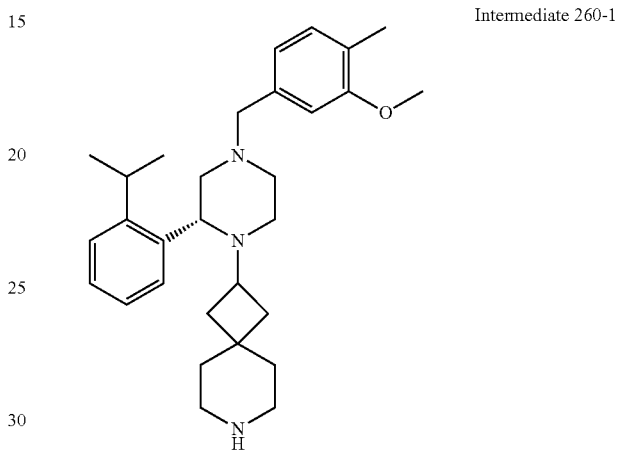

The synthesis procedures were similar to Intermediate 149-1. The compound (R)-2-(2-(2-isopropylphenyl)-4-(3-methoxy-4-methylbenzyl)piperazin-1-yl)-7-azaspiro[3.5]nonane was a light yellow solid. ¹H NMR (400 MHz, CDCl₃) δ ppm: 7.49 (d, J=4.4 Hz, 1H), 7.22-7.20 (m, 2H), 7.13-7.160 (m, 1H), 7.03 (d, J=7.2 Hz, 1H), 6.81-6.77 (m, 2H), 3.83 (s, 3H), 3.66-3.64 (m, 1H), 3.49 (s, 2H), 3.40 (s, 1H), 3.05-2.89 (m, 3H), 2.76-2.59 (m, 4H), 2.30-2.28 (m, 2H), 2.18 (s, 4H), 1.83-1.60 (m, 4H), 1.38-1.26 (m, 8H), 1.16 (d, J=6.4 Hz, 3H). MS (ESI, m/e) [M+1]⁺462.3.

Intermediate 263-1: (R)-2-(4-(4-isopropyl-3-methoxybenzyl)-2-(2-isopropylphenyl)piperazin-1-yl)-7-azaspiro[3.5]nonane Intermediate 263-1

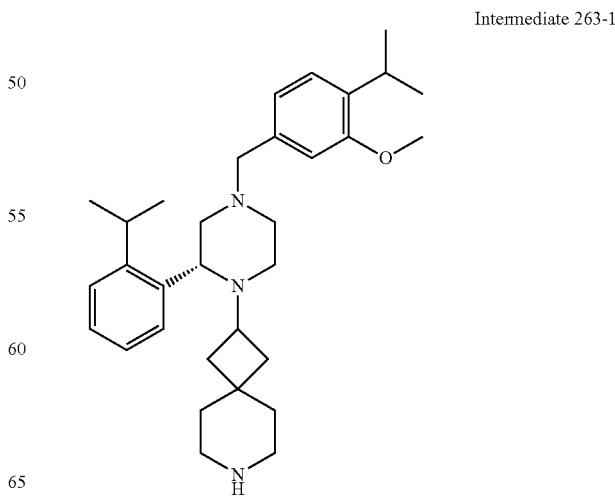

The synthesis procedures were similar to Intermediate 149-1. The compound (R)-2-(4-(4-isopropyl-3-methoxybenzyl)-2-(2-isopropylphenyl)piperazin-1-yl)-7-azaspiro[3.5]nonane was a yellow solid. $^1$H NMR (400 MHz, CDCl$_3$) δ ppm: 7.49 (s, 1H), 7.22-7.18 (m, 2H), 7.13-7.09 (m, 2H), 6.83-6.82 (m, 2H), 3.84 (s, 3H), 3.62-3.60 (m, 2H), 3.26-3.24 (m, 1H), 2.98-2.85 (m, 3H), 2.64-2.61 (m, 4H), 2.31-2.29 (m, 2H), 2.26-2.05 (m, 4H), 1.75-1.65 (m, 2H), 1.40-1.24 (m, 8H), 1.24-1.12 (m, 10H). MS (ESI, m/e) [M+1]$^+$ 490.3.

Intermediate 265-1: (R)-2-(4-(4-ethyl-3-methoxybenzyl)-2-(2-isopropylphenyl)piperazin-1-yl)-7-azaspiro[3.5]nonane

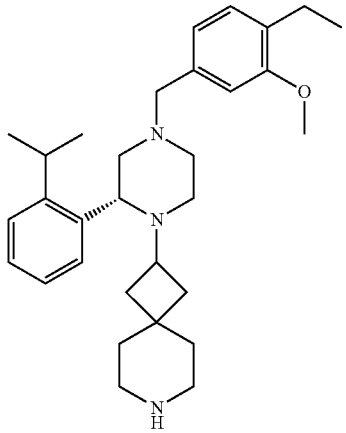

Intermediate 265-1

The synthesis procedures were similar to Intermediate 149-1. The compound (R)-2-(4-(4-ethyl-3-methoxybenzyl)-2-(2-isopropylphenyl)piperazin-1-yl)-7-azaspiro[3.5]nonane was a white solid. $^1$H NMR (400 MHz, CDCl$_3$) δ ppm: 7.49 (m, 1H), 7.25-7.17 (m, 2H), 7.16-7.08 (m, 1H), 7.05-7.03 (m, 1H), 6.85-6.78 (m, 2H), 3.82 (s, 3H), 3.71-3.61 (m, 1H), 3.54-3.46 (m, 2H), 3.45-3.32 (m, 1H), 3.05-2.97 (m, 1H), 2.97-2.87 (m, 2H), 2.72-2.53 (m, 7H), 2.32-2.30 (m, 2H), 2.19-2.15 (m, 1H), 1.74-1.62 (m, 3H), 1.41-1.28 (m, 5H), 1.26 (d, J=6.8 Hz, 3H), 1.18-1.13 (m, 6H). MS (ESI, m/e) [M+1]$^+$476.2.

Intermediate 268-1: (R)-1-(4-ethyl-3-methoxybenzyl)-3-(2-isopropylphenyl)piperazine

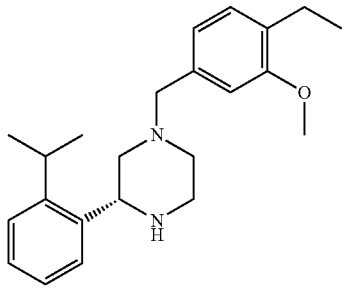

Intermediate 268-1

The synthesis procedures were similar to Intermediate 182-1. The compound (R)-1-(4-ethyl-3-methoxybenzyl)-3-(2-isopropylphenyl)piperazine was a yellow oil. $^1$H NMR (400 MHz, CDCl$_3$) δ ppm: 7.54-7.53 (m, 1H), 7.26-7.20 (m, 2H), 7.19-7.14 (m, 1H), 7.07-7.05 (m, 1H), 6.87 (s, 1H), 6.84-6.82 (m, 1H), 4.22 (br d, J=9.6 Hz, 1H), 3.84 (s, 3H), 3.61-3.46 (m, 2H), 3.27-3.22 (m, 1H), 3.14-3.12 (m, 2H), 2.96-2.81 (m, 2H), 2.61-2.59 (m, 2H), 2.29-2.20 (m, 1H), 2.07-2.01 (m, 2H), 1.23 (d, J=6.8 Hz, 3H), 1.20-1.12 (m, 6H). MS (ESI, m/e) [M+1]$^+$353.1.

Intermediate 269-1: (R)-1-(4-isopropyl-3-methoxybenzyl)-3-(2-isopropylphenyl)piperazine

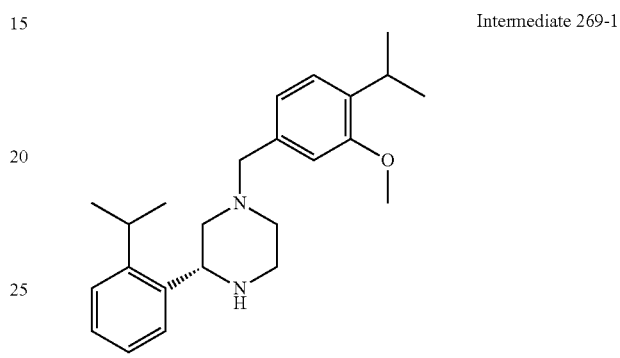

Intermediate 269-1

The synthesis procedures were similar to Intermediate 182-1. The compound (R)-1-(4-isopropyl-3-methoxybenzyl)-3-(2-isopropylphenyl)piperazine was a colorless oil. $^1$H NMR (400 MHz, CDCl$_3$) δ ppm: 7.57 (br d, J=7.2 Hz, 1H), 7.27 (s, 4H), 6.91-6.86 (m, 2H), 4.23 (dd, J=2.0, 10.0 Hz, 1H), 3.86 (s, 3H), 3.63 (d, J=12.8 Hz, 1H), 3.47 (d, J=12.8 Hz, 1H), 3.35-3.25 (m, 2H), 3.19-3.13 (m, 2H), 2.95-2.84 (m, 2H), 2.31-2.22 (m, 1H), 2.00 (t, J=10.4 Hz, 1H), 1.28-1.20 (m, 9H), 1.14 (d, J=6.8 Hz, 3H). MS (ESI, m/e) [M+1]$^+$367.1.

Intermediate 276-1: (R)-2-(4-(4-chloro-3-methoxybenzyl)-2-(2-isopropylphenyl)piperazin-1-yl)-7-azaspiro[3.5]nonane

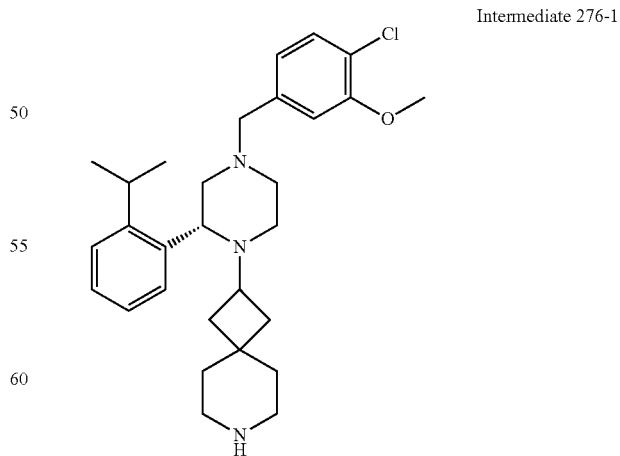

Intermediate 276-1

The synthesis procedures were similar to Intermediate 149-1. The compound (R)-2-(4-(4-chloro-3-methoxybenzyl)-2-(2-isopropylphenyl)piperazin-1-yl)-7-azaspiro[3.5]

nonane was a yellow solid. ¹H NMR (400 MHz, CDCl₃) δ ppm: 7.52-7.43 (m, 1H), 7.26-7.18 (m, 3H), 7.16-7.08 (m, 1H), 6.94 (d, 1H), 6.85-6.82 (m, 1H), 3.90 (s, 3H), 3.64 (br d, 1H), 3.48 (s, 2H), 3.43-3.33 (m, 1H), 3.02-2.97 (m, 1H), 2.94-2.87 (m, 1H), 2.80-2.64 (m, 4H), 2.31-2.29 (m, 2H), 2.22-2.15 (m, 1H), 1.82-1.77 (m, 2H), 1.73-1.69 (m, 1H), 1.47-1.45 (m, 4H), 1.33-1.24 (m, 6H), 1.16 (s, 3H). MS (ESI, m/e) [M+1]⁺482.3.

Intermediate 277-1: (R)-2-(2-(2-isopropylphenyl)-4-(3-methoxy-4-(trifluoromethyl)benzyl)piperazin-1-yl)-7-azaspiro[3.5]nonane

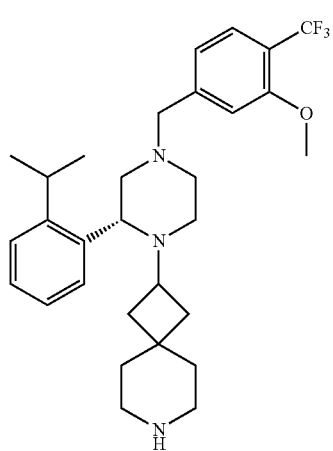

Intermediate 277-1

The synthesis procedures were similar to Intermediate 149-1. The compound (R)-2-(2-(2-isopropylphenyl)-4-(3-methoxy-4-(trifluoromethyl)benzyl)piperazin-1-yl)-7-azaspiro[3.5]nonane was a white oil. ¹H NMR (400 MHz, CDCl₃) δ ppm: 7.46 (br d, J=7.6 Hz, 2H), 7.25-7.19 (m, 2H), 7.15-7.10 (m, 1H), 7.02 (s, 1H), 6.95 (d, J=7.6 Hz, 1H), 3.91 (s, 3H), 3.75-3.59 (m, 2H), 3.58-3.50 (m, 2H), 3.39 (br s, 1H), 3.04-3.00 (m, 1H), 2.96-2.87 (m, 2H), 2.70-2.52 (m, 5H), 2.34-2.30 (m, 2H), 2.23-2.20 (m, 1H), 1.79-1.74 (m, 1H), 1.69-1.63 (m, 2H), 1.39-1.29 (m, 5H), 1.27 (d, J=6.8 Hz, 3H), 1.15 (d, J=6.8 Hz, 3H). MS (ESI, m/e) [M+1]⁺ 516.1.

Intermediate 280-1: (R)-2-(2-(2-isopropylphenyl)-4-((7-methoxybenzofuran-5-yl)methyl)piperazin-1-yl)-7-azaspiro[3.5]nonane

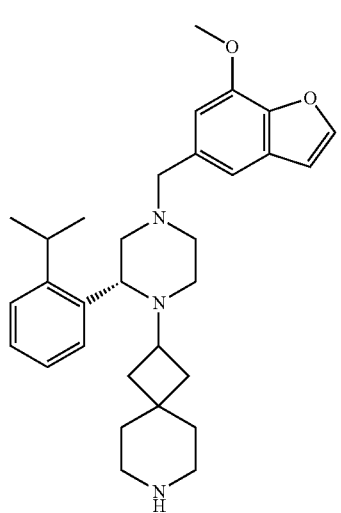

Intermediate 280-1

The synthesis procedures were similar to Intermediate 306-1. The compound (R)-2-(2-(2-isopropylphenyl)-4-((7-methoxybenzofuran-5-yl)methyl)piperazin-1-yl)-7-azaspiro[3.5]nonane was a yellow solid. ¹H NMR (400 MHz, CDCl₃) δ ppm: 7.59 (s, 1H), 7.53-7.43 (m, 1H), 7.24-7.19 (m, 2H), 7.14-7.09 (m, 2H), 6.83 (s, 1H), 6.69-6.68 (m, 1H), 4.01 (s, 3H), 3.71-3.61 (m, 1H), 3.58 (s, 2H), 3.43-3.28 (m, 1H), 3.01-2.89 (m, 3H), 2.83-2.67 (m, 5H), 2.88-2.64 (m, 1H), 2.30-2.28 (m, 2H), 2.19-2.16 (m, 1H), 1.82-1.69 (m, 2H), 1.57-1.46 (m, 4H), 1.37-1.30 (m, 1H), 1.24 (d, J=6.8 Hz, 3H), 1.13 (d, J=6.8 Hz, 3H). MS (ESI, m/e) [M+1]+ 488.2.

Intermediate 282-1: (R)-2-(4-(chroman-7-ylmethyl)-2-(2-isopropylphenyl)piperazin-1-yl)-7-azaspiro[3.5]nonane

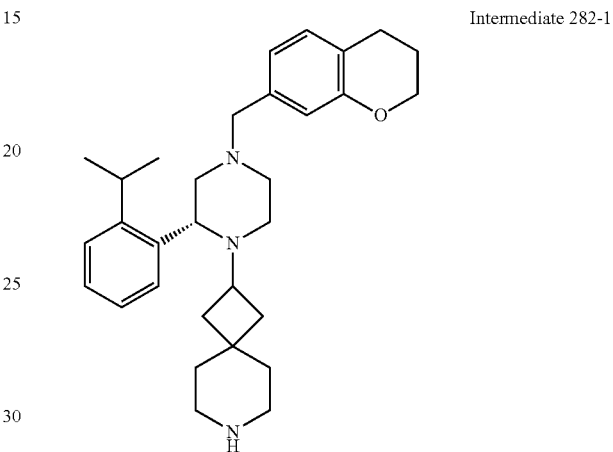

Intermediate 282-1

The synthesis procedures were similar to Intermediate 149-1. The compound (R)-2-(4-(chroman-7-ylmethyl)-2-(2-isopropylphenyl)piperazin-1-yl)-7-azaspiro[3.5]nonane was a white solid. ¹H NMR (400 MHz, CDCl₃) δ ppm: 7.55-7.40 (m, 1H), 7.25-7.17 (m, 2H), 7.15-7.08 (m, 1H), 6.95 (d, J=7.6 Hz, 1H), 6.81-6.76 (m, 1H), 6.75 (s, 1H), 4.19-4.12 (m, 2H), 3.65 (d, J=8.0 Hz, 1H), 3.52-3.33 (m, 3H), 3.00-2.86 (m, 3H), 2.76-2.73 (m, 2H), 2.70-2.54 (m, 5H), 2.32-2.24 (m, 2H), 2.22-2.14 (m, 1H), 2.08-1.89 (m, 3H), 1.72-1.62 (m, 3H), 1.41-1.28 (m, 5H), 1.25 (d, J=6.8 Hz, 3H), 1.16 (d, J=6.8 Hz, 3H). MS (ESI, m/e) [M+1]⁺474.2

Intermediate 286-1: (R)-2-(2-(2-isopropylphenyl)-4-((7-methoxy-3,3-dimethyl-2,3-dihydrobenzofuran-5-yl)methyl)piperazin-1-yl)-7-azaspiro[3.5]nonane

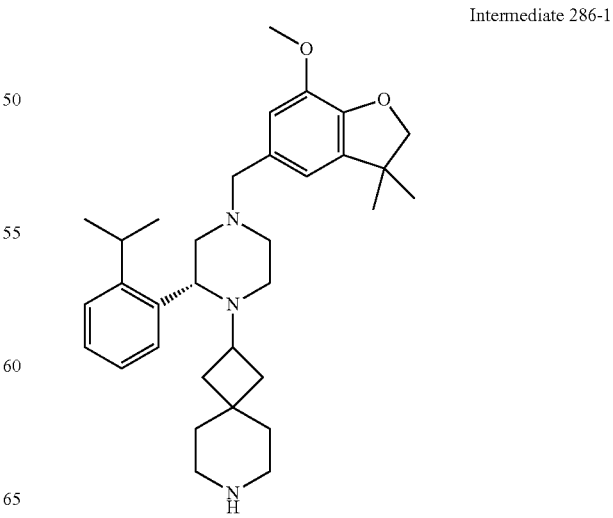

Intermediate 286-1

The synthesis procedures were similar to Intermediate 295-1. The compound (R)-2-(2-(2-isopropylphenyl)-4-((7-methoxy-3,3-dimethyl-2,3-dihydrobenzofuran-5-yl)methyl)piperazin-1-yl)-7-azaspiro[3.5]nonane was a white solid. ¹H NMR (400 MHz, CDCl₃) δ ppm: 7.49 (d, J=5.6 Hz, 1H), 7.25-7.18 (m, 2H), 7.15-7.10 (m, 1H), 6.69 (d, J=11.6 Hz, 2H), 4.26 (s, 2H), 3.86 (s, 3H), 3.65 (d, J=8.0 Hz, 1H), 3.55-3.49 (m, 1H), 3.46-3.32 (m, 2H), 3.07-2.99 (m, 1H), 2.97-2.87 (m, 2H), 2.71-2.56 (m, 5H), 2.36-2.27 (m, 2H), 2.15-2.13 (m, 1H), 1.91 (br s, 3H), 1.81-1.74 (m, 1H), 1.72-1.65 (m, 1H), 1.41-1.34 (m, 3H), 1.31 (d, J=4.0 Hz, 6H), 1.26 (d, J=6.8 Hz, 3H), 1.14 (d, J=6.8 Hz, 3H). MS (ESI, m/e) [M+1]⁺518.3

Intermediate 287-1: (R)-2-(4-(4-(difluoromethyl)-3-methoxybenzyl)-2-(2-isopropylphenyl)piperazin-1-yl)-7-azaspiro[3.5]nonane

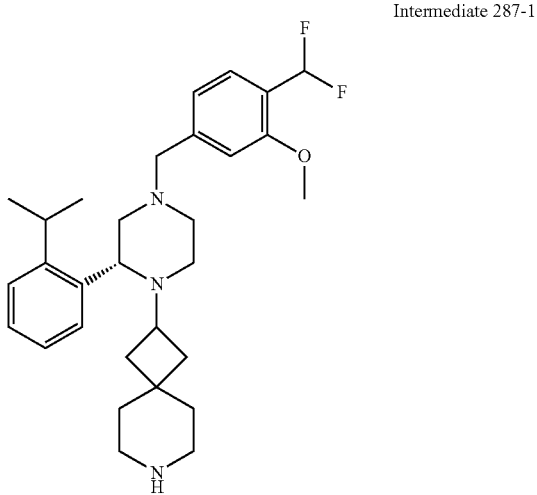 [SMILES: COc1cc(CN2CCN(C3CC4(CCNCC4)C3)[C@H](c3ccccc3C(C)C)C2)ccc1C(F)F]

Intermediate 287-1

The synthesis procedures were similar to Intermediate 149-1. The compound (R)-2-(4-(4-(difluoromethyl)-3-methoxybenzyl)-2-(2-isopropylphenyl)piperazin-1-yl)-7-azaspiro[3.5]nonane was a yellow solid. ¹H NMR (400 MHz, CDCl₃) δ ppm: 7.50-7.45 (m, 2H), 7.26-7.19 (m, 2H), 7.14-7.12 (m, 1H), 7.05-6.77 (m, 3H), 3.87 (s, 3H), 3.66-3.64 (m, 1H), 3.53-3.52 (m, 2H), 3.38-3.37 (m, 11H), 2.96-2.89 (m, 5H), 2.69-2.64 (m, 5H), 2.31-2.26 (m, 2H), 2.20-2.15 (m, 2H), 1.77-1.74 (m, 1H), 1.70-1.67 (m, 1H), 1.41-1.37 (m, 5H), 1.26 (d, J=6.8 Hz, 3H), 1.15 (d, J=6.8 Hz, 3H). MS (ESI, m/e) [M+1]⁺498.2.

Intermediate 289-1: (R)-3-(2-isopropylphenyl)-1-(3-methoxy-4-(trifluoromethyl)benzyl)piperazine

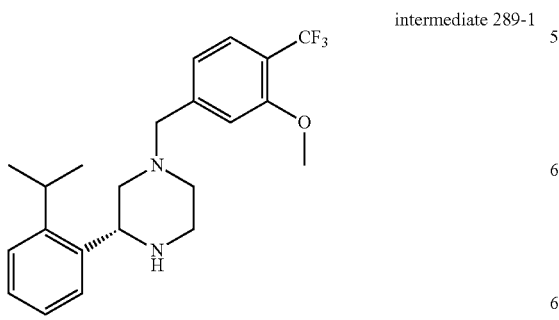

intermediate 289-1

The synthesis procedures were similar to Intermediate 182-1. The compound (R)-3-(2-isopropylphenyl)-1-(3-methoxy-4-(trifluoromethyl)benzyl)piperazine was a yellow oil. ¹H NMR (400 MHz, CDCl₃) δ ppm: 7.55 (d, J1=7.6 Hz, 1H), 7.48 (d, J=8.0 Hz, 1H), 7.14-7.26 (m, 3H), 7.06 (s, 1H), 6.97 (d, J=8.0 Hz, 1H), 4.22 (d, J=9.6 Hz, 1H), 3.92 (s, 3H), 3.49-3.66 (m, 2H), 3.20-3.31 (m, 1H), 3.08-3.18 (m, 2H), 2.77-2.90 (m, 2H), 2.29-2.28 (m, 1H), 2.01-2.11 (m, 2H), 1.25 (d, J=6.8 Hz, 3H), 1.13 (d, J=6.8 Hz, 3H). MS (ESI, m/e) [M+1]⁺363.0

Intermediate 292-1: 2-(2-(2-isopropylphenyl)-4-((4-methoxybicyclo[4.2.0]octa-1(6),2,4-trien-7-yl)methyl)piperazin-1-yl)-7-azaspiro[3.5]nonane

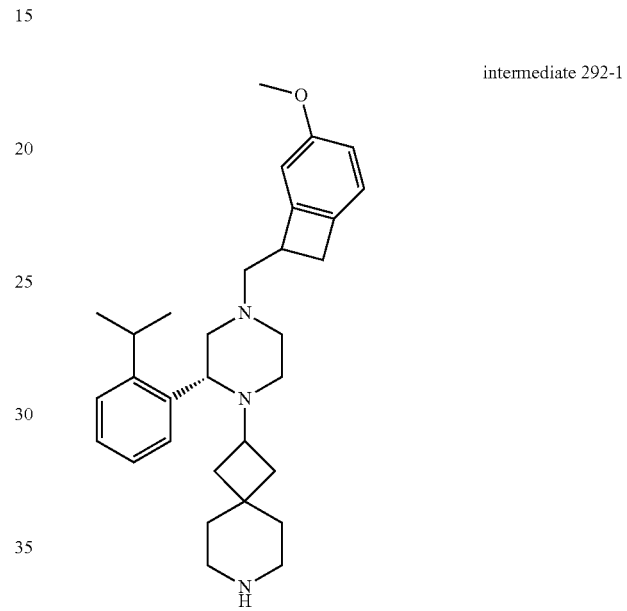

intermediate 292-1

The synthesis procedures were similar to Intermediate 149-1. The compound 2-(2-(2-isopropylphenyl)-4-((4-methoxybicyclo[4.2.0]octa-1(6),2,4-trien-7-yl)methyl)piperazin-1-yl)-7-azaspiro[3.5]nonane was a yellow oil. ¹H NMR (400 MHz, CDCl₃) δ ppm: 7.27-7.52 (m, 1H), 7.23-7.25 (m, 2H), 7.14-7.23 (m, 1H), 6.94-6.96 (m, 1H), 6.64-6.76 (m, 2H), 3.62-3.76 (m, 5H), 2.64-3.26 (m, 8H), 2.29-2.32 (m, 8H), 0.84-1.44 (m, 14H). MS (ESI, m/e) [M+1]⁺ 474.3.

Intermediate 295-1: (R)-3-(2-isopropylphenyl)-1-((7-methoxy-3,3-dimethyl-2,3-dihydrobenzofuran-5-yl)methyl)piperazine

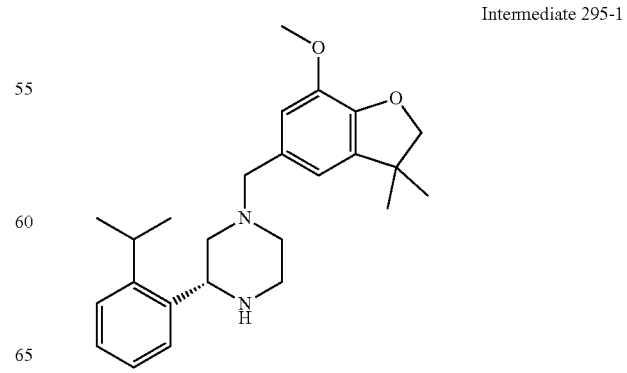

Intermediate 295-1

Step 1: 3-iodo-5-methoxy-4-((2-methylallyl)oxy)benzaldehyde

To a solution of 4-hydroxy-3-iodo-5-methoxybenzaldehyde (4.0 g, 14.39 mmol) and 3-bromo-2-methylprop-1-ene (2.91 g, 21.58 mmol) in MeCN (40 mL) was added K$_2$CO$_3$ (3.98 g, 28.77 mmol). The mixture was stirred at 80° C. for 12 hrs. The mixture was poured into H$_2$O (30 mL), extracted with EtOAc 30 mL (10 mL×3). The combined organic layers were washed with brine, dried over Na$_2$SO$_4$, filtered and concentrated under reduced pressure. The residue was purified by column chromatography (silica gel, eluent: PE/EA (v/v)=100/1 to EA) to give 3-iodo-5-methoxy-4-((2-methylallyl)oxy)benzaldehyde (4.5 g, yield: 94%) as a colorless oil. )H NMR (400 MHz, CDCl$_3$) δ ppm: 9.82 (s, 1H), 7.85 (d, J=1.6 Hz, 1H), 7.40 (d, J=1.6 Hz, 1H), 5.17 (d, J=0.4 Hz, 1H), 5.01 (s, 1H), 4.53 (s, 2H), 3.91 (s, 3H), 1.94 (s, 3H).

Step 2: 7-methoxy-3,3-dimethyl-2,3-dihydrobenzofuran-5-carbaldehyde

To a solution of 3-iodo-5-methoxy-4-((2-methylallyl)oxy) benzaldehyde (5.2 g, 15.66 mmol) in DMF (20 mL) at 20° C. were added Pd(OAc)$_2$ (1.46 g, 6.52 mmol), K$_2$CO$_3$ (2.16 g, 15.66 mmol), HCOONa (1.02 g, 15 mmol) and TBAB (4.21 g, 13.05 mmol). The mixture was stirred at 100° C. for 3 hrs. The mixture was poured into H$_2$O (20 mL), extracted with EtOAc (15 mL×3). The combined organic layers were washed with brine, dried over Na$_2$SO$_4$, filtered and concentrated under reduced pressure. The residue was purified by column chromatography (silica gel, eluent: PE/EA (v/v)= 100/1 to EA) to give 7-methoxy-3,3-dimethyl-2,3-dihydrobenzofuran-5-carbaldehyde (770 mg, yield: 23%) as a colorless oil. $^1$H NMR (400 MHz, CDCl$_3$) δ ppm: 9.83 (s, 1H), 7.31 (d, J=3.2 Hz, 2H), 4.43 (s, 2H), 3.94 (s, 3H), 1.39 (s, 6H).

Step 3: (R)-3-(2-isopropylphenyl)-1-((7-methoxy-3,3-dimethyl-2,3-dihydrobenzofuran-5-yl)methyl)piperazine To a solution of 7-methoxy-3,3-dimethyl-2,3-dihydrobenzofuran-5-carbaldehyde (470 mg, 2.28 mmol) and (R)-2-(2-isopropylphenyl)piperazine (512.17 mg, 2.51 mmol) in DCM (30 mL) was added NaBH(OAc)$_3$ (965.99 mg, 4.56 mmol) at 0° C. The mixture was stirred at 20° C. for 2 hrs. The reaction mixture was poured into aqueous Na$_2$CO$_3$ (20 mL), extracted with DCM (20 mL×3). The combined organic layers were washed with brine, dried over Na$_2$SO$_4$, filtered and concentrated under reduced pressure. The residue was purified by column chromatography (silica gel, eluent: PE/EA (v/v)=100/1 to EA) to give (R)-3-(2-isopropylphenyl)-1-((7-methoxy-3,3-dimethyl-2,3-dihydrobenzofuran-5-yl)methyl)piperazine (527 mg, yield: 58%) as a colorless oil. $^1$H NMR (400 MHz, CDCl$_3$) δ ppm: 7.56 (d, J=7.6 Hz, 1H), 7.27-7.15 (m, 3H), 6.78-6.66 (m, 2H), 4.28 (s, 2H), 4.22 (d, J=8.4 Hz, 1H), 3.88 (s, 3H), 3.58 (d, J=12.8 Hz, 1H), 3.42 (d, J=13.2 Hz, 1H), 3.27-3.25 (m, 1H), 3.18-3.11 (m, 2H), 2.94-2.83 (m, 2H), 2.64-2.46 (m, 1H), 2.27-2.24 (m, 1H), 2.01 (br s, 1H), 1.32 (d, J=2.8 Hz, 6H), 1.24 (d, J=6.8 Hz, 3H), 1.13 (d, J=6.8 Hz, 3H). MS (ESI, m/e) [M+1]$^+$395.2.

Intermediate 297-1: (R)-1-((2,3-dihydrobenzofuran-6-yl)methyl)-3-(2-isopropylphenyl)piperazine

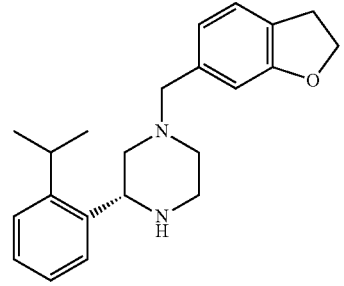

Intermediate 297-1

The synthesis procedures were similar to Intermediate 182-1. The compound (R)-1-((2,3-dihydrobenzofuran-6-yl) methyl)-3-(2-isopropylphenyl)piperazine was a colorless oil. $^1$H NMR (400 MHz, CDCl$_3$) δ ppm: 7.55 (br d, J=7.6 Hz, 1H), 7.30-7.26 (in, 1H), 7.26-7.21 (m, 1H), 7.20-7.14 (m, 1H), 7.12 (d, J=7.6 Hz, 1H), 6.88-6.77 (m, 2H), 4.58-4.54 (m, 2H), 4.25-4.18 (m, 1H), 3.56-3.47 (m, 2H), 3.35-3.29 (m, 1H), 3.22-3.08 (m, 4H), 2.87-2.84 (m, 2H), 2.22-2.20 (m, 1H), 2.08-2.03 (m, 1H), 1.82 (s, 1H), 1.25 (d, J=6.8 Hz, 3H), 1.19 (d, J=6.8 Hz, 3H). MS (ESI, m/e) [M+1]$^+$ 337.1.

Intermediate 299-1: (R)-2-(2-(2-isopropylphenyl)-4-((8-methoxychroman-6-yl)methyl)piperazin-1-yl)-7-azaspiro[3.5]nonane

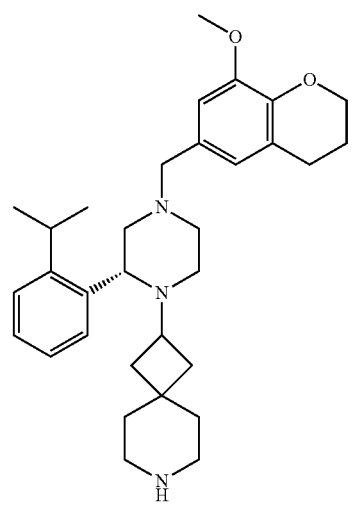

intermediate 299-1

The synthesis procedures were similar to Intermediate 312-1. The compound (R)-2-(2-(2-isopropylphenyl)-4-((8-methoxychroman-6-yl)methyl)piperazin-1-yl)-7-azaspiro [3.5]nonane was a yellow solid. $^1$H NMR (400 MHz, CDCl$_3$) δ ppm: 7.54-7.44 (m, 1H), 7.25-7.18 (m, 2H), 7.15-7.09 (m, 1H), 6.69 (s, 1H), 6.57 (s, 1H), 4.26-4.22 (m, 2H), 3.85 (s, 3H), 3.69-3.61 (m, 1H), 3.48-3.34 (m, 3H), 3.04-2.98 (m, 1H), 2.95-2.88 (m, 2H), 2.74 (br t, J=6.4 Hz, 2H), 2.70-2.61 (m, 4H), 2.34-2.26 (m, 11H), 2.20-2.05 (m, 2H), 2.02-1.93 (m, 6H), 1.80-1.67 (m, 2H), 1.46-1.28 (m, 6H), 1.26 (d, J=6.8 Hz, 3H), 1.15 (d, J=6.8 Hz, 3H). MS (ESI, m/e) [M+1]+504.3.

Intermediate 304-1: (R)-2-(4-((2,3-dihydrobenzofuran-6-yl)methyl)-2-(2-isopropylphenyl)piperazin-1-yl)-7-azaspiro[3.5]nonane

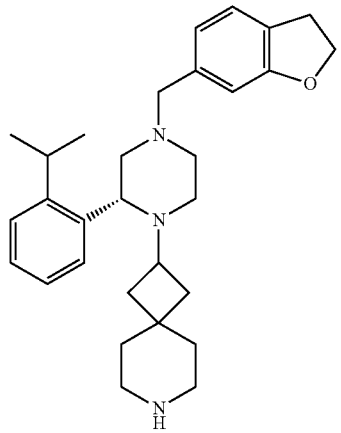

Intermediate 304-1

The synthesis procedures were similar to Intermediate 149-1. The compound (R)-2-(4-((2,3-dihydrobenzofuran-6-yl)methyl)-2-(2-isopropylphenyl)piperazin-1-yl)-7-azaspiro[3.5]nonane was a white solid. $^1$H NMR (400 MHz, CDCl$_3$) δ ppm: 7.48 (s, 1H), 7.26-7.17 (m, 2H), 7.15-7.05 (m, 2H), 6.82-6.73 (m, 2H), 4.54 (t, J=8.8 Hz, 2H), 3.65 (d, J=8.4 Hz, 1H), 3.52-3.32 (m, 3H), 3.17-3.13 (m, 2H), 3.01-2.86 (m, 3H), 2.69-2.52 (m, 5H), 2.32-2.24 (m, 2H), 2.18 (t, J=10.4 Hz, 1H), 1.75 (d, J=3.2 Hz, 1H), 1.68-1.62 (m, 1H), 1.41-1.27 (m, 5H), 1.25 (d, J=6.8 Hz, 3H), 1.15 (br d, J=6.8 Hz, 3H). MS (ESI, m/e) [M+1]$^+$460.2.

Intermediate 306-1: (R)-3-(2-isopropylphenyl)-J-((7-methoxybenzofuran-S-yl)methyl)piperazine

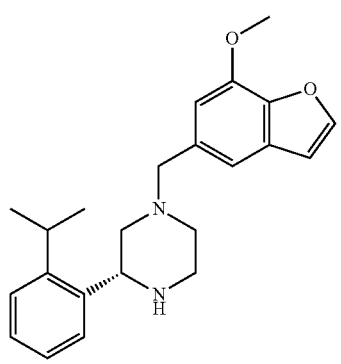

Intermediate 306-1

Step 1: 4-hydroxy-3-methoxy-5-((trimethylsilyl)ethynyl)benzaldehyde

To a solution of 4-hydroxy-3-iodo-5-methoxybenzaldehyde (10 g, 35.97 mmol) and ethynyltrimethylsilane (5.65 g, 57.54 mmol) in THF (100 mL) and TEA (20 mL) was added Pd(PPh$_3$)$_2$Cl2 (1.26 g, 1.80 mmol) and CuI (684 mg, 3.60 mmol) at 25° C. The mixture was stirred at 25° C. for 16 hrs. The reaction mixture was filtered through a celites pad and washed with THF (100 mL). The filtrate was concentrated under reduced pressure. The residue was purified by MPLC (silica gel, eluent: PE/EA (v/v)=10/1 to 2/1) to give 4-hydroxy-3-methoxy-5-((trimethylsilyl)ethynyl)benzaldehyde (7 g, yield: 78%) as a yellow solid. $^1$H NMR (400 MHz, DMSO-d$_6$) δ ppm:10.50 (s, 1H), 9.76 (s, 1H), 7.56 (d, J=2.0 Hz, 1H), 7.39 (s, 1H), 3.89 (s, 3H), 0.23-0.22 (m, 9H).

Step 2: 7-methoxybenzofuran-5-carbaldehyde

To a solution of 4-hydroxy-3-methoxy-5-((trimethylsilyl)ethynyl)benzaldehyde (3.0 g, 12.08 mmol) in THF (15 mL) was added TBAF (15 mL, 15.34 mmol) at 20° C. The mixture was stirred at 70° C. for 12 hrs. The reaction mixture was diluted with H$_2$O (20 mL) and extracted with EtOAc (20 mL×3). The combined organic layers were washed with brine, dried over Na$_2$SO$_4$, filtered and concentrated under reduced pressure. The residue was purified by MPLC (silica gel, eluent: PE/EA (v/v)=10/1 to 2/1) to give 7-methoxybenzofuran-5-carbaldehyde (1.0 g, yield: 46%) as a white solid. $^1$H NMR (400 MHz, CDCl$_3$) δ ppm: 9.94 (s, 1H), 7.74-7.63 (m, 2H), 7.31 (s, 1H), 6.83 (d, J=2.0 Hz, 1H), 4.00 (s, 3H).

Step 3: (R)-3-(2-isopropylphenyl)-1-((7-methoxybenzofuran-5-yl)methyl)piperazine To a solution of 7-methoxybenzofuran-5-carbaldehyde (700.0 mg, 3.97 mmol) and (R)-2-(2-isopropylphenyl)piperazine (893.0 mg, 4.37 mmol) in DCM (10 mL) was added NaBH(OAc)$_3$ (2.1 g, 9.93 mmol) at 0° C. The mixture was stirred at 25° C. for 12 hrs. The reaction mixture was diluted with aqueous NaHCO$_3$ (20 mL) and extracted with DCM (20 mL×3). The combined organic layers were washed with brine, dried over anhydrous Na$_2$SO$_4$, filtered and concentrated under reduced pressure. The residue was purified by MPLC (silica gel, eluent: PE/EA (v/v)=10/1 to 2/1 to EA/MeOH (v/v)=5/1) to give (R)-3-(2-isopropylphenyl)-1-((7-methoxybenzofuran-5-yl)methyl) piperazine (744 mg, yield: 51%) as a yellow oil. $^1$H NMR (400 MHz, CDCl$_3$) δ ppm: 7.60 (d, J=2.0 Hz, 1H), 7.56 (d, J=7.6 Hz, 1H), 7.26-7.20 (m, 2H), 7.19-7.15 (m, 1H), 7.13 (s, 1H), 6.88 (s, 1H), 6.71 (d, J=2.0 Hz, 1H), 4.24 (d, J=9.2 Hz, 1H), 4.03 (s, 3H), 3.70-3.65 (m, 1H), 3.62-3.56 (m, 1H), 3.32-3.23 (in, 1H), 3.14 (d, J=5.2 Hz, 2H), 2.93-2.86 (m, 2H), 2.30-2.27 (m, 1H), 2.12-1.98 (m, 2H), 1.24 (d, J=6.8 Hz, 3H), 1.10 (d, J=6.8 Hz, 3H). MS (ESI, m/e) [M+1]$^+$365.1.

Intermediate 311-1: (R)-1-((3,3-dimethyl-2,3-dihydrobenzofuran-6-yl)methyl)-3-(2-isopropylphenyl)piperazine

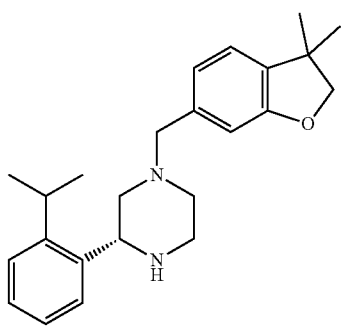

Intermediate 311-1

The synthesis procedures were similar to Intermediate 182-1. The compound (R)-1-((3,3-dimethyl-2,3-dihydrobenzofuran-6-yl)methyl)-3-(2-isopropylphenyl)piperazine was a yellow oil. $^1$H NMR (400 MHz, CDCl$_3$) δ ppm: 7.55-7.53 (m, 1H), 7.25-7.22 (m, 2H), 7.19-7.16 (m, 1H), 7.01 (d, J=7.2 Hz, 1H), 6.85-6.79 (m, 2H), 4.24-4.20 (m, 3H), 3.60-3.55 (in, 1H), 350-3.44 (m, 1H), 3.30-3.23 (m, 1H), 3.16-3.09 (m, 2H), 2.91 (d, J=10.8 Hz, 1H), 2.84 (d, J=10.8 Hz, 1H), 2.30-2.24 (m, 1H), 2.05-1.98 (m, 1H), 1.32 (d, J=2.0 Hz, 6H), 1.24 (d, J=6.8 Hz, 3H), 1.12 (d, J=6.8 Hz, 3H). MS (ESI, m/e) [M+1]$^+$365.2.

Intermediate 312-1: (R)-3-(2-isopropylphenyl)-1-((8-methoxychroman-6-yl)methyl)piperazine

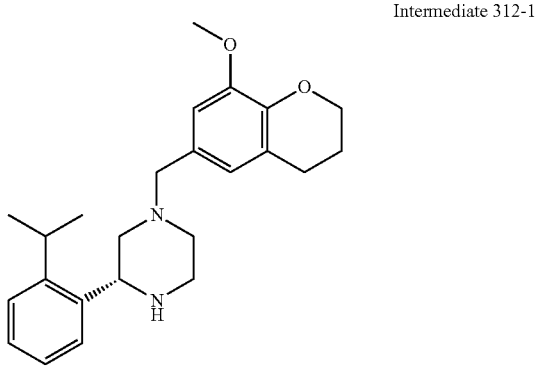 [SMILES: COc1cc(CN2CCN[C@H](c3ccccc3C(C)C)C2)cc2c1OCCC2]

Intermediate 312-1

Step 1: 3-(4-bromo-2-methoxyphenoxy)propanoic acid

To a solution of 4-bromo-2-methoxyphenol (5.0 g, 24.63 mmol) in DMF (50 mL) was added NaH (5.1 g, 28.06 mmol, 60 wt %) at 20° C. After stirred at 25° C. for 30 min, 3-bromopropanoic acid (9.0 g, 59.10 mmol) in DMF (25 mL) was added dropwise at 25° C. The mixture was stirred at 50° C. for 24 hrs. The mixture was added water (200 mL) and IN HCl (100 mL), extracted with EtOAc (100 mL×3). The combined organic layers were washed with brine, dried over anhydrous Na$_2$SO$_4$, filtered and concentrated under reduced pressure. The crude product was purified by column chromatography (silica gel, eluent: PE/EA (v/v)=100/1 to 1/1) to give 3-(4-bromo-2-methoxyphenoxy)propanoic acid (2.2 g, yield: 33%) as a white solid. $^1$H NMR (400 MHz, CDCl$_3$) δ ppm: 7.04-7.01 (m, 1H), 7.01-6.99 (m, 1H), 6.81 (d, J=8.4 Hz, 1H), 4.28 (t, J=6.4 Hz, 2H), 3.85 (s, 3H), 2.90 (t, J=6.4 Hz, 2H).

Step 2: 6-bromo-8-methoxychroman-4-one

To a solution of 3-(4-bromo-2-methoxyphenoxy)propanoic acid (3.0 g, 10.91 mmol) in DCM (50 mL) was added oxalyl dichloride (2.8 g, 21.81 mmol) at 0° C. After stirred at 25° C. for 30 min, the mixture was concentrated in vacuum. The residue was dissolved into DCM (50 mL), AlCl$_3$ (2.9 g, 21.81 mmol) was added at 0° C. The mixture was stirred at 25° C. for 1 hr. The mixture was added water, extracted with DCM, the organic layer was washed with brine, dried over anhydrous Na$_2$SO$_4$, filtered and concentrated under reduced pressure. The crude product was purified by column chromatography (silica gel, eluent: PE/EA (v/v)=100/1 to 1/1) to give 6-bromo-8-methoxychroman-4-one (2.6 g, yield: 93%) as a white solid. $^1$H NMR (400 MHz, CDCl$_3$) δ ppm: 7.63 (d, J=2.4 Hz, 1H), 7.13 (d, J=2.4 Hz, 1H), 4.65-4.60 (m, 2H), 3.91 (s, 3H), 2.86-2.82 (m, 2H).

Step 3: 6-bromo-8-methoxychromane

To a solution of 6-bromo-8-methoxychroman-4-one (2.6 g, 10.11 mmol) in AcOH (150 mL) was added Zinc powder (16.5 g, 252.84 mmol) at 25° C. The mixture was stirred at 100° C. for 12 hrs. The mixture was concentrated under reduced pressure. The residue was poured into H$_2$O (50 mL), extracted with EtOAc (50 mL×3). The combined organic layers were washed with aqueous NaHCO$_3$, dried over anhydrous Na$_2$SO$_4$, filtered and concentrated under reduced pressure. The crude product was purified by column chromatography (silica gel, eluent: PE/EA (v/v)=100/1 to 1/1) to give 6-bromo-8-methoxychroman (2.2 g, yield: 90%) as a colorless oil.

$^1$H NMR (400 MHz, CDCl$_3$) δ ppm: 6.81 (s, 2H), 4.28-4.23 (m, 2H), 3.85 (s, 3H), 2.76 (t, J=6.4 Hz, 2H), 2.04-1.97 (m, 2H).

Step 4: 8-methoxychromane-6-carbaldehyde

To a solution of 6-bromo-8-methoxychroman (1.0 g, 4.11 mmol) in THF (15 mL) was added n-BuLi (3.3 mL, 8.23 mmol, 2.5 N) at −70° C. After stirred at −70° C. for 5 min, DMF (601 mg, 8.23 mmol) was added dropwise at −70° C. The mixture was stirred at −70° C. for 1 hr. The mixture was poured into aqueous NH$_4$Cl (20 mL), extracted with EtOAc (50 mL×3). The combined organic layers were washed with brine, dried over anhydrous Na$_2$SO$_4$, filtered and concentrated under reduced pressure. The crude product was purified by column chromatography (silica gel, eluent: PE/EA (v/v)=100/1 to 5/1) to give 8-methoxychroman-6-carbaldehyde (520 mg, yield: 66%) as a yellow solid. $^1$H NMR (400 MHz, CDCl$_3$) δ ppm: 9.81 (d, J=1.4 Hz, 1H), 7.26 (s, 1H), 7.22 (s, 1H), 4.37 (t, J=4.8 Hz, 2H), 3.94 (s, 3H), 2.87 (t, J=6.4 Hz, 2H), 2.11-2.04 (in, 2H).

Step 5: (R)-3-(2-isopropylphenyl)-1-((8-methoxychroman-6-yl)methyl)piperazine

To a solution of 8-methoxychroman-6-carbaldehyde (640 mg, 3.33 mmol) in DCM (10 mL) was added (R)-2-(2-isopropylphenyl)piperazine (700 mg, 3.43 mmol) and NaBH(OAc)$_3$ (2.1 g, 9.99 mmol) at 0° C. The mixture was stirred at 0° C. for 4 hrs. The mixture was added aqueous Na$_2$CO$_3$ to pH=8-9, extracted with DCM. The combined organic layers were washed with brine, dried over anhydrous Na$_2$SO$_4$, filtered and concentrated under reduced pressure. The residue was purified by column chromatography (silica gel, eluent: PE/EA (v/v)=10/1 to 2/1 to EA) to give (R)-3-(2-isopropylphenyl)-1-((8-methoxychroman-6-yl)methyl) piperazine (925 mg, yield: 73%) as a yellow oil. $^1$H NMR (400 MHz, CDCl$_3$) δ ppm: 7.57 (d, J=7.6 Hz, 1H), 7.27-7.21 (m, 2H), 7.20-7.15 (m, 1H), 6.76 (s, 1H), 6.60 (s, 1H), 4.30-4.21 (m, 3H), 3.88 (s, 3H), 3.56-3.52 (m, 1H), 3.44-3.40 (m, 1H), 3.27 (m, 1H), 3.19-3.10 (m, 2H), 2.97-2.83 (m, 2H), 2.76-2.73 (m, 2H), 2.30 (s, 1H), 2.08-1.92 (m, 4H), 1.25 (d, J=6.8 Hz, 3H), 1.15 (d, J=6.8 Hz, 3H). MS (ESI, m/e) [M+1]$^+$381.2.

Intermediate 313-1: (R)-8-((3-(2-isopropylphenyl)piperazin-1-yl)methyl)-2,2-dimethyl-2,3-dihydro-[1,4]dioxino[2,3-b]pyridine

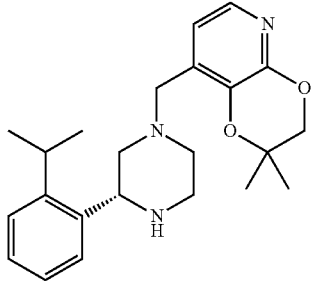

Intermediate 313-1

The synthesis procedures were similar to Intermediate 182-1. The compound (R)-8-((3-(2-isopropylphenyl)piperazin-1-yl)methyl)-2,2-dimethyl-2,3-dihydro-[1,4]dioxino[2,3-b]pyridine was a colorless oil. $^1$H NMR (400 MHz, CDCl$_3$) δ ppm: 7.77 (d, J=5.2 Hz, 1H), 7.55 (d, J=7.6 Hz, 1H), 7.27 (s, 1H), 7.26-7.21 (m, 1H), 7.19-7.14 (m, 1H), 7.05 (d, J=5.2 Hz, 1H), 4.25 (dd, J=2.0, 10.0 Hz, 1H), 4.03 (s, 2H), 3.98-3.83 (m, 1H), 3.58 (s, 2H), 3.30 (td, J=6.8, 13.6 Hz, 1H), 3.17-3.08 (m, 2H), 2.86 (br t, J=10.8 Hz, 2H), 2.37 (dt, J=4.4, 10.8 Hz, 1H), 2.17 (t, J=10.8 Hz, 1H), 1.32 (d, J=5.6 Hz, 6H), 1.26 (d, J=6.8 Hz, 3H), 1.19 (d, J=6.8 Hz, 3H). MS (ESI, m/e) [M+1]$^+$382.1.

Intermediate 315-1: (R)-1-((2,2-dimethyl-2,3-dihydrobenzo[b][1,4]dioxin--yl)methyl)-3-(2-isopropylphenyl)piperazine

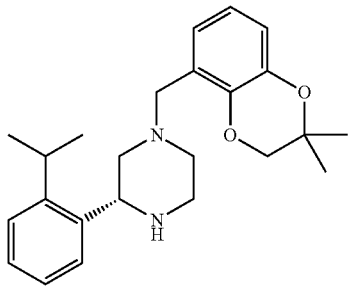

Intermediate 315-1

The synthesis procedures were similar to Intermediate 182-1. The compound (R)-1-((2,2-dimethyl-2,3-dihydrobenzo[b][1,4]dioxin-5-yl)methyl)-3-(2-isopropylphenyl)piperazine was a yellow oil. $^1$H NMR (400 MHz, CDCl$_3$) δ ppm: 7.53 (d, J=7.2 Hz, 1H), 7.29-7.27 (m, 1H), 7.26-7.20 (m, 1H), 7.19-7.13 (m, 1H), 6.93 (d, J=7.6 Hz, 1H), 6.83-6.79 (m, 1H), 6.78-6.72 (m, 1H), 4.28 (d, J=9.6 Hz, 1H), 3.86 (s, 2H), 3.79-3.61 (m, 2H), 3.33-3.30 (m, 1H), 3.19-3.08 (m, 2H), 2.98-2.87 (m, 2H), 2.41-2.34 (m, 1H), 2.21-2.15 (m, 1H), 1.32 (d, J=1.6 Hz, 6H), 1.25 (d, J=6.4 Hz, 3H), 1.19 (d, J=6.8 Hz, 3H). MS (ESI, m/e) [M+1]$^+$381.1.

Intermediate 316-1: (R)-8-((3-(2-isopropylphenyl)piperazin-1-yl)methyl)-3,3-dimethyl-2,3-dihydro-[1,4]dioxino[2,3-b]pyridine

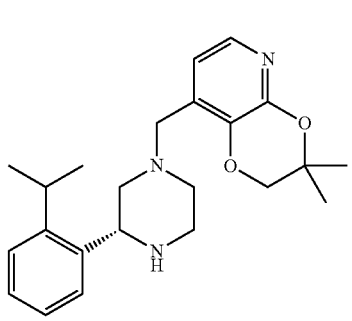

Intermediate 316-1

The synthesis procedures were similar to Intermediate 182-1. The compound (R)-8-((3-(2-isopropylphenyl)piperazin-1-yl)methyl)-3,3-dimethyl-2,3-dihydro-[1,4]dioxino[2,3-b]pyridine was a yellow solid. $^1$H NMR (400 MHz, CDCl$_3$) δ ppm: 7.78-7.77 (m, 1H), 7.53-7.51 (m, 1H), 7.27-7.13 (m, 3H), 7.01-7.00 (m, 1H), 4.25-4.24 (m, 1H), 3.85 (s, 2H), 3.61 (s, 2H), 3.30-3.28 (m, 2H), 3.14-3.11 (m, 2H), 2.89-2.82 (m, 2H), 2.30-2.26 (m, 1H), 2.14-2.11 (m, 1H), 1.37 (s, 6H), 1.25 (d, J=6.8 Hz, 3H), 1.17 (d, J=6.8 Hz, 3H). MS (ESI, m/e) [M+1]+382.2.

Intermediate 321-1: (R)-1-(4-cyclopropoxy-3-methoxybenzyl)-3-(2-isopropylphenyl)piperazine

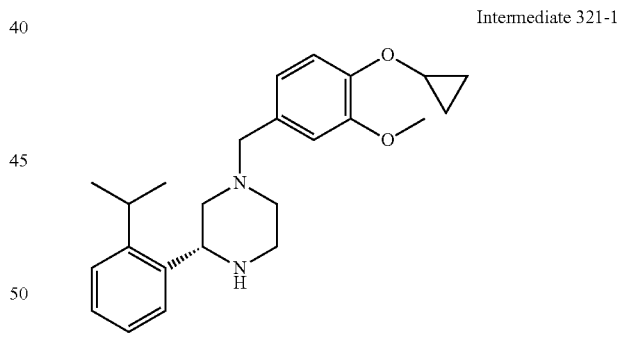

Intermediate 321-1

The synthesis procedures were similar to Intermediate 182-1. The compound (R)-1-(4-cyclopropoxy-3-methoxybenzyl)-3-(2-isopropylphenyl)piperazine was a yellow oil. $^1$H NMR (400 MHz, CDCl$_3$) δ ppm: 7.56 (d, J=7.6 Hz, 1H), 7.27-7.21 (m, 2H), 7.20-7.13 (m, 2H), 6.93 (s, 1H), 6.87-6.78 (m, 1H), 4.22 (s, 1H), 3.88 (s, 3H), 3.74-3.71 (m, 1H), 3.56 (s, 1H), 3.49-3.45 (m, 1H), 3.22-3.27 (m, 1H), 3.14 (s, 1H), 2.87 (s, 1H), 2.26 (s, 1H), 2.05-1.88 (m, 1H), 1.23 (d, J=6.8 Hz, 1H), 1.14 (d, J=6.8 Hz, 3H), 0.87-0.82 (m, 2H), 0.75-0.80 (m, 2H). MS (ESI, m/e) [M+1]$^+$381.1.

Intermediate 322-1: (R)-3-(2-isopropylphenyl)-1-((7-(methoxy-d3)benzofuran-5-yl)methyl)piperazine

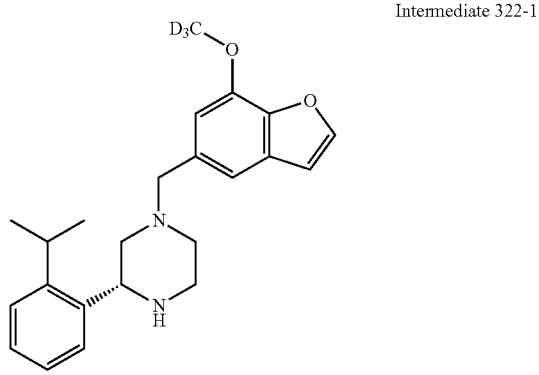 [SMILES: [2H]C([2H])([2H])Oc1cc(CN2CCN[C@H](c3ccccc3C(C)C)C2)cc2ccoc12]

Intermediate 322-1

Step 1: 7-hydroxybenzofuran-5-carbaldehyde

To a solution of 7-methoxybenzofuran-5-carbaldehyde (2.0 g, 11.35 mmol) in DCM (20 mL) was added $BBr_3$ (5.69 g, 22.71 mmol) at 0° C. and stirred at 25° C. for 2 hrs. The mixture was added water (20 mL), extracted with EtOAc (20 mL×3), the organic layer was washed with brine, dried over anhydrous $Na_2SO_4$, filtered and concentrated under reduced pressure. The crude product was purified by column chromatography (silica gel, eluent: PE/EA (v/v)=10/1 to 1/1) to give 6-bromo-8-methoxychroman-4-one (0.34 g, yield: 18%) as a white solid. 7-hydroxybenzofuran-5-carbaldehyde. $^1H$ NMR (400 MHz, $CDCl_3$) δ ppm: 10.01 (s, 1H), 7.80-7.80 (m, 2H), 7.42 (s, 1H), 6.93 (d, J=2.0 Hz, 1H), 5.70 (br s, 1H).

Step 2: 7-(methoxy-d3)benzofuran-5-carbaldehyde

To a solution of 7-hydroxybenzofuran-5-carbaldehyde (0.34 g, 2.10 mmol) in DMF (20 mL) was added $K_2CO_3$ (579 mg, 4.19 mmol) and $CD_3I$ (1.52 g, 10.48 mmol) at 20° C. The mixture was stirred at 20° C. for 2 hrs. The mixture was poured into $H_2O$ (20 mL), extracted with EtOAc (20 mL×3). The combined organic layers were washed with brine, dried over anhydrous $Na_2SO_4$, filtered and concentrated under reduced pressure. The crude product was purified by column chromatography (silica gel, eluent: PE/EA (v/v)=100/1 to 1/1) to give 7-(methoxy-d3)benzofuran-5-carbaldehyde (0.43 g, crude) as a colorless oil. MS (ESI, m/e) [M+1]+180.2.

Step 3: (R)-3-(2-isopropylphenyl)-1-((7-(methoxy-d3)benzofuran-5-yl)methyl)piperazine To a solution of (R)-2-(2-isopropylphenyl)piperazine (490 mg, 2.40 mmol) in DCM (20 mL) was added 7-(methoxy-d3)benzofuran-5-carbaldehyde (430 mg, 2.40 mmol) and $NaBH(OAc)_3$ (1.27 g, 6.00 mmol) was added at 0° C. The mixture was stirred at 20° C. for 4 hrs.

The mixture was added aqueous $Na_2CO_3$ (20 mL), extracted with EtOAc (20 mL×3). The combined organic layers were washed with brine, dried over anhydrous $Na_2SO_4$, filtered and concentrated under reduced pressure. The residue was purified by column chromatography ((silica gel, eluent: PE/EA (v/v)=10/1 to EA) to give (R)-3-(2-isopropylphenyl)-1-((7-d3-methoxybenzofuran-5-yl) methyl)piperazine (300 mg, yield: 33%) as a yellow oil. $^1H$ NMR (400 MHz, $CDCl_3$) δ ppm: 7.61-7.56 (m, 2H), 7.26-7.21 (m, 2H), 7.18-7.12 (m, 1H), 6.91 (s, 1H), 6.71 (d, J=2.4 Hz, 1H), 4.36 (d, J=9.2 Hz, 1H), 3.70 (m, 3H), 3.27-3.22 (m, 1H), 3.18-3.17 (m, 2H), 3.01-2.91 (m, 2H), 2.45-2.41 (m, 1H), 2.25-2.18 (m, 1H), 1.29-1.20 (m, 2H), 1.26-1.23 (m, 1H), 1.10 (d, J=6.8 Hz, 3H). MS (ESI, m/e) [M+1]+368.2.

Intermediate 324-1: (R)-3-(2-isopropylphenyl)-1-((7-(methoxy-d3)-3,3-dimethyl-2,3-dihydrobenzofuran-S-yl)methyl)piperazine

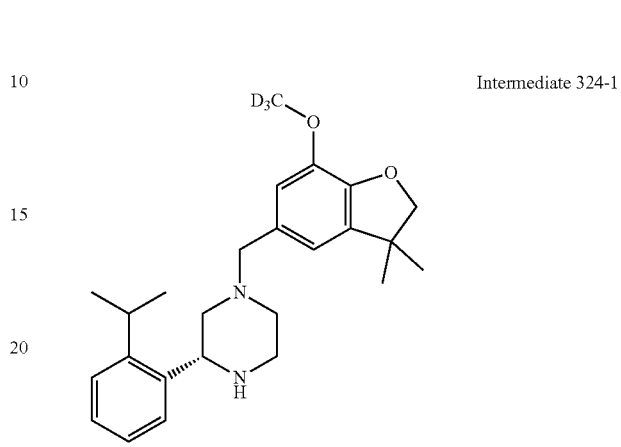

Intermediate 324-1

Step 1: 7-hydroxy-3,3-dimethyl-2,3-dihydrobenzofuran-5-carbaldehyde

To a solution of 7-methoxy-3,3-dimethyl-2,3-dihydrobenzofuran-5-carbaldehyde (4.0 g, 19.4 mmol) in DCM (40 mL) was added $BBr_3$ (14.6 g, 58.19 mmol) at 0° C. The mixture was stirred at 20° C. for 12 hrs. The mixture was added water (200 mL) and extracted with DCM (30 mL×3). The combined organic layers were washed with brine, dried over anhydrous $Na_2SO_4$, filtered and concentrated under reduced pressure. The crude product was purified by column chromatography (silica gel, eluent: PE/EA (v/v)=100/1 to 1/1) to give 7-hydroxy-3,3-dimethyl-2,3-dihydrobenzofuran-5-carbaldehyde (2.8 g, yield: 75%) as a colorless oil. $^1H$ NMR (400 MHz, $CDCl_3$) δ ppm: 9.79 (s, 1H), 7.32 (dd, J=1.2, 14.4 Hz, 2H), 5.97-5.85 (m, 1H), 4.41 (s, 2H), 1.38 (s, 6H).

Step 2: 7-(methoxy-d3)-3,3-dimethyl-2,3-dihydrobenzofuran-5-carbaldehyde

To a solution of 7-hydroxy-3,3-dimethyl-2,3-dihydrobenzofuran-5-carbaldehyde (1.0 g, 5.2 mmol) in DMF (20 mL) was added $CD_3I$ (1.5 g, 10.41 mmol) and $K_2CO_3$ (2.2 g, 15.61 mmol) at 0° C. The mixture was stirred at 20° C. for 6 hrs. The mixture was added water (30 mL) and extracted with EtOAc (20 mL×3). The combined organic layers were washed with brine, dried over anhydrous $Na_2SO_4$, filtered and concentrated under reduced pressure. The crude product was purified by column chromatography (silica gel, eluent: PE/EA (v/v)=100/1 to 1/1) to give 7-(methoxy-d3)-3,3-dimethyl-2,3-dihydrobenzofuran-5-carbaldehyde (1.0 g, yield: 92%) as a colorless oil. $^1H$ NMR (400 MHz, $CDCl_3$) δ ppm: 9.83 (s, 1H), 7.32-7.30 (m, 2H), 4.43 (s, 2H), 1.39 (s, 6H)

Step 3: (R)-3-(2-isopropylphenyl)-1-((7-(methoxy-d3)-3,3-dimethyl-2,3-dihydrobenzofuran-5-yl)methyl)piperazine To a solution of 7-(methoxy-d3)-3,3-dimethyl-2,3-dihydrobenzofuran-5-carbaldehyde (700 mg, 3.35 mmol) and (R)-2-(2-isopropylphenyl)piperazine (683.5 mg, 3.35 mmol) in DCM (10 mL) was added $NaBH(OAc)_3$ (1.77 g, 8.36 mmol) at 0° C. The mixture was stirred at 20° C. for 2 hrs. The reaction mixture was quenched by addition aqueous $NaHCO_3$ (20 mL) at 20° C., extracted with DCM (10 mL×3). The combined organic layers were washed with brine, dried over Na₂SO₄, filtered and concentrated under reduced pressure. The residue was purified by column chromatography (silica gel, eluent: PE/EA (v/v)=100/1 to EA) to give (R)-3-(2-isopropylphenyl)-1-((7-(methoxy-d3)-3,3-dimethyl-2,3-dihydrobenzofuran-5-yl)methyl)piperazine (617 mg, yield: 46%) as a colorless oil. ¹H NMR (400 MHz, CDCl₃) δ ppm: 7.58 (d, J=7.6 Hz, 1H), 7.27 (s, 3H), 6.81-6.66 (m, 2H), 4.30 (s, 2H), 4.27-4.21 (m, 1H), 3.60 (d, J=12.8 Hz, 1H), 3.44 (d, J=12.8 Hz, 1H), 3.27 (td, J=6.8, 13.6 Hz, 1H), 3.20-3.12 (m, 2H), 2.97-2.85 (m, 2H), 2.60-2.49 (m, 1H), 2.33-2.22 (m, 1H), 2.02-1.96 (m, 1H), 1.34 (d, J=2.4 Hz, 6H), 1.26 (d, J=6.8 Hz, 3H), 1.15 (d, J=6.8 Hz, 3H). MS (ESI, m/e) [M+1]⁺398.1.

Intermediate 325-1: (R)-1-(4-chloro-3-methoxybenzyl)-3-(2-isopropylphenyl)piperazine

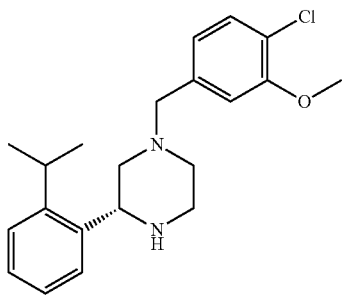

intermediate 325-1

The synthesis procedures were similar to Intermediate 182-1. The compound (R)-1-(4-chloro-3-methoxybenzyl)-3-(2-isopropylphenyl)piperazine was a yellow oil. ¹H NMR (400 MHz, CDCl₃) δ ppm: 7.59 (d, J=7.6 Hz, 1H), 7.32-7.29 (m, 1H), 7.24-7.22 (m, 1H), 7.23-7.13 (m, 2H), 7.02-7.00 (br d, 1H), 6.86-6.84 (m, 1H), 4.28 (br s, 1H), 3.92 (s, 3H), 3.39-3.73 (m, 3H), 3.20-3.28 (m, 1H), 3.13 (br s, 2H), 2.80-2.94 (m, 2H), 2.36 (br s, 1H), 2.14 (br s, 1H), 1.26 (d, J=7.6 Hz, 3H), 1.14 (d, J=7.6 Hz, 3H). MS (ESI, m/e) [M+1]⁺359.0.

Intermediate 327-1: (R)-1-(4-cyclopropyl-3,5-dimethoxybenzyl)-3-(2-isopropylphenyl)piperazine

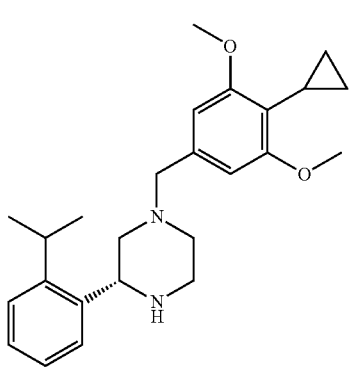

intermediate 327-1

The synthesis procedures were similar to Intermediate 182-1. The compound (R)-1-(4-cyclopropyl-3,5-dimethoxybenzyl)-3-(2-isopropylphenyl)piperazine was a colorless oil. ¹H NMR (400 MHz, CDCl₃) δ ppm: 7.55 (d, J=7.6 Hz, 1H), 7.27-7.14 (m, 3H), 6.53 (s, 2H), 4.21 (d, J=10.0 Hz, 1H), 3.81 (s, 6H), 3.61-3.55 (m, 1H), 3.45-3.40 (m, 1H), 3.29-3.26 (m, 1H), 3.14 (d, J=6.4 Hz, 2H), 2.93-2.82 (m, 2H), 2.28-2.21 (m, 1H), 2.05-1.93 (m, 2H), 1.85-1.76 (m, 1H), 1.25 (d, J=6.8 Hz, 3H), 1.14 (d, J=6.8 Hz, 3H), 0.93-0.88 (m, 2H), 0.84-0.79 (m, 2H). MS (ESI, m/e) [M+1]⁺395.2.

Intermediate 329-1: (R)-3-(2-isopropylphenyl)-1-((8-methoxy-2,2-dimethyl-2H-chromen-6-yl)methyl)piperazine

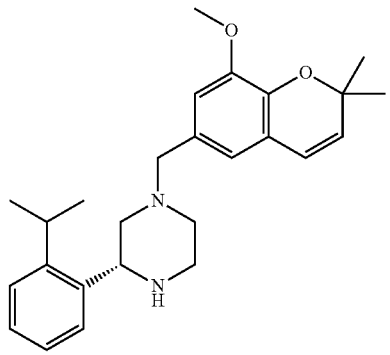

intermediate 329-1

The synthesis procedures were similar to Intermediate 182-1. The compound (R)-3-(2-isopropylphenyl)-1-((8-methoxy-2,2-dimethyl-2H-chromen-6-yl)methyl)piperazine was a yellow oil. ¹H NMR (400 MHz, CDCl₃) δ ppm: 7.56-7.53 (m, 1H), 7.27-7.17 (m, 3H), 6.79 (d, J=1.6 Hz, 1H), 6.59 (d, J=1.6 Hz, 1H), 6.28 (d, J=9.6 Hz, 1H), 5.60 (d, J=9.6 Hz, 1H), 4.21-4.18 (m, 1H), 3.87 (s, 3H), 3.54-3.49 (m, 1H), 3.40-3.35 (m, 1H), 3.28-3.23 (m, 1H), 3.17-3.11 (m, 2H), 2.93-2.83 (m, 2H), 2.24-2.18 (m, 1H), 1.98-1.93 (m, 1H), 1.90-1.82 (m, 1H), 1.46 (d, J=2.8 Hz, 6H), 1.23 (d, J=6.8 Hz, 3H), 1.14 (d, J=6.8 Hz, 3H). MS (ESI, m/e) [M+1]⁺407.1.

Intermediate 331-1: (R)-3-(2-isopropylphenyl)-1-((4-methoxybenzofuran-6-yl)methyl)piperazine

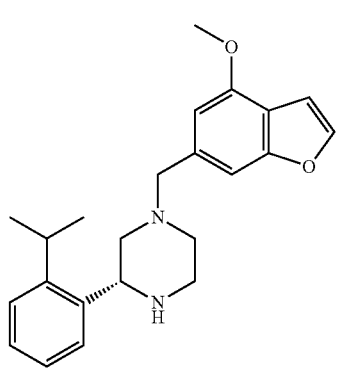

intermediate 331-1

The synthesis procedures were similar to Intermediate 182-1. The compound (R)-3-(2-isopropylphenyl)-1-((4-methoxybenzofuran-6-yl)methyl)piperazine was a yellow oil. ¹H NMR (400 MHz, CDCl₃) δ ppm: 7.48-7.41 (m, 2H), 7.18-7.06 (m, 3H), 7.04 (s, 1H), 6.74-6.73 (m, 1H), 6.64 (s, 1H), 4.19-4.16 (m, 1H), 3.87 (s, 3H), 3.65-3.52 (m, 2H), 3.25-3.14 (m, 1H), 3.11-3.04 (m, 2H), 2.89-2.78 (m, 2H), 2.29-2.17 (m, 1H), 2.03-2.00 (d, J=10.8 Hz, 1H), 1.16 (d, J=6.8 Hz, 3H), 1.03 (d, J=6.8 Hz, 3H). MS (ESI, m/e) [M+1]⁺365.1.

Intermediate 333-1: (R)-3-(2-isopropylphenyl)-1-((8-methoxy-4,4-dimethylchroman-6-yl)methyl)piperazine

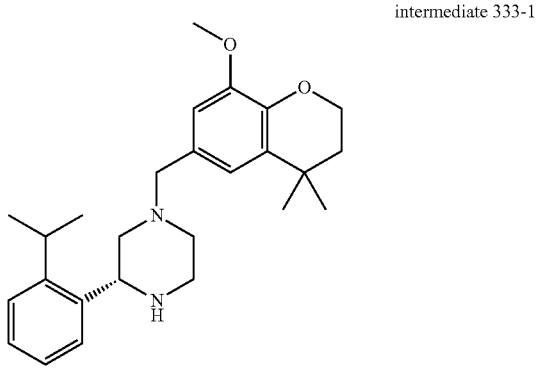 [SMILES: COc1cc(CN2CCN[C@H](c3ccccc3C(C)C)C2)cc2c1OCCC2(C)C]

intermediate 333-1

Step 1: methyl 3-(4-bromo-2-methoxyphenoxy)propanoate

A mixture of 4-bromo-2-methoxyphenol (10.0 g, 49.25 mmol) in methyl acrylate (100 mL) was added to triton B (1.0 mL) and MeOH (1.0 mL). The mixture was stirred reflux for 12 hrs. The mixture was cooled to room temperature and then concentrated under reduced pressure.

The residue was poured into water (100 mL), extracted with EtOAc (100 mL×3). The combined organic layers were washed with brine, dried over anhydrous Na₂SO₄, filtered and concentrated under reduced pressure. The crude product was purified by phase separation to give methyl 3-(4-bromo-2-methoxyphenoxy)propanoate (5.6 g, yield: 39%) as a yellow oil. ¹H NMR (400 MHz, CDCl₃) δ ppm: 6.97-7.05 (m, 2H), 6.80 (d, J=8.8 Hz, 1H), 4.29-4.26 (m, 2H), 3.84 (s, 3H), 3.73 (s, 3H), 2.87-2.83 (m, 2H).

Step 2: 4-(4-bromo-2-methoxyphenoxy)-2-methylbutan-2-ol.

A mixture of methyl 3-(4-bromo-2-methoxyphenoxy)propanoate (5.1 g, 17.64 mmol) in THF (50 mL) MeMgBr (17.64 mL, 52.92 mmol, 3.ON) was added at −70° C. The mixture was stirred at −70° C. for 3 hrs. The residue was poured into ice water (100 mL), extracted with EtOAc (100 mL×3). The combined organic layers were washed with brine, dried over anhydrous Na₂SO₄, filtered and concentrated under reduced pressure. The crude product was purified by column chromatography (silica gel, eluent: PE/EA (v/v)=100/1 to 1/1) to give 4-(4-bromo-2-methoxyphenoxy)-2-methylbutan-2-ol (4.5 g, yield: 88%) as a yellow solid. MS (ESI, m/e) [M+1]⁺290.1.

Step 3: 6-bromo-8-methoxy-4,4-dimethylchromane

A mixture of 4-(4-bromo-2-methoxyphenoxy)-2-methylbutan-2-ol (3.5 g, 12.1 mmol) in MeNO₂ (30 mL) was added to AlCl₃ (2.3 g, 16.39 mmol) in MeNO₂ (250 mL) at 0° C. and the mixture was stirred at 25° C. for 2 hrs. The residue was poured into ice water (100 mL), extracted with EtOAc (50 mL×3). The combined organic layers were washed with brine, dried over anhydrous Na₂SO₄, filtered and concentrated under reduced pressure. The residue was purified by column chromatography (silica gel, eluent: PE/EA (v/v)=100/1 to 1/1) to give 6-bromo-8-methoxy-4,4-dimethylchroman (2.4 g, yield: 73%) as a yellow oil. ¹H NMR (400 MHz, CDCl₃) δ ppm: 7.00 (d, J=2.0 Hz, 1H), 6.80 (d, J=2.4 Hz, 1H), 4.30-4.24 (m, 2H), 3.85 (s, 3H), 1.87-1.81 (m, 2H), 1.32 (s, 6H).

Step 4: 8-methoxy-4,4-dimethylchromane-6-carbaldehyde

To a solution of 6-bromo-8-methoxy-4,4-dimethylchroman (2.4 g, 8.9 mmol) in THF (30 mL) was added n-BuLi (8.9 mL, 22.1 mmol, 2.5 N) at −70° C. After stirred at −70° C. for 5 min, DMF (3.2 g, 44.3 mmol) was added dropwise at −70° C. The mixture was stirred at −70° C. for 2 hrs. The mixture was poured into aqueous. NH₄Cl (50 mL), extracted with EtOAc (30 mL×3).

The combined organic layers were washed with brine, dried over anhydrous Na₂SO₄, filtered and concentrated under reduced pressure. The crude product was purified by column chromatography (silica gel, eluent: PE/EA (v/v)= 100/1 to 5/1) to give 8-methoxy-4,4-dimethylchroman-6-carbaldehyde (1.4 g, yield: 72%) as a light yellow solid. ¹H NMR (400 MHz, CDCl₃) δ ppm: 9.82 (s, 1H), 7.44 (d, J=1.6 Hz, 1H), 7.23 (d, J=1.6 Hz, 1H), 7.26-7.20 (m, 1H), 4.40-4.33 (m, 2H), 3.92 (s, 3H), 1.92-1.86 (m, 2H), 1.38 (s, 6H).

Step 5: (R)-3-(2-isopropylphenyl)-1-((8-methoxy-4,4-dimethylchroman-6-yl)methyl)piperazine To a solution of (R)-2-(2-isopropylphenyl)piperazine (843 mg, 4.1 mmol) in DCM (30 mL) was added 8-methoxy-4,4-dimethylchroman-6-carbaldehyde (1 g, 4.5 mmol) and NaBH(OAc)₃ (2.2 g, 10.3 mmol) at 0° C. and the mixture was stirred at 25° C. for 12 hrs. The mixture was added aqueous NaHCO₃ (30 mL), extracted with DCM (30 mL×3). The combined organic layers were washed with brine, dried over anhydrous Na₂SO₄, filtered and concentrated under reduced pressure. The residue was purified by column chromatography (silica gel, eluent: PE/EA (v/v)=100/1 to EA) to give (R)-3-(2-isopropylphenyl)-1-((8-methoxy-4,4-dimethylchroman-6-yl)methyl)piperazine (1149 mg, yield: 68%) as a yellow solid. ¹H NMR (400 MHz, CDCl₃) δ ppm: 7.56-7.53 (m, 1H), 7.27-7.16 (m, 3H), 6.81 (d, J=1.6 Hz, 1H), 6.73 (d, J=1.6 Hz, 1H), 4.28-4.24 (m, 2H), 4.23-4.21 (m, 1H), 3.87 (s, 3H), 3.58-3.53 (m, 1H), 3.44-3.38 (m, 1H), 3.30-3.23 (m, 1H), 3.16-3.11 (m, 2H), 2.92-2.81 (m, 2H), 2.24-2.20 (m, 1H), 2.20-1.98 (m, 1H), 1.85-1.82 (m, 2H), 1.32 (d, J=5.6 Hz, 6H), 1.24 (d, J=6.8 Hz, 3H), 1.14 (d, J=6.8 Hz, 3H). MS (ESI, m/e) [M+1]⁺409.1.

Intermediate 335-1: (R)-3-(2-isopropylphenyl)-1-((9-methoxy-3,4-dihydro-2H-benzo[b][1,4]dioxepin-7-yl)methyl)piperazine

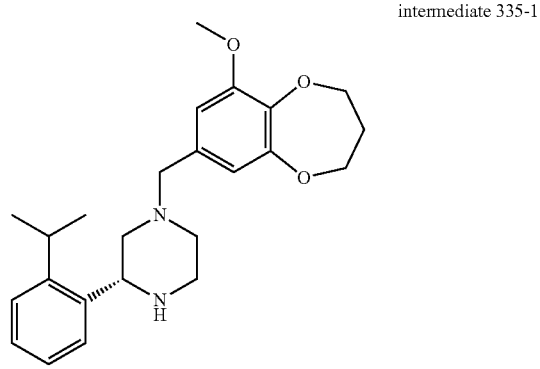 [SMILES: COc1cc(CN2CCN[C@H](c3ccccc3C(C)C)C2)cc2c1OCCCO2]

intermediate 335-1

The synthesis procedures were similar to Intermediate 182-1. The compound (R)-3-(2-isopropylphenyl)-1-((9-methoxy-3,4-dihydro-2H-benzo[b][1,4]dioxepin-7-yl)methyl)piperazine was a yellow oil. ¹H NMR (400 MHz, CDCl₃) δ ppm: 7.47 (d, J=7.6 Hz, 1H), 7.19-7.06 (m, 3H), 6.55 (s, 1H), 6.50 (s, 1H), 4.20-4.17 (m, 2H), 4.15-4.12 (m, 3H), 3.79 (s, 3H), 3.47-3.39 (m, 1H), 3.35-3.27 (m, 1H), 3.23-3.16 (m, 1H), 3.06 (d, J=6.0 Hz, 2H), 2.86-2.73 (m, 2H), 2.22-2.10 (m, 3H), 1.97-1.89 (m, 1H), 1.16 (d, J=6.8 Hz, 3H), 1.08 (d, J=6.8 Hz, 3H). MS (ESI, m/e) [M+1]397.2.

Intermediate 338-1: synthesis of (R)-3-(2-isopropylphenyl)-1-((7-methoxy-2-methylbenzofuran-5-yl)methyl)piperazine intermediate 338-1

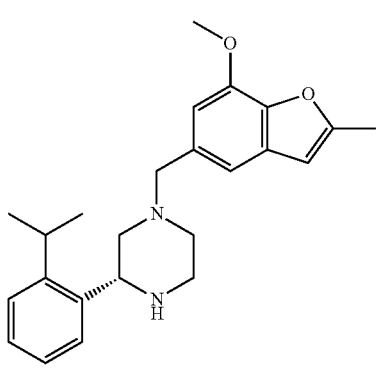

Step 1: synthesis of 3-methoxy-4-(prop-2-yn-1-yloxy)benzaldehyde.

To a solution of 4-hydroxy-3-methoxybenzaldehyde (50 g, 328.63 mmol) in DMF (80 mL) was added 3-bromoprop-1-yne (78 g, 657.26 mmol), K₂CO₃ (90.84 g, 657.26 mmol) at 20° C. The mixture was stirred at 80° C. for 12 hrs. The mixture was cooled to room temperature and was diluted with water (80 mL) and then extracted with EtOAc (500 mL×3). The combined organic layer was washed with brine, dried over anhydrous Na₂SO₄, filtered and concentrated under reduced pressure.

The crude product was purified by column chromatography (silica gel, eluent: PE/EA (v/v)=100/1 to 1/1) to give 3-methoxy-4-(prop-2-yn-1-yloxy)benzaldehyde (58 g, yield: 93%) as a white solid.

¹H NMR (400 MHz, CDCl₃) δ ppm: 9.89 (s, 1H), 7.48-7.44 (m, 2H), 7.16 (d, J=8.4 Hz, 1H), 4.87 (d, J=2.4 Hz, 2H), 3.95 (s, 3H), 2.57 (t, J=2.4 Hz, 1H).

Step 2: synthesis of 7-methoxy-2-methylbenzofuran-5-carbaldehyde.

To a solution of 3-methoxy-4-(prop-2-yn-1-yloxy)benzaldehyde (39 g, 31.55 mmol) was added PEG-600 (200 mL) at 20° C. The mixture was stirred at 220° C. for 4 hrs. The mixture was cooled to room temperature and was diluted with water (200 mL) and extracted with EtOAc (200 mL×3). The combined organic layer was washed with brine, dried over anhydrous Na₂SO₄, filtered and concentrated under reduced pressure. The crude product was purified by column chromatography (silica gel, eluent: PE/EA (v/v)=100/1 to 1/1) to give 7-methoxy-2-methylbenzofuran-5-carbaldehyde (14 g, yield: 35%) as a white solid. ¹H NMR (400 MHz, CDCl₃) δ ppm: 10.00 (s, 1H), 7.64 (s, 1H), 7.34 (s, 1H), 6.51 (s, 1H), 4.07 (s, 3H), 2.54 (s, 3H).

Step 3: synthesis of (R)-3-(2-isopropylphenyl)-1-((7-methoxy-2-methylbenzofuran-5-yl)methyl)piperazine.

To a solution of (R)-2-(2-isopropylphenyl)piperazine (10 g, 48.94 mmol) in DCM (200 mL) was added 7-methoxy-2-methylbenzofuran-5-carbaldehyde (9.31 g, 48.94 mmol) and NaBH(OAc)₃ (25.93 g, 122.38 mmol) at 0° C. The mixture was then stirred at room temperature for 12 hrs. The mixture was quenched with aqueous Na₂CO₃ (6M, 200 mL), extracted with EtOAc (200 mL×3). The combined organic layer was washed with brine, dried over anhydrous Na₂SO₄, filtered and concentrated under reduced pressure. The residue was purified by column chromatography (silica gel, eluent: PE/EA (v/v)=100/1 to EA) to give (R)-3-(2-isopropylphenyl)-1-((7-methoxy-2-methylbenzofuran-5-yl)methyl)piperazine (12.2 g, yield: 64%). ¹H NMR (400 MHz, CDCl₃) δ ppm: 7.56-7.54 (m, 1H), 7.24-7.21 (m, 3H), 7.01 (s, 1H), 6.79 (s, 1H), 6.30 (d, J=1.2 Hz, 1H), 4.23-4.20 (m, 1H), 4.02 (s, 3H), 3.65-3.53 (m, 2H), 3.33-3.23 (m, 1H), 3.15-3.12 (m, 2H), 2.96-2.83 (m, 2H), 2.46 (d, J=0.4 Hz, 3H), 2.31-2.20 (m, 1H), 2.04-1.99 (t, J=10.6 Hz, 1H), 1.24 (d, J=6.8 Hz, 3H), 1.12 (d, J=6.8 Hz, 3H). MS (ESI, m/e) [M+1]⁺379.2.

Intermediate 341-1: (R)-1-(4-cyclobutyl-3-methoxybenzyl)-3-(2-isopropylphenyl)piperazine intermediate 341-1

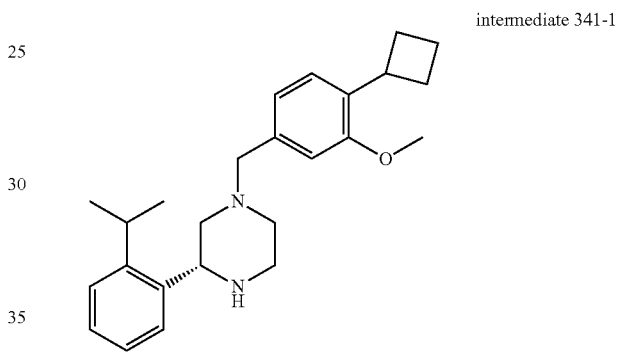

The synthesis procedures were similar to Intermediate 182-1. The compound (R)-1-(4-cyclobutyl-3-methoxybenzyl)-3-(2-isopropylphenyl)piperazine was a yellow oil. ¹H NMR (400 MHz, CDCl₃) δ ppm: 7.58 (d, J=7.6 Hz, 1H), 7.27-7.21 (m, 2H), 7.18-7.12 (m, 2H), 6.93-6.83 (m, 2H), 4.35-4.33 (m, 1H), 3.82 (s, 3H), 3.74-3.54 (m, 4H), 3.36-3.14 (m, 2H), 2.99-2.88 (m, 2H), 2.35-2.25 (m, 3H), 2.14-2.02 (m, 5H), 1.84-1.78 (m, 1H), 1.27-1.24 (m, 3H), 1.13 (d, J=6.8 Hz, 3H). MS (ESI, m/e) [M+1]⁺379.1.

Intermediate 345-1: (R)-3-(2-isopropylphenyl)-1-(3-methoxy-4-(oxetan-3-yl)benzyl)piperazine intermediate 345-1

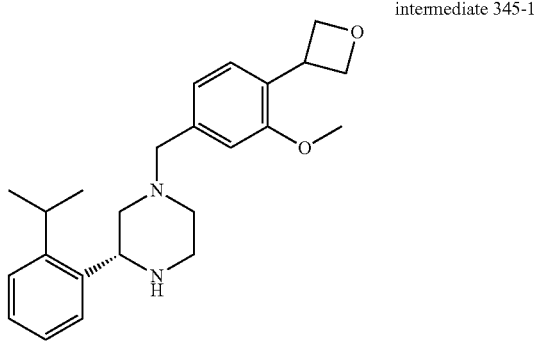 [SMILES: COc1cc(CN2CCN[C@H](c3ccccc3C(C)C)C2)ccc1C1COC1]

The synthesis procedures were similar to Intermediate 182-1. The compound (R)-3-(2-isopropylphenyl)-1-(3-methoxy-4-(oxetan-3-yl)benzyl)piperazine was a yellow oil. $^1$H NMR (400 MHz, CDCl$_3$) δ ppm: 7.57 (d, J=7.6 Hz, 1H), 7.26-7.14 (m, 4H), 6.96-6.84 (m, 2H), 5.01-4.97 (m, 2H), 4.84-4.79 (m, 2H), 4.51-4.49 (m, 1H), 4.26 (s, 1H), 3.81 (s, 3H), 3.68-3.59 (m, 1H), 3.51-3.49 (m, 1H), 3.30-3.21 (m, 1H), 3.14 (d, J=5.6 Hz, 2H), 2.95-2.81 (m, 2H), 2.39-2.28 (m, 1H), 2.13-2.06 (m, 1H), 1.25 (d, J=6.8 Hz, 3H), 1.13 (d, J=6.8 Hz, 3H). MS (ESI, m/e) [M+1]$^+$381.2.

Intermediate 347-1: (R)-3-(2-isopropylphenyl)-1-((9-methoxy-2,3,4,5-tetrahydrobenzo[b]oxepin-7-yl)methyl)piperazine

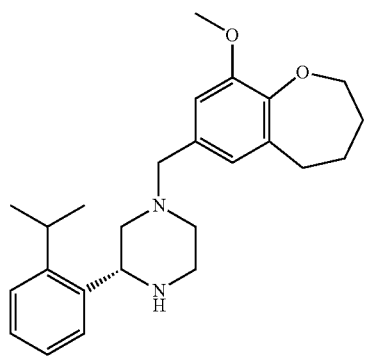

intermediate 347-1

The synthesis procedures were similar to Intermediate 182-1. The compound (R)-3-(2-isopropylphenyl)-1-((9-methoxy-2,3,4,5-tetrahydrobenzo[b]oxepin-7-yl)methyl)piperazine was a yellow solid. $^1$H NMR (400 MHz, CDCl$_3$) δ ppm: 7.56-7.54 (m, 1H), 7.29-7.25 (m, 2H), 7.21-7.19 (m, 1H), 6.80 (s, 1H), 6.68 (s, 1H), 4.32-4.30 (m, 1H), 4.01-4.00 (m, 2H), 3.86 (s, 3H), 3.60-3.43 (m, 2H), 3.25-3.20 (m, 3H), 2.80-2.79 (m, 2H), 2.78-2.77 (m, 2H), 2.35-2.31 (m, 1H), 2.09-2.07 (m, 1H), 2.00-1.96 (m, 2H), 1.72-1.71 (m, 2H), 1.26 (d, J=6.8 Hz, 3H), 1.15 (d, J=6.8 Hz, 3H). MS (ESI, m/e) [M+1]$^+$395.2.

Intermediate 349-1: (R)-1-(4-isopropoxy-3-methoxybenzyl)-3-(2-isopropylphenyl)piperazine

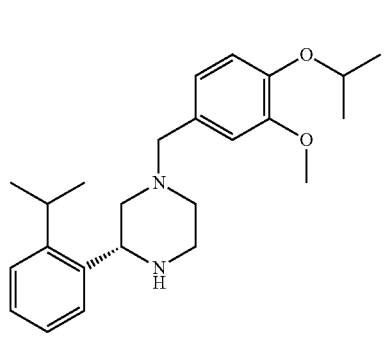

intermediate 349-1

The synthesis procedures were similar to Intermediate 182-1. The compound (R)-1-(4-isopropoxy-3-methoxybenzyl)-3-(2-isopropylphenyl)piperazine was a yellow oil. $^1$H NMR (400 MHz, CDCl$_3$) δ ppm: 7.56 (d, J=7.6 Hz, 1H), 7.27-7.19 (m, 3H), 6.94-6.74 (m, 4H), 5.52-5.46 (m, 1H), 4.50-4.47 (m, 2H), 4.34-4.31 (m, 1H), 3.86 (s, 3H), 3.62-3.51 (m, 2H), 3.23-3.16 (m, 2H), 2.95-2.90 (m, 2H), 1.36-1.32 (m, 6H), 1.24 (d, J=6.8 Hz, 3H), 1.12 (d, J=6.8 Hz, 3H). MS (ESI, m/e) [M+1]$^+$383.2.

Intermediate 350-1: (R)-1-(4-cyclobutoxy-3-methoxybenzyl)-3-(2-isopropylphenyl)piperazine

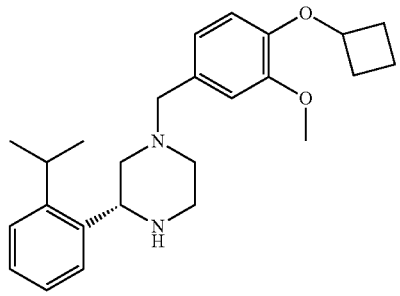

intermediate 350-1

The synthesis procedures were similar to Intermediate 182-1. The compound (R)-1-(4-cyclobutoxy-3-methoxybenzyl)-3-(2-isopropylphenyl)piperazine was a yellow oil. $^1$H NMR (400 MHz, CDC$_3$) δ ppm: 7.55-7.53 (m, 1H), 7.25-7.14 (m, 3H), 6.91 (s, 1H), 6.78-6.76 (m, 1H), 6.66-6.64 (m, 1H), 4.66-4.59 (m, 1H), 4.18-4.08 (m, 1H), 3.88 (s, 3H), 3.57-3.53 (m, 2H), 3.45-3.43 (m, 1H), 3.14-3.12 (m, 2H), 2.45-2.44 (m, 2H), 2.27-2.24 (m, 4H), 2.23 (s, 1H), 2.22-2.05 (m, 1H), 1.83-1.68 (m, 1H), 1.23-1.22 (m, 3H), 1.13-1.12 (m, 3H). MS (ESI, m/e) [M+1]$^+$395.2.

Intermediate 351-1: (R)-3-(2-isopropylphenyl)-1-(3-methoxy-4-(oxetan-3-yloxy)benzyl)piperazine

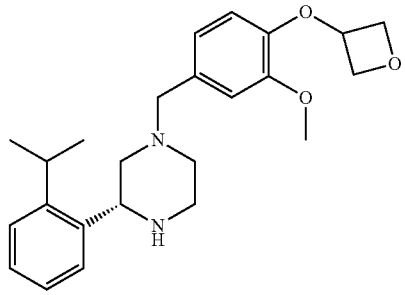

intermediate 351-1

The synthesis procedures were similar to Intermediate 182-1. The compound (R)-3-(2-isopropylphenyl)-1-(3-methoxy-4-(oxetan-3-yloxy)benzyl)piperazine was a yellow oil. $^1$H NMR (400 MHz, CDC$_3$) δ ppm: 7.56 (d, J=7.6 Hz, 1H), 7.27-7.24 (m, 2H), 7.18-7.16 (m, 1H), 6.99 (s, 1H), 6.78-6.76 (m, 1H), 6.40 (d, J=8.0 Hz, 1H), 5.20-5.16 (m, 1H), 4.96-4.92 (m, 2H), 4.85-4.82 (m, 2H), 4.31 (d, J=7.2 Hz, 1H), 3.90 (s, 3H), 3.63-3.47 (m, 2H), 3.30-3.09 (m, 3H), 2.97-2.83 (m, 2H), 2.43-2.29 (m, 1H), 2.19-2.09 (m, 1H), 1.26-1.23 (m, 3H), 1.12 (d, J=7.2 Hz, 3H). MS (ESI, m/e) [M+1]$^+$397.2.

Intermediate 361-1: (R)-4-(4-((3-(2-isopropylphenyl)piperazin-1-yl)methyl)-2-methoxyphenyl)morpholine

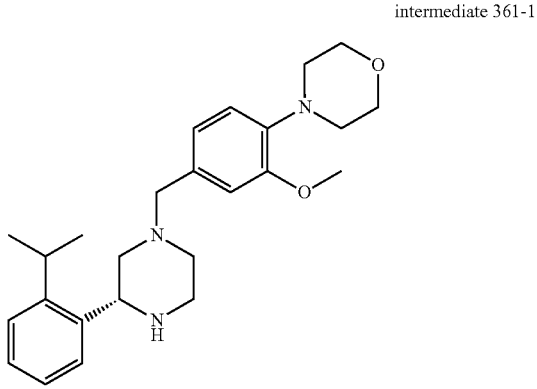 [SMILES: COc1cc(CN2CCN[C@H](c3ccccc3C(C)C)C2)ccc1N1CCOCC1]

intermediate 361-1

Step 1: 3-methoxy-4-morpholinobenzaldehyde

To a solution of 4-fluoro-3-methoxybenzaldehyde (2 g, 12.98 mmol) in DMSO (15 mL) was added morpholine (1.6 g, 12.98 mmol), $K_2CO_3$ (3.59 g, 25.95 mmol) at 100° C. The mixture was stirred at 100° C. for 12 hrs. The mixture was added water (30 mL) and extracted with EtOAc (30 mL×3). The combined organic layer was washed with brine, dried over anhydrous $Na_2SO_4$, filtered and concentrated under reduced pressure. The crude product was purified by column chromatography (silica gel, eluent: PE/EA (v/v)=100/1 to 1/1) to 3-methoxy-4-morpholinobenzaldehyde (2.23 g, yield: 87%) as a white solid. $^1$H NMR (400 MHz, $CDCl_3$) δ ppm: 9.86 (s, 1H), 7.45 (d, J=2.0 Hz, 1H), 7.43 (d, J=2.0 Hz, 1H), 6.99-6.97 (m, 1H), 3.93 (s, 3H), 3.90-3.88 (m, 4H), 3.22-3.20 (m, 4H).

Step 2: (R)-4-(4-((3-(2-isopropylphenyl)piperazin-1-yl)methyl)-2-methoxyphenyl)morpholine To a solution of 3-methoxy-4-morpholinobenzaldehyde (600 mg, 2.58 mmol) in DCM (10 mL) was added 3-methoxy-4-(oxetan-3-yloxy)benzaldehyde (554.06 mg, 2.58 mmol) and $NaBH(OAc)_3$ (1.15 g, 5.16 mmol) was added at 0° C. The mixture was stirred at 20° C. for 12 hrs.

The mixture was added aqueous $Na_2CO_3$ (20 mL), extracted with EtOAc (20 mL×3). The combined organic layers were washed with brine, dried over anhydrous $Na_2SO_4$, filtered and concentrated under reduced pressure. The residue was purified by column chromatography (silica gel, eluent: PE/EA (v/v)=100/1 to EA) to give (R)-4-(4-((3-(2-isopropylphenyl)piperazin-1-yl)methyl)-2-methoxyphenyl)morpholine (600 mg, yield: 66%) as a yellow oil. $^1$H NMR (400 MHz, $CDCl_3$) δ ppm: 7.56 (d, J=7.6 Hz, 1H), 7.25-7.22 (m, 2H), 7.21-7.15 (m, 1H), 6.93 (s, 1H), 6.85-6.84 (m, 2H), 4.22 (d, J=8.0 Hz, 1H), 3.90-3.88 (m, 8H), 3.59-3.56 (m, 1H), 3.47-3.45 (m, 1H), 3.28-3.25 (m, 1H), 3.14-3.12 (m, 2H), 3.05-3.03 (m, 4H), 2.91-2.80 (m, 2H), 2.26-2.21 (m, 1H), 2.03-1.99 (m, 1H), 1.24 (d, J=6.8 Hz, 3H), 1.14 (d, J=6.8 Hz, 3H). MS (ESI, m/e) [M+1]$^+$410.3.

Intermediate 362-1: (R)-3-(2-isopropylphenyl)-1-(4-(oxetan-3-yl)benzyl)piperazine

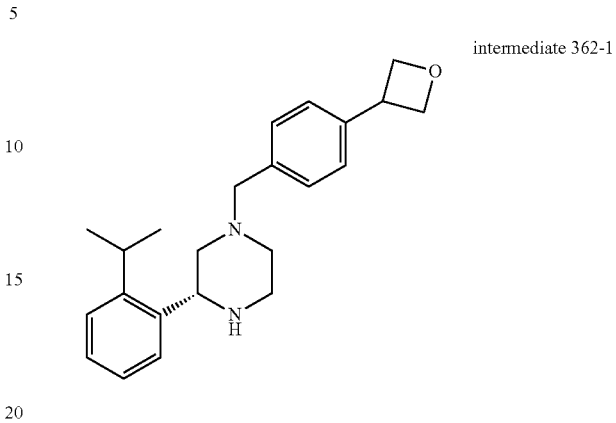

intermediate 362-1

The synthesis procedures were similar to Intermediate 182-1. The compound (R)-3-(2-isopropylphenyl)-1-(4-(oxetan-3-yl)benzyl)piperazine as a yellow oil. $^1$H NMR (400 MHz, $CDCl_3$) δ ppm: 7.46 (d, J=8.0 Hz, 1H), 7.20-7.14 (m, 6H), 7.12-7.09 (m, 1H), 5.01-4.98 (m, 2H), 4.70-4.67 (m, 2H), 4.19-4.09 (m, 2H), 3.57-3.41 (m, 2H), 3.25-3.14 (m, 1H), 3.09-3.01 (m, 2H), 2.85-2.72 (m, 2H), 2.18-2.17 (m, 1H), 1.99-1.94 (m, 1H), 1.16 (d, J=6.8 Hz, 3H), 1.06 (d, J=6.8 Hz, 3H). MS (ESI, m/e) [M+1]$^+$351.2.

Intermediate 363-1: (R)-1-(3,4-dicyclopropoxybenzyl)-3-(2-isopropylphenyl)piperazine

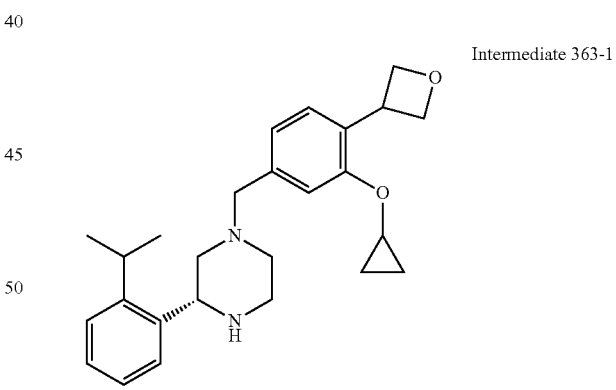

Intermediate 363-1

The synthesis procedures were similar to Intermediate 182-1. The compound (R)-1-(3,4-dicyclopropoxybenzyl)-3-(2-isopropylphenyl)piperazine was a yellow oil. $^1$H NMR (400 MHz, $CDCl_3$) δ ppm: 7.55-7.53 (m, 1H), 7.27-7.13 (m, 5H), 6.88-6.84 (m, 1H), 4.21 (d, J=8.8 Hz, 1H), 3.79-3.69 (m, 2H), 3.62-3.55 (m, 1H), 3.50-3.42 (m, 1H), 3.14-3.06 (m, 2H), 2.94-2.81 (m, 2H), 2.29-2.21 (m, 1H), 2.06-2.05 (m, 1H), 1.23 (d, J=6.8 Hz, 3H), 1.14 (d, J=6.8 Hz, 3H), 0.83-0.74 (m, 8H). MS (ESI, m/e) [M+1]$^+$407.3.

3Example 3

2-((1H-pyrrolo[2,3-b]pyridin-5-yl)oxy)-N-((4-(((((1r,4r)-4-hydroxy-4-methylcyclohexyl)methyl)amino)-3-nitrophenyl)sulfonyl)-4-(2-(4-isopropyl-2-(2-isopropylphenyl)piperazin-1-yl)-7-azaspiro[3.5]nonan-7-yl)benzamide

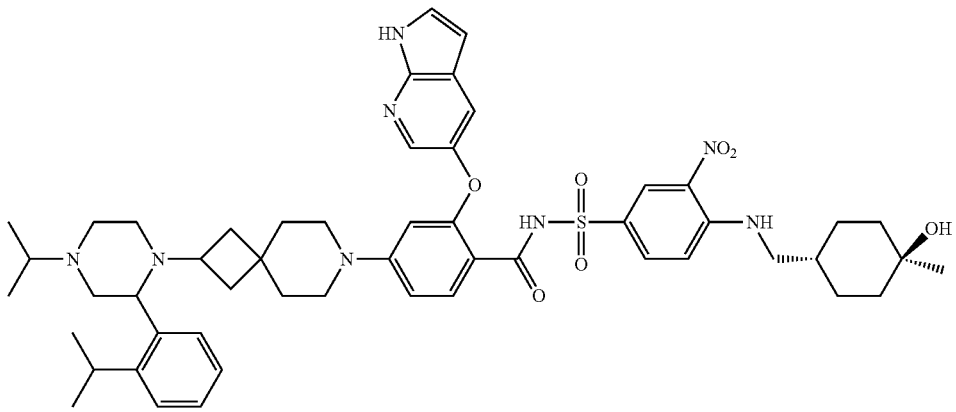 [SMILES: CC(C)c1ccccc1C1CN(C(C)C)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

Intermediate 3-1: 2-(4-isopropyl-2-(2-isopropylphenyl)piperazin-1-yl)-7-azaspiro[3.5]nonane

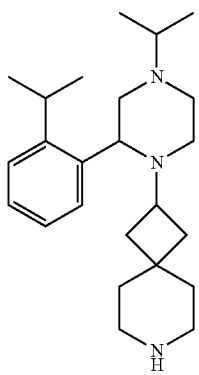

Intermediate 3-1

Step 1: tert-butyl 2-(2-bromophenyl)-3-oxopiperazine-1-carboxylate.

To a solution of 3-(2-bromophenyl)piperazin-2-one (31.2 g, 122.3 mmol) in DCM (300 mL) was added TEA (24.75 g, 244.6 mmol) and Boc$_2$O (29.36 g, 134.43 mmol) at 0° C. The mixture was stirred at 25° C. for 5 hrs. The reaction mixture was poured into H$_2$O (400 mL), extracted with DCM (300 mL×3). The combined organic layers were washed with brine, dried over Na$_2$SO$_4$, filtered and concentrated under reduced pressure. The residue was purified by MPLC. The compound tert-butyl 2-(2-bromophenyl)-3-oxopiperazine-1-carboxylate (34.2 g, yield: 78%) was obtained as a yellow solid. MS (ESI, m/e) [M+1]$^+$355.0.

Step 2: tert-butyl 3-oxo-2-(2-(prop-1-en-2-yl)phenyl)piperazine-1-carboxylate.

To a solution of tert-butyl 2-(2-bromophenyl)-3-oxopiperazine-1-carboxylate (34.2 g, 96.28 mmol) and 4,4,5,5-tetramethyl-2-(prop-1-en-2-yl)-1,3,2-dioxaborolane (9.41 g, 115.53 mmol) in dioxane (400 mL) and H$_2$O (40 mL) was added Cs$_2$CO$_3$ (62.74 g, 192.55 mmol) and Pd(dppf)Cl$_2$.DCM (7.86 g, 9.63 mmol) under N$_2$. The mixture was stirred at 100° C. for 12 hrs. The reaction mixture was filtered and concentrated under reduced pressure. The residue was poured into H$_2$O (200 mL), extracted with EtOAc (200 mL×3). The combined organic layers were washed with brine, dried over Na$_2$SO$_4$, filtered and concentrated under reduced pressure. The residue was purified by MPLC. The compound tert-butyl 3-oxo-2-(2-(prop-1-en-2-yl)phenyl)piperazine-1-carboxylate (28.2 g, yield: 92%) was obtained as a yellow solid. $^1$H NMR (400 MHz, CDCl$_3$) δ ppm: 7.57 (br s, 1H), 7.31-7.14 (m, 4H), 6.05 (s, 1H), 5.22 (s, 1H), 5.01 (s, 1H), 4.02-3.92 (m, 1H), 3.53-3.43 (m, 1H), 3.36-3.24 (m, 2H), 2.08 (s, 3H), 1.39 (s, 9H).

Step 3: tert-butyl 2-(2-isopropylphenyl)-3-oxopiperazine-1-carboxylate.

To a solution of tert-butyl 3-oxo-2-(2-(prop-1-en-2-yl)phenyl)piperazine-1-carboxylate (28.2 g, 89.13 mmol) in MeOH (100 mL) was added Pd/C (3.8 g, 3.16 mmol). The mixture was stirred at 50° C. under H$_2$ (50 psi) for 12 hrs. The reaction mixture was filtered and concentrated under reduced pressure to give tert-butyl 2-(2-isopropylphenyl)-3-oxopiperazine-1-carboxylate (25.2 g, yield: 88%) as a yellow solid. $^1$H NMR (400 MHz, CDCl$_3$) δ ppm: 7.55-7.40 (m, 1H), 7.40-7.36 (m, 1H), 7.35-7.29 (m, 1H), 7.26-7.21 (m, 1H), 7.20-7.13 (m, 1H), 6.04 (s, 1H), 3.94 (d, J=11.6 Hz, 1H), 3.61-3.51 (m, 2H), 3.38-3.21 (m, 2H), 1.48 (s, 9H), 1.30 (d, J=6.8 Hz, 3H), 1.18 (d, J=6.8 Hz, 3H).

Step 4: 3-(2-isopropylphenyl)piperazin-2-one.

A mixture of tert-butyl 2-(2-isopropylphenyl)-3-oxopiperazine-1-carboxylate (20 g, 62.81 mmol) in DCM (100 mL) and TFA (50 mL) was stirred at 25° C. for 6 hrs. The reaction mixture was concentrated under reduced pressure. The residue was diluted with H$_2$O (100 mL) and the mixture was adjusted to pH=9 with saturated aq. Na$_2$CO$_3$. The mixture was extracted with DCM (100 mL×3). The combined organic layers were washed with brine, dried over Na$_2$SO$_4$, filtered and concentrated under reduced pressure to give 3-(2-isopropylphenyl)piperazin-2-one (13.7 g, crude) as a yellow solid. $^1$H NMR (400 MHz, CDCl$_3$) δ ppm: 7.45-7.32 (m, 3H), 7.30 (br, 1H), 7.28-7.22 (m, 1H), 4.88 (s, 1H), 3.63 (m, 1H), 3.49-3.33 (m, 2H), 3.31-3.21 (m, 1H), 3.20-3.10 (m, 1H), 1.89 (s, 1H), 1.39 (d, J=6.8 Hz, 3H), 1.35 (d, J=6.8 Hz, 3H).

Step 5: tert-butyl 2-(2-(2-isopropylphenyl)-3-oxopiperazin-1-yl)-7-azaspiro[3.5]nonane-7-carboxylate.

To a solution of 3-(2-isopropylphenyl)piperazin-2-one (13.7 g, 62.76 mmol) and tert-butyl 2-oxo-7-azaspiro[3.5]

nonane-7-carboxylate (16.52 g, 69.04 mmol) in DCE (200 mL) was added AcOH (7.54 g, 125.52 mmol) and NaBH(OAc)$_3$ (26.6 g, 125.52 mmol). The mixture was stirred at 25° C. for 12 hrs. The reaction mixture was poured into aq. Na$_2$CO$_3$ (300 mL), extracted with DCM (200 mL×3). The combined organic layers were washed with brine, dried over Na$_2$SO$_4$, filtered and concentrated under reduced pressure. The residue was purified by MPLC. The compound tert-butyl 2-(2-(2-isopropylphenyl)-3-oxopiperazin-1-yl)-7-azaspiro[3.5]nonane-7-carboxylate (20 g, yield: 72%) was obtained as a yellow solid. $^1$H NMR (400 MHz, CDCl$_3$) δ ppm: 7.31-7.28 (m, 1H), 7.24 (m, 1H), 7.17-7.07 (m, 2H), 4.12-4.05 (m, 1H), 3.60-3.49 (m, 1H), 3.41 (m, 1H), 3.37-3.31 (m, 1H), 3.25 (m, 2H), 3.18 (m, 2H), 3.11-2.98 (m, 2H), 2.51-2.35 (m, 1H), 1.97-1.86 (m, 1H), 1.64 (m, 1H), 1.50-1.44 (m, 2H), 1.42 (s, 9H), 1.41-1.37 (m, 2H), 1.32 (m, 2H), 1.28 (d, J=6.8 Hz, 3H), 1.20 (d, J=6.8 Hz, 3H).

Step 6: tert-butyl 2-(4-isopropyl-2-(2-isopropylphenyl)-3-oxopiperazin-1-yl)-7-azaspiro[3.5]nonane-7-carboxylate.

To a solution of tert-butyl 2-(2-(2-isopropylphenyl)-3-oxopiperazin-1-yl)-7-azaspiro[3.5]nonane-7-carboxylate (4.0 g, 9.06 mmol) in THF (40 mL) was added NaH (1.06 g, 27.17 mmol) at 0° C. The mixture was stirred at 0° C. for 10 min, then 2-iodopropane (4.62 g, 27.17 mmol) was added at 0° C. The mixture was stirred at 65° C. for 48 hrs. The reaction mixture was poured into H$_2$O (40 mL), extracted with EtOAc (40 mL×3). The combined organic layers were washed with brine, dried over Na$_2$SO$_4$, filtered and concentrated under reduced pressure.

The residue was purified by MPLC. The compound tert-butyl 2-(4-isopropyl-2-(2-isopropylphenyl)-3-oxopiperazin-1-yl)-7-azaspiro[3.5]nonane-7-carboxylate (1.0 g, yield: 223%) was obtained as a yellow solid. $^1$H NMR (400 MHz, CDCl$_3$) δ ppm: 7.29-7.23 (m, 3H), 7.11-7.06 (m, 1H), 4.15 (s, 1H), 3.69 (m, 1H), 3.49-3.36 (m, 2H), 3.29-3.22 (m, 3H), 3.18 (s, 2H), 3.10 (m, 1H), 3.02-2.93 (m, 2H), 2.47 (m, 1H), 2.05-1.99 (m, 1H), 1.94-1.86 (m, 1H), 1.73-1.60 (m, 2H), 1.50-1.43 (m, 2H), 1.42 (s, 9H), 1.41-1.37 (m, 2H), 1.33 (s, 1H), 1.30 (d, J=6.8 Hz, 3H), 1.19 (d, J=6.8 Hz, 3H), 0.91 (m, 6H).

Step 7: tert-butyl 2-(4-isopropyl-2-(2-isopropylphenyl)piperazin-1-yl)-7-azaspiro[3.5]nonane-7-carboxylate.

A mixture of tert-butyl 2-(4-isopropyl-2-(2-isopropylphenyl)-3-oxopiperazin-1-yl)-7-azaspiro[3.5]nonane-7-carboxylate (1.0 g, 2.07 mmol) in BH$_3$·THF (10 mL) was stirred at 70° C. for 12 hrs. The reaction mixture was quenched by MeOH (5 mL) at 0° C. and stirred at 25° C. for 30 min. The mixture was concentrated under reduced pressure to afford tert-butyl 2-(4-isopropyl-2-(2-isopropylphenyl)piperazin-1-yl)-7-azaspiro[3.5]nonane-7-carboxylate (970 mg, crude) was obtained as a colorless oil. MS (ESI, m/e) [M+1]$^+$470.3.

Step 8: 2-(4-isopropyl-2-(2-isopropylphenyl)piperazin-1-yl)-7-azaspiro[3.5]nonane (Intermediate 3-1).

A mixture of tert-butyl 2-(4-isopropyl-2-(2-isopropylphenyl)piperazin-1-yl)-7-azaspiro[3.5]nonane-7-carboxylate (970 mg, 2.07 mmol) in HCl/EtOAc (10 mL) was stirred at 25° C. for 2 hrs. The reaction mixture was concentrated under reduced pressure. The residue was purified by prep-HPLC (HCl condition) according to HPLC. The residue was dilute with H$_2$O (10 mL) and added Na$_2$CO$_3$ to pH=9. The mixture was extracted with EtOAc (10 mL×3). The combined organic layers were washed with brine, dried over Na$_2$SO$_4$, filtered and concentrated under reduced pressure to give 2-(4-isopropyl-2-(2-isopropylphenyl)piperazin-1-yl)-7-azaspiro[3.5]nonane (455 mg, yield: 58%) as a yellow oil. $^1$H NMR (400 MHz, CDCl$_3$) δ ppm: 7.51 (d, J=6.4 Hz, 1H), 7.27-7.20 (m, 2H), 7.17-7.11 (m, 1H), 3.63 (d, J=9.2 Hz, 1H), 3.41 (s, 1H), 3.06 (d, J=11.2 Hz, 1H), 2.99-2.87 (m, 2H), 2.71-2.55 (m, 6H), 2.44 (m, 1H), 2.28 (m, 2H), 1.94-1.81 (m, 2H), 1.80-1.72 (m, 1H), 1.71-1.64 (m, 1H), 1.41-1.28 (m, 5H), 1.25 (d, J=6.8 Hz, 3H), 1.20 (d, J=6.8 Hz, 3H), 1.04 (m, 6H). MS (ESI, m/e) [M+1]$^+$370.3.

Synthesis of methyl 2-((1 H-pyrrolo[2,3-b]pyridin-5-yl)oxy)-4-(2-(4-isopropyl-2-(2-isopropylphenyl)piperazin-1-yl)-7-azaspiro[3.5]nonan-7-yl)benzoate To a solution of 2-(4-isopropyl-2-(2-isopropylphenyl)piperazin-1-yl)-7-azaspiro[3.5]nonane (200 mg, 0.541 mmol, Intermediate 3-1) in DMSO (10 mL) was added methyl 2-((1 H-pyrrolo[2,3-b]pyridin-5-yl)oxy)-4-fluorobenzoate (154.8 mg, 0.541 mmol) and Na$_2$CO3 (573.5 mg, 541 mmol). The mixture was stirred at 100° C. overnight. The mixture was cooled to room temperature, diluted with ethyl acetate (100 mL) and water (100 mL) under stirring. The organic layer was separated and washed with brine (100 mL), dried over Na$_2$SO$_4$, filtered and concentrated in vacuum. The residue was purified by chromatography column (silica gel, eluent: DCM/MeOH (v/v)=50/1 to 20/1) to give the title compound (120 mg, yield: 35%). MS (ESI, m/e) [M+1]$^+$636.0.

Synthesis of 2-((1H-pyrrolo[2,3-b]pyridin-5-yl)oxy)-4-(2-(4-isopropyl-2-(2-isopropylphenyl)piperazin-1-yl)-7-azaspiro[3.5]nonan-7-yl)benzoic acid To a solution of methyl 2-((1H-pyrrolo[2,3-b]pyridin-5-yl)oxy)-4-(2-(4-isopropyl-2-(2-isopropylphenyl)piperazin-1-yl)-7-azaspiro[3.5]nonan-7-yl)benzoate (120 mg, 0.189 mmol) in THF (5 mL) and MeOH (5 mL) was added aq. NaOH (2 mL, 6 N). The mixture was stirred at 50° C. for 2 hours. After the reaction solution was cooled to room temperature, the mixture was diluted with DCM (50 mL). The mixture was stirred and was adjusted to pH value ~4-5 with HCl acid (10 mL, 1M). The organic layer was separated, dried over Na$_2$SO$_4$, filtered and concentrated in vacuum. The residue was purified by chromatography column on silica gel (eluent: DCM/MeOH (v/v)=10/1). 2-((1H-pyrrolo[2,3-b]pyridin-5-yl)oxy)-4-(2-(4-isopropyl-2-(2-isopropylphenyl)piperazin-1-yl)-7-azaspiro[3.5]nonan-7-yl) benzoic acid was obtained (80 mg, yield: 68%). MS (ESI, m/e) [M+1]$^+$622.0.

Synthesis of 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4(2-(4-isopropyl-2(2-isopropylphenyl)piperazin-1-yl)-7-azaspiro[3.5]nonan-7-yl) benzamide (Example 3):

To a solution of 2-((1H-pyrrolo[2,3-b]pyridin-5-yl)oxy)-4-(2-(4-isopropyl-2-(2-isopropylphenyl)piperazin-1-yl)-7-azaspiro[3.5]nonan-7-yl)benzoic acid (80 mg, 0.129 mmol) in DCM (20 mL) was added 4-((((1r,4r)-4-hydroxy-4-methylcyclohexyl)methyl)amino)-3-nitrobenzenesulfonamide (44 mg, 0.129 mmol), EDCI (32 mg, 0.168 mmol), DMAP (31.5 mg, 0.258 mmol) and TEA (65 mg, 0.645 mmol). The mixture was stirred at room temperature for overnight. Then the reaction mixture was washed with acetic acid (30 mL, 10%), saturated aq.

NaHCO$_3$ (30 mL) and brine (20 mL) sequentially. The organic layer was separated, dried over anhydrous NaSO$_4$ and concentrated in vacuum. The residue was purified by chromatography column (silica gel, eluent: DCM/EA (v/v)= 1/1, then DCM/MeOH (v/v)=20/1) to give a crude solid. The crude was further purified by prep-TLC (eluent: DCM/MeOH (v/v)=20/1). The compound 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-(4-isopropyl-2(2-isopropylphenyl)piperazin-1-yl)-7-azaspiro[3.5]nonan-7-yl)benzamide was obtained (20 mg, yield:

16%) $^1$H NMR (400 MHz, DMSO-d$_6$) δ ppm: 11.60 (s, 1H), 8.60-8.24 (m, 2H), 7.96 (s, 1H), 7.82-6.77 (m, 10H), 6.77-6.50 (m, 1H), 6.33 (s, 1H), 6.17 (s, 1H), 4.24 (s, 1H), 3.29-3.18 (m, 4H), 3.09-2.77 (m, 9H), 2.02-1.95 (m, 1H), 1.80-1.47 (m, 8H), 1.38-1.26 (m, 7H), 1.23-1.12 (m, 9H), 1.12-0.99 (m, 10H). MS (ESI, m/e) [M+1]$^+$948.0.

Intermediate 3-1a: 2-(4-isopropyl-2-(2-isopropylphenyl) piperazin--yl)-7-azaspiro[3.5]nonane was separated by SFC (Instrument: Waters SFC80 preparative SFC; Column: Lux Cellulose-2, 250×30 mm i.d. 10 um; Mobile phase: A for CO2 and B for MeOH (0.1% NH$_3$·H$_2$O); Gradient: B%=50% isocratic mode; Flow rate: 80 g/min; Wavelength: 220 nm; Column temperature: 40° C.; System back pressure: 150 bar).

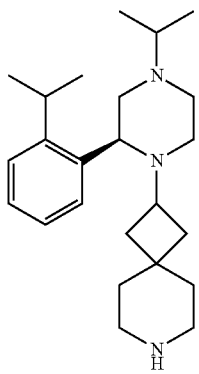

Intermediate 3-1a or

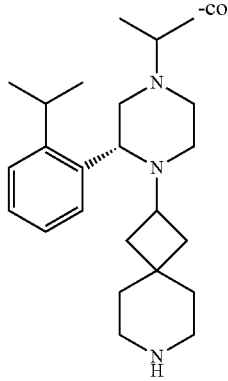

-continued (R or S)-2-(4-isopropyl-2-(2-isopropylphenyl)piperazin-1-yl)-7-azaspiro[3.5]nonane (300 mg, retention time: 1.76 min) was obtained, yield: 37.5%. 1H NMR (400 MHz, CDCl$_3$) δ ppm: 7.51 (br, 1H), 7.26-7.21 (m, 2H), 7.14 (t, 1H), 3.63 (m, 1H), 3.41 (br, 1H), 3.06 (m, 1H), 2.96-2.89 (m, 2H), 2.70-2.58 (m, 6H), 2.47-2.41 (m, 1H), 2.31-2.24 (m, 2H), 2.16 (m, 1H), 1.90 (br, 2H), 1.77 (br, 1H), 1.71-1.65 (m, 1H), 1.37-1.29 (m, 5H), 1.25 (d, J=6.8 Hz, 3H), 1.20 (br d, J=6.8 Hz, 3H), 1.04 (t, 6H). MS (ESI, m/e) [M+1]$^+$370.3.

Intermediate 3-1b: (S or R)-2-(4-isopropyl-2-(2-isopropylphenyl)piperazin-1-yl)-7-azaspiro[3.5]nonane (330 mg, retention time: 2.05 min) was obtained, yield: 41%. MS (ESI, m/e) [M+1]$^+$370.3.

Following essentially identical procedures described for Example 3 or using similar synthetic methods or strategies, Example 2, and Examples 4-18 listed in Table 1 were prepared.

TABLE 1

| Example | Structure | Compound name | Data |
|---|---|---|---|
| 2 | 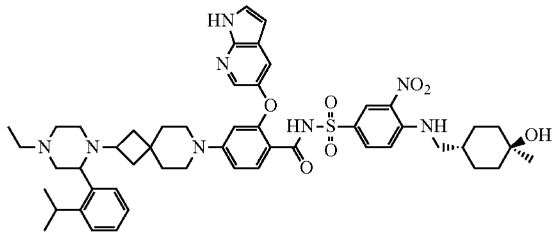 [SMILES: CCN1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)C(c2ccccc2C(C)C)C1] | 2-((1H-pyrrolo[2,3-b]pyridin-5-yl)oxy)-4-(2-(4-ethyl-2-(2-isopropylphenyl)piperazin-1-yl)-7-azaspiro[3.5]nonan-7-yl)-N-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.61 (s, 1H), 10.45 (br, 1H), 8.49-8.42 (m, 2H), 7.97 (d, J = 2.4 Hz, 1H), 7.69 (d, J = 9.2 Hz, 1H), 7.52 (d, J = 8.8 Hz, 1H), 7.47-7.40 (m, 2H), 7.39-7.35 (m, 1H), 7.30-7.18 (m, 2H), 7.17-7.12 (m, 1H), 6.94 (d, J = 9.2 Hz, 1H), 6.63 (d, J = 8.8 Hz, 1H), 6.34-6.31 (m, 1H), 6.17 (s, 1H), 4.24 (s, 1H), 3.69-3.52 (m, 1H), 3.33-3.17 (m, 4H), 3.14-2.80 (m, 8H), 2.74-2.60 (m, 2H), 2.50-2.40 (m, 1H), 2.27-2.19 (m, 1H), 1.72-1.50 (m, 8H), 1.39-1.12 (m, 18H), 1.08-1.03 (m, 3H) MS (ESI, m/e) [M + 1]⁺ 934.0. |
| 3a | 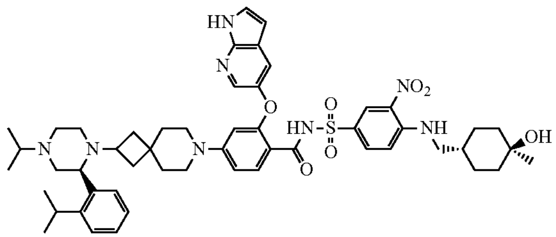 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((S or R)-4-isopropyl-2-(2-isopropylphenyl)piperazin-1-yl)-7-azaspiro[3.5]nonan-7-yl)benzamide | ¹H NMR (400 MHz, DMSO-d₆) δ ppm: 11.61 (s, 1H), 10.45 (br, 1H), 8.49-8.42 (m, 2H), 7.97 (d, J = 2.4 Hz, 1H), 7.69 (d, J = 9.2 Hz, 1H), 7.52 (d, J = 8.8 Hz, 1H), 7.47-7.40 (m, 2H), 7.39-7.35 (m, 1H), 7.30-7.18 (m, 2H), 7.17-7.12 (m, 1H), 6.94 (d, J = 9.2 Hz, 1H), 6.63 (d, J = 8.8 Hz, 1H), 6.34-6.31 (m, 1H), 6.17 (s, 1H), 4.24 (s, 1H), 3.69-3.52 (m, 1H), 3.33-3.17 (m, 4H), 3.14-2.80 (m, 8H), 2.74-2.60 (m, 2H), 2.50-2.40 (m, 1H), 2.27-2.19 (m, 1H), 1.72-1.50 (m, 8H), 1.39-1.12 (m, 18H), 1.08-1.03 (m, 3H). MS (ESI, m/e) [M + 1]⁺ 948.2. |
| | or | | |
| 3b | 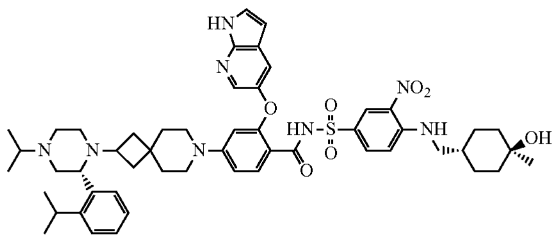 [SMILES: CC(C)c1ccccc1[C@@H]1CN(C(C)C)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R or S)-4-isopropyl-2-(2-isopropylphenyl)piperazin-1-yl)-7-azaspiro[3.5]nonan-7-yl)benzamide | ¹H NMR (400 MHz, DMSO-d₆) δ ppm: 11.67 (s, 1H), 11.43-10.96 (m, 1H), 8.53 (s, 2H), 8.01 (s, 1H), 7.76 (d, J = 8.4 Hz, 1H), 7.48 (d, J = 8.4 Hz, 4H), 7.28-7.27 (m, 2H), 7.17 (s, 1H), 7.05 (s, 1H), 6.64 (d, J = 8.6 Hz, 1H), 6.37 (s, 1H), 6.14 (s, 1H), 4.24 (s, 1H), 4.03 (s, 1H), 3.38 (s, 1H), 3.27 (s, 3H), 2.95-2.93 (m, 10H), 1.75-1.60 (m, 7H), 1.40-1.11 (m, 17H), 1.10 (s, 4H), 1.01 (s, 1H). MS (ESI, m/e) [M + 1]⁺ 948.2. |

TABLE 1-continued

| Example | Structure | Compound name | Data |
|---|---|---|---|
| 4 | (structure) | 2-((1H-pyrrolo[2,3-b]pyridin-5-yl)oxy)-4-(2-((R or S)-4-cyclopropyl-2-(2-isopropylphenyl)piperazin-1-yl)-7-azaspiro[3.5]nonan-7-yl))-N-((((1r,4r)-4-hydroxy-4-methylcyclohexyl)methyl)amino)-3-nitrophenyl)sulfonyl)benzamide | $^1$H NMR(400 MHz, DMSO-d$_6$) δ ppm: 11.68 (s, 1H), 11.42 (s, 1H), 10.28-10.10 (m, 1H), 8.55 (m, 2H), 8.02 (s, 1H), 7.77 (s, 1H), 7.72 (s, 1H), 7.50 (s, 2H), 7.47-7.45 (m, 1H), 7.39 (s, 1H), 7.26 (s, 2H), 7.09-7.04 (m, 1H), 6.66 (s, 1H), 6.37 (s, 1H), 6.16 (s, 1H), 4.53 (s, 1H), 4.24 (s, 1H), 3.78-3.68 (m, 1H), 3.40 (s, 1H), 3.28 (s, 2H), 3.13 (s, 1H), 3.02-2.81 (m, 7H), 1.99-1.98 (m, 2H), 1.86 (s, 1H), 1.68-1.65 (m, 6H), 1.37-1.21 (m, 12H), 1.13-1.10 (m, 9H), 0.77-0.68 (m, 1H), 0.38-0.35 (m, 4H). MS (ESI, m/e) [M + l]$^+$ 946.1. |
| 5 | (structure) | 2-((1H-pyrrolo[2,3-b]pyridin-5-yl)oxy)-4-(2-(4-cyclobutyl-2-(2-isopropylphenyl)piperazin-1-yl)-7-azaspiro[3.5]nonan-7-yl))-N-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.70 (s, 1H), 11.23 (br, 1H), 8.64-8.52 (m, 2H), 8.03 (s, 1H), 7.79 (d, J = 8.8 Hz, 1H), 7.53-7.12 (m, 7H), 6.94 (d, J = 9.2 Hz, 1H), 7.08 (d, J = 8.8 Hz, 1H), 6.66 (d, J = 8.8 Hz, 1), 6.38 (s, 1H), 6.14 (s, 1H), 4.26 (s, 1H), 3.99-3.62 (m, 1H), 3.59-3.42 (m, 1H), 3.33-3.17 (m, 4H), 3.17-2.60 (m, 9H), 2.50-2.38 (m, 1H), 2.27-1.85 (m, 4H), 1.78-1.50 (m, 9H), 1.39-1.14 (m, 19H). MS (ESI, m/e) [M + H]$^+$ 960.0. |
| 6 | (structure) | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(oxetan-3-yl)piperazin-1-yl)-7-azaspiro[3.5]nonan-7-yl)benzamide | $^1$H NMR (400 MHz, DMSO-d$_6$) δ ppm: 11.69 (s, 1H), 11.41 (br, 1H), 8.60-8.57 (m, 2H), 8.03 (s, 1H), 7.79 (d, J = 8.8 Hz, 1H), 7.54-7.35 (m, 4H), 7.28-7.03 (m, 3H), 6.66 (d, J = 8.8 Hz, 1H), 6.14 (s, 1H), 6.37 (s, 1H), 3.33-3.24 (m, 2H), 3.07-2.82 (m, 6H), 2.50-2.35 (m, 1H), 2.23-2.19 (m 3H), 1.74-1.50 (m, 7H), 1.39-1.12 (m, 16H), 1.08-1.03 (m, 4H), 4.25 (s, 1H), 3.60-3.39 (m, 2H), 4.59-4.33 (m 4H). MS (ESI, m/e) $^+$ 962.1. |

TABLE 1-continued

| Example | Structure | Compound name | Data |
|---|---|---|---|
| 6a | | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((S or R)-2-(2-isopropylphenyl)-4-(oxetan-3-yl)piperazin-1-yl)-7-azaspiro[3.5]nonan-7-yl)benzamide | ¹H NMR (400 MHz, DMSO-d₆) δ ppm: 11.69 (s, 1H), 11.40 (s, 1H), 8.54 (s, 2H), 8.02 (s, 1H), 7.77 (d, J = 9.0 Hz, 1H), 7.49-7.46 (m, 4H), 7.14-7.10 (m, 4H), 6.65 (d, J = 9.0 Hz, 1H), 6.37 (s, 1H), 6.15 (s, 1H), 4.57-4.31 (m, 4H), 4.25 (s, 1H), 3.40 (s, 1H), 3.28 (s, 3H), 2.96-2.90 (m, 7H), 2.46-2.35 (m, 1H), 2.01-2.00 (m 3H), 1.69-1.65 (m, 4H), 1.56-1.53 (m, 2H), 1.39-1.12 (m, 15H), 1.13-1.10 (m, 5H). MS (ESI, m/e) [M + 1]⁺ 961.6. |
| 6b | | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R or S)-2-(2-isopropylphenyl)-4-(oxetan-3-yl)piperazin-1-yl)-7-azaspiro[3.5]nonan-7-yl)benzamide | ¹H NMR(400 MHz, DMSO-d₆) δ ppm: 11.68 (s, 1H), 11.41 (br, 1H), 8.62-8.50 (m, 2H), 8.02 (s, 1H), 7.79 (d, J = 8.8 Hz, 1H), 7.52-7.35 (m, 4H), 7.28-7.14 (m, 2H), 7.12-7.01 (m, 2H), 6.66 (d, J = 8.8 Hz, 1H), 6.37 (s, 1H), 6.14 (s, 1H), 4.56-4.40 (m, 3H), 4.38-4.34 (m, 1H), 4.25 (s, 1H), 3.57-3.35 (trs, 2H), 3.30-3.25 (m, 3H), 3.03-2.70 (m, 8H), 2.46-2.38 (m, 1H), 2.21-1.85 (m 4H), 1.74-1.50 (m, 8H), 1.39-1.22 (m, 12H), 1.18-1.06 (m, 4H). MS (ESI, m/e) [M+H] 961.6. |
| 7 | 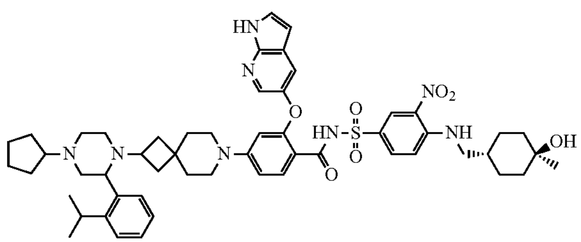 [SMILES: CC(C)c1ccccc1C1CN(C2CCCC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-cyclopentyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.70 (s, 1H), 11.43 (s, 1H), 9.79 (s, 1H), 8.57-8.55 (m, 2H), 8.02 (s, 1H), 7.78-7.77 (m, 1H), 7.49-7.47 (m, 4H), 7.29-7.28 (m, 2H), 7.17 (s, 1H), 7.08 (s, 1H), 6.65 (d, J = 8.8 Hz, 1H), 6.37 (s, 1H), 6.13 (s, 1H), 4.26 (s, 1H), 3.87 (s, 1H), 3.28 (s, 3H), 3.00-2.92 (m, 10H), 2.01-1.98 (m, 3H), 1.66 (s, 13H), 1.55-1.54 (m, 4H), 1.40-1.15 (m, 17H), 1.13-1.10 (m, 5H). MS (ESI, m/e) [M + 1]⁺ 974. |

| Example | Structure | Compound name | Data |
|---|---|---|---|
| 8 | 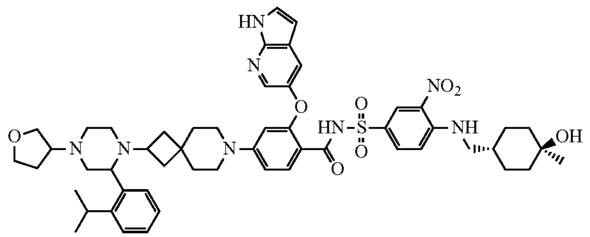 [SMILES: CC(C)c1ccccc1C1CN(C2CCOC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(tetrahydrofuran-3-yl)piperazin-1-yl)-7-azaspiro[3.5]nonan-7-yl)benzamide | ¹H NMR (400 MHz, DMSO-d₆) δ ppm: 11.69 (s, 1H), 11.44 (br, 1H), 8.63-8.54 (m, 2H), 8.03 (s, 1H), 7.99-7.85 (m, 1H), 7.79 (d, J = 8.4 Hz, 1H), 7.54-7.35 (m, 4H), 7.34-7.13 (m, 2H), 7.09 (d, J = 8.4 Hz, 1H), 6.67 (d, J = 8.4 Hz, 1H), 6.37 (s, 1H), 6.19-6.13 (m, 1H), 4.63-4.56 (m, 1H), 4.24-3.83 (m, 4H), 3.64-3.52 (m, 1H), 3.33-3.24 (m, 2H), 3.19-2.72 (m, 12H), 2.26-1.93 (m, 5H), 1.74-1.60 (m, 4H), 1.57-1.42 (m, 4H), 1 39-1 27 (m, 7H), 1.18-1.03 (m, 9H). MS (ESI, m/e) [M + 1]⁺ 976.1 |
| 9 | 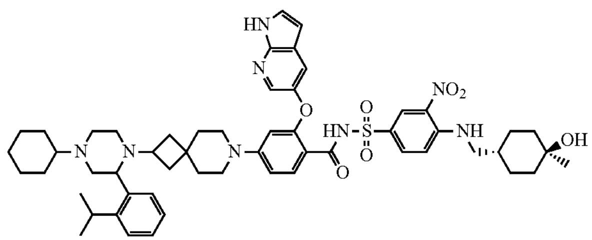 [SMILES: CC(C)c1ccccc1C1CN(C2CCCCC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2- 4-cyclohexyl-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.70 (s, 1H), 11.42 (s, 0.5H), 9.72 (s, 0.5H), 8.65-8.48 (m, 2H), 8.06-7.97(m, 1H), 7.82-7.71 (m, 1H), 7.59-7.43 (m, 4H), 7.40-6.97 (m, 5H), 6.78-6.55 (m, 1H), 6.38 (s, 1H), 6.13 (s, 1H), 4.26 (s, 1H), 4.04-3.92 (m, 1H), 3.60-3.44 (m, 1H), 3.32-3.21 (m, 3H), 3.19-2.81 (m, 11H), 2.13-1.94 (m, 3H), 1.84-1.48 (m, 11H), 1.43-1.28 (m, 6H), 1.22-1.14 (m, 8H), 1.14-0.99(m, 7H). MS (ESI, m/e) [M + 1]⁺ 988.0 |
| 10 | 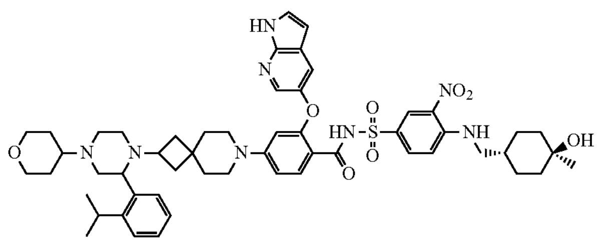 [SMILES: CC(C)c1ccccc1C1CN(C2CCOCC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(tetrahydro-2H-pyran-4-yl)piperazin-1-yl)-7-azaspiro[3.5]nonan-7-yl)benzamide | ¹H NMR (400 MHz, DMSO-d₆) δ ppm: 11.69 (s, 1H), 8.57-8.55 (m, 2H), 8.03 (s, 1H), 7.77 (d, J = 9.2 Hz, 1H), 7.56-7.42 (m, 4H), 7.28 (s, 2H), 7.16 (s, 1H), 7.07 (d, J = 9.2 Hz, 1H), 6.66-6.64 (m, 1H), 6.37 (s, 1H), 6.14 (s, 1H), 4.26 (s, 1H), 3.90 (s, 3H), 3.27-3.25 (m, 5H), 2.96-2.94 (m, 9H), 1.91 (s, 2H) 1.63-1.59 (m, 9H), 1.38-1.12 (m, 16H), 1.10 (s, 4H). MS (ESI, m/e) [M + 1]⁺ 990.2. |
| 11 | 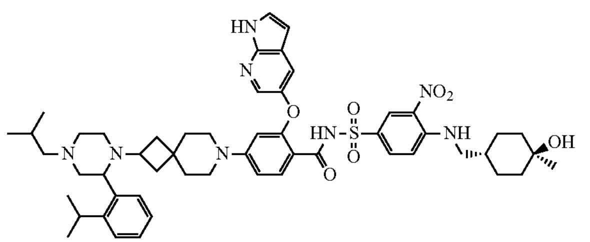 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(4-isobutyl-2-(2-isopropylphenyl)piperazin-1-yl)-7-azaspiro[3.5]nonan-7-yl)benzamide | ¹H NMR (400 MHz, DMSO-d₆) δ ppm: 11.64 (s, 1H), 10.95 (br, 1H), 8.51-8.45 (m, 2H), 8.00 (d, J = 2.4 Hz, 1H), 7.74 (d, J = 9.2 Hz, 1H), 7.52-7.35 (m, 4H), 7 29-7.09 (m, 3H), 7.05-6.96 (m, 1H), 6.64 (d, J = 8.8 Hz, 1H), 6.35(s, 1H), 6.15 (s, 1H), 4.24 (s, 1H), 3.65-3.50 (m, 1H), 3.33-3.22 (m, 3H), 3.04-2.80 (m, 7H), 2.70-2.60 (m, 1H), 2.24-2.00 (m, 5H), 1.76-1.50 (m, 8H), 1.39-1.12 (m, 15H), 1.08-1.03 (m, 4H), 0.85 (d, J = 6.8 Hz, 6H). MS (ESI, m/e) [M + 1]⁺ 962.0. |

TABLE 1-continued

| Example | Structure | Compound name | Data |
|---|---|---|---|
| 12 | 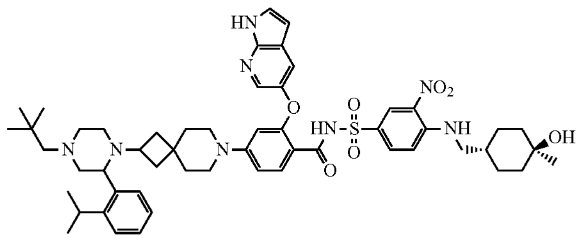 [SMILES: CC(C)c1ccccc1C1CN(CC(C)(C)C)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-neopentylpiperazin-1-yl)-7-azaspiro[3.5]nonan-7-yl)benzamide | $^1$H NMR (400 MHz, DMSO-d$_6$) δ ppm: 11.69 (s, 1H), 11.43 (s, 1H), 10.09 (s, 1H), 8.66-8.40 (m, 2H), 8.03 (s, 1H), 7.88-7.63 (m 2H), 7.55-7.33 (m, 4H), 7.31-7.05 (m, 3H), 6.75-6.55 (m, 1H), 6.37 (s, 1H), 6.20-6.05 (m, 1H), 4.67-4.54 (m, 1H), 4.25 (s, 1H), 3.92-3.74 (m, 1H), 3.29-3.25 (ns, 2H), 3.10-2.78 (m, 8H), 2.22-2.14 (m, 1H), 2.08-1.90 (m, 3H), 1.75-1.43 (m, 6H), 1.38-1.24 (m, 11H), 1.17-1.00 (m, 9H), 0.90-0.70 (s, 9H). MS (ESI, m/e) [M + 1]$^+$ 488.8 |
| 13 | 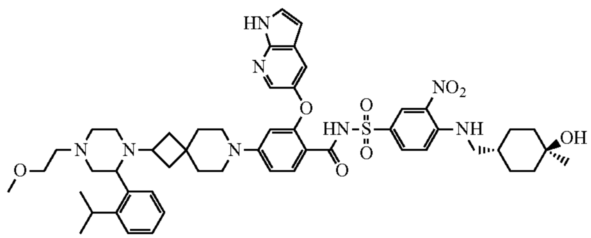 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-7-methoxyethyl)piperazin-1-yl)-7-azaspiro[3.5]nonan-7-yl)benzamide | $^1$H NMR (400 MHz, DMSO-d$_6$) δ ppm: 11.68 (s, 1H), 8.60-8.50 (m, 2H), 8.03-8.02 (m, 1H), 7.80-7.75 (m, 1H), 7.52-7.45 (m, 4H), 7.17-7.11 (m, 2H), 7.10-7.00 (m, 1H), 7.10-7.05 (m, 1H), 6.65-6.60 (m, 1H), 6.38 (s, 1H), 6.15 (s, 1H), 4.30-4.25 (m, 1H), 3.55-3.50 (m, 2H), 3.35-3.25 (m, 6H), 3.10-2.95 (m, 9H), 1.65-1.35 (m, 8H), 1.30-1.10 (m, 23H). MS (ESI, m/e) [M + 1]$^+$ 962.9 |
| 13a | 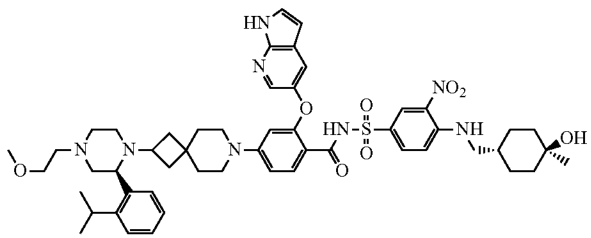 [SMILES: COCCN1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)[C@H](c2ccccc2C(C)C)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((S or R)-2-isopropylphenyl)-7-methoxyethyl)piperazin-1-yl)-7-azaspiro[3.5]nonan-7-yl)benzamide | $^1$H NMR (400 MHz, DMSO-d$_6$) δ ppm: 11.68 (S, 1H), 8.53 (s, 2H), 8.02 (s, 1H), 7.75 (s, 1H), 7.49-7.47 (m, 4H), 7.27 (s, 2H), 7.15 (s, 1H), 7.04 (s, 1H), 6.66 (s, 1H), 6.37 (s, 1H), 6.14 (s, 1H), 4.25 (s, 1H), 3.82-3.67 (m, 1H), 3.55 (s, 2H), 3.48-3.40 (m, 1H), 3.28-3.26 (m, 6H), 2.95-2.94 (m, 9H), 1.99 (s, 1H), 1.73-1.50 (m, 7H), 1.26-1.10 (m 18H), 1.09 (s, 5H).MS (ESI, m/e) [M + 1]$^+$ 964.1 |
| 13b | 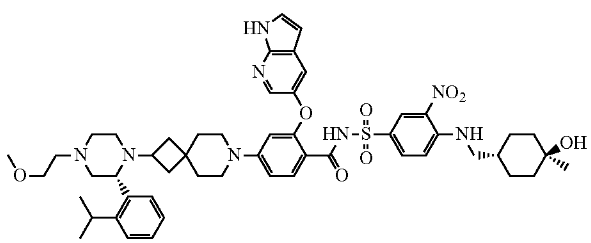 | 2-((1H-pyrrolo[2,3-b]pyridin-5-yl)oxy)-N-((4-(((1r,4r)-4-bydroxy-4-methylcyclohexyl)methyl)amino)-3-nitrophenyl)sulfonyl)-4-(2-((R or S)-2-isopropylphenyl)-7-methoxyethyl)piperazin-1-yl)-7-azaspiro[3.5]nonan-7-yl)benzamide | $^1$H NMR (400 MHz, DMSO-d$_6$) δ ppm: 11.69 (s, 1H), 11.18 (br, 1H), 8.61-8.53 (m, 2H), 8.02 (s, 1H), 7.89-7.75 (m, 1H), 7.53-7.10 (m, 7H), 7.08 (d, J = 8.4 Hz, 1H), 6.66 (d, J =8.4 Hz, 1H), 6.37 (s, 1H), 6.13 (s, 1H), 4.24 (s, 1H), 3.93-3.54 (m, 2H), 3.47-3.34 (m, 1H), 3.32-2.80 (m, 18H), 2.49-2.36 (m, 1H), 2.19-1.93 (m, 1H), 1.74-1.49(m, 7H), 1.39-1.08 (m, 18H). MS (ESI, m/e) [M + 1] 964.2. |

TABLE 1-continued

| Example | Structure | Compound name | Data |
|---|---|---|---|
| 14 | 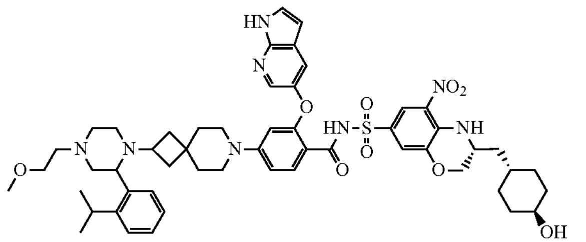 [SMILES: COCCN1CCN(C2CC3(CCN(c4ccc(C(=O)NS(=O)(=O)c5cc6c(c([N+](=O)[O-])c5)N[C@H](C[C@H]5CC[C@H](O)CC5)CO6)c(Oc5cnc6[nH]ccc6c5)c4)CC3)C2)C(c2ccccc2C(C)C)C1] | 2-((1H-pyrrolo[2,3-b]pyridin-5-yl)oxy)-N-(((R)-3-(((1r,4R)-4-hydroxycyclohexyl)methyl)-5-nitro-3,4-dihydro-2H-benzo[b][1,4]oxazin-7-yl)sulfonyl)-4-(2-(2-(2-isopropylphenyl)-4-(2-methoxy ethyl)piperazin-1-yl)-7-azaspiro[3.5]nonan-7-yl)benzamide | ¹H NMR (400 MHz, DMSO-d₆) δ ppm: 11.94 (s, 1H), 8.74 (s, 1H), 8.16 (s, 1H), 8.01 (s, 1H), 7.49-7.35 (m, 4H), 7.33-7.10 (m 4H), 6.65 (d, J = 8.4 Hz, 1H), 6.36 (s, 1H), 6.13 (s, 1H), 4.48-4.46 (m, 1H), 4.14-4.02 (m, 2H), 3.83-3.74 (m, 2H), 3.57-3.50 (m, 2H), 3.32-3.18 (m, 4H), 3.15-2.80 (m, 12H), 2.04-1.96(m, 1H), 1.87-1.53(m, 7H), 1.49-1.32(m, 5H), 1.22-1.08 (m, 10H), 1.05-0.85 (m, 4H). MS (ESI, m/e) [M + 1]⁺ 992.0. |
| 15 | 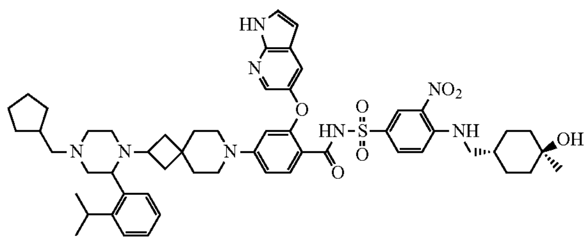 [SMILES: CC(C)c1ccccc1C1CN(CC2CCCC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(cyclopentylmethyl)piperazin-1-yl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | ¹H NMR (400 MHz, DMSO-d₆) δ ppm: 11.68 (s, 1H), 11.16 (br, 1H), 8.62-8.52 (m, 2H), 8.01 (s, 1H), 7.79-7.73 (m, 1H), 7.53-7.40 (m, 4H), 7.33-7.12 (m, 3H), 7.08-7.00 (m, 1H), 6.68-6.64 (m, 1H), 6.36 (s, 1H), 6.15 (s, 1H), 4.26 (s, 1H), 3.78-3.65 (m, 1H), 3.45-3.37 (m, 1H), 3.31-3.26 (m, 3H), 3.19-2.75 (m, 10H), 2.65-2.55 (m, 1H), 2.22-1.95 (m, 2H), 1.79-1.42 (m, 14H), 1.38-1.23 (m 10H), 1.15-1.08 (m, 10H). MS (ESI, m/e) [M + 1]⁺ 987.9. |
| 16 | 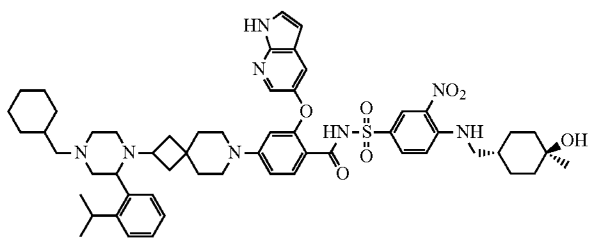 [SMILES: CC(C)c1ccccc1C1CN(CC2CCCCC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(cyclohexylmethyl)piperazin-1-yl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | ¹H NMR (400 MHz, DMSO-d₆) δ ppm: 11.67 (s, 1H), 8.51 (s, 2H), 8.00 (s, 1H), 7.73 (s, 1H), 7.49-7.43 (m, 3H), 7.31-7.19 (m, 2H), 7.13 (s, 1H), 7.01 (s, 1H), 6.64 (d, J = 8.2 Hz, 1H), 6.35 (s, 1H), 6.15 (s, 1H), 4.25 (s, 1H), 3.33 (s, 3H), 3.29-3.23 (m, 2H), 3.17 (d, J = 5.2 Hz, 1H), 3.04-2.80 (m, 8H), 2.25-2.15 (m, 1H), 1.77-1.50 (m, 14H), 1.38-1.08 (m, 21H), 0.93-078 (m, 3H). MS (ESI, m/e) [M + 1]⁺ 1001.6. |
| 17 | 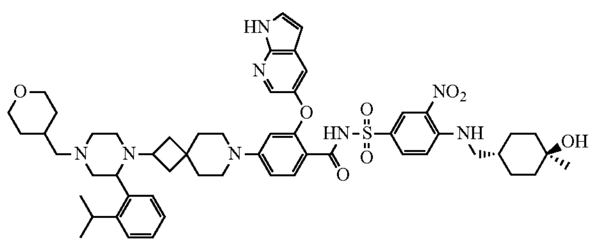 [SMILES: CC(C)c1ccccc1C1CN(CC2CCOCC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-isopropylphenyl)-4-((tetrahydro-2H-pyran-4-yl)methyl)piperazin-1-yl)-7-azaspiro[3.5]nonan-7-yl)benzamide | ¹H NMR (400 MHz, DMSO-d₆) δ ppm: 11.69 (s, 1H), 11.44 (s, 1H), 8.64-8.47 (m, 2H), 8.02 (s, 1H), 7.84-7.72 (m, 1H), 7.71-7.34 (m, 5H), 7.34-6.98 (m, 4H), 6.72-6.58 (m, 1H), 6.37 (s, 1H), 6.13 (s, 1H), 4.26 (s, 1H), 3.89-3.72 (m, 2H), 3.32-3.20 (m, 5H), 3.15-2.79 (m, 9H), 2.05-1.92 (m, 2H), 1.78-1.50 (m, 8H), 1.38-1.02 (m, 25H). MS (ESI, m/e) [M + 1]⁺ 1004.0 |

TABLE 1-continued

| Example | Structure | Compound name | Data |
|---|---|---|---|
| 18 | 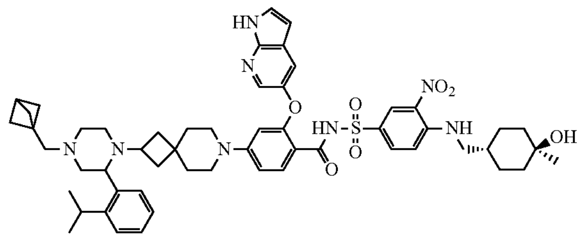 [SMILES: CC(C)c1ccccc1C1CN(CC23CC(C2)C3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(bicyclo[1.1.1]pentan-1-ylmethyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.24 (br, 1H), 8.55-8.49 (m, 2H), 8.02 (s, 1H), 7.75 (d, J = 8.0 Hz, 1H), 7.53-7.35 (m, 4H), 7.30-7.02 (m, 4H), 6.66 (d, J = 8.0 Hz, 1H), 6.37 (s, 1H), 6.14 (s, 1H), 4.25 (s, 1H), 3.84-3.40 (m, 1H), 3.30-3.05 (m, 4H), 3.02-2.60 (m, 9H), 2.46-2.30 (m, 3H), 2.07-1.87 (m, 1H), 1.81-1.58 (m, 10H), 1.57-1.50 (m, 2H), 1.39-1.18 (m, 13H), 1.16-1.07 (m, 7H). MS (ESI, m/e) [M + 1]⁺ 985.5. |

Example 19a
2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4(2-((R or S)-2-(2-isopropylphenyl)-4-(4-methoxybenzyl)piperazin-1-yl)-7-azaspiro[3.5]nonan-7-yl)benzamide (herein referred to as "Example 19a synthesized from intermediate 19-1a in Method A")
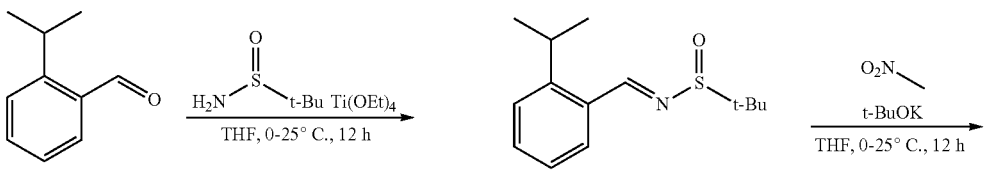
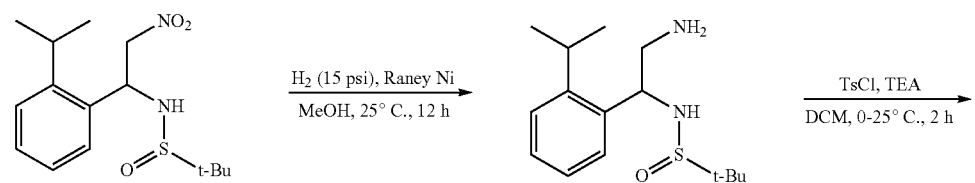
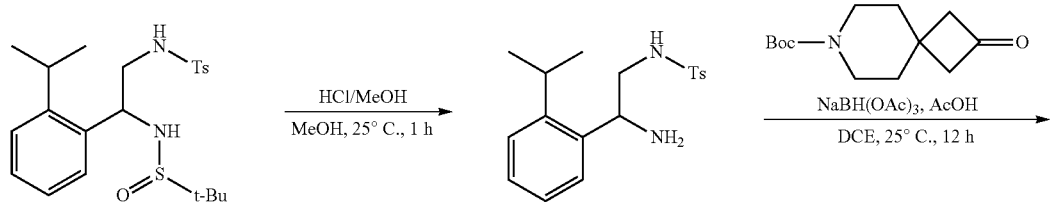
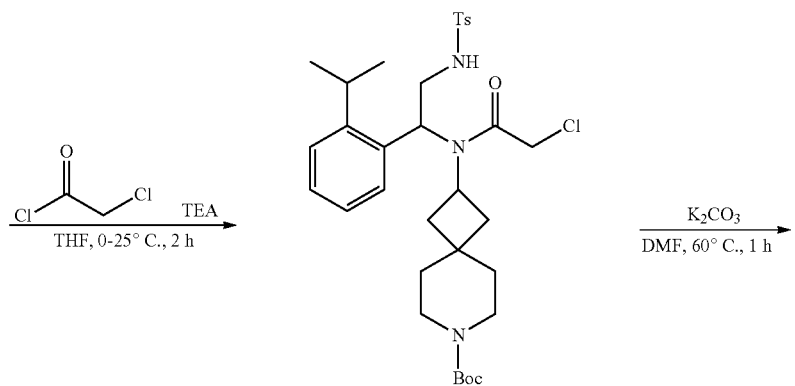
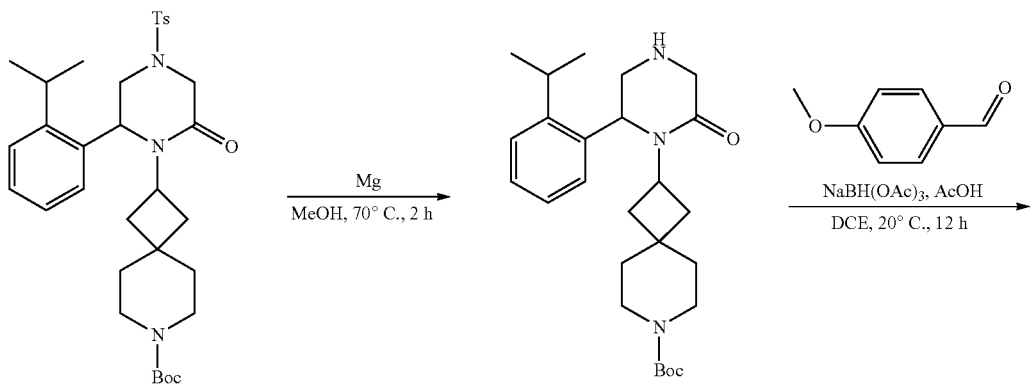

257 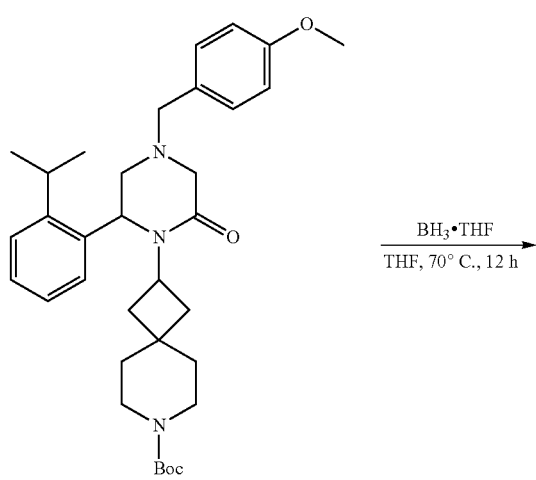 258 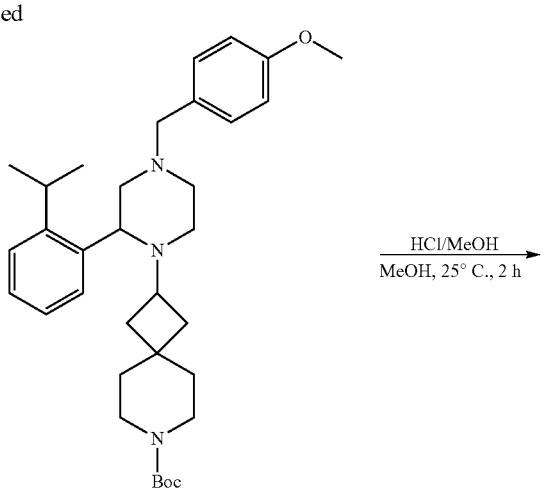
-continued
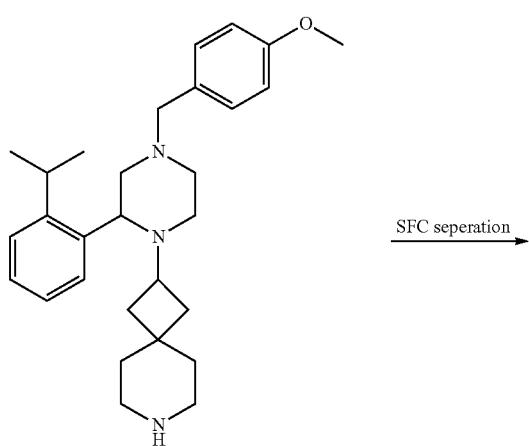
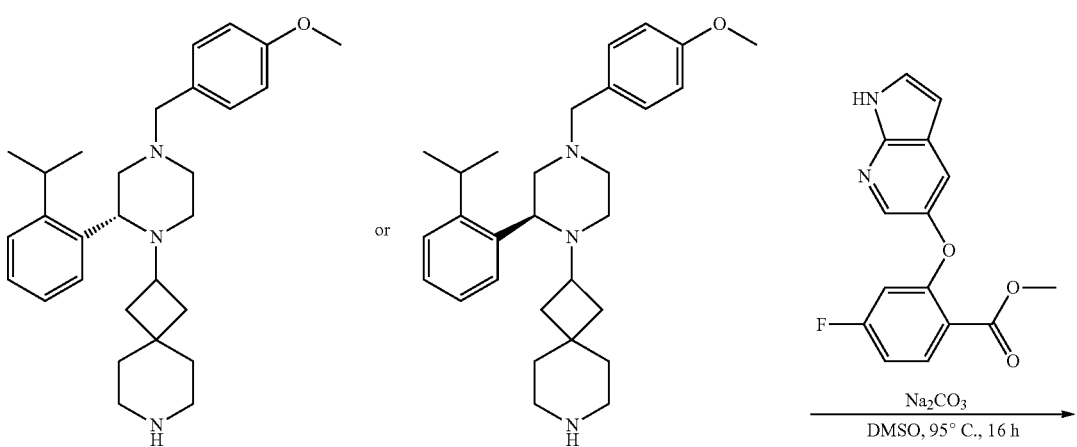
Intermediate 19-1a -continued
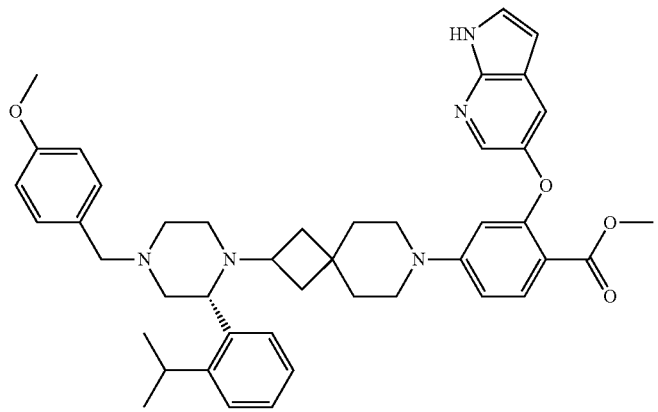
or
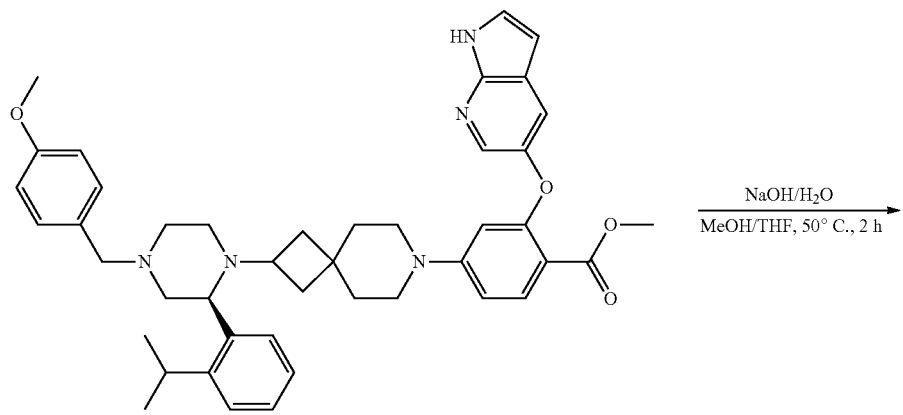
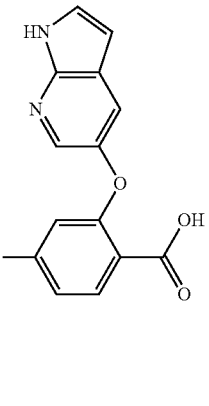
or
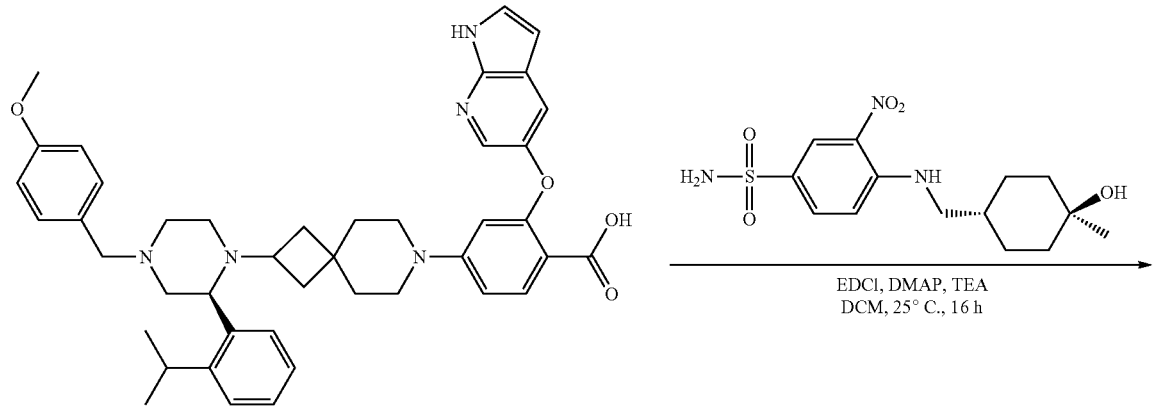

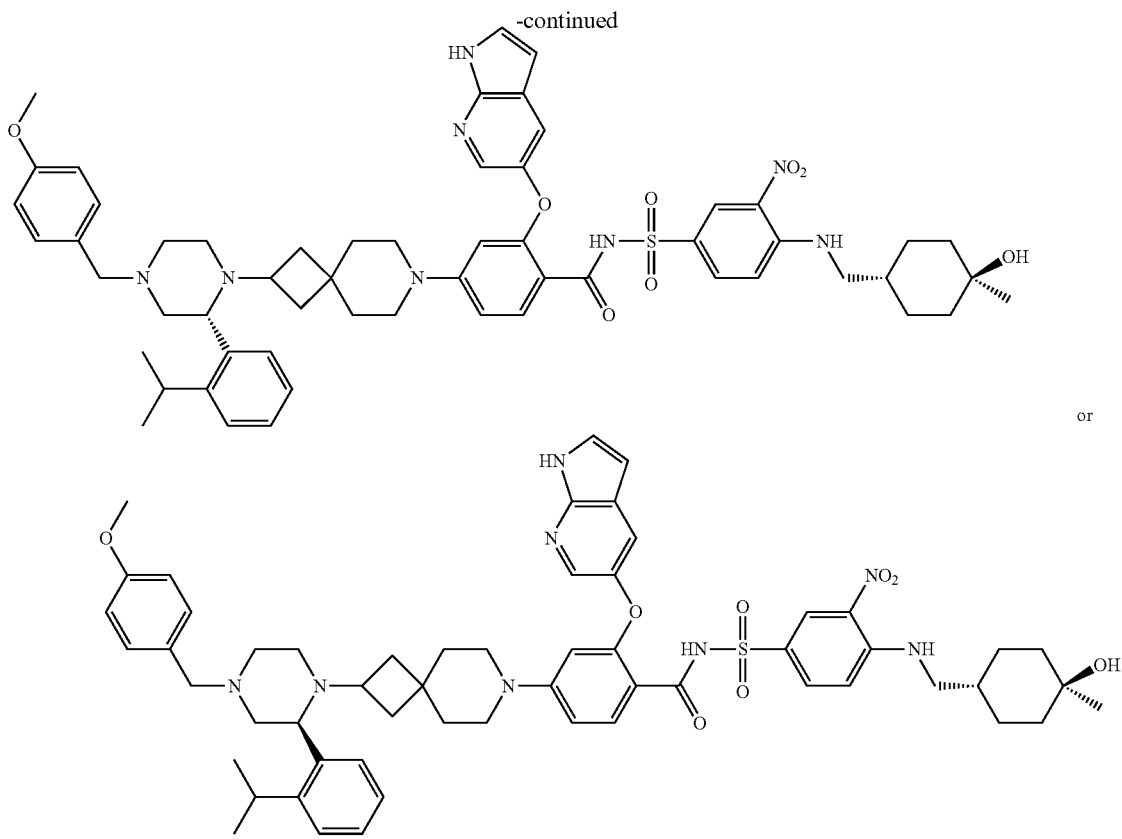

example 19a

The following Steps 1-12 and SFC separation were described as Method A for synthesis of intermediate 19-1a Step 1: synthesis of (E)-N-(2-isopropylbenzylidene)-2-methylpropane-2- sulfinamide

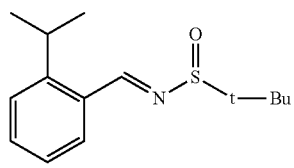

To a solution of 2-isopropylbenzaldehyde (20 g, 0.135 mol) in THF (200 mL) was added 2-methylpropane-2-sulfinamide (18 g, 0.148 mmol). After cooling to 0° C., Ti(OEt)$_4$ (62 g, 0.27 mol) was added slowly. The mixture was stirred at 25° C. for 12 hrs. The reaction mixture was quenched with water (100 mL), and then filtered through a celite pad. The filtrate was extracted with EA (100 mL×3) and washed with brine (100 mL). The combined organic layer was dried over Na$_2$SO$_4$, filtered and concentrated in vacuum. The residue was purified by column chromatography on silica gel (eluent: PE/EA (v/v)=100/1 to 20/1) to give (E)-N-(2-isopropylbenzylidene)-2-methylpropane-2-sulfinamide (32.5 g, yield: 96%). $^1$H NMR (400 MHz, CDCl$_3$) δ ppm: 9.00 (s, 1H), 7.96 (dd, J=8.0, 2.4 Hz, 1H), 7.51-7.45 (m, 1H), 7.44-7.40 (m, 1H), 7.32-7.27 (m, 1H), 3.72 (m, 1H), 1.33-1.25 (m, 15H).

Step 2: synthesis of N-(1-(2-isopropylphenyl)-2-nitroethyl)-2-methylpropane-2-sulfinamide

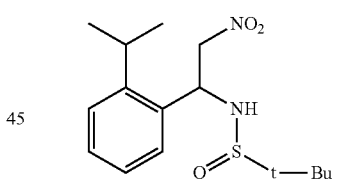

To a solution of (E)-N-(2-isopropylbenzylidene)-2-methylpropane-2-sulfinamide (32 g, 0.13 mol) in THF (300 mL) was added t-BuOK (21 g, 0.19 mol) in several portions at 0° C. After stirring for 1 hr at 0° C., Nitromethane (77 g, 1.27 mmol) was then added. The mixture was further stirred at 25° C. for 12 hrs. Water (100 mL) was added to the mixture, and then extracted with EA (100 mL×3). The combined organic layer was dried, filtered and concentrated in vacuum. The residue was purified by column chromatography on silica gel (eluent: PE/EA (v/v)=10/1 to 2/1) to give N-(1-(2-isopropylphenyl)-2-nitroethyl)-2-methylpropane-2-sulfinamide (26.5 g), yield: 67%. $^1$H NMR (400 MHz, CDCl$_3$) δ ppm: 7.40-7.34 (m, 2H), 7.34-7.28 (m, 1H), 7.26-7.21 (m, 1H), 5.53-5.44 (m, 1H), 4.88-4.78 (m, 1H), 4.76-4.65 (m, 1H), 4.30-4.20 (m, 1H), 3.35-3.22 (m, 1H), 1.34-1.26 (m, 6H), 1.27-1.20 (m, 9H).

Step 3: Synthesis of N-(2-amino-1-(2-isopropylphenyl)ethyl)-2-methylpropane-2-sulfinamide

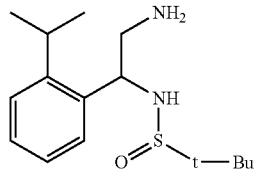

To a solution of N-(1-(2-isopropylphenyl)-2-nitroethyl)-2-methylpropane-2-sulfinamide (23 g, 0.074 mol) in MeOH (200 mL) was added Raney-Ni (5 g). The mixture was stirred under H₂ (15 psi) atmosphere at 25° C. for 12 hrs. After filtration through a celite pad, the filtrate was concentrated under reduced pressure to give N-(2-amino-1-(2-isopropylphenyl)ethyl)-2-methylpropane-2-sulfinamide (17.6 g, crude), which was used in the next step without further purification. MS (ESI, m/e) [M+1]⁺283.1.

Step 4: synthesis of N-(2-((tert-butylsulfinyl)amino)-2-(2-isopropylphenyl)ethyl)-4-methylbenzenesulfonamide

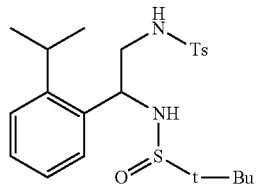

To a solution of N-(2-amino-1-(2-isopropylphenyl)ethyl)-2-methylpropane-2-sulfinamide (23 g, 0.081 mol) in DCM (300 mL) was added TEA (24.5 g, 0.243 mol). After the mixture was cooled to 0° C., TsCl (17 g, 0.09 mol) was added in several portions. After addition, the mixture was stirred at 25° C. for 2 hrs and was then quenched with aqueous NH₄Cl (100 mL, 1M). The mixture was extracted with DCM (100 mL×3). The combined organic layer was washed with brine, dried over anhydrous Na₂SO₄, filtered and concentrated in vacuum. The residue was purified by column chromatography on silica gel (eluent: PE/EA (v/v)= 20/1 to 5/1) to give N-(2-((tert-butylsulfinyl)amino)-2-(2-isopropylphenyl)ethyl)-4-methylbenzenesulfonamide (23 g, yield: 65%). ¹H NMR (400 MHz, CDCl₃) δ ppm: 7.79 (d, J=8.4 Hz, 2H), 7.32-7.26 (m, 4H), 7.20-7.12 (m, 1H), 4.82-4.69 (m, 1H), 4.25 (br, 1H), 3.14 (br, 4H), 3.07-2.97 (m, 1H), 2.41 (s, 3H), 1.42 (t, 6H), 1.23 (s, 9H).

Step 5: synthesis of N-(2-amino-2-(2-isopropylphenyl)ethyl)-4-methylbenzenesulfonamide

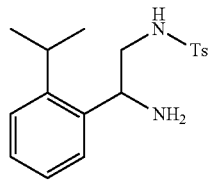 [SMILES: Cc1ccc(S(=O)(=O)NCC(N)c2ccccc2C(C)C)cc1]

To a solution of N-(2-((tert-butylsulfinyl)amino)-2-(2-isopropylphenyl)ethyl)-4-methylbenzenesulfonamide (5.0 g, 11 mmol) in MeOH (20 mL) was added HCl solution (10 mL, 4M in MeOH). The mixture was stirred at 25° C. for 1 hr and was then concentrated in vacuum. The residue was portioned with water (50 mL). To the mixture was added aqueous Na₂CO₃ to adjust the pH=9. The mixture was extracted with EA (50 mL×3). The combined organic layer was dried over Na₂SO₄, filtered and concentrated in vacuum to give N-(2-amino-2-(2-isopropylphenyl)ethyl)-4-methylbenzenesulfonamide (3.8 g, crude), which was used in next step without further purification. ¹H NMR (400 MHz, CDCl₃) δ ppm: 7.74 (d, J=8.0 Hz, 2H), 7.32-7.23 (m, 5H), 7.21-7.13 (m, 1H), 4.36 (m, 1H), 3.17-3.03 (m, 2H), 2.93 (m, 1H), 2.43 (s, 3H), 1.21-1.18 (m, 6H). MS (ESI, m/e) [M+1]⁺333.1.

Step 6: tert-butyl 2-((1-(2-isopropylphenyl)-2-(4-methylphenylsulfonamido)ethyl)amino)-7-azaspiro[3.5]nonane-7-carboxylate

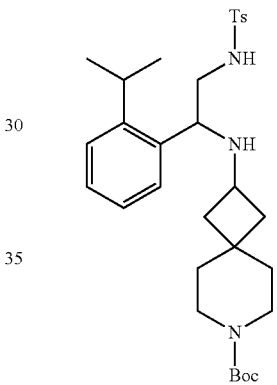

To a solution of N-(2-amino-2-(2-isopropylphenyl)ethyl)-4-methylbenzenesulfonamide (4 g, 0.012 mol) in DCE (50 mL) was added tert-butyl 2-oxo-7-azaspiro[3.5]nonane-7-carboxylate (3.2 g, 0.013 mol) and HOAc (1.44 g, 0.024 mol) and the mixture was stirred at 25° C. for 1 hr. After NaBH(OAc)₃ (5.1 g, 0.024 mol) was added, the mixture was stirred at 25° C. for 12 hrs. The reaction was quenched with aqueous NH₄Cl (50 mL) and the mixture was extracted with DCM (50 mL×3). The combined organic layer was washed with brine (50 mL×2), dried over anhydrous Na₂SO₄, filtered and concentrated in vacuum. The residue was purified by column chromatography on silica gel (eluent: PE/EA (v/v)=10/1 to 5/1) to give tert-butyl 2-((1-(2-isopropylphenyl)-2-(4-methylphenylsulfonamido)ethyl)amino)-7-azaspiro[³0.5]nonane-7-carboxylate (4.3 g), yield: 64%. ¹H NMR (400 MHz, CDCl₃) δ ppm: 7.73 (d, J=8.0 Hz, 2H), 7.32-7.25 (m, 4H), 7.19-7.13 (m, 2H), 4.02 (m, 1H), 3.30-3.22 (m, 4H), 3.09-2.98 (m, 3H), 2.88 (m, 1H), 2.43 (s, 3H), 2.02-1.88 (m, 2H), 1.75 (br, 3H), 1.44 (s, 9H), 1.40 (m, 3H), 1.17 (m, 6H). MS (ESI, m/e) [M+1]⁺556.4.

Step 7: synthesis of tert-butyl 2-(2-chloro-N-(1-(2-isopropylphenyl)-2-(4-methylphenylsulfonamido)ethyl)acetamido)-7-azaspiro[3.5]nonane-7-carboxylate

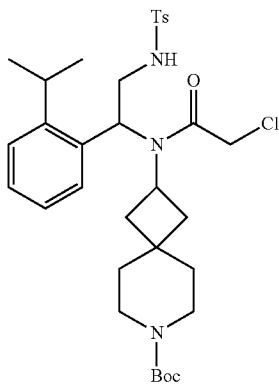 [SMILES: Cc1ccc(S(=O)(=O)NCC(c2ccccc2C(C)C)N(C(=O)CCl)C2CC3(CCN(C(=O)OC(C)(C)C)CC3)C2)cc1]

To a solution of tert-butyl 2-((1-(2-isopropylphenyl)-2-(4-methylphenylsulfonamido)ethyl)amino)-7-azaspiro[3.5]nonane-7-carboxylate (4.3 g, 7.74 mmol) in THF (50 mL) was added TEA (1.56 g, 15.48 mmol), 2-chloroacetyl chloride (0.96 g, 8.51 mmol) was then added dropwise at 0° C. The mixture was stirred at 25° C. for 2 hrs. The mixture was poured into aqueous NH₄Cl solution (50 mL, 1M), extracted with EA (50 mL×3). The combined organic layer was washed with brine (50 mL×2), dried over anhydrous Na₂SO₄, filtered and concentrated in vacuum. The residue was purified by column chromatography on silica gel (eluent: PE/EA (v/v)=20/1 to 5/1) to give tert-butyl 2-(2-chloro-N-(1-(2-isopropylphenyl)-2-(4-methylphenylsulfonamido)ethyl)acetamido)-7-azaspiro[3.5]nonane-7-carboxylate (4.6 g, yield: 94%). ¹H NMR (400 MHz, CDCl₃) δ ppm: 7.74 (d, J=8.0 Hz, 2H), 7.32-7.27 (m, 4H), 7.20 (m, 1H), 7.15-7.10 (m, 1H), 5.31-5.20 (m, 1H), 5.08 (br, 4H), 4.22 (d, J=2.8 Hz, 2H), 4.13 (m, 2H), 3.30 (m, 2H), 3.23 (m, 3H), 2.38 (s, 3H), 2.05 (s, 3H), 1.65 (br, 3H), 1.48-1.45 (m, 3H), 1.44 (s, 9H), 1.27 (m, 6H). MS (ESI, m/e) [M−100]⁺532.3.

Step 8: synthesis of tert-butyl 2-(2-(2-isopropylphenyl)-6-oxo-4-tosylpiperazin-1-yl)-7-azaspiro[3.5]nonane-7-carboxylate

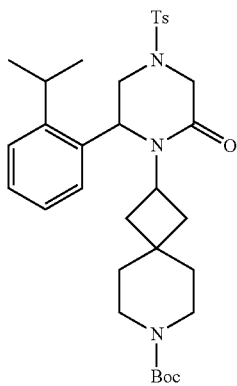 [SMILES: Cc1ccc(S(=O)(=O)N2CC(=O)N(C3CC4(CCN(C(=O)OC(C)(C)C)CC4)C3)C(c3ccccc3C(C)C)C2)cc1]

To a solution of tert-butyl 2-(2-chloro-N-(1-(2-isopropylphenyl)-2-(4-methylphenylsulfonamido)ethyl)acetamido)-7-azaspiro[3.5]nonane-7-carboxylate (4.6 g, 7.28 mmol) in DMF (50 mL) was added K₂CO₃ (2.0 g, 14.55 mmol). The mixture was stirred at 60° C. for 1 hr. The mixture was then poured into ice/water (50 mL) and was extracted with EA (50 mL×3). The combined organic layer was washed with brine (50 mL×2), dried over anhydrous Na₂SO₄, filtered and concentrated in vacuum. The residue was purified by column chromatography on silica gel (eluent: PE/EA (v/v)=20/1 to 5/1) to give tert-butyl 2-(2-(2-isopropylphenyl)-6-oxo-4-tosylpiperazin-1-yl)-7-azaspiro[3.5]nonane-7-carboxylate (2.6 g), yield: 62%. ¹H NMR (400 MHz, CDCl₃) δ ppm: 7.47 (d, J=8.0 Hz, 2H), 7.36-7.30 (m, 2H), 7.23 (d, J=8.0 Hz, 2H), 7.16-7.10 (m, 1H), 6.89 (d, J=8.0 Hz, 1H), 5.07 (t, 1H), 4.30 (br, 1H), 4.16-4.10 (m, 1H), 3.97-3.88 (m, 1H), 3.81-3.70 (m, 1H), 3.39 (m, 2H), 3.27-3.21 (m, 2H), 3.21-3.13 (m, 2H), 3.12-3.06 (m, 1H), 2.99-2.85 (m, 1H), 2.41 (s, 3H), 2.22-2.14 (m, 1H), 1.85 (br, 1H), 1.73-1.58 (m, 2H), 1.46 (m, 2H), 1.41 (s, 9H), 1.30-1.26 (m, 6H). MS (ESI, m/e) [M−100]⁺496.3.

Step 9: synthesis of tert-butyl 2-(2-(2-isopropylphenyl)-6-oxopiperazin-1-yl)-7-azaspiro[3.5]nonane-7-carboxylate

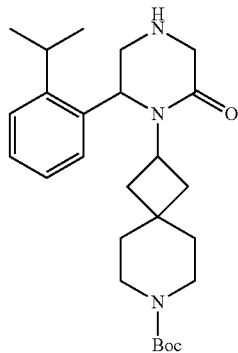 [SMILES: CC(C)c1ccccc1C1CNCC(=O)N1C1CC2(CCN(C(=O)OC(C)(C)C)CC2)C1]

To a solution of tert-butyl 2-(2-(2-isopropylphenyl)-6-oxo-4-tosylpiperazin-1-yl)-7-azaspiro[3.5]nonane-7-carboxylate (2.6 g, 4.47 mmol) in MeOH (50 mL) was added Mg (1.07 g, 44.7 mmol). The mixture was stirred at 70° C. for 2 hrs. After the mixture was cooled to room temperature, the upper layer of solution was decanted into water (50 mL) and EA (50 mL), and then filtered through a celite pad. The filtrate was extracted with EA (50 mL×3). The combined organic layer was washed with brine (50 mL×2), dried over anhydrous Na₂SO₄, filtered and concentrated in vacuum. The compound tert-butyl 2-(2-(2-isopropylphenyl)-6-oxopiperazin-1-yl)-7-azaspiro[3.5]nonane-7-carboxylate (1.3 g, crude) was obtained, yield: 66%. This product was used in next step without further purification. MS (ESI, m/e) [M+1]⁺442.3.

Step 10: synthesis of tert-butyl 2-(2-(2-isopropylphenyl)-4-(4-methoxybenzyl)-6-oxopiperazin-1-yl)-7-azaspiro[3.5]nonane-7-carboxylate

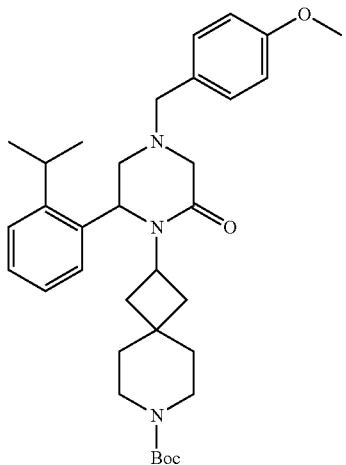 [SMILES: COc1ccc(CN2CC(=O)N(C3CC4(CCN(C(=O)OC(C)(C)C)CC4)C3)C(c3ccccc3C(C)C)C2)cc1]

To a solution of tert-butyl 2-(2-(2-isopropylphenyl)-6-oxopiperazin-1-yl)-7-azaspiro[3.5]nonane-7-carboxylate (3.5 g, 7.93 mmol) and 4-methoxybenzaldehyde (1.29 g, 9.51 mmol) in DCE (50 mL) were added AcOH (951.96 mg, 15.85 mmol) and NaBH(OAc)$_3$ (3.36 g, 15.85 mmol). The mixture was stirred at 25° C. for 12 hrs. The reaction mixture was poured into aqueous Na$_2$CO$_3$ (50 mL), extracted with and DCM (50 mL×3), dried over Na$_2$SO$_4$, filtered and concentrated in vacuum. The residue was further purified by MPLC (eluent: PE/EA (v/v)=10/1 to 2/1). The compound tert-butyl 2-(2-(2-isopropylphenyl)-4-(4-methoxybenzyl)-6-oxopiperazin-1-yl)-7-azaspiro[3.5]nonane-7-carboxylate (4.2 g) was obtained in a yield of 94%. $^1$H NMR (400 MHz, CDCl$_3$) δ ppm: 7.33-7.26 (m, 2H), 7.22-7.17 (m, 1H), 7.14-7.08 (m, 1H), 6.78 (m, 2H), 6.63 (m, 2H), 4.94 (m, 1H), 3.73 (s, 3H), 3.57-3.44 (m, 2H), 3.33-3.11 (m, 6H), 2.98 (m, 1H), 2.71-2.56 (m, 2H), 2.30-2.17 (m, 1H), 1.93 (m, 1H), 1.81-1.67 (m, 2H), 1.53-1.44 (m, 2H), 1.41 (s, 9H), 1.37-1.29 (m, 2H), 1.22 (m, 3H), 0.95 (m, 3H). MS (ESI, m/e) [M+1]$^+$562.2.

Step 11: synthesis of tert-butyl 2-(2-(2-isopropylphenyl)-4-(4-methoxybenzyl)piperazin-1-yl)-7-azaspiro[3.5]nonane-7-carboxylate

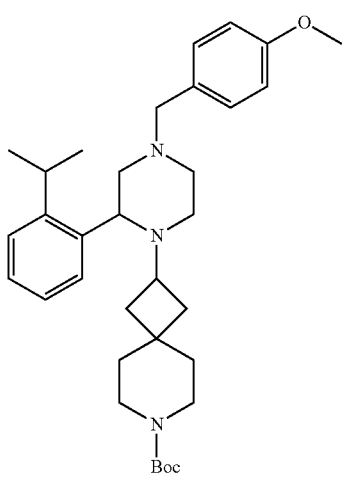 [SMILES: COc1ccc(CN2CCN(C3CC4(CCN(C(=O)OC(C)(C)C)CC4)C3)C(c3ccccc3C(C)C)C2)cc1]

A mixture of tert-butyl 2-(2-(2-isopropylphenyl)-4-(4-methoxybenzyl)-6-oxopiperazin-1-yl)-7-azaspiro[3.5]nonane-7-carboxylate (4.2 g, 7.48 mmol) in BH$_3$·THF (40 mL) was stirred at 70° C. for 12 hr. The reaction mixture was quenched by MeOH (50 mL) at 0° C. and stirred at 25° C. for 30 min. After the mixture was concentrated under reduced pressure, tert-butyl 2-(2-(2-isopropylphenyl)-4-(4-methoxybenzyl)piperazin-1-yl)-7-azaspiro[3.5]nonane-7-carboxylate (4.1 g, crude) was obtained. MS (ESI, m/e) [M+1]$^+$548.3.

Step 12: synthesis of 2-(2-(2-isopropylphenyl)-4-(4-methoxybenzyl) piperazin-1-yl)-7-azaspiro[3.5]nonane

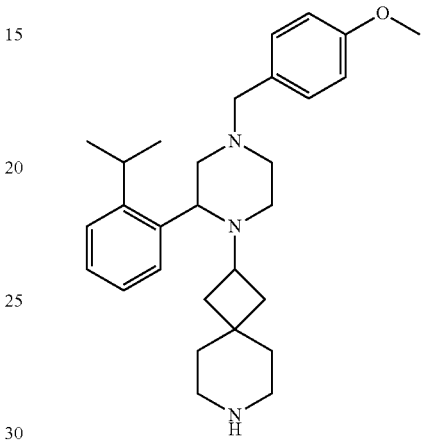

A mixture of tert-butyl 2-(2-(2-isopropylphenyl)-4-(4-methoxybenzyl)piperazin-1-yl)-7-azaspiro[3.5]nonane-7-carboxylate (4.1 g, 7.48 mmol) in HCl solution (50 mL, 4M in CH$_3$OH) was stirred at 25° C. for 2 hrs. The reaction mixture was concentrated under reduced pressure. The residue was purified by prep-HPLC (TFA condition). The residue was diluted with H$_2$O (30 mL) and basified by aq. Na$_2$CO$_3$ solution to pH=9. The mixture was extracted with EA (30 mL×3). The combined organic layers were dried over Na$_2$SO$_4$, filtered and concentrated under reduced pressure to give 2-(2-(2-isopropylphenyl)-4-(4-methoxybenzyl) piperazin-1-yl)-7-azaspiro[3.5]nonane (2.7 g, yield: 80%). MS (ESI, m/e) [M+1]$^+$448.3.

2-(2-(2-isopropylphenyl)-4-(4-methoxybenzyl)piperazin-1-yl)-7-azaspiro[3.5]nonane was separated by SFC (Instrument: Waters SFC80 preparative SFC; Column: Chiralpak IG, 250×30 mm i.d. 10 um; Mobile phase: A for CO$_2$ and B for EtOH(0.I % NH$_3$·H$_2$O); Gradient: B % =40% isocratic mode; Flow rate:65 g/min; Wavelength:220 nm; Column temperature: 40° C.; System back pressure: 100 bar).

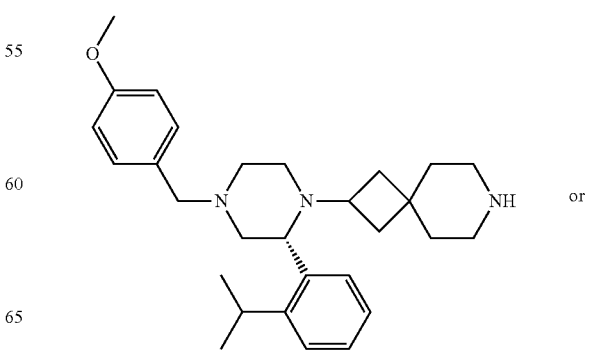

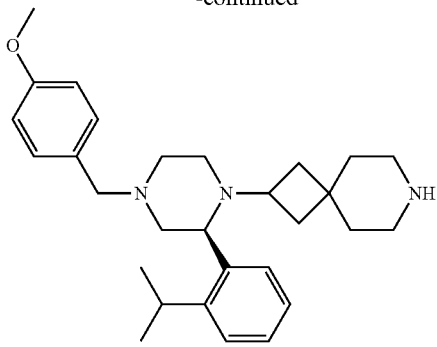

(R or S)-2-(2-(2-isopropylphenyl)-4-(4-methoxybenzyl)piperazin-1-yl)-7-azaspiro[3.5]nonane (faster peak, retention time: 1.64 min, 853 mg) was obtained (sometimes referred to as "intermediate 19-1a in Method A"), yield: 31%. $^1$H NMR (400 MHz, CDCl$_3$) δ ppm: 7.48 (m, 1H), 7.26-7.18 (m, 4H), 7.15-7.09 (m, 1H), 6.82 (m, 2H), 3.78 (s, 3H), 3.64 (m, 1H), 3.50-3.43 (m, 2H), 3.39 (m, 1H), 3.04-2.96 (m, 1H), 2.95-2.85 (m, 2H), 2.70-2.53 (m, 5H), 2.34-2.24 (m, 2H), 2.16 (m, 1H), 1.79-1.71 (m, 11H), 1.70-1.62 (m, 1H), 1.50 (s, 1H), 1.40-1.28 (m, 5H), 1.25 (m, 3H), 1.14 (m, 3H). MS (ESI, m/e) [M+1]$^+$448.3.

The other isomer intermediate 19-1b (S or R)-2-(2-(2-isopropylphenyl)-4-(4-methoxybenzyl)piperazin-1-yl)-7-azaspiro[3.5]nonane (slower peak, retention time: 1.74 min, 890 mg) was obtained (sometimes referred to as "intermediate 19-1b in Method A"), yield: 33%. MS (ESI, m/e) [M+1]$^+$448.3.

The above separated isomers Intermediate 19-1a and Intermediate 19-1b in Method A was further analyzed by the following Chiral HPLC method.

| Column | Lux ® Amylose-1 (Phenomenex, 00F-4732-E0) |
|---|---|
| Column size | 4.6 × 150 mm, 5 um |
| Mobile phase | Hexane:EtOH (0.1% DEA) = 90:10 |
| Flow rate | 0.8 mL/min |
| Wave length | UV 214 nm |
| Temperature | 22° C. |
| Retention time of intermediate 19-1a in Method A | 3.9 min |
| Retention time of intermediate 19-1b in Method A | 4.4 min |

Step 13: synthesis of methyl (R or S)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzoate

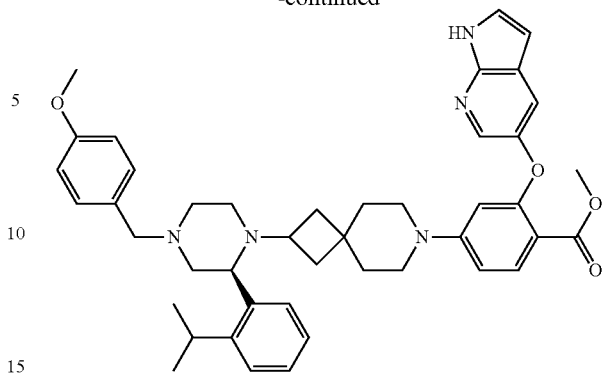

A mixture of methyl 2-((1H-pyrrolo[2,3-b]pyridin-5-yl)oxy)-4-fluorobenzoate (5.7 g, 20.13 mmol), intermediate 19-1a in Method A (R or S )-2-(2-(2-isopropylphenyl)-4-(4-methoxybenzyl)piperazin-1-yl)-7-azaspiro[3.5]nonane (7.5 g, 16.78 mmol) and Na$_2$CO$_3$ (17.8 g, 167.8 mmol) in DMSO (110 mL) was stirred in a 95° C. for 16 hrs. After the reaction was cooled to room temperature, the mixture was partitioned with EA (300 mL) and H$_2$O (300 mL). The EA layer was collected and the aqueous layer was extracted with EA (300 mL). The combined organic layers were washed with H$_2$O (200 mL×4) and brine (100 mL), dried over anhydrous Na$_2$SO$_4$, and concentrated in vacuum. The residue was purified by column chromatography on silica gel (eluent: EA/DCM (v/v)=1/4, then MeOH/DCM (v/v)=1/100 to 1/20) to give (R or S )-methyl 2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzoate (9.2 g), yield: 76.7%. $^1$H NMR (400 MHz, DMSO-d$_6$) δ ppm: 11.62 (s, 1H), 7.96 (s, 1H), 7.71 (d, J=8.4 Hz, 1H), 7.46 (s, 1H), 7.38 (s, 2H), 7.16 (s, 4H), 7.08 (s, 1H), 6.84 (s, 2H), 6.72 (s, 1H), 6.36 (s, 11H), 6.31 (s, 1H), 3.70 (s, 3H), 3.62 (s, 3H), 3.49 (s, 1H), 3.39-3.36 (m, 1H), 3.05-2.99 (m, 4H), 2.90 (s, 1H), 2.81 (s, 1H), 2.54 (s, 2H), 2.14 (s, 2H), 1.99 (s, 2H), 1.64 (s, 2H), 1.29-1.25 (m, 6H), 1.18 (s, 4H), 1.05 (s, 4H). MS (ESI, m/e) [M+1]$^+$714.4.

Step 14: synthesis of (R or S )-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzoic acid

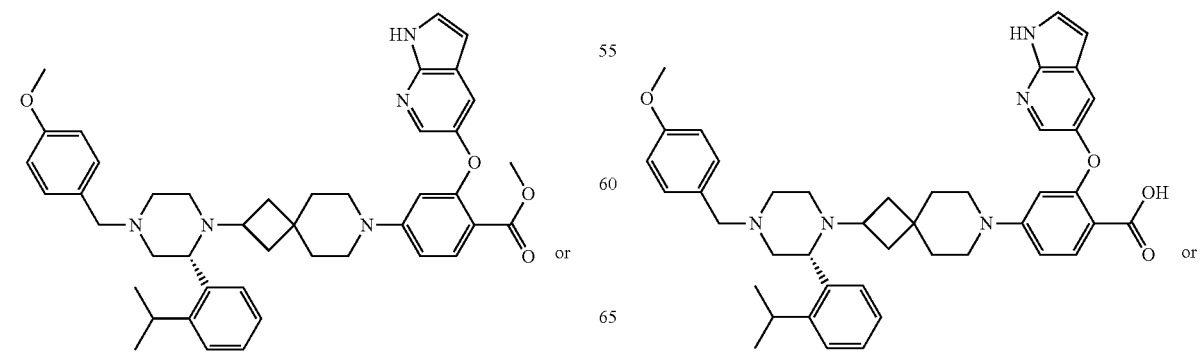

-continued

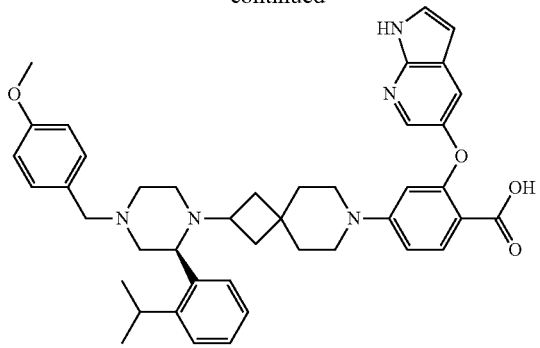

To A solution of (R or S )-2-(2-(2-isopropylphenyl)-4-(4-methoxybenzyl)piperazin-1-yl)-7-azaspiro[3.5]nonane (9.2 g, 12.90 mmol) in CH$_3$OH (50 mL) and THF (50 mL) was added NaOH solution (20 mL, 6 N in water). The mixture was stirred at 50° C. for 2.5 hrs. After the reaction solution was cooled to room temperature, the mixture was diluted with DCM (100 mL).

The mixture was stirred and was adjusted to pH value ~5 with HCl acid (70 mL, 2M). The organic layer was separated, dried over Na$_2$SO$_4$, concentrated in vacuum to get powder. The crude product was further purified by slurry in EA (100 mL) at reflux for 30 min. The solid was filtered and dried under vacuum at 50° C. to give (R or S )-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzoic acid (8.4 g), yield: 93.3%. $^1$H NMR (400 MHz, DMSO-d$_6$) δ ppm: 11.56 (s, 1H), 7.94 (s, 1H), 7.60 (d, J=8.0 Hz, 1H), 7.42 (s, 2H), 7.31 (s, 1H), 7.16 (s, 4H), 7.08 (s, 1H), 6.83 (s, 2H), 6.63 (d, J=8.0 Hz, 1H), 6.32 (s, 1H), 6.26 (s, 1H), 3.70 (s, 3H), 3.44 (s, 4H), 2.89-2.83 (m, 8H), 2.47 (s, 1H), 2.14 (s, 2H), 1.94 (s, 1H), 1.64 (s, 2H), 1.30 (s, 5H), 1.18 (s, 3H), 1.04 (s, 4H). MS (ESI, m/e) [M+1]$^+$700.4.

Step 15: synthesis of 2-((1H-pyrrolo[2,3-b]pyridin-5-yl)oxy)-N-((4-((((r,4r)-4-hydroxy-4-methylcyclohexyl)methyl)amino)-3-nitrophenyl)sulfonyl)-4(2-((R or S)-2-(2-isopropylphenyl)-4-(4-methoxybenzyl)piperazin-1-yl)-7-azaspiro[3.5]nonan-7-yl)benzamide (sometimes referred to as "Example 19a synthesized from intermediate 19-1a in Method A")

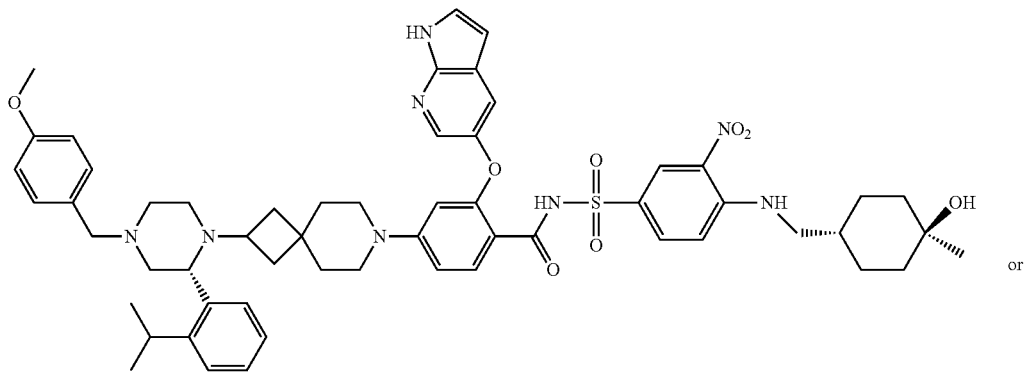 or

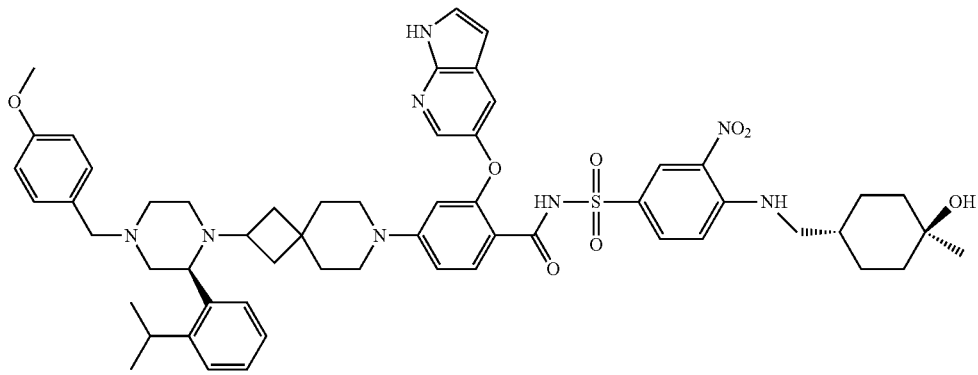

To the solution of (R or S )-2-((1 H-pyrrolo[2,3-b]pyridin-5-yl)oxy)-4-(2-(2(2-isopropylphenyl)-4-(4-methoxybenzyl)piperazin-1-yl)-7-azaspiro[3.5]nonan-7-yl)benzoic acid (8.4 g, 12.02 mmol), 4-((((1r,4r)-4-hydroxy-4-methylcyclohexyl)methyl)amino)-3-nitrobenzenesulfonamide (4.3 g, 12.62 mmol), EDCI (3.0 g, 15.62 mmol) and DMAP (4.5 g, 36.05 mmol) in DCM was added TEA (6.1 g, 60.08 mmol). The mixture was stirred at room temperature for 16 hrs. The reaction mixture was washed with 10% acetic acid (100 mL×2), saturated aq. NaHCO$_3$ (200 mL) and brine (150 mL). The organic layer was separated and dried over anhydrous Na$_2$SO$_4$, filtered and concentrated in vacuum. The residue was purified by column chromatograph on silica gel (eluent: EA/DCM (v/v)=1/1, then MeOH/EA/DCM (v/v/v) =1/40/40 to 1/15/15). 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((R or S)-2-(2-isopropylphenyl)-4-(4-methoxybenzyl)piperazin-1-yl)-7-azaspiro[3.5]nonan-7-yl)benzamide (8.0 g,) was obtained in a yield of 65.0%. $^1$H NMR (400 MHz, DMSO-d$_4$) δ ppm: 11.66 (s, 1H), 11.12 (s, 1H), 8.52 (s, 2H), 8.00 (s, 1H), 7.74 (d, J=12.0 Hz, 1H), 7.57-7.31 (m, 4H), 7.27-6.99 (m, 6H), 6.91-6.78 (m, 2H), 6.68-6.56 (m, 1H), 6.35 (s, 1H), 6.15 (s, 1H), 4.25 (s, 1H), 3.71 (s, 3H), 3.64-3.39 (m, 3H), 3.31-3.18 (m, 3H), 3.02-2.78 (m, 7H), 2.66-2.53 (m, 1H), 2.37-1.97 (m, 3H), 1.78-1.50 (m, 7H), 1.38-1.02 (m, 19H). MS (ESI, m/e) [M+1]$^+$1025.6.

The absolute configuration of Example 19a synthesized from intermediate 19-1a in Method A was determined by the conventional skills in the art. Example 19a synthesized from intermediate 19-1a in Method A is assigned as (R)-configuration on the chiral carbon atom of the piperazine ring base on its co-crystal structure with Bcl-2 G101V protein. The detailed method for the determination was described as below.

Recombinant Bcl-2 G101V mutant protein with His and SUMO tag was expressed in *E. coli* BL21 (DE3), induced with 0.3 mM IPTG for 16 h at 16° C. The cells were harvested by centrifugation at 5,000 g for 15 min, resuspended in lysis buffer containing 20 mM Tris, pH 8.0, 300 mM NaCl and 5 mM Imidazole, and lysed by sonication. After centrifugation at 20,000 g for 40 min, the supernatant was incubated with His tag affinity resin at 4° C. for 30 min. The resin was rinsed three times with the lysis buffer, followed by treatment with ULP1 protease at 4° C. overnight. The flow through was concentrated and sequentially applied to a size-exclusion chromatography column (Superdex-75, GE Healthcare) in a buffer containing 20 mM Tris, pH 8.0 and 150 mM NaCl. The peak was collected and concentrated to approximately 10 mg/ml. The protein solution was incubated with Example 19a synthesized from intermediate 19-1a in Method A for 30 min at 4° C., and then mixed with a reservoir solution containing 0.1 M MES, pH 6.5, 0.01 M CoCl$_2$ and 1.8 M (NH$_4$)$_2$SO$_4$. Co-crystals of Bcl-2 G101V mutant with Example 19a were obtained by vapor diffusion from hanging drops cultured at 20° C.

X-Ray Data Collection and Structural Determination

Nylon loops were used to harvest the co-crystals and then immersed the crystals in the reservoir solution supplemented with 20% glycerol for 10 sec. Diffraction data were collected at beamline BL17U1, Shanghai Synchrotron Radiation Facility, and were processed with XDS program. The phase was solved with program PHASER using the Bcl-2/ABT-199 crystal structure (PDB code: 6OOK) as the molecular replacement searching model. Phenix.refine was used to perform rigid body, TLS, restrained refinement against X-ray data, followed by manually adjustment in COOT program and further refinement in Phenix.refine program.

Data Collection and Refinement Statistics

|  | Bcl-2 G101V + Example 19a |
|---|---|
| Data collection |  |
| Beamline | BL17U1 |
| Space group | P 21 21 21 |
| Cell dimensions (Å) | a = 32.57 b = 49.81 c = 95.35 |
| Angles (°) | α = 90.00 β = 90.00 γ = 90.00 |
| Resolution (Å) | 34.44-1.45 (1.47-1.45) |
| Total number of reflections | 352471 (13533) |
| Number of unique reflections | 28364 (1393) |
| Completeness (%) | 100 (100) |
| Average redundancy | 12.4 (9.7) |
| Rmerge$^a$ | 0.066 (0.678) |
| I/sigma (I) | 24.2 (3.7) |
| Wilson B factor (Å) | 12.05 |
| Refinement |  |
| Resolution (Å) | 26.89-1.45 |
| Number of reflections | 28298 |
| rmsd bond lengths (Å) | 0.007 |
| rmsd bond angles (°) | 1.132 |
| R$_{work}$$^b$ (%) | 15.96 |
| R$_{free}$$^c$ (%) | 18.75 |
| Average B-factors of protein | 17.55 |
| Ramachandran plot (%) |  |
| Favored | 100 |
| Allowed | 0.00 |
| Outliers | 0.00 |

Values in parentheses refer to the highest resolution shell.

$^a$Rmerge = Σ Σ$_j$|I(h)$_j$ − ⟨(I(h)⟩|/Σ Σ$_j$|I(h)$_j$|, where ⟨I(h)⟩ is the mean intensity of equivalent.

$^b$R$_{work}$ = Σ|Fo − Fc|/Σ|Fo|, where Fo and Fc are the observed and calculated structure factor amplitudes, respectively.

$^c$R$_{free}$ = Σ|Fo − Fc|/Σ|Fo|, calculated using a test data set, 5% of total data randomly selected from the observed reflections.

As shown in FIG. 1A, the absolute stereochemistry of Example 19a is assigned as (R)-configuration on the chiral carbon atom of the piperazine ring (arrow pointed carbon) based on its co-crystal structure with Bcl-2 G101V protein.

Therefore, Example 19a synthesized from intermediate 19-1a in Method A, obtained in Step 15, has the chemical name of 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((R)-2(2-isopropylphenyl)-4-(4-methoxybenzyl)piperazin-1-yl)-7-azaspiro[3.5]nonan-7-yl)benzamide and the chemical structure

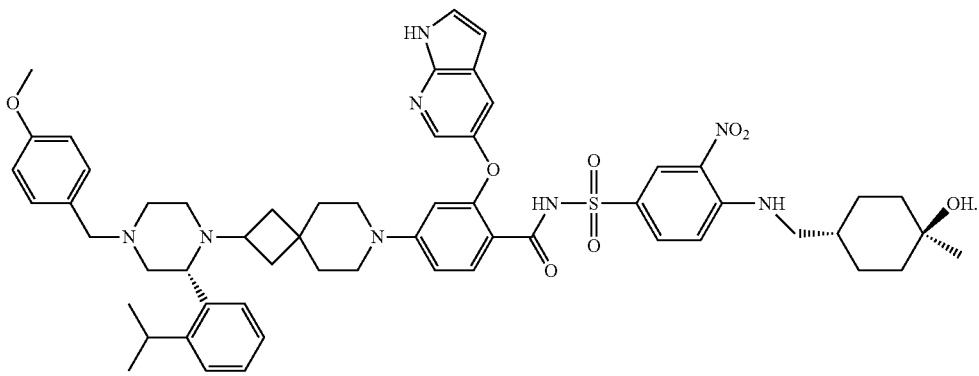 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc1]

Given that the absolute stereochemistry of Example 19a synthesized from intermediate 19-1a in Method A is assigned as (R)-configuration by co-crystal structure with Bcl-2 G101V protein. Intermediate 19-1a in Method A is deduced as having (R)-configurations as well understood by organic chemists.

Method B for Synthesis of Intermediate 19-1a

Intermediate 19-1a (R)-2-(2-(2-isopropylphenyl)-4-(4-methoxybenzyl)piperazin-1-yl)-7-azaspiro[3.5]nonane was also prepared by alternative procedure as described below.

Intermediate 19-1a in Method B

Synthesis of (R)-2-(2-(2-isopropylphenyl)-4-(4-methoxybenzyl)piperazin-1-yl)-7-azaspiro[3.5]nonane (intermediate 19-1a in Method B)

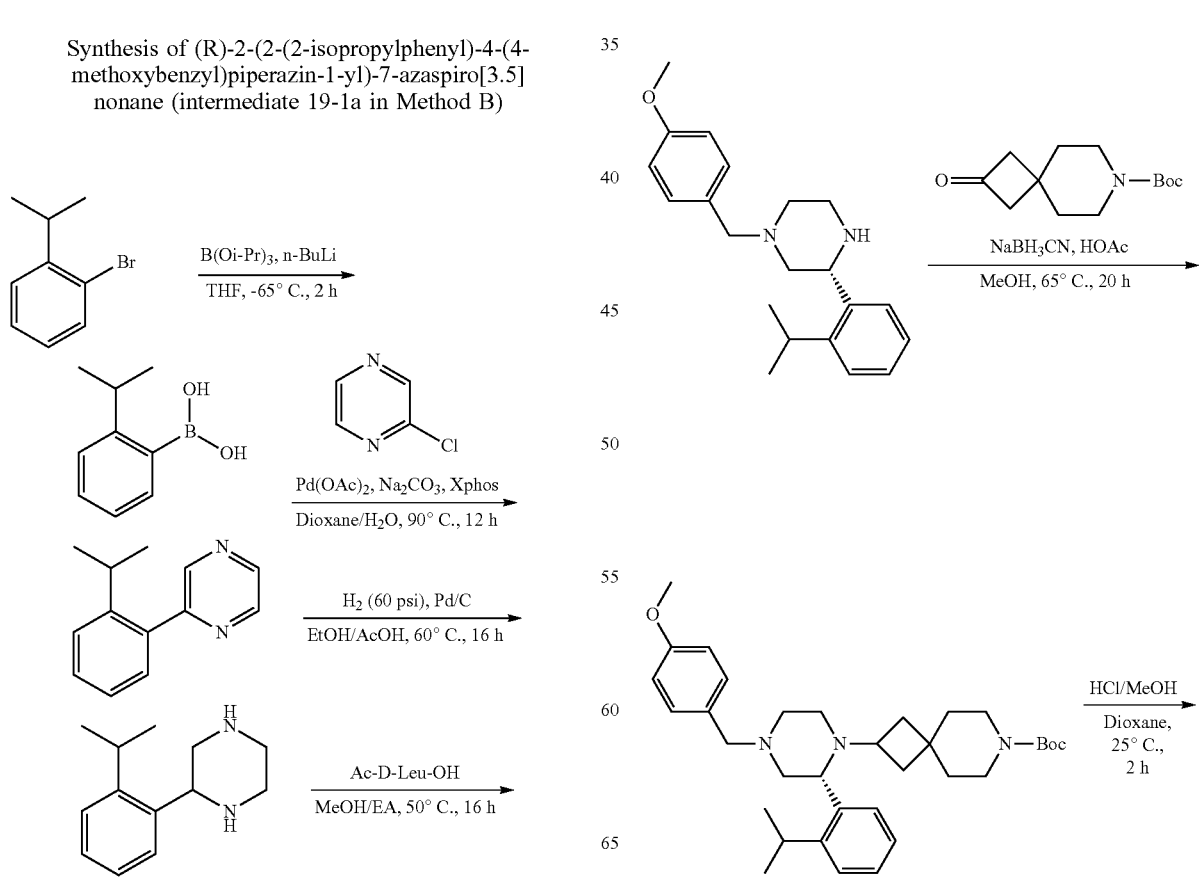

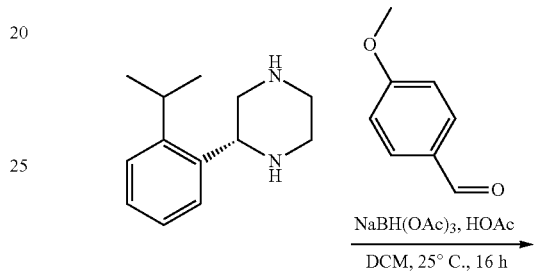

-continued

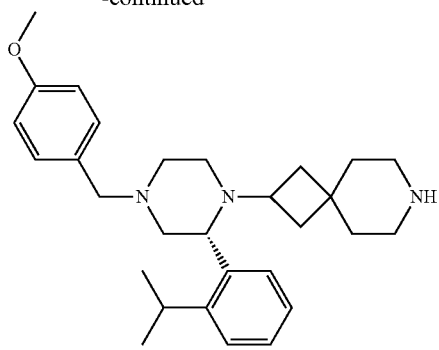

Intermediate 19-1a

Step 1: Synthesis of (2-isopropylphenyl)boronic acid

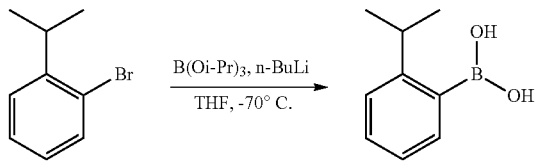

To a solution of 1-bromo-2-isopropylbenzene (200 g, 1.00 mol) in THF (2000 mL) was added n-BuLi (442.0 mL, 1.11 mol, 2.5 M in hexane) dropwise at −65° C. The solution was stirred at −65° C. for 1 hr. Triisopropyl borate (453.4 g, 2.41 mmol) in THF (500 mL) was then added dropwise at −65° C. The solution was further stirred at −65° C. for 1 hr. The mixture was warmed to 20° C. and stirred for another 1 hr. Aqueous HCl acid (1.5 L, 1.5 mol, 1 N) was added dropwise at 20° C. under stirring. The mixture was stirred at 20° C. for another 1 hr and was then extracted with EtOAc (2 L×3). The combined organic layers were dried over Na₂SO₄, filtered and concentrated under reduced pressure to give (2-isopropylphenyl)boronic acid (165 g, crude) as a yellow oil, which was used for next step directly without further purification.

Step 2: Synthesis of 2-(2-isopropylphenyl)pyrazine

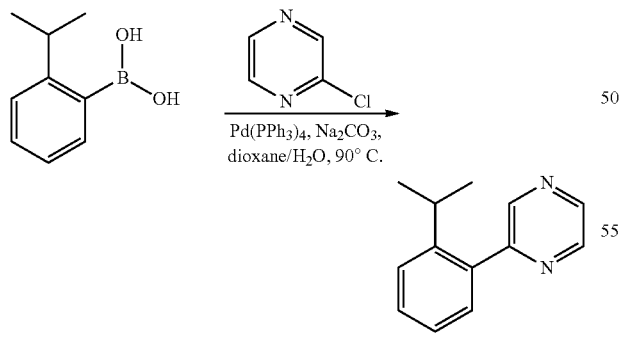

To a solution of (2-isopropylphenyl)boronic acid (165 g, 1.0 mol) in dioxane (1500 mL) and H₂O (150 mL) was added 2-chloropyrazine (138.3 g, 1.21 mol) and Pd(PPh₃)₄ (17.4 g, 15.10 mmol) and Na₂CO₃ (213.3 g, 2.01 mmol). The mixture was stirred at 90° C. for 12 hrs. After cooling to room temperature, the mixture was filtered through a Celite pad and washed with EtOAc (1 L). The filtrate was concentrated under reduced pressure. The residue was purified by column chromatography on silica gel (eluent: PE/EA (v/v)=400/1 to 1/1) to give 2-(2-isopropylphenyl)pyrazine (130 g, yield: 65%) as a yellow oil.

Step 3: Synthesis of 2-(2-isopropylphenyl)piperazine

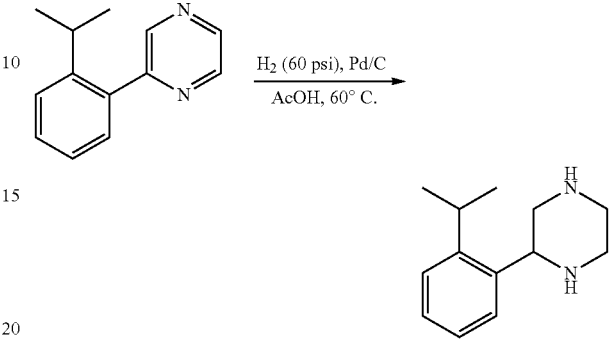

To a solution of 2-(2-isopropylphenyl)pyrazine (102 g, 515.5 mmol) in EtOH (1.5 L) and HOAc (100 mL) was added Pd/C (50 g, wet). The mixture was stirred at 60° C. for 16 hrs under H₂ (60 psi). The mixture was filtered through a Celite. The filter cake was washed with MeOH (3 L) and H₂O (1 L). The filtrate was concentrated under reduced pressure to remove most of MeOH and then extracted with EtOAc (1 L). The aqueous phase was basified with 10% NaOH aq. to pH=13-14. The mixture was extracted with DCM (1500 mL×3). The combined organic phases (DCM solution) were concentrated in vacuum to give 2-(2-isopropylphenyl)piperazine (96.6 g, yield: 91%) as a yield solid. ¹H NMR (400 MHz, CDCl₃) δ ppm: 7.62-7.55 (m, 1H), 7.32-7.15 (m, 3H), 4.09 (dd, J=10.0 Hz, 2.4 Hz, 1H), 3.41-3.29 (m, 1H), 3.16-3.13 (m, 1H), 3.07-2.85 (m, 4H), 2.74-2.71 (m, 1H), 1.26 (d, J=6.8 Hz, 6H). MS (ESI, m/e) [M+1]⁺205.5.

Step 4: Preparation of (R)-2-(2-isopropylphenyl)piperazine (the absolute configuration "R" is deduced from that of Intermediate 19-1a in Method B as described below)

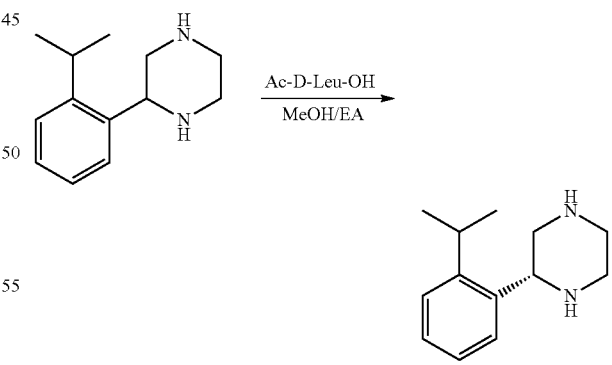

The compound of step 3 was resolved in accordance with the resolving method in the art (e.g., Bioorganic & Medicinal Chemistry Letters 12 (2002) 3161-3165). To a solution of 2-(2-isopropylphenyl)piperazine (20.0 g, 98 mmol) in MeOH/EA (v/v=1/10, 650 mL) was added the resolving agent Ac-D-Leu-OH commercial available from Bidepharma (17.0 g) at −50° C. The mixture was heated to reflux. After additional 20 mL of MeOH was added, a clear solution was formed. The solution was then cooled to room temperature slowly (observed solid precipitation) and stirred for additional 16 hrs. After the suspension was filtered, the cake was washed with EA (100 mL), collected and dried in vacuum at 45° C. (1 hr) to give ~15 g powder, which was then partitioned between 1N NaOH (100 mL) and DCM (150 mL). The organic layer was separated and collected, and the aqueous layer was extracted with DCM (50 mL). The combined organic layers were dried over Na₂SO₄, concentrated to get solid, dried in air to give (R)-2-(2-isopropylphenyl)piperazine (5.3 g, yield: 26.5%, >99% ee) as a white powder. MS (ESI, m/e) [M+1]⁺205.5.

Step 5: Synthesis of (R)-3-(2-isopropylphenyl)-1-(4-methoxybenzyl)piperazine

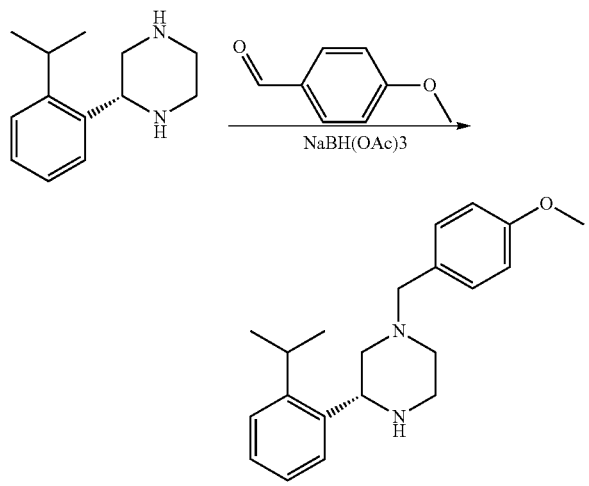

A mixture of (R)-2-(2-isopropylphenyl)piperazine (1.5 g, 7.353 mmol), 4-methoxybenzaldehyde (1.0 g, 7.353 mmol) and NaBH(OAc)₃ (2.4 g, 11.63 mmol) in DCM(30 mL) was stirred at room temperature for 16 hrs. The reaction was quenched by saturated NaHCO₃ (20 mL). The organic layer was dried over anhydrous Na₂SO₄, concentrated in vacuum to get a residue and purified by column chromatograph on silica gel (eluent: MeOH/DCM (v/v)=0/20 to 1/20) to give the product as a yellow oil. (1.5 g, yield: 63.0%). MS (ESI, m/e) [M+1]⁺325.2.

Step 6: Synthesis of tert-butyl (R)-2-(2-(2-isopropylphenyl)-4-(4-methoxybenzyl)piperazin-1-yl)-7-azaspiro[3.5]nonane-7-carboxylate

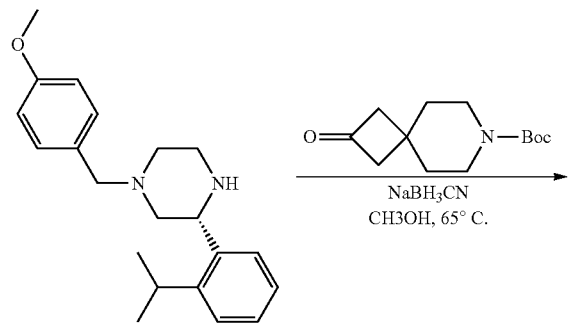

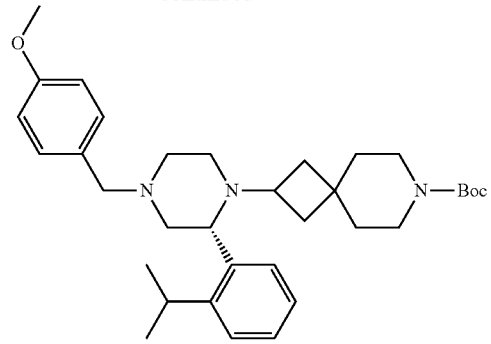

A mixture of (R)-3-(2-isopropylphenyl)-1-(4-methoxybenzyl)piperazine (130 mg, 0.401 mmol), tert-butyl 2-oxo-7-azaspiro[3.5]nonane-7-carboxylate (240 mg, 1.003 mmol), HOAc (60 mg, 1.003 mmol) and NaBH₃CN (64 mg, 1.003 mmol) was stirred at 65° C. for 20 hrs. The reaction mixture was quenched by saturated NaHCO₃ (20 mL). The organic layer was dried over anhydrous Na₂SO₄, concentrated in vacuum to get a residue and then purified by pre-TLC (eluent: EA/DCM (v/v)=1/1) to give the product as a yellow oil. (150 mg, yield: 68.3%). MS (ESI, m/e) [M+1]⁺548.4.

Step 7: Synthesis of (R)-2-(2-(2-isopropylphenyl)-4-(4-methoxybenzyl)piperazin-1-yl)-7-azaspiro[3.5]nonane (intermediate 19-1a in Method B)

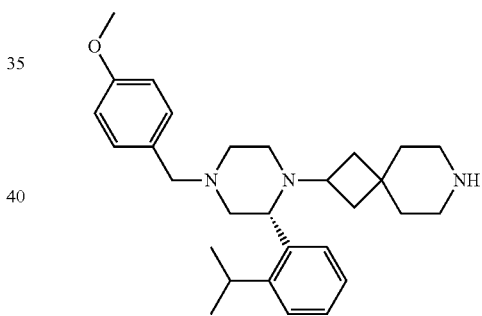

To a solution of tert-butyl (R)-2-(2-(2-isopropylphenyl)-4-(4-methoxybenzyl)piperazin-1-yl)-7-azaspiro[3.5]nonane-7-carboxylate (150 mg, 0.274 mmol) in MeOH (10 mL) was added 4M HCl in 1,4-dioxane (3 mL). The solution was stirred at room temperature for 2 hrs. The reaction mixture was concentrated. The residue partitioned between DCM (20 mL) and 1N NaOH (10 mL), the organic layer was separated, dried over Na₂SO₄ and concentrated to give (R)-2-(2-(2-isopropylphenyl)-4-(4-methoxybenzyl)piperazin-1-yl)-7-azaspiro[3.5]nonane (100 mg, yield: 81.6%). MS (ESI, m/e) [M+1]+448.3.

Intermediate 19-1a in Method B was also analyzed the following Chiral HPLC method. 1

| Column | Lux ® Amylose-1 (Phenomenex, 00F-4732-E0) |
|---|---|
| Column size | 4.6 × 150 mm, 5 um |
| Mobile phase | Hexane:EtOH (0.1% DEA) = 90:10 |
| Flow rate | 0.8 mL/min |
| Wave length | UV 214 nm |

| | |
|---|---|
| Temperature | 22° C. |
| Retention time of intermediate 19-1a in Method B | 3.9 min |

Intermediate 19-1a in Method B was found to have a retention time of 3.9 min, which was consistent with the retention time of Intermediate 19-1a in Method A. The consistency between the retention time of the two intermediates confirmed that Intermediate 19-1a in Method B has the (R)-configuration on the chiral carbon atom of the piperazine ring.

Method C for synthesis of Intermediate 19-1a

Intermediate 19-1a (R)-2-(2-(2-isopropylphenyl)-4-(4-methoxybenzyl)piperazin-1-yl)-7-azaspiro[3.5]nonane was also prepared by another procedure as described below.

Intermediate 19-1a in Method C

Synthesis of (R or S)-2-(2-(2-isopropylphenyl)-4-(4-methoxybenzyl)piperazin-1-yl)-7-azaspiro[3.5]nonane (intermediate 19-1a in Method C)

Step 1: Synthesis of (R or S)-tert-butyl 2-(2-(2-isopropylphenyl)-4-(4-methoxybenzyl)-6-oxopiperazin-1-yl)-7-azaspiro[3.5]nonane-7-carboxylate To a solution of (R or S)-tert-butyl 2-(2-(2-isopropylphenyl)-6-oxopiperazin-1-yl)-7-azaspiro[3.5]nonane-7-carboxylate (3 g, 6.79 mmol) and 4-methoxybenzaldehyde (1.11 g, 8.15 mmol) in DCE (40 mL) was added AcOH (815.91 mg, 13.59 mmol) and NaBH(OAc)$_3$ (4.32 g, 20.38 mmol). The mixture was stirred at 25° C. for 12 hrs. The reaction mixture was poured into aqueous Na$_2$CO3 (50 mL) and extracted with DCM (50 mL×3). The combined organic layer was dried over Na$_2$SO$_4$, filtered and concentrated in vacuum. The residue was purified by MPLC (silica gel, eluent: PE/EA (v/v)=10/1 to 2/1) to give (R or S)-tert-butyl 2-(2-(2-isopropylphenyl)-4-(4-methoxybenzyl)-6-oxopiperazin-1-yl)-7-azaspiro[3.5]nonane-7-carboxylate (3.6 g), yield: 94%. $^1$H NMR (400 MHz, CDCl$_3$) δ ppm: 7.33-7.26 (m, 2H), 7.22-7.17 (m, 1H), 7.14-7.08 (m, 1H), 6.78 (m, 2H), 6.63 (m, 2H), 4.94 (m, 1H), 3.73 (s, 3H), 3.57-3.44 (m, 2H), 3.33-3.11 (m, 6H), 2.98 (m, 1H), 2.71-2.56 (m, 2H), 2.30-2.17 (m, 1H), 1.93 (m, 1H), 1.81-1.67 (m, 2H), 1.53-1.44 (m, 2H), 1.41 (s, 9H), 1.37-1.29 (m, 2H), 1.22 (m, 3H), 0.95 (m, 3H).

Step 2: Synthesis of (R or S)-tert-butyl 2-(2-(2-isopropylphenyl)-4-(4-methoxybenzyl)piperazin-1-yl)-7-azaspiro[3.5]nonane-7-carboxylate A mixture of (R or S)-tert-butyl 2-(2-(2-isopropylphenyl)-4-(4-methoxybenzyl)-6-oxopiperazin-1-yl)-7-azaspiro[3.5]nonane-7-carboxylate (3.6 g, 6.41 mmol) in BH$_3$·THF (40 mL) was stirred at 70° C. for 12 hrs. The reaction mixture was quenched by MeOH (50 mL) at 0° C. and stirred at 25° C. for 30 min. The mixture was concentrated under reduced pressure to afford (R or S)-tert-butyl 2-(2-(2-isopropylphenyl)-4-(4-methoxybenzyl)piperazin-1-yl)-7-azaspiro[3.5]nonane-7-carboxylate (3.5 g, crude) as a white solid. MS (ESI, m/e) [M+1]$^+$548.3.

Step 3: Synthesis of (R or S)-2-(2-(2-isopropylphenyl)-4-(4-methoxybenzyl)piperazin-1-yl)-7-azaspiro[3.5]nonane (intermediate 19-1a in Method C)

A mixture of (R or S)-tert-butyl 2-(2-(2-isopropylphenyl)-4-(4-methoxybenzyl)piperazin-1-yl)-7-azaspiro[3.5]nonane-7-carboxylate (3.5 g, 6.39 mmol) in HCl solution (40 mL, 4M in MeOH) was stirred at 25° C. for 2 hrs. The reaction mixture was concentrated under reduced pressure. The residue was purified by prep-HPLC (TFA condition). The residue was diluted with H$_2$O (30 mL) and the mixture was basified with saturated aq. Na$_2$CO$_3$ to pH=9. The mixture was extracted with EtOAc (30 mL×3). The combined organic layers were dried over anhydrous Na$_2$SO$_4$, filtered and concentrated in vacuum to give (R or S)-2-(2-(2-isopropylphenyl)-4-(4-methoxybenzyl)piperazin-1-yl)-7-azaspiro[3.5]nonane (2.21 g), yield: 73%. $^1$H NMR (400 MHz, CDCl$_3$) δ ppm: 7.46 (m, 1H), 7.25-7.16 (m, 4H), 7.13-7.07 (m, 1H), 6.82 (m, 2H), 3.78 (s, 3H), 3.68-3.58 (m, 1H), 3.50-3.41 (m, 2H), 3.40-3.27 (m, 1H), 2.94 (m, 1H), 2.92-2.68 (m, 6H), 2.65 (m, 1H), 2.31-2.20 (m, 2H), 2.20-2.10 (m, 1H), 1.81-1.65 (m, 2H), 1.64-1.45 (m, 4H), 1.35-1.27 (m, 1H), 1.22 (m, 3H), 1.13 (m, 3H). MS (ESI, m/e) [M+1]$^+$448.3.

Example 19b 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S or R)-2-(2-isopropylphenyl)-4-(4-methoxybenzyl)piperazin-1-yl)-7-azaspiro[3.5]nonan-7-yl)benzamide

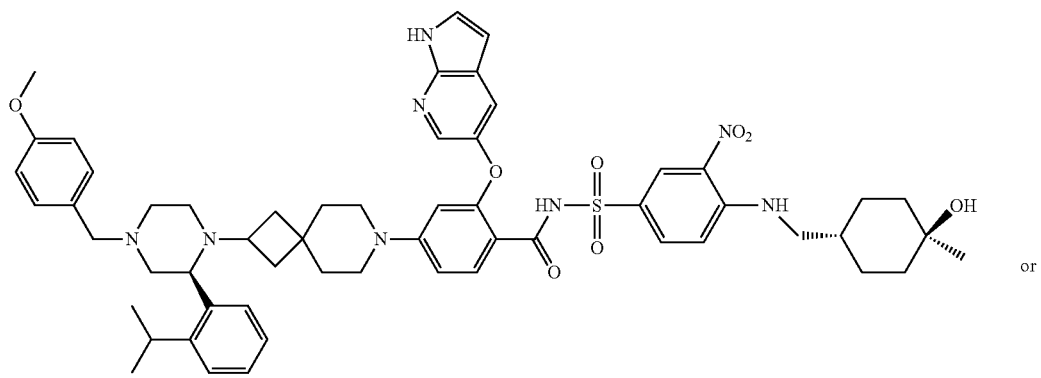

or

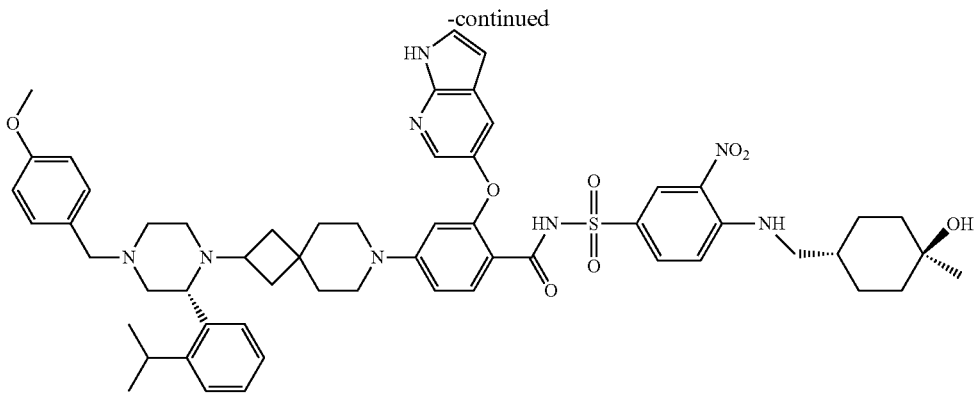

The compound Example 19b was synthesized following the similar procedures of Example 19a with (S or R)—2-(2-(2-isopropylphenyl)-4-(4-methoxybenzyl) piperazin-1-yl)-7-azaspiro[3.5]nonane (intermediate 19-1b) as material. (S or R)—2-(2-(2-isopropylphenyl)-4-(4-methoxybenzyl) piperazin-1-yl)-7-azaspiro[3.5]nonane (intermediate 19-1b) was prepared following the similar methods of preparing intermediate 19-1a as described above. MS (ESI, m/e) [M+1]⁺1025.6.

Given that the absolute stereochemistry of Example 19a synthesized from intermediate 19-1a in Method A as well as intermediate 19-1a in Method A have (R)-configurations, the other isomer with slower peal from the SFC separation, i.e., intermediate 19-1b in Method A, has (S)-configuration. Compound Example 19b from intermediate 19-1b in Method A is deduced to be (S)-configuration as well understood by organic chemists. It has the chemical name of 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-isopropylphenyl)-4-(4-methoxybenzyl)piperazin-1-yl)-7-azaspiro[3.5]nonan-7-yl)benzamide and the chemical structure:

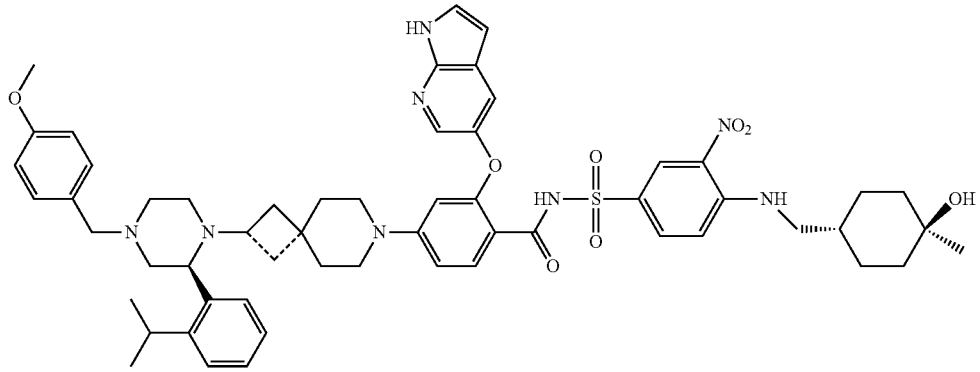

Example 32

(R or S)-2-((1 H-pyrrolo[2,3-b]pyridin-5-yl)oxy)-N-((4-((((4-fluorotetrahydro-2H-pyran-4-yl)methyl)amino)-3-nitrophenyl)sulfonyl)-4-(2-(2-(2-isopropylphenyl)-4-(4-methoxybenzyl)piperazin-1-yl)-7-azaspiro[3.5]nonan-7-yl)benzamide

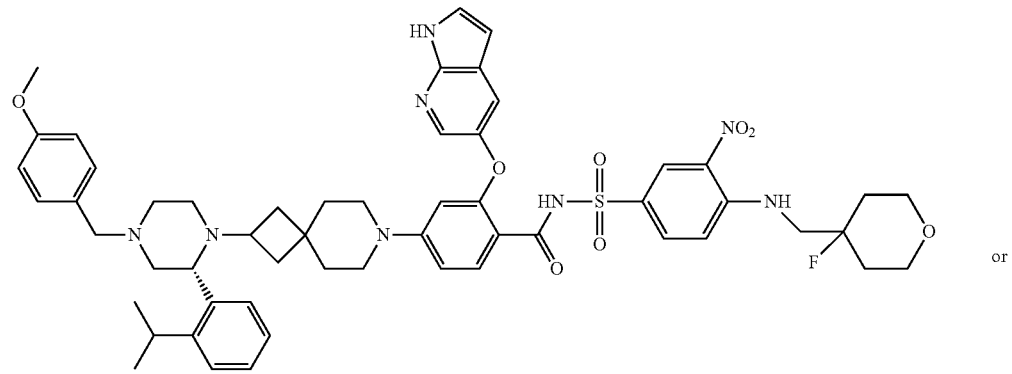

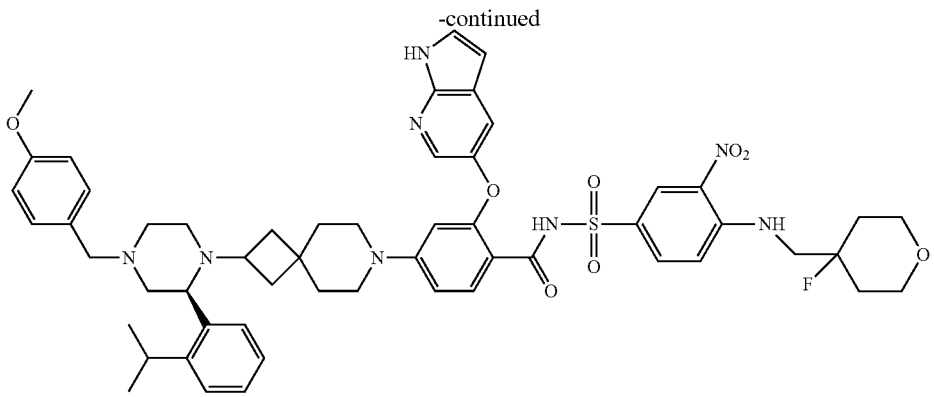

To a solution of (R or S)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzoic acid (50 mg, 0.07 mmol), 4-(((4-fluorotetrahydro-2H-pyran-4-yl)methyl)amino)-3-nitrobenzenesulfonamide (22 mg, 0.07 mmol), EDCI (13 mg, 0.07 mmol), DMAP (17 mg, 0.14 mmol) in DCM (20 mL) was added TEA (21 mg, 0.21 mmol). The reaction was stirred at room temperature for 18 hrs. Then the reaction mixture was washed with acetic acid (30 mL, 10%), saturated aq. NaHCO$_3$ (30 mL) and brine (20 mL) sequentially. The organic layer was separated, dried over anhydrous NaSO$_4$ and concentrated in vacuum. The residue was purified by prep-TLC (eluent: DCM/MeOH (v/v)=20/1). (R or S)-2-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4-(2-(2-(2-isopropylphenyl)-4-(4-methoxybenzyl)piperazin-1-yl)-7-azaspiro[3.5]nonan-7-yl)benzamide was obtained (12 mg) in a yield of 19.30%. $^1$H NMR (400 MHz, DMSO-d$_6$) δ ppm: 11.68 (s, 1H), 11.37 (br, 1H), 8.63 (s, 1H), 8.56 (s, 1H), 8.01 (s, 1H), 7.79 (d, J=8.6 Hz, 1H), 7.48-7.46 (m, 3H), 7.19-7.16 (m, 7H), 6.90 (s, 2H), 6.64 (d, J=9.4 Hz, 1H), 6.36 (s, 1H), 6.13 (s, 1H), 3.72 (s, 9H), 3.52 (s, 3H), 2.95-2.92 (m, 7H), 2.78-2.69 (m, 1H), 2.30-2.18 (m, 1H), 1.79-1.76 (m, 4H), 1.64 (s, 2H), 1.23-1.20 (m, 11H), 1.07-1.01 (m, 4H). MS (ESI) m/e [M+1]$^+$1015.5.

Example 33

N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((R or S)-2-(2-isopropylphenyl)-4-(4-methoxybenzyl)piperazin-1-yl)-7-azaspiro[3.5]nonan-7-yl)benzamide

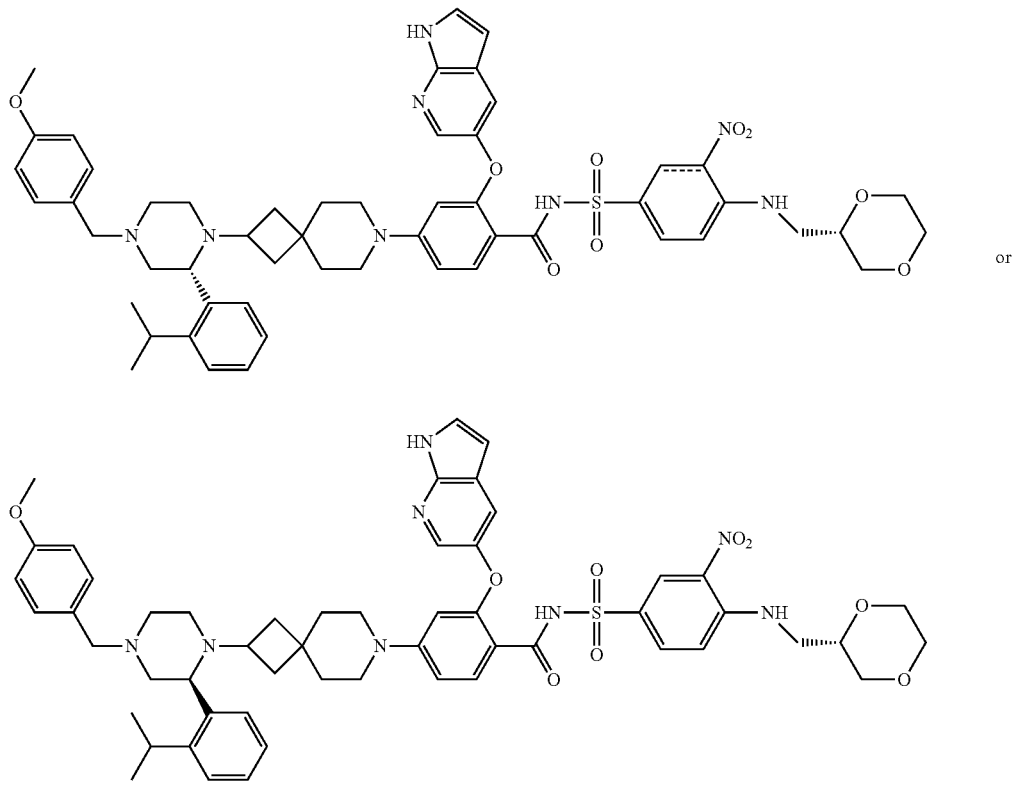

To a solution of (R or S)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzoic acid (50 mg, 0.07 mmol) (S)-4-(((1,4-dioxan-2-yl)methyl)amino)-3-nitrobenzenesulfonamide (22 mg, 0.07 mmol), EDCI (13 mg, 0.07 mmol), DMAP (17 mg, 0.14 mmol) in DCM(20 mL) was added TEA (21 mg, 0.21 mmol). The reaction was stirred at room temperature for 18 hrs. Then the reaction mixture was washed with acetic acid (30 mL, 10%), saturated aq. NaHCO$_3$ (30 mL) and brine (20 mL) sequentially. The organic layer was separated, dried over anhydrous NaSO$_4$ and concentrated in vacuum. The residue was purified by prep-TLC. (R or S)—N-((4-((((S)-1,4-dioxan-2-yl)methyl)amino)-3-nitrophenyl)sulfonyl)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)benzamide (14 mg) was obtained, Yield: 19.61%. $^1$H NMR (400 MHz, DMSO-d$_6$) δ ppm: 11.64 (s, 1H), 11.22 (s, 1H), 8.51 (s, 2H), 7.99 (s, 1H), 7.75 (d, J=8.4 Hz, 1H), 7.46-7.44 (m, 4H), 7.22-7.20 (m, 4H), 7.08-7.03 (m, 2H), 6.86 (d, J=7.8 Hz, 2H), 6.63 (d, J=8.8 Hz, 1H), 6.35 (s, 1H), 6.15 (s, 1H), 3.79 (d, J=8.8 Hz, 3H), 3.71 (s, 3H), 3.68-3.43 (m, 7H), 3.36 (s, 1H), 3.29 (s, 1H), 3.26-3.17 (m, 1H), 2.93-2.90 (m, 7H), 2.55 (s, 1H), 2.18 (s, 2H), 1.61 (s, 2H), 1.23-1.18 (m, 10H), 1.09-1.03 (m, 4H). MS (ESI) m/e [M+1]$^+$999.5.

Example 81a 2-((1H-pyrrolo[2,3-b]pyridin-5-yl)oxy)-4-(2-((R)-4-(3,4-dimethoxybenzyl)-2-(2-isopropylphenyl)piperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

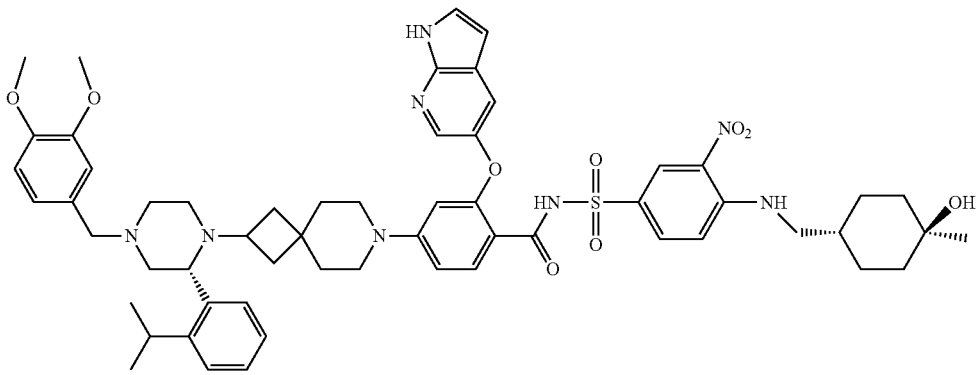 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc1OC]

Synthesis of (R)-1-(3,4-dimethoxybenzyl)-3-(2-isopropylphenyl)piperazine

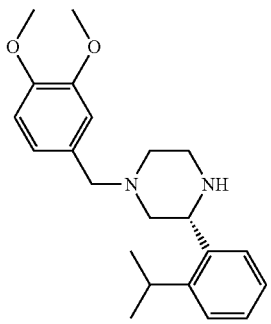 [SMILES: COc1ccc(CN2CCN[C@H](c3ccccc3C(C)C)C2)cc1OC]

A mixture of (R)-2-(2-isopropylphenyl)piperazine (5.2 g, 25.49 mmol), 3,4-dimethoxybenzaldehyde (4.2 g, 25.49 mmol) and NaBH(OAc)$_3$ (10.8 g, 50.98 mmol) in DCM (100 mL) was stirred at room temperature for 16 hrs. The reaction was quenched by saturated NaHCO$_3$ (50 mL). The organic layer was separated, dried over anhydrous Na$_2$SO$_4$ and concentrated in vacuum. The residue was purified by column chromatograph on silica gel (eluent: MeOH/DCM (v/v)=0/20 to 1/20) to give the title product (6.2 g, yield: 68.7%) as a yellow oil. MS (ESI, m/e) [M+1]$^+$355.2.

Synthesis of methyl (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)benzoate

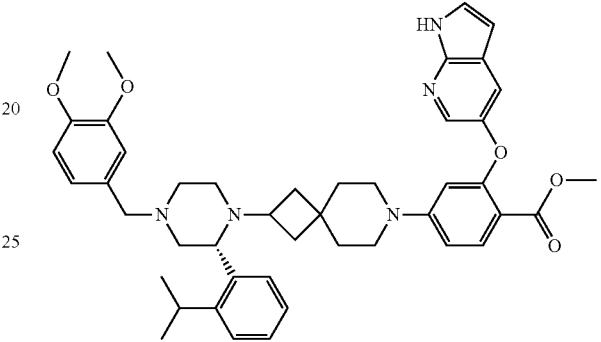

A mixture of (R)-1-(3,4-dimethoxybenzyl)-3-(2-isopropylphenyl)piperazine (2.6 g, 7.345 mmol), methyl 2-((1H-pyrrolo[2,3-b]pyridin-5-yl)oxy)-4-(2-oxo-7-azaspiro[3.5]nonan-7-yl)benzoate (3.6 g, 8.814 mmol), HOAc (440 mg, 7.345 mmol) and NaBH$_3$CN (925 mg, 14.69 mmol) in MeOH (100 mL) was stirred at 60° C. for 4 hrs. After the reaction was cooled to room temperature, the mixture was concentrated in vacuum. The residue was partitioned between DCM (100 mL) and brine (20 mL). The organic layer was separated, dried over Na$_2$SO$_4$, concentrated in vacuum. The residue was purified by column chromatograph on silica gel (eluent: MeOH/DCM (v/v)=0/25 to 1/25) to obtain methyl (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)benzoate as a white solid. (2.5 g, 45.8%). $^1$H NMR (400 MHz, DMSO-d$_6$) δ ppm: 11.61 (s, 1H), 8.00-7.93 (m, 1H), 7.71 (d, J=9.2 Hz, 1H), 7.51-7.32 (m, 3H), 7.25-7.01 (m, 3H), 6.91-6.64 (m, 4H), 6.36 (s, 1H), 6.31 (s, 1H), 3.75-3.67 (m, 6H), 3.62 (s, 3H), 3.55-3.33 (m, 3H), 3.31-3.20 (m, 11H), 3.09-2.76 (m, 7H), 2.25-2.08 (m, 2H), 1.98-1.87 (m, 11H), 1.72-1.56 (m, 2H), 1.39-1.00 (m, 13H). MS (ESI, m/e) [M+1]$^+$744.5.

Synthesis of (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)benzoic acid

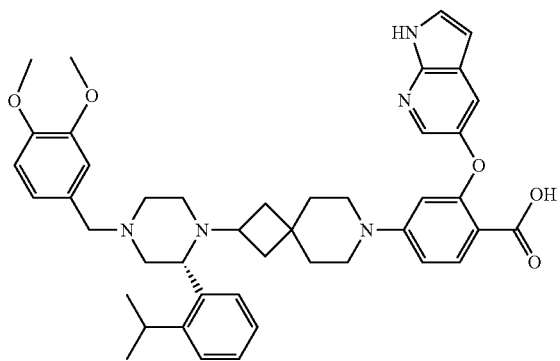 [SMILES: COc1ccc(CN2CCN(C3CC4(CCN(c5ccc(C(=O)O)c(Oc6cnc7[nH]ccc7c6)c5)CC4)C3)[C@H](c3ccccc3C(C)C)C2)cc1OC]

To the solution of methyl (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)benzoate (1.5 g, 2.019 mmol) in CH$_3$OH (20 mL) and THF (20 mL) was added aq. NaOH solution (6 N, 10 mL).

The reaction mixture was stirred at 55° C. for 1 hr. After the reaction was cooled to room temperature, DCM (50 mL) and HCl acid (6N, 70 mL) was added and the PH value of the mixture was adjusted to - 4-5. The organic layer was separated, dried over Na$_2$SO$_4$ and concentrated in vacuum to obtain (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)benzoic acid as a white solid (1.5 g, crude), which was used directly in next step without further purification. $^1$H NMR (400 MHz, DMSO-d$_6$) δ ppm: 12.05 (s, 1H), 11.59 (s, 1H), 8.00-7.90 (m, 1H), 7.71 (d, J=9.2 Hz, 1H), 7.50-7.30 (m, 3H), 7.25-7.03 (m, 3H), 6.91-6.63 (m, 4H), 6.35 (s, 1H), 6.30 (s, 1H), 3.76-3.65 (m, 6H), 3.58-3.31 (m, 4H), 3.07-2.79 (m, 7H), 2.26-2.09 (m, 2H), 1.99-1.86 (m, 1H), 1.73-1.55 (m, 2H), 1.42-0.95 (m, 13H). MS (ESI, m/e) [M+1]$^+$730.5.

Synthesis of 2-((1 H-pyrrolo[2,3-b]pyridin-5-yl)oxy)-4-(2-((R)-4-(3,4-dimethoxybenzyl)-2-(2-isopropylphenyl)piperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide (Example 81a)

A solution of (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)benzoic acid (1.5 g, 2.058 mmol), 4-((((1r,4r)-4-hydroxy-4-methylcyclohexyl)methyl)amino)-3-nitrobenzenesulfonamide (865 mg, 2.469 mmol), EDCI (593 mg, 3.086 mmol), DMAP (753 mg, 6.173 mmol) and TEA (623 mg, 6.173 mmol) in DCM (100 mL) was stirred at room temperature for 16 hrs. The reaction solution was washed with 10% HOAc (50 mL×2), saturated aq. NaHCO$_3$ (80 mL), concentrated and purified by column chromatograph on silica gel (eluent: EA/DCM (v/v)= 1/1 to MeOH/DCM (v/v)=1/10) to give the crude product, which was purified by prep-TLC (eluent: DCM/EA/MeOH (v/v/v)=10/5/1) and lyophilized. Example 81a was obtained (750 mg, 35.0%). $^1$H NMR (400 MHz, DMSO-d$_6$) δ ppm: 11.71 (s, 1H), 11.43 (br, 1H), 8.57 (s, 2H), 8.04 (s, 1H), 7.80 (d, J=8.8 Hz, 1H), 7.57-7.45 (m, 3H), 7.34-7.02 (m, 5H), 6.90 (s, 2H), 6.65 (d, J=8.4 Hz, 1H), 6.38 (s, 1H), 6.16 (s, 1H), 4.28 (s, 1H), 4.05-3.62 (m, 9H), 3.32-3.23 (m, 3H), 3.19-2.58 (m, 11H), 1.80-1.49 (m, 7H), 1.38-1.01 (m, 19H). MS (ESI, m/e) [M+1]$^+$1056.2.

Example 127

4-(2-((R)-4-(3,4-dimethoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide

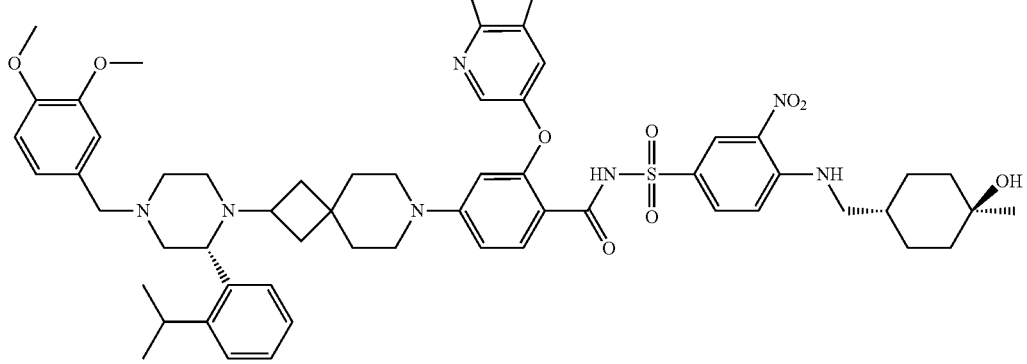

Step 1: synthesis of tert-butyl (R)-2-(2-(2-isopropylphenyl)-4-(3,4-dimethoxybenzyl)piperazin-1-yl)-7-azaspiro[3.5]nonane-7-carboxylate A solution of (R)-1-(3,4-dimethoxybenzyl)-3-(2-isopropylphenyl)piperazine (12.3 g, 34.75 mmol), tert-butyl 2-oxo-7-azaspiro[3.5]nonane-7-carboxylate (16.6 g, 69.49 mmol) in MeOH (200 mL) was added HOAc (4.2 g, 69.49 mmol) and NaBH$_3$CN (4.4 g, 69.49 mmol). The mixture was stirred at 60° C. for 16 hrs. The mixture was cooled to room temperature and concentrated in vacuum. The residue was diluted with DCM (100 mL), washed with saturated aq.

NaHCO$_3$ (50 mL) and brine (50 mL×2). The organic layer was separated, dried over anhydrous Na$_2$SO$_4$ and concentrated in vacuum. The residue was purified by column chromatograph on silica gel (eluent: EA/PE (v/v)=0/1 to 1/1). Tert-butyl (R)-2-(2-(2-isopropylphenyl)-4-(3,4-dimethoxybenzyl)piperazin-1-yl)-7-azaspiro[3.5]nonane-7-carboxylate was obtained (20.7 g). MS (ESI, m/e) [M+1]$^+$ 578.4.

Step 2: (R)-2-(4-(3,4-dimethoxybenzyl)-2-(2-isopropylphenyl)piperazin-1-yl)-7-azaspiro[3.5]nonane.

To a solution of tert-butyl (R)-2-(4-(3,4-dimethoxybenzyl)-2-(2-isopropylphenyl)piperazin-1-yl)-7-azaspiro[3.5]nonane-7-carboxylate (20.7 g, 35.81 mmol) in MeOH (200 mL) was added 4M HCl in 1,4-dioxane (200 mL). The solution was stirred at room temperature for 6 hrs. After the mixture was concentrated under reduced pressure, the residue was partitioned between DCM (300 mL) and H$_2$O (200 mL). The aqueous layer was separated and was adjusted to PH -14 with aq. NaOH (2 N), extracted with DCM (200 mL×3). The combined organic layers were dried over Na$_2$SO$_4$ and concentrated in vacuum to give the title product (11.7 g, yield: 68.8%). MS (ESI, m/e) [M+1]$^+$478.3.

Step 3: methyl (R)-4-(2-(4-(3,4-dimethoxybenzyl)-2-(2-isopropylphenyl)piperazin-1-yl)-7-azaspiro[3.5]nonan-7-yl)-2-((3-fluoro-1 H-pyrrolo[2,3-b]pyridin-5-yl)oxy)benzoate A mixture of (R)-2-(4-(3,4-dimethoxybenzyl)-2-(2-isopropylphenyl)piperazin-1-yl)-7-azaspiro[3.5]nonane (3.9 g, 8.176 mmol), methyl 4-fluoro-2-((3-fluoro-1H-pyrrolo[2,3-b]pyridin-5-yl)oxy)benzoate (2.5 g, 8.176 mmol) and Na$_2$CO$_3$ (8.7 g, 81.76 mmol) in DMSO (100 mL) was stirred at 95° C. for 30 hrs. The mixture was cooled to room temperature and poured into H$_2$O (150 mL). After extracted with EA (150 mL×2), the combined organic layer was washed with brine (50 mL×2), dried over anhydrous Na$_2$SO$_4$ and concentrated in vacuum. The residue was purified by column chromatograph on silica gel (eluent: MeOH/DCM (v/v)=0/30 to 1/30). Methyl (R)-4-(2-(4-(3,4-dimethoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)benzoate was obtained (4.3 g, yield: 69.4%). $^1$H NMR (400 MHz, DMSO-d$_6$) δ ppm: 11.47 (s, 1H), 8.04 (d, J=2.4 Hz, 1H), 7.73 (d, J=8.8 Hz, 1H), 7.52-7.29 (m, 3H), 7.24-7.04 (m, 3H), 6.91-6.67 (m, 4H), 6.38 (s, 1H), 3.75-3.67 (m, 6H), 3.61 (s, 3H), 3.55-3.34 (m, 3H), 3.32-3.22 (1m, 1H), 3.11-2.79 (m, 7H), 2.25-2.09 (m, 2H), 2.03-1.86 (m, 1H), 1.74-1.58 (m, 2H), 1.40-0.99 (m, 13H). MS (ESI, m/e) [M+1]$^+$762.5.

Then following the similar procedures of Example 81a, 4-(2-((R)-4-(3,4-dimethoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide was obtained (350 mg, 38.1%). $^1$H NMR (400 MHz, DMSO-d$_6$) δ ppm: 11.75-10.80 (m, 2H), 8.52 (s, 2H), 8.06 (s, 1H), 7.76 (s, 1H), 7.54-6.82 (m, 10H), 6.68 (s, 1H), 6.22 (s, 1H), 4.26 (s, 1H), 4.14-3.62 (m, 9H), 3.30-2.58 (m, 14H), 1.85-1.48 (m, 7H), 1.45-1.04 (m, 19H). MS (ESI, m/e) [M+1]$^+$1074.2.

Example 141a 4-(6-((R)-4-(3,4-dimethoxybenzyl)-2-(2-isopropylphenyl)piperazin-1-yl)-2-azaspiro[3.3]heptan-2-yl)-2-((3-fluoro-1 H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide

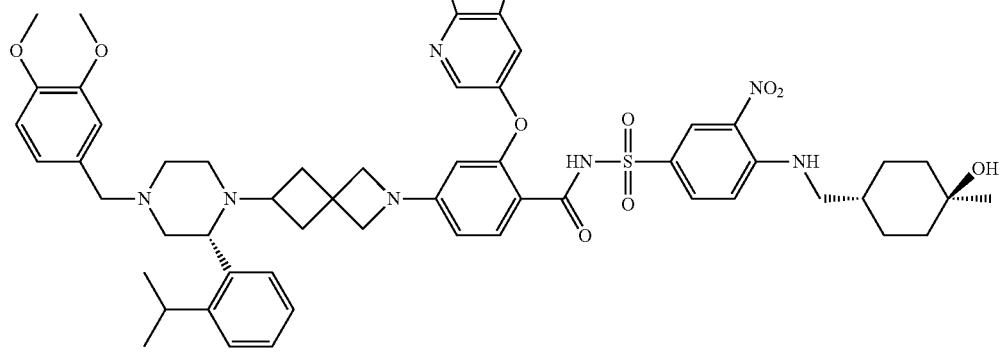

Step 1: synthesis of 6,6-dimethoxy-2-azaspiro[3.3]heptane hydrogen chloride

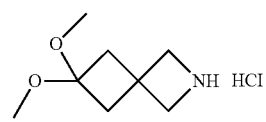

The mixture of tert-butyl 6-oxo-2-azaspiro[3.3]heptane-2-carboxylate (4.22 g, 20 mmol) in HCl solution (4M in CH$_3$OH, 20 mL) was stirred for 4 hrs at room temperature. After concentrated in vacuum, MeOH (50 mL) was added into the residue and then the resulting mixture was concentrated in vacuum (repeated this work-up twice). The brown residue was suspended in EA (150 mL) and stirred for 1 hour. The solid precipitation was filtered and dried in vacuum to afford the title product as an off-white powder (3.61 g, yield: 83.2%). $^1$H NMR (400 MHz, DMSO-d$_6$) δ ppm: 9.38 (br, 1H), 3.95-2.86 (m, 4H), 3.02 (s, 6H), 2.33-2.29 (m, 4H).

Step 2: synthesis of methyl 4-(6,6-dimethoxy-2-azaspiro[3.3]heptan-2-yl)-2-((3-fluoro-1H-pyrrolo[2,3-b]pyridin-5-yl)oxy)benzoate

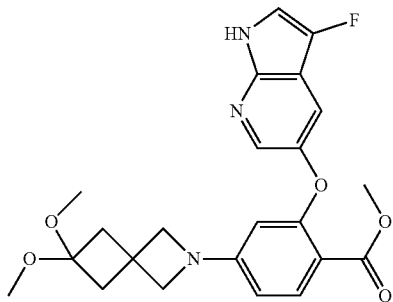 [SMILES: COC(=O)c1ccc(N2CC3(C2)CC(OC)(OC)C3)cc1Oc1cnc2[nH]cc(F)c2c1]

The mixture of 6,6-dimethoxy-2-azaspiro[3.3]heptane hydrogen chloride (1.27 g, 6.58 mmol), methyl 4-fluoro-2-((3-fluoro-1H-pyrrolo[2,3-b]pyridin-5-yl)oxy)benzoate (1.0 g, 3.29 mmnol) and Na$_2$CO$_3$ (3.49 g, 32.9 mmol) in DMSO (20 mL) was heated to 80° C. and stirred for 16 hrs. The reaction was cooled to room temperature and then quenched with brine (200 mL). The mixture was extracted with DCM (150 mL×2), washed with brine (200 mL×3), dried over anhydrous Na$_2$SO$_4$ and concentrated in vacuum. The residue was purified by chromatography on silica gel (eluent: DCM/EA (v/v)=5/1) to give methyl 4-(6,6-dimethoxy-2-azaspiro[3.3]heptan-2-yl)-2-((3-fluoro-1H-pyrrolo[2,3-b]pyridin-5-yl)oxy)benzoate (1.1 g, yield: 75.6%) as an off-white solid. MS (ESI, m/e) [M+1]$^+$442.2.

Step 3: synthesis of methyl 2-((3-fluoro-1H-pyrrolo[2,3-b]pyridin-5-yl)oxy)-4-(6-oxo-2-azaspiro[3.3]heptan-2-yl)benzoate

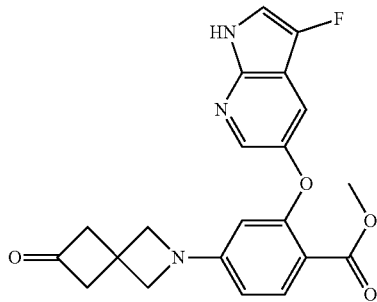 [SMILES: COC(=O)c1ccc(N2CC3(CC(=O)C3)C2)cc1Oc1cnc2[nH]cc(F)c2c1]

The mixture of methyl 4-(6,6-dimethoxy-2-azaspiro[3.3]heptan-2-yl)-2-((3-fluoro-1H-pyrrolo[2,3-b]pyridin-5-yl)oxy)benzoate (1.1 g, 2.49 mmol) and HCl acid (1N, 10 mL) in THF(10 mL) was stirred for 4 hrs. The reaction was quenched with aq. NaOH (6 N) and adjusted to pH value 8~10. The mixture was extracted with DCM (150 mL), dried over anhydrous Na$_2$SO$_4$ and concentrated in vacuum. The residue was purified by chromatography on silica gel (eluent: DCM/EA (v/v)=5/1). Methyl 2-((3-fluoro-1H-pyrrolo[2,3-b]pyridin-5-yl)oxy)-4-(6-oxo-2-azaspiro[3.3]heptan-2-yl)benzoate (940 mg, yield: 95.5%) was obtained as a off-white solid. $^1$H NMR (400 MHz, DMSO-d$_6$) δ ppm: 11.52 (s, 1H), 8.10-8.05 (m, 1H), 7.79 (d, J=8.8 Hz, 1H), 7.53-7.48 (m, 1H), 7.47-7.44 (m, 1H), 6.33-6.25 (m, 1H), 5.85 (s, 1H), 4.04 (s, 4H), 3.65 (s, 3H), 3.31 (s, 4H). MS (ESI, m/e) [M+1]$^+$396.1.

Step 4: synthesis of methyl (R)-4-(6-(4-(3,4-dimethoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoate

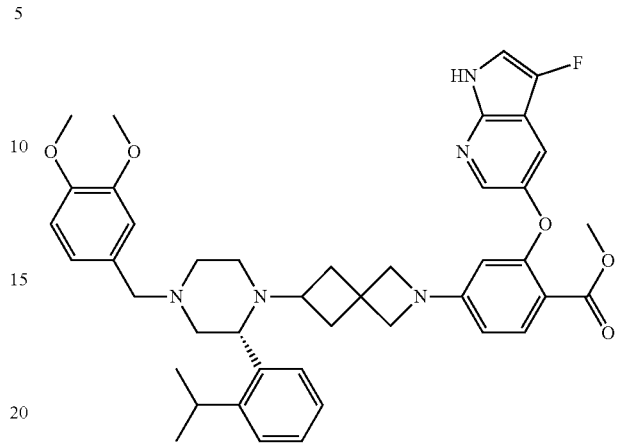

To the mixture of (R)-1-(3,4-dimethoxybenzyl)-3-(2-isopropylphenyl)piperazine (844 mg, 2.38 mmol) and methyl 2-((3-fluoro-1H-pyrrolo[2,3-b]pyridin-5-yl)oxy)-4-(6-oxo-2-azaspiro[3.3]heptan-2-yl)benzoate (940 mg, 2.38 mmol) in CH$_3$OH (100 mL) was added NaBH$_3$CN (450 mg, 7.14 mmol) and AcOH (286 mg, 4.76 mmol). The mixture was heated to reflux and stirred overnight. The mixture was cooled to room temperature and concentrated in vacuum. The residue was diluted with DCM (100 mL), washed with brine (50 mL×2), dried over anhydrous Na$_2$SO$_4$ and purified by chromatography on silica gel (eluent: DCM/EA (v/v)=1/1 to DCM/MeOH (v/v)=20/1). methyl (R)-4-(6-(4-(3,4-dimethoxybenzyl)-2-(2-isopropylphenyl)piperazin-1-yl)-2-azaspiro[3.3]heptan-2-yl)-2-((3-fluoro-1 H-pyrrolo[2,3-b]pyridin-5-yl)oxy)benzoate (820 mg, yield: 47.1%) was obtained as an off-white solid. MS (ESI, m/e) [M+1]$^+$734.4.

Step 5: synthesis of (R)-4-(6-(4-(3,4-dimethoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoic acid

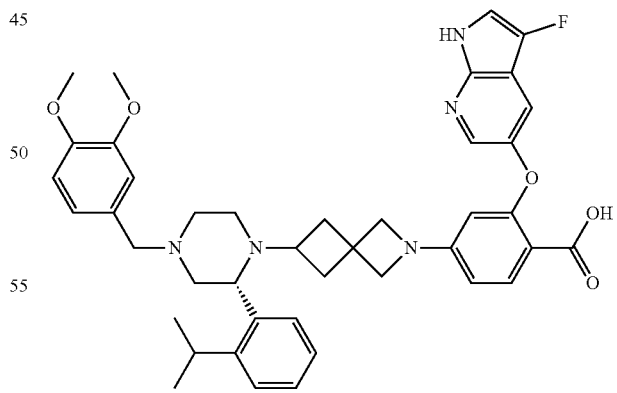

To the solution of methyl (R)-4-(6-(4-(3,4-dimethoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoate (820 mg, 1.12 mmol) in THF/MeOH(10 mL/10 mL) was added aq.
NaOH (10 mL, 6 M). The mixture was heated to 50° C. and stirred for 2 hrs. The reaction was quenched with HCl acid (1 N) and adjusted pH value to 4-6. The mixture was extracted with DCM (100 mL), dried over anhydrous Na₂SO₄ and concentrated in vacuum. The residue was purified by chromatography on silica gel (eluent: DCM/EA (v/v)=1/1 to DCM/MeOH (v/v)=20/1). (R)-4-(6-(4-(3,4-dimethoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoic acid (330 mg, yield: 40.9%) was obtained as an off-white solid. ¹H NMR (400 MHz, DMSO-d₆) δ ppm: 12.00 (br, 1H), 11.48 (s, 1H), 8.06-7.98 (m, 1H), 7.71 (d, J=8.8 Hz, 1H), 7.53-7.18 (m, 6H), 7.05-6.73 (m, 5H), 3.32-3.10 (m, 3H), 3.05-2.55 (m, 5H), 2.42-2.28 (m, 1H), 2.06-1.93 (m, 2H), 1.75-1.50 (m, 7H), 1.39-1.10 (m, 9H), 1.08-1.00 (m, 4H). MS (ESI, m/e) [M+1]⁺1046.1.

Example 145

2-((1H-pyrrolo[2,3-b]pyridin-5-yl)oxy)-4-(6-((R)-4-(3,4-dimethoxybenzyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide

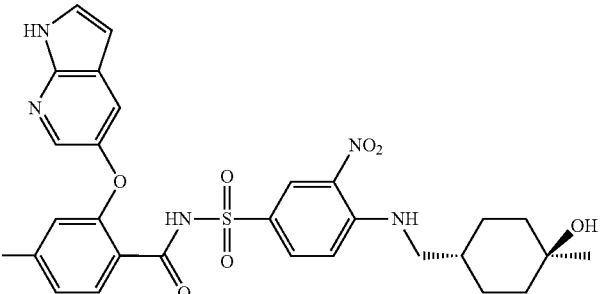

3H), 6.16-6.10 (m, 1H), 5.74-5.72 (m, 1H), 3.80-3.72 (m, 6H), 3.68-3.36 (m, 3H), 3.10-2.70 (m, 5H), 2.42-1.85 (m, 4H), 1.76-1.61 (m, 1H), 1.20-1.00 (m, 6H). MS (ESI, m/e) [M+1]⁺720.3.

Step 6: synthesis of example 141a: 4-(6-((R)-4-(3,4-dimethoxybenzyl)-2-(2-isopropylphenyl)piperazin-1-yl)-2-azaspiro[3.3]heptan-2-yl)-2-((3-fluoro-1 H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide To the mixture of (R)-4-(6-(4-(3,4-dimethoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoic acid (540 mg, 0.75 mmol) and 4-((((1r,4r)-4-hydroxy-4-methylcyclohexyl)methyl)amino)-3-nitrobenzenesulfonamide (386 mg, 1.13 mmol), EDCI (215 mg, 1.13 mmol), DMAP (275 mg, 1.13 mmol) in DCM (100 mL) was added TEA (227 mg, 2.25 mmol). The mixture was stirred at room temperature for overnight. Then the reaction mixture was washed with acetic acid (100 mL×2, 10%), saturated aq. NaHCO₃ (150 mL) and brine (100 mL) sequentially. The organic layer was separated, dried over anhydrous NaSO₄ and concentrated in vacuum. The residue was purified by chromatography on silica gel (eluent: DCM/EA (v/v)=1/1 to DCM/MeOH (v/v)=20/1) to give a crude product. 4-(6-((R)-4-(3,4-dimethoxybenzyl)-2-(2-isopropylphenyl)piperazin-1-yl)-2-azaspiro[3.3]heptan-2-yl)-2-((3-fluoro-1 H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide (330 mg, yield: 42.1%) was obtained after further purification by Pre-TLC (eluent: DCM/MeOH (v/v) =20/1). ¹H NMR (400 MHz, DMSO-d₆) δ ppm: 11.55 (s, 1H), 11.19 (br, 1H), 8.60-8.52 (m, 2H), 8.08 (s, 1H), 7.85 (d, J=8.8 Hz, 1H), 7.58-7.38 (m, 4H), 7.29-7.08 (m, 5H), 6.95-6.80 (m, 2H), 6.09-6.04 (m, 1H), 5.54 (s, 1H), 4.25 (s, 1H), 3.98-3.76 (m, 3H), 3.74 (s, 6H), 3.68-3.36 (m, Step 1: synthesis of methyl (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)benzoate

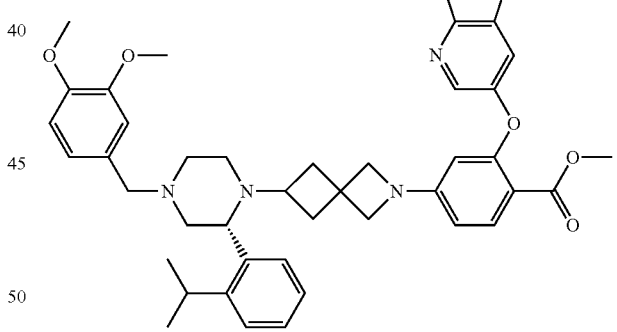

To the solution of (R)-1-(3,4-dimethoxybenzyl)-3-(2-isopropylphenyl)piperazine (704 mg, 1.989 mmol) in MeOH (50 mL) was added methyl 2-((1H-pyrrolo[2,3-b]pyridin-5-yl)oxy)-4-(6-oxo-2-azaspiro[3.3]heptan-2-yl)benzoate(750 mg, 1.989 mmol), HOAc (239 mg, 3.978 mmol) and NaBH₃CN (251 mg, 3.978 mmol). The mixture was stirred at 60° C. for 16 hrs. The mixture was cooled to room temperature and concentrated in vacuum. The residue was diluted with DCM (100 mL), washed with aq. NaOH (1N, 10 mL) and brine (50 mL×2). The organic layer was separated, dried over anhydrous Na$_2$SO$_4$ and concentrated in vacuum. The residue was purified by column chromatograph on silica gel (eluent: EA/DCM (v/v)=1/1 then MeOH/DCM (v/v)=0/50 to 1/50). methyl (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)benzoate (620 mg, yield: 43.6%) was obtained as a white solid. MS (ESI, m/e) [M+1]$^+$716.4.

Step 2: (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)benzoic acid

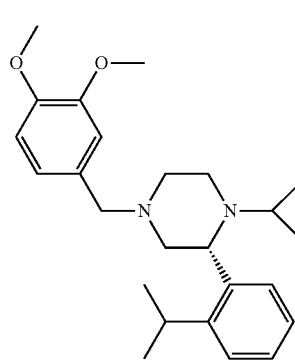

A solution of methyl (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)benzoate (620 mg, 0.867 mmol) in CH$_3$OH (10 mL) and THF (10 mL) was added aq. NaOH (6N, 3 mL). The mixture was stirred at 50° C. for 3.5 hrs and then was cooled to room temperature. After the mixture was concentrated under reduced pressure, the residue was poured into DCM (40 mL) and HCl acid (6 N, 3.5 mL). The mixture was adjusted to PH value ~4 with diluted HCl acid. The organic layer was separated, dried over Na$_2$SO$_4$ and concentrated in vacuum to give (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)benzoic acid as a yellow solid. (590 mg, crude). MS (ESI, m/e) [M+1]$^+$702.4.

Step 3: synthesis of example 145: 2-((1H-pyrrolo[2,3-b]pyridin-5-yl)oxy)-4-(6-((R)-4-(3,4-dimethoxybenzyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide

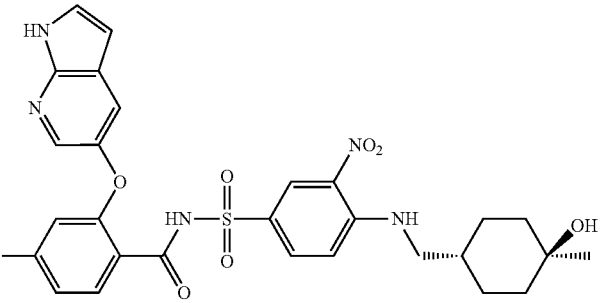

A mixture of (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)benzoic acid (550 mg, 0.785 mmol), 4-((((1r,4r)-4-hydroxy-4-methylcyclohexyl)methyl)amino)-3-nitrobenzenesulfonamide (404 mg, 1.177 mmol), EDCI (226 mg, 1.177 mmol), DMAP (383 mg, 3.138 mmol) and TEA (317 mg, 3.138 mmol) in DCM (20 mL) was stirred at room temperature for 16 hrs. The reaction mixture was then diluted with DCM (100 mL) and washed with 10% HOAc (20 mL×2), saturated aq. NaHCO$_3$ (20 mL). The organic layer was separated, anhydrous Na$_2$SO$_4$ and concentrated in vacuum. The residue was purified by column chromatograph on silica gel (eluent: EA/DCM (v/v)=1/1 then MeOH/DCM (v/v)=1/10) to give the crude product. After further purified by pre-TLC (DCM/ACN/MeOH (v/v)=20/10/1), 2-((1H-pyrrolo[2,3-b]pyridin-5-yl)oxy)-4-(6-((R)-4-(3,4-dimethoxybenzyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide (280 mg, yield: 34.8%) was obtained. $^1$H NMR (400 MHz, DMSO-d4) δ ppm: 11.73 (s, 1H), 11.22 (s, 1H), 8.66-8.48 (m, 2H), 8.07-8.00 (m, 1H), 7.83 (d, J=8.8 Hz, 1H), 7.62-7.07 (m, 9H), 6.92 (s, 2H), 6.40 (s, 1H), 6.04 (d, J=8.4 Hz, 1H), 5.49 (s, 1H), 4.25 (s, 1H), 4.12-3.83 (m, 2H), 3.74 (d, J=7.6 Hz, 6H), 3.64-3.44 (m, 4H), 3.32-3.26 (m, 3H), 3.17-2.66 (m, 6H), 2.15-1.83 (m, 2H), 1.73-1.50 (m, 6H), 1.41-0.96 (m, 16H). MS (ESI, m/e) [M+1]$^+$1028.2.

Example 155

2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(4-methoxybenzyl)piperazin-1-yl)-2-azaspiro[3.3]heptan-2-yl)benzamide

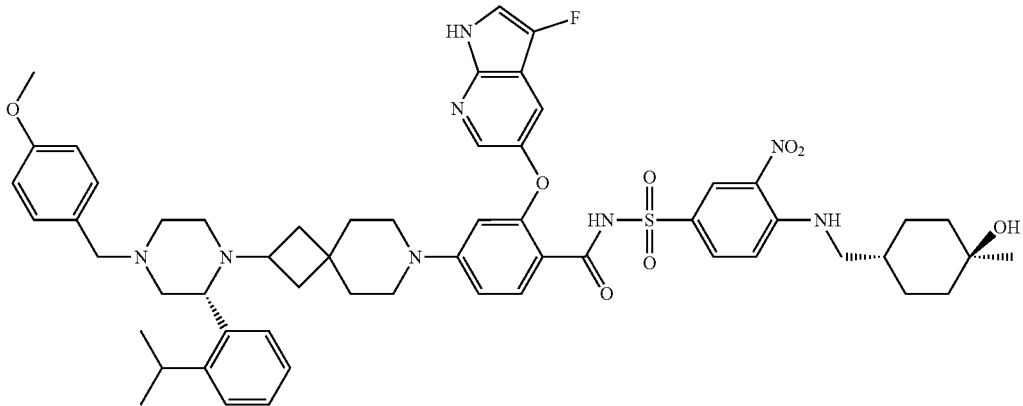 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)cc1]

Step 1: synthesis of methyl (R)-2-((3-fluoro-1H-pyrrolo[2,3-b]pyridin-5-yl)oxy)-4-(6-(2-(2-isopropylphenyl)-4-(4-methoxybenzyl)piperazin-1-yl)-2-azaspiro[3.3]heptan-2-yl)benzoate

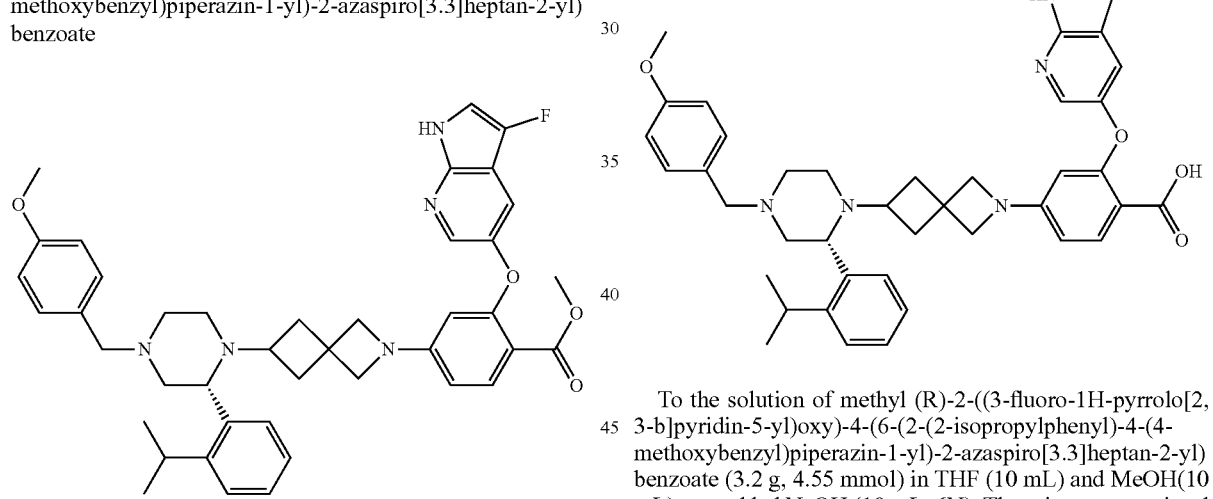

To the mixture of (R)-3-(2-isopropylphenyl)-1-(4-methoxybenzyl)piperazine (2.05 g, 6.33 mmol), methyl 2-((3-fluoro-1H-pyrrolo[2,3-b]pyridin-5-yl)oxy)-4-(6-oxo-2-azaspiro[3.3]heptan-2-yl)benzoate (2.5 g, 6.33 mmol) in MeOH (150 mL) was added NaBH$_3$CN (1.20 g, 19 mmol) and AcOH (1.14 g, 19 mmol). The mixture was heated to reflux and stirred for overnight. After cooled to room temperature, the reaction mixture was concentrated in vacuum and the residue was diluted with DCM (100 mL). This mixture was washed with brine (50 mL×2), and then with water (50 mL). The organic solution was dried over anhydrous Na$_2$SO$_4$, filtered and concentrated in vacuum. The residue was purified by chromatography on silica gel (eluent: DCM/EA (v/v)=1/1 to DCM/MeOH (v/v)=20/1). Methyl (R)-2-((3-fluoro-1H-pyrrolo[2,3-b]pyridin-5-yl)oxy)-4-(6-(2-(2-isopropylphenyl)-4-(4-methoxybenzyl)piperazin-1-yl)-2-azaspiro[3.3]heptan-2-yl)benzoate (3.2 g) was obtained in a yield of 71.8%. [M+1]$^+$704.4.

Step 2: synthesis of (R)-2-((3-fluoro-1H-pyrrolo[2,3-b]pyridin-5-yl)oxy)-4-(6(2-(2-isopropylphenyl)-4-(4-methoxybenzyl)piperazin-1-yl)-2-azaspiro[3.3]heptan-2-yl)benzoic acid To the solution of methyl (R)-2-((3-fluoro-1H-pyrrolo[2,3-b]pyridin-5-yl)oxy)-4-(6-(2-(2-isopropylphenyl)-4-(4-methoxybenzyl)piperazin-1-yl)-2-azaspiro[3.3]heptan-2-yl)benzoate (3.2 g, 4.55 mmol) in THF (10 mL) and MeOH(10 mL) was added NaOH (10 mL, 6N). The mixture was stirred at 40° C. for 4 hrs. Then the reaction mixture was washed with acetic acid (100 mL×2, 10%), saturated aq. NaHCO$_3$ (150 mL) and brine (100 mL) sequentially. The organic layer was separated, dried over anhydrous NaSO$_4$ and concentrated in vacuum. The residue was purified by chromatography on silica gel (eluent: DCM/EA (v/v)=1/1 to DCM/MeOH (v/v)=20/1). (R)-2-((3-fluoro-1H-pyrrolo[2,3-b]pyridin-5-yl)oxy)-4-(6-(2-(2-isopropylphenyl)-4-(4-methoxybenzyl)piperazin-1-yl)-2-azaspiro[3.3]heptan-2-yl)benzoic acid (2.2 g) was obtained in a yield of 70.1%. $^1$H NMR (400 MHz, DMSO-d$_6$) δ ppm: 11.96 (br, 1H), 11.47 (s, 1H), 8.03-7.98 (m, 1H), 7.71 (d, J=8.8 Hz, 1H), 7.53-7.08 (m, 8H), 7.05-6.73 (m, 2H), 6.16-6.10 (m, 1H), 5.74-5.72 (m, 1H), 3.80-3.36 (m, 10H), 3.10-2.70 (m, 7H), 2.42-1.85 (m, 3H), 1.76-1.61 (m, 1H), 1.41-1.30 (m, 1H), 1.20-1.00 (m, 6H). MS (ESI, m/e) [M+1]$^+$690.7.

Step 3: synthesis of 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-

(2-isopropylphenyl)-4-(4-methoxybenzyl)piperazin-1-yl)-2-azaspiro[3.3]heptan-2-yl)benzamide Example 155

To the mixture of (R)-2-((3-fluoro-1H-pyrrolo[2,3-b]pyridin-5-yl)oxy)-4-(6(2-(2-isopropylphenyl)-4-(4-methoxybenzyl)piperazin-1-yl)-2-azaspiro[3.3]heptan-2-yl)benzoic acid (2.0 g, 2.90 mmol) and 4-((((1r,4r)-4-hydroxy-4-methylcyclohexyl)methyl)amino)-3-nitrobenzenesulfonamide (1.50 g, 4.35 mmol) in DCM (200 mL) was added EDCI (826 mg, 4.35 mmol), DMAP (1.06 g, 8.70 mmol) and TEA (879 mg, 8.70 mmol). The mixture was stirred at room temperature for overnight. The reaction was quenched with brine (100 mL), washed with a solution of AcOH/H$_2$O (1/10, 100 mL×2), followed with aq. NaHCO$_3$ (250 mL). The organic layer was separated, dried over Na$_2$SO$_4$ and concentrated in vacuum. The residue was purified by chromatography on silica gel (eluent: DCM/EA (v/v)=1/1 to DCM/MeOH (v/v)=20/1) to give a crude product. The crude product was further purified by Prep-TLC (eluent: DCM/CH$_3$CN/MeOH (v/v/v)=25/25/2). 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(4-methoxybenzyl)piperazin-1-yl)-2-azaspiro[3.3]heptan-2-yl)benzamide (972 mg) was obtained in a yield of 33.0%. $^1$H NMR (400 MHz, DMSO-d$_6$) δ ppm: 11.55 (s, 1H), 11.23 (br, 1H), 8.63-8.54 (m, 2H), 8.08 (s, 1H), 7.85-7.78 (m, 1H), 7.57-7.48 (m, 2H), 7.47-7.08 (m, 8H), 6.95-6.84 (m, 2H), 6.09-6.04 (m, 1H), 5.53 (s, 1H), 4.25 (s, 1H), 3.73 (s, 3H), 3.68-3.36 (m, 7H), 3.32-3.10 (m, 3H), 3.05-2.55 (m, 6H), 2.30-1.90 (m, 3H), 1.70-1.42 (m, 7H), 1.38-1.10 (m, 8H), 1.08-1.00 (m, 5H). MS (ESI, m/e) [M+1]$^+$1016.1.

Example 232

4-(6-((R)-4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide Step 1: synthesis of 4-cyclopropyl-3-methoxybenzaldehyde

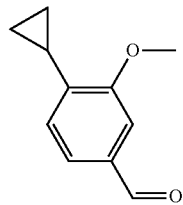

To a solution of 4-bromo-3-methoxybenzaldehyde (25.0 g, 116.3 mmol) in 1,4-dioxane (500 mL) was added cyclopropylboronic acid (31.0 g, 348.8 mmol), K$_2$CO$_3$ (16.0 g, 116.3 mmol), H$_2$O (10 mL) and Pd(dppf)Cl$_2$ (1.7 g, 2.33 mmol). The mixture was stirred at 80° C. under N2 atmosphere for 48 hrs. The reaction mixture was cooled to room temperature, and was then filtered. The resulting cake was washed with EA (200 mL). The combined filtrate was dried over anhydrous Na$_2$SO$_4$, filtered and concentrated. The residue was purified by column chromatograph (silica gel, 100-200 mesh, eluent: EA/PE (v/v)=0/10 to 1/10). 4-cyclopropyl-3-methoxybenzaldehyde (19.5 g) was obtained in a yield of 95.1%. MS (ESI, m/e) [M+1]$^+$177.2.

Step 2: synthesis of (R)-1-(4-cyclopropyl-3-methoxybenzyl)-3-(2-isopropylphenyl)piperazine

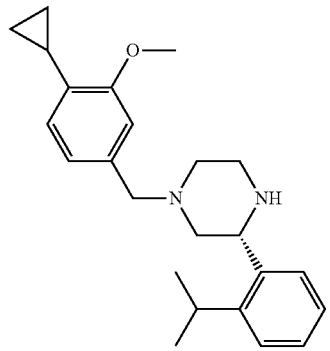 [SMILES: COc1cc(CN2CCN[C@H](c3ccccc3C(C)C)C2)ccc1C1CC1]

To a solution of (R)-2-(2-isopropylphenyl)piperazine (8.7 g, 42.6 mmol) in DCM (200 mL) was added 4-cyclopropyl-3-methoxybenzaldehyde (7.5 g, 42.6 mmol) and NaBH

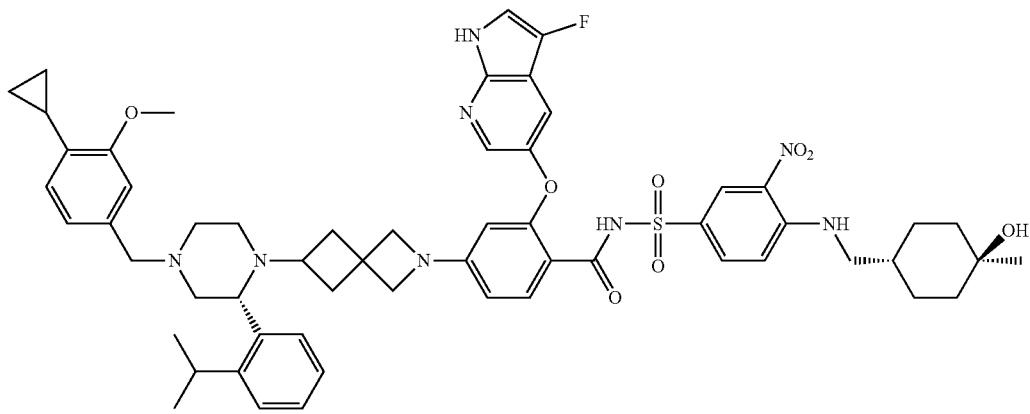

(OAc)₃ (10.8 g, 51.2 mmol). The mixture was stirred at room temperature for 20 hrs. The reaction solution was washed with 10% HOAc (100 mL×2) and saturated aq. NaHCO₃ (200 mL) sequencely. The organic layer was separated, dried over anhydrous Na₂SO₄, filtered and concentrated. The resulting crude product was further purified by column chromatograph (silica gel, 200-300 mesh, eluent: EA/PE (v/v)=1/5 then MeOH/DCM (v/v)=0/30 to 1/30). (R)-1-(4-cyclopropyl-3-methoxybenzyl)-3-(2-isopropylphenyl)piperazine (9.8 g) was obtained in a yield of 63.2%. MS (ESI, m/e) [M+1]⁺365.3.

Step 3: synthesis of methyl (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoate

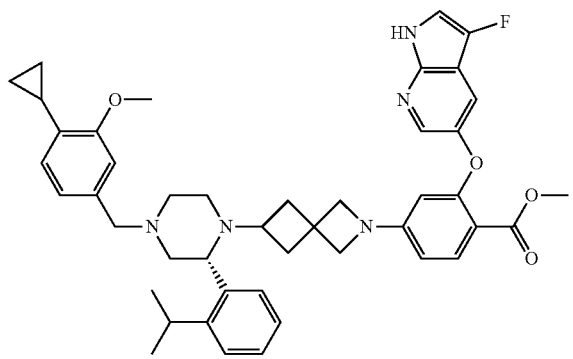 [SMILES: COC(=O)c1ccc(N2CC3(CC(N4CCN(Cc5ccc(C6CC6)c(OC)c5)C[C@H]4c4ccccc4C(C)C)C3)C2)cc1Oc1cnc2[nH]cc(F)c2c1]

To a solution of (R)-1-(4-cyclopropyl-3-methoxybenzyl)-3-(2-isopropylphenyl)piperazine (9.4 g, 25.8 mmol) in MeOH (200 mL) was added methyl 2-((3-fluoro-1H-pyrrolo[2,3-b]pyridin-5-yl)oxy)-4-(6-oxo-2-azaspiro[3.3]heptan-2-yl)benzoate (11.3 g, 28.4 mmol), HOAc (3.1 g, 51.6 mmol) and NaBH₃CN (9.7 g, 154.9 mmol). The mixture was stirred at reflux for 16 hrs. The reaction was cooled to room temperature and concentrated in vacuum. The resulting residue was partitioned between DCM (300 mL) and saturated aq. NaHCO₃ (100 mL). The organic layer was separated, dried over anhydrous Na₂SO₄, filtered and concentrated. The crude product was further purified by column chromatograph (silica gel, 200-300 mesh, eluent: MeOH/DCM (v/v)=0/50 to 1/50). Methyl (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoate (18.0 g, yield: 93.7%) was obtained as a white solid, ¹H NMR (400 MHz, DMSO-d₆) δ ppm: 11.50 (s, 1H), 8.03 (d, J=2.8 Hz, 1H), 7.70 (d, J=8.4 Hz, 1H), 7.52-7.30 (m, 3H), 7.25-6.99 (m, 3H), 6.84 (s, 1H), 6.75-6.67 (m, 2H), 6.13 (dd, J=2.0 Hz, 8.8 Hz, 11H), 5.74 (d, J=2.0 Hz, 11H), 3.77 (s, 3H), 3.70-3.58 (m, 6H), 3.56-3.41 (m, 3H), 3.40-3.13 (m, 3H), 2.92-2.67 (m, 3H), 2.24-1.86 (m, 6H), 1.76-1.61 (m, 1H), 1.44-1.31 (m, 1H), 1.24-1.13 (m, 3H), 1.09-0.98 (m, 3H), 0.88-0.78 (m, 2H), 0.58-0.49 (m, 2H). MS (ESI, m/e) [M+1]⁺744.7.

Step 4: synthesis of (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoic acid

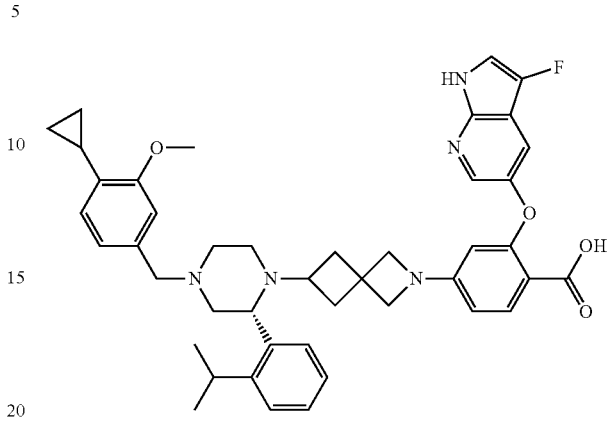

To a solution of methyl (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoate (18.0 g, 24.2 mmol) in THF (100 mL) and MeOH (100 mL) was added aq. NaOH solution (9.7 g, 242.3 mmol, in 100 mL H₂O). The mixture was stirred at 50° C. for 3 hrs.

After the reaction mixture was cooled to room temperature, DCM (300 mL) was added into it. The resulting mixture was further cooled to −10° C. The PH value of the mixture was adjusted to - 5 with 6N HCl acid. The organic layer was separated and washed with saturated aq. NaHCO₃ (100 mL), dried over anhydrous Na₂SO₄, filtered and concentrated. The residue was purified by column chromatography (silica gel, 200-300 mesh, eluent: MeOH/DCM (v/v)=0/10 to 1/10). (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoic acid (15.0 g, yield: 84.9%) was obtained as a white solid. ¹H NMR (400 MHz, DMSO-d₆) δ ppm: 11.99 (s, 1H), 11.49 (s, 1H), 8.03 (d, J=2.4 Hz, 1H), 7.71 (d, J=7.6 Hz, 1H), 7.51-7.32 (m, 3H), 7.25-6.99 (m, 3H), 6.85 (s, 1H), 6.76-6.66 (m, 2H), 6.12 (dd, J=2.0 Hz, 8.8 Hz, 1H), 5.75 (d, J=2.0 Hz, 11H), 3.77 (s, 3H), 3.70-3.15 (m, 9H), 2.93-2.66 (m, 3H), 2.24-1.88 (m, 6H), 1.75-1.61 (m, 1H), 1.44-1.30 (m, 1H), 1.24-1.13 (m, 3H), 1.09-0.98 (m, 3H), 0.88-0.78 (m, 2H), 0.58-0.49 (m, 2H). MS (ESI, m/e) [M+1]⁺730.6.

Step 5: synthesis of Example 232

To the mixture of (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)benzoic acid (15.0 g, 20.6 mmol) and 4-((((1r,4r)-4-hydroxy-4-methylcyclohexyl)methyl)amino)-3-nitrobenzenesulfonamide (7.1 g, 20.58 mmol) in DCM (300 mL) were added EDCI (5.9 g, 30.9 mmol), DMAP (10.0 g, 82.30 mmol) and TEA (8.3 g, 82.3 mmol).

The mixture was stirred at room temperature for 16 hrs. The reaction was quenched with brine (100 mL), washed with a solution of 10% HOAc (100 mL×2), followed with saturated aq. NaHCO₃ (250 mL). The organic layer was separated, dried over Na₂SO₄ and concentrated in vacuum. The residue was purified by chromatography on silica gel (200-300 mesh, eluent: MeOH/DCM (v/v)=0/30 to 1/30). The title product 4-(6-((R)-4-(4-cyclopropyl-3-methoxybenzyl)-2-(2-isopropylphenyl)piperazin-1-yl)-2-azaspiro[3.3]

heptan-2-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide (10.0 g) was obtained in a yield of 46.1%. $^1$H NMR (400 MHz, DMSO-$d_6$) δ ppm: 11.52 (s, 1H), 11.18 (s, 1H), 8.52 (s, 2H), 8.06 (s, 1H), 7.78 (d, J=9.2 Hz, 1H), 7.54-7.30 (m, 4H), 7.27-6.98 (m, 4H), 6.86 (s, 1H), 6.73 (s, 2H), 6.06 (d, J=8.4 Hz, 1H), 5.56 (s, 1H), 4.25 (s, 1H), 3.77 (s, 3H), 3.67-3.42 (m, 7H), 3.32-3.14 (m, 3H), 2.96-2.82 (m, 2H), 2.78-2.64 (m, 1H), 2.62-2.52 (m, 1H), 2.34-2.14 (m, 2H), 2.13-1.88 (m, 4H), 1.74-1.49 (m, 6H), 1.33 (t, J=11.6 Hz, 3H), 1.24-0.96 (m, 11H), 0.89-0.78 (m, 2H), 0.60-0.48 (m, 2H). MS (ESI, m/e) [M+1]$^+$1055.8.

Example 233

2-((1H-pyrrolo[2,3-b]pyridin-5-yl)oxy)-4-(6-((R)-4-(4-cyclopropyl-3-methoxybenzyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide To a solution of (R)-1-(4-cyclopropyl-3-methoxybenzyl)-3-(2-isopropylphenyl)piperazine (2.0 g, 5.495 mmol) in MeOH (50 mL) was added methyl 2-((1H-pyrrolo[2,3-b]pyridin-5-yl)oxy)-4-(6-oxo-2-azaspiro[3.3]heptan-2-yl)benzoate (2.3 g, 6.044 mmol), HOAc (0.6 g, 10.99 mmol) and NaBH$_3$CN (2.1 g, 32.97 mmol). The mixture was stirred for 5 hrs under reflux. The reaction was cooled to room temperature and concentrated in vacuum. The resulting residue was partitioned between DCM (100 mL) and saturated aq. NaHCO$_3$ (50 mL). The organic layer was separated, dried over anhydrous Na$_2$SO$_4$, filtered and concentrated. The residue was further purified by column chromatograph (silica gel, 200-300 mesh, eluent: MeOH/DCM (v/v)=0/50 to 1/50). methyl (R)-2-((1H-pyrrolo[2,3-b]pyridin-5-yl)oxy)-4-(6-(4-(4-cyclopropyl-3-methoxybenzyl)-2-(2-isopropylphenyl)piperazin-1-yl)-2-azaspiro[3.3]heptan-2-yl)benzoate (3.0 g, yield: 75.4%) was obtained. MS (ESI, m/e) [M+1]$^+$726.7.

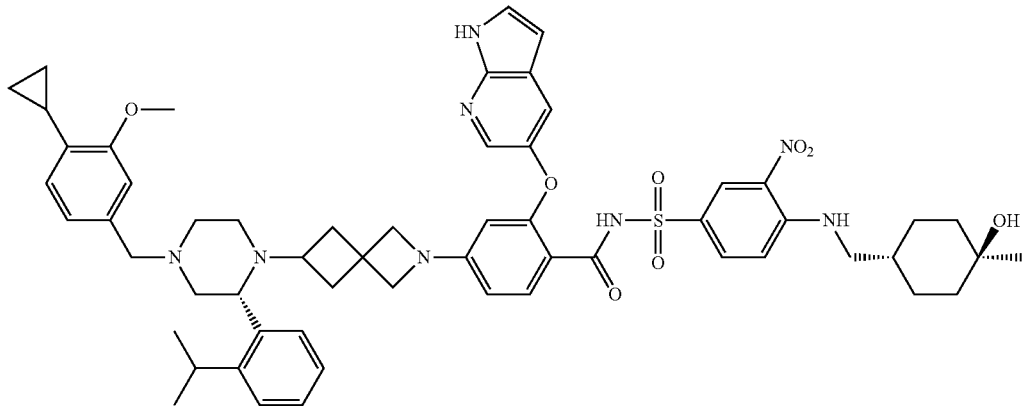 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)ccc1C1CC1]

Step 1: synthesis of methyl (R)-2-((1H-pyrrolo[2,3-b]pyridin-5-yl)oxy)-4-(6-(4-(4-cyclopropyl-3-methoxybenzyl)-2-(2-isopropylphenyl)piperazin-1-yl)-2-azaspiro[3.3]heptan-2-yl)benzoate Step 2: synthesis of (R)-2-((1H-pyrrolo[2,3-b]pyridin-5-yl)oxy)-4-(6-(4-(4-cyclopropyl-3-methoxybenzyl)-2-(2-isopropylphenyl)piperazin-1-yl)-2-azaspiro[3.3]heptan-2-yl)benzoic acid

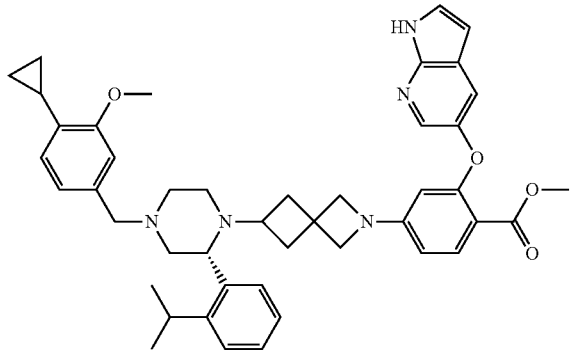 [SMILES: COC(=O)c1ccc(N2CC3(CC(N4CCN(Cc5ccc(C6CC6)c(OC)c5)C[C@H]4c4ccccc4C(C)C)C3)C2)cc1Oc1cnc2[nH]ccc2c1]

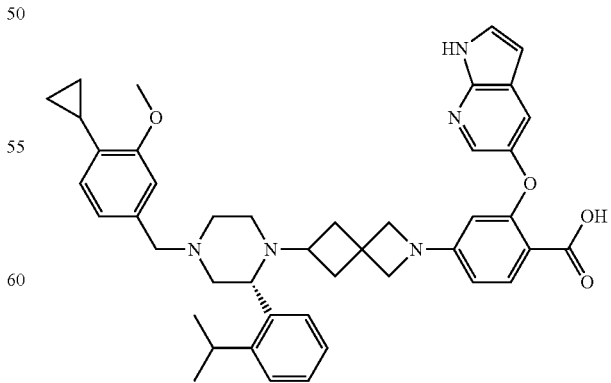

To a solution of methyl (R)-2-((1H-pyrrolo[2,3-b]pyridin-5-yl)oxy)-4-(6-(4-(4-cyclopropyl-3-methoxybenzyl)-2-(2- isopropylphenyl)piperazin-1-yl)-2-azaspiro[3.3]heptan-2-yl)benzoate (3.0 g, 4.138 mmol) in THF (30 mL) and MeOH (20 mL) was added aq. NaOH solution (1.7 g, 41.4 mmol, in 20 mL H₂O). The mixture was stirred at 50° C. for 3 hrs. After the reaction mixture was cooled to room temperature, DCM (100 mL) was added into it. The resulting mixture was further cooled to 10' C. The PH value of the mixture was adjusted to ~5 with 6N HCl acid. The organic layer was separated, dried over anhydrous Na₂SO₄, concentrated, and purified by column chromatography on silica gel (silica gel, 200-300 mesh, eluent: MeOH/DCM (v/v)=0/10 to 1/10). The acid product (2.7 g, yield: 91.8%) was obtained as a white solid. MS (ESI, m/e) [M+1]⁺712.7.

Step 3: synthesis of Example 233

To the mixture of (R)-2-((1H-pyrrolo[2,3-b]pyridin-5-yl)oxy)-4-(6-(4-(4-cyclopropyl-3-methoxybenzyl)-2-(2-isopropylphenyl)piperazin-1-yl)-2-azaspiro[3.3]heptan-2-yl)benzoic acid (2.7 g, 3.797 mmol), 4-(((((1r,4r)-4-hydroxy-4-methylcyclohexyl)methyl)amino)-3-nitrobenzenesulfonamide (1.3 g, 3.797 mmol) in DCM (100 mL) were added EDCI (1.1 g, 5.696 mmol), DMAP (1.8 g, 15.19 mmol) and TEA (1.5 g, 15.19 mmol). The mixture was stirred at room temperature for 16 hrs. The reaction was washed with a solution of 10% HOAc (50 mL×2), followed with saturated aq. NaHCO₃ (50 mL). The organic layer was separated, dried over Na₂SO₄ and concentrated in vacuum. The residue was purified by chromatography on silica gel (200-300 mesh, eluent: MeOH/DCM (v/v)=0/30 to 1/30)). 2-((I H-pyrrolo[2,3-b]pyridin-5-yl)oxy)-4-(6-((R)-4-(4-cyclopropyl-3-methoxybenzyl)-2-(2-isopropylphenyl)piperazin-1-yl)-2-azaspiro[3.3]heptan-2-yl)-N-((4-(((((1r,4r)-4-hydroxy-4-methylcyclohexyl)methyl)amino)-3-nitrophenyl)sulfonyl)benzamide (2.5 g, yield: 53.6%) was obtained. ¹H NMR (400 MHz, DMSO-d) 6 ppm: 11.70 (s, 1H), 11.11 (s, 1H), 8.55 (s, 2H), 8.02 (s, 1H), 7.80 (d, J=8.4 Hz, 1H), 7.60-7.28 (m, 4H), 7.26-7.00 (m, 4H), 6.85 (s, 1H), 6.72 (s, 2H), 6.38 (s, 1H), 6.03 (d, J=7.6 Hz, 1H), 5.50 (s, 1H), 4.25 (s, 1H), 3.77 (s, 3H), 3.66-3.40 (m, 7H), 3.31-3.14 (m, 3H), 2.96-2.80 (m, 2H), 2.78-2.64 (m, 1H), 2.61-2.52 (m, 1H), 2.32-2.12 (m, 2H), 2.11-1.86 (m, 4H), 1.76-1.48 (m, 6H), 1.33 (t, J=6.8 Hz, 3H), 1.23-0.96 (m, 11H), 0.88-0.78 (m, 2H), 0.60-0.48 (m, 2H). MS (ESI, m/e) [M+1]⁺1038.2.

Example 338

2-((3-fluoro-1H-pyrrolo[2,3-b]pyridin-5-yl)oxy)-N-((4-(((((1r,4r)-4-hydroxy-4-methylcyclohexyl)methyl)amino)-3-nitrophenyl)sulfonyl)-4-(6-((R)-2-(2-isopropylphenyl)-4-((7-methoxy-2-methylbenzofuran-5-yl)methyl)piperazin-1-yl)-2-azaspiro[3.3]heptan-2-yl)benzamide

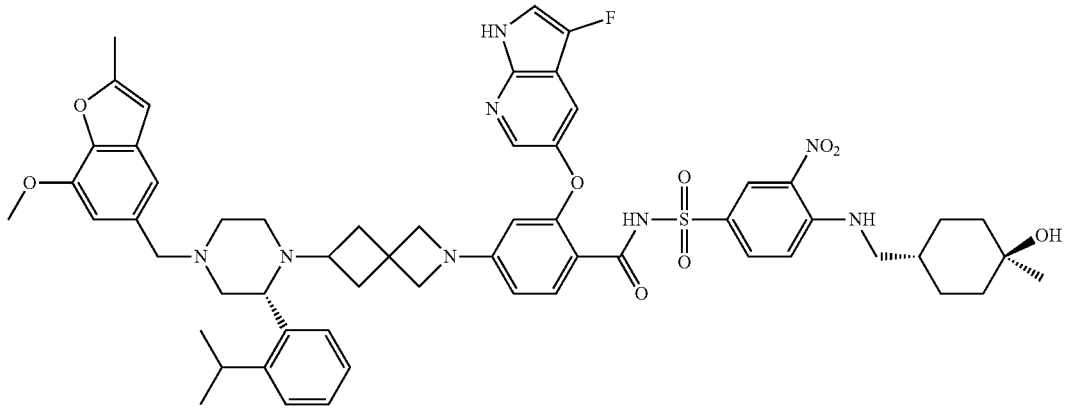

Step 1: synthesis of methyl (R)-2-((3-fluoro-1H-pyrrolo[2,3-b]pyridin-5-yl)oxy)-4-(6(2-(2-isopropylphenyl)-4-((7-methoxy-2-methylbenzofuran-5-yl)methyl)piperazin-1-yl)-2-azaspiro[3.3]heptan-2-yl)benzoate

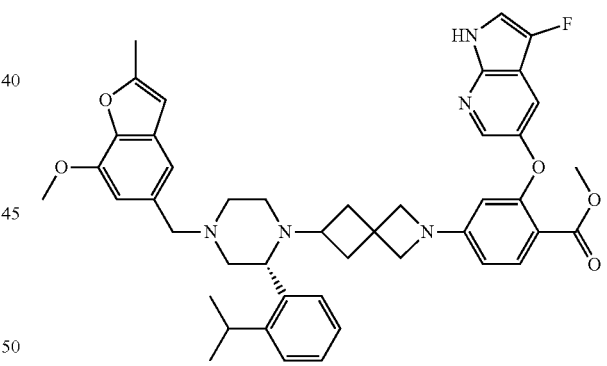

To a solution of (R)-3-(2-isopropylphenyl)-1-((7-methoxy-2-methylbenzofuran-5-yl)methyl)piperazine (9.0 g, 23.81 mmol) in DCE (300 mL) was added methyl 2-((3-fluoro-1H-pyrrolo[2,3-b]pyridin-5-yl)oxy)-4-(6-oxo-2-azaspiro[3.3]heptan-2-yl)benzoate (12.3 g, 30.95 mmol), HOAc (2.9 g, 47.62 mmol) and NaBH(OAc)₃ (10.0 g, 47.62 mmol). The mixture was stirred at 70° C. for 4 hrs. The reaction was cooled to room temperature and quenched by saturated aq. NaHCO₃ (300 mL). The organic layer was then separated, dried over anhydrous Na₂SO₄, filtered and concentrated. The residue was purified by column chromatograph on silica gel (eluent: MeOH/DCM (v/v)=0/50 to 1/50). Methyl (R)-2-((3-fluoro-1H-pyrrolo[2,3-b]pyridin-5-yl)oxy)-4-(6-(2-(2-isopropylphenyl)-4-((7-methoxy-2-methylbenzofuran-5-yl)methyl)piperazin-1-yl)-2-azaspiro

[3.3]heptan-2-yl)benzoate (13.0 g, yield: 72.1%) was obtained. ¹H NMR (DMSO-d₆) δ ppm: 11.51 (d, J=2.4 Hz, 1H), 8.04 (d, J=2.8 Hz, 1H), 7.70 (d, J=8.4 Hz, 1H), 7.50 (t, J=2.4 Hz, 1H), 7.46-7.33 (m, 2H), 7.24-7.04 (m, 3H), 6.97 (s, 1H), 6.77 (s, 1H), 6.45 (s, 1H), 6.12 (dd, J=2.0 Hz, 8.8 Hz, 1H), 5.74 (d, J=2.0 Hz, 1H), 3.87 (s, 3H), 3.70-3.40 (m, 10H), 3.33-3.17 (m, 1H), 2.93-2.81 (m, 2H), 2.79-2.65 (m, 1H), 2.58-2.51 (m, 1H), 2.39 (s, 3H), 2.25-1.86 (m, 5H), 1.76-1.60 (m, 1H), 1.44-1.30 (m, 1H), 1.19 (d, J=6.8 Hz, 3H), 1.01 (d, J=6.0 Hz, 3H). MS (ESI, m/e) [M+1]⁺758.5.

Step 2: synthesis of (R)-2-((3-fluoro-1 H-pyrrolo[2,3-b]pyridin-5-yl)oxy)-4-(6(2-(2-isopropylphenyl)-4-((7-methoxy-2-methylbenzofuran-5-yl)methyl)piperazin-1-yl)-2-azaspiro[3.3]heptan-2-yl)benzoic acid

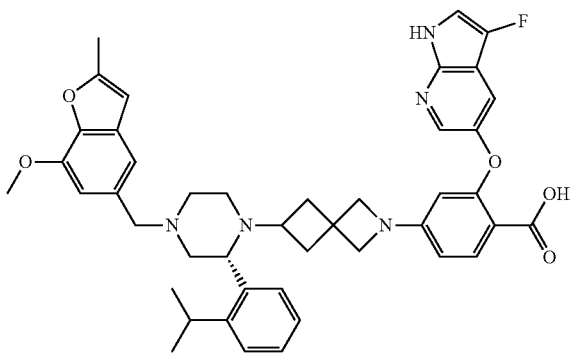 [SMILES: COc1cc(CN2CCN(C3CC4(C3)CN(c3ccc(C(=O)O)c(Oc5cnc6[nH]cc(F)c6c5)c3)C4)[C@H](c3ccccc3C(C)C)C2)cc2cc(C)oc12]

To a solution of methyl (R)-2-((3-fluoro-1H-pyrrolo[2,3-b]pyridin-5-yl)oxy)-4-(6(2-(2-isopropylphenyl)-4-((7-methoxy-2-methylbenzofuran-5-yl)methyl)piperazin-1-yl)-2-azaspiro[3.3]heptan-2-yl)benzoate (13.0 g, 17.17 mmol) in THF (65 mL) and MeOH (65 mL) was added aq. NaOH solution (6.9 g, 171.7 mmol, in 65 mL H₂O). The mixtures was stirred at 55° C. for 2 hrs. Then the reaction was cooled to 35° C. and was further stirred for 16 hrs. After cooled to ~10° C., the mixture was diluted with DCM (200 mL) and was then adjusted to PH ~5 with 6N HCl acid.

The organic layer was separated, washed with saturated aq. NaHCO₃ (100 mL), dried over anhydrous Na₂SO₄ and concentrated. The residue was purified by column chromatography on silica gel (eluent: MeOH/DCM (v/v)=0/15 to 1/15). (R)-2-((3-fluoro-1H-pyrrolo[2,3-b]pyridin-5-yl)oxy)- 4-(6-(2-(2-isopropylphenyl)-4-((7-methoxy-2-methylbenzofuran-5-yl)methyl)piperazin-1-yl)-2-azaspiro[3.3]heptan-2-yl)benzoic acid (11.0 g) was obtained in a yield of 86.2%. ¹H NMR (DMSO-d₆) δ ppm: 12.07 (s, 1H), 11.52 (s, 1H), 8.03 (d, J=2.4 Hz, 1H), 7.72 (d, J=8.8 Hz, 1H), 7.53-6.95 (m, 8H), 6.62-6.39 (m, 1H), 6.13 (d, J=8.4 Hz, 1H), 5.75 (s, 1H), 4.47-4.15 (m, 1H), 3.93 (s, 3H), 3.79-3.33 (m, 7H), 3.14-2.58 (m, 5H), 2.42 (s, 3H), 2.29-1.83 (m, 3H), 1.77-1.55 (m, 1H), 1.46-0.92 (m, 8H), 1.42-1.27 (m, 3H), 1.24-0.99 (m, 11H). MS (ESI, m/e) [M+1]⁺744.5.

Step 3: synthesis of Example 338

To the solution of (R)-2-((3-fluoro-1H-pyrrolo[2,3-b]pyridin-5-yl)oxy)-4-(6-(2-(2-isopropylphenyl)-4-((7-methoxy-2-methylbenzofuran-5-yl)methyl)piperazin-1-yl)-2-azaspiro[3.3]heptan-2-yl)benzoic acid (11.0 g, 14.80 mmol), 4-((((1r,4r)-4-hydroxy-4-methylcyclohexyl)methyl)amino)-3-nitrobenzenesulfonamide (5.6 g, 16.29 mmol) in DCM (500 mL) were added EDCI (4.3 g, 22.21 mmol), DMAP (7.3 g, 59.22 mmol) and TEA (6.0 g, 59.22 mmol). The mixture was stirred at room temperature for 16 hrs. N,N-Dimethylethylenediamine (10 mL) was then added into the reaction mixture and the mixture was further stirred at room temperature for 6 hrs. The mixture was washed with a solution of 10% HOAc (300 mL×2), followed with saturated aq. NaHCO₃ (400 mL). The organic layer was separated, dried over Na₂SO₄ and concentrated in vacuum. The residue was purified by column chromatography on silica gel (eluent: MeOH/DCM (v/v)=0/30 to 1/30). 2-((3-fluoro-1 H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((7-methoxy-2-methylbenzofuran-5-yl)methyl)piperazin-1-yl)-2-azaspiro[3.3]heptan-2-yl)benzamide (Example 338, 7.5 g, yield: 47.3%) was obtained. ¹H NMR (DMSO-d₆) δ ppm: 11.48 (s, 1H), 8.55-8.38 (m, 2H), 8.01 (s, 1H), 7.72 (d, J=8.8 Hz, 1H), 7.50-7.26 (m, 4H), 7.22-6.90 (m, 5H), 6.75 (s, 1H), 6.43 (s, 1H), 6.01 (d, J=8.8 Hz, 1H), 5.51 (s, 1H), 4.21 (s, 1H), 3.83 (s, 3H), 3.65-3.39 (m, 7H), 3.26-3.12 (m, 3H), 2.94-2.78 (m, 2H), 2.74-2.50 (m, 2H), 2.34 (s, 3H), 2.30-1.83 (m, 5H), 1.68-1.44 (m, 6H), 1.36-1.22 (m, 3H), 1.18-0.92 (m, 11H). MS (ESI, m/e) [M+1]⁺1069.9.

Following substantially identical procedures to those of Example 19a or using similar synthetic methods or strategies, Examples 19-31 and Examples 34-371 in Table 2 were prepared from the respective intermediates.

| Ex. | structure | Compound name | Data |
|---|---|---|---|
| 19 | 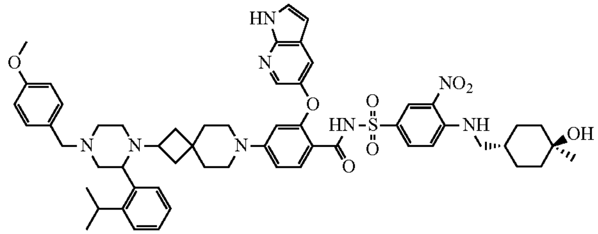 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methoxybenzyl)piperazin-1-yl)-7-azaspiro[3.5]nonan-7-yl)benzamide | $^1$H NMR (400 MHz, DMSO-$d_6$) δ ppm: 11.68 (s, 1H), 11.25 (s, 1H), 8.54 (s, 2H), 8.02 (s, 1H), 7.76 (s, 1H), 7.48-7.46 (m, 3H), 7.24 (s, 5H), 7.13 (s, 1H), 7.07 (s, 1H), 6.90 (s, 2H), 6.64 (d, J = 8.6 Hz, 1H), 6.37 (s, 1H), 6.13 (s, 1H), 4.24 (s, 1H), 3.73 (s, 4H), 3.28 (s, 3H), 2.96-2.93 (m, 7H), 2.27 (s, 1H), 2.01-1.99 (m, 1H), 1.62-1.60 (m, 7H), 1.37-1.03 (m 21H). MS (ESI, m/e) [M + 1]$^+$ 1027.0. |
| 20 | 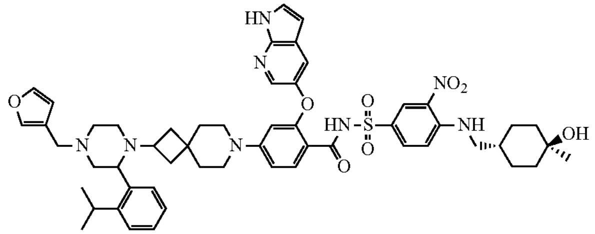 [SMILES: CC(C)c1ccccc1C1CN(Cc2ccoc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(furan-3-ylmethyl)-2-(2-isopropylphenyl)piperazin-1-yl)-7-azaspiro[3.5]nonan-7-y))-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.74 (s, 1H), 11.32 (s, 1H), 8.68-8.55 (m, 2H), 8.08 (s, 1H), 7.83 (d, J = 9.4 Hz, 1H), 7.75-7.68 (m, 2H), 7.59-7.03 (m, 9H), 6.71 (d, J = 8.7 Hz, 1H), 6.62-6.48 (m, 1H), 6.43 (s, 1H), 6.20 (s, 1H), 4.31 (s, 1H), 3.93-3.65(m, 1H), 3.36-3.27 (m, 4H), 3.18-2.76 (m, 9H), 2.39-1.99 (m, 2H), 1.80-1.55 (m, 7H), 1.44-1.26 (m, 10H), 1.21-1.11 (m, 9H). MS (ESI, m/e) [M + 1]$^+$ 986.1 |
| 21 | 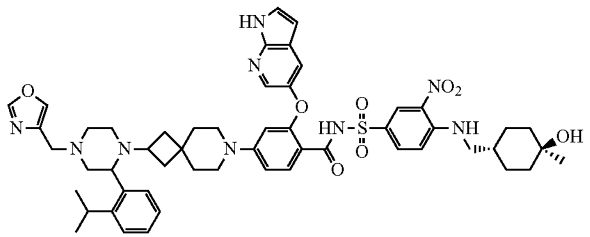 | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-(2-(2-isopropylphenyl)-4-(oxazol-4-ylmethy)piperazin-1-y))-7-azaspiro[3.5]nonan-7-yl)benzamide | $^1$H NMR (400 MHz, DMSO-$d_6$) δ ppm: 11.69 (s, 1H), 11.49-11.13 (m, 1H), 10.99-10.76 (m, 1H), 8.57-8.54 (m, 2H), 8.35 (s, 1H), 8.02 (s, 2H), 7.77 (d, J = 9.0 Hz, 1H), 7.56-7.41 (m, 3H), 7.29 (s, 3H), 7.07-7.05 (m, 1H), 6.65 (d, J = 9.0 Hz, 1H), 6.37 (s, 1H), 6.15 (s, 1H), 4.27 (s, 1H), 3.59 (s, 3H), 3.28 (s, 2H), 2.96-2.94 (m, 8H), 1.99 (s, 1H), 1.62-1.60 (m, 6H), 1.23 (s, 14H), 1.10 (s, 7H) MS (ESI, m/e) [M + 1]$^+$ 990.2. |
| 22 | 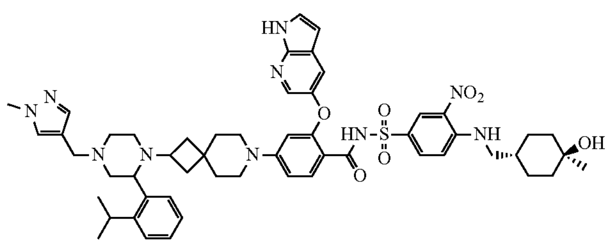 [SMILES: CC(C)c1ccccc1C1CN(Cc2cnn(C)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-((l-methyl-1H-pyrazol-4-yl)methyl)piperazin-1-yl)-7-azaspir[3.5]nonan-7-yl)benzamide | $^1$H NMR (400 MHz, DMSO-$d_6$) δ ppm: 11.66 (s, 1H), 11.26-10.82 (m, 1H), 8.52 (s, 2H), 8.00 (s, 1H), 7.74 (s, 1H), 7.67 (s, 1H), 7.48 (s, 3H), 7.39 (s, 2H), 7.25 (s, 2H), 7.13 (s, 1H), 7.05 (s, 1H), 6.64 (d, J = 9.2 Hz, 1H), 6.36 (s, 1H), 6.14 (s, 1H), 4.24 (s, 1H), 3.79 (s, 5H), 3.28-3.25 (m, 2H), 2.96-2.90 (m, 8H), 2.34-2.30 (m, 1H), 1.99 (s, 1H), 1.68-1.60 (m, 7H), 1.30-1.18 (m, 14H), 1.11-1.08 (m, 7H). MS (ESI, m/e) [M + 1]$^+$ 999.9. |

| Ex. | structure | Compound name | Data |
|---|---|---|---|
| 22a | | 2-((1H-pyrrolo[2,3-b]pyridin-5-yl)oxy)-N-((4-(((1r,4r)-4-hydroxy-4-methylcyclohexyl)methyl)sulfonyl)amino)-3-nitrophenyl)-4-(2-((R or S)-2-(2-isopropylphenyl)-4-((1-methyl-1H-pyrazol-4-yl)methyl)piperazin-1-yl)-7-azaspiro[3.5]nonan-7-yl)benzamide | $^1$H NMR (400 MHz, DMSO-$d_6$) δ ppm: 11.68 (s, 1H), 11.08 (s, 1H), 8.62-8.45 (m, 2H), 8.01 (s, 1H), 7.89-7.63 (m, 2H), 7.57-6.95 (m, 9H), 6.72-6.56 (m, 1H), 6.36 (s, 1H), 6.14 (s, 1H), 4.25 (s, 1H), 3.95-3.65 (m, 5H), 3.34-3.21 (m, 5H), 3.20-2.79 (m, 8H), 2.72-2.52 (m, 2H), 2.40-2.23 (m, 1H), 1.80-1.49 (m, 7H), 1.40-1.24 (m, 6H), 1.22-1.02 (m 12H). MS (ESI, m/e) [M + 1]$^+$ 999.6 |
| 22b | | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((S or R)-2-(2-isopropylphenyl)-4-((1-methyl-1H-pyrazol-4-yl)methyl)piperazin-1-yl)-7-azaspiro[3.5]nonan-7-yl)benzamide | $^1$H NMR (400 MHz, DMSO-$d_6$) δ ppm: 11.64 (s, 1H), 11.05 (br, 1H), 8.55-8.45 (m, 2H), 7.98 (s, 1H), 7.70 (d, J = 8.8 Hz, 1H), 7.58 (s, 1H), 7.49-7.36 (m, 4H), 7.30 (s, 1H), 7.26-7.15 (m, 2H), 7.16-7.05 (m, 1H), 6.98 (d, J = 8.8 Hz, 1H), 6.63 (d, J = 8.8 Hz, 1H), 6.34 (s, 1H), 6.15 (s, 1H), 4.25 (s, 1H), 3.76 (s, 3H), 3.62-3.40 (m, 3H), 3.32-3.20 (m, 3H), 3.06-2.80 (m, 8H), 2.70-2.61 (m, 1H), 2.35-1.93 (m, 3H), 1.73-1.52 (m, 7H), 1.38-1.20 (m, 10H), 1.15-1.08 (m, 8H). MS (ESI, m/e) [M + 1]$^+$ 999.6. |
| 23 | 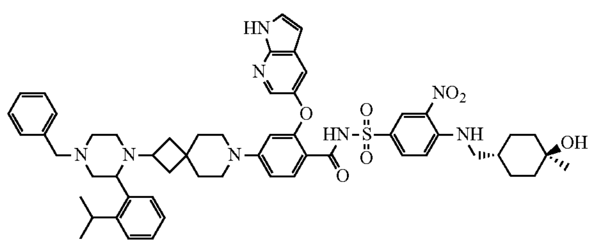 [SMILES: CC(C)c1ccccc1C1CN(Cc2ccccc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-y)oxy)-4-(2-(4-benzyl-2-(2-isopropylphenyl)piperazin-1-y))-7-azaspiro[3.5]nonan-7-yl)-N-((4-(((1r,4r)-4-hydroxy-4-methylcyclohexyl)methyl)amino)-3-nitrophenyl)sulfony)benzamide | $^1$H NMR (400 MHz, DMSO-$d_6$) δ ppm: 11.66 (s, 1H), 11.30 (br, 1H), 8.49-8.55 (m, 2H), 8.02 (s, 1H), 7.74 (d, J = 8 Hz, 1H), 7.40-7.51 (m, 4H), 7.02-7.28 (m, 10H), 6.63 (d, J = 8 Hz, 1H), 6.35 (s, 1H), 6.14 (s, 1H), 4.25 (s, 1H), 3.49-3.54 (m, 2H), 3.25-3.28 (m, 2H), 2.89-2.95 (m, 7H), 2.54 (s, 1H), 2.21-2.01 (m, 3H), 1.63-1.69 (m, 4H), 1.52-1.55 (m, 2H), 1.02-1.26 (m, 22H). MS (ESI, m/e) [M + 1]$^+$ 995.6 |

| Ex. | structure | Compound name | Data |
|---|---|---|---|
| 24a | 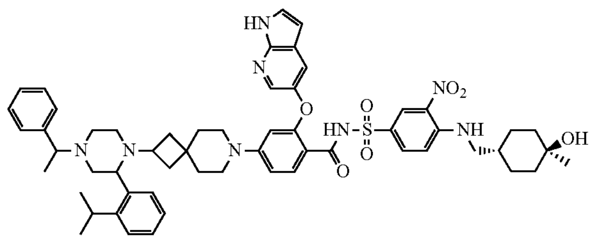 [SMILES: CC(C)c1ccccc1C1CN(C(C)c2ccccc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(1-phenylethyl)piperazin-1-yl)-7-azaspiro[3.5]nonan-7-yl)benzamide | $^1$H NMR (400 MHz, DMSO-d$_6$) δ ppm: 11.68 (s, 1H), 11.36 (br, 1H), 8.60-8.52 (m, 2H), 8.01 (s, 1H), 7.80-7.70 (m, 1H), 7.52-7.45 (m, 3H), 7.43-7.01 (m, 10H), 6.68-6.62 (m, 1H), 6.36 (s, 1H), 6.13 (s, 1H), 4.25 (s, 1H), 3.78-3.67 (m, 1H), 3.45-3.37 (m, 1H), 3.31-3.26 (m, 2H), 3.19-2.75 (m, 9H), 2.65-2.55 (m, 1H), 2.25-1.95 (m, 2H), 1.74-1.52 (m, 7H), 1.38-1.23 (m, 14H), 1.15-1.08 (m, 8H). MS (ESI, m/e) [M + 1]$^+$ 1009.9. |
| 24b | | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(1-phenylethyl)piperazin-1-yl)-7-azaspiro[3.5]nonan-7-yl)benzamide | $^1$H NMR (400 MHz, DMSO-d$_6$) δ ppm: 11.69 (s, 1H), 11.47 (br, 1H), 8.60-8.52 (m, 2H), 8.02 (s, 1H), 7.80-7.75 (m, 1H), 7.54-7.45 (m, 3H), 7.40-7.01 (m, 10H), 6.68-6.63 (m, 1H), 6.37 (s, 1H), 6.13 (s, 1H), 4.25 (s, 1H), 3.78-3.72 (m, 1H), 3.59-3.42 (m, 2H), 3.31-3.26 (m, 2H), 3.23-2.85 (m, 8H), 2.65-2.55 (m, 1H), 2.09-1.95 (m, 2H), 1.74-1.50 (m, 7H), 1.38-1.23 (m, 14H), 1.17-1.08 (m, 8H). MS (ESI, m/e) [M + 1]$^+$ 1009.9. |
| 25a | 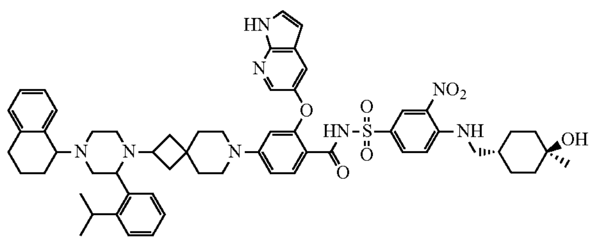 [SMILES: CC(C)c1ccccc1C1CN(C2CCCc3ccccc32)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(1,2,3,4-tetrahydronaphthalen-1-yl)piperazin-1-yl)-7-azaspiro[3.5]nonan-7-yl)benzamide | $^1$H NMR (400 MHz, DMSO-d$_6$) δ ppm: 11.69 (s, 1H), 11.44 (s, 1H), 8.54 (s, 2H), 8.02 (s, 1H), 7.76 (s, 1H), 7.62 (s, 1H), 7.48-7.46 (m, 3H), 7.39 (s, 1H), 7.26 (s, 1H), 7.12-7.00 (m, 5H), 6.66-6.64 (m, 1H), 6.37 (s, 1H), 6.15 (s, 1H), 4.27 (s, 1H), 3.88-3.85 (m, 2H), 3.28 (s, 3H), 2.92 (s, 6H), 2.67 (s, 2H), 1.96-1.93 (m, 4H), 1.60-1.56 (m, 9H), 1.25-1.22 (m, 13H), 1.17-1.06 (m, 9H). MS (ESI, m/e) [M + 1]$^+$ 1035.9. |
| 25b | 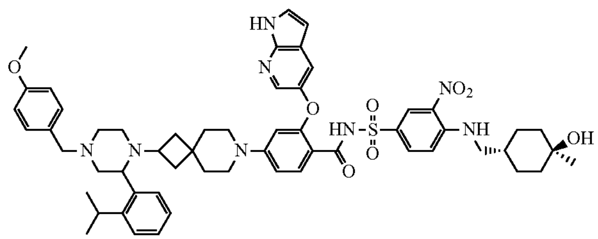 | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(1,2,3,4-tetrahydronaphthalen-1-yl)piperazin-1-yl)-7-azaspiro[3.5]nonan-7-yl)benzamide | $^1$H NMR (400 MHz, DMSO-d$_6$) δ ppm: 11.70 (s, 1H), 11.45 (s, 1H), 11.08 (s, 1H), 8.54 (s, 2H), 8.02 (s, 1H), 7.83-7.81 (m, 2H) 7.65 (s, 1H), 7.49-7.47 (m, 3H), 7.29 (s, 2H), 7.05-7.02 (m, 8 Hz, 7H), 6.66 (d, J = 8.6 Hz, 1H), 6.37 (s, 2H), 6.16 (s, 1H), 4.27 (s, 1H), 4.01 (s, 1H), 3.82 (s, 1H), 3.28 (s, 2H), 2.98-2.96 (m, 3H), 2.62 (s, 1H), 2.15-2.13 (m, 1H), 1.90 (s, 1H), 1.62-1.60 (m, 5H), 1.24 (s, 7H), 1.11 (s, 3H), 0.98-0.95 (m, 2H). MS (ESI, m/e) [M + 1]$^+$ 1035.9. |

-continued

| Ex. | structure | Compound name | Data |
|---|---|---|---|
| 26 | 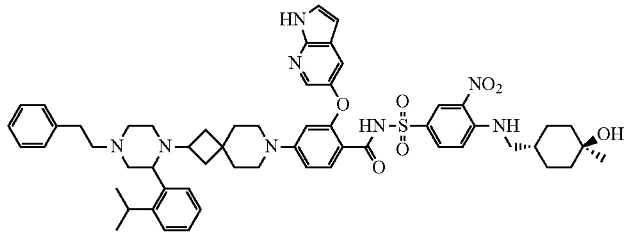 [SMILES: CC(C)c1ccccc1C1CN(CCc2ccccc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((1r,4r)-4-hydroxy-4-methylcyclohexyl)methyl)sulfonyl)-4-(2-(2-isopropylphenyl)-4-phenethylpiperazin-1-yl)-7-azaspiro[3.5]nonan-7-yl)benzamide | $^{1}$H NMR (400 MHz, DMSO-d$_6$) δ ppm 11.70 (s, 1H), 11.43-10.78 (m, 1H), 8.65-8.47(m 2H), 8.03 (s, 1H), 7.90-7.70 (m 1H), 7.58-7.37 (m, 4H), 7.37-7.11 (m, 8H), 7.11-6.96 (m, 1H), 6.69-6.58 (m, 1H), 6.37 (s, 1H), 6.19-6.05 (m, 1H), 4.25 (s, 1H), 3.97-3.67 (m, 1H), 3.60-3.40 (m, 1H), 3.29-2.55 (m, 17H), 2.08-1.93 (m, 1H), 1.82-1.49 (m, 7H), 1.3.8-1.25 (m, 6H), 1.22-1.14 (m, 6H), 1.14-1.05 (m, 5H). MS (ESI, m/e) [M + 1]$^+$ 1010.1 |
| 27 | 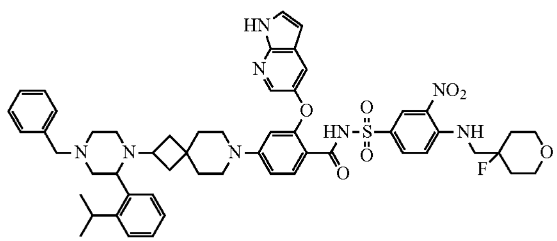 [SMILES: CC(C)c1ccccc1C1CN(Cc2ccccc2)CCN1C1CC2(CCN(c3ccc(C(=O)NS(=O)(=O)c4ccc(NCC5(F)CCOCC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-benzyl-2-(2-isopropylphenyl)piperazin-1-yl)-7-azaspiro[3.5]nonan-7-yl)-N-(4-((4-fluorotetrahydro-2H-pyran-4-yl)methyl)amino)-3-nitrophenyl)sulfonyl)benzamide | $^{1}$H NMR (400 MHz, DMSO-d$_6$) δ ppm 11.67 (s, 1H), 11.47-11.20 (m, 1H), 8.62 (s, 1H), 8.54 (s, 1H), 8.01 (s, 1H), 7.79 (d, J = 8.8 Hz, 1H), 7.48-7.47 (m, 3H), 7.28-7.27 (m, 10H), 6.64 (d, J = 8.8 Hz, 1H), 6.36 (s, 1H), 6.14 (s, 1H), 3.73-3.70 (m, 5H), 3.66-3.58 (m, 1H), 3.52 (s, 2H), 2.95-2.94 (m, 7H), 2.29-2.16 (m, 1H), 1.99 (s, 1H), 1.78-1.76 (m, 4H), 1.67-1.56 (m, 1H), 1.49-1.41 (m, 1H), 1.24-1.20 (m, 12H), 1.04 (s, 4H). MS (ESI, m/e) [M + 1]$^+$ 986.0. |
| 28 | 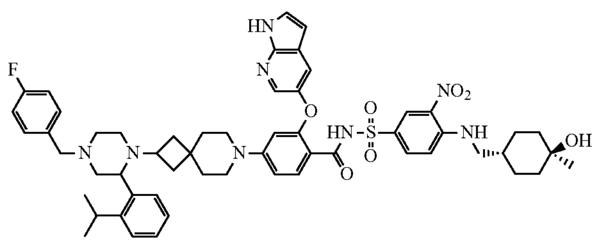 [SMILES: CC(C)c1ccccc1C1CN(Cc2ccc(F)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(4-fluorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^{1}$H NMR (400 MHz, DMSO-d$_6$) δ ppm: 11.68 (s, 1H), 11.29 (s, 1H), 8.55 (d, J = 7.8 Hz, 2H), 8.02 (s, 1H), 7.78-7.76 (m, 1H), 7.49-7.46 (m, 3H), 7.36 (s, 3H), 7.26-7.00 (m, 6H), 6.64 (d, J = 8.6 Hz, 1H), 6.37 (s, 1H), 6.14 (s, 1H), 4.25 (s, 1H), 3.62. (s, 2H), 3.28 (s, 3H), 2.96-2.93 (m, 7H), 2.67 (s, 1H), 2.24 (s, 1H), 2.10-1.93 (m, 1H), 1.65-1.56 (m, 7H), 1.26-1.05 (m, 21H), MS (ESI, m/e) [M + 1]$^+$ 1014.1 |
| 28a | or | 2-((1H-pyrrolo[2,3-b]pyridin-5-yl)oxy)-4-(2-((R or S)-4-(4-fluorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^{1}$H NMR (400 MHz, DMSO-d$_6$) δ ppm: 11.69 (s, 1H), 11.42-11.17 (m, 1H), 8.57-8.54 (m, 2H), 8.02 (s, 1H), 7.76 (s, 1H), 7.50-7.46 (m, 3H), 7.36 (s, 3H), 7.15-7.10 (m, 5H), 6.66 (s, 1H), 6.37 (s, 1H), 6.13 (s, 1H), 4.25 (s, 1H), 3.62 (s, 2H), 3.38 (s, 1H), 3.28 (s, 3H), 2.96-2.90 (m, 7H), 2.67-2.58 (m, 1H), 2.31-2.16 (m 1H), 2.00 (s, 1H), 1.66 (s, 4H), 1.57-1.52 (m, 2H), 1.30-1.26 (m, 10H), 1.15-1.10 (m, 11H). MS (ESI, m/e) [M + 1]$^+$ 1013.7. |

| Ex. | structure | Compound name | Data |
|---|---|---|---|
| 29 | 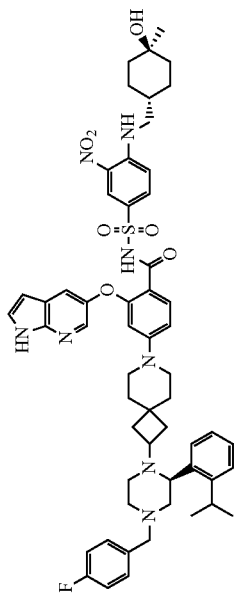 | 2-((1H-pyrrolo[2,3-b]pyridin-5-yl)oxy)-4-(2-(4-(4-chlorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.70 (s, 1H), 11.34 (s, 0.7H), 10.78 (s, 0.3H), 8.63-8.48 (m, 2H), 8.02 (s, 1H), 7.91-7.62 (m, 2H), 7.57-7.01 (m, 12H), 6.73-6.54 (m, 1H), 6.37 (s, 1H), 6.14 (s, 1H), 4.72-4.48 (m, 0.5H), 4.26 (s, 1H), 3.89-3.50 (m, 2.5H), 3.45-3.36 (m, 1H), 3.34-3.10 (m, 4H), 3.10-2.82 (m, 6H), 2.82-2.58 (m, 2H), 2.34-2.16 (m, 1H), 2.15-1.91 (m, 1H), 1.75-1.50 (m, 6H), 1.48-1.27 (m, 5H), 1.23-0.95 (m 13H). MS (ESI, m/e) [M + 1]⁺ 1030.8. |
| 29a | 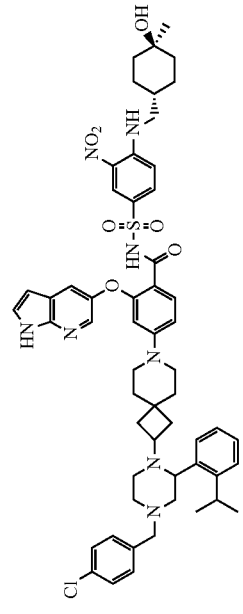 or 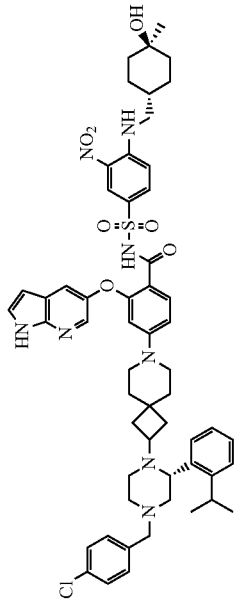<br>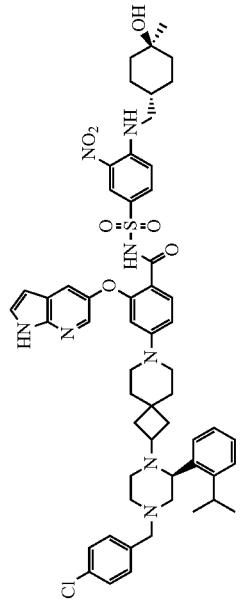 | 2-((1H-pyrrolo[2,3-b]pyridin-5-yloxy)-4-(2-((R or S)-4-(4-chlorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.69 (s, 1H), 11.33 (s, 1H), 8.6-3.8-48 (m, 2H), 8.03 (s, 1H), 7.83-7.73 (m, 1H), 7.55-7.44 (m, 3H), 7.44-7.30 (m 5H), 7.30-7.15 (m, 2H), 7.15-7.01 (m, 2H), 6.72-6.55 (m, 1H), 6.37 (s, 1H), 6.14 (s, 1H), 4.25 (s, 1H), 3.68-3.50 (m, 2H), 3.48-3.36 (m, 1H), 3.32-3.13 (m, 3H), 3.11-2.80 (m, 7H), 2.72-2.52 (m, 2H), 2.30-2.11 (m, 1H), 2.11-1.92 (m, 1H), 1.74-1.50 (m, 6H), 1.39-1.23 (m 8H), 1.23-1.15 (m, 4H), 1.15-1.00 (m, 7H). MS (ESI, m/e) [M + 1]⁺ 1030.6. |

| Ex. | structure | Compound name | Data |
|---|---|---|---|
| 30 | 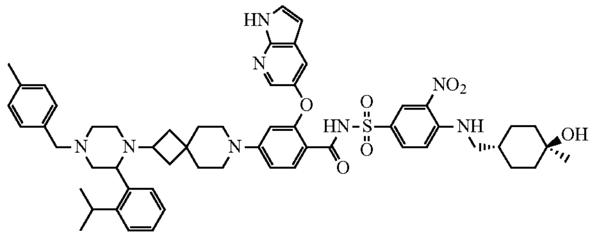 [SMILES: Cc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methylbenzyl)piperazin-1-yl)-7-azaspiro[3.5]nonan-7-yl)benzamide | ¹H NMR (400 MHz, DMSO-d₆) δ ppm: 11.67 (s, 1H), 11 41 (s, 1H), 8.52 (s, 2H), 8.00 (s, 1H), 7.79-7.68 (m, 1H), 7.52-7.46 (m 3H), 7.44-7.38 (m, 1H), 7.34 (s, 1H), 7.29-7.08 (m, 7H), 7.03 (s, 1H), 6.64 (d, J = 8.2 Hz, 1H), 6.35 (s, 1H), 6.19-6.11 (m, 1H), 4.25 (s, 1H), 3.81-3.66 (m, 1H), 3.29-3.22 (m, 3H), 3.05-2.81 (m, 8H), 2.29-2.23 (m, 4H), 1.75-1.58 (m, 5H) 1.54 (d, J = 12.8 Hz, 3H) 1.41-1.20 (m, 10H), 1.19-1 14 (m 3H), 1.13 (s, 1H), 1.12-0.95 (m, 9H). MS (ESI, m/e) [M + 1]⁺ 1009.5. |
| 31 | 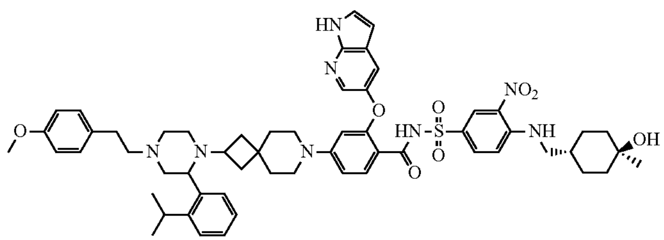 [SMILES: COc1ccc(CCN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-y)oxy)-N-((4-(1r,4r)-4-hydroxy-4-methylcyclohexyl)methyl)amino)-3-nitrophenyl)sulfonyl)-4-(2-(2-(2-isopropylphenyl)-4-(4-methoxyphenethyl)piperazin-1-yl)-7-azaspiro[3.5]nonan-7-yl)benzamide | ¹H NMR (400 MHz, DMSO-d₆) δ ppm: 11.65 (s, 1H), 11.29 (s, 1H), 8.50 (s, 2H), 7.99 (s, 1H), 7.78-7.65 (m, 1H), 7.57-7.36 (m, 4H), 7.31-7.18 (m, 2H), 7.17-7.06 (m, 3H), 7.03-6.95 (m, 1H), 6.84 (d, J = 8.0 Hz, 2H), 6.64 (d, J = 8.0 Hz, 1H), 6.35 (s, 1H), 6.15 (s, 1H), 4.24 (s, 1H), 3.70 (s, 3H), 3.29-3.21 (m, 3H), 3.16-3.14 (m, 1H), 3.09-2.71 (m, 11H), 2.69-2.61 (m, 1H), 1.75-1.49 (m 7H), 1.37-1.24 (m, 7H), 1.22-1.12 (m, 7H), 1.10 (s, 6H). MS (ESI, m/e) [M + 1]⁺ 1039.5. |
| 34 | 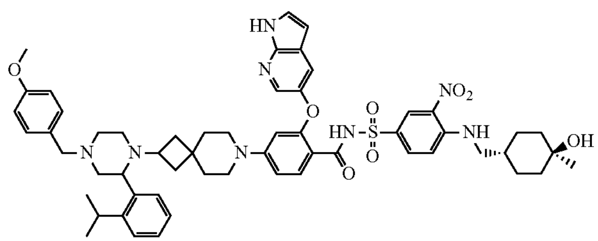 | 2-((1H-pyrrolo[2,3-b]pyridin-5-y)oxy)-N-((4-(((1r,4r)-4-hydroxy-4-methylcyclohexyl)methyl)amino)-3-nitrophenyl)sulfonyl)-4-(2-(4-(4-methoxybenzyl)-2-(o-tolyl)piperazin-1-yl)-7-azaspiro[3.5]nonan-7-yl)benzamide | ¹H NMR (400 MHz, DMSO-d₆) δ ppm: 11.69 (s, 1H), 8.54 (s, 2H), 8.02 (s, 1H), 7.76 (s, 1H), 7.49-7.47 (m, 3H), 7.29 (s, 3H), 7.12-6.98 (m, 3H), 6.91 (s, 2H), 6.65 (d, J = 8.0 Hz, 1H), 6.37 (s, 1H), 6.12 (s, 1H), 4.25 (s, 1H), 3.73 (s, 4H), 3.58 (s, 1H), 3.28 (s, 2H), 2.96-2.93 (m, 8H), 2.27 (s, 5H), 1.99 (s, 1H), 1.72-1.49 (m, 7H), 1.29-1.26 (m, 10H), 1.13-1.10 (m, 6H). MS (ESI, m/e) [M + l]⁺ 997.5. |
| 35 | 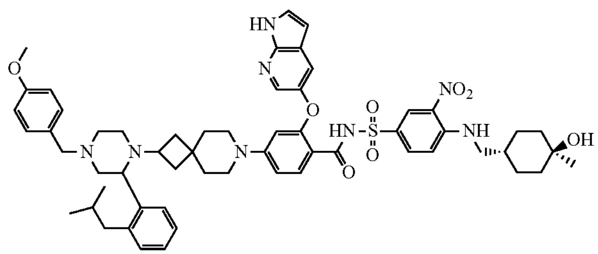 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3CC(C)C)C2)cc1] | 2-((1H-pyrrolo[2,3-b]pyridin-5-y)oxy)-N-((4-(((1r,4r)-4-hydroxy-4-methylcyclohexyl)methyl)amino)-3-nitrophenyl)sulfonyl)-4-(2-(2-(2-isobutylphenyl)-4-(4-methoxybenzyl)piperazin-1-yl)-7-azaspiro[3.5]nonan-7-yl)benzamide | MS (ESI, m/e) [M + l]⁺ 1039.6. |

| Ex. | structure | Compound name | Data |
|---|---|---|---|
| 36 | 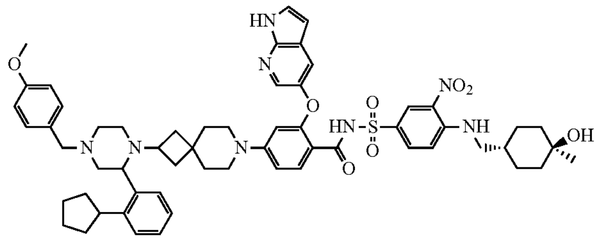 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C3CCCC3)C2)cc1] | 2-((1H-pyrrolo[2,3-b]pyridin-5-yl)oxy)-4-(2-(2-cyclopentylpheny)-4-(4-methoxybenzyl)piperazin-1-yl)-7-azaspiro[3.5]nonan-7-yl)-N-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.68 (s, 1H), 11.24 (br, 1H), 8.60-8.51 (m, 2H), 8.01 (s, 1H), 7.77 (d, J = 8.4 Hz, 1H), 7.53-7.45 (m, 3H), 7.30-7.02 (m, 7H), 6.89 (d, J = 8.4 Hz, 1H), 6.65 (d, J = 8.4 Hz, 1H), 6.36 (s, 1H), 6.13 (s, 1H), 4.25 (s, 1H), 3.72 (s, 3H), 3.61-3.50 (m, 1H), 3.30-3.25 (m, 3H), 3.07-2.83 (m, 9H), 2.30-2.15 (m, 1H), 2.03-1.87 (m, 3H), 1.84-1.72 (m, 8H), 1.57-1.50 (m, 4H), 1.39-1.26 (m, 7H), 1.19-1.07 (m, 6H). MS (ESI, m/e) [M + 1]+ 1052.5. |
| 37 | 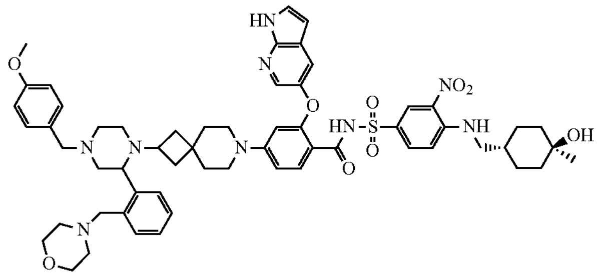 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3CN3CCOCC3)C2)cc1] | 2-((1H-pyrrolo[2,3-b]pyridin-5-yl)oxy)-N-((4-(((1r,4r)-4-hydroxy-4-methylcyclohexy)amino)-3-nitrophenyl)sulfonyl)-4-(2-(4-(4-methoxybenzyl)-2-(2-(morpholinomethyl)phenyl)piperazin-1-yl)-7-azaspiro[3.5]nonan-7-yl)benzamide | 1H NMR (400 MHz, DMSO-d6) δ ppm: 11.65 (s, 1H), 8.48 (s, 2H), 8.01 (s, 1H), 7.78-7.69 (m, 1H), 7.65-7.55 (s, 2H), 7.54-7.47 (m, 1H), 7.42-7.24 (m, 5H), 7.21-7.14 (m, 2H), 6.96-6.83 (m, 3H), 6.76-6.63 (m, 1H), 6.39 (s, 1H), 6.27 (s, 1H), 4.33 (s, 1H), 3.79 (s, 3H), 3.70-3.51 (m, 3H), 3.35-3.17 (m, 6H), 3.03-2.87 (m, 7H), 2.32 (s, 3H), 2.22 (s, 3H), 1.81-1.72 (m, 3H), 1.71-1.58 (m, 4H), 1.50-1.35 (dm, 6H), 1.32 (s, 2H), 1.25-1.14 (m, 6H), 1.10-1.03 (m, 1H), 0.97-0.88 (m, 1H). MS (ESI, m/e) [M + 1]+ 1082.6 |
| 38 | 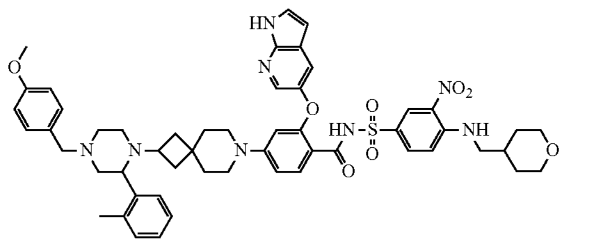 [SMILES: COc1ccc(CN2CCN(C3CC4(CCN(c5ccc(C(=O)NS(=O)(=O)c6ccc(NCC7CCOCC7)c([N+](=O)[O-])c6)c(Oc6cnc7[nH]ccc7c6)c5)CC4)C3)C(c3ccccc3C)C2)cc1] | 2-((1H-pyrrolo[2,3-b]pyridin-5-yl)oxy)-4-(2-(4-(4-methoxybenzyl)-2-(o-tolyl)piperazin-1-yl)-7-azaspiro[3.5]nonan-7-yl)-N-(3-nitro-4-(((tetrahydro-2H-pyran-4-yl)methyl)amino)phenyl)sulfonyl)benzamide | 1H NMR (400 MHz, DMSO-d6) δ ppm: 11.29-10.96 (m, 1.0 H), 8.54 (s, 2H), 8.01 (s, 1H), 7.77 (d, J = 9.0 Hz, 1H), 7.49-7.46 (m, 3H), 7.20-7.15 (m, 7H), 6.89 (s, 2H), 6.65 (d, J = 9.0 Hz, 1H), 6.37 (s, 1H), 6.13 (s, 1H), 3.85-3.83 (m, 2H), 3.73 (s, 3H), 3.55 (s, 1H), 3.30-3.20 (m, 4H), 2.94-2.92 (m, 8H), 2.28 (s, 4H), 1.96-1.90 (m, 2H), 1.63-1.60 (m, 4H), 1.28-1.21 (m, 10H), 1.06 (s, 1H), 0.85 (s, 1H). MS (ESI, m/e) [M + 1]+ 969.6. |
| 39 | 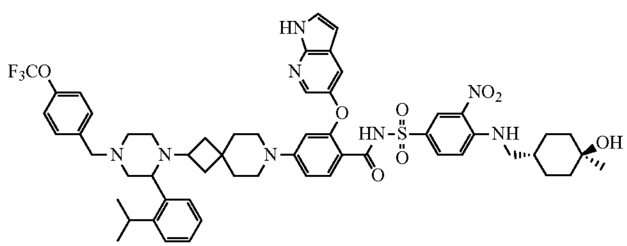 [SMILES: CC(C)c1ccccc1C1CN(Cc2ccc(OC(F)(F)F)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(4-(trifluoromethoxy)benzyl)piperazin-1-yl)-7-azaspiro[3.5]nonan-7-yl)benzamide | 1H NMR (400 MHz, DMSO-d6) δ ppm 11.62 (s, 1H), 11.42 (s, 1H), 8.47 (s, 2H), 7.97 (s, 1H), 7.68 (s, 1H), 7.53-7.35 (m, 6H), 7.31-7.25 (m, 2H), 7.12-7.04 (m, 1H), 6.94 (s, 1H), 6.62 (d, J = 8.0 Hz, 1H), 6.33 (s, 1H), 6.16 (s, 1H), 4.25 (s, 1H), 3.56-3.42 (m, 3H), 3.29-3.19 (m, 3H), 3.01-2.82 (m, 7H), 2.25-2.15 (m, 2H), 2.04-1.93 (m, 1H), 1.72-1.58 (m, 5H), 1.57-1.48 (m, 3H), 1.37-1.25 (m, 8H), 1.18-1.07 (m, 9H), 1.04-0.95 (m, 3H). MS (ESI, m/e) [M + 1]+ 1080.5. |

| Ex. | structure | Compound name | Data |
|---|---|---|---|
| 40 | 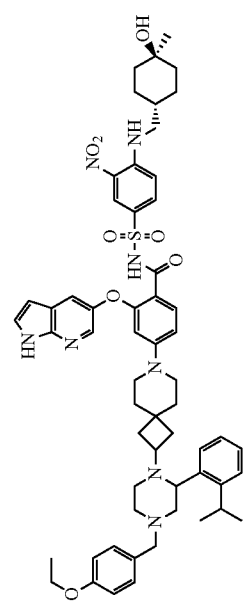 | 2-((1H-pyrrolo[2,3-b]pyridin-5-yloxy)-4-(2-(4-(4-ethoxybenzyl)-2-(2-isopropylphenyl)piperazin-1-yl)-7-azaspir[3.5]nonan-7-yl)-N-(4-(((1r,4r)-4-hydroxy-4-methylcyclohexyl)methylamino)-3-nitrophenyl)sulfonyl)benzamide | $^1$H NMR (400 MHz, DMSO-d$_6$) δ ppm: 11.69 (s, 1H), 11.17 (br, 1H), 8.54-8.55 (m, 2H), 8.02 (s, 1H), 7.77 (d, J = 8 Hz, 1H), 7.05-7.49 (m, 10H), 6.84-6.92 (m, 2H), 6.64 (d, J = 8 Hz, 1H), 6.37 (s, 1H), 6.14 (s, 1H), 4.26 (s, 1H), 3.96-4.01 (m, 2H), 3.69-3.86 (m, 2H), 3.55 (s, 1H), 3.26-3.29 (m, 2H), 2.91-2.97 (m, 7H), 2.67-2.75 (m, 2H), 2.01-2.33 (m, 2H), 1.52-1.69 (m, 7H), 1.07-1.36 (m, 24H). MS (ESI, m/e) [M +1]$^+$ 1039.7 |
| 41 | 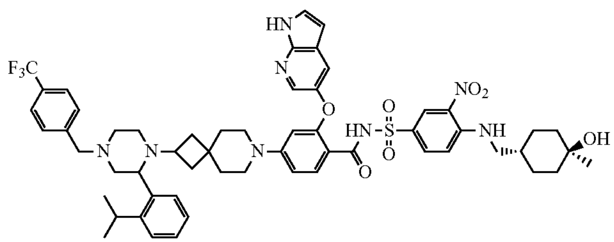 [SMILES: CC(C)c1ccccc1C1CN(Cc2ccc(C(F)(F)F)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-(trifluoromethyl)benzyl)piperazin-1-yl)-7-azaspiro[3.5]nonan-7-yl)benzamide | $^1$H NMR (400 MHz, DMSO-d$_6$) δ ppm: 11.67 (s, 1H), 11.39 (br, 1H), 8.51-8.55 (m, 2H), 8.01 (s, 1H), 7.76 (d, J = 8 Hz, 1H), 7.66 (d, J = 4 Hz, 1H), 7.46-7.53 (m, 5H), 7.16-7.19 (m, 2H), 7.05-7.08 (m, 2H), 6.64 (d, J = 8 Hz, 1H), 6.36 (s, 1H), 6.14 (s, 1H), 4.25 (s, 1H), 3.51-3.57 (m, 2H), 3.25-3.28 (m, 2H), 2.90-2.96 (m, 5H), 2.18-2.23 (m, 2H), 1.99-2.00 (m, 1H), 1.52-1.69 (m, 7H), 1 02-1,35 (m, 24H). MS (ESI, m/e) [M + 1]$^+$ 1064.5 |
| 42 | 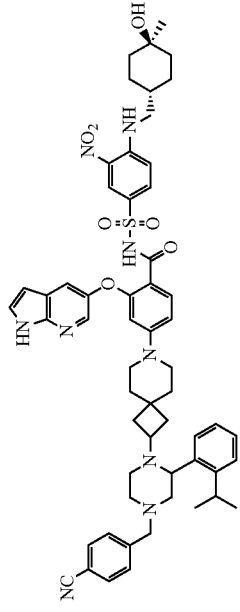 | 2-((1H-pyrrolo[2,3-b]pyridin-5-yl)oxy)-4-(2-(4-(4-cyanobenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.64 (s, 1H), 8.55-8.31 m, 2H), 7.97 (s, 1H), 7.77 (d, J = 8.0 Hz, 2H), 7.71-7.61 (m, 1H), 7.58-7.32 (m, 7H), 7.24-7.05 (m, 3H), 6.62 (d, J = 8.0 Hz, 1H), 6.33 (s, 1H), 6.16 (s, 1H), 4.27 (s, 1H), 3.77-3.66 (m 1H), 3.64-3.50 (m 3H), 3.28-3.19 (m, 3H), 3.02-2.76 (m, 9H), 2.32-2.10 (m, 2H), 2.08-1.97 (m, 1H), 1.74-1.57 (m, 6H), 1.54-1.48 (m, 3H), 1.37-1.25 (m, 8H), 1.23 (s, 3H), 1.21-1.09 (m, 5H), 1.09 (s, 5H), 1.04-0.97 (m, 4H). MS (ESI, m/e) [M + 1]$^+$ 1020.5. |

| Ex. | structure | Compound name | Data |
|---|---|---|---|
| 43 | 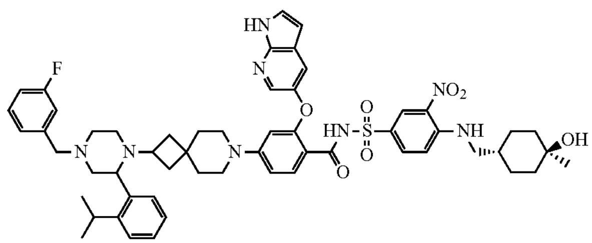 [SMILES: CC(C)c1ccccc1C1CN(Cc2cccc(F)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(3-fluorobenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.44 (s, 1H), 8.57-8.55 (m, 2H), 8.02 (s, 1H), 7.78 (d, J = 9.2 Hz, 1H), 7.50 (s, 2H), 7.47-7.46 (m, 1H), 7.35 (s, 3H), 7.21-7.18 (m, 3H), 7.07 (d, J = 9.2 Hz, 2H), 6.66 (d, J = 8.8 Hz, 1H), 6.37 (s, 1H), 6.16 (s, 1H), 4.64 (s, 1H), 4.25 (s, 1H), 3.73 (s, 1H), 3.65 (s, 1H), 3.39 (s, 1H), 3.28 (s, 2H), 3.17 (s, 1H), 2.98 (s, 7H), 2.72 (s, 2H), 2.19 (s, 1H), 2.01 (s, 1H), 1.65-1.58 (m, 6H), 1.32-1.30 (m, 10H), 1.13-1.12 (m, 5H), 1.04 (s, 3H). MS (ESI, m/e) [M + 1]$^+$ 1014.1. |
| 44 | 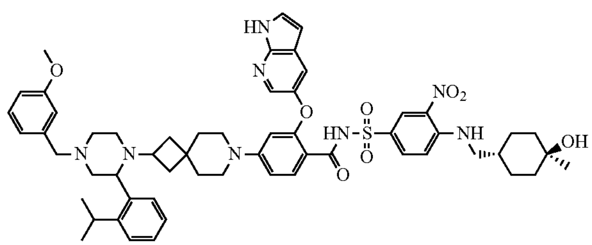 [SMILES: COc1cccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)c1] | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-(2-(2-isopropylphenyl)-4-(3-methoxybenzyl)piperazin-1-yl)-7-azaspiro[3.5]nonan-7-yl)benzamide | $^1$H NMR (400 MHz, DMSO-d$_6$) δ ppm: 11.69 (s, 1H), 11.40 (br, 1H), 8.62-8.53 (m, 2H), 8.02 (s, 1H), 7.94-7.75 (m, 2H), 7.54-7.45 (m, 3H), 7.37-7.32 (m, 1H), 7.31-7.20 (m, 4H), 7.08 (d, J = 8.4 Hz, 1H), 6.93-6.78 (m, 2H), 6.68-6.62 (m, 1H), 6.37 (s, 1H), 6.18-6.12 (m, 1H), 4.68-4.59 (m, 1H), 4.24 (s, 1H), 3.79-3.71 (m, 4H), 3.60 (s, 1H), 3.45-3.37 (m, 2H), 3.33-3.14 (m 3H), 3.08-2.80 (m, 7H), 2.77-2.57 (m, 2H), 2.09-1.95 (m 2H), 1.74-1.61 (m, 4H), 1.58-1.50 (m, 2H), 1.48-1.40 (m, 1H), 1.39-1.26 (m, 7H), 1.19-1.02 (m, 10H). MS (ESI, m/e) [M + 1]$^+$ 1026.0. |
| 45 | 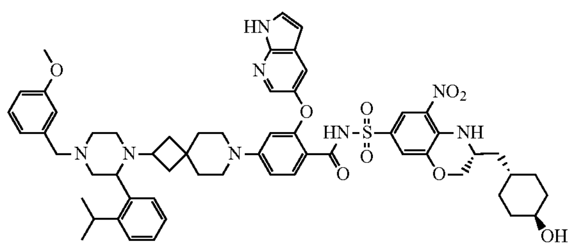 [SMILES: COc1cccc(CN2CCN(C3CC4(CCN(c5ccc(C(=O)NS(=O)(=O)c6cc7c(c([N+](=O)[O-])c6)N[C@H](C[C@H]6CC[C@H](O)CC6)CO7)c(Oc6cnc7[nH]ccc7c6)c5)CC4)C3)C(c3ccccc3C(C)C)C2)c1] | 2-((1H-pyrrolo[2,3-b]pyridin-5-yloxy)-N-(((1R,4R)-4-hydroxycyclohexyl)methyl)-5-nitro-3,4-dihydro-2H-benzo[b][1,4]oxazin-7-yl)sulfonyl)-4-(2-(2-(2-isopropylphenyl)-4-(3-methoxybenzyl)piperazin-1-yl)-7-azaspiro[3.5]nonan-7-yl)benzamide | $^1$H NMR (400 MHz, DMSO-d$_6$) δ ppm: 11.68 (s, 1H), 11.41 (br, 1H), 8.81 (s, 1H), 8.18 (s, 1H), 8.02 (s, 1H), 7.59-7.45 (m, 3H), 7.43-7.10 (m, 6H), 7.03-6.80 (m, 3H), 6.67 (d, J = 8.4 Hz, 1H), 6.37 (s, 1H), 6.15(d, J = 10.8 Hz, 1 H), 4.70-4.60 (m, 1H), 4.49 (s, 1H), 4.13-4.02 (m, 2H), 3.83-3.70 (m, 5H), 3.63-3.58 (m, 1H), 3.47-3.40 (m, 1H), 3.32-2.80 (m, 8H), 2.79-2.56 (m, 2H), 2.07-1.94 (m, 1H), 1.86-1.50 (m, 5H), 1.49-1.32 (m, 7H), 1.22-1.02 (m, 14H). MS (ESI, m/e) [M + 1]$^+$ 1054.1. |

| Ex. | structure | Compound name | Data |
|---|---|---|---|
| 46 | 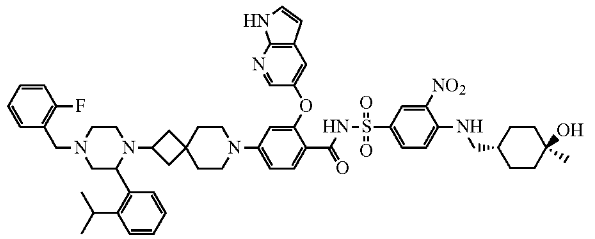 [SMILES: CC(C)c1ccccc1C1CN(Cc2ccccc2F)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(2-fluorobenzyl)-2-(2-isopropylphenyl)piperazin-1-yl)-7-azaspiro[3.5]nonan-7-yl)-N-(4-(((1r,4r)-4-hydroxy-4-methylcyclohexyl)methylamino)-3-nitrophenyl)sulfonyl)benzamide | ¹H NMR (400 MHz, DMSO-d₆) δ ppm: 11.69 (s, 1H), 11.41 (s, 1H), 8.55 (s, 2H), 8.02 (s, 1H), 7.90 (s, 1H), 7.76 (s, 1H), 7.49-7.36 (m, 7H), 7.17-7.07 (m, 6H), 6.65 (d, J = 8.2 Hz, 1H), 6.37 (s, 1H), 6.16-6.13 (m, 1H), 4.25 (s, 1H), 3.71-3.65 (m, 3H), 3.31-3.24 (m, 3H), 2.94 (m, 8H), 2.33-2.08 (m, 4H), 1.75-1.42 (m, 7H), 1.41-1.18 (m, 10H), 1.13-1.07 (m, 10H). MS (ESI, m/e) [M + 1]⁺ 1014.0. |
| 47 | 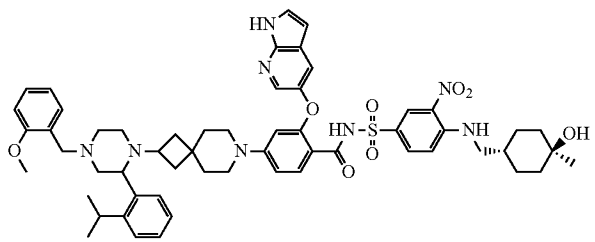 [SMILES: COc1ccccc1CN1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)C(c2ccccc2C(C)C)C1] | 2-((1H-pyrrolo[2,3-b]pyridin-5-yl)oxy)-N-(4-(((1r,4r)-4-hydroxy-4-methylcyclohexyl)methyl)amino)-3-nitrophenyl)sulfonyl)-4-(2-(2-isopropylphenyl)-4-(2-methoxybenzyl)piperazin-1-yl)-7-azaspiro[3.5]nonan-7-yl)benzamide | ¹H NMR (400 MHz, DMSO-d₆) δ ppm: 11.69 (s, 1H), 11.42 (s, 1H), 8.64-8.48 (m, 2H), 8.06-7.96 (m, 1H), 7.94-7.64 (m, 1H), 7.59-7.16 (m, 8H), 7.16-6.77 (m, 3H), 6.72-6.60 (m, 1H), 6.37 (s, 1H), 6.14 (s, 1H), 4.30 (s, 1H), 3.79 (s, 3H), 3.52-3.38 (m, 6H), 3.32-2.75 (m, 15H), 2.10-1.92 (m, 1H), 1.78-1.50 (m, 5H), 1.46-1.24 (m, 7H), 1.19-1.01 (m, 8H). MS (ESI, m/e) [M + 1]⁺ 1026.2. |
| 48 | 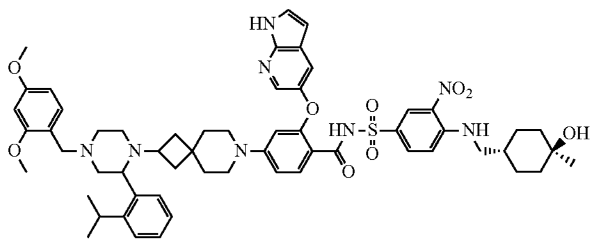 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)c(OC)c1] | 2-((1H-pyrrolo[2,3-b]pyridin-5-yl)oxy)-4-(2-(4-(2,4-dimethoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.69 (s, 1H), 11.41 (s, 1H), 8.62-8.53 (m, 2H), 8.02 (s, 1H), 7.78 (d, J = 8.8 Hz, 1H), 7.54-7.45 (m, 3H), 7.37-7.32 (m, 2H), 7.31-7.20 (m, 2H), 7.19-7.15 (m, 1H), 7.08 (d, J = 8.8 Hz, 1H), 6.68-6.44 (m, 3H), 6.37 (s, 1H), 6.13 (s, 1H), 4.26 (s, 1H), 4.19-3.83 (m, 2H), 3.77 (s, 6H), 3.60-3.44 (m, 1H), 3.30-3.22 (m, 3H), 3.17-2.80 (m, 8H), 2.77-2.57 (m, 1H), 2.44-2.30 (m, 1H), 2.09-1.95 (m, 1H), 1.74-1.61 (m, 4H), 1.52 (s, 3H), 1.49-1.16 (m, 12H), 1.14-1.00 (m, 7H). MS (ESI, m/e) [M + 1]⁺ 1055.9. |
| 48a | 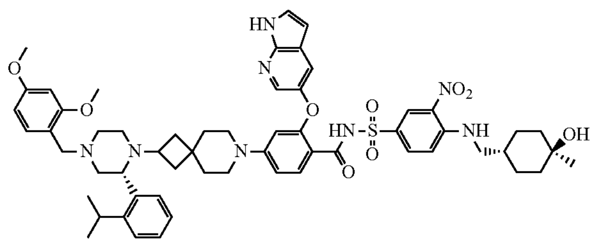 | 2-((1H-pyrrolo[2,3-b]pyridin-5-yl)oxy)-4-(2-((R or S)-4-(2,4-dimethoxybenzyl)-2-(2-isopropylphenyl)piperazin-1-y)-7-azaspiro[3.5]nonan-7-yl)-N-(4-(((1r,4r)-4-hydroxy-4-methylcyclohexyl)methyl)amino)-3-nitrophenyl)sulfonyl)benzamide or | ¹H NMR (400 MHz, DMSO-d₆) δ ppm: 11.70 (s, 1H), 11.29 (br, 1H), 8.61-8.53 (m, 2H), 8.03 (s, 1H), 7.83-7.74 (m, 1H), 7.54-7.32 (m, 5H), 7.30-7.03 (m, 4H), 6.70-6.44 (m, 3H), 6.37 (s, 1H), 6.13 (s, 1H), 4.25 (s, 1H), 4.20-3.82 (m, 1H), 3.74-3.65 (m, 6H), 3.60-3.37 (m, 1H), 3.30-3.20 (m, 3H), 3.09-2.60 (m, 9H), 2.45-2.25 (m, 1H), 2.09-1.95 (m, 1H), 1.73-1.51 (m, 6H), 1.39-1.15 (m, 12H), 1.14-1.00 (m, 9H). MS (ESI, m/e) [M + 1]⁺ 1056.2. |

| Ex. | structure | Compound name | Data |
|---|---|---|---|
| 49 | 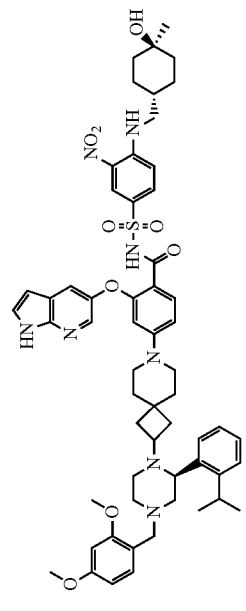 | 2-((1H-pyrrolo[2,3-b]pyridin-5-yl)oxy)-4-(2-(4-(3,5-dimethoxybenzyl)-2-(2-isopropylphenyl)piperazin-1-yl)-7-azaspiro[3.5]nonan-7-yl)-N-(4-((((1r,4r)-4-hydroxy-4-methylcyclohexyl)methyl)amino)-3-nitrophenyl)sulfonyl)benzamide | $^1$H NMR ((400 MHz, DMSO-d$_6$) δ ppm: 11.69 (s, 1H), 11.51-11.23 (m, 1H), 10.62-10.36 (m, 1H), 8.57-8.55 (m, 2H), 8.03 (s, 1H), 7.78 (d, J = 8.8 Hz, 1H), 7.55-7.44 (m, 3H), 7.36 (s, 1H), 7.23 (s, 2H), 7.07 (d, J = 8.8 Hz, 2H), 6.65 (d, J = 8.8 Hz, 1H), 6 49 (s, 2H), 6.37 (s, 2H), 6.14 (s, 1H), 4.25 (s, 1H), 3.71 (s, 7H), 3.57 (s, 1H), 3.42 (s, 1H), 3.28 (s, 3H), 2.97-2.93 (m, 7H), 2.01 (s, 1H), 1.66 (s, 4H), 1.55-1.53 (m, 2H), 1.28-1.25 (m, 13H), 1.13-1.10 (m, 8H). MS (ESI, m/e) [M + 1]$^+$ 905.1. |
| 50 | 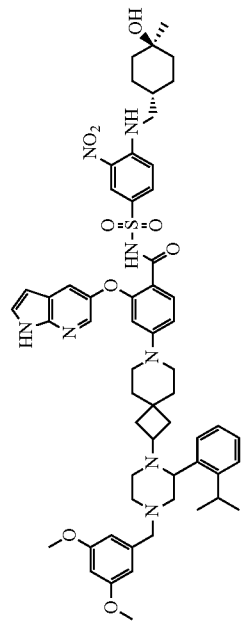 | 2-((1H-pyrrolo[2,3]-b]pyridin-5-yl)oxy)-4-(2-(4-(2,4-difluorobenzyl)-2-(2-isopropylphenyl)piperazin-1-yl)-7-azaspiro[3.5]nonan-7-yl)-N-(4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.49 (s, 1H), 8.31-8.24 (m, 1H), 7.87 (s, 1H), 7.54 (t, J = 9.6 Hz, 2H), 7.48-7.35 (m, 3H), 7.26-7.12 (m, 5H), 7.11-7.06 (m, 1H), 7.05-7.00 (m, 1H), 6.72 (d, J = 8.8 Hz, 1H), 6.58 (d, J = 8.8 Hz, 1H), 6.26 (s, 1H), 6.21 (s, 1H), 4.24 (s, 1H), 3.49 (s, 3H), 3.26-3.17 (m, 3H), 2.93-2.80 (m, 7H), 2.23-2.14 (m 2H), 2.09-1.94 (m, 2H), 1.71-1.59 (m, 5H), 1.57-3.50 (m, 2H), 1 37-1.29 (m, 6l-1), 1.24 (s, 3H), 1.19-1.15 (m, 3H), 1.12 (s, 1H) 1.09 (s, 3H), 1.07-1.04 (m, 2H). MS (ESI, m/e) [M + 1]$^+$ 1031.1. |
| 51 | 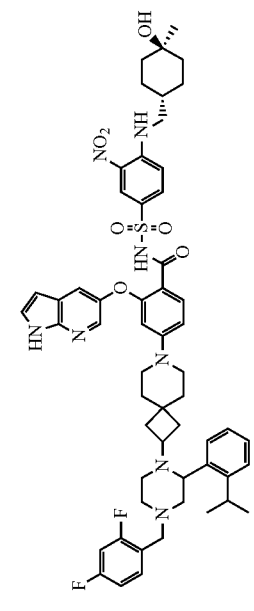 | 2-((1H-pyrrolo[2,3-b]pyridin-5-yl)oxy)-4-(2-(4-(3,5-difluorobenzyl)-2-(2-isopropylphenyl)piperazin-1-yl)-7-azaspiro[3.5]nonan-7-yl)-N-(4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.67 (s, 1H), 11.41 (s, 1H), 8.64-8.40 (m, 2H), 8.01 (s, 1H), 7.84-7.68 (m, 1H) 7.461-7.34(m, 4H), 7.34-6.90 (m, 5H), 6.70-6.57 (m, 1H), 6.36 (s, 1H), 6.14 (s, 1H), 4.25 (s, 1H), 3.65-3.44 (m, 4H), 3.31-3.20 (m, 4H), 3.10-2.76 (m ,8H), 2.31-2.11 (m, 2H), 2.06-1.92 (m 1H), 1.76-1.49 (m, 7H), 1.39-1.28 (m, 4H), 1.20-1.02 (m, 12H). MS (ESI, m/e) [M + 1]$^+$ 1031.7 |

-continued

| Ex. | structure | Compound name | Data |
|---|---|---|---|
| 52 | 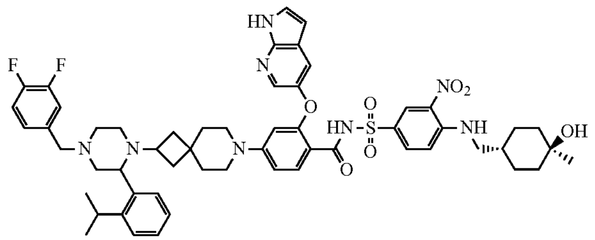 [SMILES: CC(C)c1ccccc1C1CN(Cc2ccc(F)c(F)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(3,4-difluorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.69 (s, 1H), 11.38 (br. 1H), 8.54-8.57 (m, 2H), 8.02 (s, 1H), 7.77 (d, J = 8 Hz, 1H), 7.37-7.50 (m, 5H), 7.06-7.20 (m, 4H), 6.65 (d, J = 8 Hz, 1H), 6.37 (s, 1H), 6.14 (s, 1H), 4.25 (s, 1H), 3.53-3.63 (m, 2H), 3.26-3.33 (m, 2H), 2.91-2.97 (m, 8H), 2.01-2.33 (m, 3H), 1.52-1.69 (m, 7H), 1.04-1.36 (m, 10H) MS (ESI, m/e) (M + 1)$^+$ 1031.6 |
| 52a | or | 2-((1H-pyrrolo[2,3-b]pyridin-5-yl)oxy)-4-(2-(4-(3,4-difluorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.75 (s, 1H), 11.45 (s, 1H), 8.68-8.57 (m, 2H), 8.08 (s, 1H), 7.88-7.78 (m, 1H), 7.59-7.50 (m, 3H), 7.49-7.37 (m, 3H), 7.27 (s, 1H), 7.25-7.19 (m, 2H), 7.17-7.08 (m, 2H), 6.74-6.67 (m, 1H), 6.43 (s, 1H), 6.19 (s, 1H), 4.31 (s, 1H), 3.78-3.46 (m, 3H), 3.34 (s, 3H), 3.12-2.88 (m, 7H), 2.32-2.23 (m, 1H), 2.14-2.03 (m, 1H), 1.79-1.69 (m, 4H), 1.65-1.55 (m, 3H), 1.43-1.35 (m, 4H), 1.34-1.21 (m, 5H), 1.25-1.21 (m, 2H), 1.20-1.18 (m, 1H), 1.18-1.14 (m, 4H), 1.13-1.06 (ns, 4H) MS (ESI, m/e) [M + 1]$^+$ 1031.9. |
| 53 | 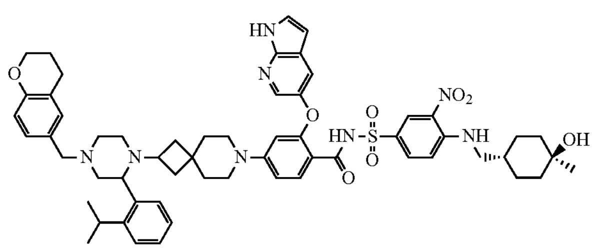 [SMILES: CC(C)c1ccccc1C1CN(Cc2ccc3c(c2)CCCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-y)oxy)-4-(2-(4-(chroman-6-ylmethyl))-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.68 (s, 1H), 11.23-10.95 (m, 1H), 10.74-10.62 (m, 0.5H), 8.57-8.54 (m, 1H), 8.02 (s, 1H), 7.77 (d, J = 8.8 Hz, 1H), 7.49-7.46 (m, 3H), 7.42-7.31 (m 1H), 7.25 (s, 2H), 7.08-7.05 (m, 4H), 6.65-6.63 (m, 2H), 6.37 (s, 1H), 6.14 (s, 1H), 4.24 (s, 1H), 4.10 (s, 2H), 3.75 (s, 2H), 3.50 (s, 1H), 3.28 (s, 3H), 2.96-2.91 (m, 8H), 2.69 (s, 3H), 2.08 (s, 1H), 1.88 (s, 2H), 1.68-1.58 (m, 7H), 1.38-1.15 (m, 11H), 1.12-1.10 (m, 9H). MS (ESI, m/e) [M + l]$^+$ 1051.7. |

| Ex. | structure | Compound name | Data |
|---|---|---|---|
| 54 | 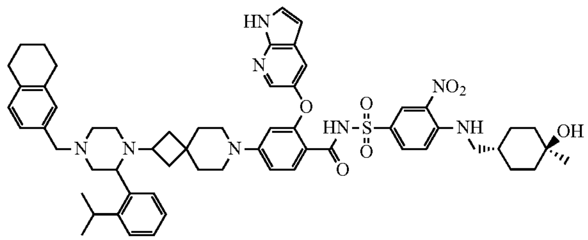 [SMILES: CC(C)c1ccccc1C1CN(Cc2ccc3c(c2)CCCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-((5,6,7,8-tetrahydronaphthalen-2-yl)methyl)piperazin-1-yl)-7-azaspiro[3.5]nonan-7-yl)benzamide | $^{1}$H NMR (400 MHz, DMSO-d$_6$) δ ppm: 11.68 (s, 1H), 11.17 (br, 1H), 8.62-8.53 (m, 2H), 8.02 (s, 1H), 7.78 (d, J = 8.4 Hz, 1H), 7.52-7.45 (m, 3H), 7.38-7.10 (m, 4H), 7.09-6.96 (m, 2H), 6.66 (d, J = 8.4 Hz, 1H), 6.37 (s, 1H), 6.14 (s, 1H), 4.25 (s, 1H), 3.84-3.35 (m, 3H), 3.30-3.25 (m, 3H), 3.07-2.72 (m, 8H), 2.69-2.60 (m, 5H), 2.35-1.95 (m, 2H), 1.74-1.51 (m, 10H), 1.39-1.15 (m, 12H), 1.14-1.02 (m, 8H). MS (ESI, m/e) [M + 1]$^+$ 1049.7. |
| 55 | 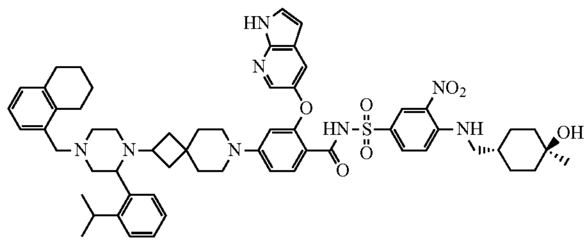 [SMILES: CC(C)c1ccccc1C1CN(Cc2cccc3c2CCCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-((5,6,7,8-tetrahydronaphthalen-1-yl)methyl)piperazin-1-yl)-7-azaspiro[3.5]nonan-7-yl)benzamide | $^{1}$H NMR (400 MHz, DMSO-d$_6$) δ ppm: 11.68 (s, 1H), 11.47-11.33 (m, 1H), 8.54 (s, 2H), 8.01 (s, 1H), 7.76 (s, 1H), 7.49 (s, 3H), 7.15-7.12 (m, 8H), 6.66 (s, 1H), 6.36 (s, 1H), 6.13 (s, 1H), 4.25 (s, 1H), 3.53 (s, 1H), 3.27 (s, 2H), 2.96-2.94 (m, 7H), 2.69 (s, 5H), 1.98 (s, 1H), 1.69-1.63 (m, 6H), 1.56-1.52 (m, 2H), 1.36-1.30 (m, 5H), 1.26-1.20 (m, 12H), 1.19-1.16 (m, 2H), 1.13 (s, 1H), 1.10-1.06 (m, 4H), 1.03 (s, 2H). MS (ESI, m/e) [M + 1]$^+$ 1049.7. |
| 56 | 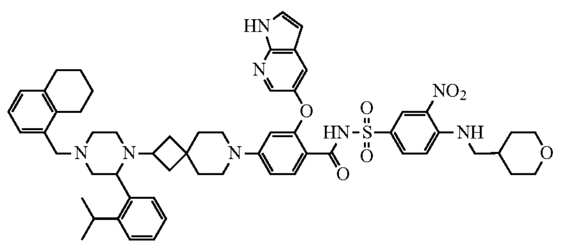 [SMILES: CC(C)c1ccccc1C1CN(Cc2cccc3c2CCCC3)CCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(2-(2-isopropylphenyl)-4-((5,6,7,8-tetrahydronaphthalen-1-yl)methyl)piperazin-1-yl)-7-azaspir[3.5]nonan-7-yl)-N-((3-nitro-4-(((tetrahydro-2H-pyran-4-yl)methyl)amino)phenyl)sulfonyl)benzamide | $^{1}$H NMR (400 MHz, DMSO-d$_6$) δ ppm: 11.30 (s, 1H), 8.58-8.56 (m, 2H), 8.02 (d, J = 2.2 Hz, 1H), 7.77 (d, J = 8.8 Hz, 1H), 7.49-7.46 (m, 3H), 7.22 (s, 2H), 7.12-7.02 (m, 2H), 7.02-6.91 (m, 2H), 6.65 (d, J = 8.8 Hz, 1H), 6.37 (s, 1H), 6.14 (s, 1H), 3.84 (d, J = 8.4 Hz, 2H), 3.51 (s, 2H), 3.32-3.22 (m, 5H), 2.98-2.91 (m, 7H), 2.73-2.70 (m, 6H), 2.20 (s, 1H), 2.08 (s, 1H), 2.01 (s, 1H), 1.91-1.90 (m, 1H), 1.79-1.55 (m, 8H), 1.36-1.15 (m, 11H), 1.03 (s, 4H). MS (ESI, m/e) [M + 1]$^+$ 1021.7. |

| Ex. | structure | Compound name | Data |
|---|---|---|---|
| 57 | 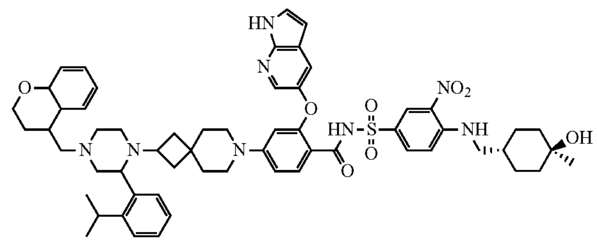 [SMILES: CC(C)c1ccccc1C1CN(CC2CCOC3C=CC=CC23)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yloxy)-4-(2-(4-(chroman-4-ylmethyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.55 (s, 1H), 8.40 (s, 2H), 7.92 (s, 1H), 7.65-7.55 (m, 1H), 7.54-7.46 (m, 1H), 7.42 (s, 2H), 7.31 (s, 1H), 7.26-7.06 (m, 5H), 7.04-6.97(m, 1H), 6.90-6.74 (m, 2H), 6.68 (d, J = 8.0 Hz, 1H), 6.59 (d, J = 8.0 Hz, 1H), 6.30 (s, 1H), 6.17 (s, 1H), 4.28 (s, 1H), 4.15-3.98 (m, 3H), 3.26-3.18 (m, 2H), 3.03 (brs, 1H), 2.98-2.80 (m, 8H), 2.73-2.64 (m, 1H), 2.31-2.15 (m, 2H), 1.96-1.83 (m, 2H), 1.70-1.58 (m, 5H), 1.52 (d, J = 12.0 Hz, 2H), 1.38-1.24 (m, 7H), 1.26-1.17 (m, 5H), 1.16-1.11 (m, 4H), 1.08 (s, 5H). MS (ESI, m/e) [M + 1]⁺ 1051.6. |
| 58 | 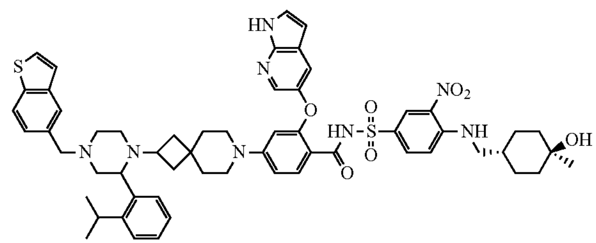 [SMILES: CC(C)c1ccccc1C1CN(Cc2ccc3sccc3c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(benzo[b]thiophen-5-ylmethyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.67 (s, 1H), 11.32 (s, 1H), 8.54 (s, 2H), 8.02 (s, 1H), 7.95 (d, J = 8.4 Hz, 1H), 7.83 (s, 1H), 7.78-7.75 (m, 2H), 7.48-7.46 (m, 3H), 7.43-7.41 (m, 1H), 7.36 (d, J = 7.4 Hz, 1H), 7.22 (s, 3H), 7.06-7.04 (m, 1H), 6.64 (d, J = 9.2 Hz, 1H), 6.37 (s, 1H), 6.14 (s, 1H), 4.24 (s, 1H), 3.78 (s, 3H), 3.29-3.26 (m, 3H), 2.96-2.94 (m, 7H), 2.72 (s, 1H), 2.33 (s, 1H), 1.63-1.60 (m, 7H), 1.29-1.20 (m, 13H), 1.13-1.10 (m, 4H), 1.05-1.02 (m, 3H). MS (ESI, m/e) [M + 1]⁺ 1051.7 |
| 59 | 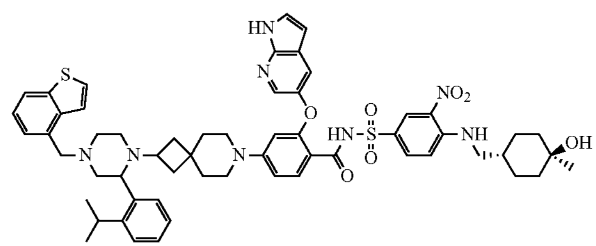 [SMILES: CC(C)c1ccccc1C1CN(Cc2cccc3sccc23)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(benzo[b]thiophen-4-ylmethyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.35 (s, 1H), 8.60-8.45 (m, 2H), 8.02 (s, 1H), 7.98-7.85 (m, 1H), 7.83-7.60 (m, 3H), 7.57-6.84 (m 11H), 6.72-6.59 (m, 2H), 6.37 (s, 1H), 6.13 (s, 1H), 4.24 (s, 1H), 4.10-3.90 (m, 1H), 3.88-3.36 (m, 2H), 3.33-3.22 (m, 3H), 3.05-2.75 (m, 7H), 2.75-2.58 (m, 1H), 2.28-1.93 (m, 2H), 1.76-1.49 (m, 6H), 1.39-1.28 (m 4H), 1.19-1.06 (m, 8H), 1.05-0.90 (m, 4H). MS (ESI, m/e) [M + 1]⁺ 1051.7 |
| 60 | 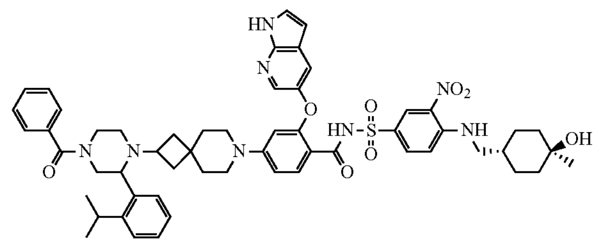 [SMILES: CC(C)c1ccccc1C1CN(C(=O)c2ccccc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-benzoyl-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-1-nitrophenyl)sulfonyl)benzamide | ¹H NMR (400 MHz, DMSO-d₆) δ ppm: 11.69 (s, 1H), 11.40 (br, 1H), 8.54-8.52 (m, 2H), 8.03 (d, J = 2.4 Hz, 1H), 7.79 (d, J = 8.8 Hz, 1H), 7.63-7.32 (m, 9H), 7.30-7.05 (m, 4H), 6.66 (d, J = 8.8 Hz, 1H), 6.38 (s, 1H), 6.13 (s, 1H), 4.53-4.35 (m, 1H), 4.24 (s, 1H), 3.69-3.42 (m, 1H), 3.33-2.80 (m, 12H), 2.27-2.19 (m, 1H), 1.72-1.50 (m, 7H), 1.39-1.12 (m, 11H), 1.08-1.03 (m, 8H). MS (ESI, m/e) [M + 1]⁺ 1010.0. |

| Ex. | structure | Compound name | Data |
|---|---|---|---|
| 61 | 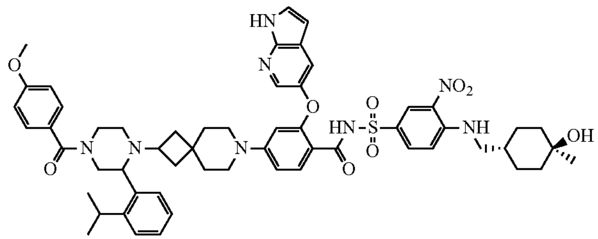 [SMILES: COc1ccc(C(=O)N2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methoxybenzoyl)piperazin-1-yl)-7-azaspiro[3.5]nonan-7-yl)benzamide | $^1$H NMR (400 MHz, DMSO-$d_6$) δ ppm: 11.69 (s, 1H), 11.41 (br, 1H), 8.55-8.57 (m, 2H), 8.03 (s, 1H), 7.78 (d, J = 8 Hz, 1H), 7.37-7.50 (m, 6H), 7.07-7.20 (m, 4H), 6.91-6.99 (m, 2H), 6.65 (d, J = 8 Hz, 1H), 6.38 (s, 1H), 6.13 (s, 1H), 4.25 (s, 1H), 3.75 (s, 3H), 3.43 (s, 1H), 3.27-3.40 (m, 2H), 2.92-2.97 (m, 6H), 1.99-2.09 (m, 2H), 1.52-1.69 (ns, 8H), 1.09-1.36 (m, 21) MS (ESI, m/e) [M + 1]$^+$ 1039.6. |
| 62 | 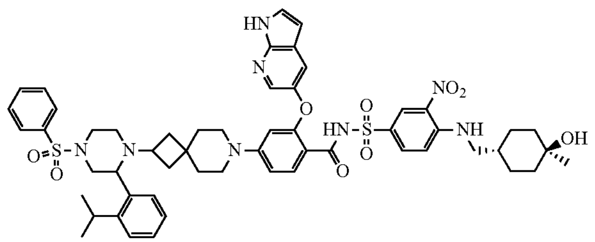 [SMILES: CC(C)c1ccccc1C1CN(S(=O)(=O)c2ccccc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-1-(phenylsulfonyl)piperazin-1-yl)-7-azaspiro[3.5]nonan-7-yl)benzamide | $^1$H NMR (400 MHz, DMSO-$d_6$) δ ppm: 11.69 (s, 1H), 11.41 (s, 1H), 8.50-8.40 (m, 2H), 8.02 (m, 1H), 7.84-7.65 (m, 6H), 7.55-7.40 (m, 3H), 7.35-7.05 (m, 5H), 6.35(m, 1H), 6.13 (s, 1H), 6.01 (s, 1H), 4.25 (s, 1H), 3.71 (m, 1H), 3.52 (m, 1H), 3.26 (s, 3H), 3.20-2.70 (m, 6H), 2.45-2.30 (m, 1H), 2.21 (m, 2H), 1.78-1.50 (m, 8H), 1.40-1.05 (m, 20H). MS (ESI, m/e) [M + 1]$^+$ 1045.5. |
| 63 | 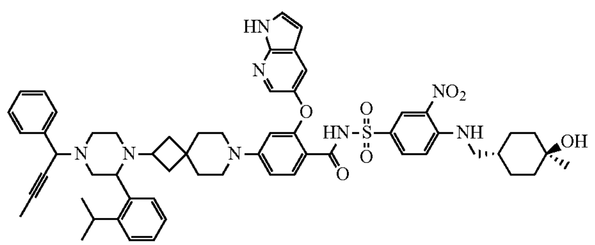 [SMILES: CC#CC(c1ccccc1)N1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)C(c2ccccc2C(C)C)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(1-phenylbut-2-yn-1-yl)piperazin-1-yl)-7-azaspiro[3.5]nonan-7-yl)benzamide | $^1$H NMR (400 MHz, DMSO-$d_6$) δ ppm: 11.67 (s, 1H), 11.43 (br, 1H), 8.60-8.45 (m, 2H), 8.01 (s, 1H), 7.80-7.70 (m, 1H), 7.54-7.42 (m, 5H), 7.37-7.01 (m, 8H), 6.68-6.62 (m, 1H), 6.36 (s, 1H), 6.13 (s, 1H), 4.56 (br, 1H), 4.26 (s, 1H), 3.58-3.35 (m, 2H), 3.31-3.22 (m, 3H), 3.04-2.80 (m, 7H), 2.35-2.21 (m, 2H), 2.09-1.95 (m, 2H), 1.91 (s, 3H), 1.73-1.52 (m, 8H), 1.38-1.20 (m, 7H), 1.15-1.08 (m, 10H). MS (ESI, m/e) [M + 1]$^+$ 1033.6. |
| 64a | 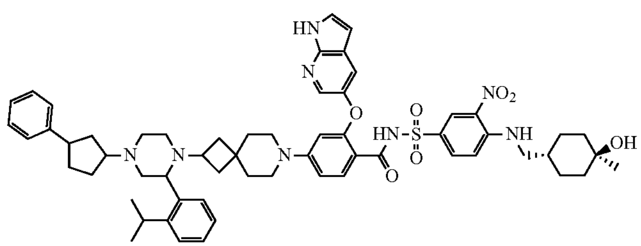 [SMILES: CC(C)c1ccccc1C1CN(C2CCC(c3ccccc3)C2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(3-phenylcyclopentyl)piperazin-1-yl)-7-azaspiro[3.5]nonan-7-yl)benzamide | $^1$H NMR (400 MHz, DMSO-$d_6$) δ ppm: 11.68 (s, 1H), 11.21 (br, 1H), 8.60-8.53 (m, 2H), 8.02 (s, 1H), 7.78 (d, J = 8.8 Hz, 1H), 7.52-7.43 (m, 4H), 7.33-7.13 (m, 8H), 7.07 (d, J = 8.8 Hz, 1H), 6.66 (d, J = 8.8 Hz, 1H), 6.37 (s, 1H), 6.14 (s, 1H), 4.24 (s, 1H), 3.90-3.81 (m, 1H), 3.60-3.41 (m, 2H), 3.30-3.24 (m, 2H), 3.17-2.80 (m, 10H), 2.44-1.37 (m, 2H), 2.20-1.90 (m, 4H), 1.74-1.51 (m, 9H), 1.39-1.26 (m, 15H), 1.24-1.05 (m, 4H) MS (ESI, m/e) [M + 1]$^+$ 1050.8. |

| Ex. | Compound name | Data |
|---|---|---|
| 64b | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-phenylpiperazin-1-yl)-7-azaspir[3.5]nonan-7-yl)benzamide | $^1$H NMR (400 MHz, DMSO-$d_6$) δ ppm: 11.68 (s, 1H), 11.21 (br, 1H), 8.62-8.53 (m, 2H), 8.02 (s, 1H), 7.78 (d, J = 8.8 Hz, 1H), 7.53-7.43 (m, 4H), 7.33-7.15 (m, 8H), 7.07 (d, J = 8.8 Hz, 1H), 6.66 (d, J = 8.8 Hz, 1H), 6.37 (s, 1H), 6.14 (s, 1H), 4.24 (s, 1H), 3.90-3.85 (m, 1H), 3.60-3.41 (m, 2H), 3.30-3.24 (m, 2H), 3.14-2.80 (m, 10H), 2.44-1.32 (m, 2H), 2.15-1.90 (m, 4H), 1.74-1.51 (m, 9H), 1.39-1.26 (m, 15H), 1.24-1.05 (m, 4H) MS (ESI, m/e) [M + 1]$^+$ 1050.7. |
| 65 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(methylsulfonyl)piperazin-1-yl)-7-azaspir[3.5]nonan-7-yl)benzamide | $^1$H NMR (400 MHz, DMSO-$d_6$) δ ppm: 11.72 (s, 1H), 8.70-8.53 (m, 2H), 8.03-8.02 (m, 1H), 7.82 (d, J = 9.1 Hz, 1H), 7.52-7.49 (m, 3H), 7.27-7.21 (m, 5H), 7.14-7.05 (m, 3H), 7.10-7.05 (m, 2H), 6.85-6.80 (m, 1H), 6.65-6.60 (m, 1H), 6.37 (s, 1H), 6.13 (s, 1H), 4.75-4.65 (m, 1H), 4.30-4.25 (m, 1H), 3.35-3.30 (m, 6H), 3.10-2.95 (m, 5H), 1.95-1.85 (m, 5H), 1.80-1.50 (m, 3H), 1.45-1.35 (m, 8H), 1.34-1.22 (m, 8H), 1.18-1.10 (m, 4H) MS (ESI, m/e) [M + 1]$^+$ 982.1 |
| 66 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)piperidin-1-yl)-7-azaspiro[3.5]nonan-7-yl)benzamide | $^1$H NMR (400 MHz, DMSO-$d_6$) δ ppm 11.69 (s, 1H), 11.41 (br, 1H), 8.63-8.53 (m, 2H), 8.03 (s, 1H), 7.79 (d, J = 8.8 Hz, 1H), 7.52 (d, J = 8.8 Hz, 1H), 7.47-7.40 (m, 3H), 7.33-7.06 (m, 4H), 6.66 (d, J = 8.8 Hz, 1H), 6.38 (s, 1H), 6.13 (s, 1H), 4.25 (s, 1H), 3.56 (d, J = 9.6 Hz, 2H), 3.33-3.24 (m, 3H), 3.23-3.02 (m, 2H), 2.84-2.74 (m, 1H), 2.25-2.15 (m, 1H), 1.74-1.50 (m, 9H), 1.39-1.12 (m, 16H), 1.08-1.03 (m, 3H) MS (ESI, m/e) [M + 1]$^+$ 984.0. |
| 67 | 2-((1H-pyrrolo[2,3-b]pyridin-5-yl)oxy)-4-(2-(4-benzyl-2-(2-isopropylphenyl)piperidin-1-yl)-7-azaspiro[3.5]nonan-7-yl)-N-((4-(((1r,4r)-4-hydroxy-4-methylcyclohexyl)methyl)amino)-3-nitrophenyl)benzamide | $^1$H NMR (400 MHz, DMSO-$d_6$) δ ppm 11.68 (s, 1H), 11.45 (s, 1H), 8.63-8.40 (m, 2H), 8.02 (s, 1H), 7.85-7.70 (m, 2H), 7.58-7.42 (m, 3H), 7.38-7.15 (m, 8H), 7.12-6.98 (m, 1H), 6.73-6.60 (m, 1H), 6.37 (s, 1H), 6.18 (s, 1H), 4.90-4.70 (m, 1H), 4.25 (s, 1H), 3.84-3.65 (m, 1H), 3.61-3.48 (m, 1H), 3.28 (s, 3H), 3.05-2.80 (m, 6H), 2.35-1.94 (m, 5H), 1.74-1.58 (m, 4H), 1.58-1.49 (m, 2H), 1.49-1.23 (m, 12H), 1.17-1.05 (m, 8H) MS (ESI, m/e) [M + 1]$^+$ 994.7 |

-continued

| Ex. | structure | Compound name | Data |
|---|---|---|---|
| 68 | 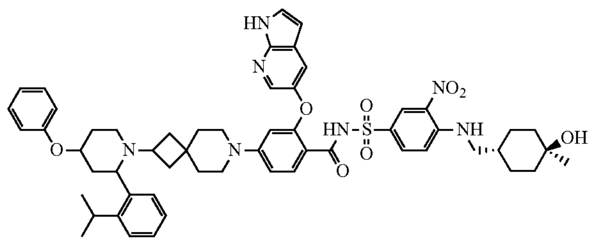 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-phenoxypiperidin-1-yl)-7-azaspiro[3.5]nonan-7-yl)benzamide | ¹H NMR (400 MHz, DMSO-d₆) δ ppm 11.69 (s, 1H), 11.43 (s, 1H), 8.56-8.54 (m, 2H), 8.02 (s, 2H), 7.77 (d, J = 9.0 Hz, 1H), 7.48-7.46 (m, 3H), 7.29-7.26 (m, 5H), 7.06 (d, J = 8.0 Hz, 3H), 6.96-6.93 (m, 1H), 6.66 (d, J = 9.0 Hz, 1H), 6.37 (s, 1H), 6.18 (s, 1H), 4.85-4.83 (m, 2H), 4.26 (s, 1H), 3.83 (s, 1H), 3.28 (s, 3H), 2.92-2.90 (m, 5H), 2.46-2.36 (m, 1H), 2.05-2.01 (m, 5H), 1.69-1.65 (m, 1H), 1.55-1.53 (m, 3H), 1.33-1.30 (m 16H) 1.13-1.10 (m, 5H), 0.85-0.83 (m, 4H), 0.58 (s, 1H). MS (ESI, m/e) [M + I]⁺ 996.6. |
| 69 | | (R or S)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)-N-((3-nitro-4-(((tetrahydro-2H-pyran-4-yl)methyl)amino)phenyl)sulfonyl)benzamide | ¹H NMR (400 MHz, DMSO-d₆) δ ppm:: 11.68 (s, 1H), 11.30 (s, 1H), 8.60 (s, 1H), 8.54 (s, 1H), 8.01 (s, 1H), 7.76 (s, 1H), 7.49 (s, 3H), 7.43-7.32 (m, 1H), 7.24 (s, 4H), 7.09 (s, 2H), 6.90 (s, 2H), 6.64 (d, J = 8.4 Hz, 1H), 6.37 (s, 1H), 6.14 (s, 1H), 3.87-3.83 (m, 2H), 3.72 (s, 4H), 3.63-3.5.3 (m, 1H), 3.30-3.22 (m, 4H), 2.96-2.90 (m, 8H), 2.28-2.15 (m, 1H), 1.88 (s, 1H), 1.63-1.60 (m, 4H), 1.23-1.10 (m, 13H), 1.06 (s, 4H). MS (ESI) m/e [M + I]⁺ 998.0. | or

| Ex. | structure | Compound name | Data |
|---|---|---|---|
| 70 | 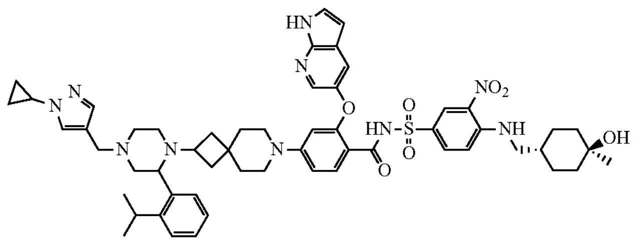 [SMILES: CC(C)c1ccccc1C1CN(Cc2cnn(C3CC3)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-((1-cyclopropyl-1H-pyrazol-4-yl)methyl)-2-(4-((1-isopropylphenyl)piperazin-1-yl)-7-azaspiro[3.5]nonan-7-yl)-N-(4-(((1r,4r)-4-hydroxy-4-methylcyclohexyl)amino)-3-nitrophenyl)sulfonyl)benzamide | ¹H NMR (400 MHz, DMSO-d₆) δ ppm: 11.73 (s, 1H), 11.12 (s, 1H), 8.58 (s, 2H), 8.06 (s, 1H), 7.87-7.75 (m, 2H), 7.58-7.49 (m, 3H), 7.48-7.40 (m, 2H), 7.35-7.25 (m, 2H), 7.19 (s, 1H), 7.09 (d, J = 8.8 Hz, 1H), 6.69 (d, J = 8.8 Hz, 1H), 6.42 (s, 1H), 6.20 (s, 1H), 4.30 (s, 1H), 3.82-3.63 (m, 3H), 3.56-3.47 (m, 1H), 3.37-3.28 (m, 3H), 3.15-2.79 (m, 9H), 2.37-2.28 (m, 1H), 1.80-1.65 (m, 5H), 1.64-1.56 (m, 3H), 1.43-1.35 (m, 4H), 1.29 (s, 4H), 1.24 (s, 3H), 1.15 (s, 6H), 1.07-0.93 (m, 6H). MS (ESI, m/e) [M + 1]⁺ 1025.6. |
| 71 | 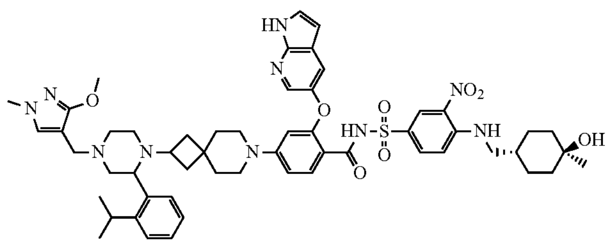 [SMILES: COc1nn(C)cc1CN1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)C(c2ccccc2C(C)C)C1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-((3-methoxy-1-methyl-1H-pyrazol-4-yl)methyl)piperazin-1-yl)-7-azaspiro[3.5]nonan-7-yl)benzamide | ¹H NMR (DMSO-d₆) δ 11.69 (s, 1H), δ.65-8.51 (m, 2H), 8.02 (s, 1H), 7.77 (d, J = 7.6 Hz, 1H), 7.61 (s, 1H), 7.55-7.45 (m, 3H), 7.42 (s, 1H), 7.34-7.22 (m, 2H), 7.16 (s, 1H), 7.07 (d, J = 8.4 Hz, 1H), 6.66 (d, J = 8.4 Hz, 1H), 6.37 (s, 1H), 6.13 (s, 1H), 4.25 (s, 1H), 3.81-3.74(m, 4H), 3.71-3.63 (s, 3H), 3.32-3.23 (m, 4H), 3.08 (s, 4H), 2.99-2.79 (m, 7H), 2.36-2.28 (m, 1H), 2.06-1.93 (m, 1H), 1.73-162 (m, 4H), 1.58-1.50 (m, 3H), 1.37-1.2.9 (m, 4H), 1.26-1.22 (m 4H), 1.21-1.18 (m, 3H), 1.06 (s, 6H). MS (ESI, m/e) [M + 1]⁺ 1029.5. |
| 72 | 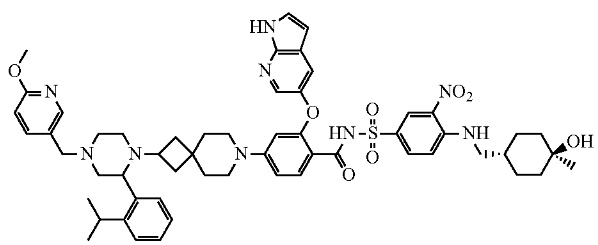 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cn1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-((6-methoxypyridin-3-yl)methyl)piperazin-1-yl)-7-azaspiro[3.5]nonan-7-yl)benzamide | ¹H NMR (400 MHz, DMSO-d₆) δ ppm: 11.69 (s, 1H), 11.29 (br, 1H), 8.62-8.53 (m, 2H), 8.09-8.01 (m, 2H), 7.81-7.74 (m, 1H), 7.70-7.64 (m, 1H), 7.54-7.44 (m, 3H), 7.43-7.03 (m, 5H), 6.82-6.76 (m, 1H), 6.68-6.62 (m, 1H), 6.37 (s, 1H), 6.14 (s, 1H), 4.25 (s, 1H), 3.81 (s, 3H), 3.64-3.45 (m, 2H), 3.30-3.25 (m, 2H), 3.07-2.72 (m, 7H), 2.69-2.54 (m, 2H), 2.45-1.85 (m, 7H), 1.74-1.51 (m, 7H), 1.39-1.15 (m, 13H), 1.14-1.02 (m, 7H). MS (ESI, m/e) [M + 1]⁺ 1027.1. |

| Ex. | structure | Compound name | Data |
|---|---|---|---|
| 73 | 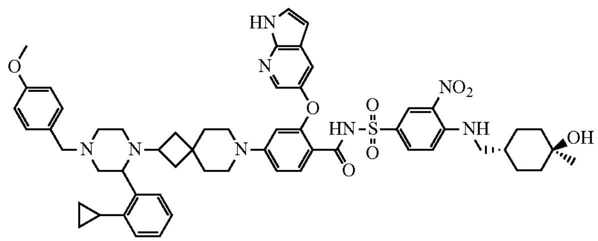 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C3CC3)C2)cc1] | 2-((1H-pyrrolo[2,3-b]pyridin-5-yl)oxy)-4-(2-(2-(2-cyclopropylphenyl)-4-(4-methoxybenzyl)piperazin-1-yl)-7-azaspiro[3.5]nonan-7-yl)-N-(4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.67 (s, 1H), 11.29-11.06 (m, 1H), 8.53 (s, 2H), 8.01 (s, 1H), 7.77 (s, 1H), 7.48 (s, 4H), 7.25 (s, 3H), 7.11 (s, 3H), 6.89 (s, 3H), 6.65 (s, 1H), 6.36 (s, 1H), 6.14 (s, 1H), 4.25 (s, 1H), 3.72 (s, 4H), 3.62-3.47 (m, 1H), 3.27 (s, 2H), 2.98-2.90 (m, 8H), 1.99 (s, 1H), 1.66 (s, 3H), 1.56-1.50 (m, 3H), 1.30-1.26 (m, 11H), 1.09 (s, 5H), 0.87-0.83 (m, 5H). MS (ESI) m/e [M + 1]$^+$ 1024.1. |
| 74 | 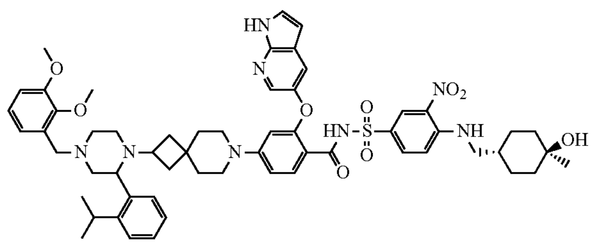 [SMILES: COc1cccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)c1OC] | 2-((1H-pyrrolo[2,3-b]pyridin-5-yl)oxy)-4-(2-(4-(2,3-dimethoxybenzyl)-2-(2-isopropylphenyl)piperazin-1-yl)-7-azaspiro[3.5]nonan-7-yl)-N-(4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.41-11.12 (m, 1H), 8.57-8.54 (m, 2H), 8.02 (s, 1H), 7.77 (d, J = 8.0 Hz, 1H), 7.49-7.43 (m, 4H), 7.28-6.84 (m, 7H), 6.65 (d, J = 8.0 Hz, 1H), 6.14 (s, 1H), 4.25 (s, 1H), 3.79 (s, 3H), 3.63-3.60 (m, 5H), 3.28 (s, 2H), 2.98-2.90 (m, 7H), 2.68 (s, 1H), 2.03 (s, 1H), 1.73-1.49 (m, 7H), 1.37-0.97 (m, 22H). MS (ESI) m/e [M +1]$^+$ 1056.1. |
| 75 | 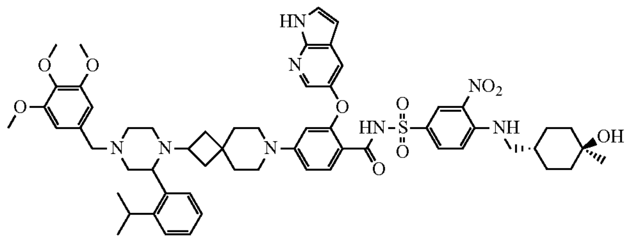 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc(OC)c1OC] | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-(2-(2-isopropylphenyl)-4-(3,4,5-trimethoxybenzyl)piperazin-1-yl)-7-azaspiro[3.5]nonan-7-yl)benzamide | $^1$H NMR (400 MHz, DMSO-d$_6$) δ ppm: 11.69 (s, 1H), 11.29 (br, 1H), 8.61-8.53 (m, 2H), 8.02 (s, 1H), 7.81-7.74 (m, 1H), 7.54-7.44 (m, 3H), 7.43-7.03 (m, 5H), 6.74-6.59 (m, 3H), 6.37 (s, 1H), 6.14 (s, 1H), 4.25 (s, 1H), 3.74 (s, 6H), 3.61 (s, 3H), 3.64-3.45 (m, 2H), 3.30-3.20 (m, 3H), 3.09-2.82 (m, 7H), 2.79-2.55 (m, 1H), 2.45-2.25 (m, 1H), 2.09-1.95 (m, 1H), 1.73-1.51 (m, 6H), 1.39-1.15 (m, 12H), 1.14-1.02 (m, 9H). MS (ESI, m/e) [M + 1]$^+$ 1085.5. |
| 76 | 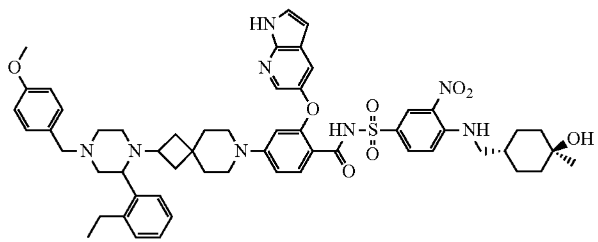 [SMILES: CCc1ccccc1C1CN(Cc2ccc(OC)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(2-(2-ethylphenyl)-4-(4-methoxybenzyl)piperazin-1-yl)-7-azaspiro[3.5]nonan-7-yl)-N-(4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.17 (br, 1H), 8.62-8.53 (m, 2H), 8.02 (s, 1H), 7.82 (d, J = 8.0 Hz, 1H), 7.54-7.44 (m, 3H), 7.43-7.03 (m, 7H), 6.94-6.85 (m, 2H), 6.65 (d, J = 8.0 Hz, 1H), 6.37 (s, 3H), 6.14 (s, 1H), 4.25 (s, 1H), 3.72 (s, 3H), 3.64-3.47 (m, 3H), 3.30-3.24 (m, 2H), 3.15-2.55 (m, 11H), 2.35-1.95 (m, 2H), 1.72-1.51 (m, 6H), 1.39-1.19 (m, 8H), 1.18-1.00 (m, 9H). MS (ESI, m/e) [M + 1]$^+$ 1011.5. |

| Ex. | structure | Compound name | Data |
|---|---|---|---|
| 77 | 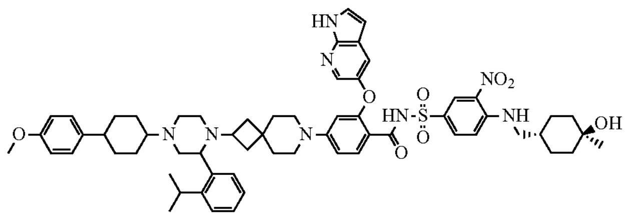 [SMILES: COc1ccc(C2CCC(N3CCN(C4CC5(CCN(c6ccc(C(=O)NS(=O)(=O)c7ccc(NC[C@H]8CC[C@](C)(O)CC8)c([N+](=O)[O-])c7)c(Oc7cnc8[nH]ccc8c7)c6)CC5)C4)C(c4ccccc4C(C)C)C3)CC2)cc1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(4-methoxyphenyl)cyclohexyl)piperazin-1-yl)-7-azaspiro[3.5]nonan-7-yl)benzamide | ¹H NMR (400 MHz, DMSO-d₆) δ ppm 11.70 (s, 1H), 11.44 (s, 1H), 8.65-8.48 (m, 2H), 8.19-7.87 (m, 2H), 7.85-7.74 (m, 1H), 7.59-7.13 (m, 8H), 7.11-6.98 (m, 1H), 6.94-6.81 (m, 2H), 6.75-6.81 (m, 1H), 6.37 (s, 1H), 6.37 (s, 1H), 6.16 (s, 1H), 5.81-5.39 (m, 1H), 3.89-3.57 (m, 9H), 3.46-3.34 (m, 4H), 3.34-3.22 (m, 3H), 3.09-2.65 (m, 6H), 2.29-1.76 (m, 8H), 1.76-1.47 (m, 9H), 1.41-1.27 (m, 6H), 1.20-1.01 (m, 9H). MS (ESI, m/e) [M + 1]⁺ 1093.5 |
| 78 | 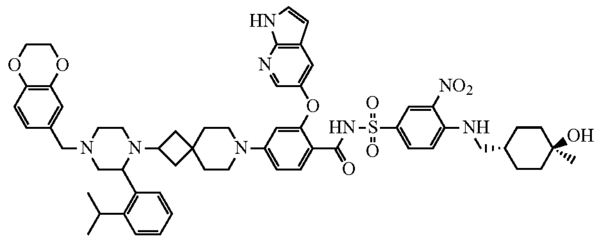 [SMILES: CC(C)c1ccccc1C1CN(Cc2ccc3c(c2)OCCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(2,3-dihydrobenzo[b][1,4]dioxin-6-yl)methyl)piperazin-1-yl)-2-(2-isopropylphenyl))-7-azaspiro[3.5]nonan-7-yl)-N-((4-(((1r,4r)-4-hydroxy-4-methylcyclohexyl)amino)-3-nitrophenyl)sulfonyl)benzamide | ¹H NMR (400 MHz, DMSO-d₆) δ ppm 11.69 (s, 1H), 11.18 (s, 1H), 8.64-8.46 (m, 2H), 8.02 (s, 1H), 7.84-7.62 (m, 1H), 7.57-7.36 (m, 4H), 7.35-7.10 (m, 3H), 7.10-6.99 (m, 1H), 6.96-6.72 (m, 3H), 6.72-6.58 (m, 1H), 6.37 (s, 1H), 6.14 (s, 1H), 4.26 (s, 1H), 4.24-4.17 (m, 4H), 3.91-3.43 (m, 3H), 3.32-3.17 (m, 5H), 3.10-2.55 (m, 9H), 1.78-1.50 (m, 6H), 1.41-1.24 (m, 6H), 1.22-1.15 (m, 4H), 1.15-0.98 (m, 9H ). MS (ESI, m/e) [M + 1]⁺ 1053.5 |
| 79 | 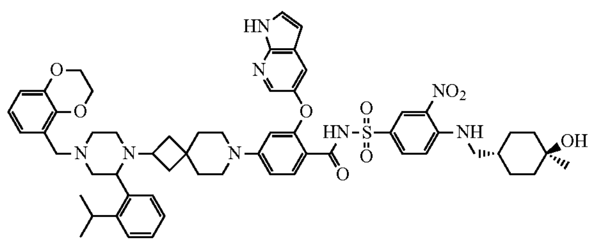 [SMILES: CC(C)c1ccccc1C1CN(Cc2cccc3c2OCCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-((2,3-dihydrobenzo[b][1,4]dioxin-5-yl)methyl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | ¹H NMR (400 MHz, DMSO-d₆) δ ppm: 11.70 (s, 1H), 11.44 (br, 1H), 8.61-8.53 (m, 2H), 8.03 (s, 1H), 7.89-7.74 (m, 2H), 7.54-7.42 (m, 3H), 7.40-7.13 (m, 3H), 7.12-6.62 (m, 5H), 6.38 (s, 1H), 6.16 (s, 1H), 4.28-4.17 (m, 5H), 3.78-3.55 (m, 2H), 3.45-3.35 (m, 5H), 3.30-2.63 (m, 10H), 2.09-1.95 (m, 1H), 173-1.51 (m, 6H), 1.39-1.15 (m, 11H), 1.14-1.02 (m, 8H). MS (ESI, m/e) [M + 1]⁺ 1054.1. |
| 79a | 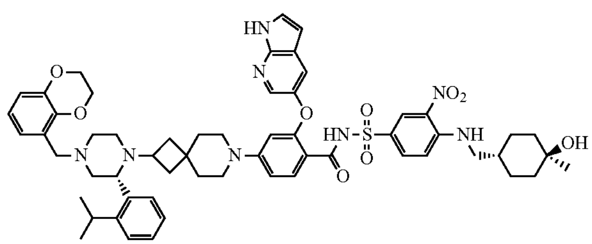 [SMILES: CC(C)c1ccccc1[C@@H]1CN(Cc2cccc3c2OCCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yloxy)-4-(2-(R-4-((2,3-dihydrobenzo[b][1,4]dioxin-5-yl)methyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.70 (s, 1H), 11.15 (br, 1H), 8.61-8.53 (m, 2H), 8.03 (s, 1H), 7.89-7.74 (m, 1H), 7.54-7.13 (m, 6H), 7.12-6.62 (m, 5H), 6.37 (s, 1H), 6.15 (s, 1H), 4.28-4.17 (m, 5H), 3.94-3.55 (m, 2H), 3.45-3.25 (m, 2H), 3.20-2.63 (m, 12H), 2.09-1.93 (m, 1H), 1.73-1.51 (m, 6H), 1.39-1.15 (m, 10H), 1.14-1.02 (m, 9H).MS (ESI, m/e) [M + 1]⁺ 1053.8. |

| Ex. | structure | Compound name | Data |
|---|---|---|---|
| 79b | 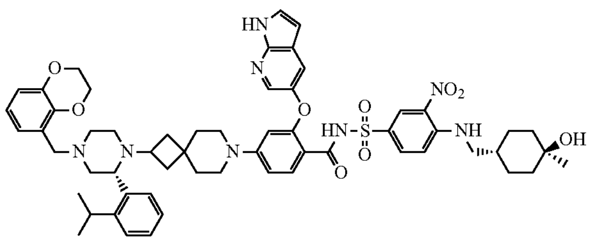 | 2-((1H-pyrrolo[2,3-b]pyridin-5-yl)oxy)-4-(2-(S-4-((2,3-dihydrobenzo[b][1,4]dioxin-5-yl)methyl)-2-(2-isopropylphenyl)piperazin-1-yl)-7-azaspiro[3.5]nonan-7-yl))-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.70 (s, 1H), 11.45-11.00 (m, 1H), 8,63-8.45 (m, 2H), 8.03 (s, 1H), 7.78 (d, J = 9.2 Hz, 1H), 7.55-6.73 (m, 10H), 6.66 (d, J = 8.4 Hz, 1H), 6.38 (s, 1H), 6.15 (s, 1H), 4.36-3.90 (m, 6H), 3.81-3.39 (m, 2H), 3.31-2.61 (m, 12H), 2.46-2.28 (m, 1H), 2,19-1,93 (m, 1H), 1.73-1.46 (m, 6H), 1.40-0.87 (m, 20H). MS (ESI, m/e) [1/2M + 1]$^+$ 527.8 |
| 80a | 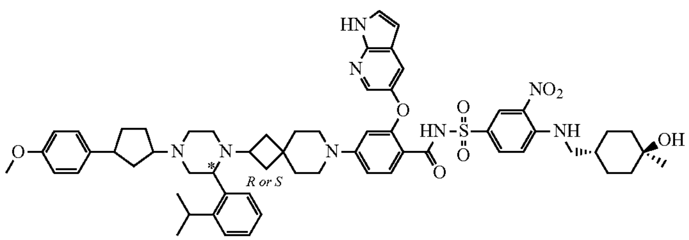 [SMILES: COc1ccc(C2CCC(N3CCN(C4CC5(CCN(c6ccc(C(=O)NS(=O)(=O)c7ccc(NC[C@H]8CC[C@](C)(O)CC8)c([N+](=O)[O-])c7)c(Oc7cnc8[nH]ccc8c7)c6)CC5)C4)C(c4ccccc4C(C)C)C3)C2)cc1] | (R or S)-2-(1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-(2-(2-isopropylphenyl)-4-(3-(cis or trans)(4-methoxyphenyl)cyclopentyl)piperazin-1-yl)-7-azaspiro[3.5]nonan-7-yl)benzamide; | $^1$H NMR (400 MHz, DMSO-$d_6$) δ ppm: 11.69 (s, 1H), 8.66-8.50 (m, 2H), 8.03 (s, 1H), 7.78 (d, J = 8.0 Hz, 1H), 7.56-7.42 (m, 4H), 7.36-7.04 (m, 6H), 6.94-6.80 (m 2H), 6.71-6.60 (m, 1H), 6.38 (s, 1H), 6.14 (s, 1H), 4.25 (s, 1H), 4.02-3.85 (m, 1H), 3.72 (s, 3H), 3.64-3.42 (m, 2H), 3.31-3.25 (m, 2H), 3.18-2.81 (m, 10H), 2.46-2.24 (m, 1H), 2.14-1.82 (m, 4H), 1.73-150 (m, 8H), 1.40-0.95 (m, 20H). MS (ESI, m/e) [M/2 + 1]$^+$ 540.6. |
| 80b | | (R or S)-2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-(2-(2-isopropylphenyl)-4-(3-(trans or cis)-(4-methoxyphenyl)cyclopentyl)piperazin-1-yl)-7-azaspiro[3.5]nonan-7-yl)benzamide | $^1$H NMR (400 MHz, DMSO-$d_6$) δ ppm: 11.69 (s, 1H), 8.66-8.50 (m, 2H), 8.03 (s, 1H), 7.78 (d, J = 8.0 Hz, 1H), 7.58-7.42 (m, 4H), 7.34-7.02 (m, 6H), 6.90-6.78 (m, 2H), 6.71-6.61 (m 1H), 6.38 (s, 1H), 6.14 (s, 1H), 4.25 (s, 1H), 4.01-3.85 (m , 1H), 3.70 (s, 3H), 3.62-3.40 (m, 2H), 3.30-3.25 (m, 2H), 3.16-2.81 (m, 10H), 2.10-1.49 (m, 12H), 1.44-0.93 (m, 20H). 2.44-2.19 MS (ESI, m/e) [M/2 + 1]$^+$ 540.7. |
| 81 | 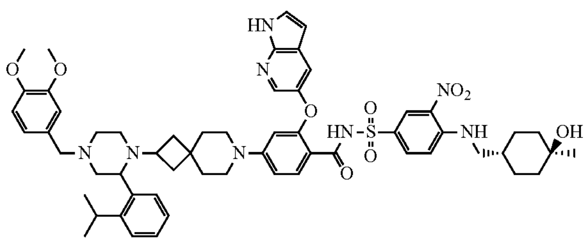 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1OC] | 2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.69 (s, 1H), 8.57-8.55 (m, 2H), 8.02 (s, 1H), 7.77 (s, 1H), 7.49-7.46 (m, 3H), 7.36 (s, 1H), 7.25 (s, 2H), 7.15 (s, 1H), 7.08 (s, 1H), 6.91 (s, 2H), 6.66 (s, 1H), 6.37 (s, 1H), 6.13 (s, 1H), 4.25 (s, 1H), 3.73 (s, 7H), 3.56 (s, 1H), 3.28 (s, 3H), 3.05-2.93 (m, 8H), 2.03 (s, 1H), 1.73-1.50 (m, 7H), 1.39-0.96 (m, 21H). MS (ESI, m/e) [M + 1]$^+$ 1055.7. |

| Ex. | structure | Compound name | Data |
|---|---|---|---|
| 81b | 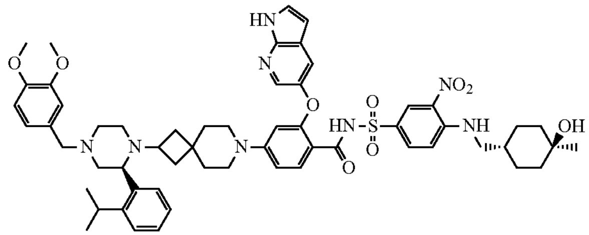 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@@H](c3ccccc3C(C)C)C2)cc1OC] | 2-((1H-pyrrolo[2,3-b]pyridin-5-yl)oxy)-4-(2-((S)-4-(3,4-dimethoxybenzyl)-2-(2-isopropylphenyl)piperazin-1-yl))-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.69 (s, 1H), 11.25 (br, 1H), 8.62-8.53 (m, 2H), 8.02 (s, 1H), 7.82-7.75 (m, 1H), 7.54-7.04 (m, 8H), 6.96-6.76 (m, 2H), 6.68-6.63 (m, 1H), 6.37 (s, 1H), 6.14 (s, 1H), 4.25 (s, 1H), 3.98-3.80 (m, 2H), 3.73 (s, 6H), 3.62-3.40 (m, 2H), 3.32-3.25 (m, 2H), 3.20-2.75 (m, 10H), 2.10-1.94 (m, 4H), 1.75-1.52 (m, 7H), 1.39-1.15 (m, 13H), 1.14-1.02 (m, 7H). MS (ESI, m/e) [M + 1]$^+$ 1055.8. |
| 82 | 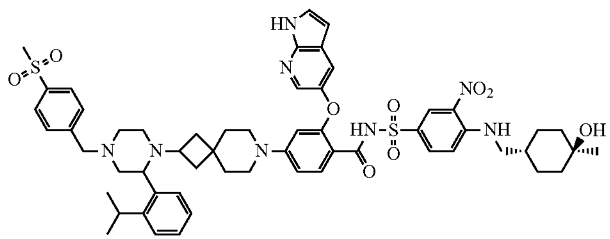 [SMILES: CC(C)c1ccccc1C1CN(Cc2ccc(S(C)(=O)=O)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(4-(methylsulfonyl)benzyl)piperazin-1-yl)-7-azaspiro[3.5]nonan-7-yl)benzamide | $^1$H NMR (400 MHz, DMSO-$d_6$) δ ppm 11.69 (s, 1H), 11.41 (s, 1H), 10.41 (s, 0H), 8.57-8.55 (m, 2H), 8.03 (s, 1H), 7.88 (s, 2H), 7.77 (s, 1H), 7.59 (s, 2H), 7.50-7.46 (m, 3H), 7.37 (s, 1H), 7.21 (s, 2H), 7.09 (s, 1H), 6.66 (s, 1H), 6.37 (s, 1H), 6.14 (s, 1H), 4.68 (s, 0H), 4.25 (s, 1H), 3.78 (s, 4H), 3.28 (s, 2H), 3.18 (s, 3H), 2.98-2.96 (m, 8H), 2.22 (s, 1H), 2.05-1.93 (m, 1H), 1.74-1.49 (m, 7H), 1.29-1.20 (m, 11H), 1.18-1.14 (m, 3H) 1.10 (m, 4H), 1.06-1.03 (m, 3H). MS (ESI, m/e) [M + 1]$^+$ 1074.3. |
| 83 | 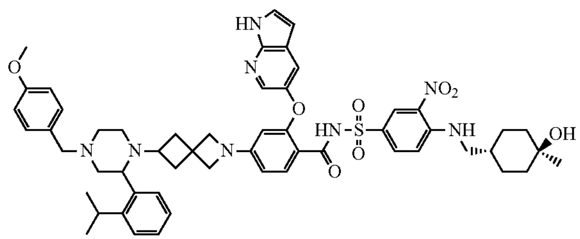 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-(2-(2-isopropylphenyl)-4-(4-methoxybenzyl)piperazin-1-yl)-2-azaspiro[3.3]heptan-2-yl)benzamide | $^1$H NMR (400 MHz, DMSO-$d_6$) δ ppm 11.72 (s, 1H), 11.26 (s, 1H), 8.72-8.51 (m, 2H), 8.03 (s, 1H), 7.86-7.77 (m, 1H), 7.71-6.98 (m, 11H), 6.97-6.78 (m, 2H), 6.40 (s, 1H), 6.10-5.95 (m, 1H), 5.48 (s, 1H), 4.24 (s, 1H), 3.72 (s, 3H), 3.68-3.41 (m, 6H), 3.33-3.16 (m, 4H), 3.10-2.82 (m, 3H), 2.77-2.61 (m, 2H), 2.28-2.15 (m, 1H), 2.03-1.90 (m, 2H), 1.75-1.47 (m, 6H), 1.40-1.28 (m, 3H), 1.21-1.00 (m, 11H). MS (ESI) [M + 1]$^+$ 998.0. |
| 84 | 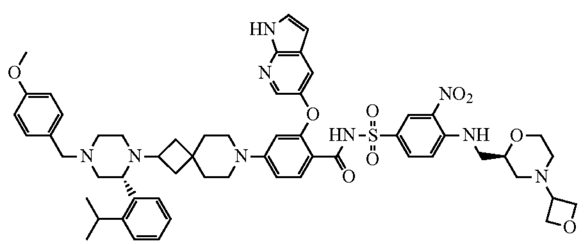 | 2-((1H-pyrrolo[2,3-b]pyridin-5-yl)oxy)-4-(2-((R or S)-2-(2-isopropylphenyl)-4-(4-methoxybenzyl)piperazin-1-yl)-7-azaspiro[3.5]nonan-7-yl)-N-((3-nitro-4-((R)-4-(oxetan-3-yl)morpholin-2-yl)methyl)amino)phenyl)sulfonyl)benzamide or | $^1$H NMR (400 MHz, DMSO-$d_6$) δ ppm 11.67 (s, 1H), 8.59 (s, 1H), 8.53 (s, 1H), 8.01 (s, 1H), 7.77 (s, 1H), 7.48 (s, 4H), 7.23 (s, 6H), 6.89 (s, 2H), 6.66 (s, 1H), 6.36 (s, 1H), 6.14 (s, 1H), 4.54 (s, 2H), 4.45 (s, 2H), 3.87-3.84 (m, 1H), 3.73-3.70 (m, 5H), 3.56 (s, 3H), 3.43 (s, 2H), 3.24-3.14 (m, 1H), 2.96-2.91 (m, 7H), 2.78-2.76 (m, 1H), 1.99 (s, 2H), 1.80 (s, 1H), 1.68-1.53 (2H), 1.25-1.20 (s, 15H), 1.06 (s, 4H). MS (ESI, m/e) [M + 1]$^+$ 1055.4. |

| Ex. | structure | Compound name | Data |
|---|---|---|---|
| 85 | 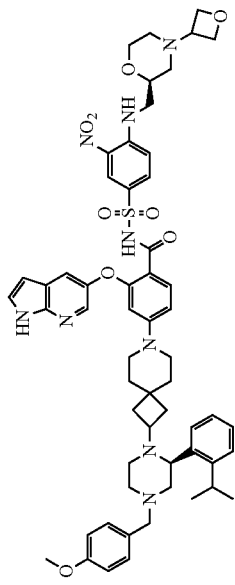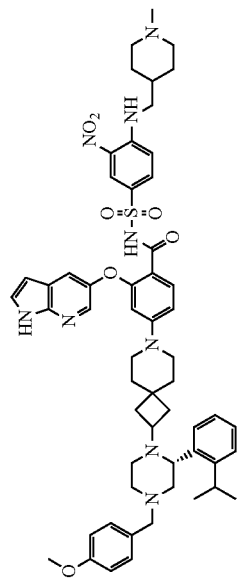 or 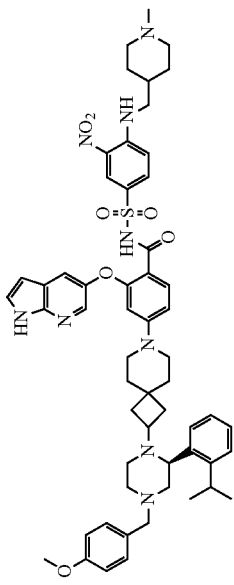 | (R or S)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)-N-((4-(((1-methylpiperidin-4-yl)methyl)amino)-3-nitrophenyl)sulfonyl)benzamide | $^1$H NMR (400 MHz, DMSO-d$_6$) δ ppm.: 11.65 (s, 1H), 11.51-11.18 (m, 1H), 8.57-8.55 (m, 2H), 7.98 (s, 1H), 7.72 (s, 1H), 7.45-7.43 (m, 5H), 7.22 (s, 4H), 7.11 (s, 2H), 6.87 (s, 2H), 6.64 (s, 1H), 6.35 (s, 1H), 6.15 (s, 1H), 3.72 (s, 4H), 2.94-2.90 (m, 9H), 2.67 (s, 4H), 2.27-2.11 (m, 1H), 1.99 (s, 2H), 1.89-1.86 (m, 3H), 1.64 (s, 2H), 1.47-1.46 (m, 3H), 1.30-1.28 (m, 3H), 1.20-1.17 (s, 4H), 1.06-1.04 (m, 5H), 0.86-0.84 (m, 3H). MS (ESI, m/e) [M + 1]$^+$ 1010.4. |

-continued

| Ex. | structure | Compound name | Data |
|---|---|---|---|
| 86 | | 2-((1H-pyrrolo[2,3-b]pyridin-5-yl)oxy)-4-(2-((R or S)-2-(2-isopropylphenyl)-4-(4-methoxybenzyl)piperazin-1-yl)-7-azaspiro[3.5]nonan-7-yl)-N-((3-nitro-4-((((S)-1-(tetrahydro-2H-pyran-4-yl)pyrrolidin-3-yl)methylamino)phenyl)sulfonyl)benzamide | $^1$H NMR (400 MHz, DMSO-d$_6$) δ ppm 11.70 (s, 1H), 8.72 (s, 1H), 8.56 (s, 1H), 8.04 (d, J = 9.2 Hz, 1H), 7.81 (d, J = 9.2 Hz, 1H), 7.59-7.52 (m, 2H), 7.49-7.40 (m, 2H), 7.35-7.21 (m, 4H), 7.19-7.04 (m, 2H), 6.97-6.88 (m, 2H), 6.68 (d, J = 9.2 Hz, 1H), 6.41 (s, 1H), 6.21 (s, 1H), 3.96 (d, J = 12.0 Hz, 2H), 3.77 (s, 3H), 3.69-3.58 (m, 2H), 3.55-3.50 (m, 2H), 3.39 (s, 4H), 3.32 (t, J = 12.0 Hz, 3H), 3.05-2.87 (m, 7H), 2.73 (s, 1H), 2.29-2.23 (m, 1H), 2.18-2.11 (m, 1H), 2.01-1.92 (m, 2H), 1.79-1.59 (m, 5H), 1.42-1.29 (m, 8H), 1.27-1.21 (m, 4H), 1.14-1.06 (m, 4H), 0.92-0.88 (m, 1H). MS (ESI, m/e) [M + 1]$^+$ 1066.7. |
| 87 | 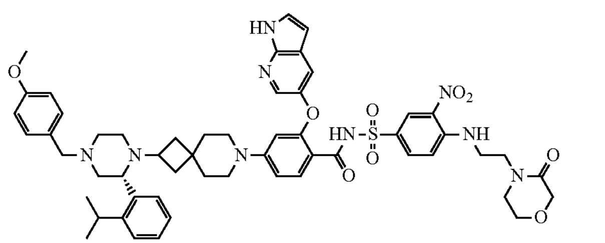 [SMILES: COc1ccc(CN2CCN(C3CC4(CCN(c5ccc(C(=O)NS(=O)(=O)c6ccc(NCCN7CCOCC7=O)c([N+](=O)[O-])c6)c(Oc6cnc7[nH]ccc7c6)c5)CC4)C3)[C@@H](c3ccccc3C(C)C)C2)cc1] | (R or S)-2-(1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)-N-((2-(3-oxomorpholino)ethyl)amino)phenyl)sulfonyl)benzamide | $^1$H NMR (400 MHz, DMSO-d$_6$) δ ppm: 11.68 (s, 1H), 11.29 (br, 1H), 8.61-8.55 (m, 1H), 8.54 (s, 1H), 8.02 (s, 1H), 7.86-7.75 (m, 1H), 7.54-7.44 (m, 3H), 7.43-7.10 (m, 7H), 6.97-6.83 (m, 2H), 6.69-6.63 (m, 1H), 6.37 (s, 1H), 6.13 (s, 1H), 3.99 (s, 2H), 3.81-3.70 (m, 6H), 3.64-3.53 (m, 5H), 3.43-3.37 (m, 2H), 3.34 (s, 3H), 3.07-3.83 (m, 7H), 2.79-2.60 (m, 2H), 2.35-2.25 (m, 1H), 2.09-1.96 (m, 1H), 1.70-1.53 (m, 1H), 1.34-1.13 (m, 8H), 1.12-0.99 (m, 4H). MS (ESI, m/e) [M + 1]$^+$ 1026.4. |

-continued
| Ex. | structure | Compound name | Data |
|---|---|---|---|
| 88 | 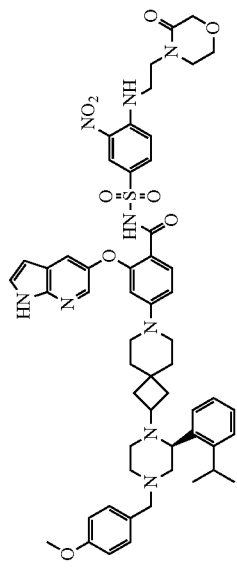 or 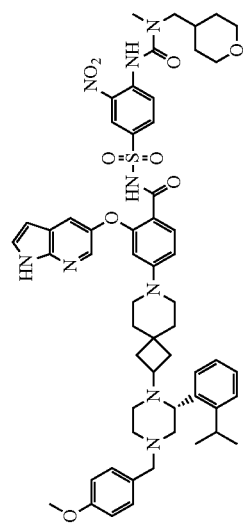 or 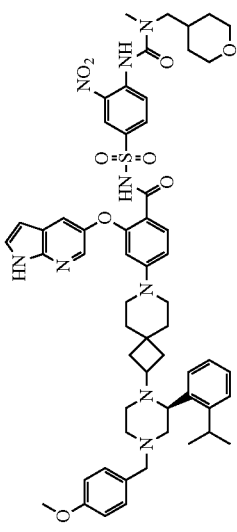 | (R or S)-2-((1H-pyrrolo[2,3-b]pyridin-5-yl)oxy)-4-(2-(2-(2-isopropylphenyl)-4-(4-methoxybenzyl)piperazin-1-yl)-7-azaspiro[3.5]nonan-7-yl)-N-((4-(3-methyl-3-((tetrahydro-2H-pyran-4-yl)methyl)ureido)-3-nitrophenyl)sulfonyl)benzamide | ¹H NMR (400 MHz, DMSO-d₆) δ ppm: 11.69 (s, 1H), 11.50 (br, 1H), 9.72 (s, 2H), 8.46 (s, 2H), 8.19-8.00 (m, 3H), 7.59-7.12 (m, 9H), 7.00-6.85 (m, 2H), 6.67-6.62 (m, 1H), 6.38 (s, 1H), 6.11 (s, 1H), 3.89-3.83 (m 2H), 3.78-3.70 (m, 3H), 3.46-3.37 (m, 1H), 3.32-3.13 (m, 6H), 3.08-2.80 (m, 10H), 2.74-2.54 (m, 1H), 2.35-2.30 (m, 1H), 2.05-1.86 (m, 2H), 1.60-1.52 (m, 3H), 1.42-0.85 (m, 18H). MS (ESI, m/e) [M + 1]⁺ 1054.5. |

| Ex. | structure | Compound name | Data |
|---|---|---|---|
| 89 | | (R or S)-2-((1H-pyrrolo[2,3-b]pyridin-5-yl)oxy)-4-(2-(2-isopropylphenyl)-4-(4-methoxybenzyl)piperazin-1-yl)-7-azaspiro[3.5]nonan-7-yl)-N-(3-nitro-4-((2-(tetrahydro-2H-pyran-4-yl)-2-azaspiro[3.3] heptam-6-yl)amino)phenyl)sulfonyl)benzamide | 1H NMR (400 MHz, DMSO-d6) δ ppm 11.68 (s, 1H), 8.53 (s, 1H), 8.31 (s, 1H), 8.01 (s, 1H), 7.79 (s, 1H), 7.57-7.55 (m, 2H), 7.49-7.36 (m, 2H), 7.31-7.20 (m, 4H), 7.17 (s, 1H), 6.93 (d, J = 7.6 Hz, 2H), 6.87-6.77 (m, 1H), 6.69 (d, J = 7.6 Hz, 1H), 6.39 (s, 1H), 6.23 (s, 1H), 4.22-4.06 (m, 4H), 4.01 (d, J = 12.0 Hz, 3H), 3.77 (s, 3H), 3.29 J = 12.0 Hz, 3H), 3.04-2.89 (m, 7H), 2.39 (s, 2H), 1.86 (d, J = 12.0 Hz, 3H), 1.68 (s, 3H), 1.43-1.38 (m, 3H), 1.37-1.29 (m, 8H), 1.26-1.21 (m, 4H), 1.14-1.09 (m, 4H), 0.94-0.87 (m, 3H). MS (ESI, m/e) [M + 1]+ 1079.0. |
| 90 | | (R or S)-2-((1H-pyrrolo[2,3-b]pyridin-5-yl)oxy)-N-((4-((4-fluoro-1-(tetrahydro-2H-pyran-4-yl)piperidin-4-yl)methoxy)-3-nitrophenyl)sulfonyl)-4-(2-(2-isoptopylphenyl)-4-(4-methoxybenzyl)piperazin-1-yl)-7-azaspiro[3.5]nonan-7-yl)benzamide | 1H NMR (400 MHz, DMSO-d6) δ ppm: 11.56 (s, 1H), 8.21 (s, 1H), 7.95-7.79 (m, 2H), 7.2-7.52 (m, 1H), 7.48-7.35 (m, 2H), 7.35-7.00 (m, 8H), 6.95-6.77 (m, 2H), 6.70-6.52 (m, 1H), 6.30 (s, 1H), 6.19 (s, 1H), 4.39-4.20 (m, 2H), 3.99-3.85 (m, 2H), 3.70 (s, 3H), 3.61-3.57 (m, 2H), 3.33-3.21 (m, 4H), 3.16-3,04 (m, 2H), 2,99-2.80 (m, 7H), 2.78-2.59 (m, 3H), 2.43-2.12 (m, 3H), 2.09-1.98 (m, 2H), 1.97-1.75 (m, 4H), 1.70-1.44 (m, 4H), 1.38-1.25 (m 4H), 1.20-0.95 (m, 8H). MS (ESI, m/e) [M + 1]+ 1099.6. |

| Ex. | structure | Compound name | Data |
|---|---|---|---|
| 91 | 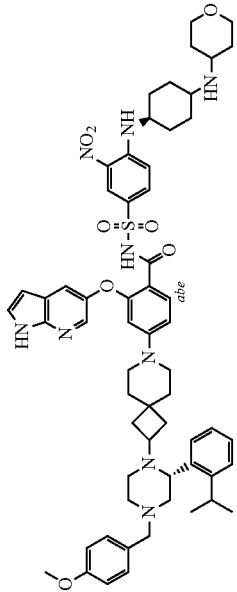 or 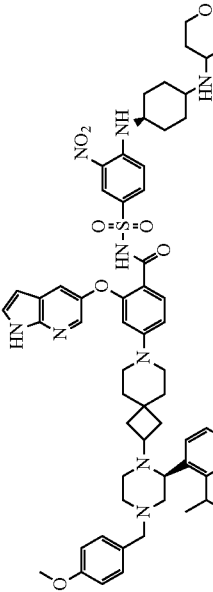 | 2-((1H-pyrrolo[2,3-b]pyridin-5-yl)oxy)-4-(2-((R or S)-2-(2-isopropylphenyl)-4-(4-methoxybenzyl)piperazin-1-yl)-7-azaspiro[3.5]nonan-7-yl)-N-((3-nitro-4-((4-((tetrahydro-2H-pyran-4-yl)amino)cyclohexyl)amino)phenyl)sulfonyl)benzamide | $^1$H NMR (400 MHz, DMSO-$d_6$) δ ppm: 11.52 (s, 1H), 8.65-8.10 (m, 2H), 8.02-7.85 (m, 2H), 7.72-7.55 (m, 2H), 7.50-7.30 (m, 2H), 7.28-7.01 (m, 6H), 6.95-6.75 (m, 3H), 6.64-6.52 (m, 1H), 6.28 (s, 1H), 6.21 (s, 1H), 3.92-3.82 (m, 2H), 3.69 (s, 3H), 3.53-3.37 (m, 6H), 3.32-3.25 (m, 3H), 3.12-3.00 (m, 1H), 2.96-2.76 (m, 7H), 2.20-1.85 (m, 9H), 1.69-1.30 (m, 11H), 1.20-0.99 (m, 8H). MS (ESI, m/e) [M + 1]$^+$ 1081.5 |
| 92 | 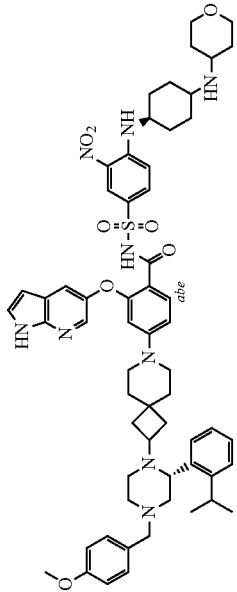 or 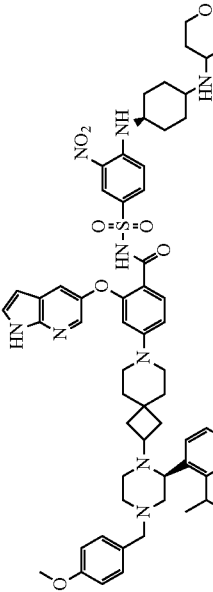 | 2-((1H-pyrrolo[2,3-b]pyridin-5-yl)oxy)-4-(2-((R or S)-2-(2-isopropylphenyl)-4-(4-methoxybenzyl)piperazin-1-yl)-7-azaspiro[3.5]nonan-7-yl)-N-((4-((4-(methylsulfonyl)morpholin-2-yl)methyl)amino)-3-nitrophenyl)sulfonyl)benzamide | $^1$H NMR (400 MHz, DMSO-$d_6$) δ ppm: 11.67 (s, 1H), 8.62 (s, 1H), 8.55 (s, 1H), 8.02 (s, 1H), 7.85-7.72 (m, 1H), 7.56-7.03 (m, 10H), 6.99-6.84 (m, 2H), 6.69-6.59 (m, 1H), 6.37 (s, 1H), 6.20-6.07 (m, 1H), 4.01-3.94 (m, 1H), 3.83-3.40 (m, 11H), 3.24-2.59 (m, 16H), 2.35-1.92 (m, 2H), 1.72-1.52 (m, 1H), 1.37-1.00 (m, 13H). MS (ESI, m/e) [M + 1]$^+$ 1076.7. |

| Ex. | structure | Compound name | Data |
|---|---|---|---|
| 93 | 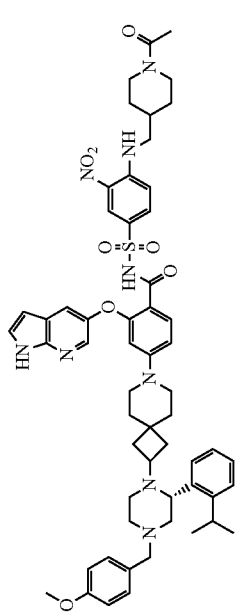 or 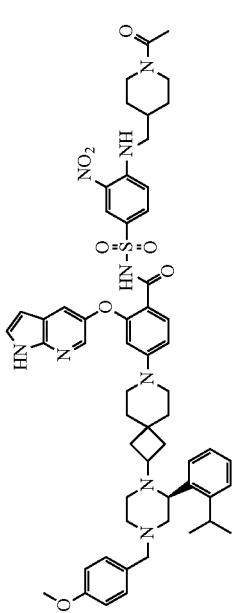 | (R or S)-2-((1H-pyrrolo[2,3-b]pyridin-5-yl)oxy)-N-((4-((1-acetylpiperidin-4-yl)methyl)amino)-3-nitrophenyl)sulfonyl)-4-(2-(2-isopropylphenyl)-4-(4-methoxybenzyl)piperazin-1-yl)-7-azaspiro[3.5]nonan-7-yl)benzamide | $^1$H NMR (400 MHz, DMSO-$d_6$) δ ppm: 11.70 (s, 1H), 11.40-10.95 (m, 1H), 8.64 (s, 1H), 8.56 (s, 1H), 8.02 (s, 1H), 7.84-7.72 (m, 1H), 7.58-7.06 (m, 10H), 6.92 (s, 2H), 6.65 (d, J = 8.8 Hz, 1H), 6.37 (s, 1H), 6.14 (s, 1H), 4.37 (d, J = 13.2 Hz, 1H), 4.02-3.69 (m, 6H), 3.34-3.22 (m, 4H), 3.18-2.62 (m, 11H), 2.48-2.32 (m, 1H), 1.98 (s, 3H), 1.92-1.47 (m, 5H), 1.41-0.74 (m, 15H). MS (ESI, m/e) [M + 1]$^+$ 1038.6. |
| 94 | 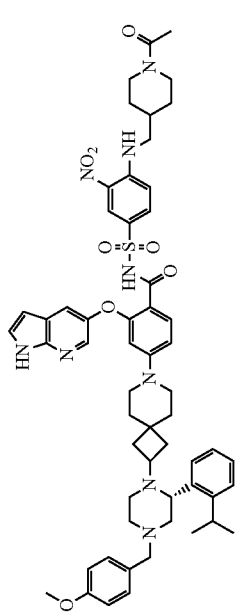 or 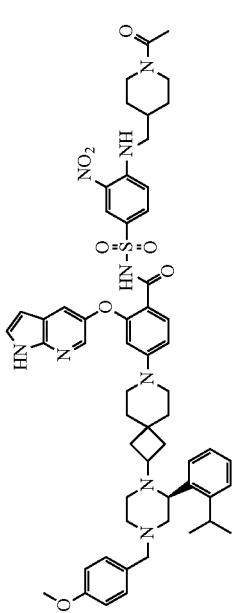 | (R or S)-2-((1H-pyrrolo[2,3-b]pyridin-5-yl)oxy)-4-(2-(2-(2-isopropylphenyl)-4-(4-methoxybenzyl)piperazin-1-yl-7-azaspiro[3.5]nonan-7-yl)-N-((4-((2-morpholinoethyl)amino)-3-nitrophenyl)sulfonyl)benzamide | $^1$H NMR (400 MHz, DMSO-$d_6$) δ ppm: 11.70 (s, 1H), 8.80 (s, 1H), 8.55 (s, 1H), 8.01 (s, 1H), 7.80 (d, J = 8.8 Hz, 1H), 7.53-7.13 (m, 9H), 7.06-6.85 (m, 3H), 6.65 (d, J = 8.4 Hz, 1H), 6.37 (s, 1H), 6.14 (s, 1H), 3.73 (s, 3H), 3.66-3.41 (m, 8H), 3.28-2.61 (m, 14H), 2.41-1.93 (m, 4H), 1.68-1.53 (m, 1H), 1.34-0.98 (m, 14H). MS (ESI, m/e) [M + 1]$^+$ 1012.7. |

| Ex. | structure | Compound name | Data |
|---|---|---|---|
| 95 | 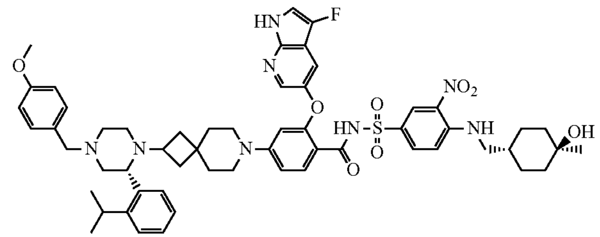 | 2-(3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((R or S)-2-(2-isopropylphenyl)-4-(4-methoxybenzyl)piperazin-1-yl)-7-azaspiro[3.5]nonan-7-yl)benzamide | $^1$H NMR (400 MHz, DMSO-$d_6$) δ ppm: 11.57 (s, 1H), 8.62 (s, 1H), 8.58 (s, 1H), 7.88-7.76 (m, 1H), 7.59-7.21 (m, 8H), 8.12 (s, 1H), 6.79-6.68 (m, 1H), 6.33-6.22 (m, 1H), 4.31 (s, 1H), 3.87-3.47 (m, 6H), 3.37-3.29 (m, 3H), 3.22-2.66 (m, 10H), 2.45-1.99 (m 2H), 1.78-1.55 (m, 6H), 1.44-1.05 (m, 19H). MS (ESI, m/e) [M + 1]$^+$ 1044.3. |
| 96 | 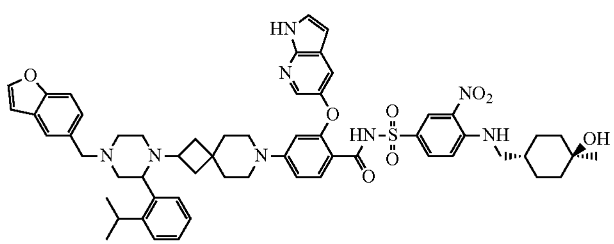 [SMILES: CC(C)c1ccccc1C1CN(Cc2ccc3occc3c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(benzofuran-5-ylmethyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.70 (s, 1H), 11.28-11.20 (m, 1H), 8.57-8.54 (m, 2H), 8.03 (s, 2H), 7.79-7.72 (m, 2H), 7.59 (s, 1H), 7.50-7.46 (m, 3H), 7.32-7.20 (m, 4H), 7.07 (d, J = 8.0 Hz, 1H), 6.96 (s, 1H), 6.65 (d, J = 8.0 Hz, 1H), 6.37 (s, 1H), 6.14 (s, 1H), 4.26 (s, 1H), 3.86 (s, 1H), 3.72 (s, 1H), 3.28 (s, 2H), 3.12-2.68 (m, 9H), 2.33 (s, 1H), 2.09-2.06 (m, 1H), 1.72-1.42 (m, 6H), 1.38-1.25 (m, 12H), 1.10 (s, 4H), 1.04 (s, 4H). MS (ESI, m/e) [M + 1]$^+$ 1035.7. |
| 97 | 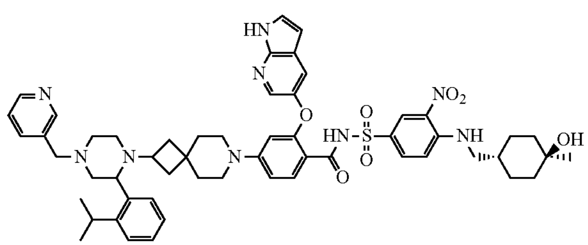 [SMILES: CC(C)c1ccccc1C1CN(Cc2cccnc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(pyridin-3-ylmethyl)piperazin-1-yl)-7-azaspiro[3.5]nonan-7-yl)benzamide | $^1$H NMR (400 MHz, DMSO-$d_6$) δ ppm 11.69 (s, 1H), 11.37 (s, 1H), 8.65-8.40 (m, 4H), 8.03 (s, 1H), 7.77 (s, 3H), 7.50-7.46 (m 4H), 7.36 (s, 2H), 7.22 (s, 2H), 7.09-7.06 (m, 2H), 6.65 (d, J = 8.8 Hz, 1H), 6.37 (s, 1H), 6.14 (s, 1H), 4.25 (s, 1H), 3.69-3.65 (m, 3H), 3.28 (s, 3H), 3.02-2.90 (m, SH), 2.22 (s, 1H), 2.01 (s, 1H), 1.73-1.50 (m, 7H), 1 36-1 23 (m, 14H), 1.20-1.15 (m, 6H), 1.10 (s, 4H), 1.04 (s, 4H). MS (ESI, m/e) [M + 1]$^+$ 996.7. |

| Ex. | structure | Compound name | Data |
|---|---|---|---|
| 98 | 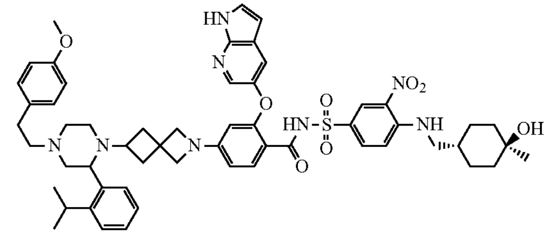 [SMILES: COc1ccc(CCN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)C(c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(6-(2-(2-isopropylphenyl)-4-(4-methoxyphenethyl)piperazin-1-yl)-2-azaspiro[3.3]heptan-2-yl)benzamide | $^1$H NMR (400 MHz, DMSO-d$_6$) δ ppm 11.73 (s, 1H), 10.98 (s, 1H), 8.70-8.45 (m, 2H), 8.03 (s, 1H), 7.87-7.73 (m, 1H), 7.63-7.37 (m, 4H), 7.35-6.97 (m 7H), 6.91-6.77 (m, 2H), 6.39 (s, 1H), 6.09-5.97 (m, 1H), 5.49 (s, 1H), 4.25 (s, 1H), 3.92-3.75 (m, 1H), 3.70 (s, 3H), 3.65-3.42 (m, 5H), 3.31-3.22 (m, 4H), 3.16-2.59 (m, 9H), 2.46-2.27 (m, 1H), 2.08-1.86 (m, 2H), 1.74-1.49 (m, 6H), 1.39-1.26 (m, 3H), 1.20-1.13 (m, 5H), 1.13-1.04 (m 4H). MS (ESI, m/e) [M + 1]$^+$ 1011.8. |
| 99 | 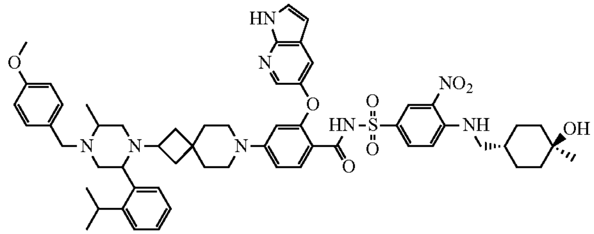 | 2-((1H-pyrrolo[2,3-b]pyridin-5-yloxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methoxybenzyl)piperazin-1-yl)-5-methylpiperazin-1-yl)-7-azaspiro[3.5]nonan-7-yl)benzamide | $^1$H NMR (400 MHz, DMSO-d$_6$) δ ppm 11.76 (s, 1H), 11.45 (s, 1H), 8.72-8.55 (m, 2H), 8.09 (s, 1H), 7.92-7.77 (m, 1H), 7.69-7.46 (m, 6H), 7.43-7.18 (m, 4H), 7.18-7.10 (m, 1H), 7.10-6.95 (m, 2H), 6.78-6.65 (m, 1H), 6.44 (s, 1H), 6.19 (s, 1H), 4.32 (s, 1H), 4.20-3.95 (m, 1H), 3.79 (s, 3H), 3.38-3.28 (m, 5H), 3.10-2.85 (m, 7H), 2.76-2.63 (m, 1H), 1.81-1.65 (m, 4H), 1.65-1.45(m, 6H), 1.45-1.28 (m, 10H), 1.22-1.06 (m, 10H). MS (ESI, m/e) [M + 1]$^+$ 1031.9. |
| 100 | 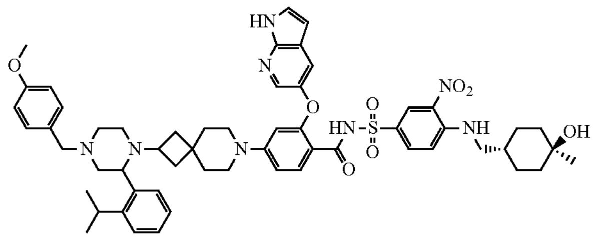 | 2-((1H-pyrrolo[2,3-b]pyridin-5-yloxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methoxybenzyl)piperazin-1-yl)piperazin-1-yl)-7-azaspiro[3.5]nonan-7-yl)benzamide | $^1$H NMR (400 MHz, DMSO-d$_6$) δ ppm: 11.67 (s, 1H), 11.29 (br, 1H), 8.60-8.52 (m, 2H), 8.01 (s, 1H), 7.79-7.72 (m, 1H), 7.52-7.30 (m, 4H), 7.29-7.00 (m, 4H), 6.68-6.61 (m, 1H), 6.36 (s, 1H), 6.14 (s, 1H), 4.25 (s, 1H), 3.32-3.27 (m, 3H), 3.20 (s, 3H), 3.07-2.83 (m, 1H), 2.30-2.12 (m, 2H), 2.03-1.92 (m, 3H), 1.79-1.58 (m, 7H), 1.52-1.40 (m, 4H), 1.38-1.18 (m, 15H), 1.17-1.12 (m, 4H), 1.07-0.96 (m, 3H). MS (ESI, m/e) [M + 1]$^+$ 1040.3. |
| 101 | 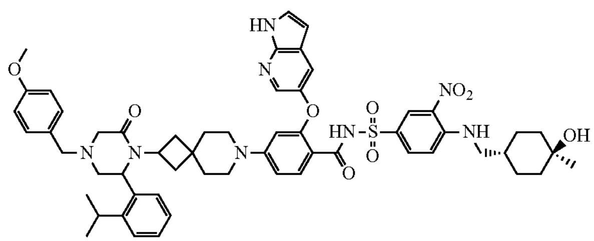 [SMILES: COc1ccc(CN2CC(=O)N(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yloxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methoxybenzyl)-6-oxopiperazin-1-yl)-7-azaspiro[3.5]nonan-7-yl)benzamide | 1H NMR (400 MHz, DMSO-d$_6$) δ ppm: 11.69 (s, 1H), 11.42 (br, 1H), 8.63-8.54 (m, 2H), 8.04 (s, 1H), 7.80 (d, J = 8.8 Hz, 1H), 7.55-7.43 (m, 3H), 7.29-7.22 (m, 2H), 7.19-7.16 (m, 1H), 7.10 (d, J = 8.8 Hz, 1H), 6.97-6.94 (m, 1H), 6.74-6.57 (m, 5H), 6.38 (s, 1H), 6.16 (s, 1H), 5.03 (s, 1H), 4.45-4.32 (m, 1H), 4.25 (s, 1H), 3.65 (s, 3H), 3.54-3.46 (m, 1H), 3.30-3.16 (m, 4H), 3.10-2.87 (m, 7H), 2.08-1.84 (m, 3H), 1.74-1.58 (m, 5H), 1.57-1.40 (m, 6H), 1.38-1.18 (m, 9H), 0.90-0.78 (m, 4H). MS (ESI, m/e) [M + 1]$^+$ 1039.6 |

| Ex. | structure | Compound name | Data |
|---|---|---|---|
| 102 | | 2-((1H-pyrrolo[2,3-b]pyridin-5-yl)oxy)-4-(2-(4-(2-chloro-4-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.67 (s, 1H), 11.38 (br, 1H), 8.60-8.51 (m, 2H), 8.00 (s, 1H), 7.85-7.73 (m, 1H), 7.55-7.28 (m, 6H), 7.27-6.95 (m, 4H) 6.93-6.85 (m, 1H), 6.68-6.60 (m, 1H), 6.35 (s, 1H), 6.13 (s, 1H), 4.23 (s, 1H), 3.72 (s, 3H), 3.70-3.54 (m, 2H), 3.45-3.34 (m, 1H), 3.30-3.23 (m, 2H), 3.05-2.67 (m, 8H), 2.28-1.90 (m, 2H), 1.70-1.47 (m, 6H), 1.45-1.12 (m, 13H), 1.10-0.99 (m 8H). MS (ESI, m/e) [M + 1]⁺ 1060.7. |
| 103 | 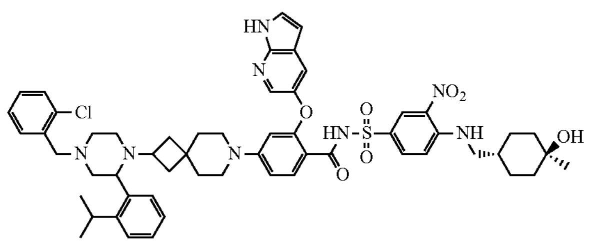 [SMILES: CC(C)c1ccccc1C1CN(Cc2ccccc2Cl)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(2-chlorobenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.67 (s, 1H), 11.38 (br. 1H), 8.60-8.51 (m, 2H), 8.00 (s, 1H), 7.85-7.73 (m, 1H), 7.55-7.35 (m, 6H), 7.33-7.15 (m, 5H), 7.10-7.03 (m, 1H), 6.68-6.60 (m, 1H), 6.35 (s, 1H), 6.13 (s, 1H), 4.23 (s, 1H), 3.83-3.37 (m, 5H), 3.30-3.23 (m, 2H), 3.08-2.69 (m, 9H), 2.28-1.90 (m, 3H), 1.70-1.47 (m, 7H), 1.45-1.12 (m, 13H), 1.10-0.99 (m, 4H). MS (ESI, m/e) [M + 1]⁺ 1030.7. |
| 104 | 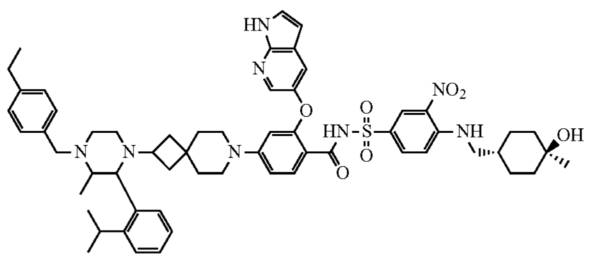 [SMILES: CCc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2C)cc1] | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-(2-(2-isopropylphenyl)-4-(4-methoxybenzyl)-3-methylpiperazin-1-yl)-7-azaspiro[3.5]nonan-7-yl)benzamide | ¹H NMR (400 MHz, DMSO-d₆) δ ppm:11.75 (s, 1H), 11.48 (s, 1H), 8.67-8.57 (m, 2H), 8.09 (s, 1H), 7.85 (d, J = 12.0 Hz, 1H), 7.67-7.46 (m, 4H), 7.44-7.37 (m, 1H), 7.36-7.23 (m, 3H), 7.19 (s, 1H), 7.14 (d, J = 8.0 Hz, 1H), 7.06-6.98 (m, 1H), 6.94 (d, J = 8.0 Hz, 1H), 6.77-6.67 (m, 1H), 6.43 (s, 1H), 6.26-6.15 (m, 1H), 4.31 (s, 1H), 3.80 (d, J = 8.0 Hz, 3H), 3.34 (s, 3H), 3.25-3.14 (m, 2H), 3.08-2.93 (m, 5H), 2.85-2.70 (m, 1H), 2.26-2.15 (m, 1H), 2.04-1.90 (m, 2H), 1.78-1.64 (m, 4H), 1.62-1.55 (m, 2H), 1.46-1.3.3 (m, 6H), 1.32-1.24 (m, 4H), 1.22-1.09 (m, 10H), 1.08-1.01 (m, 4H), 0.95-0.83 (m, 2H), MS (ESI, m/e) [M + 1]⁺ 1039.8. |

| Ex. | structure | Compound name | Data |
|---|---|---|---|
| 105 | 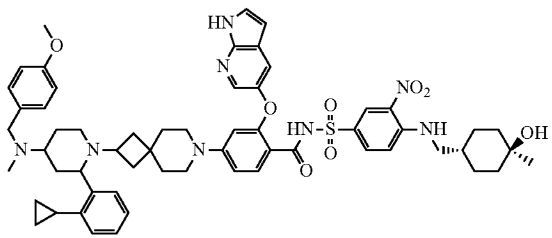 [SMILES: COc1ccc(CN(C)C2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C3CC3)C2)cc1] | 2-((1H-pyrrolo[2,3-b]pyridin-5-yl)oxy)-4-(2-(2-(2-cyclopropylphenyl)-4-((4-methoxybenzyl)(methyl)amino)piperidin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.74 (s, 1H), 11.50 (s, 1H), 10.28 (s, 1H), 8.68-8.54 (m, 2H), 8.08 (s, 1H), 7.90-7.76 (m, 2H), 7.62-7.50 (m, 3H), 7.36-7.31 (m, 3H), 7.17-7.06 (m, 2H), 6.94 (d, J = 8.0 Hz, 2H), 6.73 (d, J = 6.8 Hz, 1H), 6.43 (s, 1H), 6.23 (s, 1H), 5.19 (s, 1H), 4.31 (s, 1H), 4.02-3.92 (m, 1H), 3.80 (s, 3H), 3.66-3.48(m, 2H), 3.33 (s, 3H), 3.11-3.06 (m, 1H), 3.04-2.97 (m, 2H), 2.96-2.89 (m, 1H), 2.64 (s, 1H), 2.44-2.37 (m, 1H), 2.32-2.24 (m, 2H), 2.23-2.16 (m, 2H), 2.12 (s, 3H) 2.06-2.00 (m, 1H), 1.78-1.74 (m 1H), 1.73-1.70 (m, 1H), 1.62-1.57 (m, 2H), 1.48 (s, 1H), 1.43-1.37 (m, 4H), 1.36-1.33 (m, 2H), 1.29 (s, 2H), 1.20-1.18 (m, 1H), 1.15 (m, 3H), 1.05-1.01 (m, 1H), 0.94-0.87 (m, 2H), 0.84-0.80 (m, 1H), 0.78-0.70 (m, 2H), 0.65-0.58 (m, 1H). MS (ESI, m/e) [M + 1]⁺ 1051.7 |
| 106 | 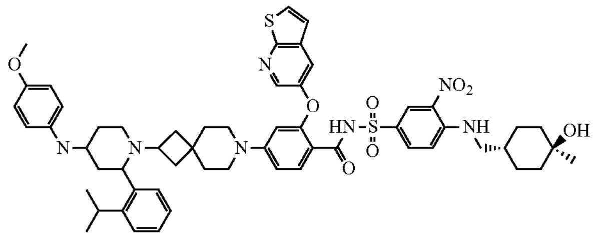 | 2-(benzo[b]thiophen-5-yloxy)-N-((4-((((1r,4r)-4-hydroxy-4-methylcyclohexyl)methyl)amino)-3-nitrophenyl)sulfonyl)-4-(2-(2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm: 11.25 (s, 1H), 8.60-8.40 (m, 2H), 7.97-7.84 (m, 1H), 7.79-7.70 (m, 1H), 7.64-7.54 (m, 1H), 7.54-7.46 (m, 1H), 7.46-7.07 (m, 8H), 7.07-6.83 (m 4H), 6.85-6.63(m, 1H), 6.35 (s, 1H), 6.35 (s, 1H), 426 (s, 1H), 4.18-3.67 (m, 6H), 3.65-3.39 (m, 3H), 3.28-3.14 (m, 3H), 3.14-2.73 (m, 7H), 2.14 (m, 1H), 1.75-1.50 (m, 6H), 1.50-0.96 (m, 19H). MS (ESI, m/e) [M + 1]⁺ 1042.6 |
| 107 | 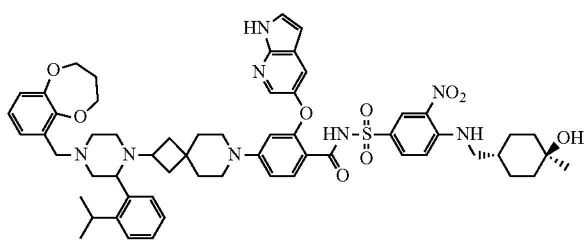 [SMILES: CC(C)c1ccccc1C1CN(Cc2cccc3c2OCCCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yloxy)-4-(2-(4-((3,4-dihydro-2H-benzo[b][1,4]dioxepin-6-yl)methyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.69 (s, 1H), 11.22 (s, 1H), 8.66-8.46 (m, 2H), 8.03 (s, 1H), 7.97-7.70 (m, 2H), 7.63-6.80 (m, 11H), 6,80-6.55 (m, 1), 6.37 (s, 1H), 6.14 (s, 1H), 4.25 (s, 1H), 4.15-4.01 (m, 4H), 3.98-3.56 (m 3H), 3.48-3.40 (m, 1H), 3.33-3.23 (m, 3H), 3.23-3.13 (m, 1H), 3.13-2.83 (m, 6H), 2.81-2,62 (m, 2H), 2.16-1.94 (m, 3H), 1.78-1.50 (m, 6H), 1.48-1.15 (m, 11H), 1.15-0.96 (m, 8H). MS (ESI, m/e) [M + 1] 1067.7 |

| Ex. | structure | Compound name | Data |
|---|---|---|---|
| 108 | 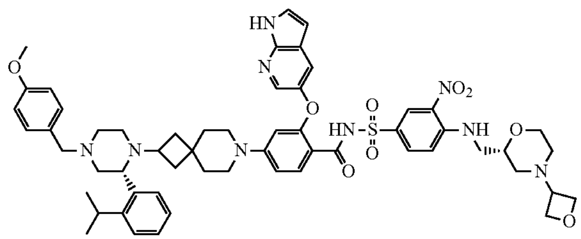 [SMILES: COc1ccc(CN2CCN(C3CC4(CCN(c5ccc(C(=O)NS(=O)(=O)c6ccc(NC[C@H]7CN(C8COC8)CCO7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-4-(2-(R)-2-(2-isopropylphenyl)-4-(4-methoxybenzyl)piperazin-1-yl)-7-azaspiro[3.5]nonan-7-yl)-N-(3-nitro-4-((((S)-4-(oxetan-3-yl)morpholin-2-yl)methyl)amino)phenyl)sulfonyl)benzamide | $^1$H NMR (400 MHz, DMSO-d$_6$) δ ppm: 11.66 (s, 1H), 8.58 (s, 1H), 8.53 (s, 1H), 8.00 (s, 1H), 7.77 (s, 1H), 7.55-7.35 (m, 4H), 7.24 (s, 4H), 7.10-7.02 (m, 2H), 6.89 (s, 2H), 6.66-6.65 (m, 1H), 6.36 (s, 1H), 6.15 (s, 1H), 4.54 (s, 2H), 4.45 (s, 2H), 3.88-3.85 (m, 1H), 3.72 (s, 5H), 3.58-3.53 (m, 3H), 3.43 (s, 3H), 3.10-2.82 (m, 7H), 2.78-2.72 (m, 1H), 2.60-2.54 (m, 1H), 1.96 (s, 2H), 1.82-1.80 (m, 1H), 1.58 (s, 2H), 1.30-1.21 (m, 9H), 1.18 (s, 3H), 1.06 (s, 3H). MS (ESI, m/e) [M + l]$^+$ 1054.6. |
| 109 | 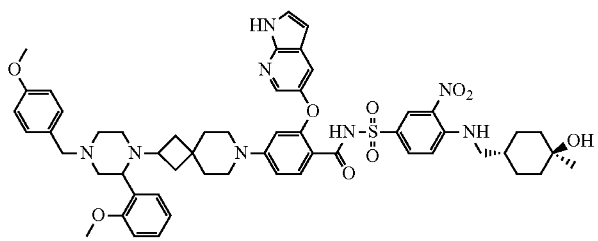 | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-(4-(4-methoxybenzyl)-2-(2-methoxyphenyl)piperazin-1-yl)-7-azaspiro[3.5]nonan-7-yl)benzamide | $^1$H NMR (400 MHz, DMSO-d$_6$) δ ppm: 11.75 (s, 1H), 11.51-10.95 (m, 1H), 8.68-8.54 (m, 2H), 8.08 (s, 1H), 7.83 (d, J = 8.8 Hz, 1H), 7.59-7.49 (m, 3H), 7.45-7.2.4 (m, 3H), 7.12 (d, J = 8.8 Hz 1H), 7.09-6.88 (m, 4H), 6.71 (d, J = 7.6 Hz, 1H), 6.43 (s, 1H), 6.20 (s, 1H), 4.31 (s, 1H), 3.91-3.82 (m, 3H), 3.78 (s, 3H), 3.62-3.52 (m, 1H), 3.33 (s, 2H), 3.18-2.88 (m, 7H), 2.87-2.63 (m, 3H), 2.17-2.00 (m, 1H), 1.79-1.64 (m, 4H), 1.59 (d, J = 11.6 Hz, 3H), 1.48-1.24 (m, 8H), 1.23-1.10 (m, 6H), 1.00-0.86 (m, 1H) MS (ESI, m/e) [M + 1]$^+$ 1014.1 |
| 110 | 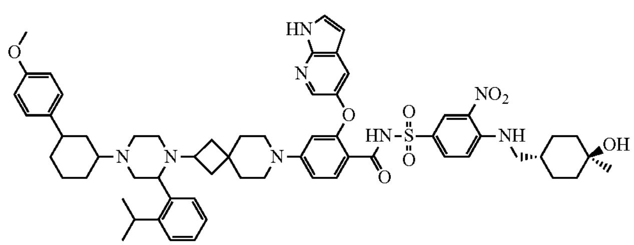 [SMILES: COc1ccc(C2CCCC(N3CCN(C4CC5(CCN(c6ccc(C(=O)NS(=O)(=O)c7ccc(NC[C@H]8CC[C@](C)(O)CC8)c([N+](=O)[O-])c7)c(Oc7cnc8[nH]ccc8c7)c6)CC5)C4)C(c4ccccc4C(C)C)C3)C2)cc1] | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-(2-isopropylphenyl)-4-(4-methoxyphenyl)piperazin-1-yl)-7-azaspiro[3.5]nonan-7-yl)benzamide | $^1$H NMR (400 MHz, DMSO-d$_6$) δ ppm: 11.70 (s, 1H), 11.43 (br, 1H), 8.62-8.54 (m, 2H), 8.03 (s, 1H), 7.84-7.75 (m, 1H), 7.54-6.96 (m, 10H), 6.88-6.63 (m, 3H), 6.38 (s, 1H), 6.14 (s, 1H), 4.25 (s, 1H), 3.70 (s, 3H), 3.54-3.41 (m, 1H), 3.20-2.75 (m, 11H), 2.29-1.80 (m, 5H), 1.79-1.41 (m, 12H), 1.15 (m, 15H), 1.14-1.02 (m, 7H). MS (ESI, m/e) [M + l]$^+$ 1093.8. |
| 111 | | | $^1$H NMR (400 MHz, DMSO-d$_6$) δ ppm: 11.70 (s, 1H), 11.43 (br, 1H), 8.62-8.54 (m, 2H), 8.03 (s, 1H), 7.84-7.75 (m, 1H), 7.54-6.96 (m, 10H), 6.88-6.63 (m, 3H), 6.38 (s, 1H), 6.14 (s, 1H), 4.25 (s, 1H), 3.70 (s, 3H), 3.54-3.41 (m, 1H), 3.20-2.75 (m, 11H), 2.29-1.80 (m, 5H), 1.79-141 (m 12H), 1.39-1.15 (m, 15H), 1.14-1.02 (m, 7H). MS (ESI, m/e) [M + 1]$^+$ 1093.8. |

| Ex. | structure | Compound name | Data |
|---|---|---|---|
| 112 | | 2-((1H-pyrrolo[2,3-b]pyridin-5-yl)oxy)-N-((4-(((1r,4r)-4-hydroxy-4-methylcyclohexyl)methyl)amino)-3-((trifluoromethyl)sulfonyl)phenyl)sulfonyl)-4-(2-(R)-2-(2-isopropylphenyl)-4-(4-methoxybenzyl)piperazin-1-yl)-7-azaspiro[3.5]nonan-7-yl)benzamide | $^{1}$H NMR (400 MHz, DMSO-d$_6$) δ ppm: 11.63 (s, 1H), 8.60-8.48 (m, 2H), 8.03 (s, 1H), 7.84-7.75 (m, 1H), 7.54-6.96 (m, 10H), 6.88-6.62 (m, 3H), 6.39 (s, 1H), 6.16 (s, 1H), 4.25 (s, 1H), 3.70 (s, 3H), 3.54-3.41 (m, 1H), 3.20-2.75 (m, 11H), 2.29-1.80 (m, 5H), 1.79-1.52 (m, 9H), 1.51-1.15 (m, 21H), 1.14-1.02 (m, 4H). MS (ESI, m/e) [M + 1]$^{+}$ 1093.9 |
| 113 | 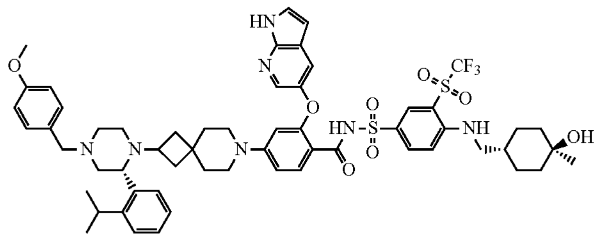 [SMILES: COc1ccc(CN2CCN(C3CC4(CCN(c5ccc(C(=O)NS(=O)(=O)c6ccc(NC[C@H]7CC[C@](C)(O)CC7)c(S(=O)(=O)C(F)(F)F)c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-4-(2-(4-(4-(dimethylamino)benzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^{1}$H NMR (400 MHz, DMSO-d$_6$) δ ppm 11.72 (s, 1H), 8.15 (s, 1H), 8.03 (s, 1H), 7.93-7.79 (m, 1H), 7.55-6.83 (m, 13H), 6.66 (s, 1H), 6.39 (s, 1H), 6.19-6.07 (m, 1H), 4.25 (s, 1H), 4.16-3.86 (m, 1H), 3.81-3.38 (m, 5H), 3.23 (s, 3H), 3.08-2.56 (m, 9H), 2.44-1.96 (m, 2H), 1.72-1.49 (m, 6H), 1.37-0.95 (m, 19H). MS (ESI, m/e) [M + 1]$^{+}$ 1112.8. |
| 114 | 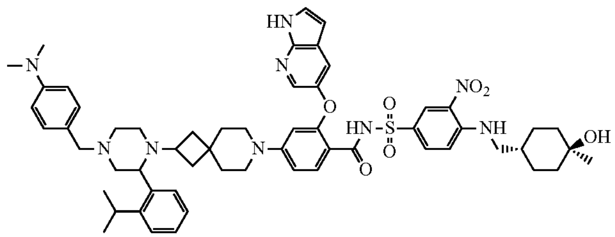 | 2-((1H-pyrrolo[2,3-b]pyridin-5-yl)oxy)-4-(2-(4-(4-(dimethylamino)benzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^{1}$H NMR (400 MHz, DMSO-d$_6$) δ ppm 11.70 (s, 1H), 11.36 (s, 1H), 8.75-8.46 (m, 2H), 8.03 (s, 1H), 7.87-7.72 (m, 1H), 7.60-7.32 (m, 5H), 7.33-6.99 (m, 6H), 6.78-6.60 (m, 3H), 6.38 (s, 1H), 6.23-6.06 (s, 1H), 4.26 (s, 1H), 4.20-3.65 (m, 3H), 3.55-3.35 (m, 2H), 3.32-3.15 (m, 4H), 3.09-2.79 (m, 14H), 2.42-2.31 (m, 1H), 2.12-1.92 (m, 1H), 1.76-1.60 (m, 4H), 1.60-1.46 (m, 3H), 1.42-1.26 (m, 5H), 1.23-1.15 (m, 3H), 1.15-1.00 (m, 9H). MS (ESI, m/e) [M + 1]$^{+}$ 1039.3 |
| 115 | 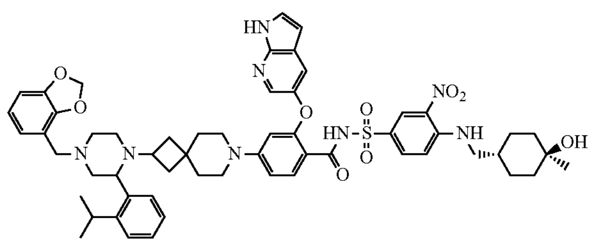 [SMILES: CC(C)c1ccccc1C1CN(Cc2cccc3c2OCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(benzo[d][1,3]dioxol-4-ylmethyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^{1}$H NMR (400 MHz, DMSO-d$_6$) δ ppm 11.69 (s, 1H), 11.35 (br, 1H), 8.62-8.54 (m, 2H), 8.03 (s, 1H), 7.81-7.75 (m, 1H), 7.54-7.45 (m, 3H), 7.44-7.05 (m, 5H), 6.90-6.77 (m, 3H), 6.68-6.63 (m, 1H), 6.37 (s, 1H), 5.97 (s, 2H), 4.25 (s, 1H), 3.82-3.38 (m, 4H), 3.32-3.25 (m, 2H), 3.20-2.60 (m, 10H), 2.30-1.96 (m, 2H), 1.74-1.50 (m, 6H), 1.39-1.15 (m, 13H), 1.14-1.02 (m, 8H). MS (ESI, m/e) [M + 1]$^{+}$ 1040.2. |

| Ex. | structure | Compound name | Data |
|---|---|---|---|
| 116 | 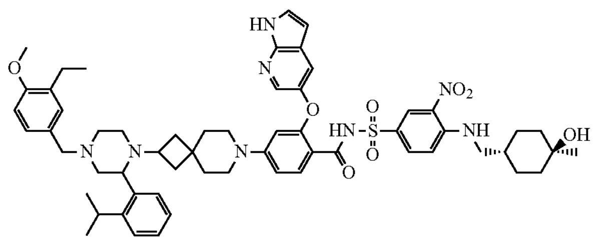 [SMILES: CCc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)ccc1OC] | 2-((1H-pyrrolo[2,3-b]pyridin-5-yloxy)-4-(2-(4-(3-ethyl-4-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.71 (s, 1H), 11.25 (s, 1H), 8.62-8.51 (m, 2H), 8.03 (s, 1H), 7.79 (d, J = 9.2 Hz, 1H), 7.56-6.81 (m, 1H), 6.65 (d, J = 8.0 Hz, 1H), 6.38 (s, 1H), 6.15 (s, 1H), 4.26 (s, 1H), 4.12-3.49 (m, 6H), 3.32-3.23 (m, 3H), 3.20-2.60 (m, 10H), 2.33-1.87 (m 1H), 1.79-1.47 (m, 7H), 1.43-0.86 (m, 24H). MS (ESI, m/e) [M + 1]⁺ 1053.8. |
| 117 | 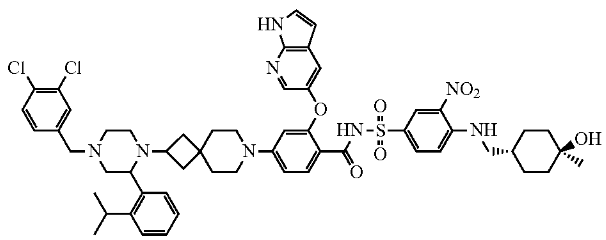 [SMILES: CC(C)c1ccccc1C1CN(Cc2ccc(Cl)c(Cl)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yloxy)-4-(2-(4-(3,4-dichlorobenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.70 (s, 1H), 11.40 (s, 1H), 8.6.3-8.51 (m, 2H), 8.03 (s, 1H), 7.79 (d, J = 9.2 Hz, 1H), 7.70-6.69 (m, 11H), 6.66 (d, J = 9.2 Hz, 1H), 6.38 (s, 1H), 6.16 (s, 1H), 4.26 (s, 1H), 3.85-3.38 (m, 4H), 3.33-3.11 (m, 4H), 3.05-2.62 (m, 8H), 2.38-1.93 (m, 2H), 1.75-1.49 (m, 6H), 1.39-0.99 (m, 19H). MS (ESI, m/e) [M + 1]⁺ 1065.5. |
| 118 | 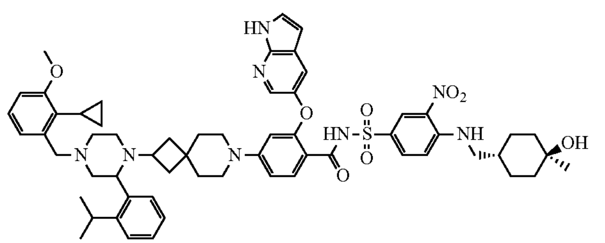 [SMILES: COc1cccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)c1C1CC1] | 2-((1H-pyrrolo[2,3-b]pyridin-5-yl)oxy)-4-(2-(4-(2-cyclopropyl-3-methoxybenzyl)-2-(2-isopropylphenyl)piperazin-1-yl)-7-azaspiro[3.5]nonan-7-y)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.73 (s, 1H), 11.41 (s, 1H), 8.58 (s, 2H), 8.07 (s, 1H), 7.80 (s, 1H), 7.59-7.39 (m, 4H), 7.33-7.20 (m, 2H), 7.19-7.12 (m, 2H), 7.09 (s, 1H), 7.01 (d, J = 8.0 Hz, 1H), 6.86 (d, J = 8.4 Hz, 1H), 6.70 (d, J = 8.4 Hz, 1H), 6 42 (s, 1H), 6.21 (s, 1H), 4.31 (s, 1H), 3.77 (s, 3H), 3.74-3.67 (m, 1H), 3.36-3.30 (m, 2H), 3.14-2.83 (m, 8H), 2.36-2.19 (m, 2H), 1.80-1.64 (m, 6H), 1.60 (d, J = 12.0 Hz, 2H), 1.45-1.28 (m, 9H), 1.27-1.21 (m, 3H), 1.19 (s, 1H), 1.16 (s, 4H), 1.13-1.07 (m, 3H), 0.96-0.87 (m, 3H), 0.69-0.60 (m, 2H), MS (ESI. m/e) [M + 1]⁺ 1065.6 |

| Ex. | structure | Compound name | Data |
|---|---|---|---|
| 119 | | 2-((1H-pyrrolo[2,3-b]pyridin-5-yl)oxy)-4-(2-(4-(3-chloro-2-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.69 (s, 1H), 11.44 (s, 1H), 8.55 (s, 2H), 8.04 (s, 1H), 7.77 (s, 1H), 7.57-7.48 (m 3H), 7.46-7.36 (m 3H), 7.33-7.20 (m, 2H), 7.19-7.11 (m,2H), 7.03 (s, 1H), 6.68 (d, J = 8.0 Hz, 1H), 6.640 (s, 1H),6.21 (s, 1H), 4.30 (s, 1H), 3.82 (s, 3H), 3.60-3.55 (m, 2H), 3.34-3.30 (m, 2H), 3.06-2.86 (m, 8H), 2.34-2.18 (m, 2H), 1.80-1.55 (m, 8H), 1.43-1.28 (m, 9H) 1.23 (d, J = 4.8 Hz, 3H), 1.20-1.18 (m, 1H), 1.15 (s, 4H), 1.13-1.06 (s, 4H). MS (ESI, m/e) [M + 1]⁺ 1060.6 |
| 120 | 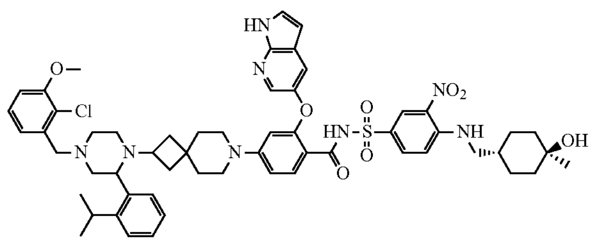 [SMILES: COc1cccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)c1Cl] | 2-((1H-pyrrolo[2,3-b]pyridin-5-yl)oxy)-4-(2-(4-(2-chloro-3-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.69 (s, 1H), 11.41 (s, 1H), 8.56-8.55 (m, 2H), 8.03 (s, 1H), 7.50-7.46 (m, 3H), 7.38 (s, 1H), 7.27 (s, 3H), 7.08 (S, 4H), 6.66 (s, 1H), 6.37 (s, 1H), 4.25 (s, 1H), 3.82 (s, 4H), 3.76-3.70 (m, 1H), 3.43 (s, 2H), 3.29-3.25 (m, 2H), 2.93-2.90 (m, 7H), 1.99 (s, 2H), 1.62-1.56 (m, 7H), 1.32-1.28 (m, 12H), 1.15-1.12 (m, 2H), 1.10 (s, 5H), 1.05 (s, 3H). MS (ESI. m/e) [M + 1]⁺ 1060.6. |
| 121 | | 2-((1H-pyrrolo[2,3-b]pyridin-5-yl)oxy)-4-(2-(4-(4-fluoro-3-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.69 (s, 1H), 11.32 (s, 1H), 8.55 (s, 2H), 8.03 (d, J = 8.4 Hz, 1H), 7.78 (d, J = 8.4 Hz, 1H), 7.50-7.46 (m, 3H), 7.36-7.00 (m, 6H), 6.89 (s, 1H), 6.65 (d, J = 8.0 Hz, 1H), 6.37 (s, 1H), 6.14 (s, 1H), 4.25 (s, 1H), 3.81 (s, 3H), 3.63 (s, 2H), 3.28 (s, 3H), 2.98-2.91 (m, 7H), 2.68 (s, 2H), 2.33 (s, 1H), 2.02 (s, 1H), 1.67-1.52 (m, 6H), 1.39-1.20 (m, 11H), 1.20-1.01 (m, 9H). MS (ESI, m/e) [M + 1]⁺ 1043.9. |
| 121a | 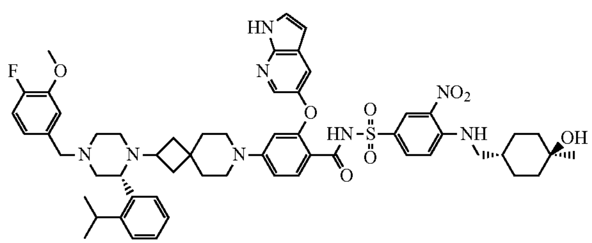 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1F] | 2-((1H-pyrrolo[2,3-b]pyridin-5-yl)oxy)-4-(2-((R)-4-(4-fluoro-3-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.30 (br, 1H), 8.54 (s, 2H), 8.02 (s, 1H), 7.77 (d, J = 7.8 Hz, 1H), 7.50-7.45 (m, 3H), 7.30-7.05 (m, 7H), 6.87 (s, 1H), 6.64 (d, J = 7.8 Hz, 1H), 6.37 (s, 1H), 6.14 (s, 1H), 4.24 (s, 1H), 3.89-3.80 (m, 4H), 3.60 (s, 2H), 3.28 (s, 2H), 3.05-2.95 (m, 7H), 2.61 (s, 1H), 2.25 (s, 1H), 1.99 (s, 1H), 1.75-1.50 (m, 6H), 1.37-1.17 (m, 12H), 1.14-1.01 (m, 9H). MS (ESI. m/e) [M + 1]⁺ 1043.9. |

-continued

| Ex. | structure | Compound name | Data |
|---|---|---|---|
| 122 | 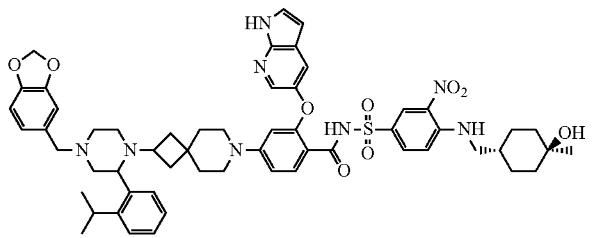 [SMILES: CC(C)c1ccccc1C1CN(Cc2ccc3c(c2)OCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yloxy)-4-(2-(4-(benzo[d][1,3]dioxol-5-ylmethyl)-2-(2-isopropylphenyl)piperazin-1-yl)-7-azaspiro[3.5]nonan-7-yl)-N-((1r,4r)-4-hydroxy-4-methylcyclohexyl)methyl)amino)-3-nitrophenyl)sulfonyl)benzamide | 1H NMR (400 MHz, DMSO-d$_6$) δ ppm 11.69 (s, 1H), 11.23 (s, 1H), 8.55 (s, 2H), 8.02 (s, 1H), 7.78 (d, J = 8.4 Hz, 1H), 7.50-7.46 (m, 3H), 7.31-7.10 (m, 3H), 7.06 (d, J = 9.0 Hz, 1H), 6.96 (s, 1H), 6.88-6.83 (m, 2H), 6.65 (d, J = 8.4 Hz, 1H), 6.37 (s, 1H), 6.15 (s, 1H), 5.99 (s, 2H), 4.25 (s, 1H), 3.70 (s, 3H), 3.28 (s, 3H), 2.98-2.90 (m, 7H), 2.73 (s, 1H), 2.33 (s, 1H), 1.72-1.50 (m, 7H), 1.39-0.99 (m, 20H). MS (ESI, m/e) [M + 1]$^+$ 1039.8. |
| 123 | 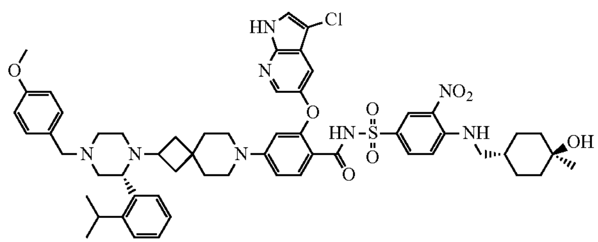 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(Cl)c7c6)c5)CC4)C3)[C@H](c3ccccc3C(C)C)C2)cc1] | 2-(3-chloro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-((R)-2-(2-isopropylphenyl)-4-(4-methoxybenzyl)piperazin-1-yl)-7-azaspiro[3.5]nonan-7-yl)benzamide | $^1$H NMR (400 MHz, DMSO-d$_6$) δ ppm: 11.69 (s, 1H), 11.36 (br, 1H), 8.63-8.54 (m, 2H), 8.03 (s, 1H), 7.88-7.75 (m, 1H), 7.54-7.44 (m, 3H), 7.43-7.04 (m, 6H), 6.96-6.88 (m, 1H), 6.68-6.63 (m, 1H), 6.37 (s, 1H), 6.15 (s, 1H), 4.25 (s, 1H), 3.84 (s, 3H), 3.82-3.58 (m, 2H), 3.48-3.37 (m, 1H), 3.32-3.15 (m, 3H), 3.12-2.56 (m, 9H), 2.45-2.26 (m, 1H), 2.14-1.94 (m, 7H), 1.38-1.16 (m, 10H), 1.14-1.00 (m, 8H). MS (ESI, m/e) [M + 1]$^+$ 1060.9. |
| 124 | 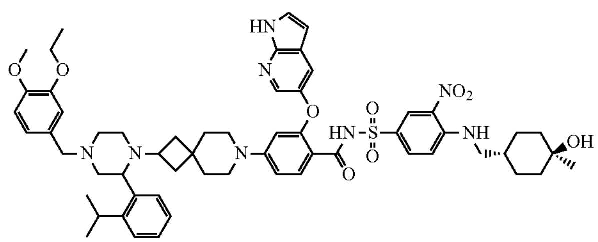 [SMILES: CCOc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)ccc1OC] | 2-((1H-pyrrolo[2,3-b]pyridin-5-yloxy)-4-(2-(4-(3-ethoxy-4-methoxybenzyl)-2-(2-isopropylphenyl)piperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.25 (br, 1H), 8.64-8.53 (m, 2H), 8.02 (s, 1H), 7.82-7.75 (m, 1H), 7.54-7.04 (m, 9H), 6.96-6.76 (m, 2H), 6.68-6.63 (m, 1H), 6.37 (s, 1H), 6.13 (s, 1H), 4.25 (s, 1H), 4.05-3.90 (m, 3H), 3.73 (s, 3H), 3.60-3.40 (m, 2H), 3.32-3.25 (m, 2H), 3.20-2.75 (m, 11H), 2.10-1.94 (m, 1H), 1.75-1.52 (m, 7H), 1.39-1.15 (m, 15H), 1.14-1.02 (m, 8H).MS (ESI, m/e) [M + 1]$^+$ 1070.0. |
| 125 | 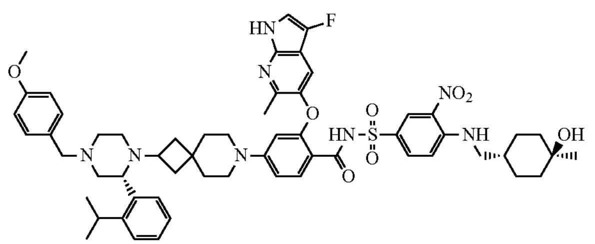 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cc7c(F)c[nH]c7nc6C)c5)CC4)C3)[C@H](c3ccccc3C(C)C)C2)cc1] | 2-(3-fluoro-6-methyl-1H-pyrrolo[2,3-b]pyridin-5-yloxy)-N-((4-((((1r,4r)-4-hydroxy-4-methylcyclohexyl)methyl)amino)-3-nitrophenyl)sulfonyl)-4-(2-((R)-2-(2-isopropylphenyl)piperazin-1-yl)-7-(4-methoxybenzyl)-7-azaspiro[3.5]nonan-7-yl)benzamide | $^1$H NMR (400 MHz, DMSO-d$_6$) δ ppm: 11.27 (s, 1H), 8.63-8.39 (m, 2H), 7.71 (d, J = 7.6 Hz, 1H), 7.51-6.79 (m, 12H), 6.68 (d, J = 8.0 Hz, 1H), 6.14 (s, 1H), 4.26 (s, 1H), 3.74 (s, 3H), 3.31-3.12 (m, 5H), 3.05-2.58 (m, 9H), 2.46-2.25 (m, 4H), 2.16-1.91 (m, 1H), 1.76-1.45 (m 7H), 1.40-0.93 (m, 21H). MS (ESI, m/e) [M + 1]$^+$ 1057.9 |

| Ex. | structure | Compound name | Data |
|---|---|---|---|
| 126 | 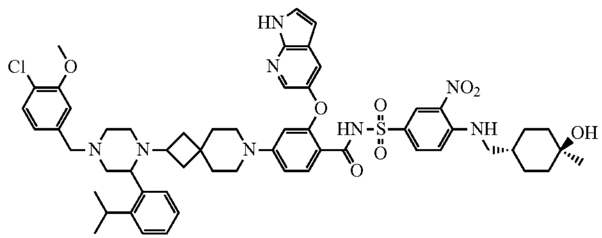 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)ccc1Cl] | 2-((1H-pyrrolo[2,3-b]pyridin-5-yl)oxy)-4-(2-(4-(4-chloro-3-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 12.00 (s, 1H), 11.52 (br, 1H), 8.59-8.47 (m, 2H), 8.08 (s, 1H), 7.80-7.74 (m, 1H), 7.68 (s, 1H), 7.50-7.10 (m, 8H), 7.09-6.86 (m, 3H), 6.68-6.64 (m, 1H), 6.23 (s, 1H), 4.24 (s, 1H), 3.98-3.80 (m, 1H), 3.74 (s, 3H), 3.62-3.40 (m, 1H), 3.32-3.25 (m, 2H), 3.20-2.57 (m, 11H), 2.45-2.30 (m, 1H), 2.10-1.94 (m, 1H), 1.75-1.52 (m, 7H), 1.39-1.15 (m, 12H), 1.14-1.02 (m, 7H). MS (ESI, m/e) [M + 1]$^+$ 1060.7. |
| 128 | 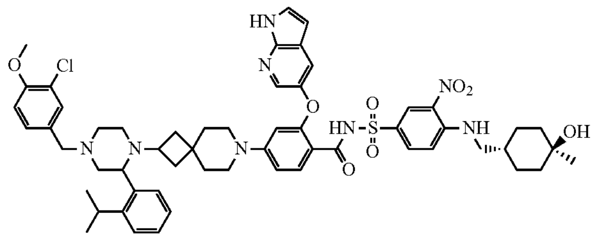 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1Cl] | 2-((1H-pyrrolo[2,3-b]pyridin-5-yl)oxy)-4-(2-(4-(3-chloro-4-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm 11.69 (s, 1H), 11.31 (s, 1H), 8.71-8.50 (m, 2H), 8.02 (s, 1H), 7.82-7.73 (m, 1H), 7.66-7.31 (m, 6H), 7.31-6.98 (m, 6H), 6.70-6.60 (m, 1H), 6.37 (s, 1H), 6.14 (s, 1H), 4.25 (s, 1H), 3.82 (s, 3H), 3.78-3.38 (m, 7H), 3.32-3.24 (m, 2H), 3.10-2.80 (m, 6H), 2.78-2.54 (m, 3H), 2.12-1.93 (m, 1H), 1.75-1.49 (m, 6H), 1.39-1.25 (m, 6H), 1.22-1.00 (m, 1H) MS (ESI, m/e) [M + 1]$^+$ 1060.7 |
| 129 | 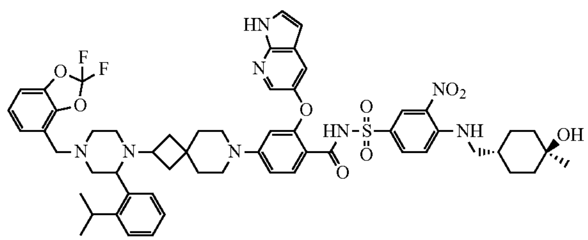 [SMILES: CC(C)c1ccccc1C1CN(Cc2cccc3c2OC(F)(F)O3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-((2,2-difluorobenzo[d][1,3]dioxol-4-yl)methyl)-7-azaspiro[3.5]nonan-7-yl)-2-(2-isopropylphenyl) piperazin-1-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm 11.68 (s, 1H), 11.40 (s, 1H), 8.65-8.50 (m, 2H), 8.02 (s, 1H), 7.85-7.60 (m, 2H), 7.55-7.43 (m, 3H), 7.43-7.00 (m, 8H), 6.70-6.57 (m, 1H), 6.37 (s, 1H), 6.14 (s, 1H), 4.25 (s, 1H), 3.90-3.40 (m, 4H), 3.32-3.16 (m, 4H), 3.12-2.65 (m, 9H), 2.28-1.90 (m, 3H), 1.72-1.51 (m, 6H), 1.42-1.26 (m, 5H), 1.20-1.00 (m, 1H) MS (ESI, m/e) [M + 1]$^+$ 1075.8 |
| 130 | 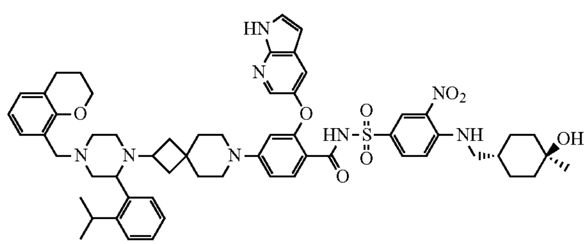 [SMILES: CC(C)c1ccccc1C1CN(Cc2cccc3c2OCCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(chroman-8-ylmethyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm 11.74 (s, 1H), 8.65-8.56 (m, 2H), 8.08 (s, 1H), 7.84 (d, J = 8.0 Hz, 1H), 7.58-7.39 (m, 4H), 7.36-6.97 (m, 6H), 6.86 (s, 1H), 6.71 (d, J = 8.0 Hz, 1H), 6.43 (s, 1H), 6.19 (s, 1H), 4.30 (s, 1H), 4.24-4.14 (m, 2H), 3.90-3.75 (m, 1H), 3.69-3.58 (m, 1H), 3.52-3.42 (m, 1H), 3.35-3.32 (m, 2H), 3.08-2.90 (m, 6H), 2.82-2.76 (m, 2H), 2.42-2.29 (m, 1H), 2.15-2.03 (m, 1H), 1.98-1.91 (m, 2H), 1.78-1.67 (m 4H), 1.64-1.56 (m, 3H), 1.43-1.35 (m, 4H), 1.33-1.28 (m, 5H), 1.26-1.23 (m, 2H), 1.19-1.13 (m, 8H), 0.94-0.86 (m, 4H). MS (ESI, m/e) [M + 1]$^+$ 1051.7 |

-continued

| Ex. | structure | Compound name | Data |
|---|---|---|---|
| 131 | 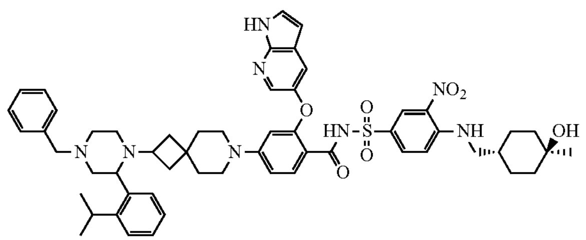 [SMILES: CC(C)c1ccccc1C1CN(Cc2ccccc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(pyridin-2-ylmethyl)piperazin-1-yl)-7-azaspiro[3.5]nonan-7-yl)benzamide | $^1$H NMR (400 MHz, DMSO-$d_6$) δ ppm: 11.66 (s, 1H), 8.51-8.48 (m, 3H), 7.99 (s, 1H), 7.75 (s, 2H), 7.46-7.44 (m, 4H), 7.30-7.10 (m, 5H), 6.63 (s, 1H), 6.35 (s, 1H), 6.12 (s, 1H), 4.23 (s, 1H), 3.82-3.50 (m, 4H), 3.25 (s, 2H), 2.90-2.80 (m, 7H), 2.27-2.16 (m, 1H), 1.96 (s, 1H), 1.68-1.60 (m, 5H), 1.52-1.50 (m, 2H), 1.35-1.20 (m, 10H), 1.15 (s, 3H), 1.10-1.00 (m, 8H). MS (ESI, m/e) [M + 1]$^+$ 996.7. |
| 132 | 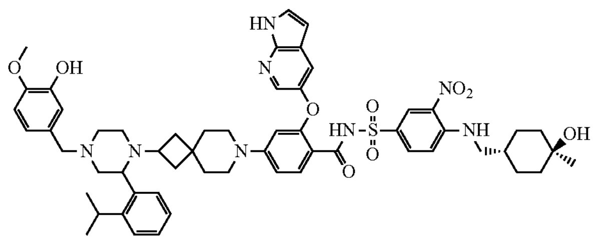 | 2-((1H-pyrrolo[2,3-b]pyridin-5-yl)oxy)-4-(2-(4-(3-cyano-4-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | $^1$H NMR (400 MHz, DMSO-$d_6$) δ ppm: 11.68 (s, 1H), 11.35 (br, 1H), 8.60-8.52 (m, 2H), 8.01 (d, J = 2.4 Hz, 1H), 7.80-7.76 (m, 1H), 7.68-7.52 (m, 2H), 7.52-7.45 (m, 3H), 7.38-7.15 (m, 5H), 6.66-6.60 (m, 1H), 6.36-6.34 (m, 1H), 6.17-6.07 (m, 1H), 4.24 (s, 1H), 3.86 (s, 6H), 3.79-3.40 (m, 4H), 3.32-3.25 (m, 3H), 2.30-1.94 (m, 3H), 1.70-1.51 (m, 7H), 1.37-1.15 (m, 13H), 1.14-1.02 (m, 4H). MS (ESI, m/e) [M + 1]$^+$ 1051.0. |
| 133 | 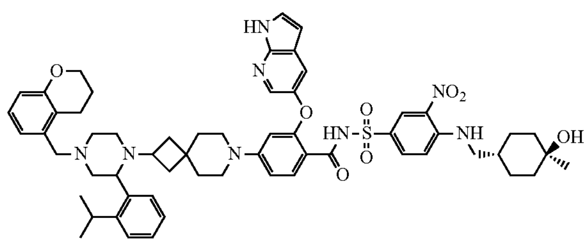 [SMILES: CC(C)c1ccccc1C1CN(Cc2cccc3c2CCCO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(chroman-5-ylmethyl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | $^1$H NMR (400 MHz, DMSO-$d_6$) δ ppm: 11.68 (s, 1H), 11.40 (br, 1H), 8.60-8.52 (m, 2H), 8.01 (d, J = 2.4 Hz, 1H), 7.80-7.52 (m, 2H), 7.50-7.42 (m, 3H), 7.35-7.15 (m, 3H), 7.07-6.92 (m, 2H), 6.80-6.74 (m, 1H), 6.66-6.57 (m, 2H), 6.36-6.34 (m, 1H), 6.17-6.07 (m, 1H), 4.24 (s, 1H), 4.09-3.97 (m, 2H), 3.79-3.40 (m, 4H), 3.32-3.05 (m, 3H), 3.03-2.80 (m, 7H), 2.79-2.60 (m, 4H), 2.13-1.94 (m, 2H), 1.92-1.84 (m, 2H), 1.70-1.40 (m 8H), 1.35-1.15 (m 14H), 1.14-1.02 (m, 3H). MS (ESI, m/e) [M + 1]$^+$ 1052.1. |
| 134 | 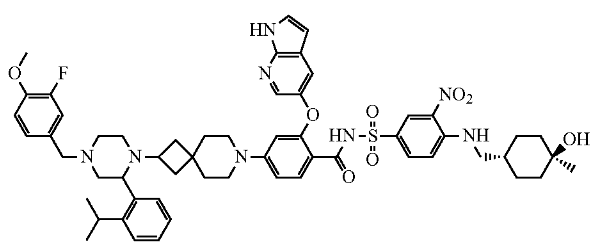 | 2-((1H-pyrrolo[2,3-b]pyridin-5-yl)oxy)-4-(2-(4-(3-fluoro-4-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | $^1$H NMR (400 MHz, DMSO-$d_6$) δ ppm: 11.68 (s, 1H), 11.35 (br, 1H), 8.60-8.52 (m, 2H), 8.01 (d, J = 2.4 Hz, 1H), 7.80-7.76 (m, 1H), 7.52-7.43 (m, 3H), 7.38-7.05 (m, 8H), 6.66-6.60 (m, 1H), 6.36-6.34 (m, 1H), 6.17-6.08 (m, 1H), 4.24 (s, 1H), 3.78 (s, 3H), 3.79-3.40 (m, 3H), 3.32-3.10 (m, 3H), 3.08-2.52 (m, 10H), 2.30-1.94 (m, 3H), 1.70-1.47 (m, 7H), 1.38-1.10 (m, 14H), 1.08-1.00 (m, 3H). MS (ESI, m/e) [M + 1]$^+$ 1044.0. |

-continued

| Ex. | Compound name | Data |
|---|---|---|
| 135 | 2-((1H-pyrrolo[2,3-b]pyridin-5-yl)oxy)-N-((4-((1r,4r)-4-hydroxy-4-methylcyclohexyl)amino)-3-nitrophenyl)sulfonyl)-4-(2-(2-(2-isopropylphenyl)-4-(2-(4-methoxyphenyl)cyclopentyl)piperazin-1-yl)-7-azaspiro[3.5]nonan-7-yl)benzamide | ¹H NMR (400 MHz,DMSO-d₆) δ ppm: 11.67 (s, 1H), 11.43 (s, 1H), 10.64-10.42 (m, 1H), 8.60-8.54 (m, 2H), 7.99 (s, 1H), 7.74 (s, 2H), 7.53-7.37 (m, 3H), 7.30-7.15 (m, 3H), 7.07 (s, 3H), 6.75-6.71 (m, 2H), 6.63 (s, 1H), 6.34 (s, 1H), 6.12 (s, 1H), 4.24 (s, 1H), 4.07 (s, 1H), 3.67 (s, 3H), 3.27-3.23 (m, 2H), 2.98-2.85 (m, 7H), 2.05-1.99 (m, 5H), 1.75-1.45 (m, 11H), 1.35-1.0 (m, 20H), 0.72 (s, 2H). MS (ESI, m/e) [M + 1]⁺ 1080.8. |
| 136 | 2-((1H-pyrrolo[2,3-b]pyridin-5-yl)oxy)-4-(2-(4-(3-cyclopropyl-4-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz. DMSO-d₆) δ ppm: 11.71 (s, 1H), 11.41 (s, 1H), 8.68-8.46 (m, 2H), 8.02 (s, 1H), 7.82-7.67 (m, 1H), 7.55-6.72 (m, 11H), 6.72-6.58 (m, 1H), 6.36 (s, 1H), 6.20-6.05 (m, 1H), 4.26 (s, 1H), 4.20-3.95 (m, 2H), 3.83-3.66 (m, 3H), 3.58-3.40 (m, 1H), 3.33-3.21 (m, 3H), 3.20-2.72 (m, 9H), 2.69-2.53 (m, 1H), 2.25-1.90 (m, 2H), 1.70-1.48 (m 6H), 1.37-1.24 (m, 5H), 1.21-0.96 (m, 13H), 0.95-0.75 (m, 3H), 0.72-0.45 (m, 3H) MS (ESI, m/e) [M + 1]⁺ 1066.7 |
| 137 | 2-((1H-pyrrolo[2,3-b]pyridin-5-yl)oxy)-4-(2-(4-(benzofuran-7-ylmethyl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | ¹H NMR (400 MHz, DMSO-d₆) δ ppm: 11.70 (s, 1H), 11.43 (s, 1H), 11.08 (s, 1H), 8.65-8.45 (m, 2H), 8.10-7.95 (m, 2H), 7.95-7.83 (m, 1H), 7.83-7.70 (m 1H), 7.68-6.90 (m, 11H), 6.80-6.57 (m, 1H), 6.37 (s, 1H), 6.22-6.04 (m, 1H), 4.74-4.56 (m, 1H), 4.26 (s, 1H), 3.99-3.67 (m, 2H), 3.46-3.35 (m, 2H), 3.31-2.59 (m, 13H), 2.20-1.92 (m, 2H), 1.78-1.43 (m, 6H), 1.39-1.24 (m, 5H), 1.22-0.94 (m 11H). MS (ESI, m/e) [M + 1]⁺ 1036.6 |
| 138 | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-(2-(2-isopropylphenyl)-4-(4-methoxyphenoxy)piperidin-1-yl)-7-azaspiro[3.5]nonan-7-yl)benzamide | ¹H NMR (400 MHz, DMSO-d₆) δ ppm: 11.68 (s, 1H), 11.43 (s, 1H), 8.64-8.40 (m, 2H), 8.10-7.88 (m, 2H), 7.85-7.67 (m, 1H), 7.54-6.96 (m, 8H), 6.96-6.73 (m, 4H), 6.73-6.57 (m, 1H), 6.35 (s, 1H), 6.14 (s, 1H), 4.76-4.55 (m, 1H), 4.24 (s, 1H), 3.72-3.58 (m, 3H), 3.58-3.34 (m, 3H), 3.30-3.21 (m, 2H), 3.21-2.58 (m, 6H), 2.35-1.85 (m, 6H), 1.73-1.43 (m, 6H), 1.3-1.21 (m, 6H), 1.19-0.94 (m, 10H). MS (ESI, m/e) [M + 1]⁺ 1027.6 |

-continued

| Ex. | structure | Compound name | Data |
|---|---|---|---|
| 139 | 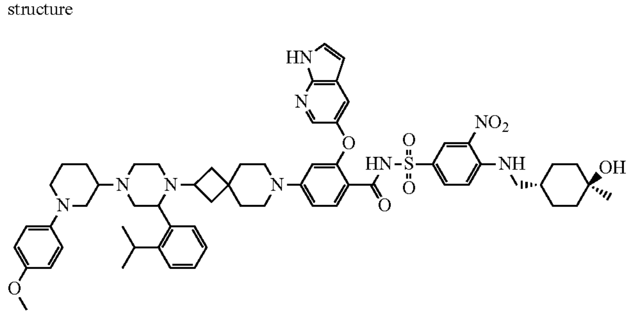 | 2-(1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-(4-methoxyphenyl)piperidin-3-yl)piperazin-1-yl)-7-azaspiro[3.5]nonan-7-yl)benzamide | $^1$H NMR (400 MHz, DMSO-d$_6$) δ ppm: 11.68 (s, 1H), 11.43 (br, 1H), 8.52-8.56 (m 2H), 8.00 (s, 1H), 7.75-7.78 (m, 1H), 7.43-7.49 (m, 3H), 7.36 (s, 1H), 7.06-7.24 (m, 4H), 6.74 (s, 2H), 6.64 (s, 1H), 6.51 (s, 1H), 6.35 (s, 1H), 6.12 (d, J = 8.0 Hz, 1H), 4.25-4.23 (m, 1H), 3.60-3.63 (m, 3H), 3.26-3.27 (m, 3H), 2.90-2.97 (m, 7H), 1.64-1.67 (m, 3H), 1.50-1.54 (m, 3H), 1.07-1.30 (m, 25H). MS (ESI, m/e) [M + 1]$^+$ 1095.6 |
| 140 | 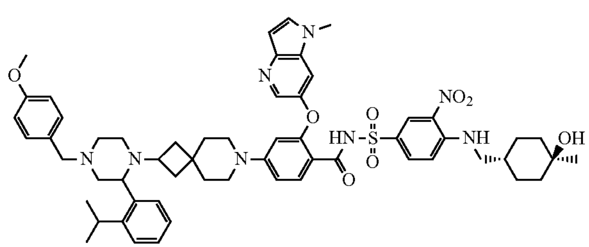 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7ccn(C)c7c6)c5)CC4)C3)C(c3ccccc3C(C)C)C2)cc1] | N-((4-(((1r,4r)-4-hydroxy-4-methylcyclohexyl)methyl)amino)-3-nitrophenyl)sulfonyl)-4-(2-(2-(2-isoptopylphenyl)-4-(4-methoxybenzyl)piperazin-1-yl)-7-azaspiro[3.5]nonan-7-yl)-2-((1-methyl-1H-pyrrolo[3,2-b]pyridin-6-yl)oxy)benzamide | $^1$H NMR (400 MHz,DMSO-d$_6$) δ ppm: 11.40-10.53 (m, 1H), 8.53 (s, 1H), 8.46 (d, J = 2.4 Hz, 1H), 8.06 (d, J = 2.4 Hz, 1H), 7.72 (d, J = 9.0 Hz, 1H), 7.50 (d, J = 3.4 Hz, 1H), 7.45 (d, J = 9.0 Hz, 1H), 7.40-7.10 (m, 6H), 7.00 (d, J = 9.4 Hz, 1H), 6.89 (s, 2H), 6.65 (d, J = 7.0 Hz, 1H), 6.46 (d, J = 3.4 Hz, 1H), 6.20 (s, 1H), 4.24 (s, 1H), 3.71 (s, 3H), 3.66 (s, 3H), 3 49 (s, 1H), 3.37 (s, 1H), 3.28-3.22 (m, 3H), 2.85-3.00 (m, 7H), 2.31 (s, 1H), 1.99-1.97 (m, 1H), 1.61-1.70 (m, 4H), 1.53-1.50 (m 2H), 1.36-1.10 (m, 13H), 1.10-1.0 (m, 7H). MS (ESI, m/e) [M + 1]$^+$ 1039.7. |
| 141b | 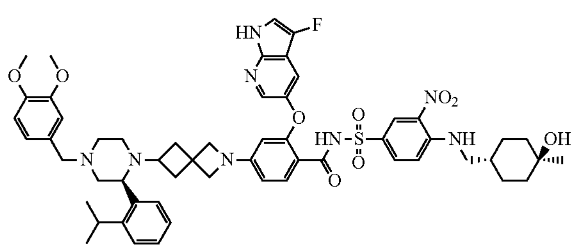 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@@H](c3ccccc3C(C)C)C2)cc1OC] | 4-(6-((S)-4-(3,4-dimethoxybenzyl) piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm 11.52 (s, 1H), 11.30 (br, 1H), 8.53-8.51 (m, 2H), 8.05 (s, 1H), 7.77 (d, J = 8.8 Hz, 1H), 7.50-7.47 (m, 2H), 7.41 (d, J = 8.8 Hz, 2H), 7.20-7.11 (m, 5H), 6.86 (s, 4H), 6.04 (d, J = 9.4 Hz, 1H), 5.30 (s, 1H), 4.24 (s, 1H), 3.75-3.70 (m, 6H), 3.59 (s, 1H), 3.53 (s, 2H), 3.49 (s, 1H), 2.97-2.85 (m, 5H), 2.70 (s, 2H), 2.2,3-2.16 (m, 2H), 1.99-1.95 (m, 4H), 1.67-1.63 (m, 5H), 1.53-1.50 (m, 3H), 1.35-1.25 (m, 4H), 1.22-1.15 (m 11H), 1.09-1.5 (m, 8H). MS (ESI, m/e) [M + 1]$^+$ 1046.0. |

-continued

| Ex. | structure | Compound name | Data |
|---|---|---|---|
| 142 | 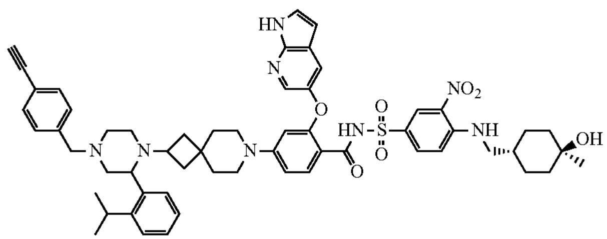 [SMILES: C#Cc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-4-(2-(4-(4-ethynylbenzyl)-2-(2-isopropylphenyl)piperazin-1-yl)-7-azaspiro[3.5]nonan-7-yl)-N-(4-((1r,4r)-4-hydroxy-4-methylcyclohexyl)methyl)benzamide | $^1$H NMR (400 MHz, DMSO-d$_6$) δ ppm: 11.68 (s, 1H), 11.33 (br, 1H), 8.60-8.52 (m, 2H), 8.05-7.98 (m, 1H), 7.80-7.74 (m, 1H), 7.53-7.40 (m, 5H), 7.38-7.05 (m, 6H), 6.66-6.60 (m, 1H), 6.36-6.34 (m, 1H), 6.17-6.08 (m, 1H), 4.24 (s, 1H), 4.19-4.13 (m, 1H), 3.79-3.53 (m, 3H), 3.43-3.34 (m, 1H), 3.32-3.10 (m, 3H), 3.05-2.55 (m, 9H), 2.30-1.94 (m 3H), 1.70-1.42 (m 7H), 1.38-1.10 (m, 11H), 1.08-1.00 (m, 8H). MS (ESI, m/e) [M + 1]$^+$ 1019.8 |
| 143 | 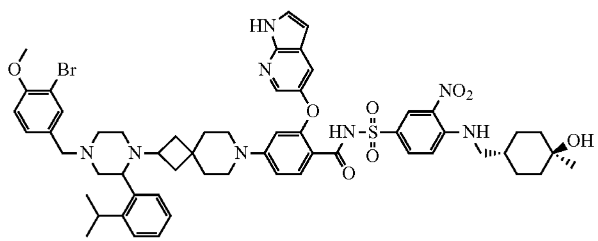 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1Br] | 2-((1H-pyrrolo[2,3-b]pyridin-5-yl)oxy)-4-(2-(4-(3-bromo-4-methoxybenzyl)-2-(2-isopropylphenyl)piperazin-1-yl)-7-azaspiro[3.5]nonan-7-yl)-N-(4-((1r,4r)-4-hydroxy-4-methylcyclohexyl)methyl)benzamide | $^1$H NMR (400 MHz, DMSO-d$_6$) δ ppm: 11.68 (s, 1H), 8.69-8.44 (m, 2H), 8.00 (s, 1H), 7.85-7.64 (m, 1H), 7.64-6.95 (m, 11H), 6.70-6.55 (m, 1H), 6.35-5.34 (m, 1H), 6.12 (s, 1H), 4.23 (s, 1H), 3.90-3.45 (m, 6H), 3.45-3.34 (m, 1H), 3.32-3.13 (m, 4H), 3.05-2.78 (m, 6H), 2.75-2.54 (m, 2H), 2.32-2.15 (m, 1H), 2.10-1.92 (m, 1H), 1.71-1.44 (m, 6H), 1.37-1.22 (m, 12H) MS (ESI, m/e) [M + 1]$^+$ 1105.6 |
| 144 | 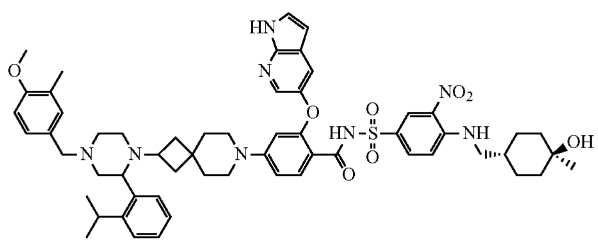 | 2-((1H-pyrrolo[2,3-b]pyridin-5-yl)oxy)-N-((4-((1r,4r)-4-hydroxy-4-methylcyclohexyl)methyl)amino)-3-nitrophenyl)sulfonyl)-4-(2-(2-(2-isopropylphenyl)piperazin-1-yl)-4-methoxy-3-methylbenzyl)-7-azaspiro[3.5]nonan-7-yl)benzamide | $^1$H NMR (400 MHz, DMSO-d$_6$) δ ppm: 11.68 (s, 1H), 8.64-8.43 (m, 2H), 8.05-7.93 (m, 1H), 7.86-7.68 (m, 2H), 7.58-6.77 (m, 11H), 6.70-6.55 (m, 1H), 6.42-6.29 (m 1H), 6.19-6.05 (m 1H), 4.24 (s, 1H), 4.10-3.65 (m, 5H), 3.57-3.35 (m, 2H), 3.30-3.18 (m, 3H), 3.07-2.55 (m, 9H), 2.43-2.22 (m, 1H), 2.16-1.89 (m, 4H), 1.77-1.38 (m, 7H), 1.38-1.22 (m, 5H), 1.20-0.94 (m, 12H) MS (ESI, m/e) [M + 1]$^+$ 1040.0 |
| 146 | 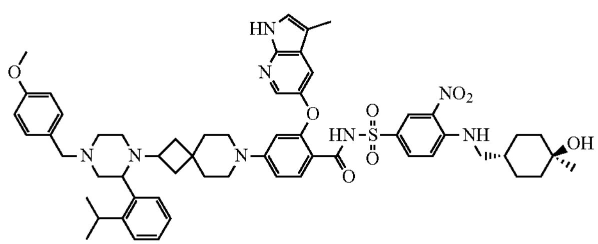 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(C)c7c6)c5)CC4)C3)C(c3ccccc3C(C)C)C2)cc1] | N-((4-((1r,4r)-4-hydroxy-4-methylcyclohexyl)methyl)amino)-3-nitrophenyl)sulfonyl)-4-(2-((R)-2-(2-isopropylphenyl)-4-methoxybenzyl)piperazin-1-yl)-7-azaspiro[3.5]nonan-7-yl)-2-(3-methyl-1H-pyrrolo[2,3-b]pyridin-5-yl)oxy)benzamide | $^1$H NMR (400 MHz, DMSO-d$_6$) δ ppm: 11.34 (s, 1H), 8.55-8.58 (m, 2H), 8.00 (s, 1H), 7.82 (d, J = 12.0 Hz, 1H), 7.35-7.51 (m, 5H), 7.17-7.26 (m, 4H), 7.10 (d, J = 8.0 Hz, 1H), 6.68 (d, J = 8.0 Hz, 1H), 6.87 (d, J = 8.0 Hz, 3H), 6.64 (d, J = 8.0 Hz, 1H), 6.09-6.12 (m, 1H), 4.24 (s, 1H), 3.71-3.76 (m, 3H), 3.56 (s, 1H), 3.55 (s, 1H), 3.27-3.29 (m, 2H), 2.91-2.96 (m, 8H), 2.16 (s, 2H), 1.99-2.07 (m, 2H), 1.66-1.69 (m, 3H), 1.52-1.56 (m, 31-1), 1.02-1.37 (m, 25H), MS (ESI, m/e) [M + 1]$^+$ 1039.9 |

| Ex. | structure | Compound name | Data |
|---|---|---|---|
| 147 | 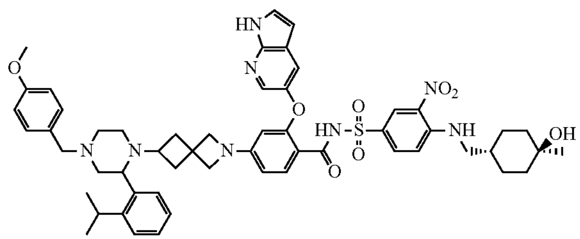 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)C(c3ccccc3C(C)C)C2)cc1] | 2-((1H-pyrrolo[2,3-b]pyridin-5-yl)oxy)-N-((4-(((1r,4r)-4-hydroxy-4-methyl(cyclohexyl)methyl)amino)-3-nitrophenyl)sulfonyl)-4-(6-((R)-4-(4-methoxybenzyl)-2-(2-isopropylphenyl)piperazin-1-yl)-2-azaspiro[3.3]heptan-2-yl)benzamide | ¹H NMR (400 MHz, DMSO-d₆) δ ppm: 11.73 (s, 1H), 11.23 (br, 1H), 8.63-8.54 (m, 2H), 8.07-8.02 (m, 1H), 7.62-7.51 (m, 2H), 7.47-7.08 (m, 8H), 6.97-6.80 (m, 2H), 6.43-6.37 (m, 1H), 6.06-6.02 (m, 1H), 5.49 (s, 1H), 4.25 (s, 1H), 3.73 (s, 3H), 3.68-3.36 (m, 7H), 3.32-3.10 (m, 3H), 3.05-2.55 (m, 6H), 2.30-1.94 (m, 3H), 1.70-1.42 (m, 7H), 1.38-1.10 (m, 8H), 1.08-1.00 (m, 5H). MS (ESI, m/e) [M + 1]⁺ 997.9. |
| 148 | 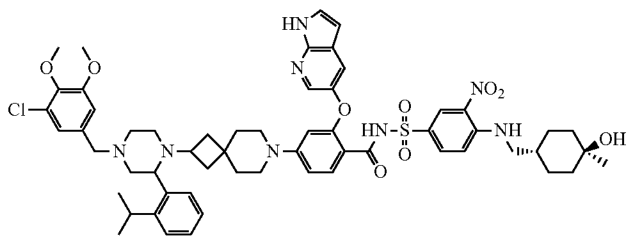 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc(Cl)c1OC] | 2-((1H-pyrrolo[2,3-b]pyridin-5-yl)oxy)-4-(2-(4-(3-chloro-4,5-dimethoxybenzyl)-2-(2-isopropylphenyl)piperazin-1-yl)-7-azaspiro[3.5]nonan-7-yl)-N-(4-(((1r,4r)-4-hydroxy-4-methyl(cyclohexyl)methyl)amino)-3-nitrophenyl)sulfonyl)benzamide | ¹H NMR (400 MHz, DMSO-d₆) δ ppm: 11.69 (s, 1H), 11.45-11.22 (m, 1H), 8.57-8.55 (m, 2H), 8.03 (s, 1H), 7.78 (d, J = 8.2 Hz, 1H), 7.50 (s, 3H), 7.42-7.31 (m, 1H), 7.22 (s, 2H), 7.07 (d, J = 9.2 Hz, 2H), 6.99 (s, 2H), 6.65 (d, J = 8.8 Hz, 1H), 6.37 (s, 1H), 6.14 (s, 1H), 4.25 (s, 1H), 3.80 (s, 4H), 3.70 (s, 3H), 3.59 (s, 3H), 3.28 (s, 2H), 3.08-2.85 (m, 7H), 2.25 (s, 1H), 1.99 (s, 1H), 1.75-1.50 (m, 7H), 1.40-1.19 (m, 12H), 1.10-1.08 (m, 9H). MS (ESI, m/e) [M + 1]⁺ 1090.9. |
| 149a | 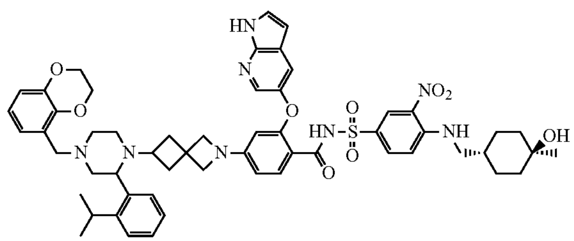 [SMILES: CC(C)c1ccccc1C1CN(Cc2cccc3c2OCCO3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]ccc4c3)c1)C2] | 2-((1H-pyrrolo[2,3-b]pyridin-5-yl)oxy)-4-(6-((R)-4-((2,3-dihydrobenzo[b][1,4]dioxin-5-yl)methyl)-2-(2-isopropylphenyl)piperazin-1-yl)-2-azaspiro[3.3]heptan-2-yl)-N-((4-(((1r,4r)-4-hydroxy-4-methyl(cyclohexyl)methyl)amino)-3-nitrophenyl)sulfonyl)benzamide | ¹H NMR (400 MHz, DMSO-d₆) δ ppm: 11.73 (s, 1H), 11.04 (s, 1H), 8.74-8.34 (m, 2H), 8.03 (s, 1H), 7.90-7.74 (m, 1H), 7.67-7.34 (m, 4H), 7.34-7.04 (m, 5H), 7.04-6.87 (m, 1H), 6.87-6.65 (m, 2H), 6.39 (s, 1H), 6.10-5.95 (m, 1H), 5.48 (s, 1H), 4.30-4.15 (m, 5H), 3.87-3.45 (m, 8H), 3.30-3.23(m, 3H), 3.14-2.61 (m, 5H), 2.38-2.18 (m, 2H), 2.10-1.88 (m 2H), 1.75-1.45 (m, 6H), 1.42-1.27 (m, 3H), 1.20-1.00 (m, 10H), MS (ESI, m/e) [M + 1]⁺ 1026.6 |
| 149b | 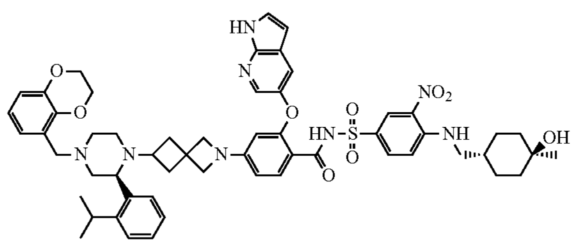 [SMILES: CC(C)c1ccccc1[C@H]1CN(Cc2cccc3c2OCCO3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]ccc4c3)c1)C2] | 2-((1H-pyrrolo[2,3-b]pyridin-5-yl)oxy)-4-(6-((S)-4-((2,3-dihydrobenzo[b][1,4]dioxin-5-yl)methyl)-2-(2-isopropylphenyl)piperazin-1-yl)-2-azaspiro[3.3]heptan-2-yl)-N-((4-(((1r,4r)-4-hydroxy-4-methyl(cyclohexyl)methyl)amino)-3-nitrophenyl)sulfonyl)benzamide | ¹H NMR (400 MHz,DMSO-d₆) δ ppm: 11.73 (s, 1H), 11.17 (br, 1H), 8.58-8.55 (m, 2H), 8.04 (s, 1H), 7.82 (d, J = 9.0 Hz, 1H), 7.58 (s, 1H), 7.52 (s, 1H), 7.44 (d, J = 9.0 Hz, 2H), 7.24 (s, 2H), 7.11 (d, J = 8.0 Hz, 2H), 6.90 (s, 1H), 6.78 (s, 2H), 6.40 (s, 1H), 6.04 (d, J = 8.8 Hz, 1H), 5.48 (s, 1H), 4.28-4.20 (m, 5H), 3.56-3.50 (m 7H), 3.29 (s, 2H), 2.92-2.87 (m, 3H), 2.71 (s, 2H), 2.25 (s, 1H), 1.97 (s, 6H), 1.73-1.49 (m, 6H), 1.38-1.30 (m, 3H), 1.25-1.02 (m, 12H). MS (ESI, m/e) [M + 1]⁺ 1025.9. |

| Ex. | structure | Compound name | Data |
|---|---|---|---|
| 150 | 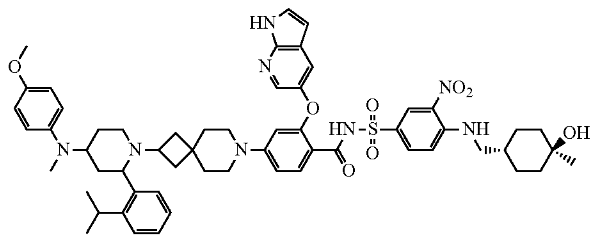 | 2-((1H-pyrrolo[2,3-b]pyridin-5-yl)oxy)-N-((1r,4r)-4-hydroxy-4-methyl)cyclohexyl)methyl)-3-nitrophenyl)sulfonyl)-4-(2-(2-isopropylphenyl)-(methyl)amino)-4-((4-methoxyphenyl)(methyl)amino)piperidin-1-yl)-7-azaspiro[3.5]nonan-7-yl)benzamide | ¹H NMR (400 MHz,DMSO-d₆) δ ppm: 11.70 (s, 1H), 11.45 (s, 1H), 10.35 (s, 1H), 8.56 (s, 2H), 8.03 (s, 1H), 7.76 (s, 2H), 7.50 (s, 3H), 7.30-7.21 (m, 5H), 7.08 (s, 1H), 6.87 (s, 2H), 6.66 (s, 1H), 6.38 (s, 1H), 6.17 (s, 1H), 4.82 (s, 1H), 4.26 (s, 1H), 3.82 (s, 1H), 3.69 (s, 3H), 3.39 (s, 1H), 3.28 (s, 4H), 2.99-2.80 (m, 5H), 2.60 (s, 3H), 2.21-1.95 (m, 5H), 1.70-1.49 (m, 5H), 1.40-1.20 (m, 12H), 1.15-1.10 (m, 4H), 0.89 (s, 3H), 0.60 (s, 1H). MS (ESI, m/e) [M + 1]⁺ 1039.8. |
| 151 | 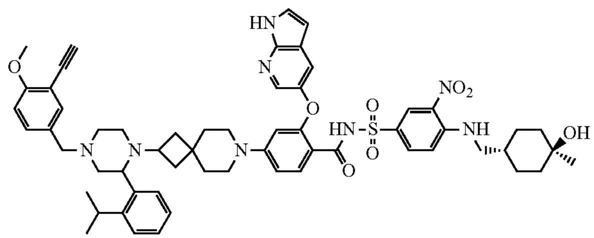 [SMILES: C#Cc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)ccc1OC] | 2-((1H-pyrrolo[2,3-b]pyridin-5-yl)oxy)-4-(2-(4-(3-ethynyl-4-methoxybenzyl)-2-(2-isopropylphenyl)piperazin-1-yl)-7-azaspiro[3.5]nonan-7-yl)-N-((4-(((1r,4r)-4-hydroxy-4-methyl)cyclohexyl)methyl)amino)-3-nitrophenyl)sulfonyl)benzamide | ¹H NMR (400 MHz, DMSO-d₆) δ ppm 11.69 (s, 1H), 11.41 (s, 0.6H), 10.69 (s, 0.4H), 8.64-8.48 (m, 1H), 8.03 (s, 1H), 7.90-7.71 (m, 2H), 7.67-6.95 (m, 11H), 6.74-6.57 (s, 1H), 6.37 (s, 1H), 6.20-6.05 (m, 1H), 4.69-4.52 (s, 0.5H), 4.31-4.18 (m, 1.5H), 3.88-3.70 (m, 4H), 3.63-3.48 (m, 1H), 3.46-3.38 (m, 1H), 3.35-3.16 (m, 5H), 3.16-2.80 (m, 7H), 2.80-2.57 (m, 2H), 2.09-1.97 (m, 1H), 1.76-1.49 (m, 6H), 1.48-1.26 (m, 6H), 1.23-0.94 (m, 12H). MS (ESI, m/e) [M + 1]⁺ 1050.5 |
| 152 | 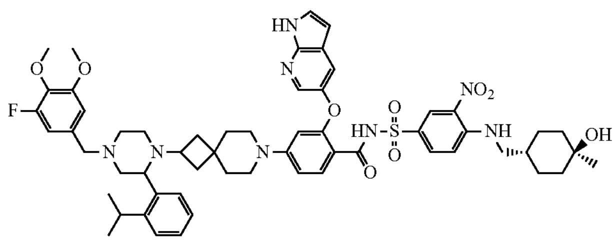 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc(F)c1OC] | 2-((1H-pyrrolo[2,3-b]pyridin-5-yl)oxy)-4-(2-(4-(3-fluoro-4,5-dimethoxybenzyl)-2-(2-isopropylphenyl)piperazin-1-yl)-7-azaspiro[3.5]nonan-7-yl)-N-((4-(((1r,4r)-4-hydroxy-4-methyl)cyclohexyl)methyl)amino)-3-nitrophenyl)sulfonyl)benzamide | ¹H NMR (400 MHz, DMSO-d₆) δ ppm 11.70 (s, 1H), 11.34 (s, 0.6H), 10.59 (s, 0.4H), 8.68-8.45 (m, 1H), 8.02 (s, 1H), 7.90-7.64 (m, 2H), 7.61-7.01 (m, 8H), 6.97-6.75 (m, 2H), 6.75-6.55 (m, 1H), 6.37 (s, 1H), 6.14 (s, 1H), 4.25 (s, 1H), 3.79 (s, 3H), 3.73 (s, 3H), 3.67-3.41 (m, 4H), 3.32-3.24 (m, 3H), 3.08-2.80 (m, 6H), 2.78-2.54 (m, 2H), 2.37-1.94 (m, 2H), 1.73-1.48 (m, 6H), 1.46-1.24 (m, 8H), 1.21-0.95 (m, 11H). MS (ESI, m/e) [M + 1]⁺ 1074 |
| 153 | 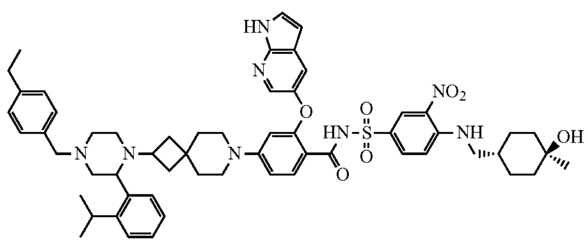 [SMILES: CCc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-4-(2-(4-(4-ethylbenzyl)-2-(2-isopropylphenyl)piperazin-1-yl)-7-azaspiro[3.5]nonan-7-yl)-N-((4-(((1r,4r)-4-hydroxy-4-methyl)cyclohexyl)methyl)amino)-3-nitrophenyl)sulfonyl)benzamide | ¹H NMR (400 MHz, DMSO-d₆) δ ppm: 11.70 (s, 1H), 11.34 (br, 1H), 8.64-8.53 (m, 2H), 8.03 (s, 1H), 7.82-7.74 (m, 1H), 7.54-7.30 (m, 5H), 7.38-7.05 (m, 6H), 6.68-6.62 (m, 1H), 6.37 (s, 1H), 6.19-6.10 (m, 1H), 4.25 (s, 1H), 4.09-3.54 (m, 1H), 3.65-3.43 (m, 3H), 3.32-3.10 (m 3H), 3.05-2.85 (m, 7H), 2.75-2.55 (m, 3H), 2.30-1.94 (m, 2H), 1.74-1.50 (m, 7H) 1.38-1.10 (m, 16H), 1.08-1.00 (m, 3H). MS (ESI, m/e) [M + 1]⁺ 1024.0. |

| Ex. | Compound name | Data |
|---|---|---|
| 154 | 2-((1H-pyrrolo[2,3-b]pyridin-5-yloxy)-N-(4-(((1r,4r)-4-hydroxy-4-methylcyclohexyl)methyl)amino)-3-nitrophenyl)sulfonyl)-4-(2-(2-(2-isopropylphenyl)-4-((5-methoxypyrazin-2-yl)methyl)piperazin-1-yl)-7-azaspiro[3.5]nonan-7-yl)benzamide | ¹H NMR (400 MHz, DMSO-d₆) δ ppm: 11.69 (s, 1H), 11.40 (br, 1H), 8.64-8.54 (m, 2H), 8.31-8.19 (m, 2H), 8.02 (s, 1H), 7 83-7.76 (m, 1H), 7.54-7.43 (m, 3H), 7.40-7.35 (m, 1H), 7.30-7.04 (m, 4H), 6.68-6.62 (m, 1H), 6.39-6.35 (m, 1H), 6.17-6.10 (m, 1H), 4.25 (s, 1H), 3.89 (s, 3H), 3.85-3.65 (m, 3H), 3.45-3.35 (m, 1H), 3.32-3.25 (m, 2H), 3.08-2.52 (m, 10H), 2.30-1.94 (m, 3H), 1.74-1.50 (m, 7H), 1.38-1.10 (m, 14H), 1.08-1.00 (m, 3H). MS (ESI, m/e) [M + 1]⁺ 1027 8 |
| 156 | 2-((1H-pyrrolo[2,3-b]pyridin-5-yloxy)-4-(2-(4-(4-cyclopropyl-3-methoxybenzyl)-2-(2-isopropylphenyl)piperazin-1-yl)-7-azaspiro[3.5]nonan-7-y)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.50 (s, 1H), 8.28-8.33 (m, 2H), 7.87 (s, 1H), 7.52-7.57 (m, 2H), 7.38 (s, 1H), 7.10-7.19 (m, 3H), 7.06-7.10 (m, 1H), 6.65 (s, 1H), 6.71-6.73 (m, 3H), 6.58 (d, J = 8.0 Hz, 2H), 4.26 (s, 1H), 3.77 (s, 3H), 3.44-3.51 (m, 3H), 3.20 (s, 2H), 2.84-2.90 (m, 7H), 2.15-2.19 (m, 2H), 1.99-2.03 (m, 2H), 1.61-1.69 (m, 4H), 1.52-1.55 (m, 2H), 1.18-1.33 (m, 16H), 1.05-1.12 (m, 8H), 0.82-0.84 (m, 2H), 0.54 (s, 2H). MS (ESI, m/e) [M + 1]⁺ 1065.9 |
| 157 | 2-((1H-pyrrolo[2,3-b]pyridin-5-yloxy)-N-(4-(((1r,4r)-4-hydroxy-4-methylcyclohexyl)methyl)amino)-3-nitrophenyl)sulfonyl)-4-(2-(2-(4-isopropylpyridin-3-yl)-4-(4-methoxybenzyl)piperazin-1-yl)-7-azaspiro[3.5]nonan-7-yl)benzamide | ¹H NMR (400 MHz, DMSO-d₆) δ ppm 11.67 (s, 1H), 11.34-11.07 (m, 1H), 8.53 (s, 2H), 8.32 (s, 1H), 8.02 (s, 1H), 7.77 (d, J = 8.2 Hz, 1H), 7.50-7.48 (m, 3H), 7.23-7.22 (m, 3H), 7.05 (d, J = 9.4 Hz, 1H), 6.89-6.85 (m, 2H), 6.64 (d, J = 8.6 Hz, 1H), 6.37 (s, 1H), 6.14 (s, 1H), 4.24 (s, 1H), 3.71 (s, 3H), 3.52 (s, 3H), 3.28 (s, 2H), 3.05-2.91 (m, 7H), 2.14 (s, 1H), 1.75-1 51 (m, 7H), 1.21-1.35-1.21 (m, 10H), 1.03 (m, 13H). MS (ESI, m/e) [M + 1]⁺ 1026.8. |
| 158 | 2-((1H-pyrrolo[2,3-b]pyridin-5-yl)oxy)-4-(2-(4-(3,4-ditethoxy-5-methylbenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.24 (s, 1H), 8.55 (s, 2H), 8.02 (s, 1H), 7.78 (d, J = 8.4 Hz, 1H), 7.50-7.46 (m, 4H), 7.40-7.00 (m, 5H), 6.90-6.83 (m, 1H), 6.76-6.57 (m, 2H), 6.37 (s, 1H), 6.14 (s, 1H), 4.24 (s, 1H), 3.80-3.65 (m, 10H), 3.28 (s, 3H), 3.05-2.85 (m, 8H), 2.71 (s, 1H), 2.14 (s, 3H), 1.65-1.55 (m, 8H), 1.37-1.02 (m, 24H). MS (ESI, m/e) [M + 1]⁺ 1070.1. |

| Ex. | structure | Compound name | Data |
|---|---|---|---|
| 159 | 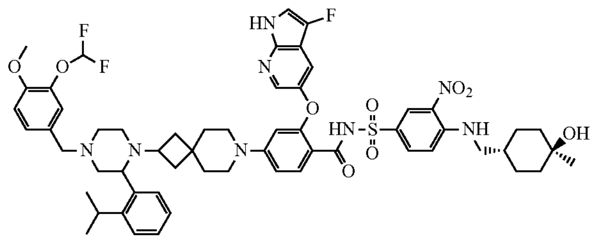 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)C(c3ccccc3C(C)C)C2)cc1OC(F)F] | 4-(2-(4-(3-(difluoromethoxy)-4-methoxybenzyl)-2-isopropylpiperazin-1-yl)-7-azaspiro[3.5]nonan-7-yl)-2-((3-fluoro-1H-pyrrolo[2,3-b]pyridin-5-yl)oxy)-N-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.67-10.87 (m, 2H), 8.67-8.31 (m, 1H), 8.08-7.99 (m, 1H), 7.81-7.70 (m, 1H), 7.53-7.37 (m, 3H), 7.36-6.95 (m, 9H), 6.74-6.60 (m, 1H), 6.21 (s, 1H), 4.24 (s, 1H), 3.93-3.50 (m, 5H), 3.31-3.20 (m, 5H), 3.10-2.88 (m, 7H), 2.78-2.60 (m 2H), 2.36-2.18 (m, 1H), 2.10-1.92 (m, 1H), 1.75-1.44 (m, 7H), 1.39-1.25 (m, 6H), 1.21-11 5 (m, 3H), 1.15-1.02 (m 9H). MS (ESI, m/e) [M + 1]⁺ 1109.8. |
| 160 | 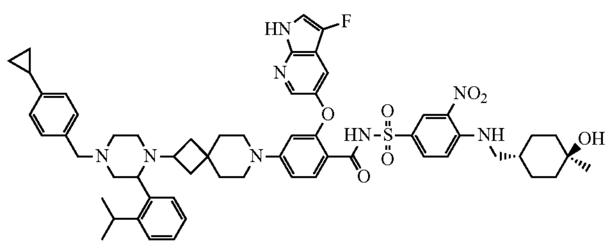 [SMILES: CC(C)c1ccccc1C1CN(Cc2ccc(C3CC3)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]cc(F)c5c4)c3)CC2)C1] | 4-(2-(4-(4-cyclopropylbenzyl)-2-isopropylphenyl)piperazin-1-yl)-7-azaspiro[3.5]nonan-7-yl)-2-((3-fluoro-1H-pyrrolo[2,3-b]pyridin-5-yl)oxy)-N-((((1r,4r)-4-hydroxy-4-methylcyclohexyl)methyl)amino)-3-nitrophenyl)sulfonyl)benzamide | ¹H NMR (400 MHz, CDCl₃) δ ppm: 12.98-12.02 (m, 0.5H), 10.43-9.67 (m, 0.5H), 8.90-8.81 (m, 0.5 H), 8.74-8.56 (m, 0.5H), 8.56-8.42 (m, 1H), 8.27-8.05 (1H, 2H), 7.98-7.85 (m, 1H), 7.72-7.62 (m, 1H), 7.55-7.30 (m, 1H), 7.23-7.06 (m, 5H), 7.04-6.95 (m, 2H), 6.93-6.83 (m, 1H), 6.57-6.45 (m, 1H), 5.90 (s, 1H), 3.72-3.38 (m, 3H), 3.33-3.10 (m, 4H), 3.05-2.60 (m, 9H), 2.08-1.93 (m, 1H), 1.93-1.81 (m, 3H), 1.81-1.70 (m 5H), 1.56-1.44 (m 6H), 1.44-1.30 (m, 7H), 1.17-1.01 (m, 6H), 0.97-0.90 (m, 2H), 0.68-0.60 (m, 2H). MS (ESI, m/e) [M + 1]⁺ 1053.8. |
| 161 | 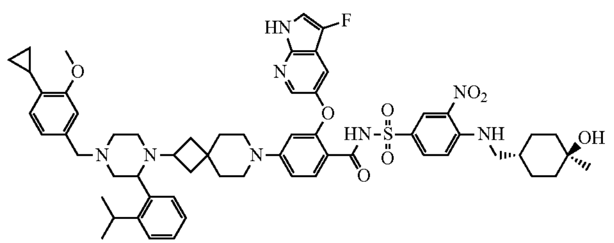 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)C(c3ccccc3C(C)C)C2)ccc1C1CC1] | 4-(2-(4-(4-cyclopropyl-3-methoxybenzyl))-2-isopropylphenyl) piperazin-1-yl)-7-azaspiro[3.5]nonan-7-yl)-2-((3-fluoro-1H-pyrrolo[2,3-b]pyridin-5-yl)oxy)-N-((((1r,4r)-4-hydroxy-4-methylcyclohexyl)methyl)amino)-3-nitrophenyl)sulfonyl)benzamide | 1H NMR (400 MHz, CDCl₃) δ ppm: 12.69-12.21 (m, 0.2H), 10.06-9.94 (m, 0.811), 8.87-8.80 (m, 0.5H), 8.70-8.57 (m, 0.5H), 8.55-8.45 (m, 1H), 8.27-8.08 (m, 2H), 7.95-7.85 (m, 1H), 7.72-7.61 (m, 1H), 7.48-7.27 (m, 3H), 7.25-7.06 (m, 2H), 6.94-6.85 (m, 1H), 6.83-6.70 (m, 2H), 6.56-6.46 (m, 1H), 5.96-5.81 (m, 1H), 4.02-3.80 (m, 3H), 3.70-3.33 (m, 4H), 3.31-3,12 (m, 4H), 3.10-2.75 (m, 8H), 2.17-1.96 (m, 3H), 1.92-170 (m, 7H), 1.52-1.43 (m, 4H), 1.40-1.29 (m, 8H), 1.21-1.03 (m, 8H), 0.66-0.53 (m, 2H). MS (ESI, m/e) [M + 1]⁺ 1083.8. |

| Ex. | structure | Compound name | Data |
|---|---|---|---|
| 162 | 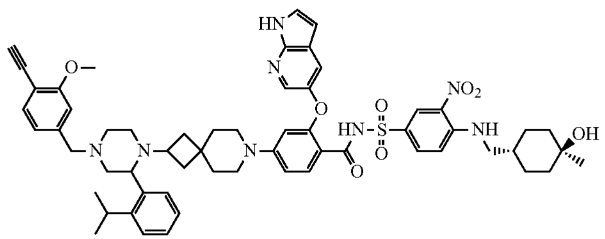 [SMILES: C#Cc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1OC] | 2-((1H-pyrrolo[2,3-b]pyridin-5-yl)oxy)-4-(2-(4-(4-ethynyl-3-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.66 (s, 1H), 11.33 (br, 1H), 8.58-8.52 (m, 2H), 8.01 (s, 1H), 7.77 (d, J = 9.6 Hz, 1H), 7.52-7.00 (m, 8H), 6.98 (s, 1H), 6.87 (d, J = 7.6 Hz, 1H), 6.65 (d, J = 9.6 Hz, 1H), 6.36 (s, 1H), 6.14 (s, 1H), 4.24 (s, 1H), 4.16 (s, 1H), 3.78 (s, 3H), 3.60-3.40 (m, 3H), 3.30-3.23 (m, 3H), 3.00-2.80 (m 7H), 2.27-2.15 (m, 2H), 2.09-1.95 (m, 1H), 1.73-1.51 (m, 2H), 1.39-1.15 (m, 13H), 1.12-1.02 (m, 7H). MS (ESI, m/e) [M + 1]$^+$ 1050.1. |
| 163 | 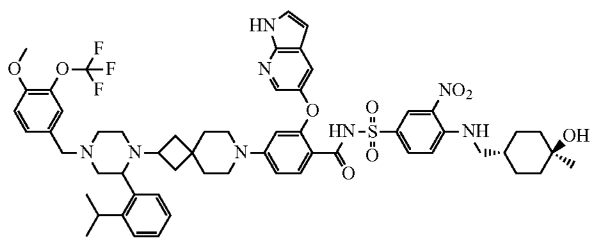 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1OC(F)(F)F] | 2-((1H-pyrrolo[2,3-b]pyridin-5-yl)oxy)-N-((((1r,4r)-4-hydroxy-4-methylcyclohexyl)methyl)amino)-3-nitrophenyl)sulfonyl)-4-(2-(2-isopropylphenyl)-4-(4-methoxy-3-(trifluoromethoxy)benzyl)piperazin-1-yl)-7-azaspiro[3.5]nonan-7-yl)benzamide | $^1$H NMR (400 MHz, DMSO-$d_6$) δ ppm: 11.68 (s, 1H), 11.34 (br, 1H), 8.58-8.52 (m, 2H), 8.03 (s, 1H), 7.77-7.75 (m, 1H), 7.54-7.03 (m, 11H), 6.66 (d, J = 9.6 Hz, 1H), 6.37 (s, 1H), 6.14 (s, 1H), 4.24 (s, 1H), 3.96 (s, 3H), 3.65-3.40 (m, 2H), 3.30-3.23 (m, 3H), 3.09-2.52 (m, 9H), 2.27-2.15 (m, 1H), 2.09-1.95 (m, 2H), 1.73-1.51 (m, 7H), 1.39-1.15 (m, 13H), 1.12-1.02 (m, 7H). MS (ESI, m/e) [M + 1]$^+$ 1109.8. |
| 164 | 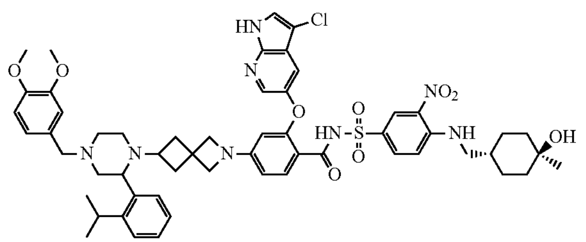 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(Cl)c6c5)c3)C4)C(c3ccccc3C(C)C)C2)cc1OC] | 2-(3-chloro-1H-pyrrolo[2,3-b]pyridin-5-yl)oxy)-4-(6-((R)-4-(3,4-dimethoxybenzyl)-2-(2-isopropylphenyl)piperazin-1-yl)-2-azaspiro[3.3]heptan-2-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 12.04 (s, 1H), 11.45 (br, 1H), 8.60-8.52 (m, 2H), 8.10 (s, 1H), 7.80 (d, J = 9.6 Hz, 1H), 7.73-7.69 (m, 1H), 7.47-7.05 (m, 8H), 6.95-6.85 (m, 2H), 6.09-6.04 (m, 1H), 5.54 (s, 1H), 4.24 (s, 1H), 3.79-3.65 (m, 8H), 3.68-3.36 (m, 6H), 3.32-3.10 (m, 3H), 3.05-2.65 (m, 5H), 2.42-2.28 (m, 1H), 2.06-1.93 (m 2H), 1.77-1.50 (m, 7H), 1.39-1.10 (m, 13H). MS (ESI, m/e) [M + 1]$^+$ 1063.0. |
| 165 | 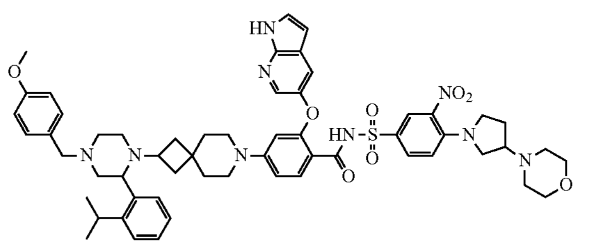 [SMILES: COc1ccc(CN2CCN(C3CC4(CCN(c5ccc(C(=O)NS(=O)(=O)c6ccc(N7CCC(N8CCOCC8)C7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yloxy)-4-(2-((R)-2-isopropylphenyl)-4-(4-methoxybenzyl)piperazin-1-yl)-7-azaspiro[3.5]nonan-7-yl)-N-(4-(3-morpholinopyrrolidin-1-yl)-3-nitrophenyl)sulfonyl)benzamide | $^1$H NMR (400 MHz, DMSO-$d_6$) δ ppm: 11.72 (s, 1H), 11.47-11.08 (m, 1H), 8.22 (s, 1H), 8.04 (s, 1H), 7.75 (s, 1H), 7.57-7.43 (m, 3H), 7.40-7.15 (m, 5H), 7.05 (d, J = 8.0 Hz, 1H), 6.95-6.90 (m, 2H), 6.64 (d, J = 8.4 Hz, 1H), 6.40 (s, 1H), 6.11 (s, 1H), 3.73 (s, 3H), 3.59 (s, 4H), 3.21 (s, 5H), 3.10-2.85 (m, 9H), 2.40 (s, 3H), 2.17 (s, 1H), 1.99 (s, 1H), 1.79 (s, 1H), 1.65-1.60 (m, 2H), 1.35-1.10 (m, 12H), 1.09-1.00 (m, 4H). MS (ESI, m/e) [M + 1]$^+$ 1038.9. |

-continued

| Ex. | structure | Compound name | Data |
|---|---|---|---|
| 166 | 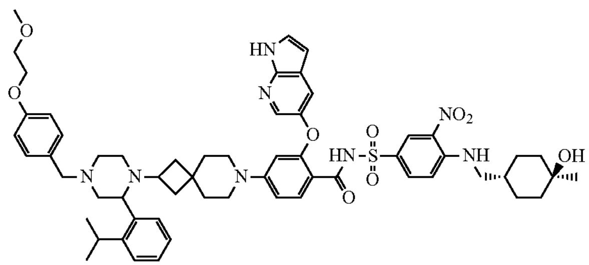 [SMILES: COCCOc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-(((1r,4r)-4-hydroxy-4-methyl)cyclohexyl)amino)-3-nitrophenyl)sulfonyl)-4-(2-(2-(2-isopropylphenyl)-4-(4-(2-methoxyethoxy)benzyl)piperazin-1-yl)-7-azaspiro[3.5]nonan-7-yl)benzamide | $^1$H NMR (400 MHz, DMSO-d$_6$) δ ppm: 11.69 (s, 1H), 11.51-11.10 (m, 1H), 8.55-8.53 (m, 2H), 8.02 (s, 1H), 7.76 (s, 1H), 7.50 (s, 3H), 7.40-7.20 (m, 6H), 7.08 (s, 1H), 6.91 (s, 2H), 6.65 (d, J = 8.4 Hz, 1H), 6.37 (s, 1H), 6.13 (s, 1H), 4.25 (s, 1H), 4.06 (s, 2H), 3.65-3.62 (m 3H), 3.29 (s, 6H), 3.05-2.85 (m, 8H), 1.99 (s, 1H), 1.72-1.49 (m, 7H), 1.37-1.00 (m, 24H). MS (ESI, m/e) [M + 1]$^+$ 1070.9. |
| 167 | 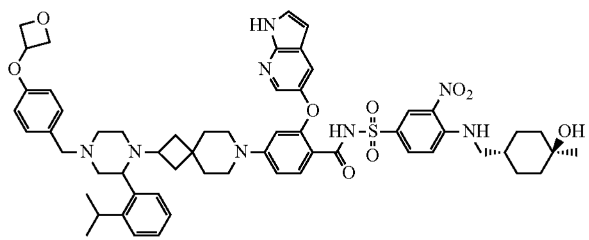 [SMILES: CC(C)c1ccccc1C1CN(Cc2ccc(OC3COC3)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methyl)cyclohexyl)amino)-3-nitrophenyl)sulfonyl)-4-(2-(2-(2-isopropylphenyl)-4-(4-(oxetan-3-yloxy)benzyl)piperazin-1-yl)-7-azaspiro[3.5]nonan-7-yl)benzamide | $^1$H NMR (400 MHz, DMSO-d$_6$) δ ppm: 11.68 (s, 1H), 8.55-8.53 (m, 2H), 8.02 (s, 1H), 7.76 (s, 1H), 7.49-7.46 (m, 3H), 7.40-7.10 (m, 6H), 6.75 (s, 2H), 6.64 (s, 1H), 6.37 (s, 1H), 6.14 (s, 1H), 5.24 (s, 1H), 4.90 (s, 2H), 4.50 (s, 2H), 4.25 (s, 1H), 3.56 (s, 2H), 3.28 (s, 3H), 3.05 -2.85 (m, 7H), 2.67 (s, 1H), 2.29-2.16 (m, 1H), 1.99 (s, 1H), 1.75-1.50 (m, 7H), 1.35-1.00 (m, 22H). MS (ESI, m/e) [M + 1]$^+$ 1067.9. |
| 168 | 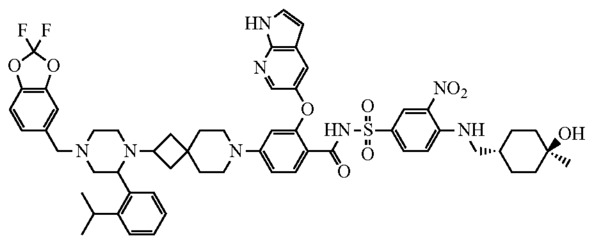 [SMILES: CC(C)c1ccccc1C1CN(Cc2ccc3c(c2)OC(F)(F)O3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(2,2-difluorobenzo[d][1,3]dioxol-5-yl)methyl)piperazin-1-yl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm 11.68 (s, 1H), 11.35 (s, 1H), 8.54-8.56 (m, 2H), 8.01-8.02 (m, 1H), 7.77 (d, J = 8.0 Hz, 1H), 7.32-7.55 (m, 7H), 7.05-7.19 (m, 4H), 6.65 (d, J = 8.0 Hz, 1H), 6.37 (s, 1H), 6.14 (s, 1H), 4.25 (s, 1H), 3.51-3.71 (m, 3H), 3.28 (s, 2H), 2.91-2.98 (m, 7H), 2.20-2.24 (m, 1H), 1.97-2.03 (m, 1H), 1.63-1.70 (m, 3H), 1.52-1.56 (m, 2H), 1.01-1.36 (m, 24H). MS (ESI, m/e) [M + 1]$^+$ 1076.0 |
| 169 | 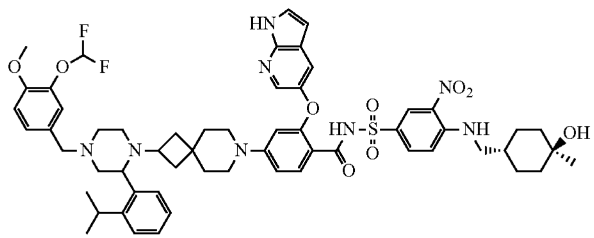 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1OC(F)F] | 2-((1H-pyrrolo[2,3-b]pyridin-5-yl)oxy)-4-(2-(4-(3-(difluoromethoxy)-4-methoxybenzyl)piperazin-1-yl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.67 (s, 1H), 11.28 (s, 1H), 8.63-850 (m, 2H), 8.06-7.97 (m, 1H), 7.81-7.72 (m, 1H), 7.56-7.43 (m, 3H), 7.43-6.97 (m, 9H), 6.76-6.58 (m, 1H), 6.37 (s, 1H), 6.14 (s, 1H), 4.24 (s, 1H), 3.86-3.75 (m, 4H), 3.69-3.48 (m, 5H), 3.30-3.24 (m, 1H), 3.09-2.81 (m, 6H), 2.74-2.54 (m, 2H), 2.30-2.09 (m, 1H), 1.78-1.47 (m, 7H), 1.38-1.25 (m, 6H), 1.23-1.01 (m, 13H). MS (ESI, m/e) [M + 1]$^+$ 1092.0. |

| Ex. | structure | Compound name | Data |
|---|---|---|---|
| 170 | 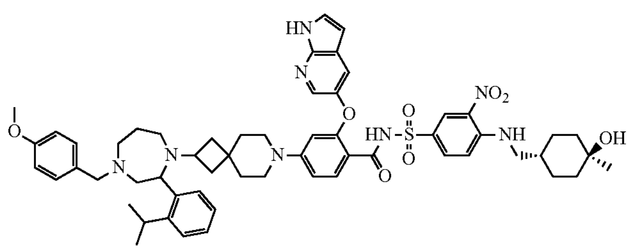 [SMILES: COc1ccc(CN2CCCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-((1r,4r)-4-hydroxy-4-methylcyclohexyl)amino)-3-nitrophenyl)sulfonyl)-4-(2-(2-isopropylphenyl)-4-(4-methoxybenzyl)-1,4-diazepan-1-yl)-7-azaspiro[3.5]nonan-7-yl)benzamide | 1H NMR (400 MHz, DMSO-d6) δ ppm: 11.69 (s, 1H), 11.38 (s, 1H), 8.69-8.40 (m, 2H), 8.12-7.93 (m, 1H), 7.84-7.69 (m, 1H), 7.62-7.24 (m, 6H), 7.25-6.99 (m, 5H), 6.96-6.80 (m, 2H), 6.72-6.61 (m, 1H), 6.38 (s, 1H), 6.16 (s, 1H), 4.25 (s, 1H), 3.73 (s, 3H), 3.33-3.10 (m, 11H), 3.07-2.86 (m, 5H), 2.80-2.58 (m, 2H), 2.15-1.80 (m, 2H), 1.76-1.49 (m, 6H), 1.49-1.25 (m, 7H), 1.18-0.98 (m, 8H), 0.77-0.61 (m, 3H). MS (ESI, m/e) [M + 1]+ 1039.8. |
| 171 | 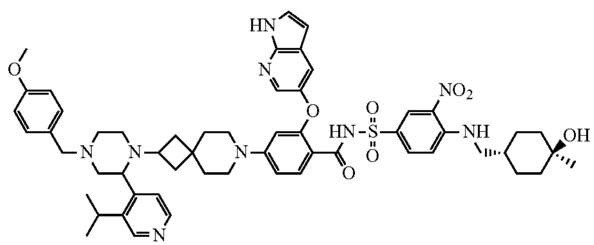 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccncc3C(C)C)C2)cc1] | 2-((1H-pyrrolo[2,3-b]pyridin-5-yl)oxy)-N-((4-((1r,4r)-4-hydroxy-4-methylcyclohexyl)amino)-3-nitrophenyl)sulfonyl)-4-(2-(2-(3-isopropylpyridin-4-yl)-4-(4-methoxybenzyl)piperazin-1-yl)-7-azaspiro[3.5]nonan-7-yl)benzamide | 1H NMR (400 MHz, CDCl3) δ ppm: 10.10 (s, 1H), 8.88 (s, 1H), 8.65-8.27(m, 3H), 8.27-8.00 (m, 2H), 7.96-7.80 (m, 1H), 7.70 (s, 1H), 7.58-7.28 (m, 3H), 6.94-6.70 (m, 3H), 6.63-6.32 (m, 2H), 5.93 (s, 1H), 3.79 (s, 3H), 3.66-3.36 (m, 2H), 3.35-3.18 (m, 3H), 3.06-2.76 (m, 7H), 1.93-1.80 (m, 3H), 1.80-1.60 (m, 11H), 1.57-1.43 (m, 4H), 1.39-1.32 (m, 4H), 1.23-1.15 (m, 9H). MS (ESI, m/e) [M + 1]+ 1026.8. |
| 172 | 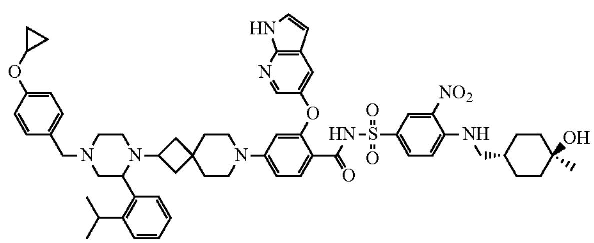 [SMILES: CC(C)c1ccccc1C1CN(Cc2ccc(OC3CC3)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-cyclopropoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.68 (s, 1H), 11.21 (s, 1H), 8.62-8.50 (m, 2H), 8.02 (s, 1H), 7.82-7.71 (m, 1H), 7.59-7.39 (m, 4H), 7.38-6.84 (m, 9H), 6.72-6.50 (m, 1H), 6.37 (s, 1H), 6.14 (s, 1H), 4.75-4.31 (m, 1H), 4.25 (s, 1H), 3.99-3.55 (m, 3H), 3.33-3.22 (m, 5H), 3.07-2.85 (m, 6H), 2.80-2.70 (m, 3H), 1.82-1.45 (m, 7H), 1.41-1.16 (m, 11H), 1.14-0.92 (m, 9H), 0.83-0.70 (m, 2H), 0.65-0.52 (m, 2H). MS (ESI, m/e) [M + 1]+ 1051.9. |
| 173 | 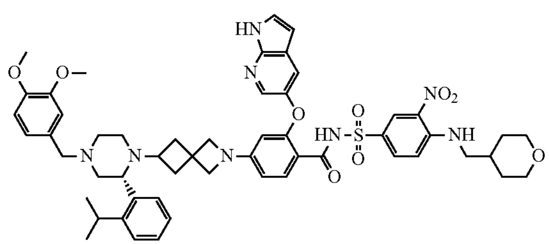 [SMILES: COc1ccc(CN2CCN(C3CC4(C3)CN(c3ccc(C(=O)NS(=O)(=O)c5ccc(NCC6CCOCC6)c([N+](=O)[O-])c5)c(Oc5cnc6[nH]ccc6c5)c3)C4)[C@H](c3ccccc3C(C)C)C2)cc1OC] | (R)-2-((1H-pyrrolo[2,3-b]pyridin-5-yl)oxy)-4-(6-(4-(3,4-dimethoxybenzyl)-2-(2-isopropylphenyl)piperazin-1-yl)-2-azaspiro[3.3]heptan-2-yl)-N-((3-nitro-4-(((tetrahydro-2H-pyran-4-yl)methyl)amino)phenyl)sulfonyl)benzamide | 1H NMR (400 MHz, DMSO-d6) δ ppm: 11.72 (s, 1H), 11.08 (s, 1H), 8.68-8.53 (m, 2H), 8.08-8.00 (m, 1H), 7.83 (d, J = 8.8 Hz, 1H), 7.62-7.04 (m, 9H), 6.91 (s, 2H), 6.40 (s, 1H), 6.04 (d, J = 8.4 Hz, 1H), 5.49 (s, 1H), 4.04-3.80 (m, 4H), 3.78-3.69 (m, 6H), 3.66-3.43 (m, 5H), 3.32-3.20 (m, 4H), 3.18-2.64 (m, 6H), 2.46-2.31 (m, 1H), 2.07-1.82 (m, 3H), 1.70-1.55 (m, 3H), 1.36-0.99 (m, 10H). MS (ESI, m/e) [M + 1]+ 1000.1. |

| Ex. | structure | Compound name | Data |
|---|---|---|---|
| 174 | 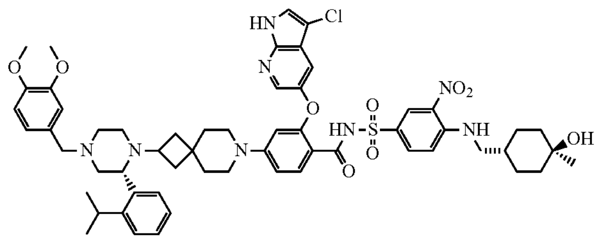 | 2-((3-chloro-1H-pyrrolo[2,3-b]pyridin-5-yl)oxy)-4-(2-((R)-4-(3,4-dimethoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | 1H NMR (400 MHz, DMSO-d6) δ ppm:: 11.93 (s, 1H), 11.45 (br, 1H), 8.53-8.42 (m 2H), 8.06 (s, 1H), 7.74-7.63 (m, 2H), 7.50 (d, J = 8.4 Hz, 1H), 7.46-6.76 (m, 9H), 6.68 (d, 7- 8.4 Hz, 1H), 6.24 (s, 1H), 4.23 (s, 1H), 3.72 (s, 3H), 3.70 (s, 3H), 3.64-3.40 (m, 4H), 3.30-3.2.3 (m, 3H), 3.06-2.60 (m, 10H), 2.27-2.15 (m, 2H), 2.09-1.95 (m, 1H), 1.74-1.50 (m, 7H), 1.39-1.15 (m, 14H), 1.12-1.02 (m 3H) MS (ESI, m/e) [M + 1]+ 1091.1. |
| 175 | 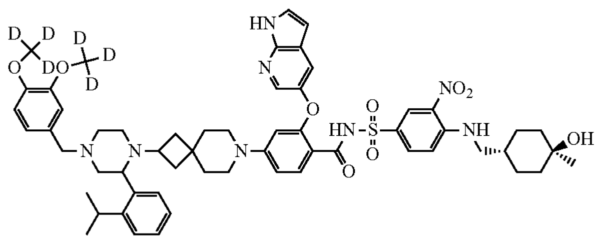 [SMILES: [2H]C([2H])([2H])Oc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1OC([2H])([2H])[2H]] | 2-((1H-pyrrolo[2,3-b]pyridin-5-yl)oxy)-4-(2-(4-(3,4-bis(methoxy-d3)benzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.68 (s, 1H), 11.34 (br, 1H), 8.59-8.54 (m, 2H), 8.02 (s, 1H), 7.79 (d, J = 8.8 Hz, 1H), 7.53-7.06 (m, 8H), 6.95-6.75 (m, 2H), 6.66 (d, J = 8.0 Hz, 1H), 6.37 (s, 1H), 4.23 (s, 1H), 3.96-3.40 (m, 4H), 3.30-3.23 (m, 3H), 3.09-2.52 (m 9H), 2.44-2.30 (m, 1H), 2.09-1.90 (m, 2H), 1.75-1.51 (m, 7H), 1.39-1.15 (m, 14H), 1.12-1.02 (m, 3H). MS (ESI, m/e) [M + I]+ 1062.3 |
| 176 | 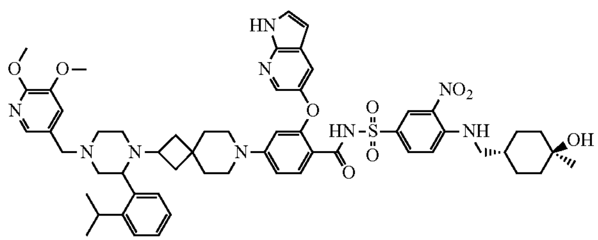 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cnc1OC] | 2-((1H-pyrrolo[2,3-b]pyridin-5-yl)oxy)-4-(2-(4-((5,6-dimethoxypyridin-1-yl)piperazin-1-yl)-7-azaspiro[3.5]nonan-7-y)-N-(4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.68 (s, 1H), 11.47 (br, 1H), 8.60-8.52 (m, 2H), 8.03 (s, 1H), 7.79 (d, J = 8.8 Hz, 1H), 7.65-7.05 (m, 10H), 6.68-6.64 (m, 1H), 6.37 (m, 1H), 6.18-6.12 (m, 1H), 4.23 (s, 1H), 3.82 (s, 3H), 3.77 (s, 3H), 3.66-3.40 (m, 4H), 3.30-3.25 (m, 3H), 3.09-2.60 (m, 10H), 2.27-2.15 (m, 1H), 2.09-1.95 (m, 2H), 1.74-1.50 (m, 7H), 1.39-1.15 (m, 14H), 1.12-1.02 (m, 3H). MS (ESI, m/e) [M + 1]+ 1057.3. |
| 177 | 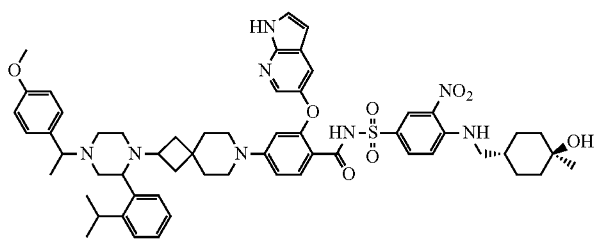 [SMILES: COc1ccc(C(C)N2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(1-(4-methoxyphenyl)ethyl)piperazin-1-yl)-7-azaspiro[3.5]nonan-7-yl)benzamide | 1H NMR (400 MHz, DMSO-d6) δ ppm: 11.68 (s, 1H), 11.38 (s, 1H), 8.57-8.55 (m, 2H), 8.03-8.02 (m, 1H), 7.78 (d, J = 8.0 Hz, 1H), 7.50-7.45 (m, 4H), 7.36-7.16 (m 5H),7.09-7.07 (m, 1H), 6.99-6.90 (m, 2H), 6.65 (d, J = 8.0 Hz, 1H), 6.37 (s, 1H), 6.13 (s, 1H), 4.25 (s, 1H), 3.77-3.74 (m, 4H), 3.34-3.28 (m, 7H), 2.04-1.98 (m, I), 1.66-1.53 (m, 9H), 1.33-1.10 (m, 25H). MS (ESI, m/e) [M + 1]+ 1040.2. |

-continued

| Ex. | structure | Compound name | Data |
|---|---|---|---|
| 178 | 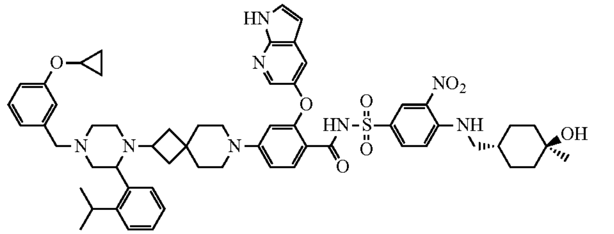 [SMILES: CC(C)c1ccccc1C1CN(Cc2cccc(OC3CC3)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(3-cyclopropoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.29 (s, 1H), 8.55 (s, 2H), 8.02 (d, J = 8.4 Hz, 1H), 7.5.3-7.43 (m, 3H), 7.41-6.87 (m, 8H), 6.65 (d, J = 8.6 Hz, 1H), 6.37 (s, 1H), 6.14 (s, 1H), 4.23 (s, 1H), 3.75-3.70 (m, 4H), 3.28 (s, 2H), 3.10-2.89 (m, 7H), 2.67 (s, 2H), 2.07 (s, 1H), 1.75-1.50 (m, 7H), 1.40-0.97 (m, 20H), 0.76 (s, 2H), 0.60 (s, 2H).MS (ESI, m/e) [M + 1]⁺ 1052.1 |
| 179 | 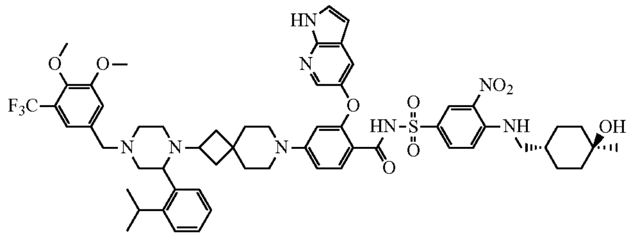 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc(C(F)(F)F)c1OC] | 2-((1H-pyrrolo[2,3-b]pyridin-5-yl)oxy)-4-(2-(4-(3,4-dimethoxy-5-(trifluoromethyl)benzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.35 (s, 1H), 8.55 (s, 2H), 8.03 (s, 1H), 7.78 (d, J = 8.8 Hz, 1H), 7.57-7.01 (m, 9H), 6.65 (d, J = 8.4 Hz, 1H), 6.37 (s, 1H), 6.15 (s, 1H), 4.23 (s, 1H), 3.90-3.70 (m, 9H), 3.42 (s, 1H), 3.28 (s, 2H), 3.10-2.85 (m, 7H), 2.70 (s, 2H), 2.05 (s, 1H), 1.75-1.51 (m, 6H), 1.48-0.96 (m, 21H). MS (ESI, m/e) [M + 1]⁺ 1125.1. |
| 180 | 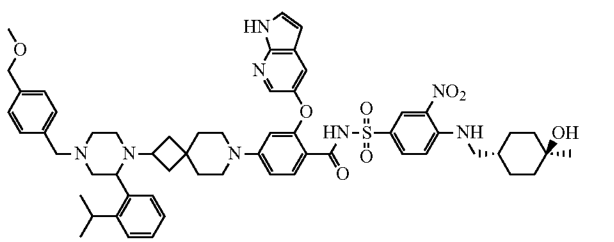 [SMILES: COCc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(4-(1-isopropyl-1H-(methoxymethyl)benzyl)piperazin-1-yl)-7-azaspiro[3.5]nonan-7-yl)benzamide | ¹H NMR (400 MHz, DMSO-d₆) δ ppm: 11.68 (s, 1H), 11.38-11.06 (m, 1H), 8 55 (s, 2H), 8.02 (s, 1H), 7.78 (d, J = 9.0 Hz, 1H), 7.50-7.10 (m, 11H), 6.65 (d, J = 8.4 Hz, 1H), 6.37 (s, 1H), 6.14 (s, 1H), 4.37 (s, 2H), 4.23 (s, 1H), 3.80-3.67 (m, 2H), 3.29-3.25 (m, 6H), 3.10-2.85 (m, 7H), 2.71-2.70 (m, 2H), 2.03 (s, 1H), 1.40-0.97 (m, 22H). MS (ESI, m/e) [M + 1]⁺ 1040.1. |
| 181 | 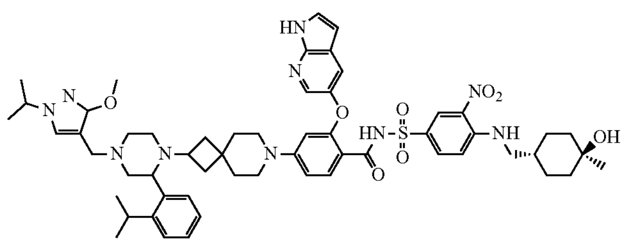 [SMILES: COC1NN(C(C)C)C=C1CN1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)C(c2ccccc2C(C)C)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-2-(4-(1-isopropyl-3-methoxy-1H-pyrazol-4-yl)methyl)-2-(2-isopropylphenyl)piperazin-1-yl)-7-azaspiro[3.5]nonan-7-yl)benzamide | ¹H NMR (400 MHz, DMSO-d₆) δ ppm: 11.68 (s, 1H), 11.39 (br, 1H), 8.62-8.54 (m, 2H), 8.02 (s, 1H), 7.80 (d, J = 8.8 Hz, 1H), 7.54-7.15 (m, 8H), 7.09 (d, J = 8.8 Hz, 1H), 6.66 (d, J = 7.6 Hz, 1H), 6.38 (s, 1H), 6.18-6.10 (m, 1H), 4.49-4.35 (m, 1H), 4.24 (s, 1H), 3.98-3.75 (m, 5H), 3.47-3.40 (m, 1H), 3.30-3.23 (m, 3H), 3.06-2.60 (m, 10H), 2.37-2.30 (m, 1H), 2.09-1.95 (m, 2H), 1.74-1.50 (m, 7H), 1.39-1.15 (m, 20H), 1.12-1.02 (m, 3H) MS (ESI, m/e) [M + 1]⁺ 1058.1. |

| Ex. | structure | Compound name | Data |
|---|---|---|---|
| 182 | 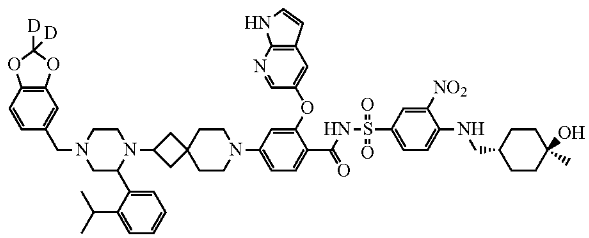 [SMILES: [2H]C1([2H])Oc2ccc(CN3CCN(C4CC5(CCN(c6ccc(C(=O)NS(=O)(=O)c7ccc(NC[C@H]8CC[C@](C)(O)CC8)c([N+](=O)[O-])c7)c(Oc7cnc8[nH]ccc8c7)c6)CC5)C4)C(c4ccccc4C(C)C)C3)cc2O1] | 2-((1H-pyrrolo[2,3-b]pyridin-5-yl)oxy)-4-(2-(4-((benzo[d][1,3]dioxol-5-yl-2,2-d2)methyl)-2-(2-isopropylphenyl) piperazin-1-yl)-7-azaspiro[3.5]nonan-7-y)-N-(4-(((1r,4r)-4-hydroxy-4-methylcyclohexyl)amino)-3-nitrophenyl)sulfonyl)benzamide | $^1$H NMR (400 MHz, DMSO-d$_6$) δ ppm: 11.68 (s, 1H), 11.39 (br, 1H), 8.63-8.54 (m, 2H), 8.02 (s, 1H), 7.79 (d, J = 8.8 Hz 1H), 7.54-7.12 (m, 8H), 7.09 (d, J = 8.8 Hz, 1H), 6.97-6.75 (m, 2H), 6.66 (d, J = 8.0 Hz, 1H), 6.37 (s, 1H), 6.18-6.11 (m, 1H), 4.24 (s, 1H), 3.96-3.40 (m, 3H), 3.30-3.23 (m, 3H), 3.09-2.54 (m, 10H), 2.44-2.30 (m, 1H), 2.09-1.94 (m, 2H), 1.75-151 (m, 7H), 1.39-1.15 (m, 14H) 1.12-1.02 (m, 3H) MS (ESI, m/e) [M + 1]$^+$ 1042.1 |
| 183 | | (R)-2-((3-fluoro-1H-pyrrolo[2,3-b]pyridin-5-yl)oxy)-4-(6-(2-(2-isopropylphenyl)-4-(4-methoxybenzyl)piperazin-1-yl)-2-azaspiro[3.3]heptan-2-y))-N-((3-nitro-4-(((tetrahydro-2H-pyran-4-yl)methyl)amino)phenyl)sulfonyl)benzamide | $^1$H NMR (400 MHz, DMSO-d$_6$) δ ppm: 11.53 (s, 1H), 10.91 (br, 1H), 8.64-8.52 (m, 2H), 8.07 (s, 1H), 7.83(d, J = 8.0 Hz, 1H), 7.57-7.08 (m, 10H), 6.98-6.80 (m, 2H), 6.10-6.04 (m 1H), 5.53 (s, 1H), 4.20-3.81 (m, 3H), 3.74 (s, 3H), 3.68-3.39 (m, 5H), 3.32-3.10 (m, 6H), 3.09-2.55 (m, 6H), 2.44-2.30 (m, 1H), 2.24-1.82 (m, 3H), 1.63 (d, J = 11.6 Hz, 2H), 1.35-1.15 (m, 7H), 1.08-1.00 (m, 2H). MS (ESI, m/e) [M + 1]$^+$ 988.0. |
| 184 | 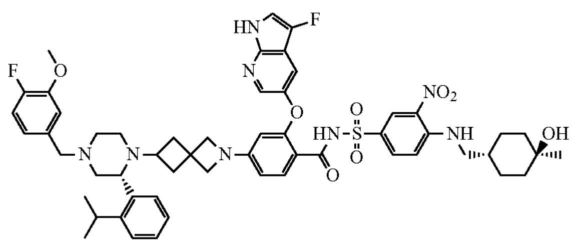 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1F] | 2-((3-fluoro-1H-pyrrolo[2,3-b]pyridin-5-yloxy)-4-(6-((R)-4-(4-fluoro-3-methoxybenzyl)-2-(2-isopropylphenyl)piperazin-1-yl)-2-azaspiro[3.3]heptan-2-yl)-N-(4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.54 (s, 1H), 11.45-11.25 (m, 1H), 8.56-8.54 (m, 2H), 8.07 (s, 1H), 7.81 (d, J = 8.2 Hz, 1H), 7.51 (s, 2H), 7.42 (s, 2H), 7.30-7.10 (m, 6H), 6.87 (s, 1H), 6.07 (s, 1H), 5.53 (s, 1H), 4.23 (s, 1H), 3.82 (s, 3H), 3.70-3.45 (m, 5H), 3.29-3.26 (m, 2H), 2.95 (s, 3H), 2.73 (s, 1H), 1.99 (s, 3H), 1.78-1.48 (m, 7H), 1.40-1.15 (m, 12H), 1.14-1.00 (m, 8H). MS (ESI, m/e) [M + 1]$^+$ 1034.1. |
| 185 | 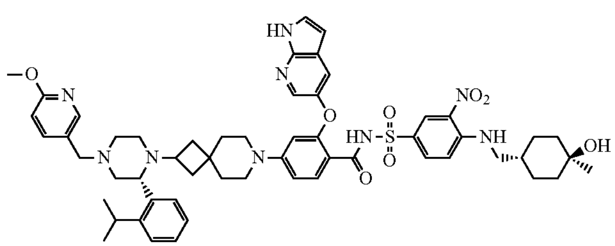 | 2-((1H-pyrrolo[2,3-b]pyridin-5-yl)oxy)-N-((4-((1,4r)-4-hydroxy-4-methylcyclohexyl)methyl)amino)-3-nitrophenyl)sulfonyl)-4-(2-((R)-2-(2-isopropylphenyl)-4-((6-methoxypyridin-3-yl)methyl)piperazin-1-yl)-7-azaspiro[3.5]nonan-7-yl)benzamide | $^1$H NMR (400 MHz, DMSO-d$_6$) δ ppm: 11.70 (s, 1H), 11.41 (s, 1H), 8.67-8.45 (m, 2H), 8.19-7.95 (m, 2H), 7.89-7.42 (m, 6H), 7.42-7.00 (m, 5H), 6.87-6.77 (m, 1H), 6.75-6.60 (m, 1H), 6.38 (s, 1H), 6.15 (s, 1H), 4.26 (s, 1H), 3.82 (s, 3H), 3.77-3.54 (m, 2H), 3.35-3.21 (m, 1H), 3.16-2.56 (m, 10H), 1.78-1.49 (m, 6H), 1.43-1.23 (m, 7H), 1.20-0.97 (m, 10H). MS (ESI, m/e) [M + 1]$^+$ 1026.9 |

| Ex. | structure | Compound name | Data |
|---|---|---|---|
| 186 | 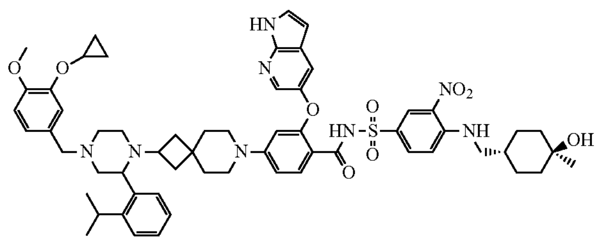 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1OC1CC1] | 2-((1H-pyrrolo[2,3-b]pyridin-5-yl)oxy)-4-(2-(4-(3-cyclopropoxy-4-methoxybenzyl) piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | $^1$H NMR (400 MHz, DMSO-d$_6$) δ ppm 11.68 (s, 1H), 11.21 (s, 1H), 8.69-8.40 (m, 2H), 8.07-7.98 (m, 1H), 7.85-7.74 (m, 1H), 7.60-7.01 (m, 10H), 7.01-6.77 (m, 2H), 6.75-6.60 (m, 1H), 6.37 (s, 1H), 6.14 (s, 1H), 4.25 (s, 1H), 4.00-3.82 (m, 1H), 3.82-3.49 (m, 6H), 3.3 1-3.22 (m, 4H), 3.15-2.61 (m, 10H), 1.80-1.48 (m, 7H), 1.42-1.28 (m, 5H), 1.22-1.15 (m, 3H), 1.15-1.00 (m, 10H), 0.79-0.70 (m, 2H), 0.67-0.55 (m, 2H). MS (ESI, m/e) [M + 1]$^+$ 1082.2 |
| 187 | 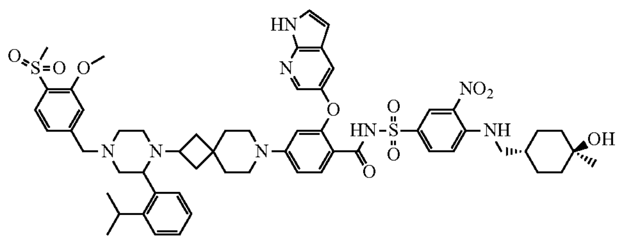 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)ccc1S(C)(=O)=O] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-(2-(2-isopropylphenyl)-4-(3-methoxy-4-(methylsulfonyl)benzyl)piperazin-1-yl)-7-azaspiro[3.5]nonan-7-yl)benzamide | $^1$H NMR (400 MHz, DMSO-d$_6$) δ ppm 11.69 (s, 1H), 11.42 (s, 1H), 8.70-8.47 (m, 2H), 8.09-8.00 (m, 1H), 7.98-7.71 (m, 3H), 7.65-7.02 (m, 10H), 6.73-6.60 (m, 1H), 6.43-6.32 (m 1H), 6.15 (s, 1H), 4.25 (s, 1H), 3.94 (s, 3H), 3.85-3.60 (m, 3H), 3.33-3.24 (m, 4H), 3.24-3.14 (m, 4H), 3.07-2.80 (m, 6H), 2.80-2.60 (m, 2H), 2.18-1.95 (m, 1H), 1.79-1.43 (m, 7H), 1.43-1.24 (m, 7H), 122-0.95 (m, 10H). MS (ESI, m/e) [M + 1]$^+$ 1104.4 |
| 188 | 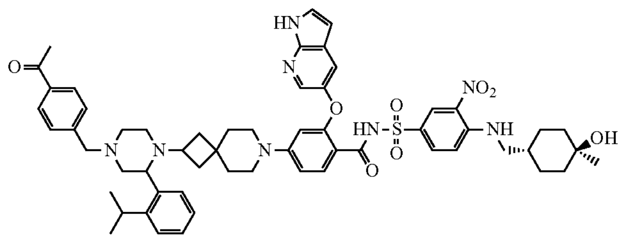 [SMILES: CC(=O)c1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 2-((1H-pyrrolo[2,3-b]pyridin-5-yl)oxy)-4-(2-(4-(4-acetylbenzyl)-2-(2-isopropylphenyl)piperazin-1-yl)-7-azaspiro[3.5]nonan-7-yl)-N-((4-(((1r,4r)-4-hydroxy-4-methylcyclohexyl)amino)-3-nitrophenyl)sulfonyl)benzamide | $^1$H NMR (400 MHz, DMSO-d$_6$) δ ppm 11.69 (s, 1H), 11.31 (s, 1H), 8.66-8.41 (m, 2H), 8.07-7.98 (m, 1H), 7.97-7.65 (m, 4H), 7.55-7.41 (m, 5H), 7.41-7.00 (m, 5H), 6.75-6.60 (m 1H), 6.42-6.33 (m 1H), 6.15 (s, 1H), 4.26 (s, 1H), 3.82-3.65 (m, 2H), 3.35-3.22 (m, 9H), 3.07-2.83 (m, 6H), 2.79-2.61 (m, 2H), 2.55 (s, 3H), 1.76-1.50 (m, 6H), 1.42-1.23 (m, 7H), 1.19-0.97 (m, 10H). MS (ESI, m/e) [M + 1]$^+$ 1038.3 |
| 189 | 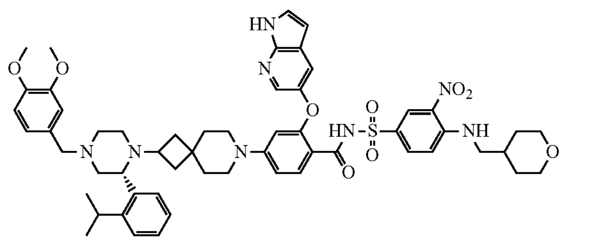 [SMILES: COc1ccc(CN2CCN(C3CC4(CCN(c5ccc(C(=O)NS(=O)(=O)c6ccc(NCC7CCOCC7)c([N+](=O)[O-])c6)c(Oc6cnc7[nH]ccc7c6)c5)CC4)C3)[C@H](c3ccccc3C(C)C)C2)cc1OC] | (R)-2-((1H-pyrrolo[2,3-b]pyridin-5-yl)oxy)-4-(2-(4-(3,4-dimethoxybenzyl)-2-(2-isopropylphenyl)piperazin-1-yl)-7-azaspiro[3.5]nonan-7-yl)-N-((3-nitro-4-(((tetrahydro-2H-pyran-4-yl)methyl)amino)phenyl)sulfonyl)benzamide | $^1$H NMR (400 MHz, DMSO-d$_6$) δ ppm: 11.66 (s, 1H), 8.68-8.41 (m, 2H), 8.01 (s, 1H), 7.76 (d, J = 8.4 Hz, 1H), 7.62-6.73 (m, 11H), 6.64 (d, J = 7.6 Hz, 1H), 6.36 (s, 1H), 6.15 (s, 1H), 3.95-3.52 (m, 11H), 3.47-3.11 (m, 7H), 3.08-2.77 (m, 7H), 2.74-2.60 (m, 1H), 2.44-2.14 (m 2H), 1.97-1.80 (m, 1H), 1.70-1.51 (m, 3H), 1.08-0.94 (m, 14H). MS (ESI, m/e) [M + 1]$^+$ 1028.2 |

| Ex. | structure | Compound name | Data |
|---|---|---|---|
| 190 | 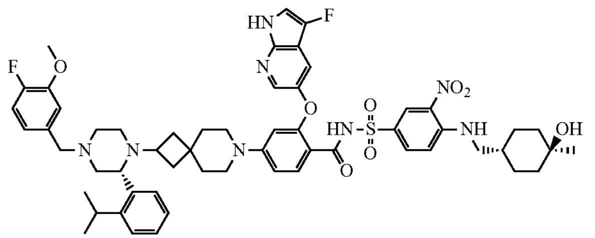 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)ccc1F] | 2-((3-fluoro-1H-pyrrolo[2,3-b]pyridin-5-yl)oxy)-4-(2-((R)-4-(4-fluoro-3-methoxybenzyl)-2-(2-isopropylphenyl)piperazin-1-yl)-7-azaspiro[3.5]nonan-7-yl)-N-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.50 (s, 1H), 8.60-8.45 (m, 2H), 8.06 (s, 1H), 7.80 (d, J = 8.8 Hz, 1H), 7.53-7.01 (m, 10H), 6.89 (s, 1H), 6.67 (d, J = 8.4 Hz, 1H), 6.21 (s, 1H), 4.24 (s, 1H), 3.88-3.34 (m, 7H), 3.30-2.58 (m, 12H), 2.15-1.96 (m, 1H), 1.73-1.90 (m, 6H), 1.39-1.01 (m, 19H). MS (ESI, m/e) [M + 1]$^+$ 1062.1 |
| 191 | 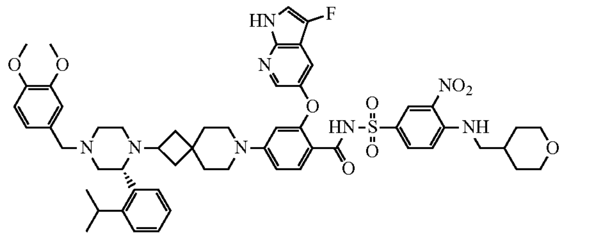 [SMILES: COc1ccc(CN2CCN(C3CC4(CCN(c5ccc(C(=O)NS(=O)(=O)c6ccc(NCC7CCOCC7)c([N+](=O)[O-])c6)c(Oc6cnc7[nH]cc(F)c7c6)c5)CC4)C3)[C@H](c3ccccc3C(C)C)C2)cc1OC] | (R)-4-(2-(4-(3,4-dimethoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((3-nitro-4-(((tetrahydro-2H-pyran-4-yl)methyl)amino)phenyl)sulfonyl)benzamide | $^1$H NMR (400 MHz, DMSO-d$_6$) δ ppm: 11.46 (s, 1H), 8.63-8.40 (m, 2H), 8.04 (s, 1H), 7.73 (d, J = 8.8 Hz, 1H), 7.55-6.75 (m, 11H), 6.66 (d, J = 8.4 Hz, 1H), 6.22 (s, 1H), 3.91-3.80 (m, 2H), 3.77-3.49 (m, 9H), 3.32-3.20 (m, 6H), 3.08-2.82 (m, 7H), 2.72-2.59 (m, 1H), 2.46-2.12 (m, 2H), 1.95-1.82 (m, 1H), 1.78-1.53 (m 4H), 1.41-0.99 (m, 14H). MS (ESI, m/e) [M + H]$^+$ 1046.1 |
| 192 | 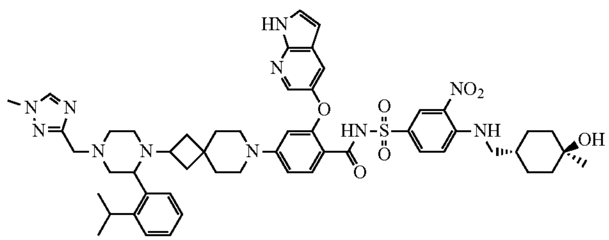 | 2-((1H-pyrrolo[2,3-b]pyridin-5-yl)oxy)-N-((((1r,4r)-4-hydroxy-4-methylcyclohexyl)methyl)amino)-3-nitrophenyl)sulfonyl)-4-(2-(2-(2-isopropylphenyl)-4-((1-methyl-1H-1,2,4-triazol-3-yl)methyl)piperazin-1-yl)-7-azaspiro[3.5]nonan-7-yl)benzamide | $^1$H NMR (400 MHz, DMSO-d$_6$) δ ppm: 11.68 (s, 1 H), 11.40 (s, 1H), 8.57-8.55 (m, 2H), 8.03-8.02 (m, 1H), 7.79-7.77 (m, 2H), 7.50-7.06 (m, 8H), 6.65 (d, J = 8.0 Hz, 1H), 6.37 (s, 1H), 6.14 (s, 1H), 4.25 (s, 1H), 3.85 (s, 3H), 3.76-3.67 (m, 2H), 3.29-3.28 (m, 2H), 2.97-2.91 (m, 6H), 2.18-1.97 (m, 2H), 1.70-1.53 (m, 7H), 1.33-1.05 (m, 24H). MS (ESI, m/e) [M + 1]$^+$ 1001.1 |
| 193 | 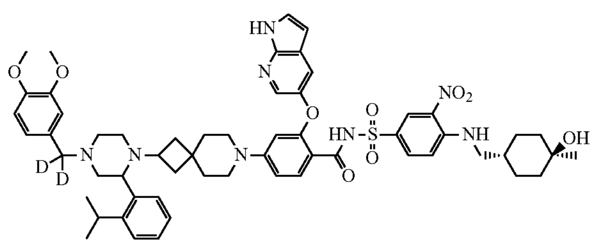 [SMILES: [2H]C([2H])(c1ccc(OC)c(OC)c1)N1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)C(c2ccccc2C(C)C)C1] | 2-((1H-pyrrolo[2,3-b]pyridin-5-yl)oxy)-4-(2-(4-(3,4-dimethoxyphenyl)methyl-d$_2$)-2-(2-isopropylphenyl)piperazin-1-yl)-7-azaspiro[3.5]nonan-7-y)-N-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.68 (s, 1H), 11.23 (s, 1H), 8.57-8.55 (m, 2H), 8.02 (s, 1H), 7.78 (d, J = 8.4 Hz, 1H), 7.57-7.01 (m, 8H), 6.95-6.93 (m, 2H), 6.65 (d, J = 8.4 Hz, 1H), 6.37 (s, 1H), 6.14 (s, 1H), 4.24 (s, 1H), 3.78-3.74 (m, 6H), 3.28 (s, 2H), 3.19-3.10 (m, 1H), 3.05-2.85 (m, 7H), 2.70 (s, 1H), 1.71-1.45 (m, 7H), 1.40-0.98 (m, 20H). MS (ESI, m/e) [M + 1]$^+$ 1058.1. |

| Ex. | structure | Compound name | Data |
|---|---|---|---|
| 194 | 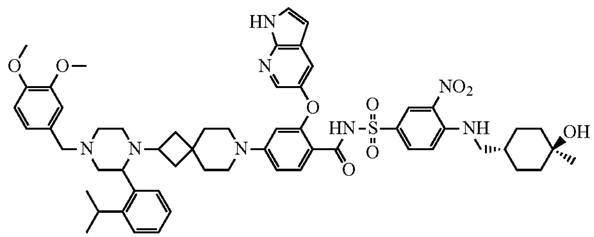 | 2-((1H-pyrrolo[2,3-b]pyridin-5-yl)oxy)-4-(2-(4-(5,6-dimethoxypyridin-2-yl)methyl)piperazin-1-yl)-7-azaspiro[3.5]nonan-7-yl))-N-((((1r,4r)-4-hydroxy-4-methylcyclohexyl)methyl)amino)-3-nitrophenyl)sulfonyl)benzamide | $^1$H NMR (400 MHz DMSO-d$_6$) δ ppm: 11.69 (s, 1H), 11.45 (br, 1H), 8.63-8.54 (m, 2H), 8.02 (s, 1H), 7.82 (d, J = 9.2 Hz, 1H), 7.57-7.40 (m, 3H), 7.39-6.92 (m, 6H), 6.69-6.64 (m, 1H), 6.37 (s, 1H), 6.18-6.10 (m, 1H), 4.24 (s, 1H), 3.88-3.56 (m, 7H), 3.45-3.36 (m, 1H), 3.32-3.12 (m, 4H), 3.10-2.55 (m, 9H), 2.45-2.30 (m, 1H), 2.09-1.94 (m, 1H), 1.74-1.50 (m, 6H), 1.42-1.15 (m, 13H), 1.14-1.05 (m, 9H). MS (ESI, m/e) [M + 1]$^+$ 1057.1 |
| 195 | 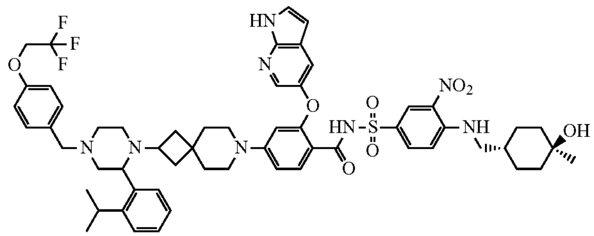 [SMILES: CC(C)c1ccccc1C1CN(Cc2ccc(OCC(F)(F)F)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-((1r,4r)-4-hydroxy-4-methylcyclohexy)methyl)amino)-3-nitrophenyl)sulfonyl)-4-(2-(2-isopropylphenyl)piperazin-1-yl)-7-azaspiro[3.5]nonan-7-yl)-4-(2,2,2-trifluoroethoxy)benzyl)benzamide | $^1$H NMR (400 MHz, DMSO-d6)δppm: 11.69 (s, 1H), 11.27 (br, 1H), 8.63-8.54 (m, 2H), 8.03 (s, 1H), 7.79 (d, J = 8.0 Hz, 1H), 7.57-6.96 (m, 12H), 6.69-6.62 (m, 1H), 6.37 (s, 1H), 6.18-6.10 (m, 1H), 4.82-4.54 (m, 2H), 4.24 (s, 1H), 3.88-3.46 (m, 3H), 3.32-3.12 (m, 4H), 3.10-2.55 (m, 9H), 2.45-2.30 (m, 1H), 2.09-1.94 (m, 1H), 1.74-1.50 (m, 6H), 1.42-1.15 (m, 14H), 1.14-1.05 (m 5H). MS (ESI, live) [M+1]* 1094.1. |
| 196 | 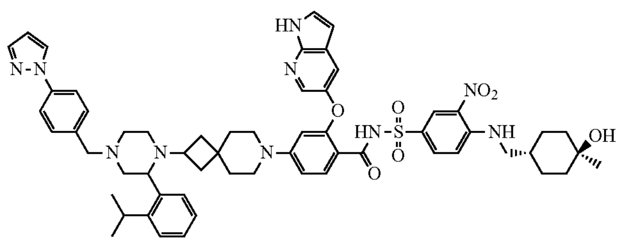 [SMILES: CC(C)c1ccccc1C1CN(Cc2ccc(-n3cccn3)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 4-(2-(4-(4-(1H-pyrazol-1-yl)benzyl)-2-(2-isopropylphenyl) piperazin-1-yl)-7-azaspiro[3.5]nonan-7-yl)-2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.66 (s, 1H), 11.29 (br, 1H), 8.60-8.52 (m, 1H), 8.49-8.45 (m, 1H), 8.01 (s, 1H), 7.83-7.70 (m, 4H), 7.54-7.35 (m, 6H), 7.25-7.00 (m, 4H), 6.67-6.60 (m, 1H), 6.52 (s, 1H), 6.36 (s, 1H), 6.14 (s, 1H), 4.23 (s, 1H), 3.68-3.40 (m, 4H), 3.32-3.20 (m, 3H), 3.10-2.80 (m, 8H), 2.65-2.55 (m, 1H), 2.30-2.15 (m, 1H), 2.05-1.94 (m, 1H), 1 74-1.50 (m, 1H), 1.39-1.17 (m, 14H), 1.14-1.05 (m, 3H). MS (ESI, m/e) [M + 1]$^+$ 1063.0. |
| 197 | 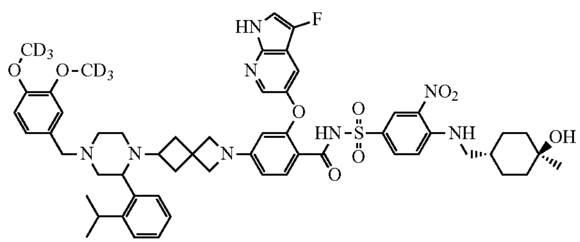 | 4-(6-((R)-4-(3,4-bis(methoxy-d3)benzyl)-2-(2-isopropylphenyl)piperazin-1-yl)-2-azaspiro[3.3]heptan-2-yl)-2-(3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.55 (s, 1H), 11.32 (br, 1H), 8.61-8.52 (m, 1H), 8.08 (s, 1H), 7.82 (d, J = 8.8 Hz, 1H), 7.57-7.08 (m, 8H), 6.98-6.75 (m, 2H), 6.18-6.02 (m, 1H), 5.53 (s, 1H), 4.2.4 (s, 1H), 4.20-3.36 (m, 7H), 3.32-3.10 (m, 3H), 3.10-2.55 (m, 6H), 2.45-2.30 (m, 1H), 2.05-1.92 (m, 2H), 1.74-1.50 (m, 6H), 1.39-1.15 (m, 10H), 1.14-1.05 (m, 5H). MS (ESI, m/e) [M + 1]$^+$ 1052.3. |

| Ex. | Compound name | Data |
|---|---|---|
| 198 | 4-(2-((R)-4-(3,4-bis(methoxy-d3)benzyl)-2-(2-isopropylphenyl)piperazin-1-yl)-7-azaspiro[3.5]nonan-7-yl)-2-(3-fluoro-1H-pyrrolo[2,3-b]pyridin-5-yloxy)-N-((1r,4r)-4-hydroxy-4-methylcyclohexyl)methyl)amino)-3-nitrophenyl)sulfonyl)benzamide | 1H NMR (400 MHz, DMSO-d6) δ ppm: 11.48 (s, 1H), 11.42 (br, 1H), 8.59-8.45 (m, 2H), 8.06 (s, 1H), 7.79 (d, J = 8.8 Hz, 1H), 7.50-7.10 (m, 7H), 7.09-6.64 (m, 4H), 6.26-6.17 (m, 1H), 4.24 (s, 1H), 4.13-3.36 (m 4H), 3.32-3.12 (m 3H), 3.10-2.55 (m, 9H), 2.45-2.30 (m, 1H), 2.09-1.94 (m, 1H), 1.74-1.50 (m, 6H), 1.41-1.15 (m, 11H), 1.14-1.00 (m, 8H). MS (ESI, m/e) [M + 1]+ 1080.2. |
| 199 | 2-((1H-pyrrolo[2,3-b]pyridin-5-yl)oxy)-4-(2-(4-(4-carbamoylbenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.64 (s, 1H), 8.53 (s, 2H), 8.02 (s, 1H), 7.93-7.71 (m, 4H), 7.54-7.00 (m, 11H), 6.64 (d, J = 8.8 Hz, 1H), 6.37 (s, 1H), 6.14 (s, 1H), 4.21 (s, 1H), 3.69-3.46 (m, 3H), 3.30-3.18 (m 2H), 3.10-2.77 (m 8H), 2.27-1.99 (m, 2H), 1.76-1.49 (m, 7H), 1.42-0.96 (m, 21H). MS (ESI, m/e) [M + 1]+ 1039.0 |
| 200 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-methyl-3,4-dihydro-2H-benzo[b][1,4]oxazin-5-yl)methyl)piperazin-1-yl)-7-azaspiro[3.5]nonan-7-yl)benzamide | 1H NMR (400 MHz, DMSO-d6) δ ppm: 11.69 (s, 1H), 11.45-10.97 (m, 1H), 8.63-8.52 (m, 2H), 8.05-8.00 (m, 1H), 7.97-7.85 (m, 1H), 7.85-7.72 (m, 1H), 7.57-7.61 (m, 12H), 6.43-6.30 (m, 1H), 6.28-6.05 (m, 1H), 4.70-4.50 (m, 1H), 4.24 (s, 1H), 4.20-4.05 (m, 2H), 3.85-3.70 (m, 1H), 3.70-3.59 (m, 1H), 3.50-3.40 (m, 1H), 3.32-3.24 (m, 5H), 3.24-2.59 (m, 16H), 2.19-2.00 (m, 1H), 1.80-1.61 (m, 7H), 1.61-1.20-0.93 (m, 10H). MS (ESI, m/e) [M + 1]+ 1066.8 |
| 201 | 2-((1H-pyrrolo[2,3-b]pyridin-5-yl)oxy)-4-(2-(4-(2,2-dimethylbenzo[d][1,3]dioxol-4-yl)methyl)-2-(2-isopropylphenyl) piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm 11.68 (s, 1H), 11.48-11.24 (m, 1H), 10.49-10.07 (m, 1H), 8.55 (s, 2H), 8.02 (s, 1H), 7.75-7.73 (m, 1H), 7.48-7.42 (m, 4H), 7.20-7.15 (m 3H), 6.76 (s, 3H), 6.66 (s, 1H), 6.37 (s, 1H), 6.15-6.13 (m, 1H), 4.62 (s, 1H), 4.24 (s, 1H), 3.76 (s, 1H), 3.60 (s, 1H), 3.41 (s, ,1H), 3.28 (s, 2H), 3.05-2.85 (m, 8H), 2.67 (s, 1H), 1.99 (s, 2H), 1.70-1.45 (m, 12H), 1.37-1.23 (m, 10H), 1.17 (s, 2H), 1.13-1.10 (m, 8H). MS (ESI, m/e) [M + 1]+ 1068.1. |

| Ex. | Compound name | Data |
|---|---|---|
| 202 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-(quinoxalin-5-ylmethyl)piperazin-1-yl)-7-azaspiro[3.5]nonan-7-yl)benzamide | ¹H NMR (400 MHz, DMSO-d₆) δ ppm 11.68 (s, 1H), 11.54-11.27 (m, 1H), 10.53-10.30 (m, 1H), 8.97 (s, 1H), 8.58-8.54 (m, 2H), 8.03 (s, 2H), 7.97-7.71 (m, 3H), 7.53-7.42 (m, 3H), 7.36 (s, 1H), 7.23 (s, 2H), 7.09-7.06 (m, 1H), 6.65 (d, J = 8.8 Hz, 1H), 6.37 (s, 1H), 6.14 (s, 1H), 4.33 (s, 1H), 4.24 (s, 1H), 3.77 (s, 1H), 3.41 (s, 1H), 3.28 (s, 2H), 3.17-3.07 (m, 1H), 3.05-2.85 (m, 8H), 2.01 (s, 1H), 1.72-1.49 (m, 6H), 1.40-1.04 (m, 21H). MS (ESI, m/e) [M + 1]⁺ 1048.1 |
| 203 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-isopropylphenyl)-4-((8-methoxy-2,3-dihydrobenzo[b][1,4]dioxin-5-yl)methyl)piperazin-1-yl)-7-azaspiro[3.5]nonan-7-yl)benzamide | ¹H NMR (400 MHz, DMSO-d₆) δ ppm 11.70 (s, 1H), 11.51-10.89 (m, 1H), 8.62-8.43 (m, 2H), 8.03 (s, 1H), 7.94-7.71 (m, 1H), 7.61-6.92 (m, 9H), 6.81-6.49 (m, 3H), 6.37 (s, 1H), 6.24-6.07 (m, 1H), 4.31-3.88 (m, 7H), 3.82-3.66 (m 3H), 3.62-3.36 (m, 2H), 3.32-3.22 (m, 3H), 3.20-2.62 (m, 10H), 2.15-1.96 (m, 1H), 1.77-1.42 (m, 7H), 1.40-1.27 (m, 4H), 1.23-0.96 (m, 13H). MS (ESI, m/e) [M + 1]⁺ 1084.1 |
| 204 | 2-((1H-pyrrolo[2,3-b]pyridin-5-yl)oxy)-4-(2-(4-(4-(dimethylphosphoryl)benzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.62 (s, 1H), 8.55-8.43 (m, 2H), 7.96 (s, 1H), 7.78-7.57 (m, 3H), 7.48-7.29 (m, 6H), 7.23-6.93 (m, 4H), 6.59 (d, J = 8.8 Hz, 1H), 6.32 (s, 1H), 6.09 (m, 1H), 4.19 (s, 1H), 3.60-3.40 (m, 3H), 3.25-2.15 (m, 3H), 2.98-2.72 (m, 7H), 2.24-1.94 (m, 2H), 1.72-1.44 (m, 14H), 1.34-0.91 (m, 20H). MS (ESI, m/e) [M + 1]⁺ 1073.0 |
| 205 | 4-(6-(R)-4-((5,6-dimethoxypyridin-3-yl)methyl)-2-(2-isopropylphenyl)piperazin-1-yl)-2-azaspiro[3.3]heptan-2-yl)-2-(3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.55 (s, 1H), 11.45 (br, 1H), 8.60-8.54 (m, 2H),8.08 (s, 1H), 7.82 (d, J = 8.4 Hz, 1H), 7.70-7.08 (m, 13H), 6.09-6.04 (m, 1H), 5.53 (s, 1H), 4.24 (s, 1H), 3.83 (s, 1H), 3.78 (s, 1H), 3.70-3.36 (m, 6H), 3.32-3.10 (m, 3H), 3.10-2.55 (m, 6H), 2.40-2.25 (m, 1H), 2.05-1.92 (m, 6H), 1.74-1.50 (m, 6H), 1.39-1.15 (m, 9H), 1.14-1.05 (m, 5H). MS (ESI, m/e) [M + 1]⁺ 1047.1. |

| Ex. | structure | Compound name | Data |
|---|---|---|---|
| 206 | 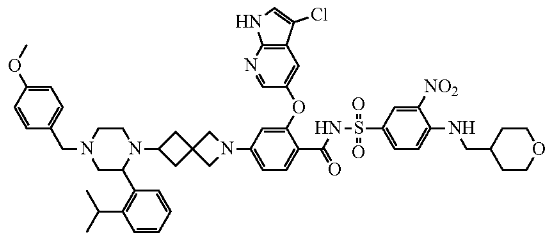 | (R)-2-((3-chloro-1H-pyrrolo[2,3-b]pyridin-5-yl)oxy)-4-(6-(2-(2-isopropylphenyl)-4-(4-methoxybenzyl)piperazin-1-yl)-2-azaspiro[3.3]heptan-2-yl)-N-((3-nitro-4-(((tetrahydro-2H-pyran-4-yl)methyl)amino)phenyl)sulfonyl)benzamide | $^1$H NMR (400 MHz, DMSO-d$_6$) δ ppm: 12.06 (s, 1H), 11.02 (br, 1H), 8.64-8.52 (m, 2H), 8.01 (s, 1H), 7.81 (d, J = 8.4 Hz, 1H), 7.47-7.08 (m, 9H), 6.95-6.85 (m, 2H), 6.09-6.04 (m, 1H), 5.54 (s, 1H), 4.30-3.82 (m 3H), 3.75 (s, 3H), 3.66-3.45 (m, 4H), 3.32-3.10 (m, 6H), 3.05-2.62 (m, 5H), 2.48-2.25 (m, 1H), 2.03-1.83 (m, 3H), 1.63 (d, J = 12.4 Hz, 1H), 1.34-1.15 (m, 6H), 1.13-0.95 (m, 4H). MS (ESI, m/e) [M + 1]$^+$ 1003.8. |
| 207 | 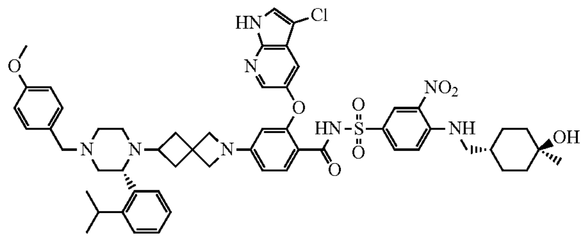 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(Cl)c6c5)c3)C4)[C@H](c3ccccc3C(C)C)C2)cc1] | 2-(3-chloro-1H-pyrrolo[2,3-b]pyridin-5-yl)oxy)-N-((((1r,4r)-4-hydroxy-4-methylcyclohexyl)methyl)amino)-3-nitrophenyl)sulfonyl)-4-(6-((R)-2-(2-isopropylphenyl)-4-(4-methoxybenzyl)piperazin-1-yl)-2-azaspiro[3.3]heptan-2-yl)benzamide | $^1$H NMR(400 MHz, DMSO+JSppm: 12.06 (s, 1H), 11.38 (br, 1H), 8.59-8.53 (m, 2H), 8.10 (s, 1H), 7.81 (d, J = 8.0 Hz, 1H), 7.72 (s, 1H), 7.47-7.05 (m, 9H) 6.95-6.85 (m, 2H), 6.14-6.04 (m, 1H), 5.54 (s, 1H), 4.25 (s, 1H), 4.18-3.85 (m, 2H), 3.75 (s, 3H), 3.68-3.45 (m, 5H), 3.32-3.10 (m, 3H), 3.05-2.62 (m, 6H), 2.48-2.30 (m, 1H), 2.03-1.93 (m, 2H), 1.74-1.51 (m, 6H), 1.49-1.15 (m, 8H), 1.10-1.00 (m, 4H). MS (ESI, m/e) [M + 1]$^+$ 1032.9. |
| 208 | 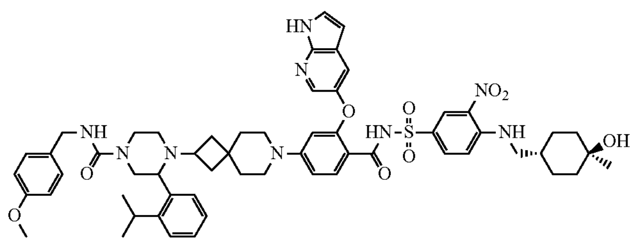 [SMILES: COc1ccc(CNC(=O)N2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1] | 4-(7-(3-((1H-pyrrolo[2,3-b]pyridin-5-yl)oxy)-4-((((1r,4r)-4-hydroxy-4-methylcyclohexyl)methyl)amino)-3-nitrophenyl)sulfonyl)carbamoyl)phenyl)-7-azaspiro[3.5]nonan-2-yl)-3-(2-(4-((1-isopropyl-1H-pyrazol-4-yl)methyl)-2-(2-isopropylphenyl)piperazin-1-yl)-2-azaspiro[3.5]nonan-7-yl)benzamide | $^1$H NMR (400 MHz, DMSO-d$_6$) δ ppm: 11.69 (s, 1H), 11.41 (s, 1H), 8.58-8.55 (m, 2H), 8.03 (s, 1H), 7.80-7.78 (m, 1H), 7.52-7.07 (m, 11H), 6.85-6.83 (m, 2H), 6.65 (d, J = 8.0 Hz, 1H), 6.38 (s, 1H), 6.15-6.13 (m, 1H), 4.43 (s, 1H), 4.17-4.15 (m, 2H), 4.01-3.99 (m, 1H), 3.71 (s, 4H), 3.28-3.24 (m, 2H), 2.98-2.87 (m, 6H), 2.01-1.97 (m, 1H), 1.69-1.53 (m, 7H), 1.36-1.10 (m, 23H). MS (ESI, m/e) [M + 1]$^+$ 1069.1. |
| 209 | 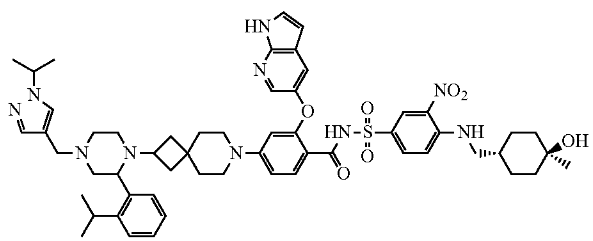 [SMILES: CC(C)c1ccccc1C1CN(Cc2cnn(C(C)C)c2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(4-((1-isopropyl-1H-pyrazol-4-yl)methyl)-2-(2-isopropylphenyl)piperazin-1-yl)-2-azaspiro[3.5]nonan-7-yl)benzamide | $^1$H NMR (400 MHz, DMSO-d$_6$) δ ppm: 11.61 (s, 1H), 8.47-8.45 (m, 1H), 7.97-7.95 (m, 1H), 7.69 (d, J = 8.0 Hz, 1H), 7.63 (s, 1H), 7.51-7.39 (m, 4H), 7.30 (s, 1H), 7.22-7.11 (m, 3H), 6.94 (d, J = 8.0 Hz, 1H), 6.92 (d, J = 8.0 Hz, 1H), 6.33 (s, 1H), 6.16 (s, 1H), 4.45-4.38 (m, 1H), 4.24 (s, 1H), 3.51-3.45 (m, 2H), 3.26-3.24 (m, 2H), 2.94-2.88 (m, 6H), 2.63-2.61 (m, 2H), 2.20-2.18 (m, 1H), 2.01-1.99 (m, 1H), 1.69-1.52 (m, 7H), 1.38-1.05 (m, 29H). MS (ESI, m/e) [M + 1]$^+$ 1028.2 |

| Ex. | structure | Compound name | Data |
|---|---|---|---|
| 210 | 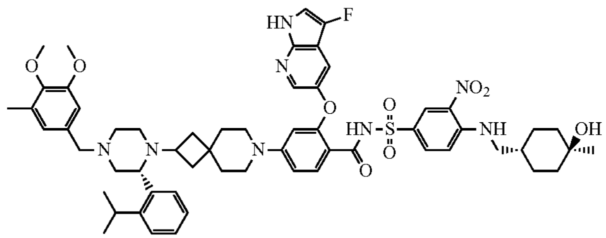 | 4-(2-((R)-4-(3,4-dimethoxy-5-methylbenzyl)-2-(2-isopropylphenyl)piperazin-1-yl)-7-azaspiro[3.5]nonan-7-yl)-2-(3-fluoro-1H-pyrrolo[2,3-b]pyridin-5-yl)oxy)-N-((1r,4r)-4-hydroxy-4-methylcyclohexyl)methyl)amino)-3-nitrophenyl)sulfonyl)benzamide | ¹H NMR (400 MHz, DMSO-A) δ ppm: 11.50 (s, 1H), 8.60-8.46 (m, 2H), 8.05 (s, 1H), 7.88-7.70 (m, 1H), 7.52-6.60 (m, 11H), 6.20 (s, 1H), 4.25 (s, 1H), 4.06-3.37 (m, 9H), 3.31-3.23 (m, 3H), 3.12-2.82 (m, 7H), 2.79-2.53 (m, 2H), 2.44-2.26 (m, 1H), 2.19-1.96 (m, 4H), 1.75-1.50 (m, 6H), 1.40-0.96 (m, 20H). MS (ESI, m/e) [M + 1]⁺ 1089.0 |
| 211 | 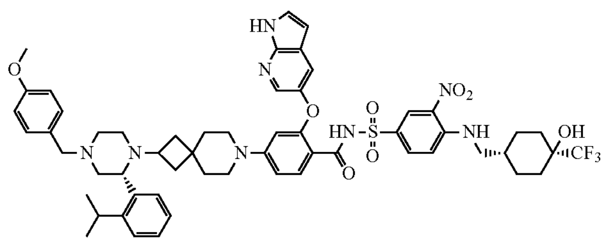 [SMILES: COc1ccc(CN2CCN(C3CC4(CCN(c5ccc(C(=O)NS(=O)(=O)c6ccc(NC[C@H]7CC[C@@](O)(C(F)(F)F)CC7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-((1r,4r)-4-hydroxy-4-(trifluoromethyl)cyclohexyl)methyl)amino)-3-nitrophenyl)sulfonyl)-4-(2-((R)-2-(2-isopropylphenyl)-4-(4-methoxybenzyl)piperazin-1-yl-7-azaspiro[3.5]nonan-7-yl)benzamide | ¹H NMR (400 MHz, DMSO-d₆) δ ppm 11.68 (s, 1H), 11.48-11.21 (m, 1H), 8.63 (s, 1H), 8.55 (s, 1H), 8.02 (s, 1H), 7.76 (d, J = 8.6 Hz, 1H), 7.54-7.44 (m, 3H), 7.36 (s, 2H), 7.23 (s, 2H), 7.09 (s, 2H), 6.93 (s, 2H), 6.65 (s, 1H), 6.37 (s, 1H), 6.13 (s, 1H), 5.66 (s, 1H), 3.74 (s, 4H), 3.56 (s, 1H), 3.29 (s, 1H), 3.05-2.85 (m, 8H), 2.58 (s, 1H), 2.02 (s, 1H), 1.80-1.55 (m, 7H), 1.46 (s, 2H), 1.40-1.15 (m, 11H), 1.09 (s, 4H). MS (ESI, m/e) [M + 1]⁺ 1080.1 |
| 212 | 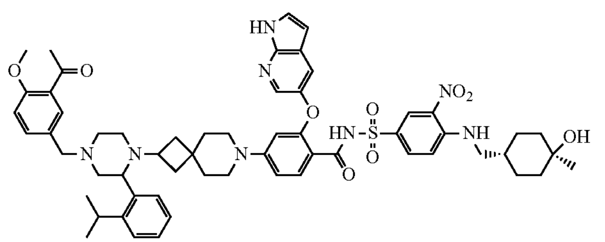 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1C(C)=O] | 2-((1H-pyrrolo[2,3-b]pyridin-5-yl)oxy)-4-(2-(4-(3-acetyl-4-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methylamino)-3-nitrophenyl)sulfonyl)benzamide | ¹H NMR (400 MHz, DMSO-d₆) δ ppm 11.68 (s, 1H), 11.49-11.22 (m, 1H), 8.55 (s, 2H), 8.02 (s, 1H), 7.78 (d, J = 8.6 Hz, 2H), 7.67-7.31 (m, 6H), 7.25-7.05 (m, 4H), 6.65 (d, J = 9.0 Hz, 1H), 6.37 (s, 1H), 6.13 (s, 1H), 4.24 (s, 1H), 3.87 (s, 3H), 3.82-3.70 (m, 1H), 3.60 (s, 1H), 3.39 (s, 1H), 3.28 (s, 2H), 3.05-2.85 (m, 7H), 2.78-2.70 (m, 1H), 2.68-2.60 (m, 1H), 2.33 (s, 1H), 2.03 (s, 1H), 1.77-1.45 (m, 7H), 1.44-0.94 (m, 20H). MS (ESI, m/e) [M + 1]⁺ 1068.2. |
| 213 | 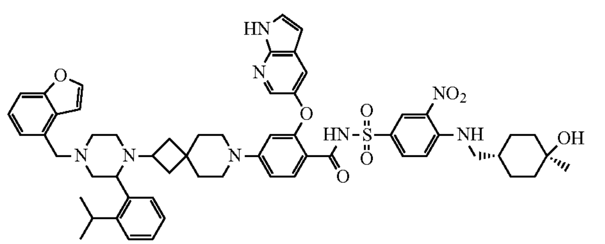 [SMILES: CC(C)c1ccccc1C1CN(Cc2cccc3occc23)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(4-(benzofuran-4-ylmethyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.68 (s, 1H), 11.39 (s, 1H), 8 55 (s, 2H), 8.02 (s, 2H), 7.77 (s, 2H), 7.47 (d, J = 17.8 Hz, 4H), 7.34 (s, 1H), 7.30-7.15 (m, 5H), 7.09 (s, 1H), 6.66 (s, 1H), 6.37 (s, 1H), 6.13 (s, 1H), 4.24 (s, 1H), 3.90 (s, 1H), 3.83-3.69 (m, 1H), 3.28 (s, 2H), 3.05-2.85 (m, 9H), 2.67 (s, 2H), 2.00 (s, 2H), 1.78-1.50 (m, 7H), 1.40-1.22 (m, 11H), 1.19-1.08 (m, 7H), 0.96 (s, 3H). MS (ESI. m/e) 1036.1. |

| Ex. | structure | Compound name | Data |
|---|---|---|---|
| 214 | 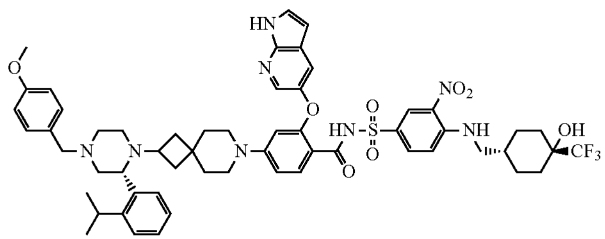 [SMILES: COc1ccc(CN2CCN(C3CC4(CCN(c5ccc(C(=O)NS(=O)(=O)c6ccc(NC[C@H]7CC[C@](O)(C(F)(F)F)CC7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-((4-((1s,4s)-4-hydroxy-4-(trifluoromethyl)cyclohexyl)methyl)amino)-3-nitrophenyl)sulfonyl)-4-(2-((R)-2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm: 11.68 (s, 1H), 11.39-10.98 (m, 1H), 8.65 (s, 1H), 8.55 (s, 1H), 8.02 (s, 1H), 7.78 (d, J = 8.8 Hz, 1H), 7.50 (s, 3H), 7.24 (s, 5H), 7.05 (d, J = 9.4 Hz, 1H), 6.91 (s, 2H), 6.64 (d, J = 8.8 Hz, 1H), 6.37 (s, 1H), 6.13 (s, 1H), 5.69 (s, 1H), 3.73 (s, 4H), 3.37 (s, 2H), 3.27-3.21 (m, 8H), 1.96 (s, 2H), 1.85-1.75 (m, 4H), 1.65 (s, 4H), 1.55-3.40 (m, 5H), 1.39-1.27 (m, 3H), 1.25-1.15 (m, 10H), 1.07 (s, 4H). MS (ESI, m/e) [M + 1]⁺ 1080.2. |
| 215 | 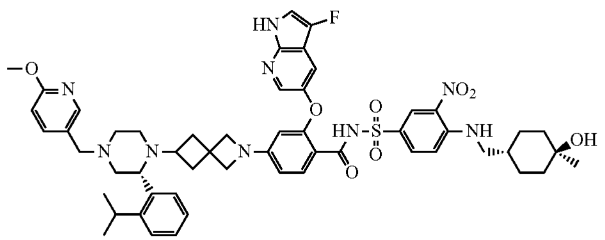 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cn1] | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-methoxypyridin-3-yl)methyl)piperazin-3-yl)methyl)heptan-2-yl)azaspiro[3.3]heptan-2-yl)benzamide | ¹H NMR (400 MHz, DMSO-d₆) δ ppm 11.55 (s, 1H), 11.26 (s, 1H), 8.70-8.52 (m, 2H), 8.30-7.98 (m, 2H), 7.92-7.58 (m, 3H), 7.59-7.32 (m, 4H), 7.32-7.00 (m, 4H), 6.92-6.70 (m, 1H), 6.20-5.91 (m 1H), 5.53 (s, 1H), 4.24 (s, 1H), 3.88-3.79 (m, 3H), 3.77-3.39 (m, 7H), 3.32-3.16 (m, 4H), 2.11-2.87 (m, 2H), 2.82-2.60 (m, 2H), 2.37-2.16 (m, 1H), 2.09-1.89 (m, 2H), 1.83-1.47 (m, 6H), 1.39-1.27 (m, 3H), 1.25-0.95 (m, 11H). MS (ESI, m/e) [M + 1]⁺ 1017.1 |
| 216 | 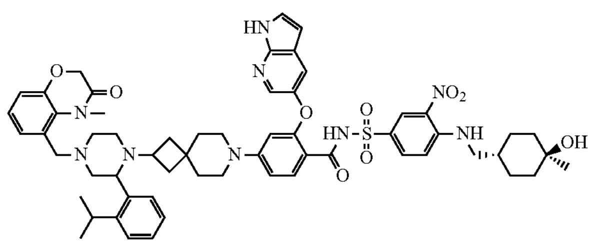 [SMILES: CC(C)c1ccccc1C1CN(Cc2cccc3c2N(C)C(=O)CO3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-(2-(2-isopropylphenyl)-4-methyl-3-oxo-3,4-dihydro-2H-benzo[b][1,4]oxazin-5-yl)methyl)piperazin-1-yl)-7-azaspiro[3.5]nonan-7-yl)benzamide | ¹H NMR (400 MHz, DMSO-d₆) δ ppm 11.69 (s, 1H), 11.41 (s, 1H), 8.64-8.50 (m, 1H), 8.07-7.97 (m, 1H), 7.96-7.71 (m, 2H), 7.68-6.81 (m, 11H), 6.75-6.59 (m, 1H), 6.43-6.30 (m, 1H), 6.15 (s, 1H), 4.62-4.47 (m 1H) 4.47-4.32 (m, 1H), 4.25 (s, 1H), 3.92-3.64 (m, 2H), 3.51-3.35 (m, 5H), 3.33-3.21 (m, 4H), 3.07-2.59 (m, 8H), 2.16-1.90 (m, 2H), 1.76-1.48 (m, 6H), 1.47-1.24 (m, 7H), 1.21-0.90 (m, 11H). MS (ESI, m/e) [M + 1]⁺ 1081.1 |
| 217 | 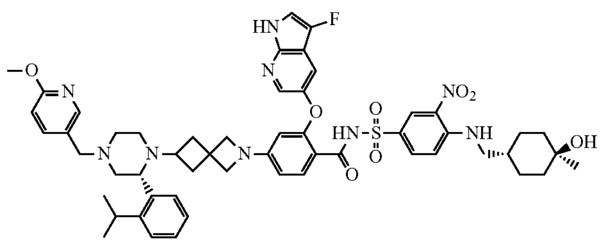 | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R)-2-(2-isopropylphenyl)-4-((6-methoxypyridin-3-yl)methyl)piperazin-1-yl)-7-azaspiro[3.5]nonan-7-yl)benzamide | ¹H NMR (400 MHz, DMSO-d₆) δ ppm: 11.55 (s, 1H), 11.44 (s, 1H), 8.66-8.46 (m, 2H), 8.17-8.07 (m, 2H), 7.89-7.61 (m, 3H), 7.57-7.06 (m, 8H), 6.91-6.80 (m, 1H), 6.77-6.68 (m, 1H), 6.26 (s, 1H), 4.30 (s, 1H), 3.87 (s, 3H), 3.66 (s, 3H), 3.38-3.25 (m, 3H), 3.11-2.88 (m, 6H), 2.82-2.60 (m, 2H), 2.36-2.00 (m 2H), 1.84-1.55 (m, 7H), 1.52-1.23 (m, 11H), 1.20-1.03 (m, 8H). MS (ESI, m/e) [M + 1]⁺ 1045.1 |

-continued

| Ex. | structure | Compound name | Data |
|---|---|---|---|
| 218 | 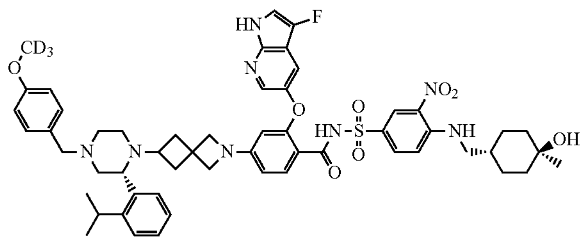 [SMILES: [2H]C([2H])([2H])Oc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc1] | 2-((3-fluoro-1H-pyrrolo[2,3-b]pyridin-5-yl)oxy)-N-((4-(((1r,4r)-4-hydroxy-4-methylcyclohexyl)methylamino)-3-nitrophenyl)sulfonyl)-4-(6-((R)-2-(2-isopropylphenyl)-4-(4-(methoxy-d3)benzyl)piperazin-1-yl)-2-azaspiro[3.3]heptan-2-yl)benzamide | ¹H NMR (400 MHz, DMSO-d₆) δ ppm: 11.56 (s, 1H), 11.25 (br, 1H), 8.59-8.52 (m, 2H), 8.08 (s, 1H), 7.82-7.75 (m, 1H), 7.52-7.03 (m, 10H), 6.89-6.85 (m, 2H), 6.09-6.06 (m, 1H), 5.53 (s, 1H), 4.24 (s, 1H), 3.65-3.45 (m, 6H), 3.32-3.15 (m, 3H), 3.05-2.62 (m, 6H), 2.28-2.15 (m, 1H), 2.06-1.90 (m, 2H), 1.74-1.51 (m, 6H), 1.39-1.15 (m, 8H), 1.05-1.00 (m, 6H). MS (ESI, m/e) [M + 1]⁺ 1019.2. |
| 219 | 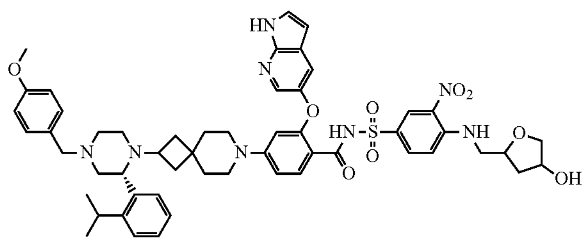 [SMILES: COc1ccc(CN2CCN(C3CC4(CCN(c5ccc(C(=O)NS(=O)(=O)c6ccc(NCC7CC(O)CO7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-((4-(((4-hydroxytetrahydrofuran-2-yl)methyl)amino)-3-nitrophenyl)sulfonyl)-4-(2-((R)-2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm: 11.66 (s, 1H), 11.44-11.05 (m, 1H), 8.69-8.50 (m, 2H), 8.01 (s, 1H), 7.79-7.76 (m, 1H), 7.49-7.46 (m, 3H), 7.29-7.19 (m, 5H), 7.11 (s, 2H), 6.90 (s, 2H), 6.64 (d, J = 9.0 Hz, 1H), 6.36 (s, 1H), 6.14 (s, 1H), 5.05-4.95 (m, 1H), 4.33 (s, 2H), 4.14 (s, 1H), 3.85 (s, 1H), 3.75-3.69 (m, 5H), 3.54 (s, 2H), 3.39 (s, 1H), 3.26-3.15 (m, 1H), 3.05-2.95 (m, 7H), 2.79-2.70 (m, 1H), 2.64-2.55 (m, 1H), 2.22 (s, 2H), 1.89-1.85 (m, 1H), 1.58 (s, 3H), 1.35-1.15 (m, 9H), 1.07 (s, 4H). MS (ESI, m/e) [M + 1]⁺ 999.9. |
| 220 | 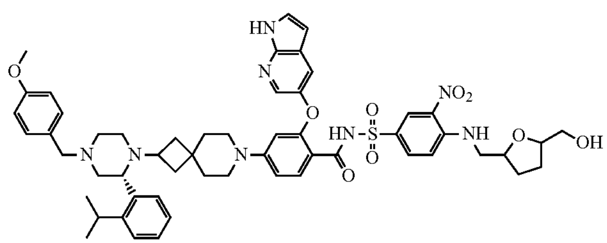 [SMILES: COc1ccc(CN2CCN(C3CC4(CCN(c5ccc(C(=O)NS(=O)(=O)c6ccc(NCC7CCC(CO)O7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-((4-(((5-(hydroxymethyl)tetrahydrofuran-2-yl)methyl)amino)-3-nitrophenyl)sulfonyl)-4-(2-((R)-2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm: 11.66 (s, 1H), 11.54-11.14 (m, 1H), 8.56-8.55 (m, 2H), 8.01 (s, 1H), 7.77 (s, 1H), 7.52-7.43 (m, 3H), 7.36 (s, 2H), 7.23 (s, 3H), 7.10 (s, 2H), 6.95-6.89 (m, 2H), 6.66 (s, 1H), 6.36 (s, 1H), 6.14 (s, 1H), 4.66 (s, 1H), 4.15-4.10 (m, 2H), 3.97-3.94 (m, 2H), 3.74 (s, 4H), 3.56 (s, 1H), 3.37 (s, 2H), 3.05-2.85 (m, 9H), 1.98 (d, J = 34.8 Hz, 3H), 1.67 (s, 3H), 1.10-1.05 (m, 4H). MS (ESI, m/e) [M + 1]⁺ 1014.1. |
| 221 | 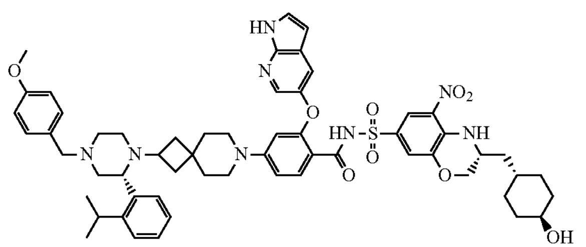 [SMILES: COc1ccc(CN2CCN(C3CC4(CCN(c5ccc(C(=O)NS(=O)(=O)c6cc7c(c([N+](=O)[O-])c6)N[C@H](C[C@H]6CC[C@H](O)CC6)CO7)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-(((R)-3-((1r,4R)-4-hydroxycyclohexyl)methyl)-5-nitro-3,4-dihydro-2H-benzo[b][1,4]oxazin-7-yl)sulfonyl)-4-(2-((R)-2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm: 11.69 (s, 1H), 11.40 (s, 1H), 10.59-10.31 (m, 1H), 8.56-8.55 (m, 2H), 8.03 (s, 1H), 7.78 (d, J = 8.8 Hz, 1H), 7.55-7.02 (m, 11H), 6.65 (d, J = 8.7 Hz, 1H), 6.37 (s, 1H), 6.15 (s, 1H), 4.24 (s, 1H), 3.85-3.80 (m, 5H), 3.42 (s, 1H), 3.10-2.85 (m, 7H), 2.67 (s, 2H), 2.31-2.17 (m, 1H), 2.04 (s, 1H), 1.73-1.49 (m, 6H), 1.41-0.95 (m, 20H). MS (ESI, m/e) [M + 1]⁺ 1054.8. |

| Ex. | structure | Compound name | Data |
|---|---|---|---|
| 222 | 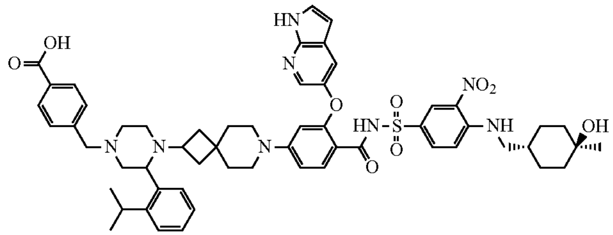 [SMILES: CC(C)c1ccccc1C1CN(Cc2ccc(C(=O)O)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 4-((4-(7-(3-((1H-pyrrolo[2,3-b]pyridin-5-yl)oxy)-4-((((1r,4r)-4-hydroxy-4-methylcyclohexyl)methyl)amino)-3-nitrophenyl)sulfonyl)carbamoyl)phenyl)-7-azaspiro[3.5]nonan-2-yl)-3-(2-isopropylphenyl)piperazin-1-yl)methyl)benzoic acid | $^1$H NMR (400 MHz, DMSO-$d_6$) δ ppm 12.87 (s, 1H), 11.68 (s, 1H), 11.36 (s, 1H), 8.65-8.45 (m, 2H), 8.02 (s, 1H), 7.93-7.83 (m, 2H), 7.82-7.71 (m, 1H), 7.57-7.00 (m, 10H), 6.66 (s, 1H), 6.37 (s, 1H), 6.14 (s, 1H), 4.25 (s, 1H), 3.79-3.50 (m, 4H), 3.30-3.18 (m, 3H), 3.06-2.79(m, 7H), 2.35-2.08 (m, 2H), 1.74-1.48 (m, 7H), 1.40-0.97 (m, 20H). MS (ESI, m/e) [M + 1]$^+$ 1040.1 |
| 223 | 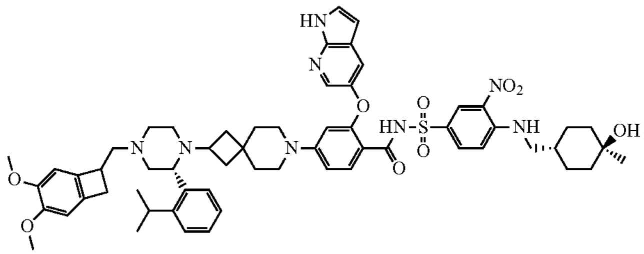 | 2-((1H-pyrrolo[2,3-b]pyridin-5-yl)oxy)-4-(2-((2R)-4-((3,4-dimethoxybicyclo[4.2.0]octa-1(6),2,4-trien-7-yl)methyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.69 (s, 1H), 11.35 (s, 1H), 8.65-8.47 (m, 2H), 8.09-7.95 (m, 1H), 7.88-7.72 (m, 1H), 7.59-7.41 (m, 4H), 7.41-6.98 (m, 5H), 6.86-6.56 (m, 3H), 6.38 (s, 1H), 6.20-6.05 (m, 1H), 4.25 (s, 1H), 3.75-3.58 (m, 7H), 3.56-3 40 (m 2H), 3.32-3.25 (m, 3H), 3.24-2.65 (m, 12H), 2.11-1.95 (m, 1H), 1.87-1.50 (m, 7H), 1.46-1.22 (m, 9H), 1.21-0.98 (m, 10H). MS (ESI, m/e) [M + 1]$^+$ 1083.0 |
| 224 | 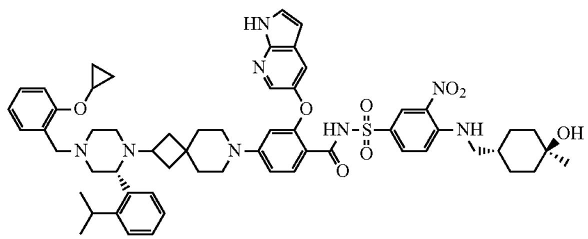 [SMILES: CC(C)c1ccccc1[C@@H]1CN(Cc2ccccc2OC2CC2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-2-(2-cyclopropoxybenzyl)-N-(2-(4-(2-cyclopropoxybenzyl)-7-azaspiro[3.5]nonan-7-yl)-N-((4-((((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.64 (s, 1H), 11.31 (s, 1H), 8.52-8.50 (m, 2H), 7.97 (s, 1H), 7.73 (d, J = 8.0 Hz, 1H), 7.49-7.11 (m, 11H), 7.03-6.87 (m, 2H), 6.60 (d, J = 8.0 Hz, 1H), 6.32 (s, 1H), 6.10 (s, 1H), 4.21 (s, 1H), 3.80 (s, 1H), 3.49-3.46 (m, 4H), 3.71 (s, 4H), 3.24-3.23 (m, 3H), 2.91-2.87 (m, 6H), 2.69-2.63 (m, 1H), 1.98-1.92 (m, 1H), 1.64-1.48 (m, 7H), 1.18-1.05 (m, 24H), 0.82-0.79 (m, 1H), 0.69-0.68 (m, 2H), 0.56-0.48 (m, 2H). MS (ESI, m/e) [M + 1]$^+$ 1052.1 |
| 225 | 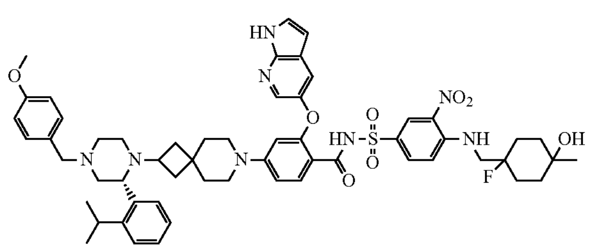 [SMILES: COc1ccc(CN2CCN(C3CC4(CCN(c5ccc(C(=O)NS(=O)(=O)c6ccc(NCC7(F)CCC(C)(O)CC7)c([N+](=O)[O-])c6)c(Oc6cnc7[nH]ccc7c6)c5)CC4)C3)[C@H](c3ccccc3C(C)C)C2)cc1] | (R)-2-((1H-pyrrolo[2,3-b]pyridin-5-yl)oxy)-N-(4-(((1-fluoro-4-hydroxy-4-methylcyclohexyl)methyl)amino)-3-nitrophenyl)sulfonyl)-4-(2-(2-isopropylbenzyl)-4-(4-methoxybenzyl)piperazin-1-yl)-7-azaspiro[3.5]nonan-7-yl)benzamide | $^1$H NMR (400 MHz, DMSO-$d_6$) δ ppm: 11.69 (s, 1H), 11.40 (s, 1.0H), 8.56-8.55 (m, 2H), 8.03 (s, 1H), 7.79-7.76 (m, 1H), 7.55-7.02 (m, 10H), 6.92-6.90 (m,2H), 6.65 (d, J = 8.8 Hz, 1H), 6.37 (s, 1H), 6.15 (s, 1H), 4.36 (s, 1H), 3.85-3.80 (m, 8H), 3.42 (s, 1H), 3.10-2.85 (m, 8H), 2.69-2.65 (m, 2H), 2.31-2.17 (m, 1H), 2.04 (s, 1H), 1.95-1.90 (m, 2H), 1.73-1.49 (m, 6H), 1.41-0.95 (m, 18H). MS (ESI, m/e) [M + 1]$^+$ 1044. |

| Ex. | structure | Compound name | Data |
|---|---|---|---|
| 226 | 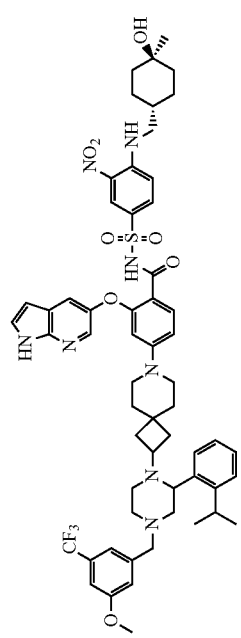 | 2-((1H-pyrrolo[2,3-b]pyridin-5-yl)oxy)-N-((4-((1r,4r)-4-hydroxy-4-methylcyclohexyl)methyl)amino)-3-nitrophenyl)sulfonyl)-4-(2-(2-isopropylphenyl)-4-(3-methoxy-5-(trifluoromethyl)benzyl)piperazin-1-yl)-7-azaspiro[3.5]nonan-7-yl)benzamide | $^1$H NMR (400 MHz, DMSO-$d_6$) δ ppm 11.69 (s, 1H), 11.40 (s, 1H), 8.56-8.55 (m, 2H), 8.03 (s, 1H), 7.79-7.76 (m, 1H), 7.55-7.02 (m, 10H), 6.92-6.90 (m, 2H), 6.65 (d, J = 8.8 Hz, 1H), 6.37 (s, 1H), 6.15 (s, 1H), 4.36 (s, 1H), 3.85-3.80 (m 8H), 3.42 (s, 1H), 3.10-2.85 (m, 7H), 2.69-2.65 (m, 2H), 2.31-2.17 (m, 1H), 2.04 (s, 1H), 1.95-1.90 (m,3H), 1.73-1.49 (m, 5H), 1.41-0.95 (m, 16H). MS (ESI, m/e) [M + 1]$^+$ 1044. |
| 227 | 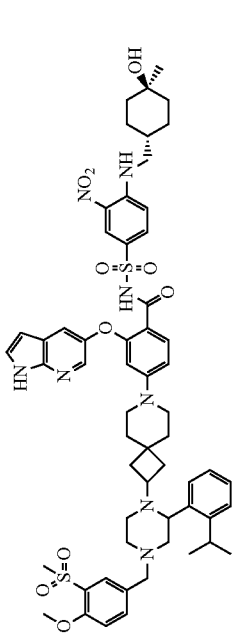 | 2-((1H-pyrrolo[2,3-b]pyridin-5-yl)oxy)-N-((4-((1r,4r)-4-hydroxy-4-mnethylcyclohexyl)methyl)amino)-3-nitrophenyl)sulfonyl)-4-(2-(2-isopropylphenyl)-4-(4-methoxy-3-(methylsulfonyl)benzyl)piperazin-1-yl)-7-azaspiro[3.5]nonan-7-yl)benzamide | $^1$H NMR (400 MHz, DMSO-$d_6$) δ ppm: 11.69 (s, 1H), 11.40 (s, 1H), 8.56-8.55 (m, 2H), 8.03 (s, 1H), 7.79-7.76 (m, 1H), 7.55-7.02 (m, 11H), 6.65 (d, J = 8.8 Hz, 1H), 6.37 (s, 1H), 6.15 (s, 1H), 4.24 (s, 1H), 3.85-3.80 (m, 5H), 3.42 (s, 1H), 3.10-2.85 (m, 7H), 2.67 (s, 2H), 2.31-2.17 (m, 1H), 2.04 (s, 1H), 1.73-1.49 (m, 6H), 1.41-0.95 (m, 20H). MS (ESI, m/e) [M + 1]$^+$ 1094.8. |
| 228 | 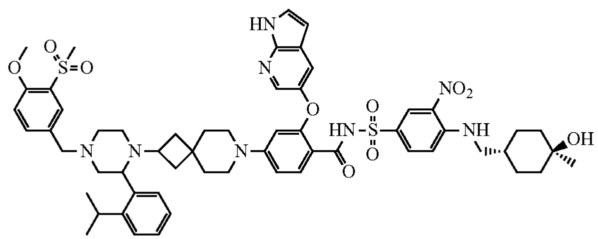 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1S(C)(=O)=O] | 2-((1H-pyrrolo[2,3-b]pyridin-5-yl)oxy)-N-((4-((1r,4r)-4-hydroxy-4-mnethylcyclohexyl)methyl)amino)-3-nitrophenyl)sulfonyl)-4-(2-(2-isopropylphenyl)-4-(4-methoxy-3-(methylsulfonyl)benzyl)piperazin-1-yl)-7-azaspiro[3.5]nonan-7-yl)benzamide | $^1$H NMR (400 MHz, DMSO-$d_6$) δ ppm: 11.69 (s, 1H), 11.38 (br, 1H), 8.61-8.54 (m, 2H), 8.02 (s, 1H), 7.90-7.55 (m, 3H), 7.52-7.05 (m, 9H), 6.69-6.63 (m, 1H), 6.37 (s, 1H), 6.18-6.10 (m, 1H), 3.93 (s, 3H), 3.85-3.35 (m 4H), 3.32-3.10 (m, 6H), 3.10-2.55 (m, 9H), 2.38-1.95 (m, 3H), 1.74-1.41 (m, 7H), 1.39-1.15 (m, 13H), 1.07-1.00 (m, 3H) MS (ESI, m/e) [M + 1]$^+$ 1104.0. |
| 229 | 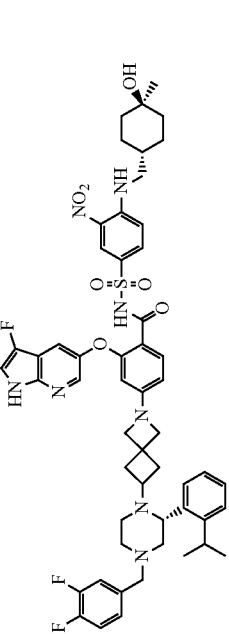 | 4-(6-((R)-4-(3,4-difluorobenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.55 (s, 1H), 11.45 (br, 1H), 8.63-8.53 (m, 2H), 8.08 (s, 1H), 7.88-7.78 (m, 1H), 7.59-7.00 (m, 10H), 6.16-6.04 (m, 1H), 5.53 (s, 1H), 4.24 (s, 1H), 3.79-3.44 (m, 8H), 3.32-3.12 (m, 3H), 3.05-2.62 (m, 5H), 2.38-2.15 (m, 1H), 2.05-1.80 (m, 2H), 1.74-1.50 (m, 6H), 1.39-1.15 (m, 8H), 1.15-1.00 (m, 7H). MS (ESI, m/e) [M + 1]$^+$ 1022.2. |

| Ex. | structure | Compound name | Data |
|---|---|---|---|
| 230 | 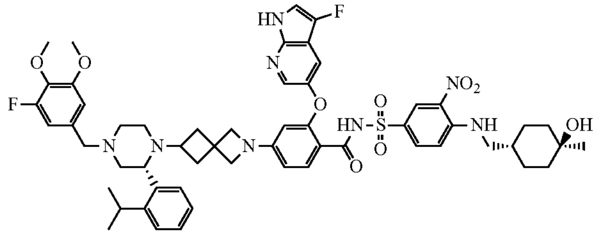 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc(F)c1OC] | 2-((3-fluoro-1H-pyrrolo[2,3-b]pyridin-5-yl)oxy)-4-(6-((R)-4-(3-fluoro-4,5-dimethoxybenzyl)-2-(2-isopropylphenyl)piperazin-1-yl)-2-azaspiro[3.3]heptan-2-yl)-N-(4-(((1r,4r)-4-hydroxy-4-methyl)cyclohexyl)amino)-3-nitrophenyl)sulfonyl)benzamide | $^1$H NMR (400 MHz, DMSO-$d_6$) δ ppm: 11.56 (s, 1H), 11.47 (br, 1H), 8.63-8.53 (m, 2H), 8.08 (s, 1H), 7.88-7.78 (m, 1H), 7.59-6.78 (m, 10H), 6.12-6.04 (m, 1H), 5.54 (s, 1H), 4.25 (s, 1H), 3.81 (s, 3H), 3.75 (s, 3H), 3.71-3.49 (m, 7H), 3.32-3.12 (m, 3H), 3.09-2.55 (m, 6H), 2.44-2.25 (m, 1H), 2.05-1.90 (m, 2H), 1.74-1.50 (m, 6H), 1.39-1.15 (m, 8H), 1.15-1.00 (m, 7H). MS (ESI, m/e) [M + 1]$^+$ 1064.1. |
| 231 | 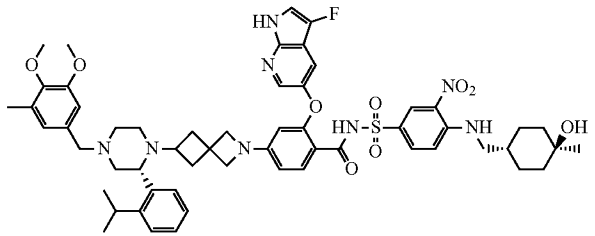 | 4-(6-((R)-4-(3,4-dimethoxy-5-methylbenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((1r,4r)-4-hydroxy-4-methylcyclohexyl)methyl)amino)-3-nitrophenyl)sulfonyl)benzamide | $^1$H NMR (400 MHz, DMSO-$d_6$) δ ppm 11.52 (s, 1H), 8.60-8.46 (m, 2H), 8.07 (s, 1H), 7.78 (d, J = 8.8 Hz, 1H), 7.56-7.30 (m, 4H), 7.27-7.01 (m, 4H), 6.80 (s, 1H), 6.69 (s, 1H), 6.06 (d, J = 8.4 Hz, 1H), 5.55 (s, 1H), 4.24 (s, 1H), 3.74 (s, 3H), 3.69 -3.41 (m, 10H), 3.31-3.18 (m, 4H), 3.00-2.83 (m, 2H), 2.78-2.65 (m, 1H), 2.63-2.52 (m, 1H), 2.36-2.16 (m, 2H), 2.13 (s, 3H), 2.09-1.91 (m, 2H), 1.75-1.59 (m, 4H), 1.58-149 (m, 2H), 1.42-1.27 (m, 3H), 1.24-0.99 (m, 11H). MS (ESI, m/e) [M + 1]$^+$ 1060.3 |
| 234 | 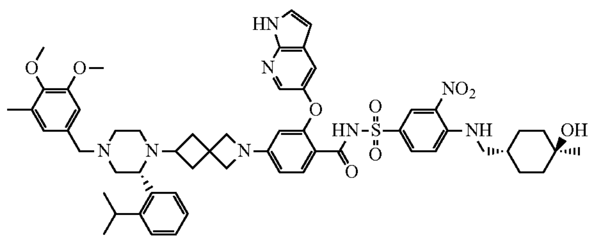 | 2-((1H-pyrrolo[2,3-b]pyridin-5-yl)oxy)-4-(6-((R)-4-(3,4-dimethoxy-5-methylbenzyl)-2-(2-isopropylphenyl)piperazin-1-yl)-2-azaspiro[3.3]heptan-2-yl)-N-((4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.70 (s, 1H), 11.14 (s, 1H), 8.65-8.45 (m, 2H), 8.07-7.98 (m, 1H), 7.80 (d, J = 7.6 Hz, 1H), 7.59-6.32 (m, 4H), 7.26-7.00 (m, 4H), 6.78 (s, 1H), 6.67 (s, 1H), 6.39 (s, 1H), 6.03 (d, J = 6.8 Hz, 1H), 5.50 (s, 1H), 4.24 (s, 1H), 3.74 (s, 3H), 3.65-3.36 (m, 10H), 3.31-3.16 (m, 3H), 2.96-2.82 (m, 2H), 2.79-2.65 (m, 1H), 2.59-2.52 (m 1H), 2.30-1.87 (m, 8H), 1.73-1.49 (m, 6H), 1.33 (t, J = 11.6 Hz, 3H), 1.22-0.98 (m, 11H). MS (ESI, m/e) [M + 1]$^+$ 1042.0 |
| 235 | 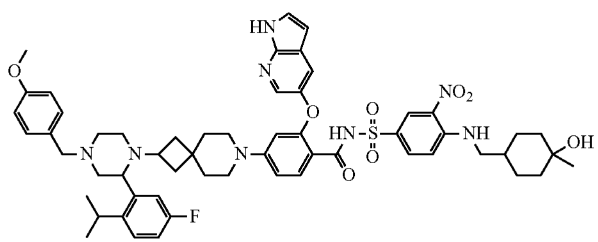 [SMILES: COc1ccc(CN2CCN(C3CC4(CCN(c5ccc(C(=O)NS(=O)(=O)c6ccc(NCC7CCC(C)(O)CC7)c([N+](=O)[O-])c6)c(Oc6cnc7[nH]ccc7c6)c5)CC4)C3)C(c3cc(F)ccc3C(C)C)C2)cc1] | 2-((1H-pyrrolo[2,3-b]pyridin-5-yl)oxy)-4-(2-(2-(5-fluoro-2-isopropylphenyl)-4-(4-methoxybenzyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm:: 11.68 (s, 1H), 11.4-10.85 (m, 1H), 8.67-8.42 (m, 2H), 8.10-7.93 (m, 1H), 7.89-7.72 (m, 1H), 7.55-7.12 (m, 8H), 7.12-6.98 (m, 2H), 6.96-6.84 (m, 2H), 6.75-6.57 (m, 1H), 6.43-6.30 (m, 1H), 6.14 (s, 1H), 4.25 (s, 1H), 3.90-3.66 (m, 5H), 3.27-2.78 (m, 13H), 2.06-1.92 (m, 1H), 1.72-1.50 (m, 7H), 1.41-1.27 (m, 6H), 1.19-1.00 (m, 13H). MS (ESI, m/e) [M + 1]$^+$ 1044.1 |

| Ex. | Compound name | Data |
|---|---|---|
| 236 | (R)-2-((1H-pyrrolo[2,3-b]pyridin-5-yl)oxy)-N-((4-((4-hydroxy-4-methylcyclohexyl)methoxy)-3-nitrophenyl)sulfonyl)-4-(2-(2-isopropylphenyl)-4-(4-methoxybenzyl)piperazin-1-yl)-7-azaspiro[3.5]nonan-7-yl)benzamide | $^1$H NMR (400 MHz, DMSO-$d_6$) δ ppm: 11.68 (s, 1H), 8.34 (s, 1H), 8.01 (s, 2H), 7.55-7.20 (m, 10H), 6.95-6.90 (m, 2H), 6.64 (d, J = 9.0 Hz, 1H), 6.38 (s, 1H), 6.14 (s, 1H), 4.27 (s, 1H), 4.07 (s, 2H), 3.74 (s, 4H), 3.56 (s, 1H), 3.26-3.13 (m, 1H), 3.05-2.85 (m, 8H), 2.01 (s, 1H), 1.75-1.65 (m, 4H), 1.60-1.52 (m, 3H), 1.42-1.14 (m, 15H), 1.15-1.02 (m, 7H). MS (ESI, m/e) [M + 1]$^+$ 1026.9. |
| 237 | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((S)-2-(2-isopropylphenyl)-4-(4-methoxybenzyl)piperazin-1-yl)-2-azaspiro[3.3]heptan-2-yl)benzamide | $^1$H NMR (400 MHz, DMSO-$d_6$) δ ppm: 11.70 (s, 1H), 11.63-10.90 (m, 1H), 8.38-8.28 (m, 1H), 8.10-7.80 (m, 3H), 7.58-7.13 (m, 10H), 7.02-6.80 (m 2H), 6.70-6.60 (m, 1H), 6.39 (s, 1H), 6.22-6.07 (m, 1H), 4.72-3.83 (m, 5H), 3.83-3.51 (m, 4H), 3.25-2.55 (m, 12H), 2.14-1.90 (m, 1H), 1.75-1.26 (m, 15H), 1.19-0.96 (m, 9H). MS (ESI, m/e) [M + 1]$^+$ 1027.0 |
| 238 | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-((R)-2-(2-isopropylphenyl)-4-(4-methoxybenzyl)piperazin-1-yl)-7-azaspiro[3.5]nonan-7-yl)benzamide | $^1$H NMR (400 MHz, DMSO-$d_6$) δ ppm: 11.55 (s, 1H), 8.56-8.50 (m, 2H), 8.08 (s, 1H), 7.81 (d, J = 9.0 Hz, 1H), 7.55-7.50 (m, 2H), 7.47-7.07 (m, 8H), 6.97 (s, 2H), 6.07 (s, 1H), 5.52 (s, 1H), 4.24 (s, 1H), 3.75 (s, 4H), 3.65-3.50 (m, 6H), 3.29 (s, 1H), 3.21 (s, 1H), 3.00 (s, 3H), 2.73 (s, 1H), 2.33 (s, 1H), 1.99 (s, 2H), 1.73-1.49 (m, 6H), 1.38-0.97 (m, 18H). MS (ESI, m/e) [M + 1]$^+$ 1015.9. |
| 239 | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-((R)-2-(2-isopropylphenyl)-4-((7-methoxy-2,3-dihydrobenzofuran-5-yl)methyl)piperazin-1-yl)-7-azaspiro[3.5]nonan-7-yl)benzamide | $^1$H NMR (400 MHz, DMSO-$d_6$) δ ppm: 11.68 (s, 1H), 11.42-0.99 (m, 1H), 8.55 (s, 2H), 8.02 (s, 1H), 7.78 (d, J = 8.4 Hz, 1H), 7.49-7.45 (m 3H), 7.34-7.10 (m, 4H), 6.86 (s, 2H), 6.65 (d, J = 7.6 Hz, 1H), 6.37 (s, 1H), 6.13 (s, 1H), 4.50 (s, 2H), 4.24 (s, 1H), 3.74 (s, 4H), 3.42 (s, 1H), 3.28 (s, 2H), 3.18-2.78 (m, 11H), 2.60 (s, 2H), 2.40-2.29 (m, 1H), 2.07 (s, 1H), 1.78-1.48 (m, 7H), 1.38-0.99 (m, 21H). MS (ESI, m/e) [M + 1]$^+$ 1067.9. |

| Ex. | structure | Compound name | Data |
|---|---|---|---|
| 240 | 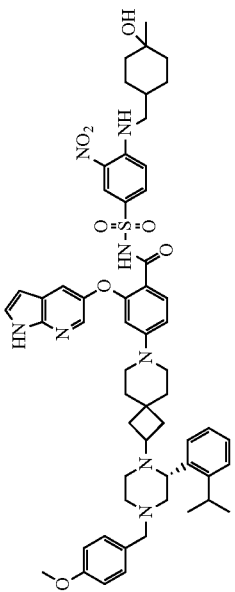 | (R)-2-((1H-pyrrolo[2,3-b]pyridin-5-yl)oxy)-N-((4-((3-hydroxy-3-methylcyclobutyl)methyl)amino)-3-nitrophenyl)sulfonyl)-4-(2-(2-(2-isopropylphenyl)-4-(4-methoxybenzyl)piperazin-1-yl)-7-azaspiro[3.5]nonan-7-yl)benzamide | 1H NMR (400 MHz, DMSO-d6) δ ppm: 11.64 (s, 1H), 11.14 (s, 1H), 8.57-8.46 (m, 1H), 8.46-8.38 (m, 1H), 8.03-7.95 (m, 1H), 7.77-6.98 (m, 1H), 7.52-7.33 (m, 4H), 7.30-7.04 (m, 5H), 7.03-6.80 (m, 3H), 6.70-6.57 (m, 1H), 6.40-6.30 (m, 1H), 6.15 (s, 1H), 4.90 (s, 1H), 3.71 (s, 3H), 3.60-3.37 (m, 7H), 3.02-2.80 (m, 6H), 2.63-2.55 (m, 1H), 2.33-1.92 (m, 6H), 1.84-1.72 (m, 2H), 1.72-1.55 (m, 2H), 1.50-1.28 (m, 5H), 1.23-0.97 (m, 11H). MS (ESI, m/e) [M + 1]+ 997.9 |
| 241 | 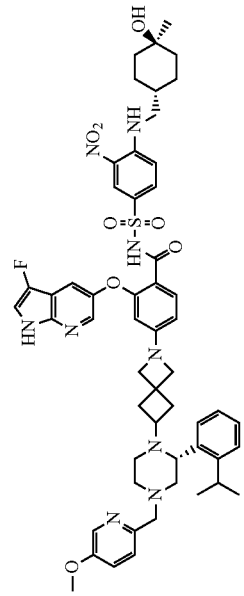 | 2-((3-fluoro-1H-pyrrolo[2,3-b]pyridin-5-yl)oxy)-N-(((1r,4r)-4-hydroxy-4-methylcyclohexyl)methyl)amino)-3-nitrophenyl)sulfonyl)-4-(6-((R)-2-(2-isopropylphenyl)-4-((5-methoxypyridin-2-yl)methyl)piperazin-1-yl)-2-azaspiro[3.3]heptan-2-yl)benzamide | 1H NMR (400 MHz, DMSO-d6) δ ppm: 11.53 (s, 1H), 11.22 (br, 1H), 8.59-8.52 (m, 2H), 8.20 (s, 1H), 8.06 (s, 1H), 7.82-7.76 (m 1H), 7.55-7.04 (m, 10H), 6.12-6.04 (m, 1H), 5.55 (s, 1H), 4.24 (s, 1H), 3.80 (s, 3H), 3.79-3.40 (m, 7H), 3.32-3.15 (m, 3H), 3.09-2.60 (m, 5H), 2.30-2.15 (m, 1H), 2.05-1.90 (m, 2H), 1.74-1.50 (m, 6H), 1.39-1.15 (m, 8H), 1.15-1.00 (m, 7H). MS (ESI, m/e) [M + 1]+ 1017.1 |
| 242 | 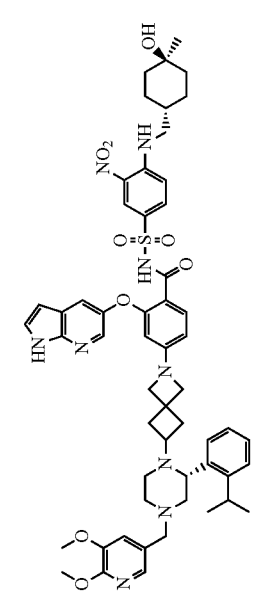 | 2-((1H-pyrrolo[2,3-b]pyridin-5-yl)oxy)-4-(6-((R)-4-((5,6-dimethoxypyridin-3-yl)methyl)-2-(2-isopropylphenyl)piperazin-1-yl)-2-azaspiro[3.3]heptan-2-yl)-4-hydroxy-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.72 (s, 1H), 11.21 (br, 1H), 8.62-8.55 (m, 2H), 8.04 (s, 1H), 7.85-7.80 (m, 1H), 7.68-7.08 (m, 10H), 6.40 (s, 1H), 6.09-6.02 (m, 1H), 5.48 (s, 1H), 4.24 (s, 1H), 3.82 (s, 3H), 3.77 (s, 3H), 3.70-3.35 (m, 7H), 3.32-3.10 (m, 3H), 3.09-2.62 (m, 5H), 2.38-2.25 (m, 1H), 2.05-1.90 (m, 2H), 1.73-1.50 (m, 6H), 1.36-1.15 (m, 8H), 1.12-1.05 (m, 7H). MS (ESI, m/e) [M + 1]+ 1029.2. |
| 243 | 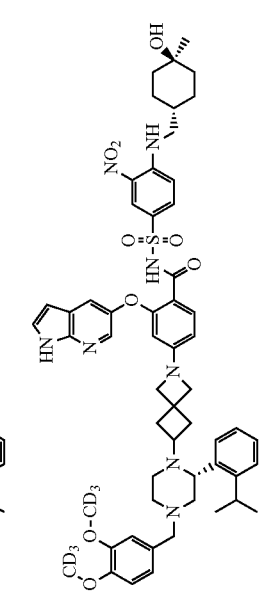 | 2-((1H-pyrrolo[2,3-b]pyridin-5-yl)oxy)-4-(6-((R)-4-(3,4-bis(methoxy-d3)benzyl)-2-(2-isopropylphenyl)piperazin-1-yl)-2-azaspiro[3.3]heptan-2-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.73 (s, 1H), 11.16 (br, 1H), 8.62-8.56 (m, 2H), 8.04 (s, 1H), 7.83 (d, J = 8.8 Hz, 1H), 7.61-7.09 (m, 9H), 6.98-6.84 (m, 2H), 6.40 (s, 1H), 6.09-6.01 (m, 1H), 5.48 (s, 1H), 4.24 (s, 1H), 4.18-3.85 (m, 2H), 3.69-3.40 (m, 5H), 3.32-3.15 (m, 3H), 3.09-2.60 (m, 6H), 2.45-2.30 (m, 1H), 2.05-1.90 (m, 2H), 1.74-1.50 (m, 6H), 1.39-1.15 (m, 8H), 1.15-1.05 (m, 7H). MS (ESI, m/e) [M + 1]+ 1034.0. |

-continued

| Ex. | structure | Compound name | Data |
|---|---|---|---|
| 244 | 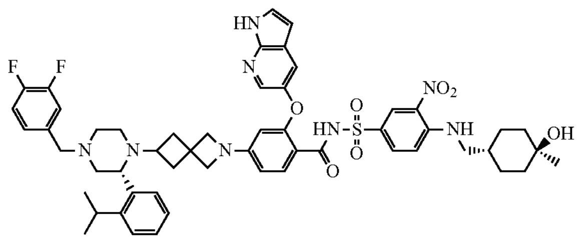 [SMILES: CC(C)c1ccccc1[C@@H]1CN(Cc2ccc(F)c(F)c2)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]ccc4c3)c1)C2] | 2-((1H-pyrrolo[2,3-b]pyridin-5-yl)oxy)-4-(6-((R)-4-(3,4-difluorobenzyl)-2-(2-isopropylphenyl)piperazin-1-yl)-2-azaspiro[3.3]heptan-2-yl)-N-(4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.72 (s, 1H), 11.27 (br, 1H), 8.62-8.55 (m, 2H), 8.04 (s, 1H), 7.84 (d, J = 9.2 Hz, 1H), 7.75-7.05 (m, 12H), 6.40 (s, 1H), 6.09-6.01 (m, 1H), 5.48 (s, 1H), 4.24 (s, 1H), 3.65-3.40 (m, 7H) 3.32-3.15 (m, 3H), 3.09-2.60 (m, 6H), 2.30-2.05 (m, 1H), 2.05-1.90 (m, 2H), 1.73-1.50 (m, 6H), 1.15-1.00 (m, 7H). MS (ESI, m/e) [M + 1]$^+$ 1004.1. |
| 245 | 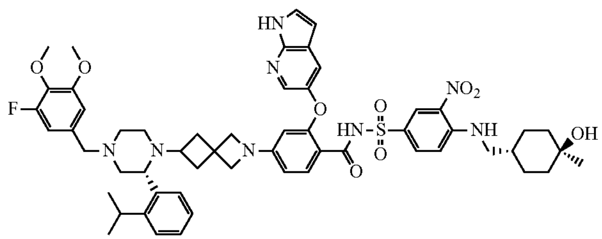 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc(F)c1OC] | 2-((1H-pyrrolo[2,3-b]pyridin-5-yl)oxy)-4-(6-((R)-4-(3-fluoro-4,5-dimethoxybenzyl)-2-(2-isopropylphenyl)piperazin-1-yl)-2-azaspiro[3.3]heptan-2-yl)-N-(4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.73 (s, 1H), 11.27 (br, 1H), 8.63-8.58 (m, 2H), 8.05 (s, 1H), 7.84 (d, J = 8.8 Hz, 1H), 7.62-6.75 (m, 10H), 6.40 (s, 1H), 6.02 (m, 1H), 5.49 (s, 1H), 4.24 (s, 1H), 3.80 (s, 3H), 3.80 (s, 3H), 3.67-3.40 (m, 6H), 3.32-3.15 (m, 3H), 3.09-2.60 (m, 6H), 2.40-2.25 (m, 1H), 2.05-1.90 (m, 2H), 1.74-1.50 (m, 6H), 1.39-1.15 (m, 8H), 1.15-1.00 (m, 7H). MS (ESI, m/e) [M + 1]$^+$ 1046.0. |
| 246 | 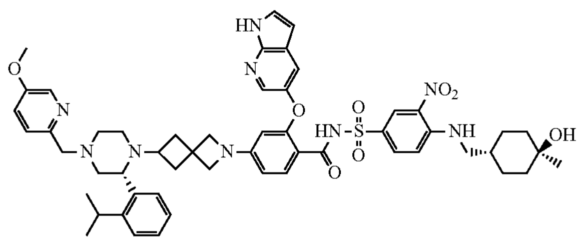 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)nc1] | 2-((1H-pyrrolo[2,3-b]pyridin-5-yl)oxy)-N-(4-(((1r,4r)-4-hydroxy-4-methylcyclohexyl)methyl)amino)-3-nitrophenyl)sulfonyl)-4-(6-((R)-2-(2-isopropylphenyl)-4-((5-methoxypyridin-2-yl)methyl)piperazin-1-yl)-2-azaspiro[3.3]heptan-2-yl)benzamide | $^1$H NMR (400 MHz, DMSO-d$_6$) δ ppm: 11.70 (s, 1H), 11.27 (br, 1H), 8.60-8.53 (m, 2H), 8.18 (s, 1H), 8.03 (s, 1H), 7.81 (d, J = 8.8 Hz, 1H), 7.58-7.35 (m, 6H), 7.25-7.05 (m, 4H), 6.39 (s, 1H), 6.06-6.03 (m, 1H), 5.49 (s, 1H), 4.24 (s, 1H), 3.80 (s, 3H), 3.70-3.40 (m, 7H), 3.32-3.15 (m, 3H), 3.09-2.60 (m, 6H), 2.25-2.15 (m, 1H), 2.05-1.90 (m, 2H), 1.74-1.50 (m, 6H), 1.39-1.15 (m, 8H), 1.13-1.00 (m, 7H). MS (ESI, m/e) [M + 1]$^+$ 999.1 |
| 247 | 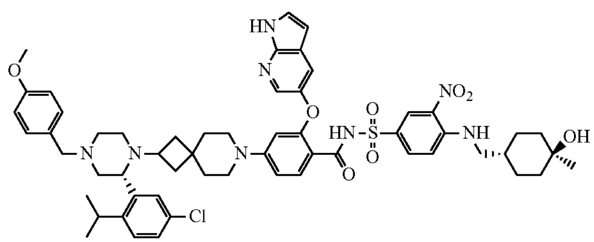 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3cc(Cl)ccc3C(C)C)C2)cc1] | 2-((1H-pyrrolo[2,3-b]pyridin-5-yl)oxy)-4-(2-(2-(5-chloro-2-isopropylphenyl)-4-(4-methoxybenzyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.67 (s, 1H), 8.54 (s, 2H), 8.02 (s, 1H), 7.76 (s, 1H), 7.49 (s, 5H), 7.25 (s, 4H), 7.10-7.01 (m, 1H), 6.88 (s, 2H), 6.66 (s, 1H), 6.37 (s, 1H), 6.14 (s, 1H), 4.23 (s, 1H), 3.72 (s, 4H), 3.05-2.85 (m, 9H), 1.75-1.52 (m, 9H), 1.38-1.22 (m, 13H), 1.20-1.08 (m, 14H). MS (ESI, m/e) [M + 1]$^+$ 1060.2. |

| Ex. | structure | Compound name | Data |
|---|---|---|---|
| 248 | 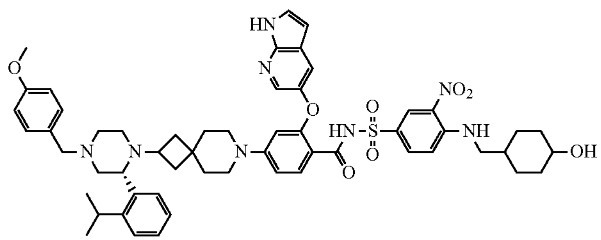 [SMILES: COc1ccc(CN2CCN(C3CC4(CCN(c5ccc(C(=O)NS(=O)(=O)c6ccc(NCC7CCC(O)CC7)c([N+](=O)[O-])c6)c(Oc6cnc7[nH]ccc7c6)c5)CC4)C3)[C@H](c3ccccc3C(C)C)C2)cc1] | (R)-2-((1H-pyrrolo[2,3-b]pyridin-5-yl)oxy)-N-((4-((4-hydroxycyclohexyl)amino)-3-nitrophenyl)-4-(2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm 11.68 (s, 1H), 11.55-11.23 (m, 1H), 8.55 (s, 2H), 8.02 (s, 1H), 7.77 (s, 1H), 7.54-7.12 (m, 8H), 7.07 (d, J = 8.4 Hz, 1H), 6.95-6.90 (m, 2H), 6.64 (s, 1H), 6.37 (s, 1H), 6.13 (s, 1H), 4.31 (s, 1H), 3.76-3.73 (m, 5H), 3.56 (s, 1H), 3.40 (s, 1H), 3.26 (s, 3H), 3.05-2.85 (m, 8H), 2.79-2.69 (m, 1H), 2.66-2.55 (m, 1H), 2.03 (s, 1H), 1.62 (s, 4H), 1.47-0.96 (m, 20H). MS (ESI, m/e) [M + 1]⁺ 1012.0. |
| 249 | 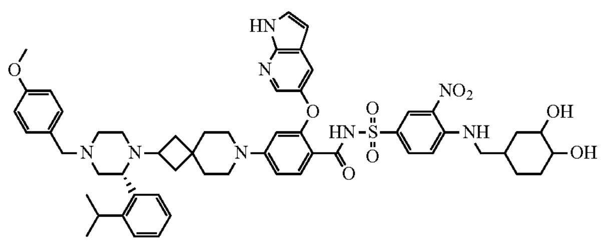 [SMILES: COc1ccc(CN2CCN(C3CC4(CCN(c5ccc(C(=O)NS(=O)(=O)c6ccc(NCC7CCC(O)C(O)C7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-((4-((3,4-dihydroxycyclohexyl)methyl)amino)-3-nitrophenyl)sulfonyl)-4-(2-((R)-2-(2-isopropylphenyl)-4-(4-methoxybenzyl)piperazin-1-yl)-7-azaspiro[3.5]nonan-7-yl)benzamide | ¹H NMR (400 MHz, DMSO-d₆) δ ppm:11.68 (s, 1H), 11.28 (s, 1H), 8.55 (s, 2H), 8.02 (s, 1H), 7.77 (d, J = 8.8 Hz, 1H), 7.57-6.80 (m, 12H), 6.65 (d, J = 9.0 Hz, 1H), 6.37 (s, 1H), 6.14 (s, 1H), 4.38-4.36 (m, 1H), 4.23-4.21 (m, 1H), 3.91 (s, 2H), 3.73 (s, 5H), 3.55 (s, 1H), 3.22 (s, 2H), 3.05-2.85 (m, 8H), 1.83-1.45 (m, 6H), 1.42-0.93 (m, 15H). MS (ESI, m/e) [M + 1]⁺ 1027.8. |
| 250 | 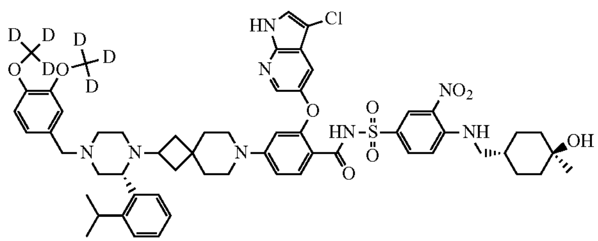 [SMILES: [2H]C([2H])([2H])Oc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(Cl)c7c6)c5)CC4)C3)[C@H](c3ccccc3C(C)C)C2)cc1OC([2H])([2H])[2H]] | 4-(2-((R)-4-(3,4-bis(methoxy-d3)benzyl)-2-(2-isopropylphenyl)piperazin-1-yl)-7-azaspiro[3.5]nonan-7-yl)-2-((3-chloro-1H-pyrrolo[2,3-b]pyridin-5-yl)oxy)-N-((4-((((1,4r)-4-hydroxy-4-methylcyclohexyl)methyl)amino)-3-nitrophenyl)sulfonyl)benzamide | ¹H NMR (400 MHz, DMSO-d₆) δ ppm: 12.01 (s, 1H), 11.42 (br, 1H), 8.60-8.50 (m, 2H), 8.09 (s, 1H), 7.78 (d, J = 8.4 Hz, 1H), 7.69 (s, 1H), 7.48-7.12 (m, 6H), 7.09-6.65 (m, 4H), 6.25-6.20 (m, 1H), 4.24 (s, 1H), 4.23-3.40 (m, 5H), 3.32-3.15 (m, 3H), 3.09-2.60 (m, 9H), 2.20-1.95 (m, 1H), 1.74-1.50 (m, 7H), 1.39-1.15 (m, 11H), 1.13-1.00 (m, 8H). MS (ESI, m/e) [M + 1]⁺ 1095.9. |
| 251 | 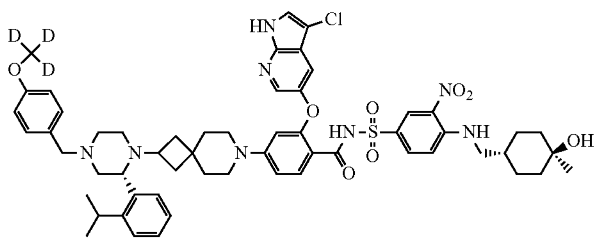 [SMILES: [2H]C([2H])([2H])Oc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(Cl)c7c6)c5)CC4)C3)[C@H](c3ccccc3C(C)C)C2)cc1] | 2-((3-chloro-1H-pyrrolo[2,3-b]pyridin-5-yl)oxy)-N-((4-((((1,4r)-4-hydroxy-4-methylcyclohexyl)methyl)amino)-3-nitrophenyl)sulfonyl)-4-(2-((R)-2-(2-isopropylphenyl)-4-(4-(methoxy-d3)benzyl)piperazin-1-yl)-7-azaspiro[3.5]nonan-7-yl)benzamide | ¹H NMR (400 MHz, DMSO-d₆) δ ppm: 12.01 (s, 1H), 11.33 (br, 1H), 8.59-8.49 (m, 2H), 8.08 (s, 1H), 7.77 (d, J = 8.4 Hz, 1H), 7.68 (s, 1H), 7.49-7.10 (m, 6H), 7.09-6.65 (m, 4H), 6.28-6.18 (m, 1H), 4.24 (s, 1H), 4.23-3.40 (m, 4H), 3.32-3.15 (m, 3H), 3.09-2.60 (m, 10H), 2.21-1.96 (m, 1H), 1.74-1.50 (m, 7H), 1.39-1.15 (m, 11H), 1.13-1.00 (m, 8H). MS (ESI, m/e) [M + 1]⁺ 1062.8. |

| Ex. | structure | Compound name | Data |
|---|---|---|---|
| 252 | 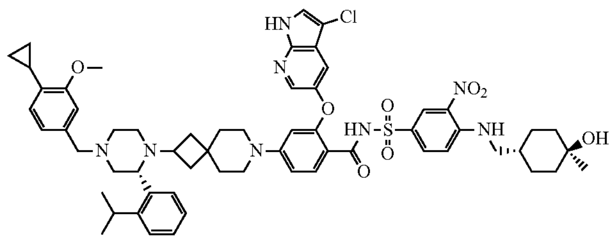 | 2-((3-chloro-1H-pyrrolo[2,3-b]pyridin-5-yl)oxy)-4-(2-((R)-4-(4-cyclopropyl-3-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 12.01 (s, 1H), 11.48 (br, 1H), 8.59-8.50 (m, 2H), 8.09 (s, 1H), 7.75 (d, J = 8.4 Hz, 1H), 7.69 (s, 1H), 7.49-7.10 (6H), 7.09-6.65 (m, 5H), 6.28-6.20 (m, 1H), 4.24 (s, 1H), 4.18-3.90 (m, 1H), 3.85-3.70 (m, 3H), 3.73-3.35 (m, 2H), 3.30-3.25 (m, 3H), 3.09-2.60 (m, 9H), 2.20-1.96 (m, 2H), 1.74-1.50 (m, 7H), 1.39-1.15 (m, 11H), 1.13-1.00 (m, 9H), 0.95-0.80 (m, 2H), 0.65-0.52 (m, 2H). MS (ESI, m/e) [M + 1]+ 1099.8. |
| 253 | 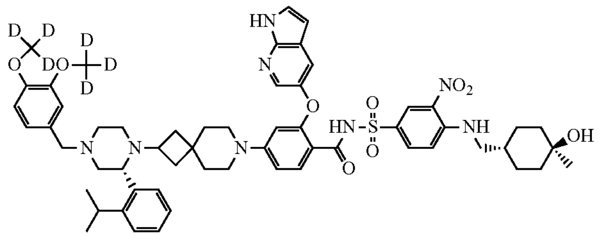 [SMILES: [2H]C([2H])([2H])Oc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc1OC([2H])([2H])[2H]] | 2-((1H-pyrrolo[2,3-b]pyridin-5-yl)oxy)-4-(2-((R)-4-(3,4-bis(methoxy-d3)benzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm 11.65 (s, 1H), 8.58-8.44 (m, 2H), 8.01 (d, J = 2.8 Hz, 1H), 7.76 (d, J = 7.2 Hz, 1H), 7.55-7.35 (m, 4H), 7.26-7.06 (m, 3H), 7.00 (d, 7 = 9.2 Hz, 1H), 6.93-6.75 (m, 3H), 6.63 (d, J = 7.6 Hz, 1H), 6.35 (s, 1H), 6.15 (s, 1H), 4.25 (m, 1H), 3.70-3.46 (m, 4H), 3.30-3.22 (m, 3H), 3.05-2.80 (m, 7H), 2.68-2.56 (m, 1H), 2.41-2.05 (m, 3H), 1 76-1.49 (m, 7H), 1.40-1.22 (m, 6H), 1.20-0.96 (m, 12H). MS (ESI, m/e) [M + 1]+ 1062.1 |
| 254 | 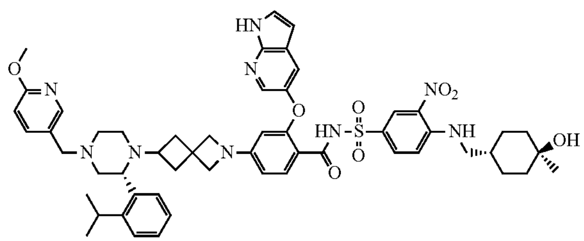 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cn1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((6-methoxypyridin-3-yl)methyl)piperazin-1-yl)-2-azaspiro[3.3]heptan-2-yl)benzamide | 1H NMR (400 MHz, DMSO-d6) δ ppm: 11.72 (s, 1H), 11.20 (br, 1H), 8.62-8.55 (m, 2H), 8.22-8.20 (m, 1H), 8.04 (s, 1H), 7.85-7.08 (m, 9H), 6.88-6.72 (m, 1H), 6.40 (s, 1H), 6.09-6.02 (m, 1H), 5.48 (s, 1H), 4.24 (s, 1H), 3.53 (s, 3H), 3.48-3.35 (m, 7H), 3.32-3.10 (m, 3H), 3.09-2.62 (m, 5H), 2.38-2.25 (m, 1H), 2.05-1.90 (m, 2H), 1.73-1.50 (m, 6H), 1.36-1.15 (m, 8H), 1.12-105 (m, 7H). MS (ESI, m/e) [M + 1]+ 998.9. |
| 255 | 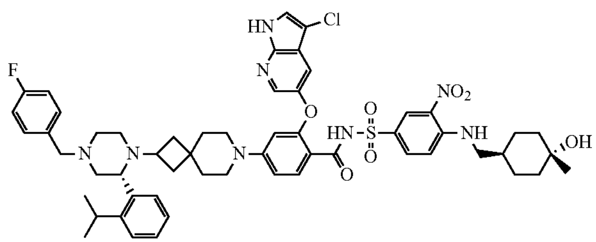 [SMILES: CC(C)c1ccccc1[C@@H]1CN(Cc2ccc(F)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]cc(Cl)c5c4)c3)CC2)C1] | 2-((3-chloro-1H-pyrrolo[2,3-b]pyridin-5-yl)oxy)-2-(2-isopropylphenyl)piperazin-1-yl)-7-(4-fluorobenzyl)-4-(((1r,4r)-4-hydroxy-4-methylcyclohexyl)methyl)amino)-3-nitrophenyl)sulfonyl)benzamide | 1H NMR (400 MHz, DMSO-d6) δ ppm 12.00 (s, 1H), 11.44 (s, 1H), 8.58-8.48 (m, 2H), 8.12-8.05 (s, 1H), 7.91-7.61 (m, 3H), 7.58-6.95 (m, 11H), 6.71-6.63 (m, 1H), 6.24 (s, 1H), 4.69-4.55 (m, 1H), 4.25 (s, 1H), 3.87-3.54 (m, 3H), 3.47-3.37 (m, 1H), 3.32-3.15 (m, 4H), 3.10-2.82 (m, 6H), 2.77-2.59 (m, 2H), 2.11-1.97 (m, 1H), 1.76-1.50 (m, 6H), 1.47-1.23 (m, 8H), 1.22-0.96 (m, 11H). MS (ESI, m/e) [M + 1]+ 1047.9 |

| Ex. | Compound name | Data |
|---|---|---|
| 256 | 2-((3-chloro-1H-pyrrolo[2,3-b]pyridin-5-yl)oxy)-4-(2-((R)-4-(4-chlorobenzyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | 1H NMR (400 MHz, DMSO-d6) δ ppm: 12.00 (s, 1H), 11.47 (s, 1H), 8.57-8.47 (m, 2H), 8.13-8.02 (m, 1H), 7.80-7.62 (m, 3H), 7.53-7.08 (m, 10H), 7.08-7.00 (m, 1H), 6.75-6.62 (m, 1H), 6.24 (s, 1H), 4.25 (s, 1H), 3.78-3.50 (m, 3H), 3.46-3.37 (m, 1H), 3.32-3.15 (m, 4H), 3.11-2.81 (m, 7H), 2.75-2.60 (m 1H), 2.32-2.18 (m, 1H), 1.72-1.50 (m, 5H), 1.45-1.24 (m, 8H), 1.19-0.97 (m, 11H). MS (ESI, m/e) [M + 1]+ 1065.9 |
| 257 | 2-((1H-pyrrolo[2,3-b]pyridin-5-yl)oxy)-4-(2-((R)-4-4-cyclopropyl-3-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.65 (s, 1H), 8.61-8.41 (m, 2H), 8.01 (s, 1H), 7.75 (d, J = 8.8 Hz, 1H), 7.55-7.33 (m, 4H), 7.28-6.97 (m 4H), 6.87 (s, 1H), 6.79-6.69 (m, 2H), 6.63 (d, J = 8.4 Hz, 1H), 6.40-6.31 (m, 1H), 6.15 (s, 1H), 4.25 (s, 1H), 3.77 (s, 3H), 3.63-3.45 (m, 3H), 3.30-2.21 (m, 3H), 3.06-2.78 (m, 7H), 2.65-2.53 (m, 1H), 2.39-2.10 (m, 2H), 2.08-1.98 (m, 1H), 1.78-1.47 (m, 7H), 1.43-0.94 (m, 20H), 0.89-0.78 (m, 2H), 0.61-0.48 (m, 2H) MS (ESI, m/e) [M + 1]+ 1066.1 |
| 258 | 4-(2-((R)-4-(4-cyclopropyl-3-methoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide | 1H NMR (400 MHz, DMSO-d6) δ ppm: 11.45 (s, 1H), 8.56-8.41 (m, 2H), 8.03 (s, 1H), 7.72 (d, J = 9.2 Hz, 1H), 7.55-7.30 (m, 4H), 7.28-6.94 (m, 4H), 6.87 (s, 1H), 6.80-6.61 (m, 3H), 6.22 (s, 1H), 4.24 (s, 1H), 3.78 (s, 3H), 3.65-3.46 (m, 2H) 3.30-2.20 (m, 3H), 3.09-2.80 (m, 7H), 2.68-2.54 (m, 1H), 2.39-2.12 (m, 2H), 2.09-1.98 (m, 1H), 1.75-1.49 (m, 7H), 1.40-0.97 (m, 20H), 0.89-0.78 (m 2H), 0.60-0.50 (m, 2H). MS (ESI, m/e) [M + 1]+ 1084.2 |
| 259 | 2-((1H-pyrrolo[2,3-b]pyridin-5-yl)oxy)-4-(2-((2R)-4-((1R,3S,5R)-adamantan-2-yl)methyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.70 (s, 1H), 11.45 (br, 1H), 8.63-8.54 (m, 2H), 8.02 (s, 1H), 7.82 (d, J = 9.2 Hz, 1H), 7.57-7.40 (m, 7H), 6.69-6.64 (m, 1H), 6.38 (s, 1H), 6.18-6.10 (m, 10H), 4.24 (s, 1H), 3.88-3.56 (m, 3H), 3.32-3.12 (m, 3H), 3.10-2.55 (m, 10H), 2.09-1.94 (m, 1H), 1.74-1.50 (m, 21H), 1.42-1.02 (m, 19H). MS (ESI, m/e) [M + 1]+ 1054.1. |

| Ex. | structure | Compound name | Data |
|---|---|---|---|
| 260 | 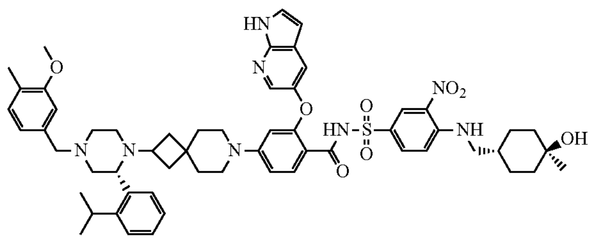 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1C] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-((R)-2-(2-isopropylphenyl)-4-(3-methoxy-4-methylbenzyl)piperazin-1-yl)-7-azaspiro[3.5]nonan-7-yl)benzamide | ¹H NMR (400 MHz, DMSO-d₆) δ ppm: 11.69 (s, 1H), 11.49-11.28 (m, 1H), 10.53-10.29 (m, 1H), 8.60-8.55 (m, 2H) 8.02 (s, 1H), 7.77 (s, 1H), 7.54-7.39 (m, 3H), 7.36 (s, 1H), 7.30-7.10 (m, 3H), 7.09-7.05 (m, 2H), 6.90-6.75 (m, 1H), 6.65 (d, J = 8.8 Hz, 1H), 6.38 (s, 1H), 6.14 (d, J = 9.0 Hz, 1H), 4.24 (s, 1H), 3.80-3.75 (m, 4H), 3.60 (s, 1H), 3.41 (s, 1H), 3.29-3.25 (m, 3H), 3.05-2.85 (m, 7H), 2.15-1.95 (m, 4H), 1.75-1.50 (m, 6H), 1.40-1.15 (m, 14H), 1.14-1.00 (m, 7H). MS (ESI, m/e) [M + 1]⁺ 1040.0. |
| 261 | 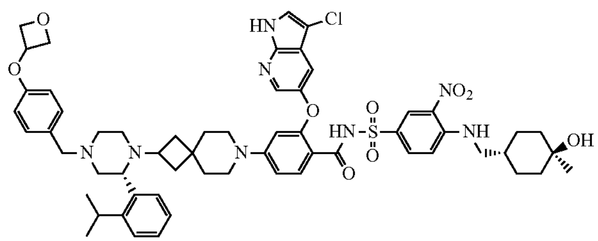 [SMILES: CC(C)c1ccccc1[C@@H]1CN(Cc2ccc(OC3COC3)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]cc(Cl)c5c4)c3)CC2)C1] | 2-((3-chloro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-((R)-2-(2-isopropylphenyl)-4-(4-(oxetan-3-yloxy)benzyl)piperazin-1-yl)-7-azaspiro[3.5]nonan-7-yl)benzamide | ¹H NMR (400 MHz, DMSO-d₆) δ ppm: 11.99 (s, 1H), 11.59-10.99 (m, 1H), 8.61-8.44 (m, 2H), 8.08 (d, J = 2.4 Hz, 1H), 7.81-7.68 (m, 2H), 7.50-7.10 (m, 8H), 7.04 (s, 1H), 6.84-6.64 (m, 3H), 6.23 (s, 1H), 5.25 (s, 1H), 4.92-4.90 (m 2H), 4.58-4.44 (m, 2H), 4.24 (s, 1H), 3.77 (s, 2H), 3.29-3.20 (m, 2H), 3.05-2.85 (m, 7H), 2.72 (s, 2H), 2.01-1.98 (m, 1H), 1.75-1.50 (m, 7H), 1.45-0.93 (m, 21H). MS (ESI, m/e) [M + 1]⁺ 1101.9. |
| 262 | 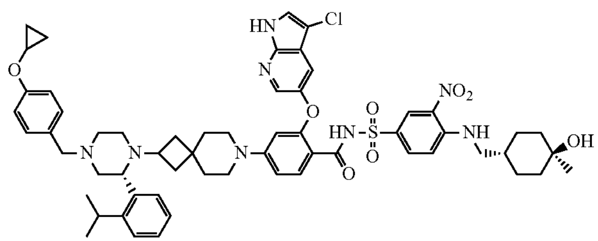 [SMILES: CC(C)c1ccccc1[C@@H]1CN(Cc2ccc(OC3CC3)cc2)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]cc(Cl)c5c4)c3)CC2)C1] | 2-((3-chloro-1H-pyrrolo[2,3-b]pyridin-5-yl)oxy)-4-(2-((R)-4-(4-cyclopropoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 12.00 (s, 1H), 11.65-11.35 (m, 1H), 8.57-8.55 (m, 2H), 8.08 (d, J = 2.4 Hz, 1H), 7.78-7.70 (m, 1H), 7.68 (d, J = 2.6 Hz, 1H), 7.61-7.20 (m, 7H), 7.06 (s, 3H), 6.68 (d, J = 9.0 Hz, 1H), 6.22 (s, 1H), 4.24 (s, 1H), 3.83 (s, 2H), 3.63-3.42 (m, 1H), 3.29-3.13 (m, 4H), 3.05-2.85 (m, 7H), 2.67 (s, 2H), 2.44-2.30 (m, 1H), 2.12-1.93 (m, 1H), 1.75-1.50 (m, 6H), 1.35-1.02 (m, 20H), 0.76 (s, 3H) 0.76 (s, 2H). MS (ESI, m/e) [M + 1]⁺ 1085.9. |
| 263 | 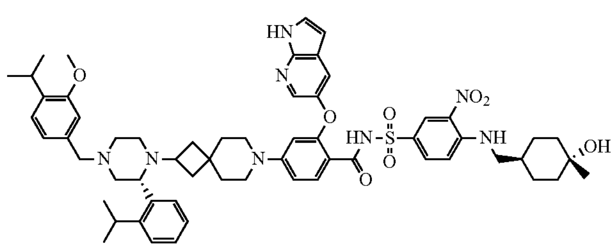 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1C(C)C] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R)-4-(4-isopropyl-3-methoxybenzyl)-2-(2-isopropylphenyl)piperazin-1-yl)-7-azaspiro[3.5]nonan-7-yl)benzamide | ¹H NMR (400 MHz, DMSO-d₆) δ ppm 11.67 (s, 1H), 11.25 (s, 1H), 8.65-8.41 (m, 2H), 8.10-7.95 (m, 1H), 7.82-7.72 (m, 1H), 7.64-7.37 (m, 4H), 7.34-6.78 (m, 8H), 6.70-6.54 (m 1H), 6.45-6.30 (m, 1H), 6.14 (s, 1H), 4.26 (s, 1H), 3.86-3.60 (m, 5H), 3.30-3.14 (m, 6H), 2.06-2.85 (m, 6H), 2.73-2.63 (m, 1H), 2.43-2.28 (m, 1H), 1.79-1.49 (m, 7H), 1.40-1.25 (m, 6H), 1.22-0.87 (m, 19H), MS (ESI, m/e) [M + 1]⁺ 1068.1 |

| Ex. | Compound name | Data |
|---|---|---|
| 264 | 2-((3-fluoro-1H-pyrrolo[2,3-b]pyridin-5-yl)oxy)-N-(4-(((1r,4r)-4-hydroxy-4-methylcyclohexyl)methyl)amino)-3-nitrophenyl)sulfonyl)-4-(2-((R)-4-(4-isopropyl-3-methoxybenzyl)-2-(2-isopropylphenyl)piperazin-1-yl)-7-azaspiro[3.5]nonan-7-yl)benzamide | ¹H NMR (400 MHz, DMSO-d₆) δ ppm: 11.57-11.03 (m, 2H), 8.57-8.40 (m, 2H), 8.06-7.95 (m, 1H), 7.92-7.63 (m, 2H), 7.60-6.73 (m, 11H), 6.70-6.54 (m, 1H), 6.16 (s, 1H) 4.21 (s, 1H), 4.12-3.37 (m, 13H), 3.15-2.81 (m, 5H), 2.77-2.59 (m, 1H), 2.03-1.90 (m, 1H), 1.75-1.43 (m, 7H), 1.42-1.20 (m, 9H), 1.17-0.93 (m, 16H). MS (ESI, m/e) [M + 1]⁺ 1086.1 |
| 265 | 2-((1H-pyrrolo[2,5-b]pyridin-5-yl)oxy)-4-(2-((R)-4-(4-ethyl-3-methoxybenzyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.68 (s, 1H), 11.27 (s, 1H). 8.68-8.46 (m, 2H), 8.14-7.97 (m, 1H), 7.87-7.68 (m, 1H), 7.64-6.80 (m, 12H), 6.72-6.60 (m, 1H), 6.48-6.30 (m, 1H), 6.15 (s, 1H), 4.25 (s, 1H), 3.90-3.63 (m, 6H), 3.33-3.16 (m, 6H), 2.13-2.81 (m, 7H), 2.79-2.56 (m, 2H), 2.47-2.25 (m, 1H), 1.73-1.50 (m, 6H), 1.40-1.22 (m, 9H), 1.17-0.98 (m, 13H). MS (ESI, m/e) [M + 1]⁺ 1054.2 |
| 266 | 4-(2-((R)-4-(4-ethyl-3-methoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.58-11.10 (m, 2H), 8.64-8.47 (m, 2H), 8.15-7.98 (m, 1H), 7.98-7.69 (m, 2H), 6.73-6.60 (m, 11H), 6.21 (s, 1H), 4.25 (s, 1H), 3.99-3.71 (m, 6H), 3.70-3.47 (m, 5H), 3.30-2.54 (m, 10H), 2.12-1.92 (m, 1H), 1.87-1.45 (m 8H), 1.40-1.26 (m, 7H), 1.20-1.00 (m, 13H). MS (ESI, m/e) [M + 1]⁺ 1072.89 |
| 267 | (R)-2-(((1H-pyrrolo[2,3-b]pyridin-5-yl)oxy)-4-(2-(2-isopropylphenyl)-4-(4-methoxybenzyl)piperazin-1-yl)-7-azaspiro[3.5]nonan-7-yl)-N-((4-(((4-methoxycyclohexyl)methyl)amino)-3-nitrophenyl)sulfonyl)benzamide | ¹H NMR (400 MHz, DMSO-d₆) δ ppm 11.69 (s, 1H), 11.44-11.17 (m, 1H), 8.59-8.56 (m, 2H), 8.02 (s, 1H), 7.89-7.73 (m, 1H), 7.53-7.11 (m, 9H), 7.06 (d, J = 9.0 Hz, 1H), 6.99-6.85 (m, 2H), 6.65 (d, J = 9.0 Hz, 1H), 6.37 (s, 1H), 6.13 (s, 1H), 4.06-3.85 (m, 1H), 3.74 (s, 4H), 3.55 (s, 1H), 3.25-3.20 (m, 6H), 3.10-2.79 (m, 9H), 2.02-1.99 (m, 3H), 1.79-1.76 (m, 2H), 1.57 (s, 3H), 1.35-1.00 (m, 18H). MS (ESI, m/e) [M + 1]⁺ 1025.9 |

-continued

| Ex. | structure | Compound name | Data |
|---|---|---|---|
| 268 | 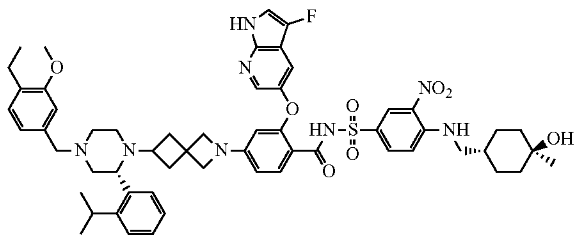 [SMILES: CCc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc1OC] | 4-(6-((R)-4-(4-ethyl--methoxybenzyl)-2-(2-isopropylphenyl)piperazin-1-yl)-2-azaspiro[3.3]heptan-2-yl)-2-(3-fluoro-1H-pyrrolo [2,3-b]pyridin-5-yl)oxy)-N-(4-(((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.53 (s, 1H), 11.19 (s, 1H), 8.66-8.45 (m, 2H), 8.12-8.03 (m, 1H), 7.89-7.76 (m, 1H), 7.60-7.32 (m, 4H), 7.32-7.02 (m, 5H), 7.02-6.77 (m, 2H), 6.20-5.91 (m, 1H), 5.54 (s, 1H), 4.23 (s, 1H), 3.93-3.45 (m, 10H), 3.42-3.34 (m, 1H), 3.31-3.16 (m, 3H), 3.13-2.58 (m, 4H), 2.56-2.50 (m, 3H), 2.37-2.20 (m, 1H), 2.08-1.90 (m, 2H), 1.82-1.48 (m, 6H), 1.42-1.27 (m, 3H), 1.22-1.00 (m, 13H). MS (ESI, m/e) [M + 1]$^+$ 1044.2 |
| 269 | 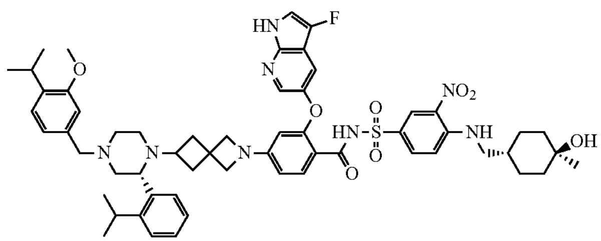 | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-4-(4-isopropyl-3-methoxybenzyl)-2-(2-isopropylphenyl)piperazin-1-yl)-2-azaspiro[3.3]heptan-2-yl)benzamide | $^1$H NMR (400 MHz, DMSO-$d_6$) δ ppm: 11.55 (s, 1H), 11.22 (br, 1H), 8.60-8.54 (m, 2H), 8.08 (s, 1H), 7.82-7.76 (m, 1H), 7.55-7.03 (m, 8H), 6.95-6.83 (m, 1H), 6.10-6.03 (m, 1H), 5.54 (s, 1H), 4.24 (s, 1H), 3.98-3.80 (m, 2H), 3.78 (s, 3H), 3.68-3.40 (m, 5H), 3.32-3.15 (m, 4H), 3.10-2.62 (m, 5H), 2.41-2.28 (m, 1H), 2.07-1.90 (m, 2H), 1.74-1.51 (m, 6H), 1.39-1.15 (m, 8H), 1.05-1.00 (m, 11H) MS (ESI, m/e) [M + 1]$^+$ 1058.3. |
| 270 | 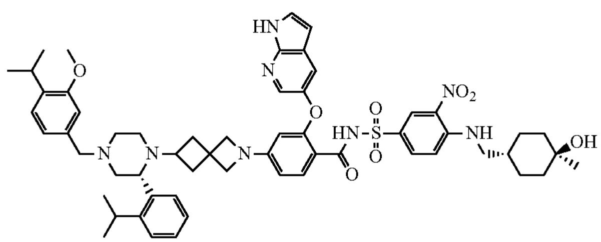 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)ccc1C(C)C] | 2-((1H-pyrrolo[2,3-b]pyridin-5-yl)oxy)-N-((4-((((1r,4r)-4-hydroxy-4-mmethylcyclohexyl)methyl)amino)-3-nntrophenyl)sulfonyl)-4-(6-((R)-4-(4-isopropyl-3-methoxybenzyl)-2-(2-isopropylphenyl)piperazin-1-yl)-2-azaspiro[3.3]heptan-2-yl)benzamide | $^1$H NMR (400 MHz, DMSO-$d_6$) δ ppm: 11.72 (s, 1H), 11.24 (br, 1H), 8.64-8.57 (m, 2H), 8.04 (s, 1H), 7.85-7.80 (m, 1H), 7.62-7.03 (m, 10H), 6.95-6.83 (m, 1H), 6.43-6.37 (m, 1H), 6.10-6.03 (m, 1H), 5.48 (s, 1H), 4.24 (s, 1H), 4.06-3.83 (m, 2H), 3.79 (s, 3H), 3.66-3.43 (m, 5H), 3.31-3.17 (m, 4H), 3.10-2.62 (m, 5H), 2.44-2.25 (m, 1H), 2.03-1.95 (m, 2H), 1.73-1.50 (m, 6H), 1.39-11.5 (m, 8H), 1.05-1.00 (m, 13H). MS (ESI, m/e) [M + 1]$^+$ 1040.2. |
| 271 | 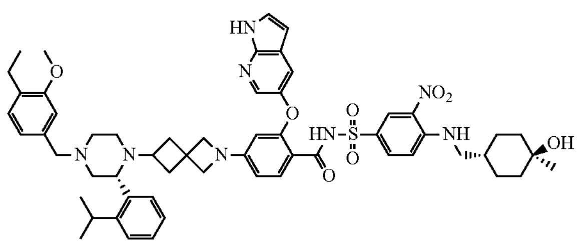 [SMILES: CCc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc1OC] | 2-((1H-pyrrolo[2,3-b]pyridin-5-yl)oxy)-4-(6-((R)-4-(4-ethyl-3-methoxybenzyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.72 (s, 1H), 11.11 (s, 1H), 8.64-8.48 (m, 2H), 8.10-7.97 (m, 1H), 7.85-7.72 (m, 1H), 7.63-6.72 (m, 12H), 6.44-6.30 (m, 1H), 6.08-5.95 (m, 1H), 5.48 (s, 1H), 4.24 (s, 1H), 3.97-3.70 (m, 4H), 3.68-3.40 (m, 5H), 3.32-3.22 (m, 4H), 3.15-2.87 (m, 3H), 2.82-2.64 (m, 3H), 2.57-2.52 (m, 1H), 2.41-2.28 (m, 1H), 2.06-1.92 (m, 2H), 1 73-1.49 (m, 6H), 1.40-1.27 (m, 3H), 0.99 (m, 15H). MS (ESI, m/e) [M + 1]$^+$ 1026.0 |

| Ex. | structure | Compound name | Data |
|---|---|---|---|
| 272 | 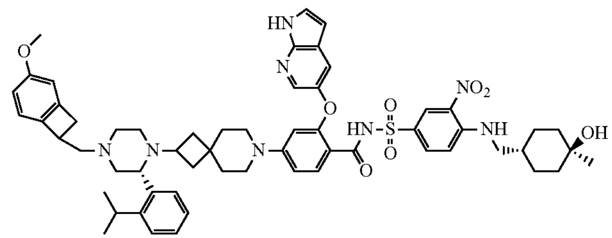 [SMILES: COc1ccc2c(c1)CC2CN1CCN(C2CC3(CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)C2)[C@H](c2ccccc2C(C)C)C1] | 2-((1H-pyrrolo[2,3-b]pyridin-5-yl)oxy)-N-((4-(((1r,4r)-4-hydroxy-4-methylcyclohexyl)amino)-3-nitrophenyl)sulfonyl)-4-(2-((2R)-2-(2-isopropylphenyl)-4-((3-methoxybicyclo[4.2.0]octa-1(6),2,4-trien-7-yl)methyl)piperazin-1-yl)-7-azaspiro[3.5]nonan-7-yl)benzamide | $^1$H NMR (400 MHz, DMSO-d$_6$) δ ppm 11.69 (s, 1H), 11.38-11.19 (m, 1H), 8.56-8.55 (m, 2H), 8.02 (s, 1H), 7.78 (d, J = 8.6 Hz, 1H), 7.55-7.45 (m, 4H), 7.46 (s, 1H), 7.40-7.15 (m, 4H), 7.10-6.95 (m, 2H), 6.73 (s, 2H), 6.69-6.65 (m, 1H), 6.37 (s, 1H), 6.14 (s, 1H), 4.24 (s, 1H), 3.69 (s, 5H), 3.28 (s, 3H), 3.05-2.85 (m, 8H), 2.02-1.99 (m, 1H), 1.75-1.59 (m, 5H), 1.56-1.50 (m, 2H), 1.40-1.05 (m, 27H). MS (ESI, m/e) [M + 1]$^+$ 1052.1 |
| 273 | 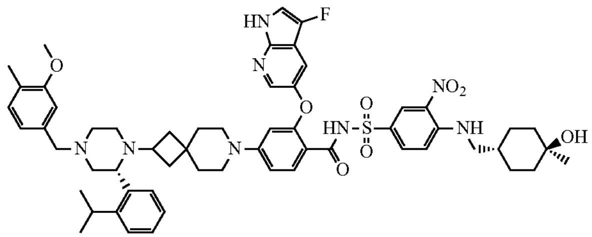 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)ccc1C] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((R)-2-(2-isopropylphenyl)-4-(3-methoxy-4-methylbenzyl)piperazin-1-yl)-7-azaspiro[3.5]nonan-7-yl)benzamide | $^1$H NMR (400 MHz, DMSO-d$_6$) δ ppm 11.51 (s, 1H), 11.24 (s, 1H), 8.59-8.56 (m, 2H), 8.09-8.0 (m, 1H), 7.78 (d, J = 9.0 Hz, 1H), 7.53-7.40 (m, 3H), 7.40-7.15 (m, 4H), 7.09-7.05 (m, 2H), 6.95-6.80 (m, 1H), 6.68 (d, J = 8.8 Hz, 1H), 6.25-6.20 (m, 1H), 4.25 (s, 1H), 4.10 (m, 1H), 3.85-3.74 (m, 4H), 3.59 (s, 1H), 3.39 (s, 1H), 3.29-3.20 (m, 2H), 3.22-3.13 (m, 1H), 3.05-2.85 (m, 7H), 2.80-2.65 (m, 1H), 2.18-2.02 (m, 4H), 1.72-1.50 (m, 7H), 142-0.97 (m, 19H). MS (ESI, m/e) [M + 1]$^+$ 1058.0. |
| 274 | 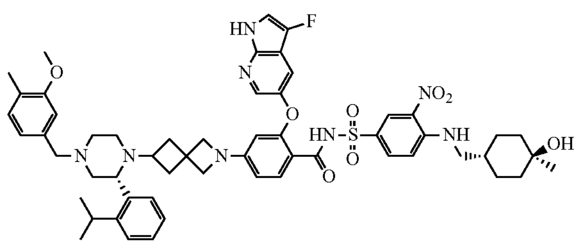 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1C] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-methylbenzyl)piperazin-1-yl)-2-azaspiro[3.3]heptan-2-yl)benzamide | $^1$H NMR (400 MHz, DMSO-d$_6$) δ ppm 11.55 (s, 1H), 11.45-11.04 (m, 1H), 8.59-8.50 (m, 2H), 8.08 (d, J = 2.2 Hz, 1H), 7.81 (d, J = 9.0 Hz, 1H), 7.51 (s, 2H), 7.45-7.40 (m, 2H), 7.25 (s, 2H), 7.18-7.05 (m, 3H), 6.87 (s, 1H), 6.06 (d, J = 8.8 Hz, 1H), 5.52 (s, 1H), 4.24 (s, 1H), 3.78 (s, 3H), 3.65-3.52 (m, 5H), 3.29-3.26 (m, 2H), 2.97 (s, 3H), 2.74 (s, 2H), 2.33 (s, 1H), 2.11 (s, 3H), 1.99 (s, 2H), 1.75-1.50 (m, 6H), 1.39-0.98 (m, 17H). MS (ESI, m/e) [M + 1]$^+$ 1030.1 |
| 275 | 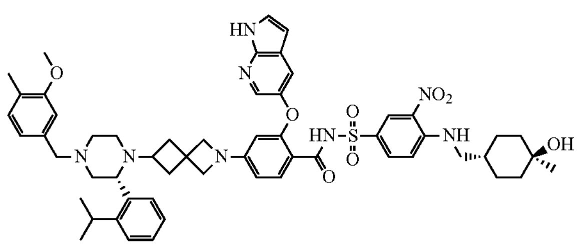 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)ccc1C] | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-methylbenzyl)piperazin-1-yl)-2-azaspiro[3.3]heptan-2-yl)benzamide | $^1$H NMR (400 MHz, DMSO-d$_6$) δ ppm: 11.73 (s 1H), 11.29 (s, 1H), 8.59-8.56 (m, 2H), 8.03 (d, J = 4.0 Hz 1H), 7.83-7.81 (m, 1H), 7.59-7.58 (m, 1H), 7.52-7.51 (m, 1H), 7.45-7.40 (m, 2H), 7.25-7.20 (m, 6H), 6.87 (s, 1H), 6.40-6.39 (m, 1H), 6.04 (d, J = 8.0 Hz 1H), 5.49 (s, 1H), 4.26 (s, 1H), 3.95 (s, 1H), 3.77 (s, 3H), 3.63-3.46 (m, 5H), 3.30-3.27 (m, 3H), 3.09-2.94 (m, 2H), 2.74-2.72 (m, 2H), 2.51-2.50 (m, 3H), 2.11 (s, 1H), 1.98-1.96 (m, 2H), 1.69-1.52 (m, 6H), 1.36-1.08 (m, 16H). MS (ESI, m/e) [M + 1]$^+$ 1012.1 |

| Ex. | structure | Compound name | Data |
|---|---|---|---|
| 276 | 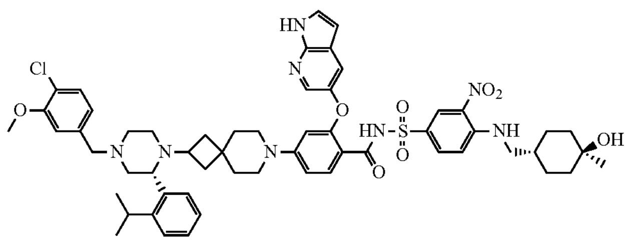 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1Cl] | 2-((1H-pyrrolo[2,3-b]pyridin-5-yl)oxy)-4-(2-((R)-4-(4-chloro-3-methoxybenzyl)-2-(2-isopropylphenyl)piperazin-1-yl)-7-azaspiro[3.5]nonan-7-yl)-N-(4-(((1r,4r)-4-hydroxy-4-methylcyclohexyl)amino)-3-nitrophenyl)sulfonyl)benzamide | $^1$H NMR (400 MHz, DMSO-d$^6$) δ ppm: 11.69 (s, 1H), 11.40 (br, 1H), 8.62-8.49 (m, 2H), 8.02 (s, 1H), 7.79-7.73 (m, 1H), 7.54-6.89 (m, 11H), 6.68-6.63 (m, 1H), 6.37 (s, 1H), 6.18-6.12 (m, 1H), 4.24 (s, 1H), 3.83 (s, 3H), 3.80-3.60 (m, 2H), 3.47-3.35 (m, 2H), 3.31-3.17 (m, 3H), 3.09-2.65 (m, 10H), 2.12-1.95 (m, 2H), 1.73-1.45 (m, 7H), 1.39-1.25 (m 5H), 1.20-1.00 (m, 12H). MS (ESI, m/e) [M + I]$^+$ 1060.1. |
| 277 | 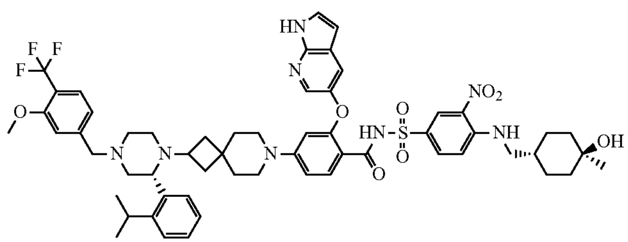 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1C(F)(F)F] | 2-((1H-pyrrolo[2,3-b]pyridin-5-yl)oxy)-N-((((1r,4r)-4-hydroxy-4-methylcyclohexyl)amino)-3-nitrophenyl)sulfonyl)-4-(2-((R)-2-(2-isopropylphenyl)benzyl)piperazin-1-yl)-4-(trifluoromethyl)benzyl)piperazin-1-yl)-7-azaspiro[3.5]nonan-7-yl)benzamide | $^1$H NMR (400 MHz, DMSO-d$_6$) δ ppm: 11.69 (s, 1H), 11.41 (br, 1H), 8.62-8.47 (m, 2H), 8.02 (s, 1H), 7.79-7.73 (m, 1H), 7.59-7.03 (m, 11H), 6.68-6.3 (m, 1H), 6.37 (s, 1H), 6.17-6.13 (m, 1H), 4.24 (s, 1H), 3.87 (s, 3H), 3.80-3.68 (m, 2H), 3.47-3.38 (m, 2H), 3.31-3.17 (m, 3H), 3.09-2.65 (m, 10H), 2.13-1.96 (m, 2H), 1.73-1.45 (m, 7H), 1.39-1.25 (m, 7H), 1.20-1.00 (m, 10H). MS (ESI, m/e) [M + I]$^+$ 1094.2. |
| 278 | 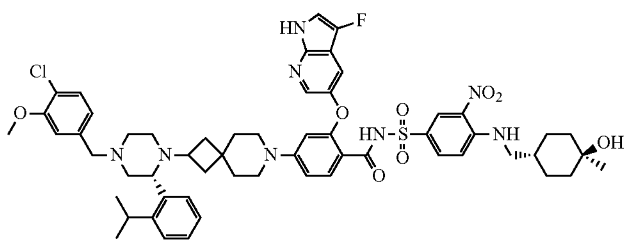 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)ccc1Cl] | 4-(2-((R)-4-(4-chloro-3-methoxybenzyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-((((1r,4r)-4-hydroxy-4-methylcyclohexyl)amino)-3-nitrophenyl)sulfonyl)benzamide | $^1$H NMR (400 MHz, DMSO-d$_6$) δ ppm: 11.51 (s, 1H), 11.42 (br, 1H), 8.60-8.51 (m, 2H), 8.05 (s, 1H), 7.54-6.89 (m, 11H), 6.72-6.64 (m, 1H), 6.25-6.17 (m, 1H), 4.25 (s, 1H), 3.84 (s, 3H), 3.80-3.60 (m, 2H), 3.49-3.35 (m, 2H), 3.31-3.25 (m, 3H), 3.20-2.65 (m, 10H), 2.20-1.96 (m, 2H), 1.75-1.45 (m, 7H), 1.39-1.25 (m, 6H), 1.20-1.00 (m, 1H) MS (ESI, m/e) [M + 1]$^+$ 1078.0. |
| 279 | 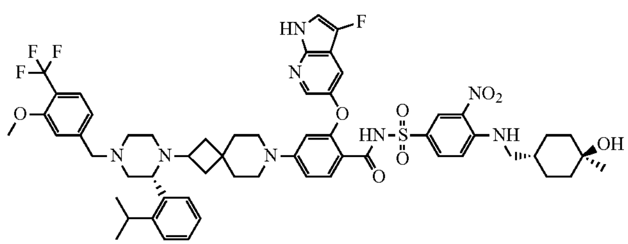 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)ccc1C(F)(F)F] | 2-((3-fluoro-1H-pyrrolo[2,3-b]pyridin-5-yl)oxy)-N-((4-((((1r,4r)-4-hydroxy-4-methylcyclohexyl)amino)-3-nitrophenyl)sulfonyl)-4-(2-((R)-2-(2-isopropylphenyl)benzyl)piperazin-1-yl)-7-azaspiro[3.5]nonan-7-yl)benzamide | $^1$H NMR (400 MHz, DMSO-d$_6$) δ ppm: 11.51 (s, 1H), 11.49 (br, 1H), 8.59-8.51 (m, 2H), 8.06 (s, 1H), 7.58-7.04 (m, 11H), 6.69-6.65 (m, 1H), 6.25-6.17 (m, 1H), 4.25 (s, 1H), 3.87 (s, 3H), 3.81-3.68 (m, 2H), 3.47-3.37 (m, 2H), 3.31-3.17 (m, 3H), 3.09-2.65 (m, 10H), 2.19-1.95 (m, 2H), 1.73-1.45 (m, 7H), 1.39-1.25 (m 6H), 1.20-1.00 (m, 11H), MS (ESI, m/e) [M + I]$^+$ 1112.1. |

| Ex. | structure | Compound name | Data |
|---|---|---|---|
| 280 | 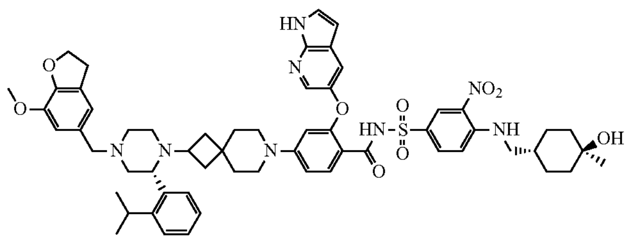 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc2c1OCC2] | 2-((1H-pyrrolo[2,3-b]pyridin-5-yl)oxy)-N-((4-((1r,4r)-4-hydroxy-4-methylcyclohexyl)methyl)amino)-3-nitrophenyl)sulfonyl)-4-(2-((R)-2-(2-isopropylphenyl)-4-((7-methoxybenzofuran-5-yl)methyl)piperazin-1-yl)-7-azaspiro[3.5]nonan-7-yl)benzamide | $^1$H NMR (400 MHz, DMSO-$d_6$) δ ppm: 11.69 (s, 1H), 8.59-8.48 (m, 2H), 8.03 (d, J = 2.8 Hz, 1H), 7.94 (d, J = 2.0 Hz, 1H), 7.78 (dd, J = 2.0 Hz, 9.2 Hz, 1H), 7.61-7.39 (m, 4H), 7.28-7.09 (m, 4H), 7.06-6.95 (m, 2H), 6.89 (d, J = 2.0 Hz, 1H), 6.64 (d, J = 8.4 Hz, 1H), 6.40-6.33 (m, 1H), 6.16 (s, 1H), 4.29 (s, 1H), 3.92 (s, 3H), 3.81-3.71 (m, 2H), 3.32-3.20 (m, 4H), 3.12-2.81 (m, 7H), 2.77-2.67 (m, 1H), 2.61-2.52 (m, 1H), 2.46-2.31 (m, 1H), 1.85-1.48 (m, 7H), 1.43-0.84 (tis, 20H). MS (ESI, m/e) [M + 1]$^+$ 1066.2 |
| 281 | 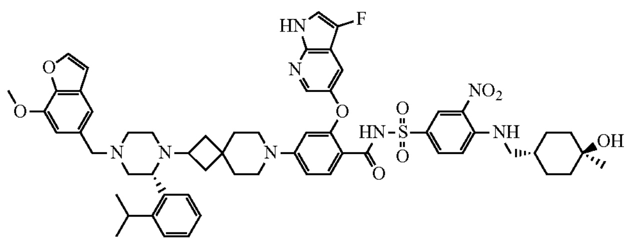 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)cc2ccoc12] | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(2-((R)-2-(2-isopropylphenyl)-4-((7-methoxybenzofuran-5-yl)methyl)piperazin-1-yl)-7-azaspiro[3.5]nonan-7-yl)benzamide | $^1$H NMR (400 MHz, DMSO-$d_6$) δ ppm: 11.48 (s, 1H), 8.58-8.44 (m, 2H), 8.04 (d, J = 2.0 Hz, 1H), 7.94 (d, J = 2.0 Hz, 1H), 7.75 (d, J = 13.2 Hz, 1H), 7.51-7.36 (m, 4H), 7.31-7.09 (m, 4H), 7.07-6.86 (m, 3H), 6.67 (d, J = 7.6 Hz, 1H), 6.22 (s, 1H), 4.26 (s, 1H), 3.92 (s, 3H), 3.88-3.67 (m, 2H), 3.31-3.20 (m, 4H), 3.12-2.86 (m, 7H), 2.81-2.61 (m, 2H), 2.47-2.32 (m, 1H), 1.78-1.48 (m, 7H), 1.41-0.96 (m, 20H). MS (ESI, m/e) [M + 1]$^+$ 1084.1 |
| 282 | 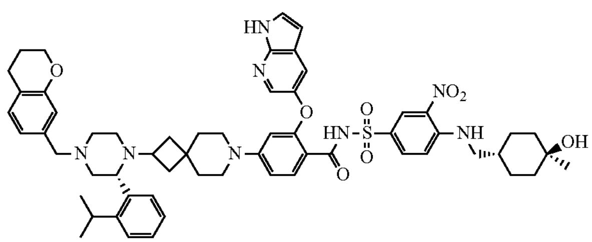 [SMILES: CC(C)c1ccccc1[C@@H]1CN(Cc2ccc3c(c2)OCCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-(R)-4-(chroman-7-ylmethyl)-2-(2-isopropylphenyl)piperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.69 (s, 1H), 11.52-11.22 (m, 1H), 8.58-8.55 (m, 2H), 8.03 (s, 1H), 7.79 (s, 1H), 7.56-7.33 (m, 4H), 7.30-6.91 (m, 4H), 6.90-6.64 (m, 3H), 6.37 (s, 1H), 6.13 (s, 1H), 4.10 (s, 2H), 3.77 (s, 1H), 3.53 (s, 1H), 3.28 (s, 2H), 3.05-2.85 (m 7H), 2.70 (s, 3H), 2.04 (s, 1H), 1.88 (s, 2H), 1.77-1.48 (m, 7H), 1.44-1.00 (m, 20H). MS (ESI, m/e) [M + 1]$^+$ 1052.0 |
| 283 | 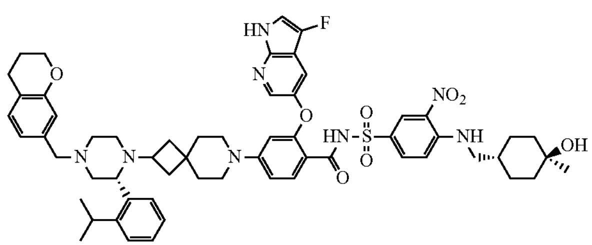 [SMILES: CC(C)c1ccccc1[C@@H]1CN(Cc2ccc3c(c2)OCCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]cc(F)c5c4)c3)CC2)C1] | 4-(2-((R)-4-(chroman-7-ylmethyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide | $^1$H NMR (400 MHz, DMSO-$d_6$) δ ppm: 11.50 (s, 1H), 8.55-8.52 (m, 2H), 8.05 (s, 1H), 7.76 (d, J = 9.0 Hz, 1H), 7.51-7.35 (m, 4H), 7.25 (s, 2H), 7.15-6.95 (m, 2H), 6.75 (s, 2H), 6.67 (d, J = 8.4 Hz, 1H), 6.20 (s, 1H), 4.25 (s, 1H), 4.09 (s, 2H), 3.53 (s, 1H), 3.40 (s, 1H), 3.29-3.21 (m, 2H), 3.05-2.85 (m, 8H), 2.70 (s, 3H), 2.03 (s, 1H), 1.88 (s, 2H), 1.72-1.50 (m, 7H), 1.43-1.00 (m, 22H). MS (ESI, m/e) [M + 1]$^+$ 1069.9. |

-continued

| Ex. | structure | Compound name | Data |
|---|---|---|---|
| 284 | 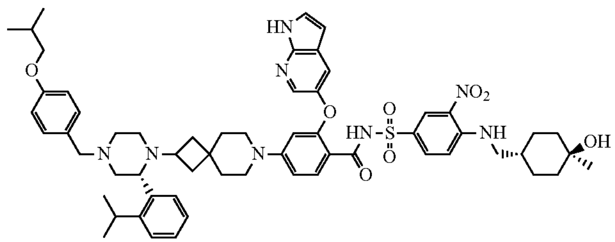 [SMILES: CC(C)COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc1] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R)-4-(4-isobutoxybenzyl)-2-isopropylphenyl)piperazin-1-yl)-7-azaspiro[3.5]nonan-7-yl)benzamide | $^1$H NMR (400 MHz, DMSO-d$_6$) δ ppm: 11.69 (s, 1H), 11.53-11.21 (m, 1H), 8.57-8.54 (m, 2H), 8.02 (s, 1H), 7.78 (d, J = 9.0 Hz, 1H), 7.54-7.44 (m, 3H), 7.45-7.15 (m, 5H), 7.10-6.95 (m, 1H), 6.96-6.84 (m, 2H), 6.68-6.62 (m, 1H), 6.37 (s, 1H), 6.15-6.12 (m, 1H), 4.25 (s, 1H), 3.76-3.70 (m, 2H), 3.55 (s, 1H), 3.39 (s, 1H), 3.29-3.20 (m, 3H), 3.05-2.85 (m, 8H), 1.99 (s, 2H), 1.75-1.50 (m, 7H), 1.38-1.00 (m, 21H), 0.96 (d, J = 6.6 Hz, 6H). MS (ESI, m/e) [M + 1]$^+$ 1068.1. |
| 285 | 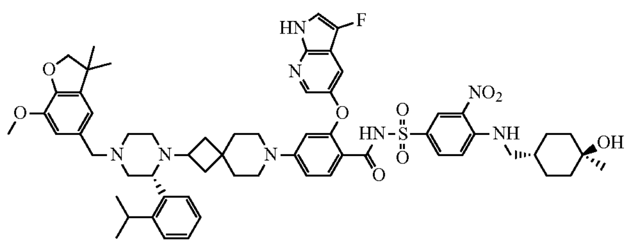 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)cc2c1OCC2(C)C] | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R)-2-(2-isopropylphenyl)-4-((7-methoxy-3,3-dimethyl-2,3-dihydrobenzofuran-5-yl)methyl)piperazin-1-yl)-7-azaspiro[3.5]nonan-7-yl)benzamide | $^1$H NMR (400 MHz, DMSO-d$_6$) δ ppm: 11.51 (s, 1H), 11.26 (s, 1H), 8.62-8.46 (m, 2H), 8.10-7.91 (m, 1H), 7.82-7.70 (m, 1H), 7.52-7.39 (m, 4H), 7.39-6.83 (m, 6H), 6.83-6.57 (m, 2H), 6.29-6.11 (m, 1H), 4.25 (s, 1H), 4.24-4.13 (m, 2H), 4.12-3.85 (m, 1H), 3.81-3.69 (m, 3H), 3.64-3.36 (m, 2H), 3.32-3.13 (m, 5H), 3.13-2.86 (m, 7H), 2.82-2.57 (m, 2H), 2.21-1.97 (m, 1H), 1.78-1.46 (m, 7H), 1.42-1.26 (m, 6H), 1.23-0.95 (m, 17H). MS (ESI, m/e) [M + 1]$^+$ 1114.2 |
| 286 | 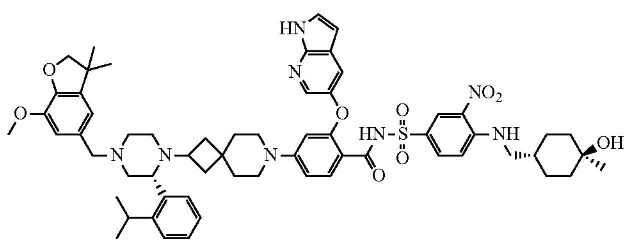 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc2c1OCC2(C)C] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R)-2-(2-isopropylphenyl)-4-((7-methoxy-3,3-dimethyl-2,3-dihydrobenzofuran-5-yl)methyl)piperazin-1-yl)-7-azaspiro[3.5]nonan-7-yl)benzamide | $^1$H NMR (400MHz, DMSO-d$_6$) δ ppm: 11.69 (s, 1H), 11.33 (s, 1H), 8.66-8.42 (m, 2H), 8.12-7.88 (m, 1H), 7.82-7.73 (m, 1H), 7.61-6.82 (m, 11H), 6.79-6.55 (m, 2H), 6.37 (s, 1H), 6.22-6.07 (m, 1H), 4.25 (s, 1H), 4.24-4.15 (m, 2H), 4.07-3.86 (m, 1H), 3.86-3.67 (m, 4H), 3.63-3.38 (m, 2H), 3.31-3.15 (m, 5I-1), 3.10-2.78 (m, 9H), 2.77-2.55 (m, 2H), 2.07-1.94 (m, 1H), 1.76-1.47 (m, 8H), 1.41-1.27 (m, 6H), 1.17-0.91 (m, 13H). MS (ESI, m/e) [M + 1]$^+$ 1096.1 |
| 287 | 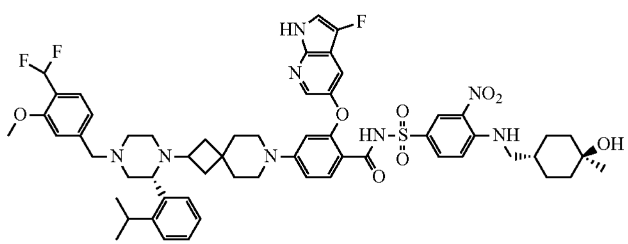 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(F)c7c6)c5)CC4)C3)[C@H](c3ccccc3C(C)C)C2)ccc1C(F)F] | 4-(2-((R)-4-(4-(difluoromethyl)-3-methoxybenzyl-2-(2-isopropylphenyl) piperazin-1-yl)-7-azaspiro[3.5]nonan-7-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.50 (s, 1H), 11.47 (br, 1H), 8.59-8.51 (m, 1H), 8.06 (s, 1H), 7.79-7.73 (m, 1H), 7.52-7.02 (m, 11H), 6.68-6.65 (m, 1H), 6.23-6.17 (m, 1H), 4.24 (s, 1H), 3.83 (s, 3H), 3.73-3.68 (m, 1H), 3.47-3.35 (m, 1H), 3.31-3.17 (m, 3H), 3.09-2.60 (m, 9H), 2.35-2.20 (m, 1H), 2.12-1.95 (m, 2H), 1.74-1.52 (m, 6H), 1.39-1.22 (m, 11H), 1.20-1.00 (m, 10H). MS (ESI, m/e) [M + 1]$^+$ 1094.2. |

| Ex. | structure | Compound name | Data |
|---|---|---|---|
| 288 | 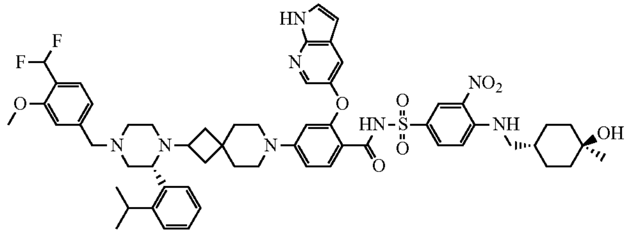 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1C(F)F] | 2-((1H-pyrrolo[2,3-b]pyridin-5-yl)oxy)-4-(2-((R)-4-(4-(difluoromethyl)-3-methoxybenzyl)-2-(2-isopropylphenyl) piperazin-1-yl)-7-azaspiro[3.5]nonan-7-yl)-N-(4-((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.39 (br, 1H), 8.61-8.52 (m, 2H), 8.02 (s, 1H), 7.83-7.75 (m, 1H), 7.55-7.00 (m, 11H), 6.68-6.62 (m, 1H), 6.37 (m, 1H), 6.18-6.10 (m, 1H), 4.25 (s, 1H), 3.83 (s, 3H), 3.73-3.68 (m, 1H), 3.47-3.35 (m, 1H), 3.31-3.17 (m, 3H), 3.09-2.60 (m, 9H), 2.42-2.20 (m, 1H), 2.12-1.95 (m, 2H), 1.74-1.52 (m, 6H), 1.39-1.22 (m, 12H), 1.20-1.00 (m, 9H). MS (ESI, m/e) [M + 1]$^+$ 1076.1. |
| 289 | 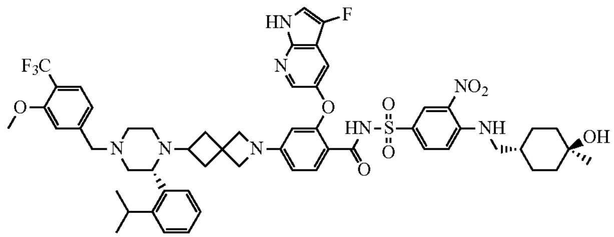 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1C(F)(F)F] | 2-(3-fluoro-1H-pyrrolo[2,3-b]pyridin-5-yl)oxy)-N-(4-(((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(trifluoromethyl)benzyl)piperazin-1-yl)-2-azaspiro[3.3]heptan-2-yl)benzamide | $^1$H NMR (400 MHz, DMSO-d$_6$) δ ppm: 11.55 (s, 1H), 11.35 (br, 1H), 8.60-8.54 (m, 2H), 8.08 (s, 1H), 7.84-7.78 (m, 1H), 7.58-7.50 (m, 3H), 7.46-7.03 (m, 8H), 6.13-6.06 (m, 1H), 5.54 (s, 1H), 4.24 (s, 1H), 3.86 (s, 3H), 3.73-3.44 (m, 7H), 3.31-3.19 (m, 3H), 2.87-2.55 (m, 4H), 2.35-2.20 (m, 1H), 2.12-1.95 (m, 2H), 1.74-1.52 (m, 6H), 1.39-1.22 (m, 9H), 1.20-1.00 (m, 7H). MS (ESI, m/e) [M + 1]$^+$ 1084.1. |
| 290 | 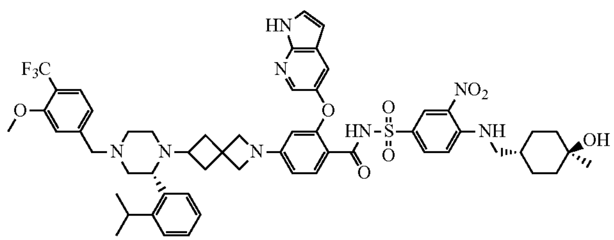 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)ccc1C(F)(F)F] | 2-(1H-pyrrolo[2,3-b]pyridin-5-yl)oxy)-N-(4-(((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(trifluoromethyl)benzyl)piperazin-1-yl)-2-azaspiro[3.3]heptan-2-yl)benzamide | $^1$H NMR (400 MHz, DMSO-d$_6$) δ ppm: 11.73 (s, 1H), 11.28 (br, 1H), 8.62-8.58 (m, 2H), 8.04 (s, 1H), 7.86-7.82 (m, 1H), 7.62-7.52 (m, 3H), 7.47-7.03 (m, 8H), 6.44-6.38 (m, 1H), 6.07-6.04 (m, 1H), 5.49 (s, 1H), 4.25 (s, 1H), 3.86 (s, 3H), 3.73-3.44 (m, 7H), 3.31-3.19 (m, 3H), 2.89-2.54 (m, 4H), 2.35-2.20 (m, 1H), 2.09-1.93 (m, 2H), 1.74-1.52 (m, 6H), 1.39-1.22 (m, 9H), 1.20-1.00 (m, 7H). MS (ESI, m/e) [M+1]$^+$ 1066.2. |
| 291 | 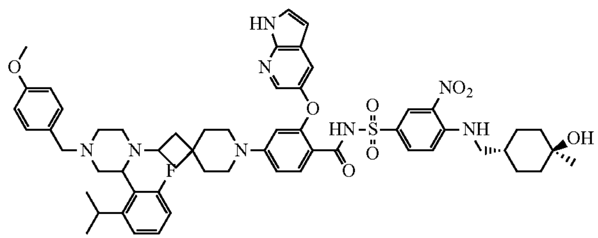 | 2-(1H-pyrrolo[2,3-b]pyridin-5-yl)oxy)-4-(2-(2-(2-fluoro-6-isopropylphenyl)-4-(4-methoxybenzyl)piperazin-1-yl)-7-azaspiro[3.5]nonan-7-yl)-N-(4-((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.51-11.18 (m, 1H), 8.56 (d, J = 7.6 Hz, 2H), 8.02 (s, 1H), 7.79-7.75 (m, 1H), 7.54-7.44 (m, 3H), 7.30-7.20 (m, 3H), 7.16 (s, 1H), 7.08 (d, J = 9.4 Hz, 1H), 6.94 (s, 3H), 6.65 (d, J = 8.2 Hz, 1H), 6.37 (s, 1H), 6.13 (s, 1H), 4.25 (s, 1H), 3.83-3.70 (m, 3H), 3.28-3.25 (m, 2H), 3.05-2.85 (m, 8H), 2.04-1.97 (m, 1H), 1.75-1.50 (m, 7H), 1.39-1.20 (m, 15H), 1.12-1.0 (m, 9H). MS (ESI, m/e) [M + 1]$^+$ 1044.0 |

-continued

| Ex. | structure | Compound name | Data |
|---|---|---|---|
| 292 | 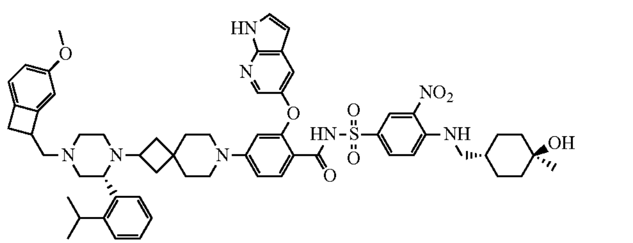 [SMILES: COc1ccc2c(c1)C(CN1CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C1)C2] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((2R)-2-isopropylphenyl)-4-(((4-methoxybicyclo[4.2.0]octa-1,3,5-trien-7-yl)methyl)piperazin-1-yl)-7-azaspiro[3.5]nonan-7-yl)benzamide | $^1$H NMR (400 MHz, DMSO-d$_6$) δ ppm 11.69 (s, 1H), 11.49-11.03 (m, 1H), 8.58-8.56 (m, 2H), 8.02 (s, 1H), 7.78 (d, J = 8.4 Hz, 1H), 7.55-7.42 (m, 3H), 7.35-7.20 (m, 3H), 7.11-6.95 (m, 2H), 6.80-6.60 (m, 3H), 6.38 (s, 1H), 6.14 (s, 1H), 4.25 (s, 1H), 3.69 (s, 5H), 3.43 (s, 1H), 3.30-3.25 (m, 3H), 3.05-2.85 (m, 10H), 2.73 (s, 1H), 2.06 (s, 1H), 1.75-1.50 (m, 7H), 1.30-1.0 (m, 21H). MS (ESI, m/e) [M + 1]$^+$ 1052.1. |
| 293 | 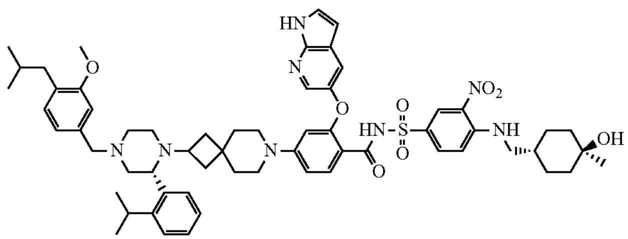 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1CC(C)C] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(2-((R)-4-(4-isobutyl-3-methoxybenzyl)piperazin-1-yl)-7-azaspiro[3.5]nonan-7-yl)benzamide | $^1$H NMR (400 MHz, DMSO-d$_6$) δ ppm: 11.69 (s, 1H), 11.51-11.24 (m, 1H), 8.58-8.56 (m, 3H), 8.02 (s, 1H), 7.78 (d, J = 8.4 Hz, 2H), 7.54-7.40 (m, 3H), 7.35 (s, 1H), 7.30-7.15 (m, 2H), 7.08 (d, J = 9.0 Hz, 1H), 6.90-6.80 (m, 3H), 6.65 (d, J = 8.6 Hz, 2H), 6.37 (s, 1H), 6.13 (s, 1H), 4.25 (s, 1H), 3.80-3.75 (m, 3H), 3.62-3.55 (m, 1H), 3.30-3.27 (s, 2H), 3.05-2.85 (m, 7H), 2.67 (s, 1H), 2.39 (s, 2H), 2.08-1.94 (m, 1H), 1.82 (s, 1H), 1.75-1.50 (m, 6H), 1.35-1.0 (m, 22H), 0.85-0.78 (m, 7H). MS (ESI, live) [M + 1]$^+$ 1082.1. |
| 294 | 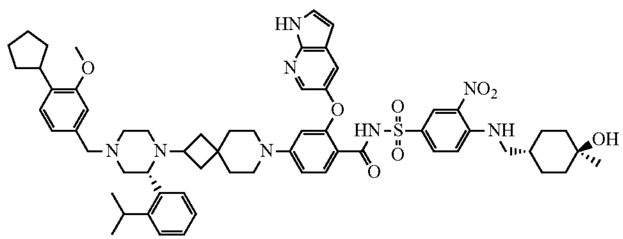 [SMILES: COc1cc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)ccc1C1CCCC1] | 2-((1H-pyrrolo[2,3-b]pyridin-5-yl)oxy)-4-(2-(R)-4-(4-cyclopentyl-3-methoxybenzyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.69 (s, 1H), 11.35 (s, 1H), 8.57-8.55 (m, 2H), 8.02 (s, 1H), 7.91-7.73 (m, 1H), 7.50-7.48 (m, 3H), 7.37-7.03 (m, 3H), 6.87-6.84 (m, 2H), 6.65 (d, J = 9.0 Hz, 1H), 6.37 (s, 1H), 6.13 (s, 1H), 4.25 (s, 1H), 3.79-3.75 (m, 4H), 3.59 (s, 1H), 3.39 (s, 1H), 3.28 (s, 4H), 3.05-2.85 (m, 7H), 2.05 (s, 1H), 1.88 (s, 2H), 1.79-1.39 (m, 14H), 1.38-1.01 (m, 20H). MS (ESI, m/e) [M +1]$^+$ 1094.1. |
| 295 | 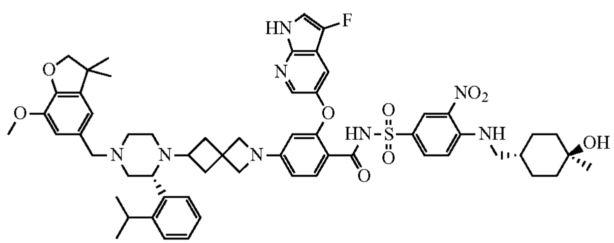 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2c1OCC2(C)C] | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((7-methoxy-3,3-dimethyl-2,3-dihydrobenzofuran-5-yl)methyl)piperazin-1-yl)-2-azaspiro[3.3]heptan-2-yl)benzamide | $^1$H NMR (400 MHz, DMSO-d$_6$) δ ppm: 11.56 (s, 1H), 11.39 (br, 1H), 8.63-8.54 (m, 2H), 8.08 (s, 1H), 7.85-7.77 (m, 1H), 7.58-6.71 (m, 10H), 6.09-6.03 (m, 1H), 5.52 (s, 1H), 4.27-3.82 (m, 4H), 3.73 (s, 3H), 3.70-3.35 (m, 7H), 3.31-3.17 (m, 3H), 3.09-2.60 (m, 6H), 2.47-2.30 (m, 1H), 2.05-1.95 (m, 2H), 1.74-1.52 (m, 6H), 1.39-1.22 (m, 14H), 1.20-1.00 (m, 6H). MS (ESI, m/e) [M + 1]$^+$ 1086.1. |

| Ex. | structure | Compound name | Data |
|---|---|---|---|
| 296 | 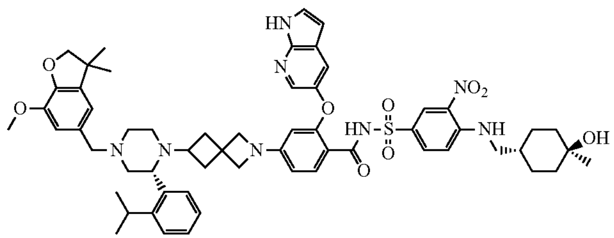 | 2-((H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropylphenyl)-4-((7-methoxy-3,3-dimethyl-2,3-dihydrobenzofuran-5-yl)methyl)piperazin-1-yl)-2-azaspiro[3.3]heptan-2-yl]benzamide | ¹H NMR (400 MHz, DMSO-d₆) δ ppm: 11.73 (s, 1H), 11.30 (br, 1H), 8.63-8.57 (m, 2H), 8.04 (s, 1H), 7.85-7.77 (m, 1H), 7.62-6.71 (m, 10H), 6.43-6.38 (m, 1H), 6.06-6.03 (m, 1H), 5.47 (s, 1H), 4.27-3.75 (m, 4H), 3.72 (s, 3H), 3.70-3.35 (m, 7H), 3.31-3.17 (m, 3H), 3.09-2.60 (m, 6H), 2.47-2.31 (m, 1H), 2.05-1.95 (m, 2H), 1.74-1.52 (m, 6H), 1.39-1.22 (m 14H), 1.20-1.00 (m, 6H). MS (ESI, m/e) [M + 1]⁺ 1068,1. |
| 297 | 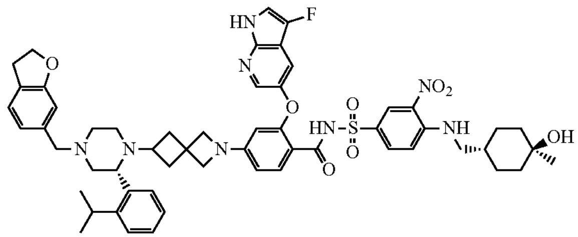 [SMILES: CC(C)c1ccccc1[C@@H]1CN(Cc2ccc3c(c2)OCC3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 4-(6-((R)-4-((2,3-dihydrobenzofuran-6-yl)methyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.55 (s, 1H), 11.50 (br, 1H), 8.61-8.57 (m, 2H), 8.08 (s, 1H), 7.83-7.79 (m, 1H), 7.58-7.05 (m, 9H), 6.87-6.64 (m, 2H), 6.06-6.03 (m, 1H), 5.52 (s, 1H), 4.52-4.48 (m, 2H), 4.24 (s, 1H), 3.73-3.44 (m, 6H), 3.31-3,19 (m, 3H), 3.17-2.55 (m, 7H), 2.35-2.20 (m, 1H), 2.06-1.95 (m, 2H), 1.74-1.52 (m, 6H), 1.39-1.22 (m, 8H), 1.20-1.00 (m, 8H). MS (ESI, m/e) [M + 1]⁺ 1027.9. |
| 298 | 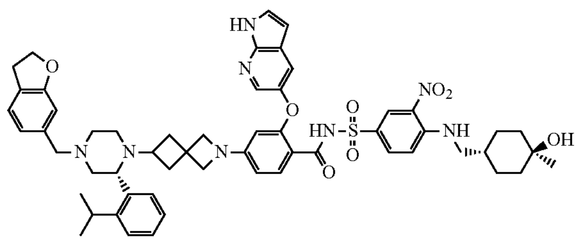 [SMILES: CC(C)c1ccccc1[C@@H]1CN(Cc2ccc3c(c2)OCC3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]ccc4c3)c1)C2] | 2-((1H-pyrrolo[2,3-b]pyridin-5-yl)oxy)-4-(6-((R)-4-((2,3-dihydrobenzofuran-6-yl)methyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.73 (s, 1H), 11.26 (br, 1H), 8.61-8.56 (m, 2H), 8.04 (s, 1H), 7.85-7.79 (m, 1H), 7.61-7.10 (m, 9H), 6.92-6.70 (m, 2H), 6.45-6.38 (m, 1H), 6.06-6.03 (m, 1H), 5.47 (s, 1H), 4.57-4.46 (m, 2H), 4.25 (s, 1H), 3.70-3,45 (m, 6H), 3.31-3.19 (m, 3H), 3.18-2.55 (m, 7H), 2.35-2.20 (m, 1H), 2.06-1.95 (m, 2H), 1.74-1.52 (m, 6H), 1.39-1.22 (m, 8H), 1.20-1.00 (m, 8H). MS (ESI, m/e) [M + 1]⁺ 1010.0. |
| 299 | 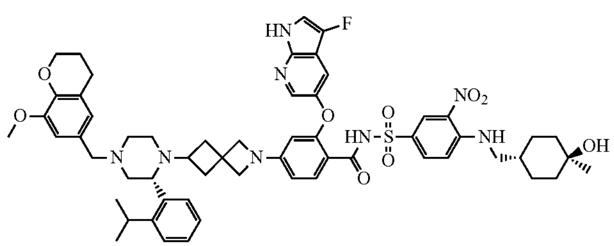 | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((R)-2-(2-isopropylphenyl)-4-((8-methoxychroman-6-yl)methyl)piperazin-1-yl)-7-azaspiro[3.5]nonan-7-yl)benzamide | ¹H NMR (400 MHz, DMSO-d₆) δ ppm: 11.50 (s, 1H), 8.59-8.46 (m, 2H), 8.05 (d, J = 2.4 Hz, 1H), 7.76 (d, J = 8.4 Hz, 1H), 7.55-7.39 (m, 4H), 7.27 (s, 3H), 7.05 (d, J = 9.0 Hz, 1H), 6.67 (d, J = 8.4 Hz, 2H), 6.21 (s, 1H), 4.25 (s, 2H), 4.09 (s, 2H), 3.88 (s, 1H), 3.70 (s, 3H), 3.28 (s, 3H), 3.05-2.85 (m, 8H), 2.67 (s, 3H), 2.39 (s, 1H), 1.86 (s, 2H), 1.75-1.50 (m, 7H), 1.38-0.98 (m, 22H). MS (ESI, m/e) [M + 1]⁺ 1100.0 |

| Ex. | Compound name | Data |
|---|---|---|
| 300 | 4-(2-((R)-4-((4,4-dimethylchroman-7-yl)methyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.51 (s, 1H), 10.93 (s, 0H), 8.57-8.50 (m, 2H), 8.05 (d, J = 2.4 Hz, 1H), 7.77 (d, J = 8.4 Hz, 1H), 7.60-7.20 (m, 8H), 7.06 (d, J = 9.2 Hz, 1H), 6.85-6.75 (m, 1H), 6.67 (d, J = 8.2 Hz, 1H), 6.20 (s, 1H), 4.26 (s, 1H), 4.11 (s, 2H), 3.76 (s, 1H), 3.51 (s, 1H), 3.28 (s, 3H), 3.05-2.85 (m, 7H), 2.73 (s, 2H), 2.13-1.96 (m, 1H), 1.78-1.49 (m, 10H), 1.40-1.05 (m, 28H). MS (ESI, m/e) [M + 1]⁺ 1097.9. |
| 301 | 2-((1H-pyrrolo[2,3-b]pyridin-5-yl)oxy)-4-(2-((R)-4-((4,4-dimethylchroman-7-yl)methyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.69 (s, 1H), 11.26 (s, 1H), 8.59-8.49 (m, 2H), 8.02 (d, J = 2.4 Hz, 1H), 7.78 (d, J = 9.4 Hz, 1H), 7.51-7.41 (m, 3H), 7.30-7.20 (m, 4H), 7.06 (d, J = 9.4 Hz, 1H), 6.65 (d, J = 8.2 Hz, 3H), 6.37 (s, 1H), 6.14 (s, 1H), 4.26 (s, 2H), 4.10 (s, 2H), 3.76 (s, 1H), 3.30-3.21 (m, 3H), 3.05-2.85 (m, 7H), 2.74-2.65 (m, 2H), 2.08 (s, 1H), 1.80-1.48 (m, 9H), 1.39-0.96 (m, 28H). MS (ESI, m/e) [M + 1]⁺ 1079.9 |
| 302 | 2-((1H-pyrrolo[2,3-b]pyridin-5-yl)oxy)-N-(((1r,4r)-4-hydroxy-4-methylcyclohexyl)methyl)amino)-3-nitrophenyl)sulfonyl)-4-(2-((R)-2-(2-isopropylphenyl)-4-((8-methoxychroman-6-yl)methyl)piperazin-1-yl)-7-azaspiro[3.5]nonan-7-yl)benzamide | ¹H NMR (400 MHz, DMSO-d₆) δ ppm: 11.68 (s, 1H), 8.56-8.53 (m, 2H), 8.01 (s, 1H), 7.77 (d, J = 9.4 Hz, 1H), 7.49-7.40 (m, 3H), 7.41-7.01 (m, 5H), 6.64 (d, J = 9.4 Hz, 2H), 6.37 (m, 2H), 6.14 (s, 1H), 4.25 (s, 1H), 4.08 (s, 2H), 3.69 (s, 3H), 3.55 (s, 3H), 3.28 (s, 3H), 3.05-2.85 (m, 7H), 2.69-2.60 (m, 3H), 1.86 (s, 2H), 1.71-1.50 (m, 7H), 1.35-1.07 (m, 22H). MS (ESI, m/e) [M + 1]⁺ 1082.9. |
| 303 | 2-((3-fluoro-1H-pyrrolo[2,3-b]pyridin-5-yl)oxy)-N-((4-(((1r,4r)-4-hydroxy-4-mmethylcyclohexyl)methyl)amino)-3-nitrophenyl)sulfonyl)-4-(2-((R)-2-(2-isopropylphenyl)-4-((7-methoxy-2,3-dihydrobenzofuran-5-yl)methyl)piperazin-1-yl)-7-azaspiro[3.5]nonan-7-yl)benzamide | ¹H NMR (400 MHz, DMSO-d₆) δ ppm: 11.50 (s, 1H), 8.58-8.44 (m, 2H), 8.05 (d, J = 2.4 Hz, 1H), 7.76 (d, J = 9.2 Hz, 1H), 7.53-7.37 (m, 3H), 7.34-7.10 (m, 3H), 7.04 (d, J = 9.2 Hz, 1H), 6.97-6.77 (m, 2H), 6.67 (d, J = 7.6 Hz, 1H), 6.22 (s, 1H), 4.50 (t, J = 8.8 Hz, 2H), 4.26 (s, 1H), 4.00-3.58 (m, 6H), 3.30-3.22 (m, 3H), 3.18-2.54 (m, 12H), 1.79-1.47 (m, 7H), 1.43-0.92 (m, 20H). MS (ESI, m/e) [M + 1]⁺ 1086.1 |

| Ex. | structure | Compound name | Data |
|---|---|---|---|
| 304 | 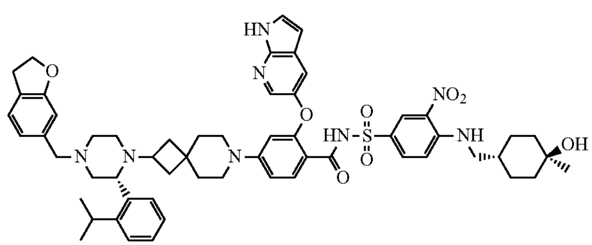 [SMILES: CC(C)c1ccccc1[C@@H]1CN(Cc2ccc3c(c2)OCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1] | 2-((1H-pyrrolo[2,3-b]pyridin-5-yl)oxy)-4-(2-((R)-4-(2,3-dihydrobenzofuran-6-yl)methyl)-2-(2-isopropylphenyl)piperazin-1-yl)-7-azaspiro[3.5]nonan-7-yl)-N-(4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.70 (s, 1H), 11.45-10.80 (m 1H), 8.66-8.49 (m, 2H), 8.07-7.97 (m, 1H), 7.85-7.71 (m, 1H), 7.67-7.40 (m, 4H), 7.40-6.98 (m, 6H), 6.96-6.71 (m, 2H), 6.70-6.58 (m, 1H), 6.42-6.32 (m, 1H), 6.15 (s, 1H), 4.57-4.42 (m, 2H), 4.28 (s, 1H), 4.10-3.52 (m, 3H), 3.36-3.22 (m, 5H), 3.22-2.54 (m, 13H), 1.76-1.49 (m, 6H), 1.47-1.24 (m, 7H), 1.21-1.01 (m, 10H). MS (ESI, m/e) [M + 1]+ 1037.9 |
| 305 | 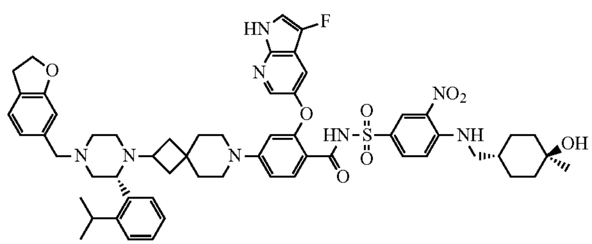 [SMILES: CC(C)c1ccccc1[C@@H]1CN(Cc2ccc3c(c2)OCC3)CCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]cc(F)c5c4)c3)CC2)C1] | 4-(2-((R)-4-((2,3-dihydrobenzofuran-6-yl)methyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.79-11.35 (m, 2H), 8.74-8.55 (m, 2H), 8.22-8.11 (m, 1H), 7.95-7.82 (m, 1H), 7.67-7.12 (m, 9H), 7.12-6.65 (m, 4H), 6.32 (s, 1H), 4.61 (s, 2H), 4.37 (s, 1H), 4.31-3.64 (m, 2H), 3.44-3.32 (m, 4H), 3.31-2.78 (m, 12H), 2.60-2.46 (m, 1H), 2.22-2.02 (m, 1H), 1.86-1.59 (m, 7H), 1.53-1.37 (m, 6H), 1.29-1.10 (m, 10H). MS (ESI, m/e) [M + 1]+ 1055.9 |
| 306 | 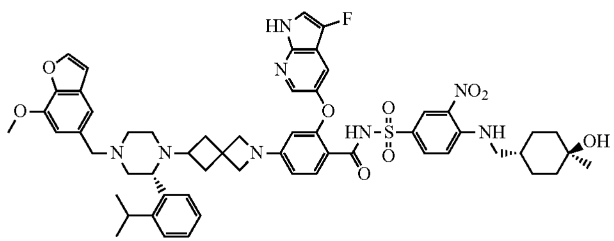 | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((7-methoxybenzofuran-5-yl)methyl)piperazin-1-yl)-2-azaspiro[3.3]heptan-2-yl)benzamide | 1H NMR (400 MHz, DMSO-d6) δ ppm: 11.56 (s, 1H), 11.22 (br, 1H), 8.60-8.53 (m, 2H), 8.08 (s, 1H), 8.00-7.76 (m, 2H), 7.58-6.85 (m, 11H), 6.09-6.03 (m, 1H), 5.32 (s, 1H), 4.25 (s, 1H), 4.19-3.95 (m, 2H), 3.94 (s, 3H), 3.73-3.44 (m, 5H), 3.31-3.19 (m, 3H), 3.17-2.55 (m, 6H), 2.47-2.30 (m, 1H), 2.05-1.93 (m, 2H), 1.74-1.52 (m, 6H), 1.39-1.16 (m, 7H), 1.12-1.00 (m, 7H). MS (ESI, m/e) [M + 1]+ 1056.0 |
| 307 | 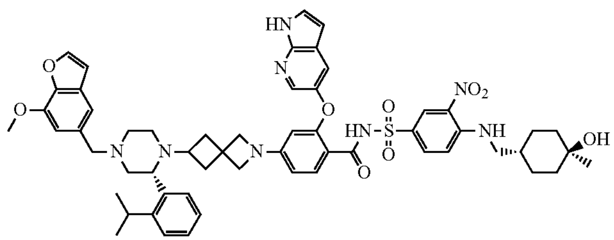 | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((7-methoxybenzofuran-5-yl)methyl)piperazin-1-yl)-2-azaspiro[3.3]heptan-2-yl)benzamide | 1H NMR (400 MHz, DMSO-d6) δ ppm: 11.73 (s, 1H), 11.26 (br, 1H), 8.63-8.56 (m, 2H), 8.03-7.93 (m, 1H), 7.84-7.80 (m, 1H), 7.60-6.85 (m, 11H), 6.43-6.39 (m, 1H), 6.07-6.02 (m, 1H), 5.47 (s, 1H), 4.24 (s, 1H), 3.94 (s, 3H), 3.92-3.89 (m, 1H), 3.73-3.44 (m, 6H), 3.31-3.19 (m, 3H), 3.17-2.68 (m, 6H), 2.39-2.30 (m, 1H), 2.05-1.93 (m, 2H), 1.73-1.50 (m, 6H), 1.38-1.14 (m, 7H), 1.12-1.00 (m, 7H). MS (ESI, m/e) [M + 1]+ 1038.1. |

| Ex. | Compound name | Data |
|---|---|---|
| 308 | 4-(2-((R)-4-((3,3-dimethyl-2,3-dihydrobenzofuran-6-yl)methyl)-2-(2-isopropylphenyl)piperazin-1-yl)-7-azaspiro[3.5]nonan-7-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.51 (s, 1H), 11.48 (br, 1H), 8.58-8.52 (m, 2H), 8.06 (s, 1H), 7.79-7.75 (m, 1H), 7.50-6.65 (m, 12H), 6.24-6.17 (m, 1H), 4.25 (s, 1H), 4.22-4.17 (m, 2H), 3.82-3.40 (m, 3H), 3.31-3.17 (m, 3H), 3.09-2.60 (m, 11H), 2.47-2.30 (m, 1H), 2.05-1.95 (m, 2H), 1.74-1.50 (m, 6H), 1.39-1.22 (m, 20H), 1.12-1.00 (m, 3H). MS (ESI, m/e) [M + 1]⁺ 1084.1. |
| 309 | 2-((1H-pyrrolo[2,3-b]pyridin-5-yl)oxy)-4-(2-((R)-4-((3,3-dimethyl-2,3-dihydrobenzofuran-6-yl)methyl)-2-(2-isopropylphenyl)piperazin-1-yl)-7-azaspiro[3.5]nonan-7-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.69 (s, 1H), 11.51 (br, 1H), 8.62-8.57 (m, 2H), 8.02 (s, 1H), 7.82-7.75 (m, 1H), 7.54-6.62 (m, 12H), 6.39-6.36 (m, 1H), 6.17-6.11 (m, 1H), 4.25 (s, 1H), 4.22-4.17 (m, 2H), 3.82-3.40 (m, 3H), 3.31-3.17 (m, 3H), 3.09-2.60 (m, 11H), 2.47-2.30 (m, 1H), 2.09-1.90 (m, 2H), 1.73-1.50 (m, 6H), 1.39-1.22 (m, 20H), 1.12-1.00 (m, 3H). MS (ESI, m/e) [M + 1]⁺ 1066.0. |
| 310 | 2-((1H-pyrrolo[2,3-b]pyridin-5-yl)oxy)-4-(6-((R)-4-((3,3-dimethyl-2,3-dihydrobenzofuran-6-yl)methyl)-2-(2-isopropylphenyl)piperazin-1-yl)-2-azaspiro[3.3]heptan-2-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.73 (s, 1H), 11.30 (s, 1H), 10.45-10.00 (m, 1H), 8.57 (s, 2H), 8.04 (s, 1H), 7.82 (d, J = 8.2 Hz, 1H), 7.58-7.54 (m, 2H), 7.47-7.06 (m, 7H), 7.00-6.74 (m, 2H), 6.40 (s, 1H), 6.05 (s, 1H), 5.49 (s, 1H), 4.30-4.13 (m, 3H), 3.58-3.50 (m, 5H), 3.01 (s, 4H), 2.70 (s, 1H), 1.97 (s, 3H), 1.70-1.42 (m, 7H), 1.40-1.0 (m, 25H). MS (ESI, m/e) [M + 1]⁺ 1038.3. |
| 311 | 4-(6-((R)-4-((3,3-dimethyl-2,3-dihydrobenzofuran-6-yl)methyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.56 (s, 1H), 11.50-11.22 (m, 1H), 8.58-8.54 (m, 2H), 8.08 (s, 1H), 7.81 (d, J = 8.6 Hz, 1H), 7.58-7.04 (m, 8H), 6.90 (s, 2H), 6.07 (s, 1H), 5.53 (s, 1H), 4.25-4.20 (m, 3H), 3.60-3.52 (m, 5H), 3.41 (s, 1H), 3.31-3.18 (m, 3H), 2.97 (s, 3H), 2.73 (s, 2H), 2.33 (s, 1H), 1.98 (s, 2H), 1.72-1.45 (m, 6H), 1.40-1.0 (m, 21H). MS (ESI, m/e) [M + 1]⁺ 1056.4. |

| Ex. | structure | Compound name | Data |
|---|---|---|---|
| 312 | 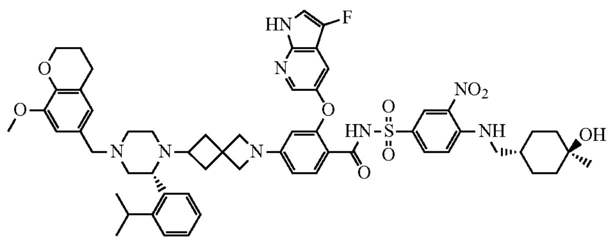 | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropyl)-4-((8-methoxychroman-6-yl)methyl)piperazin-1-yl)-2-azaspiro[3.3]heptan-2-yl)benzamide | $^1$H NMR (400 MHz, DMSO-d$_6$) δ ppm: 11.56 (s, 1H), 11.43 (br, 1H), 8.61-8.53 (m, 2H), 8.08 (s, 1H), 7.84-7.78 (m, 1H), 7.58-6.55 (m, 10H), 6.10-6.03 (m, 1H), 5.52 (s, 1H), 4.25 (s, 1H), 4.17-3.75 (m, 4H), 3.71 (s, 3H), 3.69-3.40 (m, 5H), 3.31-3.20 (m, 3H), 3.17-2.60 (m, 8H), 2.43-2.30 (m, 1H), 2.04-1.93 (m, 2H), 1.92-1.83 (m, 2H), 1.73-1.50 (m, 6H), 1.38-1.14 (m, 7H), 1.12-1.00 (m, 7H). MS (ESI, m/e) [M + 1]$^+$ 1071.9. |
| 313 | 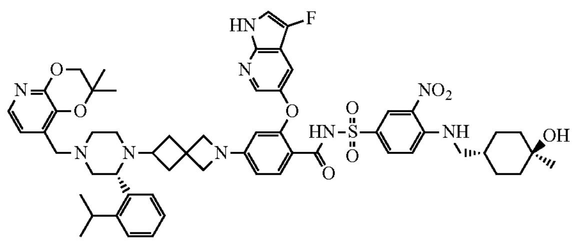 [SMILES: CC(C)c1ccccc1[C@@H]1CN(Cc2ccnc3c2OC(C)(C)CO3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 4-(6-((R)-4-((2,2-dimethyl-2,3-dihydro-[1,4]dioxino[2,3-b]pyridin-8-yl)methyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.56 (s, 1H), 11.37 (br, 1H), 8.62-8.53 (m, 2H), 8.08 (s, 1H), 7.85-7.66 (m, 2H), 7.57-6.96 (m, 9H), 6.14-6.03 (m, 1H), 5.59-5.51 (m, 1H), 4.25 (s, 1H), 4.09-4.03 (m, 2H), 3.74-3.38 (m, 7H), 3.31-3.22 (m 3H), 3.21-2.58 (m, 5H), 2.47-2.30 (m, 1H), 2.28-2.14 (m, 1H), 1.74-1.50 (m, 6H), 1.39-1.14 (m, 14H), 1.12-1 00 (m, 6H). MS (ESI, m/e) [M + 1]$^+$ 1072.9. |
| 314 | 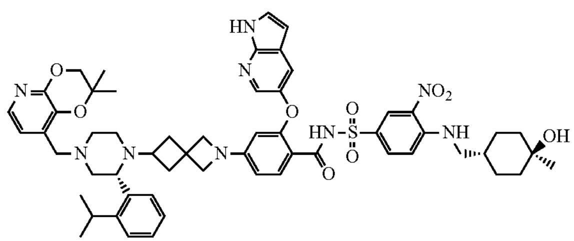 [SMILES: CC(C)c1ccccc1[C@@H]1CN(Cc2ccnc3c2OC(C)(C)CO3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]ccc4c3)c1)C2] | 2-((1H-pyrrolo[2,3-b]pyridin-5-yl)oxy)-4-(6-((R)-4-((2,2-dimethyl-2,3-dihydro-[1,4]dioxino[2,3-b]pyridin-8-yl)methyl)-2-(2-isopropylphenyl)piperazin-1-yl)-2-azaspiro[3.3]heptan-2-yl)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.73 (s, 1H), 11.29 (br, 1H), 8.63-8.56 (m, 2H), 8.04 (s, 1H), 7.87-7.66 (m, 2H), 7.61-6.96 (m, 9H), 6.43-6.37 (m, 1H), 6.09-6.00 (m, 1H), 5.53 (m, 1H), 4.25 (s, 1H), 4.09-4.03 (m, 2H), 3.70-3.36 (m, 7H), 3.31-3.20 (m 3H), 3.17-2.55 (m, 5H), 2.47-2.30 (m, 1H), 2.28-2.14 (m, 1H), 2.07-1.90 (m, 2H), 1.74-1.50 (m, 6H), 1.39-1.14 (m, 14H), 1.12-1.00 (m, 6H). MS (ESI, m/e) [M + 1]$^+$ 1054.9. |
| 315 | 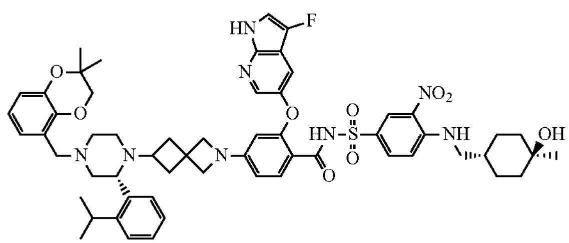 [SMILES: CC(C)c1ccccc1[C@@H]1CN(Cc2cccc3c2OCC(C)(C)O3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 4-(6-((R)-4-((2,2-dimethyl-2,3-dihydrobenzo[b][1,4]dioxin-5-yl)methyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.56 (s, 1H), 11.45-11.26 (m, 1H), 8.60-8.55 (m, 2H), 8.08 (s, 1H), 7.80 (s, 1H), 7.57-7.50 (m, 2H), 7.45-7.40 (m, 2H), 7.30-7.28 (m, 2H), 7.12 (s, 2H), 6.85 (s, 3H), 6.07 (s, 1H), 5.52 (s, 1H), 4.25 (s, 1H), 3.93 (s, 2H), 3.75-3.48 (m, 5H), 3.29 (s, 3H), 3.05-2.9 (m, 3H), 2.67 (s, 1H), 1.98 (s, 2H), 1.71 -1.48 (m, 6H), 1.39-0.99 (m, 24H). MS (ESI, m/e) [M + 1]$^+$ 1072.8. |

| Ex. | structure | Compound name | Data |
|---|---|---|---|
| 316 | 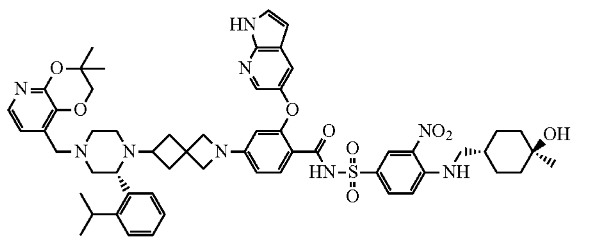 [SMILES: CC(C)c1ccccc1[C@@H]1CN(Cc2ccnc3c2OCC(C)(C)O3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]ccc4c3)c1)C2] | 2-((1H-pyrrolo[2,3-b]pyridin-5-yloxy)-4-(6-((R)-4-((3,3-dimethyl-2,3-dihydro-[1,4]dioxino[2,3-b]pyridin-8-yl)methyl)-2-(2-isopropylphenyl)piperazin-1-yl)-2-azaspiro[3.3]heptan-2-yl)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.73 (s, 1H), 11.26 (s, 1H), 8.63-8.52 (m, 2H), 8.04 (s, 1H), 7.85-7.78 (m, 1H), 7.63-7.49 (m, 2H), 7.48-7.28 (m, 3H), 7.28-7.04 (m, 4H), 6.96 (m, 1H), 6.40 (s, 1H), 6.12-5.98 (m, 1H), 5.49 (s, 1H), 4.25 (s, 1H), 3.92 (s, 2H), 3.75-3.44 (m, 7H), 3.33-3.18 (m, 3H), 3.09-2.52 (m, 5H), 2.39-1.86 (m, 5H), 1.74-1.49 (m, 6H), 1.38-1.26 (m, 7H), 1.22-1.03 (m, 11H). MS (ESI, m/e) [M + 1]⁺ 1055.0 |
| 317 | 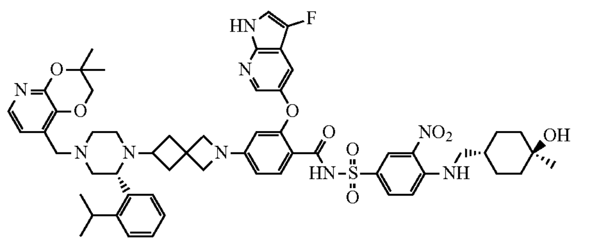 [SMILES: CC(C)c1ccccc1[C@@H]1CN(Cc2ccnc3c2OCC(C)(C)O3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 4-(6-((R)-4-((3,3-dimethyl-2,3-dihydro-[1,4]dioxino[2,3-b]pyridin-8-yl)methyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | ¹H NMR (400 MHz, DMSO-d₆) δ ppm 11.56 (s, 1H), 11.35 (s, 1H), 8.63-8.45 (m, 2H), 8.08 (s, 1H), 7.87-7.76 (m, 1H), 7.59-7.47 (m, 2H), 7.47-7.30 (m, 2H), 7.30-7.03 (m, 4H) 6.97 (s, 1H), 6.14-6.00 (m, 1H), 5.54 (s, 1H), 4.25 (s, 1H), 3.93 (s, 2H), 3.77-3.46 (m, 7H), 3.33-3.21 (m, 3H), 3.05-2.56 (m, 4H), 2.34-1.88 (m, 4H), 1.77-1.50 (m, 6H), 1.42-1.25 (m, 8H), 1 23-1 02 (m, 12H). MS (ESI, m/e) [M +1]⁺ 1073.0 |
| 318 | 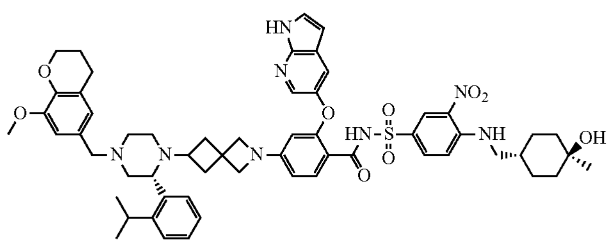 | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)piperazin-1-yl)-(8-methoxychroman-6-yl)methyl)piperazin-1-yl)-2-azaspiro[3.3]heptan-2-yl)benzamide | ¹H NMR (400 MHz, DMSO-d₆) δ ppm: 11.73 (s, 1H), 11.08 (br, 1H), 8.63-8.56 (m, 2H), 8.04 (s, 1H), 7.84-7.79 (m, 1H), 7.60-7.08 (m, 8H), 6.94-6.55 (m, 2H), 6.43-6.38 (m, 1H), 6.07-6.02 (m, 1H), 5.48 (s, 1H), 4.25 (s, 1H), 4.13-3.75 (m, 4H), 3.70 (s, 3H), 3.65-3.40 (m, 5H), 3.31-3.20 (m, 3H), 3.17-2.60 (m, 8H), 2.39-2.30 (m, 1H), 2.05-1.93 (m, 2H), 1.92-1.83 (m, 2H), 1 73-1.50 (m, 6H), 1.38-1.14 (m, 7H), 1.12-1.00 (m, 7H). MS (ESI, m/e) [M + 1]⁺ 1054.0. |
| 319 | 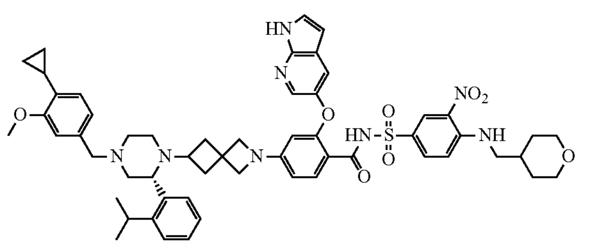 [SMILES: COc1cc(CN2CCN(C3CC4(C3)CN(c3ccc(C(=O)NS(=O)(=O)c5ccc(NCC6CCOCC6)c([N+](=O)[O-])c5)c(Oc5cnc6[nH]ccc6c5)c3)C4)[C@H](c3ccccc3C(C)C)C2)ccc1C1CC1] | (R)-2-((1H-pyrrolo[2,3-b]pyridin-5-yl)oxy)-4-6-(4-(4-cyclopropyl-3-methoxybenzyl)-2-(2-isopropylphenyl)piperazin-1-yl)-2-azaspiro[3.3]heptan-2-yl)-N-((3-nitro-4-(((tetrahydro-2H-pyran-4-yl)methyl)amino)phenyl)sulfonyl)benzamide | ¹H NMR (400 MHz, DMSO-d₆) δ ppm: 11.68 (s, 1H), 8.64-8.44 (m, 2H), 7.98 (s, 1H), 7.82-7.72 (m, 1H), 7.56-7.32 (m, 3H), 7.26-6.86 (m, 5H), 6.81-6.62 (m, 1H), 6.34 (s, 1H), 5.98 (d, J = 8.7 Hz, 1H), 5.44 (s, 1H), 3.86-3.62 (m, 7H), 3.58-3.38 (m, 5H), 3.28-3.12 (m, 7H), 3.02-2.80 (m, 2H), 2.74-2.60 (m, 1H), 2.44-2.20 (m, 2H), 2.08-1.75 (m, 4H), 1.68-1.46 (m, 3H), 1.32-1.08 (m, 6H), 0.99 (s, 3H), 0.86-0.72 (m, 2H), 0.56-0.44 (m, 2H). MS (ESI, m/e) [M +1]⁺ 1009.9. |

| Ex. | structure | Compound name | Data |
|---|---|---|---|
| 320 | 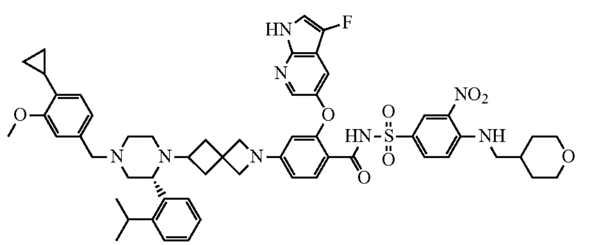 [SMILES: COc1cc(CN2CCN(C3CC4(C3)CN(c3ccc(C(=O)NS(=O)(=O)c5ccc(NCC6CCOCC6)c([N+](=O)[O-])c5)c(Oc5cnc6[nH]cc(F)c6c5)c3)C4)[C@H](c3ccccc3C(C)C)C2)ccc1C1CC1] | (R)-4-(6-(4-(4-cyclopropyl-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((3-nitro-4-(((tetrahydro-2H-pyran-4-yl)methyl)amino)phenyl)sulfonyl)benzamide | $^1$H NMR (400 MHz, DMSO-$d_6$) δ ppm: 11.55 (s, 1H), 8.64-8.44 (m, 2H), 8.07 (s, 1H), 7.86-7.75 (m, 1H), 7.57-7.37 (m, 3H), 7.30-6.92 (m, 5H), 6.86-6.68 (m, 2H), 6.06 (d, J = 8.7 Hz, 1H), 5.55 (s, 1H), 3.91-3.67 (m, 7H), 3.66-3.45 (m, 5H), 3.33-3.18 (m, 7H), 3.08-2.88 (m, 2H), 2.77-2.66 (m, 1H), 2.49-2.22 (m, 2H), 2.12-1.82 (m, 4H), 1.76-1.54 (m, 3H), 1.40-1.14 (m, 6H), 1.06 (s, 3H), 0.92-0.78 (m, 2H), 0.64-0.50 (m, 2H). MS (ESI, m/e) [M + 1]$^+$ 1028.1. |
| 321 | 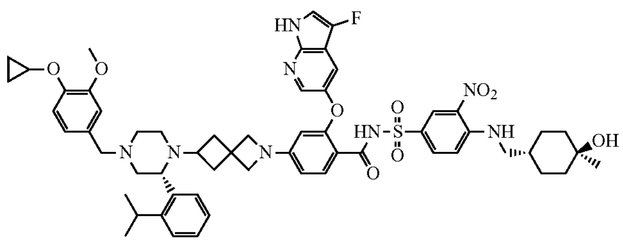 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1OC1CC1] | 4-(6-((R)-4-(4-cyclopropoxy-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexy)methyl)amino)-3-nitrophenyl)sulfonyl)benzamide | $^1$H NMR (400 MHz, DMSO-$d_6$) δ ppm: 11.57 (s, 1H), 11.41 (br, 1H), 8.62-8.53 (m, 2H), 8.08 (s, 1H), 7.85-7.78 (m, 1H), 7.59-680 (m, 11H), 6.10-6.04 (m, 1H), 5.52 (s, 1H), 4.35-4.02 (m, 3H), 3.85-3.38 (m, 10H), 3.31-3.22 (m, 3H), 3.13-2.55 (m, 6H), 2.05-1.91 (m 2H), 1.74-1.50 (m, 6H), 1.39-1.05 (m, 14H), 0.80-0.57 (m, 4H). MS (ESI, m/e) [M + 1]$^+$ 1072.1. |
| 322 | 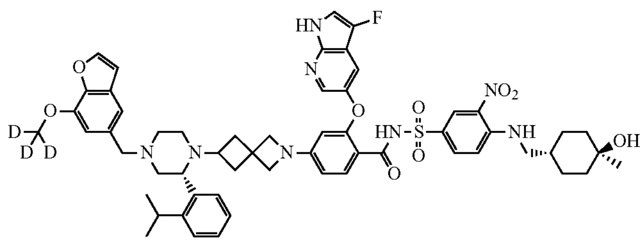 [SMILES: [2H]C([2H])([2H])Oc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2ccoc12] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((7-(methoxy-d3)benzofuran-5-yl)methyl)piperazin-1-yl)-2-azaspiro[3.3]heptan-2-yl)benzamide | $^1$H NMR (400 MHz, DMSO-$d_6$) δ ppm: 11.56 (s, 1H), 11.45 (br, 1H), 8.61-8.53 (m, 2H), 8.08 (s, 1H), 8.04-7.92 (m, 1H), 7.84-7.78 (m, 1H), 7.58-6.85 (m, 11H), 6.12-6.04 (m, 1H), 5.52 (s, 1H), 4.10-3.41 (m, 7H), 3.31-3.20 (m, 3H), 3.17-2.65 (m, 6H), 2.43-2.35 (m, 1H), 2.04-1.93 (m, 2H), 1.73-1.50 (m, 6H), 1.38-1.14 (m, 8H), 1.12-100 (m, 6H). MS (ESI, m/e) [M + 1]$^+$ 1059.1. |
| 323 | 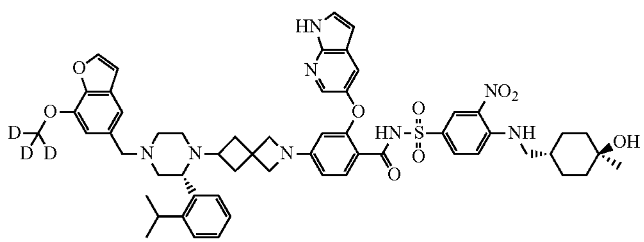 [SMILES: [2H]C([2H])([2H])Oc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2ccoc12] | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((7-(methoxy-d3)benzofuran-5-yl)methyl)piperazin-1-yl)-2-azaspiro[3.3]heptan-2-yl)benzamide | $^1$H NMR (400 MHz, DMSO-$d_6$) δ ppm: 11.73 (s, 1H), 11.29 (br, 1H), 8.63-8.55 (m, 2H), 8.04 (s, 1H), 8.02-7.92 (m, 1H), 7.86-7.79 (m, 1H), 7.58-6.85 (m, 11H), 6.43-6.38 (m, 1H), 6.10-6.02 (m, 3H), 5.47 (s, 1H), 4.25 (s, 1H), 4.10-3.41 (m, 7H), 3.31-3.20 (m, 3H), 3.17-2.65 (m, 6H), 2.43-2.35 (m, 1H), 2.04-1.93 (m, 2H), 1.73-1.50 (m, 6H), 1.38-1.14 (m, 8H), 1.12-1.00 (m, 6H). MS (ESI, m/e) [M + 1]$^+$ 1041.0. |

| Ex. | structure | Compound name | Data |
|---|---|---|---|
| 324 | 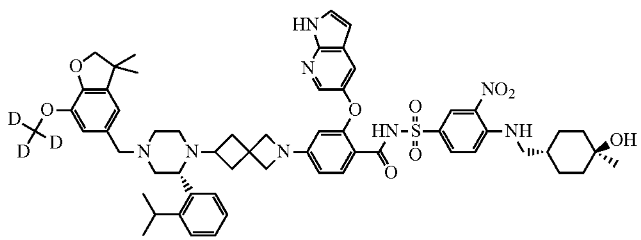 [SMILES: [2H]C([2H])([2H])Oc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2c1OCC2(C)C] | 2-((1H-pyrrolo[2,3-b]pyridin-5-yl)oxy)-N-((4-(1r,4r)-4-hydroxy-4-methylcyclohexyl)amino)-3-nitrophenyl)sulfonyl)-4-(6-((R)-2-(2-isopropylphenyl)-4-((7-(methoxy-d3)-3,3-dimethyl-2,3-dihydrobenzofuran-5-yl)methyl)piperazin-1-yl)-2-azaspiro[3.3]heptan-2-yl)benzamide | 1H NMR (400 MHz, DMSO-d6) δ ppm: 11.73 (s, 1H), 11.30 (s, 1H), 8.58 (s, 2H), 8.04 (s, 1H), 7.82 (s, 1H), 7.60-7.50 (m, 2H), 7.48-7.08 (m, 6H), 6.99-6.90 (m, 2H), 6.40 (s, 1H), 6.05 (s, 1H), 5.46 (s, 1H), 4.35-4.10 (m, 2H), 3.65-3.53 (m, 3H), 1.97 (s, 1H), 1.75-1.50 (m, 4H), 1.40-1.0 (m, 14H). MS (ESI, m/e) [M + 1]+ 1070.9. |
| 325 | 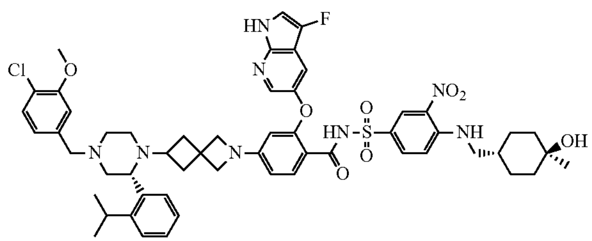 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1Cl] | 4-(6-((R)-4-(4-chloro-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm: 11.56 (s, 1H), 11.47-11.27 (m, 1H), 8.58-8.55 (m, 2H), 8.08 (s, 1H), 7.80 (s, 1H), 7.52 (s, 2H), 7.47-7.33 (m, 4H), 7.25 (s, 2H), 7.15-7.09 (m, 2H), 6.91 (s, 1H), 6.07 (s, 1H), 5.52 (s, 1H), 4.25 (s, 1H), 3.86 (s, 3H), 3.70-3.50 (m, 6H), 3.29 (s, 3H), 2.97 (s, 3H), 2.73 (s, 2H), 2.33 (s, 1H), 1.98 (s, 1H), 1.74-1.48 (m, 6H), 1.39-0.97 (m, 15H). MS (ESI, m/e) [M + 1]+ 1049.9. |
| 326 | 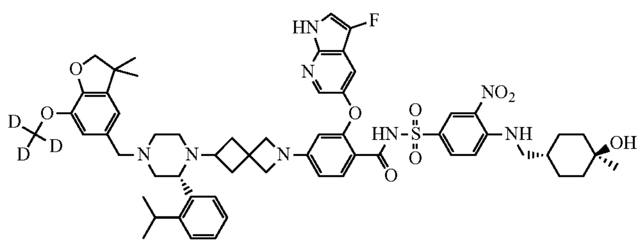 [SMILES: [2H]C([2H])([2H])Oc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2c1OCC2(C)C] | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((7-(methoxy-d3)-3,3-dimethyl-2,3-dihydrobenzofuran-5-yl)methyl)piperazin-1-yl)-2-azaspiro[3.3]heptan-2-yl)benzamide | 1H NMR (400 MHz, DMSO-d6) δ ppm 11.56 (s, 1H), 11.41 (s, 1H), 8.58-8.56 (m, 2H), 8.08 (s, 1H), 7.81 (s, 1H), 7.60-7.50 (m, 2H), 7.45-7.40 (m,2H), 7.38-7.15 (m, 3H), 7.15-7.05 (m, 2H), 6.94 (s, 1H), 6.09-6.02 (m, 1H), 5.52 (s, 1H), 4.30-4.10 (m, 5H), 3.60-3.53 (m, 5H), 3.29 (s, 3H), 3.06 (s, 5H), 2.73 (s, 2H), 1.99 (s, 2H), 1.70-1.50 (m, 6H), 140-1.20 (m, 241), 1.15-1.05 (m, 4H). MS (ESI, m/e) [M + 1]+ 1089.2 |
| 327 | 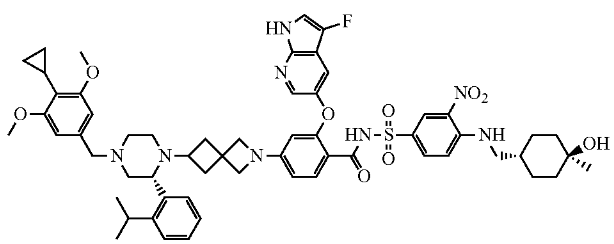 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc(OC)c1C1CC1] | 4-(6-((R)-4-(4-cyclopropyl-3,5-dimethoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | 1H NMR (400 MHz, DMSO-d6) δ ppm 11.91 (s, 1H), 11.40 (s, 1H), 8.83-8.65 (m, 2H), 8.22 (s, 1H), 8.08-7.95 (m, 1H), 7.84-7.67 (m, 2H), 7.67-7.19 (m, 7H), 7.03-6.67 (m, 2H), 6.58 (s, 1H), 6.29-6.15 (m, 1H), 5.65 (s, 1H), 4.42 (s, 1H), 4.32-4.13 (m, 1H), 4.00-3.58 (m, 13H), 3.48-3.31 (m, 5H), 3.28-3.05 (m, 3H), 3.02-2.78 (m, 2H), 2.21-2.08 (m, 2H), 2.04-1.92 (m, 1H), 1.91-1.65 (m, 7H), 1.57-1.28 (m, 10H), 1.2-1.18 (m, 1H), 1.12-1.00 (m, 2H), 0.93-0.83 (m, 2H) MS (ESI, m/e) [M + 1]+ 1085.9. |

| Ex. | structure | Compound name | Data |
|---|---|---|---|
| 328 | 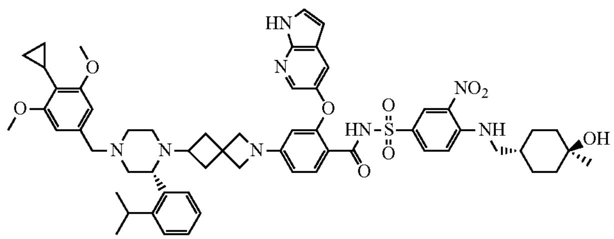 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc(OC)c1C1CC1] | 2-((1H-pyrrolo[2,3-b]pyridin-5-yl)oxy)-4-(6-((R)-4-(4-cyclopropyl-3,5-dimethoxybenzyl)-2-(2-isopropylphenyl)piperazin-1-yl)-2-azaspiro[3.3]heptan-2-yl)-N-((4-((1r,4r)-4-hydroxy-4-methylcyclohexyl)amino)-3-nitrophenyl)sulfonyl)benzamide | 1H NMR (400 MHz, DMSO-d6) δ ppm:: 11.56 (s, 1H), 11.30 (s, 1H), 8.63-8.42 (m, 2H), 8.08 (s, 1H), 7.88-7.74 (m, 1H), 7.61-6.99 (m, 10H), 6.91-6.60 (m, 2H), 6.18-6.00 (m, 1H), 5.52 (s, 1H), 4.25 (s, 1H), 4.16-3.90 (m, 1H), 3.77-3.46 (m, 12H), 3.32-3.16 (m, 7H), 3.12-2.90 (m, 3H), 2.82-2.63 (m, 2H), 1.98 (s, 2H), 1.86-1.42 (m, 8H), 1.40-1.15 (m, 8H), 1.06-0.97 (m, 2H), 0.94-0.86 (m, 2H), 0.75-0.65 (m, 2H). MS (ESI, m/e) [M + 1]+ 1067.9 |
| 329 | 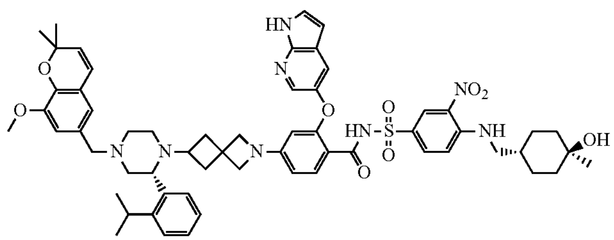 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2c1OC(C)(C)C=C2] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((8-methoxy-2,2-dimethyl-2H-chromen-6-yl)methyl)piperazin-1-yl)-2-azaspiro[3.3]heptan-2-yl)benzamide | 1H NMR (400 MHz. DMSO-d6) δ ppm: 11.68 (s, 1H), 11.25 (s, 1H), 8.52 (s, 2H), 7.99 (s, 1H), 7.78 (d, J = 8.4 Hz, 1H), 7.55-7.10 (m, 9H), 6.72-6.68 (m, 1H), 6.38-6.21 (m, 2H), 5.99 (s, 1H), 5.75-5.70 (m, 1H), 5.45-5.40 (m, 1H), 4.20 (s, 1H), 3.75-3.68 (m, 3H), 3.55-3.48 (m, 5H), 2.96 (s, 4H), 2.68 (s, 1H), 1.92 (s, 2H), 1.70-1.50 (m, 6H), 1.36-0.95 (m, 24H). MS (ESI, m/e) [M + 1]+ 1079.9 |
| 330 | 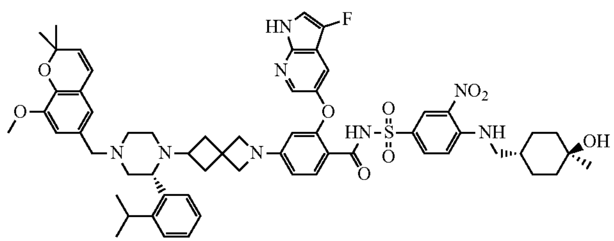 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2c1OC(C)(C)C=C2] | 2-((3-fluoro-1H-pyrrolo[2,3-b]pyridin-5-yl)oxy)-N-(4-(((1r,4r)-4-hydroxy-4-methylcyclohexyl)methyl)amino)-3-nitrophenyl)sulfonyl)-4-(6-((R)-2-(2-isopropylphenyl)-4-((8-methoxy-2,2-dimethyl-2H-chromen-6-yl)methyl)piperazin-1-yl)-2-azaspiro[3.3]heptan-2-yl)benzamide | 1H NMR (400 MHz, DMSO-d6) δ ppm: 11.51 (s, 2H), 8.53-8.50 (m, 2H), 8.03 (s, 1H), 7.75 (s, 1H), 7.56-6.92 (m, 9H), 6.68 (s, 1H), 6.32-6.28 (m, 1H), 6.02 (s, 1H), 5.69 (s, 1H), 5.47 (s, 1H), 4.20 (s, 1H), 4.04-3.85 (m, 1H), 3.74-3.41 (m, 9H), 3.19-3.11 (m, 1H), 2.94 (s, 3H), 2.69 (s, 1H), 1.93 (s, 2H), 1.72-1.42 (m, 7H), 1.35-0.97 (m 22H). MS (ESI) [M + 1]+ 1097.9 |
| 331 | 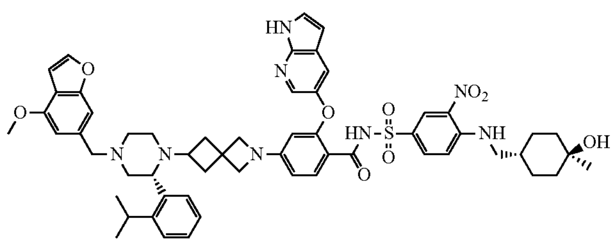 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2occc12] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((4-methoxybenzofuran-6-yl)methyl)piperazin-1-yl)-2-azaspiro[3.3]heptan-2-yl)benzamide | 1H NMR (400 MHz, DMSO-d6) δ ppm: 11.68 (s, 1H), 11.13 (s, 1H), 8.52 (s, 2H), 7.99 (s, 1H), 7.90-7.71 (m, 2H), 7.55-7.30 (m, 4H), 7.26-6.99 (m, 5H), 6.85 (s, 1H), 6.35 (s, 1H), 6.00 (s, 1H), 5.43 (s, 1H), 4.20 (s, 4H), 3.84 (s, 4H), 3.53-3.45 (m, 6H), 3.24-3.18 (m, 2H), 2.98-2.90 (m, 2H), 2.66 (s, 2H), 1.93 (s, 2H), 1.68-1.44 (m, 6H), 1.35-0.90 (m, 17H). MS (ESI, m/e) [M + 1]+ 1037.9 |

| Ex. | structure | Compound name | Data |
|---|---|---|---|
| 332 | 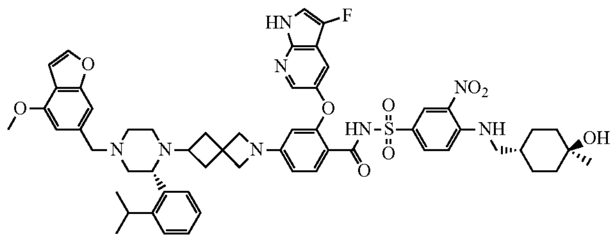 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2occc12] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((4-methoxybenzofuran-6-yl)methyl)piperazin-1-yl)-2-azaspiro[3.3]heptan-2-yl)benzamide | ¹H NMR (400 MHz, DMSO-d₆) δ ppm.: 11.51 (s, 2H), 11.30 (s, 1H), 8.53-8.50 (m, 2H), 8.03 (s, 1H), 7.85-7.80 (m, 2H), 7.55-6.90 (m, 12H), 6.02 (s, 1H), 5.48 (s, 1H), 4.20 (s, 1H), 3.85 (s, 4H), 3.60-3.50 (m, 5H), 3.24 (s, 4H), 2.89-2.70 (m, 4H), 1.93 (s, 2H), 170-1.43 (m, 7H), 1.34-0.91 (m, 17H). MS (ESI, m/e) [M + 1]⁺ 1055.9 |
| 333 | 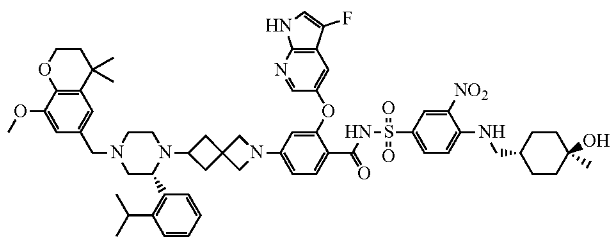 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2c1OCCC2(C)C] | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropylphenyl)-4-((8-methoxy-4,4-dimethylchroman-6-yl)methyl)piperazin-1-yl)-2-azaspiro[3.3]heptan-2-yl)benzamide | ¹H NMR (400 MHz, DMSO-d₆) δ ppm: 11.57 (s, 1H), 11.28 (s, 1H), 8.57-8.54 (m, 2H), 8.08 (s, 1H), 7.82-7.80 (m, 1H), 7.55-7.51 (m, 2H), 7.44-7.39 (m, 2H), 7.27-7.25 (m, 2H), 7.16-7.10 (m 3H), 6.98 (s, 1H), 6.06 (d, J = 8.0 Hz, 1H), 5.53 (s, 1H), 4.26 (s, 1H), 4.11 (s, 3H), 3.71-3.51 (m, 9H), 3.29-3.28 (m, 3H), 3.02-3.00 (m, 2H), 2.75-2.73 (m, 1H), 1.99-1.98 (m 2H), 1.74-1.66 (m, 6H), 1.56-1.53 (m, 2H), 1.36-1.10 (m, 24H). MS (ESI, m/e) [M + 1]⁺ 1100.0. |
| 334 | 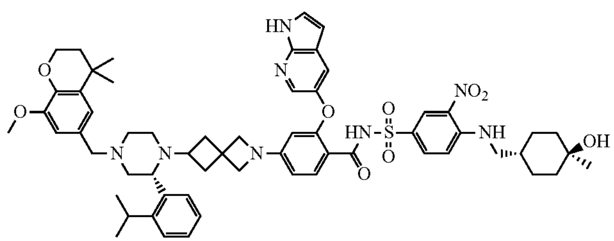 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2c1OCCC2(C)C] | 2-((1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropylphenyl)-4-((8-methoxy-4,4-dimethylchroman-6-yl)methyl)piperazin-1-yl)-2-azaspiro[3.3]heptan-2-yl)benzamide | ¹H NMR (400 MHz, DMSO-d₆) δ ppm: 11.73 (s, 1H), 11.30 (s, 1H), 8.59-8.57 (m, 2H), 8.04 (s, 1H), 7.59 (s, 1H), 7.52 (s, 1H), 7.45-7.39 (m, 2H), 7.27-7.24 (m, 2H), 7.16-7.11 (m, 2H), 7.05 (s, 1H), 6.93 (s, 1H), 6.40 (s, SH), 6.05-6.03 (m, 1H), 5,47 (s,1H), 4.26 (s, 1H), 4.11 (s, 3H), 3.71-3.48 (m, 9H), 3.29-3.28 (m, 3H), 3,02-3,00 (m, 2H), 2.75-2.73 (m, 1H), 1.99-1.98 (m 2H), 1.74-1.66 (m, 6H), 1.55-1.52 (m, 2H), 1.36-1.09 (m, 24H). MS (ESI, m/e) [M + 1]⁺ 1081.9. |
| 335 | 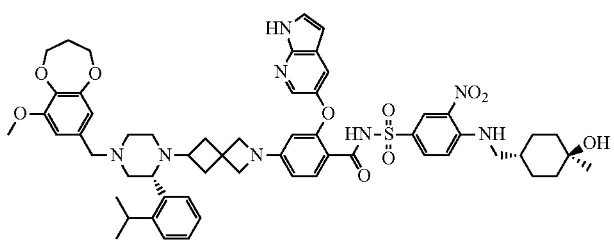 | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((9-methoxy-3,4-dihydro-2H-benzo[b][1,4]dioxepin-7-yl)methyl)piperazin-1-yl)-2-azaspiro[3.3]heptan-2-yl)benzamide | ¹H NMR (400 MHz, DMSO-d₆) δ ppm: 11.53 (s, 1H), 11.29 (s, 1H), 8.55-8.52 (m, 2H), 8.07 (s, 1H), 7.80-7.78 (m, 1H), 7.50-7.39 (m, 4H), 7.21-7.09 (m, 4H), 6.63 (s, 1H), 6.52 (s, 1H), 6.06 (d, J = 8.0 Hz. 1H), 5.54 (s, 1H), 4.24 (s, 1H), 4.05-4.01 (m, 4H), 3.70 (s, 3H), 3.62-3.50 (m, 6H), 3.29-3.28 (m, 2H), 2.91-2.90 (m, 2H), 2.73-2.71 (m, 1H), 2.22-2.20 (m, 1H), 2.04-1.96 (m, 5H), 1.69-1.52 (m, 7H), 1.36-1.30 (m, 3H), 1.23-1.06 (m 14H). MS (ESI, m/e) [M + 1]⁺ 1087.9. |

| Ex. | structure | Compound name | Data |
|---|---|---|---|
| 336 | 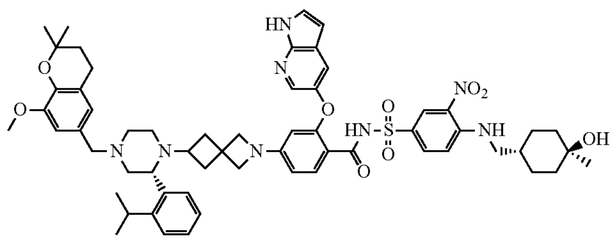 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2c1OC(C)(C)CC2] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((8-methoxy-2,2-dimethylchroman-6-yl)methyl)piperazin-1-yl)-2-azaspiro[3.3]heptan-2-yl)benzamide | $^1$H NMR (400 MHz, DMSO-d$_6$) δ ppm: 11.73 (s, 1H), 1141 (br, 1H), 8.61-8.53 (m, 2H), 8.04 (s, 1H), 7.90-7.79 (m, 1H), 7.62-7.08 (m, 8H), 6.95-6.62 (m, 2H), 6.43-6.38 (m, 1H), 6.07-5.97 (m, 1H), 5.47 (s, 1H), 4.25 (s, 1H), 3.75-3.41 (m, 9H), 3.31-3.20 (m, 3H), 3.10-2.90 (m, 3H), 2.80-2.60 (m, 4H), 2.43-2.35 (m, 1H), 2.04-1.93 (m, 2H), 1.73-1.50 (m, 8H), 1.38-1.14 (m, 16H), 1.12-1.00 (m, 6H). MS (ESI, m/e) [M + 1]$^+$ 1082.0. |
| 337 | 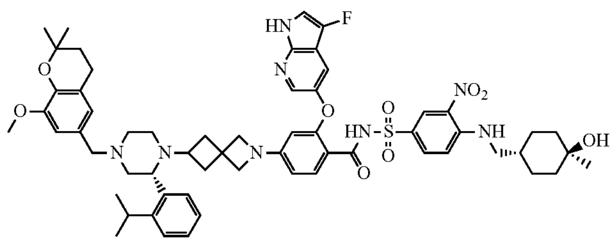 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2c1OC(C)(C)CC2] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((8-methoxy-2,2-dimethylchroman-6-yl)methyl)piperazin-1-yl)-2-azaspiro[3.3]heptan-2-yl)benzamide | $^1$H NMR (400 MHz, DMSO-d$_6$) δ ppm: 11.55 (s, 1H), 11.32 (br, 1H), 8.61-8.53 (m, 2H), 8.07 (s, 1H), 7.82-7.76 (m, 1H), 7.58-7.08 (m, 8H), 6.95-6.60 (m, 2H), 6.08-5.99 (m, 1H), 5.53 (s, 1H), 4.25 (s, 1H), 3.90-3.41 (m 9H), 3.31-3.20 (m, 3H), 3.10-2.90 (m, 3H), 2.80-2.60 (m, 4H), 2.43-2.35 (m, 1H), 2.04-1.92 (m, 2H), 1.75-1.50 (m, 8H), 1.38-1.12 (m 16H), 1.12-1.00 (m, 6H). MS (ESI, m/e) [M + 1]$^+$ 1099.9. |
| 339 | 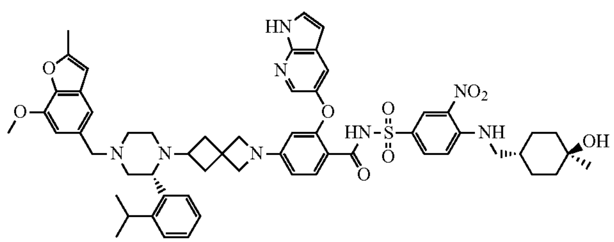 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc2cc(C)oc12] | 2-((1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-((7-methoxy-2-methylbenzofuran-5-yl)methyl)piperazin-1-yl)-2-azaspiro[3.3]heptan-2-yl)benzamide | $^1$H NMR (400 MHz, DMSO-d6)δppm: 11.68 (s, 1H), 11.06 (br. 1H), 8.59-8.51 (m, 2H), 7.99 (s, 1H), 7.80-7.76 (m, 1H), 7.58-7.00 (m, 10H), 7.21-6.81 (m, 6H), 6.44-6.42 (m, 1H), 6.35(s, 1H), 6.01-5.95 (m, 1H), 5.43 (s, 1H), 4.20 (s, 1H), 3.84 (s, 3H), 3.75-3.34 (m, 7H), 3.31-3.20 (m, 3H), 3.10-2.50 (m, 6H), 2.35 (s, 3H), 2.30-2.25 (m, 1H), 1.98-1.86 (m, 2H), 1.68-1.45 (m, 6H), 1.32-1.06 (m, 14H), 1.02-0.93 (m, 3H) MS (ESI, m/e) [M + 1]$^+$ 1051.9 |
| 340 | 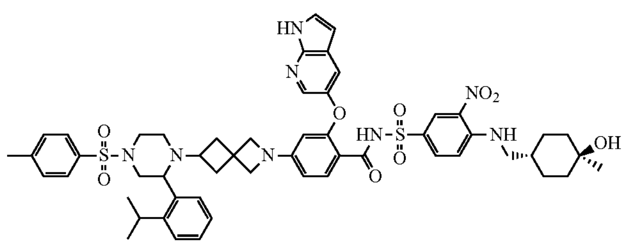 [SMILES: Cc1ccc(S(=O)(=O)N2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)C(c3ccccc3C(C)C)C2)cc1] | 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-(2-(2-isopropylphenyl)-4-tosylpiperazin-1-yl)-2-azaspiro[3.3]heptan-2-yl)benzamide | $^1$H NMR (400 MHz, DMSO-d$_6$) δ ppm: 11.68 (s, 1H), 11.25 (br, 1H), 8.58-8.52 (m, 2H), 7.99 (s, 1H), 7.82-7.74 (m, 1H), 7.57-7.35 (m, 7H), 7.23-6.97 (m, 5H), 6.34 (s, 1H), 6.01-5.94 (m, 1H), 5.41 (s, 1H), 4.20 (s, 1H), 3.65-3.34 (m, 7H), 3.31-3.20 (m, 3H), 2.93-2.84 (m, 1H), 2.68-2.57 (m, 1H), 2.34 (s, 3H), 2.32-2.25 (m, 1H), 2.17-2.06 (m, 2H), 1.95-1.82 (m, 2H), 1 67-1.45 (m, 6H), 1.33-1.12 (m, 7H), 1.12-1.00 (m, 7H). MS (ESI, m/e) [M + 1]$^+$ 1031.7 |

| Ex. | structure | Compound name | Data |
|---|---|---|---|
| 341 | | 4-(6-((R)-4-(4-cyclobutyl-3-methoxybenzyl)-2-(2-isopropylphenyl)piperazin-1-yl)-2-azaspiro[3.3]heptan-2-yl)-2-(3-fluoro-1H-pyrrolo[2,3-b]pyridin-5-yl)oxy)-N-((4-((((1r,4r)-4-hydroxy-4-methyl)cyclohexyl)methyl)amino)-3-nitrophenyl)sulfonyl)benzamide | 1H NMR (400 MHz, DMSO-d6) δ ppm: 11.55 (s, 1H), 11.36-11.06 (m, 1H), 8.57-8.53 (m, 2H), 8.07 (s, 1H), 7.80 (d, J = 8.0 Hz, 1H), 7.55-7.35 (m, 4H), 7.30-6.85 (m, 7H), 6.06 (d, J = 8.0 Hz, 1H), 5.53 (s, 1H), 4.24 (s, 1H), 3.80-3.45 (m, 10H), 3.28 (s, 3H), 2.94 (s, 2H), 2.73 (s, 2H), 2.19 (s, 2H), 1.96 (s, 5H), 1.80-1.45 (m, 7H), 1.40-1.0 (m, 15H). MS (ESI, m/e) [M + 1]+ 1069.8. |
| 342 | 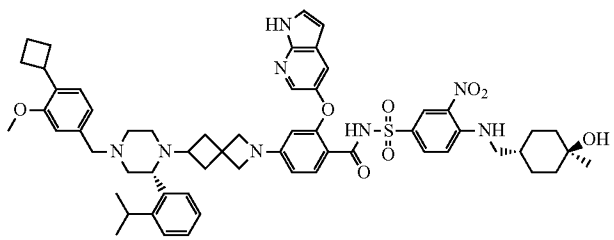 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)ccc1C1CCC1] | 2-((1H-pyrrolo[2,5-b]pyridin-5-yl)oxy)-4-(6-((R)-4-(4-cyclobutyl-3-methoxybenzyl)-2-(2-isopropylphenyl) piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide | 1H NMR (400 MHz, DMSO-d6) δ ppm 11.72 (s, 1H), 11.38-10.93 (m, 1H), 8.57 (s, 2H), 8.04 (s, 1H), 7.82 (d, J = 8.8 Hz, 1H), 7.60-7.50 (m, 2H), 7.48-7.40 (m, 2H), 7.30-7.1 (m, 5H), 6.86 (s, 2H), 6.40 (s, 1H), 6.04 (d, J = 8.0 Hz, 1H), 5.49 (s, 1H), 4.25 (s, 1H), 3.80-3.50 (m, 10H), 3.29 (s, 3H), 2.92 (s, 2H), 2.72 (s, 2H), 2.19 (s, 3H), 1.97 (s, 5H), 1.80-1.50 (m, 7H), 1.40-1.0 (m, 15H). MS (ESI, m/e) [M + 1]+ 1051.8 |
| 343 | 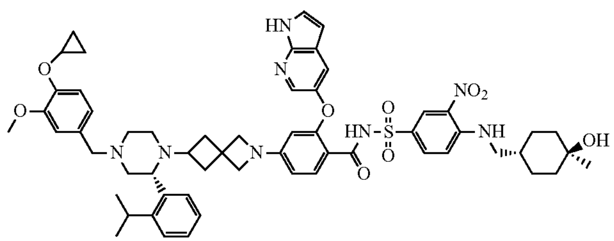 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)ccc1OC1CC1] | 2-((1H-pyrrolo[2,3-b]pyridin-5-yl)oxy)-4-(6-((R)-4-(4-cyclopropoxy-3-methoxybenzyl)-2-(2-isopropylphenyl)piperazin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide | 1H NMR (400 MHz, DMSO-d6) δ ppm: 11.68 (s, 1H), 11.25 (br, 1H), 8.58-8.49 (m, 2H), 7.99 (s, 1H), 7.80-7.74 (m, 1H), 7.56-6.72 (m, 11H), 6.35 (s, 1H), 6.02-5.90 (m, 1H), 5.43 (s, 1H), 4.20 (s, 1H), 3.77-3.34 (m, 12H), 3.31-3.20 (m, 3H), 3.10-2.80 (m, 3H), 2.73-2.57 (m, 2H), 2.32-2.20 (m, 1H), 2.10-1.85 (m, 2H), 1.68-1.45 (m, 6H), 1.33-1.12 (m 10H), 1.05-1.00 (m, 4H), 0.73-0.65 (m, 2H), 0.60-0.53 (m 2H). MS (ESI, m/e) [M + 1]+ 1053.9 |
| 344 | 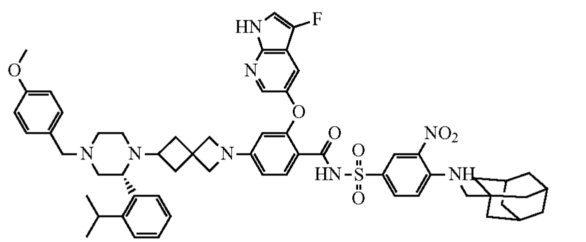 [SMILES: COc1ccc(CN2CCN(C3CC4(C3)CN(c3ccc(C(=O)NS(=O)(=O)c5ccc(NCC67CC8CC(CC(C8)C6)C7)c([N+](=O)[O-])c5)c(Oc5cnc6[nH]cc(F)c6c5)c3)C4)[C@H](c3ccccc3C(C)C)C2)cc1] | N-((4-(((1s,3R,5S)-adamantan-1-yl)methyl)amino)-3-nitrophetyl)sulfonyl)-2-(3-fluoro-1H-pyrrolo[2,3-b]pyridin-5-yl)oxy)-4-(6-((R)-4-(4-methoxybenzyl)piperazin-1-yl)-2-azaspiro[3 3]heptan-2-yl)benzamide | 1H NMR (400 MHz, DMSO-d6) δ ppm: 11.49 (s, 1H), 8.47 (s, 2H), 8.01 (s, 1H), 7.73-7.71 (m, 1H), 7.48-7.44 (m, 2H), 7.39-7.37 (m, 2H), 7.19-7.07 (m, 7H), 6.85 (s, 2H), 6.01 (d, J 8.0 Hz, 1H), 5.49 (s,1H), 3.67 (s, 3H), 3.56-3.45 (m, 6H), 3.03 (s, 2H), 2.90-2.88 (m, 2H), 2.65-2.63 (m 1H), 1.93-1.89 (s, 2H), 1.64-1.50 (m, 5H), 1.18-1.13 (m, 7H), 1.00 (s, 3H). MS (ESI, m/e) [M + 1]+ 1037.9. |

| Ex. | structure | Compound name | Data |
|---|---|---|---|
| 345 | 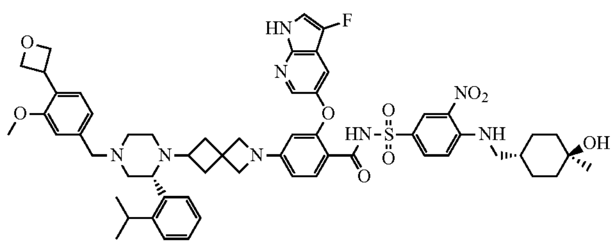 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1C1COC1] | 2-(3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(oxetan-3-yl)benzyl)piperazin-1-yl)-2-azaspiro[3.3]heptan-2-yl)benzamide | $^1$H NMR (400 MHz, DMSO-d$_6$) δ ppm: 11.51 (s, 1H), 11.23 (br, 1H), 8.52-8.48 (m, 2H), 8.02 (s, 1H), 7.76-7.74 (m, 1H), 7.48-7.46 (m, 2H), 7.39-7.37 (m, 2H), 7.19-7.04 (m, 6H), 6.90 (s, 1H), 6.01 (d, J = 8.0 Hz, 1H), 5.49 (s,1H), 4.78 (s, 2H), 4.55 (s, 2H), 4.32-4.31 (m, 1H), 4.21 (s, 1H), 3.68 (s, 3H), 3.58-3.45 (m, 6H), 3.23 (s, 3H), 2.97-2.89 (m, 2H), 2.69-2.67 (m, 2H), 2.30-2.26 (m, 1H), 1.94 (s, 2H), 1.64-1.60 (m, 3H), 1.50-1.47 (m, 2H), 1.30-1.00 (m, 18H). MS (ESI, m/e) [M + 1]$^+$ 1071.9 |
| 346 | 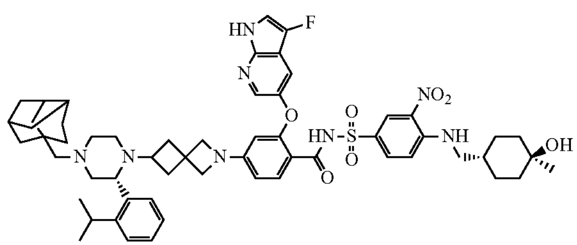 [SMILES: CC(C)c1ccccc1[C@@H]1CN(CC23CCC4CC(CC4C2)C3)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 2-(3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((2R)-2-(2-isopropylphenyl)-4-((octahydro-5H-2,5-methanoinden-5-yl)methyl)piperazin-1-yl)-2-azaspiro[3.3]heptan-2-yl)benzamide | $^1$H NMR (400 MHz, DMSO-d$_6$) δ ppm: 11.61 (s, 1H), 11.47 (s, 1H), 8.62-8.59 (m, 2H), 8.13 (s, 1H), 7.86 (s, 1H), 7.60-7.45 (m, 4H), 7.28-7.16 (m, 4H), 6.13-6.11 (m, 1H), 5.81 (s, 1H), 5.60 (s, 1H), 5.30 (s, 1H), 5.16-5.09 (m, 1H), 4.60-4.44 (m, 1H), 4.31 (s, 1H), 3.15-2.97 (m, 10H), 2.68-1.94 (m, 9H), 1.71-1.60 (m, 11H), 1.49-1.41 (m 6H), 1.35-1.29 (m 7H), 1.19-1.15 (m, 5H), 0.91 (s, 2H). MS (ESI, m/e) [M + 1]$^+$ 1043.6. |
| 347 | 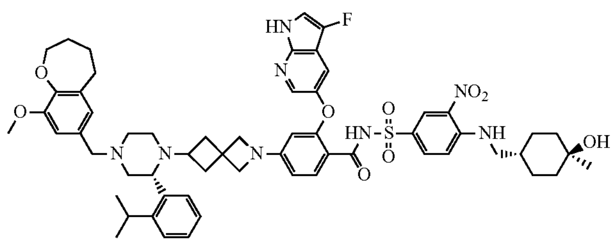 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc2c1OCCCC2] | 2-(3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-((9-methoxy-2,3,4,5-tetrahydrobenzo[b]oxepin-7-yl)methyl)piperazin-1-yl)-2-azaspiro[3.3]heptan-2-yl)benzamide | $^1$H NMR (400 MHz, DMSO-d$_6$) δ ppm: 11.56 (s, 1H), 11.43-11.07 (m, 1H), 8.58-8.55 (m, 2H), 8.08 (s, 1H), 7.80 (s, 1H). 7.52-7.44 (m, 4H), 7.19-7.16 (m, 4H), 6.75-6.65 (m, 2H), 6.07 (s, 1H), 5.55 (s, 1H), 4.27 (s, 1H), 3.88-3.51 (m, 12H), 2.94 (s, 2H), 2.68 (s, 4H), 2.30-2.24 (m, 4H), 1.99 (s, 3H), 1.86 (s, 2H), 1.73-1.50 (m, 9H), 1.40-1.0 (m, 17H). MS (ESI, m/e) [M + H]$^+$ 1085.7. |
| 348 | 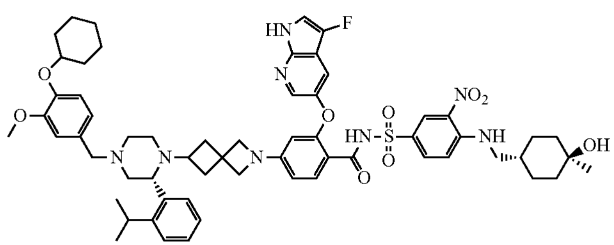 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1OC1CCCCC1] | 4-(6-((R)-4-(4-(cyclohexyloxy)-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.59 (s, 1H), 11.30 (br, 1H), 8.60-8.57 (m, 2H), 8.11 (s, 1H), 7.85-7.83 (m, 1H), 7.55 (s, 2H), 7.49-7.47 (m, 2H), 7.28-7.25 (m, 2H), 7.14-7.12 (m, 3H), 6.95-6.86 (m, 2H), 6.10 (d, J = 8.0 Hz, 1H), 5.58 (s,1H), 4.30 (s, 1H), 4.24 (s, 1H), 3.77 (m, 3H), 3.66-3.55 (m, 5H), 3.33 (s, 3H), 3.09-2.99 (m, 2H), 2.79-2.77 (m, 1H), 2.38-2.36 (m 3H), 2.04-2.01 (m, 2H), 1.88 (m, 2H), 1.73-1.71 (m, 6H), 1.59-1.56 (m 3H), 1.43-1.08 (m, 24H). MS (ESI, m/e) [M + 1]$^+$ 1113.9. |

| Ex. | structure | Compound name | Data |
|---|---|---|---|
| 349 | 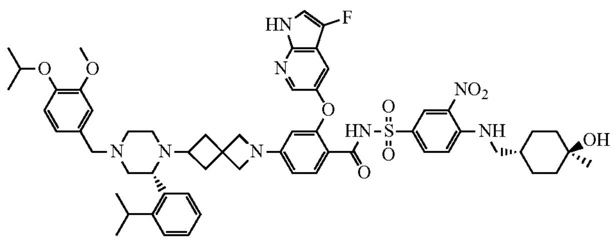 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1OC(C)C] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-4-(4-isopropoxy-3-methoxybenzyl)-2-(2-isopropylphenyl)piperazin-1-yl)-2-azaspiro[3.3]heptan-2-yl)benzamide | $^{1}$H NMR (400 MHz, DMSO-$d_6$) δ ppm: 11.46 (s, 1H), 8.4-8.45 (m, 2H), 8.00 (s, 1H), 7.73-7.70 (m, 1H), 7.43-7.35 (m, 4H), 7.16-6.99 (m, 4H), 6.85-6.79 (m, 2H), 6.72-6.70 (m, 1H), 6.01-5.99 (m, 1H), 5.50 (s, 1H), 4.41 (s, 1H), 4.20 (s, 1H), 3.65 (s, 3H), 3.56-3.45 (m, 6H), 3.22-3.16 (m, 4H-1), 2.87 (s, 3H), 2.68 (s, 3H), 2.16 (s, 3H), 1.98-1.91 (m, 3H), 1.64-1.61 (m, 4H), 1.31-1.24 (m, 3H), 1.14-0.96 (m, 12H). MS (ESI, m/e) [M + 1]$^+$ 1074.65. |
| 350 | 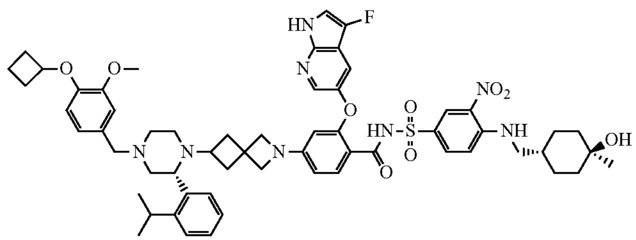 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1OC1CCC1] | 4-(6-((R)-4-(4-cyclobutoxy-3-methoxybenzyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)benzamide | $^{1}$H NMR (400 MHz, DMSO-$d_6$) δ ppm: 11.52 (s, 1H), 8.55-8.51 (m, 2H), 8.06 (s, 1H), 7.79-7.76 (m, 1H), 7.49 (s, 1H), 7.44-7.39 (m, 3H), 7.22-7.05 (m, 4H), 6.93 (s, 1H), 6.75-6.71 (m, 2H), 6.07-6.05 (m, 1H), 5.54 (s, 1H), 4.57 (s, 1H), 4.25 (s, 1H), 3.71 (s, 3H), 3.61-3.49 (m, 6H), 3.27-3.21 (m, 4H), 2.93 (s, 3H), 2.72 (s, 3H), 2.35 (s, 3H), 2.23 (s, 3H), 2.01-1.96 (m, 4H), 1.94-1.51 (m, 9H), 1.35-1.29 (m, 3H), 1.18-1.03 (m, 12H). MS (ESI, m/e) [M + 1]$^+$ 1086.13. |
| 351 | 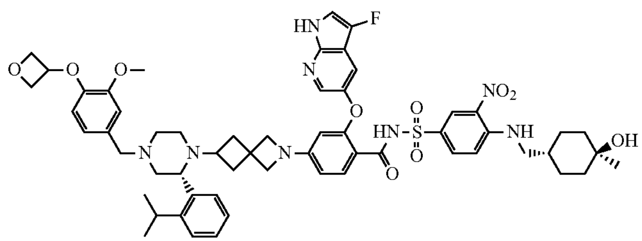 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1OC1COC1] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(oxetan-3-yloxy)benzyl)piperazin-1-yl)-2-azaspiro[3.3]heptan-2-yl)benzamide | $^{1}$H NMR (400 MHz, DMSO-$d_6$) δ ppm: 11.53 (s, 1H), 8.54-8.51 (m 2H), 8.06 (s, 1H), 7.49 (s, 1H), 7.45-7.39 (m, 3H), 7.21-7.08 (m, 4H), 6.75-6.73 (m, 1H), 6.53-6.51 (m, 1H), 6.07-6.05 (m, 1H), 5.55 (s, 1H), 5.15 (s, 1H), 4.85 (s, 2H), 4.51 (s, 2H), 4.25 (s, 1H), 3.74 (s, 3H), 3.60-3.49 (m, 6H), 3.27-3.24 (m, 4H), 2.90 (s, 2H), 2.71 (s, 1H), 2.57 (s, 1H), 2.20 (s, 2H), 2.01-1.94 (m, 3H), 1.68-1.66 (m, 4H), 1.55-1.51 (m, 2H), 1.35-1.29 (m, 3H), 1.17-1.02 (m, 12H). MS (ESI, m/e) [M + 1]$^+$ 1088.17. |
| 352 | 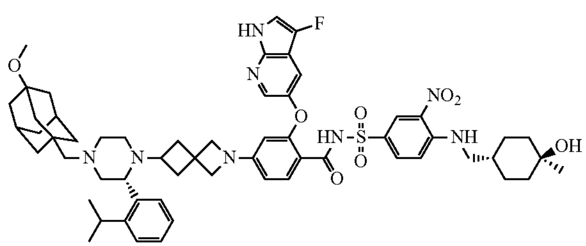 [SMILES: COC12CC3CC(CC(CN4CCN(C5CC6(C5)CN(c5ccc(C(=O)NS(=O)(=O)c7ccc(NC[C@H]8CC[C@](C)(O)CC8)c([N+](=O)[O-])c7)c(Oc7cnc8[nH]cc(F)c8c7)c5)C6)[C@H](c5ccccc5C(C)C)C4)(C3)C1)C2] | 2-((3-fluoro-1H-pyrrolo[2,3-b]pyridin-5-yl)oxy)-N-((4-((((1r,4r)-4-hydroxy-4-mmethylcyclohexyl)methyl)amino)-3-nitrophenyl)sulfonyl)-4-(6-((2R)-2-(2-isopropylphenyl)-4-(((1r,5R,7S)-3-methoxyadamantan-1-yl)methyl)piperazin-1-yl)-2-azaspiro[3.3]heptan-2-yl)benzamide | $^{1}$H NMR (400 MHz, DMSO-$d_6$) δ ppm: 11.58 (s, 1H), 11.42 (br, 1H), 8.59-8.56 (m, 2H), 8.10 (s, 1H), 7.83-7.81 on, 1H), 7.55-7.53 (m, 2H), 7.47-7.45 (m, 2H), 7.27-7.11 (m, 4H), 6.09 (d, J = 80 Hz, 1H), 5.57 (s, 1H), 4.28 (s, 1H), 3.65-3.53 (m, 5H), 3.31 (s, 3H), 3.06 (s, 3H), 2.88-2.84 (m, 2H), 2.13-2.00 (m, 5H), 1.72-1.12 (m, 39H). MS (ESI, m/e) [M + 1]$^+$ 1074.7. |

| Ex. | structure | Compound name | Data |
|---|---|---|---|
| 353 | 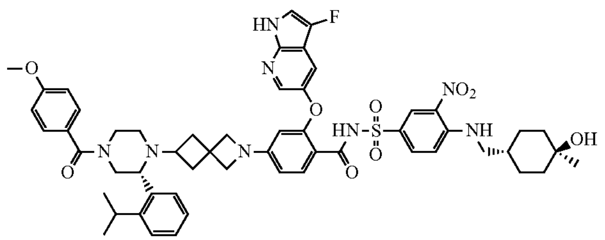 [SMILES: COc1ccc(C(=O)N2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc1] | 2-(6-((R)-4-((((1r,4r)-4-hydroxy-4-methylcyclohexyl)methyl)amino)-3-nitrophenyl)sulfonyl)-4-(6-((R)-2-(2-isopropylphenyl)-4-(4-methoxybenzoyl)piperazin-1-yl)-2-azaspiro[3.3]heptan-2-yl)benzamide | $^1$H NMR (400 MHz, DMSO-d$_6$) δ ppm: 11.55 (s, 1H), 11.41 (s, 1H), 8.57-8.54 (m, 2H), 8.08 (s, 1H), 7.82-7.80 (m, 2H), 7.55-7.51 (m, 2H), 7.44-7.36 (m, 4H), 7.20-7.10 (m, 4H), 6.93 (s, 1H), 6.07-6.05 (m, 2H), 5.53 (s, 1H), 4.25 (s, 1H), 3.75 (s, 3H), 3.61-3.51 (m, 5H), 3.28 (s, 3H), 2.96 (s, 3H), 2.76 (s, 6H), 2.07-1.95 (m, 3H), 1.69-1.66 (m, 4H), 1.55-1.52 (m, 2H), 1.36-1.29 (m, 3H), 1.16-1.09 (m, 11H), 0.84 (s, 2H). MS (ESI, m/e) [M + 1]$^+$ 1029.9. |
| 354 | 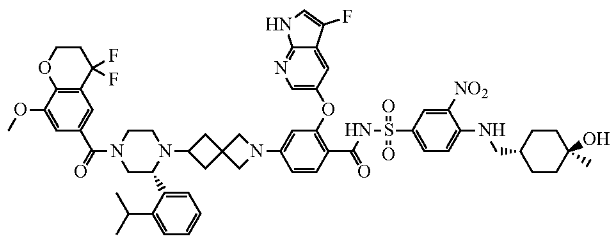 | 4-(6-((R)-4-((4,4-difluoro-8-methoxychroman-6-yl)methyl)-2-(2-isopropylphenyl)piperazin-1-yl)-2-azaspiro[3.3]heptan-2-yl)-2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)benzamide | $^1$H NMR (400 MHz, DMSO-d$_6$) δ ppm: 11.48 (s, 1H), 11.28 (br, 1H), 8.50-8.47 (m, 2H), 8.01 (s, 1H), 7.74-7.73 (m, 1H), 7.45-7.37 (m, 4H), 7.16-4H), 6.96 (m, 6H), 6.02-6.00 (m, 1H), 5.50 (s, 1H), 4.21 (s, 3H), 3.69 (s, 3H), 3.57-3.45 (m, 6H), 3.29 (s, 3H), 2.85 (s, 2H), 2.68 (s, 1H), 2.17 (s, 2H), 1.97-1.93 (m, 3H), 1.61-1.47 (m, 7H), 1.30-0.99 (m, 16H), 0.81 (s, 1H). MS (ESI, m/e) [M + 1]$^+$ 1108.1. |
| 355 | 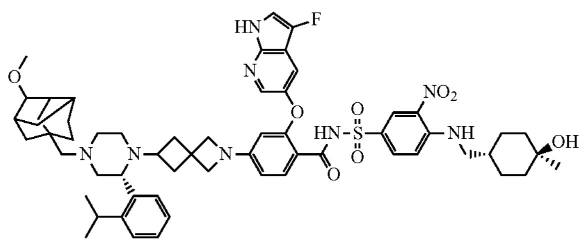 [SMILES: COC1C2CC3CCC(CN4CCN(C5CC6(C5)CN(c5ccc(C(=O)NS(=O)(=O)c7ccc(NC[C@H]8CC[C@](C)(O)CC8)c([N+](=O)[O-])c7)c(Oc7cnc8[nH]cc(F)c8c7)c5)C6)[C@H](c5ccccc5C(C)C)C4)(C2)CC31] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((2R)-2-(2-isopropylphenyl)-4-((3-methoxyoctahydro-5H-2,5-methanoinden-5-yl)methyl)piperazin-1-yl)-2-azaspiro[3.3]heptan-2-yl)benzamide | $^1$H NMR (400 MHz, DMSO-d$_6$) δ ppm: 11.53 (s, 1H), 8.54-8.51 (m, 2H), 8.06 (s, 1H), 7.78-7.77 (m, 1H), 7.49-7.39 (m, 4H), 7.22-7.09 (m, 4H), 6.07-6.05 (m, 2H), 5.55 (m, 1H), 4.25 (s, 1H), 3.61-3.50 (m, 5H), 3.28 (s, 3H), 3.19 (s, 4H), 2.79-2.72 (m, 3H), 2.19 (s, 2H), 1.99-1.92 (m, 6H), 1.81 (s, 2H), 1.69-1.52 (m, 13H), 1.39-1.29 (m, 6H), 1.21-1.09 (m, 13H). MS (ESI, m/e) [M + 1]$^+$ 1073.9. |
| 356 | | 2-((3-fluoro-1H-pyrrolo[2,3-b]pyridin-5-yl)oxy)-4-(6-((R)-2-(2-isopropylphenyl)-4-(4-methoxybenzyl)piperazin-1-yl)-2-azaspiro[3.3]heptan-2-yl)-N-((4-(((1S,3R,7S)-4-methoxyadamantan-1-yl)methyl)amino)-3-nitrophenyl)sulfonyl)benzamide | $^1$H NMR (400 MHz, DMSO-d$_6$) δ ppm: 11.50 (s, 1H), 8.48-8.45 (m, 2H), 8.02 (s, 1H), 7.74-7.72 (m, 1H), 7.46 (s, 2H), 7.37-7.35 (m, 2H), 7.22-7.08 (m, 6H), 6.87-6.85 (m, 2H), 6.01 (d, J = 8.0 Hz, 1H), 5.49 (s, 1H), 3.68 (s, 3H), 3.58-3.43 (m, 5H), 3.20-3.18 (m, 5H), 3.12-3.10 (m, 1H), 3.06-3.05 (m, 1H), 2.91-2.89 (m, 1H), 2.69-2.65 (m, 1H), 2.22-2.19 (m 1H), 2.03-1.93 (m, 5H), 1.82-1.81 (m, 1H), 1.72-1.46 (m, 9H), 1.29-1.10 (m, 10H), 1.02-1.01 (m, 31), MS (ESS, m/e) [M + 1]$^+$ 1068.0. |

| Ex. | structure | Compound name | Data |
|---|---|---|---|
| 357 | 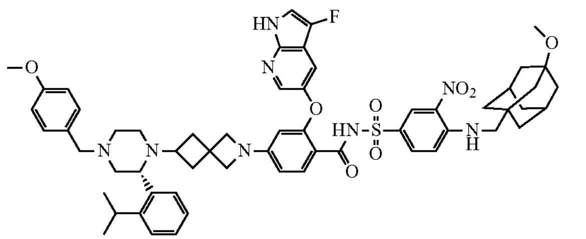 [SMILES: COc1ccc(CN2CCN(C3CC4(C3)CN(c3ccc(C(=O)NS(=O)(=O)c5ccc(NCC67CC8CC(C6)CC(OC)(C8)C7)c([N+](=O)[O-])c5)c(Oc5cnc6[nH]cc(F)c6c5)c3)C4)[C@H](c3ccccc3C(C)C)C2)cc1] | 2-((3-fluoro-1H-pyrrolo[2,3-b]pyridin-5-yl)oxy)-4-(6-((R)-2-(2-isopropylphenyl)-4-(4-methoxybenzyl)piperazin-1-yl)-2-azaspiro[3.3]heptan-2-yl)-N-(4-(((1r,5R,7S)-3-methoxyadamantan-1-yl)methyl)amino)-3-nitrophenyl)sulfonyl)benzamide | 1H NMR (400 MHz, DMSO-d6) δ ppm: 11.51 (s, 1H), 8.50 (s, 2H), 8.05 (s, 1H), 7.76-7.73 (m, 1H), 7.49-7.39 (m, 4H), 7.21-7.10 (m, 6H), 6.87-6.85 (m, 2H), 6.06-6.04 (m, 1H), 5.55 (s, 1H), 3.71 (s, 3H), 3.62-3.46 (m, 7H), 3.31 (s, 2H), 3.21-3,19 (m, 3H), 3.08 (s, 3H), 2.89-2.87 (m, 2H), 2.71 (s, 1H), 2.17 (s, 4H), 2.01-1.94 (m, 2H), 1.64-1.55 (m, 5H), 1.50-1.41 (m, 8H), 1.34-1.29 (m, 1H), 1.18-1.17 (m, 3H), 1.04-1.03 (m 3H). MS (ESI, m/e) [M + 1]+ 1068.4. |
| 358 | 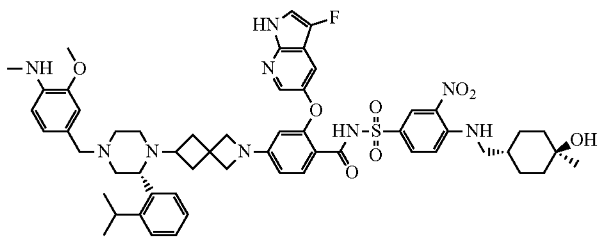 [SMILES: CNc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc1OC] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(methylamino)benzyl)piperazin-1-yl)-2-azaspiro[3.3]heptan-2-yl)benzamide | 1H NMR (400 MHz, DMSO-d6) δ ppm: .11.61 (s, 1H), 8.62-8.59 (m, 2H), 8.14-8.13 (m, 1H), 7.86-7.84 (m, 1H), 7.57 (s, 2H), 7.52-7.47 (m, 2H), 7.33-7.30 (m, 2H), 7.24-7.21 (m, 2H), 7.15-7.13 (m, 1H), 6.97-6.87 (m, 2H), 6.48-6.46 (m, 1H), 6.14-6.11 (m, 1H), 5.61 (s, 1H), 4.32 (s, 1H), 3.85-3.82 (m, 4H), 3.70-3.55 (m, 6H), 3.36-3.33 (m, 2H), 3.06-3.04 (m, 2H), 2.75-2.73 (m, 4H), 2.08-2.04 (m, 2H), 1.76-1.70 (m, 4H), 1.62-1.59 (m, 2H), 1.42-1.16 (m, 21H), MS (ESI, m/e) [M + 1]+ 1045.2. |
| 359 | 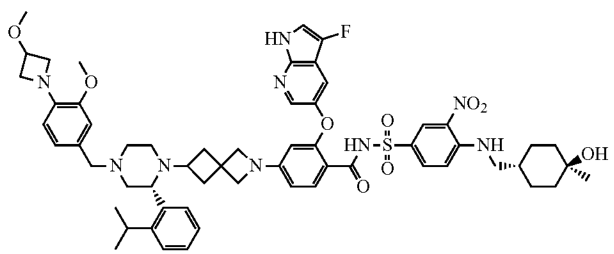 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1N1CC(OC)C1] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(3-methoxyazetidin-1-yl)benzyl)piperazin-1-yl)-2-azaspiro[3.3]heptan-2-yl)benzamide | 1H NMR (400 MHz, DMSO-d6) δ ppm: 11.51 (s, 1H), 8.50-8.49 (m, 2H), 8.04 (s, 1H), 7.76-7.74 (m, 1H), 7.48-7.39 (m, 4H), 7.21-7.10 (m, 4H), 6.81-6.67 (m, 2H), 6.31-6.29 (m, 1H), 6.05 (d, J = 8.0 Hz, 1H), 5.55 (s,1H), 4.24 (s, 1H), 4.39-4.17 (m, 1H), 4.04-4.01 (m, 2H), 3.68 (s, 3H), 3.62-3.60 (m, 1H), 3.56-3.47 (m, 5H), 3.26-3.25 (m, 2H), 3.19 (s, 1H), 2.89-2.87 (m, 1H), 2.72-2.70 (m, 1H), 2.22-2.20 (m, 1H), 2.02-1.97 (m, 3H), 1.68-1.65 (m, 4H), 1.54-1.51 (m, 2H), 1.34-1.05 (m, 22H), MS (ESI, m/e) [M + 1]+ 1101.5. |

| Ex. | structure | Compound name | Data |
|---|---|---|---|
| 360 | 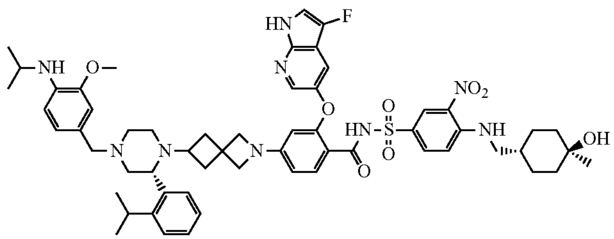 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1NC(C)C] | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-4-(4-(isopropylamino)-3-methoxybenzyl)-2-(2-isopropylphenyl)piperazin-3-yl)-2-azaspiro[3.3]heptan-2-yl)benzamide | ¹H NMR (400 MHz, DMSO-d₆) δ ppm: 11.60 (s, 1H), 8.62-8.58 (m, 2H), 8.13-8.12 (m, 1H), 7.86-7.83 (m, 1H), 7.56-7.46 (m, 4H), 7.32-7.12 (m, 5H), 7.02-7.00 (m, 1H), 6.87-6.85 (m, 1H), 6.56-6.54 (m, 1H), 6.12 (d, J = 8.0 Hz, 1H), 5.60 (s, 1H), 4.56 (br, 1H), 4.32 (s, 1H), 3.96 (br, 1H), 3.85-3.82 (m, 4H), 3.69-3.54 (m, 6H), 3.35-3.32 (m, 3H), 3.05-3.03 (m, 1H), 2.80-2.78 (m, 1H), 2.46-2.44 (m, 1H), 2.04-2.03 (m, 2H), 1.75-1.70 (m, 4H), 1.61-1.58 (m, 2H), 1.41-1.35 (m, 3H), 1.29-1.25 (m, 4H), 1.19-1.15 (m, 16H). MS (ESI, m/e) [M + 1]⁺ 1072.6. |
| 361 | 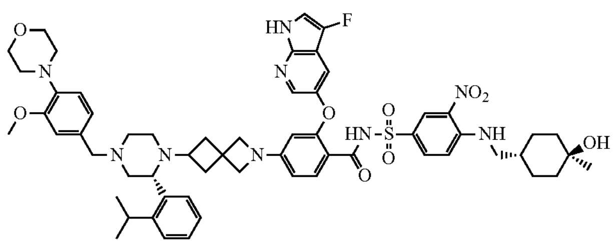 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1N1CCOCC1] | 2-((3-fluoro-1H-pyrrolo[2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-morpholinobenzyl)piperazin-1-yl)-2-azaspiro[3.3]heptan-2-yl)benzamide | ¹H NMR (400 MHz, DMSO-d₆) δ ppm: 11.52 (s, 1H), 8.53-8.50 (m, 2H), 8.06-8.05 (m, 1H), 7.78-7.76 (m, 1H), 7.49-7.39 (m, 4H), 7.21-7.04 (m, 4H), 6.89 (s, 1H), 6.79 (s, 2H), 6.07-6.04 (m, 1H), 5.55 (s, 1H), 4.25 (s, 1H), 3.75 (s, 3H), 3.69-3.67 (m, 4H), 3.62-3.47 (m, 7H), 3.31 (s, 2H), 3.28-3.25 (m, 2H), 2.91-2.88 (m, 6H), 2.72 (s, 1H), 2.59 (s, 1H), 2.23-2.19 (m, 1H), 2.03-1.95 (m, 2H), 1.69-1.62 (m, 4H), 1.55-1.51 (m, 2H), 1.35-1.29 (m, 3H) 1.23-1.02 (m, 13H). MS (ESI, m/e) [M + 1]⁺ 1100.8. |
| 362 | 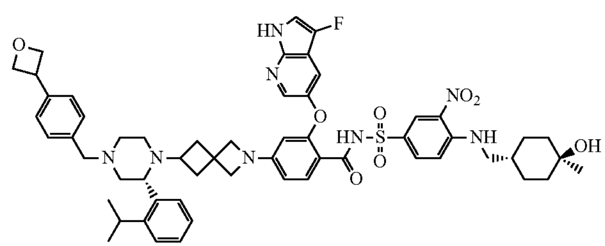 [SMILES: CC(C)c1ccccc1[C@@H]1CN(Cc2ccc(C3COC3)cc2)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 2-((3-fluoro-1H-pyrrolo [2,3-b]pyridin-5-yl)oxy)-N-((4-(((1r,4r)-4-hydroxy-4-methylcyclohexyl)methyl)amino)-3-nitrophenyl)sulfonyl)-4-(6-((R)-2-(2-isopropylphenyl)-4-(4-(oxetan-3-yl)benzyl)piperazin-1-yl)-2-azaspiro[3.3]heptan-2-yl)benzamide | ¹H NMR (400 MHz, DMSO-d₆) δ ppm: 11.54 (s, 1H), 8.56-8.52 (m, 2H), 8.07-8.06 (m, 1H), 7.80-7.78 (m, 1H), 7.51-7.50 (m, 2H), 7.44-7.42 (m, 1H), 7.35-7.29 (m, 4H), 7.22-7.15 (m, 2H), 7.09-7.07 (m, 2H), 6.05-6.04 (m, 1H), 5.53 (s, 1H), 4.93-4.89 (m, 2H), 4.58-4.54 (m, 2H), 4.25 (s, H1), 4.22-4.16 (m, 1H), 3.61-3.47 (m, 7H), 3.29-3.26 (m 4H), 2.91-2.82 (m 2H) 2.71 (s, 1H), 2.59 (s, 1H), 2.23-2.18 (m, 2H), 2.01-1.92 (m, 2H), 1.68-1.62 (m, 4H), 1.54-1.51 (m, 2H), 1.35-1.29 (m, 3H), 1.22-1.01 (m, 13H). MS (ESI, m/e) [M + 1]⁺ 1041.7. |

-continued

| Ex. | structure | Compound name | Data |
|---|---|---|---|
| 363 | 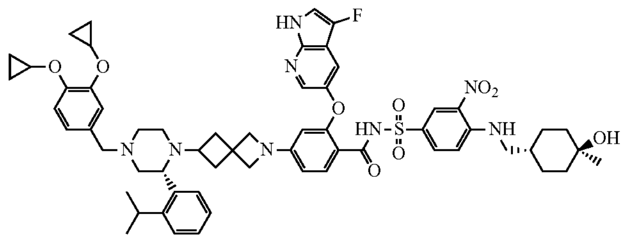 [SMILES: CC(C)c1ccccc1[C@@H]1CN(Cc2ccc(OC3CC3)c(OC3CC3)c2)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 4-(6-((R)-4-(3,4-dicyclopropoxybenzyl)-2-(2-isopropylphenyl)piperazin-1-yl)-2-azaspiro[3.3]heptan-2-yl)-2-(3-fluoro-1H-pyrrolo[2,3-b]pyridin-5-yl)oxy)-N-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.52 (s, 1H), 8.61-8.43 (m, 2H), 8.06 (d, J = 2.4 Hz, 1H), 7.77 (d, J = 8.4 Hz, 1H), 7.54-7.33 (m, 4H), 7.27-6.99 (m, 6H), 6.82 (d, J = 8.4 Hz, 1H), 6.06 (d, J = 8.8 Hz, 1H), 5.56 (s, 1H), 4.25 (s, 1H), 3.77-3.69 (m, 2H), 3.66-3.39 (m, 7H), 3.31-3.15 (m, 3H), 2.99-2.83 (m, 2H), 2.77-2.53 (m, 2H), 2.36-1.86 (m, 5H), 1.74-1.49 (m, 6H), 1.40-1.27 (m, 3H) 1.22-1.00 (m, 11H), 0.76-0.56 (m, 8H). MS (ESI, m/e) [M + 1]⁺ 1096.9. |
| 364 | | 4-(6-((R)-4-(3-cyclopropoxy-4-methoxybenzyl)piperazin-1-yl)-2-(2-isopropylphenyl)-2-azaspiro[3.3]heptan-2-yl)-2-(3-fluoro-1H-pyrrolo[2,3-b]pyridin-5-yl)oxy)-N-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.56 (s, 1H), 11.12 (s, 1H), 8.59-8.54 (m, 2H), 8.09-8.08 (m, 1H), 7.82-7.80 (m, 1H), 7.53-7.52 (m, 2H), 7.47-7.42 (m, 2H), 7.25-7.22 (m, 3H), 7.14-7.09 (m, 2H), 6.90 (s, 1H), 6.08 (d, J = 8.0 Hz, 1H), 5.56 (s, 1H), 4.27 (s, 1H), 3.80-3.50 (m, 12H), 3.24 (s, 1H), 3.32-3.28 (m, 2H), 3.04-2.97 (m, 2H), 2.73-2.69 (m, 1H), 2.30-2.28 (m, 1H), 2.02-2.00 (m, 2H), 1.71-1.65 (m, 4H), 1.57-1.54 (m, 2H), 1.37-1.31 (m, 3H), 1.25-1.08 (m, 14H), 0.76-0.73 (m, 2H), 0.65-0.62 (m, 2H). MS (ESI, m/e) [M + 1]⁺ 1071.6. |
| 365 | 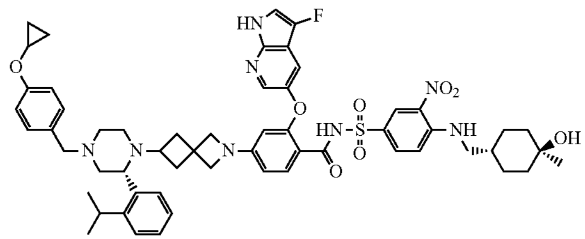 [SMILES: CC(C)c1ccccc1[C@@H]1CN(Cc2ccc(OC3CC3)cc2)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 4-(6-((R)-4-(4-cyclopropoxyphenyl)piperazin-1-yl)-2-(2-isopropylphenyl)-2-azaspiro[3.3]heptan-2-yl)-2-(3-fluoro-1H-pyrrolo[2,3-b]pyridin-5-yl)oxy)-N-((((1r,4r)-4-hydroxy-4-methylcyclohexyl)methyl)amino)-3-nitrophenyl)sulfonyl)benzamide | ¹H NMR (400 MHz, DMSO-d₆) δ ppm: 11.18 (s, 1H), 8.21-8.16 (m, 2H), 7.71-7.70 (m, 1H), 7.44-7.42 (m, 1H), 7.16-7.14 (m, 2H), 7.07-7.02 (m, 2H), 6.94-6.84 (m, 4H), 6.76-6.71 (m, 2H), 6.67-6.64 (m, 2H), 5.68 (d, J = 8.0 Hz, 1H), 5.15 (s,1H), 3.88 (s, 1H), 3.43 (s, 1H), 3.25-3.11 (m, 5H), 2.93-2.89 (m, 2H), 2.85-2.83 (m, 1H), 2.60-2.58 (m, 2H), 2.36-2.30 (m, 1H), 1.91-1.89 (m, 1H), 1.63-1.59 (m, 2H), 1.32-1.25 (m, 4H), 1.18-1.15 (m, 2H), 0.98-0.92 (m, 3H), 0.86-0.69 (m, 16H), 0.39-0.38 (m, 2H), 0.25-0.23 (m, 2H). MS (ESI, m/e) [M + 1]⁺ 1041.6. |

| Ex. | structure | Compound name | Data |
|---|---|---|---|
| 366 | 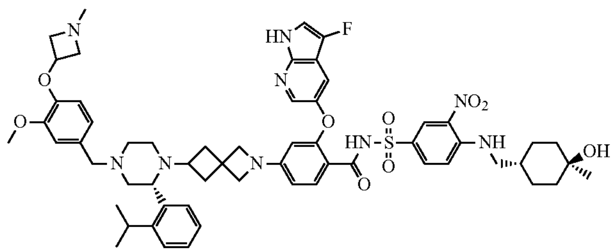 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1OC1CN(C)C1] | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(1-methylazetidin-3-yloxy)benzyl)piperazin-1-yl)-2-azaspiro[3.3]heptan-2-yl)benzamide | $^1$H NMR (400 MHz, DMSO-$d_6$) δ ppm: 11.29 (s, 1H), 8.31-8.25 (m 2H), 8.08-8.07 (m, 1H), 7.90-7.87 (m, 1H), 7.50-7.45 (m, 2H), 7.33-7.32 (m, 2H), 7.15-7.00 (m, 4H), 6.83 (s, 1H), 6.72-6.70 (m, 1H), 6.65-6.64 (m, 1H), 6.55-6.54 (m, 1H), 6.00-5.98 (m, 1H), 5.61-5.58 (m, 1H), 4.67-4.60 (m, 1H), 4.17 (s, 1H), 3.98-3.79 (m, 3H), 3.65 (s, 4H), 3.53-3.40 (m, 6H), 3.16-3.14 (m, 4H), 2.99-2.93 (m, 1H), 2.80-2.77 (m, 3H), 2.66-2.64 (m, 1H), 2.10 (s, 2H), 1.96-1.84 (m, 2H), 1.62-1.54 (m, 4H), 1.48-1.44 (m, 2H), 1.28-1.23 (m, 3H), 1.16-1.02 (m, 10H), 0.96-0.95 (m, 3H). MS (ESI, m/e) [M + 1]$^+$ 1101.01. |
| 367 | 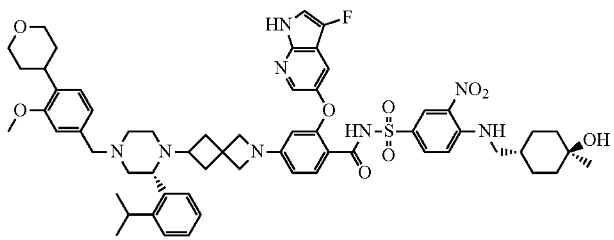 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1C1CCOCC1] | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(tetrahydro-2H-pyran-4-yl)benzyl)piperazin-1-yl)-2-azaspiro[3.3]heptan-2-yl)benzamide | $^1$H NMR (400 MHz, DMSO-$d_6$) δ ppm: 11.52 (s, 1H), 8.54-8.51 (m, 2H), 8.06-8.05 (m, 1H), 7.79-7.76 (m, 1H), 7.49-7.40 (m, 4H), 7.20-7.08 (m, 5H), 6.90 (s, 1H), 6.84-6.82 (m, 1H), 6.07-6.04 (m, 1H), 5.55 (s, 1H), 4.25 (s, 1H), 3.91-3.89 (m, 2H), 3.75 (s, 3H), 3.62-3.47 (m, 7H), 3.43-3.36 (m, 2H), 3.31 (s, 2H), 3.29-3.26 (m, 2H), 3.08-3.01 (m, 1H), 2.91-2.88 (m, 2H), 2.72 (s, 1H), 2.23-2.19 (m, 1H), 2.02-1.96 (m, 2H), 1.68-1.51 (m, 10H), 1.35-1.29 (m, 3H), 1.23-1.09 (m, 10H), 1.02-1.00 (m, 3H). MS (ESI, m/e) [M + 1]$^+$ 1099.4. |
| 368 | 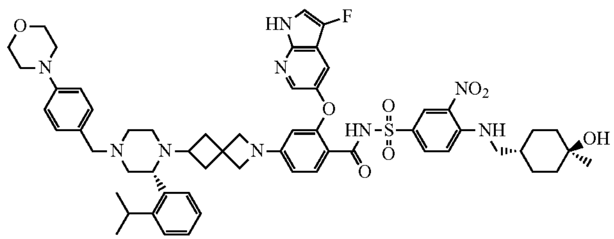 [SMILES: CC(C)c1ccccc1[C@@H]1CN(Cc2ccc(N3CCOCC3)cc2)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 2-((3-fluoro-1H-pyrrolo[2,3-b]pyridin-5-yl)oxy)-N-(4-((((1r,4r)-4-hydroxy-4-methylcyclohexyl)methyl)amino)-3-nitrophenyl)sulfonyl)-4-(6-((R)-2-(2-isopropylphenyl)-4-(4-morpholinobenzyl)piperazin-1-yl)-2-azaspiro[3.3]heptan-2-yl)benzamide | $^1$H NMR (400 MHz, DMSO-$d_6$) δ ppm: 11.51 (s, 1H), 8.57-8.43 (m, 2H), 8.05 (d, J = 2.8 Hz, 1H), 7.76 (d, J = 8.4 Hz, 1H), 7.53-7.30 (m, 4H), 7.27-6.99 (m, 6H), 6.87 (d, J = 8.4 Hz, 2H), 6.05 (dd, J = 1.6 Hz, 8.8 Hz, 1H), 5.56 (s, 1H), 4.25 (s, 1H), 3.76-3.66 (m, 4H), 3.65-3.39 (m, 7H), 3.31-3.14 (m, 3H), 3.11-3.00 (m, 4H), 2.97-2.82 (m, 2H), 2.77-2.55 (m 2H), 2.42-1.86 (m, 5H), 1.74-1.49 (m, 6H), 1.40-1.27 (m, 3H), 1.22-1.00 (m, 11H), 0.76-0.56 (m, 8H). MS (ESI, m/e) [M + 1]$^+$ 1070.9. |

| Ex. | structure | Compound name | Data |
|---|---|---|---|
| 369 | 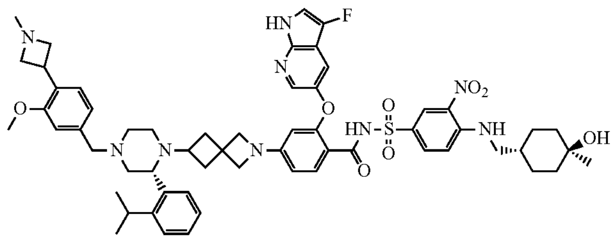 [SMILES: COc1cc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)ccc1C1CN(C)C1] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(3-methoxy-4-(1-methylazetidin-3-yl)benzyl)piperazin-1-yl)-2-azaspiro[3.3]heptan-2-yl)benzamide | $^1$H NMR (400 MHz, DMSO-$d_6$) δ ppm: 11.39 (s, 1H), 8.31-8.25 (m, 2H), 8.38 (s, 2H), 7.97 (s, 1H), 7.62-7.59 (m, 1H), 7.52-7.50 (m, 1H), 7.41 (s, 2H), 7.22-7.06 (m, 5H), 6.93 (s, 1H), 6.87-6.85 (m, 2H), 6.07-6.05 (m, 1H), 5.66 (s, 1H), 4.24 (s, 1H), 4.17 (s, 2H), 3.97 (s, 3H), 3.60-3.42 (m, 8H), 3.24-3.22 (m, 3H), 2.73 (s, 3H), 2.18-2.17 (m, 2H), 2.05-1.90 (m, 3H), 1.68-1.51 (m, 6H), 1.35-1.29 (m, 3H) 1.23-1.03 (m, 13H). MS (ESI, m/e) [M + 1]$^+$ 1084.7. |
| 370 | 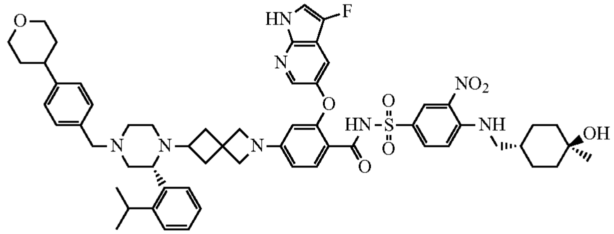 [SMILES: CC(C)c1ccccc1[C@@H]1CN(Cc2ccc(C3CCOCC3)cc2)CCN1C1CC2(C1)CN(c1ccc(C(=O)NS(=O)(=O)c3ccc(NC[C@H]4CC[C@](C)(O)CC4)c([N+](=O)[O-])c3)c(Oc3cnc4[nH]cc(F)c4c3)c1)C2] | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((R)-2-(2-isopropylphenyl)-4-(4-(tetrahydro-2H-pyran-4-yl)benzyl)piperazin-1-yl)-2-azaspiro[3.3]heptan-2-yl)benzamide | $^1$H NMR (400 MHz, DMSO-$d_6$) δ ppm: 11.53 (s, 1H), 8.54-8.51 (m, 2H), 8.06-8.05 (m, 1H), 7.78-7.76 (m 1H), 7.49-7.38 (m, 4H), 7.22-7.16 (m, 6H), 7.07-7.04 (m 2H), 6.06-6.04 (m, 1H), 5.54 (s, 1H), 4.25 (s, 1H), 3.93-3.90 (m, 2H), 3.60-3.47 (m, 6H), 3.43-3.36 (m, 2H), 3.31 (s, 1H), 3.28-3.25 (m, 2H), 2.89-2.86 (m, 2H), 2.72-2.66 (m, 2H), 2.25-2.18 (m, 2H), 2.02-1.95 (m, 3H), 1.69-1.51 (m, 11H), 1.35-1.29 (m, 3H), 1.22-1.09 (m, 10H), 1.01-0.99 (m, 3H). MS (ESI, m/e) [M + 1]$^+$ 1069.8. |
| 371 | 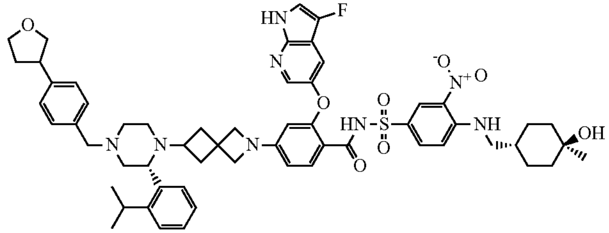 | 2-((3-fluoro-1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((2R)-2-(2-isopropylphenyl)-4-(4-(tetrahydrofuran-3-yl)benzyl)piperazin-1-yl)-2-azaspiro[3.3]heptan-2-yl)benzamide | $^1$H NMR (400 MHz, DMSO-$d_6$) δ ppm: 11.60 (s, 1H), 8.62-8.59 (m 2H), 8.13 (s, 1H), 7.86-7.84 (m, 1H), 7.57-7.49 (m, 4H), 7.28-7.14 (m, 8H), 6.13-6.11 (m, 1H), 5.60 (s, 1H), 4.32 (s, 1H), 4.01-3.94 (m, 1H), 3.86-3.80 (m, 1H), 3.67-3.52 (m, 7H), 3.34-3.33 (m, 2H), 2.95-2.94 (m, 2H), 2.78-2.77 (m, 1H), 2.34-2.25 (m, 3H), 2.07-1.89 (m, 4H), 1.75-1.58 (m, 7H), 1.41-1.36 (m, 3H), 1.29-1.08 (m, 13H). MS (ESI, m/e) [M + 1]$^+$ 1056.2. |

Biological example: Bcl-2 TR-FRET assay:

Compounds disclosed herein were tested for blocking of Bcl-2 protein with its ligand in an assay based on Time-Resolved Fluorescence Resonance Energy Transfer (TR-FRET) methodology. Recombinant human 0.05 nM Bcl-2 protein was pre-incubated with a serial dilution of compounds disclosed herein (top final concentration is 1 uM or 0.1 uM or 0.02 uM or 0.01 uM, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then the FITC labeled Bak peptide Ac-GQVGRQLAIIGDK(FITC)INR-amide (0.5 nM) and MAb Anti 6His Tb cryptate Gold were added to plate and further incubated at room temperature for 1 hour. The TR-FRET signals (337 nm-520 nm-490 nm) were read on BMG PHERAstar FSX instrument. The inhibition percentage of Bcl-2 interaction with its ligand in presence of increasing concentrations of compounds was calculated based on the TR-FRET signals. The $IC_{50}$ for each compound was derived from fitting the data to the four-parameter logistic equation by Graphpad Prism software or Dotmatics. Data are shown in Table 3.

Biological Example: Bcl-2-G101V TR-FRET Assay

Compounds disclosed herein were tested for blocking of Bcl-2-G101V protein with its ligand in an assay based on time-resolved fluorescence resonance energy transfer methodology. 0.1 nM recombinant human Bcl-2-G101 V protein was pre-incubated with a serial dilution of compounds disclosed herein (top final concentration is 10 uM or 1 uM or 0.1 uM, 4-fold or 3-fold serially diluted, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then 5 nM FITC labeled Bak peptide Ac-GQVGRQLAIIGDK(FITC) INR-amide and Mab Anti-6His Tb cryptate Gold was added to plate and further incubated at room temperature for 1 hour. The TR-FRET signals (ex337 nm, em490 nm/520 nm) were read on BMG PHERAstar FSX instrument. The inhibition percentage of Bcl-2-G101V interaction with its ligand in presence of increasing concentrations of compounds was calculated based on the ratio of fluorescence at 490 nm to that at 520 nm. The $IC_{50}$ for each compound was derived from fitting the data to the four-parameter logistic equation by Graphpad Prism software or Dotmatics. Data are shown in Table 3.

Biological Example: RS4; 11 Cell Proliferation Assay

The BCL-2 dependent acute lymphoblastic leukemia (ALL) cell line, RS4; 11, was used to study the cellular potency of BCL-2 inhibitors. The cells (ATCC, CRL-1873) were cultured in RPMI-1640 complete medium (RPMI-1640 medium, HEPES (Gibco, 22400-105) supplemented with 10% fetal bovine serum (FBS) (Gibco, 10099-1441), 100 unit/ml penicillin and 100 μg/ml streptomycin (Gibco, 15140122)) and maintained in a humidified chamber at 37° C. containing 5% $CO_2$. Each compound was serially diluted with 1 μM as the maximum concentration. To test the apoptotic effect of the compounds, the cells were seeded at 50,000 in 180 μl per well in 96-well plates and treated with 10-point dilution series of each compound for 48 hrs at 37° C. Cell viability was assessed after the treatment using CellTiter-GLO luminescent assay (Promega) according to the manufacturer's recommendations. Briefly, 30 μl of CellTiter-GLO reagent was added into 200 μl of cell culture. Mixture was agitated on an orbital shaker for 5 min to ensure cell lysis followed by 7 min incubation at room temperature to allow development and stabilization of luminescent signals, which corresponded to the quantity of ATP and thus the quantity of metabolically active cells. Luminescent signals were measured using PHERAstar FS reader (BMG). Mean $IC_{50}$ values were determined with GraphPad Prism software. Data are shown in Table 3.

Biological example: Bcl 2-G101V knock-in RS4; 11 cell proliferation assay (1) RS4; 11 H96 Bcl 2-G101V Knock-In Cell Line Generation Briefly, RS4; 11 BCL2-G101V knock-in cell pool was generated using Crisper/Cas9 gene editing system and the BCL2-G101V knock-in single clone H96 was picked from the knock-in cell pool and validated by WES (whole exome-sequencing) and RNA-seq.

The BCL-2 dependent acute lymphoblastic leukemia (ALL) cell line, RS4; 11(ATCC, CRL-1873), was cultured in RPMI-1640 complete medium (RPMI-1640 medium, HEPES (Gibco, 22400-105) supplemented with 10% fetal bovine serum (FBS) (Gibco, 10099-1441), 100 unit/ml penicillin and 100 μg/ml streptomycin (Gibco, 15140122)) and maintained in a humidified chamber at 37° C. containing 5% CO2.

To obtain BCL2-G101 V knock-in cell pool, RS4; 11 was co-transfected with the Cas9-gRNA which also expressed GFP label, and the Donor gene which contained the BCL2-G101V mutant sequence. After 48 hrs of electroporation, the GFP positive cells were collected through FACSAriaIII cell sorting system. Cell pool was recovered for 3 days and then cultured under 2 nM ABT-199 stress for 4 weeks. TA clone sequencing results showed 9% knock-in rate in the pool after ABT-199 treatment. Then cells were plated in 96 well U-plate with 1 cell/well for 10000 wells for single clone selection. After 3-5 weeks growing, clones were successively screened by PCR sequencing. And three BCL2-G101V knock-in clones: H96, H142 and H233, have been picked out.

Three clones were validated by genome DNA and cDNA (mRNA) PCR sequencing, and BCL-2, BCL-xL and MCL-1 expression using Western Blot. The H96 clone was also validated by WES (whole exome-sequencing) and RNA-seq.

(2) Bcl 2-G101V Knock-In RS4; 11 Cell Proliferation Assay

The BCL-2 G101V knock-in cell line H96 (derive from RS4; 11) were used to study the cellular potency of BCL-2 inhibitors. The cells were cultured in RPMI-1640 complete medium (RPMI-1640 medium, HEPES (Gibco, 22400-105) supplemented with 10% fetal bovine serum (FBS) (Gibco, 10099-1441), 100 unit/ml penicillin and 100 μg/ml streptomycin (Gibco, 15140122)) and maintained in a humidified chamber at 37° C. containing 5% $CO_2$. Each compound was serially diluted with 1 μM or 10 μM as the maximum concentration. To test the apoptotic effect of the compounds, the cells were seeded at 50,000 in 90 μl per well in 96-well plates and treated with 10-point dilution series of each compound for 48 hrs at 37° C. Cell viability was assessed after the treatment using CellTiter-GLO luminescent assay (Promega) according to the manufacturer's recommendations. Briefly, 30 μl of CellTiter-GLO reagent was added into 100 μl of cell culture. Mixture was agitated on an orbital shaker for 5 min to ensure cell lysis followed by 7 min incubation at room temperature to allow development and stabilization of luminescent signals, which corresponded to the quantity of ATP and thus the quantity of metabolically active cells. Luminescent signals were measured using PHERAstar FS reader (BMG). Mean $IC_{50}$ values were determined with GraphPad Prism software. Data are shown in Table 3.

TABLE 3

| Example | Biochemical assay (IC50, nM) Bcl-2 WT | Bcl-2 G101V | Ratio of Bcl-2 G101V/WT | Cellular proliferation assay (IC50, nM) RS4; 11 | RS4; 11 Bd-2 G101V knock-in |
|---|---|---|---|---|---|
| 2 | 0.011 | 0.25 | 22.7 | 0.53 | 3.94 |
| 3a | 0.034 | 2.2 | 64.7 | 3.67 | 35.07 |
| 3b | 0.0083 | 0.14 | 16.9 | | |
| 4 | 0.045 | 1.6 | 35.6 | 0.87 | 9.56 |
| 5 | 0.037 | 0.45 | 12.2 | 0.58 | 5.329 |
| 6 | 0.013 | 0.32 | 24.6 | 0.53 | 4.83 |
| 8 | 0.02 | 0.32 | 16.0 | ND | |
| 9 | 0.034 | 0.52 | 15.3 | 0.51 | 4.37 |
| 10 | 0.012 | 0.21 | 17.5 | 0.42 | 3.16 |
| 12 | 0.73 | 14 | 19.2 | 3.0 | 40.5 |
| 13 | 0.011 | 0.37 | 33.6 | 0.7 | 5.67 |
| 13a | 0.038 | 3.6 | 94.7 | 10.5 | 87.41 |
| 13b | 0.0068 | 0.15 | 22.1 | 0.32 | 2.81 |
| 14 | 0.0065 | 0.093 | 14.3 | 0.45 | 5.16 |
| 16 | 0.26 | 1.7 | 6.5 | 0.81 | 8.6 |
| 18 | 0.079 | 0.71 | 9.0 | 0.61 | 4.9 |
| 19 | 0.086 | 0.66 | 7.7 | 0.33 | 1.9 |
| 19a | 0.057 | 0.18 | 3.2 | 0.15 | 0.57 |
| 19b | 0.16 | 10 | 62.5 | 6.8 | 44 |
| 20 | 0.053 | 0.58 | 10.9 | 0.62 | 5.91 |
| 22 | 0.013 | 0.079 | 6.1 | 0.46 | 2.6 |
| 22a | 0.0079 | 0.064 | 8.1 | 0.25 | 1.35 |
| 22b | 0.038 | 1.9 | 50.0 | 7.6 | 57.3 |
| 23 | 0.45 | 2.1 | 4.7 | 0.39 | 2.66 |
| 24a | 0.37 | 6.9 | 18.6 | 3.4 | |
| 24b | 0.24 | 1.1 | 4.6 | 0.75 | 6.49 |
| 26 | 0.11 | 1.4 | 12.7 | 0.85 | 8.48 |
| 27 | 0.27 | 2.7 | 10.0 | 1.05 | 7.77 |
| 28 | 0.23 | 0.82 | 3.6 | 0.39 | 2.686 |
| 28a | 0.098 | 0.33 | 3.3 | 0.21 | 1.23 |
| 29 | 0.29 | 1.5 | 5.2 | 0.43 | 2.95 |
| 29a | 0.2 | 0.72 | 3.5 | 0.22 | 1.42 |
| 30 | 0.27 | 1.1 | 4.1 | 0.53 | 3.48 |
| 32 | 0.096 | 0.28 | 2.9 | 0.18 | 0.96 |
| 34 | 0.049 | 1.8 | 36.7 | 1.3 | 13.9 |
| 35 | 2.2 | 163 | 74.1 | ND | ND |
| 36 | 0.58 | 16 | 27.6 | ND | ND |
| 37 | 0.42 | 12 | 28.6 | 77.4 | 289 |
| 38 | 0.053 | 4.1 | 77.4 | 2.5 | 37.5 |
| 39 | 1.1 | 6.7 | 6.1 | ND | ND |
| 40 | 0.19 | 1.3 | 6.8 | 0.85 | 8.4 |
| 41 | 0.83 | 3.8 | 4.6 | 0.74 | 7.2 |
| 42 | 0.41 | 2.5 | 6.1 | 1.8 | 13.5 |
| 43 | 0.31 | 1.3 | 4.2 | 0.48 | 3.27 |
| 44 | 0.3 | 0.84 | 2.8 | 0.5 | 3.31 |
| 45 | 0.24 | 0.95 | 4.0 | 0.41 | 3.289 |
| 46 | 0.34 | 2.7 | 7.9 | 0.91 | 10.2 |
| 47 | 0.12 | 0.53 | 4.4 | 1.0 | 5.33 |
| 48 | 0.072 | 0.33 | 4.6 | 0.43 | 1.9 |
| 48a | 0.045 | 0.21 | 4.6 | 0.16 | 0.81 |
| 49 | 0.2 | 0.83 | 4.2 | 0.49 | 2.4 |
| 50 | 0.18 | 1.2 | 6.7 | 0.8 | 7.9 |
| 51 | 0.42 | 1.6 | 3.8 | 0.49 | 4.0 |
| 52 | 0.24 | 0.73 | 3.0 | 0.36 | 2.7 |
| 52a | 0.16 | 0.68 | 4.2 | 0.25 | 1.67 |
| 53 | 0.17 | 0.6 | 3.5 | 0.47 | 3.1 |
| 54 | 0.76 | 4.7 | 6.2 | 0.79 | 11.7 |
| 55 | 3.8 | 12 | 3.2 | ND | ND |
| 56 | 2.7 | 13 | 4.8 | ND | ND |
| 57 | 0.44 | 2.2 | 5.0 | 0.8 | 8.9 |
| 58 | 0.62 | 2.0 | 3.2 | 0.74 | 7.6 |
| 59 | 0.73 | 3.0 | 4.1 | 0.8 | 10.4 |
| 60 | 0.057 | 1.6 | 28.1 | 0.35 | 2.52 |
| 62 | 0.33 | 13 | 39.4 | 2.4 | 28.4 |
| 63 | 1.4 | 20 | 14.3 | ND | ND |
| 65 | 0.86 | 54 | 62.8 | 5.9 | ND |
| 66 | 0.034 | 1.6 | 47.1 | 0.6 | 6.605 |
| 68 | 0.2 | 0.81 | 4 | 0.47 | 4.7 |
| 69 | 0.041 | 0.37 | 8.9 | 0.47 | 2 |
| 70 | 0.014 | 0.13 | 9 | 0.38 | 1.5 |
| 71 | 0.02 | 0.17 | 8.3 | 0.43 | 2.0 |
| 72 | 0.05 | 0.2 | 4 | 0.45 | 1.7 |
| 73 | 0.06 | 0.47 | 7.9 | 0.37 | 2.4 |
| 75 | 0.059 | 0.28 | 4.7 | 0.35 | 1.5 |
| 76 | 0.074 | 1.3 | 17 | 0.69 | 6.5 |
| 78 | 0.21 | 0.98 | 4.6 | 0.42 | 2.6 |
| 79 | 0.16 | 0.51 | 3.2 | 0.35 | 1.0 |
| 81 | 0.038 | 0.2 | 5.2 | 0.286 | 0.878 |
| 82 | 0.031 | 0.29 | 9.5 | 0.42 | 2.67 |
| 83 | 0.079 | 0.25 | 3.1 | 0.27 | 0.73 |
| 84 | 0.028 | 0.15 | 5.2 | 0.206 | 0.6 |
| 95 | 0.23 | 0.38 | 1.7 | | |
| 105 | 0.1 | 0.25 | 2.5 | 2.12 | 16.55 |
| 79a | 0.11 | 0.25 | 2.4 | 0.104 | 0.48 |
| 79b | 0.33 | 19 | 58 | 0.16 | 0.68 |
| 107 | 0.11 | 0.56 | 5.1 | 0.33 | 1.77 |
| 81a | 0.038 | 0.075 | 2.0 | 0.146 | 0.48 |
| 81b | 0.074 | 2 | 27 | 2.85 | 11.6 |
| 114 | 0.12 | 0.83 | 6.9 | 0.6 | 3.65 |
| 115 | 0.097 | 0.37 | 3.8 | 0.42 | 2.3 |
| 116 | 0.42 | 2 | 4.7 | 0.58 | 4.76 |
| 117 | 1.6 | 7.1 | 4.4 | | |
| 119 | 0.37 | 3.1 | 8.5 | 1.44 | 14.4 |
| 120 | 0.42 | 3.4 | 8 | 1.25 | 12.7 |
| 121 | 0.28 | 1.1 | 3.8 | 0.24 | 1.13 |
| 121a | 0.12 | 0.4 | 3.4 | 0.153 | 0.603 |
| 122 | 0.19 | 0.92 | 5 | 0.3 | 2.2 |
| 123 | 0.54 | 1.8 | 3.3 | 0.25 | 1.1 |
| 124 | 0.15 | 0.51 | 3.4 | 0.24 | 1.2 |
| 125 | 0.3 | 0.71 | 2.4 | 0.15 | 0.68 |
| 126 | 0.42 | 1.9 | 4.5 | 0.18 | 3.6 |
| 127 | 0.071 | 0.13 | 1.8 | 0.167 | 0.367 |
| 128 | 0.63 | 2.6 | 4 | 0.36 | 3.94 |
| 129 | 1.8 | 7.8 | 4.4 | | |
| 130 | 0.57 | 1.9 | 3.4 | 0.34 | 2.8 |
| 131 | 0.05 | 0.51 | 10 | 0.57 | 4.34 |
| 132 | 0.26 | 0.92 | 3.5 | 0.31 | 2.05 |
| 133 | 0.57 | 1.9 | 3.4 | 0.34 | 2.8 |
| 134 | 0.35 | 1.3 | 3.8 | 0.4 | 3.1 |
| 136 | 0.75 | 2.9 | 3.8 | 0.51 | 4.6 |
| 137 | 0.62 | 3.2 | 5.1 | 0.89 | 9.6 |
| 138 | 0.36 | 1.5 | 4.1 | 0.44 | 3 |
| 139 | 0.65 | 5.6 | 8.7 | | |
| 141a | 0.054 | 0.13 | 2.5 | 0.166 | 0.268 |
| 141b | 0.059 | 2.3 | 40 | 0.659 | 4.09 |
| 142 | 0.56 | 3 | 5.3 | 0.795 | 6.22 |
| 143 | 0.48 | 2.6 | 5.5 | 0.674 | 5.15 |
| 144 | 0.26 | 1.1 | 4.1 | 0.463 | 2.8 |
| 145 | 0.028 | 0.084 | 3 | 0.104 | 0.23 |
| 147 | 0.054 | 0.17 | 3.1 | 0.14 | 0.588 |
| 148 | 0.56 | 2.0 | 3.6 | 0.46 | 2.81 |
| 149a | 0.11 | 0.27 | 2.6 | 0.17 | 0.67 |
| 149b | 0.7 | 8.4 | 12 | 5.8 | 20.4 |
| 151 | 0.43 | 2.1 | 4.9 | 0.53 | 3.86 |
| 152 | 0.25 | 0.89 | 3.5 | 0.35 | 1.31 |
| 153 | 0.6 | 2.7 | 4.4 | 0.75 | 6.48 |
| 154 | 0.05 | 0.3 | 6 | 0.38 | 2.22 |
| 155 | 0.12 | 0.22 | 1.8 | 0.2 | 0.44 |
| 156 | 0.73 | 3.6 | 4.9 | 0.375 | 1.42 |
| 158 | 0.27 | 0.75 | 2.8 | 0.322 | 1.52 |
| 159 | 0.12 | 0.4 | 3.4 | 0.386 | 1.71 |
| 160 | 1.2 | 6 | 5 | 0.564 | 2.87 |
| 161 | 0.42 | 3.9 | 6.8 | 0.46 | 1.22 |
| 162 | 0.38 | 1.5 | 3.8 | 0.373 | 2.04 |
| 163 | 1.3 | 5.5 | 4.3 | 1.08 | 9.2 |
| 164 | 0.12 | 0.35 | 3 | 0.23 | 0.82 |
| 168 | 0.79 | 4.6 | 5.9 | 0.48 | 1.68 |
| 169 | 0.62 | 2.4 | 3.9 | 0.49 | 1.5 |
| 172 | 0.35 | 1.9 | 5.5 | 0.43 | 1.64 |
| 173 | 0.017 | 0.11 | 6.5 | 0.18 | 0.6 |
| 174 | 0.096 | 0.59 | 6.1 | 0.18 | 0.49 |
| 175 | 0.041 | 0.29 | 7.0 | 0.33 | 1.0 |
| 176 | 0.035 | 0.15 | 4.3 | 0.39 | 1.0 |
| 178 | 0.52 | 1.5 | 2.9 | 0.64 | 4.87 |
| 179 | 1.5 | 6.2 | 4.3 | ND | ND |
| 183 | 0.096 | 0.18 | 1.8 | 0.10 | 0.52 |

TABLE 3-continued

| Example | Biochemical assay (IC50, nM) | | | Cellular proliferation assay (IC50, nM) | |
|---|---|---|---|---|---|
| | Bcl-2 WT | Bcl-2 G101V | Ratio of Bcl-2 G101V/WT | RS4; 11 | RS4; 11 Bd-2 G101V knock-in |
| 184 | 0.19 | 0.53 | 2.9 | 0.16 | 0.44 |
| 185 | 0.031 | 0.14 | 4.5 | 0.14 | 0.60 |
| 186 | 0.15 | 0.64 | 4.2 | 0.53 | 2.5 |
| 190 | 0.23 | 0.62 | 2.7 | 0.13 | 0.37 |
| 191 | 0.061 | 0.2 | 3.3 | 0.15 | 0.52 |
| 193 | 0.068 | 0.23 | 3.4 | 0.26 | 0.8 |
| 194 | 0.051 | 0.16 | 3.1 | 0.3 | 0.82 |
| 197 | 0.076 | 0.15 | 1.9 | 0.16 | 0.29 |
| 198 | 0.072 | 0.17 | 2.4 | 0.12 | 0.27 |
| 200 | 0.24 | 1.02 | 4.2 | 0.27 | 1.6 |
| 201 | 0.28 | 1.1 | 3.9 | 0.74 | 6.2 |
| 203 | 0.052 | 0.17 | 3.2 | 0.38 | 0.9 |
| 205 | 0.034 | 0.07 | 2 | 0.39 | 0.55 |
| 210 | 0.33 | 0.66 | 2 | 0.12 | 0.54 |
| 212 | 0.13 | 0.54 | 4.2 | 0.3 | 2.15 |
| 213 | 0.7 | 2.6 | 3.7 | 0.32 | 5.2 |
| 215 | 0.057 | 0.14 | 2.5 | 0.11 | 0.29 |
| 216 | 0.19 | 0.81 | 4.2 | 0.33 | 2.76 |
| 217 | 0.074 | 0.17 | 2.4 | 0.11 | 0.41 |
| 218 | 0.1 | 0.25 | 2.5 | 0.12 | 0.29 |
| 221 | 0.08 | 0.27 | 3.4 | 0.16 | 0.92 |
| 225 | 0.092 | 0.37 | 4 | 0.13 | 0.65 |
| 226 | 0.17 | 0.64 | 3.9 | ND | ND |
| 227 | 2.0 | 6.4 | 3.2 | ND | ND |
| 229 | 0.38 | 0.96 | 2.5 | 0.12 | 0.53 |
| 230 | 0.19 | 0.52 | 2.8 | 0.10 | 0.28 |
| 231 | 0.27 | 0.35 | 1.3 | 0.12 | 0.38 |
| 232 | 0.7 | 1.3 | 1.8 | 0.13 | 0.19 |
| 233 | 0.43 | 0.95 | 2.2 | 0.13 | 0.25 |
| 234 | 0.087 | 0.32 | 3.7 | 0.09 | 0.35 |
| 235 | 0.28 | 1.1 | 3.8 | 0.27 | 1.21 |
| 236 | 0.16 | 0.56 | 3.5 | 0.16 | 0.80 |
| 239 | 0.076 | 0.2 | 2.6 | 0.12 | 0.29 |
| 241 | 0.035 | 0.096 | 2.7 | 0.15 | 0.32 |
| 242 | 0.03 | 0.077 | 2.6 | 0.17 | 0.28 |
| 243 | 0.04 | 0.086 | 2.1 | 0.12 | 0.22 |
| 244 | 0.25 | 0.83 | 3.3 | 0.20 | 1.36 |
| 245 | 0.13 | 0.32 | 2.5 | 0.15 | 0.53 |
| 247 | 0.8 | 3.3 | 4.2 | ND | ND |
| 250 | 0.09 | 0.52 | 5.7 | 0.16 | 1.06 |
| 252 | 1.2 | 3.5 | 2.8 | 0.26 | 2.6 |
| 253 | 0.027 | 0.089 | 3.3 | 0.11 | 0.29 |
| 254 | 0.017 | 0.067 | 3.9 | 0.09 | 0.25 |
| 257 | 0.40 | 0.99 | 2.5 | 0.15 | 0.53 |
| 258 | 0.85 | 1.75 | 2.1 | 0.11 | 0.28 |
| 259 | 0.91 | 3.4 | 3.8 | 0.55 | 4.2 |
| 260 | 0.34 | 0.75 | 2.2 | 0.13 | 0.33 |
| 263 | 1.3 | 4.9 | 3.9 | 0.18 | 1.01 |
| 264 | 1.9 | 7.3 | 3.8 | 0.26 | 0.78 |
| 265 | 0.66 | 1.9 | 3 | 0.15 | 0.65 |
| 266 | 1.4 | 4.1 | 3 | 0.22 | 0.66 |
| 268 | 0.79 | 1.3 | 1.6 | 0.1 | 0.25 |
| 269 | 2.1 | 4.9 | 2.4 | 0.17 | 0.41 |
| 270 | 1.1 | 2.9 | 2.6 | 0.16 | 0.64 |
| 271 | 0.47 | 1.5 | 3.1 | 0.11 | 0.4 |
| 273 | 0.7 | 1.9 | 2.6 | 0.25 | 0.46 |
| 274 | 0.55 | 0.85 | 1.5 | 0.15 | 0.29 |
| 275 | 0.27 | 0.54 | 2 | 0.14 | 0.38 |
| 276 | 0.48 | 1.1 | 2.3 | 0.15 | 0.71 |
| 277 | 1.4 | 3.2 | 2.2 | 0.22 | 1.9 |
| 278 | 0.6 | 1.6 | 2.7 | 0.15 | 0.46 |
| 279 | 2 | 6.3 | 3.2 | ND | ND |
| 280 | 0.26 | 0.56 | 2.2 | 0.14 | 0.43 |
| 281 | 0.43 | 0.99 | 2.3 | 0.13 | 0.31 |
| 282 | 0.25 | 0.97 | 3.9 | 0.36 | 4.2 |
| 285 | 0.26 | 0.87 | 3.4 | 0.18 | 0.41 |
| 286 | 0.1 | 0.48 | 4.8 | ND | ND |
| 287 | 0.87 | 2.3 | 2.6 | 0.16 | 0.55 |
| 288 | 0.52 | 1.3 | 2.5 | 0.19 | 0.87 |
| 289 | 1.7 | 4.0 | 2.3 | ND | ND |
| 290 | 0.9 | 2.2 | 2.5 | 0.2 | 1.5 |
| 293 | 3.2 | 11 | 3.4 | ND | ND |
| 294 | 3.2 | 10 | 3.2 | ND | ND |
| 295 | 0.19 | 0.56 | 3.0 | 0.29 | 0.49 |
| 296 | 0.13 | 0.28 | 2.1 | 0.24 | 0.55 |
| 297 | 0.13 | 0.4 | 3.0 | 0.25 | 1.16 |
| 298 | 0.099 | 0.45 | 4.6 | 0.24 | 1.82 |
| 299 | 0.13 | 0.25 | 1.9 | 0.27 | 0.47 |
| 302 | 0.071 | 0.20 | 2.8 | 0.31 | 0.79 |
| 303 | 0.11 | 0.26 | 2.3 | 0.3 | 0.52 |
| 304 | 0.13 | 0.41 | 3.2 | 0.3 | 2.3 |
| 305 | 0.19 | 0.60 | 3.2 | 0.32 | 1.3 |
| 306 | 0.31 | 0.97 | 3.1 | 0.12 | 0.15 |
| 307 | 0.17 | 0.43 | 2.5 | 0.11 | 0.17 |
| 308 | 0.67 | 3.11 | 4.6 | 0.58 | 3.95 |
| 311 | 0.43 | 1.5 | 3.4 | 0.42 | 2.3 |
| 312 | 0.094 | 0.27 | 2.9 | 0.27 | 0.3 |
| 313 | 0.048 | 0.19 | 3.9 | 0.18 | 0.4 |
| 314 | 0.032 | 0.13 | 4.2 | 0.17 | 0.61 |
| 315 | 0.31 | 0.99 | 3.2 | 0.18 | 0.86 |
| 316 | 0.022 | 0.1 | 4.5 | 0.16 | 0.53 |
| 317 | 0.033 | 0.12 | 3.6 | 0.19 | 0.43 |
| 318 | 0.056 | 0.16 | 2.9 | 0.2 | 0.31 |
| 319 | 0.25 | 0.85 | 3.3 | 0.24 | 0.84 |
| 320 | 0.55 | 1.7 | 3.1 | 0.19 | 0.47 |
| 321 | 0.17 | 0.35 | 2 | 0.22 | 0.24 |
| 322 | 0.25 | 0.72 | 2.9 | 0.18 | 0.32 |
| 323 | 0.22 | 0.45 | 2.1 | 0.21 | 0.42 |
| 324 | 0.16 | 0.31 | 1.9 | 0.22 | 0.51 |
| 325 | 0.49 | 0.97 | 2 | 0.21 | 0.53 |
| 326 | 0.17 | 0.49 | 3 | 0.19 | 0.34 |
| 329 | 0.15 | 0.47 | 3.1 | 0.25 | 1.3 |
| 330 | 0.26 | 0.62 | 2.4 | 0.18 | 0.79 |
| 331 | 0.29 | 0.62 | 2.1 | 0.16 | 0.69 |
| 332 | 0.7 | 1.1 | 1.6 | 0.17 | 0.54 |
| 333 | 0.11 | 0.37 | 3.2 | 0.13 | 0.26 |
| 334 | 0.12 | 0.33 | 2.8 | 0.17 | 0.65 |
| 335 | 0.06 | 0.15 | 2.6 | 0.17 | 0.34 |
| 336 | 0.09 | 0.38 | 4.2 | 0.2 | 1.1 |
| 337 | 0.12 | 0.37 | 3 | 0.18 | 0.63 |
| 338 | 0.59 | 1.4 | 2.3 | 0.11 | 0.15 |
| 339 | 0.28 | 0.97 | 3.5 | 0.19 | 0.52 |
| 341 | 1.6 | 4.5 | 2.8 | 0.12 | 0.68 |
| 342 | 0.97 | 3.3 | 2.9 | 0.28 | 2.0 |
| 343 | 0.11 | 0.3 | 2.7 | 0.11 | 0.25 |
| 345 | 0.16 | 0.38 | 2.4 | 0.14 | 0.24 |
| 347 | 0.2 | 0.47 | 2.3 | 0.13 | 0.34 |
| 349 | 0.2 | 0.43 | 2.2 | 0.16 | 0.44 |
| 350 | 0.48 | 0.99 | 2.2 | 0.23 | 0.79 |
| 351 | 0.042 | 0.11 | 2.6 | 0.09 | 0.13 |
| 352 | 0.52 | 2.2 | 4.2 | 0.45 | 4.56 |
| 353 | 0.077 | 0.25 | 3.3 | 0.2 | 0.64 |
| 354 | 0.9 | 1.9 | 2.2 | 0.14 | 3 |
| 355 | 0.31 | 1.1 | 3.6 | 0.2 | 2.8 |
| 356 | 1.5 | 4.2 | 2.9 | 0.31 | 1.7 |
| 357 | 0.57 | 1.4 | 2.5 | 0.19 | 1 |
| 358 | 0.1 | 0.24 | 2.4 | ND | ND |
| 359 | 0.19 | 0.64 | 3.4 | 0.16 | 0.63 |
| 360 | 0.23 | 0.5 | 2.2 | 0.05 | 0.11 |
| 361 | 0.051 | 0.16 | 3.1 | 0.09 | 0.13 |
| 362 | 0.07 | 0.14 | 2 | 0.08 | 0.17 |
| 363 | 0.34 | 0.89 | 2.6 | 0.11 | 0.14 |
| 364 | 0.14 | 0.39 | 2.9 | 0.13 | 0.2 |
| 365 | 0.46 | 1.3 | 2.9 | 0.12 | 0.26 |
| 367 | 0.35 | 0.9 | 2.6 | 0.11 | 0.3 |
| 368 | 0.064 | 0.29 | 4.5 | 0.096 | 0.24 |
| 370 | 0.18 | 0.67 | 3.7 | | |
| 371 | 0.12 | 0.32 | 2.7 | | |

ND: not determined; WT: wild type.

Biological Example: Bcl-2-D103Y Biochemical Assay

Selected compounds disclosed herein were tested for blocking of Bcl-2D103Y protein with its ligand in an assay based on time-resolved fluorescence resonance energy transfer methodology. 0.05 nM recombinant human Bcl-2 D103Y protein was pre-incubated with a serial dilution of compounds disclosed herein (top final concentration is 1 uM, 4-fold serially diluted, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then 2 nM FITC labeled Bak peptide Ac-GQVGRQLAIIGDK(FITC)INR-amide and Mab Anti-6His Tb cryptate Gold was added to plate and further incubated at room temperature for 1 hour. The TR-FRET signals (ex337 nm, em490 nm/520 nm) were read on BMG PHERAstar FSX instrument. The inhibition percentage of Bcl-2 D103Y interaction with its ligand in presence of increasing concentrations of compounds was calculated based on the ratio of fluorescence at 490 nm to that at 520 nm. The IC50 for each compound was derived from fitting the data to the four-parameter logistic equation by Dotmatics.

TABLE 4 biochemical data of inhibition of mutant Bcl-2 D103Y

| Example | Bcl-2 D103Y Biochemical assay (IC50, nM) | Bcl-2 WT | Ratio of Bcl-2 D103Y/ Bcl-2 WT |
|---|---|---|---|
| F91b in WO2019210828 | 0.17 | 0.014 | 12 |
| 3 | 0.11 | 0.019 | 11 |
| 5 | 0.32 | 0.037 | 12 |
| 6 | 0.18 | 0.013 | 24 |
| 6a | 0.11 | 0.0078 | 13 |
| 10 | 0.12 | 0.012 | 10 |
| 13 | 0.14 | 0.011 | 13 |
| 13b | 0.09 | 0.068 | 12 |
| 14 | 0.084 | 0.0065 | 13 |
| 16 | 0.63 | 0.26 | 2.5 |
| 18 | 0.43 | 0.079 | 5.4 |
| 19 | 0.2 | 0.086 | 2.3 |
| 19a | 0.15 | 0.057 | 2.6 |
| 19b | 16 | 0.16 | 100 |
| 20 | 0.25 | 0.053 | 4.6 |
| 22 | 0.12 | 0.013 | 9.2 |
| 22a | 0.041 | 0.0079 | 5.2 |
| 23 | 0.26 | 0.13 | 2 |
| 24b | 0.56 | 0.24 | 2.3 |
| 26 | 0.51 | 0.11 | 4.7 |
| 27 | 0.49 | 0.27 | 1.8 |
| 28 | 0.34 | 0.23 | 1.5 |
| 28a | 0.20 | 0.098 | 2.1 |
| 29 | 0.57 | 0.29 | 1.9 |
| 29a | 0.38 | 0.2 | 1.9 |
| 30 | 0.42 | 0.27 | 1.6 |
| 32 | 0.11 | 0.096 | 1.1 |
| 33 | 0.094 | 0.038 | 2.5 |
| 39 | 3.8 | 1.1 | 3.5 |
| 40 | 0.72 | 0.19 | 3.8 |
| 41 | 3.1 | 0.83 | 3.7 |
| 42 | 1.7 | 0.41 | 4.1 |
| 43 | 0.83 | 0.31 | 2.7 |
| 45 | 0.54 | 0.24 | 2.3 |
| 46 | 1.8 | 0.34 | 5.1 |
| 47 | 0.4 | 0.12 | 3.3 |
| 48 | 0.2 | 0.072 | 2.8 |
| 48a | 0.10 | 0.045 | 2.3 |
| 49 | 0.57 | 0.2 | 2.8 |
| 50 | 1.2 | 0.18 | 6.6 |
| 51 | 1.5 | 0.42 | 3.5 |
| 52 | 0.61 | 0.24 | 2.5 |
| 52a | 0.37 | 0.16 | 2.4 |
| 53 | 0.38 | 0.17 | 2.2 |
| 58 | 1.8 | 0.62 | 2.9 |
| 59 | 3.2 | 0.73 | 4.4 |
| 68 | 0.87 | 0.2 | 4.3 |
| 70 | 0.10 | 0.014 | 7.1 |
| 71 | 0.15 | 0.02 | 7.6 |
| 72 | 0.08 | 0.05 | 1.6 |
| 73 | 0.31 | 0.06 | 5.1 |
| 75 | 0.22 | 0.059 | 3.6 |
| 78 | 0.62 | 0.21 | 2.9 |
| 79 | 0.19 | 0.16 | 1.2 |
| 81 | 0.084 | 0.038 | 2.2 |
| 82 | 0.17 | 0.031 | 5.6 |
| 83 | 0.16 | 0.079 | 2 |
| 84 | 0.049 | 0.028 | 1.8 |
| 96 | 0.23 | 0.041 | 5.6 |
| 79a | 0.2 | 0.11 | 1.9 |
| 107 | 0.31 | 0.11 | 2.8 |
| 81a | 0.54 | 0.025 | 2.2 |

TABLE 4-continued biochemical data of inhibition of mutant Bcl-2 D103Y

| Example | Bcl-2 D103Y Biochemical assay (IC50, nM) | Bcl-2 WT | Ratio of Bcl-2 D103Y/ Bcl-2 WT |
|---|---|---|---|
| 114 | 0.4 | 0.12 | 3.4 |
| 115 | 0.57 | 0.097 | 5.9 |
| 121 | 0.42 | 0.28 | 1.5 |
| 122 | 0.47 | 0.19 | 2.5 |
| 123 | 0.71 | 0.54 | 1.3 |
| 124 | 0.21 | 0.15 | 1.4 |
| 125 | 0.33 | 0.3 | 1.1 |
| 127 | 0.11 | 0.1 | 1 |
| 131 | 0.29 | 0.05 | 5.7 |
| 132 | 0.47 | 0.26 | 1.3 |
| 134 | 0.67 | 0.35 | 1.9 |
| 141a | 0.072 | 0.054 | 1.3 |
| 144 | 0.47 | 0.26 | 1.8 |
| 145 | 0.045 | 0.028 | 1.6 |
| 147 | 0.086 | 0.054 | 1.6 |
| 150 | 0.53 | 0.13 | 4.1 |
| 155 | 0.14 | 0.12 | 1.2 |
| 158 | 0.37 | 0.27 | 1.3 |
| 162 | 0.61 | 0.38 | 1.6 |
| 164 | 0.12 | 0.12 | 1 |
| 174 | 0.14 | 0.096 | 1.4 |
| 176 | 0.061 | 0.035 | 1.7 |
| 184 | 0.19 | 0.19 | 1 |
| 185 | 0.05 | 0.031 | 1.6 |
| 190 | 0.34 | 0.23 | 1.5 |
| 194 | 0.072 | 0.051 | 1.4 |
| 197 | 0.089 | 0.076 | 1.2 |
| 198 | 0.08 | 0.072 | 1.1 |
| 203 | 0.083 | 0.052 | 1.6 |
| 205 | 0.047 | 0.034 | 1.4 |
| 207 | 0.22 | 0.20 | 1.1 |
| 210 | 0.31 | 0.33 | 0.94 |
| 215 | 0.062 | 0.057 | 1.1 |
| 217 | 0.10 | 0.074 | 1.4 |
| 218 | 0.11 | 0.10 | 1.0 |
| 220 | 0.077 | 0.044 | 1.8 |
| 225 | 0.10 | 0.092 | 1.1 |
| 226 | 0.16 | 0.17 | 1 |
| 229 | 0.45 | 0.38 | 1.2 |
| 231 | 0.45 | 0.27 | 1.7 |
| 232 | 0.95 | 0.59 | 1.6 |
| 233 | 0.83 | 0.43 | 1.9 |
| 236 | 0.22 | 0.16 | 1.3 |
| 239 | 0.12 | 0.076 | 1.5 |
| 241 | 0.047 | 0.035 | 1.3 |
| 242 | 0.033 | 0.03 | 1.1 |
| 243 | 0.041 | 0.041 | 1 |
| 258 | 1.5 | 0.85 | 1.8 |
| 260 | 0.27 | 0.24 | 1.1 |
| 268 | 0.88 | 0.79 | 1.1 |
| 273 | 0.82 | 0.70 | 1.2 |
| 274 | 0.31 | 0.55 | 0.57 |
| 275 | 0.21 | 0.27 | 0.76 |
| 280 | 0.23 | 0.26 | 0.89 |
| 281 | 0.51 | 0.43 | 1.2 |
| 282 | 0.47 | 0.25 | 1.9 |
| 285 | 0.49 | 0.26 | 1.9 |
| 286 | 0.19 | 0.10 | 1.9 |
| 288 | 0.43 | 0.52 | 0.84 |
| 295 | 0.25 | 0.19 | 1.3 |
| 296 | 0.14 | 0.13 | 1.1 |
| 299 | 0.13 | 0.13 | 1.0 |
| 302 | 0.069 | 0.071 | 1.0 |
| 303 | 0.16 | 0.11 | 1.4 |
| 304 | 0.22 | 0.13 | 1.8 |
| 306 | 0.31 | 0.31 | 1.0 |
| 307 | 0.18 | 0.17 | 1.1 |
| 312 | 0.081 | 0.080 | 1.0 |
| 317 | 0.057 | 0.033 | 1.7 |
| 318 | 0.052 | 0.056 | 0.9 |
| 319 | 0.42 | 0.25 | 1.7 |
| 320 | 0.52 | 0.55 | 0.93 |
| 321 | 0.14 | 0.17 | 0.79 |
| 322 | 0.36 | 0.25 | 1.4 |
| 323 | 0.19 | 0.22 | 0.87 |

TABLE 4-continued biochemical data of inhibition of mutant Bcl-2 D103Y

| Example | Bcl-2 D103Y Biochemical assay (IC50, nM) | Bcl-2 WT | Ratio of Bcl-2 D103Y/ Bcl-2 WT |
|---|---|---|---|
| 324 | 0.14 | 0.16 | 0.87 |
| 326 | 0.25 | 0.17 | 1.5 |
| 337 | 0.39 | 0.12 | 3.2 |
| 338 | 1.0 | 0.59 | 1.7 |
| 339 | 0.71 | 0.28 | 2.5 |
| 343 | 0.09 | 0.11 | 0.8 |
| 345 | 0.13 | 0.16 | 0.8 |
| 347 | 0.28 | 0.2 | 1.4 |
| 349 | 0.17 | 0.2 | 0.9 |
| 350 | 0.65 | 0.48 | 1.4 |
| 351 | 0.07 | 0.04 | 1.7 |
| 353 | 0.12 | 0.07 | 1.5 |
| 355 | 1.8 | 0.31 | 5.8 |
| 357 | 1.0 | 0.57 | 1.8 |
| 358 | 0.11 | 0.1 | 1.1 |
| 359 | 0.44 | 0.19 | 2.4 |
| 360 | 0.31 | 0.23 | 1.4 |
| 361 | 0.079 | 0.048 | 1.6 |
| 362 | 0.095 | 0.069 | 1.4 |
| 363 | 0.36 | 0.40 | 0.9 |
| 364 | 0.14 | 0.14 | 1.0 |
| 365 | 0.51 | 0.46 | 1.1 |
| 367 | 0.40 | 0.35 | 1.2 |
| 371 | 0.31 | 0.12 | 2.6 |

WT: wild type;
Bcl-2 D103Y: Bcl-2 Asp103Tyr (D103Y) mutation

The compounds disclosed herein have an additional aromatic or carbon cycle fragment attached by a linker (—CH$_2$—, —O—, or a carbon cycle) to phenylpiperazine or phenylpiperidine moiety. As data shown in Table 3 and Table 4, this key feature structure presents the comparable or slightly better inhibitory activity for Bcl-2 wild type protein. Unexpectedly, they also show robust potency for mutant G101V and D103Y. As determined in Table 3 and Table 4, the ratio of IC50 of Bcl-2 G101V/Bcl-2 wt, such as Examples 16, 19, 19a, 23, 24b, 28-32, 39-59, 61, 68-73, 75-81, 83 and 84, 127, 141a, 145, 155, 232, 233, 338 are much lower than that of Example F132b in WO2019210828 and ABT-199 (venetoclax). The ratio of Bcl-2 D103Y/Bcl-2 wt in Table 4 also was present as this trends, such as example 16, 19a, 22a, 23, 24b, 26-30, 32-33, 39-43, 45-49, 51-53, 58, 59, 68, 72, 75, 78-81, 83 and 84, 127, 141a, 145, 155, which are significantly lower than F91b in WO2019210828. These results suggest a type of new potential Bcl-2 inhibitors without resistance concerns from mutations such as G101V and D103Y. From the aspect of neutropenia adverse effect, these compounds present the possibility of new therapy in an effective and safe dose for clinically relapse patients with mutations after the treatment with venetoclax.

Biological Example: Metabolic Stability Study

The metabolic stability of some compounds was evaluated by using the liver microsome incubation system in vitro. Briefly, the test compounds at 1 µM, were incubated with 0.5 mg/mL liver microsomes from different species (human, dog, rat and mouse) with an NADPH regenerating system at 37° C. Samples were quenched at three time points (0, 30, 60 min) with organic solvent containing internal standards, and the supernatant was analyzed for parent loss via LC-MS/MS. Midazolam was used as the positive control to validate the incubation system.

For each compound, the log percentage remaining versus incubation time was plotted and the slope of this linear regression (-k) was converted to an in vitro half-life $T_{1/2}$ and intrinsic clearance $CL_{int}$ using the equation listed below.

$$T_{1/2} = -0.693/k$$

$$CL_{int} = k/C_{protein}$$

where $C_{protein}$ is the microsomal protein concentration in the incubation system.

The value of $CL_{int}$ and $T_{1/2}$ of Example F 132b in WO2019210818 and representative compounds of the disclosure were determined, and the results are shown in Table 5.

TABLE 5

| Compound | T½ (min) Human | T½ (min) mouse | CLint (µL × min⁻¹ × mg⁻¹) Human | CLint (µL × min⁻¹ × mg⁻¹) mouse |
|---|---|---|---|---|
| Example F132b in WO2019210828 | 47.5 | 71.3 | 29.2 | 19.4 |
| Example 19a | NA# | 346 | <1.0# | 4.0 |
| Example 19 | 1228 | 292 | 1.1 | 4.7 |
| Example 28 | 135 | 200 | 10.3 | 6.9 |
| Example 29 | 245 | 2358 | 5.6 | 0.6 |
| Example 32 | 533 | 202 | 2.6 | 6.8 |
| Example 33 | 1821 | 233 | 0.8 | 5.9 |
| Example 41 | 997 | 683 | 1.4 | 2.0 |
| Example 43 | 108 | 193 | 12.8 | 7.1 |
| Example 46 | 153 | 131 | 9.1 | 10.5 |
| Example 48 | 256 | 323 | 5.4 | 4.3 |
| Example 49 | 93.4 | 205 | 14.8 | 6.7 |
| Example 51 | 234 | 306 | 5.9 | 4.5 |
| Example 52 | 145 | NA# | 9.5 | <1.0# |
| Example 67 | 309 | 272 | 4.5 | 5.1 |
| Example 72 | 491 | 159 | 2.8 | 8.7 |
| Example 79a | 253 | 124 | 5.5 | 11.2 |
| Example 81a | NA# | 219 | <1.0# | 6.32 |
| Example 127 | NA# | 182 | <1.0# | 7.63 |
| Example 141a | 343 | 18108 | 4.0 | 0.07 |
| Example 145 | 970 | 196 | 1.4 | 7.1 |
| Example 147 | NA# | 301 | <1.0# | 4.6 |
| Example 155 | 223 | 522 | 6.2 | 2.65 |

TABLE 5-continued

| Compound | T½ (min) Human | T½ (min) mouse | CLint (µL × min⁻¹ × mg⁻¹) Human | CLint (µL × min⁻¹ × mg⁻¹) mouse |
|---|---|---|---|---|
| Example 198 | 247 | 222 | 5.6 | 6.3 |
| Example 230 | 373 | 183 | 3.7 | 7.6 |
| Example 232 | 822 | 206 | 1.7 | 6.7 |
| Example 233 | 534 | 253 | 2.6 | 5.5 |
| Example 257 | 372 | 254 | 3.7 | 5.5 |

TABLE 5-continued

| Compound | T½ (min) Human | T½ (min) mouse | CLint (µL × min⁻¹ × mg⁻¹) Human | CLint (µL × min⁻¹ × mg⁻¹) mouse |
|---|---|---|---|---|
| Example 274 | 344 | 289 | 4.0 | 4.8 |
| Example 281 | 870 | 564 | 1.6 | 2.5 |
| Example 285 | 299 | 177 | 4.6 | 7.8 |
| Example 312 | 423 | 362 | 3.3 | 3.8 |
| Example 321 | 1017 | 628 | 1.4 | 2.2 |
| Example 338 | 659 | 538 | 2.1 | 2.6 |
| Example 361 | NA# | 273 | <1.0# | 5.1 |
| Example 363 | NA# | NA# | <1.0# | <1.0# | this compound is very stable, and data is beyond the detection limits
NA: not applicable As data shown in both human and mouse species, compounds in the present disclosure show much longer in vitro half-life ($T_{1/2}$) and much lower intrinsic clearance ($CL_{int}$) compared with Example F132b in WO2019210828. The metabolic stability in liver microsome of compounds in the present disclosure was significantly increased relative to Example F132b in WO2019210828.

Biological Example: Mouse PK Study

The pharmacokinetics of compounds were evaluated in male CD-1 mouse via Intravenous (dose of 1 mg/kg) and Oral Administration (dose of 10 mg/kg). For intravenous administration study, test compounds were dissolved in DMSO/EtOH/Cremophor EL/D5W (2.5/10/20/67.5, by volume) and injected with a 1 mg/kg dose via tail vein. For oral administration study, test compounds were dissolved in PEG400/Phosal 50 PG/EtOH (30/60/10, by volume) and administrated to mice at 10 mg/kg by gavage. Blood was collected into EDTA-K2 anticoagulant tube at 5 (IV only), 15, and 30 min and 1, 2, 4, 8 and 24 h after administration. Approximately 30 µL blood was collected at each time point. And then the blood was centrifuged at 3000 g for 5 min at 4° C. using a centrifuge to obtain the plasma. The plasma sample was transferred into a tube and stored in a freezer at approximately −20° C. until the determination of concentration by LC-MS/MS. Pharmacokinetic parameter were estimated by using WinNonlin software (version 8.1, Pharsight Corporation, CA, USA) with non-compartmental method. The following pharmacokinetic parameters were calculated, whenever possible from the plasma concentration-time data: CL, $V_d$, $T_{1/2}$, $AUC_{last}$, $AUC_{inf}$ for IV administration and $T_{max}$, $C_{max}$, $AUC_{last}$, $AUC_{inf}$, $T_{1/2}$ for PO administration. All animals are free fed before experiment. The results are shown in Table 6. For comparison purpose, the PK results of certain compounds in previous disclosure were obtained using the same methods.

TABLE 6

| Compound | Iv dosing (1 mg/kg) CL (mL/min/kg) | Iv dosing (1 mg/kg) $V_d$ (L/kg) | Iv dosing (1 mg/kg) AUC(0-t)) (h · ng/mL) | Po dosing (10 mg/kg) $T_{1/2}$ | Po dosing (10 mg/kg) Cmax (ng/mL) | Po dosing (10 mg/kg) AUC(0-t)) (h · ng/mL) |
|---|---|---|---|---|---|---|
| Example F132b in WO2019210828 | 12.5 | 0.73 | 1339 | 3.1 | 160 | 1062 |
| Example 19a | 1.4 | 0.48 | 12259 | NA | 1587 | 20006 |
| Example 32 | 1.5 | 0.48 | 10457 | NA | 1437 | 21215 |
| Example 52a | 2.6 | 0.62 | 6509 | 2.3 | 2140 | 20721 |
| Example 155 | 2.2 | 1.0 | 7534 | NA | 1084 | 15213 |
| Example 232 | 1.2 | 1.2 | 14419 | NA | 1088 | 18272 |
| Example 233 | 1.0 | 0.8 | 17153 | NA | 1104 | 17390 |
| Example 338 | 0.4 | 0.37 | 42870 | NA | 699 | 11604 |

NA: not applicable

As in Table 6, compounds in the present disclosure have significantly better PK than Example F132b in WO2019210828. The AUC (20006 h-ng/mL) and Cmax (1587 ng/mL) data of selected compounds in the table are at least 9 folds higher than those of Example F132b in WO2019210828 in mouse pk experiment at same dosing. The CL value in iv dosing of selected compounds is also much lower than Example F132b in WO2019210828, which is consistent with their in vitro clearance data.

What is claimed is:
1. A compound that is

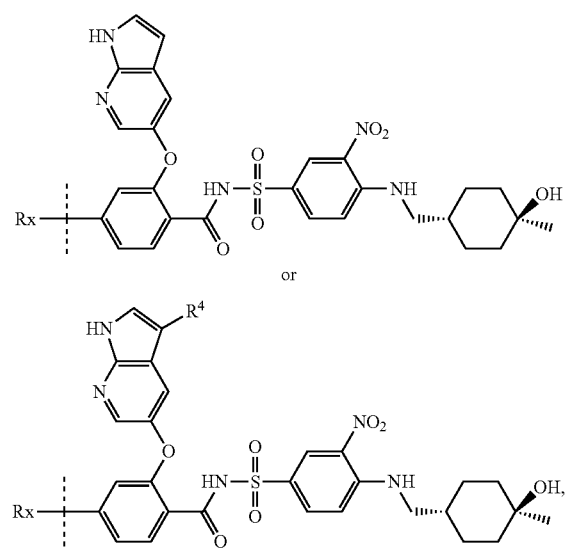

or a pharmaceutically acceptable salt thereof, wherein:
R⁴ is halogen selected from fluoro (—F), chloro (—Cl) or bromo (—Br); and Rx is selected from
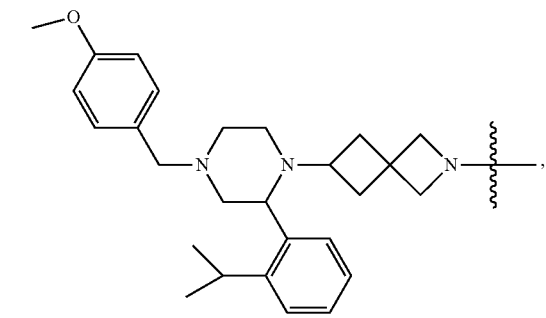,
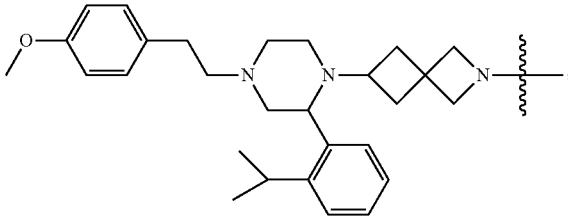,
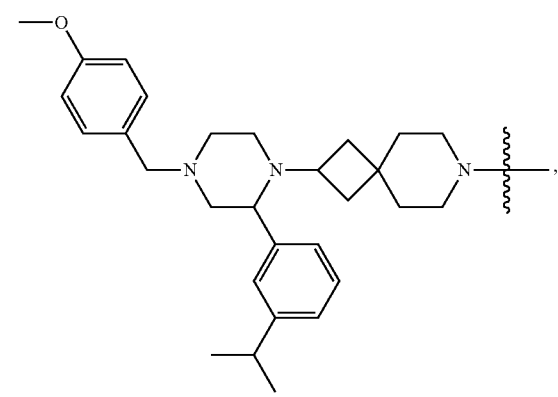,
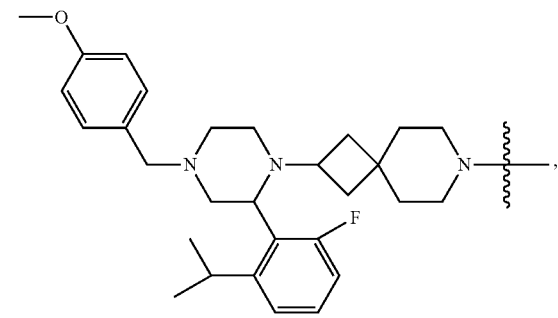,
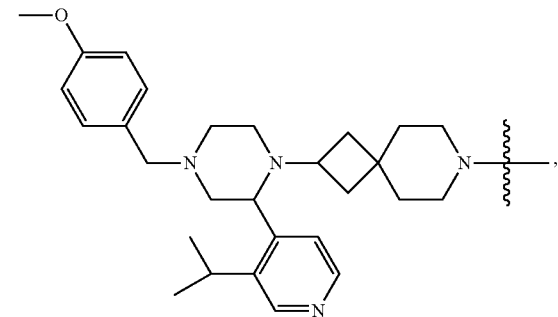,
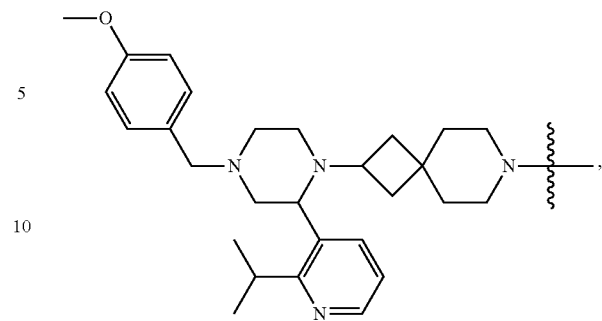,
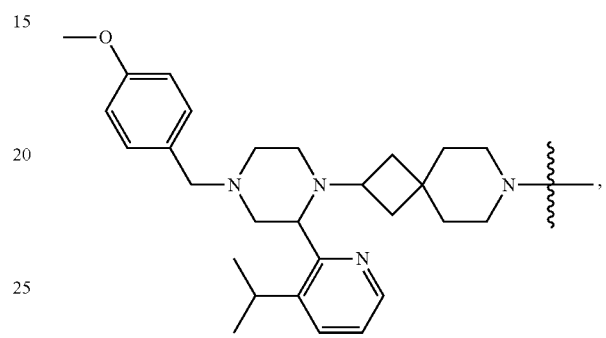,
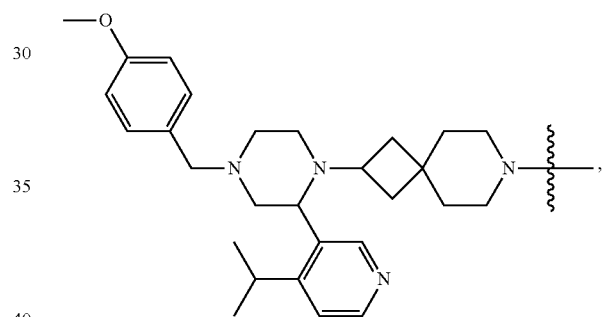,
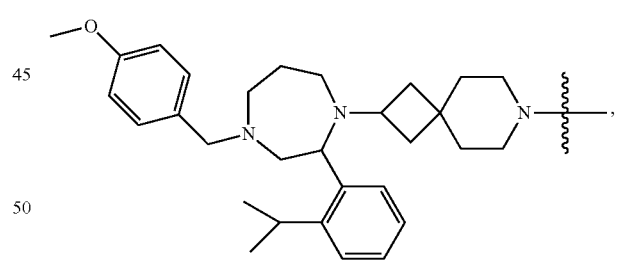,
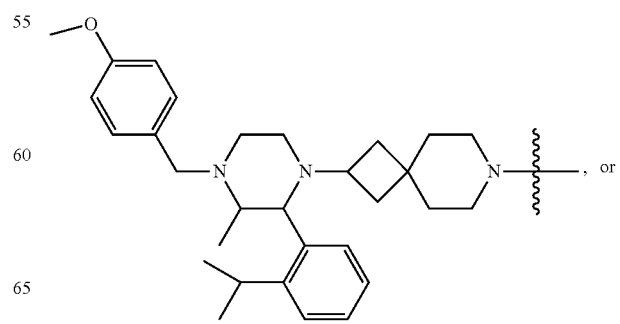, or

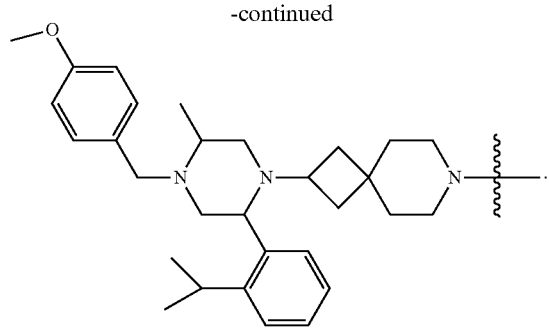
2. A compound that is selected from
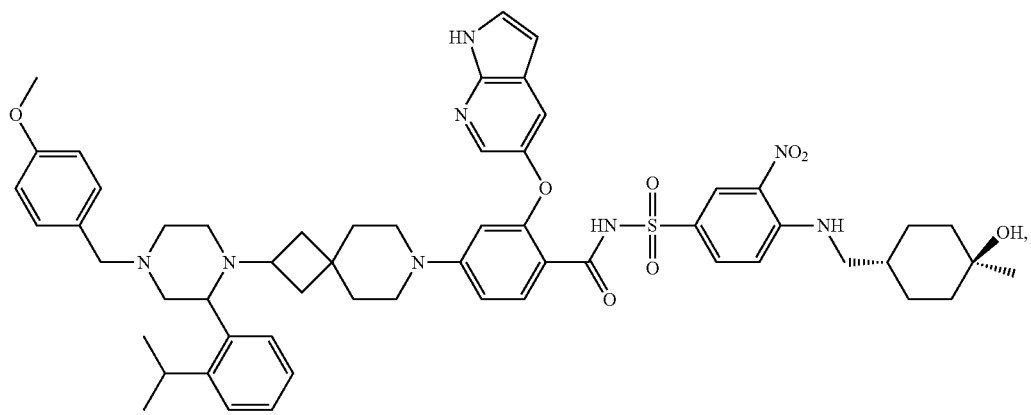 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)C(c3ccccc3C(C)C)C2)cc1]
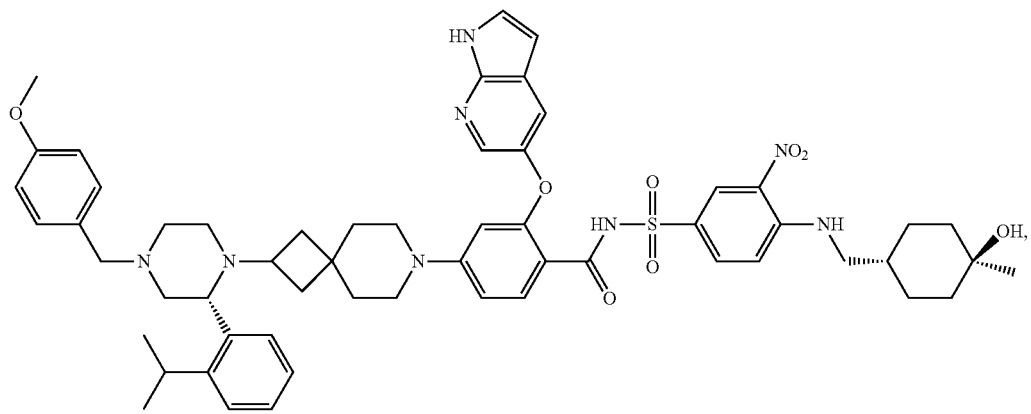
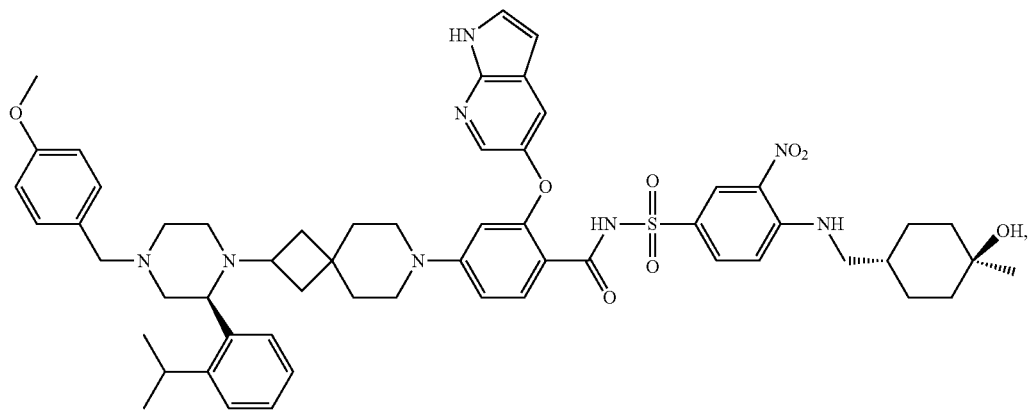

-continued
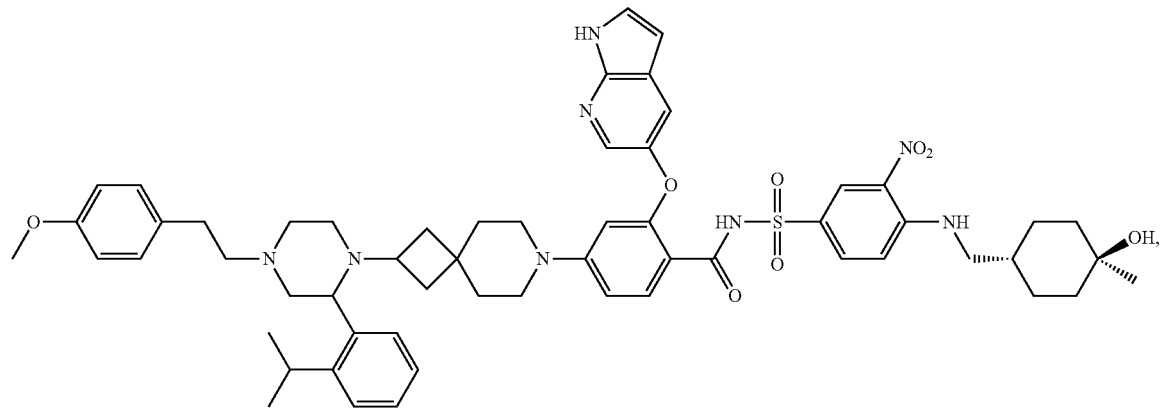
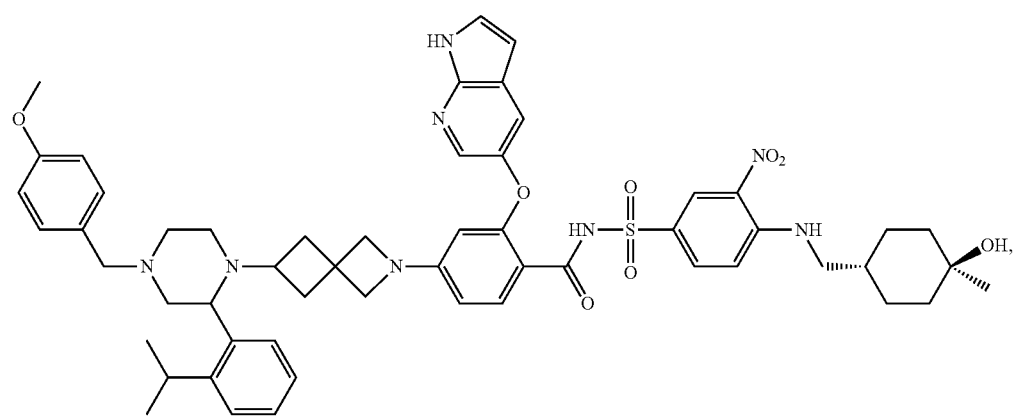
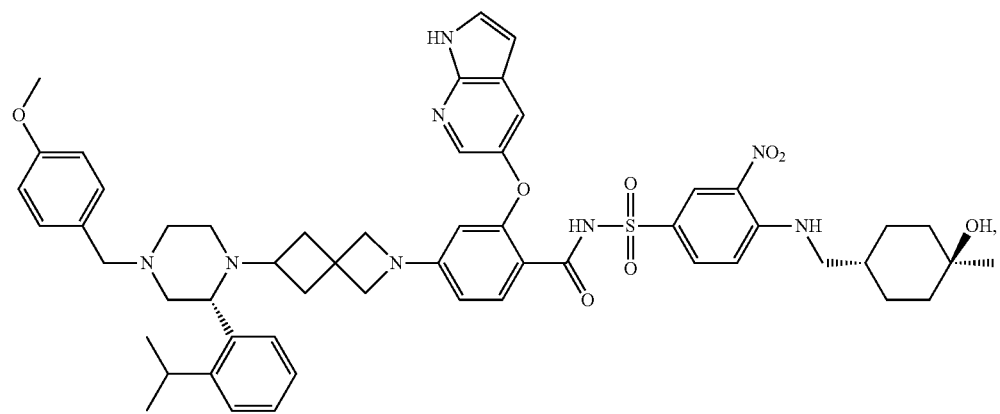
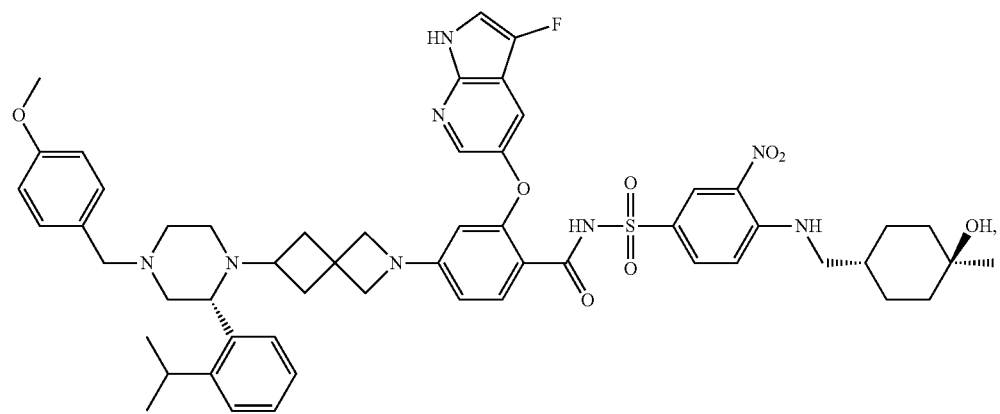

-continued

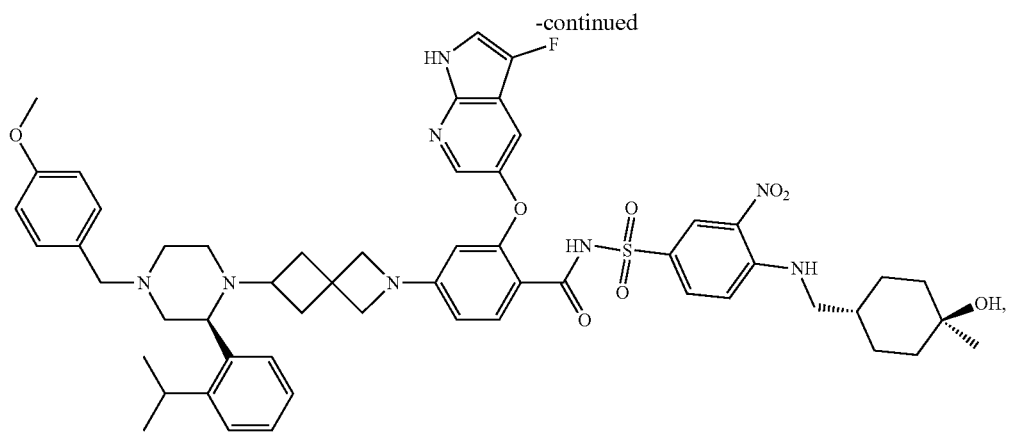

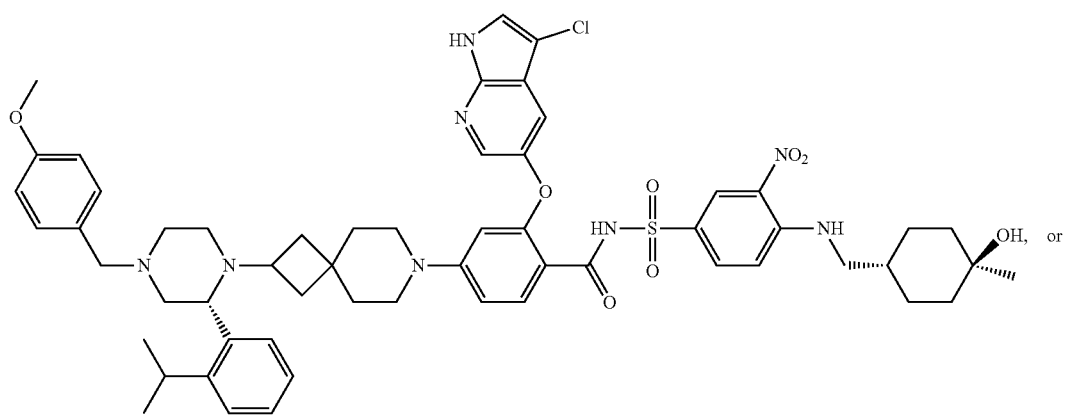

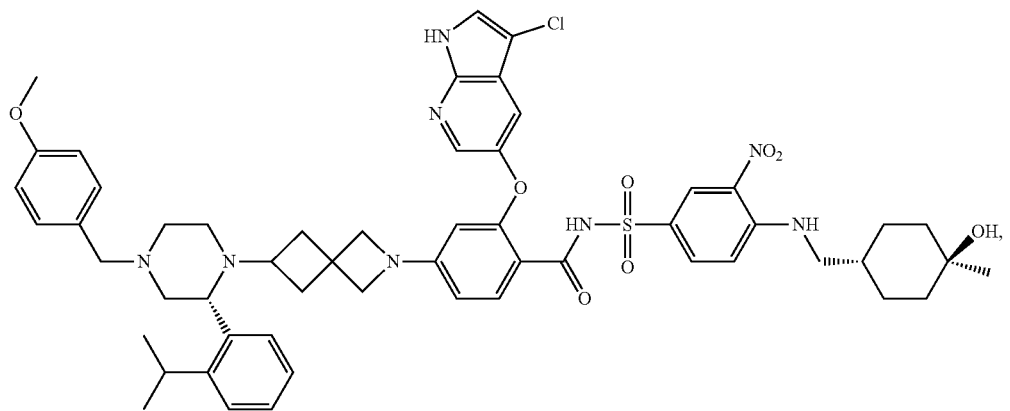

or a pharmaceutically acceptable salt thereof.

3. A pharmaceutical composition comprising the compound of claim 1, or a pharmaceutically acceptable salt thereof, and at least one pharmaceutically acceptable excipient.

4. A pharmaceutical composition comprising the compound of claim 2, or a pharmaceutically acceptable salt thereof, and at least one pharmaceutically acceptable excipient.

5. The compound of claim 2, wherein the compound is
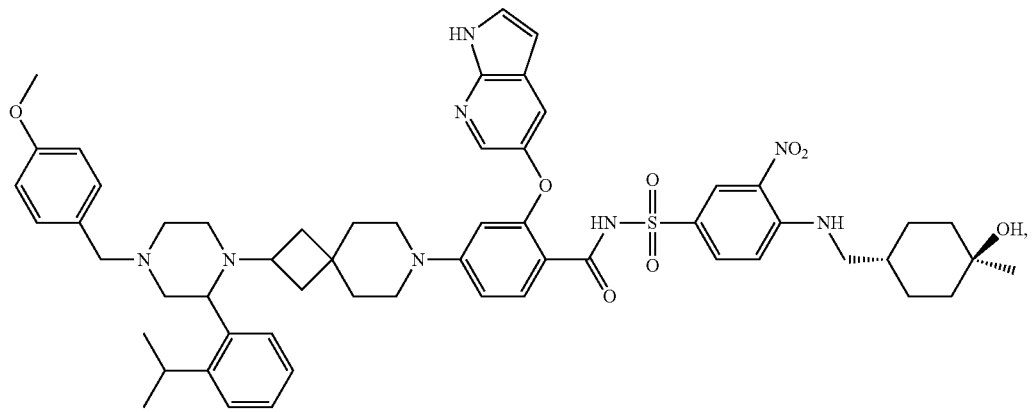
or a pharmaceutically acceptable salt thereof.
6. The compound of claim 2, wherein the compound is
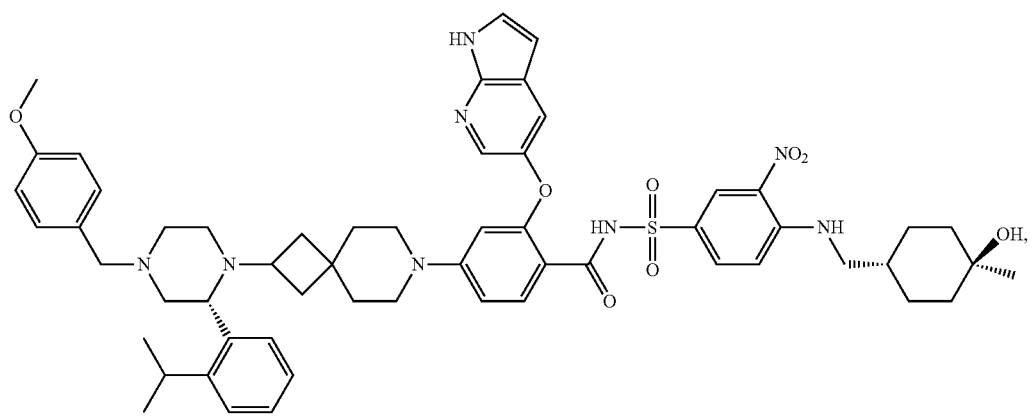 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@H](c3ccccc3C(C)C)C2)cc1]
or a pharmaceutically acceptable salt thereof.
7. The compound of claim 2, wherein the compound is
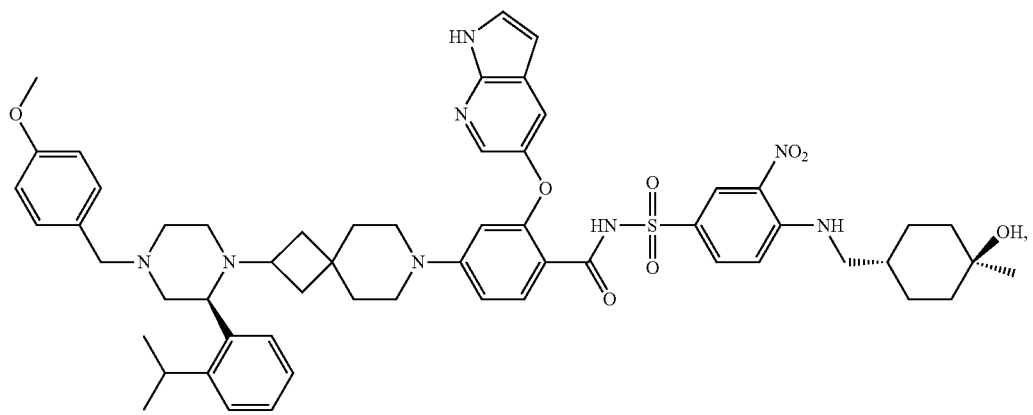 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@@H](c3ccccc3C(C)C)C2)cc1]
or a pharmaceutically acceptable salt thereof.

8. The compound of claim 2, wherein the compound is
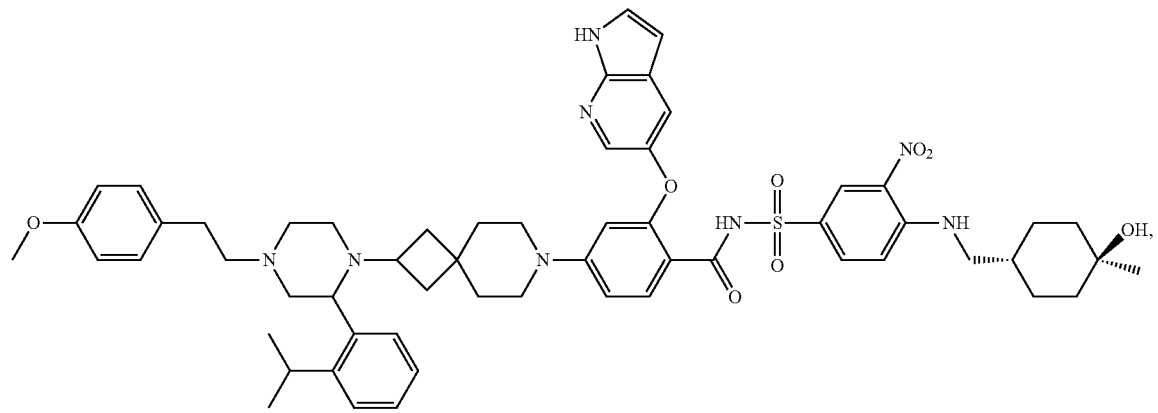
or a pharmaceutically acceptable salt thereof.
9. The compound of claim 2, wherein the compound is
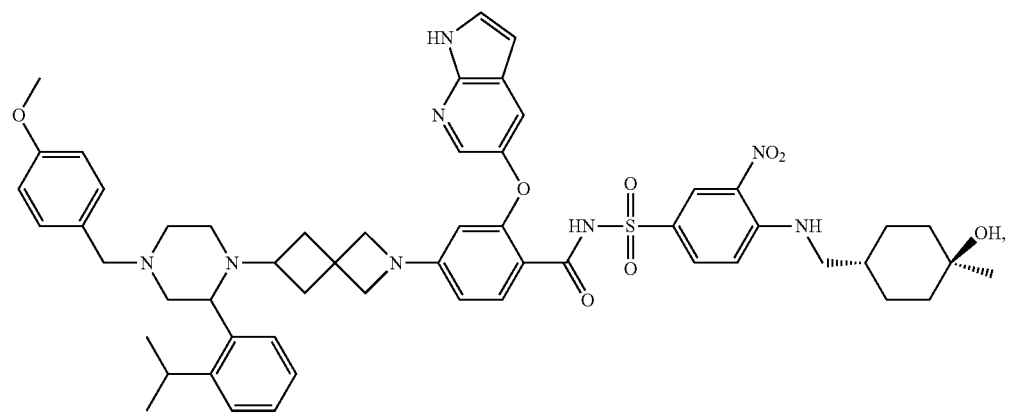 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)C(c3ccccc3C(C)C)C2)cc1]
or a pharmaceutically acceptable salt thereof.
10. The compound of claim 2, wherein the compound is
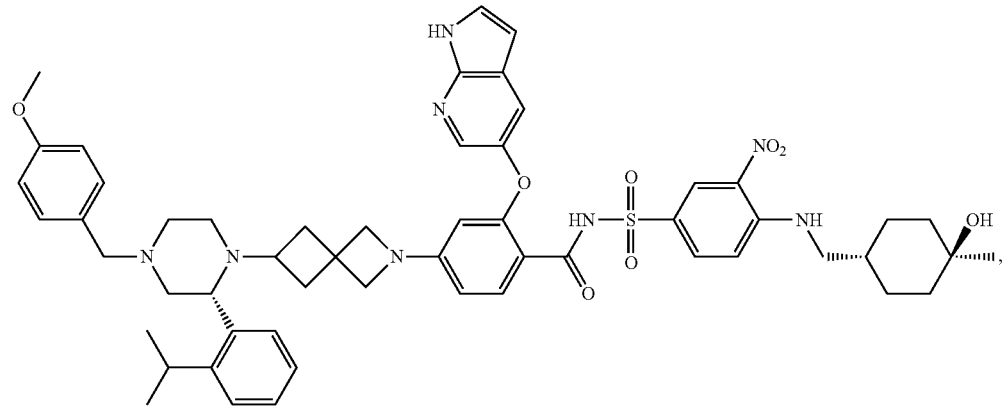 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc1]
or a pharmaceutically acceptable salt thereof.

11. The compound of claim 2, wherein the compound is
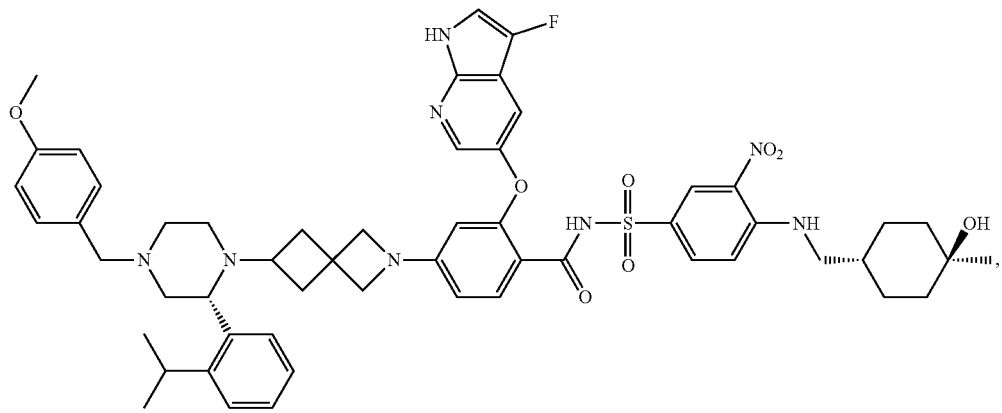 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc1]
or a pharmaceutically acceptable salt thereof.
12. The compound of claim 2, wherein the compound is
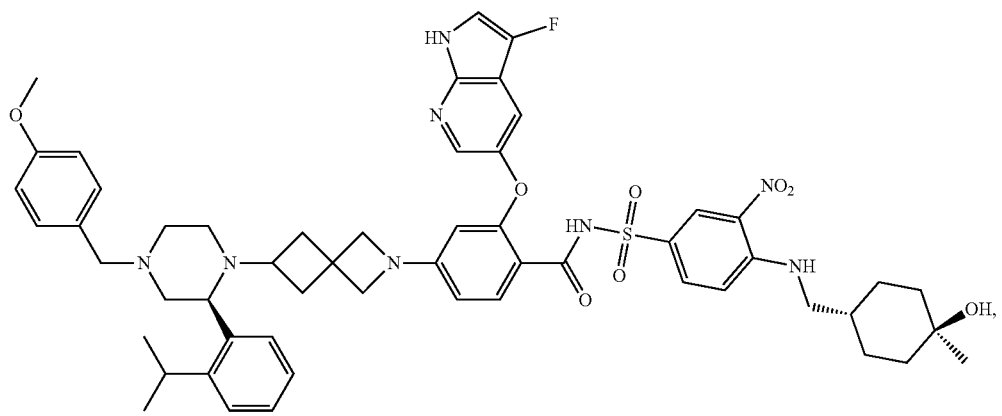 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@@H](c3ccccc3C(C)C)C2)cc1]
or a pharmaceutically acceptable salt thereof.
13. The compound of claim 2, wherein the compound is
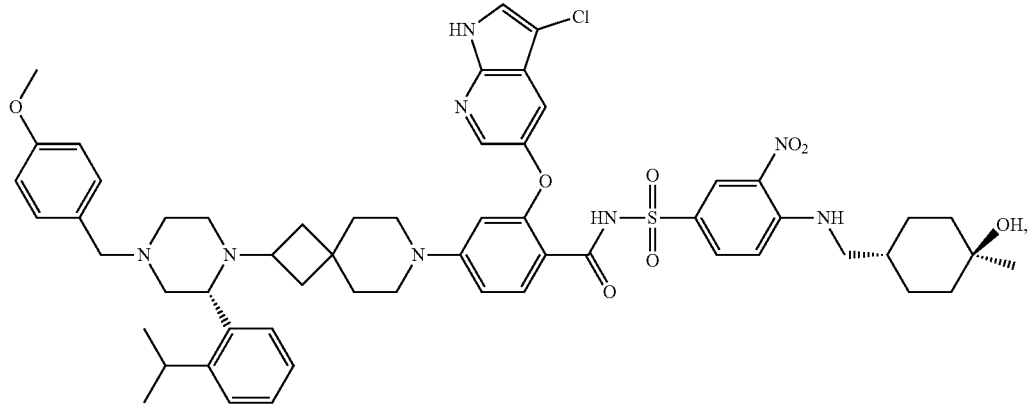
or a pharmaceutically acceptable salt thereof.

14. The compound of claim 2, wherein the compound is
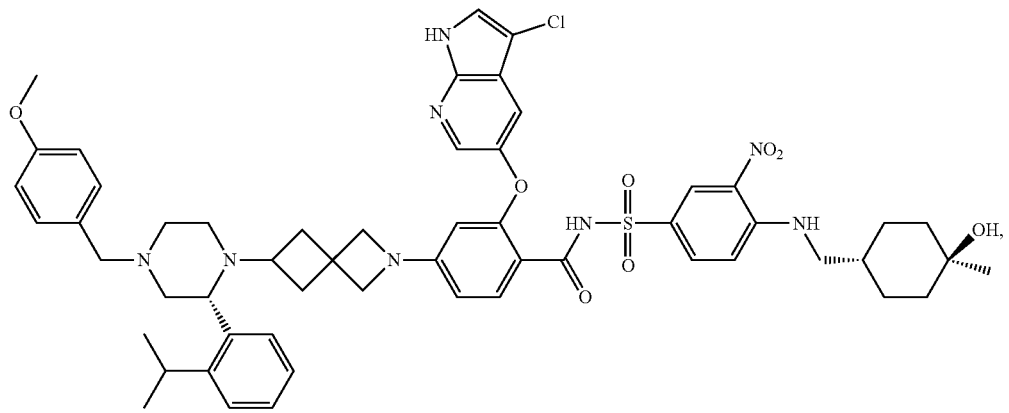
or a pharmaceutically acceptable salt thereof.
15. The pharmaceutical composition of claim 4, wherein the compound is
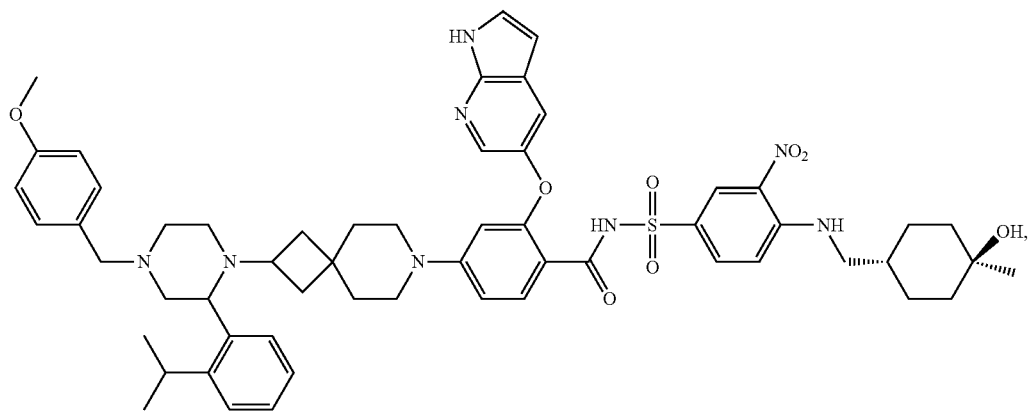
or a pharmaceutically acceptable salt thereof.
16. The pharmaceutical composition of claim 4, wherein the compound is
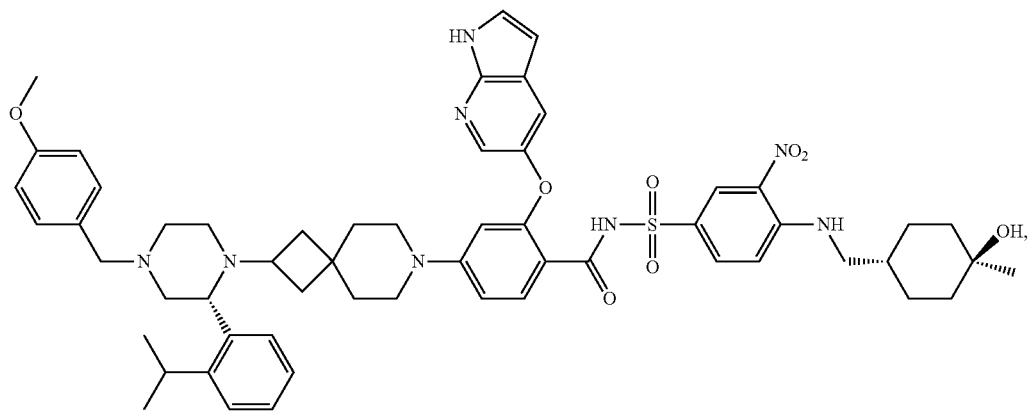
or a pharmaceutically acceptable salt thereof.

17. The pharmaceutical composition of claim 4, wherein the compound is
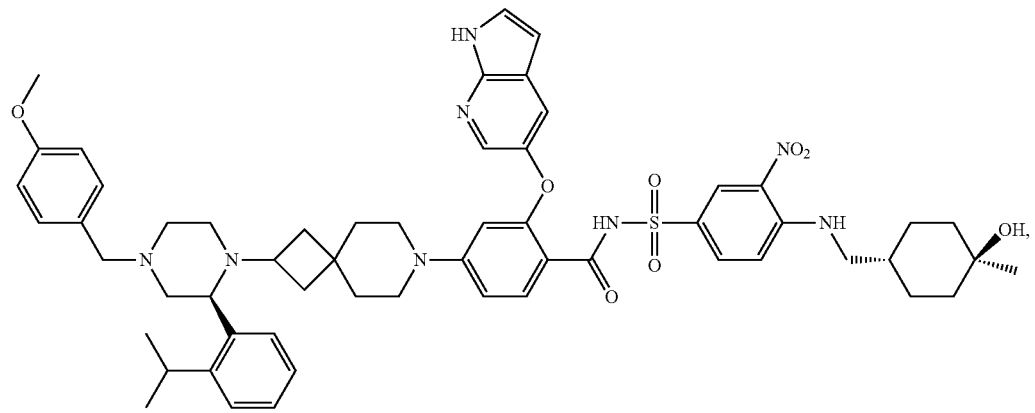 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)C3)[C@@H](c3ccccc3C(C)C)C2)cc1]
or a pharmaceutically acceptable salt thereof.
18. The pharmaceutical composition of claim 4, wherein the compound is
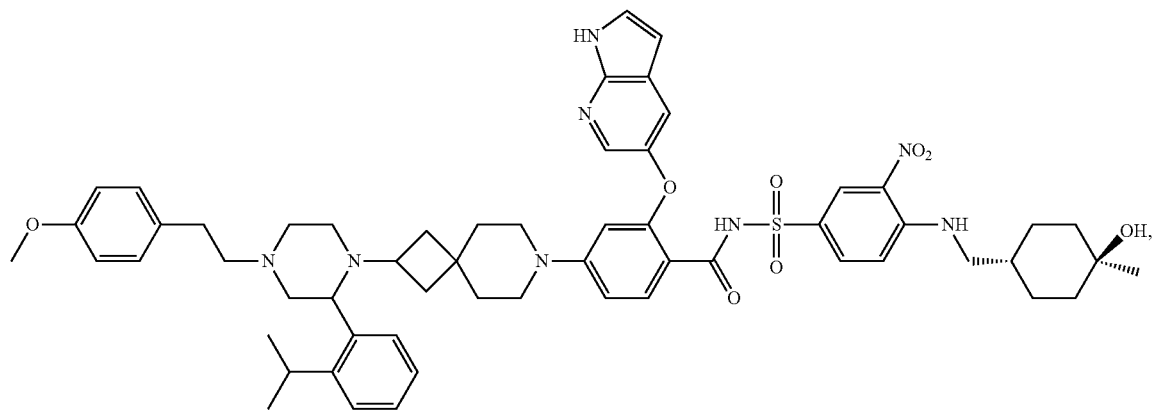
or a pharmaceutically acceptable salt thereof.
19. The pharmaceutical composition of claim 4, wherein the compound is
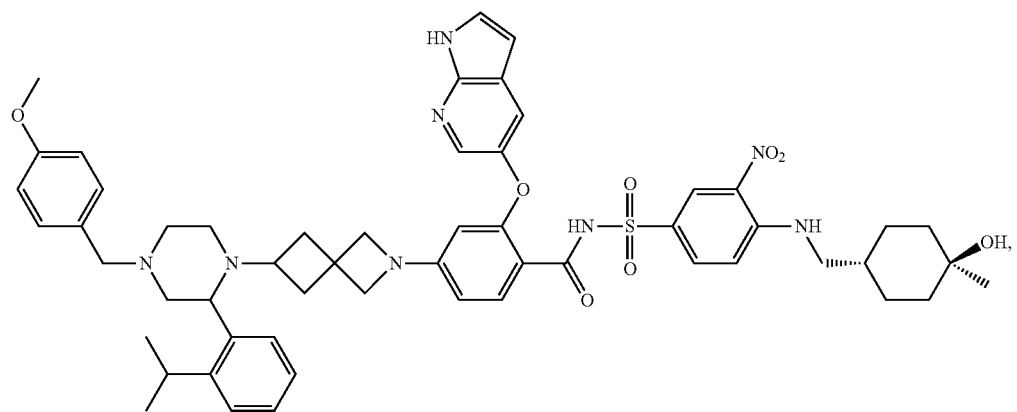 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)C(c3ccccc3C(C)C)C2)cc1]
or a pharmaceutically acceptable salt thereof.

20. The pharmaceutical composition of claim 4, wherein the compound is
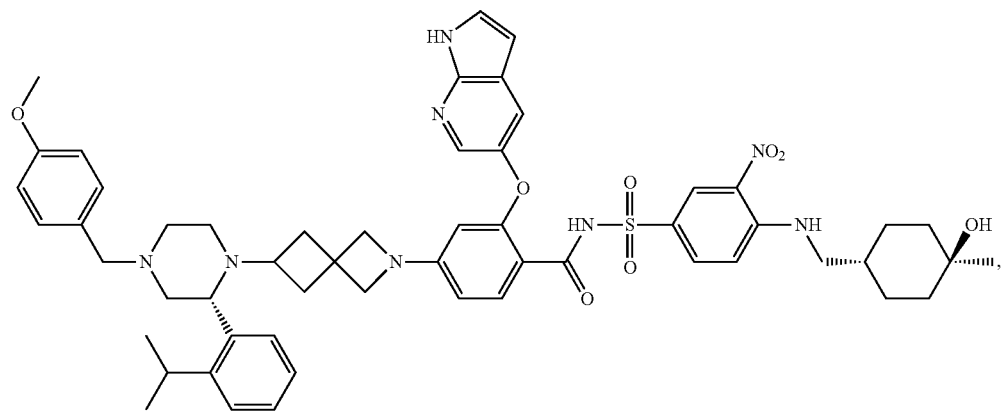 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]ccc6c5)c3)C4)[C@H](c3ccccc3C(C)C)C2)cc1]
or a pharmaceutically acceptable salt thereof.
21. The pharmaceutical composition of claim 4, wherein the compound is
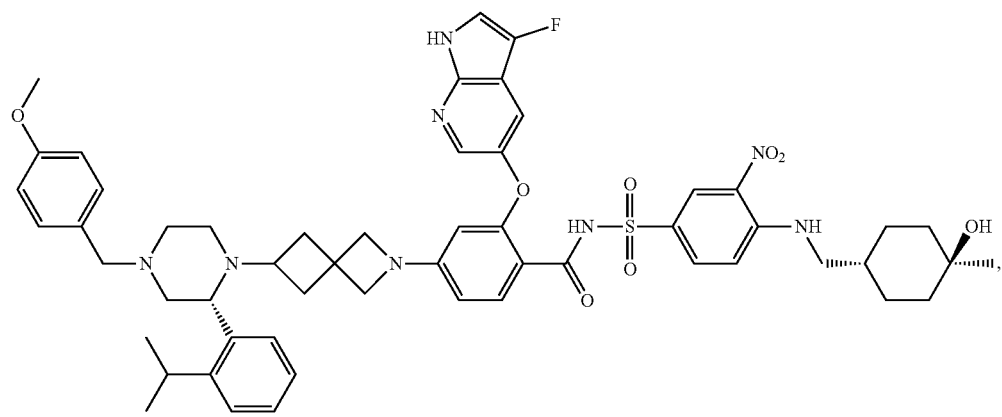 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@H](c3ccccc3C(C)C)C2)cc1]
or a pharmaceutically acceptable salt thereof.
22. The pharmaceutical composition of claim 4, wherein the compound is
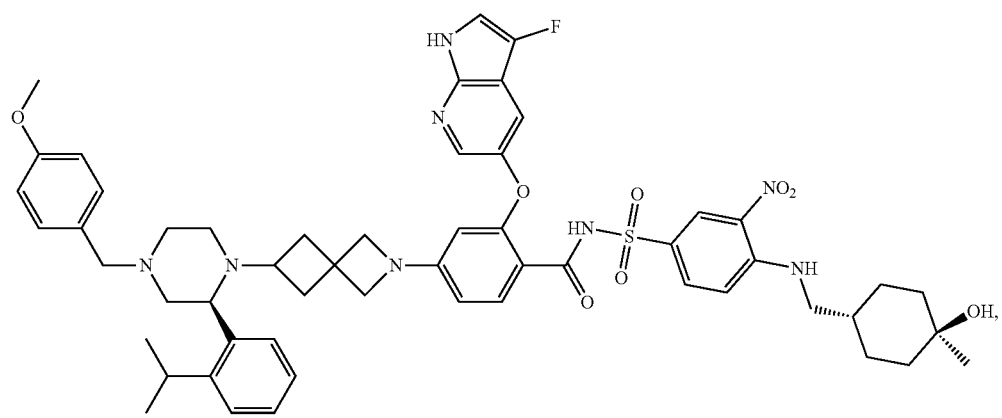 [SMILES: COc1ccc(CN2CCN(C3CC4(C3)CN(c3ccc(C(=O)NS(=O)(=O)c5ccc(NC[C@H]6CC[C@](C)(O)CC6)c([N+](=O)[O-])c5)c(Oc5cnc6[nH]cc(F)c6c5)c3)C4)[C@@H](c3ccccc3C(C)C)C2)cc1]
or a pharmaceutically acceptable salt thereof.

23. The pharmaceutical composition of claim 4, wherein the compound is
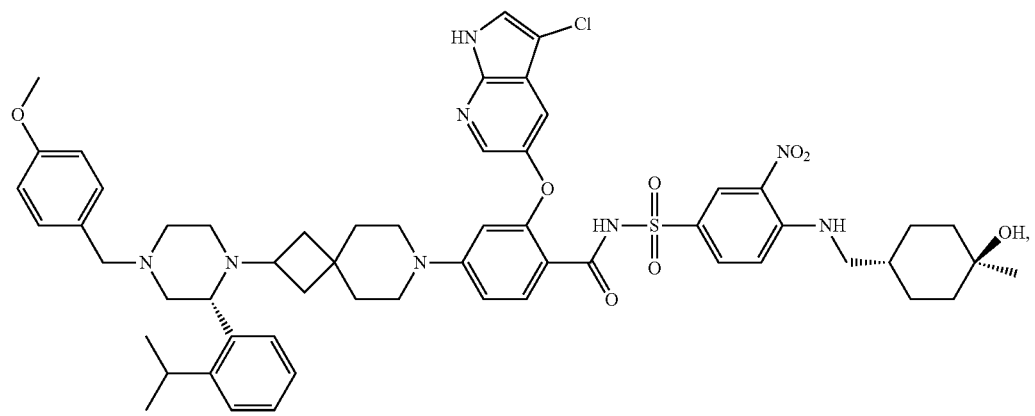 [SMILES: COc1ccc(CN2CCN(C3CC4(CCN(c5ccc(C(=O)NS(=O)(=O)c6ccc(NC[C@H]7CC[C@](C)(O)CC7)c([N+](=O)[O-])c6)c(Oc6cnc7[nH]cc(Cl)c7c6)c5)CC4)C3)[C@H](c3ccccc3C(C)C)C2)cc1]
or a pharmaceutically acceptable salt thereof.
24. The pharmaceutical composition of claim 4, wherein the compound is
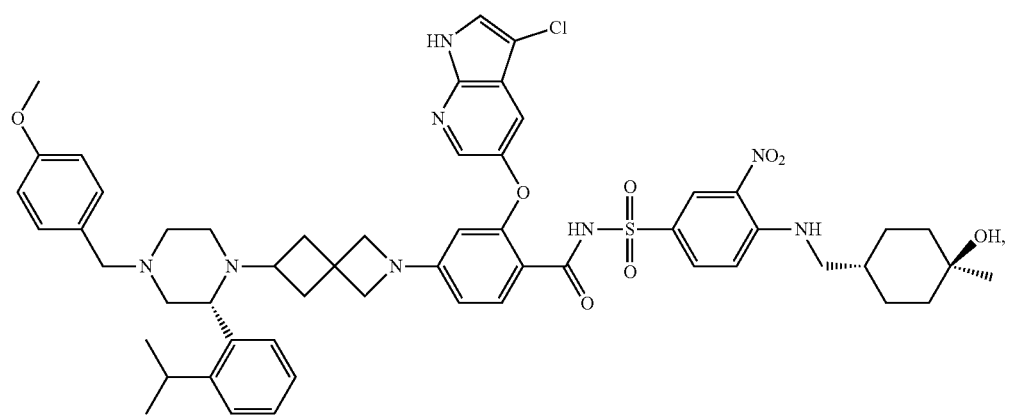
or a pharmaceutically acceptable salt thereof.
* * * * *

UNITED STATES PATENT AND TRADEMARK OFFICE
CERTIFICATE OF CORRECTION

PATENT NO. : 12,286,430 B2  
APPLICATION NO. : 17/916845  
DATED : April 29, 2025  
INVENTOR(S) : Xue et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

Signed and Sealed this  
Thirtieth Day of September, 2025

John A. Squires  
*Director of the United States Patent and Trademark Office*